US012371666B2

(12) United States Patent
Gouon-Evans et al.

(10) Patent No.: US 12,371,666 B2
(45) Date of Patent: Jul. 29, 2025

(54) NUCLEOSIDE MODIFIED mRNA AND USES THEREOF

(71) Applicants: BOSTON MEDICAL CENTER CORPORATION, Boston, MA (US); THE TRUSTEES OF THE UNIVERSITY OF PENNSYLVANIA, Philadelphia, PA (US)

(72) Inventors: Valerie Gouon-Evans, Newton, MA (US); Drew Weissman, Philadelphia, PA (US); Norbert Pardi, Philadelphia, PA (US)

(73) Assignees: BOSTON MEDICAL CENTER CORPORATION, Boston, MA (US); THE TRUSTEES OF THE UNIVERSITY OF PENNSYLVANIA, Philadelphia, PA (US)

(*) Notice: Subject to any disclaimer, the term of this patent is extended or adjusted under 35 U.S.C. 154(b) by 0 days.

(21) Appl. No.: 17/982,753

(22) Filed: Nov. 8, 2022

(65) Prior Publication Data
US 2023/0340418 A1 Oct. 26, 2023

Related U.S. Application Data

(60) Provisional application No. 63/276,868, filed on Nov. 8, 2021.

(51) Int. Cl.
| | | |
|---|---|---|
| C12N 15/88 | (2006.01) | |
| A61K 31/198 | (2006.01) | |
| C12N 5/071 | (2010.01) | |

(52) U.S. Cl.
CPC .......... *C12N 5/0679* (2013.01); *A61K 31/198* (2013.01); *C12N 15/88* (2013.01); *C12N 2501/105* (2013.01); *C12N 2501/11* (2013.01); *C12N 2501/12* (2013.01); *C12N 2501/165* (2013.01); *C12N 2501/305* (2013.01); *C12N 2501/405* (2013.01)

(58) Field of Classification Search
CPC ................ C12N 15/88; C12N 2501/10; C12N 2501/165
See application file for complete search history.

(56) References Cited

U.S. PATENT DOCUMENTS

| | | | |
|---|---|---|---|
| 2009/0275084 A1 | 11/2009 | Fares et al. | |
| 2013/0259924 A1* | 10/2013 | Bancel et al. | C12N 15/85 424/450 |
| 2016/0032316 A1* | 2/2016 | Weissman et al. | C12N 15/85 |
| 2016/0184458 A1 | 6/2016 | Heartlein | |

OTHER PUBLICATIONS

Böhm et al. (2010) "Regulation of liver regeneration by growth factors and cytokines" EMBO molecular medicine, 2(8), 294-305. (Year: 2010).*
Rizvi et al. (2023) âVEGFA mRNA-LNP promotes biliary epithelial cell-to-hepatocyte conversion in acute and chronic liver diseases and reverses steatosis and fibrosisâ Cell Stem Cell, 30(12), 1640-1657. (Year: 2023).*
Addison et al. "Sexual dimorphism of growth hormone in the hypothalamus: regulation by estradiol." Endocrinology 153.4 (2012): 1898-1907.
Avtanski et al. "Both estrogen receptor α and β stimulate pituitary GH gene expression." Molecular endocrinology 28.1 (2014): 40-52.
Bockhorn et al. "VEGF is important for early liver regeneration after partial hepatectomy." Journal of Surgical Research 138.2 (2007): 291-299.
Bohm et al. "Regulation of liver regeneration by growth factors and cytokines." EMBO molecular medicine 2.8 (2010): 294-305.
Choi et al. "Extensive conversion of hepatic biliary epithelial cells to hepatocytes after near total loss of hepatocytes in zebrafish." Gastroenterology 146.3 (2014): 776-788.
Dianat et al. "Generation of functional cholangiocyte-like cells from human pluripotent stem cells and HepaRG cells." Hepatology 60.2 (2014): 700-714.
Ding et al. "Inductive angiocrine signals from sinusoidal endothelium are required for liver regeneration." Nature 468.7321 (2010): 310-315.
Du et al. "Human hepatocytes with drug metabolic function induced from fibroblasts by lineage reprogramming." Cell stem cell 14.3 (2014): 394-403.
Du et al. "Lower susceptibility of female mice to acetaminophen hepatotoxicity: Role of mitochondrial glutathione, oxidant stress and c-jun N-terminal kinase." Toxicology and applied pharmacology 281.1 (2014): 58-66.
Fabris et al. "Effects of angiogenic factor overexpression by human and rodent cholangiocytes in polycystic liver diseases." Hepatology 43.5 (2006): 1001-1012.
Gaudio et al. "Vascular endothelial growth factor stimulates rat cholangiocyte proliferation via an autocrine mechanism." Gastroenterology 130.4 (2006): 1270-1282.
Gordillo et al. "Orchestrating liver development." Development 142.12 (2015): 2094-2108.
Gouon-Evans et al. "BMP-4 is required for hepatic specification of mouse embryonic stem cell-derived definitive endoderm." Nature biotechnology 24.11 (2006): 1402-1411.

(Continued)

*Primary Examiner* — Laura Schuberg
*Assistant Examiner* — James Joseph Graber
(74) *Attorney, Agent, or Firm* — Nixon Peabody LLP; Ronald I. Eisenstein; Nicole D. Kling

(57) ABSTRACT

The present application discloses compositions and methods for use of nucleoside modified mRNA that encode for at least one liver regenerative factor. The present invention also relates to compositions and methods for use of nucleoside modified mRNA complexed to nanoparticles. The disclosed compositions and methods are useful for treating acute liver diseases, chronic liver diseases, and/or acetaminophen (acetyl-para-aminophenol, APAP) overdose.

22 Claims, 264 Drawing Sheets
Specification includes a Sequence Listing.

(56) References Cited

OTHER PUBLICATIONS

Han et al. "An endothelial cell niche induces hepatic specification through dual repression of Wnt and Notch signaling." Stem Cells 29.2 (2011): 217-228.
Han et al. "Endothelial cells instruct liver specification of embryonic stem cell-derived endoderm through endothelial VEGFR2 signaling and endoderm epigenetic modifications." Stem Cell Research 30 (2018): 163-170.
Lau-Corona et al. "Constitutively active STAT5b feminizes mouse liver gene expression." Endocrinology 163.5 (2022): bqac046.
Ecouter et al. "Angiogenesis-independent endothelial protection of liver: role of VEGFR-1." Science 299.5608 (2003): 890-893.
Liu et al. "Glutathione metabolism during aging and in Alzheimer disease." Annals of the New York Academy of Sciences 1019.1 (2004): 346-349.
Lu et al. "Hepatic progenitor cells of biliary origin with liver repopulation capacity." Nature cell biology 17.8 (2015): 971-983.
Manco et al. "Reactive cholangiocytes differentiate into proliferative hepatocytes with efficient DNA repair in mice with chronic liver injury." Journal of hepatology 70.6 (2019): 1180-1191.
Masubuchi et al. "Sex difference in susceptibility to acetaminophen hepatotoxicity is reversed by buthionine sulfoximine." Toxicology 287.1-3 (2011): 54-60.
McClain et al. "Potentiation of acetaminophen hepatotoxicity by alcohol." Jama 244.3 (1980): 251-253.
Michalopoulos. "Hepatostat: Liver regeneration and normal liver tissue maintenance." Hepatology 65.4 (2017): 1384-1392.
Michalopoulos "Liver regeneration after partial hepatectomy: critical analysis of mechanistic dilemmas." The American journal of pathology 176.1 (2010): 2-13.
Moller et al. "Effects of growth hormone on glucose, lipid, and protein metabolism in human subjects." Endocrine reviews 30.2 (2009): 152-177.
Oe et al. "Hepatocyte growth factor as well as vascular endothelial growth factor gene induction effectively promotes liver regeneration after hepatectomy in Solt-Farber rats." Hepato-gastroenterology 52.65 (2005): 1393-1397.
Pennisi et al. "Role of growth hormone (GH) in liver regeneration." Endocrinology 145.10 (2004): 4748-4755.
Prescott "Paracetamol, alcohol and the liver." British journal of clinical pharmacology 49.4 (2000): 291-301.
Preziosi et al. "Endothelial Wnts regulate β-catenin signaling in murine liver zonation and regeneration: A sequel to the Wnt-Wnt situation." Hepatology Communications 2.7 (2018): 845-860.
Raven et al. "Cholangiocytes act as facultative liver stem cells during impaired hepatocyte regeneration." Nature 547.7663 (2017): 350-354.
Russell et al. "Hepatocyte-specific β-catenin deletion during severe liver injury provokes cholangiocytes to differentiate into hepatocytes." Hepatology 69.2 (2019): 742-759.
Sarmento-Cabral et al. "GH directly inhibits steatosis and liver injury in a sex-dependent and IGF1-independent manner." Journal of Endocrinology 248.1 (2021): 31-44.
Segal et al. "Single cell analysis of human foetal liver captures the transcriptional profile of hepatobiliary hybrid progenitors." Nature communications 10.1 (2019): 1-14.
Sourisseau et al. "Hepatic cells derived from induced pluripotent stem cells of pigtail macaques support hepatitis C virus infection." Gastroenterology 145.5 (2013): 966-969.
Veldhuis et al. "Regulated recovery of pulsatile growth hormone secretion from negative feedback: a preclinical Investigation." American Journal of Physiology-Regulatory, Integrative and Comparative Physiology 301.4 (2011): R1143-R1152.
Win et al. "Expression of mitochondrial membrane-linked SAB determines severity of sex-dependent acute liver Injury." The Journal of clinical investigation 129.12 (2019): 5278-5293.
Yang et al. "Vascular endothelial growth factor promotes fibrosis resolution and repair in mice." Gastroenterology 146.5 (2014): 1339-1350.
Yoon et al. "Acetaminophen-induced hepatotoxicity: a comprehensive update." Journal of clinical and translational hepatology 4.2 (2016): 131-142.
Rodriguez-Sanchez et al. "Paplo hamadryas growth hormone (GH) mRHA, complete cds" National Center for Biotechnology Information (2001).
Roytrakul et al. "Synthetic construct human growth hormone gene, complete cds" National Center for Biotechnology Information (2001).
Staub et al. "Synthetic construct recombinant ubiquitin-sematotropin fusion protein (Ubiq-ST) mRNA, complete cds" National Center for Biotechnology Information (2001).

* cited by examiner

*FIG. 3A (Rizvi)*

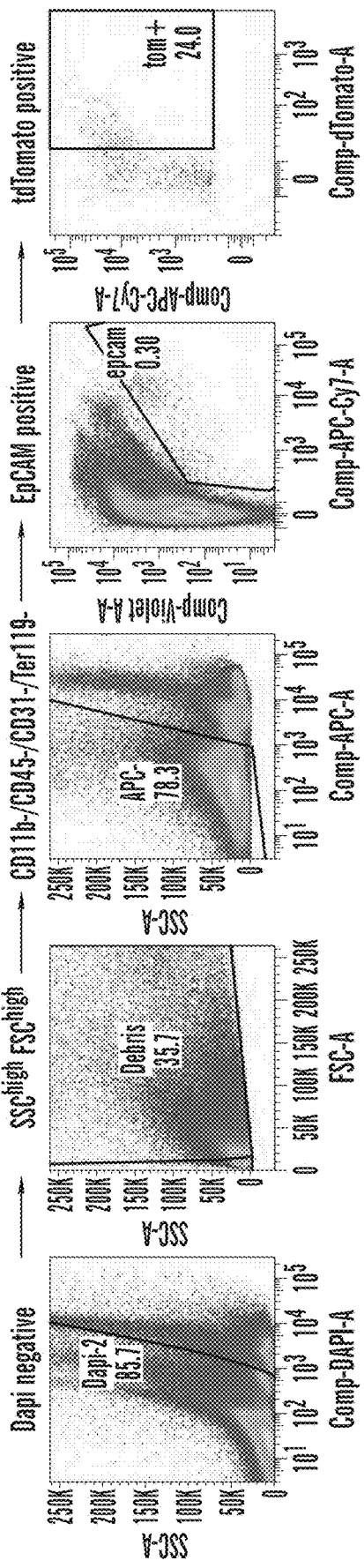
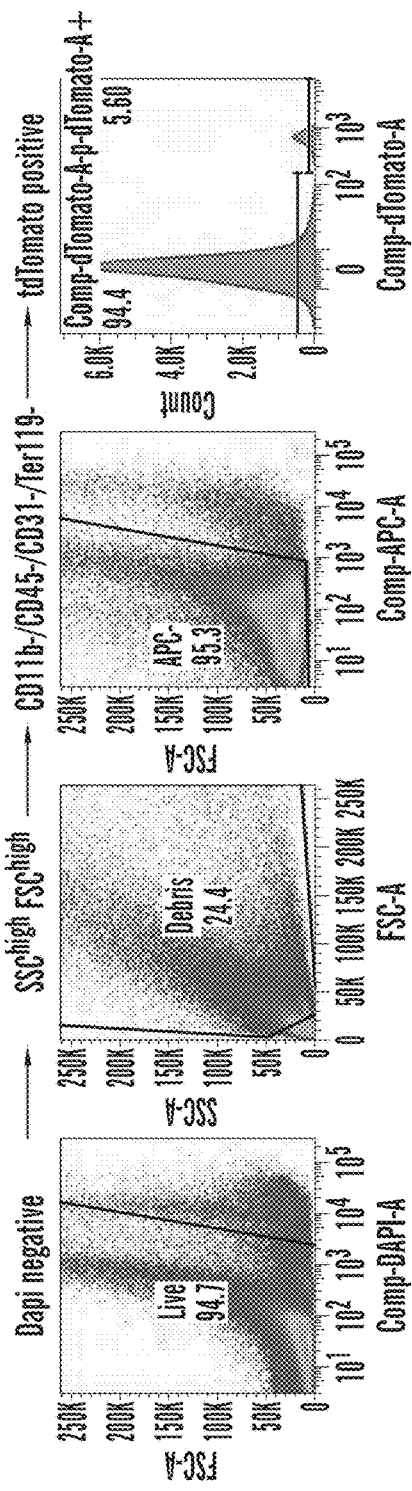
FIG. 15A
FIG. 15B

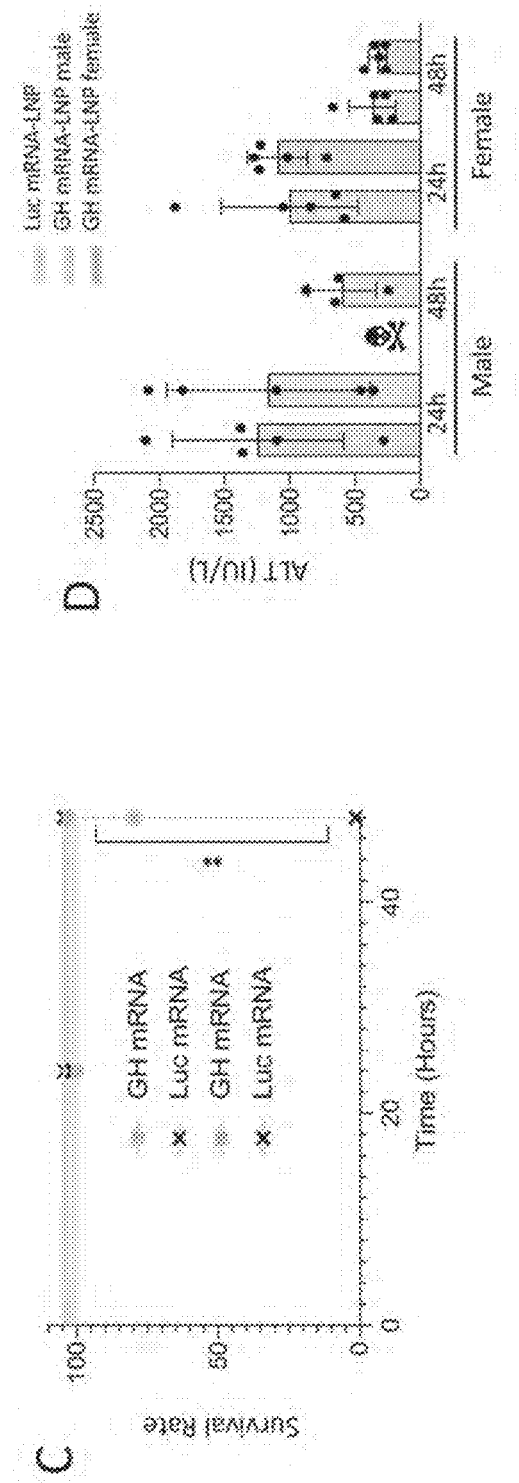
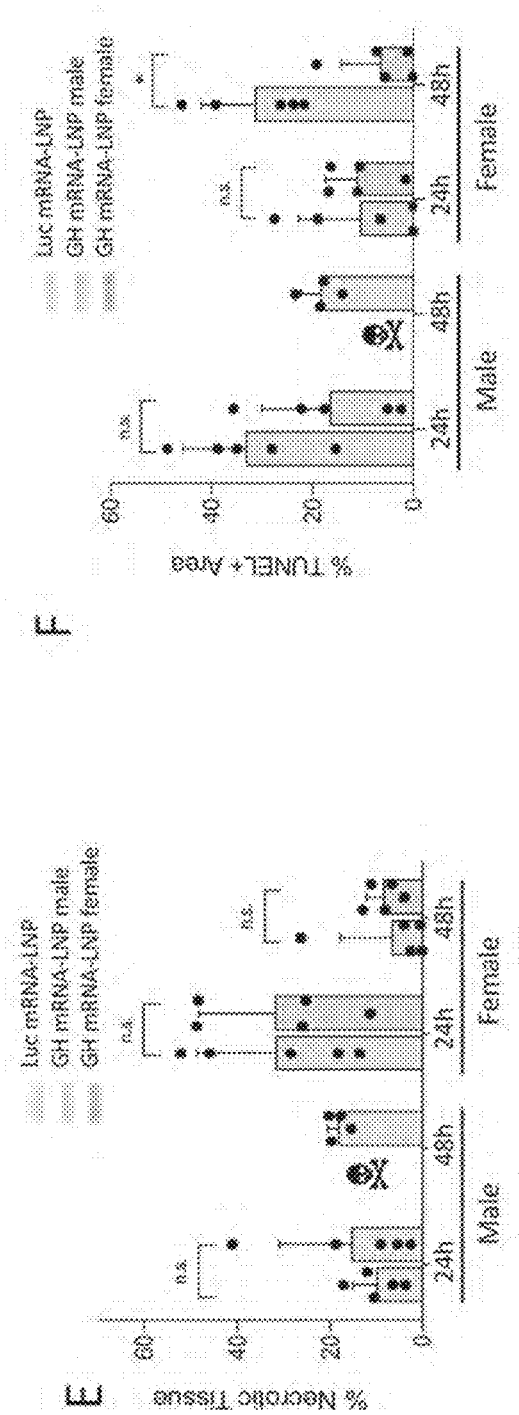
FIGs. 20C-20F

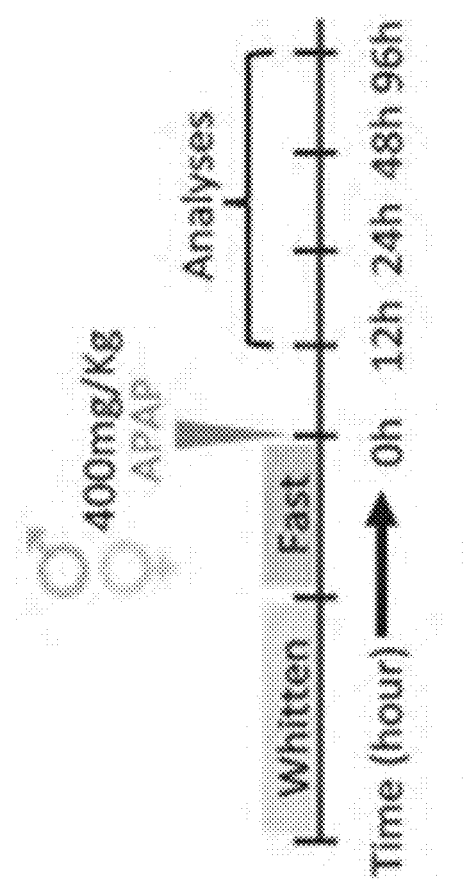
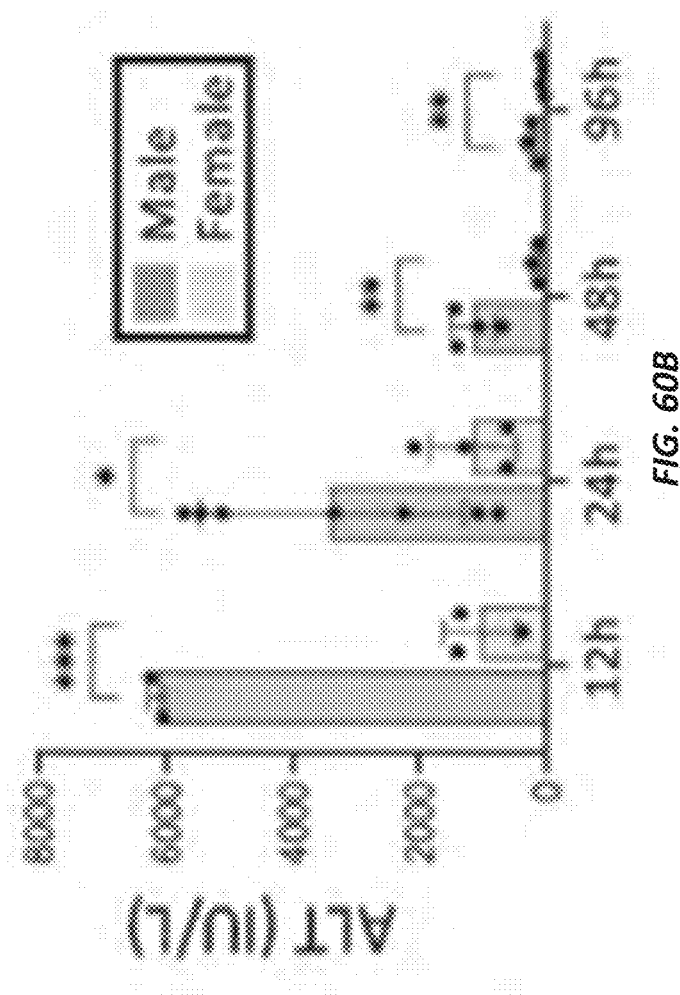
FIG. 60A
FIG. 60B

CDE: Choline-Deficient Ethionine-supplemented diet
Phenotype: steatosis, necrosis, hepatitis Arrowheads: KDR expression on a subset of cholangiocytes

- AATD is caused by a single base pair mutation of the *SERPINA1* gene.
- The PiZ mutation causes misfolded Z-AAT protein to accumulate and polymerize in hepatocytes.
- The liver disease associated with human AATD is recapitulated in the transgenic NSG-PiZ mouse model.

Borel et al., Molecular Therapy, 2017 hAlbumin

- The PiZ background favors engraftment of healthy primary human hepatocytes in the liver of mice.
- Partial hepatectomy increases human liver chimerism.

SEQUENCE LISTING

```
Sequence total quantity: 46
SEQ ID NO: 1            moltype = DNA   length = 823
FEATURE                 Location/Qualifiers
source                  1..823
                        mol_type = genomic DNA
                        organism = Homo sapiens
SEQUENCE: 1
aaggatccca aggcccaact ccccgaacca ctcagggtcc tgtggacagc tcacctagct    60
gcaatggcta caggctcccg gacgtccctg ctcctggctt ttggcctgct ctgcctgccc   120
tggcttcaag agggcagtgc cttcccaacc attcccttat ccaggctttt tgacaacgct   180
atgctccgcg cccatcgtct gcaccagctg gcctttgaca cctaccagga gtttgaagaa   240
gcctatatcc caaggaaca gaagtattca ttcctgcaga accccagac ctccctctgt    300
ttctcagagt ctattccgac accctccaac agggaggaaa cacaacagaa atccaaccta   360
gagctgctcc gcatctccct gctgctcatc cagtcgtggc tggagcccgt gcagttcctc   420
aggagtgtct tcgccaacag cctggtgtac ggcgcctctg acagcaacgt ctatgacctc   480
ctaaaggacc tagaggaagg catccaaacg ctgatgggga ggctggaaga tggcagcccc   540
cggactgggc agatcttcaa gcagacctac agcaagttcg acacaaactc acacaacgat   600
gacgcactac tcaagaacta cgggctgctc tactgcttca ggaaggacat ggacaaggtc   660
gagacattcc tgcgcatcgt gcagtgccgc tctgtggagg gcagctgtgg cttctagctg   720
cccgggtggc atccctgtga cccctcccca gtgcctcctcc tggccctgga agttgccact   780
ccagtgccca ccagcctgt cctaataaaa ttaagttgca tca                      823

SEQ ID NO: 2            moltype = DNA   length = 6388
FEATURE                 Location/Qualifiers
source                  1..6388
                        mol_type = genomic DNA
                        organism = Homo sapiens
SEQUENCE: 2
caaaaagaga aactgttggg agaggaatcg tatctccata tttcttcttt cagccccaat    60
ccaagggttg tagctggaac tttccatcag ttcttccttt cttttttcctc tctaagcctt   120
tgccttgctc tgtcacagtg aagtcagcca gagcagggct gttaaactct gtgaaatttg   180
tcataagggt gtcaggtatt tcttactggc ttccaaagaa acatagataa aagaaatcttt   240
cctgtggctt cccttggcag gctgcattca gaaggtctct cagttgaaga aagagcttgg   300
aggacaacag cacaacagga gagtaaaaga tgccccaggg ctgaggcctc cgctcaggca   360
gccgcatctg gggtcaatca tactcacctt gcccgggcca tgctccagca aaatcaagct   420
gttttctttt gaaagttcaa actcatcaag attatgctgc tcactcttat cattctgttg   480
ccagtagttt caaaatttag ttttgttagt ctctcagcac cgcagcactg gagctgtcct   540
gaaggtactc tcgcaggaaa tgggaattct acttgtgtgg gtcctgcacc cttcttaatt   600
ttctcccatg gaaatagtat ctttaggatt gacacagaag gaaccaatta tgagcaattg   660
gtggtggatg ctggtgtctc agtgatcatg gattttcatt ataatgagaa aagaatctat   720
tgggtggatt tagaaagaca acttttgcaa agagttttc tgaatgggtc aaggcaagag   780
agagtatgta atatagagaa aaatgtttct ggaatggcaa taaattggat aaatgaagaa   840
gttatttggt caaatcaaca ggaaggaatc attacagtaa cagatatgaa aggaaataat   900
tcccacattc ttttaagtgc tttaaaatat cctgcaaatg tagcagttga tccagtagaa   960
aggtttatat tttggtcttc agaggtggct ggaagccttt atagagcaga tctcgatggt  1020
gtgggagtga aggctctgtt ggagacatca gagaaaataa cagctgtgtc attggatgtg  1080
cttgataagc ggctgtttg gattcagtac aacagagaag gaagcaattc tcttatttgc  1140
tcctgtgatt atgatggagg ttctgtccac attagtaaca atccaacaca gcataattg   1200
tttgcaatgt ccccttttgg tgaccgtatc ttctattcaa catggaaaat gaagacaatt  1260
tggatagcca acaaacacac tggaaaggac atggttagaa ttaacctcca ttcatcattt  1320
gtaccacttg gtgaactgaa agtagtgcat ccacttgcac aacccaaggc agaagatgac  1380
acttgggagc ctgagcagaa actttgcaaa ttgaggaaag gaaactgcag cagcactgtg  1440
tgtgggcaag acctccagtc acacttgtgc atgtgtgcag agggatacgc cctaagtcga  1500
gaccggaagt actgtgaaga tgttaatgaa tgtgcttttt ggaatcatgg ctgtactctt  1560
gggtgtaaaa acacccctgg atcctattac tgcacgtgcc ctgtaggatt tgttctgctt  1620
cctgatggga acgatgtca tcaacttgtt cctgtccac gcaatgtgtc tgaatgcagc  1680
catgactgtg ttctgacatc agaaggtccc ttatgtttct gtcctgaagg ctcagtgctt  1740
gagagagatg ggaaaacatg tagcggttgt tcctcacccg ataatggtgg atgtagccag  1800
ctctgcgttc ctcttagccc agtatcctgg aatgtgatt gctttcctgg gtatgaccta  1860
caactggatg aaaaagctg tgcagcttca ggaccacaac catttttgct gtttgccaat  1920
tctcaagata ttcgacacat gcattttgat ggaacagata tggaactct gctcagccag  1980
cagatgggaa tggtttatgc cctagatcat gaccctgtgg aaaataagat atactttgcc  2040
catacagccc tgaagtggat agagagagct aatatggatg gttcccagcg agaaaggctt  2100
attgaggaag gagtagatgt gccagaaggt cttgctgtgg actggattgg ccgtagattc  2160
tattggacag acagagggga atctctgatt ggaaggagtg attaaaatgg aaacgttcc   2220
aaaataatca ctaaggagaa catctctcaa ccacgaggaa ttgctgttca tccaatggcc  2280
aagagattat tctggactga tacagggatt aatccacgaa ttgaaagttc ttccctccaa  2340
ggccttggcc gtcggttat agccagctct gatctaatct ggcccagtgg aataacgatt  2400
gacttcttaa ctgacaagtt gtactggtgc gatgccaagc agtctgtgat tgaaatgccc  2460
aatctggatg gttcaaaacg ccgaagactt acccagaatg atgtaggtca ccatttgct  2520
gtagcagtgt ttgaggatta tgtgtggttc tcagattggg ctatgccatc agtaatgaga  2580
gtaaacaaga ggactggcaa agatagagta cgtctccaag gcagcatgct gaagccctca  2640
tcactggttg tggttcatcc attggcaaaa cagggacga atccctgctt atatcaaaac  2700
ggaggctgtg aacatatttg caaaaagaggg cttggaactg cttggtgttc gtgtcgtgaa  2760
ggttttatga agcctcaga tgggaaaacg tgtctggctc tggatggtca tcagctgttg  2820
gcaggtggtg aagttgatct aaagaaccaa gtaacaccat tggacatctt gtccaagact  2880
agagtgtcag aagataacat tacagaatct caacacatgc tagtggctga atcatggtg  2940
tcagatcaag atgactgtgc tcctgtggga tgcagcatgt atgctcggtg tatttcagag  3000
```

```
ggagaggatg ccacatgtca gtgtttgaaa ggatttgctg gggatggaaa actatgttct   3060
gatatagatg aatgtgagat gggtgtccca gtgtgcccc ctgcctcctc caagtgcatc    3120
aacaccgaag gtggttatgt ctgccggtgc tcagaaggct accaaggaga tgggattcac    3180
tgtcttgata ttgatgagtg ccaactgggg gagcacagct gtggagagaa tgccagctgc    3240
acaaatacag agggaggcta tacctgcatg tgtgctggac gcctgtctga accaggactg    3300
atttgccctg actctactcc accccctcac ctcaggaaag atgaccacca ctattccgta    3360
agaaatagtg actctgaatg tcccctgtcc cacgatgggt actgcctcca tgatggtgtg    3420
tgcatgtata ttgaagcatt ggacaagtat gcatgcaact gtgttgttgg ctacatcggg    3480
gagcgatgtc agtaccgaga cctgaagtgg tgggaactgc gccacgctgg ccacgggcag    3540
cagcagaagg tcatcgtggt ggctgtctgc gtggtggtgc ttgtcatgct gctcctcctg    3600
agcctgtggg gggcccacta ctacaggact cagaagctgc tatcgaaaaa cccaaagaat    3660
ccttatgagg agtcgagcag agatgtgagg agtcgcaggc ctgctgacac tgaggatggg    3720
atgtcctctt gccctcaacc ttggtttgtg gttataaaag aacaccaaga cctcaagaat    3780
gggggtcaac cagtggctgg tgaggatggc caggcaggac atgggtcaat gcaaccaact    3840
tcatggaggc aggagcccca gttatgtgga atgggcacag agcaaggctg ctggattcca    3900
gtatccagtg ataagggctc ctgtcccag gtaatggagc gaagctttca tatgccctcc     3960
tatgggacac agacccttga aggggtgtc gagaagcccc attctctcct atcagctaac     4020
ccattatggc aacaaagggc cctggaccca ccacaccaaa tggagctgac tcagtgaaaa    4080
ctggaattaa aaggaaagtc aagaagaatg aactatgtcg atgcacagta tcttttcttt    4140
caaaagtaga gcaaaactat aggttttggt tccacaatct ctacgactaa tcacctactc    4200
aatgcctgga gacagatacg tagttgtgct tttgtttgct cttttaagca gtctcactgc    4260
agtcttattt ccaagtaaga gtactggag aatcactagg taacttatta gaaacccaaa     4320
ttgggacaac agtgctttgt aaattgtgtt gtcttcagca gtcaatacaa atagattttt    4380
gttttttgttg ttcctgcagc cccagaagaa attagggggtt aaagcagaca gtcacactgg   4440
tttggtcagt tacaaagtaa tttctttgat ctggacagaa catttatatc agtttcatga    4500
aatgattgga atattacaat accgttaaga tacagtgtag gcatttaact cctcattggc    4560
gtggtccatg ctgatgattt tgcaaaatga gttgtgatga atcaatgaaa aatgtaattt    4620
agaaactgat ttcttcagaa ttagatggct tattttttaa aatatttgaa tgaaaacatt    4680
ttattttaa aatattacac aggaggcttc ggagtttctt agtcattact gtccttttcc     4740
cctacagaat tttccctctt ggtgtgattg cacagattt gtatgtattt tcagttacaa     4800
gattgtaagt aaaattgcctg atttgttttc attatagaca acgatgaatt tcttctaatt    4860
atttaaataa aatcaccaaa aacataaaca ttttattgta tgcctgatta agtagtaat     4920
tatagtctaa ggcagtacta gagttgaacc aaaatgattt gtcaagcttg ctgatgtttc    4980
tgtttttcgt ttttttttt tttccggaga gaggatagga tctcactctg ttatccaggc     5040
tggagtgtgc aatggcacaa tcatagctca gtgcagcctc aaactcctgg gctcaagcaa    5100
tcctcctgcc tcagcctccc gagtaactag gaccacaggc acaggccacc atgcctggct    5160
aaggttttta ttttattttt ttgtagacat ggggatcaca caatgttgcc caggctggtc    5220
ttgaactcct ggcctcaagc aaggtcgtgc tggtaattt gcaaaatgaa ttgtgattga     5280
ctttcagcct cccaacgtat tagattatag gcattagcca tggtgcccag cccttgtaact   5340
tttaaaaaaa ttttttaatc tacaactctg tagattaaaa tttcacatgg tgttctaatt    5400
aaatatttt cttgcagcca agatattgtt actacagata acacacctg atatggtaac     5460
tttaaatttt gggggctttg aatcattcag tttatgcatt aactagtccc tttgtttatc    5520
tttcatttct caaccccttg tacttggtg ataccagaca tcagaataaa aagaaattga    5580
agtaccctgtt ttcaaaatgga tactttatag gaatttggt aaagatttgg tgatgggagg   5640
atgacttgag gtttgtggat attagttaat tattcagtat gataccctcac ccagctaatt   5700
tagatttttc tatattcggt tttgcttttca ttgacaatat cctggaggat cagaagactt    5760
gtctattttct gctgagtcac tggcctcaga aaaataataa ccataattt ccccaaggtt    5820
ttctttacct aagtgtgaat attttttctt cctccaaaag ctcactttg ggtttagatt    5880
aaatttttgt attttagcac cttttttctt taggggttca atgatgacaa agaaatgac    5940
atgagaacac ggctacccat aacataccat tatctttgta ccagaaaaat ccttgttccc    6000
ttcttaatga ctctggtacc ttagaaactg ggaccctgct aagtccttga ctaggctact    6060
taccagctcc tggtcggatt aaagaaaaaa cacactttgt gttttttaat caccaaggca    6120
ccctgcagag atatcttctt cttgcaactt cacatcttta tcagtaatgt cctctttcct   6180
ttaaaaattc aagttttaag aacagcattt tcatgtaaaa acttgatttg tgttttttcc    6240
agactgaata cttttcctcc ctaactctca tcgtctcatt gcgcgcaacg cctgattgag    6300
cttctgtttg actaaaatatc acctactatg taaaaaatga gcatattggc ctctttttcta   6360
gcatctaata aaggcttaat acactgta                                      6388
```

SEQ ID NO: 3         moltype = DNA   length = 5834
FEATURE              Location/Qualifiers
source              1..5834
                      mol_type = genomic DNA
                      organism = Homo sapiens
SEQUENCE: 3

```
aggcactgac tccgaacagg attctttcac ccaggcatct cctccagagg gatccgccag     60
cccgtccagc agcaccatgt gggtgaccaa actcctgcca gccctgctgc tgcagcatgt    120
cctcctgcat ctcctcctgc tccccatcgc catcccctat gcagagggac aaaggaaaag    180
aagaaataca attcatgaat tcaaaaaatc agcaaagact accctaatca aaatagatcc    240
agcactgaag ataaaaacca aaaagtgaa tactgcagc caatgtgcta atagatgtac    300
taggaataaa ggacttccat tcacttgcaa ggcttttgtt tttgataaag caagaaaaca   360
atgcctctgg ttccccttca atagcatgtc aagtggagtg aaaaaagaat ttggccatga   420
atttgacctc tatgaaaaca aagactacat tagaaactgc atcattggta aaggacgcag   480
ctacaaggga acagtatcta tcactaagag tggcatcaaa tgtcagccct ggagttccat   540
gataccacac gaacacagct ttttgccttc gactatcgg ggtaaagacc tacaggaaa    600
ctactgtcga aatcctcgag gggaagaagg gggaccctgg tgtttcacaa gcaatccaga   660
ggtacgctac gaagtctgtg acattcctca gtgttcagaa gttaatgca tgacctgcaa   720
tgggagagt tatcgaggtc tcatggatca tacagaatca gcaagattt gtcagcgctg    780
ggatcatcag acaccacacc ggcacaaatt cttgcctgaa agatatccg acaagggctt    840
tgatgataat tattgccgca atcccgatgg ccagccgagg ccatggtgct atactcttga    900
```

```
ccctcacacc cgctgggagt actgtgcaat taaaacatgc gctgacaata ctatgaatga    960
cactgatgtt cctttggaaa caactgaatg catccaaggt caaggagaag gctacagggg   1020
cactgtcaat accatttgga atggaattcc atgtcagcgt tgggattctc agtatcctca   1080
cgagcatgac atgactcctg aaaatttcaa gtgcaaggac ctacgagaaa attactgccg   1140
aaatccagat gggtctgaat caccctggtg ttttaccact gatccaaaca tccgagttgg   1200
ctactgctcc caaattccaa actgtgtatat gtcacatgga caagattgtt atcgtgggaa   1260
tggcaaaaat tatatgggca acttatccca aacaagatct ggactaacat gttcaatgtg   1320
ggacaagaac atgaagact tacatcgtca tatcttctgg gaaccagatg caagtaagct   1380
gaatgagaat tactgccgaa atccagatga tgatgctcat ggaccctggt gctacacggg   1440
aaatccactc attccttggg attattgccc tatttctcgt tgtgaaggtg ataccacacc   1500
tacaatagtc aatttagacc atcccgtaat atcttgtgcc aaaacgaaac aattgcgagt   1560
tgtaaatggg attccaacac gaacaaacat aggatggatg gttagtttga gatacagaaa   1620
taaacatatc tgcggaggat cattgataaa ggagagttgg gttcttactg cacgacagtg   1680
tttcccttct cgagacttga aagattatga agcttggctt ggaattcatg atgtccacgg   1740
aagaggagat gagaaatgca aacaggttct caatgtttcc cagctggtat atggccctga   1800
aggatcagat ctggttttaa tgaagcttgc caggcctgct gtcctggatg attttgttag   1860
tacgattgat ttacctaatt atggatgcac aattcctgaa aagaccagtt gcagtgttta   1920
tggctggggc tacactggat tgatcaacta tgatggccta ttacgagtgg cacatcctca   1980
tataatggga aatgagaaat gcagccagca tcatcgaggg aaggtgactc tgaatgagtc   2040
tgaaatatgt gctggggctg aaaagattgg atcaggacca tgtgaggggg attatggtgg   2100
cccacttgtt tgtgagcaac ataaaatgag aatggttctt ggtgtcattg ttcctggtcg   2160
tggatgtgcc attccaaatc gtcctggtat ttttgtccga gtagcatatt atgcaaaatg   2220
gatacacaaa attattttaa catataaggt accacagtca tagctgaagt aagtgtgtct   2280
gaagcaccca ccaatacaac tgtcttttac atgaagattt cagagaatgt ggaatttaaa   2340
atgtcactta caacaatcct aagacaacta ctggagagtc atgtttgttg aaattctcat   2400
taatgtttat gggtgtttc tgttgttttg tttgtcagtg tattttgtc aatgttgaag   2460
tgaattaagg tacatgcaag tgtaataaca tatctcctga agatacttga atggattaaa   2520
aaaacacaca ggtatatttg ctggatgata aagatttcat gggaaaaaaa atcaattaat   2580
ctgtctaagc tgctttctga tgttggtttc ttaataatga gtaaaccaca aattaaatgt   2640
tattttaacc tcaccaaaac aattatacc ttgtgtccct aaattgtagc cctatattaa   2700
attatattac atttcatatg ctatatgtta tagttcattc atttctcttc accatgtatc   2760
ctgcaatact ggtacacgaa cacactttt acaaaaccac ataccatgt acacatgcct   2820
aggtacacat gtgcatgcac tacagtttaa attatggtgt acctaatgta accctaaat   2880
attttagaag tatgtaccta tagttttacc tcaaaaaaac cagaaatctc taaagaccag   2940
tagaaatatt aaaaaatgat gcaagatcaa aatgattagc taattctcca tacataatct   3000
gcagatgatc ttcttggtt ggcatttcag gtgtggccat cacccagagt taaataacac   3060
ctaatctagg tgtttacatg tattcattat cctagttatt tcatgtagtt tctaattctt   3120
aaaggaaaga gggtaaatagt tctatttgtg taattgttt cctccaaact taaggccact   3180
tatttacaca agatatttgt agatctattt tcctaaagca tttcttaagt gctcagatca   3240
gtatctaatt gaagaagttt aaaagtgttt tggtcattaa aaatgtactt aaataggtta   3300
aatctaagcc ttgctgctgt gattggcttc tagctcactg cctttaaatt ttaaaaaatt   3360
taagaggaaa atttccaagt ctccaaagtt ttataaaatac ccttcatcaa gtcatgcatt   3420
aaagtatata ttggagaaaa aaataaaaat acttttctca actggaaga ttttagccta   3480
ataaagcttt tttgaagtaa aagacaactt gtaaaggaa agaaactagt ttgtctcaac   3540
tctgtattca tttattttt tttgaagta gagtggaatc tgttgaatca gatattttat   3600
caagatatgt ttatttttc ttatttcatt ttacaaagtt cactcctaat gccatatgta   3660
acagacattt aaatttttgtg ttctgtataa cagccaaatt atcatattta tcattgtatt   3720
tgtcatgctt agctaaagat catgtatttg ttgagaaata gaataacaaa agtaataagg   3780
ataggctttg aattttttgca gaaatcttcc tgtacaaaac accttttaaaa ataattttt   3840
gaatggtgtg aatccagtag tcccatttct ctgacttagt ttcttgagt gatttttatc   3900
aaggccaagt ccccaaacaa ttccctacca gctcttttaga gtactgttca atctggacta   3960
aaatggtttt aagtttatgg agagcttagt ccacagaata tagggcggcg agtccgaaaa   4020
tgcttataca atttttttt cataataaga tatgtgctgg catcaagaaa cttaaagtgg   4080
aagcaaaaag acatccaact agttgctggt ctctatcatc ttatctgatg gtatttctat   4140
tttccttata taatacacca tttttagtaag aactcctaga aatttcaaga gcatattgcc   4200
aaaatataaa gtatatttca tagtttcttc tggctgaacc agtgaaattt tattattgca   4260
tattaatgat atttgtaaaa cttttataaa aattgtcata atttttaaata ctcacatttt   4320
aaaaatactt ctttaatgac tcttcctcta aattcctgg aaatacagat aaagattagc   4380
tagatacaag atacagctaa gtatttagac attttgaggc tagtatttt cattttatta   4440
aaggctaaaa acaataccac caataaatca tcaaacaaat cgtacaaagt aattctctct   4500
ttgggaggct cctttcgtga tagagggaca tgggtggaat tgacaatgaa acttagatga   4560
acaaggtcca tgttatttta ggtggtagaa cagggtagag tcatgtcatt atttgctggt   4620
ggaagacact atttaccagg tgttctttgc tgaataaatc attaaacatt tttaaaaatc   4680
caacaatcca cttttattttg tgtcattgac aaaaggatct tttaaatcag aaggtttcaa   4740
tgcaattttt ggtttggctg tttgaataat ggttatgtac tgttataatt gtagacatttt  4800
tctcacgtct accaggaatt gaagtgtaaa actaaaatat ttttcataat gcctctgccg   4860
tgcagaagga atgataatcc ttttgtatac ttctttaatt ttattgtaaa atgtgtaatg   4920
acttttacct atatgctgtg gcaggtcct cagtaaaatc tattgagtca attctagta   4980
ttaacaggct tttgcttgct atctaagtgt ttcaaattat gggaagtgtg agacactgga   5040
aggcaagaaa attaacaata atggcatgtg atagcaaaat tgtatttcac ttattcctgt   5100
gaatatttct tgttggtacc aatggtactg tacaaagtga atgttatagc cacaacattc   5160
tcttgaaaag aacactgtca agaagtggga aattgctgtc aggcatttca ttgttgtttt   5220
taaactttt taaaagaaat actggttttg caatatagag atcatgtggt aagaatttt   5280
aataagatct tatactaaaa agcctaat caattttattg agattcaaaa aatactatta   5340
taattaatta catcccatac atataggcaa actcattaa aaaataaaac taattttggt   5400
aaaagtacat ggccttgttt tttaaaatac ataattttaa aataaatcac ttgtcatgat   5460
aaagtccaaa aagaagttat cattcaacat tcaactaagg ttgagctaa gaatttacta   5520
atacaaaaaa agttaaaatt ttttggacca tatatatctt gacagtgtaa cttttaagta   5580
ggttcatttc catttgcaca gaaagtttct gtctttagga aactgaaaat gaaatactgt   5640
```

```
ggatgctatg actgtttgtc ttgtatgtaa ataggaaatt aataagctgc ctattgagtg   5700
gtatagctgt atgcttaccc aaaaaaggga acactgtggt tatgacttgt attataaact   5760
ttctgtagtt aataaagttg ttattttat aaccatgatt atattattat tattaataaa   5820
atattttatc aaaa                                                    5834

SEQ ID NO: 4           moltype = DNA  length = 1943
FEATURE                Location/Qualifiers
source                 1..1943
                       mol_type = genomic DNA
                       organism = Mus musculus
SEQUENCE: 4
agtgcagggt ggtggagacc tgatgatacc caactaccag ctgtggggtg aggaggagca     60
tgaatggaga cagagacccc agataattaa ggacgtccca ctttgccagc agaataaaag    120
gtgccacagg caccatgtcc aatcctggtg atgtccgacc tgttccgcac aggagcaaag    180
tgtgccgttg tctcttcggt cccgtgggaca gtgagcagtt gcgccgtgat tgcgatgcgc    240
tcatggcggg ctgtctccag gaggcccgag aacggtggaa ctttgacttc gtcacggaga    300
cgccgctgga gggcaacttc gtctgggagc gcgttcggag cctagggctg cccaaggtct    360
acctgagccc tgggtcccgc agccgtgacg acctgggagg ggacaagagg cccagtactt    420
cctctgccct gctgcagggg ccagctccgg aggaccacgt ggccttgtcg ctgtcttgca    480
ctctggtgtc tgagcggcct gaagattccc gggtgggcc cggaacatct cagggccgaa    540
aacggaggca gaccagcctg acagatttct atcactccaa gcgcagattg gtcttctgca    600
agagaaaacc ctgaagtgcc cacggaggcc ccgccctctt ctgctgtggg tcaggaggcc    660
tcttccccat cttcggcctt agccctcact ctgtgtgtct taattattat ttgtgtttta    720
atttaaacgt ctcctgtata tacgctgcct gccctctccc agtctccaaa cttaaagtta    780
tttaaaaaaa gaacaaaaca aaacaaaaaa aaccaaaaca aaacaaacct aaattagtag    840
gacggtaggg cccttagtgt ggggatttc tattatgtag attattatta tttaagcctc    900
tcccaaccca agctctgtgt ttcctatacc ggaggaacag tcctactgat atcaaccat    960
ctgcatccgt ttcacccaac cccctcccc ccattcctg cctggttcct tgccacttct   1020
tacctggggg tgatcctcag acctgaatag cactttggaa aaatgagtag gactttgggg   1080
tctccttgtc acctctaagg ccagtcagga tgacagtgaa gcagtcacag cctagaacag   1140
ggatggcagt taggactcaa ccgtaatatc ccgactcttg acattgctca gacctgtgaa   1200
gacaggaatg gtcccactc tggatcccct ttgccactcc tggggagccc acctctcctg   1260
tgggtctctg ccagctgccc ctctatttg gagggtaat ctggtgatct gctgctcttt   1320
tccccacce catacttccc cttctgcagg tcggcaggag gcatatctag gcacttgccc   1380
cacagctcag tggactggaa gggaatgtat atgcagggta cactaagtgg gattccctgg   1440
tcttacctta ggcagctcca gtggcaaccc cctgcattgt gggtctaggg tgggtccttg   1500
gtggtgagac aggcctccca gagcattcta tggtgtgtgg tggtggggt gggcttatct   1560
gggatgggga ccccagttgg ggttctcagt gacttctccc atttcttagt agcagttgta   1620
caaggagcca ggccaagatg gtgtcttggg ggctaaggga gctcacagga cactgagcaa   1680
tggctgatcc tttctcagtg ttgaataccg tgggtgtcaa agcacttagt gggtctgact   1740
ccagccccaa acatccctgt ttctgtaaca tcctggtctg gactgtctac ccttagcccg   1800
caccccaaga acatgtattg tggctccctc cctgtctcca ctcagattgt aagcgtctca   1860
cgagaaggga cagcaccctg cattgtcccg agtcctcaca cccgacccca aagctggtgc   1920
tcaataaata cttctcgatg att                                           1943

SEQ ID NO: 5           moltype = DNA  length = 3502
FEATURE                Location/Qualifiers
source                 1..3502
                       mol_type = genomic DNA
                       organism = Homo sapiens
SEQUENCE: 5
gcggaggctt ggggcagccg ggtagctcgg aggtcgtggc gctggggggct agcaccagcg     60
ctctgtcggg aggcgcagcg gttaggtgga ccggtcagcg gactcaccgg ccagggcgct    120
cggtgctgga atttgatatt cattgatccg ggttttatcc ctcttctttt ttcttaaaca    180
ttttttta aaactgtatt gtttctcgtt ttaatttatt tttgcttgcc attcccact    240
tgaatcgggc cgacggcttg ggagattgc tctacttccc caaatcactg tggatttgt    300
aaaccagcag aaagaggaaa gaggtagcaa gagctccaga gagaagtcga ggaagagaga    360
gacgggggtca gagagagcgc gcgggcgtgc gagcagcgaa agcgacaggg gcaaagtgag    420
tgacctgctt ttgggggtga ccgccggagc gcggcgtgag ccctcccct tgggatccca    480
cagctgacca gtcgcgctga cggacagaca gacagacag gcccccagcc ccagctacca    540
cctcctcccc ggccgcggcc ggacagtgga cgcggcggcg agccgcgggc aggggccgga    600
gcccgcgccc ggaggcgggg tgagggggt cggggctcgc ggcgtcgcac tgaaactttt    660
cgtccaactt ctgggctgtt ctcgcttcgg aggagccgtg gtccgcgcgg ggaagccgaa    720
gccgagcgga gccgcgagaa gtgctagctc gggccgggga gccgcggagg cgcggagggt    780
ggaggaggaa gaagagaagg aagaggagag ggggccgcag tggcgactcg gcgctccgaa    840
gccgggctca tggacgggtg aggcggcggt gtgcgcagac agtgctccag ccgcgcgcgc    900
tccccaggcc ctgccccggg cctcgggccg ggaggaagaa gtagctcgcc gaggcgccga    960
gggagcgggg ccgccccaca gcccgagccg gagagggagc gcgccgcgcg ccggccccgg   1020
tcgggctcc gaaaccatga actttctgct gtcttggtc cattgggcc ttgccttgt    1080
gctctacctc caccatgcca agtggtccca ggctgcaccc atggcagaag gagagggca    1140
gaatcatcac gaagtggtga agttcatgga tgtctatcag cgcagctact gccatccaat    1200
cgagaccctg gtgacatct tccaggagta cctgatgag atcgagtaca tcttcaagcc    1260
atcctgtgtg cccctgatgc gatgcggggg ctgctgcaat gacgagggcc tggagtgtgt    1320
gcccactgag gagtccaaca tcaccatgca gattatgaga atcaaacctc accaaggcca    1380
gcacatagga gagatgagct tcctacagca caacaaatgt gaatgcagac caaagaaaga    1440
tagagcaaga caagaaaatc cctgtgggcc ttgctcagag cggagaaagc atttgtttgt    1500
acaagatccg cagacgtgta aatgttcctg caaaaacaca gactcgcgtt gcaagatgtg    1560
acaagccgag gcggtgagcc gggcaggagg aagagcctc cctcagggtt tcgggaacca    1620
gatctctcac caggaaagac tgatacgaaa cgatcgatac agaaaccacg ctgccgccac    1680
```

| | |
|---|---|
| cacaccatca ccatcgacag aacagtcctt aatccagaaa cctgaaatga aggaagagga | 1740 |
| gactctgcgc agagcacttt gggtccggag ggcgagactc cggcggaagc attcccgggc | 1800 |
| gggtgaccca gcacggtccc tcttggaatt ggattcgcca tttttatttt cttgctgcta | 1860 |
| aatcaccgag cccggaagat tagagagttt tatttctggg attcctgtag acacacccac | 1920 |
| ccacatacat acatttatat atatatatat tatatatata taaaaataaa tatctctatt | 1980 |
| ttatatatat aaaatatata tattcttttt ttaaattaac agtgctaatg ttattggtgt | 2040 |
| cttcactgga tgtatttgac tgctgtggac ttgagttggg aggggaatgt tcccactcag | 2100 |
| atcctgacag ggaagaggag gagatgagag actctggcat gatctttttt ttgtcccact | 2160 |
| tggtggggcc agggtcctct ccctgccca ggaatgtgca aggccagggc atggggcaga | 2220 |
| atatgaccca gttttgggaa caccgacaaa cccagccctg ggctgagcc tctctacccc | 2280 |
| aggtcagacg gacagaaaga cagatcacag gtacagggat gaggcaccg gctctgacca | 2340 |
| ggagtttggg gagcttcagg acattgctgt gctttgggga ttccctccac atgctgcacg | 2400 |
| cgcatctcgc ccccaggggc actgcctgga agattcagga gcctgggcgg ccttcgctta | 2460 |
| ctctcacctg cttctgagtt gcccaggaga ccactggcga atgtcccggc ggatccacgt | 2520 |
| gacacattgt tggaagaagc agcccatgac agctcccctt cctgggactc gccctcatcc | 2580 |
| tcttcctgct cccccttcctg gggtgcagcc taaaaggacc tatgtcctca caccattgaa | 2640 |
| accactagtt ctgtcccccc aggagacctg gttgtgtgtg tgtgagtggt tgaccttcct | 2700 |
| ccatcccctg gtccttccct tcccttcccg aggcacagag agacagggca ggatccacgt | 2760 |
| gcccattgtg gaggcagaga aaagagaaag tgtttatat acggtactta tttaatatcc | 2820 |
| cttttttaatt agaaattaaa acagttaatt taattaaaga gtagggtttt ttttcagtat | 2880 |
| tcttggttaa tatttaattt caactattta tgagatgtat cttttgctct ctcttgctct | 2940 |
| cttattttgta ccggttttg tatataaaat tcatgtttcc aatctctctc tccctgatcg | 3000 |
| gtgacagtca ctagcttatc ttgaacagat atttaattttt gctaacactc agctctgccc | 3060 |
| tccccgatcc cctggctccc cagcacacat tcctttgaaa taaggtttca atatacatct | 3120 |
| acatactata tatatatttg gcaacttgta tttgtgtgta tatatatata tatatgttta | 3180 |
| tgtatatatg tgattctgat aaaatagaca ttgctattct gtttttttata tgtaaaaaca | 3240 |
| aaacaagaaa aaatagagaa ttctacatac taaatctctc tccttttttta attttaatat | 3300 |
| ttgttatcat ttatttattg gtgctactgt ttatccgtaa taattgtggg gaaaagatat | 3360 |
| taacatcacg tctttgtctc tagtgcagtt tttcgagata ttccgtagta catatttatt | 3420 |
| tttaaacaac gacaaagaaa tacagatata tcttaaaaaa aaaaaagcat tttgtattaa | 3480 |
| agaatttaat tctgatctca aa | 3502 |

| | | |
|---|---|---|
| SEQ ID NO: 6 | moltype = DNA length = 7073 | |
| FEATURE | Location/Qualifiers | |
| source | 1..7073 | |
| | mol_type = genomic DNA | |
| | organism = Mus musculus | |
| SEQUENCE: 6 | | |

| | |
|---|---|
| actcgataac tttgccagaa gagggagaga gagagaaggc gaatgttccc ccagctgttt | 60 |
| cctgtctaca gtgtctgtgt tttgtagata aatgtgagga ttttctctaa atccctcttc | 120 |
| tgcttgctaa atctcactgt cactgctaaa ttcagagcag atagagcctg cgcaatggaa | 180 |
| taaagtcctc aaaattgaaa tgtgacattg ctctaacatc tcccatctct ctggatttct | 240 |
| ttttcgcctc attatccctg cccaccaatt catttccaga cttgtactt cagaagcgat | 300 |
| ggggaaaatc agcagccttc caactcaatt atttaagatc tgcctctgtg acttcttgaa | 360 |
| gataaagata cacatcatgt cgtcttcaca cctcttctac ctggcgctct gcttgctcac | 420 |
| cttcaccagc tccaccacag ctggaccaga dacccttgc ggggctgagc tggtggatgc | 480 |
| tcttcagttc gtgtgtggac cgaggggctt ttacttcaag cagcccacag gctatggctc | 540 |
| cagcattcgg agggcacctc agacaggcat tgtggatgag tgttgcttcc ggagctgtga | 600 |
| tctgaggaga ctggagatgt actgtgcccc actgaagcct acaaaagcag cccgctctat | 660 |
| ccgtgcccag cgccacactg acatgcccaa gactcagaag gaagtacatt tgaagaacac | 720 |
| aagtagagga agtgcaggaa acaagaccta cagaatgtga gaggagcctc ccacggaacta | 780 |
| gaaaatgcca catcaccgca ggatccttttg ctgcttgagc aacctgcaaa acatcgaaac | 840 |
| acctaccaaa taacaataat aagtccaata acattacaaa gatgggcatt ccccccaatg | 900 |
| aaatatacaa gtaaacattc caacatcgtc tttaggagtg tttgtttaaa aagctttgca | 960 |
| ccttgcaaaa gtggtcctgg cgtgggtaga ttgctgttgg tcctttatca ataacattct | 1020 |
| atagagaaaa aaaatatata tataactata tctccagtc cctgcctcta aagagccgaa | 1080 |
| aatgcatgga tgttgtagag atccagttgc tctaagtttc tctctgaatt ttggctgctg | 1140 |
| aagccattca tttagcaact gtgtagaggt ggtttatgaa tggttccctt atcttcacct | 1200 |
| cttcccacgt agctcaagct gcttgttta cagagtctaa tcatcttgtc tagctgcatt | 1260 |
| agacacaccc tttcctaaca cttgtatttg ttgaatttgg cctccttaag agcaatagca | 1320 |
| aataagtagt caagtggcct accaagtttt aacgtacctg actccatctg tggcatttgt | 1380 |
| accaaatata agttgaatgc atttattta gacacaaagc tttatttttt ttgacattgt | 1440 |
| gtttcaagaa aagaaaataga ataacaataa ctacaacttt gaggccaatc atttttaggt | 1500 |
| gtgtgtttga agcatagaac gtctcttaaa ctctcaatgt ttcaaa tgataagtta | 1560 |
| gtatgtaacc taagtatagc agtttctctc ttttttattt ttttccatat agagcactat | 1620 |
| gtaaagttag tatatcaata atacaggaaa tatcaaacag tatgtaaaac tctgttgttg | 1680 |
| ttgttttttta gtacaatggt gctattttgt agtttgttat atgaaagaat ctagtcaaca | 1740 |
| cagtaaaagg agaaagcaaa gcaaaaacaa caaacgaaag cctggagcct aagatgacaa | 1800 |
| aacgaggaag ggaactgaaa aaaaaatcc ttcctcttgg gagatgcaaa ggcctcccca | 1860 |
| attatgcctt ccaagaagaa cttaagatat agagtccatt aagacgcact tacttgtcaa | 1920 |
| gtccagagag gaagctatgg agtgggaaaa gcaagaggct agggatttgg gagtcctggt | 1980 |
| ttcttttttaa tcactgaaga agtaagtatt tgcaacctgg gtcacacaaa ctcaccaccc | 2040 |
| tgtgacctca gtcaaatcac tccacctctc ggtgcctcag ttttcctcat ctgcaaaatg | 2100 |
| ggggcaatat gtcatctacc tacctcaaag gggtggtatg aagattaaaa agtagacttt | 2160 |
| cagatttttg ttctgggttt ccaggagggt gcaacatcag aacccttgaa ttgctaggat | 2220 |
| gcaaggaatt ctgtaaataa cccactaaca atgtagctcc aaggatcatt catctgtcac | 2280 |
| tgggatgcca ccacaatatc caagttctta ttggtgaagc tgtgcaacta attagtgaca | 2340 |
| agctaaggac tcagtctccc cagcatgtca cacggcagga cacatttgat ttgcagtttt | 2400 |
| atttaacttc tgcatttgag cttatgacta taaagactag tgaaaagaag ggagagagga | 2460 |

```
gaaagaagat ccttgccaag taaagggtaa ttaattatta ttccatttat ccactctcat   2520
taaagggtaa ttaattattc catgtatcca ctctcattaa tccttccagt cacttagtat   2580
ctagaaataa ctctaacatt gtcaatgaga ctctactcag tttgccaaac acaattctcc   2640
ttccccatag catatgaaaa aaaggcgctg acattcttaa attttgaaat agtatctatt   2700
acaatcacag gttgctgtag cagatgtagt cttgcccttg tttgtacatg catgtatttt   2760
ttttttaatt ttatgaaaat gtgctagcaa gaattgctac ttgagggggca aaattcttcc   2820
ttctcaagcc tgaggttctc cctagtgtct gcttagaagg aaggatccag cttcctggaa   2880
atgtgttgga tgcattcaac tgggcattgc taaccaaaaa catttagaaa aatgttctct   2940
atgtatatag caagattgtc tccctctttt aaaaacaaaa tccaatattc acatcttatt   3000
acctacaacc ttgattctct attgcaagct tccttaatat tcttataaaa tgtattaaga   3060
aaaacaaaaa ggacaccttt agctctcctt ccgccaggtt gcctctagaa tctctgggga   3120
aatgcagaag gtgctgttga gtaaagccct cagaaggatt ggatttagga acatcaggca   3180
cgctgtacat cccctgatta ctgtagaaat gtaaatggaa taagaggtca gctgaccatc   3240
cacctgcttc cccagaagga tacagggaaa agttaggccc tcacacaccc tgggtgacac   3300
ttctgacttc tagttcttgt tcacagtgtg tacttttttca aattggtaat tcccagaaaa   3360
acacataggg ggccttctcc agatctgtgg gcttcctgcc atggttggat ttggtgattc   3420
caagtgtcta tcacatattt tgttcactta attctatcca cagtcagaaa ttctttcaat   3480
gaggaaagtt taaatatgca atcctttatc caatacctaa ttctctccaa ctgcatcata   3540
aatcaagtaa taaaaattaa ttgtactaat taatcataat aatgtaccat tgtactttta   3600
aatgaatgaa cactgcaaga caaatctatg taaactctga aaagtaactg atcattatat   3660
ggtgaatcaa aatgactcaa gattgataga aagggacatt taaaatttta caactcaaaa   3720
ttttgtagac tttgctatgg aggtaaattg ttttagtgcc tagagatgga gcggtttta   3780
taaatttaca aaagaactat aaagataggt aggaaggaat tttcatttga taggattgtt   3840
gctgattac ttactcaata cctaggtcaa atgttgatcc tattctccaa agactatcaa   3900
gtgcttgaac attgtaagat gagtctgctc cactgaaaat gtaatacatc tctccattat   3960
aatctatttt cctggggtaa aaaaatcctt ttttaaata tccacctaca tatacctacc   4020
ctacatgtgc atttgcacat gcgtgcatac gctcatgcgc cccacccccac acacacctat   4080
tcaccctaag actaagaaga aatcatttct ttgaaagtct tatctttcaa aaaaggcagc   4140
ggtgcccctt gagactcctt ctccttcttt gaatgtcaat gtgaaatgtg gcatgtctgt   4200
gtacatgaaa ccatctcata ccctatggct ccagggtttc tttatggttt gtgcacttgg   4260
gaggatgcgc agaagacagg atgcagcctg ttttgctttc cccttttactg tttggccagc   4320
tacgccaatg tggtgctatt gtttctttaa gaaagtactt gactaaaaaa aaagaaaaaa   4380
agaaaaaaag aaaagaaaaa gaaaaaagaa aaaaaagaa agcatagacc tattttttta   4440
aagtctgaaa acaacagttc tatagtagat ggcttactga gatacatta gatctagcca   4500
ccacccctagc caccacccttt caactatgtg tcactcacaa gtagaatatt gttcaccaag   4560
ttgtgagttt gggggttcag agacaaagga tggaaaagtt ttaaagttag atggctcaat   4620
catttcattg gctctcaaat ttaacaaaat tggcaatact tcacccaatc tgaagtgttg   4680
gtcaataact tgaactgggg gcaaaaataa cttcaggcaa atggcagaag aaaataatta   4740
acttacttct tgctttttttt gttgattgtt tggtttcctg ttgattttttg gttttggttt   4800
tgctgtgggt gggtgagtac atgtgtgtaa gtacgtgtgt gtgtgtgtgt gtgtgtgtgt   4860
gtgtgtgtgt tccactcaaa aacaaatact cagaaagtgg agaaaataca acgatttaa   4920
gagcatagac ttacctacta ctagaaccag cttctgtcac atcctctgga gaaggcactg   4980
atttcttgtt ttgtagaggt tgctcttcca tcagtgacct gaaagagtga ccagtctcct   5040
agagtagaca tggatctcat taggagaaga cagaagtatt tccttatgaa ttgggcttat   5100
ctactgacaa agaaagggaa gagtttatga gaagttattg aagaagatgg ctaacagtct   5160
gtgaagattt tgttctggtt ttttttgttg ttgttgttgt tgggtttggg ttttgatttt   5220
tttttttttt ttttttactt atacaatctt tatgaatgga aatcttaagt ctcaaaaaga   5280
cttggtctttt tttttctctt cgtaacagaa tggaagatga caaactcaca tagactcttt   5340
ctaggctggc tagcaaaggt gtggtttgac ttatttgaat cagaccattt taaatgttcc   5400
tctctatttt taatcataaa aggctgtcat aatttattag cgtaggccct ttttggcact   5460
tctcaaatga atgagcattc ccattcaaag catggctttc cccatggttc caaaacatga   5520
atgattaata ttaaggaatt atttacttca aaatacagta gaagtgtgag tctctgttcc   5580
cattccccac aaagatcatt aagtcctgaa tcggggcgg gggtggggcg cctggatact   5640
aagggaattt ttttgttgct tgtttttttgt tttcaatgct agtgcttaat cctatagtat   5700
acagatttgc ttcttgctat tgtgatattc tgtaagactt tcctgttagt tattagaaat   5760
tgatacataa ataccttttt tgtgtggttt ctatttaaaa ggaaagagat aagactgtct   5820
gaaccttaaa ttcgtaaggc acatgataaa gagatcacat taaataacaa gccatatctg   5880
gttcaatcct ttctttctta tcatttttaag gaaaacttgc ccagataaga cagaggccca   5940
ggggactttt gaaactctct ttgttccgcc aattcatttt ggctggtgat ggttttttca   6000
cagtgtctgc ctcagaatct tttagaggct ggccagacta aagactgtct tttaaaacac   6060
atttcacatg gttcctctta atgaatgatt acttatgt agaacatgat ttttttttct   6120
ctccacttat ttttttttttc cccatcattg ataagggttc ttaaggagaa gaattcatta   6180
acaaaactca agaaagcgta caaaaaaaaa attctaaatg tcactgccca attgaaatac   6240
gagctaaaat ggaaatactt tctccctactt aaaacccaga ctgaatcccc ttcaaaatga   6300
cctttcacaa tcttttccaat ttgccttttgt ttaaactgtc tgggcctaaa agcaagcatt   6360
attcattttc tcttgcccaa agtgaacttg tgtaaagtag gaaaattaaa agaaactgct   6420
agaaatccct tccaaccagt ggctgacccc tctcactagc tcacagcaaa gtctcctctg   6480
ttgatctatc acctagtctc atttcgtttg aatatttaca ttgtacctac tgctaaacac   6540
ttggcaggag gctccatcca tatctcctat cggtgtctct gtatccttaa accttgcaaa   6600
catcatacag tgtatattaa gtttacagga aagctccaaa tagcatatca gacctggtct   6660
ctctttgtta aagatttaag gagctatggg aatctggatt acaacgcaca ttttgcttca   6720
tttattttta tcacactttta aaggccaagg gtgatgatta acttacagac actgaattga   6780
tttccctact gaaacctgaa agtaatattt ggtcattcat tgtatgtgtt ttacacaaaa   6840
aaaacatctc ctatcaaatt actcctgatt gtatttgaag tggttattca attcatttat   6900
ggcagagcaa tatctgtcct aatgactctt ataaaatgta actaactgaa tcattatctt   6960
acatttactg tttagtaagc atattttgaa attgtatggc tagagtgtca taataaaatg   7020
gtatatcttc ctttagtaat tacattaaaa ttaatcatgt ttgattaact ggt          7073

SEQ ID NO: 7         moltype = DNA   length = 5255
```

```
FEATURE              Location/Qualifiers
source               1..5255
                     mol_type = genomic DNA
                     organism = Homo sapiens SEQUENCE: 7
ttcctgtaac atcgcagcca gtgagcagtg aacgagtgta gacagagctc tgcctctagc    60
ctggctgccc aagcccaagc cgttagaagc aggagcccct gcgcagtgcc tggtcacgga   120
gctgagctgt gtttagatgt gttggctgct gcgtggtgaa ggaagacccg tctccagaaa   180
agcaatttag gcaaaaggga ttccgtttga tggcagagtc ccagtgctag aaaggtagcg   240
aaggtggaca gcttacagtc tcaactcatt tcgtcgtaaa tgtcctcgta acgacattga   300
ttcttctacc tggataacct tttgtttgtt tgtttgtttg ttttttgtttt gttttttcccc   360
tgtaaccatt ttttttttctg acaagaaaac attttaattt tctaagcaag aagcattttt   420
caaataccat gtctgtgacc caaagtaaaa atggatgata attcatgtaa atgtgtgcaa   480
catagcaacc tgaacctgca cgcgattcgg gctctgtgtg ttgtgaacca tggctatgtg   540
gatacaggct cagcagctcc agggcgatgc ccttcaccag atgcaggcct tgtacggcca   600
gcatttcccc atcgaggtgc gacattattt atcacagtgg atcgaaagcc aagcctggga   660
ctcaatagat cttgataatc cacaggagaa cattaaggcc acccagctcc tggagggcct   720
ggtgcaggag ctgcagaaga aggcggagca ccaggtgggg aagatgggt ttttgctgaa    780
gatcaagctg gggcactatg ccacacagct ccagagcacg tacgaccgct gcccatggaa   840
gctggttcgc tgtatccggc acattctgta caacgaacag aggctggttc gcgaagccaa   900
caacggcagc tctccagctg gaagtcttgc tgacgccatg tcccagaagc accttcagat   960
caaccaaacg tttgaggagc tgcgcctgat cacacaggac acggagaacg agctgaagaa  1020
gctgcagcag acccaagagt acttcatcat ccagtaccag gagagcctgc ggatccaagc  1080
tcagttttgcc cagctgggac agctgaaccc ccaggagcgc atgagcaggg agacggccct  1140
ccagcagaag caagtgtccc tggagacctg gctgcagcga gaggcacaga cactgcagca  1200
gtaccgagtg gagctggctg agaagccaca gaagaccctc gtgcctgctgc ggaagcagca  1260
gaccatcatc ctggacgacg agctgatcca gtggaagcgg agacagcagc tggccgggaa  1320
cgggggtccc cccgagggca gcctggacgt gctgcagtcc tggtgtgaga agctggccga  1380
gatcatctgg cagaaccggc agcagatccg cagggctgag cacttgtgcc agcagctgcc  1440
catcccaggc cccgtggagg agatgctggc tgaggtcaac gccaccatca cggacatcat  1500
ctcagccctg gtcaccagca cgttcatcat cgagaagcag cctcctcagg tcctgaagac  1560
ccagaccaag tttgcagcca ccgtgcgcct gctggtgggg gggaagctga atgtgcacat  1620
gaaccccccg caggtgaagg cgaccatcat cagcgagcag caggccaagt ccctgctcaa  1680
gaatgagaac acccgcaatg attacagcgg cgagatcctg aacaactgtt gcgtcatgga  1740
gtaccaccag gccactggca cactcagcgc ccacttcaga aacatgtccc tgaaacgaat  1800
caagaggtct gaccgccgtg gggcagagtc agtaacggaa gagaagttca cgatcctgtt  1860
tgactcacag ttcagcgtcg gtggaaacga gctggtcttt caagtcaaga ccttgtcgct  1920
cccggtggtg gtgattgttc acggcagcca ggacaacaat gccacagcca ctgtcctctg  1980
ggacaacgcc tttgcagagc ctggcaggggt gccatttgcc gtgcctgaca aggtgctgtg  2040
gccgcagctg tgtgaagcgc tcaacatgaa attcaaggct gaagtacaga gcaaccgggg  2100
cttgaccaag gagaacctcg tgttcctggc acagaaactg ttcaacatca gcagcaacca  2160
cctcgaggac tacaacagca tgtccgtgtc ctggtcccag ttcaaccggg gaatttgcc   2220
aggacggaat tacactttct ggcagtggtt tgatggcgtg atggaagtat tgaaaaaaca  2280
tctcaagcct cactggaatg atgggggctat cctgggtttc gtgaacaagc aacaggccca  2340
cgacctgctc atcaacaagc cagacggggac cttcctgctg cgcttcagcg actcggaaat  2400
cggggggcatc accattgctt ggaagtttga ctctcaggag agaatgtttt ggaatctgat  2460
gccttttacc actagagact tctctatccg gtccctcgct gaccgcctgg gggacctgaa  2520
ttacctcata tatgtgtttc ctgatcggcc aaaaggatgaa gtatattcta agtactacac  2580
accggtcccc tgtgagcccg caactgcgaa agcagctgac ggatacgtga agccacagat  2640
caagcaggtg gtccccgagt ttgcaaatgc atccacagat gctgggagtg cgccaccta   2700
catggatcag gctccttccc cagtcgtgtg ccctcaggct cactacaaca tgtacccacc  2760
caacccggac tccgtccttg ataccgatgg ggacttcgat ctggaagaca cgatggacgt  2820
ggcgcggcgc gtggaagagc tcttaggccg gcccatggac agtcagtgga tccctcacgc  2880
acagtcatga ccagacctca ccacctgcag cttcatcgcc ctcgtggagg aacttcctgt  2940
ggatgtttta attccatgaa tcgcttctct ttggaaacaa tactcgtaat gtgaagtgtt  3000
aatactagtt gtgactttag tgtctctgtg catagtggca ctagtgaagg gagtgcgcgt  3060
gagtgtgagt gcatttgcac gtcgtgtttt ttcccccgcc cctgctgtcc agtctaagcc  3120
gccacgccag ggcagcggct gcgctttttt ttaccatgtg caaaaaggca gttggttccc  3180
tgaacctggc aacctggcca tgtgtcttca gggtggctga cccttgacac gtgactatcc  3240
aagtaagaaa aggacagagg aaaaagcacc ctctcctctgg ggagcctcgg ttcctctgcc  3300
aggtagtcca tagtccaagc aagcattgtc attgtctccg cctgtcttct gagatgtaga  3360
tgactgtctg atgatgaaag ccagtacctc ccgtgtcccc tgtcccctttt gcataaggaa  3420
cggaaagggg agctgaatca agggtgatgg ggcaagggtg tcacaggtt tttggatggg  3480
gagtgctgt ttccgtttc tgccacttcc gccatcttaa cactggctcc ttccctcttt    3540
gcttgctcag tctctatttc tagaactgcc actcagctta agtgcaagtg tgtctactca  3600
agtggagatg tttaacaaaa tagtggagag aagccaggc cacccagctc tgagcgtaca  3660
ggttcaggtg atgccctgtg ttccttctgt cagggcggtg cgttgtgccc aagtcctggc  3720
tccagacact gggcgtagcc tgtctgcgcc agcctcccca actcttgtct gtgctgtggc  3780
caggccgcgc ctgcgctatc caaggctttt ctccaagcgt gttgataatg gcttcctgca  3840
aacgtccggt ggtgtttttt gtttctaaat caggtctttt tttatgtttt tcccatttgc  3900
accctaattt gacatcaaat ttcccccctc ctgtatcagg tcctgggtcc tctgtaccca  3960
gatcacttca tctcccttca gtgtcacata gtgccctgag gattaggtgg taggaatggg  4020
acctgcacac ggggccagcc tgccaagcag gcagccagca ctgtacagtg ctgggtccgg  4080
ggtggccgtt gggattggg gaaatgcagt cagtcagcag gtttcctagg aagcttggaa  4140
aactaaaagc aaagtgaaag cctcagggtg atttgttcca cagtctcctc tgtagtgtct  4200
ccagaaggaa ggaaggggct gcagtgggcc gtcagggaga ggggcaagca gagagcggtt  4260
accactcagg cttgctgaga gccctccttg gcttcctctc ccaaacaagg gcagaaccgt  4320
gcccaggaga ggagccccca aaaccttatt tttatacatg caagtaaata aacatatttt  4380
ttttacaaaa ataacttctg aatttatcag tgttttactg ttaaaagaaa atactcctgt  4440
```

```
gtagtaaatt atttattggg agatgagttt ttaaaagctg ctgtttgcct tgccttggtt   4500
ttgtacactg attttttctat gcctggcggt agcctctctg cctcaggtgc tggccggatg   4560
gaggaggtgt gaggcccctc cctggcccct cagaagaaag ctggaactgc caggggagtc   4620
caggcttaag ggactcgtcc ccacctgtca tgcgactgtc ccagtaaccc tcacgagggt   4680
gtggactcga caaatatcta gatatatggt ggacatggcc ccaagtcatg gggagagtag   4740
agcagcctgg gccccccac ccccaaggtt ctaagctgac tttcaagtta ggttggagaa   4800
aagggtgcca agaagcgag acttccacat agtttttaag ctaccctgga tttactgagg   4860
gtgtacctgg acatgggaga ggtttttaac tggaaagtgt gtccctatc tgcatgctgg   4920
tctctctctc tctctgccca actcttgcac ccaaaaatga ggtgagggca ggtctccacc   4980
cacctcttgc ctgctcacag acccactcgt gagtcgggaa agcctcagct ttgggtgtg   5040
gggctttgta gaagtggaag gagatttgaa gtggctatct cctacaacgg aaaatatcct   5100
tttataattt ttcttttaa cgttttattt cagatacata ttttagtgtc gaggcagatt   5160
agtatatagc caccaaaaaa gtattgtgta taaattgagg cagccacaaa attgtgtatt   5220
ttatgttaca ataaaggcgt ctccttgaag gacaa                               5255

SEQ ID NO: 8           moltype = DNA  length = 654
FEATURE                Location/Qualifiers
source                 1..654
                       mol_type = other DNA
                       organism = synthetic construct
SEQUENCE: 8
atggccaccg gctcccgcac ctccctgctg ctggccttcg gcctgctgtg cctgccctgg   60
ctgcaggagg gctccgcctt ccccaccatc ccctgtccc gctgttcga caacgccatg   120
ctgcgcgccc accgcctgca ccagctggcc ttcgacacct accaggagtt cgaggaggcc   180
tacatcccca aggagcagaa gtactccttc ctgcagaacc cccagacctc cctgtgcttc   240
tccgagtcca tccccaccc ctccaaccgc gaggagacc agcagaagtc caacctggag   300
ctgctgcgca tctccctgct gctgatccag tcctggctgg agcccgtgca gttcctgcgc   360
tccgtgttcg ccaactccct ggtgtacggc gcctccgact ccaacgtgta cgacctgctg   420
aaggacctgg aggagggcat ccagaccctg atgggccgcc tggaggacgg ctccccccgc   480
accggccaga tcttcaagca gacctactcc aagttcgaca ccatcccca caacgacgac   540
gccctgctga gaactacgg cctgctgtac tgcttccgca aggacatgga caaggtggag   600
accttcctgc gcatcgtgca gtgccgctcc gtggagggct cctgcggctt ctaa         654

SEQ ID NO: 9           moltype = DNA  length = 3623
FEATURE                Location/Qualifiers
source                 1..3623
                       mol_type = other DNA
                       organism = synthetic construct
SEQUENCE: 9
atgctgctga ccctgatcat cctgctgccc gtggtgtcca gttctccctt cgtgtccctg   60
tccgccccc agcactggtc ctgccccgag ggcaccctgg ccggcaacgg caactccacc   120
tgcgtgggcc ccgccccctt cctgatcttc tcccacggca actccatctt ccgcatcgac   180
accgagggca ccaactacga gcagctggtg gtggacgccg agcgtccgt gatcatggac   240
ttccactaca acgagaagcg catctactgg gtggacctgg agcgccagct gctgcagcgc   300
gtgttcctga acggctcccg ccaggagcgc gtgtgcaaca tcgagaagaa cgtgtccggc   360
atggccatca actggatcaa cgaggaggtg atctggtcca ccagcagga gggcatcatc   420
accgtgaccg acatgaaggg caacaactcc cacatcctgc tgtccgccct gaagtacccc   480
gccaacgtgg ccgtggaccc cgtggagcgg ttcatcttct ggtcctccga ggtggccggc   540
tccctgtacc gcgccgacct ggacggcgtg ggcgtgaagg ccctgctgga cctccgag   600
aagatcaccg ccgtgtccct ggacgtgctg acaagcgcc tgttctggat ccagtacaac   660
cgcgaggget ccaactccct gatctgctcc tgcgactacg acggcggctc cgtgcacctc   720
tccaagcacc ccacccagca aacctgttcc gccatgtccc tgttcggcga ccgcatcttc   780
tactccacct ggaagatgaa gaccatctgg atcgccaaca gcacaccgg caaggacatg   840
gtgcgcatca acctgcactc ctccttcgtg ccctgggcg agctgaaggt ggtgcacccc   900
ctggcccagc ccaaggccga ggacgacacc tgggagcccg agcaagagt gtgcaagctg   960
cgcaagggca actgctcctc caccgtgtgc ggccaggacc tgcagtccca cctgtgcatg   1020
tgcgccgagg gctacgccct gtccgcgac cgcaagtact cgcgaggacgt gaacgagtgc   1080
gccttctgga accacggctg caccctgggc tgcaagaaca cccccggctc ctactactgc   1140
acctgcctcc tgggcttcgt gctgctgccc gacggcaagc ggtgccacca gctgtgtcc   1200
tgccccgca acgtgtccga gtgctcccac gactgcgtgc tgacctccga ggggcccctg   1260
tgcttctgcc ccgagggctc cgtgctggag cgcgacggca gacctgctc cggctgctcc   1320
tcccccgaca acggcggctg ctcccagctg tgcgtgcccc tgtcccccgt gtcctgggag   1380
tgcgactgct ccccggcta cgacctgcag ctggacagaa gtcctgcgc cgcctccggc   1440
ccccagccct tcctgctgtt cgccaactcc caggacagtc ggcacatgga cttcgacgc   1500
accgactacg gcaccctgct gtcccagcag atgggcatgg tgtacgccct ggaccacgac   1560
cccgtggaga caagatcta cttcgcccac accgccctga gtggatcga gcgcgccaac   1620
atggacggtc cccagcgcga gcgcctgatc gaggaggcg tggacgtgcc cgagggcctg   1680
gccgtggact ggatcggccg ccgcttctac tggaccgacc ggcgcaagtc cctgatcggc   1740
cgctccgacc tgaacggcaa gcggtccaca atcatccaca ggagacacat ctcccagccc   1800
cgcggcatcg ccgtgcaccc catggccaag cgcctgttct ggaccgacac cggcatcaac   1860
ccccgcatcg agtcctcctc cctgcagggc ctgggccgcc tggtgatcgc ctcctccgac   1920
ctgatcggc cctccggcat caccatcgac ttcctgaccg acaagctgta ctggtgcgac   1980
gccaagcagt ccgtgatcga gatggccaac ctggacggcc caagcgccg ccgcctgacc   2040
cagaacgtgc tgggcacccc cttccgtgg gcgtgttcc aggactacgt gttcttcacc   2100
gactgggcca tgcctccgt gatccgcgtg aacaagcgca ccggcaagga ccgcgtgcgc   2160
ctgcagggct ccatgctgaa gcctcctcc ctggtggtgg tgcaccccct ggccaagccc   2220
ggcgccgacc cctgcctgta ccagaacggc ggctgcgagc acatctgcaa gaagcgcctg   2280
ggcaccgcct ggtgctcctg ccgcgagggc ttcatgaagg cctccgacgg caagacctgc   2340
ctggcctgg acgccacca gctgctgcc ggcggcgagg tggacctgaa gaaccaggtg   2400
```

```
acccccctgg acatcctgtc caagacccgc gtgtccgagg acaacatcac cgagtcccag  2460
cacatgctgg tggccgagat catggtgtcc gaccaggacg actcgcgccc cgtgggctgc  2520
tccatgtacg cccgctgcat ctccgagggc gaggacgcca cctgccagtg cctgaagggc  2580
ttcgccggcg acggcaagct gtgctccgac atcgacgagt gcgagatggg cgtgcccgtg  2640
tgcccccccg cctcctccaa gtgcatcaac accgagggcg gctacgtgtg ccgctgctcc  2700
gagggctacc agggcgacgg catccactgc ctggacatcg acgtgcca gctgggcgtg   2760
cactcctgcg gcgagaacgc ctcctgcacc aacaccgagg gcggctacac ctgcatgtgc  2820
gccgccgcc tgtccgagcc cggcctgatc tgccccgact ccacccccc ccccacctg    2880
cgcgaggacg accaccacta ctccgtgcgc aactccgacc ccgagtgccc cctgtcccac  2940
gacggctact gcctgcacga cggcgtgtgc atgtacatcg aggcccggga caagtacgcc  3000
tgcaactgcg tggtgggcta catcggcgag cggtgccagt accgcgacct gaagtggtgg  3060
gagctgcgcc acgccggcca cggccagcag cagaaggtga tcgtggtggc cgtgtgcgtg  3120
gtggtgctgg tgatgctgct gctgctgtcc ctgtggggcg cccactacta ccgcacccag  3180
aagctgctgt ccaagaaccc caagaacccc tacgaggagt cctcccgcga cgtgcgctcc  3240
cgccgccccg ccgacaccga ggacggcatg tcctcctgcc cccagccctg gttcgtggtg  3300
atcaaggagc accaggacct gaagaacggc ggccagcccg tggccggcga ggacggccag  3360
gccgccgacg gctccatgca gcccacctcc tggcgccagg agcccagct gtgcggcatg   3420
ggcaccggag agggctgctg gatccccgtg tcctccgaca agggctcctg ccccaggtg   3480
atggagcggt ccttccacat gccctcctac ggcacccaga ccctggaggg cggcgtggag  3540
aagcccact ccctgctgtc cgccaacccc ctgtggcagc agcgcgccct ggacccccc    3600
caccgatgga gctgacccag taa                                          3623

SEQ ID NO: 10           moltype = DNA  length = 2187
FEATURE                 Location/Qualifiers
source                  1..2187
                        mol_type = other DNA
                        organism = synthetic construct
SEQUENCE: 10
atgtgggtga ccaagctgct gcccgccctg ctgctgcagc acgtgctgct gcacctgctg   60
ctgctgccca tcgccatccc ctacgccgag ggccagcgca agcgccgcaa caccatccac  120
gagttcaaga agtccgccaa gaccaccctg atcaagatcg accccgccct gaagatcaag  180
accaagaagg tgaacaccgc cgaccagctg gccaaccgct gcacccgcaa caagggcctg  240
cccttcacct gcaaggcctt cgtgttcgac aaggcccgca gcagtgcct gtggttcccc    300
ttcaactcca tgtcctccgg cgtgaagaag gagttcggcc acgagttcga cctgtacgag  360
aacaaggact acatccgcaa ctgcatcatc ggcaagggcc gctcctacaa gggcaccgtg  420
tccatcacca agtccggcat caagtgccag ccctggtcct ccatgatccc ccacgagcac  480
tccttcctgc cctcctccta ccgcggcaag gacctgcagg agaactactg ccgcaacccc  540
cgcggcgagg agggcggccc ctggtgcttc acctccaacc ccgaggtgcg ctacgaggtg  600
tgcgacatcc ccagtgctc cgaggtggag tgcatgacct gcaacggcga gtcctaccgc   660
ggcctgatgg accacaccga gtccggcaag atctgcacgc ggtgggacca ccagaccccc  720
caccgccaca agttcctgcc cgagcggtac ccgacaagg gcttcgacga caactactgc   780
cgcaaccccg acggccagcc ccgcccctgg tgctacaccc tggaccccca cacccgctgg  840
gagtactgcg ccatcaagac ctgcgccgac aacaccagga acgcaccga cgtgcccctg   900
gagaccaccg agtgcatcca gggccagggc gagggctacc gcggcaccgt gaacaccatc  960
tggaacggca tcccctgcca gcggtgggac tcccagtacc ccacgagca cgacatgacc   1020
cccgagaact tcaagtgcaa ggacctgcgc gagaactact gccgcaaccc cgacggctcc  1080
gagtcccccct ggtgcttcac caccgacccc aatatccgcg tgggctactg ctcccagatc  1140
cccaactgcg acatgtccca cggccaggac tgctaccgcg gcaacggcaa gaactactgc  1200
ggcaacctgt cccagacccg ctccggcctg acctgctcca tgtgggacaa gaacatggag  1260
gacctgcacc gccacatctt ctgggagccc gacgcctcca gctgaacga gaactactgc   1320
cgcaacccgc acgacgacgc ccacgccccc tggtgctaca ccggcaaccc cctgatcctg  1380
tgggactact gccccatctc ccgctgcgag ggcgacacca cccccaccat cgtgaacctg  1440
gaccaccccg tgatcctg cgccaagacc aagcagctgc gcgtggtgaa cggcatcccc    1500
acccgcacca acatcggctg gatggtgtcc ctgcgctacc gcaacaagca catctgcggc  1560
ggctccctga tcaaggagtc ctgggtgctg accgcccgcc agtgcttcc ctcccgcgac   1620
ctgaaggact acgaggcctg gctgggcatc cacgacgtgc acggccgcgg cgacgagaag  1680
tgcaagcagg tgctgaacgt gtccagctg gtgtacggcc ccgagggctc cgacctggtg   1740
ctgatgaagc tggcccgccc cgccgtgctg gacgacttcg tgtccaccat cgacctgccc  1800
aactacggct gcaccatccc cgagaagacc tcctgctccg tgtacggctg gggctacacc  1860
ggcctgatca actacgacgg cctgctgcgc gtgccccacc tgtacatcat gggcaacgag  1920
aagtgctccc agcaccaccg cggcaaggtg accctgaacg agtccgagat ctgcgccggc  1980
gccgagaaga tcggctccgg ccctgcgag ggcgactacg gcggccccct ggtgtgcgag   2040
cagcacaaga tgcgcatggt gctgggcgtg atcgtgcccg ccgcggctg cgccatcccc   2100
aaccgccccg gcatcttcgt gcgcgtggcc tactacgcca agtggatcca aagatcatc   2160
ctgacctaca aggtgccca gtcctaa                                        2187

SEQ ID NO: 11           moltype = DNA  length = 480
FEATURE                 Location/Qualifiers
source                  1..480
                        mol_type = other DNA
                        organism = synthetic construct
SEQUENCE: 11
atgtccaacc ccggcgacgt gcccccgtg ccccaccgct ccaaggtgtg ccgctgcctg    60
ttcggcccc tggactccga gcagctgcgc cgcgactgcg acgcctgat ggccggctgc    120
ctgcaggagc cccgcgagcg gtggaacttc gacttcgtga ccgagacccc cctggagggc  180
aacttcgtgt gggagcgcgt gcgctccctg gcctgccca agtgtacct gtcccccggc    240
tcccgctccc gcgacgacct gggcggcgac aagcgcccct ccacctcctc cgccctgctg  300
cagggccccg ccccgagga ccacgtggcc ctgtccctgt cctgcaccct ggtgtccgag  360
cgccccgagg actccccgg cggccccggc acctcccagg ccgcaagcg ccgccagacc   420
```

```
tccctgaccg acttctacca ctccaagcgc cgcctggtgt ctgcaagcg caagccctaa    480
```

SEQ ID NO: 12           moltype = DNA   length = 576
FEATURE                 Location/Qualifiers
source                  1..576
                        mol_type = other DNA
                        organism = synthetic construct
SEQUENCE: 12
```
atgaacttcc tgctgtcctg ggtgcactgg tccctggccc tgctgctgta cctgcaccac     60
gccaagtggt cccaggccgc ccccatggcc gagggcggcg ccagaaccac ccacgaggtg    120
gtgaagttca tggacgtgta ccagcggtcc tactgccacc ccatcgagac cctggtggac    180
atcttccagg agtaccccga cgagatcgag tacatcttca agccctcctg cgtgcccctg    240
atgcgctgcg gcggctgctg caacgacgag ggcctggagt gcgtgcccac cgaggagtcc    300
aacatcacca tgcagatcat gcgcatcaag ccccaccagg gcacacat cggcgagatg      360
tccttcctgc agcacaacaa gtgcgagtgc cgccccaaga aggaccgcgc cgcaggag      420
aaccctgcg gcccctgctc cgagcgccgc aagcacctgt tcgtcagga ccccagacc      480
tgcaagtgct cctgcaagaa caccgactcc cgctgcaagg cccgcagct ggagctgaac   540
gagcgcacct gccgctgcga caagccccgc cgctaa                              576
```

SEQ ID NO: 13           moltype = DNA   length = 462
FEATURE                 Location/Qualifiers
source                  1..462
                        mol_type = other DNA
                        organism = synthetic construct
SEQUENCE: 13
```
atgggcaaga tctcctccct gcccacccag ctgttcaaga tctgcctgtg cgacttcctg     60
aagatcaaga tccacatcat gtcctcctcc cacctgttct acctggccct gtgcctgctg    120
accttcacct cctccaccac cgccggcccc gagaccctgt gcggcgccga gctggtggac    180
gccctgcagt tcgtgtgcgg ccccgcggc ttctacttca caagcccac cggctacggc     240
tcctccatcc gccgcgcccc ccagaccggc atcgtggacg agtgctgctt ccgctcctgc   300
gacctgcgcc gctggagat gtactgcgcc cccctgaagc ccaccaaggc cgcccgctcc    360
atccgcgccc agcgccacac cgacatgccc aagaccagga aggaggtgca cctgaagaac   420
acctcccgcg gctccgccgg caacaagacc taccgcatgt aa                       462
```

SEQ ID NO: 14           moltype = DNA   length = 375
FEATURE                 Location/Qualifiers
source                  1..375
                        mol_type = other DNA
                        organism = synthetic construct
SEQUENCE: 14
```
atgcgcatgc agctgctgct gctgatcgcc ctgtccctgg ccctggtgac caactccggc     60
cccgagaccc tgtgcggcgc cgagctggtg gacgccctga gttcgtgtg cggccccgc      120
ggcttctact tcaacaagcc caccggctac ggctcctcca tccgccgcgc cccccagacc    180
ggcatcgtgg acgagtgctg cttccgctcc tgcgacctgc gccgcctgga gatgtactgc    240
gcccccctga gcccaccaa ggccgcccgc tccatccgcg cccagcgcca caccgacatg    300
cccaagaccc agaaggaggt gcacctgaag aacacctccc gcggctccgc cggcaacaag    360
acctaccgca tgtaa                                                      375
```

SEQ ID NO: 15           moltype = DNA   length = 243
FEATURE                 Location/Qualifiers
source                  1..243
                        mol_type = other DNA
                        organism = synthetic construct
SEQUENCE: 15
```
atggccaccg gctcccgcac ctccctgctg ctggccttcg gcctgctgtg cctgccctgg     60
ctgcaggagg gctccgccat gaactccgac tccgagtgcc ccctgtccca cgacggctac   120
tgcctgcacg acggcgtgtg catgtacatc gaggccctgg acaagtacgc ctgcaactgc    180
gtggtgggct acatcggcga gcggtgccag taccgcgacc tgaagtggtg ggagctgcgc    240
taa                                                                   243
```

SEQ ID NO: 16           moltype = DNA   length = 2397
FEATURE                 Location/Qualifiers
source                  1..2397
                        mol_type = other DNA
                        organism = synthetic construct
SEQUENCE: 16
```
atggactaca aggacgacga cgacaagggc ggcggcggct ccgccatgtg gatccaggcc     60
cagcagctgc agggcgacgc cctgaccag atgcaggccc tgtacggcca gcacttcccc    120
atcgaggtgc gccactacct gtcccagtgg atcgagtgc tgccactcc atccatccga     180
ctggacaacc cccaggagaa catcaaggcc acccagctgc tggagggcct ggtgcaggag    240
ctgcagaaga aggccgagca ccaggtgggc aggacggct tcctgctgaa gatcaagctg    300
ggccactacg ccacccagct gcagtccacc tacgaccgct gccccatgga gctggtgcgc    360
tgcatccgcc acatcctgta caacgagcag cgcctggtgc gcgaggccaa caacggctcc    420
tccccgcg gtccccttgg cgacgccatg tcccagaagc ctgcagat caacccagacc     480
ttcgaggagc tgcgcctgat cacccaggac accgagaacg agctgaagaa gctgcagcag    540
acccaggagt acttcatcat ccagtaccag gagtccctgc gcatccaggc ccagttcgcc    600
cagctgggcg agctgaaccc ccaggagcgc atgtccccgg agaccgccct gcagcagaag    660
caggtgtccc tggagacctg gctgcagcgc gaggcccaga ccctgcagca gtaccgcgtg    720
gagctggccg agaagcacca agagaccctg cagctgctgc gcaagcagca gaccatcatc    780
```

-continued

```
ctggacgacg agctgatcca gtggaagcgc cgccagcagc tggccggcaa cggcggcccc   840
cccgagggct ccctggacgt gctgcagtcc tggtgcgaga agctggccga gatcatctgg   900
cagaaccgcc agcagatccg ccgcgccgag cacctgtgcc agcagctgcc catccccggc   960
cccgtggagg agatgctggc cgaggtgaac gccaccatca ccgacatcat ctccgccctg  1020
gtgacctcca cctt catcat cgagaacgag cccccccagg tgctgaagac ccagaccaag  1080
ttcgccgcca ccgtgcgcct gctggtgggc ggcaagctga acgtgcacat gaacccccc   1140
caggtgaagg ccaccatcat ctccgagcag caggccaagt ccctgctgaa gaacgagaac  1200
acccgcaacg actactccgg cgagatcctg aacaactgct gcgtgatgga gtaccaccag  1260
gccaccggca ccctgtccgc ccacttccgc aacatgtccc tgaagcgcat caagcggtcc  1320
gaccgccgcg gcgccgagtc cgtgaccgag gagaagttca ccatcctgtt cgactcccag  1380
ttctccgtgg gcgcaacga gctggtgttc caggtgaaga ccctgtccct gcccgtggtg  1440
gtgatcgtgc acggctccca ggacaacaac gccaccgcca ccgtgctgtg ggacaacgcc  1500
ttcgccgagc ccggccgcgt gcccttcgcc gtgcccgaca aggtgctgtg gccccagctg  1560
tgcgaaggcc tgaacatgaa gttcaaggcc gaggtgcagt ccaaccgcgg cgacctgctg  1620
gagaacctgg tgttcctggc ccagaagctg ttcaacatct cctccaacca cctggaggac  1680
tacaactcca tgtccgtgtc ctggtcccag ttcaaccgcg agaacctgcc cggccgcaac  1740
tacaccttct ggcagtggtt cgacggcgtg atggaggtgc tgaagaagca cctgaagccc  1800
cactgaacg acggcgccat cctgggcttc gtgaacaagc agcggccca cgacctgctg  1860
atcaacaagc ccgacggcac cttcctgctg cgcttctccg actccgagat cggcggcatc  1920
accatcgcct ggaagttcga ctcccaggag cgcatgttct ggcacctgat gcccttcacc  1980
acccgcgact tctccatccg ctccctggcc gaccgcctgg gcgacctgaa ctacctgatc  2040
tacgtgttcc ccgaccgccc caaggacgag gtgtactcca agtactacac ccccgtgccc  2100
tgcgagcccg ccaccgccaa ggccgccgac ggctacgtga agcccagat caagcaggtg  2160
gtgcccgagt cgccaacgc ctccaccgac gccggctccg cgccaccta catgaccag  2220
gccccctccc ccgtggtgtg ccccaggcc cactacaaca tgtacccccc caaccccgac  2280
tccgtgctgg acaccgacgg cgacttcgac ctggaggaca ccatgacgt ggcccgccgc  2340
gtggaggagc tgctgggccg ccccatggac tcccagtgga tccccacgc ccagtcc    2397

SEQ ID NO: 17              moltype = DNA   length = 3197
FEATURE                    Location/Qualifiers
source                     1..3197
                           mol_type = genomic DNA
                           organism = Homo sapiens
SEQUENCE: 17
aagcctctcg gtctgtggca gcagcgttgg cccggccccg ggagcggaga gcgaggggag    60
gcggagacgg aggaaggtct gaggagcagc ttcagtcccc gccgagccgc caccgcaggt   120
cgaggacggt cggactcccg cggcgggagg agcctgttcc cctgagggta tttgaagtat   180
accatacaac tgttttgaaa atccagcgtg gacaatggct actcaagctg atttgatgga   240
gttgacatg gccatggaac cagacagaaa agcggctgtt agtcactggc agcaacgtc    300
ttacctggac tctggaatcc attctggtgc cactaccaca gctccttctc tgagtggtaa   360
aggcaatcct gaggaagagg atgtggatac ctcccaagtc ctgtatgagt gggaacaggg   420
attttctcag tccttcactc aagaacaagt agctgatatt gatggacagt atgcaatgac   480
tcgagctcag agggtacgag ctgctatgtt ccctgagaca ttagatgagg gcatgcagat   540
cccatctaca cagtttgatg ctgctcatcc cactaatgtc cagcgtttgg ctgaaccatc   600
acagatgctg aaacatgcag ttgtaaactt gattaactat caagatgatg cagaacttgc   660
cacacgtgca atccctgaac tgacaaaact gctaaatgac gaggaccagg tggtggttaa   720
taaggctgga gttatggtcc atcagctttc taaaaaggaa gcttccagac acgctatcat   780
gcgttctcct cagatggtgt ctgctattgt acgtaccatg cagaatacaa atgatgtaga   840
aacagctcgt tgtaccgctg gaccttgca taacctttcc catcatcgtg agggcttact   900
ggccatcttt aagtctggag gcattcctgc cctggtgaaa atgcttggtt caccagtgga   960
ttctgtgttg ttttatgcca ttacaactct ccacaacctt ttattacatc aagaaggagc  1020
taaaatggca gtgcgtttag ctggtgggct gcagaaaatg gttgccttgc tcaacaaaac  1080
aaatgttaaa ttcttggcta ttacgacaga ctgcctttca attttagctt atggcaacca  1140
agaaagcaag ctcatcatac tggctagtgg tggaccccaa gctttagtaa atataatgag  1200
gacctatact tacgaaaaac tactgtggac cacaagcaga gtgctgaagg tgctatctgt  1260
ctgctctagt aataagccgg ctattgtaga agctggtgga atgcaagctt taggacttca  1320
cctgacagat ccaagtcaac gtcttgttca gaactgtctt tggactctca ggaatcttc   1380
agatgctgca actaaacagg aagggatgga aggtctcctt gggactcttg ttcagcttct  1440
gggttcagat gatataaatg tggtcacctg tgcagctgga attcttttcta acctcacttg  1500
caataattat aagaacaaga tgatggtctg ccaagtgggt ggtatagagg ctcttgtgcg  1560
tactgtcctt cgggctggtg acagggaaga catcactgag cctgccatct gtgctcttcg  1620
tcatctgacc agccgacacc aagaagcaga gatggcccag aatgcagttc gccttcacta  1680
tggactacca gttgtggtta agctcttaca ccccaccatcc cactggcctc tgataaaggc  1740
tactgttgga ttgattcgaa atcttgccct ttgtcccgca aatcatgcac ctttgcgtga  1800
gcagggtgcc attccacgac tagttcagtt gcttgttcgt gcacatcagg atacccagcg  1860
ccgtacgtcc atgggtggga cacagcagca atttgtggag gggtccgca tgaagaaat    1920
agttgaaggt tgtaccggag cccttcacat cctagctcgg gatgttcaca accgaattgt  1980
tatcagagga ctaaatacca ttccattgtt tgtgcagctg ctttattctc ccattgaaaa  2040
catccaaaga gtagctggca gggtcctctg tgaacttgct caggacaagg aagctgcaga  2100
agctattgaa gctgagggag ccacagctcc tctgacagag ttacttcact ctaggaatga  2160
aggtgtggcg acatatgcag ctgctgtttt gttccgaatg tctgaggaca agccacaaga  2220
ttacaagaaa cggctttcag ttgagctgac cagctctctc ttcagaacag agccaatggc  2280
ttggaatgag actgctgatc ttggacttga tattggtgcc cagggagaac cccttggata  2340
tcgccaggat gatcctagct atcgttcttt tcactcttgc ggatatggcc aggatgcctt  2400
gggtatggac cccatgatgg aacatgagat gggtggccac caccctggtg ctgactatcc  2460
agttgatggg ctgccagatc tggggcatgc ccaggacctc atgatgggc tgcctccagg  2520
tgacagcaat cagctggcct ggtttgatac tgacctgtaa atcatccttt aggagtaaca  2580
atacaaatgg attttgggag tgactcaaga agtgaagaat gcacaagaat ggatcacaag  2640
atggaattta tcaaacccta gccttgcttg ttaaattttt tttttttttt ttttaagaat  2700
```

```
atctgtaatg gtactgactt tgcttgcttt gaagtagctc tttttttttt tttttttttt  2760
tttttgcagt aactgttttt taagtctctc gtagtgttaa gttatagtga atactgctac  2820
agcaatttct aattttttaag aattgagtaa tggtgtagaa cactaattca taatcactct  2880
aattaattgt aatctgaata aagtgtaaca attgtgtagc cttttttgtat aaaatagaca  2940
aatagaaaat ggtccaatta gttccttttt taatatgctt aaaataagca ggtggatcta  3000
tttcatgttt ttgatcaaaa actatttggg atatgtatgg gtagggtaaa tcagtaagag  3060
gtgttatttg gaaccttgtt ttggacagtt taccagttgc ctttttatccc aaagttgttg  3120
taacctgctg tgatacgatg cttcaagaga aaatgcggtt ataaaaaatg gttcagaatt  3180
aaactttttaa ttcattc                                                3197

SEQ ID NO: 18         moltype = DNA   length = 57
FEATURE               Location/Qualifiers
source                1..57
                      mol_type = other DNA
                      organism = synthetic construct
SEQUENCE: 18
atgcgcatgc agctgctgct gctgatcgcc ctgtccctgg ccctggtgac caactcc      57

SEQ ID NO: 19         moltype = DNA   length = 87
FEATURE               Location/Qualifiers
source                1..87
                      mol_type = other DNA
                      organism = synthetic construct
SEQUENCE: 19
atggccaccg gctcccgcac ctccctgctg ctggccttcg gcctgctgtg cctgccctgg  60
ctgcaggagg gctccgccat gaactcc                                       87

SEQ ID NO: 20         moltype = DNA   length = 42
FEATURE               Location/Qualifiers
source                1..42
                      mol_type = other DNA
                      organism = synthetic construct
SEQUENCE: 20
atggactaca aggacgacga cgacaagggc ggcggcggct cc                      42

SEQ ID NO: 21         moltype = DNA   length = 2340
FEATURE               Location/Qualifiers
source                1..2340
                      mol_type = other DNA
                      organism = synthetic construct
SEQUENCE: 21
gccacccagg ccgacctgat ggagctggac atggccatgg agcccgaccg caaggccgcc  60
gtgtctccact ggcagcagca gtcctacctg gactccggca cgtccaccacc           120
accgcccccct acctgtccgg caagggcaac cccgaggagg aggacgtgga cacctcccag  180
gtgctgtacg agtgggagca gggcttctcc cagtccttca cccggagca ggtggccgac    240
atcgacggcc agtacgccat gacccgcgcc cagcgcgtgc gcgccgccat gttccccgag   300
accctggacg agggcatgca gatccccctc acccagttcg acgccgccccc ccaccaac    360
gtgcagcgcc tggccgagcc ctcccagatg ctgaagcacg ccgtggtgaa cctgatcaac  420
taccaggacg acgccgagct ggccaccgcg gccatcccg agctgaccaa gctgctgaac   480
gacgaggacc aggtggtggt gaacaaggcc gccgtgatgg tgcaccagct gtccaagaag  540
gaggcctccc gccacgccat catgcgcctc ccccagatgg tgtccgccat cgtgcgcacc  600
atgcagaaca ccaacgacgt ggagaccgcc cgctgcaccg ccggcaccct gcacaacctg  660
tccaccacc gcgagggcct gctggccatc ttcaagtccg gcggcatccc cgccctggtg   720
aagatgctgg gctcccccgt ggactccgtg ctgttctacg ccatcaccac cctgcacaac  780
ctgctgctgc accaggaggg cgccaagatg ccgtgcgcg tggccggcgg cctgcagaag   840
atggtggccc tgctgaacaa gaccaacgtg aagttcctgg ccatcaccac cgactgcctg  900
cagatcctgg cctacggcaa ccaggagtcc aagctgatca tcctggcctc cggcggcccc  960
caggccctgt gaacatcat gcgcacctac acctacgaga agctgctgtg gaccacctcc   1020
cgcgtgctga aggtgctgtc cgtgtgctcc tccaacaagc ccgccatgct ggaggccggc  1080
ggcatgcagg cctgggcct gcacctgacc gaccccctcc agcgcctggt gcagaactgc  1140
ctgtggaccc tgcgcaacct gtccgacgcc gccaccaagc aggagggcat ggagggcctg  1200
ctgggcaccc tggtgcagct gctgggctcc gacgacatca acgtggtgac ctgcgccgcc  1260
ggcatcctgt ccaacctgac ctgcaacaac tacaagaaca agatgatggt gtgccaggtg  1320
ggcggcatcg aggcctggt ggcgaccgtg ctgcgcgcgg cgaccgcgga ggacatcacc  1380
gagcccgcca tctgcgccct gcgcaccctg acctccgcc accaggaggc cgagatggcc  1440
cagaacgccg tgcgcctgca ctacggcctg ccgtggtgg tgaagctgct gcaccccccc  1500
tcccactggc cctgatcaa ggccaccgtg ggcctgatcc gcaacctggc cctgtgcccc  1560
gccaaccacg cccccctgcg cgagcaggc gccatccccc gctggtgca gtgctggtg    1620
cgcgcccacc aggacaccca gcgccgcacc tccatgggg gcaccagca gcagttcgtg   1680
gagggcgtgc gcatggagga gatcgtggag ggctgcaccg gcgccctgca catcctggcc  1740
cgcgacgtgc acaaccgcat cgtgatccgc ggcctgaaca ccatccccct gttcgtgcag  1800
ctgctgtact cccccatcga gaacatccag gcgtggccg ccggcgtgct gtgcgagctg   1860
gcccaggaca aggaggccgc cgaggccatc gaggccgagg cgccaccgc ccccctgacc   1920
gagctgctgc actcccgcaa cgagggcgtg gccacctacg gctgttccgc            1980
atgtccgagg acaagcccca ggactacaag aagcgcctgt ccgtggagct gacctcctcc  2040
ctgttccgca ccgagcccat ggcctggaac gagaccgccg acctgggcct ggacatcggc  2100
gcccaggcg agcccctggg ctaccgcag gacgacccct cctaccgctc cttccactcc  2160
ggcggctacg ccaggacgc cctgggcatg gaccccatga tggagcacga gatgggcgc   2220
caccaccccg gcgccgacta ccccgtggac ggcctgcccg acctgggcca cgcccaggac  2280
```

```
ctgatggacg gcctgccccc cggcgactcc aaccagctgg cctggttcga caccgacctg    2340
```

SEQ ID NO: 22            moltype = DNA   length = 5353
FEATURE                  Location/Qualifiers
source                   1..5353
                         mol_type = genomic DNA
                         organism = Homo sapiens
SEQUENCE: 22
```
ctcagtcggg cgcagccgcc gccagggaaa agaaagggag gaaggaagga acaagaaaag      60
gaaataaaga gaaaggggag gcggggaaag gcaacgagct gtccggcctc cgtcaaggga     120
gttggaggga aaaagttctc aggcgccgca ggtccgagtg cctcgcagcc cctcccgagg     180
cgcagccgcc agaccagtgg agccgggcg cagggcgggg gcggaggcgc cggggcgggg     240
gatgcggggc cgcggcgcag ccccccggcc ctgagagcga ggacagcgcc gcccggcccg     300
cagccgtcgc cgcttctcca cctcggcccg tggagccggg gcgtccgggc gtagccctgc     360
ctcgcctggg tcagggggtg cgcgtcgggg gaggcagaag ccatggatcc cgggcagcag     420
ccgccgcctc aaccggcccc ccagggcaa gggcagccgc cttcgcagcc cccgcagggg     480
cagggcccgc cgtccggacc cgggcaaccg gcacccgcgg cgacccaggc ggcgccgcag     540
gcaccccccg ccgggcatca gatcgtgcac gtccggacga actcggagac cgacctggag     600
gcgctcttca acgccgtcat gaaccccaag acggccaacg tgcccagac cgtgcccatg     660
aggctccgga agctgcccga ctccttcttc aagccgccgg agcccaaatc ccactcccga     720
caggccagta ctgatgcagg cactgcagga gccctgactc cacagcatgt tcgagctcat     780
tcctctccag cttctctgca gttgggagct gttttctcctg ggacactgac cccactgga     840
gtagtctctg gcccagcagc tacacccaca gctcagcatc ttcgacagtc ttcttttgag     900
ataccttgatg atgtacctct gccagcaggt gggagatgg caaagacatc ttctggtcag     960
agatacttct taaatcacat cgatcagaca acaacatggc aggaccccag gaaggccatg    1020
ctgtcccaga tgaacgtcac agccccccac agtccaccag tgcagagaa tatgatgaac    1080
tcggcttcag gtcctcttcc tgatggatgg gaacaagcca tgactcagga tggaaaatt    1140
tactatataa accataagaa caagaccacc tcttggctag acccaaggct tgaccctcgt    1200
tttgccatga accagagaat cagtcagagt gctccagtga acagccacc accctggct    1260
ccccagagcc cacagggagg cgtcatgggt ggcagcaact ccaaccagca gcaacagatg    1320
cgactgcagc aactgcagat ggagaaggag aggctgcggc tgaaacagca agaactgctt    1380
cggcaggagt tagccctgcg tagccagtta ccaaacactgg agcaggatgg tgggactcaa    1440
aatccagtgt cttctcccgg gatgtctcag gaattgagaa caatgacgac caatagctca    1500
gatccttttcc ttaacagtgg cacctatcac tctcagtagta agatcaga cagtggacta    1560
agcatgagca gctacagtgt ccctcgaacc ccagatgact tcctgaacag tgtggatgaa    1620
atggatacag gtgatactat caaccaaagc accctgccct cacagcagaa ccgtttccca    1680
gactaccttg aagccattcc tgggacaaat gtggaccttg aacactgga aggagatgga    1740
atgaacatag aaggagagga gctgatgcca agtctgcagg aagctttgag ttctgacatc    1800
cttaatgaca tggagtctgt tttggctgcc accaagctag ataaagaag cttttcttaca    1860
tggttataga gccctcaggc agactgaatt ctaaatctgt gaaggatcta aggacacaca    1920
tgcaccggaa attccataa gccagttgca gttttcaggc taatacagaa aaagatgaac    1980
aaacgtccag caagatactt taatcctcta ttttgctctt ccttgtccat tgctgctgtt    2040
aatgtattgc tgacctcttt cacagttggc tctaaagaat caaaagaaaa aaacttttta    2100
tttcttttgc tattaaaact actgttcatt ttggggggctg ggggaagtga gcctgtttgg    2160
atgatggatg ccattccttt tgcccagtta aatgttcacc aatcatttta actaaatact    2220
cagacttaga agtcagatgc ttcatgtcac agcatttagt ttgttcaaca gttgtttctt    2280
cagcttcctt tgtccagtgg aaaaacatga tttactgctt tgacaagcca aaaatgttat    2340
atctgatatt aaatacttaa tgctgattttg aagagatagc tgaaccaag gctgaagact    2400
gttttacttt cagtattttc ttttcctcct agtgctatca ttagtcacat aatgaccttg    2460
attttatttt aggagcttat aaggcatgag acaatttcca tataaatata ttaattattg    2520
ccacatactc taatatagat tttggtggat aattttgtgg gtgtgcattt tgttctgtt    2580
tgttgggttt tttgttttttt ttgttttttg cagggtcggt ggggggggttg gttggttggt    2640
tggttttgtc ggaacctagg caaatgacca tattagtgaa tctgttaata gttgtagctt    2700
gggatggtta ttgtagttgt tttggtaaaa tcttcatttc ctggttttttt ttaccacctt    2760
atttaaatct cgattatctg ctctctcttt tatatacata cacacaccca aacataaat    2820
ttataatagt gtggtagtgg aatgtatcct ttttttaggtt tccctgcttt ccagttaatt    2880
tttaaaatgg tagcgctttg tatgcattta gaatacatga ctagtagttt atatttcact    2940
ggtagtttaa atcggttgg ggcagtctgc agatgtttga agtagtttag tgttctagaa    3000
agagctatta ctgtggatag tgcctagggg agtgctccac gccctctggg catacggtag    3060
atattatctg atgaattgga aaggagcaaa ccagaaatgg ctttattttc tcccttggac    3120
taatttttaa gtctcgattg gaattcagtg agtaggttca taatgtgcat gacagaaata    3180
agctttatag tggtttacct tcatttagct ttggaagttt tctttgcctt agttttgaa    3240
gtaaattcta gtttgtagtt ctcatttgta atgaacacat taacgactag attaaaatat    3300
tgcctctcaag attgttctta cttacaagac ttgctcctac ttctatgctg aaaattgacc    3360
ctggataagaa tactataagg ttttgagtta gctggaaaag tgatcagatt aataaatgta    3420
tattggtagt tgaatttagc aaagaaatag agataatcat gattatacct ttattttttac    3480
aggaagagat gatgtaacta gagtatgtgt ctacaggagt aataatggtt tccaaagagt    3540
atttttaaa ggaacaaaac agcatgaatt taactcttca atataagcta tgaagtaata    3600
gttggttgtg aattaaagtg gcaccagcta gcacctctgt gttttagggg tcttttcaatg    3660
tttctagaat aagcccttat tttcaagggt tcataacagg cataaaatct cttctcctgg    3720
caaaagctgc tatgaaaagc ctcagcttgg gaagatagat ttttttcccc caattacaa    3780
aatctaagta ttttggccct tcaatttgga ggagggcaaa agttggaagt aagaagtttt    3840
atttttaagta ctttcagtgc tcaaaaaaat gcaatcactg tgttgtatat aatagttcat    3900
aggttgatca ttcatataa ttgactctaa ggctttatt aagaaaacag cagaaagatt    3960
aaatcttgaa ttaagtctgg ggggaatgg ccactgcaga tggagttta gagtagtaat    4020
gaaattctac ctagaatgca aaattgggta tatgaattac atagcatgtt gttgggattt    4080
tttttaatgt gcaagagatc aaagctactt ggaaggagtg cctataattt gccagtagcc    4140
acagattaag attatatctt atatatcagc agattagctt tagcttaggg ggagggtggg    4200
aaagttttggg ggggggttg tgaagattta gggggaccctt gatagagaac tttataaact    4260
```

```
tctttctctt taataaagac ttgtcttaca ccgtgctgcc attaaaggca gctgttctag    4320
agtttcagtc acctaagtac acccacaaaa caatatgaat atggagatct tcctttaccc    4380
ctcaacttta atttgcccag ttatacctca gtgttgtagc agtactgtga tacctggcac    4440
agtgctttga tcttacgatg ccctctgtac tgacctgaag gagacctaag agtcctttcc    4500
cttttttgagt ttgaatcata gccttgatgt ggtctctttt tttatgtcct tgttcctaat    4560
gtaaaagtgc ttaactgctt cttggttgta ttgggtagca ttgggataag atttttaactg   4620
ggtattcttg aattgctttt acaataaacc aattttataa tctttaaatt tatcaacttt    4680
ttacatttgt gttattttca gtcagggctt cttagatcta cttatggttg atggagcaca    4740
ttgatttgga gtatttcagatc ttccaaagca ctatttgttg taataacttt tctaaatgta  4800
gtgcctttaa aggaaaaatg aacacaggga agtgactttg ctacaaataa tgttgctgtg    4860
ttaagtattc atattaaata catgccttct atatggaaca tggcagaaag actgaaaaat    4920
aacagtaatt aattgtgtaa ttcagaattc ataccaatca gtgttgaaac tcaaacattg    4980
caaaagtggg tggcaatatt cagtgcttaa cacttttcta gcgttggtac atctgagaaa    5040
tgagtgctca ggtggatttt atcctcgcaa gcatgttgtt ataagaattg tgggtgtgcc    5100
tatcataaca attgttttct gtatcttgaa aaagtattct ccacatttta aatgttttat    5160
attagagaat tctttaatgc acacttgtca aatatatata tatagtacca atgttacctt    5220
tttatttttt gttttagatg taagagcatg ctcatatgtt aggtacttac ataaattgtt    5280
acattatttt ttcttatgta atacctttttt gtttgtttat gtggttcaaa tatattcttt    5340
ccttaaactc ttc                                                       5353

SEQ ID NO: 23           moltype = DNA   length = 2115
FEATURE                 Location/Qualifiers
source                  1..2115
                        mol_type = genomic DNA
                        organism = Homo sapiens
SEQUENCE: 23
agtctcacca ctagccgcag acgcgagcgg cggggggggcg ggggcgcaga ggcgccggca     60
gccgtgacga ggcgctcccg gagctgagcg cttctgctcc gggcacgcat ggcgcccgca    120
cacgagtct gacctgatgt agacgcaagg gggttaatat gaacgtccct ctcggtggaa    180
tctggctctg gctccctctg ctcttgacct ggctcacccc tgaggtcagc tcttcatggt    240
ggtacatgag agctacaggt ggctcctcca gggtgatgtg tgagaatgtg ccaggcctgg    300
tgagccggca gcgtcagctg tgccaccgac acccagatgt gatgcgtgcc attggcctgg    360
gtgtggctga gtggactgca gagtgccaac accagttccg ccagcatcgc tggaactgca    420
acaccctgga cagagatcac agcctctttg gccgggtcct cctccgaagt agtcgggaat    480
cggcctttgt ttacgccatc tcttcagctg gcgttgtatt tgccatcacc agggcctgta    540
gccaaggaga attaaagtcc tgctcctgtg atccaaagaa gaaggaagt gccaaggaca    600
gcaaaggcac cttcgactgg ggtggctgca gtgacaatat tgactacggg atcaagtttg    660
cccgtgcctt tgtagatgcc aaggagagga aaggcaagga tgccagagcc ctgatgaacc    720
ttcacaacaa cagagctgga aggaaggctg taaagcgctt cttgaaacaa gaatgcaagt    780
gtcatggtgt gagtggctcc tgtactctga ggacatgctg gctggccatg gctgacttca    840
ggaaaacagg cgactatctc tggaggaagt acaatgggc catccaggta gtcatgaacc    900
aggatggcac tggcttcact gtagccaata agaggtttaa gaagccaacg aaaatgacc    960
tcgtgtattt tgagaattct ccagactact gtatcaggga ccgagaggca ggctccctgg   1020
gtacagcggg ccgtgtgtgc aacttgactt cccgaggcat ggacagctgc gaagttatgt   1080
gttgtgggag aggctatgac acatcccacg tcacccggat gaccaagtgt gagtgtaaat   1140
tccactggtg ctgtgccgtg cgctgtcagg actgcctgga ggcctggac gtgcacacat   1200
gcaaggcccc caagagtgcc gactgggcga gcctacatcg acctcagcag aggtcatatt   1260
cgccttttct tccctcaagg actccaatta catcttcaag gacactggac ctctgggttg   1320
ttttcagggg ctctttctta aggcatgaag ccttcatctc aagagaaacc cccttttccc   1380
tctctgggg cccccaggact gggaaccacc tgctgcacat aagtacaccc tattctgtct  1440
atcttgggca ttctgatgtc acctctcttc ctgctgatgt cttttttgaa atggcatgac   1500
aggctgttag aggaggaggg tcatagcccc ccaccactgt cacctagaca tttcctcttt   1560
ggctgcgggg agaaacatca catagcgaag gaacttcctc tgtgttttcc cagattccaa   1620
caacccagaa agtctgtgtt tccctggggc gcggggtagg gatggaaagc agaatgagct   1680
gacaccaaaa tttcctcgga tttttttaaa aaaagagtaa gcaagggctt taactaagtg   1740
atagctgttg atagcatcct tggtgacttt ctagagaaag atggcttcca ataaacatca   1800
ggttaaaaca tgtatgtctt caaagaattt attggatatt tattggctat tggatataat   1860
agggtgagaa tgtttgtcct ttcagactgt gttattttttg aactttcctg tcagccaaca   1920
ccttagaaag tgattgctat tcctcactgt cccatcagtt taaggattct taagagatga   1980
gacttctcag tgtgctctgg agagaatctg aaagggaat ggtgatctca gcaatattat    2040
ttaactactg ggtaaatatg gtttaaaat aataataact ttgtgagtgg aatatcataa    2100
atgtgcttgt atggc                                                   2115

SEQ ID NO: 24           moltype = DNA   length = 4519
FEATURE                 Location/Qualifiers
source                  1..4519
                        mol_type = genomic DNA
                        organism = Homo sapiens
SEQUENCE: 24
acgagcgcct agtggcgcga ggagatgcga gagtgcaccg gccgcctgca ccatgcgccc     60
cgcgcccgcg ctggccctgg ctgcgctctg cctgctggtg ctgcctgccg ctgccgccgc    120
cgccgcctac ttcggcctga ccggtcgtga ggtcctgaca ccctttccag gcctgggtac    180
ggcagcagcc ccggcacagg ctggtgctca cctgaagcag tgtgacctac tgaagctgtc    240
caggcggcag aagcagctct gcaggcggga gcccggcctg gctgagacgc tgagggatgc    300
tgcacacctg gggctgctgg aatgtcagtt ccagttcagg caggagcgct ggaactgcag    360
cctggagggg aggactggcc tgctccagag aggctttaag gagacggcct tcctgtatgc    420
agtgtctgca gctgccctca cgcatgcact ggccagggcc tgcagtgctg gcgcatgga    480
gcgctgtact tgtgacgact ccccaggcct ggagagccgg caggcctggc agtgggtgt    540
gtgtggtgac aatctgaagt acagcaccaa gttcctcagc aacttcctgg ggcccaagag    600
```

```
aggaagcaag gacctgaggg cgagggctga cgcccacaac acccacgtgg gcatcaaggc  660
tgtgaagagc ggcctgagaa caacctgcaa gtgccatggt gtgtcaggct cctgtgctgt  720
tcgtacctgt tggaagcagc tctcccgtt tcgcgagacc ggccaggtgc tgaagctacg  780
ctatgacacg gctgtcaagg tgtccagtgc caccaacgag gccttgggtc gtctggagct  840
atgggccccc gctaagccag gtggtcccgc caagggccta ggccctcgtc gcggggacct  900
ggtctacatg gaagattctc ccagcttctg ccggcccagc aagtactctc cgggcacggg  960
aggcagggtg tgttctcgag actccagttg cagcagccta tgctgtgggc gaggctacga 1020
cacccagagc cgcatggtgg ttttctcctg ccactgtcag gtgcagtggt gctgctacgt 1080
ggagtgccag cagtgtgcac agcaggagct cgtgtatacc tgcaagcgct aggcctccac 1140
agcgaatccc gcggaacagc gcgcaagcgc gcacctgtcg acgcacctgc cgtgcacaag 1200
agtgtgcgac tcatctctct tccccaacag atggttggcc agcccttctg ccttccccga 1260
cactcagcaa agagaaagaa agccctgcct cctagtccca ggatcaccaa cctgctggag 1320
gacttggggc cggagaacag actgagaagg ggaatctttg aggaccaggg tagggcagga 1380
atgatgctgt gcgggaagag agaaacatcc tcctatctca aggccaaaaa ctgggaggat 1440
ggggaagagg gaggcggagc cagctggagt gtggggtcag ggcatccatc tgggcgtggc 1500
cgatctcttg tggtcccact ctaatagcag agcgctctgg gtgctgcatg cctaccctgc 1560
tcttgtggct tcgtgcactg gagacttcga aatgtttatt aggagcaagg gaagcacttt 1620
aggcttgggt ggattgagtc gcagagccca tgccctgaag tcttacgtcc tggcactcag 1680
ggctgccacc ttgtcctt gtcttgagat cccctgtccc ccaaagccat tgagctctgc 1740
tcaacgagac ccctaatatg tataagaagg gtgcaggagc cagtctcctc ggtgagactc 1800
agataaacat aactagggtt gagcggggag acagtgaccc tttctctttc ctttggtcca 1860
aggaaccttt aatcacagcc cagaggtgga gagaggcagg gtccaaatgc ctggaagaga 1920
tatgacaggc tctgtattga gataccactc tggagtgtgt cctaccaatt cctgtgacca 1980
gggaccccca agaaccgagg ggcccccatc catgttagtg atacataaga acgagtgact 2040
catgggccac acgtctgctt ccaccccctg ctctcaaaga tgcttgtgca ggcttttttg 2100
ccattgctaa gtctttgcca agtctgcctc ctcaatgtct ttactcattt actaacgacc 2160
tgtcacttgg gctcccacca gaggaacaaa atgactgctg gtgaatcctt tggtcatttt 2220
taatgccccc atcaaggccc tctgtgagag gagaggaagt agtgtacagg tacaggctca 2280
cacgtgcaca cactcagcct agccaggcac agacatccca aggagcagtg cggcgtctct 2340
ccagcccagg gcaaagacct cactgggtc acttctggag gctgtgagct actccaggc 2400
agggcccaag gccaaccagg aggaagtgac ctcctttggg aagcctttgg ccatgtggct 2460
ggctgtgctg caccctcctg tgagcttcct tccaccctga aatctgttgg ggttactgtc 2520
tctctaaggg agcaggaagc ttcggaatca gccggtactc agcactactg gccctgccag 2580
ctccaggaaa gagacactgt ggcggagagg tccgtggggc agaaggggct acccttcctt 2640
cagtgcctcc gggcagcatg ctgggaagat cttgatggt ggaaagcccc gaggcggagc 2700
caccgtgacc tgagacccct ctctgggacg actttgccac ccacccgcag cttggcagga 2760
ggggtaaaca gattgggagc tgctttctac ttccctgatg aagacagatg tgttccttgg 2820
caacccaagg catccttctc tatgacccta atcctgctct ggctcgaggg tacaaggcaa 2880
gaatggagtc tggcaaaact tgggggactag cctacagcca aatcacctgt 2940
accctgactc tatggccagg agggccaggg gtggaggagg gttaaagatg aacttgaagt 3000
tgaggctgag gctgaccaac cattaagact ggtgccttaa ggcaccctca gtcaggtcct 3060
ctccctccct tctccattct ttctccaagg ccccgttccc cctaaaatcc caccatagcc 3120
atgctgggtc cccccttccc ccacactgga actttaagga agatattcac aggtatttc 3180
tgcctacctc atacatgtaa ttttcaaaaa aaattaattt atatagttaa gatatatggg 3240
aaagtatttta tgttatttat atatcttctc tatttcctgg gcaccatatg gggggttgtg 3300
tgtttaccca gaagcctctg aggaaacatg gctgggtctg tctggggcct cgcagagctg 3360
gatgcgcata gctgagaggt cacagctcct gtgtctcact gtcttggagc tcgggaagca 3420
catgtacctc ctgagataaa ccccgtgaca ccaagcaggg ccttccttgt gaagtctgtg 3480
gattctctgc ctctgccccc agaggccttt ctgctctggc ccaagggttt tgctcataaa 3540
ggacaaaaag ggtgagcagc tctggatttg taaagcactt tccatcttca gaaacactcc 3600
tctcttctct ctccctcggt tacccccggt tccctatgag gtcatgccac tgttaccacg 3660
ttccaggccc agagacggag gcaggttggt caaagccagt cactctctga acccagaggt 3720
tgaggaagag tgcatgctgc gtggaacgct ggtcttcccc catggatggc atgctagttt 3780
ctccagcaag ctgagtctca tgtccccaaa gacggggact tcctgagaag cctggagaga 3840
caagggctcc gtggatgtca ctcttaggga gggtgtcctg cagccctcat tgacctccac 3900
gactaggcta tggtccccag ccctcacag ctcgtggata atttgtgttt cttcgctttt 3960
gtttttttgtc ttttcaaagt gacttttcc ccactggatt tctaagttc tcttttgaaaa 4020
tcagttcact ggcaaatggg acctgcatcc tgacctggct gcctgcatca ggagcgcacc 4080
caaacagagt cgtgggaat cccaattgg cccagtgtcc ccggcccctt ccttaagtca 4140
cacaagctcc cgtgtggctt tcgtgagcat ggagaacctg tccccctggtc ttagaagaag 4200
ccagccattc tgccaccctc tgtttgtctg gcagacagat taccacaccg tggctgtctt 4260
tctagccaaa gcttcctctc tcaacaccca tgaacgtcca tgcttcctgt ctgagcactg 4320
aggagaaccc cagcggagct cattgttcag tgctggaata cccatccccc ctcccgttga 4380
ttatttaggg agtgtctgat aatgccaggg gatactctgg gtgctagggc gcagaagtac 4440
ttaagagcaa gtcccagcct cagggggactt atatgccggc gaggagaaag ccaacaaacc 4500
aataaaactat gcactggtt                                              4519

SEQ ID NO: 25        moltype = DNA   length = 1464
FEATURE              Location/Qualifiers
source               1..1464
                     mol_type = other DNA
                     organism = synthetic construct
SEQUENCE: 25
atggacccccg gccagcagcc ccccccccag cccgccccccc agggccaggg ccagccccccc   60
tcccagcccc cccagggcca gggccccccc tccggcccccg gccagcccgc cccgccgccc  120
acccaggccg ccccccaggc cccccccgcc ggcaccagaa tcgtgcacgt gcgcggcgac  180
tccgagaccc acctggaggc cctgttcaac gccgtgatga cccccaagac cgccaacgtg  240
ccccagaccg tgcccatgcg cctgcgcaag ctgcccgact ccttcttcaa gccccccgag  300
cccaagtccc actcccgcca ggcctccacc gacgccggca ccgccggcgc cctgacccccc  360
```

```
cagcacgtgc gcgcccacgc ctcccccgcc tccctgcagc tgggcgccgt gtccccggc    420
accctgaccc ccaccggcgt ggtgtccggc ccgccgcca cccccaccgc ccagcacctg    480
cgccagtcct ccttcgagat ccccgacgac gtgcccctgc ccgccggctg ggagatggcc    540
aagacctcct ccgccagcg ctacttcctg aaccacatcg accagaccac cacctggcag    600
gacccccgca aggccatgct gtcccagatg aacgtgcacc tccccccgtg                660
cagcagaaca tgatgaactc cgcctccggc ccctgcccg acggctggga gcaggccatg    720
acccaggacg gcgagatcta ctacatcaac cacaagaaca agaccacctc ctggctggac    780
ccccgcctgg acccccgctt cgccatgaac cagcgcatct cccagtccgc ccccgtgaag    840
cagcccccc cctggcccc ccagtccccc cagggcggcg tgatgggcgg ctccaactcc       900
aaccagcagc agcagatgcg cctgcagcag ctgcagatgg agaaggagcg cctgcgcctg    960
aagcagcagg agctgctgcg ccaggagctg gccctgcgct cccagctgcc caccctggag    1020
caggacggcg gcacccagaa ccccgtgtcc tcccccggca tgtcccagga gctgcgcacc    1080
atgaccacca actcctccga ccccttcctg aactccggca cctaccactc ccgcgacgag    1140
tccaccgact ccggcctgtc catgtcctcc tactccgtgc cccgcacccc cgacgacttc    1200
ctgaactccg tggacgagat ggacaccggc gacaccatca accagtccac cctgccctcc    1260
cagcagaacc gcttccccga ctacctggag gccatccccg gcaccaacgt ggacctgggc    1320
accctggagg gcgacggcat gaacatcgag ggcgaggagc tgatgccctc cctgcaggag    1380
gccctgtcct ccgacatcct gaacgacatg gagtccgtgc tggccgccac caagctggac    1440
aaggagtcct tcctgacctg gctg                                           1464

SEQ ID NO: 26           moltype = DNA  length = 1080
FEATURE                 Location/Qualifiers
source                  1..1080
                        mol_type = other DNA
                        organism = synthetic construct
SEQUENCE: 26
atgaacgtgc ccctgggcgg catctggctg tggctgcccc tgctgctgac ctggctgacc     60
cccgaggtgt cctcctcctg gtggtacatg cgcgccaccg gcggctcctc ccgcgtgatg    120
tgcgacaacg tgcccggcct ggtgtccgcc cagcgccagc tgtgccaccg ccaccccgac    180
gtgatgcgcg ccatcggcct gggcgtggcc gagtggaccg ccgagtgcca gcaccagttc    240
cgccagcacc gctggaactg caacaccctg gaccgcgacc actccctgtt cggccgcgtg    300
ctgctgcgct cctcccgcga gtccgccttc gtgtacgcca tctcctccgc cggcgtggtg    360
ttcgccatca cccgcgcctg ctccagggc gagctgaagt cctgctcctg cgaccccaag    420
aagaagggct ccgccaagga ctccaagggc accttcgact ggggcggctg ctccgacaag    480
atcgactacg gcatcaagtt cgcccgcgcc ttcgtggacg ccaaggagcg caagggcaag    540
gacgcccgcg ccctgatgaa cctgcacaac aaccgccgg gccgcaaggc cgtgaagcgc    600
ttcctgaagc aggagtgcaa gtgccacggc gtgtccggct cctgcaccct gcgcacctgc    660
tggctggcca tggccgactt ccgcaagacc ggcgactacc tgtggcgcaa gtacaacggc    720
gccatccagg tggtgatgaa ccaggacggc accggcttca ccgtggccaa caagcgcttc    780
aagaagccca ccaagaacga cctggtgtac ttcgagaact cccccgacta ctgcatccgc    840
gaccgcgagg ccggctccct gggcaccgcc ggccgcgtgt gcaacctgac ctcccgcggc    900
atggactcct gcgaggtgat gtgctgcggc cgcggctacg acacctccca cgtgacccgc    960
atgaccaagt gcgagtgcaa gttccactgg tgctgcgccg tgcgctgcca ggactgcctg   1020
gaggccctgg acgtgcacac ctgcaaggcc ctgcaagtccg ccgactgggc cacccccacc   1080

SEQ ID NO: 27           moltype = DNA  length = 1077
FEATURE                 Location/Qualifiers
source                  1..1077
                        mol_type = other DNA
                        organism = synthetic construct
SEQUENCE: 27
atgcgccccg cccccgccct ggccctggcc gcctgtgcc tgctggtgct gccgccgcc     60
gccgccgccg ccgcctactt cggcctgacc ggccgcgagg tgctgacccc cttccccggc    120
ctgggcaccc ccgccgcccc cgcccaggcc ggcgcccacc tgaagcagtg cgacctgctg    180
aagctgtccc gccgccagaa gcagctgtgc cgccgcgacc ccggcctggc cgagaccctg    240
cgcgacgccg cccacctggg cctgctggag tgccagttcc agttccgcca ggagcgctga    300
aactgctccc tggagggccg caccggcctg ctgcagcgcg gcttcaagga ccgccttc    360
ctgtacgccg tgtccgccgc cgccctgacc acgccctggg ccgcgcctg ctccgccggc    420
cgcatggagc gctgcacctg cgacgactcc cccggctgg agtcccgca ggcctggcag    480
tggggcgtgt gcgccgacaa cctgaagtac tccaccaagt tcctgtccaa cttcctggag    540
cccaagcgcg gctccaagga cctgcgcgcc cgcgccgacg cccacaacac ccacgtgggc    600
atcaaggccg tgaagtccgg cctgcgcacc acctgcaagt gccacggcgt gtccggctcc    660
tgcgccgtgc gcacctgctg gaagcagctg tccccttcc gcgagaccgg ccaggtgctg    720
aagctgcgct acgacaccgc cgtgaaggtg tcctccgcca ccaacgaggc cctgggccgc    780
ctggagctgt ggcccccgc caagcccggc ggccccgcca agggcctggc ccccgcccc    840
ggcgacctgg tgtacatgga ggactccccc tccttctgcc gccctccaa gtactccccc    900
ggcaccgccg ccgcgtgtg ctcccgcgac tcctcctgct cctccctgtg ctgcggccgc    960
ggctacgaca cccagtcccg catggtggtg ttcctcctgcc actgccaggt gcagtggtgc   1020
tgctacgtgg agtgccagca gtgcgcccag caggagctgg tgtacacctg caagcgc      1077

SEQ ID NO: 28           moltype = DNA  length = 48
FEATURE                 Location/Qualifiers
source                  1..48
                        mol_type = other DNA
                        organism = synthetic construct
SEQUENCE: 28
gactacaaag acgatgacga taaagcaagg ctcgaatcgg tacctatg                  48

SEQ ID NO: 29           moltype = DNA  length = 48
```

```
FEATURE                 Location/Qualifiers
source                  1..48
                        mol_type = other DNA
                        organism = synthetic construct
SEQUENCE: 29
gactacaagg acgacgacga caaggcccgc ctggagtccg tgcccatg            48

SEQ ID NO: 30           moltype = DNA   length = 30
FEATURE                 Location/Qualifiers
source                  1..30
                        mol_type = other DNA
                        organism = synthetic construct
SEQUENCE: 30
gagcaaaagc tcatttctga agaggacttg                               30

SEQ ID NO: 31           moltype = DNA   length = 30
FEATURE                 Location/Qualifiers
source                  1..30
                        mol_type = other DNA
                        organism = synthetic construct
SEQUENCE: 31
gagcagaagc tgatctccga ggaggacctg                               30

SEQ ID NO: 32           moltype = DNA   length = 20
FEATURE                 Location/Qualifiers
source                  1..20
                        mol_type = other DNA
                        organism = synthetic construct
SEQUENCE: 32
ggacatcgag atcgccacct                                          20

SEQ ID NO: 33           moltype = DNA   length = 19
FEATURE                 Location/Qualifiers
source                  1..19
                        mol_type = other DNA
                        organism = synthetic construct
SEQUENCE: 33
accgccactg ctactgcca                                           19

SEQ ID NO: 34           moltype = DNA   length = 20
FEATURE                 Location/Qualifiers
source                  1..20
                        mol_type = other DNA
                        organism = synthetic construct
SEQUENCE: 34
ctcaacacgg gaaacctcac                                          20

SEQ ID NO: 35           moltype = DNA   length = 20
FEATURE                 Location/Qualifiers
source                  1..20
                        mol_type = other DNA
                        organism = synthetic construct
SEQUENCE: 35
cgctccacca actaagaacg                                          20

SEQ ID NO: 36           moltype = DNA   length = 28
FEATURE                 Location/Qualifiers
source                  1..28
                        mol_type = other DNA
                        organism = synthetic construct
SEQUENCE: 36
actttggaag acagaaccaa attatctc                                 28

SEQ ID NO: 37           moltype = DNA   length = 17
FEATURE                 Location/Qualifiers
source                  1..17
                        mol_type = other DNA
                        organism = synthetic construct
SEQUENCE: 37
tgggcaccat tccacca                                             17

SEQ ID NO: 38           moltype = DNA   length = 24
FEATURE                 Location/Qualifiers
source                  1..24
                        mol_type = other DNA
                        organism = synthetic construct
SEQUENCE: 38
gtgaaacaca agcccaaggc aaca                                     24
```

```
SEQ ID NO: 39          moltype = DNA   length = 20
FEATURE                Location/Qualifiers
source                 1..20
                       mol_type = other DNA
                       organism = synthetic construct
SEQUENCE: 39
tcctcggcaa agcaggtctc                                                  20

SEQ ID NO: 40          moltype = DNA   length = 22
FEATURE                Location/Qualifiers
source                 1..22
                       mol_type = other DNA
                       organism = synthetic construct
SEQUENCE: 40
ggtgtccata cgcatccttg ac                                               22

SEQ ID NO: 41          moltype = DNA   length = 22
FEATURE                Location/Qualifiers
source                 1..22
                       mol_type = other DNA
                       organism = synthetic construct
SEQUENCE: 41
agccgcttga tcttccctgg at                                               22

SEQ ID NO: 42          moltype = DNA   length = 20
FEATURE                Location/Qualifiers
source                 1..20
                       mol_type = other DNA
                       organism = synthetic construct
SEQUENCE: 42
acctcctgtt taaatggaag                                                  20

SEQ ID NO: 43          moltype = DNA   length = 21
FEATURE                Location/Qualifiers
source                 1..21
                       mol_type = other DNA
                       organism = synthetic construct
SEQUENCE: 43
ccctcctggc attcctgtgt c                                                21

SEQ ID NO: 44          moltype = DNA   length = 40
FEATURE                Location/Qualifiers
source                 1..40
                       mol_type = other DNA
                       organism = synthetic construct
SEQUENCE: 44
taatacgact cactataggg catggtgggt ctgcagctgt                            40

SEQ ID NO: 45          moltype = DNA   length = 531
FEATURE                Location/Qualifiers
source                 1..531
                       mol_type = other DNA
                       organism = synthetic construct
SEQUENCE: 45
atggccaccg gctcccgcac ctccctgctg ctggccttcg gcctgctgtg cctgccctgg      60
ctgcaggagg gctccgcctt ccccaccatc cccctgtccc gcctgttcga caacgccatg     120
ctgcgcgccc accgcctgca ccagctggcc ttcgacacct accaggagtt cgaggaggcc     180
tacatcccca aggagcagaa gtactccttc ctgcagaacc cccagacctc cctgtgcttc     240
tccgagtcca tccccacccc ctccaaccgc gaggagaacc agcagaagtc caacctggag     300
ctgctgcgca tctccctgct gctgatccag tcctggctgg agcccgtgca gttcctgcgc     360
tccgtgttcg ccaactccct ggtgtacggc gcctccgact ccaacgtgta cgacctgctg     420
aaggacctgg aggagggcat ccagaccctg atgggccgcc tggaggacgg ctccccccgc     480
accggccaga tcttcaagca gacctactcc aagttcgaca ccaactccca c              531

SEQ ID NO: 46          moltype = DNA   length = 1650
FEATURE                Location/Qualifiers
source                 1..1650
                       mol_type = other DNA
                       organism = synthetic construct
SEQUENCE: 46
atggaagatg ccaaaaacat taagaagggc ccagcgccat tctacccact cgaagacggg      60
accgccggcg agcagctgca caaggccatg aagcgctacg ccctggtgcc cggcaccatc     120
gcctttaccg acgcacatat cgaggtggac attacctacg ccgagtactt cgagatgagc     180
gttcggctgt cagaagctat gaagcgctat gggctgaata caaaccatcg gatcgtggtg     240
tgcagcgaga atagcttgca gttcttcatg cccgtgttgg gtgccctgtt catcggtgtg     300
gctgtggccc cagctaacga catctacaac gagcgcgagc tgctgaacag catgggcatc     360
agccagccca ccgtcgtatt cgtgagcaag aaagggctgc aaaagatcct caacgtgcaa     420
aagaagctac cgatcataca aaagatcatc atcatggata gcaagaccga ctaccagggc     480
ttccaaagca tgtacacctt cgtgacttcc catttgccac ccggcttcaa cgagtacgac     540
```

```
ttcgtgcccg agagcttcga ccgggacaaa ccatcgccct gatcatgaac agtagtggca    600
gtaccggatt gcccaagggc gtagccctac cgcaccgcac cgcttgtgtc cgattcagtc    660
atgcccgcga ccccatcttc ggcaaccaga tcatccccga caccgctatc ctcagcgtgg    720
tgccatttca ccacggcttc ggcatgttca ccacgctggg ctacttgact ctgcggcttt    780
cgggtcgtgc tcatgtaccg cttcgaggag gagctattct tgcgcagctt gcaagactat    840
aagattcaat ctgccctgct ggtgcccaca ctgtttagct tcttcgctaa gagcactctc    900
atcgacaagt acgacctaag caacttgcac gagatcgcca gcggcggggc gccgctcagc    960
aaggaggtag gtgaggccgt ggccaaacgc ttccacctac caggcatccg acagggctac   1020
ggcctgacag aaacaaccag cgccattctg atcaccccccg aaggggacga caagcctggc   1080
gcagtaggca aggtggtgcc cttcttcgag gctaaggtgg tggacttgga caccggtaag   1140
acactgggtg tgaaccagcg cggcgagctg tgcgtccgtg gccccatgat catgagcggc   1200
tacgttaaca accccgaggc tacaaacgct ctcatcgaca aggacggctg gctgcacagc   1260
ggcgacatcg cctactggga cgaggacgag cacttcttca tcgtggaccg gctgaagtcc   1320
ctgatcaaat acaagggcta ccaggtagcc ccagccgaac tggagagcat cctgctgcaa   1380
caccccaaca tcttcgacgc cggggtcgcc ggcctgcccg acgacgatgc cggcgagctg   1440
cccgccgcag tcgtcgtgct ggaacacggt aaaaccatga ccgagaagga gatcgtggac   1500
tatgtggcca gccaggttac aaccgccaag aagctgcgcg tggtgttgt gttcgtggac   1560
gaggtgccta aaggactgac cggcaagttg gacgcccgca agatccgcga gattctcatt   1620
aaggccaaga agggcggcaa gatcgccgtg                                   1650
```

NUCLEOSIDE MODIFIED mRNA AND USES THEREOF

CROSS-REFERENCE TO RELATED APPLICATIONS

This application claims benefit under 35 U.S.C. § 119(e) of U.S. Provisional Application No. 63/276,868 filed Nov. 8, 2021 the contents of which are incorporated herein by reference in their entirety.

GOVERNMENT SUPPORT

This invention was made with Government support under DK124361-01A1 and DK133404-01 awarded by the National Institute of Health. The Government has certain rights in the invention.

SEQUENCE LISTING

The instant application contains a Sequence Listing which has been submitted electronically in XML format and is hereby incorporated by reference in its entirety. Said XML copy, created on Jan. 6, 2023, is named 701586-191080US-PX_SL.xml and is 106,377 bytes in size.

TECHNICAL FIELD

The technology described herein relates to compositions and methods for engineered mRNAs encoding liver regeneration factors, e.g., engineered sequences and/or comprising modified nucleosides, to treat acute and chronic liver diseases.

BACKGROUND

End stage liver disease (ESLD) is the 12th most common cause of death in the United States. As the result of a chronic damage of the liver tissue, ESLD begins as steatosis and inflammation and progresses to fibrosis and irreversible cirrhosis, and ultimately hepatocellular carcinoma. The current therapies to prevent the progression of the liver disease are designed to eliminate the underlying causes of injury including obesity or hepatitis C virus infection. Although some anti-fibrotic drugs are presently tested in clinical trials, none of them have been approved by the FDA. Liver transplantation remains the only treatment for ESLD, which is critically challenged by the shortage of liver donors. Currently, more than 6,000 liver transplants are performed each year in the United States, yet over 16,000 Americans are on the waiting list for a liver transplant. Given the scarcity of donor organs, hepatocyte transplantation has been attempted in patients with inherited metabolic liver and acute liver failure as treatment and a bridge for liver transplantation. Although the safety of the procedure is well established and the clinical results are encouraging, the application for liver cell therapy is still hampered by poor engraftment of transplanted cells, lack of optimal immunosuppression regiments and most importantly, a limited source of hepatocytes. The use of primary human hepatocytes could become a viable cell therapy for liver diseases only if cell engraftment mechanisms are significantly improved. Alternatively, hepatocytes derived from human induced pluripotent stem cells (hiPSC) could provide an unlimited supply for patient-specific cell replacement therapy. However, generation of iPSC-derived hepatocyte-like cells (HLC) that engraft, defined here as the ability to survive and proliferate, and are mature enough to function in a damaged liver remains a challenge, and a major gap.

Similarly, acute liver injury induced by overdose of acetaminophen (acetyl-para-aminophenol, APAP), the most common pain reliever consumed in the United States, is the leading cause of acute liver failure. Currently the only available treatment is the glutathione precursor N-acetyl cysteine (NAC), whose short window of effectiveness (~10 h) ends while organ toxicity is frequently still asymptomatic, leading to liver failure and necessitating liver transplant. Alternative treatments for acute and chronic liver injuries including cell therapies and or therapies that would harness intrinsic liver repair mechanisms are therefore urgently needed.

SUMMARY

Chronic liver disease, acute liver disease, and acetaminophen (acetyl-para-aminophenol, APAP) overdose are major health burdens, for which improved treatments are needed. Uniquely, the liver is known for its remarkable regenerative ability through proliferation of hepatocytes. Therefore, an alternative strategy would be to promote regeneration of the injured liver tissues through endogenous mechanisms. Another strategy would be to improve primary hepatocyte and iPSC-derived hepatocyte-like cell transplantation and engraftment to take advantage of promising cell therapies.

The technology described herein is directed to compositions and methods of use of engineered liver regenerative factor mRNAs complexed to lipid nanoparticles (mRNA-LNP). This technology harnesses liver regeneration to accelerate intrinsic liver repair and to enhance cell therapy to ultimately treat both acute and chronic liver injuries. This technology also improves engraftment of primary human hepatocytes as well as induced pluripotent stem cell-derived hepatocyte-like cells generated from patient cells for successful cell therapy to treat acute and chronic liver diseases.

In one aspect of any of the embodiments, described herein is a composition comprising at least one engineered liver regenerative factor mRNA, the at least one engineered liver regenerative factor mRNA comprising one or more of:

a) a sequence encoding Growth Hormone (GH) and comprising one or more of the following modifications relative to SEQ ID NO: 1 (e.g., one, two, three, four, or all of the following modifications):
deletion of nucleotides 1-63; T→C modification of nucleotide 69; A→C modification of nucleotide 72; G→C modification of nucleotide 81; G→C modification of nucleotide 84; C→G modification of nucleotide 92; T→C modification of nucleotide 99; T→C modification of nucleotide 102; C→G modification of nucleotide 111; T→G modification of nucleotide 126; A→G modification of nucleotide 129; A→T modification of nucleotide 136; G→C modification of nucleotide 137; T→C modification of nucleotide 138; A→C modification of nucleotide 147; T→C modification of nucleotide 153; T→C modification of nucleotide 157; A→G modification of nucleotide 159; A→C modification of nucleotide 163; G→C modification of nucleotide 165; T→G modification of nucleotide 168; T→C modification of nucleotide 171; T→C modification of nucleotide 180; C→G modification of nucleotide 186; T→C modification of nucleotide 195; T→C modification of nucleotide 198; T→C modification of nucleotide 216; T→C modification of nucleotide 234; A→G modification of nucleotide 237; A→G modification of nucleotide 240; T→C modification of nucleotide 246;

A→C modification of nucleotide 252; A→G modification of nucleotide 258; T→C modification of nucleotide 267; A→C modification of nucleotide 270; C→G modification of nucleotide 297; T→C modification of nucleotide 300; A→C modification of nucleotide 306; T→C modification of nucleotide 312; T→C modification of nucleotide 315; G→C modification of nucleotide 318; A→C modification of nucleotide 321; A→C modification of nucleotide 331; G→C modification of nucleotide 333; A→G modification of nucleotide 339; A→C modification of nucleotide 342; A→G modification of nucleotide 345; A→G modification of nucleotide 351; A→G modification of nucleotide 360; C→G modification of nucleotide 369; C→G modification of nucleotide 387; G→C modification of nucleotide 396; C→G modification of nucleotide 420; A→C modification of nucleotide 421; G→C modification of nucleotide 423; A→T modification of nucleotide 424; G→C modification of nucleotide 425; T→C modification of nucleotide 426; C→G modification of nucleotide 429; A→T modification of nucleotide 439; G→C modification of nucleotide 440; T→C modification of nucleotide 459; A→T modification of nucleotide 463; G→C modification of nucleotide 464; C→G modification of nucleotide 471; T→C modification of nucleotide 474; C→G modification of nucleotide 480; A→G modification of nucleotide 483; A→G modification of nucleotide 492; A→G modification of nucleotide 498; A→G modification of nucleotide 507; G→C modification of nucleotide 510; G→C modification of nucleotide 519; A→C modification of nucleotide 520; G→C modification of nucleotide 522; A→G modification of nucleotide 528; T→C modification of nucleotide 531; A→T modification of nucleotide 535; G→C modification of nucleotide 536; G→C modification of nucleotide 543; T→C modification of nucleotide 546; G→C modification of nucleotide 549; A→T modification of nucleotide 571; G→C modification of nucleotide 572; A→C modification of nucleotide 585; A→C modification of nucleotide 591; T→C modification of nucleotide 600; A→C modification of nucleotide 606; A→G modification of nucleotide 609; C→G modification of nucleotide 612; G→C modification of nucleotide 624; C→G modification of nucleotide 630; A→C modification of nucleotide 640; G→C modification of nucleotide 642; C→G modification of nucleotide 660; A→C modification of nucleotide 666; T→C modification of nucleotide 693; A→T modification of nucleotide 703; G→C modification of nucleotide 704; T→C modification of nucleotide 708; and deletion of nucleotides 717-823;

b) a sequence encoding Epidermal Growth Factor (EGF) and comprising one or more of the following modifications relative to SEQ ID NO: 2 (e.g., one, two, three, four, or all of the following modifications):

deletion of nucleotides 1-453; C→G modification of nucleotide 462; T→C modification of nucleotide 465; T→G modification of nucleotide 468; T→C modification of nucleotide 474; T→C modification of nucleotide 478; A→C modification of nucleotide 483; A→G modification of nucleotide 486; T→G modification of nucleotide 489; A→C modification of nucleotide 492; A→G modification of nucleotide 495; T→C modification of nucleotide 498; A→T modification of nucleotide 499; G→C modification of nucleotide 500; T→C modification of nucleotide 501; T→C modification of nucleotide 504; T→G modification of nucleotide 507; A→T modification of nucleotide 508; G→C modification of nucleotide 509; T→C modification of nucleotide 510; G→C modification of nucleotide 513; A→C modification of nucleotide 516; A→C modification of nucleotide 519; G→C modification of nucleotide 522; A→T modification of nucleotide 532; G→C modification of nucleotide 533; T→C modification of nucleotide 537; T→C modification of nucleotide 540; A→G modification of nucleotide 543; T→C modification of nucleotide 546; T→C modification of nucleotide 549; C→G modification of nucleotide 552; A→C modification of nucleotide 555; A→C modification of nucleotide 558; T→C modification of nucleotide 561; G→C modification of nucleotide 564; T→C modification of nucleotide 567; T→C modification of nucleotide 570; T→C modification of nucleotide 573; T→C modification of nucleotide 576; T→C modification of nucleotide 582; T→C modification of nucleotide 585; A→C modification of nucleotide 588; T→C modification of nucleotide 595; A→G modification of nucleotide 597; T→C modification of nucleotide 600; T→C modification of nucleotide 609; A→C modification of nucleotide 612; T→C modification of nucleotide 615; A→T modification of nucleotide 616; G→C modification of nucleotide 617; T→C modification of nucleotide 618; T→C modification of nucleotide 624; A→C modification of nucleotide 625; G→C modification of nucleotide 627; T→C modification of nucleotide 630; A→C modification of nucleotide 636; A→G modification of nucleotide 639; A→C modification of nucleotide 642; T→C modification of nucleotide 648; T→C modification of nucleotide 651; A→G modification of nucleotide 657; T→C modification of nucleotide 658; T→C modification of nucleotide 669; T→C modification of nucleotide 672; T→C modification of nucleotide 675; C→G modification of nucleotide 678; A→C modification of nucleotide 681; T→C modification of nucleotide 693; T→C modification of nucleotide 696; T→C modification of nucleotide 699; T→C modification of nucleotide 702; T→C modification of nucleotide 705; A→G modification of nucleotide 711; A→C modification of nucleotide 712; A→C modification of nucleotide 714; T→C modification of nucleotide 720; T→C modification of nucleotide 729; T→C modification of nucleotide 730; A→G modification of nucleotide 732; A→G modification of nucleotide 735; A→C modification of nucleotide 736; A→C modification of nucleotide 738; A→G modification of nucleotide 741; T→G modification of nucleotide 744; T→C modification of nucleotide 745; A→G modification of nucleotide 750; A→C modification of nucleotide 751; A→C modification of nucleotide 753; T→G modification of nucleotide 756; T→C modification of nucleotide 759; T→C modification of nucleotide 765; G→C modification of nucleotide 768; A→C modification of nucleotide 771; A→C modification of nucleotide 772; G→C modification of nucleotide 774; A→G modification of nucleotide 777; A→C modification of nucleotide 781; A→C modification of nucleotide 783; A→G modification of nucleotide 786; T→C modification of nucleotide 789; T→C modification of nucleotide 792; A→C modification of nucleotide 795; A→G modification of nucleotide 801; T→C modification of nucleotide 804; T→G modification of nucleotide 807; T→C modification of nucleotide 810; A→C modification of nucleotide 813; A→C modification of nucleotide 819; A→C modification of nucleotide 822; T→C modification of nucleotide 825; A→C modification of nucleotide 831; T→C modification of nucleotide 834; A→G modification of nucleotide 837; A→G modification of nucleotide 840; T→G modification of nucleotide 843; T→C modification of nucleotide 846; A→C modification of nucleotide 852; T→C modification of nucleotide 855; A→G modification of nucleotide 858; A→G modification of nucleotide 864; A→C modification of nucleotide 867; T→C modification of nucleotide 873; A→C modification of nucleotide 876; A→G modification of nucleotide 879; A→C modification of nucleotide 882; T→C modification of nucleotide 885; A→G modification of nucleotide 891; A→C modification of nucleotide 894; T→C modification of nucleotide 897; T→C modification of nucleotide 900; T→C modification of nucleotide 909; T→G modification of nucleotide 912; T→C modification of nucleotide 913; A→G modification of nucleotide 915; A→T modification of nucleotide 916; G→C modification of nucleotide 917; T→C modification of nucleotide 918; T→C modification of nucleotide 921; T→C modification of nucleotide 922; A→G modification of nucleotide 924; A→G modification of nucleotide 927; T→C modification of nucleotide 930; T→C modification of nucleotide 933; A→C modification of nucleotide 936; T→C modification of nucleotide 939; A→G modification of nucleotide 942; A→C modification of nucleotide 945; T→G modification of nucleotide 948; T→C modification of nucleotide 951; A→C modification of nucleotide 954; A→G modification of nucleotide 957; A→G modification of nucleotide 960; A→C modification of nucleotide 961; T→C modification of nucleotide 966; A→C modification of nucleotide 972; T→C modification of nucleotide 978; A→C modification of nucleotide 981; T→C modification of nucleotide 990; A→C modification of nucleotide 993; A→T modification of nucleotide 994; G→C modification of nucleotide 995; T→G modification of nucleotide 999; T→C modification of nucleotide 1002; A→C modification of nucleotide 1003; A→C modification of nucleotide 1005; A→C modification of nucleotide 1008; T→C modification of nucleotide 1011; C→G modification of nucleotide 1014; T→C modification of nucleotide 1017; T→C modification of nucleotide 1020; A→C modification of nucleotide 1026; T→C modification of nucleotide 1035; T→C modification of nucleotide 1039; A→C modification of nucleotide 1047; A→C modification of nucleotide 1050; A→G modification of nucleotide 1056; A→C modification of nucleotide 1059; A→C modification of nucleotide 1062; T→C modification of nucleotide 1065; A→C modification of nucleotide 1071; T→C modification of nucleotide 1072; T→C modification of nucleotide 1077; T→G modification of nucleotide 1083; T→C modification of nucleotide 1086; G→C modification of nucleotide 1092; T→C modification of nucleotide 1098; T→C modification of nucleotide 1104; A→C modification of nucleotide 1114; A→C modification of nucleotide 1116; A→G modification of nucleotide 1119; A→C modification of nucleotide 1122; A→T modification of nucleotide 1123; G→C modification of nucleotide 1124; T→C modification of nucleotide 1128; T→C modification of nucleotide 1131; T→G modification of nucleotide 1134; T→C modification of nucleotide 1137; T→C modification of nucleotide 1146; T→C modification of nucleotide 1149; T→C modification of nucleotide 1152; T→C modification of nucleotide 1155; A→C modification of nucleotide 1158; T→C modification of nucleotide 1161; T→C modification of nucleotide 1164; C→G modification of nucleotide 1167; T→C modification of nucleotide 1173; A→T modification of nucleotide 1174; G→C modification of nucleotide 1175; T→C modification of nucleotide 1176; A→G modification of nucleotide 1179; T→C modification of nucleotide 1182; A→C modification of nucleotide 1185; A→C modification of nucleotide 1188; T→C modification of nucleotide 1194; T→C modification of nucleotide 1197; T→C modification of nucleotide 1198; T→C modification of nucleotide 1203; A→C modification of nucleotide 1206; T→G modification of nucleotide 1215; T→C modification of nucleotide 1218; T→C modification of nucleotide 1221; T→C modification of nucleotide 1227; T→C modification of nucleotide 1236; A→C modification of nucleotide 1239; A→C modification of nucleotide 1242; A→G modification of nucleotide 1248; A→C modification of nucleotide 1257; T→C modification of nucleotide 1260; A→C modification of nucleotide 1266; A→G modification of nucleotide 1275; T→C modification of nucleotide 1281; A→C modification of nucleotide 1284; T→G modification of nucleotide 1296; A→C modification of nucleotide 1297; A→C modification of nucleotide 1299; T→C modification of nucleotide 1302; C→G modification of nucleotide 1308; T→C modification of nucleotide 1311; A→C modification of nucleotide 1314; 1→C modification of nucleotide 1317; T→C modification of nucleotide 1320; A→G modification of nucleotide 1323; A→C modification of nucleotide 1326; T→G modification of nucleotide 1329; T→C modification of nucleotide 1332; A→G modification of nucleotide 1335; A→G modification of nucleotide 1341; A→G modification of nucleotide 1344; T→C modification of nucleotide 1350; A→C modification of nucleotide 1353; T→G modification of nucleotide 1356; A→C modification of nucleotide 1359; A→G modification of nucleotide 1362; A→C modification of nucleotide 1371; A→G modification of nucleotide 1374; T→C modification of nucleotide 1377; T→C modification of nucleotide 1383; T→C modification of nucleotide 1392; A→G modification of nucleotide 1401; T→G modification of nucleotide 1404; A→G modification of nucleotide 1410; A→C modification of nucleotide 1411; A→C modification of nucleotide 1414; G→C modification of nucleotide 1416; A→G modification of nucleotide 1419; A→C modification of nucleotide 1422; A→T modification of nucleotide 1429; G→C modification of nucleotide 1430; A→T modification of nucleotide 1432; G→C modification of nucleotide 1433; T→C modification of nucleotide 1437; T→C modification of nucleotide 1443; G→C modification of nucleotide 1446; A→G modification of nucleotide 1449; C→G modification of nucleotide 1455; A→C modification of nucleotide 1461; T→C modification of nucleotide 1465; T→C modification of nucleotide 1476; A→C modification of nucleotide 1479; A→C modification of nucleotide 1485; A→G modification of nucleotide 1494; A→T modification of nucleotide 1495; G→C modification of nucleotide 1496; T→C modification of nucleotide 1497; A→C modification of nucleotide 1500; G→C modification of nucleotide 1506; T→C modification of nucleotide 1515; A→G modification of nucleotide 1518; T→C modification of nucleotide 1521; T→G modification of nucleotide 1524; T→C modification of nucleotide 1527; A→G modification of nucleotide 1530; T→C modification of nucleotide 1536; T→C modification of nucleotide 1539; T→C modification of nucleotide 1545; T→C modification of nucleotide 1548; T→C modification of nucleotide 1554; T→C modification of nucleotide 1557; T→G modification of nucleotide 1560; G→C modification of nucleotide 1563; T→C modification of nucleotide 1566; A→G modification of nucleotide 1569; T→C modification of nucleotide 1578; A→C modification of nucleotide 1581; T→C modification of nucleotide 1587; G→C modification of nucleotide 1596; T→C modification of nucleotide 1602; A→G modification of nucleotide 1605; A→C modification of nucleotide 1608; T→C modification of nucleotide 1611; T→G modification of nucleotide 1614; T→G modification of nucleotide 1620; T→C modification of nucleotide 1623; T→C modification of nucleotide 1626; G→C modification of nucleotide 1629; A→G modification of nucleotide 1632; A→G modification of nucleotide 1635; T→C modification of nucleotide 1638; T→C modification of nucleotide 1641; A→G modification of nucleotide 1644; T→G modification of nucleotide 1647; T→G modification of nucleotide 1650; T→C modification of nucleotide 1656; A→C modification of nucleotide 1659; T→C modification of nucleotide 1665; T→C modification of nucleotide 1671; A→G modification of nucleotide 1674; A→T modification of nucleotide 1678; G→C modification of nucleotide 1679; T→C modification of nucleotide 1683; T→C modification of nucleotide 1689; T→G modification of nucleotide 1692; A→C modification of nucleotide 1698; A→C modification of nucleotide 1701; A→G modification of nucleotide 1704; T→C modification of nucleotide 1707; T→C modification of nucleotide 1711; A→G modification of nucleotide 1713; T→C modification of nucleotide 1716; T→C modification of nucleotide 1722; T→C modification of nucleotide 1725; A→G modification of nucleotide 1728; A→C modification of nucleotide 1734; T→G modification of nucleotide 1740; A→C modification of nucleotide 1744; A→C modification of nucleotide 1746; T→C modification of nucleotide 1749; G→C modification of nucleotide 1752; A→G modification of nucleotide 1755; A→C modification of nucleotide 1758; T→C modification of nucleotide 1761; A→T modification of nucleotide 1762; G→C modification of nucleotide 1763; T→C modification of nucleotide 1767; T→C modification of nucleotide 1770; A→C modification of nucleotide 1776; T→C modification of nucleotide 1782; T→C modification of nucleotide 1785; T→C modification of nucleotide 1788; A→C modification of nucleotide 1791; T→C modification of nucleotide 1794; A→T modification of nucleotide 1795; G→C modification of nucleotide 1796; C→G modification of nucleotide 1803; T→G modification of nucleotide 1809; T→C modification of nucleotide 1812; T→G modification of nucleotide 1815; A→T modification of nucleotide 1816; G→C modification of nucleotide 1817; A→C modification of nucleotide 1821; A→G modification of nucleotide 1824; A→G modification of nucleotide 1833; T→C modification of nucleotide 1836; T→C modification of nucleotide 1839; T→C modification of nucleotide 1845; T→C modification of nucleotide 1848; G→C modification of nucleotide 1851; T→C modification of nucleotide 1854; A→G modification of nucleotide 1860; A→G modification of nucleotide 1863; T→C modification of nucleotide 1869; A→G modification of nucleotide 1872; A→G modification of nucleotide 1875; G→C modification of nucleotide 1877; T→C modification of nucleotide 1881; A→C modification of nucleotide 1884; T→C modification of nucleotide 1887; A→C modification of nucleotide 1890; A→C modification of nucleotide 1893; A→C modification of nucleotide 1896; A→G modification of nucleotide 1899; A→C modification of nucleotide 1902; T→C modification of nucleotide 1905; T→C modification of nucleotide 1906; T→C modification of nucleotide 1914; T→C modification of nucleotide 1920; T→C modification of nucleotide 1923; A→G modification of nucleotide 1926; T→C modification of nucleotide 1929; T→C modification of nucleotide 1932; A→C modification of nucleotide 1935; T→C modification of nucleotide 1944; T→C modification of nucleotide 1947; T→C modification of nucleotide 1950; A→C modification of nucleotide 1953; A→C modification of nucleotide 1956; T→C modification of nucleotide 1962; A→C modification of nucleotide 1965; T→C modification of nucleotide 1968; C→G modification of nucleotide 1974; A→T modification of nucleotide 1975; G→C modification of nucleotide 1976; A→C modification of nucleotide 1989; T→G modification of nucleotide 1995; T→C modification of nucleotide 1998; A→G modification of nucleotide 2004; T→C modification of nucleotide 2007; T→C modification of nucleotide 2010; T→C modification of nucleotide 2016; A→G modification of nucleotide 2022; T→C modification of nucleotide 2025; A→C modification of nucleotide 2031; T→C modification of nucleotide 2037; T→C modification of nucleotide 2043; A→C modification of nucleotide 2046; A→C modification of nucleotide 2061; A→C modification of nucleotide 2065; A→C modification of nucleotide 2067; T→C modification of nucleotide 2070; T→C modification of nucleotide 2073; T→C modification of nucleotide 2079; T→C modification of nucleotide 2082; A→C modification of nucleotide 2091; A→G modification of nucleotide 2094; A→C modification of nucleotide 2095; G→C modification of nucleotide 2097; T→G modification of nucleotide 2100; T→C modification of nucleotide 2103; A→G modification of nucleotide 2109; A→C modification of nucleotide 2112; A→G modification of nucleotide 2115; T→C modification of nucleotide 2118; A→C modification of nucleotide 2124; A→G modification of nucleotide 2127; T→C modification of nucleotide 2130; T→G modification of nucleotide 2133; T→C modification of nucleotide 2136; T→C modification of nucleotide 2148; T→C modification of nucleotide 2154; A→C modification of nucleotide 2155; A→C modification of nucleotide 2157; T→C modification of nucleotide 2163; A→C modification of nucleotide 2169; A→C modification of nucleotide 2173; A→C modification of nucleotide 2175; G→C modification of nucleotide 2178; A→G modification of nucleotide 2181; T→C modification of nucleotide 2184; T→C modification of nucleotide 2190; A→C modification of nucleotide 2193; A→C modification of nucleotide 2194; G→C modification of nucleotide 2196; A→T modification of nucleotide 2197; G→C modification of nucleotide 2198; T→C modification of nucleotide 2199; T→C modification of nucleotide 2202; T→C modification of nucleotide 2203; A→G modification of nucleotide 2205; T→C modification of nucleotide 2208; G→C modification of nucleotide 2211; A→G modification of nucleotide 2214; T→G modification of nucleotide 2217; A→G modification of nucleotide 2223; A→C modification of nucleotide 2226; T→C modification of nucleotide 2232; T→C modification of nucleotide 2247; A→G modification of nucleotide 2250; A→C modification of nucleotide 2253; A→C modification of nucleotide 2256; A→C modification of nucleotide 2259; T→C modification of nucleotide 2262; T→C modification of nucleotide 2265; T→G modification of nucleotide 2268; T→C modification of nucleotide 2271; A→C modification of nucleotide 2274; A→C modification of nucleotide 2284; A→C modification of nucleotide 2286; T→C modification of nucleotide 2287; A→G modification of nucleotide 2289; T→C modification of nucleotide 2298; T→C modification of nucleotide 2301; A→C modification of nucleotide 2304; G→C modification of nucleotide 2307; T→C modification of nucleotide 2310; T→C modification of nucleotide 2313; A→C modification of nucleotide 2316; A→C modification of nucleotide 2319; T→C modification of nucleotide 2322; A→G modification of nucleotide 2325; A→T modification of nucleotide 2326; G→C modification of nucleotide 2327; T→C modification of nucleotide 2328; T→C modification of nucleotide 2331; C→G modification of nucleotide 2337; A→G modification of nucleotide 2340; T→G modification of nucleotide 2346; T→C modification of nucleotide 2352; T→G modification of nucleotide 2358; A→C modification of nucleotide 2361; T→A modification of nucleotide 2365; G→C modification of nucleotide 2366; T→C modification of nucleotide 2370; T→C modification of nucleotide 2373; A→G modification of nucleotide 2376; A→T modification of nucleotide 2386; G→C modification of nucleotide 2387; T→C modification of nucleotide 2388; A→C modification of nucleotide 2391; A→C modification of nucleotide 2394; G→C modification of nucleotide 2397; T→C modification of nucleotide 2400; T→C modification of nucleotide 2407; A→G modification of nucleotide 2409; T→C modification of nucleotide 2412; T→C modification of nucleotide 2419; T→C modification of nucleotide 2433; T→C modification of nucleotide 2445; T→C modification of nucleotide 2451; A→G modification of nucleotide 2454; T→C modification of nucleotide 2463; T→C modification of nucleotide 2469; T→C modification of nucleotide 2472; A→C modification of nucleotide 2475; A→G modification of nucleotide 2478; A→C modification of nucleotide 2484; A→C modification of nucleotide 2485; A→C modification of nucleotide 2487; T→G modification of nucleotide 2490; T→C modification of nucleotide 2499; T→C modification of nucleotide 2502; A→G modification of nucleotide 2505; T→C modification of nucleotide 2508; A→C modification of nucleotide 2514; T→C modification of nucleotide 2517; T→C modification of nucleotide 2520; A→G modification of nucleotide 2523; A→C modification of nucleotide 2526; T→C modification of nucleotide 2532; T→C modification of nucleotide 2538; T→C modification of nucleotide 2541; A→C modification of nucleotide 2553; T→C modification of nucleotide 2556; T→C modification of nucleotide 2562; A→C modification of nucleotide 2568; A→C modification of nucleotide 2571; A→G modification of nucleotide 2574; G→C modification of nucleotide 2577; A→C modification of nucleotide 2578; A→C modification of nucleotide 2580; A→G modification of nucleotide 2583; A→C modification of nucleotide 2590; G→C modification of nucleotide 2592; T→C modification of nucleotide 2595; A→G modification of nucleotide 2601; T→C modification of nucleotide 2604; A→C modification of nucleotide 2605; A→C modification of nucleotide 2607; A→G modification of nucleotide 2610; T→C modification of nucleotide 2613; A→C modification of nucleotide 2616; A→G modification of nucleotide 2619; A→T modification of nucleotide 2623; G→C modification of nucleotide 2624; A→C modification of nucleotide 2640; A→C modification of nucleotide 2643; T→G modification of nucleotide 2649; T→G modification of nucleotide 2655; T→C modification of nucleotide 2658; A→C modification of nucleotide 2661; T→C modification of nucleotide 2662; A→C modification of nucleotide 2667; A→G modification of nucleotide 2670; A→C modification of nucleotide 2673; A→C modification of nucleotide 2676; A→C modification of nucleotide 2679; T→C modification of nucleotide 2682; T→C modification of nucleotide 2689; A→G modification of nucleotide 2691; T→C modification of nucleotide 2694; A→G modification of nucleotide 2697; A→C modification of nucleotide 2703; T→C modification of nucleotide 2709; A→G modification of nucleotide 2712; T→C modification of nucleotide 2715; T→C modification of nucleotide 2718; A→G modification of nucleotide 2724; A→C modification of nucleotide 2728; G→C modification of nucleotide 2730; T→G modification of nucleotide 2733; A→C modification of nucleotide 2736; T→C modification of nucleotide 2739; T→C modification of nucleotide 2742; T→C modification of nucleotide 2748; G→C modification of nucleotide 2751; T→C modification of nucleotide 2754; T→C modification of nucleotide 2757; A→G modification of nucleotide 2760; T→C modification of nucleotide 2763; T→C modification of nucleotide 2766; A→G modification of nucleotide 2772; A→C modification of nucleotide 2778; T→C modification of nucleotide 2781; G→C modification of nucleotide 2784; A→G modification of nucleotide 2787; G→C modification of nucleotide 2790; T→C modification of nucleotide 2793; T→C modification of nucleotide 2799; T→C modification of nucleotide 2805; T→C modification of nucleotide 2808; T→C modification of nucleotide 2811; T→C modification of nucleotide 2818; A→C modification of nucleotide 2823; T→C modification of nucleotide 2826; T→C modification of nucleotide 2829; A→G modification of nucleotide 2832; T→G modification of nucleotide 2832; T→G modification of nucleotide 2835; T→C modification of nucleotide 2838; A→G modification of nucleotide 2841; A→G modification of nucleotide 2850; A→G modification of nucleotide 2853; A→C modification of nucleotide 2856; A→C modification of nucleotide 2859; T→C modification of nucleotide 2860; T→C modification of nucleotide 2869; T→C modification of nucleotide 2880; A→C modification of nucleotide 2881; A→C modification of nucleotide 2883; A→C modification of nucleotide 2889; A→G modification of nucleotide 2892; T→C modification of nucleotide 2895; T→C modification of nucleotide 2901; A→C modification of nucleotide 2904; A→G modification of nucleotide 2907; T→C modification of nucleotide 2910; A→G modification of nucleotide 2913; A→G modification of nucleotide 2922; T→C modification of nucleotide 2928; A→G modification of nucleotide 2931; A→C modification of nucleotide 2943; T→C modification of nucleotide 2946; A→G modification of nucleotide 2949; T→C modification of nucleotide 2952; T→C modification of nucleotide 2958; T→C modification of nucleotide 2961; T→C modification of nucleotide 2964; A→C modification of nucleotide 2970; A→T modification of nucleotide 2974; G→C modification of nucleotide 2975; T→C modification of nucleotide 2982; T→C modification of nucleotide 2985; G→C modification of nucleotide 2988; T→C modification of nucleotide 2991; T→C modification of nucleotide 2994; A→C modification of nucleotide 2997; A→C modification of nucleotide 3003; T→C modification of nucleotide 3009; A→C modification of nucleotide 3015; T→C modification of nucleotide 3018; T→C modification of nucleotide 3024; T→C modification of nucleotide 3025; A→G modification of nucleotide 3030; A→C modification of nucleotide 3033; T→C modification of nucleotide 3036; T→C modification of nucleotide 3039; G→C modification of nucleotide 3042; T→C modification of nucleotide 3045; A→C modification of nucleotide 3048; A→G modification of nucleotide 3051; A→G modification of nucleotide 3054; T→C modification of nucleotide 3057; T→C modification of nucleotide 3060; T→C modification of nucleotide 3063; A→C modification of nucleotide 3066; T→C modification of nucleotide 3069; A→G modification of nucleotide 3072; T→C modification of nucleotide 3075; T→C modification of nucleotide 3084; C→G modification of nucleotide 3087; A→C modification of nucleotide 3090; T→C modification of nucleotide 3102; A→G modification of nucleotide 3129; T→C modification of nucleotide 3132; T→C modification of nucleotide 3135; T→C modification of nucleotide 3138; C→G modification of nucleotide 3141; G→C modification of nucleotide 3147; A→C modification of nucleotide 3153; A→G modification of nucleotide 3156; A→G modification of nucleotide 3165; A→C modification of nucleotide 3168; T→C modification of nucleotide 3171; G→C modification of nucleotide 3174; T→C modification of nucleotide 3177; T→C modification of nucleotide 3183; T→G modification of nucleotide 3186; T→C modification of nucleotide 3189; T→C modification of nucleotide 3192; T→C modification of nucleotide 3195; A→G modification of nucleotide 3204; G→C modification of nucleotide 3210; A→T modification of nucleotide 3212; A→T modification of nucleotide 3217; G→C modification of nucleotide 3218; T→C modification of nucleotide 3222; A→C modification of nucleotide 3225; T→C modification of nucleotide 3231; A→T modification of nucleotide 3235; G→C modification of nucleotide 3236; A→C modification of nucleotide 3243; T→C modification of nucleotide 3246; A→C modification of nucleotide 3249; A→C modification of nucleotide 3255; T→C modification of nucleotide 3261; T→C modification of nucleotide 3273; T→C modification of nucleotide 3276; A→C modification of nucleotide 3279; T→C modification of nucleotide 3288; A→G modification of nucleotide 3291; A→C modification of nucleotide 3294; A→C modification of nucleotide 3297; T→C modification of nucleotide 3303; T→C modification of nucleotide 3309; T→C modification of nucleotide 3315; T→C modification of nucleotide 3318; A→C modification of nucleotide 3321; T→C modification of nucleotide 3327; C→G modification of nucleotide 3333; A→C modification of nucleotide 3334; G→C modification of nucleotide 3336; A→G modification of nucleotide 3339; T→C modification of nucleotide 3342; T→C modification of nucleotide 3354; A→G modification of nucleotide 3360; A→C modification of nucleotide 3361; A→C modification of nucleotide 3363; T→C modification of nucleotide 3366; T→A modification of nucleotide 3367; G→C modification of nucleotide 3368; T→C modification of nucleotide 3369; T→C modification of nucleotide 3375; A→G modification of nucleotide 3378; T→C modification of nucleotide 3381; T→C modification of nucleotide 3396; G→C modification of nucleotide 3399; C→G modification of nucleotide 3408; T→C modification of nucleotide 3411; T→C modification of nucleotide 3414; T→C modification of nucleotide 3417; T→C modification of nucleotide 3429; T→C modification of nucleotide 3432; A→G modification of nucleotide 3435; A→C modification of nucleotide 3438; T→C modification of nucleotide 3439; T→C modification of nucleotide 3450; A→C modification of nucleotide 3453; T→C modification of nucleotide 3462; T→G modification of nucleotide 3465; T→G modification of nucleotide 3468; G→C modification of nucleotide 3480; A→G modification of nucleotide 3486; T→C modification of nucleotide 3489; A→C modification of nucleotide 3498; A→G modification of nucleotide 3516; T→C modification of nucleotide 3528; G→C modification of nucleotide 3537; C→G modification of nucleotide 3552; T→C modification of nucleotide 3564; C→G modification of nucleotide 3567; T→G modification of nucleotide 3582; C→G modification of nucleotide 3585; C→G modification of nucleotide 3584; C→G modification of nucleotide 3594; C→G modification of nucleotide 3597; A→T modification of nucleotide 3612; G→C modification of nucleotide 3602; G→C modification of nucleotide 3612; A→C modification of nucleotide 3625; G→C modification of nucleotide 3627; T→C modification of nucleotide 3630; A→G modification of nucleotide 3642; G→C modification of nucleotide 3645; A→G modification of nucleotide 3648; A→C modification of nucleotide 3654; T→C modification of nucleotide 3660; T→C modification of nucleotide 3663; T→C modification of nucleotide 3668; G→C modification of nucleotide 3675; A→T modification of nucleotide 3676; G→C modification of nucleotide 3677; A→C modification of nucleotide 3679; A→C modification of nucleotide 3681; T→C modification of nucleotide 3684; A→C modification of nucleotide 3688; G→C modification of nucleotide 3690; A→T modification of nucleotide 3691; G→C modification of nucleotide 3692; T→C modification of nucleotide 3693; A→C modification of nucleotide 3697; G→C modification of nucleotide 3699; T→C modification of nucleotide 3702; T→C modification of nucleotide 3705; T→C modification of nucleotide 3711; T→C modification of nucleotide 3717; G→C modification of nucleotide 3720; T→C modification of nucleotide 3729; T→C modification of nucleotide 3735; A→G modification of nucleotide 3738; T→C modification of nucleotide 3741; T→C modification of nucleotide 3747; T→G modification of nucleotide 3752; A→C modification of nucleotide 3756; A→G modification of nucleotide 3759; A→G modification of nucleotide 3762; A→G modification of nucleotide 3769; C→G modification of nucleotide 3774; T→C modification of nucleotide 3780; G→C modification of nucleotide 3783; T→C modification of nucleotide 3786; A→G modification of nucleotide 3789; A→C modification of nucleotide 3792; T→C modification of nucleotide 3798; T→C modification of nucleotide 3801; T→C modification of nucleotide 3807; A→C modification of nucleotide 3816; A→C modification of nucleotide 3819; T→C modification of nucleotide 3822; G→C modification of nucleotide 3825; A→C modification of nucleotide 3828; A→G modification of nucleotide 3834; A→C modification of nucleotide 3837; T→C modification of nucleotide 3840; A→C modification of nucleotide 3843; A→C modification of nucleotide 3847; G→C modification of nucleotide 3849; T→C modification of nucleotide 3862; A→G modification of nucleotide 3864; T→C modification of nucleotide 3867; A→C modification of nucleotide 3870; A→C modification of nucleotide 3879; A→G modification of nucleotide 3885; T→C modification of nucleotide 3897; A→C modification of nucleotide 3900; A→G modification of nucleotide 3903; A→T modification of nucleotide 3907; G→C modification of nucleotide 3908; T→C modification of nucleotide 3909; T→C modification of nucleotide 3912; T→C modification of nucleotide 3924; A→G modification of nucleotide 3933; A→G modification of nucleotide 3942; A→T modification of nucleotide 3943; G→C modification of nucleotide 3944; T→C modification of nucleotide 3948; T→C modification of nucleotide 3951; T→C modification of nucleotide 3963; G→C modification of nucleotide 3966; A→C modification of nucleotide 3969; T→G modification of nucleotide 3978; A→G modification of nucleotide 3981; G→C modification of nucleotide 3984; T→C modification of nucleotide 3987; C→G modification of nucleotide 3990; T→C modification of nucleotide 4002; T→C modification of nucleotide 4005; C→G modification of nucleotide 4008; A→G modification of nucleotide 4011; A→C modification of nucleotide 4014; T→C modification of nucleotide 4017; A→C modification of nucleotide 4023; T→C modification of nucleotide 4024; A→G modification of nucleotide 4026; A→G modification of nucleotide 4032; A→G modification of nucleotide 4035; A→C modification of nucleotide 4036; G→C modification of nucleotide 4038; A→C modification of nucleotide 4050; A→C modification of nucleotide 4053; A→G modification of nucleotide 4059; T→C modification of nucleotide 4071; and deletion of nucleotides 4076-6388;

c) a sequence encoding Hepatocyte Growth Factor (HGF) and comprising one or more of the following modifications relative to SEQ ID NO: 3 (e.g., one, two, three, four, or all of the following modifications):

deletion of nucleotides 1-76; A→G modification of nucleotide 91; C→G modification of nucleotide 94; T→C modification of nucleotide 118; C→G modification of nucleotide 121; C→G modification of nucleotide 124; T→C modification of nucleotide 130; C→G modification of nucleotide 133; C→G modification of nucleotide 136; C→G modification of nucleotide 142; T→C modification of nucleotide 160; A→C modification of nucleotide 163; A→C modification of nucleotide 169; A→G modification of nucleotide 172; A→C modification of nucleotide 173; G→C modification of nucleotide 175; A→G modification of nucleotide 178; A→C modification of nucleotide 179; A→C modification of nucleotide 181; A→C modification of nucleotide 182; A→C modification of nucleotide 184; T→C modification of nucleotide 187; A→C modification of nucleotide 190; T→C modification of nucleotide 193; T→C modification of nucleotide 196; A→G modification of nucleotide 199; A→G modification of nucleotide 205; A→G modification of nucleotide 208; A→C modification of nucleotide 211; A→C modification of nucleotide 214; T→C modification of nucleotide 220; A→G modification of nucleotide 226; A→G modification of nucleotide 232; A→C modification of nucleotide 235; T→C modification of nucleotide 238; A→C modification of nucleotide 241; A→C modification of nucleotide 244; A→C modification of nucleotide 253; A→G modification of nucleotide 256; A→G modification of nucleotide 262; A→G modification of nucleotide 265; T→C modification of nucleotide 271; T→C modification of nucleotide 274; A→C modification of nucleotide 277; A→G modification of nucleotide 283; T→C modification of nucleotide 286; T→C modification of nucleotide 289; T→C modification of nucleotide 292; A→C modification of nucleotide 293; A→C modification of nucleotide 295; T→C modification of nucleotide 298; T→C modification of nucleotide 301; A→C modification of nucleotide 302; G→C modification of nucleotide 304; T→C modification of nucleotide 307; A→G modification of nucleotide 310; A→C modification of nucleotide 313; T→G modification of nucleotide 316; A→C modification of nucleotide 319; T→C modification of nucleotide 325; T→C modification of nucleotide 334; T→C modification of nucleotide 337; T→G modification of nucleotide 340; T→C modification of nucleotide 343; T→C modification of nucleotide 346; A→G modification of nucleotide 349; A→C modification of nucleotide 352; A→C modification of nucleotide 353; A→C modification of nucleotide 355; A→G modification of nucleotide 358; A→G modification of nucleotide 361; C→G modification of nucleotide 367; T→C modification of nucleotide 382; A→T modification of nucleotide 383; G→C modification of nucleotide 384; A→C modification of nucleotide 391; A→T modification of nucleotide 392; G→C modification of nucleotide 393; T→C modification of nucleotide 394; A→C modification of nucleotide 397; A→G modification of nucleotide 403; A→G modification of nucleotide 406; A→G modification of nucleotide 409; T→C modification of nucleotide 412; T→C modification of nucleotide 418; A→G modification of nucleotide 421; T→C modification of nucleotide 424; C→G modification of nucleotide 430; T→C modification of nucleotide 433; A→G modification of nucleotide 436; A→G modification of nucleotide 442; T→C modification of nucleotide 451; A→C modification of nucleotide 452; A→C modification of nucleotide 454; T→C modification of nucleotide 466; T→C modification of nucleotide 469; A→G modification of nucleotide 472; A→C modification of nucleotide 475; A→T modification of nucleotide 479; G→C modification of nucleotide 480; A→C modification of nucleotide 490; A→C modification of nucleotide 493; A→G modification of nucleotide 496; T→C modification of nucleotide 499; T→C modification of nucleotide 505; A→T modification of nucleotide 509; G→C modification of nucleotide 510; T→C modification of nucleotide 511; A→G modification of nucleotide 520; T→C modification of nucleotide 523; A→T modification of nucleotide 533; G→C modification of nucleotide 534; T→C modification of nucleotide 535; A→C modification of nucleotide 544; A→C modification of nucleotide 547;

A→G modification of nucleotide 553; A→T modification of nucleotide 557; G→C modification of nucleotide 558; T→C modification of nucleotide 562; T→C modification of nucleotide 563; T→C modification of nucleotide 568; G→C modification of nucleotide 571; A→T modification of nucleotide 572; G→C modification of nucleotide 573; T→C modification of nucleotide 577; G→C modification of nucleotide 580; T→C modification of nucleotide 583; A→G modification of nucleotide 586; A→G modification of nucleotide 592; A→G modification of nucleotide 598; T→C modification of nucleotide 607; A→C modification of nucleotide 610; T→C modification of nucleotide 613; T→C modification of nucleotide 616; A→C modification of nucleotide 619; G→C modification of nucleotide 622; A→G modification of nucleotide 625; A→G modification of nucleotide 628; G→C modification of nucleotide 631; A→C modification of nucleotide 634; T→C modification of nucleotide 643; A→C modification of nucleotide 649; A→T modification of nucleotide 650; G→C modification of nucleotide 651; T→C modification of nucleotide 655; A→C modification of nucleotide 658; A→G modification of nucleotide 664; A→G modification of nucleotide 673; C→G modification of nucleotide 676; T→C modification of nucleotide 679; T→C modification of nucleotide 685; T→C modification of nucleotide 688; T→C modification of nucleotide 694; A→C modification of nucleotide 697; A→G modification of nucleotide 700; T→G modification of nucleotide 703; A→G modification of nucleotide 706; T→C modification of nucleotide 721; G→C modification of nucleotide 724; A→T modification of nucleotide 728; G→C modification of nucleotide 729; T→C modification of nucleotide 730; T→C modification of nucleotide 733; A→C modification of nucleotide 736; T→C modification of nucleotide 739; C→G modification of nucleotide 742; T→C modification of nucleotide 748; T→C modification of nucleotide 751; A→C modification of nucleotide 754; A→G modification of nucleotide 757; A→C modification of nucleotide 760; T→C modification of nucleotide 769; T→C modification of nucleotide 772; C→G modification of nucleotide 778; T→C modification of nucleotide 784; T→C modification of nucleotide 787; A→C modification of nucleotide 783; A→C modification of nucleotide 786; G→C modification of nucleotide 802; A→G modification of nucleotide 808; T→C modification of nucleotide 812; T→C modification of nucleotide 817; A→G modification of nucleotide 820; A→C modification of nucleotide 821; A→G modification of nucleotide 823; T→C modification of nucleotide 826; T→C modification of nucleotide 841; T→C modification of nucleotide 844; T→C modification of nucleotide 847; T→C modification of nucleotide 850; T→C modification of nucleotide 853; T→C modification of nucleotide 862; T→C modification of nucleotide 868; G→C modification of nucleotide 877; A→C modification of nucleotide 878; G→C modification of nucleotide 880; A→C modification of nucleotide 883; T→C modification of nucleotide 892; T→C modification of nucleotide 895; T→G modification of nucleotide 898; T→C modification of nucleotide 904; T→C modification of nucleotide 925; A→C modification of nucleotide 928; T→C modification of nucleotide 931; A→G modification of nucleotide 934; A→C modification of nucleotide 937; T→C modification of nucleotide 943; T→C modification of nucleotide 949; T→C modification of nucleotide 952; T→C modification of nucleotide 958; T→C modification of nucleotide 964; T→C modification of nucleotide 967; T→G modification of nucleotide 970; T→C modification of nucleotide 973; T→C modification of nucleotide 974; A→G modification of nucleotide 979; A→C modification of nucleotide 982; T→C modification of nucleotide 985; A→G modification of nucleotide 988; A→G modification of nucleotide 997; T→C modification of nucleotide 1000; A→G modification of nucleotide 1003; A→C modification of nucleotide 1006; A→G modification of nucleotide 1009; A→C modification of nucleotide 1016; G→C modification of nucleotide 1018; T→C modification of nucleotide 1024; C→G modification of nucleotide 1027; T→C modification of nucleotide 1030; T→C modification of nucleotide 1036; T→C modification of nucleotide 1042; A→C modification of nucleotide 1045; T→C modification of nucleotide 1048; A→C modification of nucleotide 1051; T→C modification of nucleotide 1054; T→G modification of nucleotide 1060; T→C modification of nucleotide 1066; T→C modification of nucleotide 1069; T→C modification of nucleotide 1075; T→C modification of nucleotide 1078; T→C modification of nucleotide 1087; T→C modification of nucleotide 1096; T→C modification of nucleotide 1099; A→G modification of nucleotide 1102; T→C modification of nucleotide 1105; A→G modification of nucleotide 1123; A→C modification of nucleotide 1126; A→G modification of nucleotide 1129; T→C modification of nucleotide 1132; A→C modification of nucleotide 1141; T→C modification of nucleotide 1144; A→C modification of nucleotide 1147; T→C modification of nucleotide 1150; G→C modification of nucleotide 1153; T→C modification of nucleotide 1156; A→G modification of nucleotide 1159; A→C modification of nucleotide 1162; T→C modification of nucleotide 1171; T→C modification of nucleotide 1174; T→C modification of nucleotide 1180; T→C modification of nucleotide 1183; A→C modification of nucleotide 1186; A→C modification of nucleotide 1195; T→G modification of nucleotide 1198; A→G modification of nucleotide 1213; T→C modification of nucleotide 1216; A→C modification of nucleotide 1219; T→C modification of nucleotide 1225; T→C modification of nucleotide 1228; A→C modification of nucleotide 1234; T→C modification of nucleotide 1237; A→C modification of nucleotide 1240; A→G modification of nucleotide 1243; T→C modification of nucleotide 1246; T→C modification of nucleotide 1249; T→C modification of nucleotide 1252; T→C modification of nucleotide 1255; G→C modification of nucleotide 1258; T→C modification of nucleotide 1261; A→G modification of nucleotide 1267; T→C modification of nucleotide 1270; T→C modification of nucleotide 1273; T→C modification of nucleotide 1283; A→G modification of nucleotide 1285; A→G modification of nucleotide 1291; A→C modification of nucleotide 1294; A→C modification of nucleotide 1295; A→C modification of nucleotide 1297; T→C modification of nucleotide 1300; A→C modification of nucleotide 1303; A→G modification of nucleotide 1306; A→C modification of nucleotide 1309; T→C modification of nucleotide 1312; A→C modification of nucleotide 1315; A→G modification of nucleotide 1336; T→C modification of nucleotide 1340; A→G modification of nucleotide 1342; T→C modification of nucleotide 1345; T→C modification of nucleotide 1348; T→C modification of nucleotide 1351; A→G modification of nucleotide 1363; A→C modification of nucleotide 1366; T→C modification of nucleotide 1369; A→C modification of nucleotide 1372; A→T modification of nucleotide 1373; G→C modification of nucleotide 1374; T→C modification of nucleotide 1375; T→C modification of nucleotide 1384; T→C modification of nucleotide 1390; A→C modification of nucleotide 1399; T→C modification of nucleotide 1402; A→C modification of nucleotide 1405; T→C modification of nucleotide 1408; T→C modification of nucleotide 1411; T→C modification of nucleotide 1414; T→C modification of nucleotide 1417; T→C modification of nucleotide 1420; A→C modification of nucleotide 1423; G→C modification of nucleotide 1438; A→C modification of nucleotide 1441; T→C modification of nucleotide 1444; A→C modification of nucleotide 1447; C→G modification of nucleotide 1450; T→C modification of nucleotide 1453; T→C modification of nucleotide 1456; T→C modification of nucleotide 1462; T→C modification of nucleotide 1465; T→C modification of nucleotide 1471; T→C modification of nucleotide 1474; T→C modification of nucleotide 1477; T→C modification of nucleotide 1480; T→C modification of nucleotide 1483; A→G modification of nucleotide 1486; T→C modification of nucleotide 1489; T→C modification of nucleotide 1492; A→C modification of nucleotide 1498; T→C modification of nucleotide 1501; A→C modification of nucleotide 1504; A→C modification of nucleotide 1507; C→G modification of nucleotide 1510; T→C modification of nucleotide 1513; T→C modification of nucleotide 1514; A→G modification of nucleotide 1516; T→C modification of nucleotide 1522; A→G modification of nucleotide 1528; A→C modification of nucleotide 1531; T→C modification of nucleotide 1534; T→C modification of nucleotide 1537; A→G modification of nucleotide 1543; G→C modification of nucleotide 1546; A→G modification of nucleotide 1549; A→G modification of nucleotide 1552; T→C modification of nucleotide 1553; A→C modification of nucleotide 1558; T→G modification of nucleotide 1561; A→G modification of nucleotide 1564; T→C modification of nucleotide 1567; G→C modification of nucleotide 1570; T→C modification of nucleotide 1573; A→C modification of nucleotide 1576; A→C modification of nucleotide 1579; A→C modification of nucleotide 1582; A→C modification of nucleotide 1585; A→C modification of nucleotide 1594; T→G modification of nucleotide 1603; A→T modification of nucleotide 1604; G→C modification of nucleotide 1605; T→C modification of nucleotide 1606; T→C modification of nucleotide 1607; A→C modification of nucleotide 1610; A→C modification of nucleotide 1612; A→C modification of nucleotide 1616; A→C modification of nucleotide 1618; T→C modification of nucleotide 1621; A→G modification of nucleotide 1624; T→C modification of nucleotide 1627; A→C modification of nucleotide 1636; A→C modification of nucleotide 1639; A→C modification of nucleotide 1642; T→C modification of nucleotide 1643; A→C modification of nucleotide 1648; A→T modification of nucleotide 1655; G→C modification of nucleotide 1656; T→C modification of nucleotide 1657; T→G modification of nucleotide 1663; T→G modification of nucleotide 1666; T→C modification of nucleotide 1669; A→C modification of nucleotide 1672; A→C modification of nucleotide 1675; T→C modification of nucleotide 1681; T→C modification of nucleotide 1687; T→C modification of nucleotide 1690; A→C modification of nucleotide 1693; T→C modification of nucleotide 1697; A→G modification of nucleotide 1702; T→C modification of nucleotide 1705; T→C modification of nucleotide 1708; A→G modification of nucleotide 1711; T→C modification of nucleotide 1714; T→G modification of nucleotide 1720; A→C modification of nucleotide 1723; T→C modification of nucleotide 1726; T→C modification of nucleotide 1729; T→C modification of nucleotide 1732; C→G modification of nucleotide 1735; A→C modification of nucleotide 1741; A→C modification of nucleotide 1742; A→C modification of nucleotide 1744; A→C modification of nucleotide 1747; T→C modification of nucleotide 1750; A→G modification of nucleotide 1756; A→G modification of nucleotide 1762; T→G modification of nucleotide 1768; C→G modification of nucleotide 1771; T→C modification of nucleotide 1774; T→G modification of nucleotide 1777; A→G modification of nucleotide 1789; T→C modification of nucleotide 1792; T→C modification of nucleotide 1798; A→G modification of nucleotide 1801; A→C modification of nucleotide 1804; A→C modification of nucleotide 1807; T→C modification of nucleotide 1810; T→G modification of nucleotide 1816; T→C modification of nucleotide 1817; A→G modification of nucleotide 1819; T→G modification of nucleotide 1828; A→C modification of nucleotide 1832; G→C modification of nucleotide 1834; T→C modification of nucleotide 1837; T→C modification of nucleotide 1840; C→G modification of nucleotide 1843; T→C modification of nucleotide 1849; T→C modification of nucleotide 1852; T→C modification of nucleotide 1855; T→G modification of nucleotide 1858; G→C modification of nucleotide 1860; T→C modification of nucleotide 1861; G→C modification of nucleotide 1863; T→C modification of nucleotide 1866; T→C modification of nucleotide 1870; T→C modification of nucleotide 1871; A→G modification of nucleotide 1873; T→C modification of nucleotide 1876; T→C modification of nucleotide 1879; T→C modification of nucleotide 1882; A→C modification of nucleotide 1885; A→C modification of nucleotide 1891; T→C modification of nucleotide 1894; T→C modification of nucleotide 1897; A→G modification of nucleotide 1900; A→T modification of nucleotide 1907; G→C modification of nucleotide 1908; T→C modification of nucleotide 1909; A→T modification of nucleotide 1913; G→C modification of nucleotide 1914; T→C modification of nucleotide 1915; T→G modification of nucleotide 1918; T→C modification of nucleotide 1921; T→C modification of nucleotide 1936; A→C modification of nucleotide 1939; T→C modification of nucleotide 1940; T→C modification of nucleotide 1951; T→C modification of nucleotide 1954; A→G modification of nucleotide 1960; T→C modification of nucleotide 1961; A→G modification of nucleotide 1963; A→C modification of nucleotide 1966; A→C modification of nucleotide 1972; T→C modification of nucleotide 1975; C→G modification of nucleotide 1978; T→C modification of nucleotide 1981; A→C modification of nucleotide 1990; T→C modification of nucleotide 1993; A→G modification of nucleotide 1999; A→T modification of nucleotide 2003; G→C modification of nucleotide 2004; T→C modification of nucleotide 2011; T→C modification of nucleotide 2014; A→C modification of nucleotide 2017; G→C modification of nucleotide 2020; T→C modification of nucleotide 2029; T→C modification of nucleotide 2035; T→C modification of nucleotide 2041; A→G modification of nucleotide 2044; A→C modification of nucleotide 2047; T→C modification of nucleotide 2050; T→C modification of nucleotide 2053; G→C modification of nucleotide 2056; T→C modification of nucleotide 2059; A→G modification of nucleotide 2062; T→C modification of nucleotide 2068; A→C modification of nucleotide 2071; A→C modification of nucleotide 2074; A→C modification of nucleotide 2077; A→C modification of nucleotide 2080; T→C modification of nucleotide 2083; G→C modification of nucleotide 2089; T→C modification of nucleotide 2092; T→C modification of nucleotide 2095; T→C modification of nucleotide 2098; A→C modification of nucleotide 2104; T→G modification of nucleotide 2107; T→G modification of nucleotide 2110; T→C modification of nucleotide 2113; A→G modification of nucleotide 2119; T→C modification of nucleotide 2122; A→G modification of nucleotide 2125; A→C modification of nucleotide 2129; A→C modification of nucleotide 2131; T→G modification of nucleotide 2137; T→G modification of nucleotide 2140; T→C modification of nucleotide 2143; C→G modification of nucleotide 2146; T→C modification of nucleotide 2149; T→G modification of nucleotide 2152; T→C modification of nucleotide 2155; T→C modification of nucleotide 2158; T→C modification of nucleotide 2161; A→C modification of nucleotide 2164; T→C modification of nucleotide 2167; T→C modification of nucleotide 2173; A→C modification of nucleotide 2176; T→C modification of nucleotide 2179; T→C modification of nucleotide 2182; T→C modification of nucleotide 2185; T→C modification of nucleotide 2188; T→C modification of nucleotide 2191; T→C modification of nucleotide 2194; C→G modification of nucleotide 2197; A→C modification of nucleotide 2200; A→G modification of nucleotide 2203; A→C modification of nucleotide 2206; T→C modification of nucleotide 2209; T→C modification of nucleotide 2212; A→C modification of nucleotide 2215; A→G modification of nucleotide 2218; A→C modification of nucleotide 2224; A→G modification of nucleotide 2230; T→C modification of nucleotide 2233; T→C modification of nucleotide 2236; T→C modification of nucleotide 2237; A→G modification of nucleotide 2239; A→C modification of nucleotide 2242; T→C modification of nucleotide 2245; A→G modification of nucleotide 2251; A→C modification of nucleotide 2254; A→C modification of nucleotide 2262; and deletion of nucleotides 2263-5834;

d) a sequence encoding Cyclin-Dependent Kinase Inhibitor 1A (P21) and comprising one or more of the following modifications relative to SEQ ID NO: 4 (e.g., one, two, three, four, or all of the following modifications):

deletion of nucleotides 1-134; T→C modification of nucleotide 143; T→C modification of nucleotide 146; T→C modification of nucleotide 149; T→C modification of nucleotide 152; C→G modification of nucleotide 155; A→C modification of nucleotide 158; T→C modification of nucleotide 161; T→G modification of nucleotide 164; G→C modification of nucleotide 167; A→C modification of nucleotide 171; G→C modification of nucleotide 173; A→T modification of nucleotide 174; G→C modification of nucleotide 175; A→G modification of nucleotide 179; T→C modification of nucleotide 188; T→C modification of nucleotide 191; C→G modification of nucleotide 194; T→C modification of nucleotide 200; A→T modification of nucleotide 210; G→C modification of nucleotide 211; T→C modification of nucleotide 212; T→C modification of nucleotide 219; T→C modification of nucleotide 227; T→C modification of nucleotide 230; T→C modification of nucleotide 236; G→C modification of nucleotide 239; C→G modification of nucleotide 242; G→C modification of nucleotide 248; T→C modification of nucleotide 254; C→G modification of nucleotide 257; A→C modification of nucleotide 269; A→G modification of nucleotide 272; T→C modification of nucleotide 284; C→G modification of nucleotide 293; G→C modification of nucleotide 296; G→C modification of nucleotide 302; G→C modification of nucleotide 305; C→G modification of nucleotide 323; T→G modification of nucleotide 335; G→C modification of nucleotide 338; A→T modification of nucleotide 339; G→C modification of nucleotide 340; A→G modification of nucleotide 344; G→C modification of nucleotide 347; C→G modification of nucleotide 359; A→T modification of nucleotide 366; G→C modification of nucleotide 367; T→C modification of nucleotide 371; G→C modification of nucleotide 374; A→T modification of nucleotide 381; G→C modification of nucleotide 382; T→C modification of nucleotide 386; A→C modification of nucleotide 398; G→C modification of nucleotide 401; A→C modification of nucleotide 408; G→C modification of nucleotide 410; A→T modification of nucleotide 414; G→C modification of nucleotide 415; T→C modification of nucleotide 416; T→C modification of nucleotide 419; T→C modification of nucleotide 425; G→C modification of nucleotide 440; A→C modification of nucleotide 443; T→C modification of nucleotide 446; G→C modification of nucleotide 449; T→C modification of nucleotide 465; G→C modification of nucleotide 470; T→C modification of nucleotide 476; T→C modification of nucleotide 482; T→C modification of nucleotide 491; G→C modification of nucleotide 497; T→C modification of nucleotide 500; A→G modification of nucleotide 503; T→C modification of nucleotide 506; G→C modification of nucleotide 512; T→C modification of nucleotide 515; G→C modification of nucleotide 518; A→C modification of nucleotide 524; A→C modification of nucleotide 527; T→C modification of nucleotide 530; A→C modification of nucleotide 539; A→G modification of nucleotide 542; G→C modification of nucleotide 545; A→C modification of nucleotide 546; G→C modification of nucleotide 548; A→G modification of nucleotide 555; G→C modification of nucleotide 556; A→C modification of nucleotide 563; T→C modification of nucleotide 566; T→C modification of nucleotide 572; A→C modification of nucleotide 585; A→C modification of nucleotide 587; T→C modification of nucleotide 588; C→G modification of nucleotide 593; A→C modification of nucleotide 603; A→C modification of nucleotide 605; A→G modification of nucleotide 608; and deletion of nucleotides 613-1943;

e) a sequence encoding Vascular Endothelial Growth Factor A (VEGFA) and comprising one or more of the following modifications relative to SEQ ID NO: 5 (e.g., one, two, three, four, or all of the following modifications):

deletion of nucleotides 1-1036; T→C modification of nucleotide 1045; T→C modification of nucleotide 1054; T→C modification of nucleotide 1063; A→T modification of nucleotide 1067; G→C modification of nucleotide 1068; T→G modification of nucleotide 1072; T→C modification of nucleotide 1076; C→G modification of nucleotide 1084; C→G modification of nucleotide 1090; T→C modification of nucleotide 1096; T→C modification of nucleotide 1114; A→C modification of nucleotide 1117; A→C modification of nucleotide 1126; A→G modification of nucleotide 1129; A→C modification of nucleotide 1132; A→C modification of nucleotide 1135; G→C modification of nucleotide 1138; T→C modification of nucleotide 1144; T→C modification of nucleotide 1147; A→G modification of nucleotide 1153; T→C modification of nucleotide 1171; C→G modification of nucleotide 1174; T→C modification of nucleotide 1177; C→G modification of nucleotide 1183; A→T modification of nucleotide 1184; G→C modification of nucleotide 1185; T→C modification of nucleotide 1195; A→C modification of nucleotide 1198; T→C modification of nucleotide 1234; T→C modification of nucleotide 1237; A→C modification of nucleotide 1261; T→C modification of nucleotide 1267; A→C modification of nucleotide 1282; G→C modification of nucleotide 1288; T→C modification of nucleotide 1300; T→C modification of nucleotide 1318; T→C modification of nucleotide 1327; T→C modification of nucleotide 1354; G→C modification of nucleotide 1360; A→G modification of nucleotide 1366; T→C modification of nucleotide 1369; A→G modification of nucleotide 1375; A→C modification of nucleotide 1387; A→C modification of nucleotide 1390; A→T modification of nucleotide 1397; G→C modification of nucleotide 1398; A→G modification of nucleotide 1405; A→G modification of nucleotide 1417; T→C modification of nucleotide 1420; A→G modification of nucleotide 1423; A→C modification of nucleotide 1427; A→C modification of nucleotide 1429; A→C modification of nucleotide 1432; A→G modification of nucleotide 1438; T→C modification of nucleotide 1441; A→C modification of nucleotide 1442; A→C modification of nucleotide 1444; A→C modification of nucleotide 1447; A→C modification of nucleotide 1448; A→C modification of nucleotide 1450; A→G modification of nucleotide 1453; A→G modification of nucleotide 1456; T→C modification of nucleotide 1459; T→C modification of nucleotide 1465; G→C modification of nucleotide 1468; T→C modification of nucleotide 1471; A→C modification of nucleotide 1477; G→C modification of nucleotide 1483; A→C modification of nucleotide 1484; A→C modification of nucleotide 1486; T→C modification of nucleotide 1492; T→C modification of nucleotide 1493; T→C modification of nucleotide 1498; A→G modification of nucleotide 1501; A→G modification of nucleotide 1504; T→C modification of nucleotide 1507; G→C modification of nucleotide 1510; G→C modification of nucleotide 1516; T→C modification of nucleotide 1519; A→G modification of nucleotide 1522; T→C modification of nucleotide 1525; A→G modification of nucleotide 1534; A→C modification of nucleotide 1540; G→C modification of nucleotide 1546; T→C modification of nucleotide 1549; and deletion of nucleotides 1556-3502;

f) a sequence encoding Insulin-like Growth Factor 1 (Igf1) and comprising one or more of the following modifications relative to SEQ ID NO: 6 (e.g., one, two, three, four, or all of the following modifications):

deletion of nucleotides 1-298; G→C modification of nucleotide 304; A→G modification of nucleotide 307; A→T modification of nucleotide 311; G→C modification of nucleotide 312; A→T modification of nucleotide 314; G→C modification of nucleotide 315; T→G modification of nucleotide 319; A→C modification of nucleotide 322; T→C modification of nucleotide 325; A→G modification of nucleotide 328; T→C modification of nucleotide 329; A→G modification of nucleotide 331; T→C modification of nucleotide 334; C→G modification of nucleotide 346; T→C modification of nucleotide 349; T→C modification of nucleotide 356; A→C modification of nucleotide 364; A→C modification of nucleotide 370; G→C modification of nucleotide 382; T→C modification of nucleotide 385; A→C modification of nucleotide 388; C→G modification of nucleotide 394; G→C modification of nucleotide 406; C→G modification of nucleotide 409; T→C modification of nucleotide 413; C→G modification of nucleotide 418; A→T modification of nucleotide 428; G→C modification of nucleotide 429; A→C modification of nucleotide 439; T→C modification of nucleotide 442; A→C modification of nucleotide 445; A→C modification of nucleotide 448; T→G modification of nucleotide 457; G→C modification of nucleotide 463; T→C modification of nucleotide 466; T→C modification of nucleotide 478; T→C modification of nucleotide 481; T→G modification of nucleotide 484; T→C modification of nucleotide 496; A→C modification of nucleotide 499; G→C modification of nucleotide 502; A→C modification of nucleotide 503; G→C modification of nucleotide 505; T→C modification of nucleotide 511; A→C modification of nucleotide 529; T→C modification of nucleotide 535; A→T modification of nucleotide 542; G→C modification of nucleotide 543; T→C modification of nucleotide 547; G→C modification of nucleotide 550; A→C modification of nucleotide 551; G→C modification of nucleotide 553; A→C modification of nucleotide 556; T→C modification of nucleotide 559; A→C modification of nucleotide 565; T→C modification of nucleotide 571; T→C modification of nucleotide 577; T→C modification of nucleotide 583; G→C modification of nucleotide 592; A→T modification of nucleotide 593; G→C modification of nucleotide 594; T→C modification of nucleotide 598; T→C modification of nucleotide 601; A→C modification of nucleotide 605; G→C modification of nucleotide 607; A→C modification of nucleotide 608; A→C modification of nucleotide 610; T→C modification of nucleotide 625; A→C modification of nucleotide 631; T→C modification of nucleotide 640; A→C modification of nucleotide 643; A→G modification of nucleotide 646; A→C modification of nucleotide 649; T→C modification of nucleotide 658; T→C modification of nucleotide 664; T→C modification of nucleotide 679; T→C modification of nucleotide 694; A→G modification of nucleotide 703; A→G modification of nucleotide 706; T→C modification of nucleotide 709; T→C modification of nucleotide 710; A→C modification of nucleotide 721; A→T modification of nucleotide 722; G→C modification of nucleotide 723; T→C modification of nucleotide 724; A→C modification of nucleotide 725; A→C modification of nucleotide 727; A→C modification of nucleotide 730; A→T modification of nucleotide 731; G→C modification of nucleotide 732; T→C modification of nucleotide 733; A→C modification of nucleotide 736; A→C modification of nucleotide 739; A→C modification of nucleotide 752; A→C modification of nucleotide 754; and deletion of nucleotides 760-7073;

g) a sequence encoding Insulin-like Growth Factor 1 (Igf1) and comprising one or more of the following modifications relative to SEQ ID NO: 6 (e.g., one, two, three, four, or all of the following modifications):

deletion of nucleotides 1-442; insertion of SEQ ID NO: 18; A→C modification of nucleotide 445; A→C modification of nucleotide 448; T→G modification of nucleotide 457; G→C modification of nucleotide 463; T→C modification of nucleotide 466; T→C modification of nucleotide 478; T→C modification of nucleotide 481; T→G modification of nucleotide 484; T→C modification of nucleotide 496; A→C modification of nucleotide 499; G→C modification of nucleotide 502; A→C modification of nucleotide 503; G→C modification of nucleotide 505; T→C modification of nucleotide 511; A→C modification of nucleotide 529; T→C modification of nucleotide 535; A→T modification of nucleotide 542; G→C modification of nucleotide 543; T→C modification of nucleotide 547; G→C modification of nucleotide 550; A→C modification of nucleotide 551; G→C modification of nucleotide 553; A→C modification of nucleotide 556; T→C modification of nucleotide 559; A→C modification of nucleotide 565; T→C modification of nucleotide 571; T→C modification of nucleotide 577; T→C modification of nucleotide 583; G→C modification of nucleotide 592; A→T modification of nucleotide 593; G→C modification of nucleotide 594; T→C modification of nucleotide 598; T→C modification of nucleotide 601; A→C modification of nucleotide 605; G→C modification of nucleotide 607; A→C modification of nucleotide 608; A→C modification of nucleotide 610; T→C modification of nucleotide 625; A→C modification of nucleotide 631; T→C modification of nucleotide 640; A→C modification of nucleotide 643; A→G modification of nucleotide 646; A→C modification of nucleotide 649; T→C modification of nucleotide 658; T→C modification of nucleotide 664; T→C modification of nucleotide 679; T→C modification of nucleotide 694; A→G modification of nucleotide 703; A→G modification of nucleotide 706; T→C modification of nucleotide 709; T→C modification of nucleotide 710; A→C modification of nucleotide 721; A→T modification of nucleotide 722; G→C modification of nucleotide 723; T→C modification of nucleotide 724; A→C modification of nucleotide 725; A→C modification of nucleotide 727; A→C modification of nucleotide 730; A→T modification of nucleotide 731; G→C modification of nucleotide 732; T→C modification of nucleotide 733; A→C modification of nucleotide 736; A→C modification of nucleotide 739; A→C modification of nucleotide 752; A→C modification of nucleotide 754; and deletion of nucleotides 760-7073;

h) a sequence encoding Epidermal Growth Factor 1 (EGF) and comprising one or more of the following modifications relative to SEQ ID NO: 2 (e.g., one, two, three, four, or all of the following modifications):

deletion of nucleotides 1-3369; insertion of SEQ ID NO: 19; T→C modification of nucleotide 3375; A→G modification of nucleotide 3378; T→C modification of nucleotide 3381; T→C modification of nucleotide 3396; G→C modification of nucleotide 3399; C→G modification of nucleotide 3408; T→C modification of nucleotide 3411; T→C modification of nucleotide 3414; T→C modification of nucleotide 3417; T→C modification of nucleotide 3429; T→C modification of nucleotide 3432; A→G modification of nucleotide 3435; A→C modification of nucleotide 3438; T→C modification of nucleotide 3439; T→C modification of nucleotide 3450; A→C modification of nucleotide 3453; T→C modification of nucleotide 3462; T→G modification of nucleotide 3465; T→G modification of nucleotide 3468; G→C modification of nucleotide 3480; A→G modification of nucleotide 3486; T→C modification of nucleotide 3489; A→C modification of nucleotide 3498; A→G modification of nucleotide 3516; and deletion of nucleotides 3523-6388;

i) a sequence encoding signal transducer and activator of transcription 5B (Stat5b) and comprising one or more of the following modifications relative to SEQ ID NO: 7 (e.g., one, two, three, four, or all of the following modifications):

deletion of nucleotides 1-532; insertion of SEQ ID NO: 20; T→C modification of nucleotide 535; A→C modification of nucleotide 544; T→C modification of nucleotide 550; C→G modification of nucleotide 559; T→C modification of nucleotide 568; T→G modification of nucleotide 574; T→C modification of nucleotide 590; T→C modification of nucleotide 604; A→C modification of nucleotide 622; T→C modification of nucleotide 625; T→C modification of nucleotide 628; T→C modification of nucleotide 629; A→G modification of nucleotide 631; A→C modification of nucleotide 634; A→G modification of nucleotide 646; A→T modification of nucleotide 647; G→C modification of nucleotide 648; A→G modification of nucleotide 652; A→C modification of nucleotide 664; A→C modification of nucleotide 667; T→C modification of nucleotide 670; T→G modification of nucleotide 673; T→C modification of nucleotide 676; T→C modification of nucleotide 679; A→C modification of nucleotide 682; T→C modification of nucleotide 694; C→G modification of nucleotide 709; G→C modification of nucleotide 745; G→C modification of nucleotide 760; A→G modification of nucleotide 763; T→C modification of nucleotide 766; G→C modification of nucleotide 769; T→C modification of nucleotide 772; T→C modification of nucleotide 773; G→C modification of nucleotide 793; T→C modification of nucleotide 799; A→C modification of nucleotide 805; C→G modification of nucleotide 811; A→T modification of nucleotide 815; G→C modification of nucleotide 816; G→C modification of nucleotide 820; T→G modification of nucleotide 847; T→C modification of nucleotide 853; G→C modification of nucleotide 859; T→C modification of nucleotide 865; A→G modification of nucleotide 877; A→C modification of nucleotide 881; G→C modification of nucleotide 883; T→G modification of nucleotide 889; A→G modification of nucleotide 895; A→T modification of nucleotide 908; G→C modification of nucleotide 909; T→C modification of nucleotide 913; A→C modification of nucleotide 916; T→C modification of nucleotide 919; A→C modification of nucleotide 922; A→T modification of nucleotide 923; G→C modification of nucleotide 924; T→C modification of nucleotide 925; T→G modification of nucleotide 928; T→C modification of nucleotide 931; T→G modification of nucleotide 955; A→G modification of nucleotide 967; G→C modification of nucleotide 970; T→C modification of nucleotide 973; A→C modification of nucleotide 994; G→C modification of nucleotide 1003; A→G modification of nucleotide 1036; A→T modification of nucleotide 1064; G→C modification of nucleotide 1065; G→C modification of nucleotide 1072; A→G modification of nucleotide 1078; T→C modification of nucleotide 1081; T→C modification of nucleotide 1087; A→C modification of nucleotide 1099; A→T modification of nucleotide 1124; G→C modification of nucleotide 1125; A→C modification of nucleotide 1127; G→C modification of nucleotide 1129; G→C modification of nucleotide 1135; C→G modification of nucleotide 1141; A→G modification of nucleotide 1153; A→C modification of nucleotide 1180; A→C modification of nucleotide 1186; A→C modification of nucleotide 1192; A→C modification of nucleotide 1207; T→C modification of nucleotide 1219; G→C modification of nucleotide 1252; G→C modification of nucleotide 1300; A→C modification of nucleotide 1301; A→C modification of nucleotide 1303; G→C modification of nucleotide 1318; G→C modification of nucleotide 1324; T→C modification of nucleotide 1327; A→T modification of nucleotide 1340; G→C modification of nucleotide 1341; T→C modification of nucleotide 1366; G→C modification of nucleotide 1399; A→C modification of nucleotide 1412; G→C modification of nucleotide 1414; T→C modification of nucleotide 1417; T→C modification of nucleotide 1424; A→C modification of nucleotide 1447; T→C modification of nucleotide 1471; C→G modification of nucleotide 1477; G→C modification of nucleotide 1492; A→C modification of nucleotide 1504; C→G modification of nucleotide 1513; A→T modification of nucleotide 1517; G→C modification of nucleotide 1518; G→C modification of nucleotide 1522; T→C modification of nucleotide 1543; T→C modification of nucleotide 1546; C→G modification of nucleotide 1552; T→C modification of nucleotide 1573; A→C modification of nucleotide 1576; G→C modification of nucleotide 1600; G→C modification of nucleotide 1603; T→C modification of nucleotide 1612; G→C modification of nucleotide 1630; G→C modification of nucleotide 1642; A→T modification of nucleotide 1652; G→C modification of nucleotide 1653; C→G modification of nucleotide 1678; T→C modification of nucleotide 1684; T→C modification of nucleotide 1699; T→C modification of nucleotide 1702; A→T modification of nucleotide 1706; G→C modification of nucleotide 1707; T→C modification of nucleotide 1729; C→G modification of nucleotide 1735; T→C modification of nucleotide 1756; A→C modification of nucleotide 1762; C→G modification of nucleotide 1765; A→T modification of nucleotide 1766; G→C modification of nucleotide 1767; A→C modification of nucleotide 1778; A→C modification of nucleotide 1780; A→G modification of nucleotide 1795; A→C modification of nucleotide 1798; A→C modification of nucleotide 1805; T→C modification of nucleotide 1810; T→C modification of nucleotide 1819; G→C modification of nucleotide 1822; A→C modification of nucleotide 1825; A→C modification of nucleotide 1831; A→G modification of nucleotide 1834; G→C modification of nucleotide 1837; A→G modification of nucleotide 1840; G→C modification of nucleotide 1852; T→C modification of nucleotide 1861; A→C modification of nucleotide 1867; A→T modification of nucleotide 1874; G→C modification of nucleotide 1875; C→G modification of nucleotide 1879; T→C modification of nucleotide 1882; A→C modification of nucleotide 1885; C→G modification of nucleotide 1897; T→C modification of nucleotide 1900; A→G modification of nucleotide 1903; C→G modification of nucleotide 1906; T→C modification of nucleotide 1913; G→C modification of nucleotide 1918; C→G modification of nucleotide 1921; G→C modification of nucleotide 1924; T→C modification of nucleotide 1936; T→G modification of nucleotide 1939; A→T modification of nucleotide 1946; G→C modification of nucleotide 1947; T→C modification of nucleotide 1960; A→C modification of nucleotide 1966; T→C modification of nucleotide 1972; C→G modification of nucleotide 1975; C→G modification of nucleotide 1978; T→C modification of nucleotide 1993; A→C modification of nucleotide 1996; T→C modification of nucleotide 2002; A→C modification of nucleotide 2006; G→C modification of nucleotide 2008; A→C modification of nucleotide 2014; T→C modification of nucleotide 2017; T→C modification of nucleotide 2026; G→C modification of nucleotide 2044; T→C modification of nucleotide 2053; A→G modification of nucleotide 2056; G→C modification of nucleotide 2059; C→G modification of nucleotide 2062; A→G modification of nucleotide 2071; T→C modification of nucleotide 2080; A→G modification of nucleotide 2083; A→G modification of nucleotide 2086; A→T modification of nucleotide 2090; G→C modification of nucleotide 2091; G→C modification of nucleotide 2098; T→C modification of nucleotide 2102; C→G modification of nucleotide 2119; A→C modification of nucleotide 2131; A→G modification of nucleotide 2137; A→T modification of nucleotide 2150; G→C modification of nucleotide 2151; A→T modification of nucleotide 2153; G→C modification of nucleotide 2154; C→G modification of nucleotide 2164; A→T modification of nucleotide 2177; G→C modification of nucleotide 2178; G→C modification of nucleotide 2209; T→C modification of nucleotide 2215; T→C modification of nucleotide 2216; A→C modification of nucleotide 2221; A→C modification of nucleotide 2224; G→C modification of nucleotide 2227; T→C modification of nucleotide 2230; T→C modification of nucleotide 2236; T→C modification of nucleotide 2251; T→C modification of nucleotide 2254; A→G modification of nucleotide 2266; A→G modification of nucleotide 2269; T→C modification of nucleotide 2270; A→G modification of nucleotide 2275; A→G modification of nucleotide 2278; T→C modification of nucleotide 2281; C→G modification of nucleotide 2284; T→C modification of nucleotide 2290; T→C modification of nucleotide 2299; T→C modification of nucleotide 2302; G→C modification of nucleotide 2305; T→C modification of nucleotide 2308; T→C modification of nucleotide 2317; A→G modification of nucleotide 2332; C→G modification of nucleotide 2350; A→C modification of nucleotide 2362; G→C modification of nucleotide 2368; A→T modification of nucleotide 2387; G→C modification of nucleotide 2388; G→C modification of nucleotide 2395; A→G modification of nucleotide 2398; G→C modification of nucleotide 2404; T→C modification of nucleotide 2416; T→C modification of nucleotide 2419; T→C modification of nucleotide 2428; T→C modification of nucleotide 2434; A→C modification of nucleotide 2441; A→C modification of nucleotide 2443; T→C modification of nucleotide 2449; A→C modification of nucleotide 2453; T→C modification of nucleotide 2455; T→C modification of nucleotide 2464; T→C modification of nucleotide 2467; T→C modification of nucleotide 2473; A→C modification of nucleotide 2474; A→C modification of nucleotide 2476; T→C modification of nucleotide 2485; G→C modification of nucleotide 2491; C→G modification of nucleotide 2497; T→C modification of nucleotide 2500; G→C modification of nucleotide 2512; T→C modification of nucleotide 2521; C→G modification of nucleotide 2527; A→C modification of nucleotide 2530; T→C modification of nucleotide 2533; T→C modification of nucleotide 2539; T→C modification of nucleotide 2542; T→C modification of nucleotide 2545; G→C modification of nucleotide 2548; A→C modification of nucleotide 2551; T→C modification of nucleotide 2557; A→G modification of nucleotide 2560; A→G modification of nucleotide 2563; T→C modification of nucleotide 2566; T→C modification of nucleotide 2569; A→C modification of nucleotide 2581; G→C modification of nucleotide 2584; C→G modification of nucleotide 2587; T→C modification of nucleotide 2593; A→C modification of nucleotide 2602; T→C modification of nucleotide 2605; G→C modification of nucleotide 2608; A→G modification of nucleotide 2611; A→C modification of nucleotide 2614; T→C modification of nucleotide 2617; A→C modification of nucleotide 2623; A→C modification of nucleotide 2635; C→G modification of nucleotide 2653; T→C modification of nucleotide 2662; A→C modification of nucleotide 2665; T→C modification of nucleotide 2668; A→C modification of nucleotide 2671; A→C modification of nucleotide 2677; T→C modification of nucleotide 2680; T→C modification of nucleotide 2683; G→C modification of nucleotide 2686; A→T modification of nucleotide 2687; G→C modification of nucleotide 2688; T→C modification of nucleotide 2689; T→C modification of nucleotide 2707; T→C modification of nucleotide 2713; T→C modification of nucleotide 2716; A→C modification of nucleotide 2722; C→G modification of nucleotide 2725; T→C modification of nucleotide 2734; T→C modification of nucleotide 2740; A→C modification of nucleotide 2758; G→C modification of nucleotide 2767; C→G modification of nucleotide 2776; T→G modification of nucleotide 2779; T→C modification of nucleotide 2782; T→C modification of nucleotide 2788; G→C modification of nucleotide 2791; T→C modification of nucleotide 2800; A→G modification of nucleotide 2806; G→C modification of nucleotide 2812; G→C modification of nucleotide 2824; G→C modification of nucleotide 2827; A→G modification of nucleotide 2836; C→G modification of nucleotide 2842; T→C modification of nucleotide 2843; A→G modification of nucleotide 2845; G→C modification of nucleotide 2851; A→T modification of nucleotide 2861; G→C modification of nucleotide 2862; T→C modification of nucleotide 2863; T→C modification of nucleotide 2875; A→C modification of nucleotide 2881; A→C modification of nucleotide 2887; and deletion of nucleotides 2888-5255;

j) a sequence encoding beta catenin (CTNNB1) and comprising one or more of the following modifications relative to SEQ ID NO: 17 (e.g., one, two, three, four, or all of the following modifications):

deletion of nucleotides 1-214; T→C modification of nucleotide 220; T→C modification of nucleotide 223; A→G modification of nucleotide 226; T→C modification of nucleotide 229; T→C modification of nucleotide 232; T→C modification of nucleotide 233; T→C modification of nucleotide 242; A→G modification of nucleotide 259; A→C modification of nucleotide 262; A→C modification of nucleotide 266; A→C modification of nucleotide 268; A→G modification of nucleotide 271; G→C modification of nucleotide 274; T→C modification of nucleotide 277; T→G modification of nucleotide 280; A→T modification of nucleotide 281; G→C modification of nucleotide 282; T→C modification of nucleotide 283; A→G modification of nucleotide 295; T→C modification of nucleotide 301; T→C modification of nucleotide 313; A→C modification of nucleotide 316; T→C modification of nucleotide 322; T→C modification of nucleotide 325; T→C modification of nucleotide 328; T→C modification of nucleotide 334; A→C modification of nucleotide 340; T→C modification of nucleotide 343; T→C modification of nucleotide 346; T→C modification of nucleotide 349; A→C modification of nucleotide 353; G→C modification of nucleotide 354; T→C modification of nucleotide 355; T→C modification of nucleotide 358; A→G modification of nucleotide 361; T→C modification of nucleotide 367; T→C modification of nucleotide 370; A→G modification of nucleotide 376; T→C modification of nucleotide 382; T→C modification of nucleotide 388; A→G modification of nucleotide 397; C→G modification of nucleotide 400; T→C modification of nucleotide 406; A→G modification of nucleotide 415; A→C modification of nucleotide 421; T→C modification of nucleotide 424; T→C modification of nucleotide 427; T→C modification of nucleotide 439; A→G modification of nucleotide 442; A→G modification of nucleotide 445; A→G modification of nucleotide 448; A→G modification of nucleotide 451; T→C modification of nucleotide 454; T→C modification of nucleotide 457; T→C modification of nucleotide 460; T→C modification of nucleotide 463; A→C modification of nucleotide 466; T→C modification of nucleotide 472; A→C modification of nucleotide 475; T→C modification of nucleotide 481; A→C modification of nucleotide 484; T→C modification of nucleotide 487; A→C modification of nucleotide 491; G→C modification of nucleotide 493; A→G modification of nucleotide 496; A→C modification of nucleotide 499; T→C modification of nucleotide 502; T→C modification of nucleotide 505; T→C modification of nucleotide 514; A→C modification of nucleotide 520; T→C modification of nucleotide 521; A→G modification of nucleotide 523; T→C modification of nucleotide 526; A→C modification of nucleotide 544; T→C modification of nucleotide 547; A→C modification of nucleotide 550; T→C modification of nucleotide 556; T→C modification of nucleotide 559; T→C modification of nucleotide 562; T→C modification of nucleotide 565; T→C modification of nucleotide 568; T→C modification of nucleotide 574; T→C modification of nucleotide 577; C→G modification of nucleotide 580; T→C modification of nucleotide 586; T→C modification of nucleotide 587; T→C modification of nucleotide 592; A→G modification of nucleotide 595; A→C modification of nucleotide 598; A→C modification of nucleotide 601; A→G modification of nucleotide 613; T→C modification of nucleotide 616; A→C modification of nucleotide 619; T→G modification of nucleotide 622; A→G modification of nucleotide 625; T→C modification of nucleotide 629; T→C modification of nucleotide 634; T→C modification of nucleotide 640; A→G modification of nucleotide 643; T→C modification of nucleotide 646; T→C modification of nucleotide 649; A→C modification of nucleotide 652; A→G modification of nucleotide 655; T→G modification of nucleotide 658; A→C modification of nucleotide 664; T→C modification of nucleotide 667; A→C modification of nucleotide 670; T→C modification of nucleotide 676; A→G modification of nucleotide 679; A→C modification of nucleotide 685; A→G modification of nucleotide 688; A→G modification of nucleotide 694; T→C modification of nucleotide 697; T→G modification of nucleotide 718; T→C modification of nucleotide 721; T→C modification of nucleotide 727; A→C modification of nucleotide 730; T→G modification of nucleotide 733; C→G modification of nucleotide 739; T→C modification of nucleotide 742; T→G modification of nucleotide 748; T→C modification of nucleotide 751; A→G modification of nucleotide 754; A→G modification of nucleotide 760; T→C modification of nucleotide 763; A→C modification of nucleotide 767; A→C modification of nucleotide 769; T→C modification of nucleotide 775; T→C modification of nucleotide 784; T→C modification of nucleotide 787; T→C modification of nucleotide 790; T→C modification of nucleotide 802; T→C modification of nucleotide 805; T→C modification of nucleotide 808; A→G modification of nucleotide 811; T→C modification of nucleotide 814; T→C modification of nucleotide 826; A→C modification of nucleotide 829; T→C modification of nucleotide 832; T→C modification of nucleotide 835; A→G modification of nucleotide 838; A→G modification of nucleotide 841; A→C modification of nucleotide 844; T→C modification of nucleotide 847; T→C modification of nucleotide 850; T→C modification of nucleotide 853; T→C modification of nucleotide 859; G→C modification of nucleotide 862; T→C modification of nucleotide 866; T→C modification of nucleotide 871; T→G modification of nucleotide 878; T→C modification of nucleotide 883; T→C modification of nucleotide 886; T→C modification of nucleotide 889; T→C modification of nucleotide 896; A→G modification of nucleotide 898; T→C modification of nucleotide 910; T→C modification of nucleotide 916; A→C modification of nucleotide 919; T→C modification of nucleotide 925; T→C modification of nucleotide 928; A→G modification of nucleotide 940; T→G modification of nucleotide 946; T→C modification of nucleotide 949; A→C modification of nucleotide 952; A→C modification of nucleotide 955; T→C modification of nucleotide 961; T→C modification of nucleotide 964; T→C modification of nucleotide 968; T→C modification of nucleotide 973; T→C modification of nucleotide 976; T→C modification of nucleotide 982; A→C modification of nucleotide 985; T→C modification of nucleotide 988; C→G modification of nucleotide 991; T→G modification of nucleotide 1000; T→C modification of nucleotide 1001; A→G modification of nucleotide 1003; T→C modification of nucleotide 1004; A→G modification of nucleotide 1006; T→C modification of nucleotide 1009; A→G modification of nucleotide 1012; A→G modification of nucleotide 1015; A→C modification of nucleotide 1018; T→C modification of nucleotide 1021; A→G modification of nucleotide 1024; A→C modification of nucleotide 1030; T→C modification of nucleotide 1036; T→C modification of nucleotide 1037; A→G modification of nucleotide 1039; T→C modification of nucleotide 1042; T→C modification of nucleotide 1045; G→C modification of nucleotide 1048; A→G modification of nucleotide 1057; T→G modification of nucleotide 1063; T→C modification of nucleotide 1067; C→G modification of nucleotide 1072; A→G modification of nucleotide 1078; A→C modification of nucleotide 1081; T→C modification of nucleotide 1084; T→G modification of nucleotide 1087; A→G modification of nucleotide 1090; T→C modification of nucleotide 1094; T→C modification of nucleotide 1099; T→C modification of nucleotide 1102; G→C modification of nucleotide 1105; A→C modification of nucleotide 1108; T→G modification of nucleotide 1117; A→G modification of nucleotide 1120; T→C modification of nucleotide 1123; T→C modification of nucleotide 1124; A→G modification of nucleotide 1126; T→C modification of nucleotide 1129; T→C modification of nucleotide 1132; A→G modification of nucleotide 1141; A→G modification of nucleotide 1144; A→T modification of nucleotide 1145; G→C modification of nucleotide 1146; C→G modification of nucleotide 1153; A→C modification of nucleotide 1159; T→C modification of nucleotide 1165; A→T modification of nucleotide 1166; G→C modification of nucleotide 1167; T→C modification of nucleotide 1168; T→C modification of nucleotide 1171; A→C modification of nucleotide 1174; A→G modification of nucleotide 1180; T→C modification of nucleotide 1183; T→C modification of nucleotide 1184; A→G modification of nucleotide 1186; A→G modification of nucleotide 1189; T→C modification of nucleotide 1192; A→C modification of nucleotide 1195; A→C modification of nucleotide 1199; G→C modification of nucleotide 1201; T→C modification of nucleotide 1207; T→C modification of nucleotide 1210; A→G modification of nucleotide 1216; A→G modification of nucleotide 1219; A→G modification of nucleotide 1222; A→C modification of nucleotide 1234; A→T modification of nucleotide 1235; G→C modification of nucleotide 1236; A→C modification of nucleotide 1238; A→C modification of nucleotide 1240; A→G modification of nucleotide 1255; T→C modification of nucleotide 1258; C→G modification of nucleotide 1261; T→C modification of nucleotide 1267; A→T modification of nucleotide 1268; G→C modification of nucleotide 1269; T→C modification of nucleotide 1270; T→C modification of nucleotide 1273; G→C modification of nucleotide 1279; T→C modification of nucleotide 1282; T→C modification of nucleotide 1285; A→G modification of nucleotide 1288; A→G modification of nucleotide 1291; T→C modification of nucleotide 1294; T→C modification of nucleotide 1297; A→C modification of nucleotide 1300; A→G modification of nucleotide 1306; T→C modification of nucleotide 1309; T→C modification of nucleotide 1310; A→G modification of nucleotide 1312; A→C modification of nucleotide 1315; T→G modification of nucleotide 1318; A→C modification of nucleotide 1327; T→C modification of nucleotide 1330; A→C modification of nucleotide 1333; A→T modification of nucleotide 1334; G→C modification of nucleotide 1335; T→C modification of nucleotide 1336; A→G modification of nucleotide 1339; T→C modification of nucleotide 1342; T→G modification of nucleotide 1345; T→G modification of nucleotide 1348; T→C modification of nucleotide 1357; T→G modification of nucleotide 1360; T→C modification of nucleotide 1366; C→G modification of nucleotide 1369; A→C modification of nucleotide 1370; G→C modification of nucleotide 1372; T→C modification of nucleotide 1375; T→G modification of nucleotide 1378; A→C modification of nucleotide 1381; T→C modification of nucleotide 1384; T→C modification of nucleotide 1387; A→C modification of nucleotide 1390; T→C modification of nucleotide 1393; A→G modification of nucleotide 1396; A→G modification of nucleotide 1402; G→C modification of nucleotide 1405; A→G modification of nucleotide 1411; T→C modification of nucleotide 1414; C→G modification of nucleotide 1417; T→G modification of nucleotide 1420; G→C modification of nucleotide 1423; T→C modification of nucleotide 1426; T→G modification of nucleotide 1429; T→G modification of nucleotide 1432; T→G modification of nucleotide 1438; T→C modification of nucleotide 1444; A→C modification of nucleotide 1447; T→C modification of nucleotide 1450; T→C modification of nucleotide 1453; A→C modification of nucleotide 1456; T→C modification of nucleotide 1459; C→G modification of nucleotide 1465; T→C modification of nucleotide 1471; A→C modification of nucleotide 1474; T→C modification of nucleotide 1477; A→C modification of nucleotide 1480; T→C modification of nucleotide 1483; T→G modification of nucleotide 1486; T→C modification of nucleotide 1489; C→G modification of nucleotide 1495; T→C modification of nucleotide 1498; T→C modification of nucleotide 1504; T→C modification of nucleotide 1507; T→C modification of nucleotide 1510; C→G modification of nucleotide 1528; A→G modification of nucleotide 1534; T→C modification of nucleotide 1540; T→C modification of nucleotide 1543; A→C modification of nucleotide 1546; T→C modification of nucleotide 1552; T→G modification of nucleotide 1555; T→C modification of nucleotide 1561; T→C modification of nucleotide 1564; C→G modification of nucleotide 1567; T→G modification of nucleotide 1570; G→C modification of nucleotide 1573; T→C modification of nucleotide 1576; T→C modification of nucleotide 1579; A→C modification of nucleotide 1583; G→C modification of nucleotide 1585; A→G modification of nucleotide 1588; T→C modification of nucleotide 1597; T→C modification of nucleotide 1603; T→C modification of nucleotide 1612; T→C modification of nucleotide 1615; T→G modification of nucleotide 1618; T→C modification of nucleotide 1621; T→C modification of nucleotide 1624; A→T modification of nucleotide 1631; G→C modification of nucleotide 1632; A→C modification of nucleotide 1636; A→G modification of nucleotide 1642; A→G modification of nucleotide 1645; A→C modification of nucleotide 1648; T→C modification of nucleotide 1663; A→C modification of nucleotide 1666; T→G modification of nucleotide 1669; T→G modification of nucleotide 1675; T→C modification of nucleotide 1681; A→C modification of nucleotide 1684; A→G modification of nucleotide 1687; A→C modification of nucleotide 1690; T→G modification of nucleotide 1693; T→G modification of nucleotide 1699; C→G modification of nucleotide 1705; T→C modification of nucleotide 1706; A→G modification of nucleotide 1708; A→C modification of nucleotide 1714; A→C modification of nucleotide 1717; T→C modification of nucleotide 1729; A→C modification of nucleotide 1735; T→C modification of nucleotide 1741; T→C modification of nucleotide 1744; T→G modification of nucleotide 1747; A→C modification of nucleotide 1750; T→C modification of nucleotide 1751; T→C modification of nucleotide 1756; A→C modification of nucleotide 1759; T→C modification of nucleotide 1762; T→G modification of nucleotide 1765; T→G modification of nucleotide 1771; T→C modification of nucleotide 1774; A→C modification of nucleotide 1780; T→C modification of nucleotide 1783; T→C modification of nucleotide 1786; A→C modification of nucleotide 1789; T→C modification of nucleotide 1792; T→C modification of nucleotide 1793; T→C modification of nucleotide 1798; T→C modification of nucleotide 1807; T→C modification of nucleotide 1813; A→C modification of nucleotide 1816; A→C modification of nucleotide 1819; A→G modification of nucleotide 1822; T→G modification of nucleotide 1825; T→C modification of nucleotide 1829; T→G modification of nucleotide 1834; T→G modification of nucleotide 1837; T→C modification of nucleotide 1840; A→C modification of nucleotide 1843; T→C modification of nucleotide 1846; T→C modification of nucleotide 1852; T→C modification of nucleotide 1864; G→C modification of nucleotide 1867; T→C modification of nucleotide 1876; G→C modification of nucleotide 1879; A→C modification of nucleotide 1882; A→G modification of nucleotide 1891; T→C modification of nucleotide 1894; G→C modification of nucleotide 1903; C→G modification of nucleotide 1906; A→G modification of nucleotide 1915; A→G modification of nucleotide 1918; A→C modification of nucleotide 1921; T→G modification of nucleotide 1924; A→G modification of nucleotide 1927; T→C modification of nucleotide 1930; T→C modification of nucleotide 1933; A→C modification of nucleotide 1939; T→G modification of nucleotide 1945; A→G modification of nucleotide 1954; T→C modification of nucleotide 1957; G→C modification of nucleotide 1960; T→C modification of nucleotide 1963; T→G modification of nucleotide 1966; A→C modification of nucleotide 1975; T→C modification of nucleotide 1978; T→G modification of nucleotide 1981; A→C modification of nucleotide 1985; A→C modification of nucleotide 1987; A→C modification of nucleotide 1990; A→G modification of nucleotide 1993; T→C modification of nucleotide 1996; T→C modification of nucleotide 2002; A→C modification of nucleotide 2005; T→C modification of nucleotide 2006; T→C modification of nucleotide 2011; T→G modification of nucleotide 2023; T→C modification of nucleotide 2026; T→C modification of nucleotide 2029; T→C modification of nucleotide 2035; A→G modification of nucleotide 2038; A→G modification of nucleotide 2047; A→C modification of nucleotide 2048; A→C modification of nucleotide 2050; A→G modification of nucleotide 2053; T→C modification of nucleotide 2056; A→C modification of nucleotide 2059; G→C modification of nucleotide 2062; C→G modification of nucleotide 2065; C→G modification of nucleotide 2068; T→C modification of nucleotide 2071; A→G modification of nucleotide 2074; T→G modification of nucleotide 2077; T→C modification of nucleotide 2080; A→G modification of nucleotide 2092; T→C modification of nucleotide 2095; A→C modification of nucleotide 2098; A→G modification of nucleotide 2101; T→C modification of nucleotide 2104; T→C modification of nucleotide 2107; A→G modification of nucleotide 2110; T→C modification of nucleotide 2113; A→C modification of nucleotide 2119; A→C modification of nucleotide 2125; T→C modification of nucleotide 2128; T→C modification of nucleotide 2131; A→C modification of nucleotide 2137; T→C modification of nucleotide 2141; A→G modification of nucleotide 2143; T→G modification of nucleotide 2146; T→C modification of nucleotide 2152; A→C modification of nucleotide 2153; G→C modification of nucleotide 2155; T→C modification of nucleotide 2158; A→G modification of nucleotide 2161; T→C modification of nucleotide 2164; G→C modification of nucleotide 2170; A→C modification of nucleotide 2173; T→C modification of nucleotide 2176; A→C modification of nucleotide 2179; T→C modification of nucleotide 2182; T→C modification of nucleotide 2185; T→G modification of nucleotide 2188; T→C modification of nucleotide 2189; A→C modification of nucleotide 2197; T→C modification of nucleotide 2203; A→C modification of nucleotide 2215; A→G modification of nucleotide 2218; T→C modification of nucleotide 2221; A→G modification of nucleotide 2230; G→C modification of nucleotide 2233; T→G modification of nucleotide 2236; A→C modification of nucleotide 2239; T→G modification of nucleotide 2242; A→T modification of nucleotide 2252; G→C modification of nucleotide 2253; T→C modification of nucleotide 2257; C→G modification of nucleotide 2260; A→C modification of nucleotide 2264; A→C modification of nucleotide 2266; A→C modification of nucleotide 2269; A→C modification of nucleotide 2275; T→C modification of nucleotide 2281; T→C modification of nucleotide 2287; T→C modification of nucleotide 2293; T→C modification of nucleotide 2296; T→C modification of nucleotide 2299; T→G modification of nucleotide 2302; A→C modification of nucleotide 2305; T→G modification of nucleotide 2308; T→C modification of nucleotide 2311; T→C modification of nucleotide 2314; T→C modification of nucleotide 2317; A→C modification of nucleotide 2326; A→G modification of nucleotide 2329; T→G modification of nucleotide 2335; A→C modification of nucleotide 2338; T→C modification of nucleotide 2341; T→C modification of nucleotide 2350; T→C modification of nucleotide 2353; T→C modification of nucleotide 2356; A→T modification of nucleotide 2357; G→C modification of nucleotide 2358; T→C modification of nucleotide 2362; T→C modification of nucleotide 2365; T→C modification of nucleotide 2368; T→C modification of nucleotide 2371; T→C modification of nucleotide 2377; T→C modification of nucleotide 2380; A→C modification of nucleotide 2383; T→C modification of nucleotide 2386; T→C modification of nucleotide 2395; T→C modification of nucleotide 2399; T→C modification of nucleotide 2404; A→G modification of nucleotide 2422; T→C modification of nucleotide 2425; T→C modification of nucleotide 2434; T→C modification of nucleotide 2447; T→C modification of nucleotide 2449; T→C modification of nucleotide 2452; T→C modification of nucleotide 2458; A→C modification of nucleotide 2461; T→G modification of nucleotide 2464; T→C modification of nucleotide 2467; G→C modification of nucleotide 2470; A→C modification of nucleotide 2476; T→C modification of nucleotide 2479; G→C modification of nucleotide 2485; T→C modification of nucleotide 2488; C→G modification of nucleotide 2500; T→C modification of nucleotide 2506; G→C modification of nucleotide 2509; T→C modification of nucleotide 2515; A→C modification of nucleotide 2518; T→C modification of nucleotide 2521; A→T modification of nucleotide 2525; G→C modification of nucleotide 2526; T→C modification of nucleotide 2530; T→C modification of nucleotide 2545; T→C modification of nucleotide 2548; T→C modification of nucleotide 2551; and deletion of nucleotides 2558-3197;

k) a sequence encoding yes-associated protein 1 (YAP) and comprising one or more of the following modifications relative to SEQ ID NO: 22 (e.g., one, two, three, four, or all of the following modifications):

deletion of nucleotides 1-402; T→C modification of nucleotide 408; G→C modification of nucleotide 414; G→C modification of nucleotide 423; G→C modification of nucleotide 426; T→C modification of nucleotide 429; A→G modification of nucleotide 432; G→C modification of nucleotide 435; A→G modification of nucleotide 450; G→C modification of nucleotide 453; G→C modification of nucleotide 459; T→C modification of nucleotide 462; G→C modification of nucleotide 465; G→C modification of nucleotide 474; G→C modification of nucleotide 480; G→C modification of nucleotide 489; G→C modification of nucleotide 492; A→C modification of nucleotide 498; G→C modification of nucleotide 504; A→G modification of nucleotide 507; G→C modification of nucleotide 510; A→C modification of nucleotide 513; G→C modification of nucleotide 519; G→C modification of nucleotide 522; G→C modification of nucleotide 531; G→C modification of nucleotide 534; G→C modification of nucleotide 537; A→C modification of nucleotide 543; G→C modification of nucleotide 555; T→C modification of nucleotide 558; C→G modification of nucleotide 573; G→C modification of nucleotide 579; G→C modification of nucleotide 585; G→C modification of nucleotide 603; C→G modification of nucleotide 606; C→G modification of nucleotide 618; G→C modification of nucleotide 633; A→C modification of nucleotide 661; G→C modification of nucleotide 663; C→G modification of nucleotide 666; G→C modification of nucleotide 669; G→C modification of nucleotide 696; G→C modification of nucleotide 699; A→G modification of nucleotide 708; A→C modification of nucleotide 720; A→T modification of nucleotide 727; G→C modification of nucleotide 728; T→C modification of nucleotide 729; T→C modification of nucleotide 732; T→C modification of nucleotide 735; A→C modification of nucleotide 738; T→C modification of nucleotide 744; A→C modification of nucleotide 747; A→C modification of nucleotide 750; T→C modification of nucleotide 759; A→C modification of nucleotide 762; T→C modification of nucleotide 768; T→G modification of nucleotide 771; A→C modification of nucleotide 774; T→C modification of nucleotide 777; T→C modification of nucleotide 780; T→G modification of nucleotide 781; T→C modification of nucleotide 786; A→C modification of nucleotide 789; T→C modification of nucleotide 792; T→C modification of nucleotide 795; T→C modification of nucleotide 802; A→C modification of nucleotide 807; T→C modification of nucleotide 810; T→G modification of nucleotide 813; T→C modification of nucleotide 816; T→C modification of nucleotide 819; T→C modification of nucleotide 822; A→C modification of nucleotide 825; T→C modification of nucleotide 837; A→C modification of nucleotide 840; A→G modification of nucleotide 843; C→G modification of nucleotide 846; T→C modification of nucleotide 849; A→C modification of nucleotide 855; A→C modification of nucleotide 858; T→C modification of nucleotide 861; A→C modification of nucleotide 864; A→C modification of nucleotide 870; T→C modification of nucleotide 873; T→C modification of nucleotide 879; T→G modification of nucleotide 882; A→C modification of nucleotide 885; T→C modification of nucleotide 891; T→C modification of nucleotide 894; T→C modification of nucleotide 897; A→C modification of nucleotide 903; T→C modification of nucleotide 906; T→C modification of nucleotide 909; T→C modification of nucleotide 912; A→G modification of nucleotide 915; T→C modification of nucleotide 918; A→C modification of nucleotide 924; A→C modification of nucleotide 927; T→C modification of nucleotide 930; A→C modification of nucleotide 942; A→C modification of nucleotide 948; T→C modification of nucleotide 951; T→C modification of nucleotide 954; T→C modification of nucleotide 957; A→C modification of nucleotide 961; A→C modification of nucleotide 963; T→C modification of nucleotide 970; A→G modification of nucleotide 972; T→C modification of nucleotide 975; T→C modification of nucleotide 984; A→C modification of nucleotide 990; A→C modification of nucleotide 993; A→C modification of nucleotide 996; A→C modification of nucleotide 1009; G→C modification of nucleotide 1011; C→G modification of nucleotide 1038; A→C modification of nucleotide 1041; A→T modification of nucleotide 1051; G→C modification of nucleotide 1052; T→C modification of nucleotide 1053; A→C modification of nucleotide 1056; A→C modification of nucleotide 1059; T→C modification of nucleotide 1071; G→C modification of nucleotide 1083; T→C modification of nucleotide 1086; A→C modification of nucleotide 1089; T→C modification of nucleotide 1092; T→C modification of nucleotide 1095; T→G modification of nucleotide 1098; T→C modification of nucleotide 1101; T→C modification of nucleotide 1104; A→C modification of nucleotide 1107; A→G modification of nucleotide 1113; A→G modification of nucleotide 1116; T→C modification of nucleotide 1125; T→C modification of nucleotide 1131; A→C modification of nucleotide 1134; A→G modification of nucleotide 1137; T→C modification of nucleotide 1140; T→C modification of nucleotide 1146; A→C modification of nucleotide 1149; T→C modification of nucleotide 1155; T→C modification of nucleotide 1173; A→G modification of nucleotide 1179; A→C modification of nucleotide 1185; A→C modification of nucleotide 1186; G→C modification of nucleotide 1188; T→G modification of nucleotide 1191; T→C modification of nucleotide 1197; T→C modification of nucleotide 1200; T→C modification of nucleotide 1203; A→C modification of nucleotide 1216; A→C modification of nucleotide 1218; A→T modification of nucleotide 1222; G→C modification of nucleotide 1223; T→C modification of nucleotide 1224; A→T modification of nucleotide 1228; G→C modification of nucleotide 1229; T→C modification of nucleotide 1230; T→C modification of nucleotide 1233; A→C modification of nucleotide 1236; A→G modification of nucleotide 1242; A→C modification of nucleotide 1248; A→C modification of nucleotide 1251; T→C modification of nucleotide 1260; A→T modification of nucleotide 1267; G→C modification of nucleotide 1268; A→C modification of nucleotide 1272; A→C modification of nucleotide 1278; C→G modification of nucleotide 1284; T→C modification of nucleotide 1290; A→T modification of nucleotide 1294; G→C modification of nucleotide 1295; A→G modification of nucleotide 1314; A→C modification of nucleotide 1323; A→G modification of nucleotide 1332; A→C modification of nucleotide 1351; G→C modification of nucleotide 1353; G→C modification of nucleotide 1359; A→G modification of nucleotide 1365; A→G modification of nucleotide 1371; A→G modification of nucleotide 1374; T→G modification of nucleotide 1380; G→C modification of nucleotide 1383; T→C modification of nucleotide 1390; A→G modification of nucleotide 1392; T→C modification of nucleotide 1401; A→T modification of nucleotide 1402; G→C modification of nucleotide 1403; T→C modification of nucleotide 1408; A→G modification of nucleotide 1410; A→C modification of nucleotide 1413; A→C modification of nucleotide 1416; T→C modification of nucleotide 1428; T→C modification of nucleotide 1431; G→C modification of nucleotide 1434; T→C modification of nucleotide 1437; A→G modification of nucleotide 1440; T→C modification of nucleotide 1443; A→C modification of nucleotide 1446; T→C modification of nucleotide 1452; T→C modification of nucleotide 1455; G→C modification of nucleotide 1461; T→C modification of nucleotide 1467; A→G modification of nucleotide 1473; T→C modification of nucleotide 1474; A→C modification of nucleotide 1477; A→C modification of nucleotide 1479; A→C modification of nucleotide 1482; G→C modification of nucleotide 1488; T→C modification of nucleotide 1494; A→T modification of nucleotide 1495; G→C modification of nucleotide 1496; A→C modification of nucleotide 1500; T→C modification of nucleotide 1503; T→C modification of nucleotide 1506; T→G modification of nucleotide 1512; A→T modification of nucleotide 1516; G→C modification of nucleotide 1517; T→C modification of nucleotide 1518; T→C modification of nucleotide 1527; T→C modification of nucleotide 1533; A→C modification of nucleotide 1536; T→C modification of nucleotide 1539; A→T modification of nucleotide 1543; G→C modification of nucleotide 1544; T→C modification of nucleotide 1545; A→C modification of nucleotide 1548; A→T modification of nucleotide 1552; G→C modification of nucleotide 1553; T→C modification of nucleotide 1554; A→C modification of nucleotide 1557; A→G modification of nucleotide 1560; A→T modification of nucleotide 1561; G→C modification of nucleotide 1562; A→T modification of nucleotide 1567; G→C modification of nucleotide 1568; A→T modification of nucleotide 1570; G→C modification of nucleotide 1571; A→T modification of nucleotide 1576; G→C modification of nucleotide 1577; T→C modification of nucleotide 1578; C→G modification of nucleotide 1581; T→C modification of nucleotide 1584; A→C modification of nucleotide 1587; A→C modification of nucleotide 1593; T→C modification of nucleotide 1596; A→T modification of nucleotide 1609; G→C modification of nucleotide 1610; T→C modification of nucleotide 1611; T→C modification of nucleotide 1617; T→C modification of nucleotide 1626; A→C modification of nucleotide 1629; T→C modification of nucleotide 1632; T→C modification of nucleotide 1635; T→C modification of nucleotide 1638; A→G modification of nucleotide 1647; A→T modification of nucleotide 1648; G→C modification of nucleotide 1649; A→C modification of nucleotide 1662; T→C modification of nucleotide 1674; A→C modification of nucleotide 1680; T→G modification of nucleotide 1689; A→G modification of nucleotide 1692; T→C modification of nucleotide 1698; T→C modification of nucleotide 1701; G→C modification of nucleotide 1704; A→C modification of nucleotide 1707; T→C modification of nucleotide 1710; T→G modification of nucleotide 1719; A→C modification of nucleotide 1722; A→C modification of nucleotide 1725; A→G modification of nucleotide 1731; A→C modification of nucleotide 1734; T→C modification of nucleotide 1737; A→C modification of nucleotide 1740; A→C modification of nucleotide 1749; A→G modification of nucleotide 1752; A→C modification of nucleotide 1755; A→C modification of nucleotide 1770; A→T modification of nucleotide 1771; G→C modification of nucleotide 1772; T→C modification of nucleotide 1773; A→G modification of nucleotide 1782; T→C modification of nucleotide 1785; T→C modification of nucleotide 1786; A→T modification of nucleotide 1789; G→C modification of nucleotide 1790; T→C modification of nucleotide 1791; T→C modification of nucleotide 1794; T→G modification of nucleotide 1803; T→C modification of nucleotide 1806; T→C modification of nucleotide 1818; T→G modification of nucleotide 1821; T→C modification of nucleotide 1822; T→C modification of nucleotide 1827; A→G modification of nucleotide 1839; T→C modification of nucleotide 1842; A→G modification of nucleotide 1845; A→G modification of nucleotide 1848; A→T modification of nucleotide 1849; G→C modification of nucleotide 1850; T→C modification of nucleotide 1854; T→G modification of nucleotide 1857; A→C modification of nucleotide 1860; and deletion of nucleotides 1864-5353;

l) a sequence encoding wingless-type MMTV integration site family, member 2 (WNT2) and comprising one or more of the following modifications relative to SEQ ID NO: 23 (e.g., one, two, three, four, or all of the following modifications):

deletion of nucleotides 1-158; C→G modification of nucleotide 167; T→C modification of nucleotide 170; C→G modification of nucleotide 173; T→C modification of nucleotide 176; A→C modification of nucleotide 179; C→G modification of nucleotide 188; C→G modification of nucleotide 194; T→C modification of nucleotide 197; C→G modification of nucleotide 203; T→C modification of nucleotide 204; C→G modification of nucleotide 215; T→C modification of nucleotide 221; C→G modification of nucleotide 227; A→T modification of nucleotide 228; G→C modification of nucleotide 229; T→C modification of nucleotide 233; A→C modification of nucleotide 236; A→C modification of nucleotide 249; A→C modification of nucleotide 251; T→C modification of nucleotide 254; A→C modification of nucleotide 257; T→C modification of nucleotide 260; A→C modification of nucleotide 270; G→C modification of nucleotide 272; T→C modification of nucleotide 281; T→C modification of nucleotide 287; A→C modification of nucleotide 293; A→T modification of nucleotide 303; G→C modification of nucleotide 304; G→C modification of nucleotide 308; T→C modification of nucleotide 314; A→C modification of nucleotide 329; A→C modification of nucleotide 335; T→C modification of nucleotide 338; T→C modification of nucleotide 347; T→C modification of nucleotide 353; T→C modification of nucleotide 362; T→C modification of nucleotide 368; T→C modification of nucleotide 377; A→C modification of nucleotide 380; A→G modification of nucleotide 389; T→C modification of nucleotide 407; A→C modification of nucleotide 432; A→C modification of nucleotide 434; T→C modification of nucleotide 437; A→T modification of nucleotide 441; G→C modification of nucleotide 442; C→G modification of nucleotide 446; T→C modification of nucleotide 449; G→C modification of nucleotide 455; T→C modification of nucleotide 458; C→G modification of nucleotide 461; C→G modification of nucleotide 464; A→C modification of nucleotide 467; A→T modification of nucleotide 468; G→C modification of nucleotide 469; T→C modification of nucleotide 470; A→T modification of nucleotide 471; G→C modification of nucleotide 472; T→C modification of nucleotide 473; G→C modification of nucleotide 476; A→G modification of nucleotide 479; G→C modification of nucleotide 482; T→C modification of nucleotide 488; T→G modification of nucleotide 491; T→C modification of nucleotide 503; A→C modification of nucleotide 506; T→C modification of nucleotide 509; T→G modification of nucleotide 515; A→G modification of nucleotide 518; T→C modification of nucleotide 521; A→C modification of nucleotide 531; G→C modification of nucleotide 533; T→C modification of nucleotide 539; A→T modification of nucleotide 540; G→C modification of nucleotide 541; A→G modification of nucleotide 545; A→C modification of nucleotide 548; A→G modification of nucleotide 551; T→C modification of nucleotide 552; A→G modification of nucleotide 554; T→C modification of nucleotide 569; T→C modification of nucleotide 572; A→C modification of nucleotide 575; A→G modification of nucleotide 584; A→C modification of nucleotide 587; A→T modification of nucleotide 588; G→C modification of nucleotide 589; T→C modification of nucleotide 590; A→T modification of nucleotide 600; G→C modification of nucleotide 601; A→G modification of nucleotide 605; T→C modification of nucleotide 623; A→T modification of nucleotide 630; G→C modification of nucleotide 631; T→C modification of nucleotide 632; T→C modification of nucleotide 638; T→C modification of nucleotide 641; G→C modification of nucleotide 650; T→C modification of nucleotide 659; T→C modification of nucleotide 665; T→C modification of nucleotide 671; A→G modification of nucleotide 674; T→C modification of nucleotide 677; A→C modification of nucleotide 687; G→C modification of nucleotide 689; A→G modification of nucleotide 692; T→C modification of nucleotide 701; A→C modification of nucleotide 705; A→C modification of nucleotide 707; T→G modification of nucleotide 722; A→C modification of nucleotide 732; A→C modification of nucleotide 734; T→C modification of nucleotide 737;

A→C modification of nucleotide 740; A→C modification of nucleotide 741; G→C modification of nucleotide 743; T→C modification of nucleotide 749; A→G modification of nucleotide 752; T→C modification of nucleotide 762; A→G modification of nucleotide 767; A→G modification of nucleotide 770; A→G modification of nucleotide 773; T→C modification of nucleotide 782; T→C modification of nucleotide 785; T→C modification of nucleotide 788; A→T modification of nucleotide 792; G→C modification of nucleotide 793; T→C modification of nucleotide 794; T→C modification of nucleotide 803; T→C modification of nucleotide 806; A→C modification of nucleotide 810; G→C modification of nucleotide 812; A→C modification of nucleotide 815; T→C modification of nucleotide 833; A→C modification of nucleotide 840; G→C modification of nucleotide 842; A→G modification of nucleotide 845; A→C modification of nucleotide 848; T→C modification of nucleotide 857; C→G modification of nucleotide 860; A→C modification of nucleotide 864; G→C modification of nucleotide 866; T→C modification of nucleotide 875; G→C modification of nucleotide 878; A→G modification of nucleotide 890; C→G modification of nucleotide 893; T→C modification of nucleotide 905; T→C modification of nucleotide 911; T→C modification of nucleotide 920; A→G modification of nucleotide 923; T→C modification of nucleotide 929; A→C modification of nucleotide 933; G→C modification of nucleotide 935; T→C modification of nucleotide 938; A→C modification of nucleotide 947; G→C modification of nucleotide 950; A→G modification of nucleotide 953; T→C modification of nucleotide 956; C→G modification of nucleotide 962; T→C modification of nucleotide 968; T→C modification of nucleotide 971; T→C modification of nucleotide 977; T→C modification of nucleotide 980; A→C modification of nucleotide 983; T→C modification of nucleotide 992; A→C modification of nucleotide 996; G→C modification of nucleotide 998; A→C modification of nucleotide 1004; A→C modification of nucleotide 1010; T→C modification of nucleotide 1022; A→C modification of nucleotide 1025; G→C modification of nucleotide 1028; T→C modification of nucleotide 1034; T→C modification of nucleotide 1044; T→C modification of nucleotide 1049; A→C modification of nucleotide 1055; A→T modification of nucleotide 1065; G→C modification of nucleotide 1066; A→G modification of nucleotide 1073; T→G modification of nucleotide 1076; T→C modification of nucleotide 1082; T→C modification of nucleotide 1085; G→C modification of nucleotide 1088; A→C modification of nucleotide 1089; A→C modification of nucleotide 1091; T→C modification of nucleotide 1097; A→C modification of nucleotide 1103; C→G modification of nucleotide 1112; G→C modification of nucleotide 1118; T→C modification of nucleotide 1130; T→C modification of nucleotide 1136; A→G modification of nucleotide 1139; T→C modification of nucleotide 1154; T→C modification of nucleotide 1166; A→C modification of nucleotide 1199; A→T modification of nucleotide 1215; G→C modification of nucleotide 1216; T→C modification of nucleotide 1217; and deletion of nucleotides 1229-2115; and/or m) a sequence encoding wingless-type MMTV integration site family, member 9B (WNT9b) and comprising one or more of the following modifications relative to SEQ ID NO: 24 (e.g., one, two, three, four, or all of the following modifications):

deletion of nucleotides 1-52; G→C modification of nucleotide 64; G→C modification of nucleotide 70; T→C modification of nucleotide 82; G→C modification of nucleotide 85; G→C modification of nucleotide 88; T→C modification of nucleotide 106; T→C modification of nucleotide 112; T→C modification of nucleotide 145; T→C modification of nucleotide 148; C→G modification of nucleotide 154; A→C modification of nucleotide 160; A→C modification of nucleotide 169; T→C modification of nucleotide 178; G→C modification of nucleotide 181; A→C modification of nucleotide 184; A→C modification of nucleotide 187; G→C modification of nucleotide 193; A→C modification of nucleotide 196; T→C modification of nucleotide 202; T→C modification of nucleotide 205; T→C modification of nucleotide 208; T→C modification of nucleotide 223; A→G modification of nucleotide 229; A→C modification of nucleotide 242; G→C modification of nucleotide 244; G→C modification of nucleotide 247; C→G modification of nucleotide 259; A→C modification of nucleotide 263; G→C modification of nucleotide 265; G→C modification of nucleotide 268; T→C modification of nucleotide 283; A→C modification of nucleotide 293; G→C modification of nucleotide 295; T→C modification of nucleotide 298; T→C modification of nucleotide 301; A→C modification of nucleotide 304; G→C modification of nucleotide 313; A→G modification of nucleotide 322; T→C modification of nucleotide 325; A→C modification of nucleotide 338; G→C modification of nucleotide 340; A→T modification of nucleotide 359; G→C modification of nucleotide 360; G→C modification of nucleotide 370; A→C modification of nucleotide 371; G→C modification of nucleotide 373; T→C modification of nucleotide 376; C→G modification of nucleotide 385; A→C modification of nucleotide 389; A→C modification of nucleotide 391; T→C modification of nucleotide 397; G→C modification of nucleotide 406; T→C modification of nucleotide 418; A→C modification of nucleotide 421; T→C modification of nucleotide 427; A→C modification of nucleotide 430; T→C modification of nucleotide 433; C→G modification of nucleotide 439; G→C modification of nucleotide 442; T→C modification of nucleotide 445; A→C modification of nucleotide 448; T→C modification of nucleotide 455; G→C modification of nucleotide 457; A→T modification of nucleotide 464; G→C modification of nucleotide 465; T→C modification of nucleotide 466; T→C modification of nucleotide 469; G→C modification of nucleotide 472; T→C modification of nucleotide 487; T→C modification of nucleotide 490; T→C modification of nucleotide 493; A→C modification of nucleotide 505; A→T modification of nucleotide 515; G→C modification of nucleotide 516; G→C modification of nucleotide 520; T→C modification of nucleotide 538; T→C modification of nucleotide 544; T→C modification of nucleotide 547; T→C modification of nucleotide 553; A→T modification of nucleotide 563; G→C modification of nucleotide 564; C→G modification of nucleotide 577; A→T modification of nucleotide 578; G→C modification of nucleotide 579; G→C modification of nucleotide 592; A→C modification of nucleotide 599; A→C modification of nucleotide 601; A→C modification of nucleotide 604; A→T modification of nucleotide 605; G→C modification of nucleotide 606; A→C modification of nucleotide 617; G→C modification of nucleotide 619; G→C modification of nucleotide 622; A→C modification of nucleotide 623; G→C modification of nucleotide 625; T→C modification of nucleotide 628; T→C modification of nucleotide 661; A→T modification of nucleotide 668; G→C modification of nucleotide 669; A→C modification of nucleotide 677; A→C modification of nucleotide 679; A→C modification of nucleotide 682; T→C modification of nucleotide 697; T→C modification of nucleotide 700; A→C modification of nucleotide 706; T→C modification of nucleotide 715; T→C modification of nucleotide 718; T→G modification of nucleotide 721; T→C modification of nucleotide 724; T→C modification of nucleotide 730; C→G modification of nucleotide 742; G→C modification of nucleotide 748; T→C modification of nucleotide 751; A→G modification of nucleotide 778; T→C modification of nucleotide 784; G→C modification of nucleotide 790; T→C modification of nucleotide 793; C→G modification of nucleotide 796; A→T modification of nucleotide 806; G→C modification of nucleotide 807; T→C modification of nucleotide 808; T→C modification of nucleotide 824; T→C modification of nucleotide 829; T→C modification of nucleotide 832; A→G modification of nucleotide 841; T→C modification of nucleotide 853; A→C modification of nucleotide 859; T→C modification of nucleotide 862; T→C modification of nucleotide 865; A→G modification of nucleotide 880; T→C modification of nucleotide 886; T→C modification of nucleotide 889; G→C modification of nucleotide 895; C→G modification of nucleotide 904; A→G modification of nucleotide 913; T→C modification of nucleotide 916; T→C modification of nucleotide 919; A→T modification of nucleotide 923; G→C modification of nucleotide 924; G→C modification of nucleotide 934; A→T modification of nucleotide 938; G→C modification of nucleotide 939; T→C modification of nucleotide 949; G→C modification of nucleotide 952; G→C modification of nucleotide 958; A→C modification of nucleotide 961; A→C modification of nucleotide 965; G→C modification of nucleotide 967; T→C modification of nucleotide 973; T→C modification of nucleotide 976; A→C modification of nucleotide 979; A→T modification of nucleotide 986; G→C modification of nucleotide 987; T→C modification of nucleotide 988; A→T modification of nucleotide 992; G→C modification of nucleotide 993; A→T modification of nucleotide 995; G→C modification of nucleotide 996; A→G modification of nucleotide 1000; T→C modification of nucleotide 1006; G→C modification of nucleotide 1009; A→C modification of nucleotide 1012; A→T modification of nucleotide 1028; G→C modification of nucleotide 1029; T→G modification of nucleotide 1042; T→C modification of nucleotide 1057; T→C modification of nucleotide 1096; A→C modification of nucleotide 1099; C→G modification of nucleotide 1111; T→C modification of nucleotide 1117; and deletion of nucleotides 1130-4519.

In some embodiments of any of the aspects, the mRNA comprises one of the foregoing sequences comprising each of the listed modifications.

In some embodiments of any of the aspects, the at least one engineered liver regenerative factor mRNA comprises one or more of:
a) SEQ ID NO: 8 (GH);
b) SEQ ID NO: 9 (EGF);
c) SEQ ID NO: 10 (HGF);
d) SEQ ID NO: 11 (p21);
e) SEQ ID NO: 12 (VEGF165);
f) SEQ ID NO: 13 (IGF-1);
g) SEQ ID NO: 14 (IGF-1 IL-2 SP);
h) SEQ ID NO: 15 (secreted EGF);
i) SEQ ID NO: 16 (stat5bca);
j) SEQ ID NO: 21 (beta catenin);
k) SEQ ID NO: 25 (YAP);
l) SEQ ID NO: 26 (WNT2); and
m) SEQ ID NO: 27 (WNT9B).

In some embodiments of any of the aspects, the at least one engineered liver regenerative factor mRNA further comprises at least one modified nucleoside.

In one aspect of any of the embodiments, described herein is a composition comprising at least one liver regenerative factor mRNAs comprising at least one modified nucleoside; wherein the at least one liver regenerative factor is selected from the group consisting of: vascular endothelial growth factor A (VEGFA); hepatocyte growth factor (HGF); growth hormone (GH); insulin-like growth factor 1 (IGF-1), epidermal growth factor (EGF); signal transducer and activator of transcription 5B (STAT5b); cyclin-dependent kinase inhibitor 1A (p21); beta catenin (CTNNB1); yes-associated protein (YAP); wingless-type MMTV integration site family, member 2 (WNT2); and wingless-type MMTV integration site family, member 9B (WNT9b).

In some embodiments of any of the aspects, the composition further comprises a carrier complexed with the at least one engineered liver regenerative factor mRNA or the at least one liver regenerative factor mRNA comprising at least one modified nucleoside. In some embodiments of any of the aspects, the carrier is a nanoparticle. In some embodiments of any of the aspects, the carrier is a polymer nanoparticle. In some embodiments of any of the aspects, the nanoparticle is a lipid nanoparticle (LNP).

In some embodiments of any of the aspects, the at least one liver regenerative factor is selected from the group consisting of: VEGFA; HGF; GH; and EGF. In some embodiments of any of the aspects, the at least one liver regenerative factor is selected from the group consisting of: HGF; GH; EGF; and p21. In some embodiments of any of the aspects, the at least one liver regenerative factor is selected from the group consisting of: HGF; GH; and EGF. In some embodiments of any of the aspects, the at least one liver regenerative factor comprises two or more liver regenerative factors selected from the group consisting of: VEGFA; HGF; GH; IGF-1; EGF; STAT5bCA; p21; CNNTB1; YAP; WNT2; and WNT9b.

In some embodiments of any of the aspects, the at least one liver regenerative factor is a human liver regenerative factor or a murine liver regenerative factor.

In some embodiments of any of the aspects, the at least one modified nucleoside comprises at least one non-natural nucleoside. In some embodiments of any of the aspects, the at least one modified nucleoside is selected from the group consisting of: pseudouridine, N1-methylpseudouridine, 2-thiouridine, 4'-thiouridine, 5-methylcytosine, 2-thio-1-methyl-1-deaza-pseudouridine, 2-thio-1-methyl-pseudouridine, 2-thio-5-aza-uridine, 2-thio-dihydropseudouridine, 2-thio-dihydrouridine, 2-thio-pseudouridine, 4-methoxy-pseudouridine, 4-thio-1-methyl-pseudouridine, 4-thiopseudouridine, 5-aza-uridine, dihydropseudouridine, 5-methyluridine, pseudouridine, and mixtures thereof, 5-methyluridine, 5-methoxyuridine, and 2'-O-methyluridine. In some embodiments of any of the aspects, the at least one modified nucleoside comprises at least one-methylpseudouridine (m1Ψ)-5' triphosphate (TriLink).

In some embodiments of any of the aspects, the LNP comprises at least one ionizable lipid, at least one phospholipid, at least one structured lipid, and at least one polyethylene glycol (PEG)-lipid. In some embodiments of any of the aspects, the at least one ionizable lipid is selected from the group consisting of: 2,2-dioleyl-4-dimethylaminoethyl-[1,3]-dioxolane (DLin-KC2-DMA); dioleyl-methyl 4-dimethylaminobutyrate (DLin-MC3-DMA); and di ((Z)-non-2-en-1-yl) 9-((4-(dimethylamino) butyryl) oxy) heptadecanedioate (L319). In some embodiments of any of the aspects, the at least one ionizable lipid has a pKA in the range of 6.0-6.5. In some embodiments of any of the aspects, the at least one phospholipid comprises phosphatidylcholine. In some embodiments of any of the aspects, the at least one structured lipid comprises cholesterol.

In some embodiments of any of the aspects, the at least one engineered liver regenerative factor mRNA or the at least one liver regenerative factor mRNA comprising at least one modified nucleoside is encapsulated in the nanoparticle. In some embodiments of any of the aspects, the at least one engineered liver regenerative factor mRNA or the at least one liver regenerative factor mRNA comprising at least one modified nucleoside is in an aqueous solution and in admixture with an ethanolic lipid mixture at acidic pH. In some embodiments of any of the aspects, the at least one engineered liver regenerative factor mRNA or the at least one liver regenerative factor mRNA comprising at least one modified nucleoside is complexed to the LNP in a way selected from the group consisting of: encapsulation in the interior of the LNP; interspersed within the lipid bilayer of the LNP; and attached to the LNP via a linking molecule.

In some embodiments of any of the aspects, the liver regenerative factor comprises GH; and the at least one engineered liver regenerative factor mRNA or the at least one liver regenerative factor mRNA comprising at least one modified nucleoside comprises a nucleotide sequence having at least 80% (e.g., at least 80%, at least 85%, at least 90%, at least 95%, at least 98% or greater) sequence identity to the nucleotide sequence set forth in SEQ ID NO: 8. In some embodiments of any of the aspects, the liver regenerative factor comprises EGF; and the at least one engineered liver regenerative factor mRNA or the at least one liver regenerative factor mRNA comprising at least one modified nucleoside comprises a nucleotide sequence having at least 80% (e.g., at least 80%, at least 85%, at least 90%, at least 95%, at least 98% or greater) sequence identity to the nucleotide sequence set forth in SEQ ID NO: 9. In some embodiments of any of the aspects, the liver regenerative factor comprises HGF; and the at least one engineered liver regenerative factor mRNA or the at least one liver regenerative factor mRNA comprising at least one modified nucleoside comprises a nucleotide sequence having at least 80% (e.g., at least 80%, at least 85%, at least 90%, at least 95%, at least 98% or greater) sequence identity to the nucleotide sequence set forth in SEQ ID NO: 10. In some embodiments of any of the aspects, the liver regenerative factor comprises p21; and the at least one engineered liver regenerative factor mRNA or the at least one liver regenerative factor mRNA comprising at least one modified nucleoside comprises a nucleotide sequence having at least 80% (e.g., at least 80%, at least 85%, at least 90%, at least 95%, at least 98% or greater) sequence identity to the nucleotide sequence set forth in SEQ ID NO: 11. In some embodiments of any of the aspects, the liver regenerative factor comprises VEGF; and the at least one engineered liver regenerative factor mRNA or the at least one liver regenerative factor mRNA comprising at least one modified nucleoside comprises a nucleotide sequence having at least 80% (e.g., at least 80%, at least 85%, at least 90%, at least 95%, at least 98% or greater) sequence identity to the nucleotide sequence set forth in SEQ ID NO: 12. In some embodiments of any of the aspects, the liver regenerative factor comprises IGF-1; and the at least one engineered liver regenerative factor mRNA or the at least one liver regenerative factor mRNA comprising at least one modified nucleoside comprises a nucleotide sequence having at least 80% (e.g., at least 80%, at least 85%, at least 90%, at least 95%, at least 98% or greater) sequence identity to the nucleotide sequence set forth in SEQ ID NO: 13. In some embodiments of any of the aspects, the liver regenerative factor comprises IGF-1 IL-2 SP; and the at least one engineered liver regenerative factor mRNA or the at least one liver regenerative factor mRNA comprising at least one modified nucleoside comprises a nucleotide sequence having at least 80% (e.g., at least 80%, at least 85%, at least 90%, at least 95%, at least 98% or greater) sequence identity to the nucleotide sequence set forth in SEQ ID NO: 14. In some embodiments of any of the aspects, the liver regenerative factor comprises secreted EGF; and the at least one engineered liver regenerative factor mRNA or the at least one liver regenerative factor mRNA comprising at least one modified nucleoside comprises a nucleotide sequence having at least 80% (e.g., at least 80%, at least 85%, at least 90%, at least 95%, at least 98% or greater) sequence identity to the nucleotide sequence set forth in SEQ ID NO: 15. In some embodiments of any of the aspects, the liver regenerative factor comprises stat5b; and the at least one engineered liver regenerative factor mRNA or the at least one liver regenerative factor mRNA comprising at least one modified nucleoside comprises a nucleotide sequence having at least 80% (e.g., at least 80%, at least 85%, at least 90%, at least 95%, at least 98% or greater) sequence identity to the nucleotide sequence set forth in SEQ ID NO: 16. In some embodiments of any of the aspects, the liver regenerative factor comprises beta catenin; and the at least one engineered liver regenerative factor mRNA or the at least one liver regenerative factor mRNA comprising at least one modified nucleoside comprises a nucleotide sequence having at least 80% (e.g., at least 80%, at least 85%, at least 90%, at least 95%, at least 98% or greater) sequence identity to the nucleotide sequence set forth in SEQ ID NO: 21. In some embodiments of any of the aspects, the liver regenerative factor comprises YAP; and the at least one engineered liver regenerative factor mRNA or the at least one liver regenerative factor mRNA comprising at least one modified nucleoside comprises a nucleotide sequence having at least 80% (e.g., at least 80%, at least 85%, at least 90%, at least 95%, at least 98% or greater) sequence identity to the nucleotide sequence set forth in SEQ ID NO: 25. In some embodiments of any of the aspects, the liver regenerative factor comprises WNT2; and the at least one engineered liver regenerative factor mRNA or the at least one liver regenerative factor mRNA comprising at least one modified nucleoside comprises a nucleotide sequence having at least 80% (e.g., at least 80%, at least 85%, at least 90%, at least 95%, at least 98% or greater) sequence identity to the nucleotide sequence set forth in SEQ ID NO: 26. In some embodiments of any of the aspects, the liver regenerative factor comprises WNT9b; and the at least one engineered liver regenerative factor mRNA or the at least one liver regenerative factor mRNA comprising at least one modified nucleoside comprises a nucleotide sequence having at least 80% (e.g., at least 80%, at least 85%, at least 90%, at least 95%, at least 98% or greater) sequence identity to the nucleotide sequence set forth in SEQ ID NO: 27.

In some embodiments of any of the aspects, the composition further comprises N-acetyl cysteine (NAC). In one aspect of any of the embodiments, described herein is the combination of a composition described herein and N-acetyl cysteine (NAC).

In one aspect of any of the embodiments, described herein is a method of treating liver injury or liver disease in a subject in need thereof, the method comprising administering the composition or combination as described herein to the subject. In one aspect of any of the embodiments, described herein is a method of accelerating intrinsic liver repair in a subject in need thereof, the method comprising administering the composition or combination as described herein to the subject. In some embodiments of any of the aspects, the subject is a subject in need of treatment for acute liver disease, chronic liver disease, or acetaminophen (acetyl-para-aminophenol, APAP) overdose. In some embodiments of any of the aspects, the acute or chronic liver disease is selected from the group consisting of: haemophilia; familial hypercholesterolemia; ornithine transcarbamylase deficiency; α-antitrypsin deficiency; non-alcoholic fatty liver disease (NAFLD); non-alcoholic steatohepatitis (NASH); liver fibrosis; liver cirrhosis; alcoholic fatty liver disease; alcohol-related liver disease (ARLD); phenylketonuria; glycogen storage disease; α1-antitrypsin deficiency; hereditary hemochromatosis; tyrosinemia type 1; argininosuccinic aciduria; hepatitis virus infection; non-viral hepatitis; autoimmune hepatitis; primary biliary cholangitis; cirrhosis, biliary atresia; liver cancer; genetic cholestasis; hemochromatosis; Gilbert syndrome; primary sclerosing cholangitis (PSC); and Wilson's disease. In some embodiments of any of the aspects, the method further comprises administering N-acetyl cysteine (NAC) to the subject.

In one aspect of any of the embodiments, described herein is a method of engrafting cells in a liver tissue, the method comprising introducing the cells into the liver tissue and contacting the cells or the liver tissue with the composition or combination described herein. In some embodiments of any of the aspects, the cells are primary human hepatocytes (PHH) or induced pluripotent stem cell-derived hepatocyte-like-cells (iPSC-HLCs). In some embodiments of any of the aspects, the liver tissue is a liver in a subject, the introducing comprises transplanting the cells into the liver, and the contacting comprises administering. In some embodiments of any of the aspects, the subject is a subject in need of treatment for acute liver disease, chronic liver disease, or genetic liver disease. In some embodiments of any of the aspects, the acute or chronic liver disease is selected from the group consisting of: haemophilia; familial hypercholesterolemia; ornithine transcarbamylase deficiency; α-antitrypsin deficiency; non-alcoholic fatty liver disease (NAFLD); non-alcoholic steatohepatitis (NASH); liver fibrosis; liver cirrhosis; alcoholic fatty liver disease; alcohol-related liver disease (ARLD); phenylketonuria; glycogen storage disease; α1-antitrypsin deficiency; hereditary hemochromatosis; tyrosinemia type 1; argininosuccinic aciduria; hepatitis virus infection; non-viral hepatitis; autoimmune hepatitis; primary biliary cholangitis; cirrhosis, biliary atresia; liver cancer; genetic cholestasis; hemochromatosis; Gilbert syndrome; primary sclerosing cholangitis (PSC); and Wilson's disease. In some embodiments of any of the aspects, the subject is a subject in need of treatment for alpha-1 antitrypsin deficiency associated liver disease (AATD).

In some embodiments of any of the aspects, the composition or combination is administered once. In some embodiments of any of the aspects, the composition or combination is administered twice or more. In some embodiments of any of the aspects, the composition or combination comprises two or more liver regenerative factor mRNAs. In some embodiments of any of the aspects, the method comprising administering a first composition or combination comprising a first liver regenerative factor mRNA and concurrently administering a second composition or combination comprising a second liver regenerative factor mRNA. In some embodiments of any of the aspects, the method comprises administering a first composition or combination comprising a first liver regenerative factor mRNA and separately administering a second composition or combination comprising a second liver regenerative factor mRNA.

In some embodiments of any of the aspects, the administering is intravenous administration. In some embodiments of any of the aspects, the administering is via the common bile duct or to the gallbladder.

BRIEF DESCRIPTION OF THE DRAWINGS

(FIG. 1A) Single-optical section images showing the expression of Bhmt, Tp1:H2B-mCherry, and fabp10a:CFP-NTR in regenerating livers (dotted lines) at R24h. Scheme illustrates the periods of Mtz and SU5416 treatments and an analysis stage. Quantification of the percentage of hepatocytes (Bhmt$^+$) among BEC-derived cells (H2B-mCherry$^+$) and quantification of liver size are shown. (FIG. 1B) Whole-mount in situ hybridization images showing gc and f5 expression (arrows) in regenerating livers at R24h. Numbers in the upper-right corner indicate the proportion of larvae exhibiting the phenotype shown. Based on the levels of hepatic gc and f5 expression, larvae were divided into three groups: no, weak, and strong. (FIG. 1C) Single-optical section images showing the expression of Tp1:H2B-mCherry, fabp10a:CFP-NTR, and Bhmt in regenerating livers (dashed lines) at R26h. To overexpress sFlt1, Tg(hs:sflt1) larvae were heat-shocked four times at A13h, A24h, A35h, and R10h. Quantification of the percentage of Bhmt$^+$ among BEC-derived cells and quantification of liver size are shown. (FIG. 1D) Maximum projection images showing the expression of hs:loxP-mCherry-loxP and Bhmt in regenerating livers (dashed lines) at R3h. The Tg(Tp1:CreERT2) and Tg(hs:loxP-mCherry-loxP-hVEGFA) lines were used to express hVEGFA in a subset of BEC-derived cells during regeneration. Larvae were treated with 10 µM 4-OHT from 2.5 to 3.5 dpf for 24 hours, heat-shocked twice at A20h and A34h, and harvested at R3h. Quantification of the percentage of Bhmt$^+$ area in the liver is shown. Data are presented as mean±SEM. (D) p<0.01, *p<0.001, and ****p<0.0001; statistical significance was calculated using an unpaired two-tailed t-test. Scale bars: 50 (FIGS. 1A, 1C, 1D), 100 (FIG. 1B) µm.

(FIG. 2A) Scheme showing key interventions in the experimental design using the KRT19-Cre$^{ERT}$, R26$^{LSL}$tdTomato mice. AAV8-Tbg-p21 vector was administered to induce hepatocyte senescence. Injury was induced by CDE diet for 2 weeks, followed by VEGFA mRNA-LNP or control Poly(C) RNA-LNP injections, 10 µg/20 g body weight. (FIG. 2B) Human-specific VEGFA ELISA in mouse serum (n=3), injected with VEGFA mRNA-LNPs. Serum was collected 5 h, 24 h, 48 h, and 72 h after injection. (FIG. 2C) Immunofluorescent images showing tdTomato+ clusters (outlined) in livers of mice given two injections of either control Poly(C) RNA-LNP (n=4) or VEGFA mRNA-LNP (n=4). The bar graph shows quantification of tdTomato+ areas in the two groups. (FIG. 2D) Representative images of tdTomato+ and KRT7+ liver cells in Poly(C) RNA-LNP- or VEGFA mRNA-LNP-treated mice. The close-up images highlight tdTomato+ hepatocytes (arrowheads) adjacent to tdTomato+ Krt7+ BECs (arrows) in VEGFA-mRNA-LNP-treated mice. * represents tdTomato+ BEC areas. (FIG. 2E) tdTomato and PAS staining on serial sections of liver tissue demonstrating glycogen storage in tdTomato+ hepatocytes. (FIG. 2F) Histograms from flow cytometry of hepatocyte fraction isolated from mouse livers. Values of histograms represent % tdTomato+ population in the hepatocyte fraction and hepatocytes from a control non-tdTomato background run simultaneously with the experimental mice. Bar graph shows the total % tdTomato+ hepatocytes calculated by extrapolating the lineage tracing efficiency as 100% across all mice. (FIG. 2G) Representative brightfield images and corresponding bar graph showing quantification of % trichrome stained area estimated from at least three different fields in each mouse in the two groups (n=4 per group). (FIG. 2H) LipidSpot staining showing the accumulation of lipid droplets in hepatocytes. The bar graph shows quantification of % LipidSpot stained area averaged from three different fields in each mouse in the two groups (n=4 per group). (FIG. 2I) Bar graph depicting total serum cholesterol levels in mice. Numerical data are presented as mean±s.d. P values were determined by two-tailed Student's t-test, *p<0.05, p<0.01, *p<0.001, ****p<0.0001.

FIGS. 3A-3F depict VEGFA mRNA-LNP administration inducing BEC-to-hepatocyte conversion in APAP/p21-induced acute liver injury in mice. (FIG. 3A) Experimental design using the Krt19-Cre$^{ERT}$, R26$^{LSL}$tdTomato mice. AAV8-Tbg-p21 vector was administered to induce hepatocyte senescence. Injury was induced by a single intraperitoneal injection of acetaminophen (APAP), followed by VEGFA mRNA-LNP or control Poly(C) RNA-LNP injections, 10 µg/20 g body weight. (FIG. 3B) Representative immunofluorescent images showing comparison of EpCAM+ BECs observed in mice treated with APAP or APAP/p21. (FIG. 3C) Immunofluorescence microscopy images of tdTomato+ areas (outlined) in livers of mice given two injections of either control Poly(C) RNA-LNP (n=3) or VEGFA mRNA-LNP (n=3). The graph shows quantification of tdTomato+ area in both groups. (FIG. 3D) Histograms from flow cytometry of hepatocyte fraction isolated from mouse livers. Values of histograms represent % tdTomato+ population in the hepatocyte fraction and hepatocytes from a control non-tdTomato background run simultaneously with experimental mouse. Bar graph shows the total % tdTomato+ hepatocytes calculated by extrapolating the lineage tracing efficiency as 100% across all mice. (FIG. 3E) Representative immunofluorescence microscopy images showing hepatocyte identity of tdTomato+ cells (arrows) with HNF4α staining in the VEGFA mRNA-LNP-treated group. Close-up images show HNF4α+ cells within a tdTomato+ biliary duct. (FIG. 3F) tdTomato and PAS staining on serial sections of liver tissue demonstrating the ability of tdTomato+ hepatocytes to store glycogen. Data are presented as mean±s.d. P values were determined by two-tailed Student's t-test, *p<0.05, p<0.01, *p<0.001, ****p<0.0001.

(FIG. 4A-4B) Expression of KDR in BECs from the CDE- and APAP-induced liver injuries in the presence of AAV8-Tbg-p21. KDR expression was observed in some of the BECs depicted by arrowheads. (FIG. 4C) Scheme showing key interventions in the experimental design using the Kdr-2A-Cre$^{ERT2}$-2A-eYFP, R26$^{LSL}$tdTomato mice to track any cell that expresses KDR using CDE/p21 injury model. Additionally, three injections of tamoxifen were given on alternate days in the second week of injury to trace any BECs expressing KDR. (FIG. 4D) Representative close-up images of a bile duct showing tdTomato+ EPCAM+ BECs. (FIG. 4E) Immunofluorescence microscopy images showing tdTomato+ areas (outlined) in livers of mice given 2 injections of either control Poly(C) RNA-LNP (n=3) or VEGFA mRNA-LNP (n=3). The bar graph shows the quantification of the tdTomato+ area in the two groups. (FIG. 4F-4G) Representative immunofluorescence images depicting hepatocyte identity of tdTomato+ cells (outlined and identified with *) with HNF4α staining, a hepatocyte marker, or CD26 staining, a mature hepatocyte marker expressed on the canalicular face of the hepatocytes. (FIG. 4H) Representative brightfield images of Oil Red O-stained liver tissues showing lipid accumulation in the liver. The bar graph shows the quantification of the % Oil Red O-stained area averaged from at least three different fields in each mouse in the two groups (n=3 per group). Numerical data are presented as mean±s.d. P values were determined by two-tailed Student's t-test, *p<0.05, **p<0.01.

(FIG. 5A) Scheme showing key interventions in the experimental design using the Kdr-2A-Cre$^{ERT2}$-2A-eYFP, R26$^{LSL}$tdTomato mice to track any cell that expresses KDR in APAP/p21 injury model. Three injections of tamoxifen are given on alternate days around injury to trace any BEC expressing KDR in response to APAP injury. (FIG. 5B) Immunofluorescent microscopy images showing tdTomato+ areas (outlined) in livers of control firefly luciferase mRNA-LNP- (n=6) or VEGFA mRNA-LNP- (n=6) treated mice. The bar graph shows quantification of tdTomato+ area in the two groups. (FIG. 5C-5D) Representative immunofluorescent images depicting hepatocyte identity of tdTomato+ cells (outlined and identified with *) with HNF4α staining, a hepatocyte marker or CD26 staining, a mature hepatocyte marker that is expressed on the canalicular face of the hepatocytes. (FIG. 5E) Immunofluorescent images showing expression of YFP in liver cells of Kdr-2A-Cre$^{ERT2}$-2A-eYFP mice three days after acute liver toxicity by intraperitoneal APAP injection (400 mg/kg to male or 500 mg/kg to female). The fields of interest have been enlarged below. Arrowheads depict BECs co-expressing YFP and EpCAM while arrows depict large intermediate hepatocyte-like cells expressing YFP. Numerical data in the figure are presented as mean±s.d. P values were determined by two-tailed Student's t-test for comparison between two groups, ***p<0.001.

(FIG. 6A) Immunofluorescent images showing small cuboidal KRT7+ BECs (arrowheads) and KRT7+ intermediate hepatocyte-like cells (arrows) largely present in the regenerative nodules (*) close to the fibrous septa (outlined). (FIG. 6B) Immunofluorescence images showing KRT7 and GS staining in human cirrhotic liver specimens. The white arrowheads depict GS+ KRT7+ BECs possessing a duct cell-like morphology. The white arrows depict the rare GS+ KRT7+ intermediate hepatocyte-like cells, while arrows depict GS+ KRT7− intermediate hepatocyte-like cells. (FIG. 6C) Immunofluorescent images of cirrhotic liver specimen showing fibrous septa stained for KRT7+ BECs and KDR+ sinusoidal endothelial cells. Numerous KRT7+ KDR+ (arrowheads) BECs can be observed (magnified images) along with larger KDR+ intermediate hepatocyte-like cells (arrows) surrounding the KRT7+ KDR+ BECs. (FIG. 6D) Relative gene expression of KDR, KRT7, HNF4α determined in hepatocytes (Heps) isolated from normal (n=5) or cirrhotic human livers, Child-Pugh B (n=5) and Child-Pugh C (n=4). (FIG. 6E) Western blots showing protein expression of KDR, KRT7, HNF4α in hepatocytes isolated from normal or cirrhotic human livers Child-Pugh B (n=3) and Child-Pugh C (n=3) analyzed above in panel d. GAPDH serves as endogenous control. Numerical data in the figure are presented as mean±s.d. P values were determined by two-tailed Student's t-test for comparison between two groups, *p<0.05.

(FIG. 7B) Representative immunofluorescent microscopy images showing extent of ductular response (KRT7+ BECs) in Krt19-Cre$^{ERT}$R26$^{LSL}$tdTomato mice treated with AAV8-Tbg-p21 vector and choline-deficient diet with 0.1% ethionine supplementation for 2 weeks, followed by VEGFA mRNA-LNP or control Poly(C) RNA-LNP injections, 10 μg/20 g body weight. The bar graph shows quantification of KRT7-positive area averaged from at least three different fields in each mouse in the two groups (n=4 per group). (FIG. 7C) KRT7 and tdTomato staining showing decrease in BEC density in regions of BEC-to-hepatocyte conversion in VEGFA mRNA-LNP-treated group (outline). (FIG. 7D) Scheme showing key interventions in the experimental design using the Krt19-Cre$^{ERT}$, R26$^{LSL}$tdTomato mice without inducing hepatocyte senescence through AAV8-Tbg-p21 vector. Injury was induced by choline-deficient diet with 0.1% ethionine supplementation for 2 weeks, followed by VEGFA mRNA-LNP or control Poly(C) RNA-LNP injections, 10 μg/20 g body weight, as indicated. (FIG. 7E) Representative immunofluorescent microscopy images showing extent of ductular response (KRT7+ biliary epithelial cells) in chronically injured liver in the absence of AAV8 p21-induced hepatic senescence. (FIG. 7F) Close-up images of tdTomato+ liver cells in Poly(C) RNA-LNP- and VEGFA mRNA-LNP-treated mice. (FIG. 7G) Representative immunofluorescent microscopy images showing tdTomato+ liver cells and p21 staining on serial sections of liver tissue demonstrating the endogenous up-regulation of p21 in areas around tdTomato+ hepatocytes. Images on the right have been magnified to reveal p21 staining. Numerical data are presented as mean±s.d. P values were determined by one-way ANOVA followed by Tukey's method for multiple comparisons. p<0.01, *p<0.001. ns=non-significant.

(FIG. 8A) Representative immunofluorescence microscope images showing expression of p21-induced by AAV8-Tbg-p21 vector as compared to mice injected with a null vector. Mice were administered with 5×10$^{11}$ gc of AAV8-Tbg-p21 vector or null vector intravenously through retro-orbital sinus injection. (FIG. 8B) Density plots from flow cytometry of NPC fraction isolated from mouse livers. The NPC fraction was gated to exclude dead cell, debris, and cells expressing CD11b, CD45, Ter119, CD31. Values show % tdTomato+ EpCAM+ population. Lower panel shows cells from a control non-tdTomato mouse run simultaneously with each experimental mouse. (FIG. 8C) Scheme showing key interventions in the experimental design using the Krt19-Cre$^{ERT}$, R26$^{LSL}$tdTomato mice without administering AAV8-Tbg-p21 vector to induce hepatocyte senescence. Injury was induced by a single intraperitoneal injection of APAP (500 mg/kg to female mice) followed by VEGFA mRNA-LNP or control Poly(C) RNA-LNP injections, 10 μg/20 g body weight. (FIG. 8D) Representative close-up images of tdTomato+ liver cells in Poly(C) RNA-LNP- and VEGFA mRNA-LNP-treated mice. HNF4α staining shows the hepatocyte identity of selected tdTomato+ cluster.

(FIG. 9A) Immunofluorescent images showing co-expression of the endothelial cell markers KDR and CD31 in the liver of uninjured mice. (FIG. 9B) Schematic structure of the Kdr-2A-Cre$^{ERT2}$-2A-eYFP construct. (FIG. 9C) Representative immunofluorescent images showing specificity and sensitivity of the Kdr-2A-Cre$^{ERT2}$-2A-eYFP construct in Kdr-2A-Cre$^{ERT2}$-2A-eYFP mice. YFP expression overlaps the KDR+ expression in the liver endothelial cells. (FIG. 9D) Scheme showing the experimental design for defining leakiness of Cre recombinase in Kdr-2A-Cre$^{ERT2}$-2A-eYFP, R26$^{LSL}$tdTomato mice. Mice were administered with three corn oil injections on alternate days and sacrificed 10 days later. (FIG. 9E) Representative immunofluorescent microscope images showing leakiness of Cre in Kdr-2A-Cre$^{ERT2}$-2A-eYFP, R26$^{LSL}$tdTomato mice (male, n=3; female n=3). Enlarged images of selected areas demonstrate KDR+ endothelial cell identity of tdTomato+ cells.

(FIGS. 10A-10D) Representative immunofluorescent microscope images of KDR+ and tdTomato+ cells and their corresponding pixel representation by ImageJ used for quantitation of percent leakiness. The bar graph depicts quantification of % tdTomato+ KDR+ cells averaged from at least four different fields in each mouse in the two groups (n=3 per group). (FIG. 10D) Bar graph representing quantitation of rare tdTomato+ hepatocytes observed in Kdr-2A-Cre$^{ERT2}$-2A-eYFP, R26$^{LSL}$tdTomato mice treated with corn oil. Numerical data are presented as mean±s.d. P values were determined by two-tailed Student's t-test. ns=non-significant.

(FIG. 11A) Representative image showing lineage tracing efficiency in KDR expressing cells. The labelling was uniform and complete in endothelial cells across all mice as shown. (FIG. 11B) Representative immunofluorescent microscope images showing ductular response (EpCAM+ BECs) in Kdr-2A-Cre$^{ERT2}$-2A-eYFP, R26$^{LSL}$tdTomato mice treated with AAV8-Tbg-p21 vector and choline-deficient diet with 0.1% ethionine supplementation for 2 weeks, followed by VEGFA mRNA-LNP or control firefly luciferase mRNA-LNP injections, 10 μg/20 g body weight. The bar graph shows quantification of area of EpCAM+ staining averaged from at least three different fields in each mouse in the two groups (n=3 per group). (FIG. 11C) Krt7 staining showing comparison of ductular response in Kdr-2A-Cre$^{ERT2}$-2A-eYFP, R26$^{LSL}$tdTomato mice treated with AAV8-Tbg-p21 vector and APAP (500 mg/kg to female mice, 300 mg/kg to male mice) followed by VEGFA mRNA-LNP or control Luciferase mRNA-LNP injections, 10 μg/20 g body weight. The bar graph represents quantification of Krt7 stained area averaged from at least three different fields in each mouse in the two groups (n=6 per group). (FIG. 11D) Scheme showing the experimental design using the Kdr-2A-Cre$^{ERT2}$-2A-eYFP, mice to capture YFP (or KDR) expressing cells after acute liver toxicity. AAV8-Tbg-p21 vector was administered to induce hepatocyte senescence and injury was induced by a single intra-peritoneal injection of acetaminophen (400 mg/kg APAP to male mice and 500 mg/kg to female mice). Mice were sacrificed three days after the injury. Numerical data are presented as mean±s.d. P values were determined by one-way ANOVA followed by Tukey's method for multiple comparisons. *p<0.001, **p<0.0001, ns=non-significant.

(FIGS. 12A-12B) Representative brightfield images of H&E-stained cirrhotic human liver specimens showing the abnormal liver morphology and thick fibrous septa around the portal tracts of the diseased human livers. Brightfield images of trichrome stained human cirrhotic liver tissues showing collagen deposition. Oil Red O-stained human cirrhotic liver tissues showing lipid accumulation in the liver. (FIG. 12C) Representative immunofluorescence images showing ductular response (KRT7+ BECs) in the tissues of human liver samples at 4× magnification. The selected regions are shown at 10× magnification to clearly visualize KRT7-positive BECs in the dense fibrous septa as depicted by DAPI staining.

(FIG. 13A) Representative immunofluorescent images of cirrhotic human liver tissues showing the GS expression in the central vein area away from the fibrous where KRT7+ BECs are located. (FIG. 13B) Representative immunofluorescent images of normal human liver tissues (n=3) showing the GS expression in the central vein areas. KRT7 depicts the portal vein area. (FIG. 13C) KDR and KRT7 staining showing the normal endothelial staining pattern in the diseased donor liver tissues. (FIG. 13D) GS and its corresponding IgG isotype staining on serial sections demonstrating the specificity of GS antibody. (FIG. 13E) Relative gene expression of albumin determined in hepatocytes isolated from normal (n=5) or cirrhotic human livers, Child Pugh B (n=5) and Child-Pugh C (n=4).

FIGS. 15A-15B depict gating strategies of hepatocyte and non-parenchymal fractions.

(FIG. 16A) Following the Whitten effect and fasting to normalize estrogen and glutathione levels, respectively, male and female 12-week-old C57BL/6J mice were injected with 400 mg/kg APAP intraperitoneally and followed for 96 hours using the injury scheme outlined. (FIG. 16B) Serum alanine aminotransferase (ALT) levels at each sacrifice time post-APAP. First series is male, second series is female. (FIG. 16C) Hematoxylin & eosin staining of representative male and female livers at each time point, shown at 40× magnification. Bar graph on the right quantifies tissue area covered by necrosis (H&E). First series is male, second series is female. (FIG. 16D) TUNEL staining of representative male and female livers at each time point, quantifying both cell apoptosis and necrosis, shown at 40×. Bar graph on the right quantifies tissue area covered by cell death (TUNEL+). First series is male, second series is female. (FIG. 16E) Serum bilirubin in each sex at each time point. N=3-6 mice per sex/time point, with 2-3 lobes averaged for histological quantification—one male mouse died before 96 hours. Statistics calculated via two-sided student's t test for unpaired comparisons; p-values *<0.05, <0.001, *<0.0001.

(FIG. 17A) Male and female mice were given equivalent doses of 400 mg/kg APAP or PBS vehicle control post-fast and Whitten (for females), then livers were perfused in situ and dissociated at 48 hours post-APAP treatment for single-cell RNA sequencing analysis. (FIG. 17B) All 4 datasets combined on a single SPRING plot (4,821 cells), with 8 different cell type clusters resolved. Hepatocytes and endothelial cells (ECs) exhibit sexually dimorphic clustering prior to APAP injury. (FIG. 17C) Subclusters of combined dataset, separated by treatment, with female cells and male cells. (FIG. 17D) Growth hormone receptor (GHR) expression of combined SPRING plot, and violin plots of PBS-treated and APAP-treated hepatocytes (Hep), endothelial cells (EC) showing differential expression of GHR between males and females. First series is female, second series is male. (FIG. 17E) Growth hormone (GH) pathway enrichment of Biocarta gene set in SPRING and violin plots of PBS-treated and APAP-treated Heps and ECs showing differential enrichment of GH pathway between males and females. First series is female, second series is male. DEG of 0.25 used for differential expression resolution. P-values *<0.05, <0.001, *<0.0001.

(FIG. 18A)

Injury and treatment scheme consisting of fast and Whitten effect (females), then differential severe doses of APAP (400 mg/kg for males, 600 mg/kg for females), followed by treatment of 2.5 mg/kg GH, 1000 mg/kg NAC, or equivalent volume of PBS vehicle control 8 hours after APAP injection. N=5-9 mice per sex/treatment/time point (GH and PBS) or N=3 per sex/time point (NAC), with 2-3 lobes averaged per mouse for histological quantification. (FIG. 18B) Serum ALT levels of GH-treated, NAC-treated, and PBS-treated male and female mice 24 and 48 hours after severe dose of APAP. (FIG. 18C-18D) Representative H&E stains of male mouse livers per treatment, and time point post-APAP at 40× magnification, and graph quantifying % necrotic tissue in males and females. (FIG. 18E-18F) Representative TUNEL stains of male mouse livers per treatment, and time point post-APAP at 40× magnification and graph quantifying % TUNEL+ tissue in males and females. Statistics calculated via two-sided student's t test for unpaired comparisons; p-values *<0.05, <0.001, *<0.0001.

(FIG. 19A) Pre-treatment scheme with AAV8-TBG-STAT5bCA given 7 days prior to 400 mg/kg severe APAP injury, in C57BL/6J male mice, and sacrificed at 48 hours post-APAP administration. (FIG. 19B) Plasma murine IGF1 concentration measured by ELISA 6 days post-AAV8 injection in Null- and STAT5bCA-injected mice. (FIG. 19C) Survival rate for STAT5bCA- (square) and Null-injected mice (x). (FIG. 19D) Representative H&E stain and TUNEL stain of STAT5bCA-injected mouse livers, with average of % necrotic tissue and % TUNEL+ cell area and standard error for treatment group. N=6 mice/treatment. Statistics calculated via two-sided student's t test for unpaired comparisons; p-values *<0.05, <0.001, *<0.0001.

FIGS. 20A-20F depict GH mRNA-LNP targets liver to promote recovery throughout the length of the APAP-induced acute injury. (FIG. 20A) C57BL/6J mice were given sub-lethal doses of APAP (400 mg/kg for males, 600 mg/kg for females), and 8 hours later were injected retro-orbitally with g of human GH mRNA-LNP or negative control Luc mRNA-LNP, then analyzed 24 and 48 hours post-APAP. (FIG. 20B) Upper panels: human GH protein levels in liver tissue homogenate (left) and serum (right) were measured 5 hours post-injection by ELISA. Lower panel: human GH protein levels in serum of mice were measured 5, 24 and 48 hours post GH mRNA-LNP injection by ELISA. N=3 mice per treatment/time point. (FIG. 20C) Survival rate of GH mRNA-LNP-treated mice (squares; males in blue, females in pink) and Luc mRNA-LNP-treated mice (black x's) 24 and 48 hours post APAP overdose. N=5 mice per sex/treatment/time point. Statistical analysis carried out using the Log-rank Mantel-Cox test. (FIG. 20D) Serum ALT of GH mRNA-LNP-treated females and males and Luc mRNA-LNP-treated mice 24 and 48 hours post APAP treatment. Note all male mice treated with Luc mRNA-LNP died by 48 hours post treatment (skull symbol). The first series in each timepoint is Luc mRNA-LNP. The second series in each timepoint is GH mRNA-LNP. (FIG. 20E) % necrotic liver tissue quantified from H&E stains in GH mRNA-LNP-treated and Luc mRNA-LNP-treated mice. The first series in each timepoint is Luc mRNA-LNP. The second series in each timepoint is GH mRNA-LNP. (FIG. 20F) % TUNEL+ area from TUNEL stain in GH mRNA-LNP-treated and control Luc mRNA-LNP-treated mice. The first series in each timepoint is Luc mRNA-LNP. The second series in each timepoint is GH mRNA-LNP. Statistics for bar graphs calculated via two-sided student's t test for unpaired comparisons; p-values *<0.05, <0.001, *<0.0001.

(FIG. 21A) Single liver hepatocytes (Hep) and endothelial cells (EC) from males and females treated with PBS or APAP harvested as described in FIG. 17 were analyzed for pathway enrichment using ENRICHR. From the SPRING plots, the list of the most enriched genes in pre-identified hepatocytes and endothelial cells in each group were defined, analyzed with ENRICHR for pathway analysis, and ranked by z-score of enrichment as defined in the Bioplanet 2019 pathways database. B/C: Violin plots from Heps and ECs of genes included in the BioCarta GH pathway activation (FIG. 21B) as well as of additional downstream genes key for GH pathway activation (FIG. 21C). T-tests were used to assess differences in gene set scores between groups for each cell type, p-values *<0.05, <0.001, *<0.0001.

(FIG. 22A) Serum ALT, % necrotic liver tissue and % TUNEL+ liver tissue quantified from H&E stain and TUNEL stain, respectively, from males and females 12 hours post-APAP treatment with doses of 400 mg/kg and 600 mg/kg, respectively. First series is male, second series is female. (FIG. 22B) Injury and treatment scheme for male and female mice injured with sex-specific doses of APAP and treated 8 hours later with 4 different doses of subcutaneous GH protein injection or PBS vehicle control, and sacrificed at either 24 hours post-treatment (females) or 48 hours post-treatment (males). (FIG. 22C) Serum ALT levels of GH-treated and PBS-treated male and female mice 24 and 48 hours after administration of APAP. First series is male, second series is female. (FIG. 22D) % Necrotic liver tissue quantified via H&E stain for males and females following PBS or GH protein treatment at 4 different doses. First series is male, second series is female. (FIG. 22E) Representative H&E images for each sex at each GH dosage shown at 40× magnification. Statistics calculated via two-sided student's t test for unpaired comparisons; p-values *<0.05, <0.001, *<0.0001.

(FIGS. 23A-23B) Pictures of livers from female mice described in FIG. 18 treated with APAP, NAC or PBS. Representative H&E stains (FIG. 23A) or TUNEL stains (FIG. 23B) from mice used in FIG. 17 of livers per treatment, and time point post-APAP at 40× magnification. (FIG. 23C) Survival rate calculated from GH-treated (squares) vs NAC-treated (black x's) mice after APAP overdose. N=6 mice per sex/treatment. Statistical analysis carried out using the Log-rank Mantel-Cox test.

(FIG. 25A) Timeline of hiPSC 2D differentiation. (FIG. 25B) Day 5 cultures generate ~100% of endoderm cells expressing CXCR4 and CKIT that in turn give rise to a homogenous population of HLCs at day 15 expressing all AFP and EPCAM while 25% express AAT. (FIG. 25C) qPCR quantification and (FIG. 25D) immunostaining for hepatic markers in day 15 HLCs.

(FIG. 26A) Bioluminescence pictures and (FIG. 26B) bioluminescence quantification representing transplanted cells in livers at T1, T3 and T7. (FIG. 26C) Immunostaining of clusters of human albumin+ cells at T7 (arrows). (FIG. 26D) ALT serum levels in mice at T-7 (7 days prior to transplantation), and after transplantation at T1, T3 and T7. N=3-5 mice per group. (FIG. 26E) Protocol of cell transplantation in FRG mice. (FIG. 26B) Presence of human albumin+ cell clusters 40 days after transplantation.

(FIG. 27A) Bioluminescence pictures of mice injected with 5 ug of luciferase-mRNA-LNP. (FIG. 27B) Luciferase activity (photon/sec) seen in (FIG. 27A) in liver areas. (FIG. 27C) GFP immunofluorescence in liver 5 hours after injection of GFP-mRNA-LNPs. Note that all HNF4α+ hepatocytes express GFP.

FIGS. 28A, 28B, 28E, and 28F) and chronic (PiZ; FIGS. 28C and 28D) liver injury models. Mice were either injected with mRNA-LNP encoding HGF, IL6, and EGF (mRNA), or PolyC control, and then $10^6$ BU3 hiPSC-derived HLCs were transplanted through the spleen of all mice 5 hours later. The following day, mice were analyzed for bioluminescence activity. (FIGS. 28A, 28C) Pictures taken 10 min after luciferin injection and (FIGS. 28B, 28D) luciferase activity in the respective liver areas quantified (circled areas). Note the greater luciferase activity in all mice treated with mRNAs in both liver injury mouse models. (FIGS. 28E, 28F) Presence of single HLCs expressing human nuclei antigen (FIG. 28E) or cluster of HLCs (FIG. 28F) detected with DsRed 1 day after cell transplantation in the APAP injury model.

(FIG. 29A) Design of the sensor/actuator circuit. (FIG. 29B) Activity of the circuit does not affect the endogenous expression of the sensor gene RPS21/EYFP. (FIG. 29C) Expression of the actuator tdTomato is proportional to the number of gRNAs integrated chromosomally downstream of endogenous RPS21 gene.

(FIG. 33A) Bi-cell transplantation design and analyses. (FIG. 33B) Ligand-mRNA-LNP conditions to be tested.

(FIG. 34A) Current primary human hepatocytes (PHH) and HLC therapies have limitations. (FIG. 34B) It is contemplated that engineering transplanted HLCs to express important dox-inducible mitogen receptors and maturation transcription factors and advantaging transplanted cells with mRNA-LNP will improve HLC repopulation in the NSG-PiZ mouse model recapitulating alpha 1 antitrypsin disease (AATD) associated liver disease.

(FIG. 35A) Z-AAT polymer accumulation in hepatocytes visualized as PAS-positive diastase-resistant. (FIG. 35B) Hepatic fibrosis as shown with picrosirius red stain.

(FIG. 36A) Serum human albumin levels quantified by ELISA biweekly post-engraftment for 10 weeks following transplantation. (FIG. 36B) Human albumin immunostaining on liver sections 10 weeks post-partial hepatectomy (PHx). (FIG. 36C) Serum human albumin after various challenges. (FIG. 36D) Serum human AAT levels quantified by ELISA at 10 weeks post-engraftment. Dotted line is therapeutic threshold, 572 mg/mL.

(FIG. 37A) Schematic of 15 day directed differentiation from iPSC to HLC. (FIG. 37B) Flow cytometry analyses of day 5 definitive endoderm culture. (FIG. 37C) Immunofluorescence of cells in culture throughout differentiation. (FIG. 37D) RT-qPCR analysis showing relative gene expression during differentiation. Fold change is relative to PHH control. Data points are mean±SEM, n=1.

(FIG. 38A) eGFP detected 5 h after mRNA-LNP injection in NSG-PiZ mice. (FIG. 38B) NSG-PiZ mice were treated with or without intravenous AAV8-P21. 7 d later, they were injected with HGF+EGF mRNA-LNP or PolyC control RNA-LNP. 48 h later, mice were injected with EdU to label proliferating cells. Livers were harvested 2 h later. (FIG. 38C) EdU stain showing proliferating cells in green. (FIG. 38D) Quantification of EdU+ hepatocytes per 10× image field. n=2 or 3 mice. Data represented as mean±SEM. (FIG. 38E) Immunofluorescence showing P21 expression in AAV8-P21 treated NSG-PiZ mice 1 week post injection and in P21 mRNA-LNP treated NSG mice 5 hrs post injection.

(FIG. 40A) Schematic of in vivo detection of transplanted HLCs. (FIG. 40B) NSG-PiZ mice were treated with either PolyC or HGF+EGF mRNA-LNP 5 h prior to transplantation with $10^6$ HLCs. Representative images of bioluminescence detected with in vivo imaging system (IVIS) 1, 3, and 5 days post transplantation. (FIG. 40C) Quantification of IVIS data represented as mean±SEM, n=5-6 per group.

(FIG. 44A) Epifluorescence images showing fabp10a:DsRed expression in the regenerating larvae at R24h and R48h. Arrows point to the liver. Quantification of the liver size is shown. (FIG. 44B) Confocal images showing Prox1 and Hnf4a expression in regenerating livers at R6h. (FIG. 44C) Confocal images showing the expression of fabp10a:CFP-NTR, Tp1:H2B-mCherry, and Bhmt in regenerating livers at R24h. Scale bars, 50 μm.

(FIG. 45A) Whole-mount in situ hybridization images showing the expression of senescence markers, tp53 and cdkn1a, at 5 dpf (FIG. 45B) SA-β-gal staining also reveals the increased senescence in Tg(fabp10a:ca-13-catenin) livers at 10 dpf Arrows point to livers. (FIG. 45C) Confocal images showing the labeling of TUNEL and nucleus (Hoechst33342) with fabp10a:GFP expression at 10 dpf TUNEL$^+$ cells (arrow) were detected in Tg(fabp10a:ca-13-catenin) livers but not in control livers. (FIG. 45D-45F) Confocal images showing the expression of mpeg1:Dendra2 (macrophages; FIG. 45D), hand2:EGFP (stellate cells; FIG. 45E), and acta2:mCherry (fibrosis; FIG. 45F). Anxa4 is a marker of BECs and LPCs. (FIG. 45G) Confocal images showing the expression of fabp10a:CFP (hepatocytes and LPCs), Tp1:H2B-mCherry (BECs and LPCs), and Bhmt (hepatocytes) in Tg(fabp10a:ca-13-catenin) livers. Arrows point to LPCs. Scale bars: 50 μm.

(FIG. 46A) Bioluminescence pictures of mice injected IV with 10 μg of luciferase mRNA-LNP. (FIG. 46B) Graph representing the luciferase activity (photon/sec) seen in (FIG. 46A). (FIG. 46C) flow cytometry analyses of dissociated liver cells and (FIG. 46D) GFP expression on liver sections 5 hours after injection of GFP mRNA-LNP. (FIG. 46E) Efficient VEGFA secretion in serum with time assessed by ELISA specific for human VEGFA after injection of 10 μg of human VEGFA mRNA-LNP (mean±SD from 3 mice/time point).

(FIG. 48A) Experimental design using the KRT19-Cre$^{ERT}$, R26$^{LSL}$tdTomato mice. (FIGS. 48B, 48C) Tomato and KRT7 immunostaining on either Poly(C)RNA-LNP (FIG. 48B, n=4) or VEGF mRNA-LNP (FIG. 48C, n=4) treated mice 5 days following the last injection of mRNA-LNPs. Note the numerous areas of Tomato+ hepatocytes (arrowheads) adjacent to Tomato+ KRT7+ BECs (arrows) in VEGFA-treated mice. * represent Tomato+ BEC areas.

(FIG. 50A) Experimental design using the KRT19-Cre$^{ERT}$, R26$^{LSL}$tdTomato mice. (FIG. 50B) Tomato and HNF4α immunostaining on Poly(C) RNA-LNP or VEGFA mRNA-LNP treated mice 5 and 14 days following the last injection of mRNA-LNPs. (FIG. 50C) Flow cytometry quantification of CD26+ Tomato+ hepatocytes, and (FIG. 50D) corrected based on the Krt19 BEC lineage tracing efficiency as measured by the percentage of Tomato+ EpCAM+ BEC for each mouse (n=4 mice/group).

(FIG. 57A) Confocal images showing the expression of fabp10a:CFP-NTR, Tp1:H2B-mCherry, and Bhmt in regenerating livers at R24h. 10 μM LY294002 was added from A18h to R24h8. (FIG. 57B) Confocal images showing pS6 expression in 5-dpf control and R6h regenerating livers. Arrows point to pS6-positive BECs; arrowheads to pS6-positive hepatocytes. Scale bars, 50 μm.

FIGS. 60A-60G depict liver necrosis, hepatocyte apoptosis and tissue recovery are sexually dimorphic following equivalent doses of APAP. (FIG. 60A) Male and female mice were injected with 400 mg/kg APAP and monitored for 96 hours using the injury scheme outlined. (FIG. 60B) Serum ALT levels with time in both sexes (each dot represents one mouse). (FIG. 60C) H&E staining at 24, 48 and 96 hours post-APAP shows less necrosis in females overtime. (100× magnification). (FIG. 60D) Graph quantifying surface area covered by necrotic (eosin+/hematoxylin−) tissue in each sex over time (n=4 mice/sex/time point, 2 lobes per mouse). (FIG. 60E) TUNEL staining representing cell apoptosis is consistent with H&E pattern (40×). (FIG. 60F) Graph quantifying surface area covered by TUNEL+ staining (n=4 mice/sex/time point). (FIG. 60G) Quantification of serum bilirubin (n=4 mice/sex/time point). Two tailed t-test, p-values *<0.05, <0.001, *<0.0001, n.s.=not significant.

(FIG. 62A-62F) SPRING plots of combined cells from APAP- and PBS-treated males and females illustrate expression for GHR, IGF1, IGF1R, IGFBP4, IGFBP7 and prolactin receptor (PRLR). The intensity represents levels of gene expression. Bars on violin plots represent average expression level in hepatocytes (Hep), ECs and KC/monocytes (M/KC). First series in each graph is female, second series is male. (FIG. 62G) Biocarta GH pathway expression is significantly higher in female hepatocytes and ECs than in male cell counterparts. Pathways with normalized enrichment scores of p>0.2 shown. Welch's two sample t-test was used to calculate statistical significance (*p<0.0001, p<0.001, *p<0.05, n.s.: not significant).

(FIG. 63A) Timeline of the experimental design. (FIG. 63B) Serum ALT levels over time in both sexes (each dot represents one mouse). (FIG. 63C) H&E stain of male and female livers given either PBS or GH 8 hours after sub-lethal sex-dependent APAP injection dosing, then euthanized 24 h or 48 h post-APAP (40× magnification). (FIG. 63D) Quantification of staining shown in C by measuring stained area on FIJI (n=3 mice/sex/treatment/time point, 2 lobes per mouse). First series is untreated, second series is treated. (FIG. 63E) TUNEL staining on subsequent tissue sections from the same mice (40×). (FIG. 63F) Quantification of staining shown in E by measuring stained area on FIJI. (n=3 mice/sex/treatment/time point, 2 lobes per mouse). First series is untreated, second series is treated. Two tailed t-test, p-values *<0.05, <0.001, *<0.0001, n.s.=not-significant.

(FIG. 64A) Bioluminescence pictures of mice injected IV with 10 µg of luciferase mRNA-LNP. (FIG. 64B) Graph representing the luciferase activity (photon/sec) seen in (FIG. 64A). (FIG. 64C) eGFP expression on liver sections 5 hours after injection of eGFP mRNA-LNP, (FIG. 64D) flow cytometry analyses of dissociated liver cells (Poly(C) RNA-LNP used as control, mean±SD from 2 mice/group measured in duplicate).[1]

(FIG. 67A-67C) SPRING plots and violin plots for expression of ERa and of early and late estrogen pathway. (FIG. 67D) Timeline of E2 treatment in male mice. (FIG. 67E) Serum ALT levels in control oil-treated and E2-treated males (each dot represents one mouse). Two tailed t-test, p-values *<0.05, n.s: not significant. Hep: hepatocyte, EC: endothelial cells.

Figure 75:
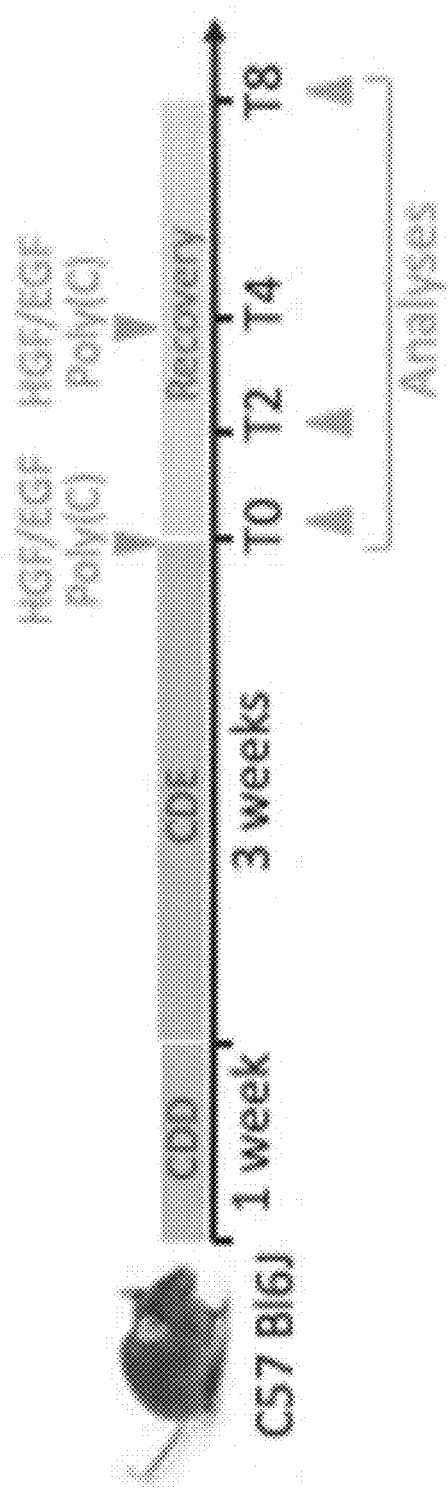
Figure 75B:
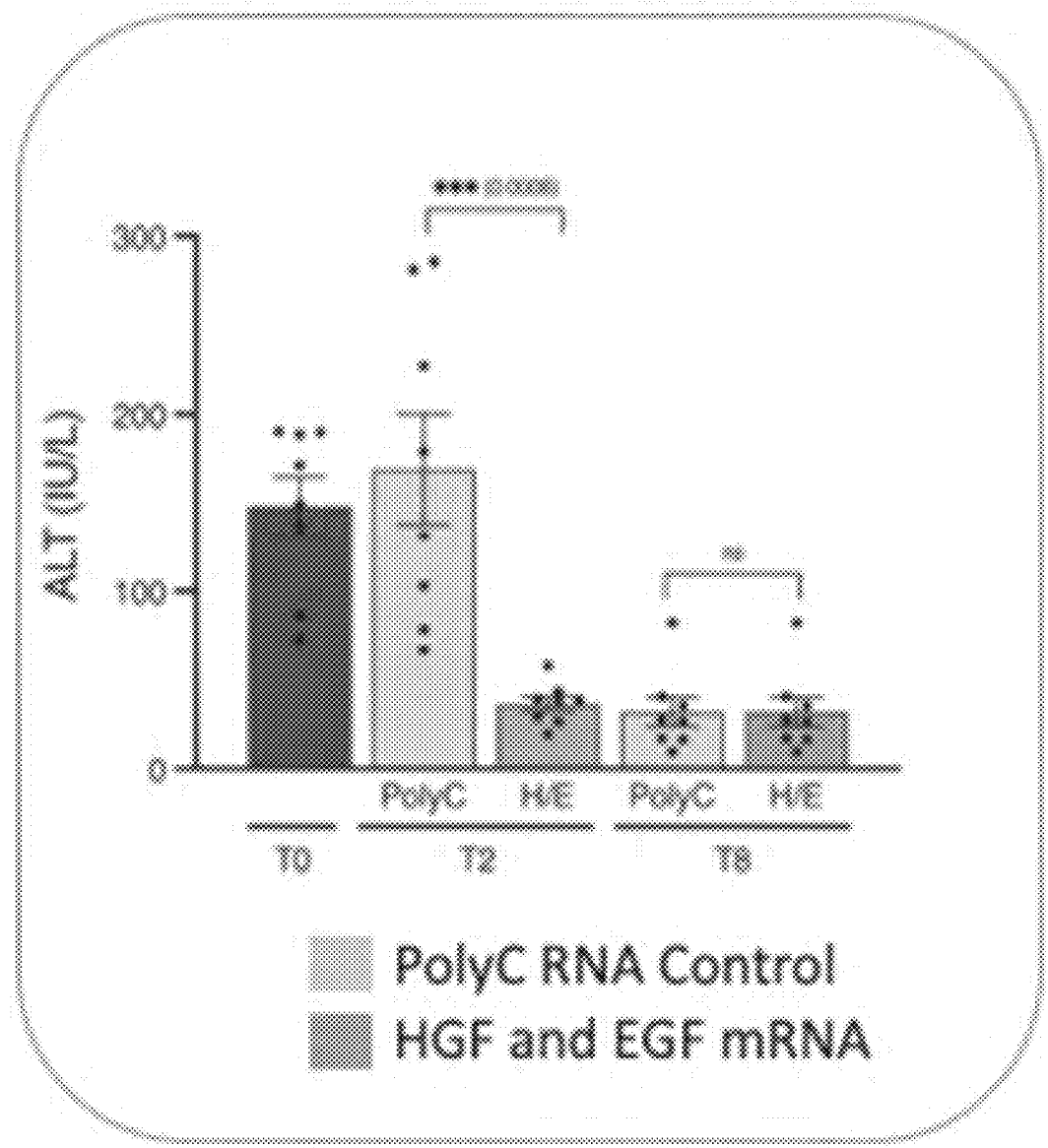
Figure 75C:
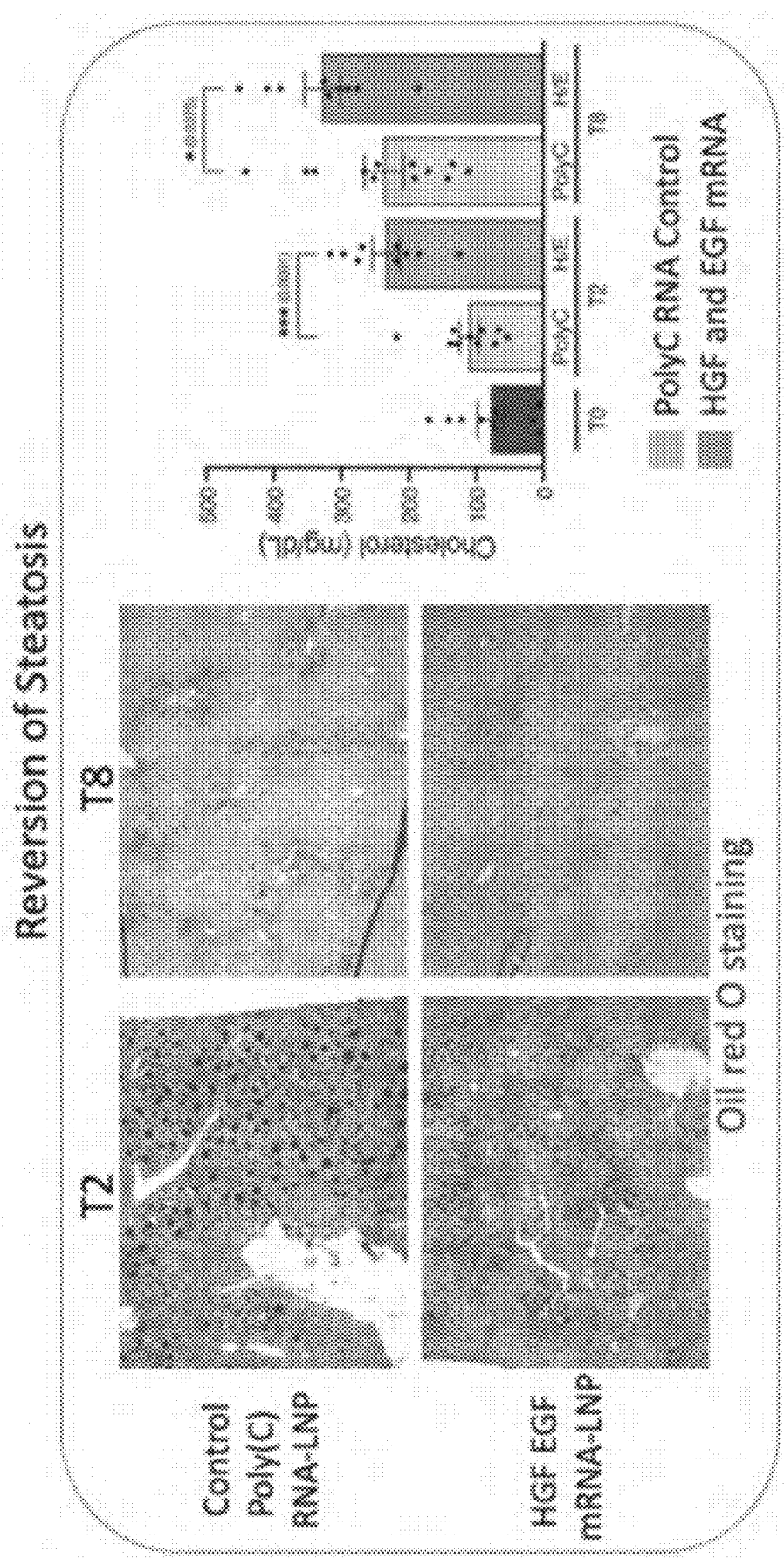

FIGS. 75A-75C depict HGF and EGF mRNA-LNPs revert liver necrosis and reduce steatosis in a chronic liver injury model. Mice were fed the choline deficient ethionine supplemented CDE diet for 3 weeks to induce steatohepatitis and hepatocyte death. Mice were then treated twice with HGF EGF mRNA LNP during the recovery period. The liver mitogen mRNA-LNP rapidly restores the serum ALT levels indicative of liver damage to normal levels 2 days after the first injection. The treatment also induced a sharp decrease of steatosis compared to that with control Poly(C)-RNA treatment, in which macrosteatosis was maintained, even 8 days after the diet was over. The levels of cholesterol found in the serum of mice were inversely proportional to the degree of steatosis seen in livers.

Figure 76A:
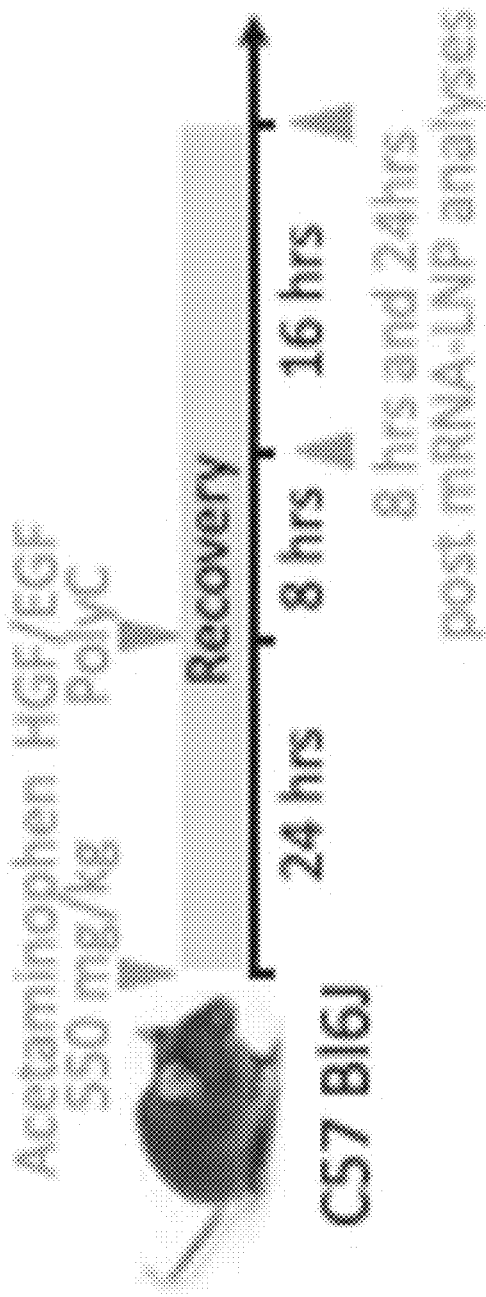
Figure 76B:
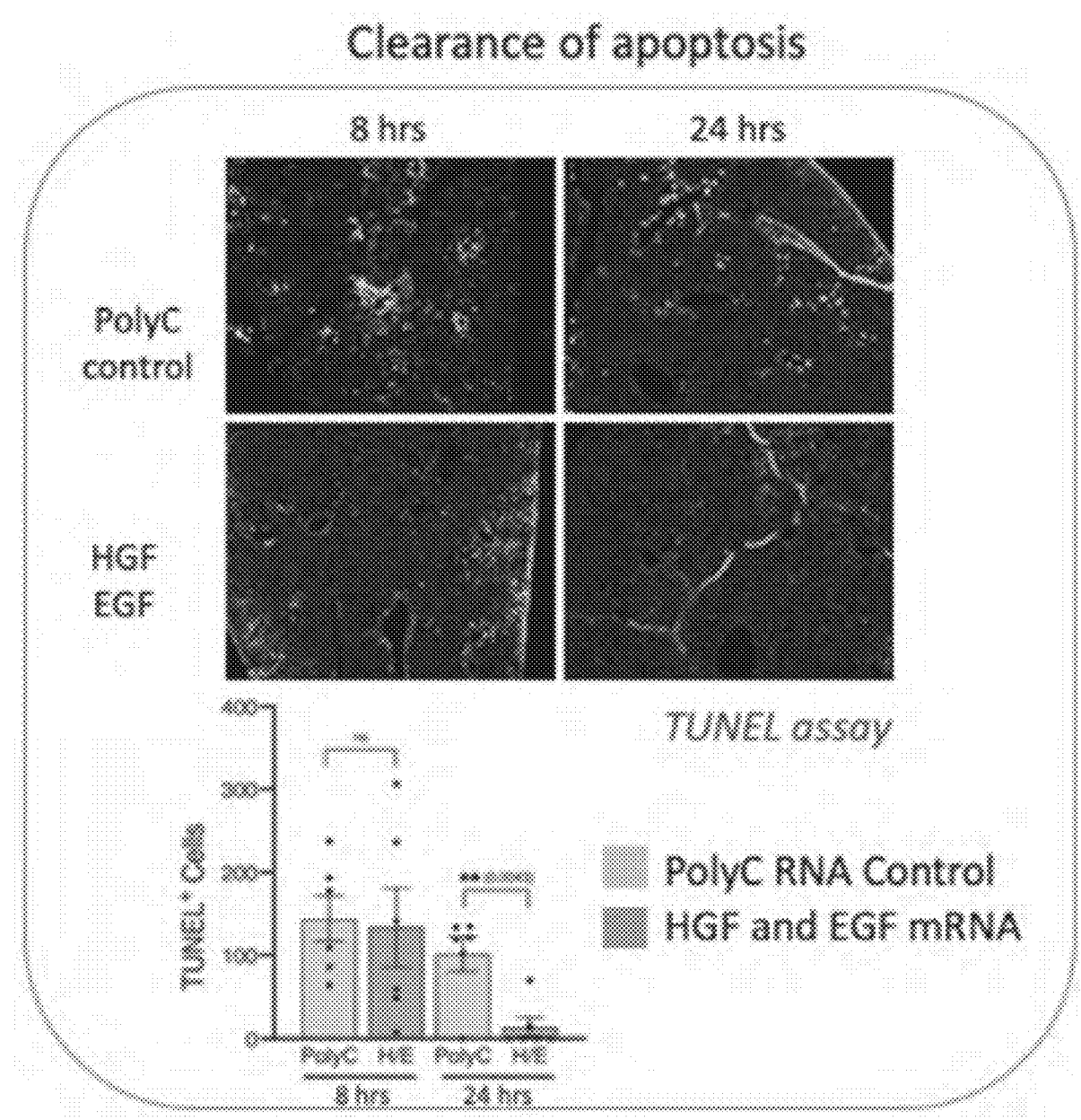
Figure 76C:
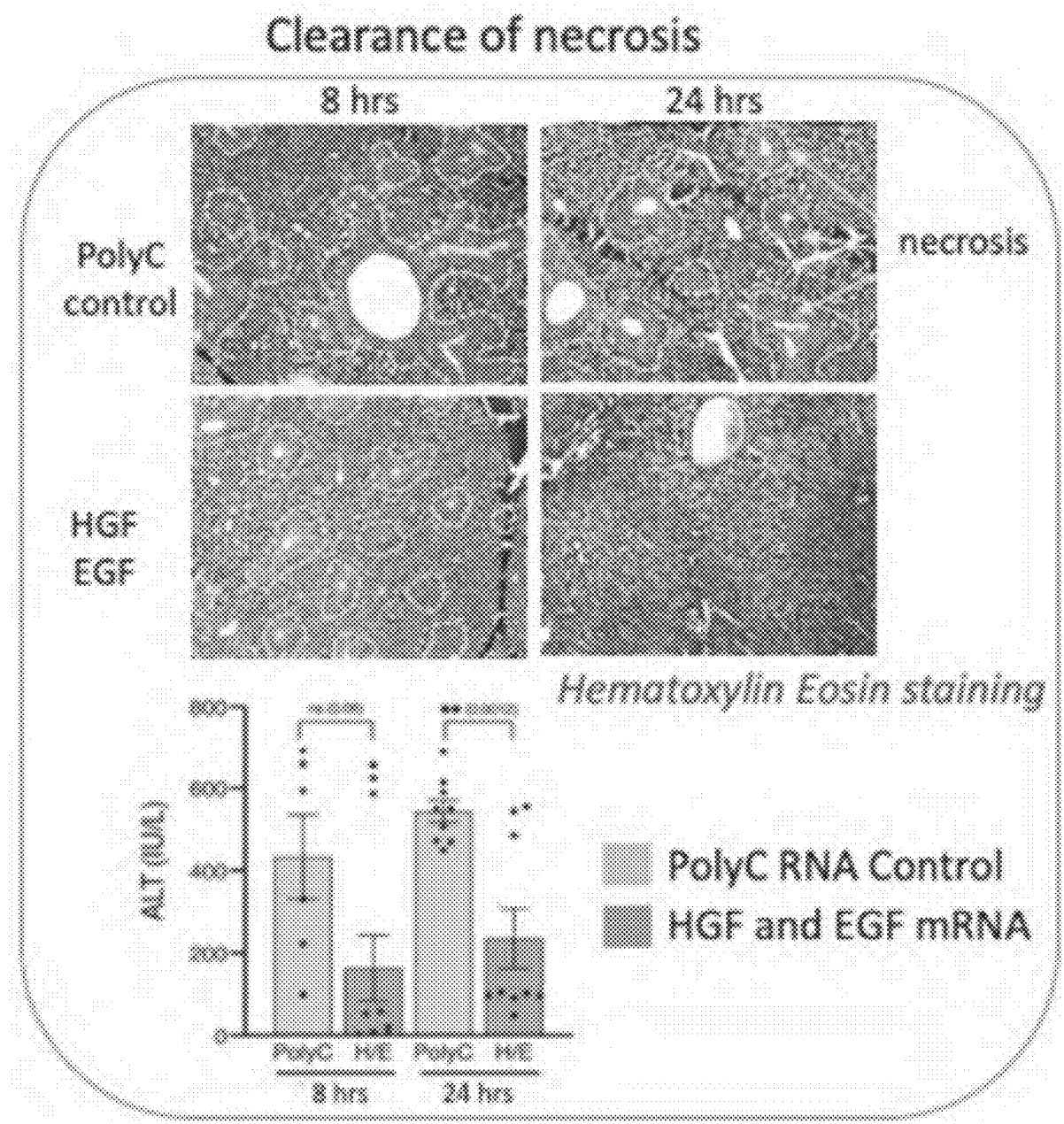

FIGS. 76A-76C depicts HGF and EGF mRNA-LNPs accelerate liver repair following acetaminophen-induced acute liver injury. A single injection of HGF and EGF mRNA-LNP was administered 24 hours after acetaminophen overdose, and mice were analyzed 8 hours and 24 hours after the mRNA-LNP injection. Beneficial effects of mRNA-LNP were consistently and significantly observed 24 hours after HGF/EGF mRNA-LNP injection with accelerated disappearance of necrotic areas that were still seen in the Poly(C) RNA-LNP-treated control group assessed by H&E staining, which was accompanied by significantly lower serum ALT levels, and absence of TUNEL cells that were still present in Poly(C) RNA-LNP control group.

Figure 77:
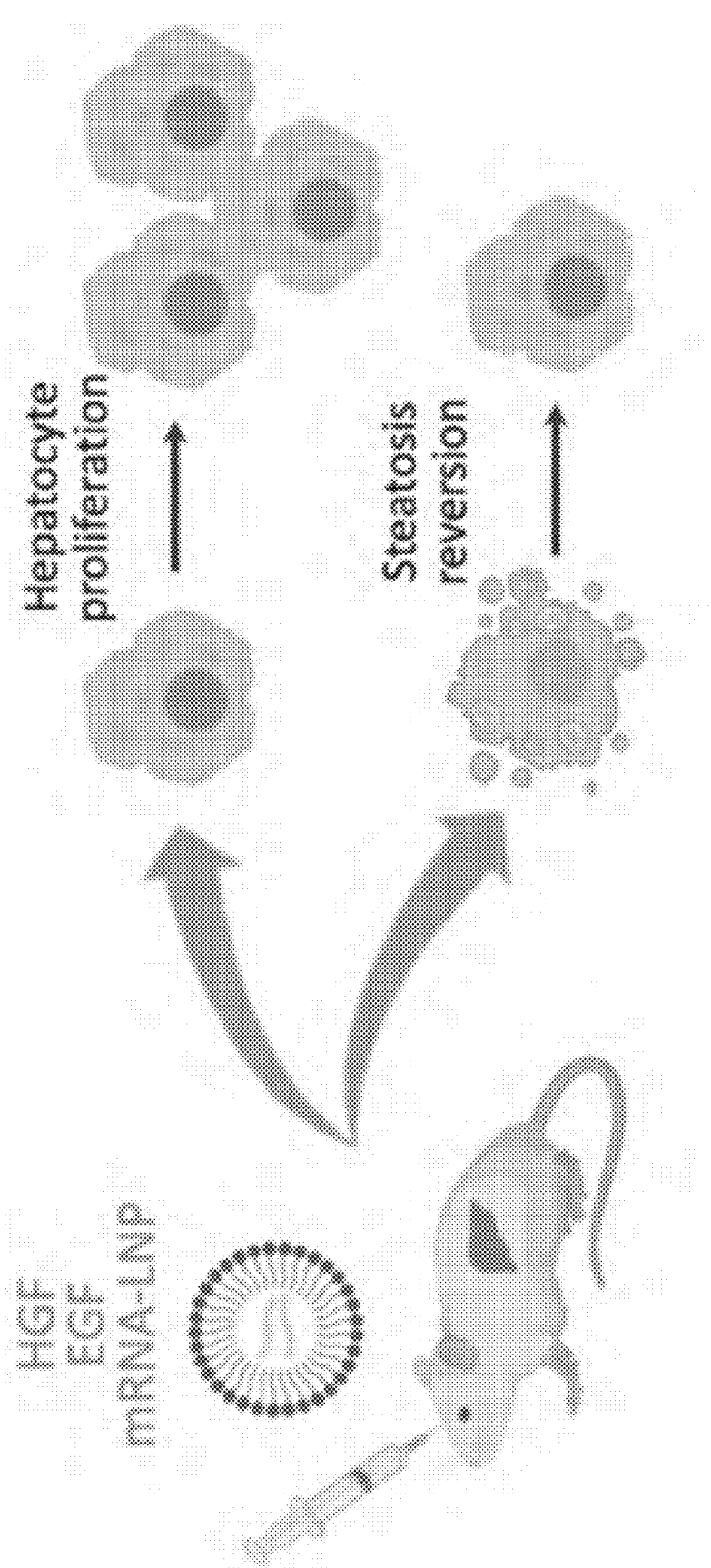

FIG. 77 depicts use of HGF/EGF mRNA-LNPs to harness hepatocyte-driven liver repair by transiently promoting hepatocyte proliferation and reverting steatosis in a chronic liver injury model.

Figure 78A:
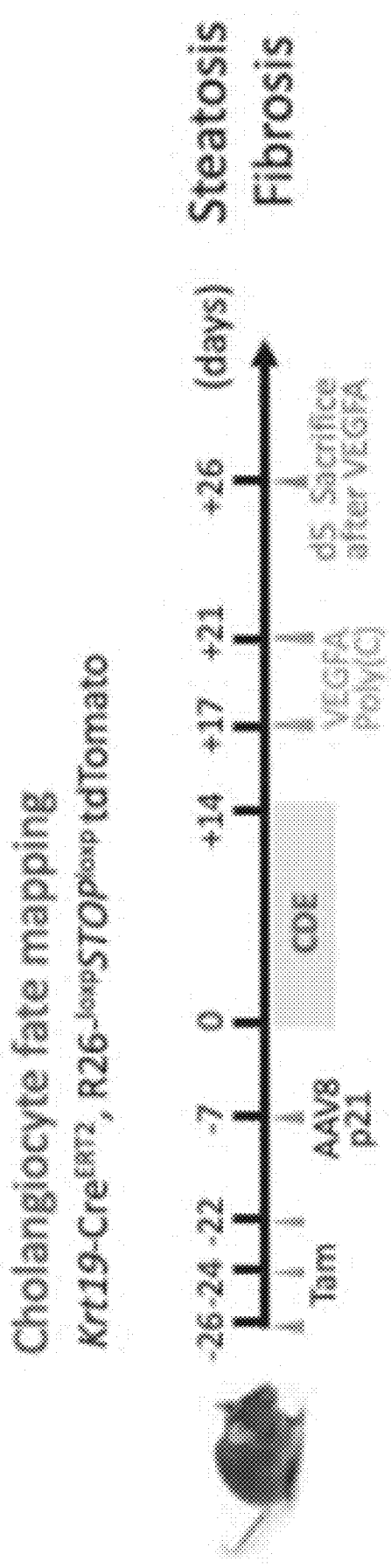
Figure 78B:
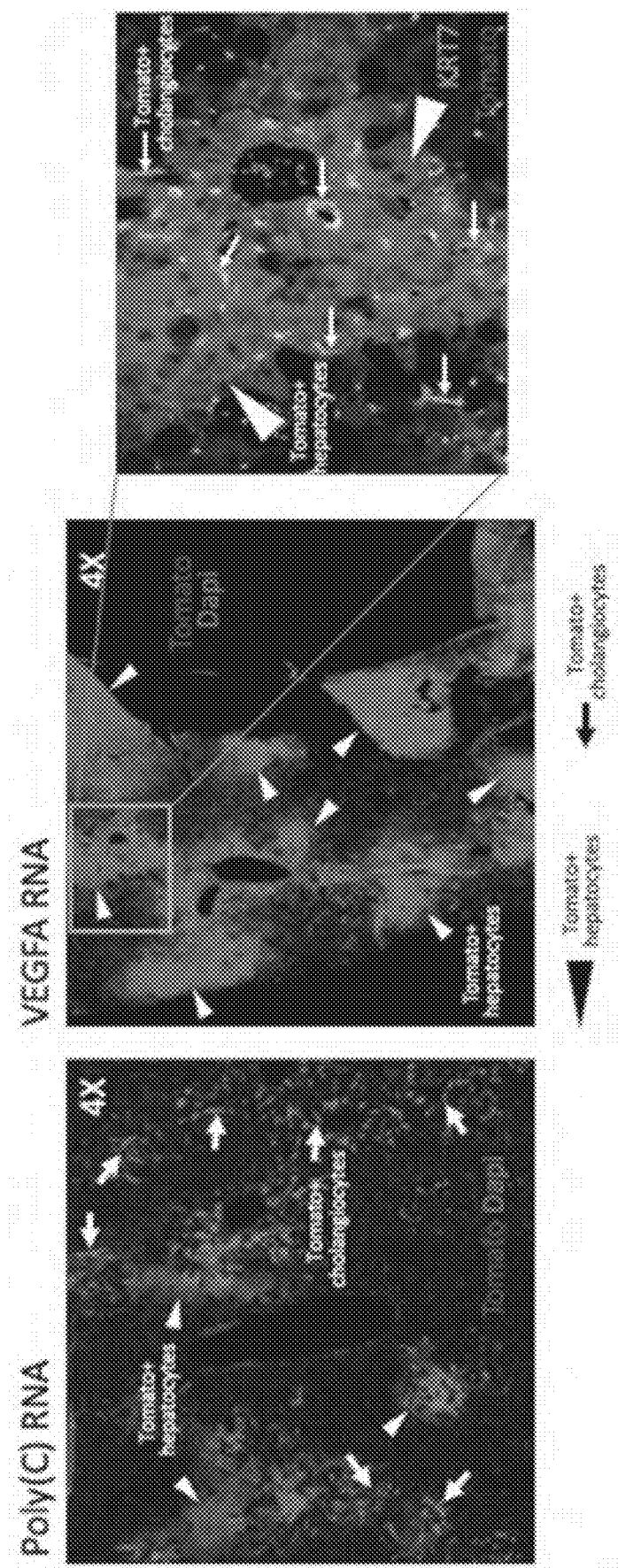
Figure 78C:
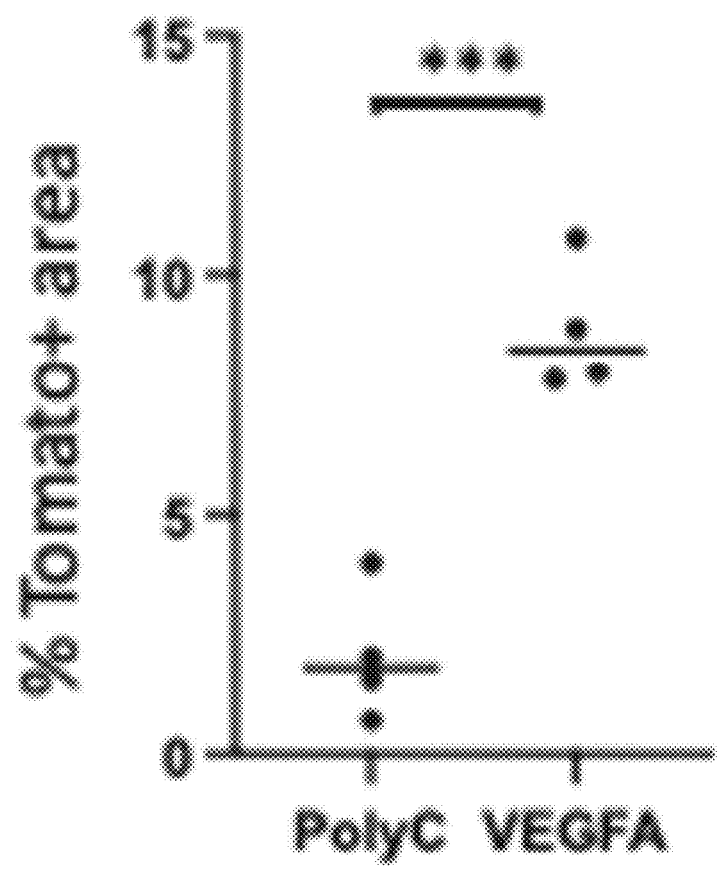

FIGS. 78A-78C depict VEGFA mRNA-LNPs promote cholangiocyte-to-hepatocyte conversion in vivo and reverse the chronic liver disease. Lineage tracing of cholangiocytes in a CDE-induced chronic liver disease mouse model treated with 2 doses of VEGFA mRNA-LNP after the CDE diet revealed VEGFA significantly induces generation of tomato+ hepatocytes throughout the liver.

Figure 79A:
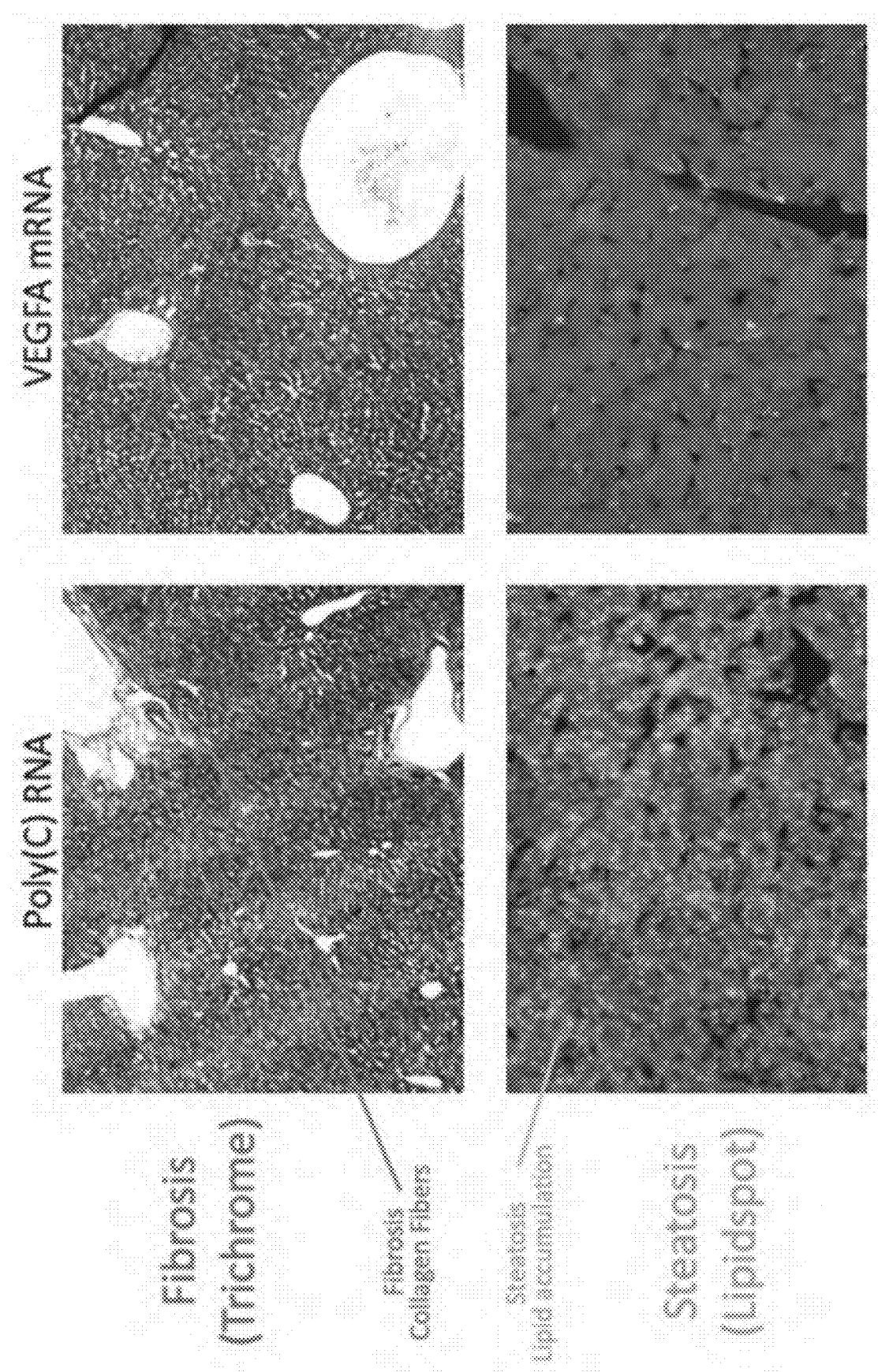
Figure 79B:
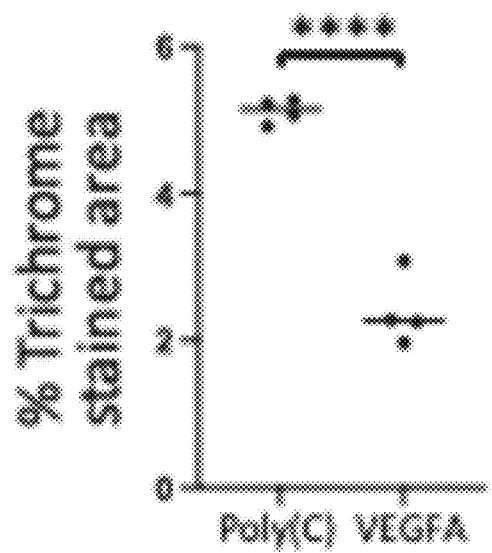
Figure 79B:
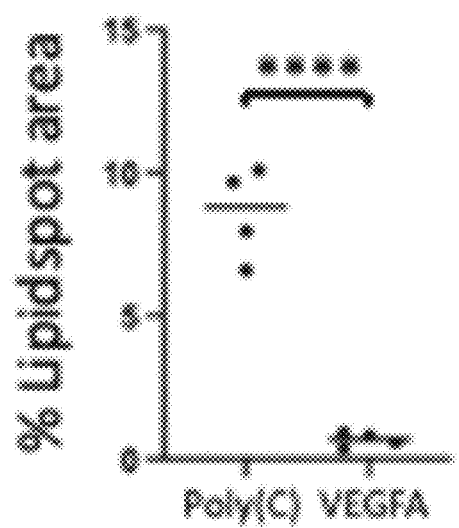

FIGS. 79A-79B depict VEGFA mRNA-LNPs promotes cholangiocyte to hepatocyte conversion and reverses steatosis and fibrosis in a chronic liver injury model. Microvesicle of fat are seen in hepatocytes in control PolyC treated mice, while these microvesicles are absent in the VEGFA mRNA-LNPs treated mice. Similarly, VEGFA mRNA-LNPs reverted fibrosis as assessed with trichrome staining. Fibrosis is still present in polyC treated mice, while it is absent in VEGFA mRNA-LNPs treated mice.

Figure 80:
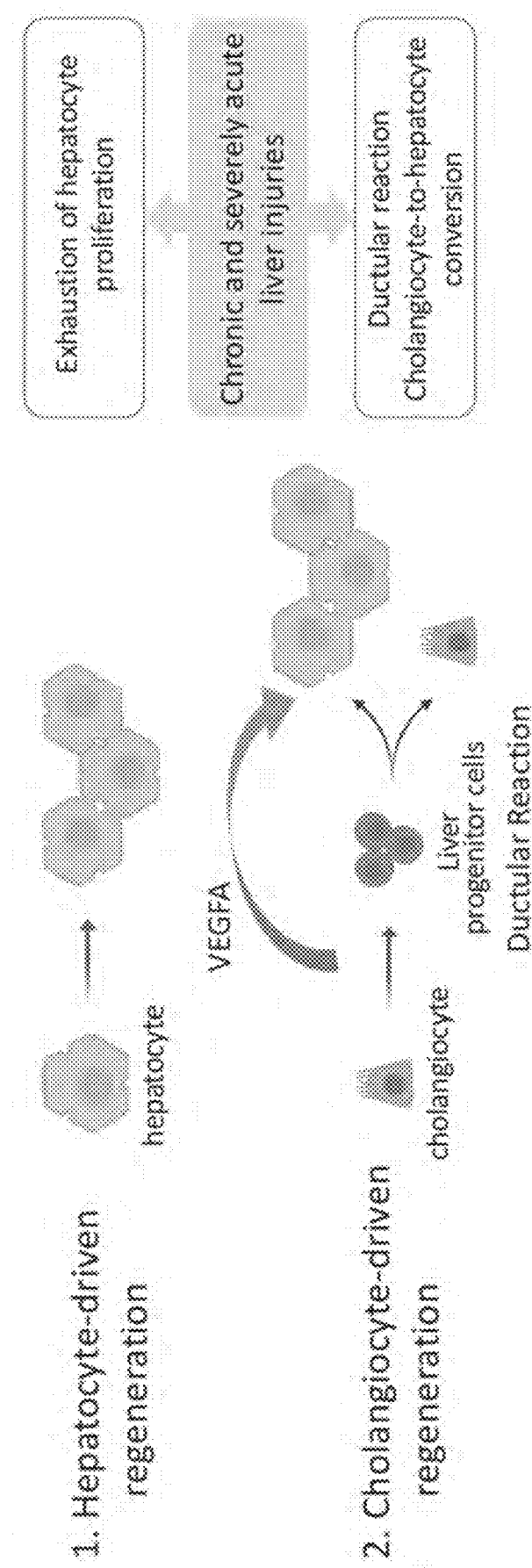

FIG. 80 depicts mechanisms of hepatocyte regeneration and the proposed experiments to promote cholangiocyte-driven liver regeneration by activating liver progenitor cells (LPCs) to differentiate into hepatocytes using VEGFA, a ligand for VEGFR2/KDR.

Figure 81A:
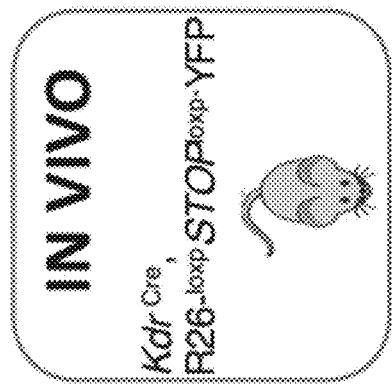
Figure 81A:
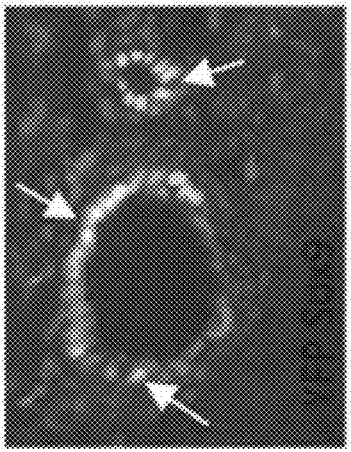
Figure 81A:
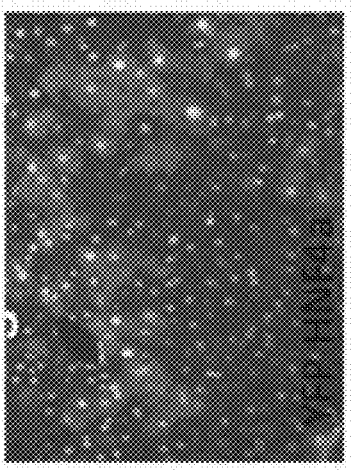
Figure 81A:
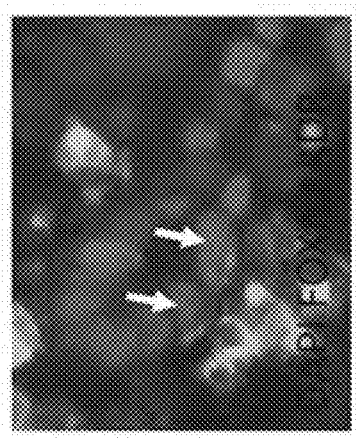
Figure 81B:
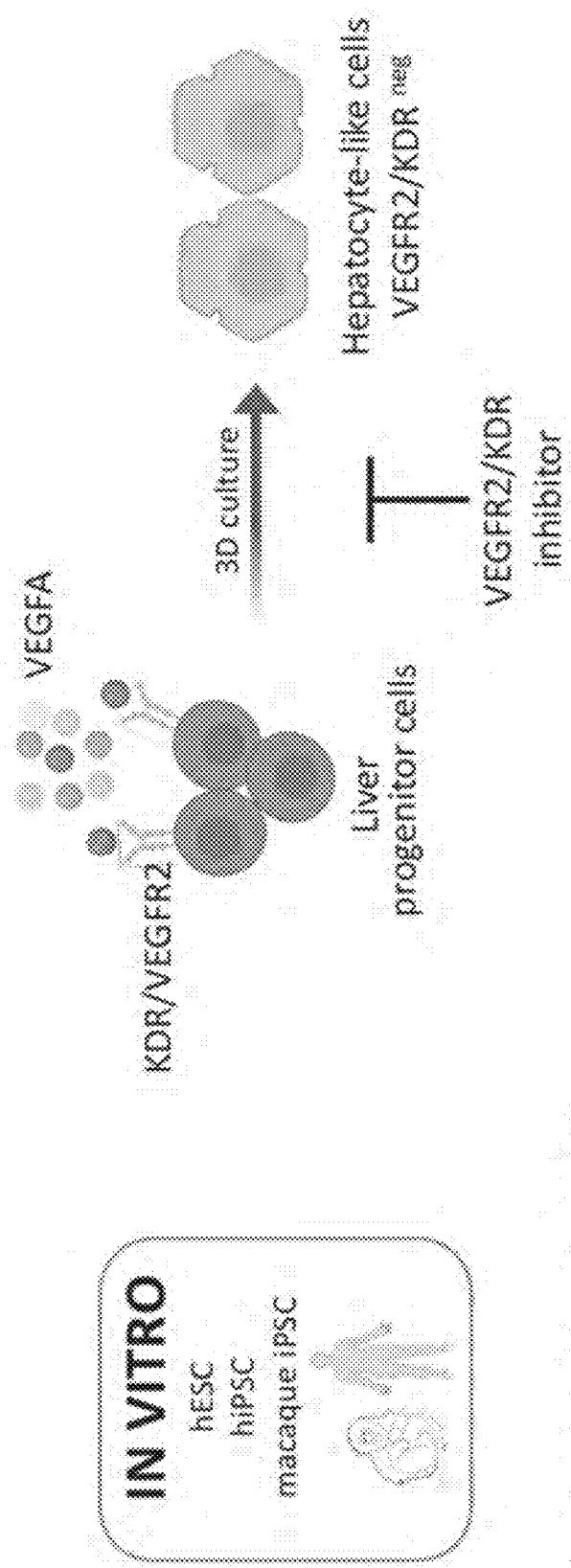

FIGS. 81A-81B depict the identification of liver progenitors expressing VEGFR2/KDR.

Figure 82:
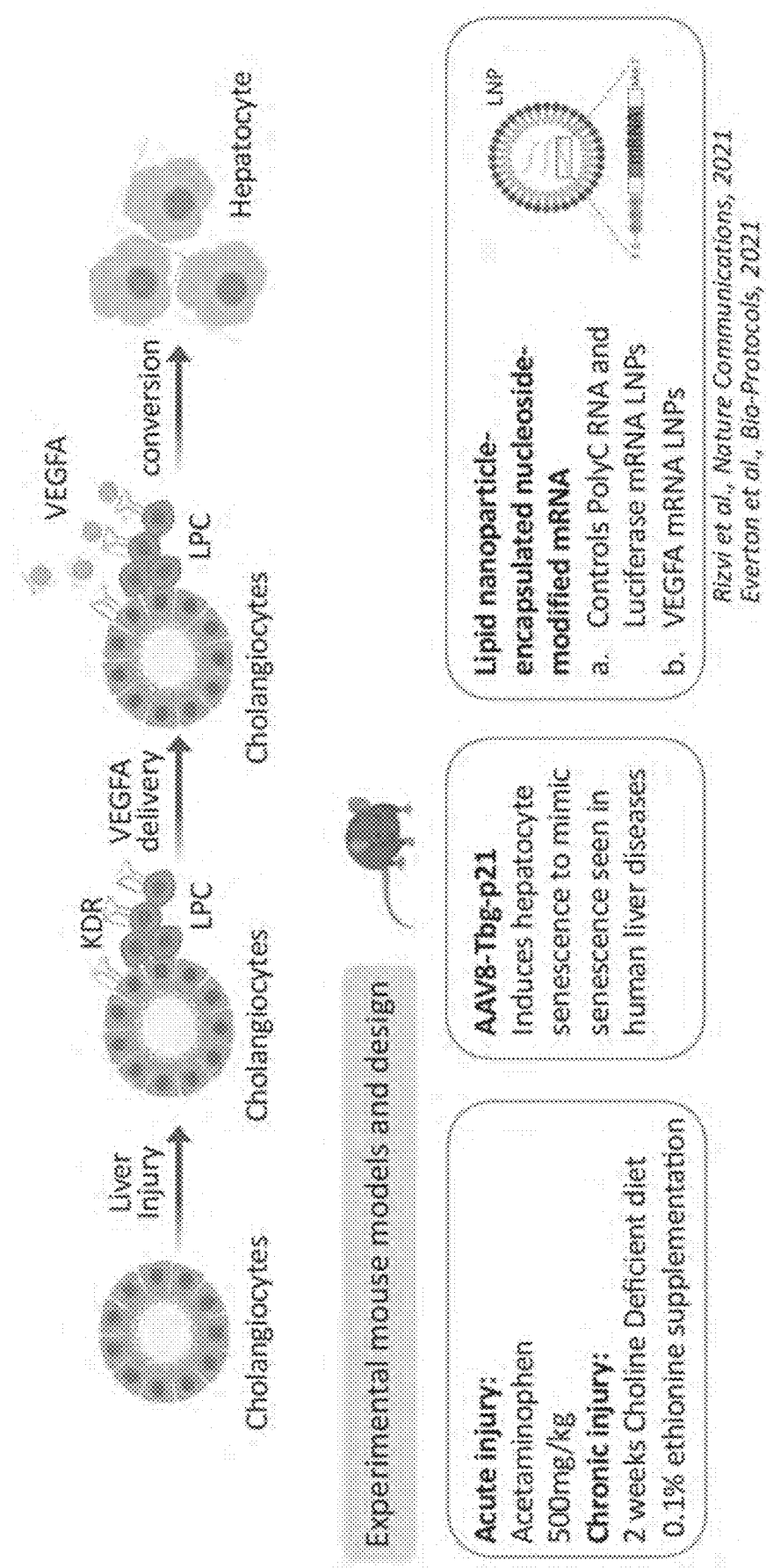

FIG. 82 depicts the experimental mouse models and design to test if VEGFA, a ligand for VEGFR2/KDR promotes cholangiocyte to hepatocyte conversion.

Figure 83:
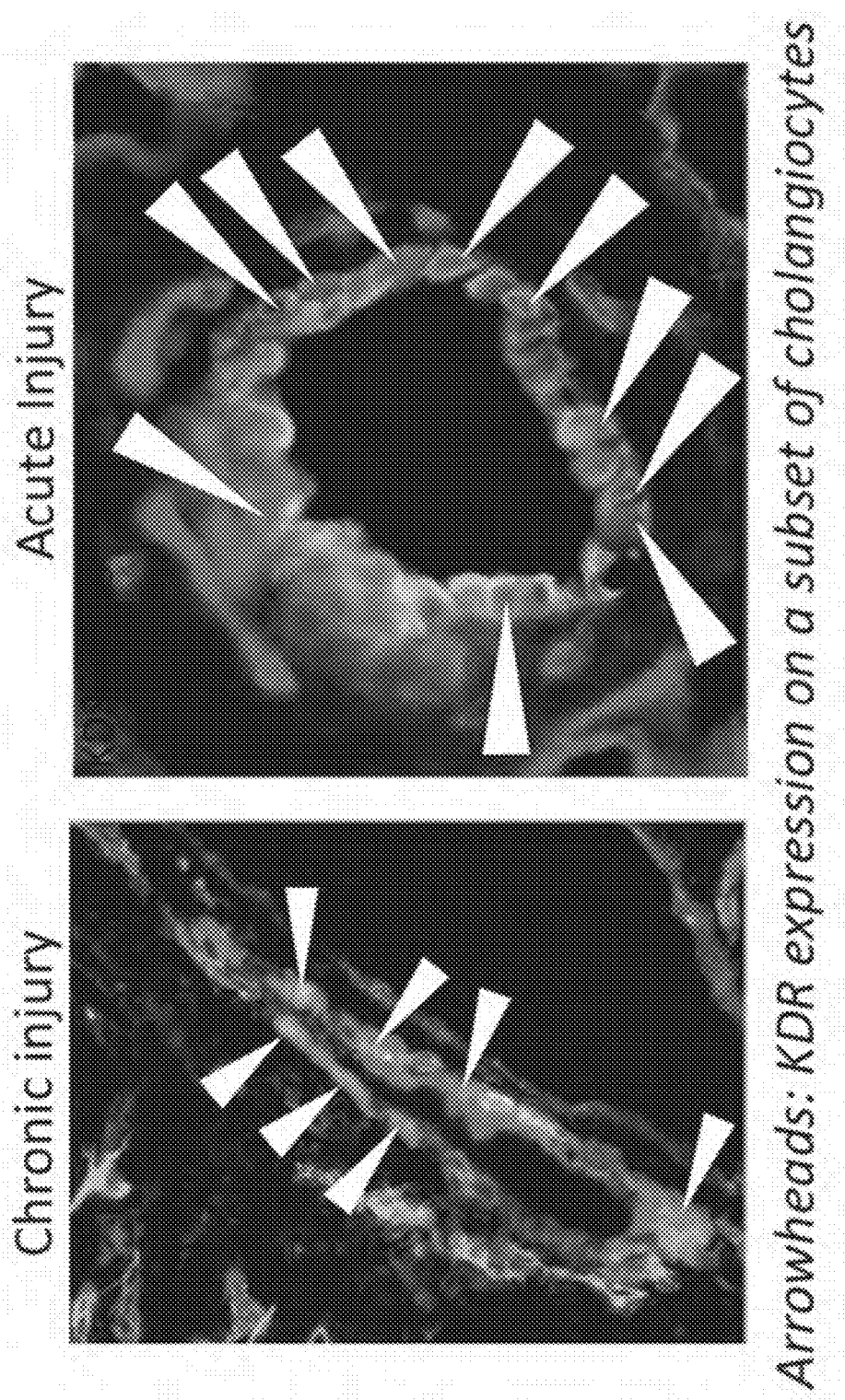

FIG. 83 depicts liver injury induces KDR expression on cholangiocytes.

Figure 84:
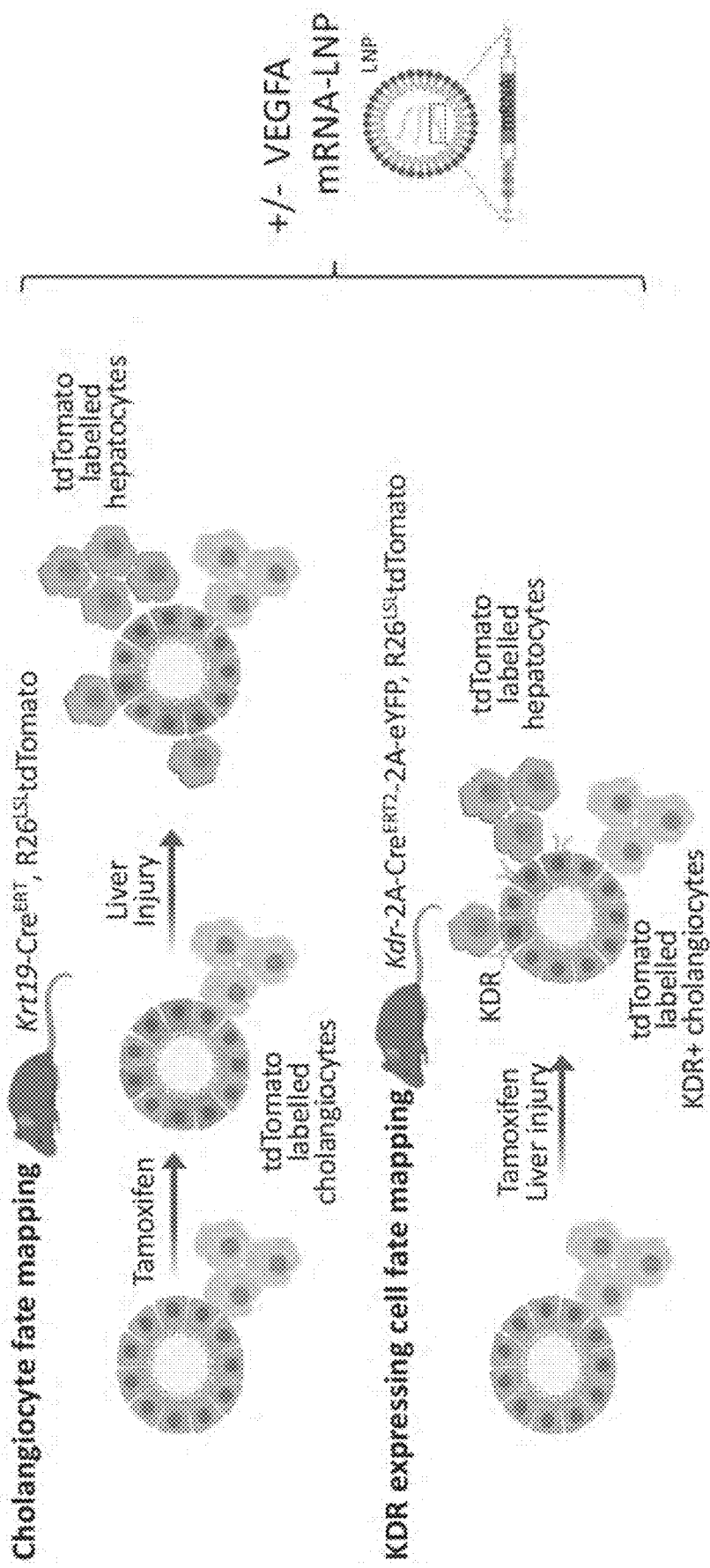
Figure 85A:
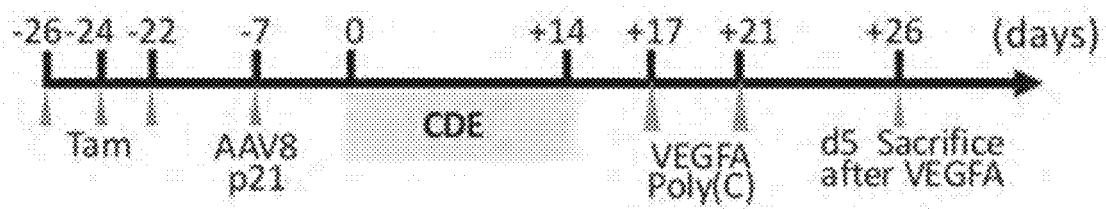
Figure 85B:
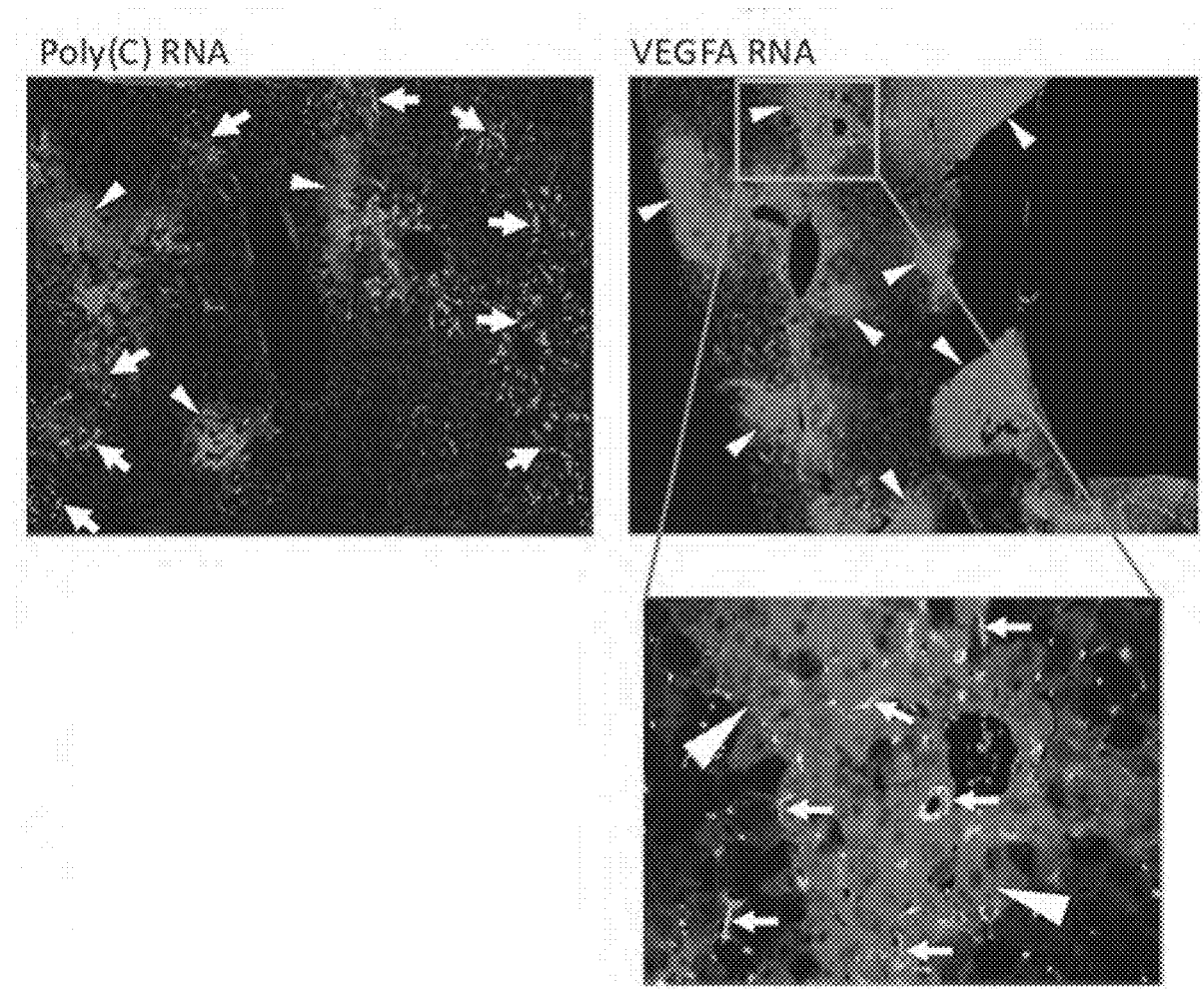
Figure 85C:
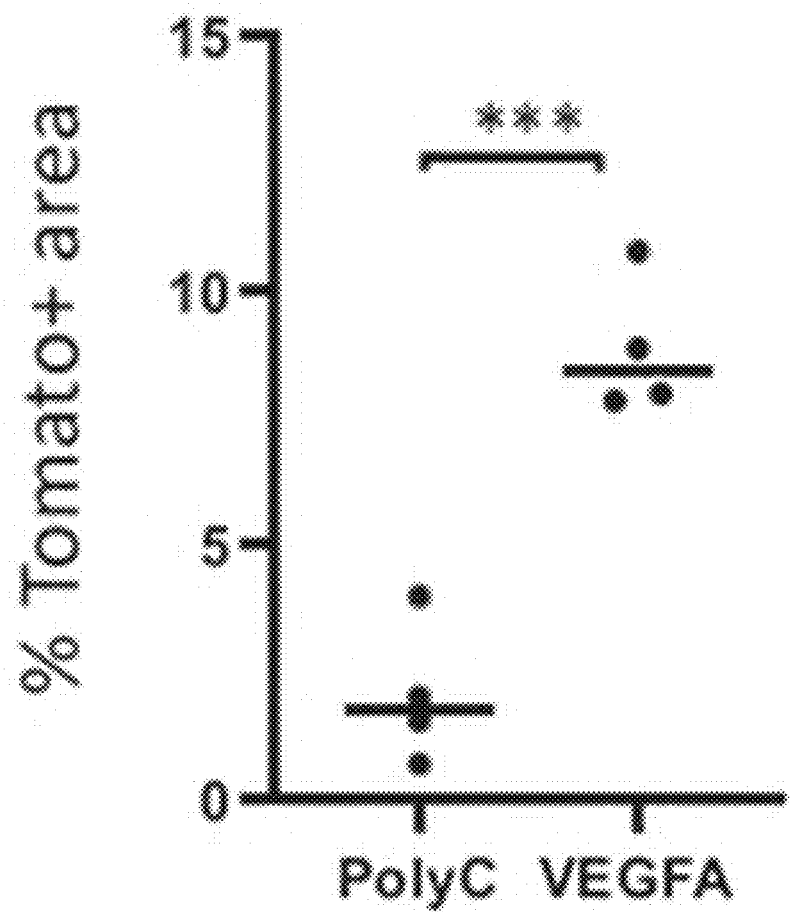
Figure 85D:
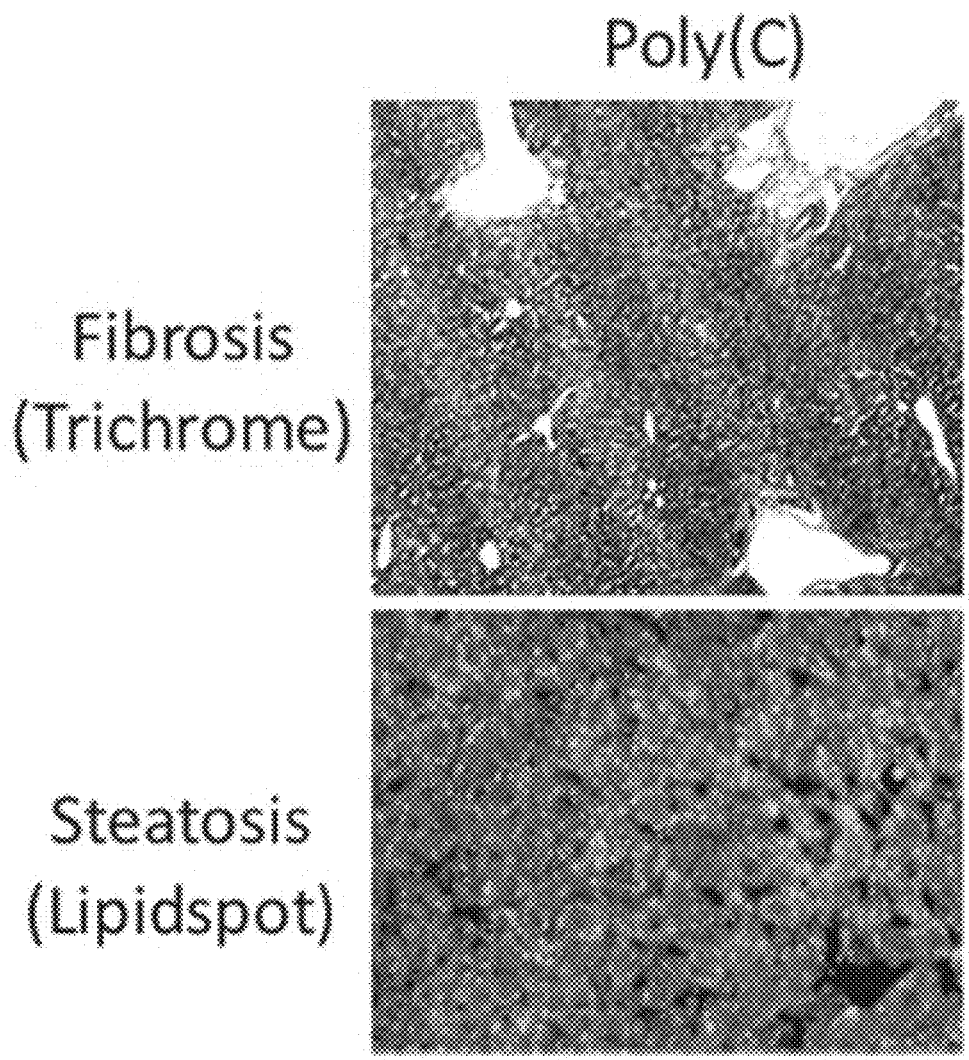
Figure 85D:
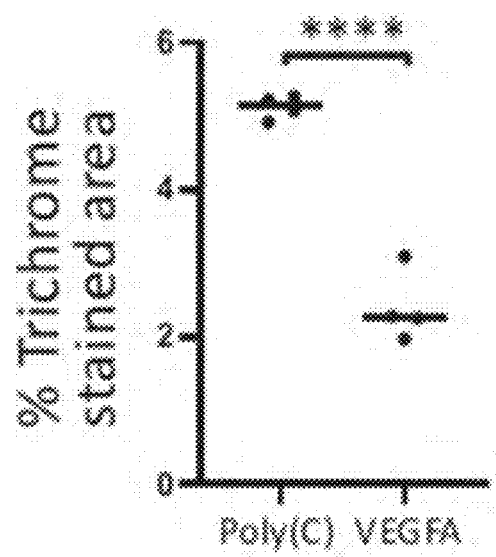
Figure 85E:
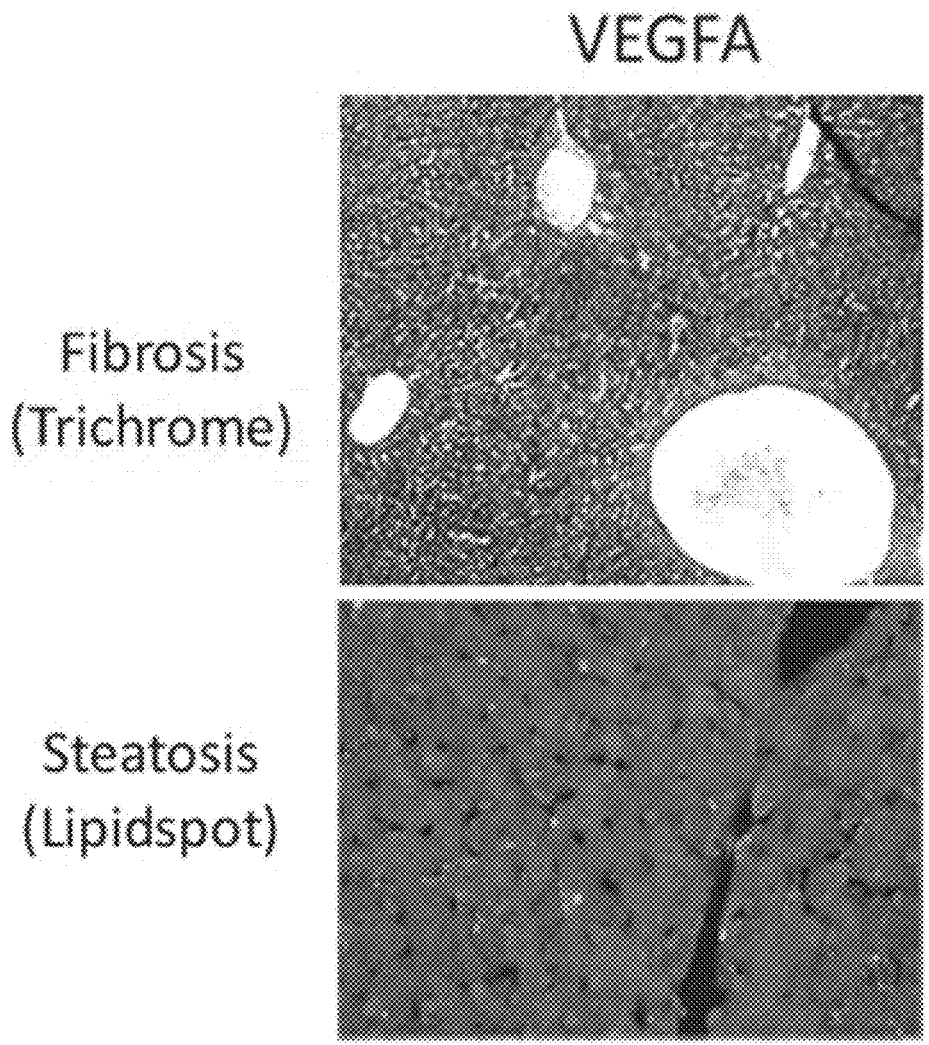
Figure 85E:
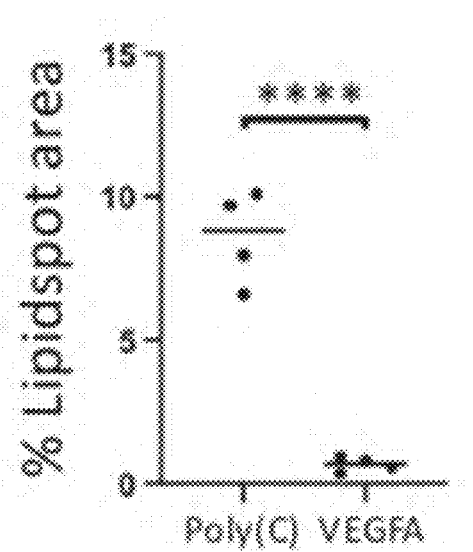
Figure 86A:
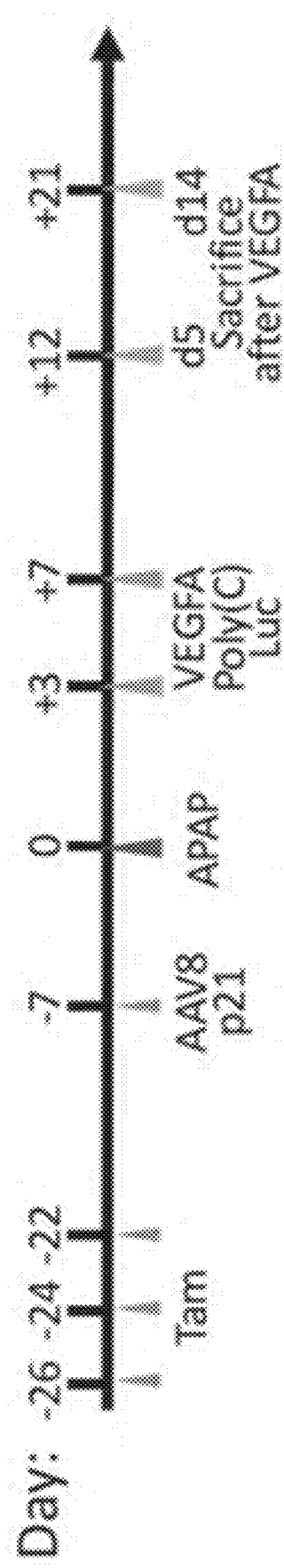
Figure 86B:
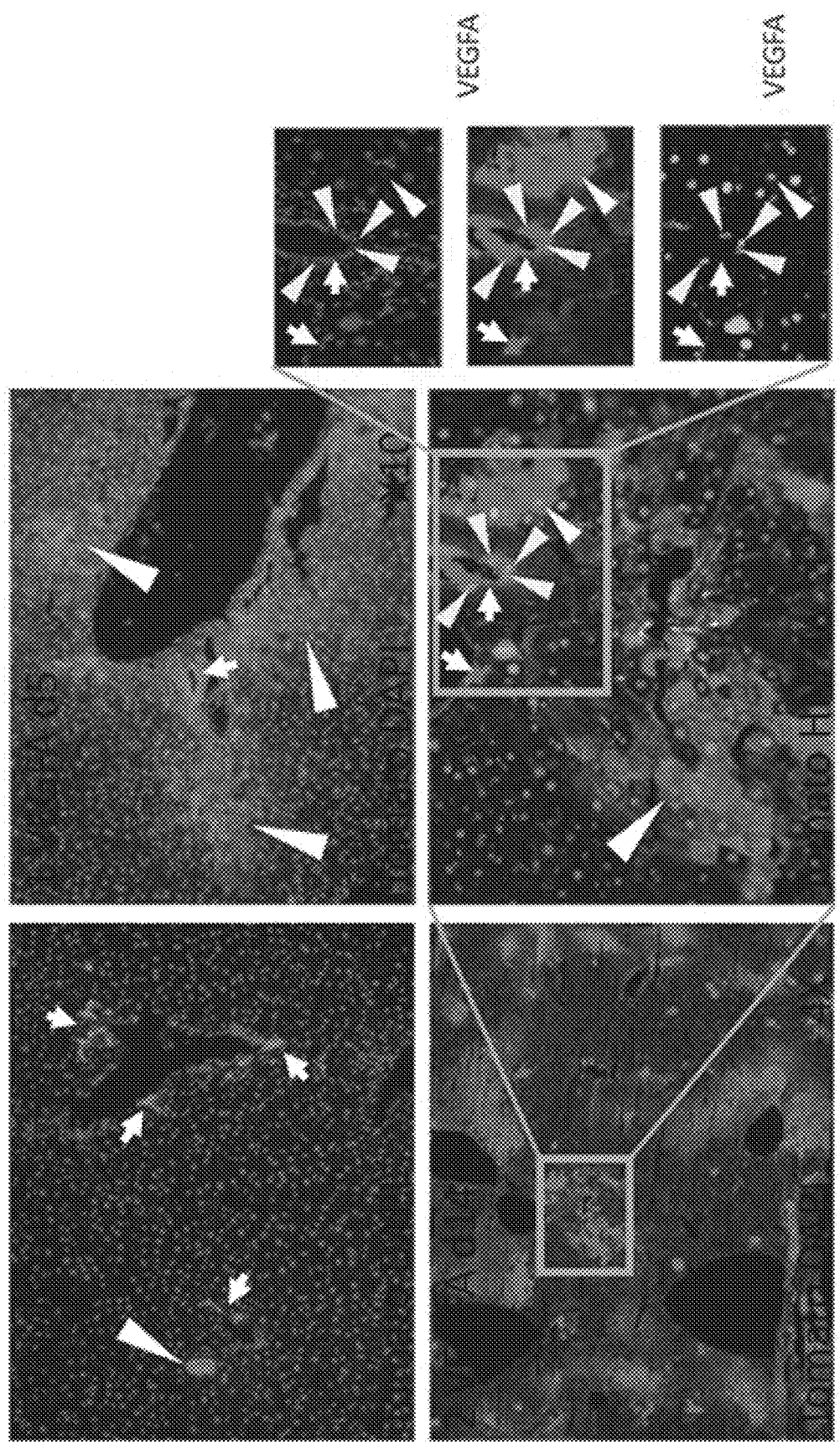
Figure 86C:
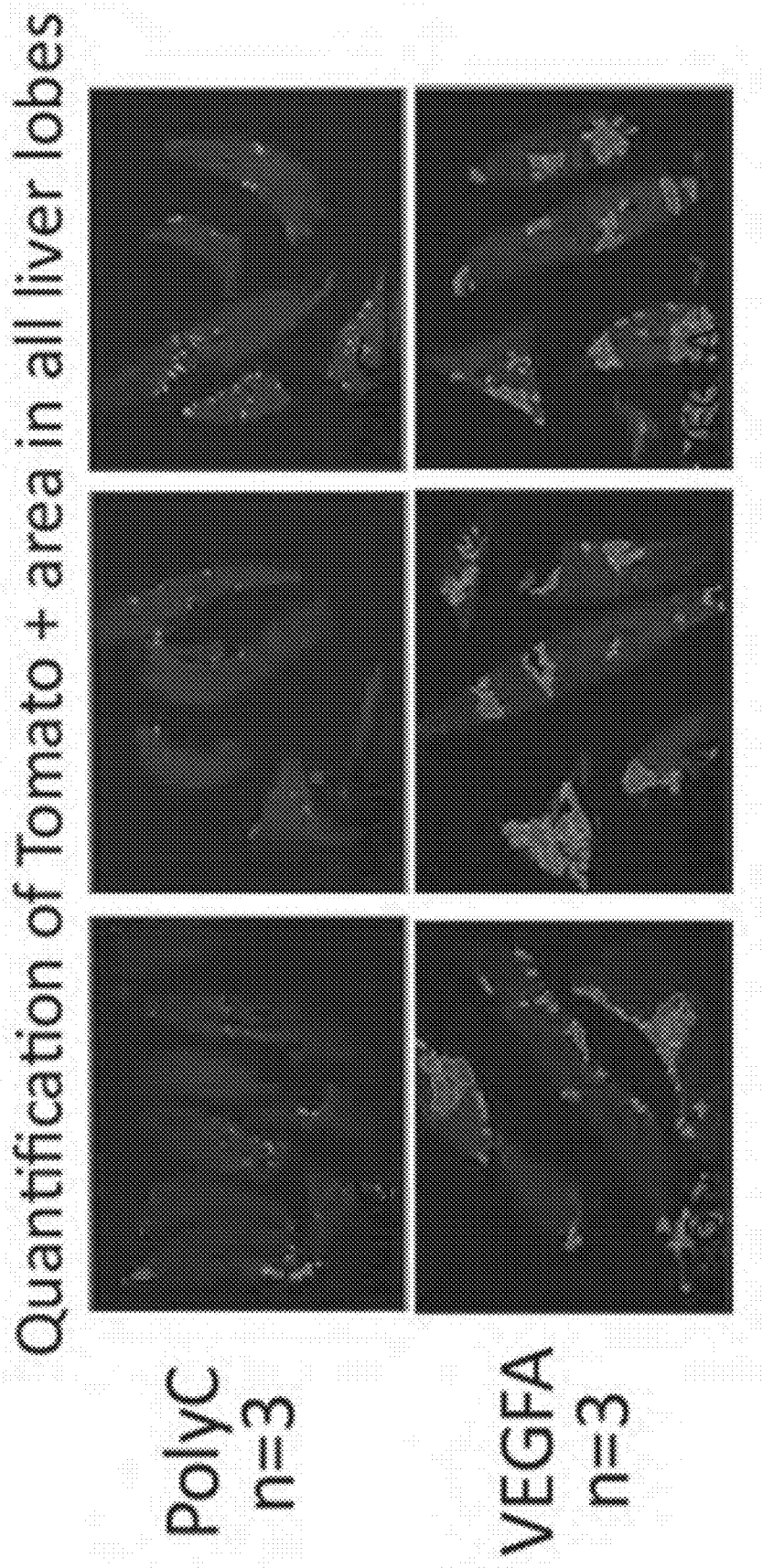
Figure 86D:
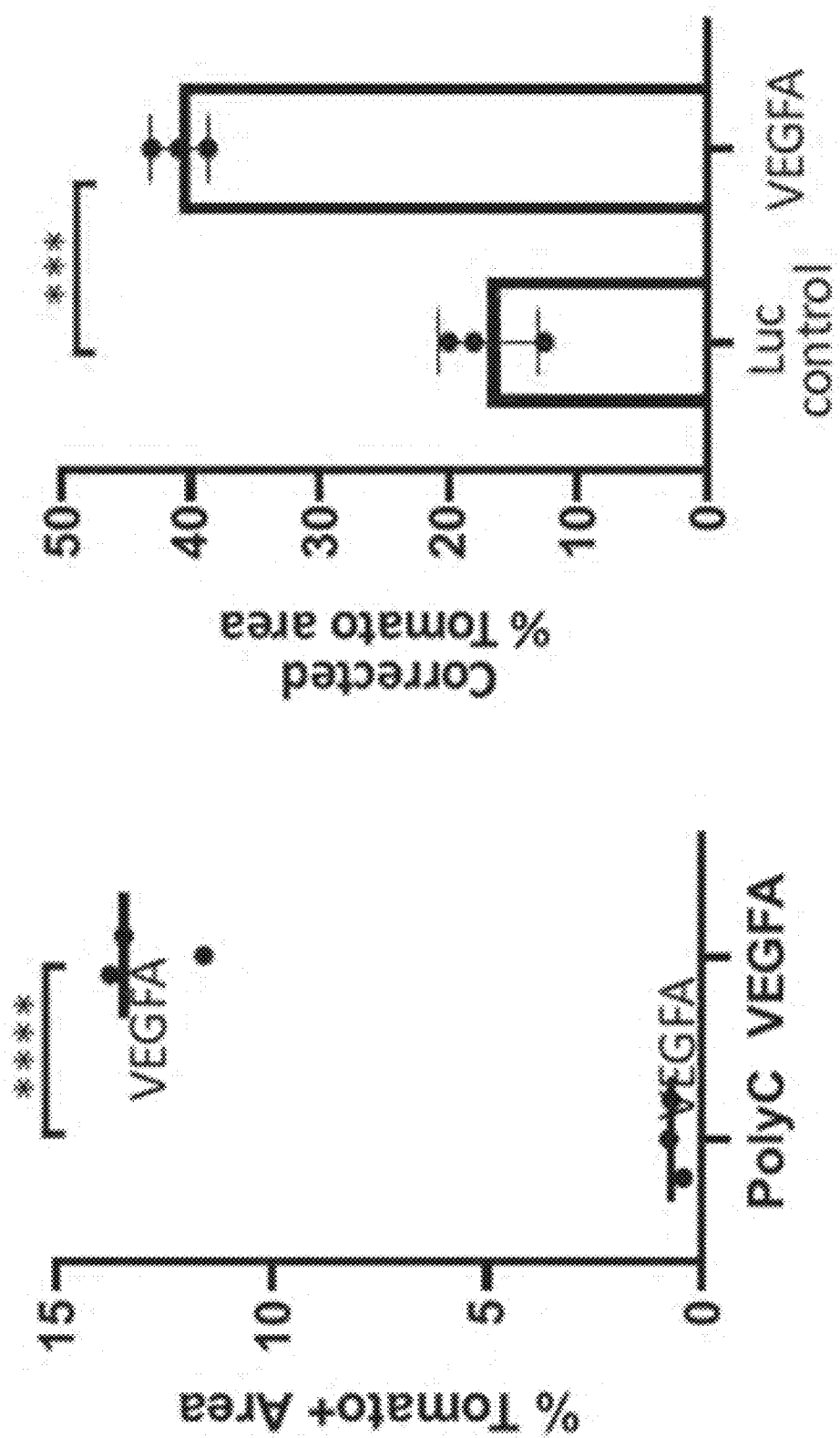
Figure 87A:
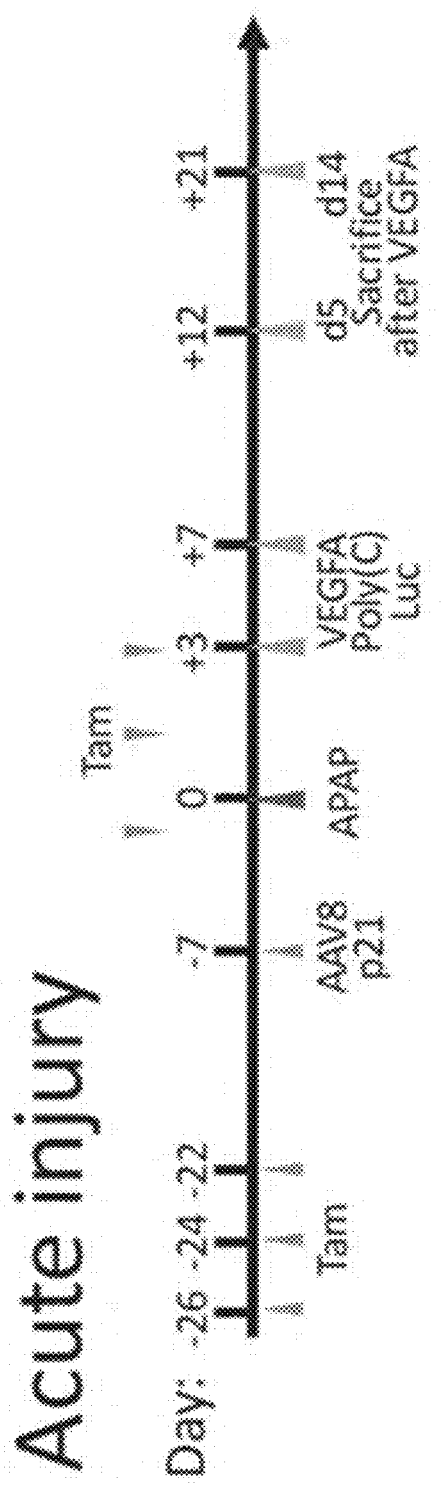
Figure 87B:
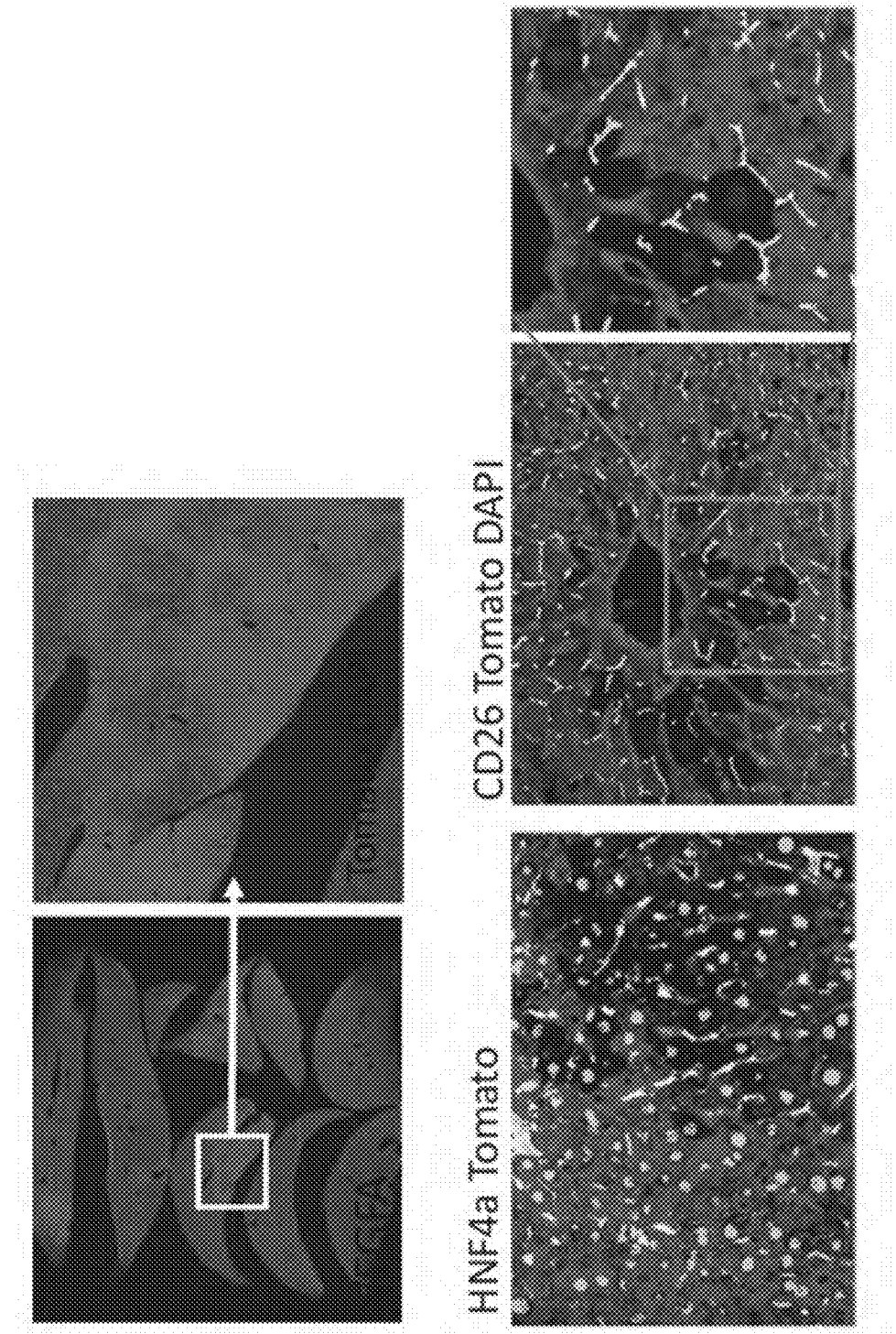
Figure 87C:
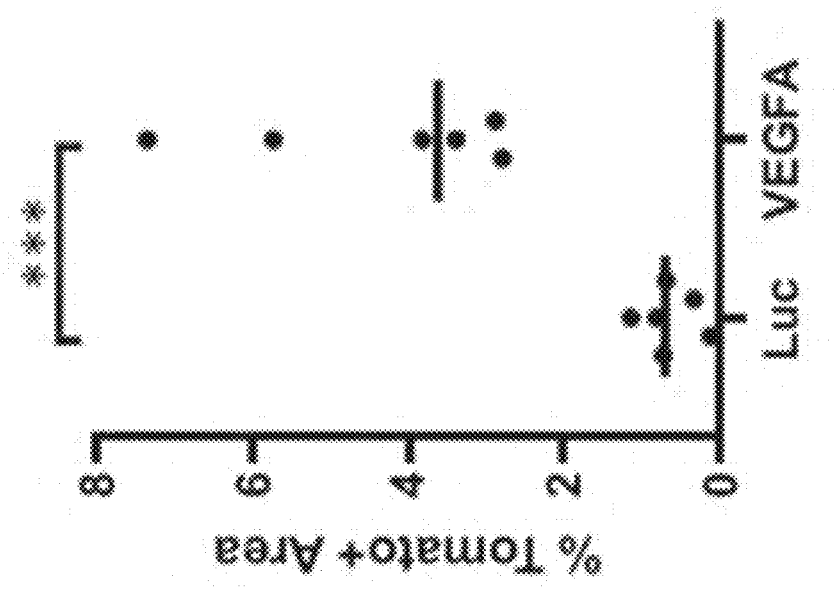
Figure 87D:
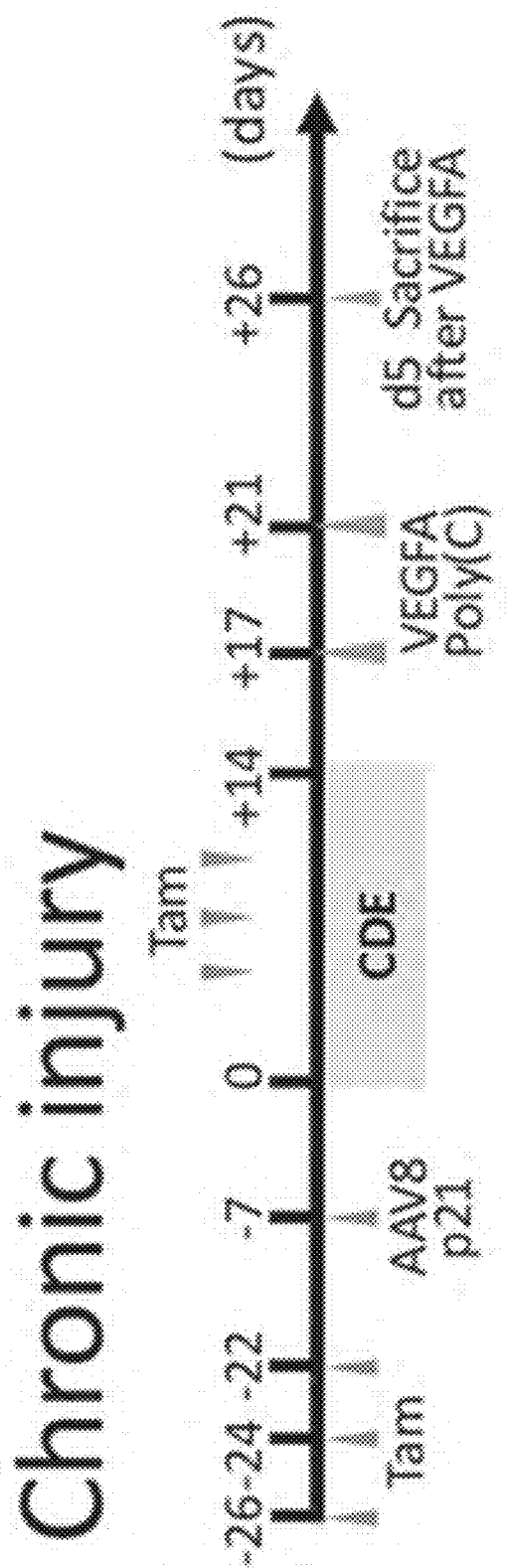
Figure 87E:
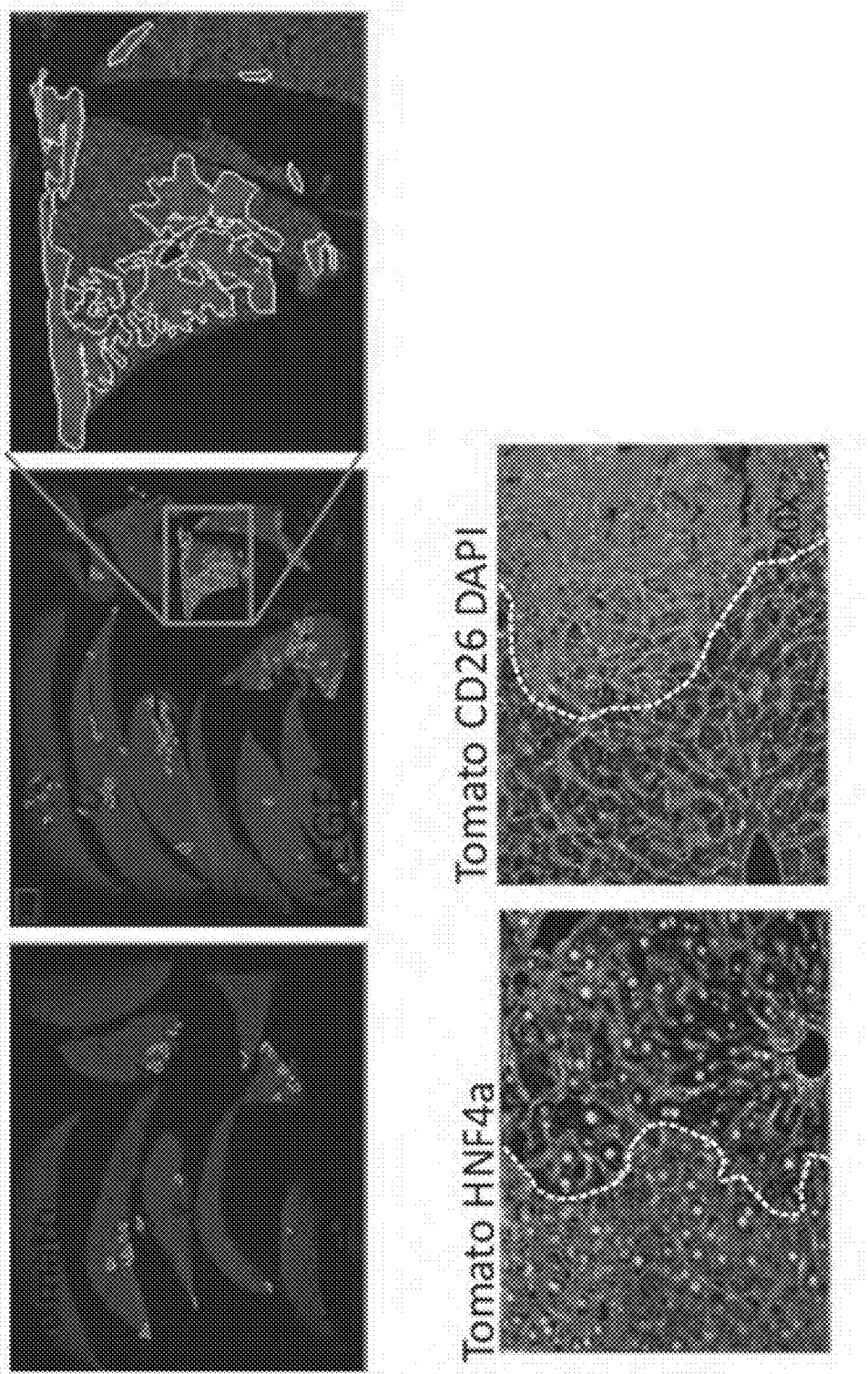
Figure 87F:
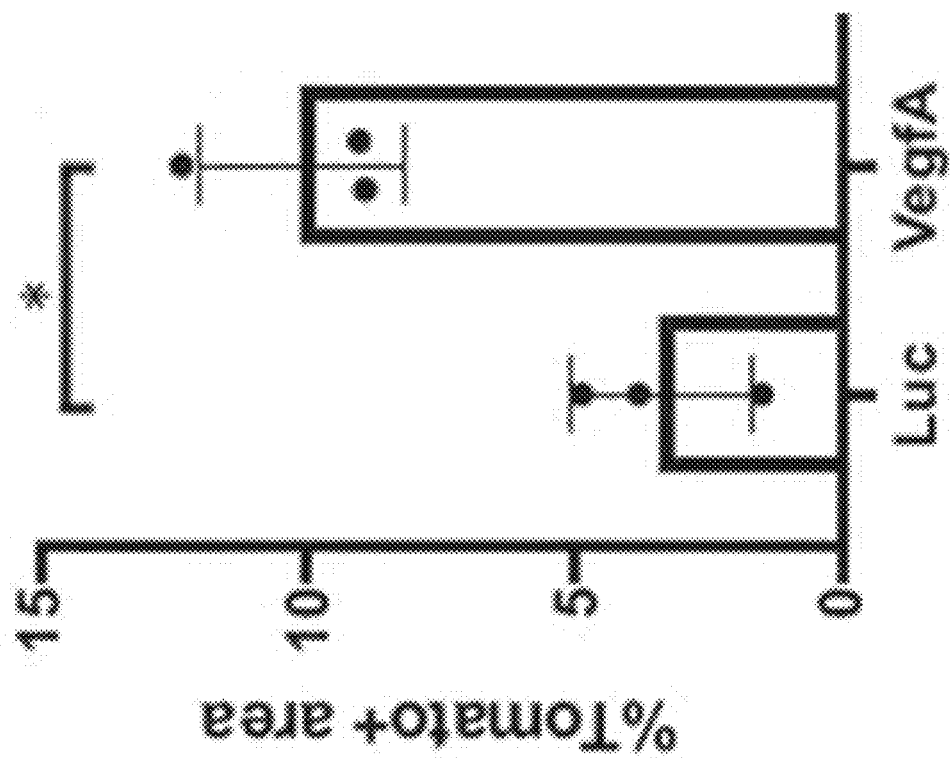

FIG. 84 depicts mapping hepatocytic fate of cholangiocytes and KDR expressing cells in VEGFA-treated mice.

FIGS. 85A-85E demonstrate VEGFA mRNA-LNPs promotes cholangiocyte to hepatocyte conversion and reverses steatosis and fibrosis in a chronic liver injury model.

FIGS. 86A-86D demonstrate that VEGFA mRNA-LNPs promotes KDR+ cell conversion to hepatocytes in acute and chronic liver injuries.

FIGS. 87A-87F summarize that KDR is expressed on a subset of cholangiocytes after acute and chronic liver injuries and that VEGFA mRNA-LNPs promotes cholangiocyte to hepatocyte conversion in acute and chronic liver injuries.

Figure 88A:
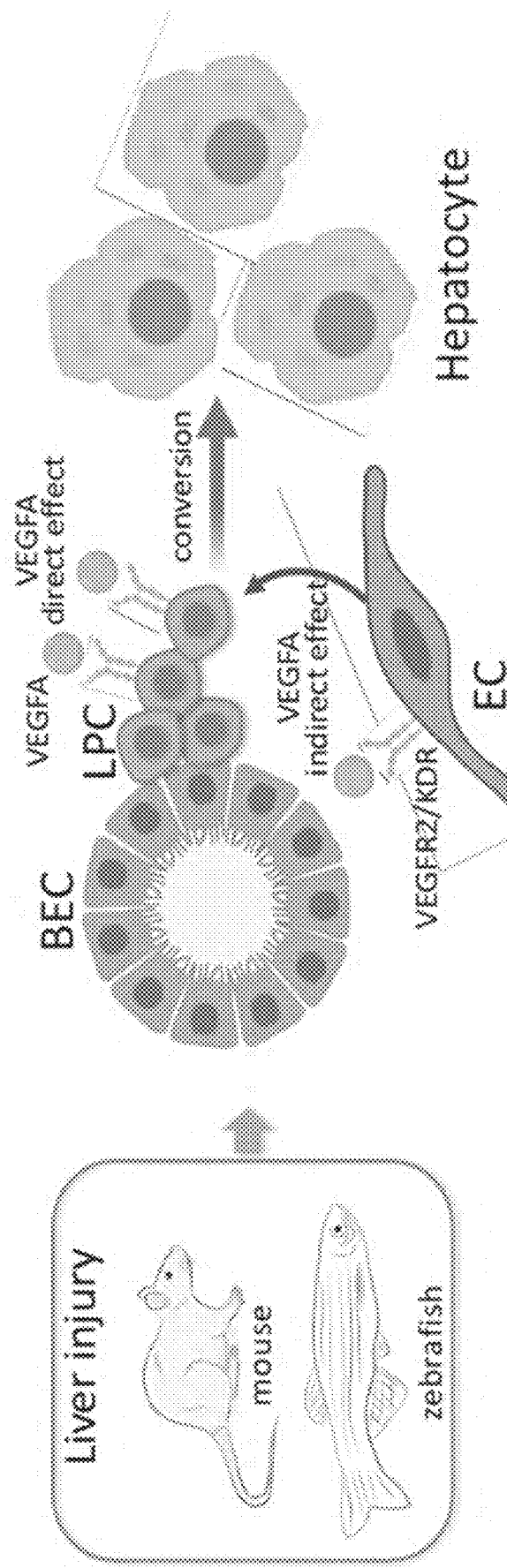
Figure 88B:
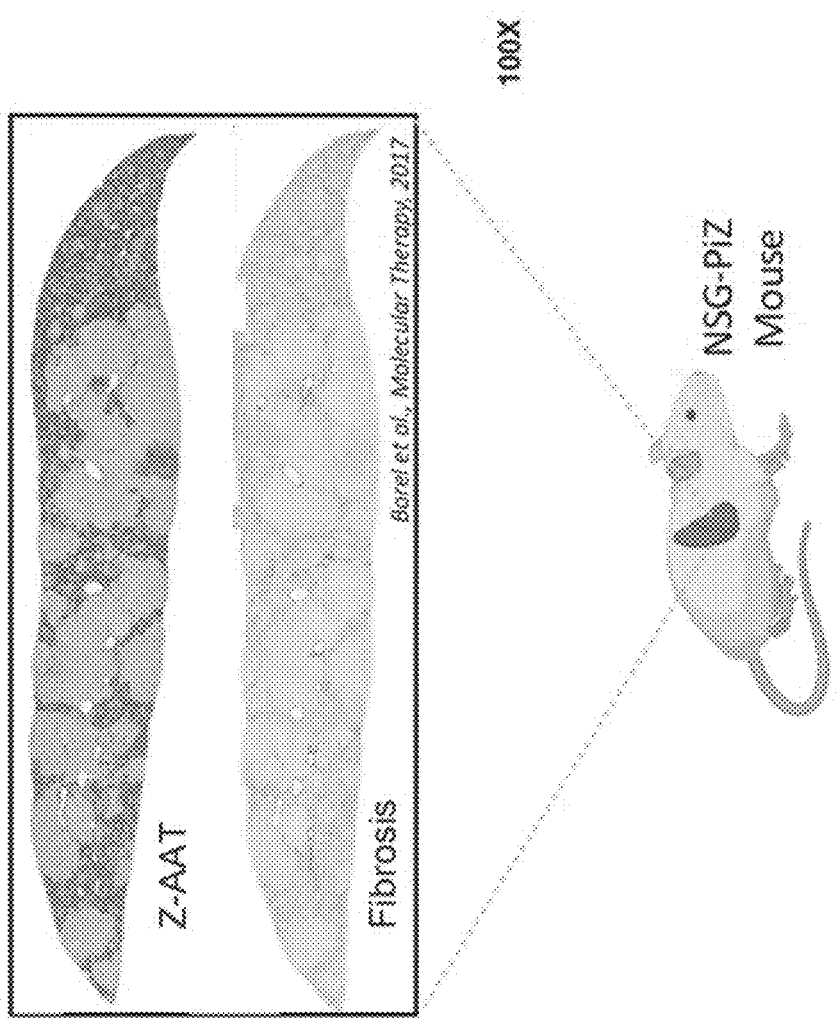

FIGS. 88A-88B depict NSG-PiZ mice recapitulate alpha-1 antitrypsin deficiency liver disease.

Figure 89:
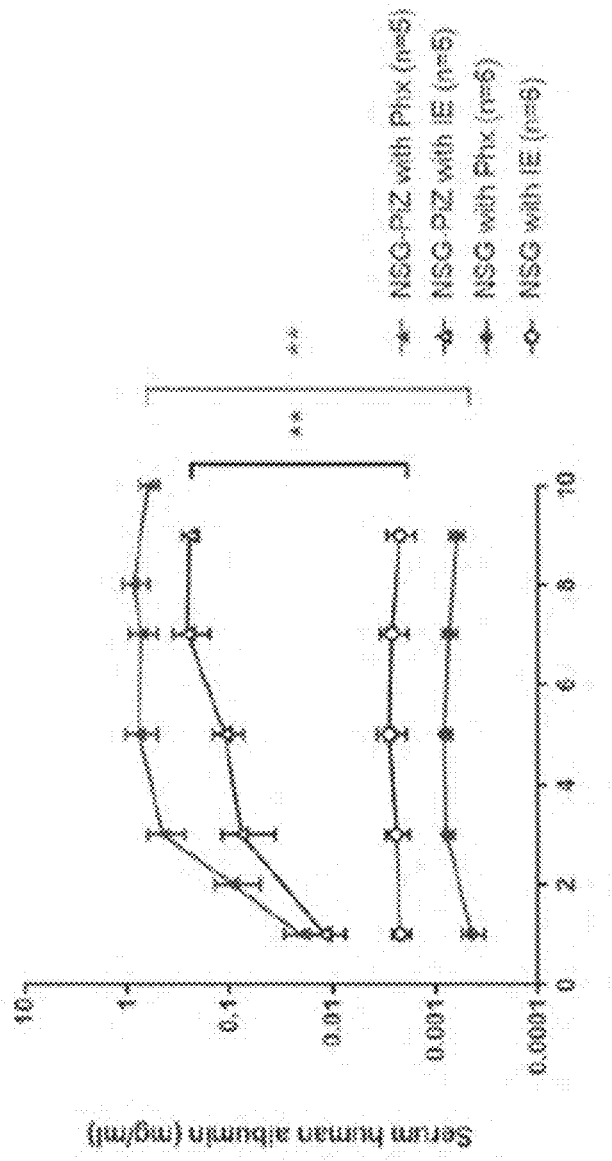
Figure 89:
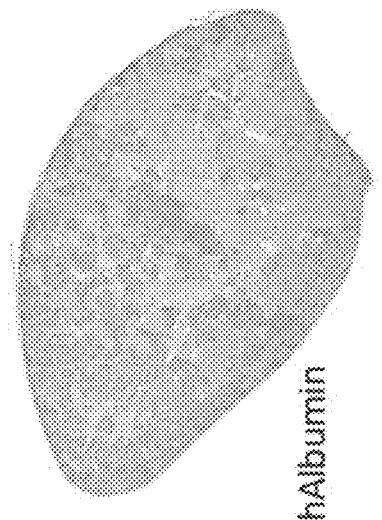

FIG. 89 depicts alpha-1 antitrypsin deficiency is an ideal candidate for liver cell therapy.

Figure 90:
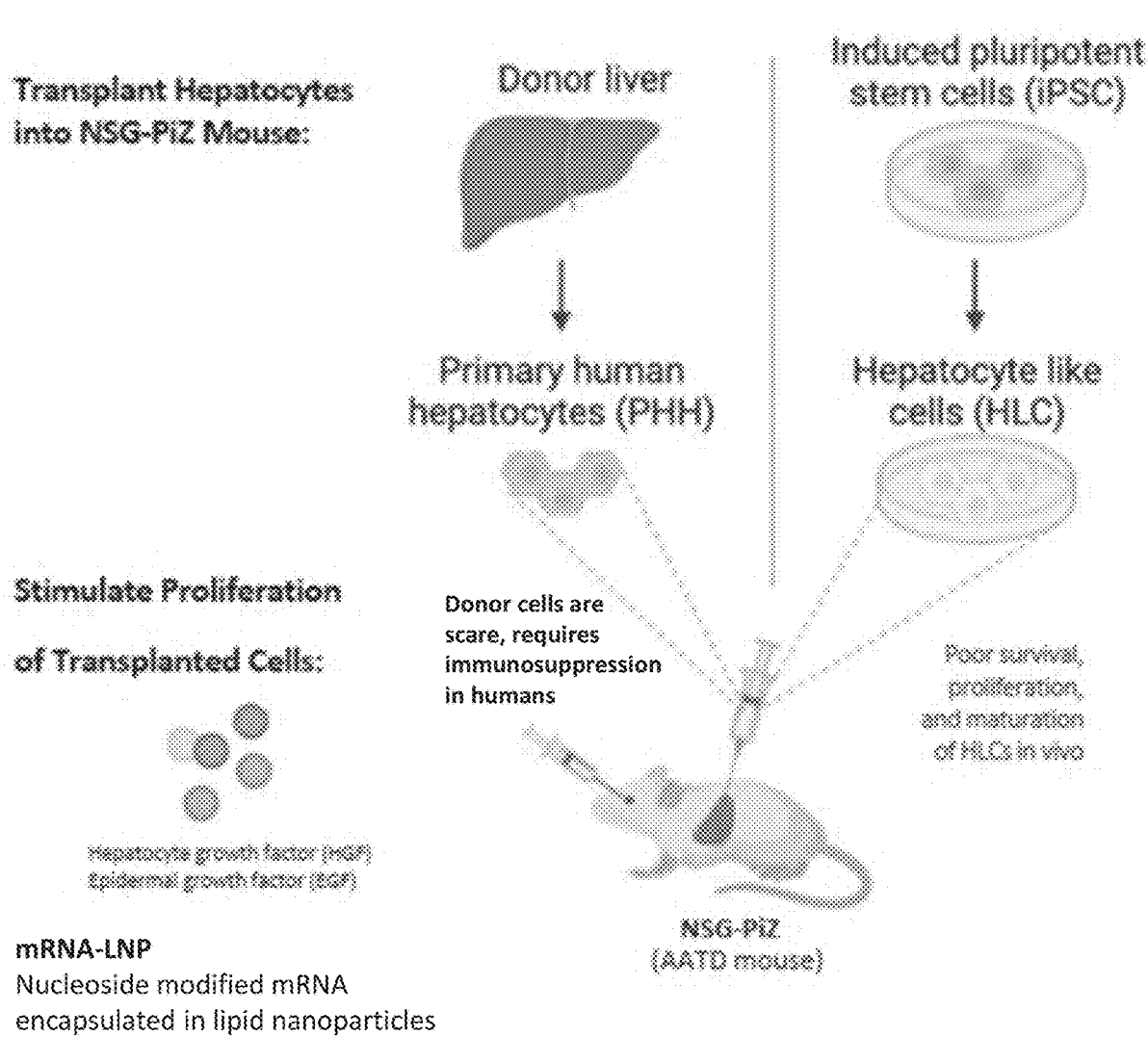

FIG. 90 depicts experimental proposal to use mRNA-LNP encoding HGF and EGF to stimulate proliferation of transplanted cells in NSG-PiZ mouse model.

Figure 91A:
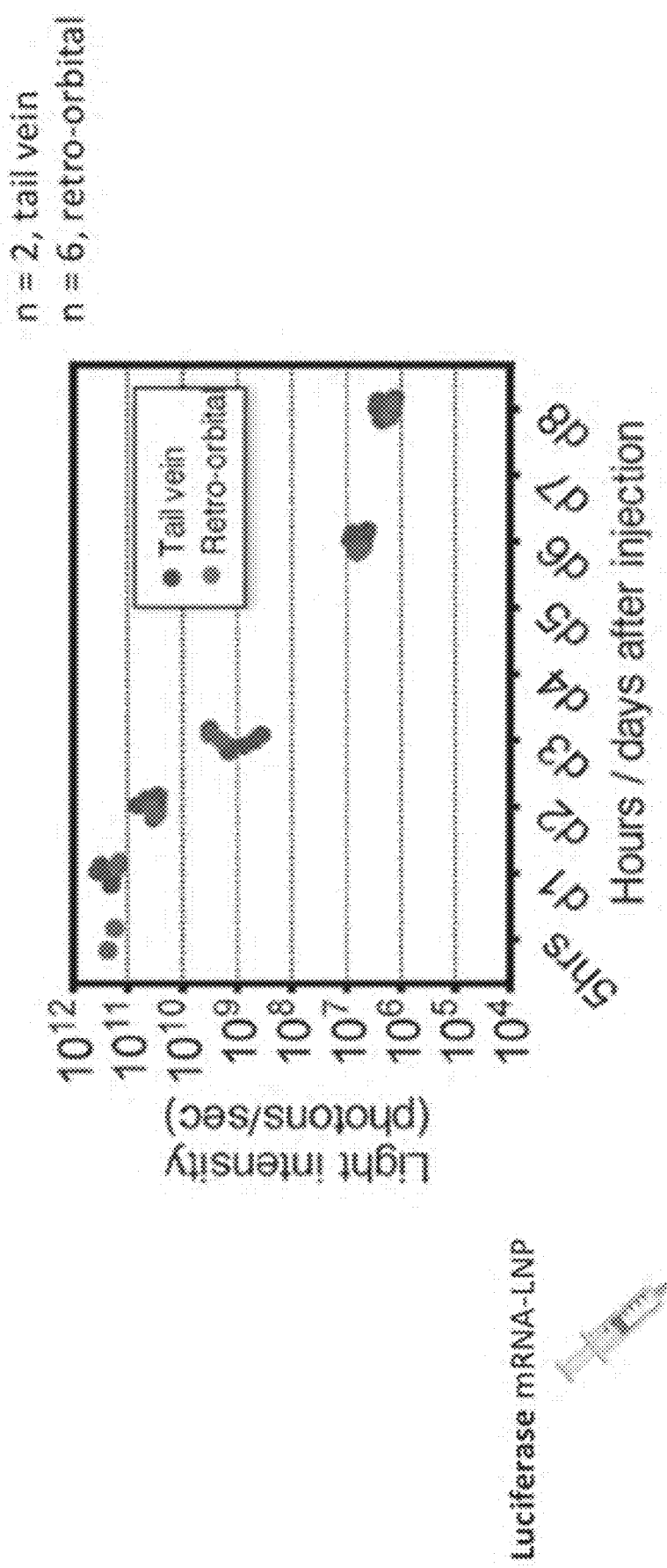
Figure 91B:
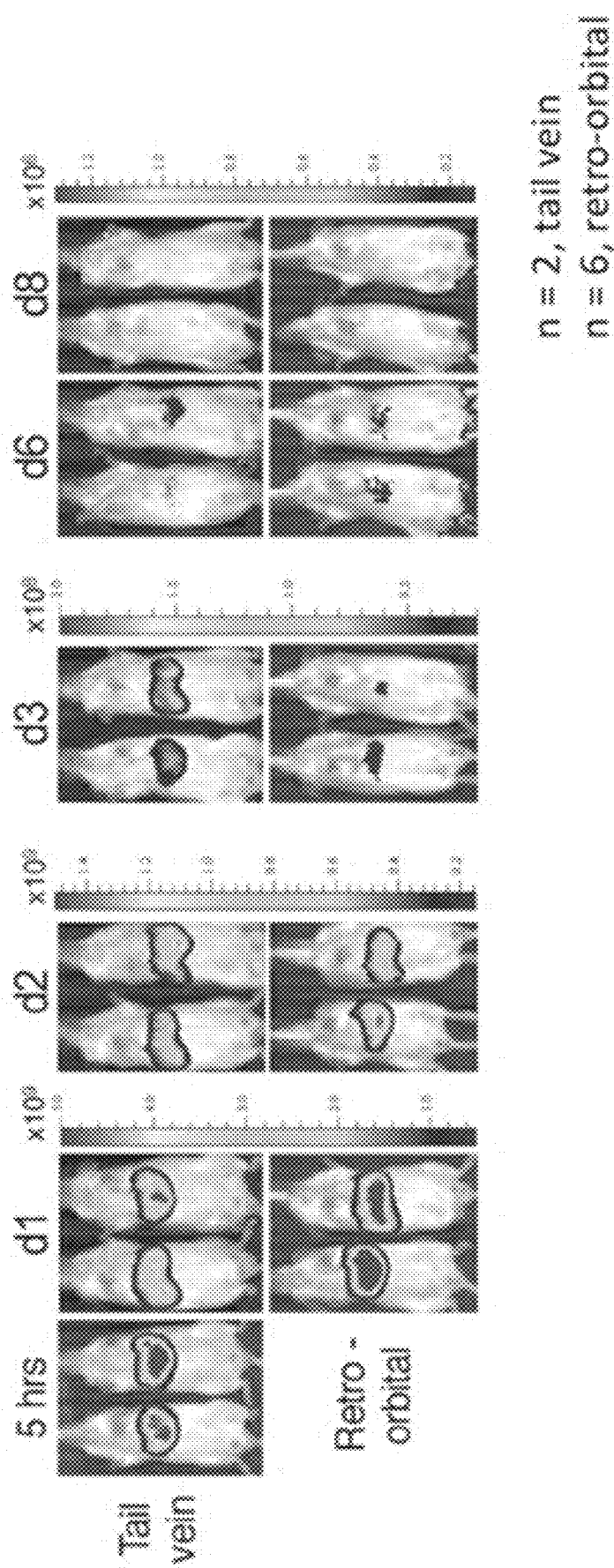

FIGS. 91A-91B depict a single IV injection of mRNA-LNP induces robust and restricted protein expression in the liver.

Figure 9A:
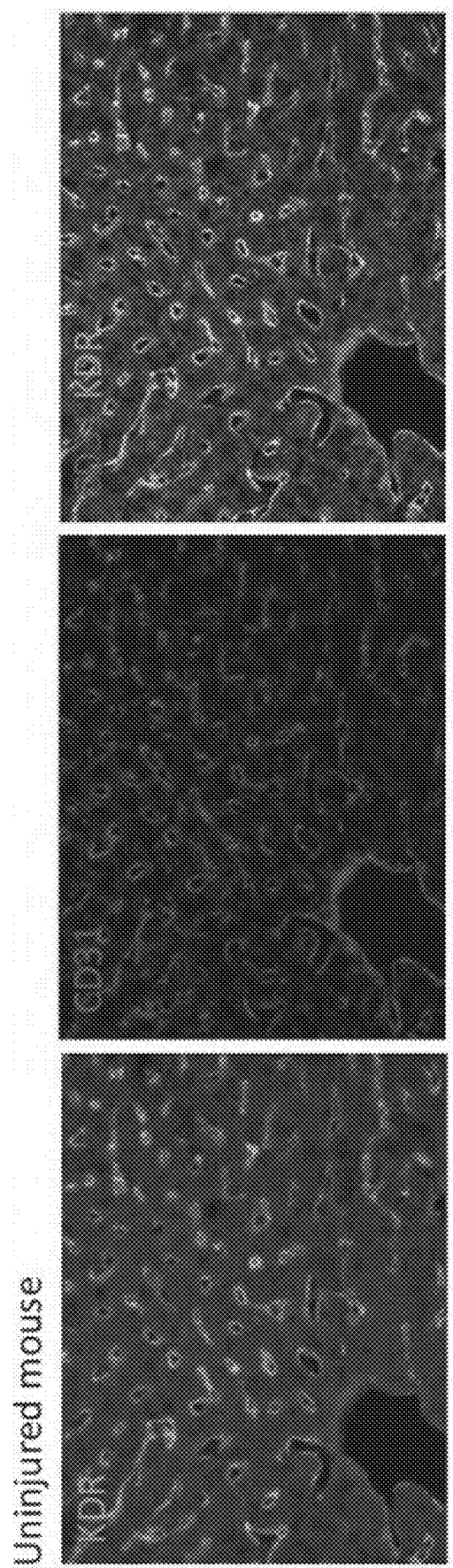
FIGS. 9A-9E depict hepatocyte generation from KDR expressing cells and experimental design.
Figure 9B:
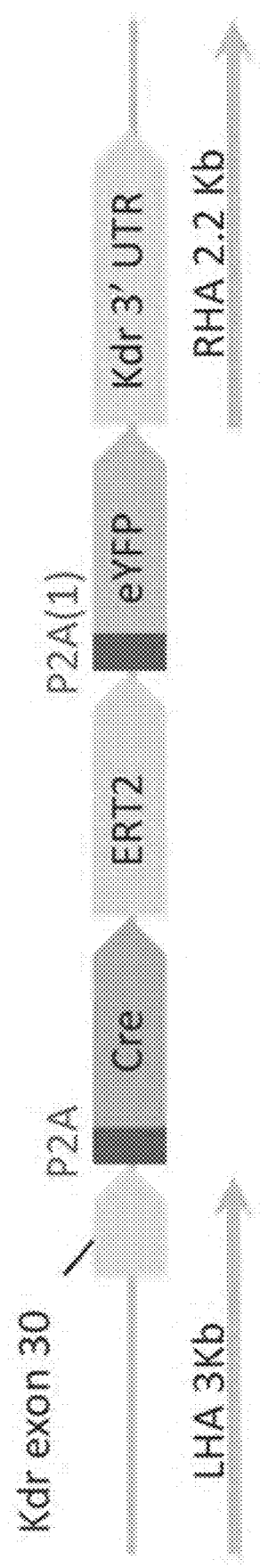
Figure 92A:
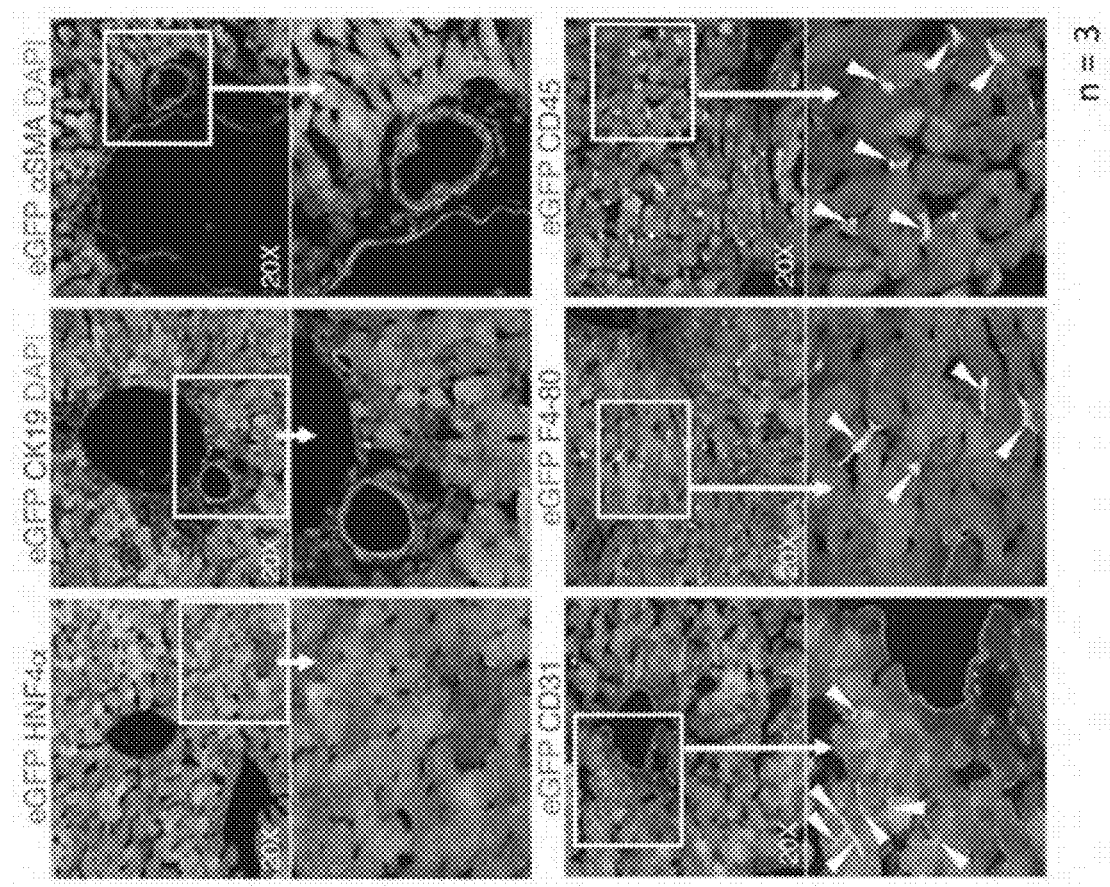
Figure 92A:
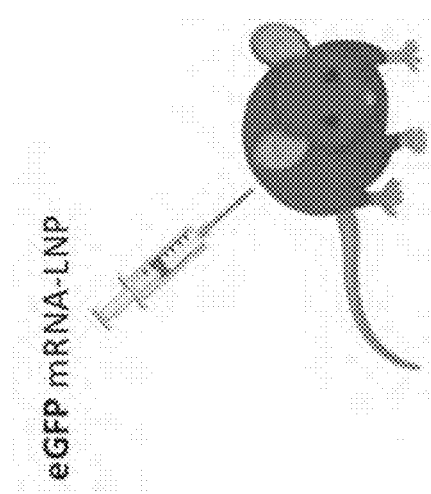
Figure 92B:
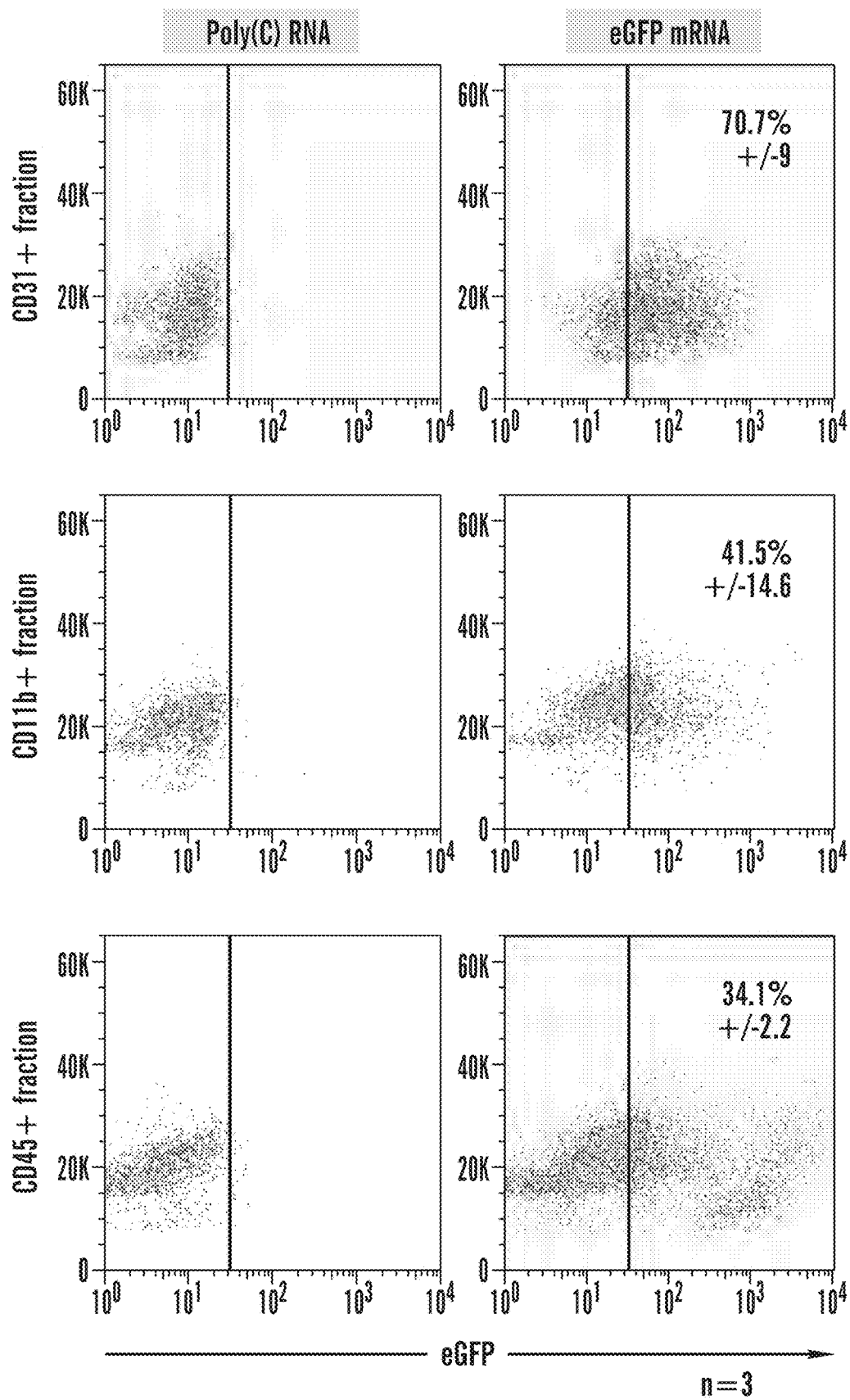

FIGS. 92A-9B show that hepatocytes are the main liver cell type transfected by mRNA-LNP.

Figure 93:
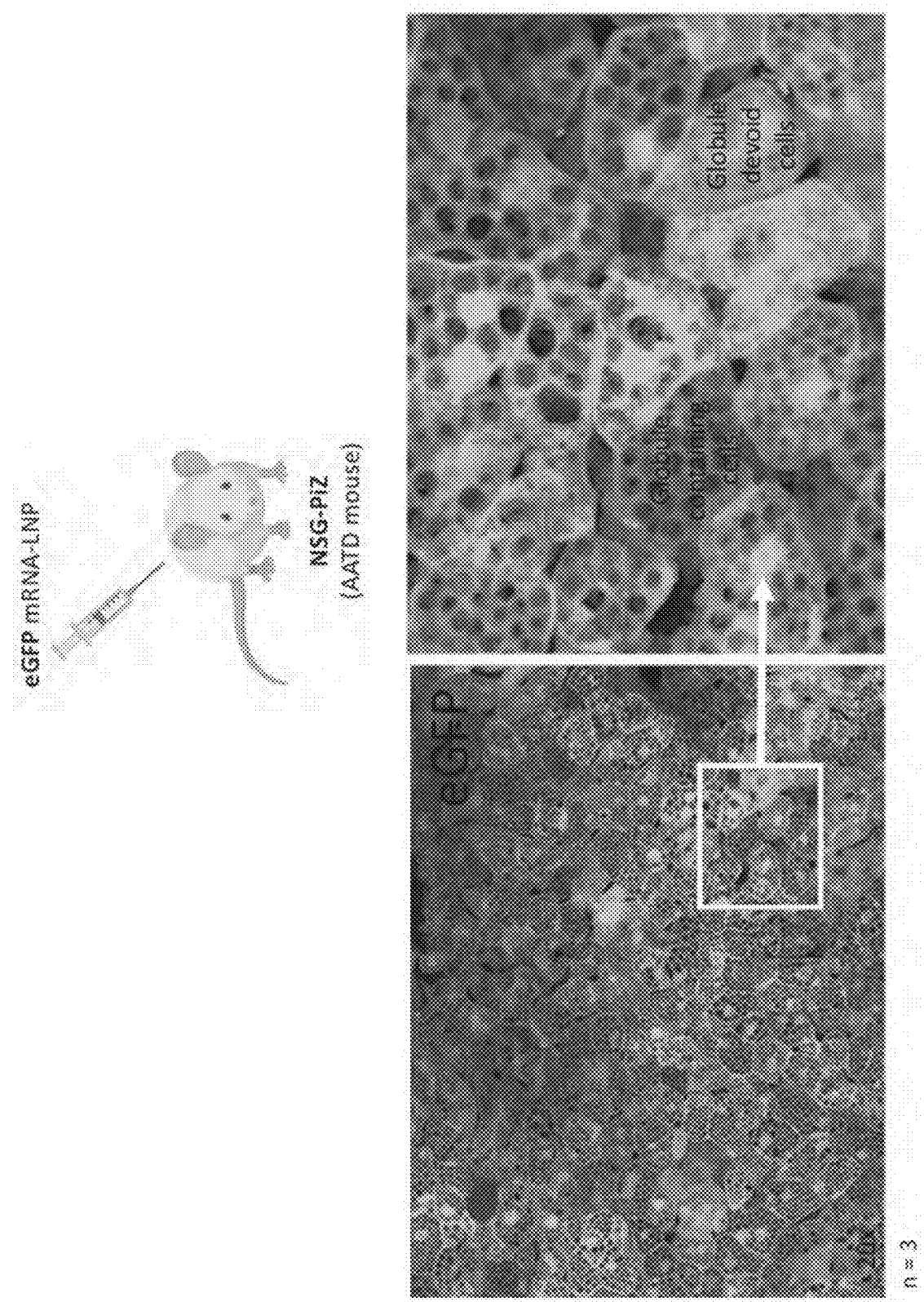

FIG. 93 shows that mRNA-LNP induces protein expression in diseased hepatocytes in NSG-PiZ mice.

Figure 94:
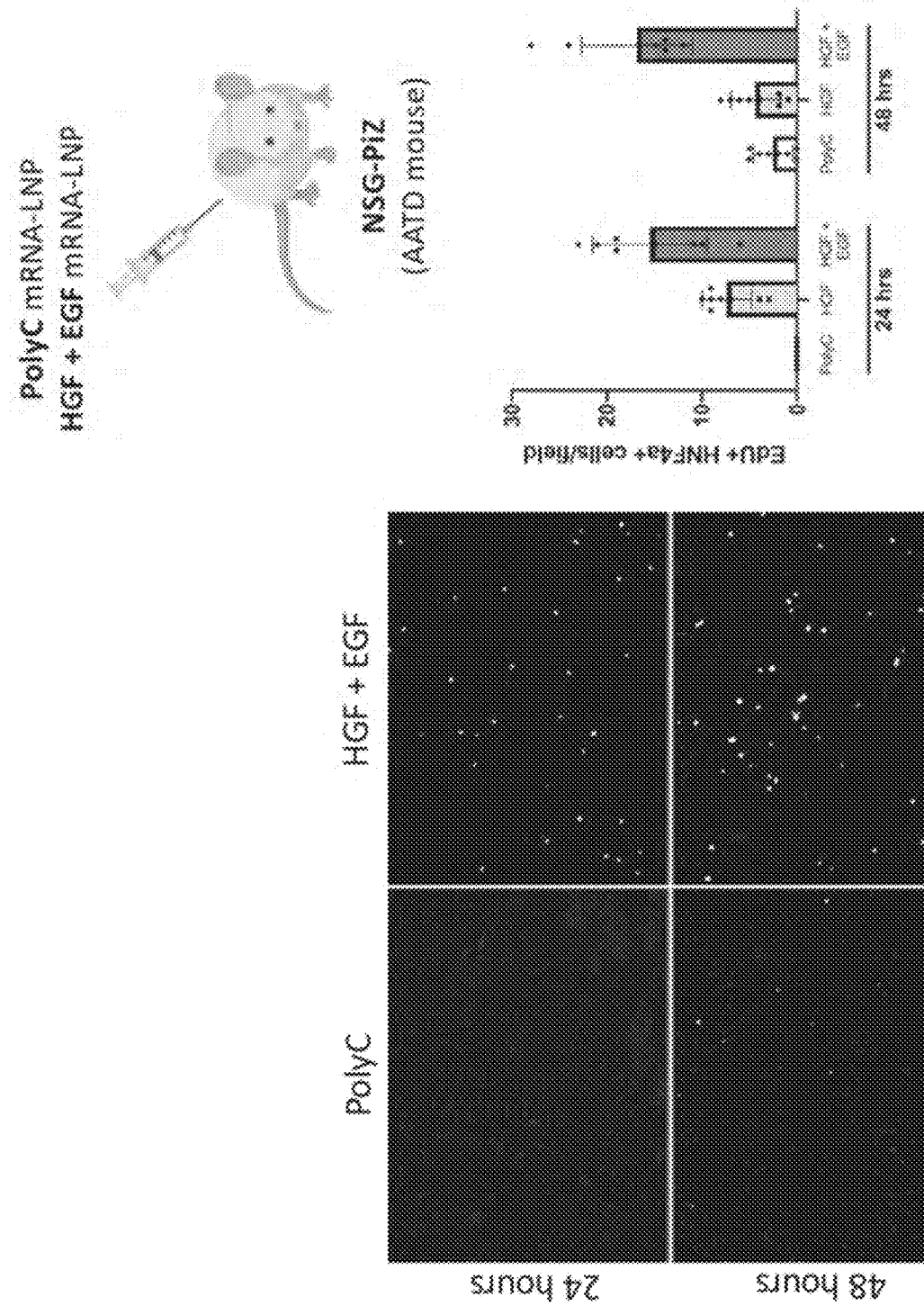

FIG. 94 shows HGF+EGF mRNA-LNP induces hepatocyte proliferation.

Figure 95:
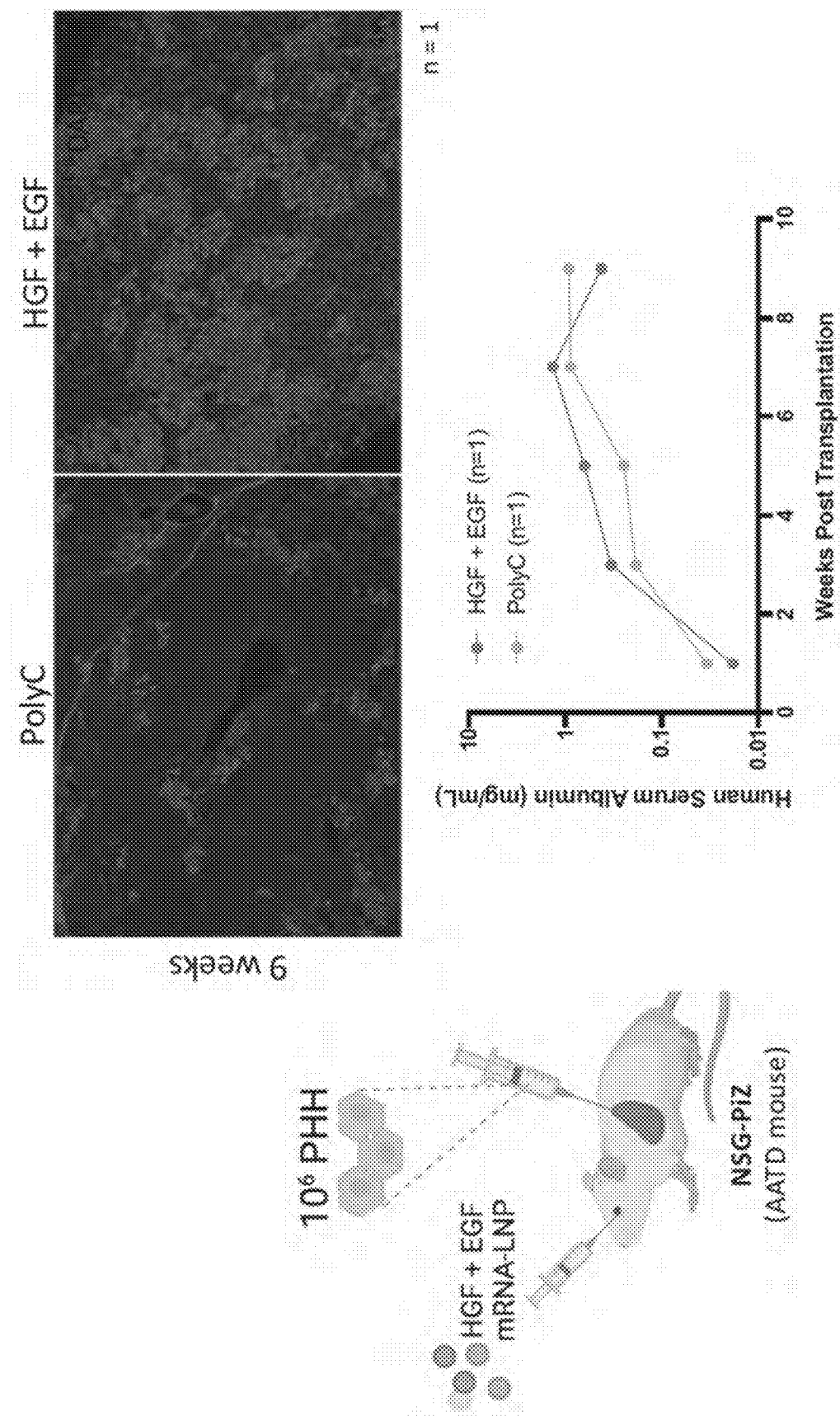

FIG. 95 shows that weekly injections of HGF+EGF mRNA-LNP increase PHH cluster size in male NSG-PiZ mice.

Figure 96A:
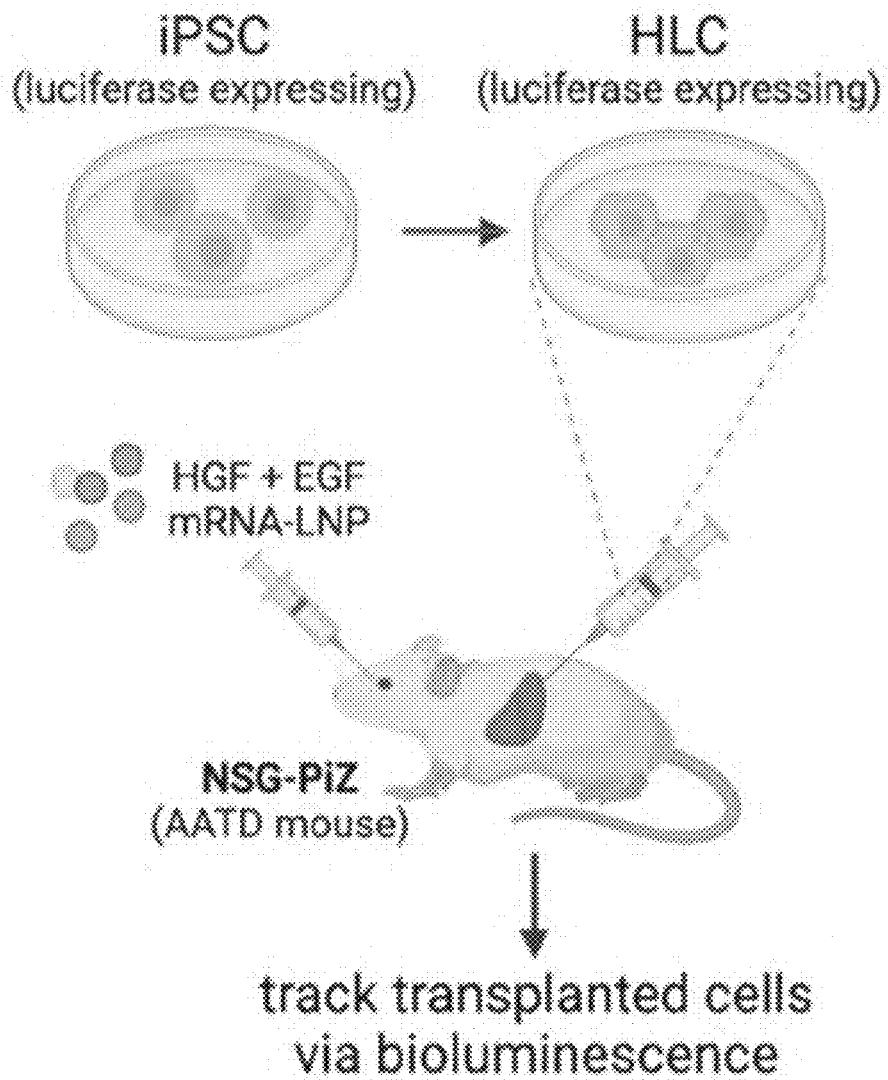
Figure 96B:
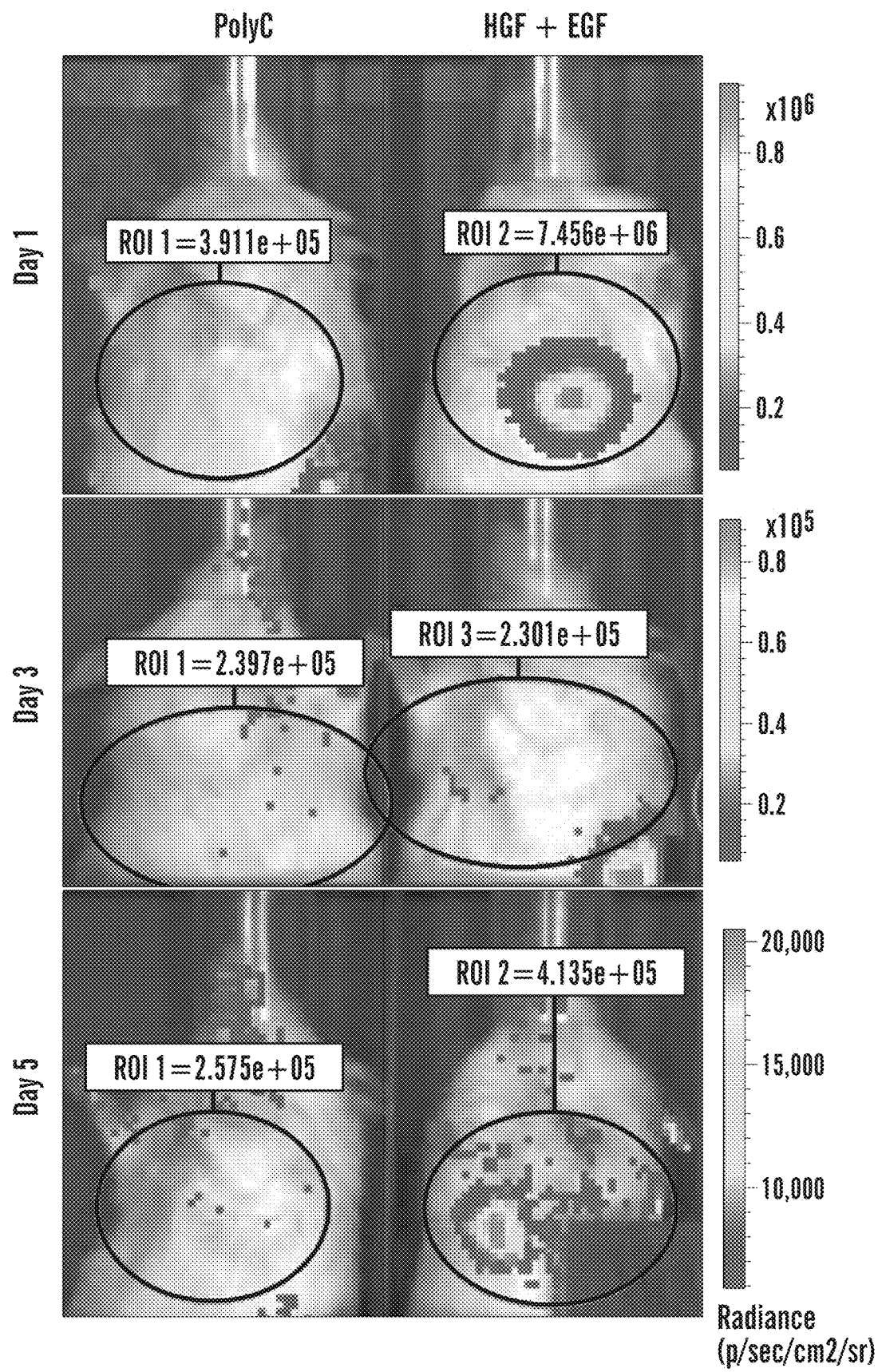
Figure 96C:
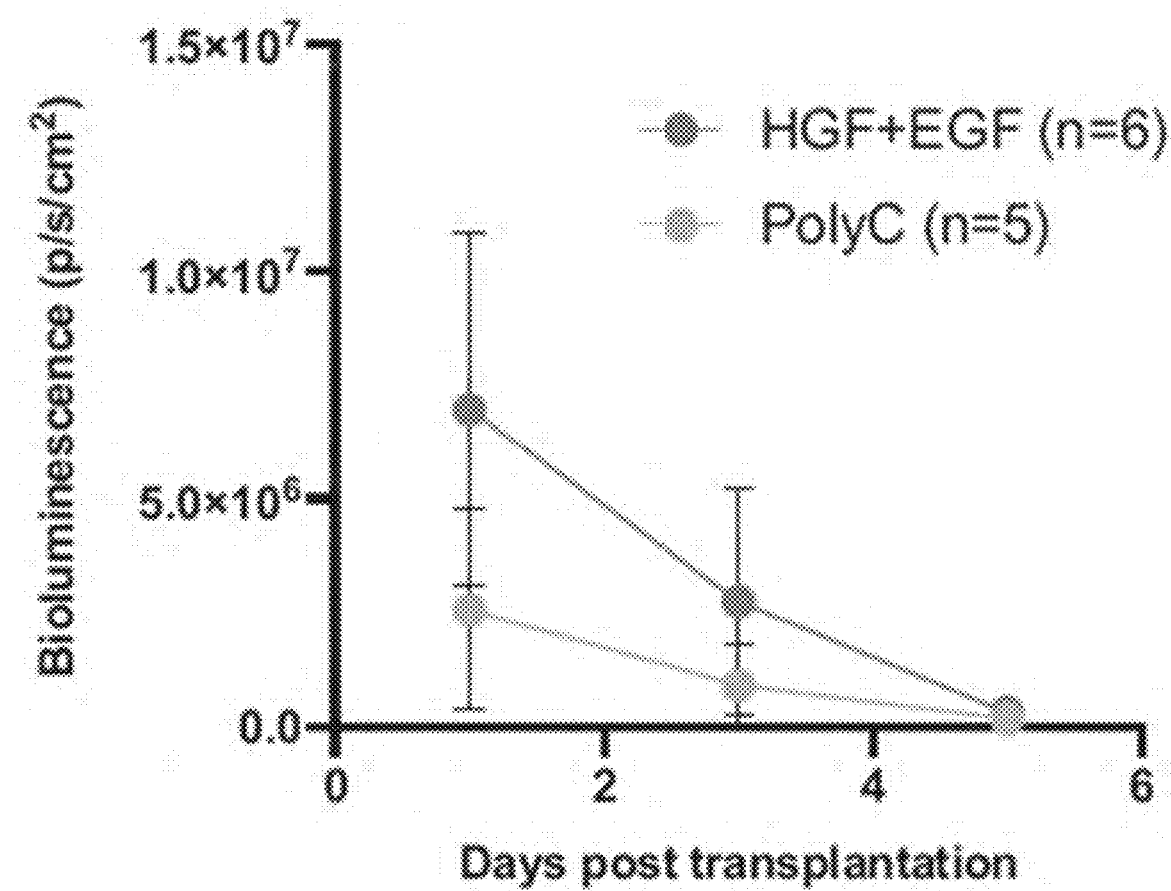

FIGS. 96A-96C show that HGF+EGF mRNA-LNP transiently improves HLC survival after transplantation.

Figure 97A:
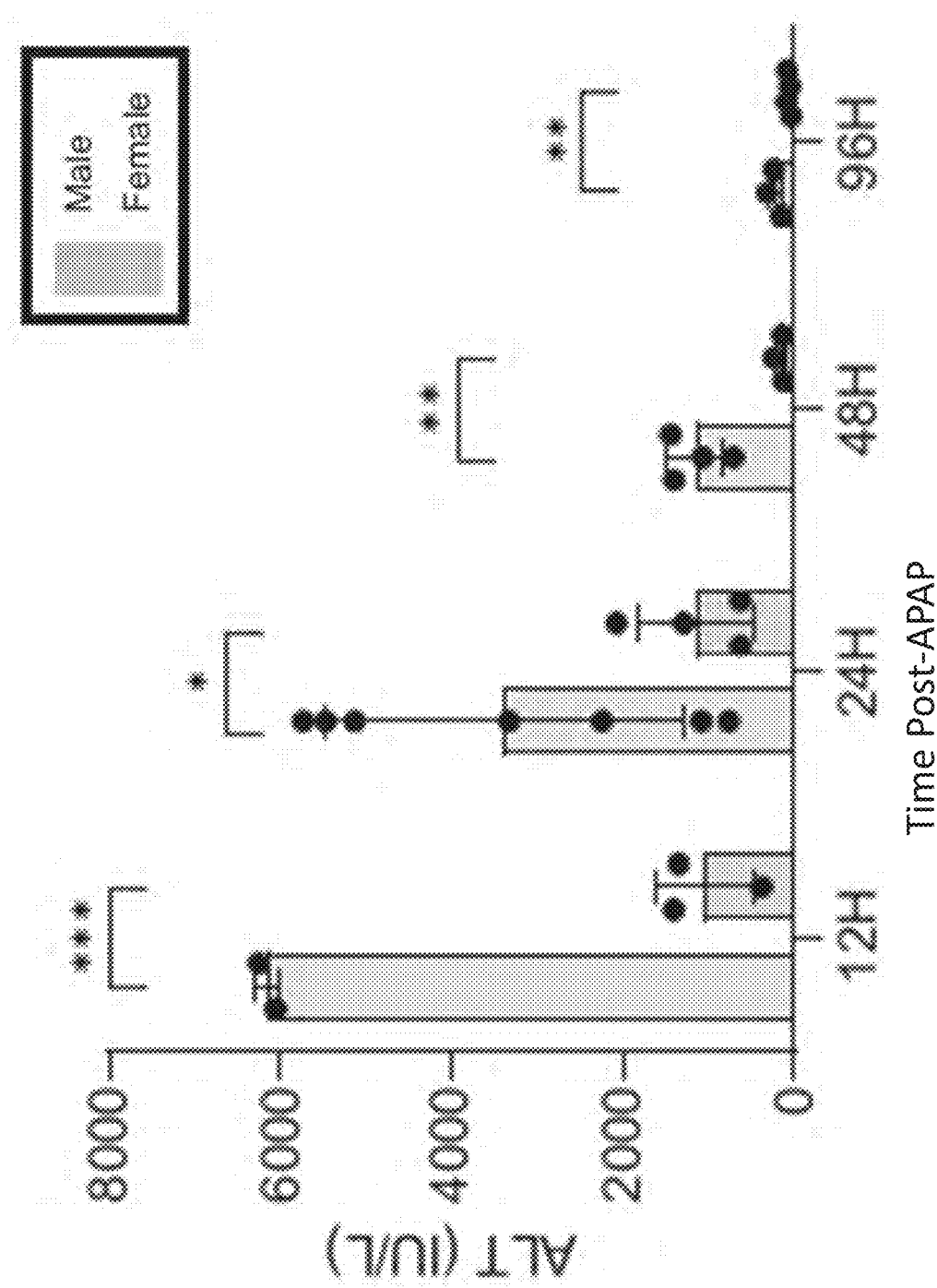
Figure 97B:
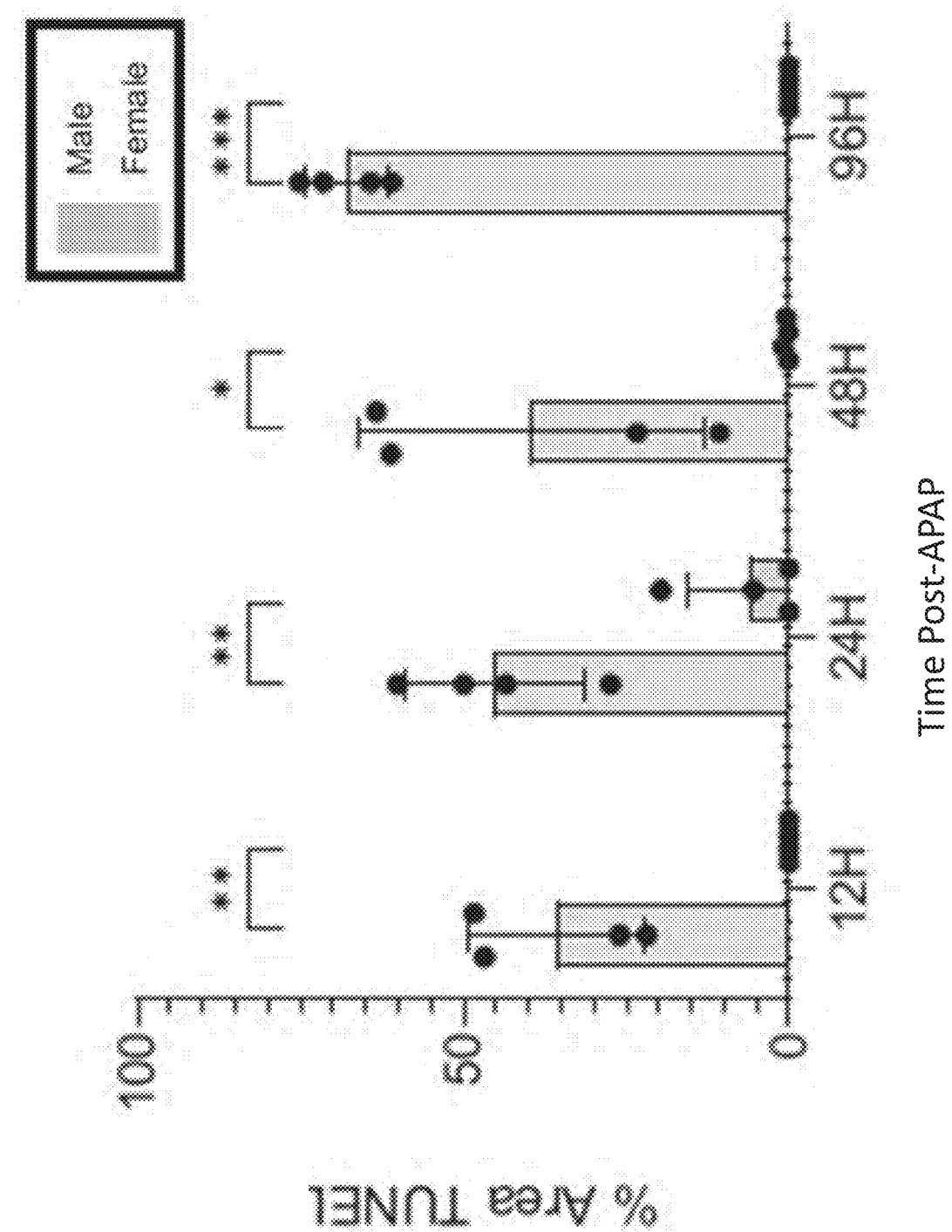
Figure 97C:
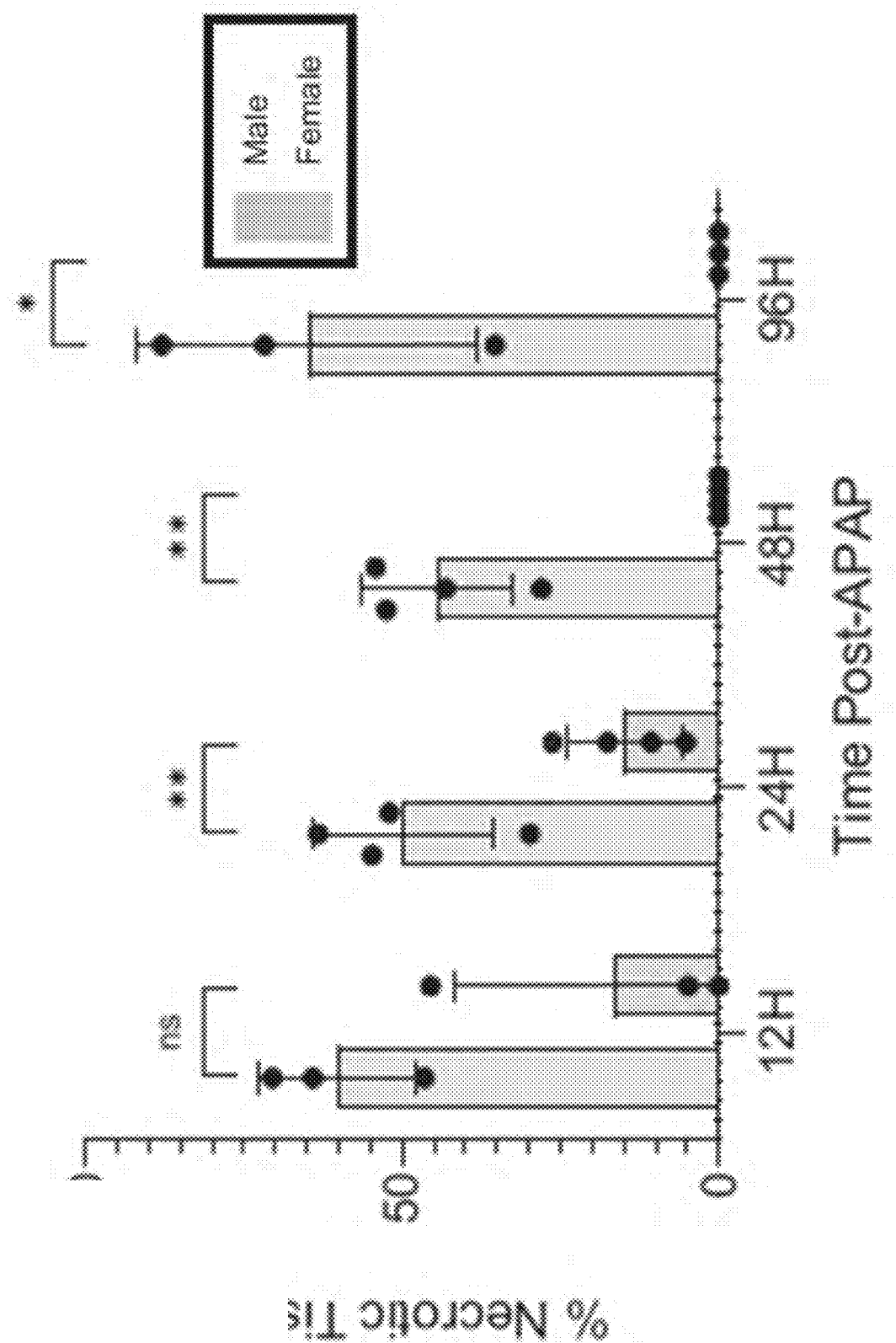
Figure 97D:
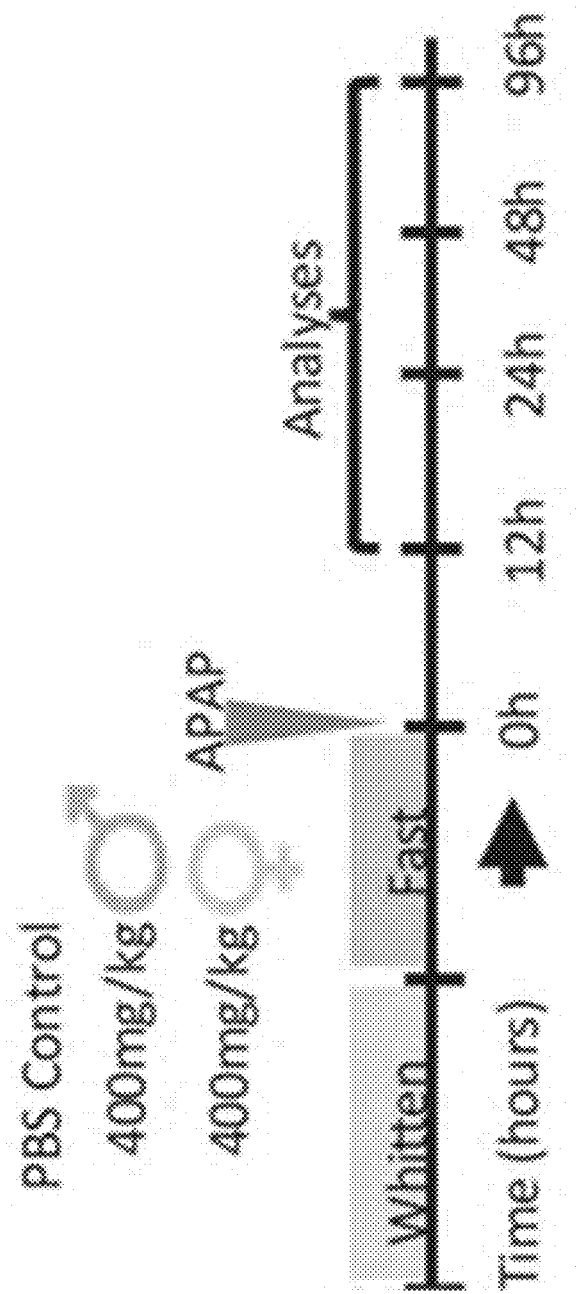
Figure 97E:
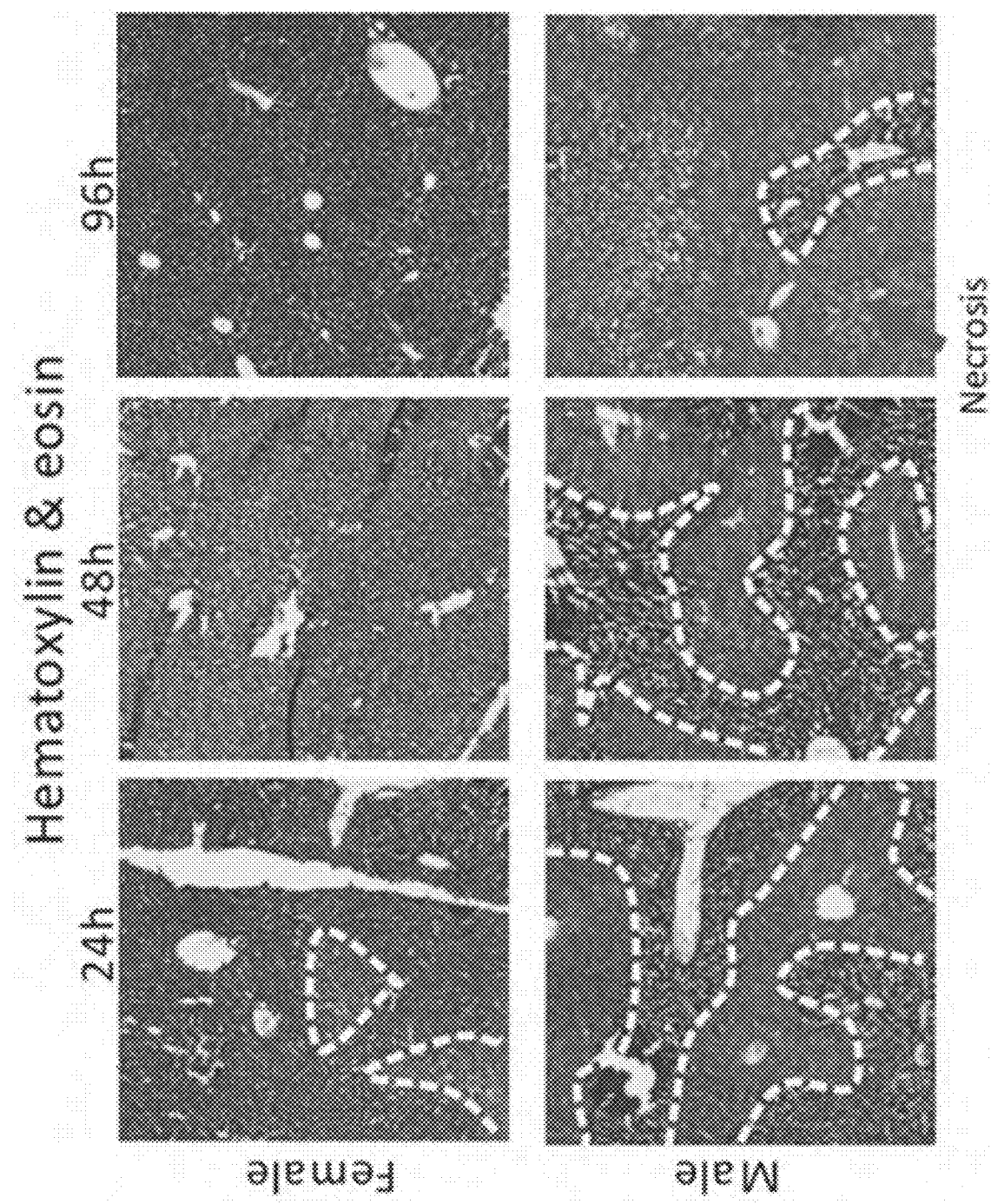

FIGS. 97A-97E show that in equivalent doses of APAP (400 mg/kg), the level and persistence of tissue necrosis and apoptosis are highly sexually dimorphic (n=4 mice/sex/time point). $P<0.05=*$, $<0.005=$, $<0.0005=*$. In FIG. 97A-97C the first series is male and the second series is female.

Figure 98A:
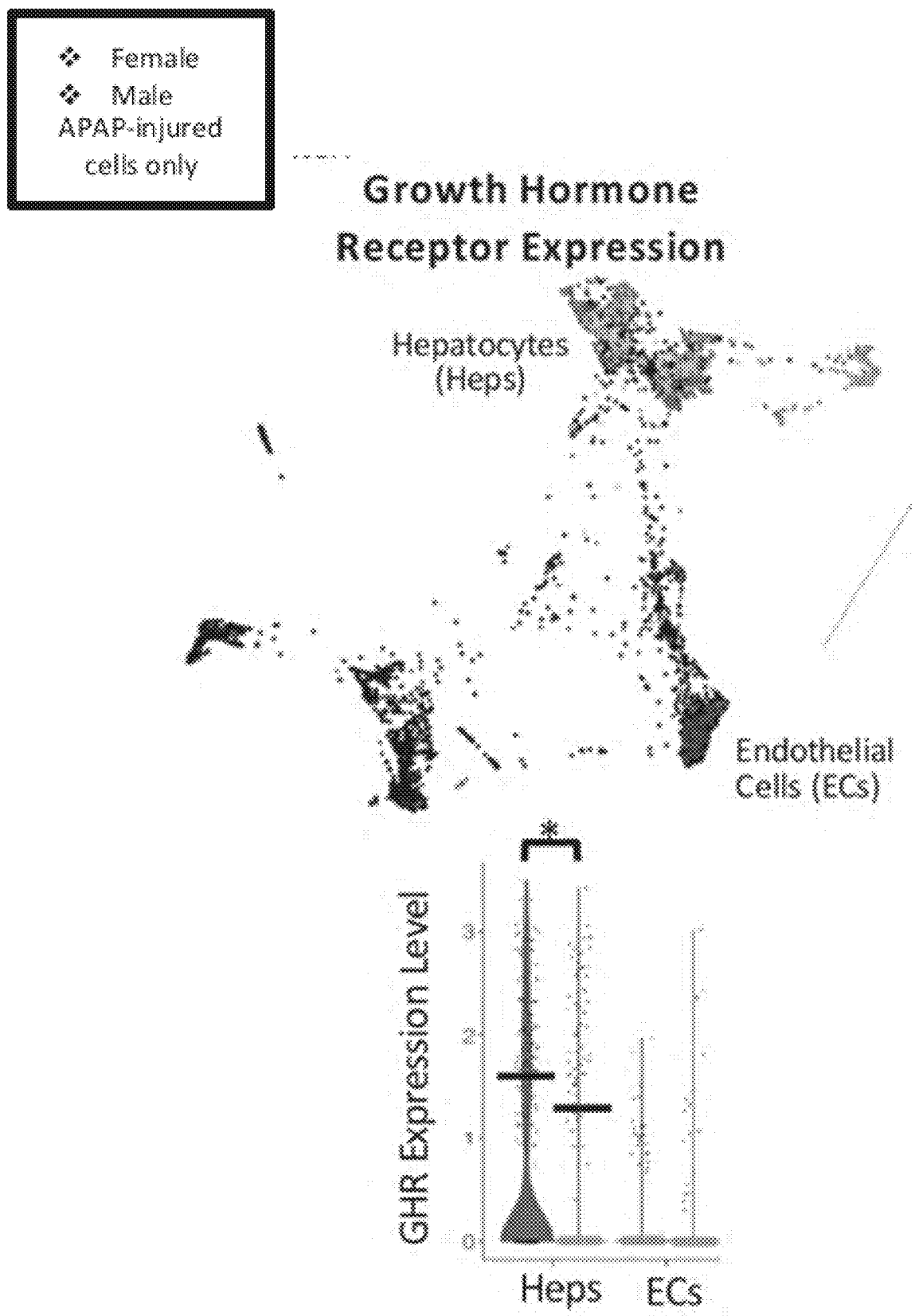
Figure 98B:
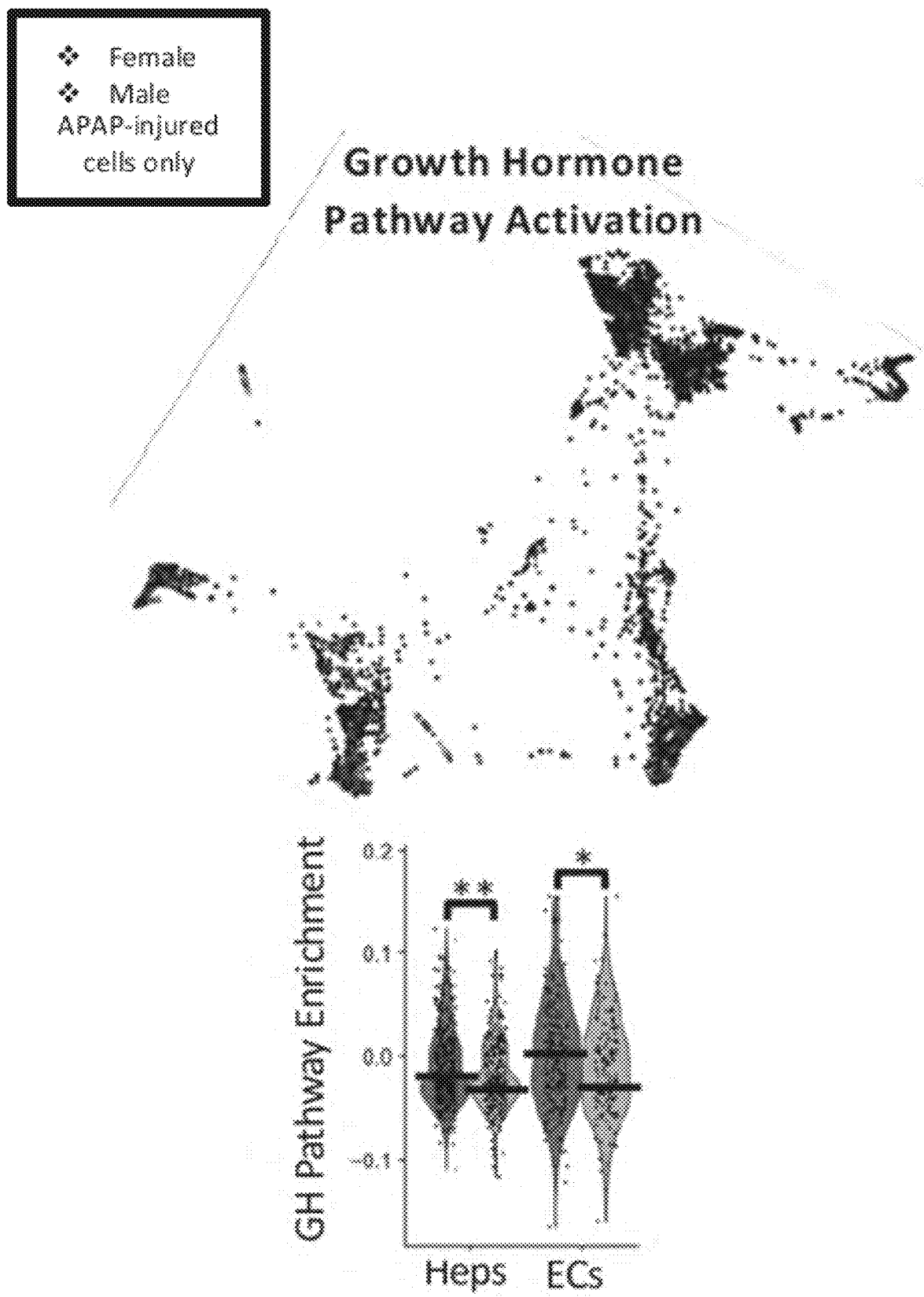
Figure 98C:
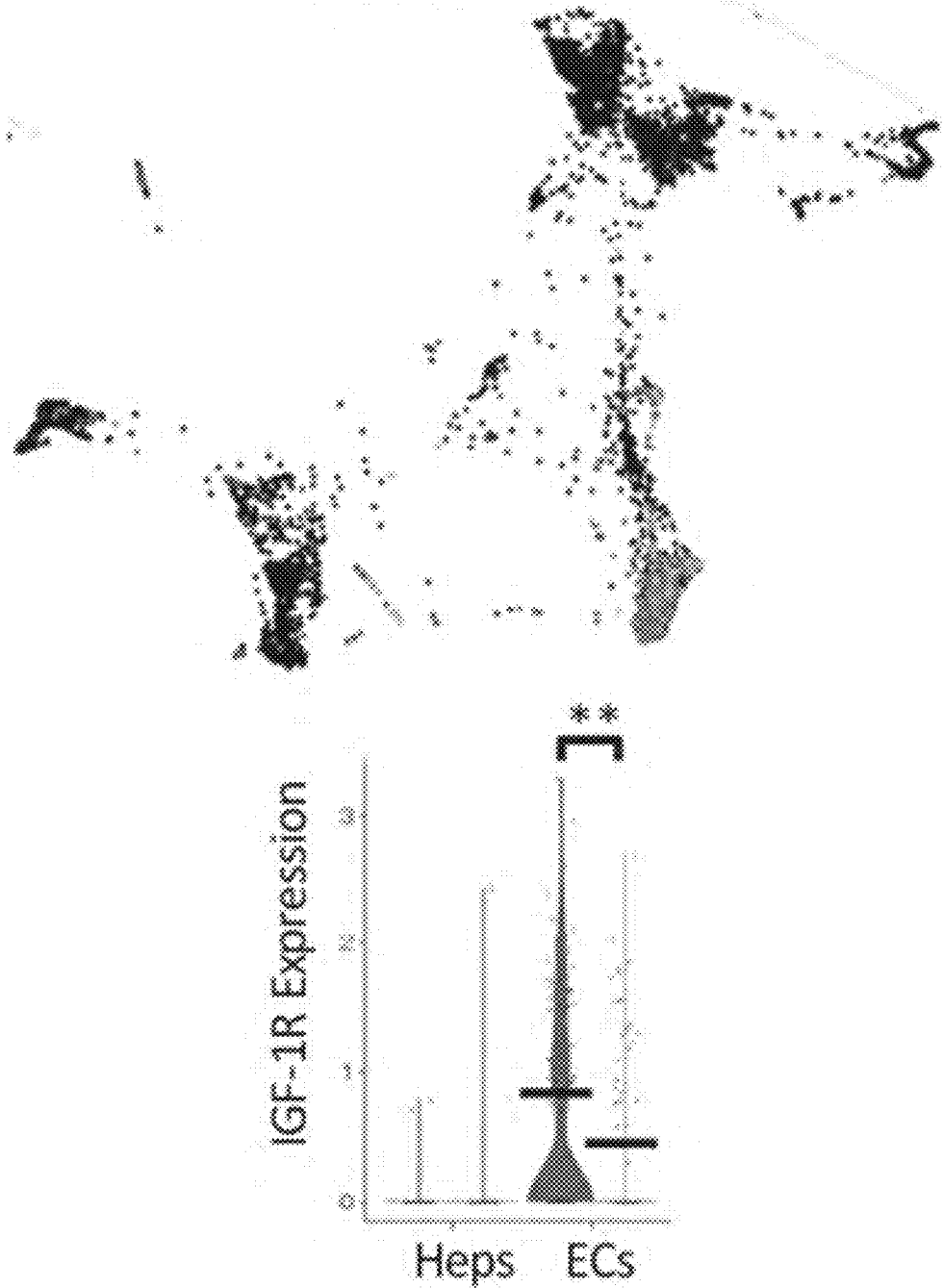
Figure 99A:
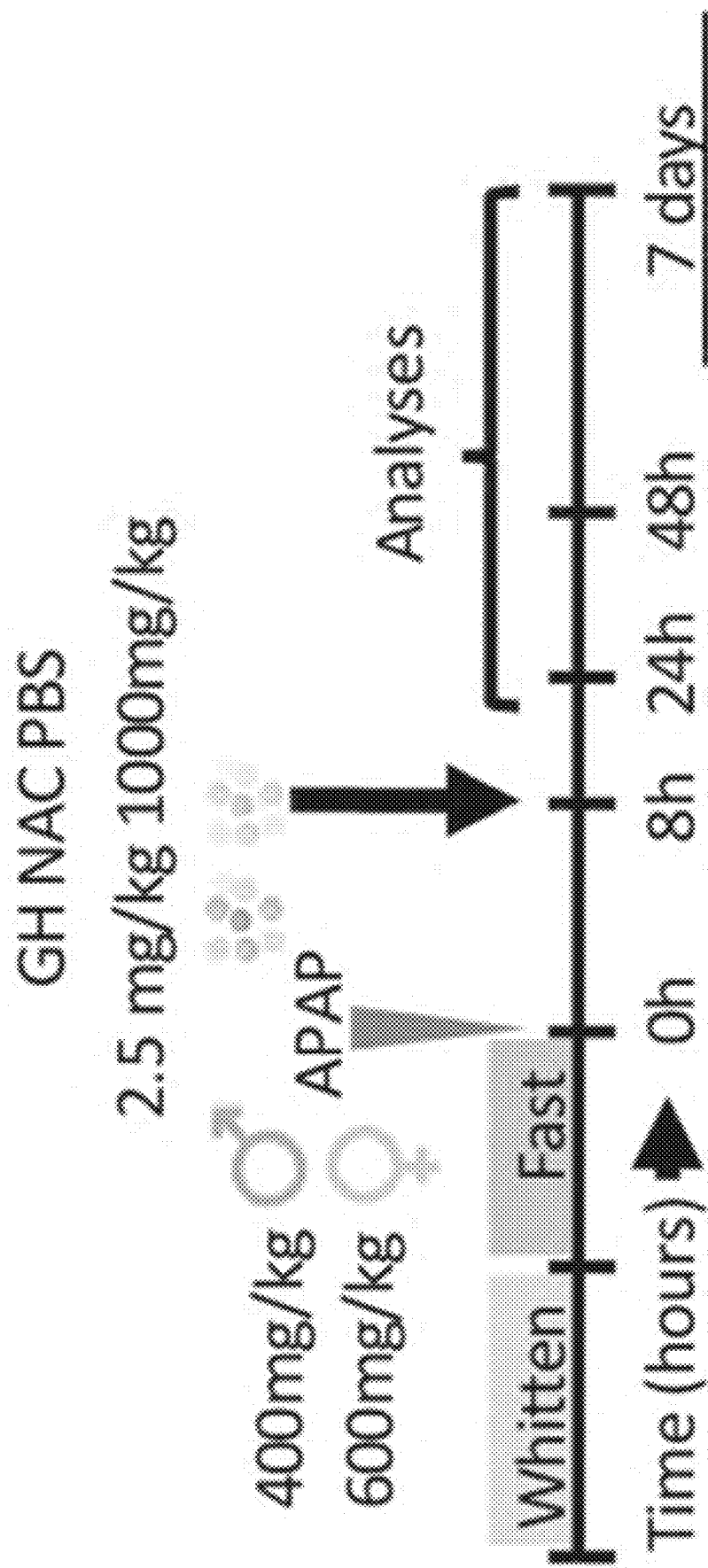
Figure 99B:
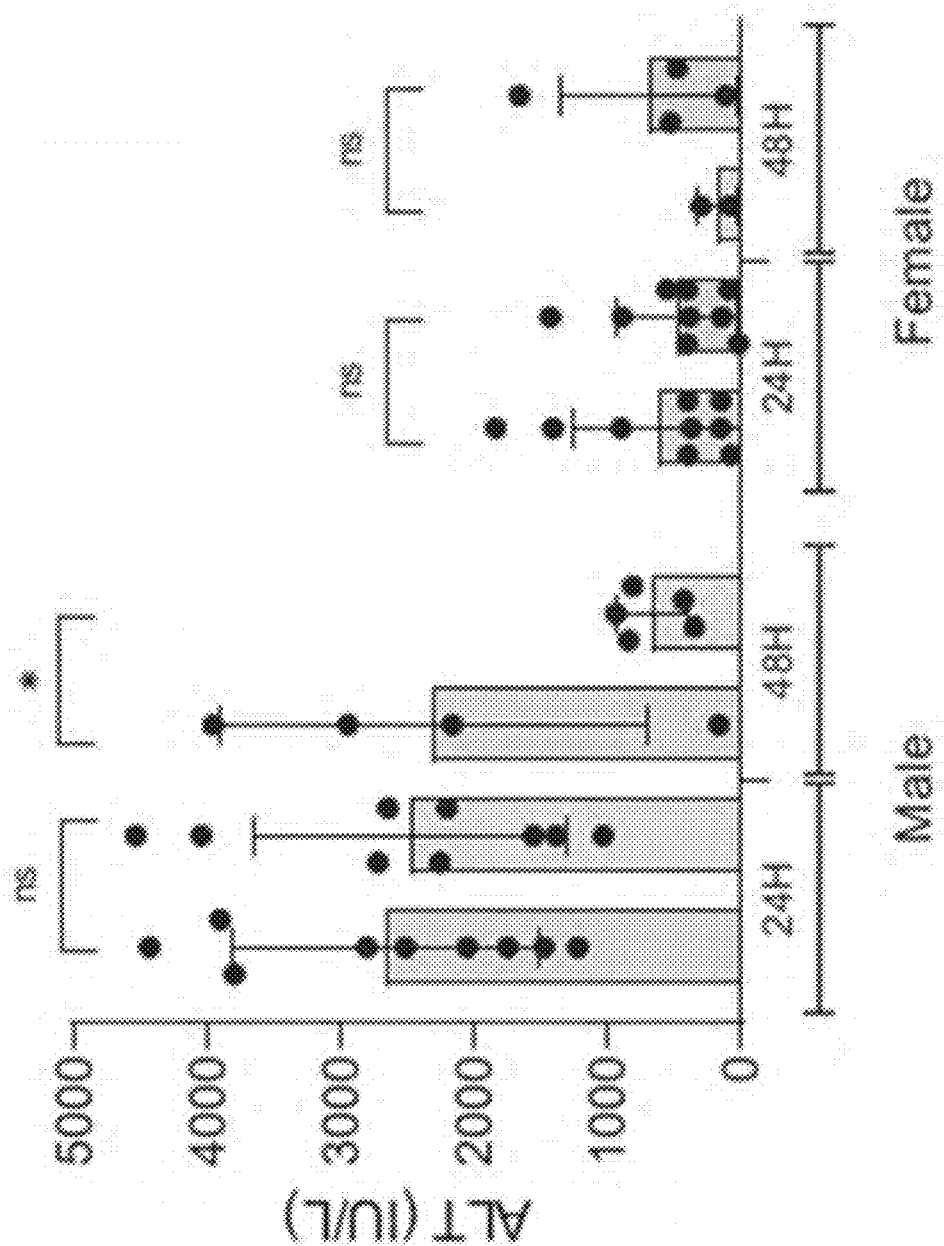
Figure 99C:
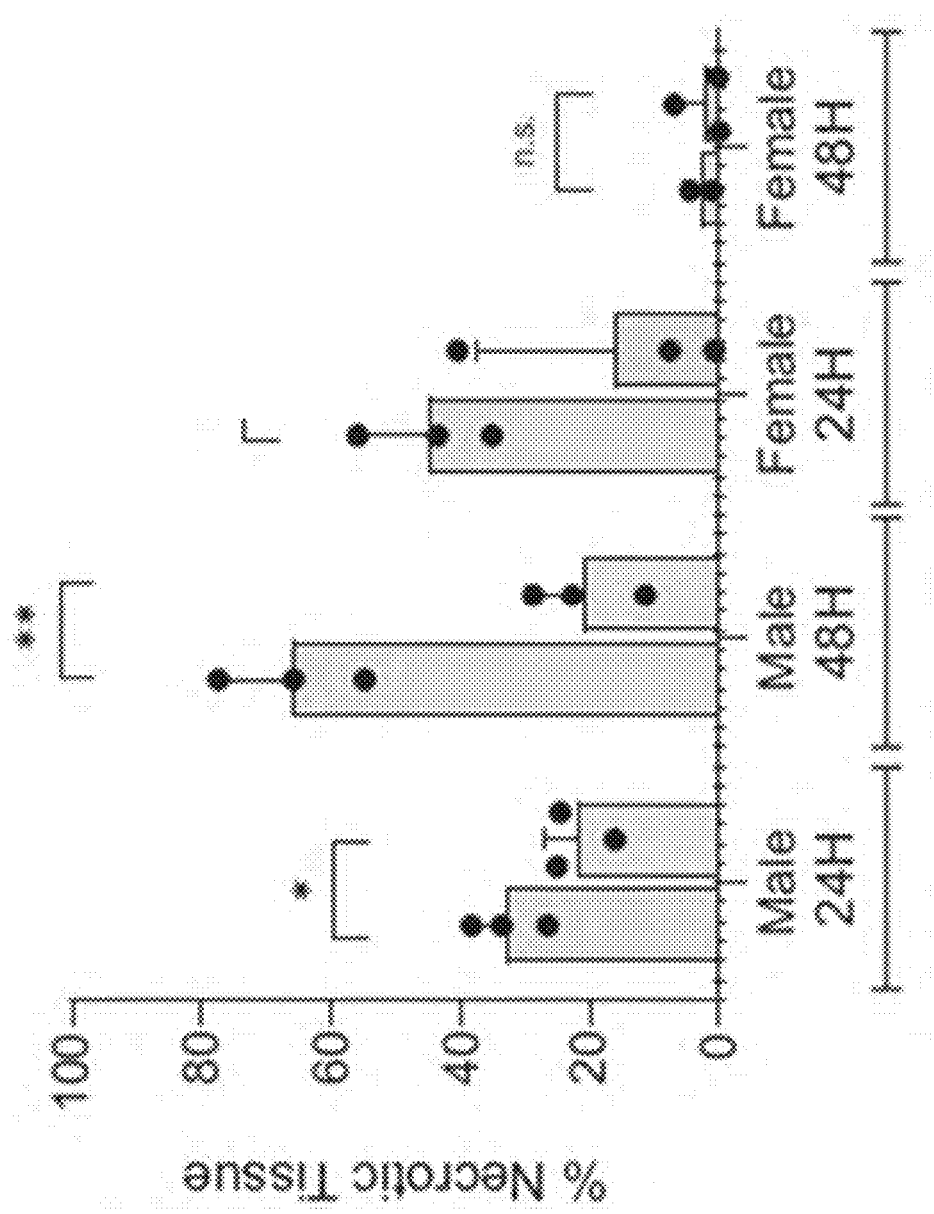
Figure 99D:
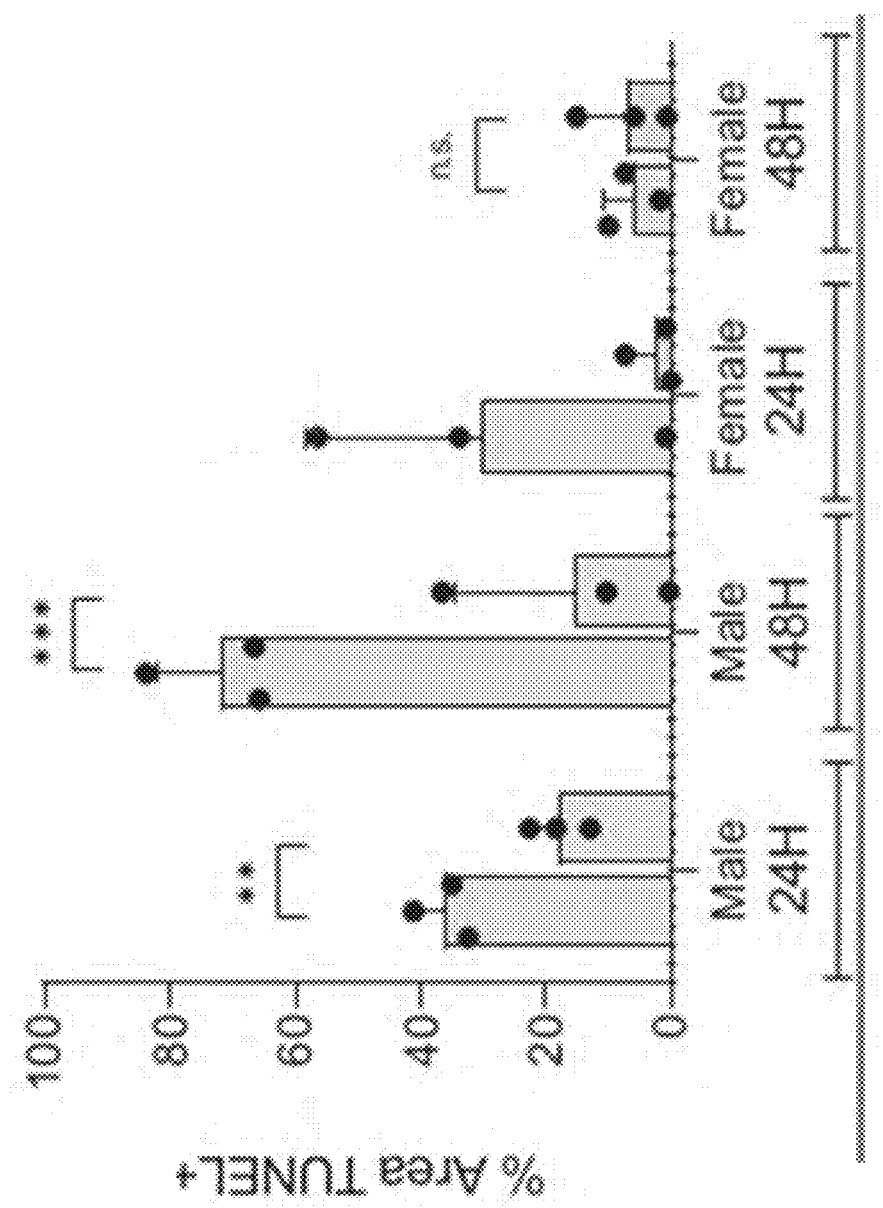
Figure 99E:
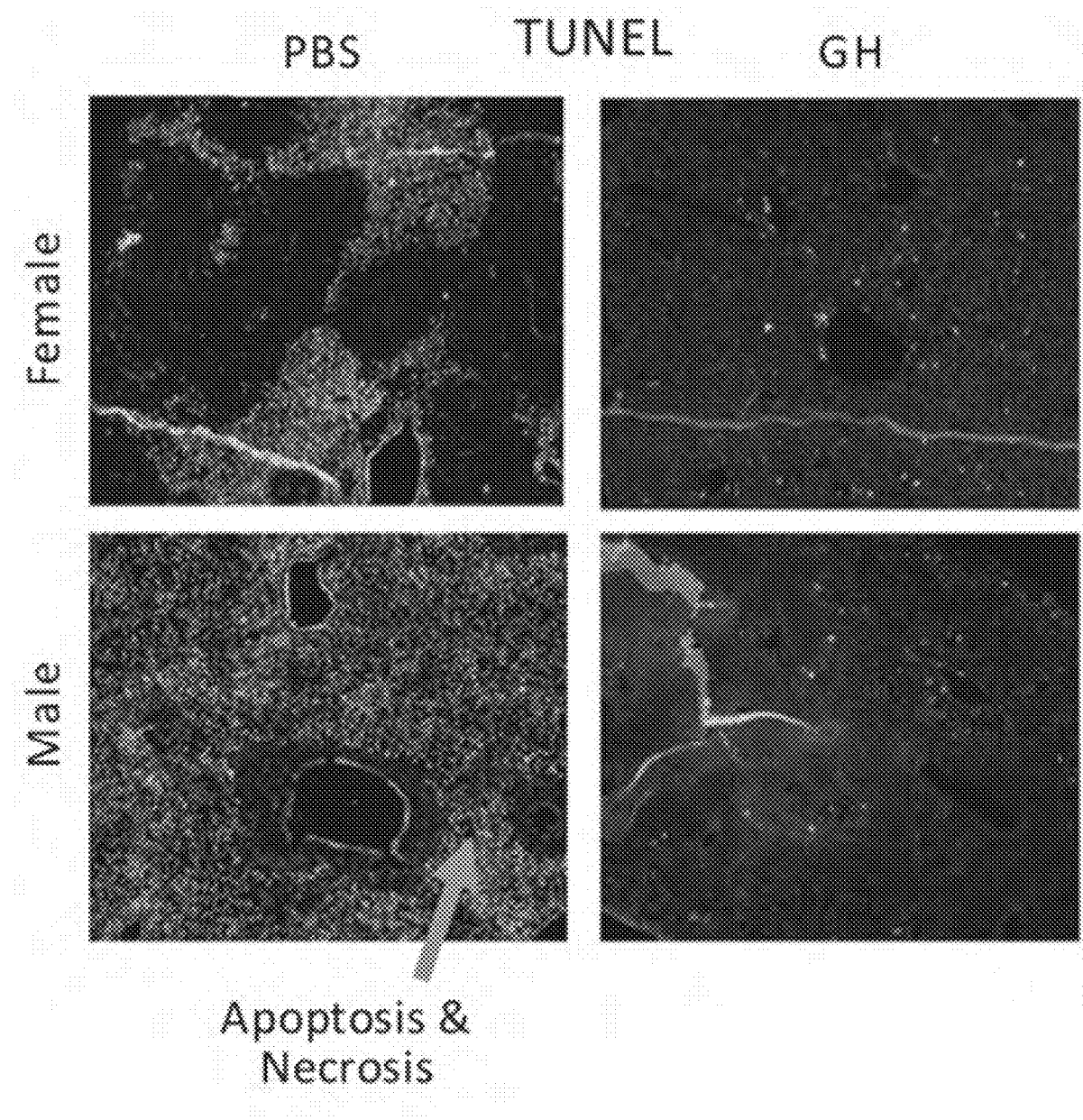

FIGS. 98A-98C show single-cell RNA sequencing of whole livers of male and female mice before and after injury reveals sexual dimorphism of growth hormone (GH) pathway activity in hepatocyte and endothelial cell transcriptomes. Data are shown on SPRING plots of combined populations, and violin plots of hepatocyte and endothelial clusters after APAP injury dissecting differences between sexes. Lines on violin plots represent mean expression level for cluster.

FIGS. 99A-99E show that a single dose of GH significantly accelerates liver regeneration after APAP-induced liver injury in both males and females, as compared to PBS-treated and NAC standard of care-treated controls. (n=5 mice/sex/treatment). Females and males were treated with sex-specific doses of APAP that generated similar liver damage. First series is untreated, second series is treated.

Figure 100A:
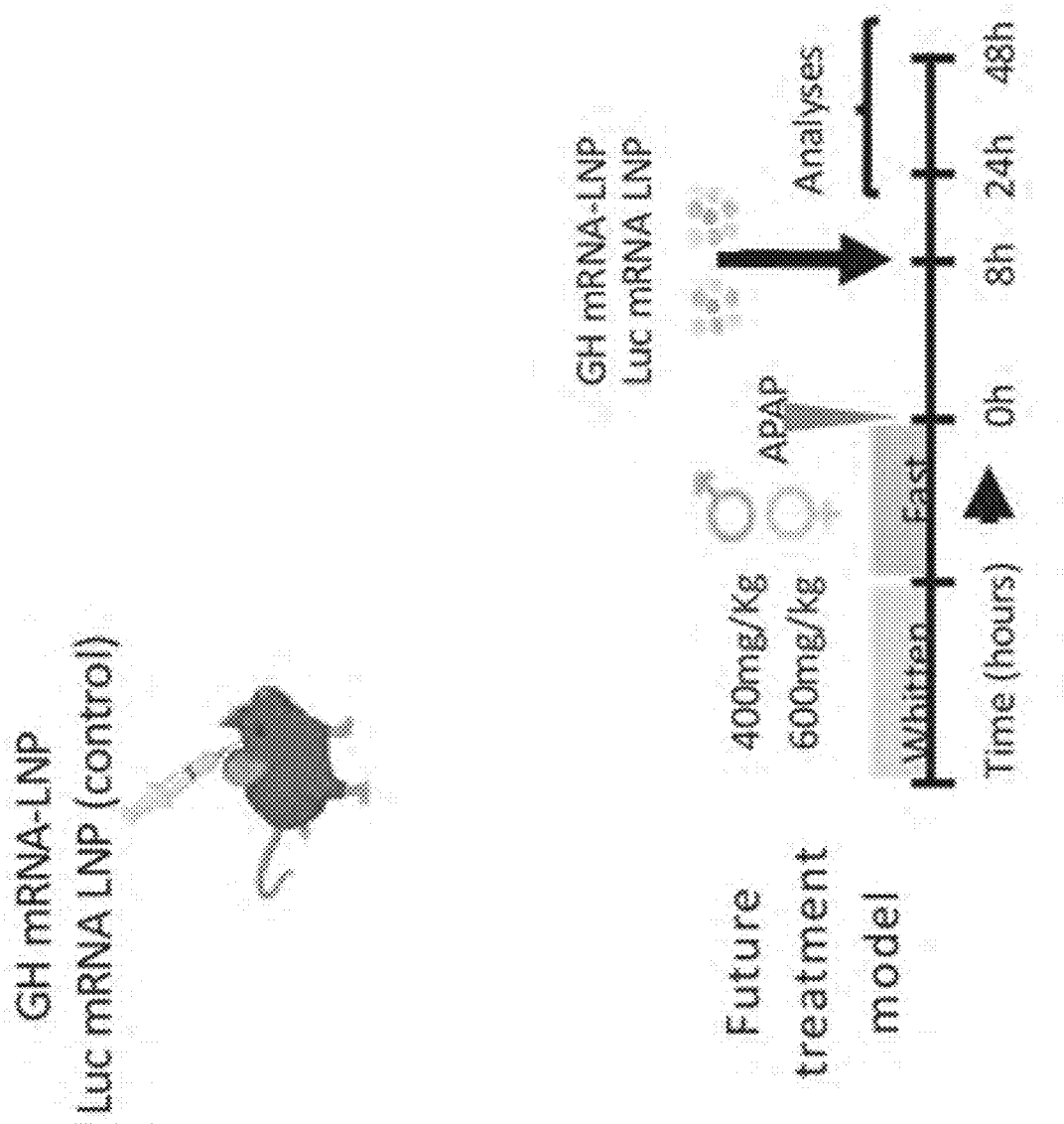
Figure 100B:
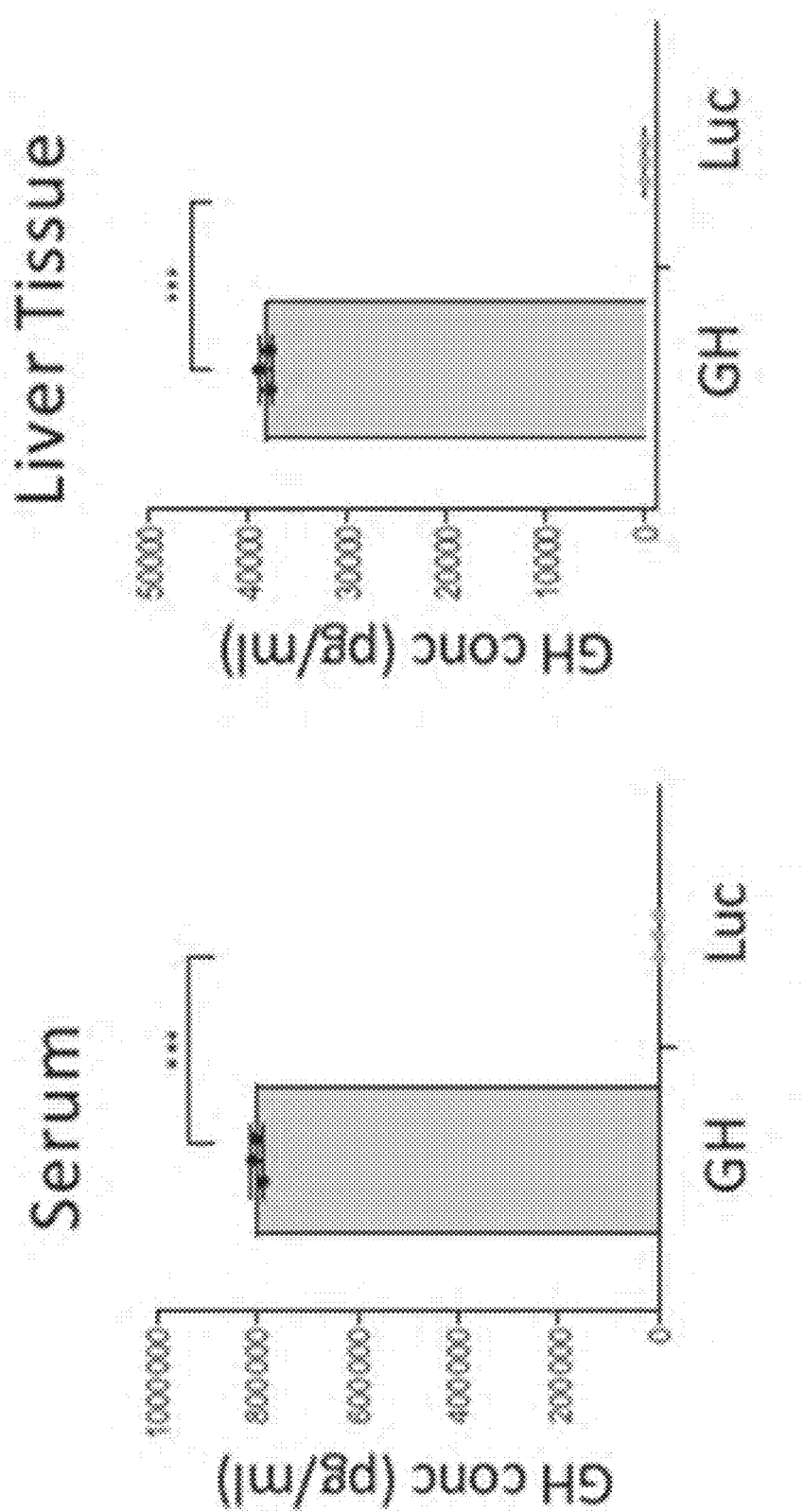

FIGS. 100A-100B show a single injection of nucleoside-modified lipid nanoparticle-encapsulated mRNA encoding GH induces robust expression of GH in the liver and serum of uninjured mice 5 hours post retroorbital injection, as compared to Luciferase mRNA-LNP (Luc) negative control. Serum concentration of GH is 30× less than acute recombinant GH injection, within safe limit for clinical application. Future treatment model will test the efficacy of promoting recovery from APAP injury compared to recombinant protein injection. (n=3 mice/treatment).

Figure 101:
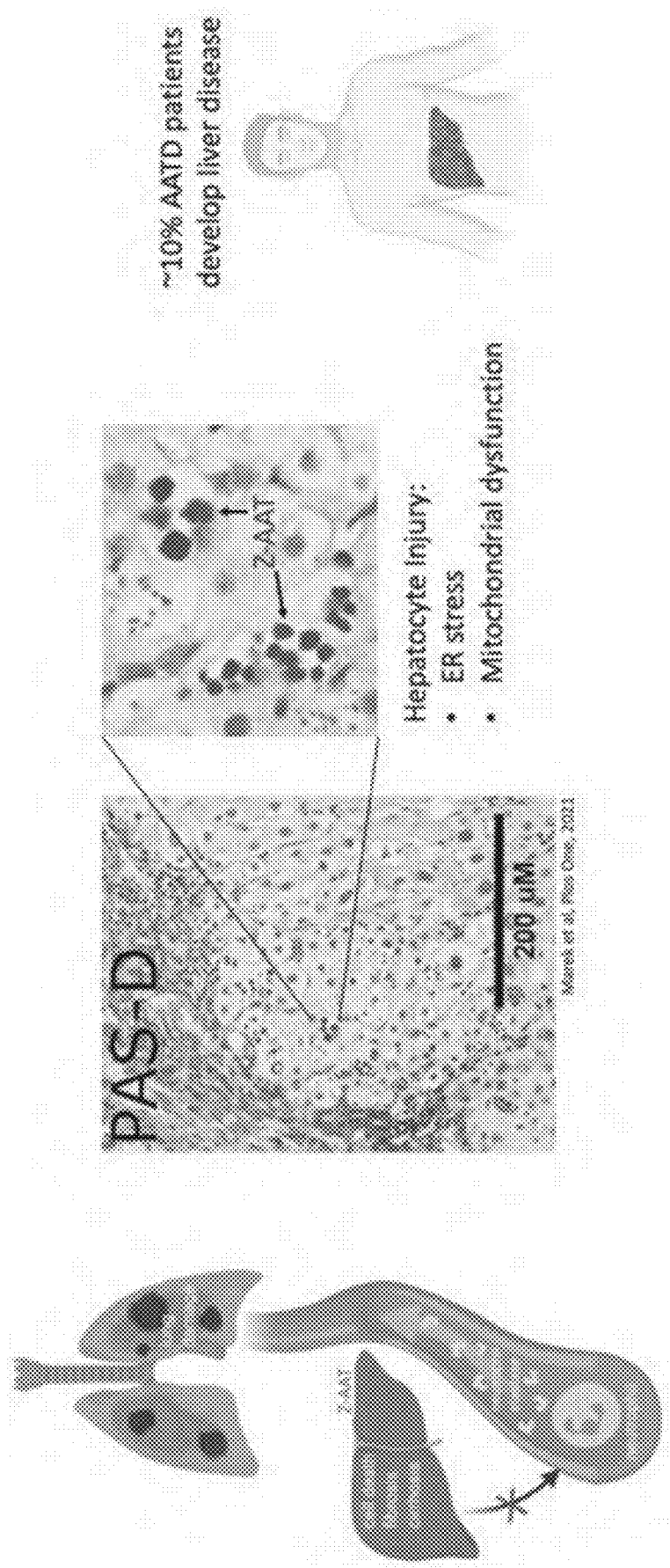

FIG. 101 depicts alpha-1 antitrypsin deficiency (AATD) increases risk for liver and lung disease.

Figure 102:
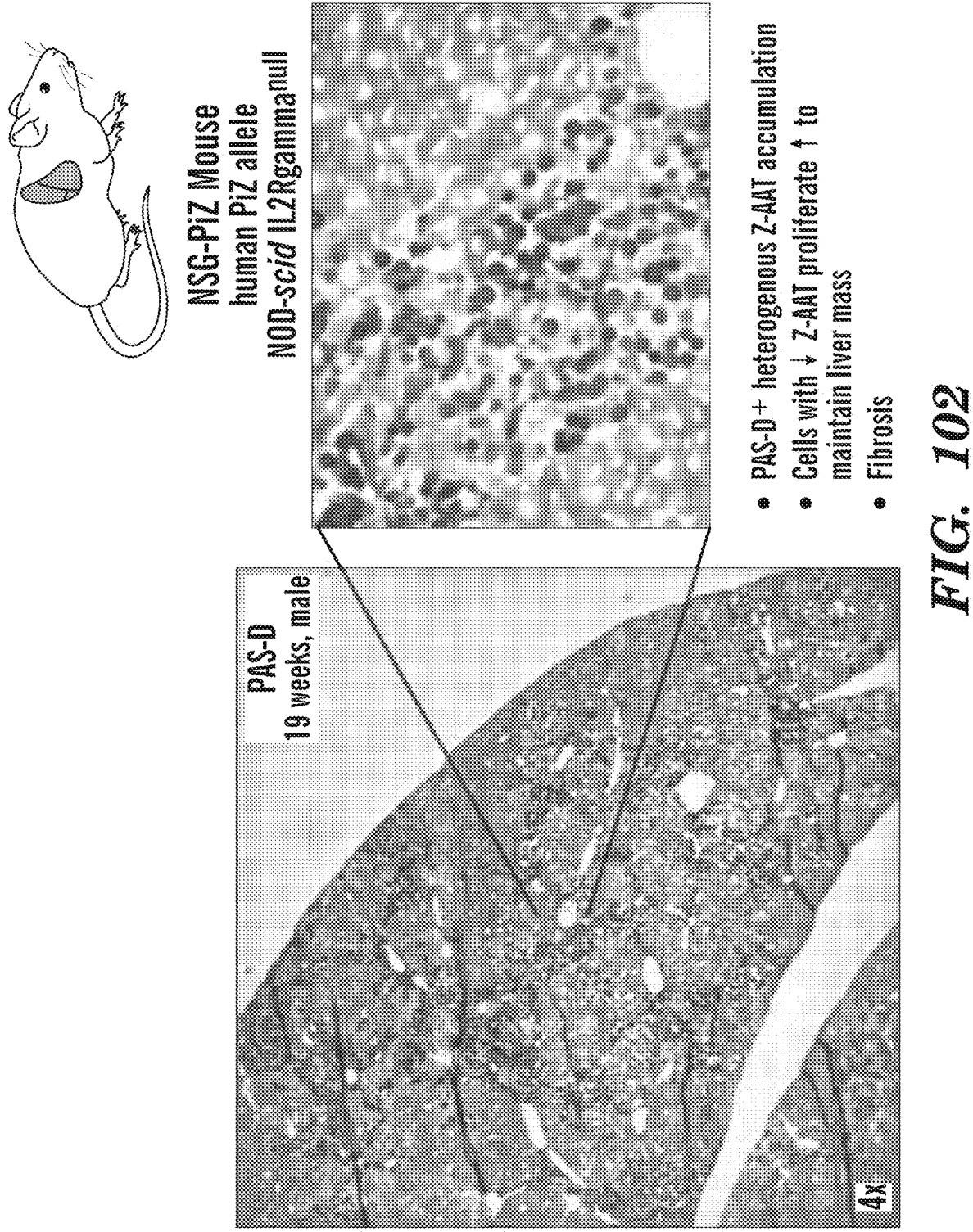

FIG. 102 depicts NSG-PiZ mice recapitulate AATD liver disease.

Figure 103:
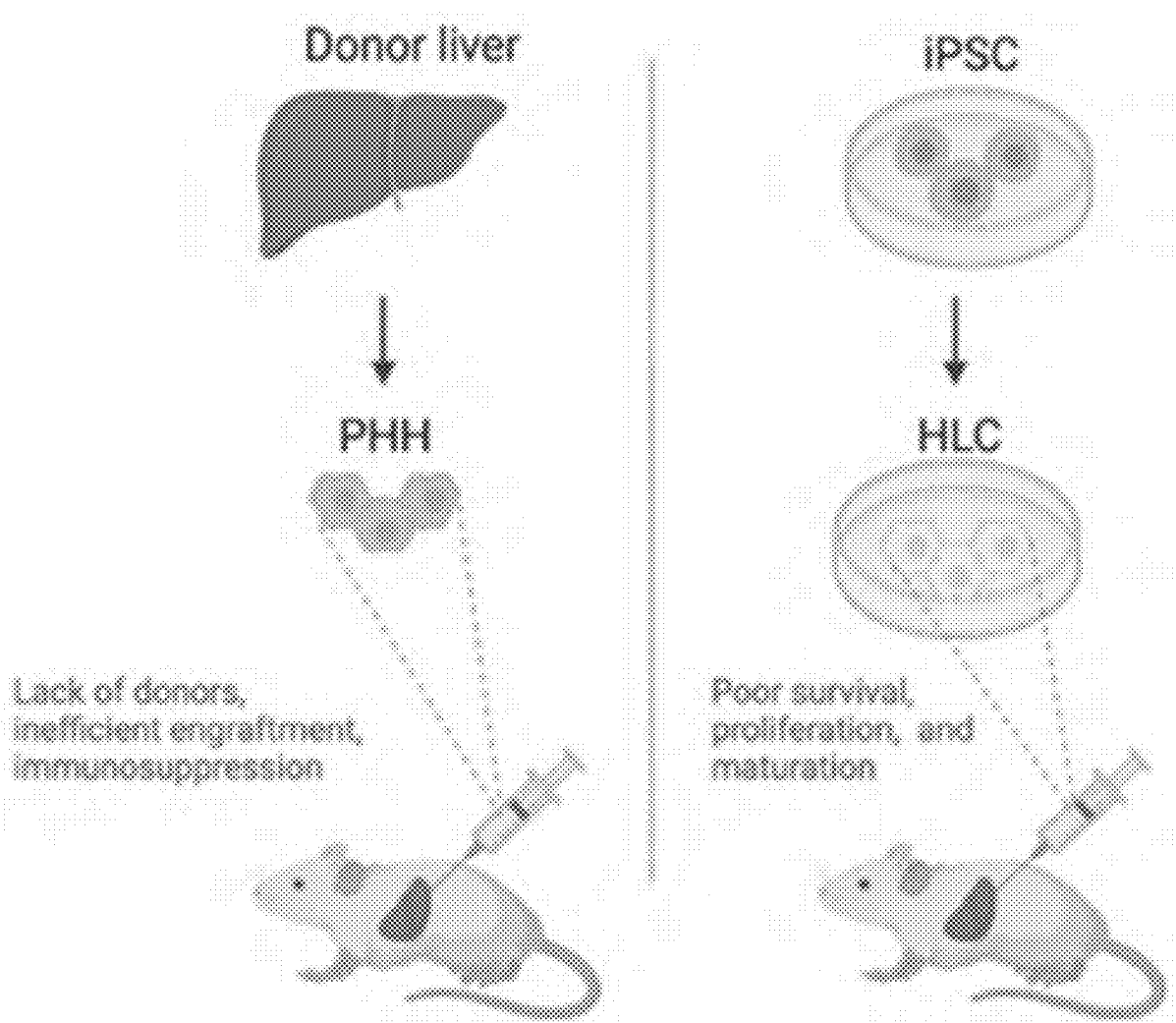

FIG. 103 depicts current liver cell therapies have limitations.

Figure 104:
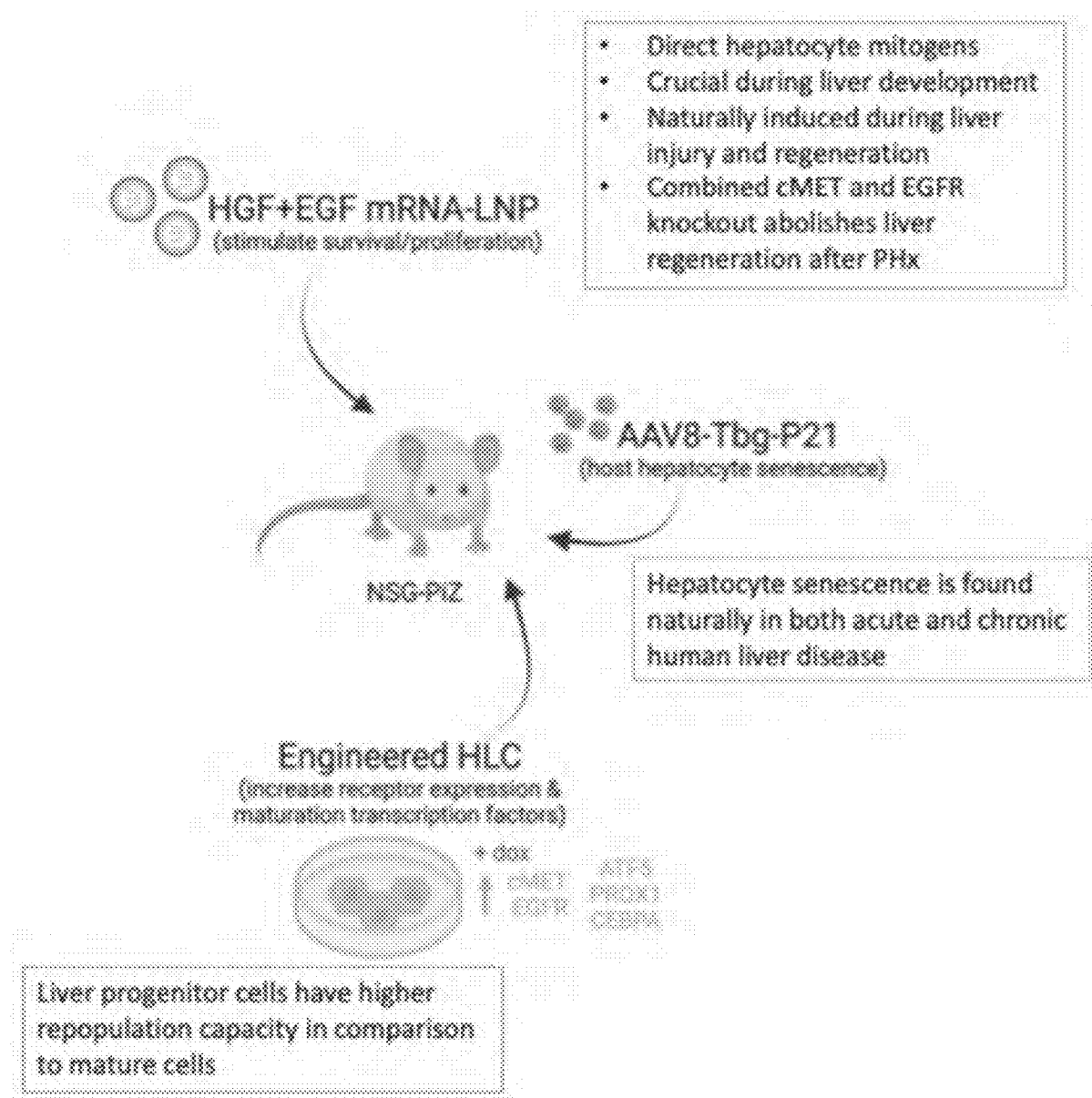
Figure 105A:
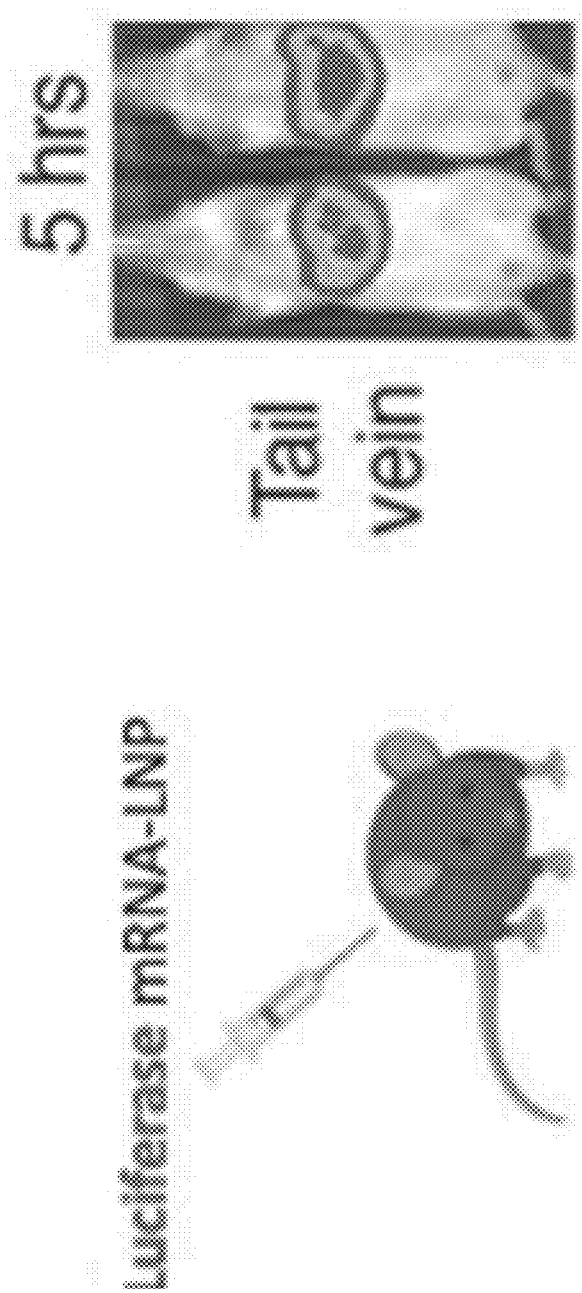
Figure 105B:
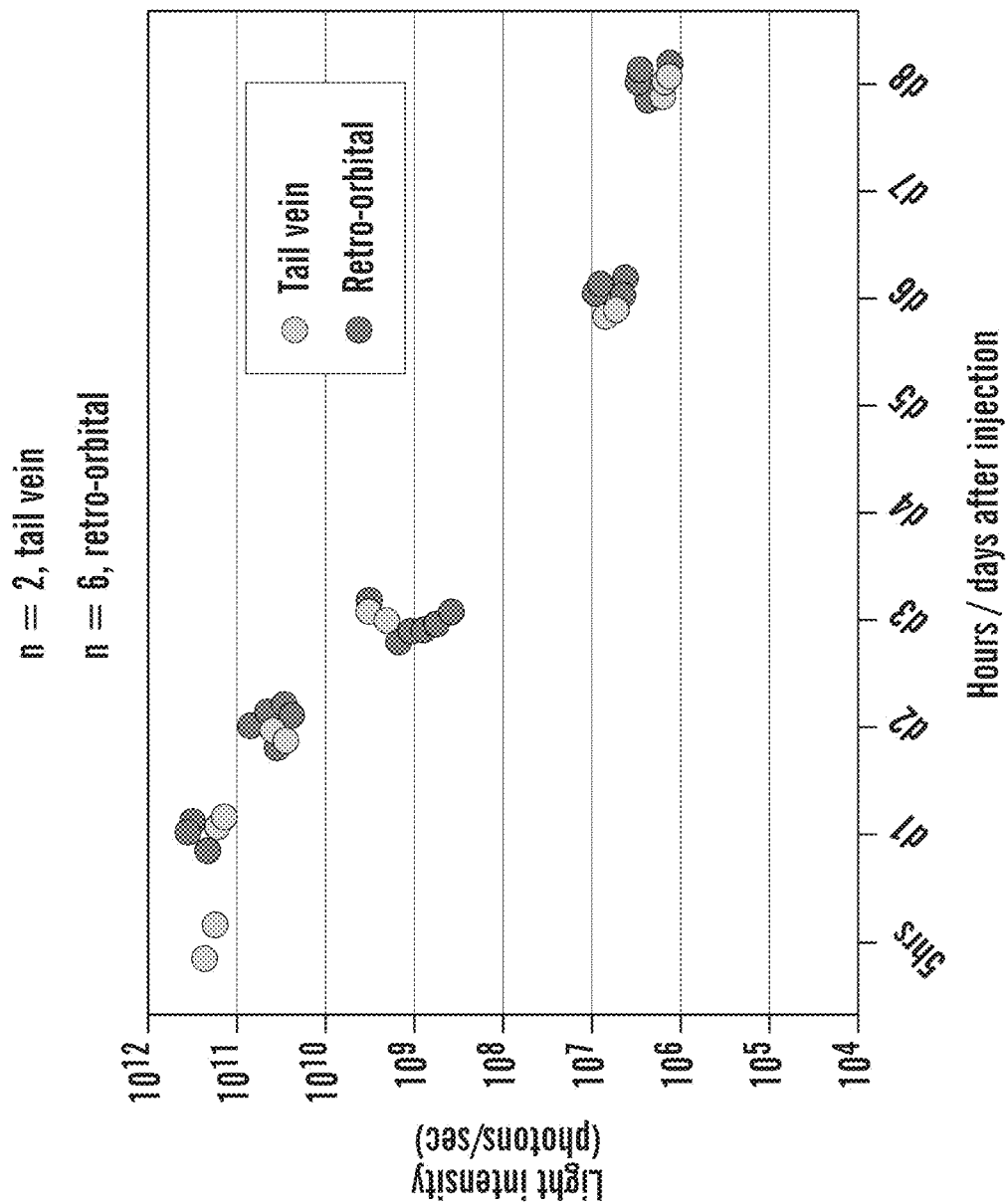
Figure 105C:
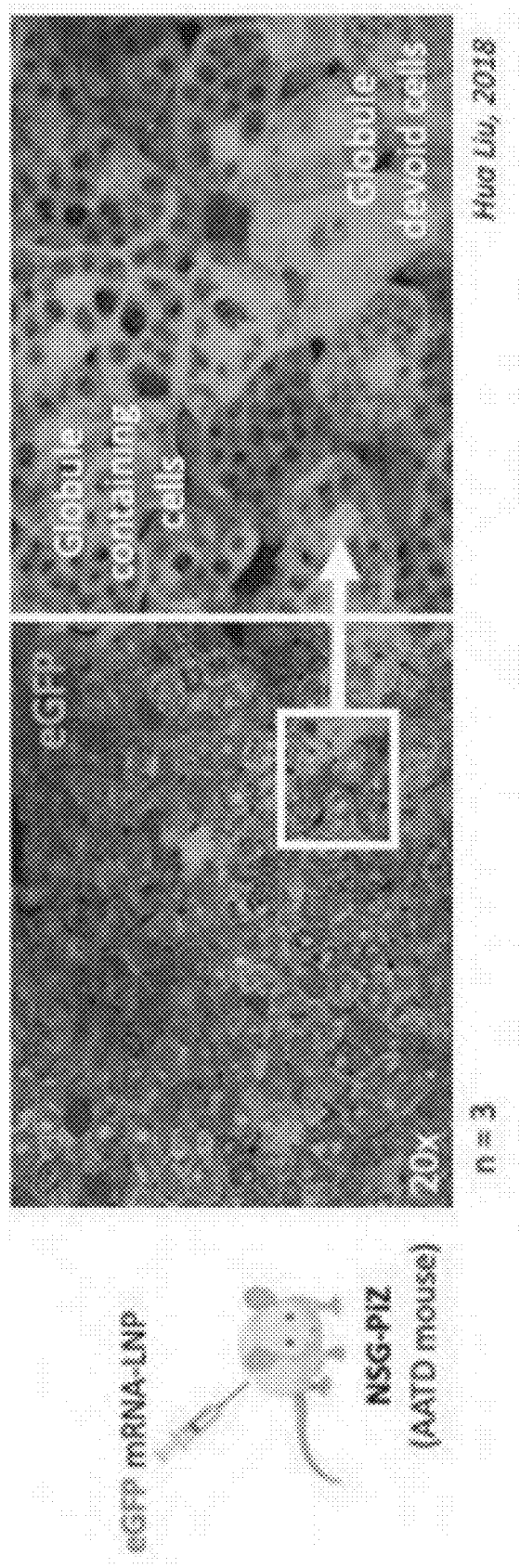
Figure 105D:
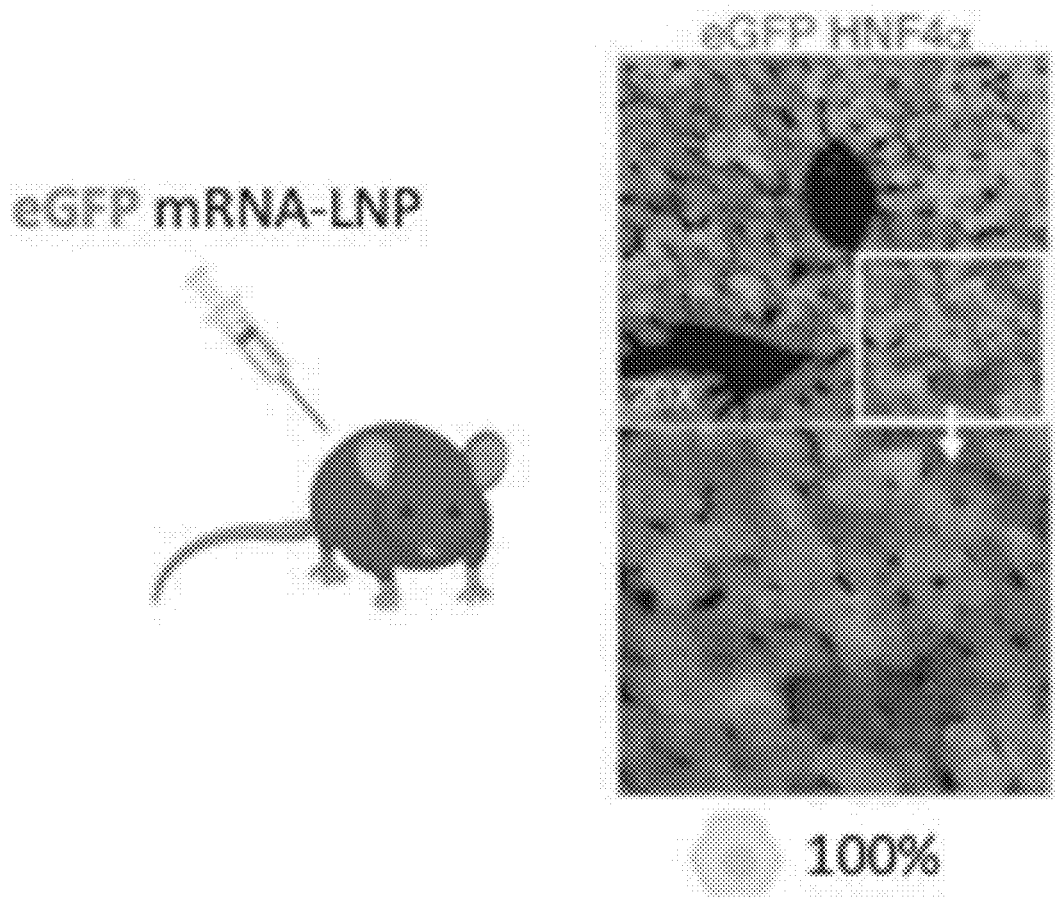

FIG. 104 depicts proposed strategies to improve survival, proliferation, maturation, and engraftment of PHHs and HLCs in NSG-PiZ mice, which include stimulating key regenerative pathways in transplanted hepatocytes; preconditioning the host liver to prevent host hepatocyte proliferation; and maturing transplanted cells in vivo.

FIGS. 105A-105D depict mRNA-LNP induces robust protein expression in the liver, mainly in hepatocytes.

Figure 106A:
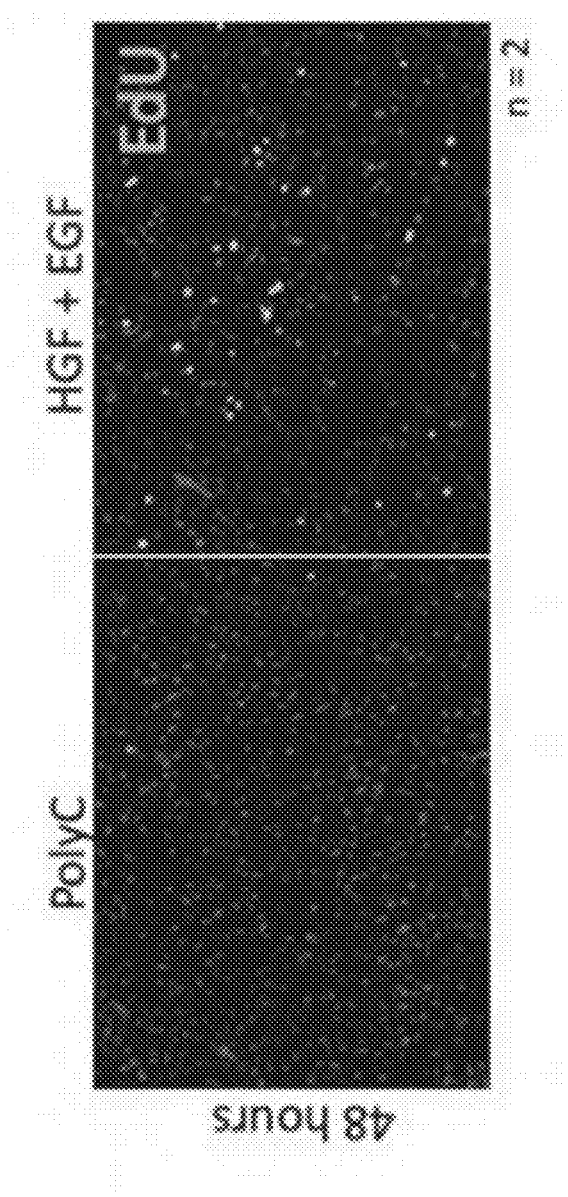
Figure 106A:
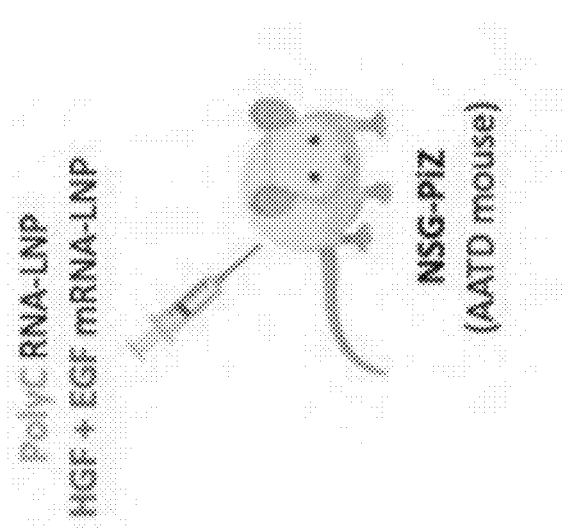
Figure 106B:
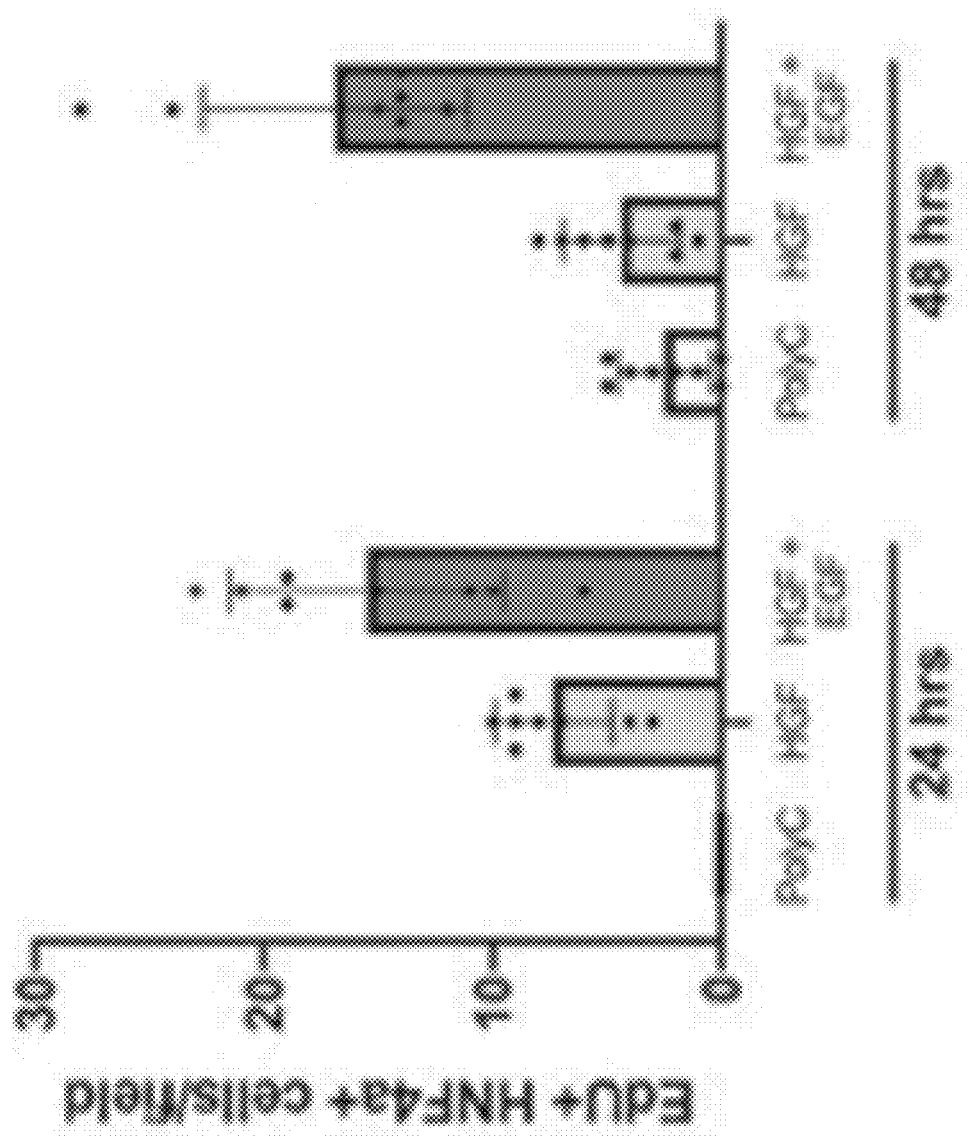
Figure 107A:
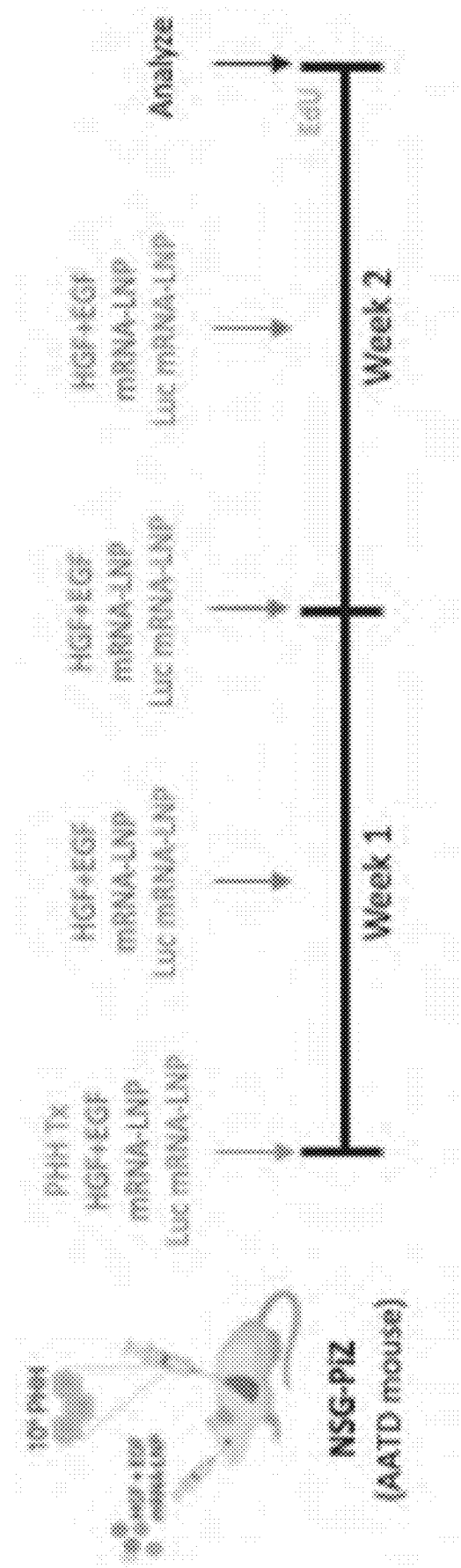
Figure 107B:
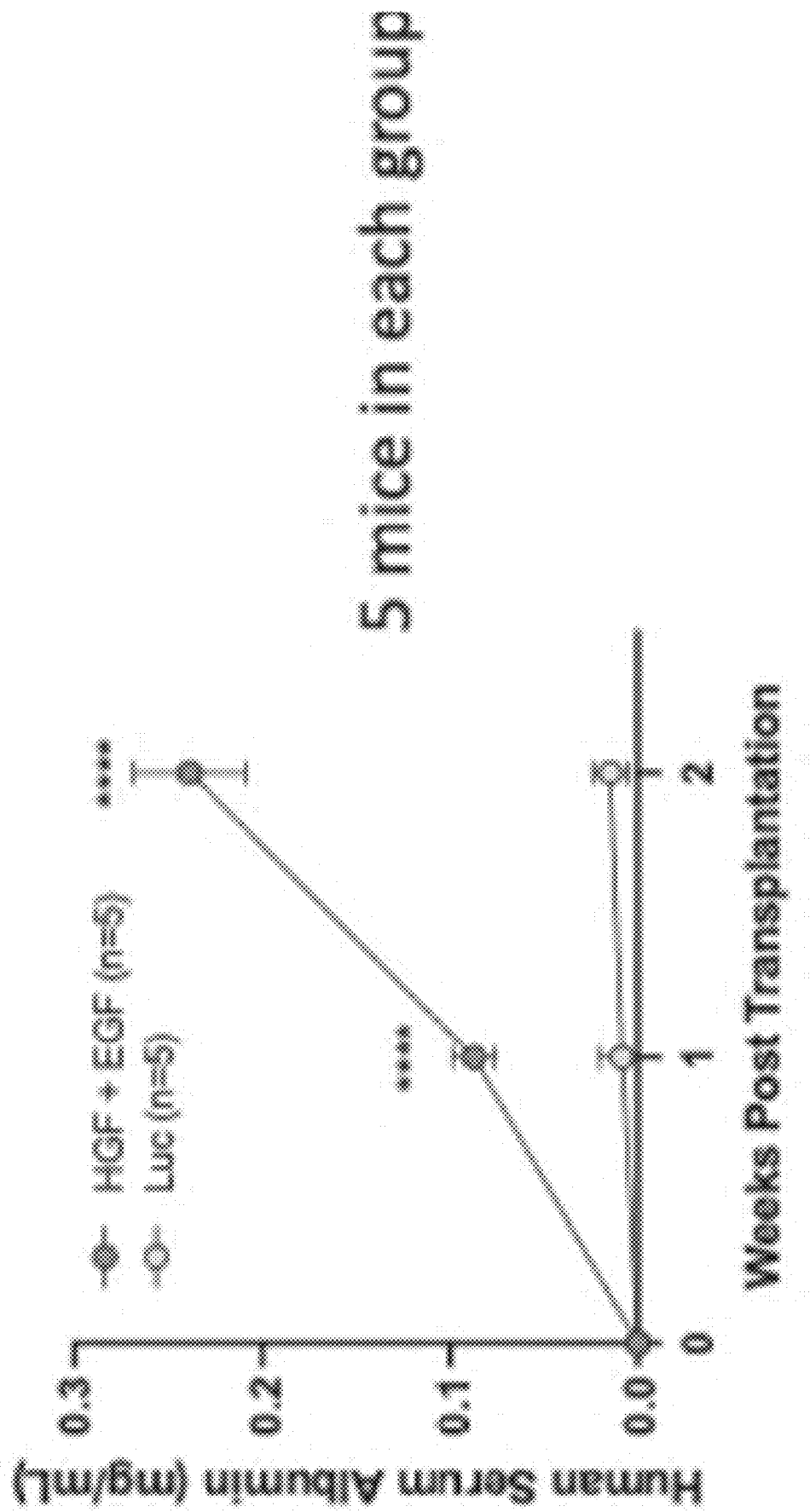
Figure 107C:
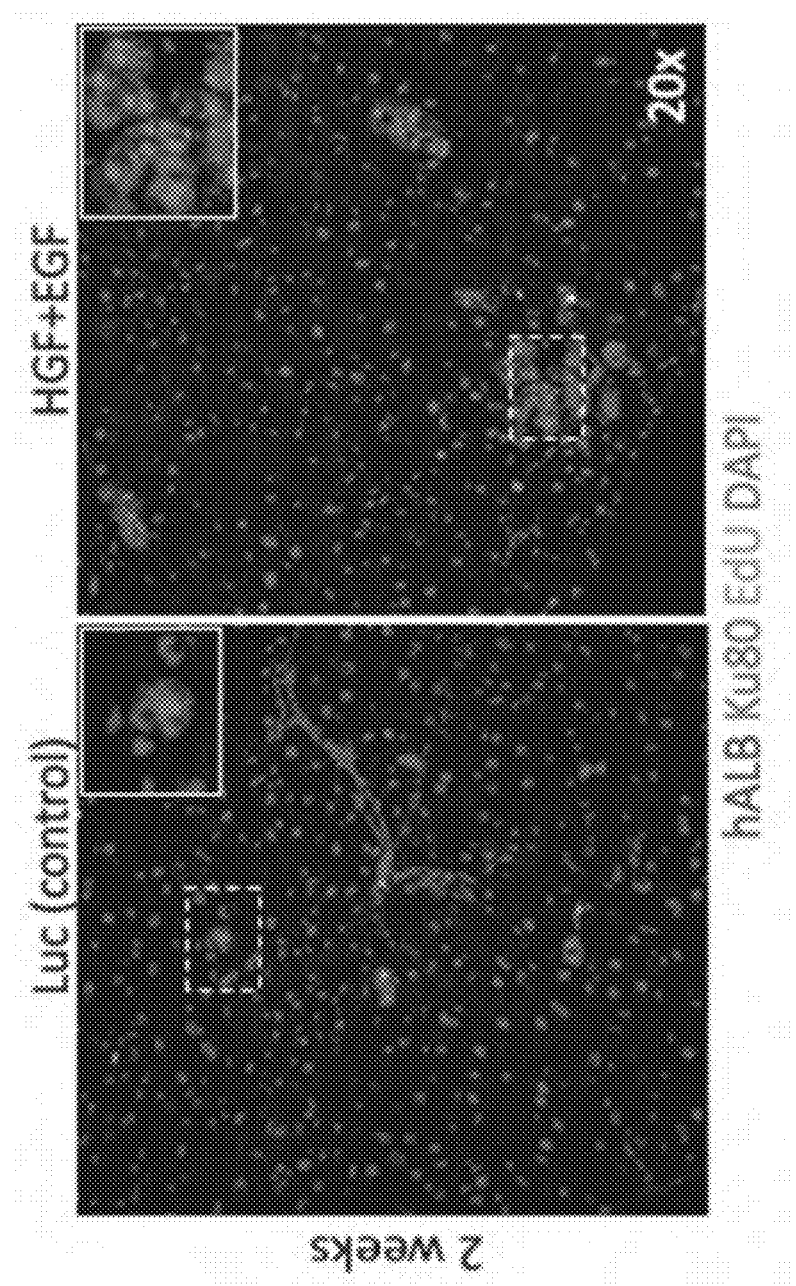
Figure 107D:
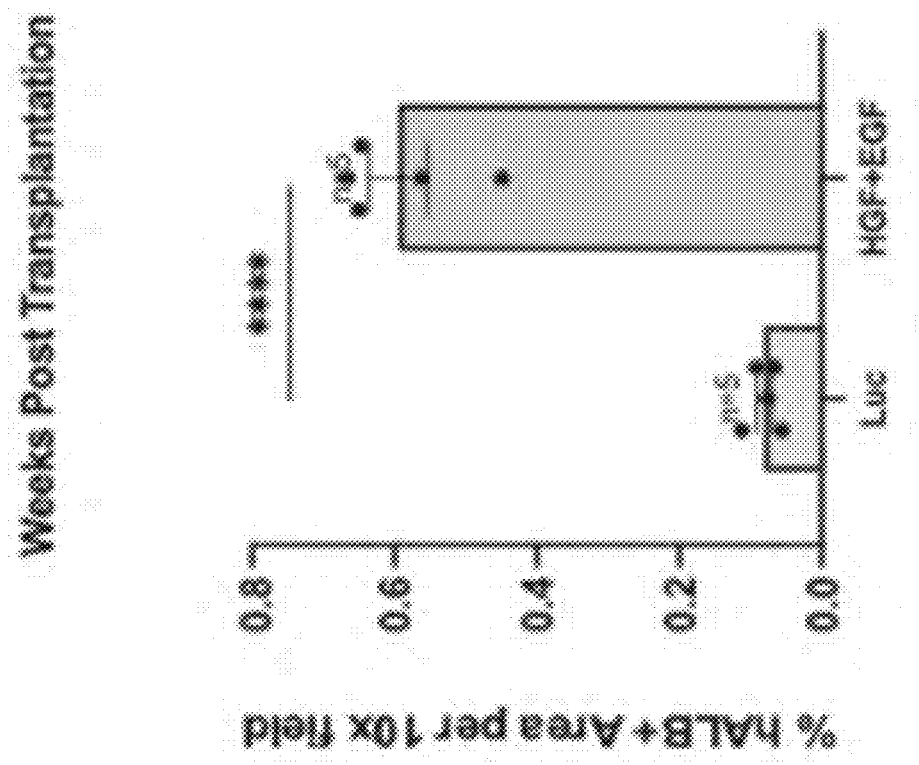

FIGS. 106A-106B depict HGF+EGF mRNA-LNP induces hepatocyte proliferation in vivo.

FIGS. 107A-107D demonstrate HGF+EGF mRNA-LNP significantly increase PHH cluster size in NSG-PiZ mice following 2 weeks engraftment.

Figure 108A:
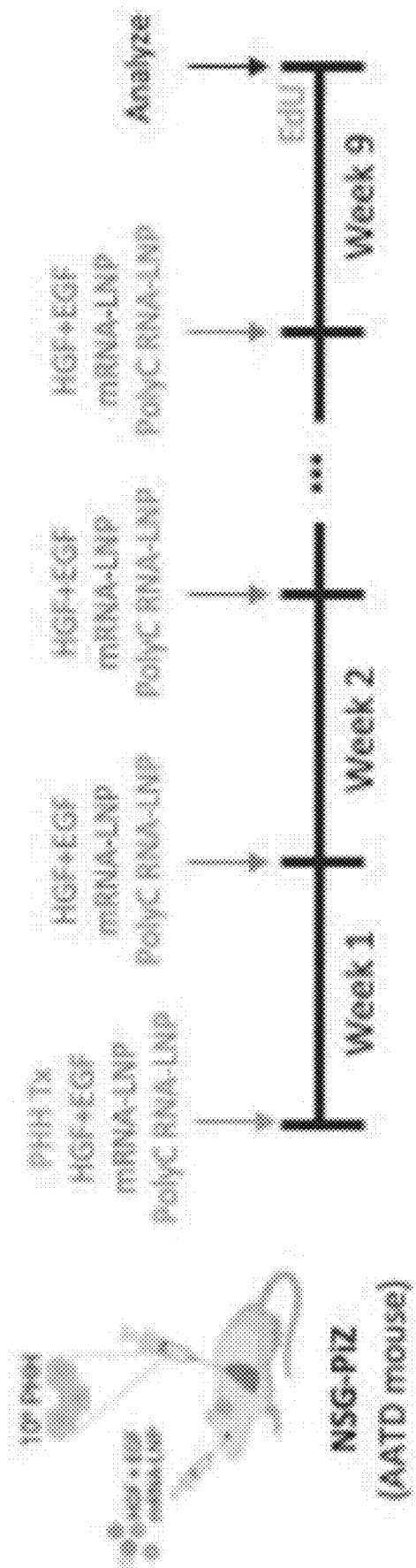
Figure 108B:
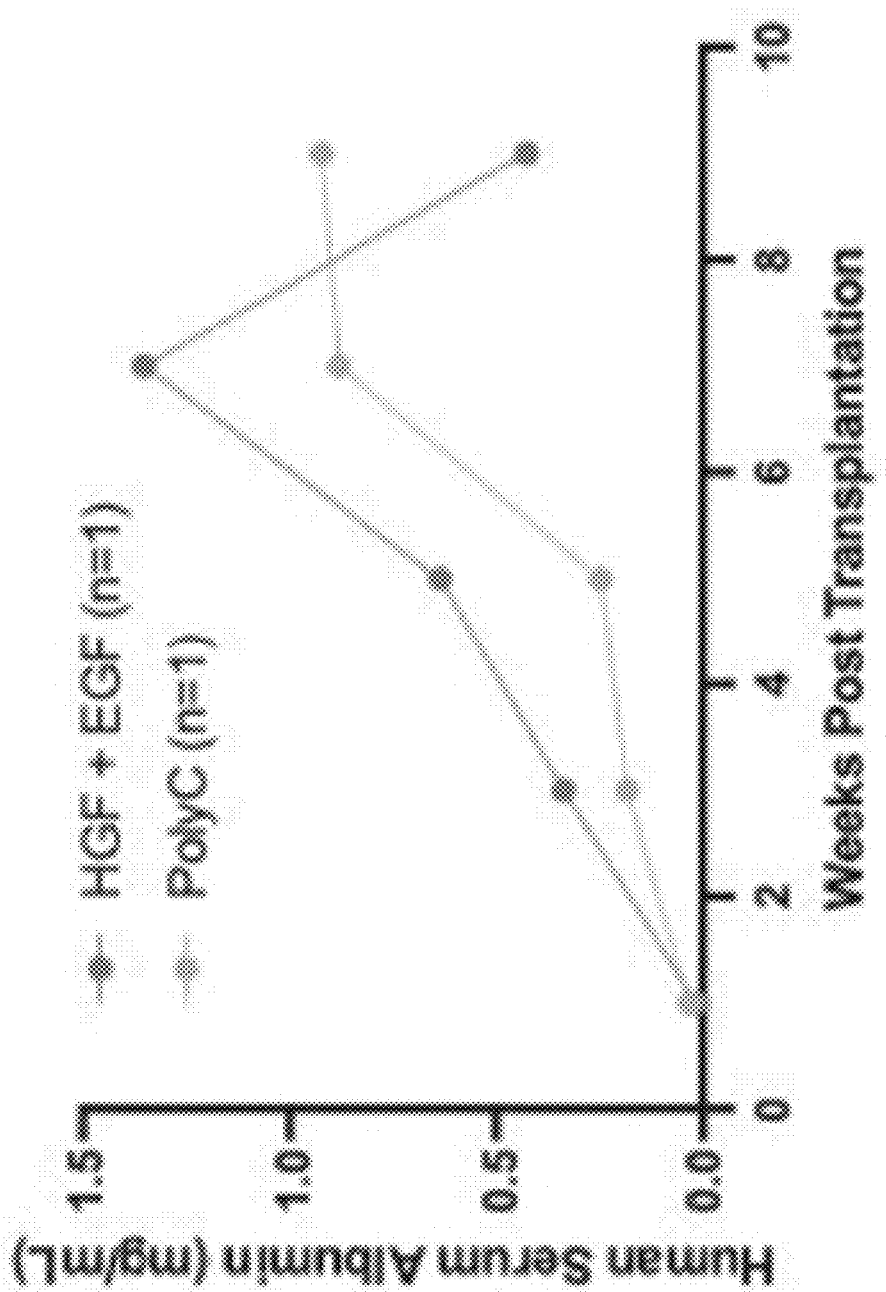
Figure 108C:
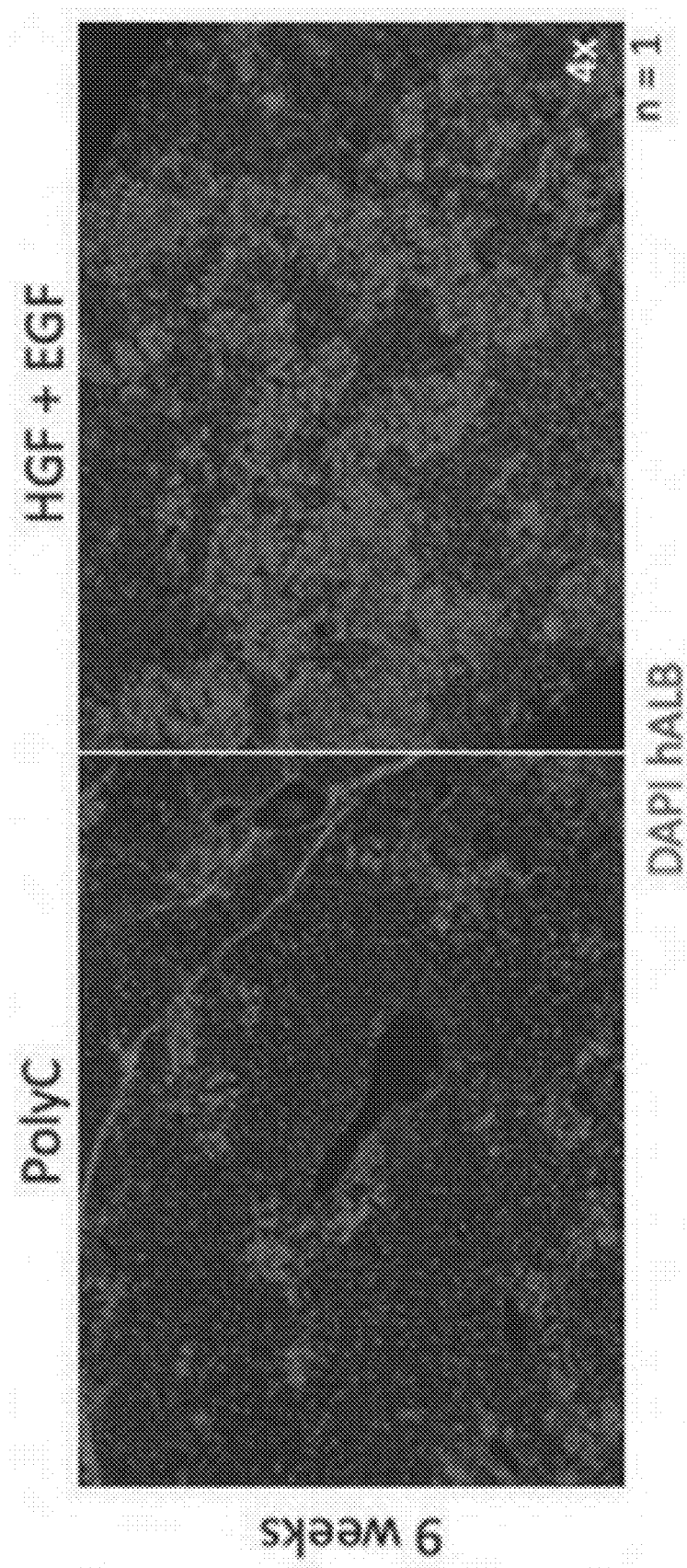

FIGS. 108A-108C demonstrate HGF+EGF mRNA-LNP significantly increase PHH cluster size in NSG-PiZ mice after 9 weeks of engraftment.

Figure 109A:
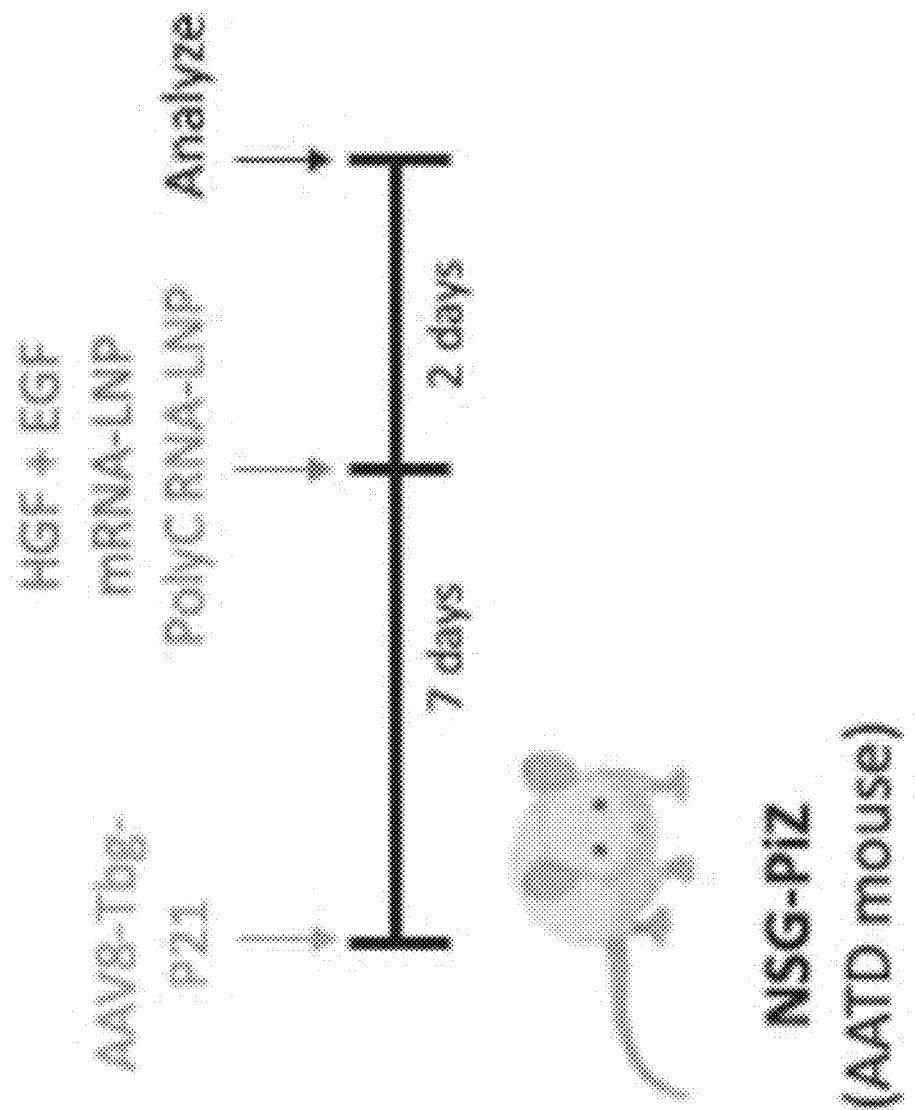
Figure 109B:
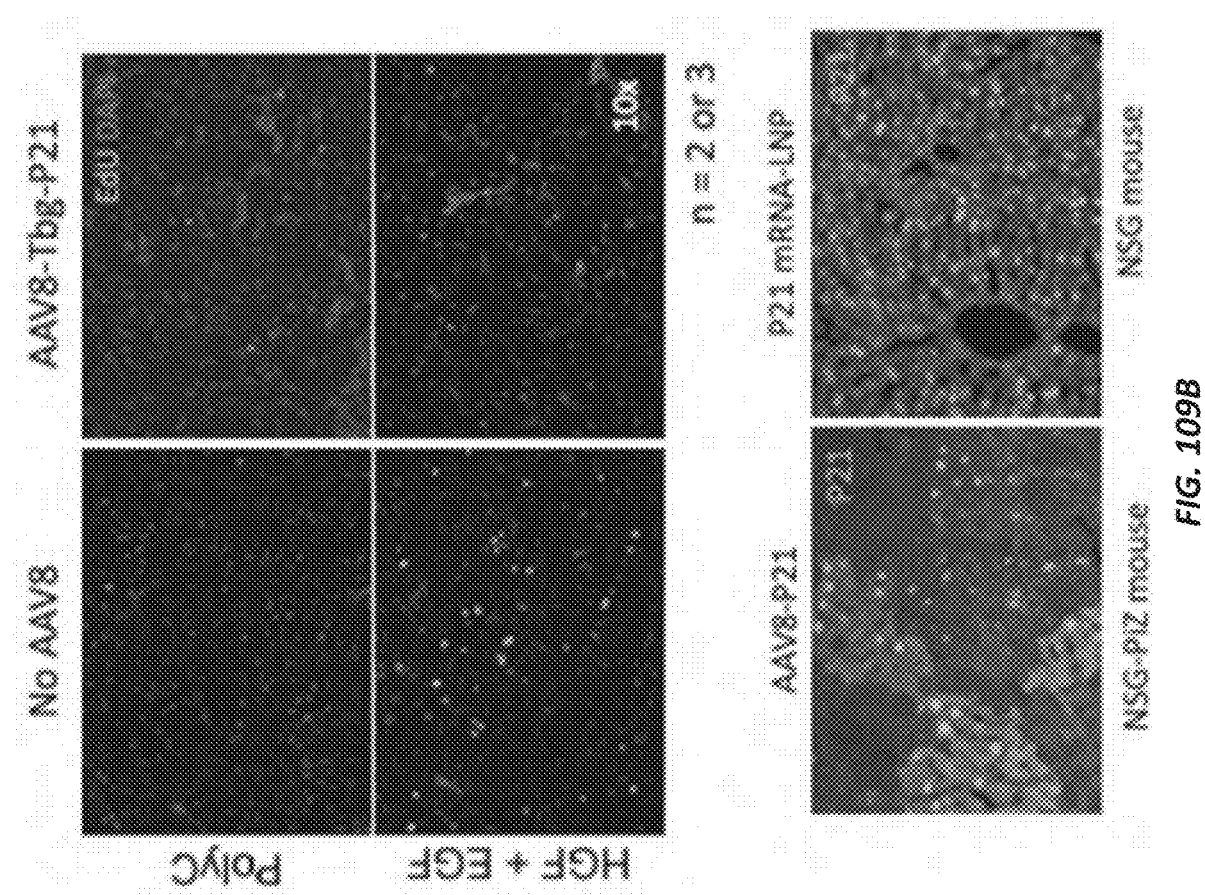
Figure 109C:
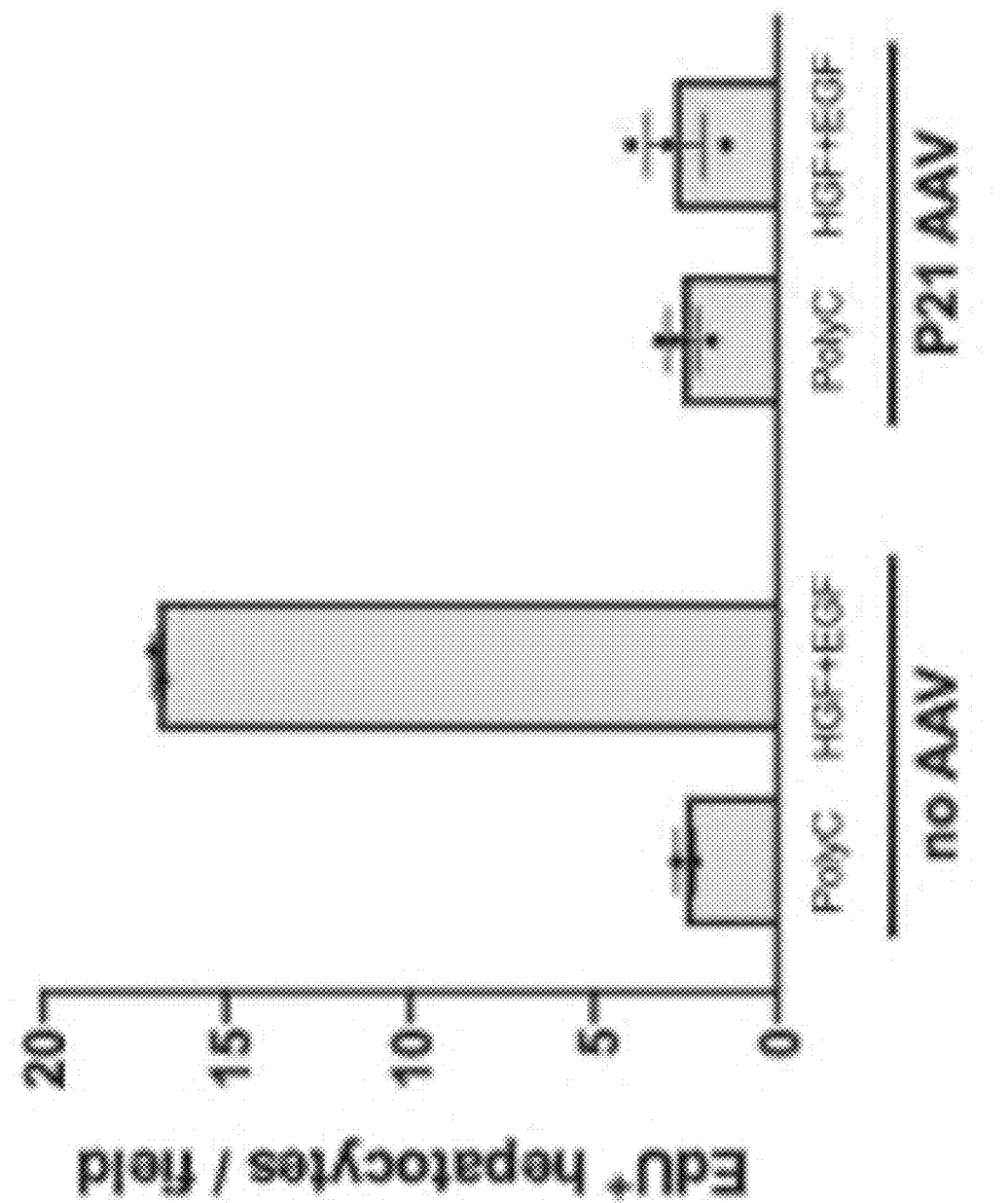
Figure 110A:
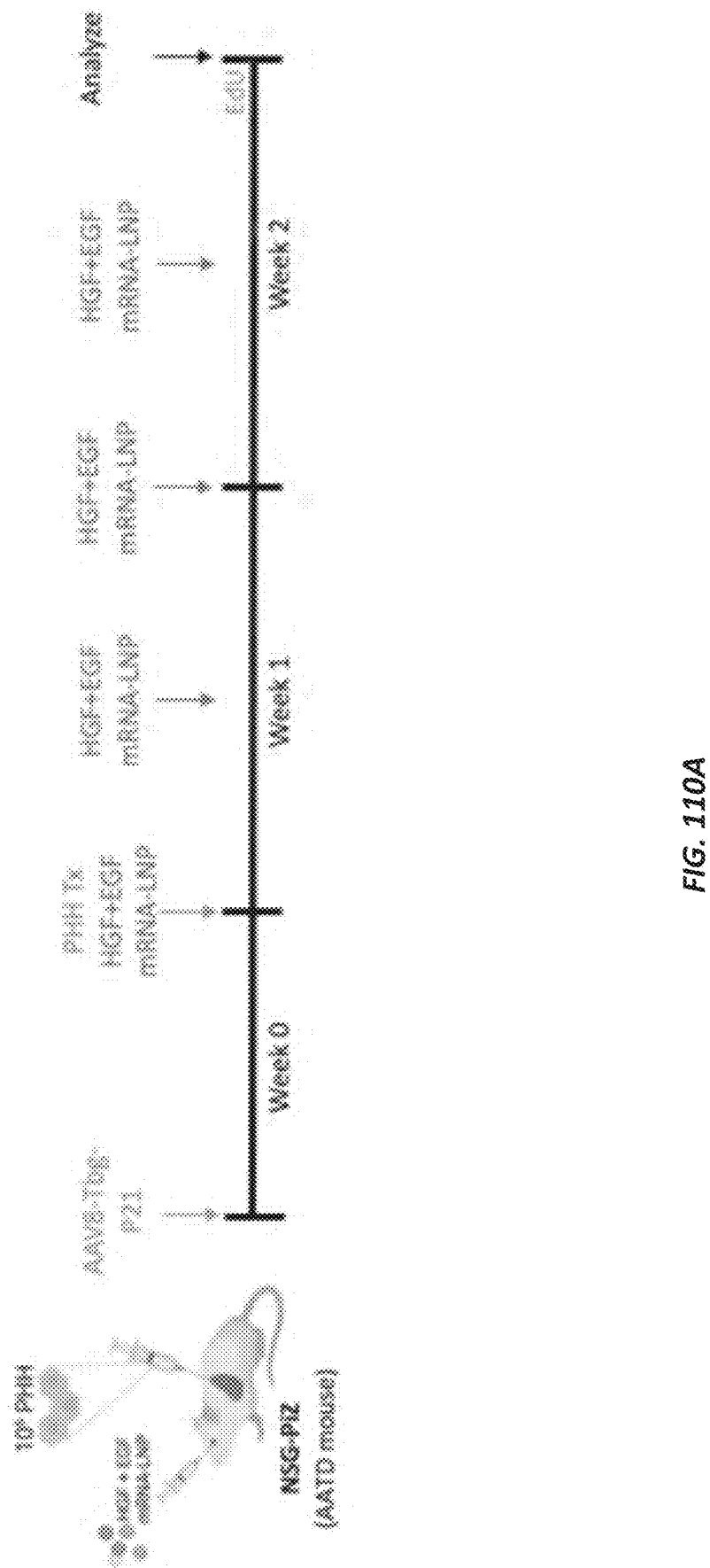
Figure 110B:
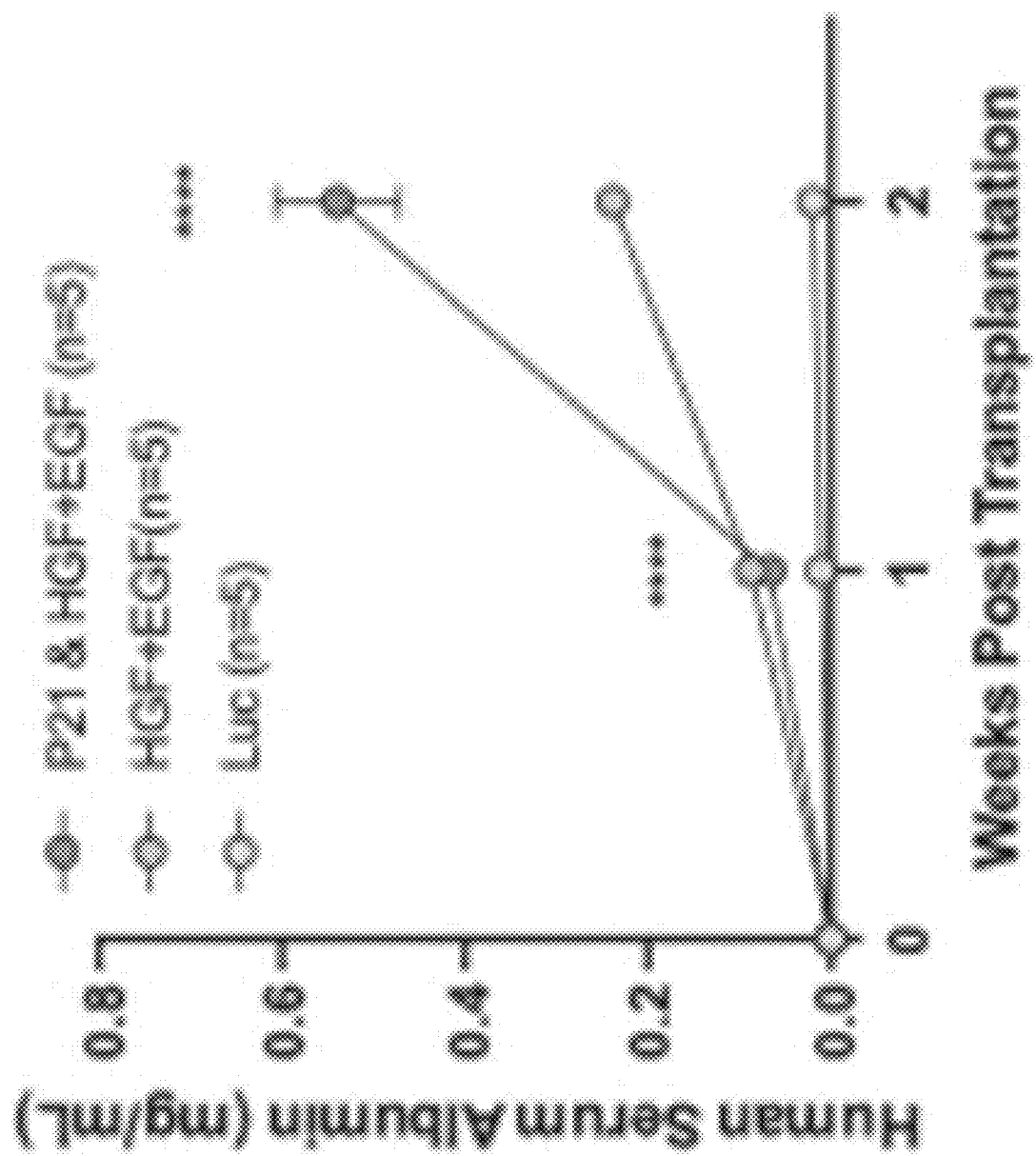
Figure 110C:
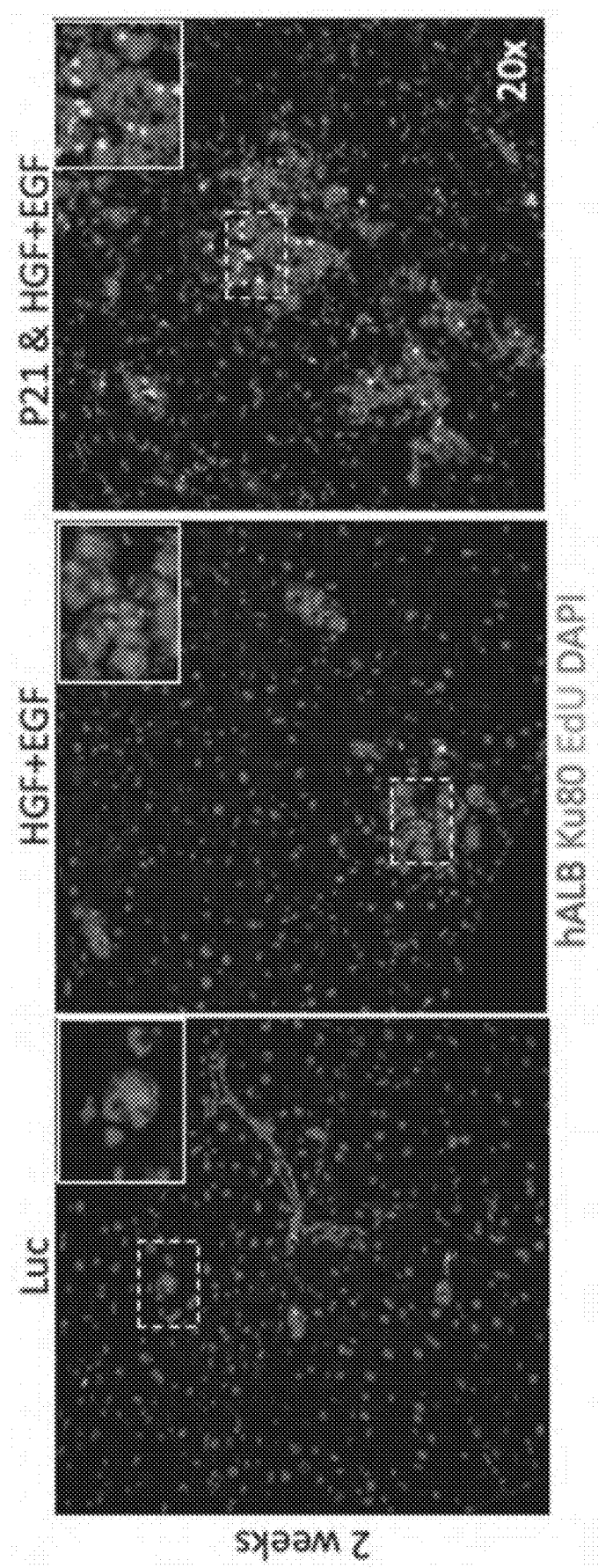
Figure 110D:
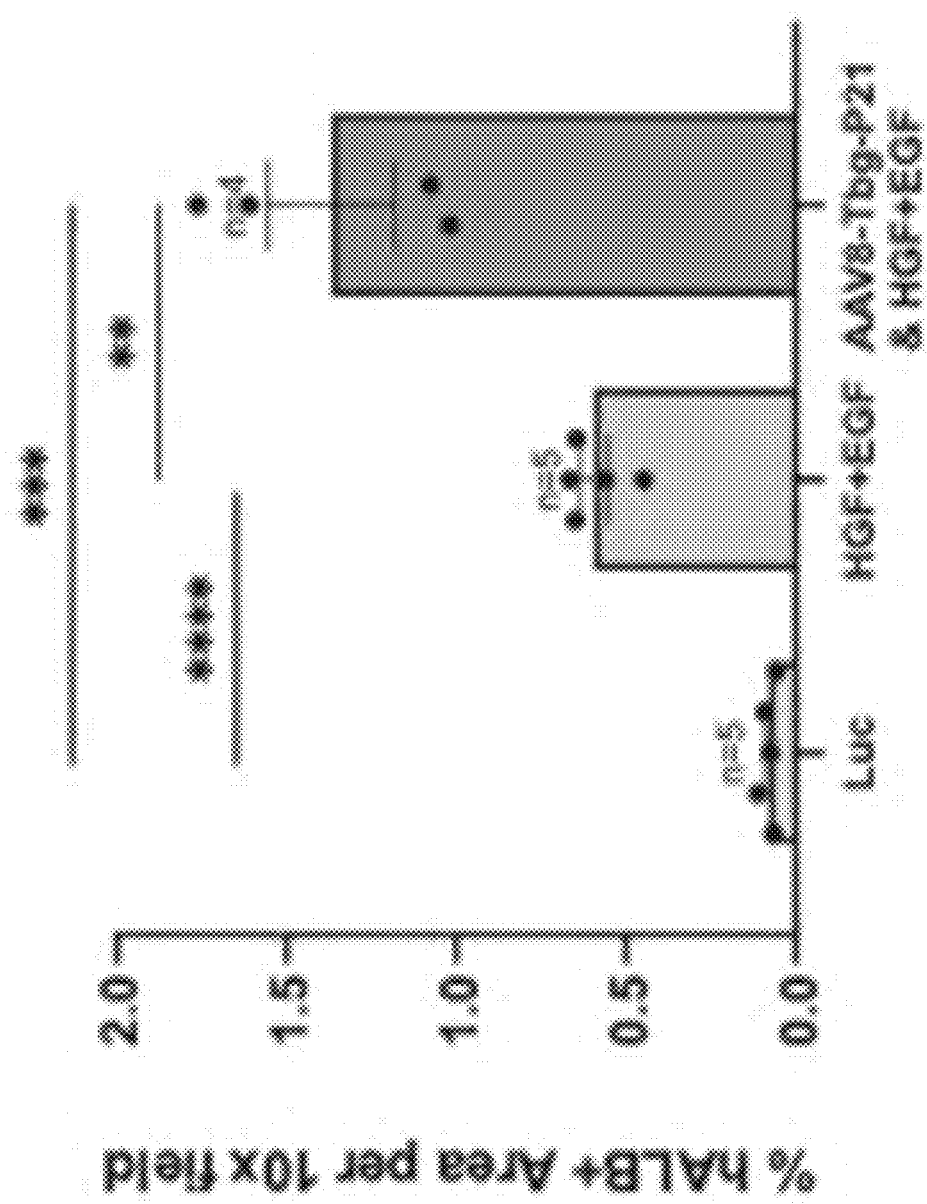

FIGS. 109A-109C demonstrate P21 expression delivered with AAV8-Tbg-p21 blocks host hepatocyte proliferation.

FIGS. 110A-110D demonstrate AAV8-Tbg-P21 in addition to HGF+EGF mRNA-LNP significantly augments PHH repopulation in NSG-PiZ mice after 2 weeks engraftment.

Figure 111A:
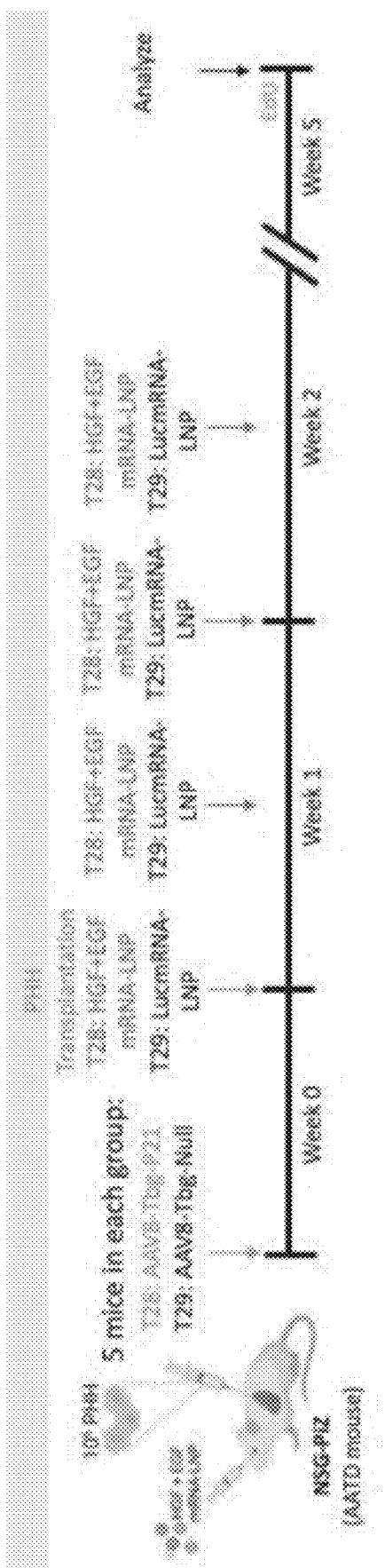
Figure 111B:
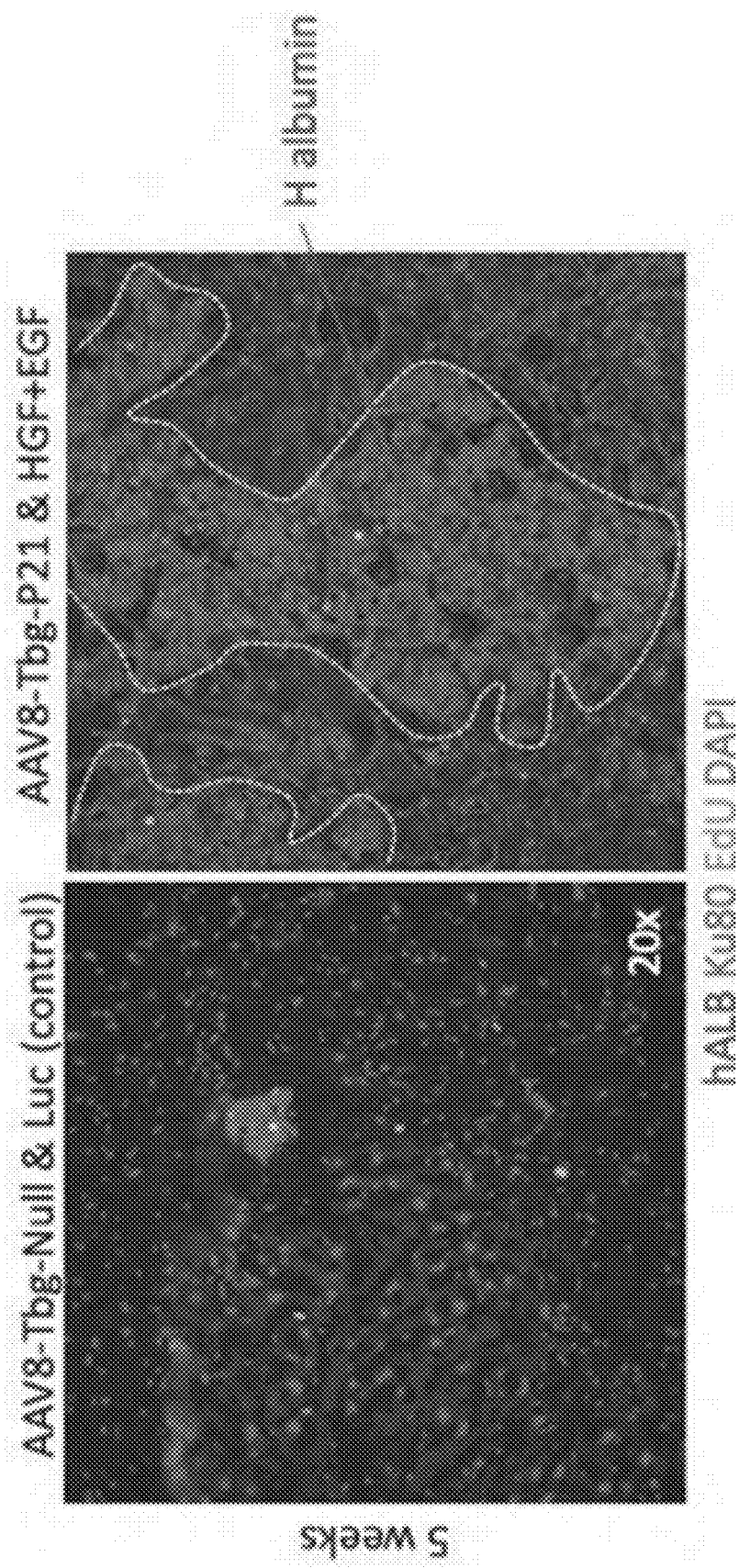
Figure 111C:
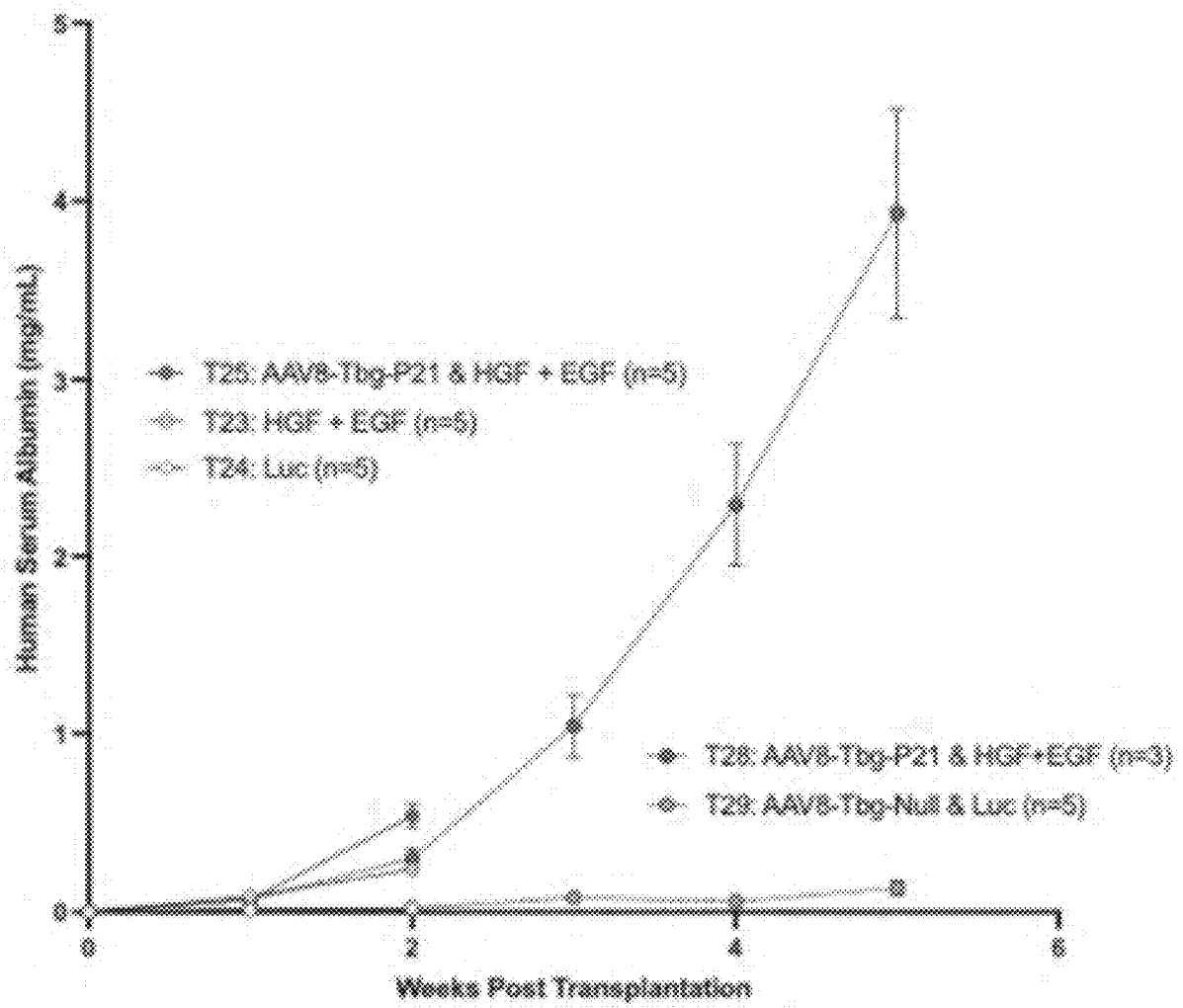

FIGS. 111A-111C demonstrate AAV8-Tbg-P21 and HGF+EGF mRNA-LNP drastically improve PHH engraftment after 5 week-engraftment.

Figure 112A:
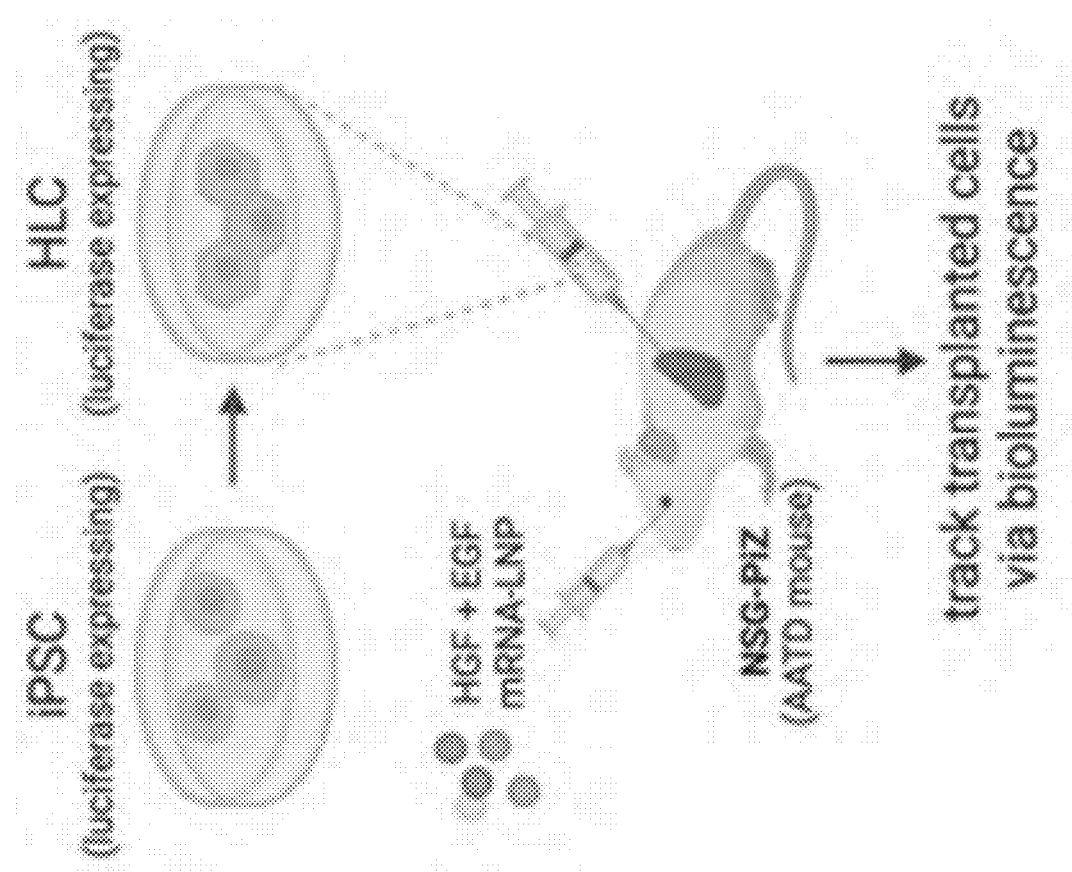
Figure 112B:
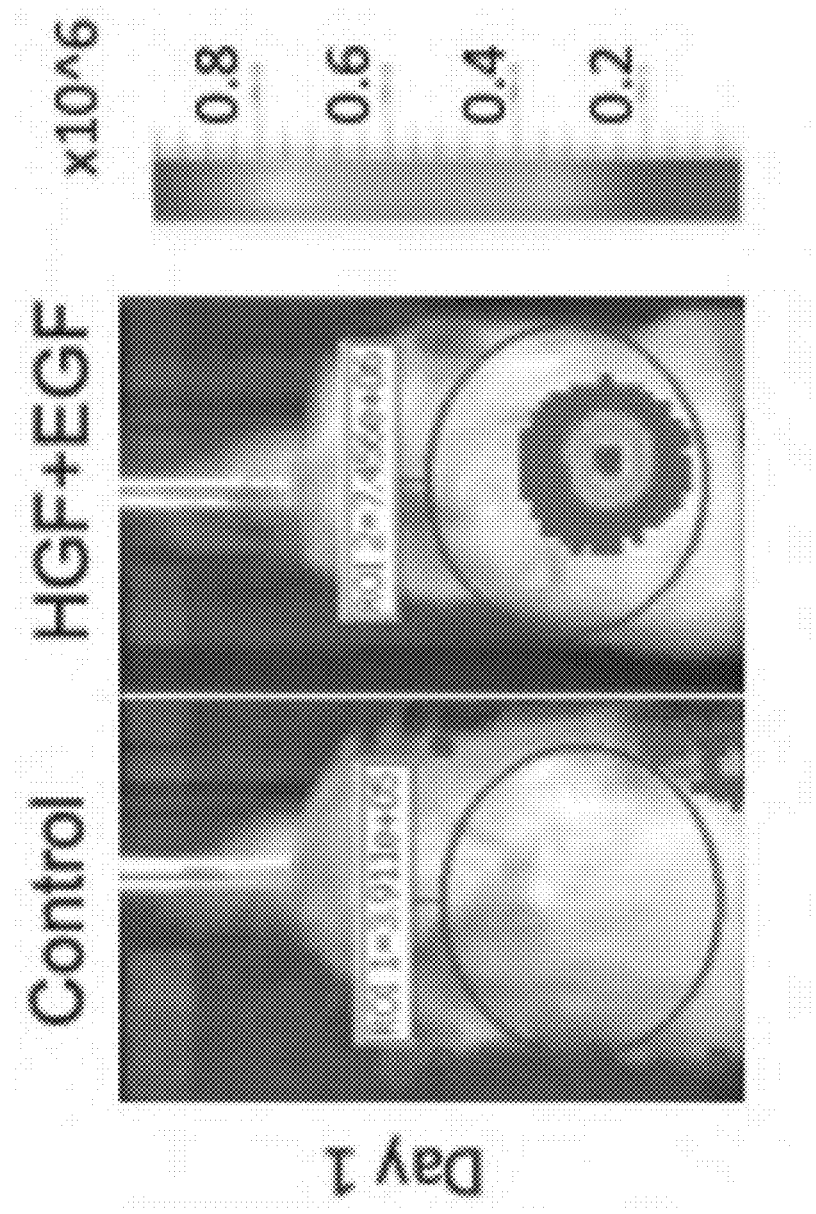
Figure 112C:
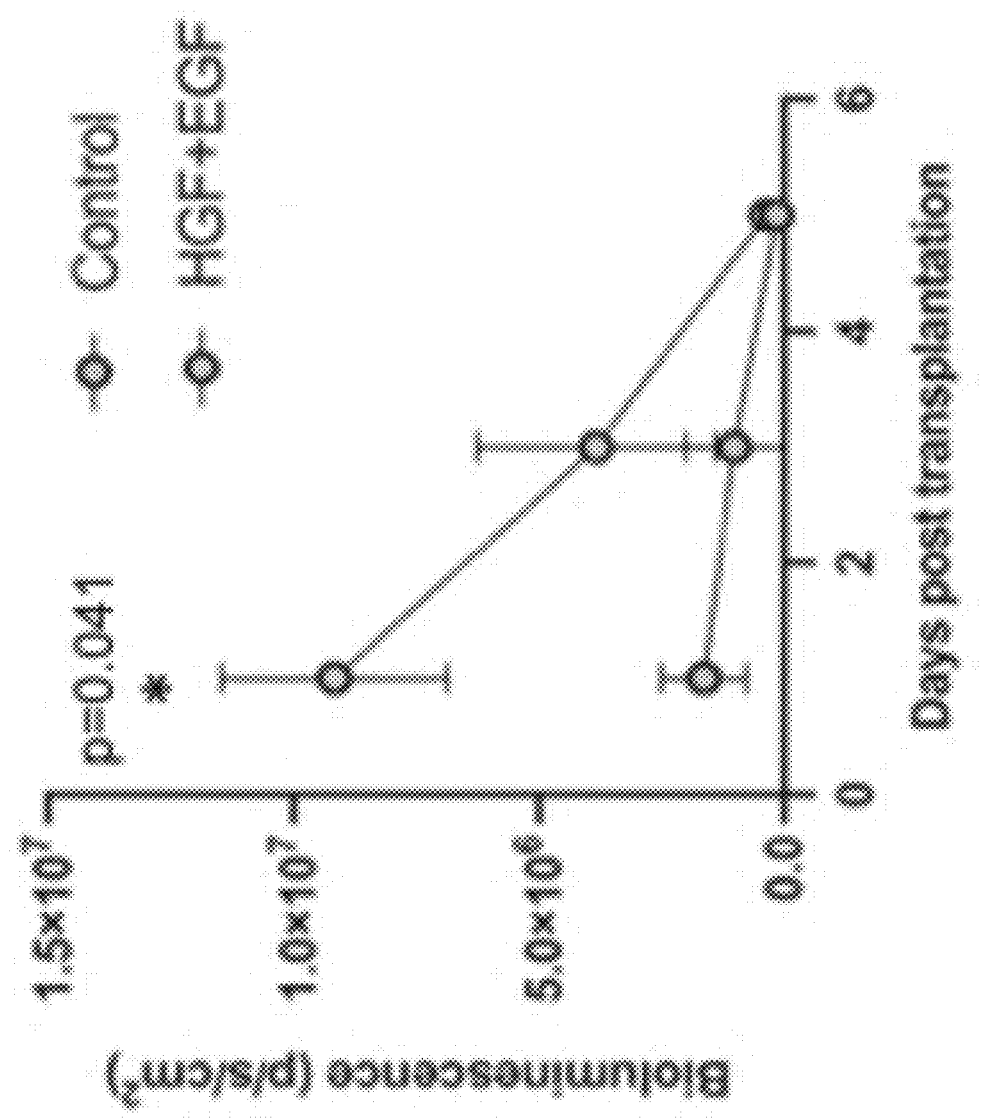

FIGS. 112A-112C demonstrate HGF+EGF mRNA-LNP transiently improves HCL survival after transplantation.

DETAILED DESCRIPTION

As described herein, the inventors have designed engineered liver regenerative factor compositions that provide improved therapeutic performance as compared to wild-type liver regenerative factors. These liver regenerative factor compositions can comprise one or more of: engineered mRNA sequences, engineered nucleosides (e.g., modified nucleosides); and carrier molecules and compositions.

As used herein, "liver regenerative factor" refers to a polypeptide that promotes or increases the growth, repair, function, or regeneration of liver tissue or cells, or a gene or mRNA encoding such a polypeptide. Such liver regenerative factors include but are not limited to: vascular endothelial growth factor A (VEGFA); hepatocyte growth factor (HGF); growth hormone (GH); insulin-like growth factor 1 (IGF-1), epidermal growth factor (EGF); signal transducer and activator of transcription 5B (STAT5b) (e.g., constitutively active STAT5b); cyclin-dependent kinase inhibitor 1A (p21); beta catenin (CTNNB1) (e.g., activated beta catenin); yes-associated protein (YAP) (e.g., activated YAP); wingless-type MMTV integration site family, member 2 (WNT2); and wingless-type MMTV integration site family, member 9B (WNT9b).

The sequences and structures of the foregoing liver regenerative factors are known in the art.

As used herein, "Growth Hormone" or "GH" refers to a polypeptide (or the gene or mRNA encoding said polypeptide) that, upon recognition by a receptor, stimulates MAPK/ERK and JAK-STAT signaling to increase IGF-1 production. The sequences of GH are known in the art for a number of species, e.g., human GH (NBCI Gene ID: 2688, polypeptide sequences NP_000506.2, NP_072053.1, NP_072054.1 and mRNA sequences NM_000515.5, NM_022559.4, and NM_022560.4) and murine GH (NBCI Gene ID: 14599, polypeptide sequence NP_032143.1 and mRNA sequence NM_008117.3). The structure and function of GH is known in the art. An exemplary wild-type mRNA sequence of GH is provided herein as SEQ ID NO: 1.

As used herein, "Epidermal Growth Factor" or "EGF" refers to a polypeptide (or the gene or mRNA encoding said polypeptide) that, upon recognition by the cognate receptor, stimulates cellular proliferation, differentiation, and survival and DNA synthesis. The sequences of EGF are known in the art for a number of species, e.g., human EGF (NBCI Gene ID: 1950, polypeptide sequences NP_001171601.1, NP_001171602.1, NP_001343950.1, and NP_001954.2 and mRNA sequences NM_001178130.3, NM_001178131.3, NM_001357021.2, and NM_001963.6) and murine EGF (NBCI Gene ID: 13645, polypeptide sequences NP_001297666.1, NP_001316523.1, and NP_034243.2 mRNA sequences NM_001310737.1, NM 001329594.1, and NM_010113.4). The structure and function of EGF is known in the art. An exemplary wild-type mRNA sequence of EGF is provided herein as SEQ ID NO: 2. As used herein, "secreted EGF" refers to a matured form of EGF in which the transmembrane region of EGF is cleaved. For example in NP_001954.2 the secreted form of EGF is provided in amino acids 971-1023.

As used herein, "Hepatocyte Growth Factor" or "HGF" refers to a polypeptide (or the gene or mRNA encoding said polypeptide) that, upon recognition by the c-Met receptor, stimulates mitogenesis, cell motility, and matrix invasion. HGF is a key factor in angiogenesis and tissue regeneration processes. The sequences of HGF are known in the art for a number of species, e.g., human HGF (NBCI Gene ID: 3082, polypeptide sequences NP_000592.3, NP_001010931.1, NP_001010932.1, NP_001010933.1, and NP_001010934.1 and mRNA sequences NM_000601.6, NM_001010931.3, NM_00101932.3, NM_001010933.3, and NM_001010934.3) and murine HGF (NBCI Gene ID: 15234, polypeptide sequences NP_001276387.1, NP_001276388.1, NP_001276389.1, NP_001276390.1, and NP_034557.3 and mRNA sequences NM_001289458.1, NM_001289459.1, NM_001289460.2, NM_001289461.1, and NM_010427.5). The structure and function of HGF is known in the art. An exemplary wild-type mRNA sequence of HGF is provided herein as SEQ ID NO: 3.

As used herein, "Cyclin-dependent Kinase inhibitor 1" or "p21" refers to a polypeptide (or the gene or mRNA encoding said polypeptide) that inhibits cyclin/CDK complexes, particularly CDK2. p21 also inhibits PCNA and apoptosis. The sequences of p21 are known in the art for a number of species, e.g., human p21 (NBCI Gene ID: 1026, polypeptide sequences NP_000380.1, NP_001207706.1, NP_001207707.1, NP_001278478.1, NP_001361438.1, NP 001361439.1, NP_001361440.1, NP_001361441.1, NP_001361442.1, and NP_510867.1 and mRNA sequences NM_000389.5, NM_001220777.2, NP_001220778.2, NM_001291549.3, NM_001374509.1, NM_001374510.1, NM_001374511.1, NM_001374512.1, NM_001374513.1, and NM_078467.3) and murine p21 (NBCI Gene ID: 12575, polypeptide sequences NP_001104569.1 and NP_031695.1 and mRNA sequences NM_001111099.2 and NM_007669.5). The structure and function of p21 is known in the art. An exemplary wild-type mRNA sequence of p21 is provided herein as SEQ ID NO: 4.

As used herein, "Vascular Endothelial Growth Factor" or "VEGF" or "VEGFA" refers to a cysteine-knot growth factor (or the gene or mRNA encoding said factor) that promotes vasculogenesis. A number of isoforms of VEGF are known, including $VEGF_{165}$. The sequences of VEGF are known in the art for a number of species, e.g., human VEGF (NBCI Gene ID: 7422, polypeptide sequences NP 001020537.2, NP_001020538.2, NP_001020539.2, NP 001020540.2, NP_001020541.2, NP 001028928.1, NP_001165093.1, NP_001165094.1, NP_001165095.1, NP_001165096.1, NP_001165097.1, NP_001165098.1, NP_001165099.1, NP 001165100.1, NP_001165101.1, NP 001191313.1, NP_001191314.1, NP_001273973.1, NP_001303939.1, and NP_003367.4 and mRNA sequences NM_001025366.3, NM_00102367.3, NM_001025368.3, NM_001025369.3, NM 001025370.3, NM 001033756.3, NM_001171622.2, NM_001171623.2, NM_001171624.2, NM 001171625.2, NM 001171626.2, NM_001171627.2, NM_001171628.2, NM_001171629.2, NM 001171630.2, NM 001204384.2, NM_001204385.2, NM_001287044.2, NM_001317010.1, NM_003376.6) and murine VEGF (NBCI Gene ID: 22339, polypeptide sequences NP_001020421.2, NP 001020428.2, NP_001103736.1, NP 00103737.1, NP 001103738.1, NP_001273985.1, NP_001273986.1, NP_001273987.1, NP_001303970.1, and NP_033531.3 and mRNA sequences NM 001025250.3, NM 001025257.3, NM_001110266.1, NM_001110267.1, NM_001110268.1, NM_001287056.1, NM_001287057.1, NM_001287058.1, NM_001317041.1, and NM_009505.4). The sequence of VEGF165 is known in the art as well, e.g., human VEGF165 mRNA is provided in NCBI as AF486837.1. The structure and function of VEGF is known in the art. An exemplary wild-type mRNA sequence of VEGF is provided herein as SEQ ID NO: 5.

As used herein, "Insulin-Like Growth Factor 1" or "IGF-1" refers to a polypeptide (or the gene or mRNA encoding said polypeptide) produced primarily in the liver in response to GH and which stimulates growth. The sequences of IGF-1 are known in the art for a number of species, e.g., human IGF-1 (NBCI Gene ID: 3479, polypeptide sequences NP_000609.1, NP_001104753.1, NP_001104754.1, and NP_001104755.1 and mRNA sequences NM_000618.5, NM_001111283.3, NM_001111284.2, and NM_001111285.3) and murine IGF-1 (polypeptide sequences NP_001104744.1, NP_001104745.1, NP_001104746.1, NP_001300939.1, and NP_034642.2 and mRNA sequences NM_001111274.1, NM_001111275.2, NM_001111276.1, NM_001314010.1, and NM_010512.5). The structure and function of IGF-1 is known in the art. An exemplary wild-type mRNA sequence of IGF-1 is provided herein as SEQ ID NO: 6.

As used herein, "Signal transducer and activator of transcription 5B" or "STAT5" refers to a polypeptide (or the gene or mRNA encoding said polypeptide) that is transcription factor responsive to IL2, IL4, CSF1, and growth factors. The sequences of STAT5B are known in the art for a number of species, e.g., human STAT5B (NBCI Gene ID: 6777, polypeptide sequences XP_047292549.1, XP_024306665.1, XP_016880466.1, XP_024306666.1, and XP_005257683.1 and mRNA sequences XM_047436593.1, XM_024450897.2, XM_017024977.2, XM_024450898.2, and XM_005257626.5) and murine STAT5B (NCBI Gene ID: 20851, polypeptide sequences NP_001107035.1, NP_001349611.1, and NP_035619.3 and mRNA sequences NM_001113563.2, NM_001362682.1, and NM_011489.3). The structure and function of STAT5B is known in the art. An exemplary wild-type mRNA sequence of STAT5B is provided herein as SEQ ID NO: 7.

As used herein, "beta catenin" or "β-catenin" or "CTNNB1" refers to a polypeptide (or the gene or mRNA encoding said polypeptide) that regulates cell to cell adhesion and gent transcription. The sequences of beta catenin are known in the art for a number of species, e.g., human beta catenin (NBCI Gene ID: 1499, polypeptide sequences NP_001091679.1, NP_001091680.1, NP_001317658.1, and NP_001895.1 and mRNA sequences NM_001098209.2, NM_001098210.2, NM_001330729.2, and NM_001904.4) and murine beta catenin (NCBI Gene ID: 12387, polypeptide sequences NP_001159374.1 and NP_031640.1 and mRNA sequences NM_001165902.1 and NM_007614.3). The structure and function of beta catenin is known in the art. An exemplary wild-type mRNA sequence of beta catenin is provided herein as SEQ ID NO: 17. In some embodiments of any of the aspects, beta catenin is activated beta-catenin.

As used herein, "Yes-associated protein 1" or "YAP" refers to a polypeptide (or the gene or mRNA encoding said polypeptide) that is a transcription co regulator of proliferation and apoptotic genes. The sequences of YAP are known in the art for a number of species, e.g., human YAP (NBCI Gene ID: 10413, polypeptide sequences NP_001123617.1, NP_001181973.1, NP_001181974.1, NP_001269026.1, NP_001269027.1, NP_001269028.1, NP_001269029.1, NP 001269030.1, NP_006097.2 and mRNA sequences NM_001130145.3, NM_001195044.2, NM_001195045.2, NM_001282097.2, NM_001282098.2, NM_001282099.2, NM_001282100.2, NM_001282101.2, and NM_006106.5) and murine YAP (NCBI Gene ID: 22601, polypeptide sequences NP_001164618.1 and NP_033560.1 and mRNA sequences NM_001171147.1 and NM_009534.3). The structure and function of YAP is known in the art. An exemplary wild-type mRNA sequence of YAP is provided herein as SEQ ID NO: 22. In some embodiments of any of the aspects, YAP is activated YAP.

As used herein, "Wingless-type MMTV integration site family, member 2" or "Wnt2" refers to a polypeptide (or the gene or mRNA encoding said polypeptide) that participates in the Wnt signaling pathway to regulate developmental and growth processes. The sequences of Wnt2 are known in the art for a number of species, e.g., human Wnt2 (NBCI Gene ID: 7472, polypeptide sequence NP_003382.1 and mRNA sequence NM_003391.3) and murine Wnt2 (NCBI Gene ID: 22413, polypeptide sequence NP_076142.3 and mRNA sequence NM_023653.5). The structure and function of Wnt2 is known in the art. An exemplary wild-type mRNA sequence of Wnt2 is provided herein as SEQ ID NO: 23.

As used herein, "Wingless-type MMTV integration site family, member 91B" or "Wnt9b" refers to a polypeptide (or the gene or mRNA encoding said polypeptide) that participates in the Wnt signaling pathway to regulate developmental and growth processes. The sequences of Wnt9b are known in the art for a number of species, e.g., human Wnt9b (NBCI Gene ID: 7484, polypeptide sequences NP_001307387.1 and NP_003387.1 and mRNA sequences NM_001320458.2 and NM_003396.3) and murine Wnt9b (NCBI Gene ID: 22412, polypeptide sequence NP_035849.3 and mRNA sequence NM_011719.4). The structure and function of Wnt9b is known in the art. An exemplary wild-type mRNA sequence of Wnt9b is provided herein as SEQ ID NO: 24.

Where reference is made herein to NCBI sequences and entries, it shall be understood that the NCBI sequences and data available under the provided numbers as of Nov. 8, 2022 are referred to.

TABLE 1

Sequences used in present disclosure

| Name | Sequence | SEQ ID NO: |
|---|---|---|
| Human Growth Hormone 1 (GH) (variant 1) NCBI Ref Seq: NM_000515.5 | AAGGATCCCAAGGCCCAACTCCCCGAACCACTCAGGGTCCTGTGGACAG CTCACCTAGCTGCAATGGCTACAGGCTCCCGGACGTCCCTGCTCCTGGCT TTTGGCCTGCTCTGCCTGCCCTGGCTTCAAGAGGGCAGTGCCTTCCCAAC CATTCCCTTATCCAGGCTTTTTGACAACGCTATGCTCCGCGCCCATCGTCT GCACCAGCTGGCCTTTGACACCTACCAGGAGTTTGAAGAAGCCTATATC CCAAAGGAACAGAAGTATTCATTCCTGCAGAACCCCCAGACCTCCCTCT GTTTCTCAGAGTCTATTCCGACACCCTCCAACAGGGAGGAAACACAACA GAAATCCAACCTAGAGCTGCTCCGCATCTCCCTGCTGCTCATCCAGTCGT GGCTGGAGCCCGTGCAGTTCCTCAGGAGTGTCTTCGCCAACAGCCTGGT GTACGGCGCCTCTGACAGCAACGTCTATGACCTCCTAAAGGACCTAGAG GAAGGCATCCAAACGCTGATGGGGAGGCTGGAAGATGGCAGCCCCCGG ACTGGGCAGATCTTCAAGCAGACCTACAGCAAGTTCGACACAAACTCAC ACAACGATGACGCACTACTCAAGAACTACGGGCTGCTCTACTGCTTCAG GAAGGACATGGACAAGGTCGAGACATTCCTGCGCATCGTGCAGTGCCGC TCTGTGGAGGGCAGCTGTGGCTTCTAGCTGCCCGGGTGGCATCCCTGTGA CCCCTCCCCAGTGCCTCTCCTGGCCCTGGAAGTTGCCACTCCAGTGCCCA CCAGCCTTGTCCTAATAAAATTAAGTTGCATCA | 1 |
| Human Epidermal Growth Factor (EGF) (Variant 1) NCBI Ref Seq: NM_001963.6 | CAAAAAGAGAAACTGTTGGGAGAGGAATCGTATCTCCATATTTCTTCTTT CAGCCCCAATCCAAGGGTTGTAGCTGGAACTTTCCATCAGTTCTTCCTTT CTTTTTCCTCTCTAAGCCTTTGCCTTGCTCTGTCACAGTGAAGTCAGCCAG AGCAGGGCTGTTAAACTCTGTGAAATTTGTCATAAGGGTGTCAGGTATTT CTTACTGGCTTCCAAAGAAACATAGATAAAGAAATCTTTCCTGGCTTC CCTTGGCAGGCTGCATTCAGAAGGTCTCTCAGTTGAAGAAAGAGCTTGG AGGACAACAGCACAACAGGAGAGTAAAAGATGCCCCAGGGCTGAGGCC TCCGCTCAGGCAGCCGCATCTGGGGTCAATCATACTCACCTTGCCCGGGC CATGCTCCAGCAAAATCAAGCTGTTTTCTTTTGAAAGTTCAAACTCATCA AGATTATGCTGCTCACTCTTATCATTCTGTTGCCAGTAGTTTCAAAATTTA GTTTTGTTAGTCTCTCAGCACCGCAGCACTGGAGCTGTCCTGAAGGTACT CTCGCAGGAAATGGGAATTCTACTTGTGTGGGTCCTGCACCCTTCTTAAT TTTCTCCCATGGAAATAGTATCTTTAGGATTGACACAGAAGGAACCAATT ATGAGCAATTGGTGGTGGATGCTGGTGTCTCAGTGATCATGGATTTTCAT TATAATGAGAAAAGAATCTATTGGGTGGATTTAGAAAGACAACTTTTGC AAAGAGTTTTTCTGAATGGGTCAAGGCAAGAGAGTATGTAATATAGA GAAAAATGTTTCTGGAATGGCAATAAATTGGATAAATGAAGAAGTTATT TGGTCAAATCAACAGGAAGGAATCATTACAGTAACAGATATGAAAGGA AATAATTCCCACATTCTTTTAAGTGCTTTAAAATATCCTGCAAATGTAGC AGTTGATCCAGTAGAAAGGTTTATATTTTGGTCTTCAGAGGTGGCTGGAA GCCTTTATAGAGCAGATCTCGATGGTGTGGGAGTGAAGGCTCTGTTGGA GACATCAGAGAAATAACAGCTGTGTCATTGGATGTGCTTGATAAGCGG CTGTTTTGGATTCAGTACAACAGAGAAGGAAGCAATTCTCTTATTTGCTC CTGTGATTATGATGGAGGTTCTGTCCACATTAGTAAACATCCAACACAGC ATAATTTGTTTGCAATGTCCCTTTTTGGTGACCGTATCTTCTATTCAACAT GGAAAATGAAGCAATTTGGATAGCCAACAAACACACTGGAAAGGACA TGGTTAGAATTAACCTCCATTCATCATTTGTACCACTTGGTGAACTGAAA GTAGTGCATCCACTTGCACAACCCAAGGCAGAAGATGACACTTGGGAGC CTGAGCAGAAACTTTGCAAATTGAGGAAAGGAAACTGCAGCAGCACTGT GTGTGGGCAAGACCTCCAGTCACACTTGTGCATGTGTGCAGAGGGATAC GCCCTAAGTCGAGACCGGAAGTACTGTGAAGATGTTAATGAATGTGCTT TTTGGAATCATGGCTGTACTCTTGGGTGTAAAAACACCCCTGGATCCTAT TACTGCACGTGCCCTGTAGGATTTGTTCTGCTTCCTGATGGGAAACGATG TCATCAACTTGTTTCCTGTCCACGCAATGTGTCTGAATGCAGCCATGACT GTGTTCTGACATCAGAAGGTCCCTTATGTTTCTGTCCTGAAGGCTCAGTG CTTGAGAGATGGGAAAACATGTAGCGGTTGTTCCTCACCCGATAATG GTGGATGTAGCCAGCTCTGCGTTCCTCTTAGCCCAGTATCCTGGGAATGT GATTGCTTTCCTGGGTATGACCTACAACTGGATGAAAAAAGCTGTGCAG CTTCAGGACCACAACCATTTTTGCTGTTTGCCAATTCTCAAGATATTCGA CACATGCATTTTGATGGAACAGACTATGGAACTCTGCTCAGCCAGCAGA TGGGAATGGTTTATGCCCTAGATCATGACCCTGTGGAAAATAAGATATA CTTTGCCCATACAGCCCTGAAGTGGATAGAGAGCTAATATGGATGGT TCCCAGCGAGAAAGGCTTATTGAGGAAGGAGTAGATGTGCCAGAAGGTC TTGCTGTGGACTGGATTGGCCGTAGATTCTATTGGACAGACAGAGGGAA ATCTCTGATTGGAAGGAGTGATTTAAATGGGAACGTTCCAAAATAATC ACTAAGGAGAACATCTCTCAACCACGAGGAATTGCTGTTCATCCAATGG CCAAGAGATTATTCTGGACTGATACAGGGATTAATCCACGAATTGAAAG TTCTTCCCTCCAAGGCCTTGGCCGTCTGGTTATAGCCAGCTCTGATCTAA TCTGGCCCAGTGGAATAACGATTGACTTCTTAACTGACAAGTTGTACTGG TGCGATGCCAAGCAGTCTGTGATTGAAATGGCCAATCTGGATGGTTCAA AACGCCGAAGACTTACCCAGAATGATGTAGGTCACCCATTTGCTGTAGC AGTGTTTGAGGATTATGTGTGGTTCTCAGATTGGGCTATGCCATCAGTAA TGAGAGTAAACAAGAGGACTGGCAAAGATAGAGTACGCTCCAAGGCA GCATGCTGAAGCCCTCATCACTGGTTGTGGTTCATCCATTGGCAAAACCA GGAGCAGATCCCTGCTTATATCAAAACGGAGGCTGTGAACATATTTGCA AAAAGAGGCTTGGAACTGCTTGGTGTTCGTGTCGTGAAGGTTTTATGAA | 2 |

TABLE 1-continued

Sequences used in present disclosure

| Name | Sequence | SEQ ID NO: |
|---|---|---|
| | AGCCTCAGATGGGAAAACGTGTCTGGCTCTGGATGGTCATCAGCTGTTG | |
| | GCAGGTGGTGAAGTTGATCTAAAGAACCAAGTAACACCATTGGACATCT | |
| | TGTCCAAGACTAGAGTGTCAGAAGATAACATTACAGAATCTCAACACAT | |
| | GCTAGTGGCTGAAATCATGGTGTCAGATCAAGATGACTGTGCTCCTGTG | |
| | GGATGCAGCATGTATGCTCGGTGTATTTCAGAGGGAGAGGATGCCACAT | |
| | GTCAGTGTTTGAAAGGATTTGCTGGGGATGGAAAACTATGTTCTGATATA | |
| | GATGAATGTGAGATGGGTGTCCCAGTGTGCCCCCCTGCCTCCTCCAAGTG | |
| | CATCAACACCGAAGGTGGTTATGTCTGCCGGTGCTCAGAAGGCTACCAA | |
| | GGAGATGGGATTCACTGTCTTGATATTGATGAGTGCCAACTGGGGGAGC | |
| | ACAGCTGTGGAGAGAATGCCAGCTGCACAAATACAGAGGGAGGCTATA | |
| | CCTGCATGTGTGCTGGACGCCTGTCTGAACCAGGACTGATTTGCCCTGAC | |
| | TCTACTCCACCCCCTCACCTCAGGGAAGATGACCACCACTATTCCGTAAG | |
| | AAATAGTGACTCTGAATGTCCCCTGTCCCACGATGGGTACTGCCTCCATG | |
| | ATGGTGTGTGCATGTATATTGAAGCATTGGACAAGTATGCATGCAACTGT | |
| | GTTGTTGGCTACATCGGGGAGCGATGTCAGTACCGAGACCTGAAGTGGT | |
| | GGGAACTGCGCCACGCTGGCCACGGGCAGCAGCAGAAGGTCATCGTGGT | |
| | GGCTGTCTGCGTGGTGGTGCTTGTCATGCTGCTCCTCCTGAGCCTGTGGG | |
| | GGGCCCACTACTACAGGACTCAGAAGCTGCTATCGAAAAACCCAAAGAA | |
| | TCCTTATGAGGAGTCGAGCAGAGATGTGAGGAGTCGCAGGCCTGCTGAC | |
| | ACTGAGGATGGGATGTCCTCTTGCCCTCAACCTTGGTTTGTGGTTATAAA | |
| | AGAACACCAAGACCTCAAGAATGGGGGTCAACCAGTGGCTGGTGAGGA | |
| | TGGCCAGGCAGCAGATGGGTCAATGCAACCAACTTCATGGAGGCAGGAG | |
| | CCCCAGTTATGTGGAATGGGCACAGAGCAAGGCTGCTGGATTCCAGTAT | |
| | CCAGTGATAAGGGCTCCTGTCCCCAGGTAATGGAGCGAAGCTTTCATAT | |
| | GCCCTCCTATGGGACACAGACCCTTGAAGGGGGTGTCGAGAAGCCCCAT | |
| | TCTCTCCTATCAGCTAACCCATTATGGCAACAAAGGGCCCTGGACCCACC | |
| | ACACCAAATGGAGCTGACTCAGTGAAAACTGGAATTAAAAGGAAAGTC | |
| | AAGAAGAATGAACTATGTCGATGCACAGTATCTTTTCTTTCAAAAGTAG | |
| | AGCAAAACTATAGGTTTTGGTTCCACAATCTCTACGACTAATCACCTACT | |
| | CAATGCCTGGAGACAGATACGTAGTTGTGCTTTTGTTTGCTCTTTTAAGC | |
| | AGTCTCACTGCAGTCTTATTTCCAAGTAAGAGTACTGGGAGAATCACTAG | |
| | GTAACTTATTAGAAACCCAAATTGGGACAACAGTGCTTTGTAAATTGTGT | |
| | TGTCTTCAGCAGTCAATACAAATAGATTTTTGTTTTTGTTGTTCCTGCAGC | |
| | CCCAGAAGAAATTAGGGGTTAAAGCAGACAGTCACACTGGTTTGGTCAG | |
| | TTACAAAGTAATTTCTTTGATCTGGACAGAACATTTATATCAGTTTCATG | |
| | AAATGATTGGAATATTACAATACCGTTAAGATACAGTGTAGGCATTTAA | |
| | CTCCTCATTGGCGTGGTCCATGCTGATGATTTTGCAAAATGAGTTGTGAT | |
| | GAATCAATGAAAAATGTAATTTAGAAACTGATTTCTTCAGAATTAGATG | |
| | GCTTATTTTTAAAATATTTGAATGAAAACATTTTATTTTAAATATTAC | |
| | ACAGGAGGCTTCGGAGTTTCTTAGTCATTACTGTCCTTTTCCCCTACAGA | |
| | ATTTTCCCTCTTGGTGTGATTGCACAGAATTTGTATGTATTTTCAGTTACA | |
| | AGATTGTAAGTAAATTGCCTGATTTGTTTTCATTATAGACAACGATGAAT | |
| | TTCTTCTAATTATTTAAATAAAATCACCAAAAACATAAACATTTTATTGT | |
| | ATGCCTGATTAAGTAGTTAATTATAGTCTAAGGCAGTACTAGAGTTGAAC | |
| | CAAAATGATTTGTCAAGCTTGCTGATGTTTCTGTTTTTCGTTTTTTTTTTT | |
| | TTCCGGAGAGAGGATAGGATCTCACTCTGTTATCCAGGCTGGAGTGTGC | |
| | AATGGCACAATCATAGCTCAGTGCAGCCTCAAACTCCTGGGCTCAAGCA | |
| | ATCCTCCTGCCTCAGCCTCCCGAGTAACTAGGACCACAGGCACAGGCCA | |
| | CCATGCCTGGCTAAGGTTTTTATTTTTATTTTTTGTAGACATGGGGATCAC | |
| | ACAATGTTGCCCAGGCTGGTCTTGAACTCCTGCCTCAAGCAAGGTCGTG | |
| | CTGGTAATTTTGCAAATGAATTGTGATTGACTTTCAGCCTCCCAACGTA | |
| | TTAGATTATAGGCATTAGCCATGGTGCCCAGCCTTGTAACTTTTAAAAAA | |
| | ATTTTTTAATCTACAACTCTGTAGATTAAAATTTCACATGGTGTTCTAATT | |
| | AAATATTTTTCTTGCAGCCAAGATATTGTTACTACAGATAACACAACCTG | |
| | ATATGGTAACTTTAAATTTTGGGGCTTTGAATCATTCAGTTTATGCATT | |
| | AACTAGTCCCTTTGTTTATCTTTCATTTCTCAACCCCTTGTACTTTGGTGA | |
| | TACCAGACATCAGAATAAAAAGAAATTGAAGTACCTGTTTTCAAATGGA | |
| | TACTTTATAGGAATTTTGGTAAAGATTTGGTGATGGGAGGATGACTTGAG | |
| | GTTTGTGGATATTAGTTAATTATTCAGTATGATACCTCACCCAGCTAATT | |
| | TAGATTTTTCTATATTCGGTTTTGCTTTCATTGACAATATCCTGGAGGATC | |
| | AGAAGACTTGTCTATTTCTGCTGAGTCACTGGCCTCAGAAAAATAATAAC | |
| | CATAATTTCCCCCAAGGTTTTCTTTACCTAAGTGTGAATATTTTTCTTCC | |
| | TCCAAAAGCTCACTTTTGGGTTTAGATTAAATTTTTGTATTTTAGCACCTT | |
| | TTTCTTTTAGGGGTTCAATGATGACAAAAGAAATGACATGAGAACACGG | |
| | CTACCCATAACATACCATTATCTTTGTACCAGAAAAATCCTTGTTTCCTTC | |
| | TTAATGACTCTGGTACCTTAGAAACTGGGACCCTGCTAAGTCCTTGACTA | |
| | GGCTATCTACCAGCTCCTGGTCGGATTAAAGAAAAAACACACTTTGTGTT | |
| | TTTTAATCACCAAGGCACCCTGCAGAGATATCTTCTTCTTGCAACTTCAC | |
| | ATCTTTATCAGTAATGTCCTCTTTCCTTTAAAAATTCAAGTTTTAAGAACA | |
| | GCATTTTCATGTAAAAACTTGATTTGTGTTTTTTCCAGACTGAATACTTTT | |
| | CCTCCCTAACTCTCATCGTCTCATTGCGCGCAACGCCTGATTGAGCTTCT | |
| | GTTTGACTAAATATCACCTACTATGTAAAAAATGAGCATATTGGCCTCTT | |
| | TTCTAGCATCTAATAAAGGCTTAATACACTGTA | |

TABLE 1-continued

Sequences used in present disclosure

| Name | Sequence | SEQ ID NO: |
|---|---|---|
| Human hepatocyte growth factor (HGF) Variant 1 NCBI Ref Seq: NM_000601.6 | AGGCACTGACTCCGAACAGGATTCTTTCACCCAGGCATCTCCTCCAGAG<br>GGATCCGCCAGCCCGTCCAGCAGCCACCATGTGGGTGACCAAACTCCTGC<br>CAGCCCTGCTGCTGCAGCATGTCCTCCTGCATCTCCTCCTGCTCCCCATC<br>GCCATCCCCTATGCAGAGGGACAAAGGAAAAGAAGAAATACAATTCAT<br>GAATTCAAAAAATCAGCAAAGACTACCCTAATCAAATAGATCCAGCAC<br>TGAAGATAAAAACCAAAAAGTGAATACTGCAGACCAATGTGCTAATAG<br>ATGTACTAGGAATAAAGGACTTCCATTCACTTGCAAGGCTTTTGTTTTTG<br>ATAAAGCAAGAAAACAATGCCTCTGGTTCCCCTTCAATAGCATGTCAAG<br>TGGAGTGAAAAAAGAATTTGGCCATGAATTTGACCTCTATGAAAACAAA<br>GACTACATTAGAAACTGCATCATTGGTAAAGGACGCAGCTACAAGGGAA<br>CAGTATCTATCACTAAGAGTGGCATCAAATGTCAGCCCTGGAGTTCCATG<br>ATACCACACGAACACAGCTTTTTGCCTTCGAGCTATCGGGGTAAAGACCT<br>ACAGGAAAACTACTGTCGAAATCCTCGAGGGGAAGAAGGGGGACCCTG<br>GTGTTTCACAAGCAATCCAGAGGTACGCTACGAAGTCTGTGACATTCCTC<br>AGTGTTCAGAAGTTGAATGCATGACCTGCAATGGGAGAGTTATCGAGG<br>TCTCATGGATCATACAGAATCAGGCAAGATTTGTCAGCGCTGGGATCAT<br>CAGACACCACACCGGCACAAATTCTTGCCTGAAAGATATCCCGACAAGG<br>GCTTTGATGATAATTATTGCCGCAATCCCGATGGCCAGCCGAGGCCATG<br>GTGCTATACTCTTGACCCTCACACCCGCTGGGAGTACTGTGCAATTAAAA<br>CATGCGCTGACAATACTATGAATGACACTGATGTTCCTTTGGAAACAACT<br>GAATGCATCCAAGGTCAAGGAGAAGGCTACAGGGGCACTGTCAATACCA<br>TTTGGAATGGAATTCCATGTCAGCGTTGGGATTCTCAGTATCCTCACGAG<br>CATGACATGACTCCTGAAAATTTCAAGTGCAAGGACCTACGAGAAAATT<br>ACTGCCGAAATCCAGATGGGTCTGAATCACCCTGGTGTTTTACCACTGAT<br>CCAAACATCCGAGTTGGCTACTGCTCCCAAATTCCAAACTGTGATATGTC<br>ACATGGACAAGATTGTTATCGTGGGAATGGCAAAAATTATATGGGCAAC<br>TTATCCCAAACAAGATCTGGACTAACATGTTCAATGTGGGACAAGAACA<br>TGGAAGACTTACATCGTCATATCTTCTGGGAACCAGATGCAAGTAAGCT<br>GAATGAGAATTACTGCCGAAATCCAGATGATGATGCTCATGGACCCTGG<br>TGCTACACGGGAAATCCACTCATTCCTTGGGATTATTGCCCTATTTCTCG<br>TTGTGAAGGTGATACCACCTACAATAGTCAATTTAGACCATCCCGTAA<br>TATCTTGTGCCAAAACGAAACAATTGCGAGTTGTAAATGGGATTCCAAC<br>ACGAACAAACATAGGATGGATGGTTAGTTTGAGATACAGAAATAAACAT<br>ATCTGCGGAGGATCATTGATAAAGGAGAGTTGGGTTCTTACTGCACGAC<br>AGTGTTTCCCTTCTCGAGACTTGAAAGATTATGAAGCTTGGCTTGGAATT<br>CATGATGTCCACGGAAGAGGAGATGAGAAATGCAAACAGGTTCTCAATG<br>TTTCCCAGCTGGTATATGGCCCTGAAGGATCAGATCTGGTTTTAATGAAG<br>CTTGCCAGGCCTGCTGTCCTGGATGATTTTGTTAGTACGATTGATTTACCT<br>AATTATGGATGCACAATTCCTGAAAAGACCAGTTGCAGTGTTTATGGCTG<br>GGGCTACACTGGATTGATCAACTATGATGGCCTATTACGAGTGGCACAT<br>CTCTATATAATGGGAAATGAGAAATGCAGCCAGCATCATCGAGGGAAGG<br>TGACTCTGAATGAGTCTGAAATATGTGCTGGGGCTGAAAAGATTGGATC<br>AGGACCATGTGAGGGGGATTATGGTGGCCCACTTGTTTGTGAGCAACAT<br>AAAATGAGAATGGTTCTTGGTGTCATTGTTCCTGGTCGTGGATGTGCCAT<br>TCCAAATCGTCCTGGTATTTTTGTCCGAGTAGCATATTATGCAAAATGGA<br>TACACAAAATTATTTTAACATATAAGGTACCACAGTCATAGCTGAAGTA<br>AGTGTGTCTGAAGCACCCACCAATACAACTGTCTTTTACATGAAGATTTC<br>AGAGAATGTGGAATTTAAAATGTCACTTACAACAATCCTAAGACAACTA<br>CTGGAGAGTCATGTTTGTTGAAATTCTCATTAATGTTTATGGGTGTTTTCT<br>GTTGTTTTGTTTGTCAGTGTTATTTTGTCAATGTTGAAGTGAATTAAGGTA<br>CATGCAAGTGTAATAACATATCTCCTGAAGATACTTGAATGGATTAAAA<br>AAACACACAGGTATATTTGCTGGATGATAAAGATTTCATGGGAAAAAAA<br>ATCAATTAATCTGTCTAAGCTGCTTTCTGATGTTGGTTTCTTAATAATGAG<br>TAAACCACAAATTAAATGTTATTTTAACCTCACCAAAACAATTTATACCT<br>TGTGTCCCTAAATTGTAGCCCTATATTAAATTATATTACATTTCATATGCT<br>ATATGTTATAGTTCATTCATTTCTCTTCACCATGTATCCTGCAATACTGGT<br>ACACGAACACACTTTTTACAAAACCACATACCCATGTACACATGCCTAG<br>GTACACATGTGCATGCACTACAGTTTAAATTATGGTGTACCTAATGTAAC<br>CCCTAAATATTTTAGAAGTATGTACCTATAGTTTTACCTCAAAAAAACCA<br>GAAATCTCTAAAGACCAGTAGAAATATTAAAAAATGATGCAAGATCAAA<br>ATGATTAGCTAATTCTCCATACATAATCTGCAGATGATCTTCTTTGGTTG<br>GCATTTCAGGTGTGGCCATCACCCAGAGTTAAATAACACCTAATCTAGGT<br>GTTTACATGTATTCATTATCCTAGTTATTTCATGTAGTTTCTAATTCTTAA<br>AGGAAAGAGGGTAATAGTTCTATTTGTGTAATTTGTTTCCTCCAAACTTA<br>AGGCCACTTATTTACACAAGATATTTGTAGATCTATTTTCCTAAAGCATT<br>TCTTAAGTGCTCAGATCAGTATCTAATTGAAGAAGTTTAAAAGTGTTTTG<br>GTCATTAAAAATGTACTTAAATAGGTTAAATCTAAGCCTTGCTGCTGTGA<br>TTGGCTTCTAGCTCACTGCCTTTAAATTTTAAAAAATTTAAGAGGAAAAT<br>TTCCAAGTCTCCAAAGTTTTATAAATACCCTTCAAGTCATGCATTAA<br>AGTATATATTGGAGAAAAAATAAAAATACTTTTCTCAACCTGGAAGAT<br>TTTAGCCTAATAAAGCTTTTTGAAGTAAAAGACAACTTGTAAAGGAA<br>AGAAACTAGTTTGTCTCAACTCTGTATTCATTTATTTTTTTTTGAAGTAG<br>AGTGGAATCTGTTGAATCAGATATTTTTATCAAGATATGTTTATTTTTTCTT<br>ATTTCATTTTACAAAGTTCACTCCTAATGCCATATGTAACAGACATTTAA | 3 |

TABLE 1-continued

Sequences used in present disclosure

| Name | Sequence | SEQ ID NO: |
|---|---|---|
| | ATTTTGTGTTCTGTATAACAGCCAAATTATCATATTTATCATTGTATTTGT<br>CATGCTTAGCTAAAGATCATGTATTTGTTGAGAAATAGAATAACAAAAA<br>GTAATAGGATAGGCTTTGAATTTTTGCAGAAATCTTCCTGTACAAAACAC<br>CTTTAAAAATAATTTTTTGAATGGTGTGAATCCAGTAGTCCCATTTCTCT<br>GACTTAGTTTTCTTGAGTGATTTTTATCAAGGCCAAGTCCCCAAACAATT<br>CCCTACCAGCTCTTTAGAGTACTGTTCAATCTGGACTAAAATGGTTTTAA<br>GTTTATGGAGAGCTTAGTCCACAGAATATAGGGCGGCGAGTCCAGAAAT<br>GCTTATACAATTTTTTTTTCATAATAAGATATGTGCTGGCATCAAGAAAC<br>TTAAAGTGGAAGCAAAAAGACATCCAACTAGTTGCTGGTCTCTATCATCT<br>TATCTGATGGTATTTCTATTTTCCTTATATAATACACCATTTTAGTAAGAA<br>CTCCTAGAAATTTCAAGAGCATATTGCCAAAATATAAAGTATATTTCATA<br>GTTTCTTCTGGCTGAACCAGTGAAATTTTATTATTGCATATTAATGATATT<br>TGTAAACTTTTATAAAAATTGTCATAATTTTAAATACTCACATTTTAAA<br>AATACTTCTTTAATGACTCTTCCTCTAAATTTCCTGGAAATACAGATAAA<br>GATTAGCTAGATACAAGATACAGCTAAGTATTTAGACATTTTGAGGCTA<br>GTATTTTCATTTTATTAAAGGCTAAAAACAATACCACCAATAAATCATC<br>AAACAAACCGTACAAAGTAATTCTCTCTTTGGGAGGCTCCTTTCGTGATA<br>GAGGGACATGGGTGGAATTGACAATGAAACTTAGATGAACAAGGTCCAT<br>GTTATTTTAGGTGGTAGAACAGGGTAGAGTCATGTCATTATTTGCTGGTG<br>GAAGACACTATTTACCAGGTGTTCTTTGCTGAATAAATCATTAAACATTT<br>TTAAAAATCCAACAATCCACTTTATTTTGTGTCATTGACAAAAGGATCTT<br>TTAAATCAGAAGGTTTCAATGCAATTTTTGGTTTGGCTGTTTGAATAATG<br>GTTATGTACTGTTATAATTGTAGACATTTTCTCACGTCTACCAGGAATTG<br>AAGTGTAAAACTAAAATATTTTTCATAATGCCTCTGCCGTGCAGAAGGA<br>ATGATAATCCTTTTGTATACTTCTTTAATTTTATTGTAAAATGTGTAATGA<br>CTTTTACCTATATGCTGTGGGCAGGTCCTCAGTAAAATCTATTGAGTCAA<br>TTTCTAGTATTAACAGGCTTTTGCTTGCTATCTAAGTGTTTCAAATTATGG<br>GAAGTGTGAGACACTGGAAGGCAAGAAAATTAACAATAATGGCATGTG<br>ATAGCAAAATTGTATTTCACTTATTCCTGTGAATATTTCTTGTTGGTACCA<br>ATGGTACTGTACAAAGTGAATGTTATAGCCACAACATTCTCTTGAAAAG<br>AACACTGTCAAGAAGTGGGAAATTGCTGTCAGGCATTTCATTGTTGTTTT<br>TAAACTTTTTTAAAAGAAATACTGGTTTTGCAATATAGAGATCATGTGGT<br>AAAGAATTTTAATAAGATCTTATACTAAAAAGCCTTAAATCAATTTATTG<br>AGATTCAAAAAATACTATTATAATTAATTACATCCCATACATATAGGCAA<br>ACTCATTTAAAAAATAAAACTAATTTTGGTAAAAGTACATGGCCTTTGTT<br>TTTAAAATACATAATTTTAAAATAAATCACTTGTCATGATAAAGTCCAAA<br>AAGAAGTTATCATTCAACATTCAACTAAGGTTGGAGCTAAGAATTTACT<br>AATACAAAAAAGTTAAAATTTTTTGGACCATATATATCTTGACAGTGTA<br>ACTTTTAAGTAGGTTCATTTCCATTTGCACAGAAAGTTTCTGTCTTTAGG<br>AAACTGAAAATGAAATACTGTGGATGCTATGACTGTTTGTCTTGTATGTA<br>AATAGGAAATTAATAAGCTGCCTATTGAGTGGTATAGCTGTATGCTTACC<br>CAAAAAAGGGAACACTGTGGTTATGACTTGTATTATAAACTTTCTGTAGT<br>TAATAAAGTTGTTATTTTTATAACCATGATTATATTATTATTATTAATAAA<br>ATATTTTATCAAAA | |
| Mouse Cyclin-<br>dependent<br>kinase<br>inhibitor<br>1A/Senescence<br>gene (p21)<br>(Cdkn1a)<br>(Variant 2)<br>NCBI Ref<br>Seq:<br>NM_001111099.2 | AGTGCAGGGTGGTGGAGACCTGATGATACCCAACTACCAGCTGTGGGGT<br>GAGGAGGAGCATGAATGGAGACAGAGACCCCAGATAATTAAGGACGTC<br>CCACTTTGCCAGCAGAATAAAAGGTGCCACAGGCACCATGTCCAATCCT<br>GGTGATGTCCGACCTGTTCCGCACAGGAGCAAAGTGTGCCGTTGTCTCTT<br>CGGTCCCGTGGACAGTGAGCAGTTGCGCCGTGATTGCGATGCGCTCATG<br>GCGGGCTGTCTCCAGGAGGCCCGAGAACGGTGGAACTTTGACTTCGTCA<br>CGGAGACGCCGCTGGAGGGCAACTTCGTCTGGGAGCGCGTTCGGAGCCT<br>AGGGCTGCCCAAGGTCTACCTGAGCCCTGGGTCCCGCAGCCGTGACGAC<br>CTGGGAGGGGACAAGAGGCCCAGTACTTCCTCTGCCCTGCTGCAGGGGC<br>CAGCTCCGGAGGACCACGTGGCCTTGTCGCTGTCTTGCACTCTGGTGTCT<br>GAGCGGCCTGAAGATTCCCCGGGTGGGCCCGGAACATCTCAGGGCGGAA<br>AACGGAGGCAGACCAGCCTGACAGATTTCTATCACTCCAAGCGCAGATT<br>GGTCTTCTGCAAGAGAAAACCCTGAAGTGCCCACGGGAGCCCCGCCCTC<br>TTCTGCTGTGGGTCAGGAGGCCTCTTCCCCATCTTCGGCCTTAGCCCTCA<br>CTCTGTGTGTCTTAATTATTATTTGTGTTTTAATTTAAACGTCTCCTGTAT<br>ATACGCTGCCTGCCCTCTCCCAGTCTCCAAACTTAAAGTTATTTAAAAAA<br>AGAACAAAACAAACAAAAAAAACCAAAACAAAACAAACCTAAATTAG<br>TAGGACGGTAGGGCCCTTAGTGTGGGGATTTCTATTATGTAGATTATTA<br>TTATTTAAGCCCCTCCCAACCCAAGCTCTGTGTTTCCTATACCGGAGGAA<br>CAGTCCTACTGATATCAACCCATCTGCATCCGTTTCACCCAACCCCCCTC<br>CCCCCATTCCCTGCCTGGTTCCTTGCCACTTCTTACCTGGGGGTGATCCTC<br>AGACCTGAATAGCACTTTGGAAAATGAGTAGGACTTTGGGGTCTCCTT<br>GTCACCTCTAAGGCCAGCTAGGATGACAGTGAAGCAGTCACAGCCTAGA<br>ACAGGGATGCAGTTAGGACTCAACCGTAATATCCCGACTCTTGACATT<br>GCTCAGACCTGTGAAGCAGGAATGGTCCCCACTCTGGATCCCCTTTGCC<br>ACTCCTGGGGAGCCCACCTCTCCTGTGGGTCTCTGCCAGCTGCCCCTCTA<br>TTTTGGAGGGTTAATCTGGTGATCTGCTGCTCTTTTCCCCCACCCCATACT<br>TCCCCTTCTGCAGGTCGGCAGGAGGCATATCTAGGCACTTGCCCCACAGC<br>TCAGTGGACTGGAAGGGAATGTATATGCAGGGTACACTAAGTGGGATTC | 4 |

TABLE 1-continued

Sequences used in present disclosure

| Name | Sequence | SEQ ID NO: |
|---|---|---|
| | CCTGGTCTTACCTTAGGCAGCTCCAGTGGCAACCCCCTGCATTGTGGGTC<br>TAGGGTGGGTCCTTGGTGGTGAGACAGGCCTCCCAGAGCATTCTATGGT<br>GTGTGGTGGTGGGGGTGGGCTTATCTGGGATGGGGACCCCAGTTGGGGT<br>TCTCAGTGACTTCTCCCATTTCTTAGTAGCAGTTGTACAAGGAGCCAGGC<br>CAAGATGGTGTCTTGGGGGCTAAGGGAGCTCACAGGACACTGAGCAATG<br>GCTGATCCTTTCTCAGTGTTGAATACCGTGGGTGTCAAAGCACTTAGTGG<br>GTCTGACTCCAGCCCCAAACATCCCTGTTTCTGTAACATCCTGGTCTGGA<br>CTGTCTACCCTTAGCCCGCACCCCAAGAACATGTATTGTGGCTCCCTCCC<br>TGTCTCCACTCAGATTGTAAGCGTCTCACGAGAAGGGACAGCACCCTGC<br>ATTGTCCCGAGTCCTCACACCCGACCCCAAAGCTGGTGCTCAATAAATAC<br>TTCTCGATGATT | |
| Human vascular endothelial growth factor A (VEGFA) (variant 5) NCBI Ref Seq: NM_001025369.3 | GCGGAGGCTTGGGGCAGCCGGGTAGCTCGGAGGTCGTGGCGCTGGGGGC<br>TAGCACCAGCGCTCTGTCGGGAGGCGCAGCGGTTAGGTGGACCGGTCAG<br>CGGACTCACCGGCCAGGGCGCTCGGTGCTGGAATTTGATATTCATTGATC<br>CGGGTTTTATCCCTCTTCTTTTTTCTTAAACATTTTTTTTTAAAACTGTATT<br>GTTTCTCGTTTTAATTTATTTTTGCTTGCCATTCCCCACTTGAATCGGGCC<br>GACGGCTTGGGGAGATTGCTCTACTTCCCCAAATCACTGTGGATTTTGGA<br>AACCAGCAGAAAGAGGAAAGAGGTAGCAAGAGCTCCAGAGAGAAGTCG<br>AGGAAGAGAGAGACGGGGTCAGAGAGAGCGCGCGGGCGTGCGAGCAGC<br>GAAAGCGACAGGGGCAAAGTGAGTGACCTGCTTTTGGGGGTGACCGCCG<br>GAGCGCGGCGTGAGCCCTCCCCCTTGGGATCCCGCAGCTGACCAGTCGC<br>GCTGACGGACAGACAGACACCGCCCCCAGCCCCAGCTACCACCTC<br>CTCCCCGGCCGGCGGCGGACAGTGGACGCGGCGGCGAGCCGCGGGCAG<br>GGGCCGGAGCCCGCGCCCGGAGGCGGGGTGGAGGGGGTCGGGGCTCGC<br>GGCGTCGCACTGAAACTTTTCGTCCAACTTCTGGGCTGTTCTCGCTTCGG<br>AGGAGCCGTGGTCCGCGCGGGGAAGCCGAGCCGAGCGGAGCCGCGAG<br>AAGTGCTAGCTCGGGCCGGGAGGAGCCGCAGCCGGAGGAGGGGGAGGA<br>GGAAGAAGAGAAGGAAGAGGAGAGGGGGCCGCAGTGGCGACTCGGCGC<br>TCGGAAGCCGGGCTCATGGACGGGTGAGGCGGCGGTGTGCGCAGACAGT<br>GCTCCAGCCGCGCGCGCTCCCCAGGCCCTGGCCCGGGCCTCGGGCCGGG<br>GAGGAAGAGTAGCTCGCCGAGGCGCCGAGGAGAGCGGGCCGCCCCACA<br>GCCCGAGCCGGAGAGGGAGCGCGAGCCGCGCCGGCCCCGGTCGGGCCT<br>CCGAAACCATGAACTTTCTGCTGTCTTGGGTGCATTGGAGCCTTGCCTTG<br>CTGCTCTACCTCCACCATGCCAAGTGGTCCCAGGCTGCACCCATGGCAGA<br>AGGAGGAGGGCAGAATCATCACGAAGTGGTGAAGTTCATGGATGTCTAT<br>CAGCGCAGCTACTGCCATCCAATCGAGACCCTGGTGGACATCTTCCAGG<br>AGTACCCTGATGAGATCGAGTACATCTTCAAGCCATCCTGTGTGCCCCTG<br>ATGCGATGCGGGGGCTGCTGCAATGACGAGGGCCTGGAGTGTGTGCCCA<br>CTGAGGAGTCCAACATCACCATGCAGATTATGCGGATCAAACCTCACCA<br>AGGCCAGCACATAGGAGAGATGAGCTTCCTACAGCACAACAAATGTGAA<br>TGCAGACCAAAGAAAGATAGAGCAAGACAAGAAAATCCCTGTGGGCCT<br>TGCTCAGAGCGGAGAAAGCATTTGTTTGTACAAGATCCGCAGACGTGTA<br>AATGTTCCTGCAAAAACACAGACTCGCGTTGCAAGATGTGACAAGCCGA<br>GGCGGTGAGCCGGGCAGGAGGAAGGAGCCTCCCTCAGGGTTTCGGGAA<br>CCAGATCTCTCACCAGGAAAGACTGATACAGAACGATCGATACAGAAAC<br>CACGCTGCCGCCACCACACCATCACCATCGACAGAACAGTCCTTAATCC<br>AGAAACCTGAAATGAAGGAAGAGGAGACTCTGCGCAGAGCACTTTGGG<br>TCCGGAGGGCGAGACTCCGGCGGAAGCATTCCCGGGCGGGTGACCCAGC<br>ACGGTCCCTCTTGGAATTGGATTCGCCATTTTATTTTTCTTGCTGCTAAAT<br>CACCGAGCCCGGAAGATTAGAGAGTTTTATTTCTGGGATTCCTGTAGACA<br>CACCCACCCACATACATACATTTATATATATATATATTATATATATATAA<br>AAATAAATATCTCTATTTTATATATATAAAATATATATATTCTTTTTTTAA<br>ATTAACAGTGCTAATGTTATTGGTGTCTTCACTGGATGTATTTGACTGCT<br>GTGGACTTGAGTTGGGAGGGGAATGTTCCCACTCAGATCCTGACAGGGA<br>AGAGGAGGAGATGAGAGACTCTGGCATGATCTTTTTTTTGTCCCACTTGG<br>TGGGGCCAGGGTCCTCTCCCCTGCCCAGGAATGTGCAAGGCCAGGGCAT<br>GGGGGCAAATATGACCCAGTTTTGGGAACACCGACAAACCCAGCCCTGG<br>CGCTGAGCCTCTCTACCCCAGGTCAGACGGACAGAAAGACAGATCACAG<br>GTACAGGGATGAGGACACCGGCTCTGACCAGGAGTTTGGGGAGCTTCAG<br>GACATTGCTGTGCTTTGGGGATTCCCTCCACATGCTGCACGCGCATCTCG<br>CCCCCAGGGGCACTGCCTGGAAGATTCAGGAGCCTGGGCGGCCTTCGCT<br>TACTCTCACCTGCTTCTGAGTTGCCCAGGAGACCACTGGCAGATGTCCCG<br>GCGAAGAGAAGAGACACATTGTTGGAAGAAGCAGCCCATGACAGCTCC<br>CCTTCCTGGGACTCGCCCTCATCCTCTTCCTGCTCCCCTTCCTGGGGTGCA<br>GCCTAAAAGGACCTATGTCCTCACACCATTGAAACCACTAGTTCTGTCCC<br>CCCAGGAGACCTGGTTGTGTGTGTGAGTGGTTGACCTTCCTCCATCCC<br>CTGGTCCTTCCCTTCCCTTCCCGAGGCACAGAGAGACAGGGCAGGATCC<br>ACGTGCCCATTGTGGAGGCAGAGAAAAGAGAAAGTGTTTTATATACGGT<br>ACTTATTTAATATCCCTTTTTAATTAGAAATTAAAACAGTTAATTTAATTA<br>AAGAGTAGGGTTTTTTTTCAGTATTCTTGGTTAATATTTAATTTCAACTAT<br>TTATGAGATGTATCTTTTGCTCTCTCTTGCTCTCTTATTTGTACCGGTTTTT<br>GTATATAAAATTCATGTTTCCAATCTCTCTCCCTGATCGGTGACAGTC<br>ACTAGCTTATCTTGAACAGATATTTAATTTTGCTAACACTCAGCTCTGCC | 5 |

TABLE 1-continued

Sequences used in present disclosure

| Name | Sequence | SEQ ID NO: |
|---|---|---|
| | CTCCCCGATCCCCTGGCTCCCCAGCACACATTCCTTTGAAATAAGGTTTC<br>AATATACATCTACATACTATATATATATTTGGCAACTTGTATTTGTGTGT<br>ATATATATATATATATGTTTATGTATATATGTGATTCTGATAAAATAGAC<br>ATTGCTATTCTGTTTTTTATATGTAAAAACAAAACAAGAAAAAATAGAG<br>AATTCTACATACTAAATCTCTCTCCTTTTTTAATTTTAATATTTGTTATCA<br>TTTATTTATTGGTGCTACTGTTTATCCGTAATAATTGTGGGGAAAAGATA<br>TTAACATCACGTCTTTGTCTCTAGTGCAGTTTTTCGAGATATTCCGTAGTA<br>CATATTTATTTTTAAACAACGACAAAGAAATACAGATATATCTTAAAAA<br>AAAAAAAGCATTTTGTATTAAAGAATTTAATTCTGATCTCAAA | |
| Mouse Insulin Growth Factor (IGF-1) Variant 4 NCBI Ref Seq: NM_001111275.2 | ACTCGATAACTTTGCCAGAAGAGGGAGAGAGAGAGAAGGCGAATGTTC<br>CCCCAGCTGTTTCCTGTCTACAGTGTCTGTGTTTTGTAGATAAATGTGAG<br>GATTTTCTCTAAATCCCTCTTCTGCTTGCTAAATCTCACTGTCACTGCTAA<br>ATTCAGAGCAGATAGAGCCTGCGCAATGGAATAAAGTCCTCAAAATTGA<br>AATGTGACATTGCTCTAACATCTCCCATCTCTCTGGATTTCTTTTTCGCCT<br>CATTATCCCTGCCCACCAATTCATTTCCAGACTTTGTACTTCAGAAGCGA<br>TGGGGAAAATCAGCAGCCTTCCAACTCAATTATTTAAGATCTGCCTCTGT<br>GACTTCTTGAAGATAAAGATACACATCATGTCGTCTTCACACCTCTTCTA<br>CCTGGCGCTCTGCTTGCTCACCTTCACCAGCTCCACCACAGCTGGACCAG<br>AGACCCTTTGCGGGGCTGAGCTGGTGGATGCTCTTCAGTTCGTGTGTGGA<br>CCGAGGGGCTTTTACTTCAACAAGCCCACAGGCTATGGCTCCAGCATTCG<br>GAGGGCACCTCAGACAGGCATTGTGGATGAGTGTTGCTTCCGGAGCTGT<br>GATCTGAGGAGACTGGAGATGTACTGTGCCCCACTGAAGCCTACAAAAG<br>CAGCCCGCTCTATCCGTGCCCAGCGCCACACTGACATGCCCAAGACTCA<br>GAAGGAAGTACATTTGAAGAACACAAGTAGAGGAAGTGCAGGAAACAA<br>GACCTACAGAATGTAGGAGGAGCCTCCCACGGAGCAGAAAATGCCACAT<br>CACCCGCAGGATCCTTTGCTGCTTGAGCAACCTGCAAAACATCGAAACAC<br>CTACCAAATAACAATAATAAGTCCAATAACATTACAAAGATGGGCATTT<br>CCCCCAATGAAATATACAAGTAAACATTCCAACATCGTCTTTAGGAGTGT<br>TTGTTTAAAAAGCTTTGCACCTTGCAAAAGTGGTCCTGGCGTGGGTAGAT<br>TGCTGTTGGTCCTTTATCAATAACATTCTATAGAGAAAAAAAATATATAT<br>ATAACTATATCTCCTAGTCCCTGCCTCTAAAGAGCCGAAAATGCATGGAT<br>GTTGTAGAGATCCAGTTGCTCTAAGTTTCTCTCTGAATTTTGGCTGCTGA<br>AGCCATTCATTTAGCAACTGTGTAGAGGTGGTTTATGAATGGTTCCCTTA<br>TCTTCACCTCTTCCCACGTAGCTCAAGCTGCTTGTTTTACAGAGTCTAATC<br>ATCTTGTCTAGCTGCATTAGACACACCCTTTCCTAACACTTGTATTTGTTG<br>AATTTGGCCTCCTTAAGAGCAATAGCAAATAAGTAGTCAAGTGGCCTAC<br>CAAGTTTTAACGTACCTGACTCCATCTGTGGCATTTGTACCAAATATAAG<br>TTGAATGCATTTATTTTAGACACAAAGCTTTATTTTTTTGACATTGTGTT<br>TCAAGAAAAAAAAATAGAATAACAATAACTACAACTTTGAGGCCAATCAT<br>TTTTAGGTGTGTGTTTGAAGCATAGAACGTCTCTTAAACTCTCAATGGTT<br>TCTTCAAATGATAAGTTAGTATGTAACCTAAGTATAGCAGTTTCTCTCTT<br>TTTTATTTTTTTCCATATAGAGCACTATGTAAAGTTAGTATATCAATAATA<br>CAGGAAATATCAAACAGTATGTAAAACTCTGTTGTTGTTGTTTTTTAGTA<br>CAATGGTGCTATTTTGTAGTTTGTTATATGAAAGAATCTAGTCAACACAG<br>TAAAAGGAGAAAGCAAAGCAAAACAACAAACGAAAGCCTGGAGCCTA<br>AGATGACAAAACGAGGAAGGGAACTGAAAAAAAAAATCCTTCCTCTTG<br>GGAGATGCAAAGGCCTCCCCAATTATGCCTTCCAAGAAGAACTTAAGAT<br>ATAGAGTCCATTAAGACGCACTTACTTGTCAAGTCCAGAGAGGAAGCTA<br>TGGAGTGGGAAAAGCAAGAGGCTAGGGATTTGGGAGTCCTGGTTTCTTT<br>TTAATCACTGAAGAAGTAAGTATTTGCAACCTGGGTCACACAAACTCAC<br>CACCCTGTGACCTCAGTCAAATCACTCCACCTCTCGGTGCCTCAGTTTTC<br>CTCATCTGCAAAATGGGGGCAATATGTCATCTACCTACCTCAAAGGGGT<br>GGTATGAAGATTAAAAAGTAGACCTTCAGATTTTTGTTCTGGGTTTCCAG<br>GAGGGTGCAACATCAGAACCCTTGAATTGCTAGGATGCAAGGAATTCTG<br>TAAATAACCCACTAACAATGTAGCTCCAAGGATCATTCATCTGTCACTGG<br>GATGCCACCACAATATCCAAGTTCTTATTGGTGAAGCTGTGCAACTAATT<br>AGTGACAAGCTAAGGACTCAGTCTCCCCAGCATGTCACACGGCAGGAGA<br>CATTTGATTTGCAGTTTTATTTAACTTCTGCATTTGAGCTTATGACTATAA<br>AGACTAGTGAAAAGAAGGGAGAGAGGAGAAAGAAGATCCTTGCCAAGT<br>AAAGGGTAATTAATTATTATTCCATTTATCCACTCTCATTAAAGGGTAAT<br>TAATTATTCCATGTATCCACTCTCATTAATCCTTCCAGTCACTTAGTATCT<br>AGAATAACTCTAACATTGTCAATGAGACTCTACTCAGTTTGCCAAACAC<br>AATTCTCCTTCCCCATAGCATATGAAAAAAAGGCGCTGACATTCTTAAAT<br>TTTGAAATAGTATCTATTACAATCACAGGTTGCTGTAGCAGATGTAGTCT<br>TGCCCTTGTTTGTACATGCATGTATTTTTTTTAATTTTATGAAAATGTG<br>CTAGCAAGAATTGCTACTTGAGGGGCAAAATTCTTCCTTCTCAAGCCTGA<br>GGTTCTCCCTAGTGTCTGCTTAGAAGGAAGGATCCAGCTTCCTGGAAATG<br>TGTTGGATGCATTCAACTGGGCATTGCTAACCAAAAACATTTAGAAAAA<br>TGTTCTCTATGTATATAGCAAGATTGTCTCCCTCTTTTAAAAACAAAATC<br>CAATATTCACATCTTATTACCTACAACCTTGATTCTCTATTGCAAGCTTCC<br>TTAATATTCTTATAAAATGTATTAAGAAAACAAAAAGGACACCTTTAG<br>CTCTCCTTCCGCCAGGTTGCCTCTAGAATCTCTGGGGAATGCAGAAGGT<br>GCTGTTGAGTAAAGCCCTCAGAAGGATTGGATTTAGGAACATCAGGCAC | 6 |

TABLE 1-continued

Sequences used in present disclosure

| Name | Sequence | SEQ ID NO: |
|---|---|---|
| | GCTGTACATCCCCTGATTACTGTAGAAATGTAAATGGAATAAGAGGTCA | |
| | GCTGACCATCCACCTGCTTCCCCAGAAGGATACAGGGAAAAGTTAGGCC | |
| | CTCACACACCCTGGGTGACACTTCTGACTTCTAGTTCTTGTTCACAGTGT | |
| | GTACTTTTTCAAATTGGTAATTCCCAGAAAAACACATAGGTGGCCTTCTC | |
| | CAGATCTGTGGGCTTCCTGCCATGGTTGGATTTGGTGATTCCAAGTGTCT | |
| | ATCACATATTTTGTTCACTTAATTCTATCCACAGTCAGAAATTCTTTCAAT | |
| | GAGGAAAGTTTAAATATGCAATCCTTTATCCAATACCTAATTCTCTCCAA | |
| | CTGCATCATAAATCAAGTAATAAAAATTAATTGTACTAATTAATCATAAT | |
| | AATGTACCATTGTACTTTTAAATGAATGAACACTGCAAGACAAATCTATG | |
| | TAAACTCTGAAAAGTAACTGATCATTATATGGTGAATCAAAATGACTCA | |
| | AGATTGATAGAAAGGGACATTTAAAATTTTACAACTCAAAATTTTGTAG | |
| | ACTTTGCTATGGAGGTAAATTGTTTTAGTGCCTAGAGATGGAGCGGTTTT | |
| | AATAAATTTACAAAAGAACTATAAAGATAGGTAGGAAGGAATTTTCATT | |
| | TGATAGGATTGTTGCTGATTTACTTACTCAATACCTAGGTCAAATGTTGA | |
| | TCCTATTCTCCAAAGACTATCAAGTGCTTGAACATTGTAAGATGAGTCTG | |
| | CTCCACTGAAATGTAATACATCTCTCCATTATAATCTATTTTCCTGGGG | |
| | TAAAAAAATCCTTTTTTTAAATATCCACCTACATATACCTACCCTACATG | |
| | TGCATTTGCACATGCGTGCATACGCTCATGCGCCCCACCCCACACACACC | |
| | TATTCACCCTAAGACTAAGAAGAAATCATTTCTTTGAAAGTCTTATCTTT | |
| | CAAAAAAGGCAGCGGTGCCCCTTGAGACTCCTTCTCCTTCTTTGAATGTC | |
| | AATGTGAAATGTGGCATGTCTGTGTACATGAAACCATCTCATACCCTATG | |
| | GCTCCAGGGTTTCTTTATGGTTTGTGCACTTGGGAGGATGCGCAGAAGAC | |
| | AGGATGCAGCCTGTTTTGCTTTCCCCTTTACTGTTTGGCCAGCTACGCCA | |
| | ATGTGGTGCTATTGTTTCTTTAAGAAAGTACTTGACTAAAAAAAAAGAA | |
| | AAAAAGAAAAAAAGAAAAGAAAAAGAAAAAGAAAAAAAAAGAAAGC | |
| | ATAGACCTATTTTTTTAAAGTCTGAAAACAACAGTTCTATAGTAGATGGC | |
| | TTACTGAGATAGCATTAGATCTAGCCACCACCCTAGCCACCACCTTTCAA | |
| | CTATGTGTCACTCACAAGTAGAATATTGTTCACCAAGTTGTGAGTTTGGG | |
| | GGTTCAGAGACAAAGGATGGAAAAGTTTTAAAGTTAGATGGCTCAATCA | |
| | TTTCATTGGCTCTCAAATTTAACAAAATTGGCAATACTTCACCCAATCTG | |
| | AAGTGTTGGTCAATAACTTGAACTGGGGGCAAAAATAACTTCAGGCAAA | |
| | TGGCAGAAGAAAATAATTAACTTACTTCTTGCTTTTTTTGTTGATTGTTTG | |
| | GTTTCCTGTTGATTTTTGGTTTTGGTTTTGCTGTGGGTGGGTGAGTACATG | |
| | TGTGTAAGTACGTGTGTGTGTGTGTGTGTGTGTGTGTGTGTGTTCC | |
| | ACTCAAAAACAAATACTCAGAAAGTGGAGAAAATACAACGATTTTAAGA | |
| | GCATAGACTTACCTACTACTAGAACCAGCTTCTGTCACATCCTCTGGAGA | |
| | AGGCACTGATTTCTTGTTTTGTAGAGGTTGCTCTTCCATCAGTGACCTGA | |
| | AAGAGTGACCAGTCTCCTAGAGTAGACATGGATCTCATTAGGAGAAGAC | |
| | AGAAGTATTTCCTTATGAATTGGGCTTATCTACTGACAAAGAAAGGGAA | |
| | GAGTTTATGAGAAGTTATTGAAGAAGATGGCTAACAGTCTGTGAAGATT | |
| | TTGTTCTGGTTTTTTTGTTGTTGTTGTTGGGTTTGGGTTTTGATTTTT | |
| | TTTTTTTTTTTTTTACTTTATACAATCTTTATGAATGGAAATCTTAATGCTC | |
| | AAAAAGACTTGGTCTTTTTTTCTCTTTCGTAACAGAATGGAAGATGACAA | |
| | ACTCACATAGACTCTTTCTAGGCTGGCTAGCAAAGGTGTGGTTTGACTTA | |
| | TTTGAATCAGACCATTTTAAATGTTCCTCTCTATTTTTAATCATAAAAGGC | |
| | TGTCATAATTTATTAGCGTAGGCCCTTTTTGGCACTTCTCAAATGAATGA | |
| | GCATTCCCATTCAAAGCATGGCTTTCCCCATGGTTCCAAAACATGAATGA | |
| | TTAATATTAAGGAATTATTTACTTCAAAATACAGTAGAAGTGTGAGTCTC | |
| | TGTTCCCATTCCCCACAAAGATCATTAAGTCCTGAATCGGGGCGGGGG | |
| | TGGGGCGCCTGGATACTAAGGGAATTTTTTTGTTGCTTGTTTTTTGTTTTC | |
| | AATGCTAGTGCTTAATCCTATAGTATACAGATTTGCTTCTTGCTATTGTG | |
| | ATATTCTGTAAGACTTTCCTGTTAGGTATTAGAAATTGATACATAAATAC | |
| | CTTTTTTGTGTGGTTTCTATTTAAAAGGAAAGAGATAAGACTGTCTGAAC | |
| | CTTAAATTCGTAAGGCACATGATAAAGAGATCACATTAAATAACAAGCC | |
| | ATATCTGGTTCAATCCTTTCTTTCTTATCATTTTAAGGAAAACTTGCCCAG | |
| | ATAAGACAGAGGCCCAGGGGACTTTTGAAACTCTCTTTGTTCCGCCAATT | |
| | CATTTTGGCTGGTGATGGTTTTTCCCCAGTGTCTGCCTCAGAATCTTTTAG | |
| | AGGCTGGCCAGACTAAAGACTGTCTTTTAAAACACATTTCACATGGTTCC | |
| | TCTTAATGAATGATTACACTTATGTAGAACATGATTTTTTTTTCTCTCCAC | |
| | TTATTTTTTTTTCCCCATCATTGATAAGGGTTCTTAAGGAGAAGAATTCA | |
| | TTAACAAAACTCAAGAAAGCGTACAAAAAAAAAATTCTAAATGTCACTG | |
| | CCCAATTGAAATACGAGCTAAAATGGAAATACTTTCTCCTACTTAAAACC | |
| | CAGACTGAATCACCTTCAAAATGACCTTTCACAATCTTTCCAATTTGCCT | |
| | TTGTTTAAACTGTCTGGGCCTAAAAGCAAGCATTATTCATTTTCTCTTGCC | |
| | CAAAGTGAACTTGTGTAAAGTAGGAAAATTAAAAGAAACTGCTAGAAAT | |
| | CCCTTCCAACCAGTGGCTGACCCCTCTCACTAGCTCACAGCAAAGTCTCC | |
| | TCTGTTGATCTATCACCTAGTCTCATTTCGTTTGAATATTTACATTGTACC | |
| | TACTGCTAAACACTTGGCAGGAGGCTCCATCCATATCTCCTATCGGTGTC | |
| | TCTGTATCCTTAAACCTTGCAAACATCATACAGTGTATATTAAGTTTACA | |
| | GGAAAGCTCCAAATAGCATATCAGACCTGGTCTCTCTTTGTTAAAGATTT | |
| | AAGGAGCTATGGGAATCTGGATTACAACGCACATTTTGCTTCATTTATTT | |
| | TTATCACACTTTAAAGGCCAAGGGTGATGATTAACTTACAGACACTGAA | |
| | TTGATTTCCCTACTGAAACCTGAAAGTAATATTTGGTCATTCATTGTATG | |
| | TGTTTTACACAAAAAAAAACATCTTCTATCAAATTACTCCTGATTGTATTT | |

TABLE 1-continued

Sequences used in present disclosure

| Name | Sequence | SEQ ID NO: |
|---|---|---|
| | GAAGTGGTTATTCAATTCATTTATGGCAGAGCAATATCTGTCCTAATGAC<br>TCTTATAAAATGTAACTAACTGAATCATTATCTTACATTTACTGTTTAGTA<br>AGCATATTTTGAAATTGTATGGCTAGAGTGTCATAATAAAATGGTATATC<br>TTTCTTTAGTAATTACATTAAAATTAATCATGTTTGATTAACTGGT | |
| Human Signal transducer and activator of transcription 5B (stat5b) (Variant 1) NCBI Ref Seq: NM_011489.3 | TTCCTGTAACATCGCAGCCAGTGAGCAGTGAACGAGTGTAGACAGAGCT<br>CTGCCTCTAGCCTGGCTGCCCAAGCCCAAGCCGTTAGAAGCAGGAGCCC<br>CTGCGCAGTGCCTGGTCACGGAGCTGAGCTGTGTTTAGATGTGTTGGCTG<br>CTGCGTGGTGAAGGAAGACCCGTCTCCAGAAAAGCAATTTAGGCAAAAG<br>GGATTCCGTTTGATGGCAGAGTCCCAGTGCTAGAAAGGTAGCGAAGGTG<br>GACAGCTTACAGTCTCAACTCATTTCGTCGTAAATGTCCTCGTAACGACA<br>TTGATTCTTCTACCTGGATAACCTTTTGTTTGTTTGTTTGTTTTGTT<br>TTGTTTTTCCCCTGTAACCATTTTTTTTCTGACAAGAAAACATTTTAATT<br>TTCTAAGCAAGAAGCATTTTTCAAATACCATGTCTGTGACCCAAAGTAAA<br>AATGGATGATAATTCATGTAAATGTGTGCAACATAGCAACCTGAACCTG<br>CACGCGATTCGGGCTCTGTAGGTTGTGAACCATGGCTATGTGGATACAG<br>GCTCAGCAGCTCCAGGGCGATGCCCTTCACCAGATGCAGGCCTTGTACG<br>GCCAGCATTTCCCCATCGAGGTGCGACATTATTTATCACAGTGGATCGAA<br>AGCCAAGCCTGGGACTCAATAGATCTTGATAATCCACAGGAGAACATTA<br>AGGCCACCCAGCTCCTGGAGGGCCTGGTGCAGGAGCTGCAGAAGAAGG<br>CGGAGCACCAGGTGGGGAAGATGGGTTTTTGCTGAAGATCAAGCTGGG<br>GCACTATGCCACACAGCTCCAGAGCACGTACGACCGCTGCCCCATGGAG<br>CTGGTTCGCTGTATCCGGCACATTCTGTACAACGAACAGAGGCTGGTTCG<br>CGAAGCCAACAACGGCAGCTCTCCAGCTGGAAGTCTTGCTGACGCCATG<br>TCCCAGAAGCACCTTCAGATCAACCAAACGTTTGAGGAGCTGCGCCTGA<br>TCACACAGGACACGGAGAACGAGCTGAAGAAGCTGCAGCAGACCCAAG<br>AGTACTTCATCATCCAGTACCAGGAGAGCCTGCGGATCCAAGCTCAGTTT<br>GCCCAGCTGGGACAGCTGAACCCCCAGGAGCGCATGAGCAGGGAGACG<br>GCCCTCCAGCAGAAGCAAGTGTCCCTGGAGACCTGGCTGCAGCGAGAGG<br>CACAGACACTGCAGCAGTACCGAGTGGAGCTGGCTGAGAAGCACCAGA<br>AGACCCTGCAGCTGCTGCGGAAGCAGCAGACCATCATCCTGGACGACGA<br>GCTGATCCAGTGGAAGCGGAGACAGCAGCTGGCCGGGAACGGGGGTCC<br>CCCCGAGGGCAGCCTGGACGTGCTGCAGTCCTGGTGTGAGAAGCTGGCC<br>GAGATCATCTGGCAGAACCGGCAGCAGATCCGCAGGGCTGAGCACTTGT<br>GCCAGCAGCTGCCCATCCCAGGCCCCGTGGAGGAGATGCTGGCTGAGGT<br>CAACGCCACCATCACGGACATCATCTCAGCCCTGGTCACCAGCACGTTC<br>ATCATCGAGAAGCAGCCTCCTCAGGTCCTGAAGACCCAGACCAAGTTTG<br>CAGCCACCGTGCGCCTGCTGGTGGGGGGGAAGCTGAATGTGCACATGAA<br>CCCCCCGCAGGTGAAGGCGACCATCATCAGCGAGCAGCAGGCCAAGTCC<br>CTGCTCAAGAATGAGAACACCCGCAATGATTACAGCGGCGAGATCCTGA<br>ACAACTGTTGCGTCATGGAGTACCACCAGGCCACTGGCACACTCAGCGC<br>CCACTTCAGAAACATGTCCCTGAAACGAATCAAGAGGTCTGACCGCCGT<br>GGGGCAGAGTCAGTAACGGAAGAGAAGTTCACGATCCTGTTTGACTCAC<br>AGTTCAGCGTCGGTGGAAACGAGCTGGTCTTTCAAGTCAAGACCTTGTC<br>GCTCCCGGTGGTGGTGATTGTTCACGGCAGCCAGGACAACAATGCCACA<br>GCCACTGTCCTCTGGGACAACGCCTTTGCAGAGCCTGGCAGGGTGCCATT<br>TGCCGTGCCTGACAAGGTGCTGTGGCCGCAGCTGTGTGAAGCGCTCAAC<br>ATGAAATTCAAGGCTGAAGTACAGAGCAACCGGGGCTTGACCAAGGAG<br>AACCTCGTGTTCCTGGCACAGAAACTGTTCAACATCAGCAGCAACCACC<br>TCGAGGACTACAACAGCATGTCCGTGTCCTGGTCCCAGTTCAACCGGGA<br>GAATTTGCCAGGACGGAATTACACTTTCTGGCAGTGGTTTGATGGCGTGA<br>TGGAAGTATTGAAAAAACATCTCAAGCCTCACTGGAATGATGGGGCTAT<br>CCTGGGTTTCGTGAACAAGCAACAGGCCCACGACCTGCTCATCAACAAG<br>CCAGACGGGACCTTCCTGCTGCGCTTCAGCGACTCGGAAATCGGGGGCA<br>TCACCATTGCTTGGAAGTTTGACTCTCAGGAGAGAATGTTTTGGAATCTG<br>ATGCCTTTTACCACTAGAGACTTCTCTATCCGGTCCCTCGCTGACCGCCT<br>GGGGGACCTGAATTACCTCATATATGTGTTTCCTGATCGGCCAAAGGATG<br>AAGTATATTCTAAGTACTACACACCGGTCCCCTGTGAGCCCGCAACTGCG<br>AAAGCAGCTGACGGATACGTGAAGCCACAGATCAAGCAGGTGGTCCCCG<br>AGTTTGCAAATGCATCCACAGATGCTGGGAGTGGCGCCACCTACATGGA<br>TCAGGCTCCTTCCCCAGTCGTGTGCCCTCAGGCTCACTACAACATGTACC<br>CACCCAACCCGGACTCCGTCCTTGATACCGATGGGGACTTCGATCTGGA<br>AGACACGATGGACGTGGCGCGGCGCGTGGAAGAGCTCTTAGGCCGGCCC<br>ATGGACAGTCAGTGGATCCCTCACGCACAGTCATGACCAGACCTCACCA<br>CCTGCAGCTTCATCGCCTCGTGGAGGAACTTCCTGTGGATGTTTTAATT<br>CCATGAATCGCTTCTCTTTGGAAACAATACTCGTAATGTGAAGTGTTAAT<br>ACTAGTTGTGACTTTAGTGTCTCTGTGCATAGTGGCACTAGTGAAGGGAG<br>TGCGCGTGAGTGTGAGTGCATTTGCACGTCGTGTTTTTTCCCCGCCCCT<br>GCTGTCCAGTCTAAGCCGCCACGCCAGGGCAGCGGCTGCGCTTTTTTTA<br>CCATGTGCAAAAAGGCAGTTGGTTCCCTGAACCCTGGAACCTGGCCATG<br>TGTCTTCAGGGTGGCTGACCCTTGACACGTGACTATCAAGTAAGAAAA<br>GGACAGAGGAAAAAGCACCCTCTCTCTGGGGAGCCTCGGTTCCTCTGCC<br>AGGTAGTCCATAGTCCAAGCAAGCATTGTCATTGTCTCCGCCTGTCTTCT<br>GAGATGTAGATGACTGTCTGATGATGAAAGCCAGTACCTCCCGTGTCCC | 7 |

TABLE 1-continued

Sequences used in present disclosure

| Name | Sequence | SEQ ID NO: |
|---|---|---|
| | CTGTCCCCTTTGCATAAGGGACGGAAAGGGGAGCTGAATCAAGGGTGAT<br>GGGGCAAGGGTGGTCACAGGTTTTTGGATGGGGAGTGGCTGTTTCCCGT<br>TTCTGCCACTTCCGCCATCTTAACACTGGCTCCTTCCCTCTCTGCTTGCTC<br>AGTCTCTATTTCTAGAACTGCCACTCAGCTTAAGTGCAAGTGTGTGTACT<br>CAAGTGGAGATGTTTAACAAATAGTGGAGAGGAAGCCAGGCCACCCA<br>GCTCTGAGCGTACAGGTTCAGGTGATGCCCTGTGTTCCTTCTGTCAGGGC<br>GGTGCGTTGTGCCCAAGTCCTGGCTCCAGACACTGGGCGTAGCCTGTCTG<br>CGCCAGCCTCCCCAACTCTTGTCTGTGCTGTGGCCAGGCCGCGCCTGCGC<br>TATCCAAGGCTTTTCTCCAAGCGTGTTGATAATGGCTTCCTGCAAACGTC<br>CGGTGGTGTTTTTGTTTCTAAATCAGGTCTTTTTTTATGTTTTTCCCATTT<br>GCACCCTAATTTGACATCAAATTTCCCCCCTCCTGTATCAGGTCCTGGGT<br>CCTCTGTACCCAGATCACTTCATCTCCCTTCAGTGTCACATAGTGCCCTG<br>AGGATTAGGTGGTAGGAATGGGACCTGCACACGGGGCCAGCCTGCCAAG<br>CAGGCAGCCAGCACTGTACAGTGCTGGGTGCCGGGTGGCCGTTGGGGAT<br>TGGGGAAATGCAGTCAGTCAGCGGGTTTCCTAGGAAGCTTGGAAAACTA<br>AAAGCAAAGTGAAAGCCTCAGGGTGATTTGTTCCACAGTCTCCTCTGTA<br>GTGTCTCCAGAAGGAAGGAAGGGGCTGCAGTGGGCCGTCAGGGAGAGG<br>GGCAAGCAGAGAGCGGTTACCACTCAGGCTTGCTGAGAGCCCTCCTTGG<br>CTTCCTCTCCCAAACAAGGGCAGAACCGTGCCCAGGAGAGGAGCCCCCA<br>AAACCTTATTTTTATACATGCAAGTAAATAAACATATTTTTTTTACAAAA<br>ATAACTTCTGAATTTATCAGTGTTTTACTGTTAAAAGAAAATACTCCTGT<br>GTAGTAAATTATTTATTGGGAGATGAGTTTTTAAAAGCTGCTGTTTGCCT<br>TGCCTTGGTTTTGTACACTGATTTTTCTATGCCTGGCGGTAGCCTCTCTGC<br>CTCAGGTGCTGGCCGGATGGAGGAGGTGTGAGGCCCCTCCCTGGCCCCT<br>CAGAAGAAAGCTGGAACTGCCAGGGGAGTCCAGGCTTAAGGGACTCGTC<br>CCCACCTGTCATGCGACTGTCCCAGTAACCCTCACGAGGGTGTGGACTCG<br>ACAAATATCTAGATATATGGTGGACATGGCCCCAAGTCATGGGGAGAGT<br>AGAGCAGCCTGGGCCCCCCCACCCCCAAGGTTCTAAGCTGACTTTCAAG<br>TTAGGTTGGAGAAAAGGGTGCCAAAGAAGCGAGACTTCCACATAGTTTT<br>TAAGCTACCCTGGATTTACTGAGGGTGTACCTGGACATGGGAGAGGTTTT<br>TAACTGGAAAGTGTGTCCCCTATCTGCATGCTGGTCTCTCTCTCTCTCTGC<br>CCAACTCTTGCACCCAAAAATGAGGTGAGGGCAGGTCTCCACCCACCTC<br>TTGCCTGCTCACAGACCCACTCGTGAGTCGGGAAAGCCTCAGCTTTGGG<br>GTGTGGGCTTTGTAGAAGTGGAAGGAGATTTGAAGTGGCTATCTCCTA<br>CAACGGAAAATATCCTTTTATAATTTTTCTTTTTAACGTTTTATTTCAGAT<br>ACATATTTTAGTGTCGAGGCAGATTAGTATATAGCCACCAAAAAGTAT<br>TGTGTATAAATTGAGGCAGCCACAAAATTGTGTATTTTATGTTACAATAA<br>AGGCGTCTCCTTGAAGGACAA | |
| Modified Human GH | ATGGCCACCGGCTCCCGCACCTCCCTGCTGCTGGCCTTCGGCCTGCTGTG<br>CCTGCCCTGGCTGCAGGAGGGCTCCGCCTTCCCCACCATCCCCCTGTCCC<br>GCCTGTTCGACAACGCCATGCTGCGCGCCCACCGCCTGCACCAGCTGGC<br>CTTCGACACCTACCAGGAGTTCGAGGAGGCCTACATCCCCAAGGAGCAG<br>AAGTACTCCTTCCTGCAGAACCCCCAGACCTCCCTGTGCTTCTCCGAGTC<br>CATCCCCACCCCCTCCAACCGCGAGGAGACCCAGCAGAAGTCCAACCTG<br>GAGCTGCTGCGCATCTCCCTGCTGCTGATCCAGTCCTGGCTGGAGCCCGT<br>GCAGTTCCTGCGCTCCGTGTTCGCCAACTCCCTGGTGTACGGCGCCTCCG<br>ACTCCAACGTGTACGACCTGCTGAAGGACCTGGAGGAGGGCATCCAGAC<br>CCTGATGGGCCGCCTGGAGGACGGCTCCCCCCGCACCGGCCAGATCTTC<br>AAGCAGACCTACTCCAAGTTCGACACCAACTCCCACAACGACGACGCCC<br>TGCTGAAGAACTACGGCCTGCTGTACTGCTTCCGCAAGGACATGGACAA<br>GGTGGAGACCTTCCTGCGCATCGTGCAGTGCCGCTCCGTGGAGGGCTCCT<br>GCGGCTTCtaa | 8 |
| Modified Human EGF | ATGCTGCTGACCCTGATCATCCTGCTGCCCGTGGTGTCCAAGTTCTCCTT<br>CGTGTCCCTGTCCGCCCCCCAGCACTGGTCCTGCCCCGAGGGCACCCTG<br>GCCGGCAACGGCAACTCCACCTGCGTGGGCCCCGCCCCCTTCCTGATCT<br>TCTCCCACGGCAACTCCATCTTCCGCATCGACACCGAGGGCACCAACTA<br>CGAGCAGCTGGTGGTGGACGCCGGCGTGTCCGTGATCATGGACTTCCAC<br>TACAACGAGAAGCGCATCTACTGGGTGGACCTGGAGCGCCAGCTGCTG<br>CAGCGCGTGTTCCTGAACGGCTCCCGCCAGGAGCGCGTGTGCAACATCG<br>AGAAGAACGTGTCCGGCATGGCCATCAACTGGATCAACGAGGAGGTGA<br>TCTGGTCCAACCAGCAGGAGGGCATCATCACCGTGACCGACATGAAGG<br>GCAACAACTCCCACATCCTGCTGTCCGCCCTGAAGTACCCCGCCAACGT<br>GGCCGTGGACCCCGTGGAGCGgTTCATCTTCTGGTCCTCCGAGGTGGCC<br>GGCTCCCTGTACCGCGCCGACCTGGACGGCGTGGGCGTGAAGGCCCTGC<br>TGGAGACCTCCGAGAAGATCACCGCCGTGTCCCTGGACGTGCTGGACA<br>AGCGCCTGTTCTGGATCCAGTACAACCGCGAGGGCTCCAACTCCCTGAT<br>CTGCTCCTGCGACTACGACGGCGGCTCCGTGCACATCTCCAAGCACCCC<br>ACCCAGCACAACCTGTTCGCCATGTCCCTGTTCGGCGACCGCATCTTCT<br>ACTCCACCTGGAAGATGAAGACCATCTGGATCGCCAACAAGCACACCG<br>GCAAGGACATGGTGCGCATCAACCTGCACTCCTCCTTCGTGCCCCTGGG<br>CGAGCTGAAGGTGGTGCACCCCCTGGCCCAGCCCAAGGCCGAGGACGA<br>CACCTGGGAGCCCGAGCAGAAGCTGTGCAAGCTGCGCAAGGGCAACTG | 9 |

TABLE 1-continued

Sequences used in present disclosure

| Name | Sequence | SEQ ID NO: |
|---|---|---|
| | CTCCTCCACCGTGTGCGGCCAGGACCTGCAGTCCCACCTGTGCATGTGC<br>GCCGAGGGCTACGCCCTGTCCCGCGACCGCAAGTACTGCGAGGACGTG<br>AACGAGTGCGCCTTCTGGAACCACGGCTGCACCCTGGGCTGCAAGAAC<br>ACCCCCGGCTCCTACTACTGCACCTGCCCCGTGGGCTTCGTGCTGCTGCC<br>CGACGGCAAGCGgTGCCACCAGCTGGTGTCCTGCCCCCGCAACGTGTCC<br>GAGTGCTCCCACGACTGCGTGCTGACCTCCGAGGGCCCCCTGTGCTTCT<br>GCCCCGAGGGCTCCGTGCTGGAGCGCGACGGCAAGACCTGCTCCGGCT<br>GCTCCTCCCCCGACAACGGCGGCTGCTCCCAGCTGTGCGTGCCCCTGTC<br>CCCCGTGTCCTGGGAGTGCGACTGCTTCCCCGGCTACGACCTGCAGCTG<br>GACGAGAAGTCCTGCGCCGCCTCCGGCCCCCAGCCCTTCCTGCTGTTCG<br>CCAACTCCCAGGACATCCGCCACATGCACTTCGACGGCACCGACTACGG<br>CACCCTGCTGTCCCAGCAGATGGGCATGGTGTACGCCCTGGACCACGAC<br>CCCGTGGAGAACAAGATCTACTTCGCCCACACCGCCCTGAAGTGGATCG<br>AGCGCGCCAACATGGACGGCTCCCAGCGCGAGCGCCTGATCGAGGAGG<br>GCGTGGACGTGCCCGAGGGCCTGGCCGTGGACTGGATCGGCCGCCGCTT<br>CTACTGGACCGACCGCGGCAAGTCCCTGATCGGCCGCTCCGACCTGAAC<br>GGCAAGCGgTCCAAGATCATCACCAAGGAGAACATCTCCCAGCCCCGCG<br>GCATCGCCGTGCACCCCATGGCCAAGCGCCTGTTCTGGACCGACACCGG<br>CATCAACCCCGCATCGAGTCCTCCTCCCTGCAGGGCCTGGGCCGCCTG<br>GTGATCGCCTCCTCCGACCTGATCTGGCCCTCCGGCATCACCATCGACTT<br>CCTGACCGACAAGCTGTACTGGTGCGACGCCAAGCAGTCCGTGATCGA<br>GATGGCCAACCTGGACGGCTCCAAGCGCCGCCGCCTGACCCAGAACGA<br>CGTGGGCCACCCCTTCGCCGTGGCCGTGTTCGAGGACTACGTGTGGTTC<br>TCCGACTGGGCCATGCCCTCCGTGATCCGCGTGAACAAGCGCACCGGCA<br>AGGACCGCGTGCGCCTGCAGGGCTCCATGCTGAAGCCCTCCTCCCTGGT<br>GGTGGTGCACCCCCTGGCCAAGCCCGGCGCCGACCCCTGCCTGTACCAG<br>AACGGCGGCTGCGAGCACATCTGCAAGAAGCGCCTGGGCACCGCCTGG<br>TGCTCCTGCCGCGAGGGCTTCATGAAGGCCTCCGACGGCAAGACCTGCC<br>TGGCCCTGGACGGCCACCAGCTGCTGGCCGGCGGCGAGGTGGACCTGA<br>AGAACCAGGTGACCCCCCTGGACATCCTGTCCAAGACCCGCGTGTCCGA<br>GGACAACATCACCGAGTCCCAGCACATGCTGGTGGCCGAGATCATGGT<br>GTCCGACCAGGACGACTGCGCCCCCGTGGGCTGCTCCATGTACGCCCGC<br>TGCATCTCCGAGGGCGAGGACGCCACCTGCCAGTGCCTGAAGGGCTTCG<br>CCGGCGACGGCAAGCTGTGCTCCGACATCGACGAGTGCGAGATGGGCG<br>TGCCCGTGTGCCCCCCCGCCTCCTCCAAGTGCATCAACACCGAGGGCGG<br>CTACGTGTGCCGCTGCTCCGAGGGCTACCAGGGCGACGGCATCCACTGC<br>CTGGACATCGACGAGTGCCAGCTGGGCGTGCACTCCTGCGGCGAGAAC<br>GCCTCCTGCACCAACACCGAGGGCGGCTACACCTGCATGTGCGCCGGCC<br>GCCTGTCCGAGCCCGGCCTGATCTGCCCCGACTCCACCCCCCCCCCCCCA<br>CCTGCGCGAGGACGACCACCACTACTCCGTGCGCAACTCCGACTCCGAG<br>TGCCCCCCTGTCCCACGACGGCTACTGCCTGCACGACGGCGTGTGCATGT<br>ACATCGAGGCCCTGGACAAGTACGCCTGCAACTGCGTGGTGGGCTACAT<br>CGGCGAGCGgTGCCAGTACCGCGACCTGAAGTGGTGGGAGCTGCGCCA<br>CGCCGGCCACGGCCAGCAGCAGAAGGTGATCGTGGTGGCCGTGTGCGT<br>GGTGGTGCTGGTGATGCTGCTGCTGCTGTCCCTGTGGGGCGCCCACTAC<br>TACCGCACCCAGAAGCTGCTGTCCAAGAACCCCAAGAACCCCTACGAG<br>GAGTCCTCCCGCGACGTGCGCTCCCGCCGCCCCGCCGACACCGAGGACG<br>GCATGTCCTCCTGCCCCCAGCCCTGGTTCGTGGTGATCAAGGAGCACCA<br>GGACCTGAAGAACGGCGGCCAGCCCGTGGCCGGCGAGGACGGCCAGGC<br>CGCCGACGGCTCCATGCAGCCCACCTCCTGGCGCCAGGAGCCCCAGCTG<br>TGCGGCATGGGCACCGAGCAGGGCTGCTGGATCCCCGTGCCTCCGACA<br>AGGGCTCCTGCCCCCAGGTGATGGAGCGgTCCTTCCACATGCCCTCCTA<br>CGGCACCCAGACCCTGGAGGGCGGCGTGGAGAAGCCCCACTCCCTGCT<br>GTCCGCCAACCCCCTGTGGCAGCAGCGCGCCCTGGACCCCCCCCACCGA<br>TGGAGCTGACCCAGtaa | |
| Modified Human HGF | ATGTGGGTGACCAAGCTGCTGCCCGCCCTGCTGCTGCAGCACGTGC<br>TGCTGCACCTGCTGCTGCTGCCCATCGCCATCCCCTACGCCGAGGGC<br>CAGCGCAAGCGCCGCAACACCATCCACGAGTTCAAGAAGTCCGCCA<br>AGACCACCCTGATCAAGATCGACCCCGCCCTGAAGATCAAGACCAA<br>GAAGGTGAACACCGCCGACCAGTGCGCCAACCGCTGCACCCGCAAC<br>AAGGGCCTGCCCTTCACCTGCAAGGCCTTCGTGTTCGACAAGGCCC<br>GCAAGCAGTGCCTGTGGTTCCCCTTCAACTCCATGTCCTCCGGCGTG<br>AAGAAGGAGTTCGGCCACGAGTTCGACCTGTACGAGAACAAGGACT<br>ACATCCGCAACTGCATCATCGGCAAGGGCCGCTCCTACAAGGGCAC<br>CGTGTCCATCACCAAGTCCGGCATCAAGTGCCAGCCCTGGTCCTCCA<br>TGATCCCCCACGAGCACTCCTTCCTGCCCTCCTCCTACCGCGGCAAG<br>GACCTGCAGGAGAACTACTGCCGCAACCCCCGCGGCGAGGAGGGC<br>GGCCCCTGGTGCTTCACCTCCAACCCCGAGGTGCGCTACGAGGTGT<br>GCGACATCCCCCAGTGCTCCGAGGTGGAGTGCATGACCTGCAACGG<br>CGAGTCCTACCGCGGCCTGATGGACCACACCGAGTCCGGCAAGATC<br>TGCCAGCGgTGGGACCACCAGACCCCCCACCGCCACAAGTTCCTGC<br>CCGAGCGgTACCCCGACAAGGGCTTCGACGACAACTACTGCCGCAA<br>CCCCGACGGCCAGCCCCGCCCCTGGTGCTACACCCTGGACCCCCAC | 10 |

TABLE 1-continued

Sequences used in present disclosure

| Name | Sequence | SEQ ID NO: |
|---|---|---|
| | ACCCGCTGGGAGTACTGCGCCATCAAGACCTGCGCCGACAACACCA<br>TGAACGACACCGACGTGCCCCTGGAGACCACCGAGTGCATCCAGGG<br>CCAGGGCGAGGGCTACCGCGGCACCGTGAACACCATCTGGAACGGC<br>ATCCCCTGCCAGCGgTGGGACTCCCAGTACCCCCACGAGCACGACA<br>TGACCCCCGAGAACTTCAAGTGCAAGGACCTGCGCGAGAACTACTG<br>CCGCAACCCCGACGGCTCCGAGTCCCCCTGGTGCTTCACCACCGAC<br>CCCAACATCCGCGTGGGCTACTGCTCCCAGATCCCCAACTGCGACA<br>TGTCCCACGGCCAGGACTGCTACCGCGGCAACGGCAAGAACTACAT<br>GGGCAACCTGTCCCAGACCCGCTCCGGCCTGACCTGCTCCATGTGG<br>GACAAGAACATGGAGGACCTGCACCGCCACATCTTCTGGGAGCCCG<br>ACGCCTCCAAGCTGAACGAGAACTACTGCCGCAACCCCGACGACGA<br>CGCCCACGGCCCCTGGTGCTACACCGGCAACCCCCTGATCCCCTGG<br>GACTACTGCCCCATCTCCCGCTGCGAGGGCGACACCACCCCCACCA<br>TCGTGAACCTGGACCACCCCGTGATCTCCTGCGCCAAGACCAAGCA<br>GCTGCGCGTGGTGAACGGCATCCCCACCCGCACCAACATCGGCTGG<br>ATGGTGTCCCTGCGCTACCGCAACAAGCACATCTGCGGCGGCTCCC<br>TGATCAAGGAGTCCTGGGTGCTGACCGCCCGCCAGTGCTTCCCCTCC<br>CGCGACCTGAAGGACTACGAGGCCTGGCTGGGCATCCACGACGTGC<br>ACGGCCGCGGCGACGAGAAGTGCAAGCAGGTGCTGAACGTGTCCCA<br>GCTGGTGTACGGCCCCGAGGGCTCCGACCTGGTGCTGATGAAGCTG<br>GCCCGCCCCGCCGTGCTGGACGACTTCGTGTCCACCATCGACCTGCC<br>CAACTACGGCTGCACCATCCCCGAGAAGACCTCCTGCTCCGTGTAC<br>GGCTGGGGCTACACCGGCCTGATCAACTACGACGGCCTGCTGCGCG<br>TGGCCCACCTGTACATCATGGGCAACGAGAAGTGCTCCCAGCACCA<br>CCGCGGCAAGGTGACCCTGAACGAGTCCGAGATCTGCGCCGGCGCC<br>GAGAAGATCGGCTCCGGCCCCTGCGAGGGCGACTACGGCGGCCCCC<br>TGGTGTGCGAGCAGCACAAGATGCGCATGGTGCTGGGCGTGATCGT<br>GCCCGGCCGCGGCTGCGCCATCCCCAACCGCCCCGGCATCTTCGTG<br>CGCGTGGCCTACTACGCCAAGTGGATCCACAAGATCATCCTGACCT<br>ACAAGGTGCCCCAGTCCtaa | |
| Modified Mouse p21 | ATGTCCAACCCCGGCGACGTGCGCCCCGTGCCCCACCGCTCCAAGGTGT<br>GCCGCTGCCTGTTCGGCCCCGTGGACTCCGAGCAGCTGCGCCGCGACTG<br>CGACGCCCTGATGGCCGGCTGCCTGCAGGAGGCCCGCGAGCGgTGGAAC<br>TTCGACTTCGTGACCGAGACCCCCCTGGAGGGCAACTTCGTGTGGGAGC<br>GCGTGCGCTCCCTGGGCCTGCCCAAGGTGTACCTGTCCCCCGGCTCCGC<br>TCCCGCGACGACCTGGGCGGCGACAAGCGCCCCTCCACCTCCTCCGCCCT<br>GCTGCAGGGCCCCGCCCCCGAGGACCACGTGGGCCCTGTCCCTGTCCTGC<br>ACCCTGGTGTCCGAGCGCCCCGAGGACTCCCCCGGCGGCCCCGGCACCTC<br>CCAGGGCCGCAAGCGCCGCCAGACCTCCCTGACCGACTTCTACCACTCCAA<br>GCGCCGCCTGGTGTTCTGCAAGCGCAAGCCCtaa | 11 |
| Modified Human VEGF165 | ATGAACTTCCTGCTGTCCTGGGTGCACTGGTCCCTGGCCCTGCTGCTGTACC<br>TGCACCACGCCAAGTGGTCCCAGGCCGCCCCCATGGCCGAGGGCGGCCGGC<br>CAGAACCACCACGAGGTGGTGAAGTTCATGGACGTGTACCAGCGGgTCCTAC<br>TGCCACCCCATCGAGACCCTGGTGGACATCTTCCAGGAGTACCCCGACGAG<br>ATCGAGTACATCTTCAAGCCCTCCTGCGTGCCCCTGATGCGCTGCGGCGGC<br>TGCTGCAACGACGAGGGCCTGGAGTGCGTGCCCACCGAGGAGTCCAACAT<br>CACCATGCAGATCATGCGCATCAAGCCCCACCAGGGCCAGCACATCGGCG<br>AGATGTCCTTCCTGCAGCACAACAAGTGCGAGTGCCGCCCCAAGAAGGAC<br>CGCGCCCGCCAGGAGAACCCCTGCGGCCCCTGCTCCGAGCGCCGCAAGCA<br>CCTGTTCGTGCAGGACCCCCAGACCTGCAAGTGCTCCTGCAAGAACACCGA<br>CTCCCGCTGCAAGGCCCGCCAGCTGGAGCTGAACGAGCGCACCTGCCGCTG<br>CGACAAGCCCCGCCGCtaa | 12 |
| Modified Mouse IGF-1 | ATGGGCAAGATCTCCTCCCTGCCCACCCAGCTGTTCAAGATCTGCCT<br>GTGCGACTTCCTGAAGATCAAGATCCACATCATGTCCTCCTCCCACC<br>TGTTCTACCTGGCCCTGTGCCTGCTGACCTTCACCTCCTCCACCACCG<br>CCCGGCCCCGAGACCCTGTGCGGCGCCGAGCTGGTGGACGCCCTGCA<br>GTTCGTGTGCGGCCCCCGCGGCTTCTACTTCAACAAGCCCACCGGCT<br>ACGGCTCCTCCATCCGCCGCGCCCCCCAGACCGGCATCGTGGACGA<br>GTGCTGCTTCCGCTCCTGCGACCTGCGCCGCCTGGAGATGTACTGCG<br>CCCCCCTGAAGCCCACCAAGGCCGCCCGCTCCATCCGCGCCCAGCGC<br>CACACCGACATGCCCAAGACCCAGAAGGAGGTGCACCTGAAGAACA<br>CCTCCCGCGGCTCCGCCGGCAACAAGACCTACCGCATGtaa | 13 |
| Modified Mouse IGF-1 IL-2 SP | ATGCGCATGCAGCTGCTGCTGCTGATCGCCCTGTCCCTGGCCCTGGTGAC<br>CAACTCCGGCCCCGAGACCCTGTGCGGCGCCGAGCTGGTGGACGCCCTG<br>CAGTTCGTGTGCGGCCCCCGCGGCTTCTACTTCAACAAGCCCACCGGCTA<br>CGGCTCCTCCATCCGCCGCGCCCCCCAGACCGGCATCGTGGACGAGTGC<br>TGCTTCCGCTCCTGCGACCTGCGCCGCCTGGAGATGTACTGCGCCCCCCT<br>GAAGCCCACCAAGGCCGCCCGCTCCATCCGCGCCCAGCGCCACACCGAC<br>ATGCCCAAGACCCAGAAGGAGGTGCACCTGAAGAACACCTCCCGCGGCT<br>CCGCCGGCAACAAGACCTACCGCATGtaa | 14 |

TABLE 1-continued

Sequences used in present disclosure

| Name | Sequence | SEQ ID NO: |
|---|---|---|
| Modified Human Secreted EGF | ATGGCCACCGGCTCCCGCACCTCCCTGCTGCTGGCCTTCGGCCTGCTGTG CCTGCCCTGGCTGCAGGAGGGCTCCGCCATGAACTCCGACTCCGAGTGC CCCCTGTCCCACGACGGCTACTGCCTGCACGACGGCGTGTGCATGTACAT CGAGGCCCTGGACAAGTACGCCTGCAACTGCGTGGTGGGCTACATCGGC GAGCGgTGCCAGTACCGCGACCTGAAGTGGTGGGAGCTGCGCtaa | 15 |
| Modified Mouse constitutively activated stat5b (stat5bCA) | ATGGACTACAAGGACGACGACGACAAGGGCGGCGGCGGCTCCGCCATG TGGATCCAGGCCCAGCAGCTGCAGGGCGACGCCCTGCACCAGATGCAGG CCCTGTACGGCCAGCACTTCCCCATCGAGGTGCGCCACTACCTGTCCCAG TGGATCGAGTCCCAGGCCTGGGACTCCATCGACCTGGACAACCCCCAGG AGAACATCAAGGCCACCCAGCTGCTGGAGGGCCTGGTGCAGGAGCTGCA GAAGAAGGCCGAGCACCAGGTGGGCGAGGACGGCTTCCTGCTGAAGAT CAAGCTGGGCCACTACGCCACCCAGCTGCAGTCCACCTACGACCGCTGC CCCATGGAGCTGGTGCGCTGCATCCGCCACATCCTGTACAACGAGCAGC GCCTGGTGCGCGAGGCCAACAACGGCTCCTCCCCCGCCGGCTCCCTGGC CGACGCCATGTCCCAGAAGCACCTGCAGATCAACCAGACCTTCGAGGAG CTGCGCCTGATCACCCAGGACACCGAGAACGAGCTGAAGAAGCTGCAGC AGACCCAGGAGTACTTCATCATCCAGTACCAGGAGTCCCTGCGCATCCA GGCCCAGTTCGCCCAGCTGGGCCAGCTGAACCCCCAGGAGCGCATGTCC CGCGAGACCGCCCTGCAGCAGAAGCAGGTGTCCCTGGAGACCTGGCTGC AGCGCGAGGCCCAGACCCTGCAGCAGTACCGCGTGGAGCTGGCCGAGA AGCACCAGAAGACCCTGCAGCTGCTGCGCAAGCAGCAGACCATCATCCT GGACGACGAGCTGATCCAGTGGAAGCGCCGCCAGCAGCTGGCCGGCAA CGGCGGCCCCCCGAGGGCTCCCTGGACGTGCTGCAGTCCTGGTGCGAG AAGCTGGCCGAGATCATCTGGCAGAACCGCCAGCAGATCCGCCGCGCCG AGCACCTGTGCCAGCAGCTGCCCATCCCCGGCCCCGTGGAGGAGATGCT GGCCGAGGTGAACGCCACCATCACCGACATCATCTCCGCCCTGGTGACC TCCACCTTCATCATCGAGAAGCAGCCCCCCAGGTGCTGAAGACCCAGA CCAAGTTCGCCGCCACCGTGCGCCTGCTGGTGGGCGGCAAGCTGAACGT GCACATGAACCCCCCCAGGTGAAGGCCACCATCATCTCCGAGCAGCAG GCCAAGTCCCTGCTGAAGAACGAGAACACCCGCAACGACTACTCCGGCG AGATCCTGAACAACTGCTGCGTGATGGAGTACCACCAGGCCACCGGCAC CCTGTCCGCCCACTTCCGCAACATGTCCCTGAAGCGCATCAAGCGgTCCG ACCGCCGCGGCGCCGAGTCCGTGACCGAGGAGAAGTTCACCATCCTGTT CGACTCCCAGTTCTCCGTGGGCGGCAACGAGCTGGTGTTCCAGGTGAAG ACCCTGTCCCTGCCCGTGGTGGTGATCGTGCACGGCTCCCAGGACAACA ACGCCACCGCCACCGTGCTGTGGGACAACGCCTTCGCCGAGCCCGGCCG CGTGCCCTTCGCCGTGCCCGACAAGGTGCTGTGGCCCCAGCTGTGCGAG GCCCTGAACATGAAGTTCAAGGCCGAGGTGCAGTCCAACCGCGGCCTGA CCAAGGAGAACCTGGTGTTCCTGGCCCAGAAGCTGTTCAACATCTCCTCC AACCACCTGGAGGACTACAACTCCATGTCCGTGTCCTGGTCCCAGTTCAA CCGCGAGAACCTGCCCGGCCGCAACTACACCTTCTGGCAGTGGTTCGAC GGCGTGATGGAGGTGCTGAAGAAGCACCTGAAGCCCCACTGGAACGAC GGCGCCATCCTGGGCTTCGTGAACAAGCAGCAGGCCCACGACCTGCTGA TCAACAAGCCCGACGGCACCTTCCTGCTGCGCTTCTCCGACTCCGAGATC GGCGGCATCACCATCGCCTGGAAGTTCGACTCCCAGGAGCGCATGTTCT GGCACCTGATGCCCTTCACCCACCCGCGACTTCTCCATCCGCTCCCTGGCC GACCGCCTGGGCGACCTGAACTACCTGATCTACGTGTTCCCCGACCGCCC CAAGGACGAGGTGTACTCCAAGTACTACACCCCCGTGCCCTGCGAGCCC GCCACCGCCAAGGCCGCCGACGGCTACGTGAAGCCCCAGATCAAGCAGG TGGTGCCCGAGTTCGCCAACGCCTCCACCGACGCCGGCTCCGGCGCCAC CTACATGGACCAGGCCCCCTCCCCCGTGGTGTGCCCCCAGGCCCACTACA ACATGTACCCCCCCAACCCCGACTCCGTGCTGGACACCGACGGCGACTT CGACCTGGAGGACACCATGGACGTGGCCCGCCGCGTGGAGGAGCTGCTG GGCCGCCCCATGGACTCCCAGTGGATCCCCCACGCCCAGTCC | 16 |
| Human Beta Catenin (CTNNB1) (variant 3) NCBI Ref Seq: NM_001098210.2 | AAGCCTCTCGGTCTGTGGCAGCAGCGTTGGCCCGGCCCCGGGAGCGGAG AGCGAGGGGAGGCGGAGACGGAGGAAGGTCTGAGGAGCAGCTTCAGTC CCCGCCGAGCCGCCACCGCAGGTCGAGGACGGTCGGACTCCCGCGGCGG GAGGAGCCTGTTCCCCTGAGGGTATTTGAAGTATACCATACAACTGTTTT GAAATCCAGCGTGGACAATGGCTACTCAAGCTGATTTGATGGAGTTGG ACATGGCCATGGAACCAGACAGAAAAGCGGCTGTTAGTCACTGGCAGCA ACAGTCTTACCTGGACTCTGGAATCCATTCTGGTGCCACTACCACAGCTC CTTCTCTGAGTGGTAAAGGCAATCCTGAGGAAGAGGATGTGGATACCTC CCAAGTCCTGTATGAGTGGGAACAGGGATTTTCTCAGTCCTTCACTCAAG AACAAGTAGCTGATATTGATGGACAGTATGCAATGACTCGAGCTCAGAG GGTACGAGCTGCTATGTTCCCTGAGACATTAGATGAGGGCATGCAGATC CCATCTACACAGTTTGATGCTGCTCATCCCACTAATGTCCAGCGTTTGGC TGAACCATCACAGATGCTGAAACATGCAGTTGTAAACTTGATTAACTATC AAGATGATGCAGAACTTGCCACACGTGCAATCCCTGAACTGACAAACT GCTAAATGACGAGGACCAGGTGGTGGTTAATAAGGCTGCAGTTATGGTC CATCAGCTTTCTAAAAGGAAGCTTCCAGACACGCTATCATGCGTTCTCC TCAGATGGTGTCTGCTATTGTACGTACCATGCAGAATACAAATGATGTAG | 17 |

TABLE 1-continued

Sequences used in present disclosure

| Name | Sequence | SEQ ID NO: |
|---|---|---|
| | AAACAGCTCGTTGTACCGCTGGGACCTTGCATAACCTTTCCCATCATCGT GAGGGCTTACTGGCCATCTTTAAGTCTGGAGGCATTCCTGCCCTGGTGAA AATGCTTGGTTCACCAGTGGATTCTGTGTTGTTTTATGCCATTACAACTCT CCACAACCTTTTATTACATCAAGAAGGAGCTAAAATGGCAGTGCGTTTA GCTGGTGGGCTGCAGAAAATGGTTGCCTTGCTCAACAAAACAAATGTTA AATTCTTGGCTATTACGACAGACTGCCTTCAAATTTTAGCTTATGGCAAC CAAGAAAGCAAGCTCATCATACTGGCTAGTGGTGGACCCCAAGCTTTAG TAAATATAATGAGGACCTATACTTACGAAAAACTACTGTGGACCACAAG CAGAGTGCTGAAGGTGCTATCTGTCTGCTCTAGTAATAAGCCGGCTATTG TAGAAGCTGGTGGAATGCAAGCTTTAGGACTTCACCTGACAGATCCAAG TCAACGTCTTGTTCAGAACTGTCTTTGGACTCTCAGGAATCTTTCAGATG CTGCAACTAAACAGGAAGGGATGGAAGGTCTCCTTGGGACTCTTGTTCA GCTTCTGGGTTCAGATGATATAAATGTGGTCACCTGTGCAGCTGGAATTC TTTCTAACCTCACTTGCAATAATTATAAGAACAAGATGATGGTCTGCCAA GTGGGTGGTATAGAGGCTCTTGTGCGTACTGTCCTTCGGGCTGGTGACAG GGAAGACATCACTGAGCCTGCCATCTGTGCTCTTCGTCATCTGACCAGCC GACACCAAGAAGCAGAGATGGCCCAGAATGCAGTTCGCCTTCACTATGG ACTACCAGTTGTGGTTAAGCTCTTACACCCACCATCCCACTGGCCTCTGA TAAAGGCTACTGTTGGATTGATTCGAAATCTTGCCCTTTGTCCCGCAAAT CATGCACCTTTGCGTGAGCAGGGTGCCATTCCACGACTAGTTCAGTTGCT TGTTCGTGCACATCAGGATACCCAGCGCCGTACGTCCATGGGTGGGACA CAGCAGCAATTTGTGGAGGGGGTCCGCATGAAGAAATAGTTGAAGGTT GTACCGGAGCCCTTCACATCCTAGCTCGGGATGTTCACAACCGAATTGTT ATCAGAGGACTAAATACCATTCCATTGTTTGTGCAGCTGCTTTATTCTCC CATTGAAAACATCCAAAGAGTAGCTGCAGGGGTCCTCTGTGAACTTGCT CAGGACAAGGAAGCTGCAGAAGCTATTGAAGCTGAGGGAGCCACAGCT CCTCTGACAGAGTTACTTCACTCTAGGAATGAAGGTGTGGCGACATATG CAGCTGCTGTTTTGTTCCGAATGTCTGAGGACAAGCCACAAGATTACAA GAAACGGCTTTCAGTTGAGCTGACCAGCTCTCTCTTCAGAACAGAGCCA ATGGCTTGGAATGAGACTGCTGATCTTGGACTTGATATTGGTGCCCAGGG AGAACCCCTTGGATATCGCCAGGATGATCCTAGCTATCGTTCTTTTCACT CTGGTGGATATGGCCAGGATGCCTTGGGTATGGACCCCATGATGGAACA TGAGATGGGTGGCCACCACCCTGGTGCTGACTATCCAGTTGATGGGCTG CCAGATCTGGGGCATGCCCAGGACCTCATGGATGGGCTGCCTCCAGGTG ACAGCAATCAGCTGGCCTGGTTTGATACTGACCTGTAAATCATCCTTTAG GAGTAACAATACAAATGGATTTTGGGAGTGACTCAAGAAGTGAAGAATG CACAAGAATGGATCACAAGATGGAATTTATCAAACCCTAGCCTTGCTTG TTAAATTTTTTTTTTTTTTTTAAGAATATCTGTAATGGTACTGACTTTG CTTGCTTTGAAGTAGCTCTTTTTTTTTTTTTTTTTTTTGCAGTAACT GTTTTTTAAGTCTCTCGTAGTGTTAAGTTATAGTGAATACTGCTACAGCA ATTTCTAATTTTTAAGAATTGAGTAATGGTGTAGAACACTAATTCATAAT CACTCTAATTAATTGTAATCTGAATAAAGTGTAACAATTGTGTAGCCTTT TTGTATAAAATAGACAAATAGAAAATGGTCCAATTAGTTTCCTTTTTAAT ATGCTTAAAATAAGCAGGTGGATCTATTTCATGTTTTTGATCAAAAACTA TTTGGGATATGTATGGGTAGGGTAAATCAGTAAGAGGTGTTATTTGGAA CCTTGTTTTGGACAGTTTACCAGTTGCCTTTTATCCCAAAGTTGTTGTAAC CTGCTGTGATACGATGCTTCAAGAGAAAATGCGGTTATAAAAAATGGTT CAGAATTAAACTTTTAATTCATTC | |
| Modified Mouse IGF-1 IL-2 SP Inserted Opening Sequence | ATGCGCATGCAGCTGCTGCTGCTGATCGCCCTGTCCCTGGCCCTGGTGAC CAACTCC | 18 |
| Modified Human EGF Secreted Inserted Opening Sequence | ATGGCCACCGGCTCCCGCACCTCCCTGCTGCTGGCCTTCGGCCTGCTGTG CCTGCCCTGGCTGCAGGAGGGCTCCGCCATGAACTCC | 19 |
| Modified Mouse stat5bCA Inserted Opening Sequence | ATGGACTACAAGGACGACGACGACAAGGGCGGCGGCGGCTCC | 20 |
| Modified Human β catenin (activated) | GCCACCCAGGCCGACCTGATGGAGCTGGACATGGCCATGGAGCCCGACC GCAAGGCCGCCGTGTCCCACTGGCAGCAGCAGTCCTACCTGGACTCCGG CATCCACTCCGGCGCCACCACCACCGCCCCCTACCTGTCCGGCAAGGGC AACCCCGAGGAGGAGGACGTGGACACCTCCCAGGTGCTGTACGAGTGGG | 21 |

TABLE 1-continued

Sequences used in present disclosure

| Name | Sequence | SEQ ID NO: |
|---|---|---|
| | AGCAGGGCTTCTCCCAGTCCTTCACCCAGGAGCAGGTGGCCGACATCGA<br>CGGCCAGTACGCCATGACCCGCGCCCAGCGCGTGCGCGCCGCCATGTTC<br>CCCGAGACCCTGGACGAGGGCATGCAGATCCCCTCCACCCAGTTCGACG<br>CCGCCCACCCCACCAACGTGCAGCGCCTGGCCGAGCCCTCCCAGATGCT<br>GAAGCACGCCGTGGTGAACCTGATCAACTACCAGGACGACGCCGAGCTG<br>GCCACCCGCGCCATCCCCGAGCTGACCAAGCTGCTGAACGACGAGGACC<br>AGGTGGTGGTGAACAAGGCCGCCGTGATGGTGCACCAGCTGTCCAAGAA<br>GGAGGCCTCCCGCCACGCCATCATGCGCTCCCCCCAGATGGTGTCCGCC<br>ATCGTGCGCACCATGCAGAACACCAACGACGTGGAGACCGCCCGCTGCA<br>CCGCCGGCACCCTGCACAACCTGTCCCACCACCGCGAGGGCCTGCTGGC<br>CATCTTCAAGTCCGGCGGCATCCCCGCCCTGGTGAAGATGCTGGGCTCC<br>CCGTGGACTCCGTGCTGTTCTACGCCATCACCACCCTGCACAACCTGCTG<br>CTGCACCAGGAGGGCGCCAAGATGGCCGTGCGCCTGGCCGGCGGCCTGC<br>AGAAGATGGTGGCCCTGCTGAACAAGACCAACGTGAAGTTCCTGGCCAT<br>CACCACCGACTGCCTGCAGATCCTGGCCTACGGCAACCAGGAGTCCAAG<br>CTGATCATCCTGGCCTCCGGCGGCCCCCAGGGCCTGGTGAACATCATGCG<br>CACCTACACCTACGAGAAGCTGCTGTGGACCACCTCCCGCGTGCTGAAG<br>GTGCTGTCCGTGTGCTCCTCCAACAAGCCCGCCATCGTGGAGGCCGGCG<br>GCATGCAGGCCCTGGGCCTGCACCTGACCGACCCCTCCCAGCGCCTGGT<br>GCAGAACTGCCTGTGGACCCTGCGCAACCTGTCCGACGCCGCCACCAAG<br>CAGGAGGGCATGGAGGGCCTGCTGGGCACCCTGGTGCAGCTGCTGGGCT<br>CCGACGACATCAACGTGGTGACCTGCGCCGCCGGCATCCTGTCCAACCT<br>GACCTGCAACAACTACAAGAACAAGATGATGGTGTGCCAGGTGGGCGGC<br>ATCGAGGCCCTGGTGCGCACCGTGCTGCGCGCCGGCGACCGCGAGGACA<br>TCACCGAGCCCGCCATCTGCGCCCTGCGCCACCTGACCTCCCGCCACCAG<br>GAGGCCGAGATGGCCCAGAACGCCGTGCGCCTGCACTACGGCCTGCCCG<br>TGGTGGTGAAGCTGCTGCACCCCCCCTCCCACTGGCCCCTGATCAAGGCC<br>ACCGTGGGCCTGATCCGCAACCTGGCCCTGTGCCCCGCCAACCACGCCC<br>CCTGCGCGAGCAGGGCGCCATCCCCCGCCTGGTGCAGCTGCTGGTGCG<br>CGCCCACCAGGACACCCAGCGCCGCACCTCCATGGGCGGCACCCAGCAG<br>CAGTTCGTGGAGGGCGTGCGCATGGAGGAGATCGTGGAGGGCTGCACCG<br>GCGCCCTGCACATCCTGGCCCGCGACGTGCACAACCGCATCGTGATCCG<br>CGGCCTGAACACCATCCCCCTGTTCGTGCAGCTGCTGTACTCCCCCATCG<br>AGAACATCCAGCGCGTGGCCGCCGGCGTGCTGTGCGAGCTGGCCCAGGA<br>CAAGGAGGCCGCCGAGGCCATCGAGGCCGAGGGCGCCACCGCCCCCCTG<br>ACCGAGCTGCTGCACTCCCGCAACGAGGGCGTGGCCACCTACGCCGCCG<br>CCGTGCTGTTCCGCATGTCCGAGGACAAGCCCAGGACTACAAGAAGCG<br>CCTGTCCGTGGAGCTGACCTCCTCCCTGTTCCGCACCGAGCCCATGGCCT<br>GGAACGAGACCGCCGACCTGGGCCTGGACATCGGCGCCCAGGGCGAGC<br>CCCTGGGCTACCGCCAGGACGACCCCTCCTACCGCTCCTTCCACTCCGGC<br>GGCTACGGCCAGGACGCCCTGGGCATGGACCCCATGATGGAGCACGAGA<br>TGGGCGGCCACCACCCCGGCGCCGACTACCCCGTGGACGGCCTGCCCGA<br>CCTGGGCCACGCCCAGGACCTGATGGACGGCCTGCCCCCCGGCGACTCC<br>AACCAGCTGGCCTGGTTCGACACCGACCTG | |
| Human yes-<br>associated<br>protein 1<br>(YAP-1)<br>(variant 3)<br>NCBI Ref<br>Seq:<br>NM_001195044.2 | CTCAGTCGGGCGCAGCCGCCGCCAGGGAAAAGAAAGGGAGGAAGGAAG<br>GAACAAGAAAAGGAAATAAAGAGAAAGGGGAGGCGGGAAAGGCAAC<br>GAGCTGTCCGGCCTCCGTCAAGGGAGTTGGAGGGAAAAAGTTCTCAGGC<br>GCCGCAGGTCCGAGTGCCTCGCAGCCCCTCCCGAGGCGCAGCCGCCAGA<br>CCAGTGGAGCCGGGGCGCAGGGCGGGGCGGAGGCGCCGGGGCGGGGG<br>ATGCGGGGCCGCGGCGCAGCCCCCGGCCCTGAGAGCGAGGACAGCGC<br>CGCCCGGCCCGCAGCCGTCGCCGCTTCTCCACCTCGGCCCGTGGAGCCG<br>GGGCGTCCGGGCGTAGCCCTCGCTCGCCTGGGTCAGGGGGTGCGCGTCG<br>GGGGAGGCAGAAGCCATGGATCCCGGGCAGCAGCCGCCGCCTCAACCG<br>GCCCCCCAGGGCCAAGGGCAGCCGCCTTCGCAGCCCCGCAGGGGCAGG<br>GCCGCCGTCCGGACCCGGGCAACCGGCACCCGCGGCGACCCAGGCGGC<br>GCCGCAGGCACCCCCGCCGGGCATCAGATCGTGCACGTCCGCGGGGAC<br>TCGGAGACCGACCTGGAGGCGCTCTTCAACGCCGTCATGAACCCCAAGA<br>CGGCCAACGTGCCCCAGACCGTGCCCATGAGGCTCCGGAAGCTGCCCGA<br>CTCCTTCTTCAAGCCGCCGGAGCCCAAATCCCACTCCCGACAGGCCAGTA<br>CTGATGCAGGCACTGCAGGAGCCCTGACTCCACAGCATGTTCGAGCTCA<br>TTCCTCTCCAGCTTCTCTGCAGTTGGGAGCTGTTTCTCCTGGGACACTGA<br>CCCCCACTGGAGTAGTCTCTGGCCCAGCAGCTACACCCACAGCTCAGCA<br>TCTTCGACAGTCTTCTTTTGAGATACCTGATGATGTACCTCTGCCAGCAG<br>GTTGGGAGATGGCAAAGACATCTTGGTCAGAGATACTTCTTAAATCA<br>CATCGATCAGACAACAACATGGCAGGACCCCAGGAAGGCCATGCTGTCC<br>CAGATGAACGTCACAGCCCCACCAGTCCACCAGTGCAGCAGAATATGA<br>TGAACTCGGCTTCAGGTCCTCTTCCTGATGGATGGGAACAAGCCATGACT<br>CAGGATGGAGAAATTTACTATATAAACCATAAGAACAAGACCACCTCTT<br>GGCTAGACCCAAGGCTTGACCCTCGTTTTGCCATGAACCAGAGAATCAG<br>TCAGAGTGCTCCAGTGAAACAGCCACCACCCCTGGCTCCCCAGAGCCCA<br>CAGGGAGGCGTCATGGGTGGCAGCAACTCCAACCAGCAGCAACAGATG<br>CGACTGCAGCAACTGCAGATGGAGAAGGAGAGGCTGCGGCTGAAACAG<br>CAAGAACTGCTTCGGCAGGAGTTAGCCCTGCGTAGCCAGTTACCAACAC | 22 |

TABLE 1-continued

Sequences used in present disclosure

| Name | Sequence | SEQ ID NO: |
|---|---|---|
| | TGGAGCAGGATGGTGGGACTCAAAATCCAGTGTCTTCTCCCGGGATGTC | |
| | TCAGGAATTGAGAACAATGACGACCAATAGCTCAGATCCTTTCCTTAAC | |
| | AGTGGCACCTATCACTCTCGAGATGAGAGTACAGACAGTGGACTAAGCA | |
| | TGAGCAGCTACAGTGTCCCTCGAACCCCAGATGACTTCCTGAACAGTGT | |
| | GGATGAGATGGATACAGGTGATACTATCAACCAAAGCACCCTGCCCTCA | |
| | CAGCAGAACCGTTTCCCAGACTACCTTGAAGCCATTCCTGGGACAAATG | |
| | TGGACCTTGGAACACTGGAAGGAGATGGAATGAACATAGAAGGAGAGG | |
| | AGCTGATGCCAAGTCTGCAGGAAGCTTTGAGTTCTGACATCCTTAATGAC | |
| | ATGGAGTCTGTTTTGGCTGCCACCAAGCTAGATAAAGAAAGCTTTCTTAC | |
| | ATGGTTATAGAGCCCTCAGGCAGACTGAATTCTAAATCTGTGAAGGATC | |
| | TAAGGAGACACATGCACCGGAAATTTCCATAAGCCAGTTGCAGTTTTCA | |
| | GGCTAATACAGAAAAAGATGAACAAACGTCCAGCAAGATACTTTAATCC | |
| | TCTATTTTGCTCTTCCTTGTCCATTGCTGCTGTTAATGTATTGCTGACCTC | |
| | TTTCACAGTTGGCTCTAAAGAATCAAAAGAAAAAAACTTTTTATTTCTTT | |
| | TGCTATTAAAACTACTGTTCATTTTGGGGGCTGGGGGAAGTGAGCCTGTT | |
| | TGGATGATGGATGCCATTCCTTTTGCCCAGTTAAATGTTCACCAATCATT | |
| | TTAACTAAATACTCAGACTTAGAAGTCAGATGCTTCATGTCACAGCATTT | |
| | AGTTTGTTCAACAGTTGTTTCTTCAGCTTCCTTTGTCCAGTGGAAAAACA | |
| | TGATTTACTGGTCTGACAAGCCAAAAATGTTATATCTGATATTAAATACT | |
| | TAATGCTGATTTGAAGAGATAGCTGAAACCAAGGCTGAAGACTGTTTTA | |
| | CTTTCAGTATTTCTTTTCCTCCTAGTGCTATCATTAGTCACATAATGACC | |
| | TTGATTTTATTTTAGGAGCTTATAAGGCATGAGACAATTTCCATATAAAT | |
| | ATATTAATTATTGCCACATACTCTAATATAGATTTTGGTGGATAATTTTGT | |
| | GGGTGTGCATTTTGTTCTGTTTTGTTGGGTTTTTTGTTTTTTTGTTTTTGG | |
| | CAGGGTCGGTGGGGGGTTGGTTGGTTGGTTGGTTTTGTCGGAACCTAG | |
| | GCAAATGACCATATTAGTGAATCTGTTAATAGTTGTAGCTTGGGATGGTT | |
| | ATTGTAGTTGTTTTGGTAAAATCTTCATTTCCTGGTTTTTTTTACCACCTT | |
| | ATTTAAATCTCGATTATCTGCTCTCTCTTTTATATACATACACACACCCAA | |
| | ACATAACATTTATAATAGTGTGGTAGTGGAATGTATCCTTTTTTAGGTTT | |
| | CCCTGCTTTCCAGTTAATTTTTAAAATGGTAGCGCTTTGTATGCATTTAGA | |
| | ATACATGACTAGTAGTTTATATTTCACTGGTAGTTTAAATCTGGTTGGGG | |
| | CAGTCTGCAGATGTTTGAAGTAGTTTAGTGTTCTAGAAAGAGCTATTACT | |
| | GTGGATAGTGCCTAGGGGAGTGCTCCACGCCCTCTGGGCATACGGTAGA | |
| | TATTATCTGATGAATTGGAAAGGAGCAAACCAGAAATGGCTTTATTTCT | |
| | CCCCTTGGACTAATTTTTAAGTCTCGATTGGAATTCAGTGAGTAGGTTCAT | |
| | AATGTGCATGACAGAAATAAGCTTTATAGTGGTTTACCTTCATTTAGCTT | |
| | TGGAAGTTTTCTTTGCCTTAGTTTTGGAAGTAAATTCTAGTTTGTAGTTCT | |
| | CATTTGTAATGAACACATTAACGACTAGATTAAAATATTGCCTTCAAGAT | |
| | TGTTCTTACTTACAAGACTTGCTCCTACTTCTATGCTGAAAATTGACCCTG | |
| | GATAGAATACTATAAGGTTTTGAGTTAGCTGGAAAAGTGATCAGATTAA | |
| | TAAATGTATATTGGTAGTTGAATTTAGCAAAGAAATAGAGATAATCATG | |
| | ATTATACCTTTATTTTTACAGGAAGAGATGATGTAACTAGAGTATGTGTC | |
| | TACAGGAGTAATAATGGTTTCCAAAGAGTATTTTTTAAAGGAACAAAAC | |
| | GAGCATGAATTAACTCTTCAATATAAGCTATGAAGTAATAGTTGGTTGTG | |
| | AATTAAAGTGGCACCAGCTAGCACCTCTGTGTTTTAAGGGTCTTTCAATG | |
| | TTTCTAGAATAAGCCCTTATTTTCAAGGGTTCATAACAGGCATAAAATCT | |
| | CTTCTCCTGGCAAAAGCTGCTATGAAAAGCCTCAGCTTGGGAAGATAGA | |
| | TTTTTTTCCCCCCAATTACAAAATCTAAGTATTTTGGCCCTTCAATTTGGA | |
| | GGAGGGCAAAAGTTGGAAGTAAGAAGTTTTATTTTAAGTACTTTCAGTG | |
| | CTCAAAAAAATGCAATCACTGTGTTGTATATAATAGTTCATAGGTTGATC | |
| | ACTCATAATAATTGACTCTAAGGCTTTTATTAAGAAAACAGCAGAAAGA | |
| | TTAAATCTTGAATTAAGTCTGGGGGGAAATGGCCACTGCAGATGGAGTT | |
| | TTAGAGTAGTAATGAAATTCTACCTAGAATGCAAAATTGGGTATATGAA | |
| | TTACATAGCATGTTGTTGGGATTTTTTTAATGTGCAGAAGATCAAAGCT | |
| | ACTTGGAAGGAGTGCCTATAATTTGCCAGTAGCCACAGATTAAGATTAT | |
| | ATCTTATATATCAGCAGATTAGCTTTAGCTTAGGGGGAGGGTGGGAAAG | |
| | TTTGGGGGGGGGTTGTGAAGATTTAGGGGGACCTTGATAGAGAACTTT | |
| | ATAAACTTCTTTCTCTTTAATAAAGACTTGTCTTACACCGTGCTGCCATTA | |
| | AAGGCAGCTGTTCTAGAGTTTCAGTCACCTAAGTACACCCACAAAACAA | |
| | TATGAATATGGAGATCTTCCTTTACCCCTCAACTTTAATTTGCCCAGTTAT | |
| | ACCTCAGTGTTGTAGCAGTACTGTGATACCTGGCACAGTGCTTTGATCTT | |
| | ACGATGCCCTCTGTACTGACCTGAAGGAGACCTAAGAGTCCTTTCCCTTT | |
| | TTGAGTTTGAATCATAGCCTTGATGTGGTCTCTTGTTTTATGTCCTTGTTC | |
| | CTAATGTAAAAGTGCTTAACTGCTTCTTGGTTGTATTGGGTAGCATTGGG | |
| | ATAAGATTTTAACTGGGTATTCTTGAATTGCTTTTACAATAAACCAATTT | |
| | TATAATCTTTAAATTTATCAACTTTTTACATTTGTGTTATTTTCAGTCAGG | |
| | GCTTCTTAGATCTACTTATGGTTGATGGAGCACATTGATTTGGAGTTTCA | |
| | GATCTTCCAAAGCACTATTTGTTGTAATAACTTTTCTAAATGTAGTGCCTT | |
| | TAAAGGAAAAATGAACACAGGGAAGTGACTTTGCTACAAATAATGTTGC | |
| | TGTGTTAAGTATTCATATTAAATACATGCCTTCTATATGGAACATGGCAG | |
| | AAAGACTGAAAAATAACAGTAATTAATTGTGTAATTCAGAATTCATACC | |
| | AATCAGTGTTGAAACTCAAACATTGCAAAAGTGGGTGGCAATATTCAGT | |
| | GCTTAACACTTTTCTAGCGTTGGTACATCTGAGAAATGAGTGCTCAGGTG | |
| | GATTTTATCCTCGCAAGCATGTTGTTATAAGAATTGTGGGTGTGCCTATC | |

TABLE 1-continued

Sequences used in present disclosure

| Name | Sequence | SEQ ID NO: |
|---|---|---|
| | ATAACAATTGTTTTCTGTATCTTGAAAAAGTATTCTCCACATTTTAAATGT<br>TTTATATTAGAGAATTCTTTAATGCACACTTGTCAAATATATATATATAG<br>TACCAATGTTACCTTTTTATTTTTTGTTTTAGATGTAAGAGCATGCTCATA<br>TGTTAGGTACTTACATAAATTGTTACATTATTTTTTCTTATGTAATACCTT<br>TTTGTTTGTTTATGTGGTTCAAATATATTCTTTCCTTAAACTCTTC | |
| Human wingless-type MMTV integration site family, member 2 (WNT2) NCBI Ref Seq: NM_023653.5 | AGTCTCACCACTAGCCGCAGACGCGAGCGGCGGGGGGGCGGGGCGCA<br>GAGGCGCCGGCAGCCGTGACGAGGCGCTCCCGGAGCTGAGCGCTTCTGC<br>TCCGGGCACGCATGGCGCCCGCACACGGAGTCTGACCTGATGTAGACGC<br>AAGGGGGTTAATATGAACGTCCCTCTCGGTGGAATCTGGCTCTGGCTCCC<br>TCTGCTCTTGACCTGGCTCACCCCTGAGGTCAGCTCTTCATGGTGGTACA<br>TGAGAGCTACAGGTGGCTCCTCCAGGGTGATGTGTGACAATGTGCCAGG<br>CCTGGTGAGCCGGCAGCGTCAGCTGTGCCACCGACACCCAGATGTGATG<br>CGTGCCATTGGCCTGGGTGTGGCTGAGTGGACTGCAGAGTGCCAACACC<br>AGTTCCGCCAGCATCGCTGGAACTGCAACACCCTGGACAGAGATCACAG<br>CCTCTTTGGCCGGGTCCTCCTCCGAAGTAGTCGGGAATCGGCCTTTGTTT<br>ACGCCATCTCTTCAGCTGGCGTTGTATTTGCCATCACCAGGGCCTGTAGC<br>CAAGGAGAATTAAAGTCCTGCTCCTGTGATCCAAAGAAGAAAGGAAGTG<br>CCAAGGACAGCAAAGGCACCTTCGACTGGGGTGGCTGCAGTGACAATAT<br>TGACTACGGGATCAAGTTTGCCCGTGCCTTTGTAGATGCCAAGGAGAGG<br>AAAGGCAAGGATGCCAGAGCCCTGATGAACCTTCACAACAACAGAGCTG<br>GAAGGAAGGCTGTAAAGCGCTTCTTGAAACAAGAATGCAAGTGTCATGG<br>TGTGAGTGGCTCCTGTACTCTGAGGACATGCTGGCTGGCCATGGCTGACT<br>TCAGGAAAACAGGCGACTATCTCTGGAGGAAGTACAATGGGGCCATCCA<br>GGTAGTCATGAACCAGGATGGCACTGGCTTCACTGTAGCCAATAAGAGG<br>TTTAAGAAGCAACGAAAAATGACCTCGTGTATTTTGAGAATTCTCCAG<br>ACTACTGTATCAGGGACCGAGAGGCAGGCTCCCTGGGTACAGCGGGCCG<br>TGTGTGCAACTTGACTTCCCGAGGCATGGACAGCTGCGAAGTTATGTGTT<br>GTGGGAGAGGCTATGACACATCCCACGTCACCCGGATGACCAAGTGTGA<br>GTGTAAATTCCACTGGTGCTGTGCCGTGCGCTGTCAGGACTGCCTGGAGG<br>CCCTGGACGTGCACACATGCAAGGCCCCCAAGAGTGCCGACTGGGCGAC<br>GCCTACATGACCTCAGCAGAGGTCATATTCGCCTTTTCTTCCCTCAAGGA<br>CTCCAATTACATCTTCAAGGACACTGGACCTCTGGGTTGTTTTCAGGGGC<br>TCTTTCTTAAGGCATGAAGCCTTCATCTCAAGAGAAACCCCCTTTCCCCT<br>CTCTGGGGGCCCCAGGACTGGGAACCACCTGCTGCACATAAGTACACCC<br>TATTCTGTCTATCTTGGGCATTCTGATGTCACCTCTCTTCCTGCTGATTTC<br>TTTTTGGAAATGGCATGACAGGCTGTTAGAGGAGGAGGGTCATAGCCCC<br>CCACCACTGTCACCTAGACATTTCCTCTTTGGCTGCGGGGAGAAACATCA<br>CATAGCGAAGGAACTTCCTCTGTGTTTTCCCAGATTCCAACAACCCAGAA<br>AGTCTGTGTTTCCCTGGGGCGCGGGGTAGGGATGGAAAGCAGAATGAGC<br>TGACACCAAAATTTCCTCGGATTTTTTTAAAAAAAGAGTAAGCAAGGGC<br>TTTAACTAAGTGATAGCTGTTGATAGCATCCTTGGTGACTTTCTAGAGAA<br>AGATGGCTTCCAATAAACATCAGGTTAAAACATGTATGTCTTCAAAGAA<br>TTTATTGGATATTTATTGGCTATTGGATATAATAGGGTGAGAATGTTTGT<br>CCTTTCAGACTGTGTTATTTTTGAACTTTCCTGTCAGCCAACACCTTAGAA<br>AGTGATTGCTATTCCTCACTGTCCCATCAGTTTAAGGATTCTTAAGAGAT<br>GAGACTTCTCAGTGTGCTCTGGAGAGAATCTGAAAGGGGAATGGATGAT<br>CTAGCAATATTATTTAACTACTGGGTAAATATGGTTTAAAAATAATAATA<br>ACTTTGTGAGTGGAATATCATAAATGTGCTTGTATGGC | 23 |
| Human wingless-type MMTV integration site family, member 9B (WNT9B) NCBI Ref Seq: NM_011719.4 | ACGAGCGCCTAGTGGCGCGAGGAGATGCGAGAGTGCACCGGCCGCCTGC<br>ACCATGCGCCCCGCGCCCGCGCTGGCCCTGGCTGCGCTCTGCCTGCTGGT<br>GCTGCCTGCCGCTGCCGCCGCCGCCGCCTACTTCGGCCTGACCGGTCGTG<br>AGGTCCTGACACCCTTCCCAGGCCTGGGTACGGCAGCAGCCCCGGCACA<br>GGCTGGTGCTCACCTGAAGCAGTGTGACCTACTGAAGCTGTCCAGGCGG<br>CAGAAGCAGCTCTGCAGGCGGGAGCCCGGCTGGCTGAGACCCTGAGGG<br>ATGCTGCACACCTGGGGCTGCTGGAATGTCAGTTCCAGTTCAGGCAGGA<br>GCGCTGGAACTGCAGCCTGGAGGGGAGGACTGGCCTGCTCCAGAGAGGC<br>TTTAAGGAGACGGCCTTCCTGTATGCAGTGTCTGCAGCTGCCCTCACGCA<br>TGCACTGGCCAGGGCCTGCAGTGCTGGGCGCATGGAGCGCTGTACTTGT<br>GACGACTCCCCAGGCCTGGAGAGCCGGCAGGCCTGGCAGTGGGGTGTGT<br>GTGGTGACAATCTGAAGTACAGCACCAAGTTCCTCAGCAACTTCCTGGG<br>GCCCAAGAGAGGAAGCAAGGACCTGAGGGCGAGGGCTGACGCCCACAA<br>CACCCACGTGGGCATCAAGGCTGTGAAGAGCGGCCTGAGAACAACCTGC<br>AAGTGCCATGGTGTGTCAGGCTCCTGTGCTGTTCGTACCTGTTGGAAGCA<br>GCTCTCCCCGTTTCGCGAGACCGGCCAGGTGCTGAAGCTACGCTATGAC<br>ACGGCTGTCAAGGTGTCCAGTGCCACCAACGAGGCCTTGGGTCGTCTGG<br>AGCTATGGGCCCCGCTAAGCCAGGTGGTCCCGCCAAGGGCCTAGCCCC<br>TCGTCCCGGGGACCTGGTCTACATGGAAGATTCTCCCAGCTTCTGCCCGG<br>CCAGCAAGTACTCTCCGGGCACGGCAGGCAGGGTGTGTTCTCGAGACTC<br>CAGTTGCAGCAGCCTATGCTGTGGGCGAGGCTACGACACCCAGAGCCGC<br>ATGGTGGTTTTCTCCTGCCACTGTCAGGTGCAGTGGTGCTGCTACGTGGA<br>GTGCCAGCAGTGTGCACAGCAGGAGCTCGTGTATACCTGCAAGCGCTAG<br>GCCTCCACAGCGAATCCCGCGGAACAGCGCGCAAGCGCGCACCTGTCGA | 24 |

TABLE 1-continued

Sequences used in present disclosure

| Name | Sequence | SEQ ID NO: |
|---|---|---|
| | CGCACCTGCCGTGCACAAGAGTGTGCGACTCATCTCTCTTCCCCAACAGA<br>TGGTTGGCCAGCCCTTCTGCCTTCCCCGACACTCAGCAAAGAGAAAGAA<br>AGCCCTGCCTCCTAGTCCCAGGATCACCAACCTGCTGGAGGACTTGGGG<br>CCGGAGAACAGACTGAGAAGGGGAATCTTTGAGGACCAGGGTAGGGCA<br>GGAATGATGCTGTGCGGGAAGAGAGAAACATCCTCCTATCTCAAGGCCA<br>AAAACTGGGAGGATGGGGAAGAGGGAGGCGGAGCCAGCTGGAGTGTGG<br>GGTCAGGGCATCCATCTGGGCGTGGCCGATCTCTTGTGGTCCCACTCTAA<br>TAGCAGAGCGCTCTGGGTGCTGCATGCCTACCCTGCTCTTGTGGCTTCGT<br>GCACTGGAGACTTCGAAATGTTTATTAGGAGCAAGGGAAGCACTTTAGG<br>CTTGGGTGGATTGAGTCGCAGAGCCCATGCCCTGAAGTCTTACGTCCTGG<br>CACTCAGGGCTGCCACCTTGTCTCCTTGTCTTGAGATCCCCTGTCCCCCA<br>AAGCCATTGAGCTCTGCTCAACGAGACCCCTAATATGTATAAGAAGGGT<br>GCAGGAGCCAGTCTCCTCGGTGAGACTCAGATAAACATAACTAGGGTTG<br>AGCGGGGAGACAGTGACCCTTTCTCTTTCCTTTGGTCCAAGGAACCTTTA<br>ATCACAGCCCAGAGGTGGAGAGAGGCAGGGTCCAAATGCCTGGAAGAG<br>ATATGACAGGCTCTGTATTGAGATACCACTCTGGAGTGTGTCCTACCAAT<br>TCCTGTGACCAGGGACCCCCAAGAACCGAGGGGCCCCCATCCATGTTAG<br>TGATACATAAGAACGAGTGACTCATGGGCCACACGTCTGCTTCCACCCC<br>CTGCTCTCAAAGATGCTTGTGCAGGCTTTTTTGCCATTGCTAAGTCTTTGC<br>CAAGTCTGCCTCCTCAATGGTCTTACTCATTTACTAACGACCTGTCACTT<br>GGGCTCCCACCAGAGGAACAAAATGACTGCTGGTGAATCCTTTGGTCAT<br>TTTTAATGCCCCCATCAAGGCCCTCTGTGAGAGGAGAGGAAGTAGTGTA<br>CAGGTACAGGCTCACACGTGCACACACTCAGCCTAGCCAGGCACAGACA<br>TCCCAAGGAGCAGTGCGGCGTCTCTCCAGCCCAGGGCAAAGACCTCACT<br>GGGGTCACTTCTGGAGGCTGTGAGCTACTCCAGGGCAGGGCCCAAGGCC<br>AACCAGGAGGAAGTGACCTCCTTTGGGAAGCCTTTGGCCATGTGGCTGG<br>CTGTGCTGCACCCTCCTGTGAGCTTCCTTCCACCCTGAAATCTGTTGGGG<br>TTACTGTCTCTCTAAGGGAGCAGGAAGCTTCGGAATCAGCCGGTACTCA<br>GCACTACTGGCCCTGCCAGCTCCAGGAAAGAGACACTGTGGCGGAGAGG<br>TCCGTGGGGCAGAAGGGGCTACCCTTTCTTCAGTGCCTCCGGGCAGCAT<br>GCTGGGAAGATCTTTGATGGTGGAAAGCCCCGAGGCGGAGCCACCGTGA<br>CCTGAGACCCTTCTCTGGGACGACTTTGCCACCCACCCGCAGCTTGGCAG<br>GAGGGGTAAACAGATTGGGAGCTGCTTTCTACTTCCCTGATGAAGACAG<br>ATGTGTTCCTTGGCAACCCAAGGCATCCTTCTCTATGACCCTAATCCTGC<br>TCTGGCTCGAGGGTACAAGGCAAGAATGGAGCCTGGCAAAACTTGGGGA<br>CTAGAACACCTGGACCTACAGCCAAATCACCTGTACCCTGACTCTATGGC<br>CAGGAGGGCCAGGGGTGGAGGAGGGTTAAAGATGAACTTGAAGTTGAG<br>GCTGAGGCTGACCAACCATTAAGACTGGTGCCTTAAGGCACCCTCAGTC<br>AGGTCCTCTCCCTCCCTTCTCCATTCTTTCTCCAAGGCCCCGTTCCCCCTA<br>AAATCCCACCATAGCCATGCTGGGTCCCCCCTTCCCCACACTGGAACTT<br>TAAGGAAGATATTCACAGGGTATTTCTGCCTACCTCATACATGTAATTTT<br>CAAAAAAAATTAATTTATATAGTTAAGATATATGGGAAAGTATTTATGTT<br>ATTTATATATCTTCTCTATTTCCTGGGCACCATATGGGGGGTTGTGTGTTT<br>ACCCAGAAGCCTCTGAGGAAACATGGCTGGGTCTGTCTGGGGCCTCGCA<br>GAGCTGGATGCGCATAGCTGAGAGGTCACAGCTCCTGTGTCTCACTGTCT<br>TGGAGCTCGGGAAGCACATGTACCTCCTGAGATAAACCCCGTGACACCA<br>AGCAGGGCCTTCCTTGTGAAGTCTGTGGATTCTCTGCCTCTGGCCCCAGA<br>GGCCTTTCTGCTCTGGCCCAAGGGTTTTGCTCATAAAGGACAAAAAGGG<br>TGAGCAGCTCTGGATTTGTAAAGCACTTTCCATCTTCAGAAACACTCCTC<br>TCTTCTCTCTCCCTCGGTTACCCCCGGTTCCCTATGAGGTCATGCCACTGT<br>TACCACGTTCCAGGCCCAGAGACGGAGGCAGGTTGGTCAAAGCCAGTCA<br>CTCTCTGAACCCAGAGGTTGAGGAAGAGTGCATGCTGCGTGGAACGCTG<br>GTCTTCCCCCATGGATGGCATGCTAGTTTCTCCAGCAAGCTGAGTCTCAT<br>GTCCCCAAAGACGGGGACTTCCTGAGAAGCCTGGAGAGACAAGGGCTCC<br>GTGGATGTCACTCTTAGGGAGGGTGTCCTGCAGCCCTCATTGACCTCCAC<br>GACTAGGCTATGGTCTCCAGCCCCTCACAGCTCGTGGATAATTTGTGTTT<br>CTTCGCTTTTGTTTTTTGTCTTTTCAAAGTGACTTTTTCCCCACTGGATTTC<br>TAAGTTTCTCTTTGAAAATCAGTTCACTGGCAAATGGGACCTGCATCCTG<br>ACCTGGCTGCCTGCATCAGGAGCGACACCAAACAGAGTGCGTGGGGATC<br>CCCAATTGGCCCAGTGTCCCCCGGCCCTTCCTTAAGTCACACAAGCTCCC<br>GTGTGGCTTTCGTGAGCATGGAGAACCTGTCCCCTGGTCTTAGAGAAAG<br>CCAGCCATTCTGCCACCCTCTGTTTGTCTGGCAGACAGATTACCACACCG<br>TGGCTGTCTTTCTAGCCAAAGCTTCCTCTCTCAACACCCATGAACGTCCA<br>TGCTTCCTGTCTGAGCACTGAGGAGAACCCCAGCGGAGCTCATTGTTCAG<br>TGCTGGAATACCCATCCCCCCTCCCGTTGATTATTTAGGGAGTGTCTGAT<br>AATGCCAGGGGATACTCTGGGTGCTAGGGCGCAGAAGTACTTAAGAGCA<br>AGTCCCAGCCTCAGGGGACTTATATGCCGGCGAGGAGAAAGCCAACAAA<br>CCAATAAACTATGCACTGGTT | |
| Modified Human YAP (activated and without tag) | ATGGACCCCGGCCAGCAGCCCCCCCCAGCCCGCCCCCCAGGGCCAGG<br>GCCAGCCCCCTCCCAGCCCCCCAGGGCCAGGGCCCCCCTCCGGCCC<br>CGGCCAGCCCGCCCCCGCCGCCACCCAGGCCGCCCCCAGGCCCCCCC<br>GCCGGCCACCAGATCGTGCACGTGCGCGGCGACTCCGAGACCGACCTGG<br>AGGCCCTGTTCAACGCCGTGATGAACCCCAAGACCGCCAACGTGCCCCA | 25 |

TABLE 1-continued

Sequences used in present disclosure

| Name | Sequence | SEQ ID NO: |
|------|----------|------------|
| | GACCGTGCCCATGCGCCTGCGCAAGCTGCCCGACTCCTTCTTCAAGCCCC<br>CCGAGCCCAAGTCCCACTCCCGCCAGGCCTCCACCGACGCCGGCACCGC<br>CGGCGCCCTGACCCCCCAGCACGTGCGCGCCCACGCCTCCCCCGCCTCCC<br>TGCAGCTGGGCGCCGTGTCCCCCGGCACCCTGACCCCCACCGGCGTGGT<br>GTCCGGCCCCGCCGCCACCCCCACCGCCCAGCACCTGCGCCAGTCCTCCT<br>TCGAGATCCCCGACGACGTGCCCCTGCCCGCCGGCTGGGAGATGGCCAA<br>GACCTCCTCCGGCCAGCGCTACTTCCTGAACCACATCGACCAGACCACC<br>ACCTGGCAGGACCCCCGCAAGGCCATGCTGTCCCAGATGAACGTGACCG<br>CCCCCACCTCCCCCCCCGTGCAGCAGAACATGATGAACTCCGCCTCCGGC<br>CCCCTGCCCGACGGCTGGGAGCAGGCCATGACCCAGGACGGCGAGATCT<br>ACTACATCAACCACAAGAACAAGACCACCTCCTGGCTGGACCCCCGCCT<br>GGACCCCCGCTTCGCCATGAACCAGCGCATCTCCCAGTCCGCCCCCGTGA<br>AGCAGCCCCCCCCCTGGCCCCCAGTCCCCCCAGGGCGGCGTGATGGG<br>CGGCTCCAACTCCAACCAGCAGCAGCAGATGCGCCTGCAGCAGCTGCAG<br>ATGGGAGAAGGAGCGCCTGCGCCTGAAGCAGCAGGAGCTGCTGCGCCAG<br>GAGCTGGCCCTGCGCTCCCAGCTGCCCACCCTGGAGCAGGACGGCGGCA<br>CCCAGAACCCCGTGTCCTCCCCCGGCATGTCCCAGGAGCTGCGCACCAT<br>GACCACCAACTCCTCCGACCCCTTCCTGAACTCCGGCACCTACCACTCCC<br>GCGACGAGTCCACCGACTCCGGCCTGTCCATGTCCTCCTACTCCGTGCCC<br>CGCACCCCCGACGACTTCCTGAACTCCGTGGACGAGATGGACACCGGCG<br>ACACCATCAACCAGTCCACCCTGCCCTCCCAGCAGAACCGCTTCCCCGAC<br>TACCTGGAGGCCATCCCCGGCACCAACGTGGACCTGGGCACCCTGGAGG<br>GCGACGGCATGAACATCGAGGGCGAGGAGCTGATGCCCTCCCTGCAGGA<br>GGCCCTGTCCTCCGACATCCTGAACGACATGGAGTCCGTGCTGGCCGCC<br>ACCAAGCTGGACAAGGAGTCCTTCCTGACCTGGCTG | |
| Modified Mouse WNT2 | ATGAACGTGCCCCTGGGCGGCATCTGGCTGTGGCTGCCCCTGCTGCTGAC<br>CTGGCTGACCCCCGAGGTGTCCTCCTCCTGGTGGTACATGCGCGCCACCG<br>GCGGCTCCTCCCGCGTGATGTGCGACAACGTGCCCGGCCTGGTGTCCCGC<br>CAGCGCCAGCTGTGCCACCGCCACCCCGACGTGATGCGCGCCATCGGCC<br>TGGGCGTGGCCGAGTGGACCGCCGAGTGCCAGCACCAGTTCCGCCAGCA<br>CCGCTGGAACTGCAACACCCTGGACCGCGACCACTCCCTGTTCGGCCGC<br>GTGCTGCTGCGCTCCTCCCGCGAGTCCGCCTTCGTGTACGCCATCTCCTC<br>CGCCGGCGTGGTGTTCGCCATCACCCGCGCCTGCTCCCAGGGCGAGCTG<br>AAGTCCTGCTCCTGCGACCCCAAGAAGAAGGGCTCCGCCAAGGACTCCA<br>AGGGCACCTTCGACTGGGGCGGCTGCTCCGACAACATCGACTACGGCAT<br>CAAGTTCGCCCGCGCCTTCGTGGACGCCAAGGAGCGCAAGGGCAAGGAC<br>GCCCGCGCCCTGATGAACCTGCACAACAACCGCGCCGGCCGCAAGGCCG<br>TGAAGCGCTTCCTGAAGCAGGAGTGCAAGTGCCACGGCGTGTCCGGCTC<br>CTGCACCCTGCGCACCTGCTGGCTGGCCATGGCCGACTTCCGCAAGACC<br>GGCGACTACCTGTGGCGCAAGTACAACGGCGCCATCCAGGTGGTGATGA<br>ACCAGGACGGCACCGGCTTCACCGTGGCCAACAAGCGCTTCAAGAAGCC<br>CACCAAGAACGACCTGGTGTACTTCGAGAACTCCCCCGACTACTGCATC<br>CGCGACCGCGAGGCCGGCTCCCTGGGCACCGCCGGCCGCGTGTGCAACC<br>TGACCTCCCGCGGCATGGACTCCTGCGAGGTGATGTGCTGCGGCCGCGG<br>CTACGACACCTCCCACGTGACCCGCATGACCAAGTGCGAGTGCAAGTTC<br>CACTGGTGCTGCGCCGTGCGCTGCCAGGACTGCCTGGAGGCCCTGGACG<br>TGCACACCTGCAAGGCCCCCAAGTCCGCCGACTGGGCCACCCCCACC | 26 |
| Modified Human WNT9B | ATGCGCCCCGCCCCCGCCCTGGCCCTGGCCGCCCTGTGCCTGCTGGTGCT<br>GCCCGCCGCCGCCGCCGCCGCCTACTTCGGCCTGACCGGCCGCGAG<br>GTGCTGACCCCCTTCCCCGGCCTGGGCACCGCCGCCGCCCCCGCCCAGGC<br>CGGCGCCCACCTGAAGCAGTGCGACCTGCTGAAGCTGTCCCGCCGCCAG<br>AAGCAGCTGTGCCGCCGCGAGCCCGGCCTGGCCGAGACCCTGCGCGACG<br>CCGCCCACCTGGGCCTGCTGGAGTGCCAGTTCCAGTTCCGCCAGGAGCG<br>CTGGAACTGCTCCCTGGAGGGCCGCACCGGCCTGCTGCAGCGCGGCTTC<br>AAGGAGACCGCCTTCCTGTACGCCGTGTCCGCCGCCGCCCTGACCCACG<br>CCCTGGCCCGCGCCTGCTCCGCCGGCCGCATGGAGCGCTGCACCTGCGA<br>CGACTCCCCCGGCCTGGAGTCCGCCAGGCCTGGCAGTGGGCGTGTGC<br>GGCGACAACCTGAAGTACTCCACCAAGTTCCTGTCCAACTTCCTGGGCCC<br>CAAGCGCGGCTCCAAGGACCTGCGCGCCCGCGCCGACGCCCACAACACC<br>CACGTGGGCATCAAGGCCGTGAAGTCCGGCCTGCGCACCACCTGCAAGT<br>GCCACGGCGTGTCCGGCTCCTGCGCCGTGCGCACCTGCTGGAAGCAGCT<br>GTCCCCCTTCCGCGAGACCGGCCAGGTGCTGAAGCTGCGCTACGACACC<br>GCCGTGAAGGTGTCCTCCGCCACCAACGAGGGCCTGGGCGCCTGGAGC<br>TGTGGGCCCCGCCAAGCCCGGCGGCCCCGCCAAGGGCCTGGCCCCCCG<br>CCCCGGCGACCTGGTGTACATGGAGGACTCCCCCTCCTTCTGCCGCCCCT<br>CCAAGTACTCCCCCGGCACCGCCGGCCGCGTGCTCCCGCGACTCCTCC<br>TGCTCCTCCCCTGTGCTGCGGCCGCGGCTACGACACCCAGTCCCGCATGGT<br>GGTGTTCTCCTGCCACTGCCAGGTGCAGTGGTGCTGCTACGTGGAGTGCC<br>AGCAGTGCGCCCAGCAGGAGCTGGTGTACACCTGCAAGGCGC | 27 |

TABLE 1-continued

Sequences used in present disclosure

| Name | Sequence | SEQ ID NO: |
|---|---|---|
| WT YAP FLAG Tag | GACTACAAAGACGATGACGATAAAGCAAGGCTCGAATCGGTACCTATG | 28 |
| Modified YAP FLAG Tag | GACTACAAGGACGACGACGACAAGGCCCGCCTGGAGTCCGTGCCCATG | 29 |
| WT beta catenin myc Tag | GAGCAAAAGCTCATTTCTGAAGAGGACTTG | 30 |
| Modified beta myc FLAG Tag | GAGCAGAAGCTGATCTCCGAGGAGGACCTG | 31 |

In some embodiments of any of the aspects, the liver regenerative factor is or is derived from a mammalian liver regenerative factor. In some embodiments of any of the aspects, the liver regenerative factor is or is derived from a primate liver regenerative factor. In some embodiments of any of the aspects, the liver regenerative factor is or is derived from a human liver regenerative factor. In some embodiments of any of the aspects, the liver regenerative factor is or is derived from a murine liver regenerative factor. In some embodiments of any of the aspects, the liver regenerative factor is or is derived from a human liver regenerative factor or a murine liver regenerative factor.

In some embodiments of any of the aspects, a liver regenerative factor composition described herein relates to one or more mRNAs in which the mRNA sequence is not a naturally-occurring sequence, e.g., in which the mRNA sequence has been engineered to comprise one or more deletions, modifications, or additions. These engineered mRNA sequences can exhibit improve therapeutic characteristics including improved expression levels, cellular specificity, or half-life. Accordingly, in one aspect of any of the embodiments, described herein is a composition comprising at least one engineered liver regenerative factor mRNA, the at least one engineered liver regenerative factor mRNA comprising one or more of the deletions, modifications, and/or additions described herein.

In some embodiments of any of the aspects, the liver regenerative factor is GH and the at least one engineered liver regenerative factor mRNA comprises SEQ ID NO: 8. In some embodiments of any of the aspects, the liver regenerative factor is EGF and the at least one engineered liver regenerative factor mRNA comprises SEQ ID NO: 9. In some embodiments of any of the aspects, the liver regenerative factor is HGF and the at least one engineered liver regenerative factor mRNA comprises SEQ ID NO: 10. In some embodiments of any of the aspects, the liver regenerative factor is p21 and the at least one engineered liver regenerative factor mRNA comprises SEQ ID NO: 11. In some embodiments of any of the aspects, the liver regenerative factor is VEGF165 and the at least one engineered liver regenerative factor mRNA comprises SEQ ID NO: 12. In some embodiments of any of the aspects, the liver regenerative factor is IGF-1 and the at least one engineered liver regenerative factor mRNA comprises SEQ ID NO: 13. In some embodiments of any of the aspects, the liver regenerative factor is IGF-1 IL-2 SP and the at least one engineered liver regenerative factor mRNA comprises SEQ ID NO: 14. In some embodiments of any of the aspects, the liver regenerative factor is secreted EGF and the at least one engineered liver regenerative factor mRNA comprises SEQ ID NO: 15. In some embodiments of any of the aspects, the liver regenerative factor is STAT5B and the at least one engineered liver regenerative factor mRNA is constitutively activated and comprises SEQ ID NO: 16. In some embodiments of any of the aspects, the liver regenerative factor is beta-catenin and the at least one engineered liver regenerative factor mRNA is activated and comprises SEQ ID NO: 21. In some embodiments of any of the aspects, the liver regenerative factor is YAP and the at least one engineered liver regenerative factor mRNA is activated and comprises SEQ ID NO: 25. In some embodiments of any of the aspects, the liver regenerative factor is WNT2 and the at least one engineered liver regenerative factor mRNA comprises SEQ ID NO: 26. In some embodiments of any of the aspects, the liver regenerative factor is WNT9b and the at least one engineered liver regenerative factor mRNA comprises SEQ ID NO: 27.

In some embodiments of any of the aspects, the liver regenerative factor is GH and the at least one engineered liver regenerative factor mRNA consists of or consists essentially of SEQ ID NO: 8. In some embodiments of any of the aspects, the liver regenerative factor is EGF and the at least one engineered liver regenerative factor mRNA consists of or consists essentially of SEQ ID NO: 9. In some embodiments of any of the aspects, the liver regenerative factor is HGF and the at least one engineered liver regenerative factor mRNA consists of or consists essentially of SEQ ID NO: 10. In some embodiments of any of the aspects, the liver regenerative factor is p21 and the at least one engineered liver regenerative factor mRNA consists of or consists essentially of SEQ ID NO: 11. In some embodiments of any of the aspects, the liver regenerative factor is VEGF165 and the at least one engineered liver regenerative factor mRNA consists of or consists essentially of SEQ ID NO: 12. In some embodiments of any of the aspects, the liver regenerative factor is IGF-1 and the at least one engineered liver regenerative factor mRNA consists of or consists essentially of SEQ ID NO: 13. In some embodiments of any of the aspects, the liver regenerative factor is IGF-1 IL-2 SP and the at least one engineered liver regenerative factor mRNA consists of or consists essentially of SEQ ID NO: 14. In some embodiments of any of the aspects, the liver regenerative factor is secreted EGF and the at least one engineered liver regenerative factor mRNA consists of or consists essentially of SEQ ID NO: 15. In some embodiments of any of the aspects, the liver regenerative factor is STAT5B and the at least one engineered liver regenerative factor mRNA is constitutively active and consists of or consists essentially of SEQ ID NO: 16. In some embodiments of any of the aspects, the liver regenerative factor is beta-catenin and the at least one engineered liver regenerative factor mRNA is activated and consists of or consists essentially of SEQ ID NO: 21. In some embodiments of any of the aspects, the liver regenerative factor is YAP and the at least one engineered liver regenerative factor mRNA is activated and consists of or consists essentially SEQ ID NO: 25. In some embodiments of any of the aspects, the liver regenerative factor is WNT2 and the at least one engineered liver regenerative factor mRNA consists of or consists essentially SEQ ID NO: 26. In some embodiments of any of the aspects, the liver regenerative factor is WNT9b and the at least one engineered liver regenerative factor mRNA consists of or consists essentially SEQ ID NO: 27.

In some embodiments of any of the aspects, the liver regenerative factor is GH and the at least one engineered liver regenerative factor mRNA comprises, consists of, or consists essentially of a sequence having at least 80%, at least 85%, at least 90%, at least 95%, or greater sequence identity to SEQ ID NO: 8. In some embodiments of any of the aspects, the liver regenerative factor is EGF and the at least one engineered liver regenerative factor mRNA comprises, consists of, or consists essentially of a sequence having at least 80%, at least 85%, at least 90%, at least 95%, or greater sequence identity to SEQ ID NO: 9. In some embodiments of any of the aspects, the liver regenerative factor is HGF and the at least one engineered liver regenerative factor mRNA comprises, consists of, or consists essentially of a sequence having at least 80%, at least 85%, at least 90%, at least 95%, or greater sequence identity to SEQ ID NO: 10. In some embodiments of any of the aspects, the liver regenerative factor is p21 and the at least one engineered liver regenerative factor mRNA comprises, consists of, or consists essentially of a sequence having at least 80%, at least 85%, at least 90%, at least 95%, or greater sequence identity to SEQ ID NO: 11. In some embodiments of any of the aspects, the liver regenerative factor is VEGF165 and the at least one engineered liver regenerative factor mRNA comprises, consists of, or consists essentially of a sequence having at least 80%, at least 85%, at least 90%, at least 95%, or greater sequence identity to SEQ ID NO: 12. In some embodiments of any of the aspects, the liver regenerative factor is IGF-1 and the at least one engineered liver regenerative factor mRNA comprises, consists of, or consists essentially of a sequence having at least 80%, at least 85%, at least 90%, at least 95%, or greater sequence identity to SEQ ID NO: 13. In some embodiments of any of the aspects, the liver regenerative factor is IGF-1 IL-2 SP and the at least one engineered liver regenerative factor mRNA comprises, consists of, or consists essentially of a sequence having at least 80%, at least 85%, at least 90%, at least 95%, or greater sequence identity to SEQ ID NO: 14. In some embodiments of any of the aspects, the liver regenerative factor is EGF and the at least one engineered liver regenerative factor mRNA comprises, consists of, or consists essentially of a sequence having at least 80%, at least 85%, at least 90%, at least 95%, or greater sequence identity to SEQ ID NO: 15. In some embodiments of any of the aspects, the liver regenerative factor is STAT5B and the at least one engineered liver regenerative factor mRNA is constitutively active and comprises, consists of, or consists essentially of a sequence having at least 80%, at least 85%, at least 90%, at least 95%, or greater sequence identity to SEQ ID NO: 16. In some embodiments of any of the aspects, the liver regenerative factor is beta-catenin and the at least one engineered liver regenerative factor mRNA is activated and comprises, consists of, or consists essentially of a sequence having at least 80%, at least 85%, at least 90%, at least 95%, or greater sequence identity to SEQ ID NO: 21. In some embodiments of any of the aspects, the liver regenerative factor is YAP and the at least one engineered liver regenerative factor mRNA is activated and comprises, consists of, or consists essentially of a sequence having at least 80%, at least 85%, at least 90%, at least 95%, or greater sequence identity to SEQ ID NO: 25. In some embodiments of any of the aspects, the liver regenerative factor is WNT2 and the at least one engineered liver regenerative factor mRNA comprises, consists of, or consists essentially of a sequence having at least 80%, at least 85%, at least 90%, at least 95%, or greater sequence identity to SEQ ID NO: 26. In some embodiments of any of the aspects, the liver regenerative factor is WNT9b and the at least one engineered liver regenerative factor mRNA comprises, consists of, or consists essentially of a sequence having at least 80%, at least 85%, at least 90%, at least 95%, or greater sequence identity to SEQ ID NO: 27.

In some embodiments of any of the aspects, the liver regenerative factor is GH and the at least one engineered liver regenerative factor mRNA comprises a sequence having at least 80% sequence identity to SEQ ID NO: 8. In some embodiments of any of the aspects, the liver regenerative factor is EGF and the at least one engineered liver regenerative factor mRNA comprises a sequence having at least 80% sequence identity to SEQ ID NO: 9. In some embodiments of any of the aspects, the liver regenerative factor is HGF and the at least one engineered liver regenerative factor mRNA comprises a sequence having at least 80% sequence identity to SEQ ID NO: 10. In some embodiments of any of the aspects, the liver regenerative factor is p21 and the at least one engineered liver regenerative factor mRNA comprises a sequence having at least 80% sequence identity to SEQ ID NO: 11. In some embodiments of any of the aspects, the liver regenerative factor is VEGF165 and the at least one engineered liver regenerative factor mRNA comprises a sequence having at least 80% sequence identity to SEQ ID NO: 12. In some embodiments of any of the aspects, the liver regenerative factor is IGF-1 and the at least one engineered liver regenerative factor mRNA comprises a sequence having at least 80% greater sequence identity to SEQ ID NO: 13. In some embodiments of any of the aspects, the liver regenerative factor is IGF-1 IL-2 SP and the at least one engineered liver regenerative factor mRNA comprises a sequence having at least 80% sequence identity to SEQ ID NO: 14. In some embodiments of any of the aspects, the liver regenerative factor is EGF and the at least one engineered liver regenerative factor mRNA comprises a sequence having at least 80% sequence identity to SEQ ID NO: 15. In some embodiments of any of the aspects, the liver regenerative factor is STAT5B and the at least one engineered liver regenerative factor mRNA is constitutively activated and comprises a sequence having at least 80% sequence identity to SEQ ID NO: 16. In some embodiments of any of the aspects, the liver regenerative factor is beta-catenin and the at least one engineered liver regenerative factor mRNA is activated and comprises a sequence having at least 80% sequence identity to SEQ ID NO: 21. In some embodiments of any of the aspects, the liver regenerative factor is YAP and the at least one engineered liver regenerative factor mRNA is activated and comprises a sequence having at least 80% sequence identity to SEQ ID NO: 25. In some embodiments of any of the aspects, the liver regenerative factor is WNT2 and the at least one engineered liver regenerative factor mRNA comprises a sequence having at least 80% sequence identity to SEQ ID NO: 26. In some embodiments of any of the aspects, the liver regenerative factor is WNT9b and the at least one engineered liver regenerative factor mRNA comprises a sequence having at least 80% sequence identity to SEQ ID NO: 27.

In some embodiments of any of the aspects, the composition comprises a liver regenerative factor and at least one internal label or tag. In some embodiments, the tag can be, for example, a myc or FLAG tag. In some embodiments, the tag is a FLAG tag, for example, a FLAG tag encoded by the nucleic acid of SEQ ID NO: 28-29. In some embodiments the tag is a myc tag, for example, a myc tag encoded by the nucleic acid of SEQ ID NO: 30-31.

In some embodiments of any of the aspects, the at least one engineered liver regenerative factor is beta catenin and the at least one internal tag is a myc tag encoded by the nucleic acid of SEQ ID NO: 30 or SEQ ID NO: 31.

In some embodiments of any of the aspects, the tag is located after between sequence nucleotide 3 and nucleotide 4 of SEQ ID NO: 21. In some embodiments of any of the aspects, the tag is located after between sequence nucleotide 3 and nucleotide 4 of SEQ ID NO: 22. In some embodiments of any of the aspects, the tag is a myc tag is located between nucleotide 3 and nucleotide 4 of SEQ ID NO: 21. In some embodiments of any of the aspects, the tag is a FLAG tag is located between nucleotide 3 and nucleotide 4 of SEQ ID NO: 22.

In some embodiments of any of the aspects, a composition comprises two or more of the engineered liver regenerative factor mRNA sequences described herein. In some embodiments of any of the aspects, a composition comprises three or more of the engineered liver regenerative factor mRNA sequences described herein. In some embodiments of any of the aspects, a composition comprises four or more of the engineered liver regenerative factor mRNA sequences described herein. In some embodiments of any of the aspects, a composition comprises five or more of the engineered liver regenerative factor mRNA sequences described herein. In some embodiments of any of the aspects, a composition comprises six or more of the engineered liver regenerative factor mRNA sequences described herein. In some embodiments of any of the aspects, a composition comprises seven or more of the engineered liver regenerative factor mRNA sequences described herein. In some embodiments of any of the aspects, a composition comprises eight or more of the engineered liver regenerative factor mRNA sequences described herein. In some embodiments of any of the aspects, a composition comprises nine or more of the engineered liver regenerative factor mRNA sequences described herein. In some embodiments of any of the aspects, a composition comprises ten or more of the engineered liver regenerative factor mRNA sequences described herein.

In some embodiments of any of the aspects, a composition comprises two or more of SEQ ID NOs: 8-16, 21, and 25-27. In some embodiments of any of the aspects, a composition comprises three or more of SEQ ID NOs: 8-16, 21, and 25-27. In some embodiments of any of the aspects, a composition comprises four or more of SEQ ID NOs: 8-16, 21, and 25-27. In some embodiments of any of the aspects, a composition comprises five or more of SEQ ID NOs: 8-16, 21, and 25-27. In some embodiments of any of the aspects, a composition comprises six or more of SEQ ID NOs: 8-16, 21, and 25-27. In some embodiments of any of the aspects, a composition comprises seven or more of SEQ ID NOs: 8-16, 21, and 25-27. In some embodiments of any of the aspects, a composition comprises eight or more of SEQ ID NOs: 8-16, 21, and 25-27. In some embodiments of any of the aspects, a composition comprises nine or more of SEQ ID NOs: 8-16, 21, and 25-27. In some embodiments of any of the aspects, a composition comprises each of.

In some embodiments of any of the aspects, a mRNA, e.g., a mRNA molecule can be polycistronic, e.g., it can comprise two or more of the engineered liver regenerative factor mRNA sequences described herein. In some embodiments of any of the aspects, a mRNA, e.g., a mRNA molecule can be polycistronic, e.g., it can comprise two or more of SEQ ID NOs: 8-16, 21, and 25-27.

In embodiments comprising two or more liver regenerative factors, any combination of the liver regenerative factors and engineered liver regenerative factor mRNAs described herein is contemplated. Merely as illustrative examples, the following tables present exemplary pair-wise combinations of liver regenerative factors and engineered liver regenerative factor mRNAs.

TABLE 2

Combinations of liver regenerative factors

|  | GH | EGF | HGF | P21 | VEGF (e.g. VEGF165) | IGF-1 | GF-1 IL-2 SP | Secreted EGF | STAT5B | Beta-catenin | YAP | Wnt9b | Wnt2 |
|---|---|---|---|---|---|---|---|---|---|---|---|---|---|
| GH |  | x | x | x | x | x | x | x | x | x | X | X | X |
| EGF | x |  | x | x | x | x | x | x | x | x | X | X | X |
| HGF | x | x |  | x | x | x | x | x | x | x | X | X | X |
| P21 | x | x | x |  | x | x | x | x | X | x | X | X | X |
| VEGF 165 | x | x | x | x |  | x | x | X | X | x | X | X | X |
| IGF-1 | x | x | x | x | x |  | x | x | X | X | X | X | X |
| IGF-1 IL2 SP | x | x | x | x | x | x |  | X | X | X | X | X | X |
| Secreted EGF | x | x | x | x | x | x | x |  | X | X | X | X | X |
| STAT 5B | x | x | x | x | x | x | x | x |  | x | X | X | X |

TABLE 2-continued

Combinations of liver regenerative factors

|  | GH | EGF | HGF | P21 | VEGF (e.g. VEGF165) | IGF-1 | GF-1 IL-2 SP | Secreted EGF | STAT5B | Beta-catenin | YAP | Wnt9b | Wnt2 |
|---|---|---|---|---|---|---|---|---|---|---|---|---|---|
| Beta-catenin | x | x | x | x | x | x | x | x | x |  | x | X | X |
| YAP | x | x | x | x | x | x | x | x | x | x |  | X | X |
| Wnt9b | x | x | x | x | x | x | x | x | x | x | x |  | X |
| Wnt2 | x | x | x | x | x | x | x | x | x | x | x | x |  |

TABLE 3

Combinations of sequences of liver regenerative factor mRNAs

SEQ ID NO:

|  |  | 8 | 9 | 10 | 11 | 12 | 13 | 14 | 15 | 16 | 21 | 25 | 26 | 27 |
|---|---|---|---|---|---|---|---|---|---|---|---|---|---|---|
| SEQ ID NO: | 8 |  | x | x | x | x | x | x | x | x | X | X | X | X |
|  | 9 | x |  | x | x | x | x | x | x | x | X | X | X | X |
|  | 10 | x | x |  | x | x | x | x | x | x | X | X | X | X |
|  | 11 | x | x | x |  | x | x | x | x | x | X | X | X | X |
|  | 12 | x | x | x | x |  | x | x | x | x | X | X | X | X |
|  | 13 | x | x | x | x | x |  | x | x | x | X | X | X | X |
|  | 14 | x | x | x | x | x | x |  | x | x | X | X | X | X |
|  | 15 | x | x | x | x | x | x | x |  | x | X | X | X | X |
|  | 16 | x | x | x | x | x | x | x | x |  | X | X | X | X |
|  | 21 | x | x | x | x | x | x | x | x | x |  | x | X | x |
|  | 25 | x | x | x | x | x | x | x | x | x | x |  | x | x |
|  | 26 | x | x | x | x | x | x | x | x | x | x | x |  | x |
|  | 27 | x | x | x | x | x | x | x | x | x | x | x | x |  |

In some embodiments of any of the aspects, a composition described herein can comprise two or more different engineered liver regenerative factor mRNAs of a single liver regenerative factor, e.g., two different GH engineered liver regenerative factor mRNAs.

In some embodiments of any of the aspects, the at least one liver regenerative factor is selected from the group consisting of VEGFA; HGF; GH; and EGF. In some embodiments of any of the aspects, the at least one liver regenerative factor is selected from the group consisting of: HGF; GH; EGF; and p21. In some embodiments of any of the aspects, the at least one liver regenerative factor is selected from the group consisting of: HGF; GH; and EGF. In some embodiments of any of the aspects, the at least one liver regenerative factor is selected from the group consisting of: VEGFA; HGF; GH; IGF-1; EGF; STAT5b; p21; CNNTB1; YAP; WNT2; and WNT9b.

In some embodiments of any of the aspects, the at least one liver regenerative factor mRNA (or engineered liver regenerative factor mRNA) is selected from the group consisting of: VEGFA mRNA; HGF mRNA; GH mRNA; and EGF mRNA. In some embodiments of any of the aspects, the at least one liver regenerative factor mRNA (or engineered liver regenerative factor mRNA) is selected from the group consisting of: HGF mRNA; GH mRNA; EGF mRNA; and p21 mRNA. In some embodiments of any of the aspects, the at least one liver regenerative factor mRNA (or engineered liver regenerative factor mRNA) is selected from the group consisting of: HGF mRNA; GH mRNA; and EGF mRNA. In some embodiments of any of the aspects, the at least one liver regenerative factor mRNA (or engineered liver regenerative factor mRNA) is selected from the group consisting of: VEGFA mRNA; HGF mRNA; GH mRNA; IGF-1 mRNA; EGF mRNA; STAT5b mRNA; p21 mRNA; CNNTB1 mRNA; YAP mRNA; WNT2 mRNA; and WNT9b mRNA.

In some embodiments of any of the aspects, the at least one liver regenerative factor is selected from the group consisting of: VEGF165; HGF; GH; and EGF. In some embodiments of any of the aspects, the at least one liver regenerative factor is selected from the group consisting of: VEGF165; HGF; GH; IGF-1; EGF; STAT5b; p21; CNNTB1; YAP; WNT2; and WNT9b.

In some embodiments of any of the aspects, the at least one liver regenerative factor mRNA (or engineered liver regenerative factor mRNA) is selected from the group consisting of: VEGF165 mRNA; HGF mRNA; GH mRNA; and EGF mRNA. In some embodiments of any of the aspects, the at least one liver regenerative factor is selected from the group consisting of: VEGF165 mRNA; HGF mRNA; GH mRNA; IGF-1 mRNA; EGF mRNA; STAT5b mRNA; p21 mRNA; CNNTB1 mRNA; YAP mRNA; WNT2 mRNA; and WNT9b mRNA.

In some embodiments of any of the aspects, the at least one liver regenerative factor does not comprise VEGFA. In some embodiments of any of the aspects, the at least one liver regenerative factor does not comprise VEGF165.

As described herein, the nucleosides of a liver regenerative factor mRNA can also be engineered, e.g., modified to provide improved performance relative to wild-type mRNAs. In some embodiments of any of the aspects, an engineered liver regenerative factor mRNA can comprise at least one modified nucleoside. In one aspect of any of the embodiments, described herein is a composition comprising at least one liver regenerative factor mRNA (e.g., having a naturally-occurring mRNA sequence) comprising at least one modified nucleoside.

As used herein, "modified nucleoside" refers to a nucleoside that is not naturally-occurring, e.g., a not naturally-occurring sugar and/or nucleobase. Exemplary modified sugars can include, e.g., one of the following at the 2' position: OH; F; O-, S-, or N-alkyl; O-, S-, or N-alkenyl; O-, S- or N-alkynyl; or O-alkyl-O-alkyl, wherein the alkyl, alkenyl and alkynyl may be substituted or unsubstituted C1 to C10 alkyl or C2 to C10 alkenyl and alkynyl. Exemplary suitable modifications include O[(CH2)nO] mCH3, O(CH2) nOCH3, O(CH2)nNH2, O(CH2)nCH3, O(CH2)nONH2, and O(CH2)nON[(CH2)nCH3)]2, where n and m are from 1 to about 10. In some embodiments of any of the aspects, a modified nucleoside can include one of the following at the 2' position: C1 to C10 lower alkyl, substituted lower alkyl, alkaryl, aralkyl, O-alkaryl or O-aralkyl, SH, SCH3, OCN, Cl, Br, CN, CF3, OCF3, SOCH3, SO2CH3, ONO2, NO2, N3, NH2, heterocycloalkyl, heterocycloalkaryl, aminoalkylamino, polyalkylamino, substituted silyl, an RNA cleaving group, a reporter group, an intercalator, a group for improving the pharmacokinetic properties of an mRNA, or a group for improving the pharmacodynamic properties of an mRNA, and other substituents having similar properties. In some embodiments of any of the aspects, the modified nucleoside includes a 2' methoxyethoxy (2'-O—CH2CH2OCH3, also known as 2'-O-(2-methoxyethyl) or 2'-MOE) (Martin et al., Helv. Chim. Acta, 1995, 78:486-504) i.e., an alkoxy-alkoxy group. Another exemplary modification is 2'-dimethylaminooxyethoxy, i.e., a O(CH2)2ON(CH3)2 group, also known as 2'-DMAOE and 2'-dimethylaminoethoxyethoxy (also known in the art as 2'-O-dimethylaminoethoxyethyl or 2'-DMAEOE), i.e., 2'-O—CH2-O—CH2-N(CH2)2.

Other modifications include 2'-methoxy (2'-OCH3), 2'-aminopropoxy (2'-OCH2CH2CH2NH2) and 2'-fluoro (2'-F). Modified nucleosides may also have sugar mimetics such as cyclobutyl moieties in place of the pentofuranosyl sugar.

A modified nucleoside can also include nucleobase (often referred to in the art simply as "base") modifications or substitutions. As used herein, "unmodified" or "natural" nucleobases include the purine bases adenine (A) and guanine (G), and the pyrimidine bases thymine (T), cytosine (C) and uracil (U). Modified nucleobases include other synthetic and natural nucleobases such as 5-methylcytosine (5-me-C), 5-hydroxymethyl cytosine, xanthine, hypoxanthine, 2-aminoadenine, 6-methyl and other alkyl derivatives of adenine and guanine, 2-propyl and other alkyl derivatives of adenine and guanine, 2-thiouracil, 2-thiothymine and 2-thiocytosine, 5-halouracil and cytosine, 5-propynyl uracil and cytosine, 6-azo uracil, cytosine and thymine, 5-uracil (pseudouracil), 4-thiouracil, 8-halo, 8-amino, 8-thiol, 8-thioalkyl, 8-hydroxyl anal other 8-substituted adenines and guanines, 5-halo, particularly 5-bromo, 5-trifluoromethyl and other 5-substituted uracils and cytosines, 7-methylguanine and 7-methyladenine, 8-azaguanine and 8-azaadenine, 7-deazaguanine and 7-deazaadenine and 3-deazaguanine and 3-deazaadenine.

In some embodiments of any of the aspects, a modified nucleoside can be pseudouridine, N1-methylpseudouridine, 2-thiouridine, 4'-thiouridine, 5-methylcytosine, 2-thio-1-methyl-1-deaza-pseudouridine, 2-thio-1-methyl-pseudouridine, 2-thio-5-aza-uridine, 2-thio-dihydropseudouridine, 2-thio-dihydrouridine, 2-thio-pseudouridine, 4-methoxy-pseudouridine, 4-thio-1-methyl-pseudouridine, 4-thio-pseudouridine, 5-aza-uridine, dihydropseudouridine, 5-methyluridine, pseudouridine, 5-methyluridine, 5-methoxyuridine, or 2'-O-methyluridine.

In some embodiments of any of the aspects, a modified nucleoside can be 2'-O-Methylpseudouridine-5'-Triphosphate; N1-Methylpseudouridine-5'-Triphosphate; N1-Methyl-2'-O-Methylpseudouridine-5'-Triphosphate; or 1-Methylpseudouridine. In some embodiments of any of the aspects, a modified nucleoside can be one-methylpseudouridine (m1Ψ)-5' triphosphate.

In some embodiments of any of the aspects, a modified nucleoside is a non-natural nucleoside. In some embodiments of any of the aspects, an engineered liver regenerative factor mRNA or liver regenerative factor mRNA described herein does not comprise a modified nucleoside, e.g., it comprises only naturally-occurring nucleosides.

In some embodiments of any of the aspects, a mRNA comprising at least one modified nucleoside comprises at least one one-methylpseudouridine (m1Ψ)-5'-triphosphate residue.

In some embodiments of any of the aspects, a mRNA comprises, relative to a reference sequence provided herein, the replacement of at least one uracil or thymine with a modified nucleoside. In some embodiments of any of the aspects, a mRNA comprises, relative to a reference sequence provided herein, the replacement of at least one uracil or thymine with one-methylpseudouridine (m1Ψ)-5'-triphosphate.

In some embodiments of any of the aspects, a mRNA comprises, relative to a reference sequence provided herein, the replacement of at least half of the uracils or thymines with modified nucleosides. In some embodiments of any of the aspects, a mRNA comprises, relative to a reference sequence provided herein, the replacement of at least half of the uracils or thymines with one-methylpseudouridine (m1Ψ)-5'-triphosphates.

In some embodiments of any of the aspects, a mRNA comprises, relative to a reference sequence provided herein, the replacement of each uracil or thymine with a modified nucleoside. In some embodiments of any of the aspects, a mRNA comprises, relative to a reference sequence provided herein, the replacement of each uracil or thymine with one-methylpseudouridine (m1Ψ)-5'-triphosphate.

In some embodiments of any of the aspects, a mRNA comprises a m7G cap.

The preparation of the modified nucleosides described above are well known in the art.

In some embodiments of any of the aspects, contacting a cell or administering to a subject one of the compositions or combinations described herein, e.g., comprising an engineered liver regenerative factor mRNA and/or liver regenerative factor mRNA comprising at least one modified nucleoside increases the protein level of the liver regenerative factor in the cell/subject. In some embodiments of any of the aspects, contacting a cell or administering to a subject one of the compositions or combinations described herein, e.g., comprising an engineered liver regenerative factor mRNA and/or liver regenerative factor mRNA comprising at least one modified nucleoside increases the protein level of the liver regenerative factor in the liver of the subject. In some embodiments of any of the aspects, the increase is relative to the absence of, or prior to, the contacting or administering. Methods of measuring the protein level of a factor are well known in the art and include, e.g, immunochemistry, immunohistochemistry ("IHC"), immunocytochemistry ("ICC"), Western blot, ELISA, and LFIA methods or the like.

In some embodiments of any of the aspects, the composition further comprises a carrier or scaffold complexed with the at least one engineered liver regenerative factor mRNA (comprising or not comprising at least one modified nucleoside) and/or the at least one liver regenerative factor mRNA comprising at least one modified nucleoside. Carrier or scaffold materials suitable for use in therapeutic compositions are known in the art and can include, but are not limited to, a nanoparticle; a matrix; a hydrogel; and a biomaterial, biocompatible, and/or biodegradable scaffold material.

In some embodiments of any of the aspects, the carrier is, comprises, or consists of a nanoparticle. As used herein, the term "nanoparticle" refers to particles that are on the order of about 10-9 or one to several billionths of a meter. The term "nanoparticle" includes nanospheres; nanorods; nanoshells; and nanoprisms; these nanoparticles may be part of a nanonetwork.

As used herein, the term "matrix" refers to a 3-dimensional structure comprising the components of a composition described herein (e.g., mRNA). Non-limiting examples of matrix structures include foams; hydrogels; electrospun fibers; gels; fiber mats; sponges; 3-dimensional scaffolds; non-woven mats; woven materials; knit materials; fiber bundles; and fibers and other material formats (See, e.g., Rockwood et al. Nature Protocols 2011 6:1612-1631 and US Patent Publications 2011/0167602; 2011/0009960; 2012/0296352; and U.S. Pat. No. 8,172,901; each of which is incorporated by reference herein in its entirety). The structure of the matrix can be selected by one of skill in the art depending upon the intended application of the composition, e.g., electrospun matrices can have greater surface area than foams.

In some embodiments, the carrier is a hydrogel. As used herein, the term "hydrogel" refers to a three-dimensional polymeric structure that is insoluble in water but which is capable of absorbing and retaining large quantities of water to form a stable, often soft and pliable, structure. In some embodiments, water can penetrate in between the polymer chains of the polymer network, subsequently causing swelling and the formation of a hydrogel. In general, hydrogels are superabsorbent. Hydrogels have many desirable properties for biomedical applications. For example, they can be made nontoxic and compatible with tissue, and they are highly permeable to water, ions, and small molecules. Hydrogels are super-absorbent (they can contain over 99% water) and can be comprised of natural (e.g., silk) or synthetic polymers, e.g., PEG.

As used herein, "biomaterial" refers to a material that is biocompatible and biodegradable. As used herein, the term "biocompatible" refers to substances that are not toxic to cells. In some embodiments, a substance is considered to be "biocompatible" if its addition to cells in vitro results in less than or equal to approximately 20% cell death. In some embodiments, a substance is considered to be "biocompatible" if its addition to cells in vivo does not induce inflammation and/or other adverse effects in vivo. As used herein, the term "biodegradable" refers to substances that are degraded under physiological conditions. In some embodiments, a biodegradable substance is a substance that is broken down by cellular machinery. In some embodiments, a biodegradable substance is a substance that is broken down by chemical processes.

The term "nanoparticles" also encompasses liposomes and lipid particles having the size of a nanoparticle. Exemplary liposomes can comprise, e.g., DSPC, DPPC, DSPG, Cholesterol, hydrogenated soy phosphatidylcholine, soy phosphatidyl choline, methoxypolyethylene glycol (mPEG-DSPE) phosphatidyl choline (PC), phosphatidyl glycerol (PG), distearoylphosphatidylcholine, and combinations thereof. In some embodiments of any of the aspects, the carrier is, comprises, or consists of a lipid nanoparticle (LNP). Lipid nanoparticles can comprise multiple components, including, e.g., ionizable lipids (such as MC3, DLin-MC3-DMA, ALC-0315, or SM-102), pegylated lipids (such as PEG2000-C-DMG, PEG2000-DMG, ALC-0159), phospholipids (such as DSPC), and cholesterol.

Generally, the lipid nanoparticles have a mean diameter selected to provide an intended therapeutic effect. Accordingly, in some aspects, the lipid nanoparticle has a mean diameter from about 30 nm to about 150 nm, more typically from about 50 nm to about 150 nm, more typically about 60 nm to about 130 nm, more typically about 70 nm to about 110 nm, most typically about 85 nm to about 105 nm, and preferably about 100 nm. In some aspects, the disclosure provides for lipid particles that are larger in relative size to common nanoparticles and about 150 to 250 nm in size. Lipid nanoparticle particle size can be determined by quasi-elastic light scattering using, for example, a Malvern Zetasizer Nano ZS (Malvern, UK) system.

Depending on the intended use of the lipid particles, the proportions of the components can be varied and the delivery efficiency of a particular formulation can be measured using, for example, an endosomal release parameter (ERP) assay.

The mRNA can be complexed with the lipid portion of the particle or encapsulated in the lipid position of the lipid nanoparticle. In some embodiments, the mRNA can be fully encapsulated in the lipid position of the lipid nanoparticle, thereby protecting it from degradation by a nuclease, e.g., in an aqueous solution. In some embodiments, the mRNA in the lipid nanoparticle is not substantially degraded after exposure of the lipid nanoparticle to a nuclease at 37° C. for at least about 20, 30, 45, or 60 minutes. In some embodiments, the mRNA in the lipid nanoparticle is not substantially degraded after incubation of the particle in serum at 37° C. for at least about 30, 45, or 60 minutes or at least about 2, 3, 4, 5, 6, 7, 8, 9, 10, 12, 14, 16, 18, 20, 22, 24, 26, 28, 30, 32, 34, or 36 hours.

In certain embodiments, the lipid nanoparticles are substantially non-toxic to mammals such as humans.

In some embodiments, lipid nanoparticles are solid core particles that possess at least one lipid bilayer. In other embodiments, the lipid nanoparticles have a non-bilayer structure, i.e., a non-lamellar (i.e., non-bilayer) morphology. Without limitations, the non-bilayer morphology can include, for example, three dimensional tubes, rods, cubic symmetries, etc. The non-lamellar morphology (i.e., non-bilayer structure) of the lipid particles can be determined using analytical techniques known to and used by those of skill in the art. Such techniques include, but are not limited to, Cryo-Transmission Electron Microscopy ("Cryo-TEM"), Differential Scanning calorimetry ("DSC"), X-Ray Diffraction, etc. . . . . For example, the morphology of the lipid nanoparticles (lamellar vs. non-lamellar) can readily be assessed and characterized using, e.g., Cryo-TEM analysis as described in US2010/0130588, content of which is incorporated herein by reference in its entirety.

In some further embodiments, the lipid nanoparticles having a non-lamellar morphology are electron dense.

In embodiments, the lipid nanoparticle is either unilamellar or multilamellar in structure. In some aspects, the disclosure provides for a lipid nanoparticle formulation that comprises multi-vesicular particles and/or foam-based particles.

The lipid nanoparticle may have positive or negative zeta potential. In various embodiments, the lipid nanoparticle has a positive zeta potential.

By controlling the composition and concentration of the lipid components, one can control the rate at which the lipid conjugate exchanges out of the lipid particle and, in turn, the rate at which the lipid nanoparticle becomes fusogenic. In addition, other variables including, e.g., pH, temperature, or ionic strength, can be used to vary and/or control the rate at which the lipid nanoparticle becomes fusogenic. Other methods which can be used to control the rate at which the lipid nanoparticle becomes fusogenic will become apparent to those of skill in the art upon reading this disclosure. Also, by controlling the composition and concentration of the lipid conjugate, one can control the lipid particle size.

The pKa of formulated cationic lipids can be correlated with the effectiveness of the LNPs for delivery of nucleic acids (see Jayaraman et al, Angewandte Chemie, International Edition (2012), 51(34), 8529-8533; Semple et al, Nature Biotechnology 28, 172-176 (2010), both of which are incorporated by reference in their entirety). The preferred range of pKa is ~5 to ~7. The pKa of the cationic lipid can be determined in lipid nanoparticles using an assay based on fluorescence of 2-(p-toluidino)-6-napthalene sulfonic acid (TNS).

Encapsulation of mRNA in lipid particles can be determined by performing a membrane-impermeable fluorescent dye exclusion assay, which uses a dye that has enhanced fluorescence when associated with nucleic acid, for example, an Oligreen® assay or PicoGreen® assay. Generally, encapsulation is determined by adding the dye to the lipid particle formulation, measuring the resulting fluorescence, and comparing it to the fluorescence observed upon addition of a small amount of nonionic detergent. Detergent-mediated disruption of the lipid bilayer releases the encapsulated mRNA, allowing it to interact with the membrane-impermeable dye. Encapsulation of mRNA can be calculated as $E=(I_0-I)/I_0$, where I and $I_0$ refers to the fluorescence intensities before and after the addition of detergent.

Lipid nanoparticles can form spontaneously upon mixing of mRNA and the lipid(s). Depending on the desired particle size distribution, the resultant nanoparticle mixture can be extruded through a membrane (e.g., 100 nm cut-off) using, for example, a thermobarrel extruder, such as Lipex Extruder (Northern Lipids, Inc). In some cases, the extrusion step can be omitted. Ethanol removal and simultaneous buffer exchange can be accomplished by, for example, dialysis or tangential flow filtration.

Generally, lipid nanoparticles can be formed by any method known in the art including. For example, the lipid nanoparticles can be prepared by the methods described, for example, in US2013/0037977, US2010/0015218, US2013/0156845, US2013/0164400, US2012/0225129, and US2010/0130588, content of each of which is incorporated herein by reference in its entirety. In some embodiments, lipid nanoparticles can be prepared using a continuous mixing method, a direct dilution process, or an in-line dilution process. The processes and apparatuses for apparatuses for preparing lipid nanoparticles using direct dilution and in-line dilution processes are described in US2007/0042031, content of which is incorporated herein reference in its entirety. The processes and apparatuses for preparing lipid nanoparticles using step-wise dilution processes are described in US2004/0142025, content of which is incorporated herein reference in its entirety.

In one non-limiting example, the lipid nanoparticles can be prepared by an impinging jet process. Generally, the particles are formed by mixing lipids dissolved in alcohol (e.g., ethanol) with mRNA dissolved in a buffer, e.g., a citrate buffer, a sodium acetate buffer, a sodium acetate and magnesium chloride buffer, a malic acid buffer, a malic acid and sodium chloride buffer, or a sodium citrate and sodium chloride buffer. The mixing ratio of lipids to mRNA can be about 45-55% lipid and about 65-45% mRNA.

The lipid solution can contain a condensing agent (e.g., a cationic lipid), a non-cationic lipid (e.g., a phospholipid, such as DSPC), PEG or PEG conjugated molecule (e.g., PEG-lipid), and a sterol (e.g., cholesterol) at a total lipid concentration of 5-30 mg/mL, more likely 5-15 mg/mL, most likely 9-12 mg/mL in an alcohol, e.g., in ethanol.

In the lipid solution, mol ratio of the lipids can range from about 25-98% for the cationic lipid, preferably about 35-65%; about 0-15% for the non-ionic lipid, preferably about 0-12%; about 0-15% for the PEG or PEG conjugated molecule, preferably about 1-6%; and about 0-75% for the sterol, preferably about 30-50%.

The mRNA solution can comprise the mRNA at a concentration range from 0.3 to 1.0 mg/mL, preferably 0.3-0.9 mg/mL in buffered solution, with pH in the range of 3.5-5.

For forming the LNPs, the two liquids are heated to a temperature in the range of about 15-40° C., preferably about 30-40° C., and then mixed, for example, in an impinging jet mixer, instantly forming the LNP. The mixing flow rate can range from 10-600 ml/min. The tube ID can have a range from 0.25 to 1.0 mm and a total flow rate from 10-600 mL/min. The combination of flow rate and tubing ID can have the effect of controlling the particle size of the LNPs between 30 and 200 nm. The solution can then be mixed with a buffered solution at a higher pH with a mixing ratio in the range of 1:1 to 1:3 vol:vol, preferably about 1:2 vol:vol. If needed this buffered solution can be at a temperature in the range of 15-40° C. or 30-40° C. The mixed LNPs can then undergo an anion exchange filtration step. Prior to the anion exchange, the mixed LNPs can be incubated for a period of time, for example 30 mins to 2 hours. The temperature during incubating can be in the range of 15-40° C. or 30-40° C. After incubating the solution is filtered through a filter, such as a 0.8 μm filter, containing an anion exchange separation step. This process can use tubing IDs ranging from 1 mm ID to 5 mm ID and a flow rate from 10 to 2000 mL/min.

After formation, the LNPs can be concentrated and diafiltered via an ultrafiltration process where the alcohol is removed and the buffer is exchanged for the final buffer solution, for example, phosphate buffered saline (PBS) at about pH 7, e.g., about pH 6.9, about pH 7.0, about pH 7.1, about pH 7.2, about pH 7.3, or about pH 7.4.

The ultrafiltration process can use a tangential flow filtration format (TFF) using a membrane nominal molecular weight cutoff range from 30-500 KD. The membrane format is hollow fiber or flat sheet cassette. The TFF processes with the proper molecular weight cutoff can retain the LNP in the retentate and the filtrate or permeate contains the alcohol; citrate buffer and final buffer wastes. The TFF process is a multiple step process with an initial concentration to a mRNA concentration of 1-3 mg/mL. Following concentration, the LNPs solution is diafiltered against the final buffer for 10-20 volumes to remove the alcohol and perform buffer exchange. The material can then be concentrated an additional 1-3 fold. The concentrated LNP solution can be sterile filtered.

In some embodiments of any of the aspects, the compositions comprising mRNA as described herein are formulated in a lipid vesicle that have crosslinks between functionalized lipid bilayers.

In some embodiments, the compositions comprising mRNA(s) as described herein are formulated in a lipid-polycation complex. The formation of the lipid-polycation complex can be accomplished by methods known in the art and/or as described in U.S. Pub. No. 20120178702, herein incorporated by reference in its entirety. As a non-limiting example, the polycation can include a cationic peptide or a polypeptide such as, but not limited to, polylysine, polyornithine and/or polyarginine. In another embodiment, the polynucleotides, primary constructs and/or mRNA can be formulated in a lipid-polycation complex which can further include a neutral lipid such as, but not limited to, cholesterol or dioleoyl phosphatidylethanolamine (DOPE).

The selection of the liposome formulation can be influenced by, for example, the selection of the cationic lipid component, the degree of cationic lipid saturation, the nature of the PEGylation, ratio of all components and biophysical parameters such as size. In some embodiments, the ratio of PEG in the LNP formulations can be increased or decreased and/or the carbon chain length of the PEG lipid can be modified from C14 to C18 to alter the pharmacokinetics and/or biodistribution of the LNP formulations. The cationic lipid can be selected from any lipid known in the art such as, but not limited to, DLin-MC3-DMA, DLin-DMA, C12-200 and DLin-KC2-DMA.

In some embodiments, the cationic lipid can be selected from, but not limited to, a cationic lipid described in International Publication Nos. WO2012040184, WO2011153120, WO2011149733, WO2011090965, WO2011043913, WO2011022460, WO2012061259, WO2012054365, WO2012044638, WO2010080724, WO201021865 and WO2008103276, U.S. Pat. Nos. 7,893, 302 and 7,404,969 and US Patent Publication No. US20100036115; each of which is herein incorporated by reference in their entireties. In another embodiment, the cationic lipid is selected from formula A described in International Publication Nos. WO2012040184, WO2011153120, WO2011149733, WO2011090965, WO2011043913, WO2011022460, WO2012061259, WO2012054365 and WO2012044638; each of which is herein incorporated by reference in their entireties. In other embodiments, the cationic lipid is selected from, formula CLI-CLXXIX of International Publication No. WO2008103276, formula CLI-CLXXIX of U.S. Pat. No. 7,893,302, formula CLI-CLXXXXII of U.S. Pat. No. 7,404, 969 and formula I-VI of US Patent Publication No. 0520100036115; each of which is herein incorporated by reference in their entireties. As non-limiting examples, the cationic lipid is selected from (20Z,23Z)—N,N-dimethyl-nonacosa-20,23-dien-10-amine, (17Z,20Z)—N,N-dimemyl-hexacosa-17,20-dien-9-amine, (1Z,19Z)—N5N.about.dimethylpentacosa.about.16,19-dien-8-amine, (13Z,16Z)—N,N-dimethyldocosa-13J16-dien-5-amine, (12Z,15Z)—NJN-dimethylhenicosa-12,15-dien-4-amine, (14Z,17Z)—N,N-dimethyltricosa-14,17-dien-6-amine, (15Z,18Z)—N,N-dimethyltetracosa-15,18-dien-7-amine, (18Z,21Z)—N,N-dimethylheptacosa-18,21-dien-10-amine, (15Z,18Z)—N,N-dimethyltetracosa-15,18-dien-5-amine, (14Z,17Z)—N,N-dimethyltricosa-14,17-dien-4-amine, (19Z,22Z)—N,N-dimeihyloctacosa-19,22-dien-9-amine, (18Z,21Z)—N,N-dimethylheptacosa-18,21-dien-8-amine, (17Z,20Z)—N,N-dimethylhexacosa-17,20-dien-7-amine, (16Z;19Z)—N,N-dimethylpentacosa-16,19-dien-6-amine, (22Z,25Z)—N,N-dimethylhentriaconta-22,25-dien-10-amine, (21Z,24Z)—N;N-dimetyltriaconta-21,24-dien-9-amine, (18Z)—N,N-dimethylheptacos-18-en-10-amine, (17Z)—N,N-dimethylhexacos-17-en-9-amine, (19Z,22Z)—NJN-dimethyloctacosa-19,22-dien-7-amine, N,N-dimethyl-heptacosan-10-amine, (20Z,23Z)—N-ethyl-N-methylnona-cosa-20J23-dien-10-amine, 1-[(11Z,14Z)-1-nonylicosa-11, 14-dien-1-yl] pyrrolidine, (20Z)—N,N-dimethylheptacos-20-en-10-amine, (15Z)—N,N-dimethyl eptacos-15-en-10-amine, (14Z)—N,N-dimethylnonacos-14-en-10-amine, (17Z)—N,N-dimethylnonacos-17-en-10-amine, (24Z)—N, N-dimethyltritriacont-24-en-10-amine, (20Z)—N,N-dim-ethylnonacos-20-en-10-amine, (22Z)—N,N-dimethylhen-triacont-22-en-10-amine, (16Z)—N,N-dimethylpentacos-16-en-8-amine, (12Z,15Z)—N,N-dimethyl-2-nonylhenicosa-12,15-dien-1-amine, (13Z,16Z)—N,N-dimethyl-3-nonyldocosa-13,16-dien-1-amine, N,N-dimethyl-1-[(1 S,2R)-2-octylcyclopropyl] eptadecan-8-amine, 1-[(1S,2R)-2-hexylcyclopropyl]-N,N-dimethylnonadecan-10-amine, N,N-dimethyl-1-[(1S,2R)-2-octylcyclopropyl]nonadecan-10-amine, N,N-dimethyl-21.about.[(1S,2R)-2-octylcyclopropyl]henicosan-1 O-amine, N,N-dimethyl-1-[(1 S,2S)-2-{[(1R,2R)-2-pentyl-cyclopropyl]methyl} cyclopropyl]nonadecan-10-amine, N,N-dimethyl-1-[(1S,2R)-2-octylcyclopropyl]hexadecan-8-amine, N,N-dimethyH-[(1R,2S)-2-undecylcyclopropyl]tet-radecan-5-amine, N,N-dimethyl-3-{7-[(1S,2R)-2-octylcy-clopropyl]heptyl} dodec-an-1-amine, 1-[(1R,2S)-2-heptylcyclopropy 1]-N,N-dimethyloctadecan-9-amine, 1-[(1S,2R)-2-decylcyclopropyl]-N,N-dimethylpentadecan-6-amine, N,N-dimethyl-1-[(1S,2R)-2-octylcyclopropyl]pen-tadecan-8-amine, R—N,N-dimethyl-1-[(9Z,12Z)-octadeca-9,12-dien-1-yloxy]-3-(octyloxy)propa-n-2-amine, S—N,N-dimethyl-1-[(9Z,12Z)-octadeca-9,12-dien-1-yloxy]-3-(octyloxy)propan-2-amine, 1-{2-[(9Z,12Z)-octadeca-9,12-dien-1-yloxy]-1-[(octyloxy) methyl]ethyl}pyrrolidine, (2S)—N,N-dimethyl-1-[(9Z,12Z)-octadeca-9,12-dien-1-yloxy]-3-[(5Z)-oct-5-en-1-yloxy]propan-2-amine, 1-{2-[(9Z,12Z)-octadeca-9,12-dien-1-yloxy]-1-[(octyloxy) methyl]ethyl}azetidine, (2S)-1-(hexyloxy)-N,N-dimethyl-3-[(9Z,12Z)-octadeca-9,12-dien-1-yloxy]pro-pan-2-amine, (2S)-1-(heptyloxy)-N,N-dimethyl-3-[(9Z,12Z)-octadeca-9, 12-dien-1-yloxy]pr-opan-2-amine, N,N-dimethyl-1-(nony-loxy)-3-[(9Z,12Z)-octadeca-9,12-dien-1-yloxy]propan-2-amine, N,N-dimethyl-1-[(9Z)-octadec-9-en-1-yloxy]-3-(octyloxy)propan-2-am-me (Compound 9); (2S)—N,N-dimethyl-1-[(6Z,9Z,12Z)-octadeca-6,9,12-trien-1-yloxy]-3-(octyl-oxy)propan-2-amine, (2S)-1-[(11Z,14Z)-icosa-11,14-dien-1-yloxy]-N,N-dimethyl-3-(pentyloxy)pro-pan-2-amine, (2S)-1-(hexyloxy)-3-[(11Z,14Z)-icosa-11,14-dien-1-yloxy]-N,N-dimethylprop-an-2-amine, 1-[(11Z,14Z)-icosa-11,14-dien-1-yloxy]-N,N-dimethyl-3-(octyloxy)propan-2-amine, 1-[(13Z,16Z)-docosa-13,16-dien-1-yloxy]-N,N-dimethyl-3-(octyloxy)pr-opan-2-amine, (2S)-1-[(13Z,16Z)-docosa-13,16-dien-1-yloxy]-3-(hexyloxy)-N,N-dimethylpro-pan-2-amine, (2S)-1-[(13Z)-docos-13-en-1-yloxy]-3-(hexyloxy)-N,N-dimethylpropan-2-amin-e, 1-[(13Z)-docos-13-en-1-yloxy]-N,N-dimethyl-3-(octyloxy) propan-2-amine, 1-[(9Z)-hexadec-9-en-1-yloxy]-N,N-dim-ethyl-3-(octyloxy)propan-2-amine, (2R)—N,N-dimethyl-H (1-metoyloctyl)oxy]-3-[(9Z,12Z)-octadeca-9,12-dien-1-yloxy]propan-2-amine, (2R)-1-[(3,7-dimethyloctyl)oxy]-N, N-dimethyl-3-[(9Z,12Z)-octadeca-9,12-di-en-1-yloxy] propan-2-amine, N,N-dimethyl-1-(octyloxy)-3-({8-[(1S, 2S)-2-{[(1R,2R)-2-pentylcyclopropyl]- methyl}cyclopropyl]octyl}oxy)propan-2-amine, N,N-dimethyl-1-{[8-(2-oclylcyclopropyl)octyl]oxy}-3-(octyloxy)propan-2-am-ine and (11E,20Z,23Z)—N;N-dimethylnonacosa-11,20,2-trien-10-amine or a pharmaceutically acceptable salt or stereoisomer thereof.

In some embodiments, the LNP formulations of the compositions comprising mRNA(s) as described herein can contain PEG-c-DOMG between and including 1.5-3% lipid molar ratio. In some embodiments, the compositions comprising the mRNA(s) described herein include at least one of the PEGylated lipids described in International Publication No. 2012099755, herein incorporated by reference. In some embodiments, the LNP formulation contains PEG-DMG 2000 (1,2-dimyristoyl-sn-glycero-3-phophoethanolamine-N-[methoxy(polyethylene glycol)-2000), a cationic lipid known in the art, and at least one other component. As a non-limiting example, the LNP formulation can contain PEG-DMG 2000, DLin-DMA, DSPC and cholesterol.

In some embodiments, the LNP formulation can be formulated by the methods described in International Publication Nos. WO2011127255 or WO2008103276, each of which is herein incorporated by reference in their entireties. As a non-limiting example, modified RNA can be encapsulated in LNP formulations as described in WO2011127255 and/or WO2008103276; each of which is herein incorporated by reference in their entireties.

In some embodiments, the LNP formulations comprise a polycationic composition. In some embodiments, the LNP formulations additionally comprise a permeability enhancer molecule. Non-limiting permeability enhancer molecules are described in US Patent Publication No. US20050222064; herein incorporated by reference in its entirety.

In some embodiments of any of the aspects, lipid nanoparticle formulations for use with compositions comprising mRNA(s) as described herein can be improved by replacing the cationic lipid with a biodegradable cationic lipid, which is known as a rapidly eliminated lipid nanoparticle (reLNP). The rapid metabolism of the rapidly eliminated lipids can improve the tolerability and therapeutic index of the lipid nanoparticles. Inclusion of an enzymatically degraded ester linkage can improve the degradation and metabolism profile of the cationic component, while still maintaining the activity of the reLNP formulation. The ester linkage can be internally located within the lipid chain or it can be terminally located at the terminal end of the lipid chain. The internal ester linkage can replace any carbon in the lipid chain. The internal ester linkage can be located on either side of the saturated carbon.

In some embodiments, compositions comprising mRNA(s) are formulated as a lipoplex, such as, without limitation, the ATUPLEX system, the DACC system, the DBTC system and other siRNA-lipoplex technology from Silence Therapeutics (London, United Kingdom), STEMFECT from STEMGENT (Cambridge, Mass.), and polyethylenimine (PEI) or protamine-based targeted and non-targeted delivery of nucleic acids (Aleku et al. Cancer Res. 2008 68:9788-9798; Strumberg et al. Int J Clin Pharmacol Ther 2012 50:76-78; Santel et al., Gene Ther 2006 13:1222-1234; Santel et al., Gene Ther 2006 13:1360-1370; Gutbier et al., Pulm Pharmacol. Ther. 2010 23:334-344; Kaufmann et al. Microvasc Res 2010 80:286-293 Weide et al. J Immunother. 2009 32:498-507; Weide et al. J Immunother. 2008 31:180-188; Pascolo Expert Opin. Biol. Ther. 4:1285-1294; Fotin-Mleczek et al., 2011 J. Immu-nother. 34:1-15; Song et al., Nature Biotechnol. 2005, 23:709-717; Peer et al., Proc Natl Acad Sci USA. 2007 6; 104:4095-4100; deFougerolles Hum Gene Ther. 2008 19:125-132; all of which are incorporated herein by reference in their entireties).

In some embodiments, the compositions comprising an mRNA(s) as described herein are formulated as a solid lipid nanoparticle. A solid lipid nanoparticle (SLN) can be spherical with an average diameter be-tween 10 to 1000 nm. SLN possess a solid lipid core matrix that can solubilize lipophilic molecules and can be stabilized with surfactants and/or emulsifiers. The lipid nanoparticle can be a self-assembly lipid-polymer nanoparticle (see Zhang et al., ACS Nano, 2008, 2 (8), pp 1696-1702; herein incorporated by reference in its entirety).

Liposomes, lipoplexes, or lipid nanoparticles can be used to improve the efficacy of protein production as these formulations can increase cell transfection by the compositions comprising mRNA(s) as described herein; and/or increase the translation of encoded protein. One such example involves the use of lipid encapsulation to enable the effective systemic delivery of polyplex plasmid DNA (Heyes et al., Mol Ther. 2007 15:713-720; herein incorporated by reference in its entirety). The liposomes, lipoplexes, or lipid nanoparticles can also be used to increase the stability of the compositions comprising mRNA(s) as described herein.

The compositions comprising RNA(s) as described herein can, in some embodiments, be encapsulated into a lipid nanoparticle or a rapidly eliminating lipid nanoparticle, and the lipid nanoparticles or a rapidly eliminating lipid nanoparticle may then be encapsulated into a polymer, hydrogel and/or surgical seal-ant described herein and/or known in the art. As a non-limiting example, the polymer, hydrogel or surgical sealant may be PLGA, ethylene vinyl acetate (EVAc), poloxamer, GELSITE (Nanotherapeutics, Inc. Alachua, Fla.), HYLENEX (Halozyme Therapeutics, San Diego Calif.), surgical sealants such as fibrinogen polymers (Ethicon Inc. Cornelia, Ga.), TISSELL (Baxter International, Inc Deerfield, Ill.), PEG-based sealants, and COSEAL. (Baxter International, Inc Deerfield, Ill.).

Compositions comprising mRNA(s) as described herein can include formulations in which the mRNA(s) is complexed or associated with one or more cationic polymers, including but not limited to polyethyleneimine and cationic dendrimers.

The compositions comprising mRNA(s) as described herein can be encapsulated in a therapeutic nanoparticle. Therapeutic nanoparticles can be formulated by methods described herein and known in the art such as, but not limited to, International Pub Nos. WO2010005740, WO2010030763, WO2010005721, WO2010005723, WO2012054923, US Pub. Nos. US20110262491, US20100104645, US20100087337, US20100068285, US20110274759, US20100068286, and U.S. Pat. No. 8,206, 747; the contents of each of which are herein incorporated by reference in their entireties.

The nanoparticles used with the compositions comprising mRNA(s) as described herein can comprise a polymeric matrix. As a non-limiting example, the nanoparticle can comprise two or more polymers such as, but not limited to, polyethylenes, polycarbonates, polyanhydrides, polyhydroxyacids, polypropylfumerates, polycaprolactones, polyamides, polyacetals, polyethers, polyesters, poly(orthoesters), pol-ycyanoacrylates, polyvinyl alcohols, polyurethanes, polyphosphazenes, polyacrylates, polymethacry-lates, polycyanoacrylates, polyureas, polystyrenes, polyamines, polylysine, poly(ethylene imine), poly(serine ester), poly(L-lactide-co-L-lysine), poly(4-hydroxy-L-proline ester) or combinations thereof.

The nanoparticles used with the compositions comprising mRNA(s) as described herein can comprise at least one acrylic polymer. Acrylic polymers include but are not limited to, acrylic acid, methacrylic acid, acrylic acid and methacrylic acid copolymers, methyl methacrylate copolymers, ethoxyethyl meth-acrylates, cyanoethyl methacrylate, amino alkyl methacrylate copolymer, poly(acrylic acid), poly(methacrylic acid), polycyanoacrylates and combinations thereof.

The nanoparticles used with compositions comprising mRNA(s) as described herein can comprise at least one cationic polymer described herein and/or known in the art.

The nanoparticles used with the compositions comprising mRNA(s) as described herein can comprise at least one amine-containing polymer such as, but not limited to polylysine, polyethylene imine, poly(amidoamine) dendrimers and combinations thereof.

The nanoparticles used with the compositions comprising mRNA(s) as described herein can comprise at least one degradable polyester that can contain polycationic side chains. Degradable polyesters include, but are not limited to, poly(serine ester), poly(L-lactide-co-L-lysine), poly(4-hydroxy-L-proline ester), and combinations thereof. In another embodiment, the degradable polyesters can include a PEG conjugation to form a PEGylated polymer.

The compositions comprising mRNA(s) as described herein can be encapsulated in, linked to and/or associated with synthetic nanocarriers. The synthetic nanocarriers can be formulated using methods known in the art and/or described herein. As a non-limiting example, the synthetic nanocarriers can be formulated by the methods described in International Pub Nos. WO2010005740, WO2010030763 and US Pub. Nos. US20110262491, US20100104645 and US20100087337, each of which is herein incorporated by reference in their entireties. In some embodiments, the synthetic nanocarriers can contain reactive groups to release the compositions comprising mRNA(s) as described herein (see International Pub. No. WO20120952552 and US Pub No. US20120171229, each of which is herein incorporated by reference in their entireties).

In some embodiments of any of the aspects, the LNP comprises at least one ionizable lipid, at least one phospholipid, and at least one polyethylene glycol (PEG)-lipid. In some embodiments of any of the aspects, the LNP comprises at least one ionizable lipid, at least one phospholipid, at least one structured lipid, and at least one polyethylene glycol (PEG)-lipid.

Exemplary ionizable lipids include but are not limited to 2,2-dioleyl-4-dimethylaminoethyl-[1,3]-dioxolane (DLin-KC2-DMA); dioleyl-methyl 4-dimethylaminobutyrate (DLin-MC3-DMA); and di ((Z)-non-2-en-1-yl) 9-((4-(dimethylamino) butyryl) oxy) heptadecanedioate (L319); ALC-0315; C12-200, cKK-E12; A6; A18-Iso5-2DC18; OF-02; 98N12-5; 9A1P9; C12-200; cKK-E12; 7C1; G0-$C_{14}$; L319; $3040_{13}$; FTT5; $306O_{110}$; DODAP; and DODMA. In some embodiments of any of the aspects, the at least one ionizable lipid comprises, consists of, or consists essentially of 2,2-dioleyl-4-dimethylaminoethyl-[1,3]-dioxolane (DLin-KC2-DMA); dioleyl-methyl 4-dimethylaminobutyrate (DLin-MC3-DMA); and/or di ((Z)-non-2-en-1-yl) 9-((4-(dimethylamino) butyryl) oxy) heptadecanedioate (L319). In some embodiments of any of the aspects, the at least one ionizable lipid has a pKA in the range of 6.0-6.5.

Exemplary phospholipids include but are not limited to phosphatidic acid (phosphatidate) (PA); phosphatidylethanolamine (cephalin) (PE); phosphatidylcholine (lecithin) (PC); phosphatidylserine (PS): phosphoinositides: phosphatidylinositol (PI); phosphatidylinositol phosphate (PIP); phosphatidylinositol bisphosphate (PIP2); phosphatidylinositol trisphosphate (PIP3); phosphatidic acid derivatives (e.g., DMPA, DPPA, DSPA); phosphatidylcholine derivatives (e.g., DDPC, DLPC, DMPC, DPPC, DSPC, DOPC, POPC, DEPC); phosphatidylglycerol derivatives (e.g., DMPG, DPPG, DSPG, POPG); phosphatidylethanolamine derivatives (e.g., DMPE, DPPE, DSPE DOPE); and phosphatidylserine derivatives (DOPS); and PEG phospholipids (e.g., mPEG-phospholipid, polyglycerin-phospholipid, functionalized-phospholipid, terminal activated-phospholipid). In some embodiments of any of the aspects, the at least one phospholipid comprises, consists of, or consists essentially of phosphatidylcholine.

In some embodiments of any of the aspects, the at least one structured lipid comprises, consists of, or consists essentially of cholesterol.

In some embodiments of any of the aspects, the at least one engineered liver regenerative factor mRNA or the at least one liver regenerative factor mRNA comprising at least one modified nucleoside is encapsulated in the carrier. In some embodiments of any of the aspects, the at least one engineered liver regenerative factor mRNA or the at least one liver regenerative factor mRNA comprising at least one modified nucleoside is encapsulated in the LNP.

In some embodiments of any of the aspects, the at least one engineered liver regenerative factor mRNA or the at least one liver regenerative factor mRNA comprising at least one modified nucleoside is in an aqueous solution and in admixture with an ethanolic lipid mixture at acidic pH.

In some embodiments of any of the aspects, the at least one engineered liver regenerative factor mRNA or the at least one liver regenerative factor mRNA comprising at least one modified nucleoside is complexed to a nanoparticle by encapsulation in the interior of the nanoparticle. In some embodiments of any of the aspects, the at least one engineered liver regenerative factor mRNA or the at least one liver regenerative factor mRNA comprising at least one modified nucleoside is complexed to a nanoparticle by being interspersed within the lipid bilayer of the nanoparticle. In some embodiments of any of the aspects, the at least one engineered liver regenerative factor mRNA or the at least one liver regenerative factor mRNA comprising at least one modified nucleoside is complexed to a nanoparticle by being attached to the nanoparticle via a linking molecule.

In some embodiments of any of the aspects, the at least one engineered liver regenerative factor mRNA or the at least one liver regenerative factor mRNA comprising at least one modified nucleoside is complexed to a LNP by encapsulation in the interior of the LNP. In some embodiments of any of the aspects, the at least one engineered liver regenerative factor mRNA or the at least one liver regenerative factor mRNA comprising at least one modified nucleoside is complexed to a LNP by being interspersed within the lipid bilayer of the LNP. In some embodiments of any of the aspects, the at least one engineered liver regenerative factor mRNA or the at least one liver regenerative factor mRNA comprising at least one modified nucleoside is complexed to a LNP by being attached to the LNP via a linking molecule.

In some embodiments of any of the aspects, the composition further comprises N-acetyl cysteine (NAC). In one aspect of any of the embodiments described herein is a combination of a composition described herein and N-acetyl cysteine (NAC). In one aspect of any of the embodiments described herein is a combination of a first composition comprising a first engineered liver regenerative factor mRNA or liver regenerative factor mRNA described herein and a second composition comprising a second engineered liver regenerative factor mRNA or liver regenerative factor mRNA described herein.

In one aspect, described herein is a kit comprising one or more compositions as described herein, e.g., a composition comprising an engineered liver regenerative factor mRNA and/or liver regenerative factor mRNA, as described herein. A kit is any manufacture (e.g., a package or container) comprising at least one reagent, e.g., an mRNA, the manufacture being promoted, distributed, or sold as a unit for performing the methods described herein.

The kits described herein can optionally comprise additional components useful for performing the methods described herein. By way of example, the kit can comprise fluids (e.g., buffers) suitable for composition comprising an mRNA as described herein, an instructional material which describes performance of a method as described herein, and the like. A kit can further comprise devices and/or reagents for delivery of the composition(s) as described herein. Additionally, the kit may comprise an instruction leaflet and/or may provide information as to the relevance of the obtained results.

The compositions and combinations described herein can promote liver repair and/or healing, or decrease the rate or degree of liver damage and/or injury. Accordingly, in one aspect of any of the embodiments, described herein is a method of treating liver injury or liver disease in a subject in need thereof, the method comprising administering the composition or combination described herein to the subject. In one aspect of any of the embodiments, described herein is a method of accelerating intrinsic liver repair in a subject in need thereof, the method comprising administering the composition or combination described herein.

As used herein, "liver injury or liver disease" refers to injuries or disorders that affect the anatomy or metabolism of normal functioning of the liver. Liver disease can be acute liver disease, chronic liver disease, and/or genetic liver disease. Liver diseases are caused by, for example, alcohol (e.g. ASH), non-alcoholic fatty liver changes (such as NAFLD including NASH), nutrition-mediated liver injury (for example starvation), other toxic liver injury (such as unspecific hepatitis induced by e.g. drugs such as but not limited to acetaminophen (paracetamol), chlorinated hydrocarbons (e.g. CC14), amiodarone (cordarone), valproate, tetracycline (only i.v.), isoniacid, or food intoxication resulting in acute or chronic liver failure, e.g. by consumption of mushrooms containing aflatoxins (preferably B1 aflatoxin) or ingestion of certain metals (such as copper or cadmium) or herbal products used in natural medicine (homeopathics such as Mild thistle, Chaparral, Kawa-Kawa), interference of bilirubin metabolism, hepatitis like syndromes, cholestasis, granulomatous lesions, intrahepatic vascular lesions and cirrhosis), trauma and surgery (e.g. Pringle maneuver), or radiation-mediated liver injury (such as caused by radiotherapy). Exemplary liver injuries and/or liver diseases include but are not limited to haemophilia (including haemophilia A or B), familial hypercholesterolemia, ornithine transcarbamylase deficiency, α-antitrypsin deficiency, non-alcoholic fatty liver disease (NAFLD), alcoholic fatty liver disease, alcohol-related liver disease (ARLD), phenylketonuria, glycogen storage disease, α1-antitrypsin deficiency, hereditary hemochromatosis, tyrosinemia type 1, arginino-succinic aciduria, hepatitis virus infection (e.g., hepatitis A, hepatitis B, or hepatitis C), non-viral hepatitis, autoimmune hepatitis, primary biliary cholangitis, cirrhosis, biliary atresia, liver cancer, genetic cholestasis, hemochromatosis, Gilbert syndrome, primary sclerosing cholangitis (PSC), and Wilson's disease. In some embodiments of any of the aspects, the subject is a subject in need of treatment for acute liver disease, chronic liver disease, or acetaminophen (acetyl-para-aminophenol, APAP) overdose.

The liver is capable of intrinsic repair processes, e.g., restoration of normal hepatic function and architecture. This process is referred to herein as "intrinsic liver repair" and can include inhibition or reversal of fibrosis, decreases in the rate or amount of collagen matrix formation, reduction of inflammatory processes, promotion of health hepatocyte gene expression, and/or promotion of healthy hepatocyte function.

In some embodiments, the methods described herein relate to treating a subject having or diagnosed as having a liver injury or liver disease with a composition or combination comprising mRNA(s) as described herein. Subjects having liver disease can be identified by a physician using current methods of diagnosing liver diseases. Symptoms and/or complications of liver diseases which characterize these conditions and aid in diagnosis are well known in the art and include but are not limited to, jaundice, abdominal pain, bruising, changes in urine or stool color, fatigue, vomiting, or edema. Tests that may aid in a diagnosis of, e.g. liver disease include, but are not limited to, liver enzyme blood tests, ultrasounds, MRI, CT scan, or a liver biopsy. A family history of liver disease, or exposure to risk factors for liver disease (e.g. alcohol consumption) can also aid in determining if a subject is likely to have liver disease or in making a diagnosis of liver disease.

In some embodiments of any of the aspects, administration or treatment according to the methods described herein can result in decreased serum ALT levels, decreased necrosis, and increased survival following APAP overdose or in response to chronic liver disease, e.g., as compared to absence of said administration or treatment. In some further embodiments of any of the aspects, administration or treatment according to the methods described herein can result in increased conversion of biliary epithelial cells into hepatocytes, decreased steatosis, decreased inflammation, and decreased fibrosis, e.g., as compared to absence of said administration or treatment. In further embodiments of any of the aspects, administration or treatment according to the methods described herein can result in increased hepatocyte proliferation, increased hepatocyte survival, and improvement of hepatocyte transplantation or engraftment, e.g., as compared to absence of said administration or treatment The compositions and methods described herein can be administered to a subject having or diagnosed as having liver disease. In some embodiments, the methods described herein comprise administering an effective amount of compositions described herein, e.g. an mRNA(s) as described herein to a subject in order to alleviate a symptom of a liver disease. As used herein, "alleviating a symptom" is ameliorating any condition or symptom associated with the disease. As compared with an equivalent untreated control, such reduction is by at least 5%, 10%, 20%, 40%, 50%, 60%, 80%, 90%, 95%, 99% or more as measured by any standard technique. A variety of means for administering the compositions described herein to subjects are known to those of skill in the art. Such methods can include, but are not limited to oral, parenteral, intravenous, intramuscular, subcutaneous, transdermal, airway (aerosol), pulmonary, cutaneous, topical, injection, or intratumoral administration. Administration can be local or systemic.

The compositions and combinations described herein can also promote engraftment of cells in liver tissue. Accordingly, in one aspect of any of the embodiments, described herein is a method of engrafting cells in a liver tissue, the method comprising introducing the cells into the liver tissue and contacting the cells or the liver tissue with a composition or combination described herein.

The introduced cells can be primary cells, differentiated cells, cultured cells, transplanted cells, autologous cells, or non-autologous cells. In some embodiments of any of the aspects, the cells are primary human hepatocytes (PHH). In some embodiments of any of the aspects, the cells are induced pluripotent stem cell-derived hepatocyte-like-cells (iPSC-HLCs).

As used herein, the terms "hepatocytes" and the like refers to cells that show liver-like qualities such as expression of liver genes and proteins and/or hepatic cells. A number of genes expressed in the liver includes carrier protein Albumin (ALB), blood coagulation factors Fibrinogen Alpha chain (FBA), Fibrinogen Beta chain (FBB), Fibrinogen Gamma chain (FBG), thrombinogen, Alpha anti-trypsin (AAT), Tyrosine metabolic genes [Fumarylacetoacetate hydrolase (FAH), tyrosine amino transferase (TAT), homogentisate 1,2-dioxygenase (HGD), 4-hydroxyphenylpyruvic acid dioxygenase (HPD), phenylalanine hydroxylase (PAH), maleylacetoacetate isomerase (MAI)], and urea metabolic genes (ARG1), ornithine carbamoyltransferase (OTC), Carbamoyl-phosphate synthase 1 (CPS1), Glutamine Synthetase (GS). The term "hepatocytes or hepatocyte-like cells" includes different hepatocyte subtypes, which includes but not limited to stem cells, progenitors, differentiated perivenous hepatocytes, and periportal hepatocytes. Furthermore, the term "hepatocyte-like cells" refers to cells that may possess liver or hepatic stem cell or progenitor properties, including but not limited to the capacity to self-renew, proliferate and differentiate. Hepatocyte-like cells may or may not be mature and functional but can engraft into the liver.

In some embodiments of any of the aspects, the liver tissue is a liver in a subject, the introducing comprises transplanting the cells into the liver, and the contacting comprises administering. Accordingly, in one aspect of any of the embodiments, described herein is a method of engrafting cells in a liver of a subject, the method comprising transplanting the cells into the liver and administering to the subject a composition or combination described herein. The administering can be performed before, during, and/or after the transplantation. In some embodiments of any of the aspects, the subject is a subject in need of treatment for acute liver disease, chronic liver disease, or genetic liver disease. In some embodiments of any of the aspects, the subject is a subject in need of treatment for alpha-1 antitrypsin deficiency associated liver disease (AATD).

The term "effective amount" as used herein refers to the amount of a composition or combination described herein needed to alleviate at least one or more symptom of the disease or disorder, and relates to a sufficient amount of pharmacological composition to provide the desired effect. The term "therapeutically effective amount" therefore refers to an amount of a composition or combination that is sufficient to provide a particular effect when administered to atypical subject. An effective amount as used herein, in various contexts, would also include an amount sufficient to delay the development of a symptom of the disease, alter the course of a symptom disease (for example but not limited to, slowing the progression of a symptom of the disease), or reverse a symptom of the disease. Thus, it is not generally practicable to specify an exact "effective amount". However, for any given case, an appropriate "effective amount" can be determined by one of ordinary skill in the art using only routine experimentation.

Effective amounts, toxicity, and therapeutic efficacy can be determined by standard pharmaceutical procedures in cell cultures or experimental animals, e.g., for determining the LD50 (the dose lethal to 50% of the population) and the ED50 (the dose therapeutically effective in 50% of the population). The dosage can vary depending upon the dosage form employed and the route of administration utilized. The dose ratio between toxic and therapeutic effects is the therapeutic index and can be expressed as the ratio LD50/ED50. Compositions and methods that exhibit large therapeutic indices are preferred. A therapeutically effective dose can be estimated initially from cell culture assays. Also, a dose can be formulated in animal models to achieve a circulating plasma concentration range that includes the IC50 (i.e., the concentration of an mRNA, which achieves a half-maximal inhibition of symptoms) as determined in cell culture, or in an appropriate animal model. Levels in plasma can be measured, for example, by high performance liquid chromatography. The effects of any particular dosage can be monitored by a suitable bioassay, e.g., assay for liver enzymes, among others. The dosage can be determined by a physician and adjusted, as necessary, to suit observed effects of the treatment.

Effective amounts, toxicity, and therapeutic efficacy can be determined by standard pharmaceutical procedures in cell cultures or experimental animals, e.g., for determining the minimal effective dose and/or maximal tolerated dose. The dosage can vary depending upon the dosage form employed and the route of administration utilized. A therapeutically effective dose can be estimated initially from cell culture assays. Also, a dose can be formulated in animal models to achieve a dosage range between the minimal effective dose and the maximal tolerated dose. The effects of any particular dosage can be monitored by a suitable bioassay, e.g., assay for liver function among others. The dosage can be determined by a physician and adjusted, as necessary, to suit observed effects of the treatment.

In some embodiments, the technology described herein relates to a pharmaceutical composition comprising mRNA(s) as described herein, and optionally a pharmaceutically acceptable carrier. In some embodiments, the active ingredients of the pharmaceutical composition comprise one or more mRNAs as described herein. In some embodiments, the active ingredients of the pharmaceutical composition consist essentially of the one or more mRNAs as described herein. In some embodiments, the active ingredients of the pharmaceutical composition consist of one or more mRNAs as described herein. In some embodiments, the active ingredients of the pharmaceutical composition comprise one or more mRNAs as described herein and a carrier (e.g, a LNP). In some embodiments, the active ingredients of the pharmaceutical composition consist essentially of the one or more mRNAs as described herein and a carrier (e.g, a LNP). In some embodiments, the active ingredients of the pharmaceutical composition consist of one or more mRNAs as described herein and a carrier (e.g, a LNP).

Pharmaceutically acceptable carriers and diluents include saline, aqueous buffer solutions, solvents and/or dispersion media. The use of such carriers and diluents is well known in the art. Some non-limiting examples of materials which can serve as pharmaceutically-acceptable carriers include: (1) sugars, such as lactose, glucose and sucrose; (2) starches, such as corn starch and potato starch; (3) cellulose, and its derivatives, such as sodium carboxymethyl cellulose, methylcellulose, ethyl cellulose, microcrystalline cellulose and cellulose acetate; (4) powdered tragacanth; (5) malt; (6) gelatin; (7) lubricating agents, such as magnesium stearate, sodium lauryl sulfate and talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol (PEG); (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) pH buffered solutions; (21) polyesters, polycarbonates and/or polyanhydrides; (22) bulking agents, such as polypeptides and amino acids (23) serum component, such as serum albumin, HDL and LDL; (22) $C_2$-$C_{12}$ alcohols, such as ethanol; and (23) other non-toxic compatible substances employed in pharmaceutical formulations. Wetting agents, coloring agents, release agents, coating agents, sweetening agents, flavoring agents, perfuming agents, preservative and antioxidants can also be present in the formulation. The terms such as "excipient", "carrier", "pharmaceutically acceptable carrier" or the like are used interchangeably herein. In some embodiments, the carrier inhibits the degradation of the active agent, e.g. mRNA(s) as described herein.

In some embodiments, the pharmaceutical composition as described herein can be a parenteral dose form. Since administration of parenteral dosage forms typically bypasses the patient's natural defenses against contaminants, parenteral dosage forms are preferably sterile or capable of being sterilized prior to administration to a patient. Examples of parenteral dosage forms include, but are not limited to, solutions ready for injection, dry products ready to be dissolved or suspended in a pharmaceutically acceptable vehicle for injection, suspensions ready for injection, and emulsions. In addition, controlled-release parenteral dosage forms can be prepared for administration of a patient, including, but not limited to, DUROS®-type dosage forms and dose-dumping.

Suitable vehicles that can be used to provide parenteral dosage forms of mRNA(s) as disclosed within are well known to those skilled in the art. Examples include, without limitation: sterile water; water for injection USP; saline solution; glucose solution; aqueous vehicles such as but not limited to, sodium chloride injection, Ringer's injection, dextrose Injection, dextrose and sodium chloride injection, and lactated Ringer's injection; water-miscible vehicles such as, but not limited to, ethyl alcohol, polyethylene glycol, and propylene glycol; and non-aqueous vehicles such as, but not limited to, corn oil, cottonseed oil, peanut oil, sesame oil, ethyl oleate, isopropyl myristate, and benzyl benzoate. Compounds that alter or modify the solubility of a pharmaceutically acceptable salt of a compound as disclosed herein can also be incorporated into the parenteral dosage forms of the disclosure, including conventional and controlled-release parenteral dosage forms.

Conventional dosage forms generally provide rapid or immediate drug release from the formulation. Depending on the pharmacology and pharmacokinetics of the drug, use of conventional dosage forms can lead to wide fluctuations in the concentrations of the drug in a patient's blood and other tissues. These fluctuations can impact a number of parameters, such as dose frequency, onset of action, duration of efficacy, maintenance of therapeutic blood levels, toxicity, side effects, and the like. Advantageously, controlled-release formulations can be used to control a drug's onset of action, duration of action, plasma levels within the therapeutic window, and peak blood levels. In particular, controlled- or extended-release dosage forms or formulations can be used to ensure that the maximum effectiveness of a drug is achieved while minimizing potential adverse effects and safety concerns, which can occur both from under-dosing a drug (i.e., going below the minimum therapeutic levels) as well as exceeding the toxicity level for the drug. In some embodiments, the composition or combination can be administered in a sustained release formulation.

Controlled-release pharmaceutical products have a common goal of improving drug therapy over that achieved by their non-controlled release counterparts. Ideally, the use of an optimally designed controlled-release preparation in medical treatment is characterized by a minimum of drug substance being employed to cure or control the condition in a minimum amount of time. Advantages of controlled-release formulations include: 1) extended activity of the drug; 2) reduced dosage frequency; 3) increased patient compliance; 4) usage of less total drug; 5) reduction in local or systemic side effects; 6) minimization of drug accumulation; 7) reduction in blood level fluctuations; 8) improvement in efficacy of treatment; 9) reduction of potentiation or loss of drug activity; and 10) improvement in speed of control of diseases or conditions. Kim, Cherng-ju, Controlled Release Dosage Form Design, 2 (Technomic Publishing, Lancaster, Pa.: 2000).

Most controlled-release formulations are designed to initially release an amount of drug (active ingredient) that promptly produces the desired therapeutic effect, and gradually and continually release other amounts of drug to maintain this level of therapeutic or prophylactic effect over an extended period of time. In order to maintain this constant level of drug in the body, the drug must be released from the dosage form at a rate that will replace the amount of drug being metabolized and excreted from the body. Controlled-release of an active ingredient can be stimulated by various conditions including, but not limited to, pH, ionic strength, osmotic pressure, temperature, enzymes, water, and other physiological conditions or compounds.

A variety of known controlled- or extended-release dosage forms, formulations, and devices can be adapted for use with the salts and compositions of the disclosure. Examples include, but are not limited to, those described in U.S. Pat. Nos. 3,845,770; 3,916,899; 3,536,809; 3,598,123; 4,008,719; 5,674,533; 5,059,595; 5,591,767; 5,120,548; 5,073,543; 5,639,476; 5,354,556; 5,733,566; and 6,365,185 B1; each of which is incorporated herein by reference. These dosage forms can be used to provide slow or controlled-release of one or more active ingredients using, for example, hydroxypropylmethyl cellulose, other polymer matrices, gels, permeable membranes, osmotic systems (such as OROS® (Alza Corporation, Mountain View, Calif USA)), or a combination thereof to provide the desired release profile in varying proportions.

In some embodiments of any of the aspects, the composition or combination described herein is administered as a monotherapy, e.g., another treatment for the liver disease is not administered to the subject.

In some embodiments of any of the aspects, the methods described herein can further comprise administering a second agent and/or treatment to the subject, e.g. as part of a combinatorial therapy. Non-limiting examples of second agents and/or treatments can include a liver transplant, transjugular intrahepatic portosystemic shunt, anti-virals, or interferon. In some embodiments of any of the aspects, a method described herein can further comprise administering N-acetyl cysteine (NAC) to the subject.

In some embodiments of any of the aspects, the administering is intravenous administration. In some embodiments of any of the aspects, the administering is via the common bile duct. In some embodiments of any of the aspects, the administering is to the gallbladder.

In certain embodiments, an effective dose of a composition or combination as described herein can be administered to a patient once. In certain embodiments, an effective dose of a composition or combination as described herein can be administered to a patient repeatedly. For systemic administration, subjects can be administered a therapeutic amount of a composition or combination as described herein, such as, e.g. 0.1 mg/kg, 0.5 mg/kg, 1.0 mg/kg, 2.0 mg/kg, 2.5 mg/kg, 5 mg/kg, 10 mg/kg, 15 mg/kg, 20 mg/kg, 25 mg/kg, 30 mg/kg, 40 mg/kg, 50 mg/kg, or more.

In some embodiments, after an initial treatment regimen, the treatments can be administered on a less frequent basis. For example, after treatment biweekly for three months, treatment can be repeated once per month, for six months or a year or longer. Treatment according to the methods described herein can reduce levels of a marker or symptom of a condition, e.g. liver disease by at least 10%, at least 15%, at least 20%, at least 25%, at least 30%, at least 40%, at least 50%, at least 60%, at least 70%, at least 80% or at least 90% or more.

The dosage of a composition as described herein can be determined by a physician and adjusted, as necessary, to suit observed effects of the treatment. With respect to duration and frequency of treatment, it is typical for skilled clinicians to monitor subjects in order to determine when the treatment is providing therapeutic benefit, and to determine whether to increase or decrease dosage, increase or decrease administration frequency, discontinue treatment, resume treatment, or make other alterations to the treatment regimen. The dosing schedule can vary from once a week to daily depending on a number of clinical factors, such as the subject's sensitivity to the active ingredient. The desired dose or amount of activation can be administered at one time or divided into subdoses, e.g., 2-4 subdoses and administered over a period of time, e.g., at appropriate intervals through the day or other appropriate schedule. In some embodiments, administration can be chronic, e.g., one or more doses and/or treatments daily over a period of weeks or months. Examples of dosing and/or treatment schedules are administration daily, twice daily, three times daily or four or more times daily over a period of 1 week, 2 weeks, 3 weeks, 4 weeks, 1 month, 2 months, 3 months, 4 months, 5 months, or 6 months, or more. A preferred example of dosing and/or treatment schedules are administration every two days, 3 times a week over a period of 1 week, 2 weeks, 3 weeks, 4 weeks, 1 month, 2 months, 3 months, 4 months, 5 months, or 6 months, or more. A composition or combination as described herein can be administered over a period of time, such as over a 5 minute, 10 minute, 15 minute, 20 minute, or 25 minute period.

In some embodiments of any of the aspects, the composition or combination is administered once. In some embodiments of any of the aspects, the composition or combination is administered twice. In some embodiments of any of the aspects, the composition or combination is administered repeatedly. When two or more individual compositions are administered, the compositions can be administered concurrently, or sequentially.

The dosage ranges for the administration of a composition or combination described herein, according to the methods described herein depend upon, for example, the form of the mRNA(s), its potency, and the extent to which symptoms, markers, or indicators of a condition described herein are desired to be reduced, for example the percentage increase desired for gene expression or liver function. The dosage should not be so large as to cause adverse side effects. Generally, the dosage will vary with the age, condition, and sex of the patient and can be determined by one of skill in the art. The dosage can also be adjusted by the individual physician in the event of any complication.

The efficacy of a composition or combination described herein in, e.g. the treatment of a condition described herein, or to induce a response as described herein (e.g. liver function and/or repair) can be determined by the skilled clinician. However, a treatment is considered "effective treatment," as the term is used herein, if one or more of the signs or symptoms of a condition described herein are altered in a beneficial manner, other clinically accepted symptoms are improved, or even ameliorated, or a desired response is induced e.g., by at least 10% following treatment according to the methods described herein. Efficacy can be assessed, for example, by measuring a marker, indicator, symptom, and/or the incidence of a condition treated according to the methods described herein or any other measurable parameter appropriate, e.g. liver function or repair. Efficacy can also be measured by a failure of an individual to worsen as assessed by hospitalization, or need for medical interventions (i.e., progression of the disease is halted). Methods of measuring these indicators are known to those of skill in the art and/or are described herein. Treatment includes any treatment of a disease in an individual or an animal (some non-limiting examples include a human or an animal) and includes: (1) inhibiting the disease, e.g., preventing a worsening of symptoms (e.g. pain or inflammation); or (2) relieving the severity of the disease, e.g., causing regression of symptoms. An effective amount for the treatment of a disease means that amount which, when administered to a subject in need thereof, is sufficient to result in effective treatment as that term is defined herein, for that disease. Efficacy of an agent can be determined by assessing physical indicators of a condition or desired response, (e.g. liver repair and/or function). It is well within the ability of one skilled in the art to monitor efficacy of administration and/or treatment by measuring any one of such parameters, or any combination of parameters. Efficacy can be assessed in animal models of a condition described herein, for example treatment of liver disease. When using an experimental animal model, efficacy of treatment is evidenced when a statistically significant change in a marker is observed, e.g. liver enzymes, liver histology normalization, or hepatocyte gene expression.

In vitro and animal model assays are provided herein which allow the assessment of a given dose of one or more mRNA(s) as described herein. By way of non-limiting example, the effects of a dose of one or more mRNA(s) as described herein can be assessed by in vitro assays for liver cell function, or an animal model, e.g., a murine model as described herein.

In one respect, the present invention relates to the herein described compositions, methods, and respective component(s) thereof, as essential to the technology, yet open to the inclusion of unspecified elements, essential or not ("comprising). In some embodiments of any of the aspects, other elements to be included in the description of the composition, method or respective component thereof are limited to those that do not materially affect the basic and novel characteristic(s) of the technology (e.g., the composition, method, or respective component thereof "consists essentially of" the elements described herein). This applies equally to steps within a described method as well as compositions and components therein. In other embodiments of any of the aspects, the compositions, methods, and respective components thereof, described herein are intended to be exclusive of any element not deemed an essential element to the component, composition or method (e.g., the composition, method, or respective component thereof "consists of" the elements described herein). This applies equally to steps within a described method as well as compositions and components therein.

For convenience, the meaning of some terms and phrases used in the specification, examples, and appended claims, are provided below. Unless stated otherwise, or implicit from context, the following terms and phrases include the meanings provided below. The definitions are provided to aid in describing particular embodiments, and are not intended to limit the claimed invention, because the scope of the invention is limited only by the claims. Unless otherwise defined, all technical and scientific terms used herein have the same meaning as commonly understood by one of ordinary skill in the art to which this invention belongs. If there is an apparent discrepancy between the usage of a term in the art and its definition provided herein, the definition provided within the specification shall prevail.

Unless otherwise defined herein, scientific and technical terms used in connection with the present application shall have the meanings that are commonly understood by those of ordinary skill in the art to which this disclosure belongs.

It should be understood that this invention is not limited to the particular methodology, protocols, and reagents, etc., described herein and as such can vary. The terminology used herein is for the purpose of describing particular embodiments only, and is not intended to limit the scope of the present invention, which is defined solely by the claims. Definitions of common terms in immunology and molecular biology can be found in The Merck Manual of Diagnosis and Therapy, 19th Edition, published by Merck Sharp & Dohme Corp., 2011 (ISBN 978-0-911910-19-3); Robert S. Porter et al. (eds.), Fields Virology, 6$^{th}$ Edition, published by Lippincott Williams & Wilkins, Philadelphia, PA, USA (2013); Knipe, D. M. and Howley, P. M. (ed.), The Encyclopedia of Molecular Cell Biology and Molecular Medicine, published by Blackwell Science Ltd., 1999-2012 (ISBN 9783527600908); and Robert A. Meyers (ed.), Molecular Biology and Biotechnology: a Comprehensive Desk Reference, published by VCH Publishers, Inc., 1995 (ISBN 1-56081-569-8); Immunology by Werner Luttmann, published by Elsevier, 2006; Janeway's Immunobiology, Kenneth Murphy, Allan Mowat, Casey Weaver (eds.), Taylor & Francis Limited, 2014 (ISBN 0815345305, 9780815345305); Lewin's Genes XI, published by Jones & Bartlett Publishers, 2014 (ISBN-1449659055); Michael Richard Green and Joseph Sambrook, Molecular Cloning: A Laboratory Manual, 4$^{th}$ ed., Cold Spring Harbor Laboratory Press, Cold Spring Harbor, N.Y., USA (2012) (ISBN 1936113414); Davis et al., Basic Methods in Molecular Biology, Elsevier Science Publishing, Inc., New York, USA (2012) (ISBN 044460149X); Laboratory Methods in Enzymology: DNA, Jon Lorsch (ed.) Elsevier, 2013 (ISBN 0124199542); Current Protocols in Molecular Biology (CPMB), Frederick M. Ausubel (ed.), John Wiley and Sons, 2014 (ISBN047150338X, 9780471503385), Current Protocols in Protein Science (CPPS), John E. Coligan (ed.), John Wiley and Sons, Inc., 2005; and Current Protocols in Immunology (CPI) (John E. Coligan, ADA M Kruisbeek, David H Margulies, Ethan M Shevach, Warren Strobe, (eds.) John Wiley and Sons, Inc., 2003 (ISBN 0471142735, 9780471142737), the contents of which are all incorporated by reference herein in their entireties.

The terms "decrease", "reduce", "inhibit", or other grammatical forms thereof are used herein to mean a decrease by a statistically significant amount. In some embodiments, "reduce" or "decrease" or "inhibit" typically means a decrease by at least 10% as compared to a reference level (e.g. the absence of a given treatment or agent) and can include, for example, a decrease by at least about 10%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 95%, at least about 98%, at least about 99%, or more. As used herein, "inhibition" does not encompass a complete inhibition as compared to a reference level. "Complete inhibition" is a 100% inhibition as compared to a reference level. Where applicable, a decrease can be preferably down to a level accepted as within the range of normal for a subject without a given disease (e.g., liver disease).

The terms "increased", "increase", "enhance", or grammatical forms thereof are used herein to mean an increase by a statically significant amount. In some embodiments, the terms "increased", "increase", or "enhance", can mean an increase of at least 10% as compared to a reference level, for example an increase of at least about 20%, or at least about 30%, or at least about 40%, or at least about 50%, or at least about 60%, or at least about 70%, or at least about 80%, or at least about 90% or up to and including a 100% increase or any increase between 10-100% as compared to a reference level, or at least about a 2-fold, or at least about a 3-fold, or at least about a 4-fold, or at least about a 5-fold or at least about a 10-fold increase, or any increase between 2-fold and 10-fold or greater as compared to a reference level.

As used herein, a "subject" means a human or animal. Usually the animal is a vertebrate such as a primate, rodent, domestic animal or game animal. Primates include, for example, chimpanzees, cynomolgus monkeys, spider monkeys, and macaques, e.g., Rhesus. Rodents include, for example, mice, rats, woodchucks, ferrets, rabbits and hamsters. Domestic and game animals include, for example, cows, horses, pigs, deer, bison, feline species, e.g., domestic cat, canine species, e.g., dog, fox, wolf, avian species, e.g., chicken, emu, ostrich, and fish, e.g., trout, catfish and salmon. In some embodiments, the subject is a mammal, e.g., a primate, e.g., a human.

Preferably, the subject is a mammal. The mammal can be a human, non-human primate, mouse, rat, dog, cat, horse, or cow, but is not limited to these examples. Mammals other than humans can be advantageously used as subjects that represent animal models of disease e.g., cancer. A subject can be male or female.

A subject can be one who has been previously diagnosed with or identified as suffering from or having a condition in need of treatment (e.g. chronic or acute liver injury or disease) or one or more complications related to such a condition, and optionally, have already undergone treatment for the condition or the one or more complications related to the condition. Alternatively, a subject can also be one who has not been previously diagnosed as having such condition or related complications. For example, a subject can be one who exhibits one or more risk factors for the condition or one or more complications related to the condition or a subject who does not exhibit risk factors.

A "subject in need" of treatment for a particular condition can be a subject having that condition, diagnosed as having that condition, or at risk of developing that condition.

As used herein, the terms "protein" and "polypeptide" are used interchangeably herein to designate a series of amino acid residues, connected to each other by peptide bonds between the alpha-amino and carboxyl groups of adjacent residues. The terms "protein", and "polypeptide" refer to a polymer of amino acids, including modified amino acids (e.g., phosphorylated, glycated, glycosylated, etc.) and amino acid analogs, regardless of its size or function. "Protein" and "polypeptide" are often used in reference to relatively large polypeptides, whereas the term "peptide" is often used in reference to small polypeptides, but usage of these terms in the art overlaps. The terms "protein" and "polypeptide" are used interchangeably herein when referring to a gene product and fragments thereof. Thus, exemplary polypeptides or proteins include gene products, naturally occurring proteins, homologs, orthologs, paralogs, fragments and other equivalents, variants, fragments, and analogs of the foregoing.

As used herein, the term "engineered" and its grammatical equivalents can refer to one or more human-designed and human-generated alterations of a nucleic acid, e.g., a mRNA. The term can refer to alterations, additions, and/or deletion of nucleotides. For example, a mRNA is considered to be "engineered" when at least one aspect of the mRNA, e.g., its sequence, has been manipulated by the hand of man to differ from the aspect as it exists in nature.

The terms "nucleic acid segment," "nucleotide sequence," or more generally "segment" will be understood by those in the art as a functional term that includes both genomic sequences, ribosomal RNA sequences, transfer RNA sequences, messenger RNA sequences, small regulatory RNAs, operon sequences and smaller engineered nucleotide sequences that express or may be adapted to express, proteins, polypeptides or peptides. Nucleic acids of the present disclosure may also be synthesized, either completely or in part, by methods known in the art. Thus, all or a portion of the nucleic acids of the present codons may be synthesized using codons preferred by a selected host. Species-preferred codons may be determined, for example, from the codons used most frequently in the proteins expressed in a particular host species. Other modifications of the nucleotide sequences may result in mutants having slightly altered activity As used herein, the term "nucleic acid" refers to a single or double-stranded polymer of deoxyribonucleotide or ribonucleotide bases read from the 5' to the 3' end. The "nucleic acid" may also optionally contain non-naturally occurring or altered nucleotide bases that permit correct read-through by a polymerase and do not reduce expression of a polypeptide encoded by that nucleic acid. The term "nucleotide sequence" or "nucleic acid sequence" refers to both the sense and antisense strands of a nucleic acid as either individual single strands or in the duplex. The term "ribonucleic acid" (RNA) is inclusive of RNAi (inhibitory RNA), dsRNA (double stranded RNA), siRNA (small interfering RNA), mRNA (messenger RNA), miRNA (micro-RNA), tRNA (transfer RNA, whether charged or discharged with a corresponding acylated amino acid), and cRNA (complementary RNA) and the term "deoxyribonucleic acid" (DNA) is inclusive of cDNA and genomic DNA and DNA-RNA hybrids.

The term "constitutive" when made in reference to a promoter means that the promoter is capable of directing transcription of an operably linked nucleic acid sequence in the absence of a stimulus (e.g., heat shock, chemicals, light, etc.). Typically, constitutive promoters are capable of directing expression of a transgene in substantially any cell and any tissue. In contrast, a "regulatable" or "inducible" promoter is one which is capable of directing a level of transcription of an operably linked nuclei acid sequence in the presence of a stimulus (e.g., heat shock, chemicals, light, etc.) which is different from the level of transcription of the operably linked nucleic acid sequence in the absence of the stimulus.

The term "expression" refers to the cellular processes involved in producing RNA and proteins and as appropriate, secreting proteins, including where applicable, but not limited to, for example, transcription, transcript processing, translation and protein folding, modification and processing. Expression can refer to the transcription and stable accumulation of sense (mRNA) or antisense RNA derived from a nucleic acid fragment or fragments of the invention and/or to the translation of mRNA into a polypeptide.

In some embodiments, the expression of a biomarker(s), target(s), or gene/polypeptide described herein is/are tissue-specific. In some embodiments, the expression of a biomarker(s), target(s), or gene/polypeptide described herein is/are global. In some embodiments, the expression of a biomarker(s), target(s), or gene/polypeptide described herein is systemic.

"Expression products" include RNA transcribed from a gene, and polypeptides obtained by translation of mRNA transcribed from a gene. The term "gene" means the nucleic acid sequence which is transcribed (DNA) to RNA in vitro or in vivo when operably linked to appropriate regulatory sequences. The gene may or may not include regions preceding and following the coding region, e.g. 5' untranslated (5'UTR) or "leader" sequences and 3' UTR or "trailer" sequences, as well as intervening sequences (introns) between individual coding segments (exons).

"Operably linked" refers to an arrangement of elements wherein the components so described are configured so as to perform their usual function. Thus, control elements operably linked to a coding sequence are capable of effecting the expression of the coding sequence. The control elements need not be contiguous with the coding sequence, so long as they function to direct the expression thereof. Thus, for example, intervening untranslated yet transcribed sequences can be present between a promoter sequence and the coding sequence and the promoter sequence can still be considered "operably linked" to the coding sequence.

In some embodiments of any of the aspects, the mRNA(s) described herein is exogenous. In some embodiments of any of the aspects, the mRNA(s) described herein is ectopic. In some embodiments of any of the aspects, the mRNA(s) described herein is not endogenous.

The term "exogenous" refers to a substance present in a cell other than its native source. The term "exogenous" when used herein can refer to a nucleic acid (e.g. a nucleic acid encoding a polypeptide) or a polypeptide that has been introduced by a process involving the hand of man into a biological system such as a cell or organism in which it is not normally found and one wishes to introduce the nucleic acid or polypeptide into such a cell or organism. Alternatively, "exogenous" can refer to a nucleic acid or a polypeptide that has been introduced by a process involving the hand of man into a biological system such as a cell or organism in which it is found in relatively low amounts and one wishes to increase the amount of the nucleic acid or polypeptide in the cell or organism, e.g., to create ectopic expression or levels. In contrast, the term "endogenous" refers to a substance that is native to the biological system or cell. As used herein, "ectopic" refers to a substance that is found in an unusual location and/or amount. An ectopic substance can be one that is normally found in a given cell, but at a much lower amount and/or at a different time. Ectopic also includes substance, such as a polypeptide or nucleic acid that is not naturally found or expressed in a given cell in its natural environment.

By "wild-type" it is intended, as will be clear to the skilled addressee, that the nucleic acid or polypeptide is not engineered and can be found in nature. Reference wild-type sequences are provided for the liver regenerative factors described herein.

In some embodiments, the methods described herein relate to measuring, detecting, or determining the level of at least one expression product. As used herein, the term "detecting" or "measuring" refers to observing a signal from, e.g. a probe, label, or target molecule to indicate the presence of an analyte in a sample. Any method known in the art for detecting a particular label moiety can be used for detection. Exemplary detection methods include, but are not limited to, spectroscopic, fluorescent, photochemical, biochemical, immunochemical, electrical, optical or chemical methods. In some embodiments of any of the aspects, measuring can be a quantitative observation.

As used herein, the terms "treat," "treatment," "treating," or "amelioration" refer to therapeutic treatments, wherein the object is to reverse, alleviate, ameliorate, inhibit, slow down or stop the progression or severity of a condition associated with a disease or disorder. The term "treating" includes reducing or alleviating at least one adverse effect or symptom of a condition, disease or disorder. Treatment is generally "effective" if one or more symptoms or clinical markers are reduced. Alternatively, treatment is "effective" if the progression of a disease is reduced or halted. That is, "treatment" includes not just the improvement of symptoms or markers, but also a cessation of, or at least slowing of, progress or worsening of symptoms compared to what would be expected in the absence of treatment. Beneficial or desired clinical results include, but are not limited to, alleviation of one or more symptom(s), diminishment of extent of disease, stabilized (i.e., not worsening) state of disease, delay or slowing of disease progression, amelioration or palliation of the disease state, remission (whether partial or total), and/or decreased mortality, whether detectable or undetectable. The term "treatment" of a disease also includes providing relief from the symptoms or side-effects of the disease (including palliative treatment).

In some embodiments of any of the aspects, described herein is a prophylactic method of treatment. As used herein "prophylactic" refers to the timing and intent of a treatment relative to a disease or symptom, that is, the treatment is administered prior to clinical detection or diagnosis of that particular disease or symptom in order to protect the patient from the disease or symptom. Prophylactic treatment can encompass a reduction in the severity or speed of onset of the disease or symptom, or contribute to faster recovery from the disease or symptom. Accordingly, the methods described herein can be prophylactic relative to liver failure, or the need for a liver transplant. In some embodiments of any of the aspects, prophylactic treatment is not prevention of all symptoms or signs of a disease.

As used herein, the term "pharmaceutical composition" refers to the active agent in combination with a pharmaceutically acceptable carrier e.g. a carrier commonly used in the pharmaceutical industry. The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio. In some embodiments of any of the aspects, a pharmaceutically acceptable carrier can be a carrier other than water. In some embodiments of any of the aspects, a pharmaceutically acceptable carrier can be a cream, emulsion, gel, liposome, nanoparticle, and/or ointment. In some embodiments of any of the aspects, a pharmaceutically acceptable carrier can be an artificial or engineered carrier, e.g., a carrier that the active ingredient would not be found to occur in in nature.

As used herein, the term "administering," refers to the placement of a compound as disclosed herein into a subject by a method or route which results in at least partial delivery of the agent at a desired site. Pharmaceutical compositions comprising the compounds disclosed herein can be administered by any appropriate route which results in an effective treatment in the subject. In some embodiments, administration comprises physical human activity, e.g., an injection, act of ingestion, an act of application, and/or manipulation of a delivery device or machine. Such activity can be performed, e.g., by a medical professional and/or the subject being treated.

As used herein, "contacting" refers to any suitable means for delivering, or exposing, an agent to at least one cell. Exemplary delivery methods include, but are not limited to, direct delivery to cell culture medium, perfusion, injection, or other delivery method well known to one skilled in the art. In some embodiments, contacting comprises physical human activity, e.g., an injection; an act of dispensing, mixing, and/or decanting; and/or manipulation of a delivery device or machine.

The term "statistically significant" or "significantly" refers to statistical significance and generally means a two standard deviation (2SD) or greater difference.

Other than in the operating examples, or where otherwise indicated, all numbers expressing quantities of ingredients or reaction conditions used herein should be understood as modified in all instances by the term "about." The term "about" when used in connection with percentages can mean±1%.

As used herein, the term "comprising" means that other elements can also be present in addition to the defined elements presented. The use of "comprising" indicates inclusion rather than limitation.

The term "consisting of" refers to compositions, methods, and respective components thereof as described herein, which are exclusive of any element not recited in that description of the embodiment.

As used herein the term "consisting essentially of" refers to those elements required for a given embodiment. The term permits the presence of additional elements that do not materially affect the basic and novel or functional characteristic(s) of that embodiment of the invention.

As used herein, where a modification (e.g. a change, addition, or deletion) is referred to as "relative to" a reference sequence, it is understood that the modification is made at a point or in a residue of an embodiment of the mRNA that corresponds to the indicated location or residue in the reference sequence. The embodied mRNA can have additional modifications, or may be shorter or longer than the reference sequence, so that the modification does not occur at a location having the same numbering as the location in the reference sequence. One of skill in the art can align sequences and determine what positions or residues correspond to a reference sequence position or residue utilizing automated alignment tools such as BLAST.

As used herein, the term "corresponding to" refers to an amino acid or nucleotide at the enumerated position in a first polypeptide or nucleic acid, or an amino acid or nucleotide that is equivalent to an enumerated amino acid or nucleotide in a second polypeptide or nucleic acid. Equivalent enumerated amino acids or nucleotides can be determined by alignment of candidate sequences using degree of homology programs known in the art, e.g., BLAST.

The singular terms "a," "an," and "the" include plural referents unless context clearly indicates otherwise. Similarly, the word "or" is intended to include "and" unless the context clearly indicates otherwise. Although methods and materials similar or equivalent to those described herein can be used in the practice or testing of this disclosure, suitable methods and materials are described below. The abbreviation, "e.g." is derived from the Latin exempli gratia, and is used herein to indicate a non-limiting example. Thus, the abbreviation "e.g." is synonymous with the term "for example."

In some embodiments of any of the aspects, the disclosure described herein does not concern a process for cloning human beings, processes for modifying the germ line genetic identity of human beings, uses of human embryos for industrial or commercial purposes or processes for modifying the genetic identity of animals which are likely to cause them suffering without any substantial medical benefit to man or animal, and also animals resulting from such processes.

Groupings of alternative elements or embodiments of the invention disclosed herein are not to be construed as limitations. Each group member can be referred to and claimed individually or in any combination with other members of the group or other elements found herein. One or more members of a group can be included in, or deleted from, a group for reasons of convenience and/or patentability. When any such inclusion or deletion occurs, the specification is herein deemed to contain the group as modified thus fulfilling the written description of all Markush groups used in the appended claims.

Other terms are defined herein within the description of the various aspects of the invention.

All patents and other publications; including literature references, issued patents, published patent applications, and co-pending patent applications; cited throughout this application are expressly incorporated herein by reference for the purpose of describing and disclosing, for example, the methodologies described in such publications that might be used in connection with the technology described herein. These publications are provided solely for their disclosure prior to the filing date of the present application. Nothing in this regard should be construed as an admission that the inventors are not entitled to antedate such disclosure by virtue of prior invention or for any other reason. All statements as to the date or representation as to the contents of these documents is based on the information available to the inventors and does not constitute any admission as to the correctness of the dates or contents of these documents.

The description of embodiments of the disclosure is not intended to be exhaustive or to limit the disclosure to the precise form disclosed. While specific embodiments of, and examples for, the disclosure are described herein for illustrative purposes, various equivalent modifications are possible within the scope of the disclosure, as those skilled in the relevant art will recognize. For example, while method steps or functions are presented in a given order, alternative embodiments may perform functions in a different order, or functions may be performed substantially concurrently. The teachings of the disclosure provided herein can be applied to other procedures or methods as appropriate. The various embodiments described herein can be combined to provide further embodiments. Aspects of the disclosure can be modified, if necessary, to employ the compositions, functions and concepts of the above references and application to provide yet further embodiments of the disclosure. Moreover, due to biological functional equivalency considerations, some changes can be made in protein structure without affecting the biological or chemical action in kind or amount. These and other changes can be made to the disclosure in light of the detailed description. All such modifications are intended to be included within the scope of the appended claims.

Specific elements of any of the foregoing embodiments can be combined or substituted for elements in other embodiments. Furthermore, while advantages associated with certain embodiments of the disclosure have been described in the context of these embodiments, other embodiments may also exhibit such advantages, and not all embodiments need necessarily exhibit such advantages to fall within the scope of the disclosure.

In some embodiments, the present technology may be defined in any of the following numbered paragraphs:

1. A composition comprising at least one engineered liver regenerative factor mRNA, the at least one engineered liver regenerative factor mRNA comprising one or more of:
   a) a sequence encoding Growth Hormone (GH) and comprising one or more of the following modifications relative to SEQ ID NO: 1:
      deletion of nucleotides 1-63; T→C modification of nucleotide 69; A→C modification of nucleotide 72; G→C modification of nucleotide 81; G→C modification of nucleotide 84; C→G modification of nucleotide 92; T→C modification of nucleotide 99; T→C modification of nucleotide 102; C→G modification of nucleotide 111; T→G modification of nucleotide 126; A→G modification of nucleotide 129; A→T modification of nucleotide 136; G→C modification of nucleotide 137; T→C modification of nucleotide 138; A→C modification of nucleotide 147; T→C modification of nucleotide 153; T→C modification of nucleotide 157; A→G modification of nucleotide 159; A→C modification of nucleotide 163; G→C modification of nucleotide 165; T→G modification of nucleotide 168; T→C modification of nucleotide 171; T→C modification of nucleotide 180; C→G modification of nucleotide 186; T→C modification of nucleotide 195; T→C modification of nucleotide 198; T→C modification of nucleotide 216; T→C modification of nucleotide 234; A→G modification of nucleotide 237; A→G modification of nucleotide 240; T→C modification of nucleotide 246; A→C modification of nucleotide 252; A→G modification of nucleotide 258; T→C modification of nucleotide 267; A→C modification of nucleotide 270; C→G modification of nucleotide 297; T→C modification of nucleotide 300; A→C modification of nucleotide 306; T→C modification of nucleotide 312; T→C modification of nucleotide 315; G→C modification of nucleotide 318; A→C modification of nucleotide 321; A→C modification of nucleotide 331; G→C modification of nucleotide 333; A→G modification of nucleotide 339; A→C modification of nucleotide 342; A→G modification of nucleotide 345; A→G modification of nucleotide 351; A→G modification of nucleotide 360; C→G modification of nucleotide 369; C→G modification of nucleotide 387; G→C modification of nucleotide 396; C→G modification of nucleotide 420; A→C modification of nucleotide 421; G→C modification of nucleotide 423; A→T modification of nucleotide 424; G→C modification of nucleotide 425; T→C modification of nucleotide 426; C→G modification of nucleotide 429; A→T modification of nucleotide 439; G→C modification of nucleotide 440; T→C modification of nucleotide 459; A→T modification of nucleotide 463; G→C modification of nucleotide 464; C→G modification of nucleotide 471; T→C modification of nucleotide 474; C→G modification of nucleotide 480; A→G modification of nucleotide 483; A→G modification of nucleotide 492; A→G modification of nucleotide 498; A→G modification of nucleotide 507; G→C modification of nucleotide 510; G→C modification of nucleotide 519; A→C modification of nucleotide 520; G→C modification of nucleotide 522; A→G modification of nucleotide 528; T→C modification of nucleotide 531; A→T modification of nucleotide 535; G→C modification of nucleotide 536; G→C modification of nucleotide 543; T→C modification of nucleotide 546; G→C modification of nucleotide 549; A→T modification of nucleotide 571; G→C modification of nucleotide 572; A→C modification of nucleotide 585; A→C modification of nucleotide 591; T→C modification of nucleotide 600; A→C modification of nucleotide 606; A→G modification of nucleotide 609; C→G modification of nucleotide 612; G→C modification of nucleotide 624; C→G modification of nucleotide 630; A→C modification of nucleotide 640; G→C modification of nucleotide 642; C→G modification of nucleotide 660; A→C modification of nucleotide 666; T→C modification of nucleotide 693; A→T modification of nucleotide 703; G→C modification of nucleotide 704; T→C modification of nucleotide 708; and deletion of nucleotides 717-823;

b) a sequence encoding Epidermal Growth Factor (EGF) and comprising one or more of the following modifications relative to SEQ ID NO: 2:

deletion of nucleotides 1-453; C→G modification of nucleotide 462; T→C modification of nucleotide 465; T→G modification of nucleotide 468; T→C modification of nucleotide 474; T→C modification of nucleotide 478; A→C modification of nucleotide 483; A→G modification of nucleotide 486; T→G modification of nucleotide 489; A→C modification of nucleotide 492; A→G modification of nucleotide 495; T→C modification of nucleotide 498; A→T modification of nucleotide 499; G→C modification of nucleotide 500; T→C modification of nucleotide 501; T→C modification of nucleotide 504; T→G modification of nucleotide 507; A→T modification of nucleotide 508; G→C modification of nucleotide 509; T→C modification of nucleotide 510; G→C modification of nucleotide 513; A→C modification of nucleotide 516; A→C modification of nucleotide 519; G→C modification of nucleotide 522; A→T modification of nucleotide 532; G→C modification of nucleotide 533; T→C modification of nucleotide 537; T→C modification of nucleotide 540; A→G modification of nucleotide 543; T→C modification of nucleotide 546; T→C modification of nucleotide 549; C→G modification of nucleotide 552; A→C modification of nucleotide 555; A→C modification of nucleotide 558; T→C modification of nucleotide 561; G→C modification of nucleotide 564; T→C modification of nucleotide 567; T→C modification of nucleotide 570; T→C modification of nucleotide 573; T→C modification of nucleotide 576; T→C modification of nucleotide 582; T→C modification of nucleotide 585; A→C modification of nucleotide 588; T→C modification of nucleotide 595; A→G modification of nucleotide 597; T→C modification of nucleotide 600; T→C modification of nucleotide 609; A→C modification of nucleotide 612; T→C modification of nucleotide 615; A→T modification of nucleotide 616; G→C modification of nucleotide 617; T→C modification of nucleotide 618; T→C modification of nucleotide 624; A→C modification of nucleotide 625; G→C modification of nucleotide 627; T→C modification of nucleotide 630; A→C modification of nucleotide 636; A→G modification of nucleotide 639; A→C modification of nucleotide 642; T→C modification of nucleotide 648; T→C modification of nucleotide 651; A→G modification of nucleotide 657; T→C modification of nucleotide 658; T→C modification of nucleotide 669; T→C modification of nucleotide 672; T→C modification of nucleotide 675; C→G modification of nucleotide 678; A→C modification of nucleotide 681; T→C modification of nucleotide 693; T→C modification of nucleotide 696; T→C modification of nucleotide 699; T→C modification of nucleotide 702; T→C modification of nucleotide 705; A→G modification of nucleotide 711; A→C modification of nucleotide 712; A→C modification of nucleotide 714; T→C modification of nucleotide 720; T→C modification of nucleotide 729; T→C modification of nucleotide 730; A→G modification of nucleotide 732; A→G modification of nucleotide 735; A→C modification of nucleotide 736; A→C modification of nucleotide 738; A→G modification of nucleotide 741; T→G modification of nucleotide 744; T→C modification of nucleotide 745; A→G modification of nucleotide 750; A→C modification of nucleotide 751; A→C modification of nucleotide 753; T→G modification of nucleotide 756; T→C modification of nucleotide 759; T→C modification of nucleotide 765; G→C modification of nucleotide 768; A→C modification of nucleotide 771; A→C modification of nucleotide 772; G→C modification of nucleotide 774; A→G modification of nucleotide 777; A→C modification of nucleotide 781; A→C modification of nucleotide 783; A→G modification of nucleotide 786; T→C modification of nucleotide 789; T→C modification of nucleotide 792; A→C modification of nucleotide 795; A→G modification of nucleotide 801; T→C modification of nucleotide 804; T→G modification of nucleotide 807; T→C modification of nucleotide 810; A→C modification of nucleotide 813; A→C modification of nucleotide 819; A→C modification of nucleotide 822; T→C modification of nucleotide 825; A→C modification of nucleotide 831; T→C modification of nucleotide 834; A→G modification of nucleotide 837; A→G modification of nucleotide 840; T→G modification of nucleotide 843; T→C modification of nucleotide 846; A→C modification of nucleotide 852; T→C modification of nucleotide 855; A→G modification of nucleotide 858; A→G modification of nucleotide 864; A→C modification of nucleotide 867; T→C modification of nucleotide 873; A→C modification of nucleotide 876; A→G modification of nucleotide 879; A→C modification of nucleotide 882; T→C modification of nucleotide 885; A→G modification of nucleotide 891; A→C modification of nucleotide 894; T→C modification of nucleotide 897; T→C modification of nucleotide 900; T→C modification of nucleotide 909; T→G modification of nucleotide 912; T→C modification of nucleotide 913; A→G modification of nucleotide 915; A→T modification of nucleotide 916; G→C modification of nucleotide 917; T→C modification of nucleotide 918; T→C modification of nucleotide 921; T→C modification of nucleotide 922; A→G modification of nucleotide 924; A→G modification of nucleotide 927; T→C modification of nucleotide 930; T→C modification of nucleotide 933; A→C modification of nucleotide 936; T→C modification of nucleotide 939; A→G modification of nucleotide 942; A→C modification of nucleotide 945; T→G modification of nucleotide 948; T→C modification of nucleotide 951; A→C modification of nucleotide 954; A→G modification of nucleotide 957; A→G modification of nucleotide 960; A→C modification of nucleotide 961; T→C modification of nucleotide 966; A→C modification of nucleotide 972; T→C modification of nucleotide 978; A→C modification of nucleotide 981; T→C modification of nucleotide 990; A→C modification of nucleotide 993; A→T modification of nucleotide 994; G→C modification of nucleotide 995; T→G modification of nucleotide 999; T→C modification of nucleotide 1002; A→C modification of nucleotide 1003; A→C modification of nucleotide 1005; A→C modification of nucleotide 1008; T→C modification of nucleotide 1011; C→G modification of nucleotide 1014; T→C modification of nucleotide 1017; T→C modification of nucleotide 1020; A→C modification of nucleotide 1026; T→C modification of nucleotide 1035; T→C modification of nucleotide 1039; A→C modification of nucleotide 1047; A→C modification of nucleotide 1050; A→G modification of nucleotide 1056; A→C modification of nucleotide 1059; A→C modification of nucleotide 1062; T→C modification of nucleotide 1065; A→C modification of nucleotide 1071; T→C modification of nucleotide 1072; T→C modification of nucleotide 1077; T→G modification of nucleotide 1083; T→C modification of nucleotide 1086; G→C modification of nucleotide 1092; T→C modification of nucleotide 1098; T→C modification of nucleotide 1104; A→C modification of nucleotide 1114; A→C modification of nucleotide 1116; A→G modification of nucleotide 1119; A→C modification of nucleotide 1122; A→T modification of nucleotide 1123; G→C modification of nucleotide 1124; T→C modification of nucleotide 1128; T→C modification of nucleotide 1131; T→G modification of nucleotide 1134; T→C modification of nucleotide 1137; T→C modification of nucleotide 1146; T→C modification of nucleotide 1149; T→C modification of nucleotide 1152; T→C modification of nucleotide 1155; A→C modification of nucleotide 1158; T→C modification of nucleotide 1161; T→C modification of nucleotide 1164; C→G modification of nucleotide 1167; T→C modification of nucleotide 1173; A→T modification of nucleotide 1174; G→C modification of nucleotide 1175; T→C modification of nucleotide 1176; A→G modification of nucleotide 1179; T→C modification of nucleotide 1182; A→C modification of nucleotide 1185; A→C modification of nucleotide 1188; T→C modification of nucleotide 1194; T→C modification of nucleotide 1197; T→C modification of nucleotide 1198; T→C modification of nucleotide 1203; A→C modification of nucleotide 1206; T→G modification of nucleotide 1215; T→C modification of nucleotide 1218; T→C modification of nucleotide 1221; T→C modification of nucleotide 1227; T→C modification of nucleotide 1236; A→C modification of nucleotide 1239; A→C modification of nucleotide 1242; A→G modification of nucleotide 1248; A→C modification of nucleotide 1257; T→C modification of nucleotide 1260; A→C modification of nucleotide 1266; A→G modification of nucleotide 1275; T→C modification of nucleotide 1281; A→C modification of nucleotide 1284; T→G modification of nucleotide 1296; A→C modification of nucleotide 1297; A→C modification of nucleotide 1299; T→C modification of nucleotide 1302; C→G modification of nucleotide 1308; T→C modification of nucleotide 1311; A→C modification of nucleotide 1314; 1→C modification of nucleotide 1317; T→C modification of nucleotide 1320; A→G modification of nucleotide 1323; A→C modification of nucleotide 1326; T→G modification of nucleotide 1329; T→C modification of nucleotide 1332; A→G modification of nucleotide 1335; A→G modification of nucleotide 1341; A→G modification of nucleotide 1344; T→C modification of nucleotide 1350; A→C modification of nucleotide 1353; T→G modification of nucleotide 1356; A→C modification of nucleotide 1359; A→G modification of nucleotide 1362; A→C modification of nucleotide 1371; A→G modification of nucleotide 1374; T→C modification of nucleotide 1377; T→C modification of nucleotide 1383; T→C modification of nucleotide 1392; A→G modification of nucleotide 1401; T→G modification of nucleotide 1404; A→G modification of nucleotide 1410; A→C modification of nucleotide 1411; A→C modification of nucleotide 1414; G→C modification of nucleotide 1416; A→G modification of nucleotide 1419; A→C modification of nucleotide 1422; A→T modification of nucleotide 1429; G→C modification of nucleotide 1430; A→T modification of nucleotide 1432; G→C modification of nucleotide 1433; T→C modification of nucleotide 1437; T→C modification of nucleotide 1443; G→C modification of nucleotide 1446; A→G modification of nucleotide 1449; C→G modification of nucleotide 1455; A→C modification of nucleotide 1461; T→C modification of nucleotide 1465; T→C modification of nucleotide 1476; A→C modification of nucleotide 1479; A→C modification of nucleotide 1485; A→G modification of nucleotide 1494; A→T modification of nucleotide 1495; G→C modification of nucleotide 1496; T→C modification of nucleotide 1497; A→C modification of nucleotide 1500; G→C modification of nucleotide 1506; T→C modification of nucleotide 1515; A→G modification of nucleotide 1518; T→C modification of nucleotide 1521; T→G modification of nucleotide 1524; T→C modification of nucleotide 1527; A→G modification of nucleotide 1530; T→C modification of nucleotide 1536; T→C modification of nucleotide 1539; T→C modification of nucleotide 1545; T→C modification of nucleotide 1548; T→C modification of nucleotide 1554; T→C modification of nucleotide 1557; T→G modification of nucleotide 1560; G→C modification of nucleotide 1563; T→C modification of nucleotide 1566; A→G modification of nucleotide 1569; T→C modification of nucleotide 1578; A→C modification of nucleotide 1581; T→C modification of nucleotide 1587; G→C modification of nucleotide 1596; T→C modification of nucleotide 1602; A→G modification of nucleotide 1605; A→C modification of nucleotide 1608; T→C modification of nucleotide 1611; T→G modification of nucleotide 1614; T→G modification of nucleotide 1620; T→C modification of nucleotide 1623; T→C modification of nucleotide 1626; G→C modification of nucleotide 1629; A→G modification of nucleotide 1632; A→G modification of nucleotide 1635; T→C modification of nucleotide 1638; T→C modification of nucleotide 1641; A→G modification of nucleotide 1644; T→G modification of nucleotide 1647; T→G modification of nucleotide 1650; T→C modification of nucleotide 1656; A→C modification of nucleotide 1659; T→C modification of nucleotide 1665; T→C modification of nucleotide 1671; A→G modification of nucleotide 1674; A→T modification of nucleotide 1678; G→C modification of nucleotide 1679; T→C modification of nucleotide 1683; T→C modification of nucleotide 1689; T→G modification of nucleotide 1692; A→C modification of nucleotide 1698; A→C modification of nucleotide 1701; A→G modification of nucleotide 1704; T→C modification of nucleotide 1707; T→C modification of nucleotide 1711; A→G modification of nucleotide 1713; T→C modification of nucleotide 1716; T→C modification of nucleotide 1722; T→C modification of nucleotide 1725; A→G modification of nucleotide 1728; A→C modification of nucleotide 1734; T→G modification of nucleotide 1740; A→C modification of nucleotide 1744; A→C modification of nucleotide 1746; T→C modification of nucleotide 1749; G→C modification of nucleotide 1752; A→G modification of nucleotide 1755; A→C modification of nucleotide 1758; T→C modification of nucleotide 1761; A→T modification of nucleotide 1762; G→C modification of nucleotide 1763; T→C modification of nucleotide 1767; T→C modification of nucleotide 1770; A→C modification of nucleotide 1776; T→C modification of nucleotide 1782; T→C modification of nucleotide 1785; T→C modification of nucleotide 1788; A→C modification of nucleotide 1791; T→C modification of nucleotide 1794; A→T modification of nucleotide 1795; G→C modification of nucleotide 1796; C→G modification of nucleotide 1803; T→G modification of nucleotide 1809; T→C modification of nucleotide 1812; T→G modification of nucleotide 1815; A→T modification of nucleotide 1816; G→C modification of nucleotide 1817; A→C modification of nucleotide 1821; A→G modification of nucleotide 1824; A→G modification of nucleotide 1833; T→C modification of nucleotide 1836; T→C modification of nucleotide 1839; T→C modification of nucleotide 1845; T→C modification of nucleotide 1848; G→C modification of nucleotide 1851; T→C modification of nucleotide 1854; A→G modification of nucleotide 1860; A→G modification of nucleotide 1863; T→C modification of nucleotide 1869; A→G modification of nucleotide 1872; A→G modification of nucleotide 1875; G→C modification of nucleotide 1877; T→C modification of nucleotide 1881; A→C modification of nucleotide 1884; T→C modification of nucleotide 1887; A→C modification of nucleotide 1890; A→C modification of nucleotide 1893; A→C modification of nucleotide 1896; A→G modification of nucleotide 1899; A→C modification of nucleotide 1902; T→C modification of nucleotide 1905; T→C modification of nucleotide 1906; T→C modification of nucleotide 1914; T→C modification of nucleotide 1920; T→C modification of nucleotide 1923; A→G modification of nucleotide 1926; T→C modification of nucleotide 1929; T→C modification of nucleotide 1932; A→C modification of nucleotide 1935; T→C modification of nucleotide 1944; T→C modification of nucleotide 1947; T→C modification of nucleotide 1950; A→C modification of nucleotide 1953; A→C modification of nucleotide 1956; T→C modification of nucleotide 1962; A→C modification of nucleotide 1965; T→C modification of nucleotide 1968; C→G modification of nucleotide 1974; A→T modification of nucleotide 1975; G→C modification of nucleotide 1976; A→C modification of nucleotide 1989; T→G modification of nucleotide 1995; T→C modification of nucleotide 1998; A→G modification of nucleotide 2004; T→C modification of nucleotide 2007; T→C modification of nucleotide 2010; T→C modification of nucleotide 2016; A→G modification of nucleotide 2022; T→C modification of nucleotide 2025; A→C modification of nucleotide 2031; T→C modification of nucleotide 2037; T→C modification of nucleotide 2043; A→C modification of nucleotide 2046; A→C modification of nucleotide 2061; A→C modification of nucleotide 2065; A→C modification of nucleotide 2067; T→C modification of nucleotide 2070; T→C modification of nucleotide 2073; T→C modification of nucleotide 2079; T→C modification of nucleotide 2082; A→C modification of nucleotide 2091; A→G modification of nucleotide 2094; A→C modification of nucleotide 2095; G→C modification of nucleotide 2097; T→G modification of nucleotide 2100; T→C modification of nucleotide 2103; A→G modification of nucleotide 2109; A→C modification of nucleotide 2112; A→G modification of nucleotide 2115; T→C modification of nucleotide 2118; A→C modification of nucleotide 2124; A→G modification of nucleotide 2127; T→C modification of nucleotide 2130; T→G modification of nucleotide 2133; T→C modification of nucleotide 2136; T→C modification of nucleotide 2148; T→C modification of nucleotide 2154; A→C modification of nucleotide 2155; A→C modification of nucleotide 2157; T→C modification of nucleotide 2163; A→C modification of nucleotide 2169; A→C modification of nucleotide 2173; A→C modification of nucleotide 2175; G→C modification of nucleotide 2178; A→G modification of nucleotide 2181; T→C modification of nucleotide 2184; T→C modification of nucleotide 2190; A→C modification of nucleotide 2193; A→C modification of nucleotide 2194; G→C modification of nucleotide 2196; A→T modification of nucleotide 2197; G→C modification of nucleotide 2198; T→C modification of nucleotide 2199; T→C modification of nucleotide 2202; T→C modification of nucleotide 2203; A→G modification of nucleotide 2205; T→C modification of nucleotide 2208; G→C modification of nucleotide 2211; A→G modification of nucleotide 2214; T→G modification of nucleotide 2217; A→G modification of nucleotide 2223; A→C modification of nucleotide 2226; T→C modification of nucleotide 2232; T→C modification of nucleotide 2247; A→G modification of nucleotide 2250; A→C modification of nucleotide 2253; A→C modification of nucleotide 2256; A→C modification of nucleotide 2259; T→C modification of nucleotide 2262; T→C modification of nucleotide 2265; T→G modification of nucleotide 2268; T→C modification of nucleotide 2271; A→C modification of nucleotide 2274; A→C modification of nucleotide 2284; A→C modification of nucleotide 2286; T→C modification of nucleotide 2287; A→G modification of nucleotide 2289; T→C modification of nucleotide 2298; T→C modification of nucleotide 2301; A→C modification of nucleotide 2304; G→C modification of nucleotide 2307; T→C modification of nucleotide 2310; T→C modification of nucleotide 2313; A→C modification of nucleotide 2316; A→C modification of nucleotide 2319; T→C modification of nucleotide 2322; A→G modification of nucleotide 2325; A→T modification of nucleotide 2326; G→C modification of nucleotide 2327; T→C modification of nucleotide 2328; T→C modification of nucleotide 2331; C→G modification of nucleotide 2337; A→G modification of nucleotide 2340; T→G modification of nucleotide 2346; T→C modification of nucleotide 2352; T→G modification of nucleotide 2358; A→C modification of nucleotide 2361; T→A modification of nucleotide 2365; G→C modification of nucleotide 2366; T→C modification of nucleotide 2370; T→C modification of nucleotide 2373; A→G modification of nucleotide 2376; A→T modification of nucleotide 2386; G→C modification of nucleotide 2387; T→C modification of nucleotide 2388; A→C modification of nucleotide 2391; A→C modification of nucleotide 2394; G→C modification of nucleotide 2397; T→C modification of nucleotide 2400; T→C modification of nucleotide 2407; A→G modification of nucleotide 2409; T→C modification of nucleotide 2412; T→C modification of nucleotide 2419; T→C modification of nucleotide 2433; T→C modification of nucleotide 2445; T→C modification of nucleotide 2451; A→G modification of nucleotide 2454; T→C modification of nucleotide 2463; T→C modification of nucleotide 2469; T→C modification of nucleotide 2472; A→C modification of nucleotide 2475; A→G modification of nucleotide 2478; A→C modification of nucleotide 2484; A→C modification of nucleotide 2485; A→C modification of nucleotide 2487; T→G modification of nucleotide 2490; T→C modification of nucleotide 2499; T→C modification of nucleotide 2502; A→G modification of nucleotide 2505; T→C modification of nucleotide 2508; A→C modification of nucleotide 2514; T→C modification of nucleotide 2517; T→C modification of nucleotide 2520; A→G modification of nucleotide 2523; A→C modification of nucleotide 2526; T→C modification of nucleotide 2532; T→C modification of nucleotide 2538; T→C modification of nucleotide 2541; A→C modification of nucleotide 2553; T→C modification of nucleotide 2556; T→C modification of nucleotide 2562; A→C modification of nucleotide 2568; A→C modification of nucleotide 2571; A→G modification of nucleotide 2574; G→C modification of nucleotide 2577; A→C modification of nucleotide 2578; A→C modification of nucleotide 2580; A→G modification of nucleotide 2583; A→C modification of nucleotide 2590; G→C modification of nucleotide 2592; T→C modification of nucleotide 2595; A→G modification of nucleotide 2601; T→C modification of nucleotide 2604; A→C modification of nucleotide 2605; A→C modification of nucleotide 2607; A→G modification of nucleotide 2610; T→C modification of nucleotide 2613; A→C modification of nucleotide 2616; A→G modification of nucleotide 2619; A→T modification of nucleotide 2623; G→C modification of nucleotide 2624; A→C modification of nucleotide 2640; A→C modification of nucleotide 2643; T→G modification of nucleotide 2649; T→G modification of nucleotide 2655; T→C modification of nucleotide 2658; A→C modification of nucleotide 2661; T→C modification of nucleotide 2662; A→C modification of nucleotide 2667; A→G modification of nucleotide 2670; A→C modification of nucleotide 2673; A→C modification of nucleotide 2676; A→C modification of nucleotide 2679; T→C modification of nucleotide 2682; T→C modification of nucleotide 2689; A→G modification of nucleotide 2691; T→C modification of nucleotide 2694; A→G modification of nucleotide 2697; A→C modification of nucleotide 2703; T→C modification of nucleotide 2709; A→G modification of nucleotide 2712; T→C modification of nucleotide 2715; T→C modification of nucleotide 2718; A→G modification of nucleotide 2724; A→C modification of nucleotide 2728; G→C modification of nucleotide 2730; T→G modification of nucleotide 2733; A→C modification of nucleotide 2736; T→C modification of nucleotide 2739; T→C modification of nucleotide 2742; T→C modification of nucleotide 2748; G→C modification of nucleotide 2751; T→C modification of nucleotide 2754; T→C modification of nucleotide 2757; A→G modification of nucleotide 2760; T→C modification of nucleotide 2763; T→C modification of nucleotide 2766; A→G modification of nucleotide 2772; A→C modification of nucleotide 2778; T→C modification of nucleotide 2781; G→C modification of nucleotide 2784; A→G modification of nucleotide 2787; G→C modification of nucleotide 2790; T→C modification of nucleotide 2793; T→C modification of nucleotide 2799; T→C modification of nucleotide 2805; T→C modification of nucleotide 2808; T→C modification of nucleotide 2811; T→C modification of nucleotide 2818; A→C modification of nucleotide 2823; T→C modification of nucleotide 2826; T→C modification of nucleotide 2829; A→G modification of nucleotide 2832; T→G modification of nucleotide 2832; T→G modification of nucleotide 2835; T→C modification of nucleotide 2838; A→G modification of nucleotide 2841; A→G modification of nucleotide 2850; A→G modification of nucleotide 2853; A→C modification of nucleotide 2856; A→C modification of nucleotide 2859; T→C modification of nucleotide 2860; T→C modification of nucleotide 2869; T→C modification of nucleotide 2880; A→C modification of nucleotide 2881; A→C modification of nucleotide 2883; A→C modification of nucleotide 2889; A→G modification of nucleotide 2892; T→C modification of nucleotide 2895; T→C modification of nucleotide 2901; A→C modification of nucleotide 2904; A→G modification of nucleotide 2907; T→C modification of nucleotide 2910; A→G modification of nucleotide 2913; A→G modification of nucleotide 2922; T→C modification of nucleotide 2928; A→G modification of nucleotide 2931; A→C modification of nucleotide 2943; T→C modification of nucleotide 2946; A→G modification of nucleotide 2949; T→C modification of nucleotide 2952; T→C modification of nucleotide 2958; T→C modification of nucleotide 2961; T→C modification of nucleotide 2964; A→C modification of nucleotide 2970; A→T modification of nucleotide 2974; G→C modification of nucleotide 2975; T→C modification of nucleotide 2982; T→C modification of nucleotide 2985; G→C modification of nucleotide 2988; T→C modification of nucleotide 2991; T→C modification of nucleotide 2994; A→C modification of nucleotide 2997; A→C modification of nucleotide 3003; T→C modification of nucleotide 3009; A→C modification of nucleotide 3015; T→C modification of nucleotide 3018; T→C modification of nucleotide 3024; T→C modification of nucleotide 3025; A→G modification of nucleotide 3030; A→C modification of nucleotide 3033; T→C modification of nucleotide 3036; T→C modification of nucleotide 3039; G→C modification of nucleotide 3042; T→C modification of nucleotide 3045; A→C modification of nucleotide 3048; A→G modification of nucleotide 3051; A→G modification of nucleotide 3054; T→C modification of nucleotide 3057; T→C modification of nucleotide 3060; T→C modification of nucleotide 3063; A→C modification of nucleotide 3066; T→C modification of nucleotide 3069; A→G modification of nucleotide 3072; T→C modification of nucleotide 3075; T→C modification of nucleotide 3084; C→G modification of nucleotide 3087; A→C modification of nucleotide 3090; T→C modification of nucleotide 3102; A→G modification of nucleotide 3129; T→C modification of nucleotide 3132; T→C modification of nucleotide 3135; T→C modification of nucleotide 3138; C→G modification of nucleotide 3141; G→C modification of nucleotide 3147; A→C modification of nucleotide 3153; A→G modification of nucleotide 3156; A→G modification of nucleotide 3165; A→C modification of nucleotide 3168; T→C modification of nucleotide 3171; G→C modification of nucleotide 3174; T→C modification of nucleotide 3177; T→C modification of nucleotide 3183; T→G modification of nucleotide 3186; T→C modification of nucleotide 3189; T→C modification of nucleotide 3192; T→C modification of nucleotide 3195; A→G modification of nucleotide 3204; G→C modification of nucleotide 3210; A→T modification of nucleotide 3212; A→T modification of nucleotide 3217; G→C modification of nucleotide 3218; T→C modification of nucleotide 3222; A→C modification of nucleotide 3225; T→C modification of nucleotide 3231; A→T modification of nucleotide 3235; G→C modification of nucleotide 3236; A→C modification of nucleotide 3243; T→C modification of nucleotide 3246; A→C modification of nucleotide 3249; A→C modification of nucleotide 3255; T→C modification of nucleotide 3261; T→C modification of nucleotide 3273; T→C modification of nucleotide 3276; A→C modification of nucleotide 3279; T→C modification of nucleotide 3288; A→G modification of nucleotide 3291; A→C modification of nucleotide 3294; A→C modification of nucleotide 3297; T→C modification of nucleotide 3303; T→C modification of nucleotide 3309; T→C modification of nucleotide 3315; T→C modification of nucleotide 3318; A→C modification of nucleotide 3321; T→C modification of nucleotide 3327; C→G modification of nucleotide 3333; A→C modification of nucleotide 3334; G→C modification of nucleotide 3336; A→G modification of nucleotide 3339; T→C modification of nucleotide 3342; T→C modification of nucleotide 3354; A→G modification of nucleotide 3360; A→C modification of nucleotide 3361; A→C modification of nucleotide 3363; T→C modification of nucleotide 3366; T→A modification of nucleotide 3367; G→C modification of nucleotide 3368; T→C modification of nucleotide 3369; T→C modification of nucleotide 3375; A→G modification of nucleotide 3378; T→C modification of nucleotide 3381; T→C modification of nucleotide 3396; G→C modification of nucleotide 3399; C→G modification of nucleotide 3408; T→C modification of nucleotide 3411; T→C modification of nucleotide 3414; T→C modification of nucleotide 3417; T→C modification of nucleotide 3429; T→C modification of nucleotide 3432; A→G modification of nucleotide 3435; A→C modification of nucleotide 3438; T→C modification of nucleotide 3439; T→C modification of nucleotide 3450; A→C modification of nucleotide 3453; T→C modification of nucleotide 3462; T→G modification of nucleotide 3465; T→G modification of nucleotide 3468; G→C modification of nucleotide 3480; A→G modification of nucleotide 3486; T→C modification of nucleotide 3489; A→C modification of nucleotide 3498; A→G modification of nucleotide 3516; T→C modification of nucleotide 3528; G→C modification of nucleotide 3537; C→G modification of nucleotide 3552; T→C modification of nucleotide 3564; C→G modification of nucleotide 3567; T→G modification of nucleotide 3582; C→G modification of nucleotide 3585; C→G modification of nucleotide 3584; C→G modification of nucleotide 3594; C→G modification of nucleotide 3597; A→T modification of nucleotide 3612; G→C modification of nucleotide 3602; G→C modification of nucleotide 3612; A→C modification of nucleotide 3625; G→C modification of nucleotide 3627; T→C modification of nucleotide 3630; A→G modification of nucleotide 3642; G→C modification of nucleotide 3645; A→G modification of nucleotide 3648; A→C modification of nucleotide 3654; T→C modification of nucleotide 3660; T→C modification of nucleotide 3663; T→C modification of nucleotide 3668; G→C modification of nucleotide 3675; A→T modification of nucleotide 3676; G→C modification of nucleotide 3677; A→C modification of nucleotide 3679; A→C modification of nucleotide 3681; T→C modification of nucleotide 3684; A→C modification of nucleotide 3688; G→C modification of nucleotide 3690; A→T modification of nucleotide 3691; G→C modification of nucleotide 3692; T→C modification of nucleotide 3693; A→C modification of nucleotide 3697; G→C modification of nucleotide 3699; T→C modification of nucleotide 3702; T→C modification of nucleotide 3705; T→C modification of nucleotide 3711; T→C modification of nucleotide 3717; G→C modification of nucleotide 3720; T→C modification of nucleotide 3729; T→C modification of nucleotide 3735; A→G modification of nucleotide 3738; T→C modification of nucleotide 3741; T→C modification of nucleotide 3747; T→G modification of nucleotide 3752; A→C modification of nucleotide 3756; A→G modification of nucleotide 3759; A→G modification of nucleotide 3762; A→G modification of nucleotide 3769; C→G modification of nucleotide 3774; T→C modification of nucleotide 3780; G→C modification of nucleotide 3783; T→C modification of nucleotide 3786; A→G modification of nucleotide 3789; A→C modification of nucleotide 3792; T→C modification of nucleotide 3798; T→C modification of nucleotide 3801; T→C modification of nucleotide 3807; A→C modification of nucleotide 3816; A→C modification of nucleotide 3819; T→C modification of nucleotide 3822; G→C modification of nucleotide 3825; A→C modification of nucleotide 3828; A→G modification of nucleotide 3834; A→C modification of nucleotide 3837; T→C modification of nucleotide 3840; A→C modification of nucleotide 3843; A→C modification of nucleotide 3847; G→C modification of nucleotide 3849; T→C modification of nucleotide 3862; A→G modification of nucleotide 3864; T→C modification of nucleotide 3867; A→C modification of nucleotide 3870; A→C modification of nucleotide 3879; A→G modification of nucleotide 3885; T→C modification of nucleotide 3897; A→C modification of nucleotide 3900; A→G modification of nucleotide 3903; A→T modification of nucleotide 3907; G→C modification of nucleotide 3908; T→C modification of nucleotide 3909; T→C modification of nucleotide 3912; T→C modification of nucleotide 3924; A→G modification of nucleotide 3933; A→G modification of nucleotide 3942; A→T modification of nucleotide 3943; G→C modification of nucleotide 3944; T→C modification of nucleotide 3948; T→C modification of nucleotide 3951; T→C modification of nucleotide 3963; G→C modification of nucleotide 3966; A→C modification of nucleotide 3969; T→G modification of nucleotide 3978; A→G modification of nucleotide 3981; G→C modification of nucleotide 3984; T→C modification of nucleotide 3987; C→G modification of nucleotide 3990; T→C modification of nucleotide 4002; T→C modification of nucleotide 4005; C→G modification of nucleotide 4008; A→G modification of nucleotide 4011; A→C modification of nucleotide 4014; T→C modification of nucleotide 4017; A→C modification of nucleotide 4023; T→C modification of nucleotide 4024; A→G modification of nucleotide 4026; A→G modification of nucleotide 4032; A→G modification of nucleotide 4035; A→C modification of nucleotide 4036; G→C modification of nucleotide 4038; A→C modification of nucleotide 4050; A→C modification of nucleotide 4053; A→G modification of nucleotide 4059; T→C modification of nucleotide 4071; and deletion of nucleotides 4076-6388;

c) a sequence encoding Hepatocyte Growth Factor (HGF) and comprising one or more of the following modifications relative to SEQ ID NO: 3:
deletion of nucleotides 1-76; A→G modification of nucleotide 91; C→G modification of nucleotide 94; T→C modification of nucleotide 118; C→G modification of nucleotide 121; C→G modification of nucleotide 124; T→C modification of nucleotide 130; C→G modification of nucleotide 133; C→G modification of nucleotide 136; C→G modification of nucleotide 142; T→C modification of nucleotide 160; A→C modification of nucleotide 163; A→C modification of nucleotide 169; A→G modification of nucleotide 172; A→C modification of nucleotide 173; G→C modification of nucleotide 175; A→G modification of nucleotide 178; A→C modification of nucleotide 179; A→C modification of nucleotide 181; A→C modification of nucleotide 182; A→C modification of nucleotide 184; T→C modification of nucleotide 187; A→C modification of nucleotide 190; T→C modification of nucleotide 193; T→C modification of nucleotide 196; A→G modification of nucleotide 199; A→G modification of nucleotide 205; A→G modification of nucleotide 208; A→C modification of nucleotide 211; A→C modification of nucleotide 214; T→C modification of nucleotide 220; A→G modification of nucleotide 226; A→G modification of nucleotide 232; A→C modification of nucleotide 235; T→C modification of nucleotide 238; A→C modification of nucleotide 241; A→C modification of nucleotide 244; A→C modification of nucleotide 253; A→G modification of nucleotide 256; A→G modification of nucleotide 262; A→G modification of nucleotide 265; T→C modification of nucleotide 271; T→C modification of nucleotide 274; A→C modification of nucleotide 277; A→G modification of nucleotide 283; T→C modification of nucleotide 286; T→C modification of nucleotide 289; T→C modification of nucleotide 292; A→C modification of nucleotide 293; A→C modification of nucleotide 295; T→C modification of nucleotide 298; T→C modification of nucleotide 301; A→C modification of nucleotide 302; G→C modification of nucleotide 304; T→C modification of nucleotide 307; A→G modification of nucleotide 310; A→C modification of nucleotide 313; T→G modification of nucleotide 316; A→C modification of nucleotide 319; T→C modification of nucleotide 325; T→C modification of nucleotide 334; T→C modification of nucleotide 337; T→G modification of nucleotide 340; T→C modification of nucleotide 343; T→C modification of nucleotide 346; A→G modification of nucleotide 349; A→C modification of nucleotide 352; A→C modification of nucleotide 353; A→C modification of nucleotide 355; A→G modification of nucleotide 358; A→G modification of nucleotide 361; C→G modification of nucleotide 367; T→C modification of nucleotide 382; A→T modification of nucleotide 383; G→C modification of nucleotide 384; A→C modification of nucleotide 391; A→T modification of nucleotide 392; G→C modification of nucleotide 393; T→C modification of nucleotide 394; A→C modification of nucleotide 397; A→G modification of nucleotide 403; A→G modification of nucleotide 406; A→G modification of nucleotide 409; T→C modification of nucleotide 412; T→C modification of nucleotide 418; A→G modification of nucleotide 421; T→C modification of nucleotide 424; C→G modification of nucleotide 430; T→C modification of nucleotide 433; A→G modification of nucleotide 436; A→G modification of nucleotide 442; T→C modification of nucleotide 451; A→C modification of nucleotide 452; A→C modification of nucleotide 454; T→C modification of nucleotide 466; T→C modification of nucleotide 469; A→G modification of nucleotide 472; A→C modification of nucleotide 475; A→T modification of nucleotide 479; G→C modification of nucleotide 480; A→C modification of nucleotide 490; A→C modification of nucleotide 493; A→G modification of nucleotide 496; T→C modification of nucleotide 499; T→C modification of nucleotide 505; A→T modification of nucleotide 509; G→C modification of nucleotide 510; T→C modification of nucleotide 511; A→G modification of nucleotide 520; T→C modification of nucleotide 523; A→T modification of nucleotide 533; G→C modification of nucleotide 534; T→C modification of nucleotide 535; A→C modification of nucleotide 544; A→C modification of nucleotide 547; A→G modification of nucleotide 553; A→T modification of nucleotide 557; G→C modification of nucleotide 558; T→C modification of nucleotide 562; T→C modification of nucleotide 563; T→C modification of nucleotide 568; G→C modification of nucleotide 571; A→T modification of nucleotide 572; G→C modification of nucleotide 573; T→C modification of nucleotide 577; G→C modification of nucleotide 580; T→C modification of nucleotide 583; A→G modification of nucleotide 586; A→G modification of nucleotide 592; A→G modification of nucleotide 598; T→C modification of nucleotide 607; A→C modification of nucleotide 610; T→C modification of nucleotide 613; T→C modification of nucleotide 616; A→C modification of nucleotide 619; G→C modification of nucleotide 622; A→G modification of nucleotide 625; A→G modification of nucleotide 628; G→C modification of nucleotide 631; A→C modification of nucleotide 634; T→C modification of nucleotide 643; A→C modification of nucleotide 649; A→T modification of nucleotide 650; G→C modification of nucleotide 651; T→C modification of nucleotide 655; A→C modification of nucleotide 658; A→G modification of nucleotide 664; A→G modification of nucleotide 673; C→G modification of nucleotide 676; T→C modification of nucleotide 679; T→C modification of nucleotide 685; T→C modification of nucleotide 688; T→C modification of nucleotide 694; A→C modification of nucleotide 697; A→G modification of nucleotide 700; T→G modification of nucleotide 703; A→G modification of nucleotide 706; T→C modification of nucleotide 721; G→C modification of nucleotide 724; A→T modification of nucleotide 728; G→C modification of nucleotide 729; T→C modification of nucleotide 730; T→C modification of nucleotide 733; A→C modification of nucleotide 736; T→C modification of nucleotide 739; C→G modification of nucleotide 742; T→C modification of nucleotide 748; T→C modification of nucleotide 751; A→C modification of nucleotide 754; A→G modification of nucleotide 757; A→C modification of nucleotide 760; T→C modification of nucleotide 769; T→C modification of nucleotide 772; C→G modification of nucleotide 778; T→C modification of nucleotide 784; T→C modification of nucleotide 787; A→C modification of nucleotide 783; A→C modification of nucleotide 786; G→C modification of nucleotide 802; A→G modification of nucleotide 808; T→C modification of nucleotide 812; T→C modification of nucleotide 817; A→G modification of nucleotide 820; A→C modification of nucleotide 821; A→G modification of nucleotide 823; T→C modification of nucleotide 826; T→C modification of nucleotide 841; T→C modification of nucleotide 844; T→C modification of nucleotide 847; T→C modification of nucleotide 850; T→C modification of nucleotide 853; T→C modification of nucleotide 862; T→C modification of nucleotide 868; G→C modification of nucleotide 877; A→C modification of nucleotide 878; G→C modification of nucleotide 880; A→C modification of nucleotide 883; T→C modification of nucleotide 892; T→C modification of nucleotide 895; T→G modification of nucleotide 898; T→C modification of nucleotide 904; T→C modification of nucleotide 925; A→C modification of nucleotide 928; T→C modification of nucleotide 931; A→G modification of nucleotide 934; A→C modification of nucleotide 937; T→C modification of nucleotide 943; T→C modification of nucleotide 949; T→C modification of nucleotide 952; T→C modification of nucleotide 958; T→C modification of nucleotide 964; T→C modification of nucleotide 967; T→G modification of nucleotide 970; T→C modification of nucleotide 973; T→C modification of nucleotide 974; A→G modification of nucleotide 979; A→C modification of nucleotide 982; T→C modification of nucleotide 985; A→G modification of nucleotide 988; A→G modification of nucleotide 997; T→C modification of nucleotide 1000; A→G modification of nucleotide 1003; A→C modification of nucleotide 1006; A→G modification of nucleotide 1009; A→C modification of nucleotide 1016; G→C modification of nucleotide 1018; T→C modification of nucleotide 1024; C→G modification of nucleotide 1027; T→C modification of nucleotide 1030; T→C modification of nucleotide 1036; T→C modification of nucleotide 1042; A→C modification of nucleotide 1045; T→C modification of nucleotide 1048; A→C modification of nucleotide 1051; T→C modification of nucleotide 1054; T→G modification of nucleotide 1060; T→C modification of nucleotide 1066; T→C modification of nucleotide 1069; T→C modification of nucleotide 1075; T→C modification of nucleotide 1078; T→C modification of nucleotide 1087; T→C modification of nucleotide 1096; T→C modification of nucleotide 1099; A→G modification of nucleotide 1102; T→C modification of nucleotide 1105; A→G modification of nucleotide 1123; A→C modification of nucleotide 1126; A→G modification of nucleotide 1129; T→C modification of nucleotide 1132; A→C modification of nucleotide 1141; T→C modification of nucleotide 1144; A→C modification of nucleotide 1147; T→C modification of nucleotide 1150; G→C modification of nucleotide 1153; T→C modification of nucleotide 1156; A→G modification of nucleotide 1159; A→C modification of nucleotide 1162; T→C modification of nucleotide 1171; T→C modification of nucleotide 1174; T→C modification of nucleotide 1180; T→C modification of nucleotide 1183; A→C modification of nucleotide 1186; A→C modification of nucleotide 1195; T→G modification of nucleotide 1198; A→G modification of nucleotide 1213; T→C modification of nucleotide 1216; A→C modification of nucleotide 1219; T→C modification of nucleotide 1225; T→C modification of nucleotide 1228; A→C modification of nucleotide 1234; T→C modification of nucleotide 1237; A→C modification of nucleotide 1240; A→G modification of nucleotide 1243; T→C modification of nucleotide 1246; T→C modification of nucleotide 1249; T→C modification of nucleotide 1252; T→C modification of nucleotide 1255; G→C modification of nucleotide 1258; T→C modification of nucleotide 1261; A→G modification of nucleotide 1267; T→C modification of nucleotide 1270; T→C modification of nucleotide 1273; T→C modification of nucleotide 1283; A→G modification of nucleotide 1285; A→G modification of nucleotide 1291; A→C modification of nucleotide 1294; A→C modification of nucleotide 1295; A→C modification of nucleotide 1297; T→C modification of nucleotide 1300; A→C modification of nucleotide 1303; A→G modification of nucleotide 1306; A→C modification of nucleotide 1309; T→C modification of nucleotide 1312; A→C modification of nucleotide 1315; A→G modification of nucleotide 1336; T→C modification of nucleotide 1340; A→G modification of nucleotide 1342; T→C modification of nucleotide 1345; T→C modification of nucleotide 1348; T→C modification of nucleotide 1351; A→G modification of nucleotide 1363; A→C modification of nucleotide 1366; T→C modification of nucleotide 1369; A→C modification of nucleotide 1372; A→T modification of nucleotide 1373; G→C modification of nucleotide 1374; T→C modification of nucleotide 1375; T→C modification of nucleotide 1384; T→C modification of nucleotide 1390; A→C modification of nucleotide 1399; T→C modification of nucleotide 1402; A→C modification of nucleotide 1405; T→C modification of nucleotide 1408; T→C modification of nucleotide 1411; T→C modification of nucleotide 1414; T→C modification of nucleotide 1417; T→C modification of nucleotide 1420; A→C modification of nucleotide 1423; G→C modification of nucleotide 1438; A→C modification of nucleotide 1441; T→C modification of nucleotide 1444; A→C modification of nucleotide 1447; C→G modification of nucleotide 1450; T→C modification of nucleotide 1453; T→C modification of nucleotide 1456; T→C modification of nucleotide 1462; T→C modification of nucleotide 1465; T→C modification of nucleotide 1471; T→C modification of nucleotide 1474; T→C modification of nucleotide 1477; T→C modification of nucleotide 1480; T→C modification of nucleotide 1483; A→G modification of nucleotide 1486; T→C modification of nucleotide 1489; T→C modification of nucleotide 1492; A→C modification of nucleotide 1498; T→C modification of nucleotide 1501; A→C modification of nucleotide 1504; A→C modification of nucleotide 1507; C→G modification of nucleotide 1510; T→C modification of nucleotide 1513; T→C modification of nucleotide 1514; A→G modification of nucleotide 1516; T→C modification of nucleotide 1522; A→G modification of nucleotide 1528; A→C modification of nucleotide 1531; T→C modification of nucleotide 1534; T→C modification of nucleotide 1537; A→G modification of nucleotide 1543; G→C modification of nucleotide 1546; A→G modification of nucleotide 1549; A→G modification of nucleotide 1552; T→C modification of nucleotide 1553; A→C modification of nucleotide 1558; T→G modification of nucleotide 1561; A→G modification of nucleotide 1564; T→C modification of nucleotide 1567; G→C modification of nucleotide 1570; T→C modification of nucleotide 1573; A→C modification of nucleotide 1576; A→C modification of nucleotide 1579; A→C modification of nucleotide 1582; A→C modification of nucleotide 1585; A→C modification of nucleotide 1594; T→G modification of nucleotide 1603; A→T modification of nucleotide 1604; G→C modification of nucleotide 1605; T→C modification of nucleotide 1606; T→C modification of nucleotide 1607; A→C modification of nucleotide 1610; A→C modification of nucleotide 1612; A→C modification of nucleotide 1616; A→C modification of nucleotide 1618; T→C modification of nucleotide 1621; A→G modification of nucleotide 1624; T→C modification of nucleotide 1627; A→C modification of nucleotide 1636; A→C modification of nucleotide 1639; A→C modification of nucleotide 1642; T→C modification of nucleotide 1643; A→C modification of nucleotide 1648; A→T modification of nucleotide 1655; G→C modification of nucleotide 1656; T→C modification of nucleotide 1657; T→G modification of nucleotide 1663; T→G modification of nucleotide 1666; T→C modification of nucleotide 1669; A→C modification of nucleotide 1672; A→C modification of nucleotide 1675; T→C modification of nucleotide 1681; T→C modification of nucleotide 1687; T→C modification of nucleotide 1690; A→C modification of nucleotide 1693; T→C modification of nucleotide 1697; A→G modification of nucleotide 1702; T→C modification of nucleotide 1705; T→C modification of nucleotide 1708; A→G modification of nucleotide 1711; T→C modification of nucleotide 1714; T→G modification of nucleotide 1720; A→C modification of nucleotide 1723; T→C modification of nucleotide 1726; T→C modification of nucleotide 1729; T→C modification of nucleotide 1732; C→G modification of nucleotide 1735; A→C modification of nucleotide 1741; A→C modification of nucleotide 1742; A→C modification of nucleotide 1744; A→C modification of nucleotide 1747; T→C modification of nucleotide 1750; A→G modification of nucleotide 1756; A→G modification of nucleotide 1762; T→G modification of nucleotide 1768; C→G modification of nucleotide 1771; T→C modification of nucleotide 1774; T→G modification of nucleotide 1777; A→G modification of nucleotide 1789; T→C modification of nucleotide 1792; T→C modification of nucleotide 1798; A→G modification of nucleotide 1801; A→C modification of nucleotide 1804; A→C modification of nucleotide 1807; T→C modification of nucleotide 1810; T→G modification of nucleotide 1816; T→C modification of nucleotide 1817; A→G modification of nucleotide 1819; T→G modification of nucleotide 1828; A→C modification of nucleotide 1832; G→C modification of nucleotide 1834; T→C modification of nucleotide 1837; T→C modification of nucleotide 1840; C→G modification of nucleotide 1843; T→C modification of nucleotide 1849; T→C modification of nucleotide 1852; T→C modification of nucleotide 1855; T→G modification of nucleotide 1858; G→C modification of nucleotide 1860; T→C modification of nucleotide 1861; G→C modification of nucleotide 1863; T→C modification of nucleotide 1866; T→C modification of nucleotide 1870; T→C modification of nucleotide 1871; A→G modification of nucleotide 1873; T→C modification of nucleotide 1876; T→C modification of nucleotide 1879; T→C modification of nucleotide 1882; A→C modification of nucleotide 1885; A→C modification of nucleotide 1891; T→C modification of nucleotide 1894; T→C modification of nucleotide 1897; A→G modification of nucleotide 1900; A→T modification of nucleotide 1907; G→C modification of nucleotide 1908; T→C modification of nucleotide 1909; A→T modification of nucleotide 1913; G→C modification of nucleotide 1914; T→C modification of nucleotide 1915; T→G modification of nucleotide 1918; T→C modification of nucleotide 1921; T→C modification of nucleotide 1936; A→C modification of nucleotide 1939; T→C modification of nucleotide 1940; T→C modification of nucleotide 1951; T→C modification of nucleotide 1954; A→G modification of nucleotide 1960; T→C modification of nucleotide 1961; A→G modification of nucleotide 1963; A→C modification of nucleotide 1966; A→C modification of nucleotide 1972; T→C modification of nucleotide 1975; C→G modification of nucleotide 1978; T→C modification of nucleotide 1981; A→C modification of nucleotide 1990; T→C modification of nucleotide 1993; A→G modification of nucleotide 1999; A→T modification of nucleotide 2003; G→C modification of nucleotide 2004; T→C modification of nucleotide 2011; T→C modification of nucleotide 2014; A→C modification of nucleotide 2017; G→C modification of nucleotide 2020; T→C modification of nucleotide 2029; T→C modification of nucleotide 2035; T→C modification of nucleotide 2041; A→G modification of nucleotide 2044; A→C modification of nucleotide 2047; T→C modification of nucleotide 2050; T→C modification of nucleotide 2053; G→C modification of nucleotide 2056; T→C modification of nucleotide 2059; A→G modification of nucleotide 2062; T→C modification of nucleotide 2068; A→C modification of nucleotide 2071; A→C modification of nucleotide 2074; A→C modification of nucleotide 2077; A→C modification of nucleotide 2080; T→C modification of nucleotide 2083; G→C modification of nucleotide 2089; T→C modification of nucleotide 2092; T→C modification of nucleotide 2095; T→C modification of nucleotide 2098; A→C modification of nucleotide 2104; T→G modification of nucleotide 2107; T→G modification of nucleotide 2110; T→C modification of nucleotide 2113; A→G modification of nucleotide 2119; T→C modification of nucleotide 2122; A→G modification of nucleotide 2125; A→C modification of nucleotide 2129; A→C modification of nucleotide 2131; T→G modification of nucleotide 2137; T→G modification of nucleotide 2140; T→C modification of nucleotide 2143; C→G modification of nucleotide 2146; T→C modification of nucleotide 2149; T→G modification of nucleotide 2152; T→C modification of nucleotide 2155; T→C modification of nucleotide 2158; T→C modification of nucleotide 2161; A→C modification of nucleotide 2164; T→C modification of nucleotide 2167; T→C modification of nucleotide 2173; A→C modification of nucleotide 2176; T→C modification of nucleotide 2179; T→C modification of nucleotide 2182; T→C modification of nucleotide 2185; T→C modification of nucleotide 2188; T→C modification of nucleotide 2191; T→C modification of nucleotide 2194; C→G modification of nucleotide 2197; A→C modification of nucleotide 2200; A→G modification of nucleotide 2203; A→C modification of nucleotide 2206; T→C modification of nucleotide 2209; T→C modification of nucleotide 2212; A→C modification of nucleotide 2215; A→G modification of nucleotide 2218; A→C modification of nucleotide 2224; A→G modification of nucleotide 2230; T→C modification of nucleotide 2233; T→C modification of nucleotide 2236; T→C modification of nucleotide 2237; A→G modification of nucleotide 2239; A→C modification of nucleotide 2242; T→C modification of nucleotide 2245; A→G modification of nucleotide 2251; A→C modification of nucleotide 2254; A→C modification of nucleotide 2262; and deletion of nucleotides 2263-5834;

d) a sequence encoding Cyclin-Dependent Kinase Inhibitor 1A (P21) and comprising one or more of the following modifications relative to SEQ ID NO: 4:

deletion of nucleotides 1-134; T→C modification of nucleotide 143; T→C modification of nucleotide 146; T→C modification of nucleotide 149; T→C modification of nucleotide 152; C→G modification of nucleotide 155; A→C modification of nucleotide 158; T→C modification of nucleotide 161; T→G modification of nucleotide 164; G→C modification of nucleotide 167; A→C modification of nucleotide 171; G→C modification of nucleotide 173; A→T modification of nucleotide 174; G→C modification of nucleotide 175; A→G modification of nucleotide 179; T→C modification of nucleotide 188; T→C modification of nucleotide 191; C→G modification of nucleotide 194; T→C modification of nucleotide 200; A→T modification of nucleotide 210; G→C modification of nucleotide 211; T→C modification of nucleotide 212; T→C modification of nucleotide 219; T→C modification of nucleotide 227; T→C modification of nucleotide 230; T→C modification of nucleotide 236; G→C modification of nucleotide 239; C→G modification of nucleotide 242; G→C modification of nucleotide 248; T→C modification of nucleotide 254; C→G modification of nucleotide 257; A→C modification of nucleotide 269; A→G modification of nucleotide 272; T→C modification of nucleotide 284; C→G modification of nucleotide 293; G→C modification of nucleotide 296; G→C modification of nucleotide 302; G→C modification of nucleotide 305; C→G modification of nucleotide 323; T→G modification of nucleotide 335; G→C modification of nucleotide 338; A→T modification of nucleotide 339; G→C modification of nucleotide 340; A→G modification of nucleotide 344; G→C modification of nucleotide 347; C→G modification of nucleotide 359; A→T modification of nucleotide 366; G→C modification of nucleotide 367; T→C modification of nucleotide 371; G→C modification of nucleotide 374; A→T modification of nucleotide 381; G→C modification of nucleotide 382; T→C modification of nucleotide 386; A→C modification of nucleotide 398; G→C modification of nucleotide 401; A→C modification of nucleotide 408; G→C modification of nucleotide 410; A→T modification of nucleotide 414; G→C modification of nucleotide 415; T→C modification of nucleotide 416; T→C modification of nucleotide 419; T→C modification of nucleotide 425; G→C modification of nucleotide 440; A→C modification of nucleotide 443; T→C modification of nucleotide 446; G→C modification of nucleotide 449; T→C modification of nucleotide 465; G→C modification of nucleotide 470; T→C modification of nucleotide 476; T→C modification of nucleotide 482; T→C modification of nucleotide 491; G→C modification of nucleotide 497; T→C modification of nucleotide 500; A→G modification of nucleotide 503; T→C modification of nucleotide 506; G→C modification of nucleotide 512; T→C modification of nucleotide 515; G→C modification of nucleotide 518; A→C modification of nucleotide 524; A→C modification of nucleotide 527; T→C modification of nucleotide 530; A→C modification of nucleotide 539; A→G modification of nucleotide 542; G→C modification of nucleotide 545; A→C modification of nucleotide 546; G→C modification of nucleotide 548; A→G modification of nucleotide 555; G→C modification of nucleotide 556; A→C modification of nucleotide 563; T→C modification of nucleotide 566; T→C modification of nucleotide 572; A→C modification of nucleotide 585; A→C modification of nucleotide 587; T→C modification of nucleotide 588; C→G modification of nucleotide 593; A→C modification of nucleotide 603; A→C modification of nucleotide 605; A→G modification of nucleotide 608; and deletion of nucleotides 613-1943;

e) a sequence encoding Vascular Endothelial Growth Factor A (VEGFA) and comprising one or more of the following modifications relative to SEQ ID NO: 5:

deletion of nucleotides 1-1036; T→C modification of nucleotide 1045; T→C modification of nucleotide 1054; T→C modification of nucleotide 1063; A→T modification of nucleotide 1067; G→C modification of nucleotide 1068; T→G modification of nucleotide 1072; T→C modification of nucleotide 1076; C→G modification of nucleotide 1084; C→G modification of nucleotide 1090; T→C modification of nucleotide 1096; T→C modification of nucleotide 1114; A→C modification of nucleotide 1117; A→C modification of nucleotide 1126; A→G modification of nucleotide 1129; A→C modification of nucleotide 1132; A→C modification of nucleotide 1135; G→C modification of nucleotide 1138; T→C modification of nucleotide 1144; T→C modification of nucleotide 1147; A→G modification of nucleotide 1153; T→C modification of nucleotide 1171; C→G modification of nucleotide 1174; T→C modification of nucleotide 1177; C→G modification of nucleotide 1183; A→T modification of nucleotide 1184; G→C modification of nucleotide 1185; T→C modification of nucleotide 1195; A→C modification of nucleotide 1198; T→C modification of nucleotide 1234; T→C modification of nucleotide 1237; A→C modification of nucleotide 1261; T→C modification of nucleotide 1267; A→C modification of nucleotide 1282; G→C modification of nucleotide 1288; T→C modification of nucleotide 1300; T→C modification of nucleotide 1318; T→C modification of nucleotide 1327; T→C modification of nucleotide 1354; G→C modification of nucleotide 1360;

A→G modification of nucleotide 1366; T→C modification of nucleotide 1369; A→G modification of nucleotide 1375; A→C modification of nucleotide 1387; A→C modification of nucleotide 1390; A→T modification of nucleotide 1397; G→C modification of nucleotide 1398; A→G modification of nucleotide 1405; A→G modification of nucleotide 1417; T→C modification of nucleotide 1420; A→G modification of nucleotide 1423; A→C modification of nucleotide 1427; A→C modification of nucleotide 1429; A→C modification of nucleotide 1432; A→G modification of nucleotide 1438; T→C modification of nucleotide 1441; A→C modification of nucleotide 1442; A→C modification of nucleotide 1444; A→C modification of nucleotide 1447; A→C modification of nucleotide 1448; A→C modification of nucleotide 1450; A→G modification of nucleotide 1453; A→G modification of nucleotide 1456; T→C modification of nucleotide 1459; T→C modification of nucleotide 1465; G→C modification of nucleotide 1468; T→C modification of nucleotide 1471; A→C modification of nucleotide 1477; G→C modification of nucleotide 1483; A→C modification of nucleotide 1484; A→C modification of nucleotide 1486; T→C modification of nucleotide 1492; T→C modification of nucleotide 1493; T→C modification of nucleotide 1498; A→G modification of nucleotide 1501; A→G modification of nucleotide 1504; T→C modification of nucleotide 1507; G→C modification of nucleotide 1510; G→C modification of nucleotide 1516; T→C modification of nucleotide 1519; A→G modification of nucleotide 1522; T→C modification of nucleotide 1525; A→G modification of nucleotide 1534; A→C modification of nucleotide 1540; G→C modification of nucleotide 1546; T→C modification of nucleotide 1549; and deletion of nucleotides 1556-3502;

f) a sequence encoding Insulin-like Growth Factor 1 (Igf1) and comprising one or more of the following modifications relative to SEQ ID NO: 6:
deletion of nucleotides 1-298; G→C modification of nucleotide 304; A→G modification of nucleotide 307; A→T modification of nucleotide 311; G→C modification of nucleotide 312; A→T modification of nucleotide 314; G→C modification of nucleotide 315; T→G modification of nucleotide 319; A→C modification of nucleotide 322; T→C modification of nucleotide 325; A→G modification of nucleotide 328; T→C modification of nucleotide 329; A→G modification of nucleotide 331; T→C modification of nucleotide 334; C→G modification of nucleotide 346; T→C modification of nucleotide 349; T→C modification of nucleotide 356; A→C modification of nucleotide 364; A→C modification of nucleotide 370; G→C modification of nucleotide 382; T→C modification of nucleotide 385; A→C modification of nucleotide 388; C→G modification of nucleotide 394; G→C modification of nucleotide 406; C→G modification of nucleotide 409; T→C modification of nucleotide 413; C→G modification of nucleotide 418; A→T modification of nucleotide 428; G→C modification of nucleotide 429; A→C modification of nucleotide 439; T→C modification of nucleotide 442; A→C modification of nucleotide 445; A→C modification of nucleotide 448; T→G modification of nucleotide 457; G→C modification of nucleotide 463; T→C modification of nucleotide 466; T→C modification of nucleotide 478; T→C modification of nucleotide 481; T→G modification of nucleotide 484; T→C modification of nucleotide 496; A→C modification of nucleotide 499; G→C modification of nucleotide 502; A→C modification of nucleotide 503; G→C modification of nucleotide 505; T→C modification of nucleotide 511; A→C modification of nucleotide 529; T→C modification of nucleotide 535; A→T modification of nucleotide 542; G→C modification of nucleotide 543; T→C modification of nucleotide 547; G→C modification of nucleotide 550; A→C modification of nucleotide 551; G→C modification of nucleotide 553; A→C modification of nucleotide 556; T→C modification of nucleotide 559; A→C modification of nucleotide 565; T→C modification of nucleotide 571; T→C modification of nucleotide 577; T→C modification of nucleotide 583; G→C modification of nucleotide 592; A→T modification of nucleotide 593; G→C modification of nucleotide 594; T→C modification of nucleotide 598; T→C modification of nucleotide 601; A→C modification of nucleotide 605; G→C modification of nucleotide 607; A→C modification of nucleotide 608; A→C modification of nucleotide 610; T→C modification of nucleotide 625; A→C modification of nucleotide 631; T→C modification of nucleotide 640; A→C modification of nucleotide 643; A→G modification of nucleotide 646; A→C modification of nucleotide 649; T→C modification of nucleotide 658; T→C modification of nucleotide 664; T→C modification of nucleotide 679; T→C modification of nucleotide 694; A→G modification of nucleotide 703; A→G modification of nucleotide 706; T→C modification of nucleotide 709; T→C modification of nucleotide 710; A→C modification of nucleotide 721; A→T modification of nucleotide 722; G→C modification of nucleotide 723; T→C modification of nucleotide 724; A→C modification of nucleotide 725; A→C modification of nucleotide 727; A→C modification of nucleotide 730; A→T modification of nucleotide 731; G→C modification of nucleotide 732; T→C modification of nucleotide 733; A→C modification of nucleotide 736; A→C modification of nucleotide 739; A→C modification of nucleotide 752; A→C modification of nucleotide 754; and deletion of nucleotides 760-7073;

g) a sequence encoding Insulin-like Growth Factor 1 (Igf1) and comprising one or more of the following modifications relative to SEQ ID NO: 6:
deletion of nucleotides 1-442; insertion of SEQ ID NO: 18; A→C modification of nucleotide 445; A→C modification of nucleotide 448; T→G modification of nucleotide 457; G→C modification of nucleotide 463; T→C modification of nucleotide 466; T→C modification of nucleotide 478; T→C modification of nucleotide 481; T→G modification of nucleotide 484; T→C modification of nucleotide 496; A→C modification of nucleotide 499; G→C modification of nucleotide 502; A→C modification of nucleotide 503; G→C modification of nucleotide 505; T→C modification of nucleotide 511; A→C modification of nucleotide 529; T→C modification of nucleotide 535; A→T modification of nucleotide 542; G→C modification of nucleotide 543; T→C modification of nucleotide 547; G→C modification of nucleotide 550; A→C modification of nucleotide 551; G→C modification of nucleotide 553; A→C modification of nucleotide 556; T→C modification of nucleotide 559; A→C modification of nucleotide 565; T→C modification of nucleotide 571; T→C modification of nucleotide 577; T→C modification of nucleotide 583; G→C modification of nucleotide 592; A→T modification of nucleotide 593; G→C modification of nucleotide 594; T→C modification of nucleotide 598; T→C modification of nucleotide 601; A→C modification of nucleotide 605; G→C modification of nucleotide 607; A→C modification of nucleotide 608; A→C modification of nucleotide 610; T→C modification of nucleotide 625; A→C modification of nucleotide 631; T→C modification of nucleotide 640; A→C modification of nucleotide 643; A→G modification of nucleotide 646; A→C modification of nucleotide 649; T→C modification of nucleotide 658; T→C modification of nucleotide 664; T→C modification of nucleotide 679; T→C modification of nucleotide 694; A→G modification of nucleotide 703; A→G modification of nucleotide 706; T→C modification of nucleotide 709; T→C modification of nucleotide 710; A→C modification of nucleotide 721; A→T modification of nucleotide 722; G→C modification of nucleotide 723; T→C modification of nucleotide 724; A→C modification of nucleotide 725; A→C modification of nucleotide 727; A→C modification of nucleotide 730; A→T modification of nucleotide 731; G→C modification of nucleotide 732; T→C modification of nucleotide 733; A→C modification of nucleotide 736; A→C modification of nucleotide 739; A→C modification of nucleotide 752; A→C modification of nucleotide 754; and deletion of nucleotides 760-7073;

h) a sequence encoding Epidermal Growth Factor1 (EGF) and comprising one or more of the following modifications relative to SEQ ID NO: 2 deletion of nucleotides 1-3369; insertion of SEQ ID NO: 19; T→C modification of nucleotide 3375; A→G modification of nucleotide 3378; T→C modification of nucleotide 3381; T→C modification of nucleotide 3396; G→C modification of nucleotide 3399; C→G modification of nucleotide 3408; T→C modification of nucleotide 3411; T→C modification of nucleotide 3414; T→C modification of nucleotide 3417; T→C modification of nucleotide 3429; T→C modification of nucleotide 3432; A→G modification of nucleotide 3435; A→C modification of nucleotide 3438; T→C modification of nucleotide 3439; T→C modification of nucleotide 3450; A→C modification of nucleotide 3453; T→C modification of nucleotide 3462; T→G modification of nucleotide 3465; T→G modification of nucleotide 3468; G→C modification of nucleotide 3480; A→G modification of nucleotide 3486; T→C modification of nucleotide 3489; A→C modification of nucleotide 3498; A→G modification of nucleotide 3516; and deletion of nucleotides 3523-6388;

i) a sequence encoding signal transducer and activator of transcription 5B (Stat5b) and comprising one or more of the following modifications relative to SEQ ID NO: 7:
deletion of nucleotides 1-532; insertion of SEQ ID NO: 20; T→C modification of nucleotide 535; A→C modification of nucleotide 544; T→C modification of nucleotide 550; C→G modification of nucleotide 559; T→C modification of nucleotide 568; T→G modification of nucleotide 574; T→C modification of nucleotide 590; T→C modification of nucleotide 604; A→C modification of nucleotide 622; T→C modification of nucleotide 625; T→C modification of nucleotide 628; T→C modification of nucleotide 629; A→G modification of nucleotide 631; A→C modification of nucleotide 634; A→G modification of nucleotide 646; A→T modification of nucleotide 647; G→C modification of nucleotide 648; A→G modification of nucleotide 652; A→C modification of nucleotide 664; A→C modification of nucleotide 667; T→C modification of nucleotide 670; T→G modification of nucleotide 673; T→C modification of nucleotide 676; T→C modification of nucleotide 679; A→C modification of nucleotide 682; T→C modification of nucleotide 694; C→G modification of nucleotide 709; G→C modification of nucleotide 745; G→C modification of nucleotide 760; A→G modification of nucleotide 763; T→C modification of nucleotide 766; G→C modification of nucleotide 769; T→C modification of nucleotide 772; T→C modification of nucleotide 773; G→C modification of nucleotide 793; T→C modification of nucleotide 799; A→C modification of nucleotide 805; C→G modification of nucleotide 811; A→T modification of nucleotide 815; G→C modification of nucleotide 816; G→C modification of nucleotide 820; T→G modification of nucleotide 847; T→C modification of nucleotide 853; G→C modification of nucleotide 859; T→C modification of nucleotide 865; A→G modification of nucleotide 877; A→C modification of nucleotide 881; G→C modification of nucleotide 883; T→G modification of nucleotide 889; A→G modification of nucleotide 895; A→T modification of nucleotide 908; G→C modification of nucleotide 909; T→C modification of nucleotide 913; A→C modification of nucleotide 916; T→C modification of nucleotide 919; A→C modification of nucleotide 922; A→T modification of nucleotide 923; G→C modification of nucleotide 924; T→C modification of nucleotide 925; T→G modification of nucleotide 928; T→C modification of nucleotide 931; T→G modification of nucleotide 955; A→G modification of nucleotide 967; G→C modification of nucleotide 970; T→C modification of nucleotide 973; A→C modification of nucleotide 994; G→C modification of nucleotide 1003; A→G modification of nucleotide 1036; A→T modification of nucleotide 1064; G→C modification of nucleotide 1065; G→C modification of nucleotide 1072; A→G modification of nucleotide 1078; T→C modification of nucleotide 1081; T→C modification of nucleotide 1087; A→C modification of nucleotide 1099; A→T modification of nucleotide 1124; G→C modification of nucleotide 1125; A→C modification of nucleotide 1127; G→C modification of nucleotide 1129; G→C modification of nucleotide 1135; C→G modification of nucleotide 1141; A→G modification of nucleotide 1153; A→C modification of nucleotide 1180; A→C modification of nucleotide 1186; A→C modification of nucleotide 1192; A→C modification of nucleotide 1207; T→C modification of nucleotide 1219; G→C modification of nucleotide 1252; G→C modification of nucleotide 1300; A→C modification of nucleotide 1301; A→C modification of nucleotide 1303; G→C modification of nucleotide 1318; G→C modification of nucleotide 1324; T→C modification of nucleotide 1327; A→T modification of nucleotide 1340; G→C modification of nucleotide 1341; T→C modification of nucleotide 1366; G→C modification of nucleotide 1399; A→C modification of nucleotide 1412; G→C modification of nucleotide 1414; T→C modification of nucleotide 1417; T→C modification of nucleotide 1424; A→C modification of nucleotide 1447; T→C modification of nucleotide 1471; C→G modification of nucleotide 1477; G→C modification of nucleotide 1492; A→C modification of nucleotide 1504; C→G modification of nucleotide 1513; A→T modification of nucleotide 1517; G→C modification of nucleotide 1518; G→C modification of nucleotide 1522; T→C modification of nucleotide 1543; T→C modification of nucleotide 1546; C→G modification of nucleotide 1552; T→C modification of nucleotide 1573; A→C modification of nucleotide 1576; G→C modification of nucleotide 1600; G→C modification of nucleotide 1603; T→C modification of nucleotide 1612; G→C modification of nucleotide 1630; G→C modification of nucleotide 1642; A→T modification of nucleotide 1652; G→C modification of nucleotide 1653; C→G modification of nucleotide 1678; T→C modification of nucleotide 1684; T→C modification of nucleotide 1699; T→C modification of nucleotide 1702; A→T modification of nucleotide 1706; G→C modification of nucleotide 1707; T→C modification of nucleotide 1729; C→G modification of nucleotide 1735; T→C modification of nucleotide 1756; A→C modification of nucleotide 1762; C→G modification of nucleotide 1765; A→T modification of nucleotide 1766; G→C modification of nucleotide 1767; A→C modification of nucleotide 1778; A→C modification of nucleotide 1780; A→G modification of nucleotide 1795; A→C modification of nucleotide 1798; A→C modification of nucleotide 1805; T→C modification of nucleotide 1810; T→C modification of nucleotide 1819; G→C modification of nucleotide 1822; A→C modification of nucleotide 1825; A→C modification of nucleotide 1831; A→G modification of nucleotide 1834; G→C modification of nucleotide 1837; A→G modification of nucleotide 1840; G→C modification of nucleotide 1852; T→C modification of nucleotide 1861; A→C modification of nucleotide 1867; A→T modification of nucleotide 1874; G→C modification of nucleotide 1875; C→G modification of nucleotide 1879; T→C modification of nucleotide 1882; A→C modification of nucleotide 1885; C→G modification of nucleotide 1897; T→C modification of nucleotide 1900; A→G modification of nucleotide 1903; C→G modification of nucleotide 1906; T→C modification of nucleotide 1913; G→C modification of nucleotide 1918; C→G modification of nucleotide 1921; G→C modification of nucleotide 1924; T→C modification of nucleotide 1936; T→G modification of nucleotide 1939; A→T modification of nucleotide 1946; G→C modification of nucleotide 1947; T→C modification of nucleotide 1960; A→C modification of nucleotide 1966; T→C modification of nucleotide 1972; C→G modification of nucleotide 1975; C→G modification of nucleotide 1978; T→C modification of nucleotide 1993; A→C modification of nucleotide 1996; T→C modification of nucleotide 2002; A→C modification of nucleotide 2006; G→C modification of nucleotide 2008; A→C modification of nucleotide 2014; T→C modification of nucleotide 2017; T→C modification of nucleotide 2026; G→C modification of nucleotide 2044; T→C modification of nucleotide 2053; A→G modification of nucleotide 2056; G→C modification of nucleotide 2059; C→G modification of nucleotide 2062; A→G modification of nucleotide 2071; T→C modification of nucleotide 2080; A→G modification of nucleotide 2083; A→G modification of nucleotide 2086; A→T modification of nucleotide 2090; G→C modification of nucleotide 2091; G→C modification of nucleotide 2098; T→C modification of nucleotide 2102; C→G modification of nucleotide 2119; A→C modification of nucleotide 2131; A→G modification of nucleotide 2137; A→T modification of nucleotide 2150; G→C modification of nucleotide 2151; A→T modification of nucleotide 2153; G→C modification of nucleotide 2154; C→G modification of nucleotide 2164; A→T modification of nucleotide 2177; G→C modification of nucleotide 2178; G→C modification of nucleotide 2209; T→C modification of nucleotide 2215; T→C modification of nucleotide 2216; A→C modification of nucleotide 2221; A→C modification of nucleotide 2224; G→C modification of nucleotide 2227; T→C modification of nucleotide 2230; T→C modification of nucleotide 2236; T→C modification of nucleotide 2251; T→C modification of nucleotide 2254; A→G modification of nucleotide 2266; A→G modification of nucleotide 2269; T→C modification of nucleotide 2270; A→G modification of nucleotide 2275; A→G modification of nucleotide 2278; T→C modification of nucleotide 2281; C→G modification of nucleotide 2284; T→C modification of nucleotide 2290; T→C modification of nucleotide 2299; T→C modification of nucleotide 2302; G→C modification of nucleotide 2305; T→C modification of nucleotide 2308; T→C modification of nucleotide 2317; A→G modification of nucleotide 2332; C→G modification of nucleotide 2350; A→C modification of nucleotide 2362; G→C modification of nucleotide 2368; A→T modification of nucleotide 2387; G→C modification of nucleotide 2388; G→C modification of nucleotide 2395;

A→G modification of nucleotide 2398; G→C modification of nucleotide 2404; T→C modification of nucleotide 2416; T→C modification of nucleotide 2419; T→C modification of nucleotide 2428; T→C modification of nucleotide 2434; A→C modification of nucleotide 2441; A→C modification of nucleotide 2443; T→C modification of nucleotide 2449; A→C modification of nucleotide 2453; T→C modification of nucleotide 2455; T→C modification of nucleotide 2464; T→C modification of nucleotide 2467; T→C modification of nucleotide 2473; A→C modification of nucleotide 2474; A→C modification of nucleotide 2476; T→C modification of nucleotide 2485; G→C modification of nucleotide 2491; C→G modification of nucleotide 2497; T→C modification of nucleotide 2500; G→C modification of nucleotide 2512; T→C modification of nucleotide 2521; C→G modification of nucleotide 2527; A→C modification of nucleotide 2530; T→C modification of nucleotide 2533; T→C modification of nucleotide 2539; T→C modification of nucleotide 2542; T→C modification of nucleotide 2545; G→C modification of nucleotide 2548; A→C modification of nucleotide 2551; T→C modification of nucleotide 2557; A→G modification of nucleotide 2560; A→G modification of nucleotide 2563; T→C modification of nucleotide 2566; T→C modification of nucleotide 2569; A→C modification of nucleotide 2581; G→C modification of nucleotide 2584; C→G modification of nucleotide 2587; T→C modification of nucleotide 2593; A→C modification of nucleotide 2602; T→C modification of nucleotide 2605; G→C modification of nucleotide 2608; A→G modification of nucleotide 2611; A→C modification of nucleotide 2614; T→C modification of nucleotide 2617; A→C modification of nucleotide 2623; A→C modification of nucleotide 2635; C→G modification of nucleotide 2653; T→C modification of nucleotide 2662; A→C modification of nucleotide 2665; T→C modification of nucleotide 2668; A→C modification of nucleotide 2671; A→C modification of nucleotide 2677; T→C modification of nucleotide 2680; T→C modification of nucleotide 2683; G→C modification of nucleotide 2686; A→T modification of nucleotide 2687; G→C modification of nucleotide 2688; T→C modification of nucleotide 2689; T→C modification of nucleotide 2707; T→C modification of nucleotide 2713; T→C modification of nucleotide 2716; A→C modification of nucleotide 2722; C→G modification of nucleotide 2725; T→C modification of nucleotide 2734; T→C modification of nucleotide 2740; A→C modification of nucleotide 2758; G→C modification of nucleotide 2767; C→G modification of nucleotide 2776; T→G modification of nucleotide 2779; T→C modification of nucleotide 2782; T→C modification of nucleotide 2788; G→C modification of nucleotide 2791; T→C modification of nucleotide 2800; A→G modification of nucleotide 2806; G→C modification of nucleotide 2812; G→C modification of nucleotide 2824; G→C modification of nucleotide 2827; A→G modification of nucleotide 2836; C→G modification of nucleotide 2842; T→C modification of nucleotide 2843; A→G modification of nucleotide 2845; G→C modification of nucleotide 2851; A→T modification of nucleotide 2861; G→C modification of nucleotide 2862; T→C modification of nucleotide 2863; T→C modification of nucleotide 2875; A→C modification of nucleotide 2881; A→C modification of nucleotide 2887; and deletion of nucleotides 2888-5255;

j) a sequence encoding beta catenin (CTNNB1) and comprising one or more of the following modifications relative to SEQ ID NO: 17:
  deletion of nucleotides 1-214; T→C modification of nucleotide 220; T→C modification of nucleotide 223; A→G modification of nucleotide 226; T→C modification of nucleotide 229; T→C modification of nucleotide 232; T→C modification of nucleotide 233; T→C modification of nucleotide 242; A→G modification of nucleotide 259; A→C modification of nucleotide 262; A→C modification of nucleotide 266; A→C modification of nucleotide 268; A→G modification of nucleotide 271; G→C modification of nucleotide 274; T→C modification of nucleotide 277; T→G modification of nucleotide 280; A→T modification of nucleotide 281; G→C modification of nucleotide 282; T→C modification of nucleotide 283; A→G modification of nucleotide 295; T→C modification of nucleotide 301; T→C modification of nucleotide 313; A→C modification of nucleotide 316; T→C modification of nucleotide 322; T→C modification of nucleotide 325; T→C modification of nucleotide 328; T→C modification of nucleotide 334; A→C modification of nucleotide 340; T→C modification of nucleotide 343; T→C modification of nucleotide 346; T→C modification of nucleotide 349; A→C modification of nucleotide 353; G→C modification of nucleotide 354; T→C modification of nucleotide 355; T→C modification of nucleotide 358; A→G modification of nucleotide 361; T→C modification of nucleotide 367; T→C modification of nucleotide 370; A→G modification of nucleotide 376; T→C modification of nucleotide 382; T→C modification of nucleotide 388; A→G modification of nucleotide 397; C→G modification of nucleotide 400; T→C modification of nucleotide 406; A→G modification of nucleotide 415; A→C modification of nucleotide 421; T→C modification of nucleotide 424; T→C modification of nucleotide 427; T→C modification of nucleotide 439; A→G modification of nucleotide 442; A→G modification of nucleotide 445; A→G modification of nucleotide 448; A→G modification of nucleotide 451; T→C modification of nucleotide 454; T→C modification of nucleotide 457; T→C modification of nucleotide 460; T→C modification of nucleotide 463; A→C modification of nucleotide 466; T→C modification of nucleotide 472; A→C modification of nucleotide 475; T→C modification of nucleotide 481; A→C modification of nucleotide 484; T→C modification of nucleotide 487; A→C modification of nucleotide 491; G→C modification of nucleotide 493; A→G modification of nucleotide 496; A→C modification of nucleotide 499; T→C modification of nucleotide 502; T→C modification of nucleotide 505; T→C modification of nucleotide 514; A→C modification of nucleotide 520; T→C modification of nucleotide 521; A→G modification of nucleotide 523; T→C modification of nucleotide 526; A→C modification of nucleotide 544; T→C modification of nucleotide 547; A→C modification of nucleotide 550; T→C modification of nucleotide 556; T→C modification of nucleotide 559; T→C modification of nucleotide 562; T→C modification of nucleotide 565; T→C modification of nucleotide 568; T→C modification of nucleotide 574; T→C modification of nucleotide 577; C→G modification of nucleotide 580; T→C modification of nucleotide 586; T→C modification of nucleotide 587; T→C modification of nucleotide 592; A→G modification of nucleotide 595; A→C modification of nucleotide 598; A→C modification of nucleotide 601; A→G modification of nucleotide 613; T→C modification of nucleotide 616; A→C modification of nucleotide 619; T→G modification of nucleotide 622; A→G modification of nucleotide 625; T→C modification of nucleotide 629; T→C modification of nucleotide 634; T→C modification of nucleotide 640; A→G modification of nucleotide 643; T→C modification of nucleotide 646; T→C modification of nucleotide 649; A→C modification of nucleotide 652; A→G modification of nucleotide 655; T→G modification of nucleotide 658; A→C modification of nucleotide 664; T→C modification of nucleotide 667; A→C modification of nucleotide 670; T→C modification of nucleotide 676; A→G modification of nucleotide 679; A→C modification of nucleotide 685; A→G modification of nucleotide 688; A→G modification of nucleotide 694; T→C modification of nucleotide 697; T→G modification of nucleotide 718; T→C modification of nucleotide 721; T→C modification of nucleotide 727; A→C modification of nucleotide 730; T→G modification of nucleotide 733; C→G modification of nucleotide 739; T→C modification of nucleotide 742; T→G modification of nucleotide 748; T→C modification of nucleotide 751; A→G modification of nucleotide 754; A→G modification of nucleotide 760; T→C modification of nucleotide 763; A→C modification of nucleotide 767; A→C modification of nucleotide 769; T→C modification of nucleotide 775; T→C modification of nucleotide 784; T→C modification of nucleotide 787; T→C modification of nucleotide 790; T→C modification of nucleotide 802; T→C modification of nucleotide 805; T→C modification of nucleotide 808; A→G modification of nucleotide 811; T→C modification of nucleotide 814; T→C modification of nucleotide 826; A→C modification of nucleotide 829; T→C modification of nucleotide 832; T→C modification of nucleotide 835; A→G modification of nucleotide 838; A→G modification of nucleotide 841; A→C modification of nucleotide 844; T→C modification of nucleotide 847; T→C modification of nucleotide 850; T→C modification of nucleotide 853; T→C modification of nucleotide 859; G→C modification of nucleotide 862; T→C modification of nucleotide 866; T→G modification of nucleotide 871; T→G modification of nucleotide 878; T→C modification of nucleotide 883; T→C modification of nucleotide 886; T→C modification of nucleotide 889; T→C modification of nucleotide 896; A→G modification of nucleotide 898; T→C modification of nucleotide 910; T→C modification of nucleotide 916; A→C modification of nucleotide 919; T→C modification of nucleotide 925; T→C modification of nucleotide 928; A→G modification of nucleotide 940; T→G modification of nucleotide 946; T→C modification of nucleotide 949; A→C modification of nucleotide 952; A→C modification of nucleotide 955; T→C modification of nucleotide 961; T→C modification of nucleotide 964; T→C modification of nucleotide 968; T→C modification of nucleotide 973; T→C modification of nucleotide 976; T→C modification of nucleotide 982; A→C modification of nucleotide 985; T→C modification of nucleotide 988; C→G modification of nucleotide 991; T→G modification of nucleotide 1000; T→C modification of nucleotide 1001; A→G modification of nucleotide 1003; T→C modification of nucleotide 1004; A→G modification of nucleotide 1006; T→C modification of nucleotide 1009; A→G modification of nucleotide 1012; A→G modification of nucleotide 1015; A→C modification of nucleotide 1018; T→C modification of nucleotide 1021; A→G modification of nucleotide 1024; A→C modification of nucleotide 1030; T→C modification of nucleotide 1036; T→C modification of nucleotide 1037; A→G modification of nucleotide 1039; T→C modification of nucleotide 1042; T→C modification of nucleotide 1045; G→C modification of nucleotide 1048; A→G modification of nucleotide 1057; T→G modification of nucleotide 1063; T→C modification of nucleotide 1067; C→G modification of nucleotide 1072; A→G modification of nucleotide 1078; A→C modification of nucleotide 1081; T→C modification of nucleotide 1084; T→G modification of nucleotide 1087; A→G modification of nucleotide 1090; T→C modification of nucleotide 1094; T→C modification of nucleotide 1099; T→C modification of nucleotide 1102; G→C modification of nucleotide 1105; A→C modification of nucleotide 1108; T→G modification of nucleotide 1117; A→G modification of nucleotide 1120; T→C modification of nucleotide 1123; T→C modification of nucleotide 1124; A→G modification of nucleotide 1126; T→C modification of nucleotide 1129; T→C modification of nucleotide 1132; A→G modification of nucleotide 1141; A→G modification of nucleotide 1144; A→T modification of nucleotide 1145; G→C modification of nucleotide 1146; C→G modification of nucleotide 1153; A→C modification of nucleotide 1159; T→C modification of nucleotide 1165; A→T modification of nucleotide 1166; G→C modification of nucleotide 1167; T→C modification of nucleotide 1168; T→C modification of nucleotide 1171; A→C modification of nucleotide 1174; A→G modification of nucleotide 1180; T→C modification of nucleotide 1183; T→C modification of nucleotide 1184; A→G modification of nucleotide 1186; A→G modification of nucleotide 1189; T→C modification of nucleotide 1192; A→C modification of nucleotide 1195; A→C modification of nucleotide 1199; G→C modification of nucleotide 1201; T→C modification of nucleotide 1207; T→C modification of nucleotide 1210; A→G modification of nucleotide 1216; A→G modification of nucleotide 1219; A→G modification of nucleotide 1222; A→C modification of nucleotide 1234; A→T modification of nucleotide 1235; G→C modification of nucleotide 1236; A→C modification of nucleotide 1238; A→C modification of nucleotide 1240; A→G modification of nucleotide 1255; T→C modification of nucleotide 1258; C→G modification of nucleotide 1261; T→C modification of nucleotide 1267; A→T modification of nucleotide 1268; G→C modification of nucleotide 1269; T→C modification of nucleotide 1270; T→C modification of nucleotide 1273; G→C modification of nucleotide 1279; T→C modification of nucleotide 1282; T→C modification of nucleotide 1285; A→G modification of nucleotide 1288; A→G modification of nucleotide 1291; T→C modification of nucleotide 1294; T→C modification of nucleotide 1297; A→C modification of nucleotide 1300; A→G modification of nucleotide 1306; T→C modification of nucleotide 1309; T→C modification of nucleotide 1310; A→G modification of nucleotide 1312; A→C modification of nucleotide 1315; T→G modification of nucleotide 1318; A→C modification of nucleotide 1327; T→C modification of nucleotide 1330; A→C modification of nucleotide 1333; A→T modification of nucleotide 1334; G→C modification of nucleotide 1335; T→C modification of nucleotide 1336; A→G modification of nucleotide 1339; T→C modification of nucleotide 1342; T→G modification of nucleotide 1345; T→G modification of nucleotide 1348; T→C modification of nucleotide 1357; T→G modification of nucleotide 1360; T→C modification of nucleotide 1366; C→G modification of nucleotide 1369; A→C modification of nucleotide 1370; G→C modification of nucleotide 1372; T→C modification of nucleotide 1375; T→G modification of nucleotide 1378; A→C modification of nucleotide 1381; T→C modification of nucleotide 1384; T→C modification of nucleotide 1387; A→C modification of nucleotide 1390; T→C modification of nucleotide 1393; A→G modification of nucleotide 1396; A→G modification of nucleotide 1402; G→C modification of nucleotide 1405; A→G modification of nucleotide 1411; T→C modification of nucleotide 1414; C→G modification of nucleotide 1417; T→G modification of nucleotide 1420; G→C modification of nucleotide 1423; T→C modification of nucleotide 1426; T→G modification of nucleotide 1429; T→G modification of nucleotide 1432; T→G modification of nucleotide 1438; T→C modification of nucleotide 1444; A→C modification of nucleotide 1447; T→C modification of nucleotide 1450; T→C modification of nucleotide 1453; A→C modification of nucleotide 1456; T→C modification of nucleotide 1459; C→G modification of nucleotide 1465; T→C modification of nucleotide 1471; A→C modification of nucleotide 1474; T→C modification of nucleotide 1477; A→C modification of nucleotide 1480; T→C modification of nucleotide 1483; T→G modification of nucleotide 1486; T→C modification of nucleotide 1489; C→G modification of nucleotide 1495; T→C modification of nucleotide 1498; T→C modification of nucleotide 1504; T→C modification of nucleotide 1507; T→C modification of nucleotide 1510; C→G modification of nucleotide 1528; A→G modification of nucleotide 1534; T→C modification of nucleotide 1540; T→C modification of nucleotide 1543; A→C modification of nucleotide 1546; T→C modification of nucleotide 1552; T→G modification of nucleotide 1555; T→C modification of nucleotide 1561; T→C modification of nucleotide 1564; C→G modification of nucleotide 1567; T→G modification of nucleotide 1570; G→C modification of nucleotide 1573; T→C modification of nucleotide 1576; T→C modification of nucleotide 1579; A→C modification of nucleotide 1583; G→C modification of nucleotide 1585; A→G modification of nucleotide 1588; T→C modification of nucleotide 1597; T→C modification of nucleotide 1603; T→C modification of nucleotide 1612; T→C modification of nucleotide 1615; T→G modification of nucleotide 1618; T→C modification of nucleotide 1621; T→C modification of nucleotide 1624; A→T modification of nucleotide 1631; G→C modification of nucleotide 1632; A→C modification of nucleotide 1636; A→G modification of nucleotide 1642; A→G modification of nucleotide 1645; A→C modification of nucleotide 1648; T→C modification of nucleotide 1663; A→C modification of nucleotide 1666; T→G modification of nucleotide 1669; T→G modification of nucleotide 1675; T→C modification of nucleotide 1681; A→C modification of nucleotide 1684; A→G modification of nucleotide 1687; A→C modification of nucleotide 1690; T→G modification of nucleotide 1693; T→G modification of nucleotide 1699; C→G modification of nucleotide 1705; T→C modification of nucleotide 1706; A→G modification of nucleotide 1708; A→C modification of nucleotide 1714; A→C modification of nucleotide 1717; T→C modification of nucleotide 1729; A→C modification of nucleotide 1735; T→C modification of nucleotide 1741; T→C modification of nucleotide 1744; T→G modification of nucleotide 1747; A→C modification of nucleotide 1750; T→C modification of nucleotide 1751; T→C modification of nucleotide 1756; A→C modification of nucleotide 1759; T→C modification of nucleotide 1762; T→G modification of nucleotide 1765; T→G modification of nucleotide 1771; T→C modification of nucleotide 1774; A→C modification of nucleotide 1780; T→C modification of nucleotide 1783; T→C modification of nucleotide 1786; A→C modification of nucleotide 1789; T→C modification of nucleotide 1792; T→C modification of nucleotide 1793; T→C modification of nucleotide 1798; T→C modification of nucleotide 1807; T→C modification of nucleotide 1813; A→C modification of nucleotide 1816; A→C modification of nucleotide 1819; A→G modification of nucleotide 1822; T→G modification of nucleotide 1825; T→C modification of nucleotide 1829; T→G modification of nucleotide 1834; T→G modification of nucleotide 1837; T→C modification of nucleotide 1840; A→C modification of nucleotide 1843; T→C modification of nucleotide 1846; T→C modification of nucleotide 1852; T→C modification of nucleotide 1864; G→C modification of nucleotide 1867; T→C modification of nucleotide 1876; G→C modification of nucleotide 1879; A→C modification of nucleotide 1882; A→G modification of nucleotide 1891; T→C modification of nucleotide 1894; G→C modification of nucleotide 1903; C→G modification of nucleotide 1906; A→G modification of nucleotide 1915; A→G modification of nucleotide 1918; A→C modification of nucleotide 1921; T→G modification of nucleotide 1924; A→G modification of nucleotide 1927; T→C modification of nucleotide 1930; T→C modification of nucleotide 1933; A→C modification of nucleotide 1939; T→G modification of nucleotide 1945; A→G modification of nucleotide 1954; T→C modification of nucleotide 1957; G→C modification of nucleotide 1960; T→C modification of nucleotide 1963; T→G modification of nucleotide 1966; A→C modification of nucleotide 1975; T→C modification of nucleotide 1978; T→G modification of nucleotide 1981; A→C modification of nucleotide 1985; A→C modification of nucleotide 1987; A→C modification of nucleotide 1990; A→G modification of nucleotide 1993; T→C modification of nucleotide 1996; T→C modification of nucleotide 2002; A→C modification of nucleotide 2005; T→C modification of nucleotide 2006; T→C modification of nucleotide 2011; T→G modification of nucleotide 2023; T→C modification of nucleotide 2026; T→C modification of nucleotide 2029; T→C modification of nucleotide 2035; A→G modification of nucleotide 2038; A→G modification of nucleotide 2047; A→C modification of nucleotide 2048; A→C modification of nucleotide 2050; A→G modification of nucleotide 2053; T→C modification of nucleotide 2056; A→C modification of nucleotide 2059; G→C modification of nucleotide 2062; C→G modification of nucleotide 2065; C→G modification of nucleotide 2068; T→C modification of nucleotide 2071; A→G modification of nucleotide 2074; T→G modification of nucleotide 2077; T→C modification of nucleotide 2080; A→G modification of nucleotide 2092; T→C modification of nucleotide 2095; A→C modification of nucleotide 2098; A→G modification of nucleotide 2101; T→C modification of nucleotide 2104; T→C modification of nucleotide 2107; A→G modification of nucleotide 2110; T→C modification of nucleotide 2113; A→C modification of nucleotide 2119; A→C modification of nucleotide 2125; T→C modification of nucleotide 2128; T→C modification of nucleotide 2131; A→C modification of nucleotide 2137; T→C modification of nucleotide 2141; A→G modification of nucleotide 2143; T→G modification of nucleotide 2146; T→C modification of nucleotide 2152; A→C modification of nucleotide 2153; G→C modification of nucleotide 2155; T→C modification of nucleotide 2158; A→G modification of nucleotide 2161; T→C modification of nucleotide 2164; G→C modification of nucleotide 2170; A→C modification of nucleotide 2173; T→C modification of nucleotide 2176; A→C modification of nucleotide 2179; T→C modification of nucleotide 2182; T→C modification of nucleotide 2185; T→G modification of nucleotide 2188; T→C modification of nucleotide 2189; A→C modification of nucleotide 2197; T→C modification of nucleotide 2203; A→C modification of nucleotide 2215; A→G modification of nucleotide 2218; T→C modification of nucleotide 2221; A→G modification of nucleotide 2230; G→C modification of nucleotide 2233; T→G modification of nucleotide 2236; A→C modification of nucleotide 2239; T→G modification of nucleotide 2242; A→T modification of nucleotide 2252; G→C modification of nucleotide 2253; T→C modification of nucleotide 2257; C→G modification of nucleotide 2260; A→C modification of nucleotide 2264; A→C modification of nucleotide 2266; A→C modification of nucleotide 2269; A→C modification of nucleotide 2275; T→C modification of nucleotide 2281; T→C modification of nucleotide 2287; T→C modification of nucleotide 2293; T→C modification of nucleotide 2296; T→C modification of nucleotide 2299; T→G modification of nucleotide 2302; A→C modification of nucleotide 2305; T→G modification of nucleotide 2308; T→C modification of nucleotide 2311; T→C modification of nucleotide 2314; T→C modification of nucleotide 2317; A→C modification of nucleotide 2326; A→G modification of nucleotide 2329; T→G modification of nucleotide 2335; A→C modification of nucleotide 2338; T→C modification of nucleotide 2341; T→C modification of nucleotide 2350; T→C modification of nucleotide 2353; T→C modification of nucleotide 2356; A→T modification of nucleotide 2357; G→C modification of nucleotide 2358; T→C modification of nucleotide 2362; T→C modification of nucleotide 2365; T→C modification of nucleotide 2368; T→C modification of nucleotide 2371; T→C modification of nucleotide 2377; T→C modification of nucleotide 2380; A→C modification of nucleotide 2383; T→C modification of nucleotide 2386; T→C modification of nucleotide 2395; T→C modification of nucleotide 2399; T→C modification of nucleotide 2404; A→G modification of nucleotide 2422; T→C modification of nucleotide 2425; T→C modification of nucleotide 2434; T→C modification of nucleotide 2447; T→C modification of nucleotide 2449; T→C modification of nucleotide 2452; T→C modification of nucleotide 2458; A→C modification of nucleotide 2461; T→G modification of nucleotide 2464; T→C modification of nucleotide 2467; G→C modification of nucleotide 2470; A→C modification of nucleotide 2476; T→C modification of nucleotide 2479; G→C modification of nucleotide 2485; T→C modification of nucleotide 2488; C→G modification of nucleotide 2500; T→C modification of nucleotide 2506; G→C modification of nucleotide 2509; T→C modification of nucleotide 2515; A→C modification of nucleotide 2518; T→C modification of nucleotide 2521; A→T modification of nucleotide 2525; G→C modification of nucleotide 2526; T→C modification of nucleot T→C modification of nucleotide 2545; T→C modification of nucleotide 2548; T→C modification of nucleotide 2551; and deletion of nucleotides 2558-3197;

k) a sequence encoding yes-associated protein 1 (YAP) and comprising one or more of the following modifications relative to SEQ ID NO: 22:
deletion of nucleotides 1-402; T→C modification of nucleotide 408; G→C modification of nucleotide 414; G→C modification of nucleotide 423; G→C modification of nucleotide 426; T→C modification of nucleotide 429; A→G modification of nucleotide 432; G→C modification of nucleotide 435; A→G modification of nucleotide 450; G→C modification of nucleotide 453; G→C modification of nucleotide 459; T→C modification of nucleotide 462; G→C modification of nucleotide 465; G→C modification of nucleotide 474; G→C modification of nucleotide 480; G→C modification of nucleotide 489; G→C modification of nucleotide 492; A→C modification of nucleotide 498; G→C modification of nucleotide 504; A→G modification of nucleotide 507; G→C modification of nucleotide 510; A→C modification of nucleotide 513; G→C modification of nucleotide 519; G→C modification of nucleotide 522; G→C modification of nucleotide 531; G→C modification of nucleotide 534; G→C modification of nucleotide 537; A→C modification of nucleotide 543; G→C modification of nucleotide 555; T→C modification of nucleotide 558; C→G modification of nucleotide 573; G→C modification of nucleotide 579; G→C modification of nucleotide 585; G→C modification of nucleotide 603; C→G modification of nucleotide 606; C→G modification of nucleotide 618; G→C modification of nucleotide 633; A→C modification of nucleotide 661; G→C modification of nucleotide 663; C→G modification of nucleotide 666; G→C modification of nucleotide 669; G→C modification of nucleotide 696; G→C modification of nucleotide 699; A→G modification of nucleotide 708; A→C modification of nucleotide 720; A→T modification of nucleotide 727; G→C modification of nucleotide 728; T→C modification of nucleotide 729; T→C modification of nucleotide 732; T→C modification of nucleotide 735; A→C modification of nucleotide 738; T→C modification of nucleotide 744; A→C modification of nucleotide 747; A→C modification of nucleotide 750; T→C modification of nucleotide 759; A→C modification of nucleotide 762; T→C modification of nucleotide 768; T→G modification of nucleotide 771; A→C modification of nucleotide 774; T→C modification of nucleotide 777; T→C modification of nucleotide 780; T→G modification of nucleotide 781; T→C modification of nucleotide 786; A→C modification of nucleotide 789; T→C modification of nucleotide 792; T→C modification of nucleotide 795; T→C modification of nucleotide 802; A→C modification of nucleotide 807; T→C modification of nucleotide 810; T→G modification of nucleotide 813; T→C modification of nucleotide 816; T→C modification of nucleotide 819; T→C modification of nucleotide 822; A→C modification of nucleotide 825; T→C modification of nucleotide 837; A→C modification of nucleotide 840; A→G modification of nucleotide 843; C→G modification of nucleotide 846; T→C modification of nucleotide 849; A→C modification of nucleotide 855; A→C modification of nucleotide 858; T→C modification of nucleotide 861; A→C modification of nucleotide 864; A→C modification of nucleotide 870; T→C modification of nucleotide 873; T→C modification of nucleotide 879; T→G modification of nucleotide 882; A→C modification of nucleotide 885; T→C modification of nucleotide 891; T→C modification of nucleotide 894; T→C modification of nucleotide 897; A→C modification of nucleotide 903; T→C modification of nucleotide 906; T→C modification of nucleotide 909; T→C modification of nucleotide 912; A→G modification of nucleotide 915; T→C modification of nucleotide 918; A→C modification of nucleotide 924; A→C modification of nucleotide 927; T→C modification of nucleotide 930; A→C modification of nucleotide 942; A→C modification of nucleotide 948; T→C modification of nucleotide 951; T→C modification of nucleotide 954; T→C modification of nucleotide 957; A→C modification of nucleotide 961; A→C modification of nucleotide 963; T→C modification of nucleotide 970; A→G modification of nucleotide 972; T→C modification of nucleotide 975; T→C modification of nucleotide 984; A→C modification of nucleotide 990; A→C modification of nucleotide 993; A→C modification of nucleotide 996; A→C modification of nucleotide 1009; G→C modification of nucleotide 1011; C→G modification of nucleotide 1038; A→C modification of nucleotide 1041; A→T modification of nucleotide 1051; G→C modification of nucleotide 1052; T→C modification of nucleotide 1053; A→C modification of nucleotide 1056; A→C modification of nucleotide 1059; T→C modification of nucleotide 1071; G→C modification of nucleotide 1083; T→C modification of nucleotide 1086; A→C modification of nucleotide 1089; T→C modification of nucleotide 1092; T→C modification of nucleotide 1095; T→G modification of nucleotide 1098; T→C modification of nucleotide 1101; T→C modification of nucleotide 1104; A→C modification of nucleotide 1107; A→G modification of nucleotide 1113; A→G modification of nucleotide 1116; T→C modification of nucleotide 1125; T→C modification of nucleotide 1131; A→C modification of nucleotide 1134; A→G modification of nucleotide 1137; T→C modification of nucleotide 1140; T→C modification of nucleotide 1146; A→C modification of nucleotide 1149; T→C modification of nucleotide 1155; T→C modification of nucleotide 1173; A→G modification of nucleotide 1179; A→C modification of nucleotide 1185; A→C modification of nucleotide 1186; G→C modification of nucleotide 1188; T→G modification of nucleotide 1191; T→C modification of nucleotide 1197; T→C modification of nucleotide 1200; T→C modification of nucleotide 1203; A→C modification of nucleotide 1216; A→C modification of nucleotide 1218; A→T modification of nucleotide 1222; G→C modification of nucleotide 1223; T→C modification of nucleotide 1224; A→T modification of nucleotide 1228; G→C modification of nucleotide 1229; T→C modification of nucleotide 1230; T→C modification of nucleotide 1233; A→G modification of nucleotide 1236; A→G modification of nucleotide 1242; A→C modification of nucleotide 1248; A→C modification of nucleotide 1251; T→C modification of nucleotide 1260; A→T modification of nucleotide 1267; G→C modification of nucleotide 1268; A→C modification of nucleotide 1272; A→C modification of nucleotide 1278; C→G modification of nucleotide 1284; T→C modification of nucleotide 1290; A→T modification of nucleotide 1294; G→C modification of nucleotide 1295; A→G modification of nucleotide 1314; A→C modification of nucleotide 1323; A→G modification of nucleotide 1332; A→C modification of nucleotide 1351; G→C modification of nucleotide 1353; G→C modification of nucleotide 1359; A→G modification of nucleotide 1365; A→G modification of nucleotide 1371; A→G modification of nucleotide 1374; T→G modification of nucleotide 1380; G→C modification of nucleotide 1383; T→C modification of nucleotide 1390; A→G modification of nucleotide 1392; T→C modification of nucleotide 1401; A→T modification of nucleotide 1402; G→C modification of nucleotide 1403; T→C modification of nucleotide 1408; A→G modification of nucleotide 1410; A→C modification of nucleotide 1413; A→C modification of nucleotide 1416; T→C modification of nucleotide 1428; T→C modification of nucleotide 1431; G→C modification of nucleotide 1434; T→C modification of nucleotide 1437; A→G modification of nucleotide 1440; T→C modification of nucleotide 1443; A→C modification of nucleotide 1446; T→C modification of nucleotide 1452; T→C modification of nucleotide 1455; G→C modification of nucleotide 1461; T→C modification of nucleotide 1467; A→G modification of nucleotide 1473; T→C modification of nucleotide 1474; A→C modification of nucleotide 1477; A→C modification of nucleotide 1479; A→C modification of nucleotide 1482; G→C modification of nucleotide 1488; T→C modification of nucleotide 1494; A→T modification of nucleotide 1495; G→C modification of nucleotide 1496; A→C modification of nucleotide 1500; T→C modification of nucleotide 1503; T→C modification of nucleotide 1506; T→G modification of nucleotide 1512; A→T modification of nucleotide 1516; G→C modification of nucleotide 1517; T→C modification of nucleotide 1518; T→C modification of nucleotide 1527; T→C modification of nucleotide 1533; A→C modification of nucleotide 1536; T→C modification of nucleotide 1539; A→T modification of nucleotide 1543; G→C modification of nucleotide 1544; T→C modification of nucleotide 1545; A→C modification of nucleotide 1548; A→T modification of nucleotide 1552; G→C modification of nucleotide 1553; T→C modification of nucleotide 1554; A→C modification of nucleotide 1557; A→G modification of nucleotide 1560; A→T modification of nucleotide 1561; G→C modification of nucleotide 1562; A→T modification of nucleotide 1567; G→C modification of nucleotide 1568; A→T modification of nucleotide 1570; G→C modification of nucleotide 1571; A→T modification of nucleotide 1576; G→C modification of nucleotide 1577; T→C modification of nucleotide 1578; C→G modification of nucleotide 1581; T→C modification of nucleotide 1584; A→C modification of nucleotide 1587; A→C modification of nucleotide 1593; T→C modification of nucleotide 1596; A→T modification of nucleotide 1609; G→C modification of nucleotide 1610; T→C modification of nucleotide 1611; T→C modification of nucleotide 1617; T→C modification of nucleotide 1626; A→C modification of nucleotide 1629; T→C modification of nucleotide 1632; T→C modification of nucleotide 1635; T→C modification of nucleotide 1638; A→G modification of nucleotide 1647; A→T modification of nucleotide 1648; G→C modification of nucleotide 1649; A→C modification of nucleotide 1662; T→C modification of nucleotide 1674; A→C modification of nucleotide 1680; T→G modification of nucleotide 1689; A→G modification of nucleotide 1692; T→C modification of nucleotide 1698; T→C modification of nucleotide 1701; G→C modification of nucleotide 1704; A→C modification of nucleotide 1707; T→C modification of nucleotide 1710; T→G modification of nucleotide 1719; A→C modification of nucleotide 1722; A→C modification of nucleotide 1725; A→G modification of nucleotide 1731; A→C modification of nucleotide 1734; T→C modification of nucleotide 1737; A→C modification of nucleotide 1740; A→C modification of nucleotide 1749; A→G modification of nucleotide 1752; A→C modification of nucleotide 1755; A→C modification of nucleotide 1770; A→T modification of nucleotide 1771; G→C modification of nucleotide 1772; T→C modification of nucleotide 1773; A→G modification of nucleotide 1782; T→C modification of nucleotide 1785; T→C modification of nucleotide 1786; A→T modification of nucleotide 1789; G→C modification of nucleotide 1790; T→C modification of nucleotide 1791; T→C modification of nucleotide 1794; T→G modification of nucleotide 1803; T→C modification of nucleotide 1806; T→C modification of nucleotide 1818; T→G modification of nucleotide 1821; T→C modification of nucleotide 1822; T→C modification of nucleotide 1827; A→G modification of nucleotide 1839; T→C modification of nucleotide 1842; A→G modification of nucleotide 1845; A→G modification of nucleotide 1848; A→T modification of nucleotide 1849; G→C modification of nucleotide 1850; T→C modification of nucleotide 1854; T→G modification of nucleotide 1857; A→C modification of nucleotide 1860; and deletion of nucleotides 1864-5353;

l) a sequence encoding wingless-type MMTV integration site family, member 2 (WNT2) and comprising one or more of the following modifications relative to SEQ ID NO: 23:
deletion of nucleotides 1-158; C→G modification of nucleotide 167; T→C modification of nucleotide 170; C→G modification of nucleotide 173; T→C modification of nucleotide 176; A→C modification of nucleotide 179; C→G modification of nucleotide 188; C→G modification of nucleotide 194; T→C modification of nucleotide 197; C→G modification of nucleotide 203; T→C modification of nucleotide 204; C→G modification of nucleotide 215; T→C modification of nucleotide 221; C→G modification of nucleotide 227; A→T modification of nucleotide 228; G→C modification of nucleotide 229; T→C modification of nucleotide 233; A→C modification of nucleotide 236; A→C modification of nucleotide 249; A→C modification of nucleotide 251; T→C modification of nucleotide 254; A→C modification of nucleotide 257; T→C modification of nucleotide 260; A→C modification of nucleotide 270; G→C modification of nucleotide 272; T→C modification of nucleotide 281; T→C modification of nucleotide 287; A→C modification of nucleotide 293; A→T modification of nucleotide 303; G→C modification of nucleotide 304; G→C modification of nucleotide 308; T→C modification of nucleotide 314; A→C modification of nucleotide 329; A→C modification of nucleotide 335; T→C modification of nucleotide 338; T→C modification of nucleotide 347; T→C modification of nucleotide 353; T→C modification of nucleotide 362; T→C modification of nucleotide 368; T→C modification of nucleotide 377; A→C modification of nucleotide 380; A→G modification of nucleotide 389; T→C modification of nucleotide 407; A→C modification of nucleotide 432; A→C modification of nucleotide 434; T→C modification of nucleotide 437; A→T modification of nucleotide 441; G→C modification of nucleotide 442; C→G modification of nucleotide 446; T→C modification of nucleotide 449; G→C modification of nucleotide 455; T→C modification of nucleotide 458; C→G modification of nucleotide 461; C→G modification of nucleotide 464; A→C modification of nucleotide 467; A→T modification of nucleotide 468; G→C modification of nucleotide 469; T→C modification of nucleotide 470; A→T modification of nucleotide 471; G→C modification of nucleotide 472; T→C modification of nucleotide 473; G→C modification of nucleotide 476; A→G modification of nucleotide 479; G→C modification of nucleotide 482; T→C modification of nucleotide 488; T→G modification of nucleotide 491; T→C modification of nucleotide 503; A→C modification of nucleotide 506; T→C modification of nucleotide 509; T→G modification of nucleotide 515; A→G modification of nucleotide 518; T→C modification of nucleotide 521; A→C modification of nucleotide 531; G→C modification of nucleotide 533; T→C modification of nucleotide 539; A→T modification of nucleotide 540; G→C modification of nucleotide 541; A→G modification of nucleotide 545; A→C modification of nucleotide 548; A→G modification of nucleotide 551; T→C modification of nucleotide 552; A→G modification of nucleotide 554; T→C modification of nucleotide 569; T→C modification of nucleotide 572; A→C modification of nucleotide 575; A→G modification of nucleotide 584; A→C modification of nucleotide 587; A→T modification of nucleotide 588; G→C modification of nucleotide 589; T→C modification of nucleotide 590; A→T modification of nucleotide 600; G→C modification of nucleotide 601; A→G modification of nucleotide 605; T→C modification of nucleotide 623; A→T modification of nucleotide 630; G→C modification of nucleotide 631; T→C modification of nucleotide 632; T→C modification of nucleotide 638; T→C modification of nucleotide 641; G→C modification of nucleotide 650; T→C modification of nucleotide 659; T→C modification of nucleotide 665; T→C modification of nucleotide 671; A→G modification of nucleotide 674; T→C modification of nucleotide 677; A→C modification of nucleotide 687; G→C modification of nucleotide 689; A→G modification of nucleotide 692; T→C modification of nucleotide 701; A→C modification of nucleotide 705; A→C modification of nucleotide 707; T→G modification of nucleotide 722; A→C modification of nucleotide 732; A→C modification of nucleotide 734; T→C modification of nucleotide 737; A→C modification of nucleotide 740; A→C modification of nucleotide 741; G→C modification of nucleotide 743; T→C modification of nucleotide 749; A→G modification of nucleotide 752; T→C modification of nucleotide 762; A→G modification of nucleotide 767; A→G modification of nucleotide 770; A→G modification of nucleotide 773; T→C modification of nucleotide 782; T→C modification of nucleotide 785; T→C modification of nucleotide 788; A→T modification of nucleotide 792; G→C modification of nucleotide 793; T→C modification of nucleotide 794; T→C modification of nucleotide 803; T→C modification of nucleotide 806; A→C modification of nucleotide 810; G→C modification of nucleotide 812; A→C modification of nucleotide 815; T→C modification of nucleotide 833; A→C modification of nucleotide 840; G→C modification of nucleotide 842; A→G modification of nucleotide 845; A→C modification of nucleotide 848; T→C modification of nucleotide 857; C→G modification of nucleotide 860; A→C modification of nucleotide 864; G→C modification of nucleotide 866; T→C modification of nucleotide 875; G→C modification of nucleotide 878; A→G modification of nucleotide 890; C→G modification of nucleotide 893; T→C modification of nucleotide 905; T→C modification of nucleotide 911; T→C modification of nucleotide 920; A→G modification of nucleotide 923; T→C modification of nucleotide 929; A→C modification of nucleotide 933; G→C modification of nucleotide 935; T→C modification of nucleotide 938; A→C modification of nucleotide 947; G→C modification of nucleotide 950; A→G modification of nucleotide 953; T→C modification of nucleotide 956; C→G modification of nucleotide 962; T→C modification of nucleotide 968; T→C modification of nucleotide 971; T→C modification of nucleotide 977; T→C modification of nucleotide 980; A→C modification of nucleotide 983; T→C modification of nucleotide 992; A→C modification of nucleotide 996; G→C modification of nucleotide 998; A→C modification of nucleotide 1004; A→C modification of nucleotide 1010; T→C modification of nucleotide 1022; A→C modification of nucleotide 1025; G→C modification of nucleotide 1028;

T→C modification of nucleotide 1034; T→C modification of nucleotide 1044; T→C modification of nucleotide 1049; A→C modification of nucleotide 1055; A→T modification of nucleotide 1065; G→C modification of nucleotide 1066; A→G modification of nucleotide 1073; T→G modification of nucleotide 1076; T→C modification of nucleotide 1082; T→C modification of nucleotide 1085; G→C modification of nucleotide 1088; A→C modification of nucleotide 1089; A→C modification of nucleotide 1091; T→C modification of nucleotide 1097; A→C modification of nucleotide 1103; C→G modification of nucleotide 1112; G→C modification of nucleotide 1118; T→C modification of nucleotide 1130; T→C modification of nucleotide 1136; A→G modification of nucleotide 1139; T→C modification of nucleotide 1154; T→C modification of nucleotide 1166; A→C modification of nucleotide 1199; A→T modification of nucleotide 1215; G→C modification of nucleotide 1216; T→C modification of nucleotide 1217; and deletion of nucleotides 1229-2115; and/or m) a sequence encoding wingless-type MMTV integration site family, member 9B (WNT9b) and comprising one or more of the following modifications relative to SEQ ID NO: 24:

deletion of nucleotides 1-52; G→C modification of nucleotide 64; G→C modification of nucleotide 70; T→C modification of nucleotide 82; G→C modification of nucleotide 85; G→C modification of nucleotide 88; T→C modification of nucleotide 106; T→C modification of nucleotide 112; T→C modification of nucleotide 145; T→C modification of nucleotide 148; C→G modification of nucleotide 154; A→C modification of nucleotide 160; A→C modification of nucleotide 169; T→C modification of nucleotide 178; G→C modification of nucleotide 181; A→C modification of nucleotide 184; A→C modification of nucleotide 187; G→C modification of nucleotide 193; A→C modification of nucleotide 196; T→C modification of nucleotide 202; T→C modification of nucleotide 205; T→C modification of nucleotide 208; T→C modification of nucleotide 223; A→G modification of nucleotide 229; A→C modification of nucleotide 242; G→C modification of nucleotide 244; G→C modification of nucleotide 247; C→G modification of nucleotide 259; A→C modification of nucleotide 263; G→C modification of nucleotide 265; G→C modification of nucleotide 268; T→C modification of nucleotide 283; A→C modification of nucleotide 293; G→C modification of nucleotide 295; T→C modification of nucleotide 298; T→C modification of nucleotide 301; A→C modification of nucleotide 304; G→C modification of nucleotide 313; A→G modification of nucleotide 322; T→C modification of nucleotide 325; A→C modification of nucleotide 338; G→C modification of nucleotide 340; A→T modification of nucleotide 359; G→C modification of nucleotide 360; G→C modification of nucleotide 370; A→C modification of nucleotide 371; G→C modification of nucleotide 373; T→C modification of nucleotide 376; C→G modification of nucleotide 385; A→C modification of nucleotide 389; A→C modification of nucleotide 391; T→C modification of nucleotide 397; G→C modification of nucleotide 406; T→C modification of nucleotide 418; A→C modification of nucleotide 421; T→C modification of nucleotide 427; A→C modification of nucleotide 430; T→C modification of nucleotide 433; C→G modification of nucleotide 439; G→C modification of nucleotide 442; T→C modification of nucleotide 445; A→C modification of nucleotide 448; T→C modification of nucleotide 455; G→C modification of nucleotide 457; A→T modification of nucleotide 464; G→C modification of nucleotide 465; T→C modification of nucleotide 466; T→C modification of nucleotide 469; G→C modification of nucleotide 472; T→C modification of nucleotide 487; T→C modification of nucleotide 490; T→C modification of nucleotide 493; A→C modification of nucleotide 505; A→T modification of nucleotide 515; G→C modification of nucleotide 516; G→C modification of nucleotide 520; T→C modification of nucleotide 538; T→C modification of nucleotide 544; T→C modification of nucleotide 547; T→C modification of nucleotide 553; A→T modification of nucleotide 563; G→C modification of nucleotide 564; C→G modification of nucleotide 577; A→T modification of nucleotide 578; G→C modification of nucleotide 579; G→C modification of nucleotide 592; A→C modification of nucleotide 599; A→C modification of nucleotide 601; A→C modification of nucleotide 604; A→T modification of nucleotide 605; G→C modification of nucleotide 606; A→C modification of nucleotide 617; G→C modification of nucleotide 619; G→C modification of nucleotide 622; A→C modification of nucleotide 623; G→C modification of nucleotide 625; T→C modification of nucleotide 628; T→C modification of nucleotide 661; A→T modification of nucleotide 668; G→C modification of nucleotide 669; A→C modification of nucleotide 677; A→C modification of nucleotide 679; A→C modification of nucleotide 682; T→C modification of nucleotide 697; T→C modification of nucleotide 700; A→C modification of nucleotide 706; T→C modification of nucleotide 715; T→C modification of nucleotide 718; T→G modification of nucleotide 721; T→C modification of nucleotide 724; T→C modification of nucleotide 730; C→G modification of nucleotide 742; G→C modification of nucleotide 748; T→C modification of nucleotide 751; A→G modification of nucleotide 778; T→C modification of nucleotide 784; G→C modification of nucleotide 790; T→C modification of nucleotide 793; C→G modification of nucleotide 796; A→T modification of nucleotide 806; G→C modification of nucleotide 807; T→C modification of nucleotide 808; T→C modification of nucleotide 824; T→C modification of nucleotide 829; T→C modification of nucleotide 832; A→G modification of nucleotide 841; T→C modification of nucleotide 853; A→C modification of nucleotide 859; T→C modification of nucleotide 862; T→C modification of nucleotide 865; A→G modification of nucleotide 880; T→C modification of nucleotide 886; T→C modification of nucleotide 889; G→C modification of nucleotide 895; C→G modification of nucleotide 904; A→G modification of nucleotide 913; T→C modification of nucleotide 916; T→C modification of nucleotide 919; A→T modification of nucleotide 923; G→C modification of nucleotide 924; G→C modification of nucleotide 934; A→T modification of nucleotide 938; G→C modification of nucleotide 939; T→C modification of nucleotide 949; G→C modification of nucleotide 952; G→C modification of nucleotide 958; A→C modification of nucleotide 961; A→C modification of nucleotide 965; G→C modification of nucleotide 967; T→C modification of nucleotide 973; T→C modification of nucleotide 976; A→C modification of nucleotide 979; A→T modification of nucleotide 986; G→C modification of nucleotide 987; T→C modification of nucleotide 988; A→T modification of nucleotide 992; G→C modification of nucleotide 993; A→T modification of nucleotide 995; G→C modification of nucleotide 996; A→G modification of nucleotide 1000; T→C modification of nucleotide 1006; G→C modification of nucleotide 1009; A→C modification of nucleotide 1012; A→T modification of nucleotide 1028; G→C modification of nucleotide 1029; T→G modification of nucleotide 1042; T→C modification of nucleotide 1057; T→C modification of nucleotide 1096; A→C modification of nucleotide 1099; C→G modification of nucleotide 1111; T→C modification of nucleotide 1117; and deletion of nucleotides 1130-4519.

2. The composition of paragraph 1, wherein the at least one engineered liver regenerative factor mRNA comprises one or more of:
   a) SEQ ID NO: 8 (GH);
   b) SEQ ID NO: 9 (EGF);
   c) SEQ ID NO: 10 (HGF);
   d) SEQ ID NO: 11 (p21);
   e) SEQ ID NO: 12 (VEGF165);
   f) SEQ ID NO: 13 (IGF-1);
   g) SEQ ID NO: 14 (IGF-1 IL-2 SP);
   h) SEQ ID NO: 15 (secreted EGF);
   i) SEQ ID NO: 16 (stat5bca);
   j) SEQ ID NO: 21 (beta catenin);
   k) SEQ ID NO: 25 (YAP);
   l) SEQ ID NO: 26 (WNT2); and
   m) SEQ ID NO: 27 (WNT9B).

3. The composition of any one of the preceding paragraphs, wherein the at least one engineered liver regenerative factor mRNA further comprises at least one modified nucleoside.

4. A composition comprising at least one liver regenerative factor mRNAs comprising at least one modified nucleoside;
   wherein the at least one liver regenerative factor is selected from the group consisting of:
      vascular endothelial growth factor A (VEGFA); hepatocyte growth factor (HGF); growth hormone (GH); insulin-like growth factor 1 (IGF-1), epidermal growth factor (EGF); signal transducer and activator of transcription 5B (STAT5b); cyclin-dependent kinase inhibitor 1A (p21); beta catenin (CTNNB1); yes-associated protein (YAP); wingless-type MMTV integration site family, member 2 (WNT2); and wingless-type MMTV integration site family, member 9B (WNT9b).

5. The composition of any one of the preceding paragraphs, wherein the composition further comprises a carrier complexed with the at least one engineered liver regenerative factor mRNA or the at least one liver regenerative factor mRNA comprising at least one modified nucleoside.

6. The composition of paragraph 5, wherein the carrier is a nanoparticle.

7. The composition of paragraph 6, wherein the carrier is a polymer nanoparticle.

8. The composition of paragraph 6, wherein the nanoparticle is a lipid nanoparticle (LNP).

9. The composition of any one of the preceding paragraphs, wherein the at least one liver regenerative factor is selected from the group consisting of: VEGFA; HGF; GH; and EGF.

10. The composition of any one of the preceding paragraphs, wherein the at least one liver regenerative factor is selected from the group consisting of: HGF; GH; EGF; and p21.

11. The composition of any one of the preceding paragraphs, wherein the at least one liver regenerative factor is selected from the group consisting of: HGF; GH; and EGF.

12. The composition of any one of the preceding paragraphs, wherein the at least one liver regenerative factor comprises two or more liver regenerative factors selected from the group consisting of:
    VEGFA; HGF; GH; IGF-1; EGF; STAT5bCA; p21; CNNTB1; YAP; WNT2; and WNT9b.

13. The composition of any one of the preceding paragraphs, wherein the at least one liver regenerative factor is a human liver regenerative factor or a murine liver regenerative factor.

14. The composition of any one of the preceding paragraphs, wherein the at least one modified nucleoside comprises at least one non-natural nucleoside.

15. The composition of any one of the preceding paragraphs, wherein the at least one modified nucleoside is selected from the group consisting of:
    pseudouridine, N1-methylpseudouridine, 2-thiouridine, 4'-thiouridine, 5-methylcytosine, 2-thio-1-methyl-1-deaza-pseudouridine, 2-thio-1-methyl-pseudouridine, 2-thio-5-aza-uridine, 2-thio-dihydropseudouridine, 2-thio-dihydrouridine, 2-thio-pseudouridine, 4-methoxy-pseudouridine, 4-thio-1-methyl-pseudouridine, 4-thio-pseudouridine, 5-aza-uridine, dihydropseudouridine, 5-methyluridine, pseudouridine, and mixtures thereof, 5-methyluridine, 5-methoxyuridine, and 2'-O-methyluridine.

16. The composition of any one of the preceding paragraphs, wherein the at least one modified nucleoside comprises at least one-methylpseudouridine (m1Ψ)-5' triphosphate (TriLink).

17. The composition of any one of the preceding paragraphs, wherein the LNP comprises at least one ionizable lipid, at least one phospholipid, at least one structured lipid, and at least one polyethylene glycol (PEG)-lipid.

18. The composition of paragraph 17, wherein the at least one ionizable lipid is selected from the group consisting of:
    2,2-dioleyl-4-dimethylaminoethyl-[1,3]-dioxolane (DLin-KC2-DMA); dioleyl-methyl 4-dimethylaminobutyrate (DLin-MC3-DMA); and di ((Z)-non-2-en-1-yl) 9-((4-(dimethylamino) butyryl) oxy) heptadecanedioate (L319).

19. The composition of any one of paragraphs 17-18, wherein the at least one ionizable lipid has a pKA in the range of 6.0-6.5.

20. The composition of any one of paragraphs 17-19, wherein the at least one phospholipid comprises phosphatidylcholine.

21. The composition of any one of paragraphs 17-20, wherein the at least one structured lipid comprises cholesterol.

22. The composition of any one of the preceding paragraphs, wherein the at least one engineered liver regenerative factor mRNA or the at least one liver regenerative factor mRNA comprising at least one modified nucleoside is encapsulated in the nanoparticle.

23. The composition of any one of the preceding paragraphs, wherein the at least one engineered liver regenerative factor mRNA or the at least one liver regenerative factor mRNA comprising at least one modified nucleoside is in an aqueous solution and in admixture with an ethanolic lipid mixture at acidic pH.

24. The composition of any one of the preceding paragraphs, wherein the at least one engineered liver regenerative factor mRNA or the at least one liver regenerative factor mRNA comprising at least one modified nucleoside is complexed to the LNP in a way selected from the group consisting of:
encapsulation in the interior of the LNP; interspersed within the lipid bilayer of the LNP; and attached to the LNP via a linking molecule.

25. The composition of any one of the preceding paragraphs, wherein the liver regenerative factor comprises GH; and
the at least one engineered liver regenerative factor mRNA or the at least one liver regenerative factor mRNA comprising at least one modified nucleoside comprises a nucleotide sequence having at least 80% sequence identity to the nucleotide sequence set forth in SEQ ID NO: 8.

26. The composition of any one of the preceding paragraphs, wherein the liver regenerative factor comprises EGF; and
the at least one engineered liver regenerative factor mRNA or the at least one liver regenerative factor mRNA comprising at least one modified nucleoside comprises a nucleotide sequence having at least 80% sequence identity to the nucleotide sequence set forth in SEQ ID NO: 9.

27. The composition of any one of the preceding paragraphs, wherein the liver regenerative factor comprises HGF; and
the at least one engineered liver regenerative factor mRNA or the at least one liver regenerative factor mRNA comprising at least one modified nucleoside comprises a nucleotide sequence having at least 80% sequence identity to the nucleotide sequence set forth in SEQ ID NO: 10.

28. The composition of any one of the preceding paragraphs, wherein the liver regenerative factor comprises p21; and
the at least one engineered liver regenerative factor mRNA or the at least one liver regenerative factor mRNA comprising at least one modified nucleoside comprises a nucleotide sequence having at least 80% sequence identity to the nucleotide sequence set forth in SEQ ID NO: 11.

29. The composition of any one of the preceding paragraphs, wherein the liver regenerative factor comprises VEGF; and
the at least one engineered liver regenerative factor mRNA or the at least one liver regenerative factor mRNA comprising at least one modified nucleoside comprises a nucleotide sequence having at least 80% sequence identity to the nucleotide sequence set forth in SEQ ID NO: 12.

30. The composition of any one of the preceding paragraphs, wherein the liver regenerative factor comprises IGF-1; and
the at least one engineered liver regenerative factor mRNA or the at least one liver regenerative factor mRNA comprising at least one modified nucleoside comprises a nucleotide sequence having at least 80% sequence identity to the nucleotide sequence set forth in SEQ ID NO: 13.

31. The composition of any one of the preceding paragraphs, wherein the liver regenerative factor comprises IGF-1 IL-2 SP; and
the at least one engineered liver regenerative factor mRNA or the at least one liver regenerative factor mRNA comprising at least one modified nucleoside comprises a nucleotide sequence having at least 80% sequence identity to the nucleotide sequence set forth in SEQ ID NO: 14.

32. The composition of any one of the preceding paragraphs, wherein the liver regenerative factor comprises secreted EGF; and
the at least one engineered liver regenerative factor mRNA or the at least one liver regenerative factor mRNA comprising at least one modified nucleoside comprises a nucleotide sequence having at least 80% sequence identity to the nucleotide sequence set forth in SEQ ID NO: 15.

33. The composition of any one of the preceding paragraphs, wherein the liver regenerative factor comprises stat5b; and
the at least one engineered liver regenerative factor mRNA or the at least one liver regenerative factor mRNA comprising at least one modified nucleoside comprises a nucleotide sequence having at least 80% sequence identity to the nucleotide sequence set forth in SEQ ID NO: 16.

34. The composition of any one of the preceding paragraphs, wherein the liver regenerative factor comprises beta catenin; and
the at least one engineered liver regenerative factor mRNA or the at least one liver regenerative factor mRNA comprising at least one modified nucleoside comprises a nucleotide sequence having at least 80% sequence identity to the nucleotide sequence set forth in SEQ ID NO: 21.

35. The composition of any one of the preceding paragraphs, wherein the liver regenerative factor comprises YAP; and
the at least one engineered liver regenerative factor mRNA or the at least one liver regenerative factor mRNA comprising at least one modified nucleoside comprises a nucleotide sequence having at least 80% sequence identity to the nucleotide sequence set forth in SEQ ID NO: 25.

36. The composition of any one of the preceding paragraphs, wherein the liver regenerative factor comprises WNT2; and the at least one engineered liver regenerative factor mRNA or the at least one liver regenerative factor mRNA comprising at least one modified nucleoside comprises a nucleotide sequence having at least 80% sequence identity to the nucleotide sequence set forth in SEQ ID NO: 26.

37. The composition of any one of the preceding paragraphs, wherein the liver regenerative factor comprises WNT9b; and the at least one engineered liver regenerative factor mRNA or the at least one liver regenerative factor mRNA comprising at least one modified nucleoside comprises a nucleotide sequence having at least 80% sequence identity to the nucleotide sequence set forth in SEQ ID NO: 27.

38. The composition of any one of the preceding paragraphs, further comprising N-acetyl cysteine (NAC).

39. A combination of the composition of any one of paragraphs 1-37 and N-acetyl cysteine (NAC).

40. A method of treating liver injury or liver disease in a subject in need thereof, the method comprising administering the composition or combination of any one of the preceding paragraphs to the subject.

41. A method of accelerating intrinsic liver repair in a subject in need thereof, the method comprising administering the composition or combination of any one of the preceding paragraphs.

42. The method of any one of the preceding paragraphs, wherein the subject is a subject in need of treatment for acute liver disease, chronic liver disease, or acetaminophen (acetyl-para-aminophenol, APAP) overdose.

43. The method of paragraph 42, wherein acute or chronic liver disease is selected from the group consisting of: haemophilia; familial hypercholesterolemia; ornithine transcarbamylase deficiency; α-antitrypsin deficiency; non-alcoholic fatty liver disease (NAFLD); alcoholic fatty liver disease; alcohol-related liver disease (ARLD); phenylketonuria; glycogen storage disease; α1-antitrypsin deficiency; hereditary hemochromatosis; tyrosinemia type 1; argininosuccinic aciduria; hepatitis virus infection; non-viral hepatitis; autoimmune hepatitis; primary biliary cholangitis; cirrhosis; biliary atresia; liver cancer; genetic cholestasis; hemochromatosis; Gilbert syndrome; primary sclerosing cholangitis (PSC); and Wilson's disease.

44. The method of any one of the preceding paragraphs, further comprising administering N-acetyl cysteine (NAC) to the subject.

45. A method of engrafting cells in a liver tissue, the method comprising introducing the cells into the liver tissue and contacting the cells or the liver tissue with the composition or combination of any of one of the preceding paragraphs.

46. The method of paragraph 45, wherein the cells are primary human hepatocytes (PHH) or induced pluripotent stem cell-derived hepatocyte-like-cells (iPSC-HLCs).

47. The method of any one of paragraphs 45-46, wherein the liver tissue is a liver in a subject, the introducing comprises transplanting the cells into the liver, and the contacting comprises administering.

48. The method of paragraph 47, wherein the subject is a subject in need of treatment for acute liver disease, chronic liver disease, or genetic liver disease.

49. The method of paragraph 48, wherein acute or chronic liver disease is selected from the group consisting of: haemophilia; familial hypercholesterolemia; ornithine transcarbamylase deficiency; α-antitrypsin deficiency; non-alcoholic fatty liver disease (NAFLD); alcoholic fatty liver disease; alcohol-related liver disease (ARLD); phenylketonuria; glycogen storage disease; α1-antitrypsin deficiency; hereditary hemochromatosis; tyrosinemia type 1; argininosuccinic aciduria; hepatitis virus infection; non-viral hepatitis; autoimmune hepatitis; primary biliary cholangitis; cirrhosis; biliary atresia; liver cancer; genetic cholestasis; hemochromatosis; Gilbert syndrome; primary sclerosing cholangitis (PSC); and Wilson's disease.

50. The method of paragraph 48, wherein the subject is a subject in need of treatment for alpha-1 antitrypsin deficiency associated liver disease (AATD).

51. The method of any one of the preceding paragraphs, wherein the composition or combination is administered once.

52. The method of any one of the preceding paragraphs, wherein the composition or combination is administered twice or more.

53. The method of any one of the preceding paragraphs, wherein the composition or combination comprises two or more liver regenerative factor mRNAs.

54. The method of any one of the preceding paragraphs, comprising administering a first composition or combination of any one of paragraphs 1-39 comprising a first liver regenerative factor mRNA and concurrently administering a second composition or combination of any one of paragraphs 1-39 comprising a second liver regenerative factor mRNA.

55. The method of any one of the preceding paragraphs, comprising administering a first composition or combination of any one of paragraphs 1-39 comprising a first liver regenerative factor mRNA and separately administering a second composition or combination of any one of paragraphs 1-39 comprising a second liver regenerative factor mRNA.

56. The method of any one of the preceding paragraphs, wherein the administering is intravenous administration.

57. The method of any one of the preceding paragraphs, wherein the administering is via the common bile duct or to the gallbladder.

The technology described herein is further illustrated by the following examples which in no way should be construed as being further limiting.

EXAMPLES

Example 1: VEGFA mRNA-LNP Promotes Biliary Epithelial Cell-to-Hepatocyte Conversion in Acute and Chronic Liver Diseases and Reverses Steatosis and Fibrosis The liver is known for its remarkable regenerative ability through proliferation of hepatocytes. Yet, during chronic injury or severe hepatocyte death, proliferation of hepatocytes is exhausted. To overcome this hurdle, the inventors use vascular-endothelial-growth-factor A (VEGFA) as a therapeutic means to accelerate biliary epithelial cell (BEC)- to-hepatocyte conversion. Investigation in zebrafish establishes that blocking VEGF receptors abrogates BEC-driven liver repair, while VEGFA overexpression promotes it. Delivery of VEGFA via non-integrative and safe nucleoside-modified mRNA encapsulated into lipid-nanoparticles (mRNA-LNP) in acutely or chronically injured mouse livers induces robust BEC-to-hepatocyte conversion and reversion of steatosis and fibrosis. In human and murine diseased livers, the inventors further identified VEGFA-receptor KDR-expressing BECs associated with KDR-expressing cell-derived hepatocytes. This defines KDR-expressing cells, as being BECs, as facultative progenitors. This study reveals novel therapeutic benefits of VEGFA delivered via nucleoside-modified mRNA-LNP, whose safety is widely validated with COVID-19 vaccines, for harnessing BEC-driven repair to potentially treat liver diseases.

Mortality related to end stage liver disease (ESLD) is ranked as the 12$^{th}$ most common cause of death in the US. Liver transplantation remains the only treatment for ESLD, but this procedure is critically challenged by the shortage of organ donors. The remarkable ability of the liver to regenerate by proliferation of mature hepatocytes is well documented[1], yet in the case of severe acute hepatocyte death or chronic ESLD, proliferation of mature cells becomes exhausted[2,3] due to the escalating progression of steatosis, inflammation, fibrosis and irreversible cirrhosis. In these cases, the presence of alternative precursors of hepatocytes that derive from biliary epithelial cells (BECs) has been postulated, and these cells have been referred to by various names, including liver progenitor cells (LPCs)[4]. Expansion of LPCs from the BEC compartment, a process described as ductular reaction (DR), is present in virtually all chronic and acute human liver diseases, suggesting an alternative regeneration process by which BECs proliferate and differentiate into hepatocytes[5-15], the BEC-driven liver regeneration. The evidence for the contribution of BECs to de novo hepatocytes in humans is illustrated by the presence of hepatocytes expressing the BEC marker EpCAM emerging from highly proliferative DR areas in advanced cirrhotic livers[16], detection of "bi-phenotypic cells"[17] or "ductular hepatocytes"[18] positive for both the BEC marker KRT19 and the hepatocyte marker HNF4α[17] or HepPar1[18], and observation of budding of hepatocyte-like cells expressing the hepatocytic marker glutamine synthetase (GS) from BECs within the DRs[19-23]. Specifically, one study quantified the emerging immature hepatocytes budding from KRT19+ BECs within the septa developed in human cirrhotic livers, and estimated that they represented up to 70% of hepatocytes[19]. Importantly, a recent study showed that aberrant GS positivity adjacent to portal tracts is significantly associated with regressed cirrhosis in humans[24], suggesting the clinical benefit of LPC-derived hepatocytes in resolving human cirrhosis. In an attempt to lineage trace the LPCs among the DRs in human cirrhotic livers, recent studies have used mutational analysis in mitochondrial DNA encoding cytochrome c oxidase enzyme, and showed the descent of hepatocytes within monoclonal regenerative nodules from adjacent LPC-associated DRs[25]. In mice, lineage tracing studies have confirmed that the first and massive response to liver injury is the proliferation of mature hepatocytes[26-29]. Yet, consistent with an alternative BEC-mediated liver repair identified in human liver diseases, the BEC origin of de novo hepatocytes has been demonstrated in mouse models in which hepatocyte proliferation was significantly impaired by lack of Mdm2[30], deficiency in β1 integrin[31] or β-catenin[32], overexpression of p21 in hepatocytes[31], or following long-term chronic injuries[33] [17] In these studies, percentages of hepatocytes mapped from BECs averaged 15%[31,32] In the same line of evidence, the inventors' lineage tracing studies in zebrafish robustly demonstrated the BEC origin of the majority of hepatocytes after near complete ablation of hepatocytes[34,35].

Results

Figure 1A:
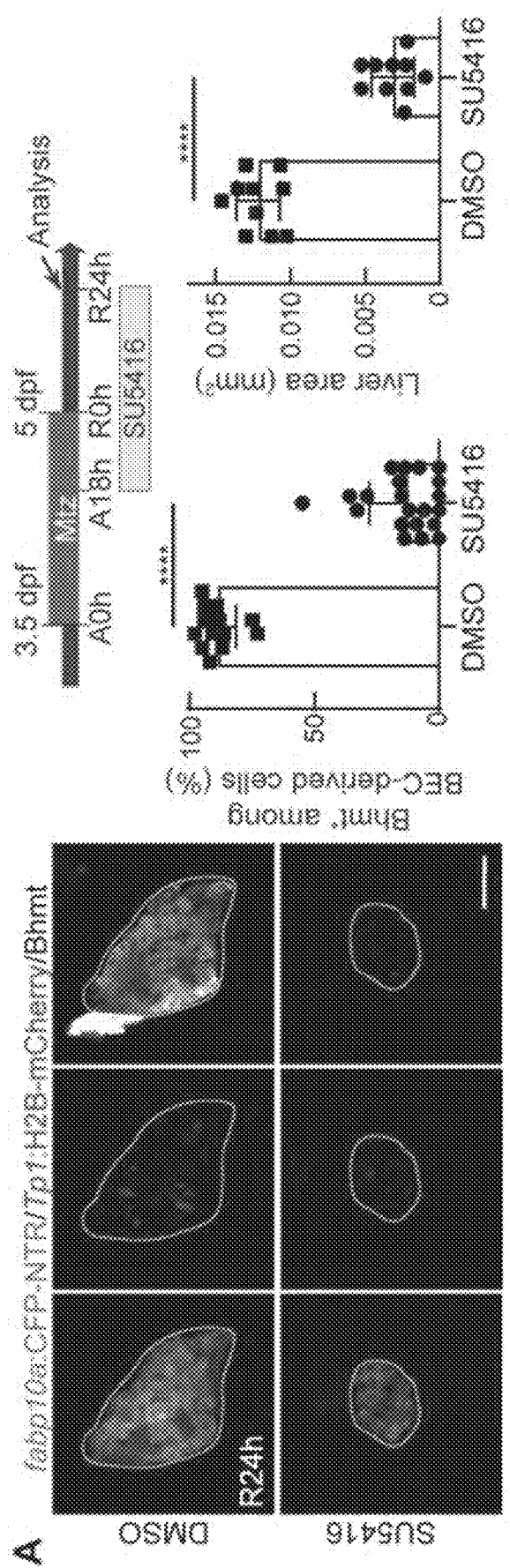
FIGS. 1A-1D depict VEGFR signaling regulating BEC-driven liver regeneration in zebrafish.
Figure 1B:
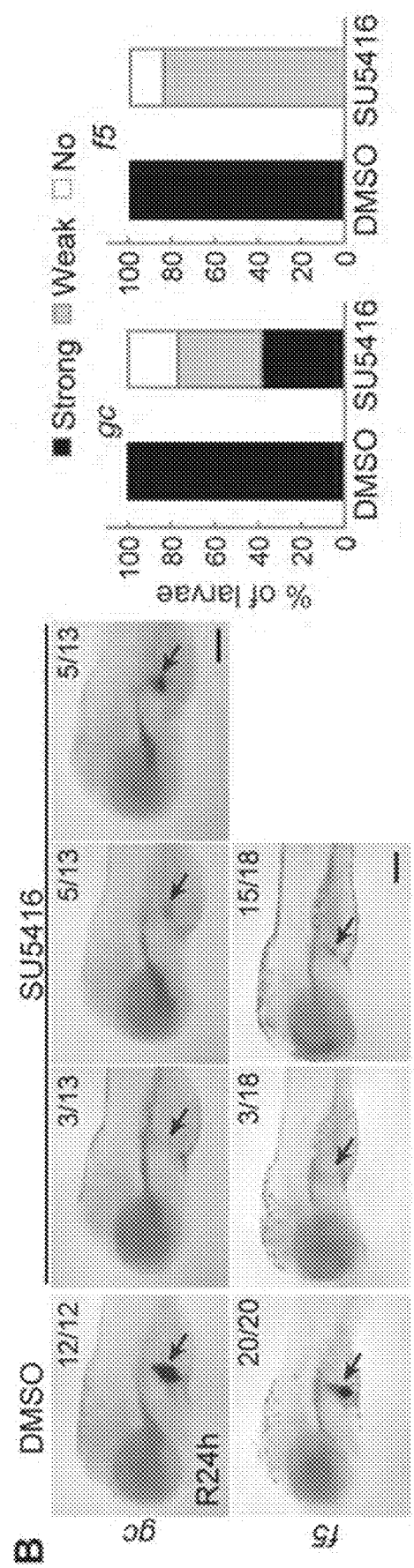
Figure 1C:
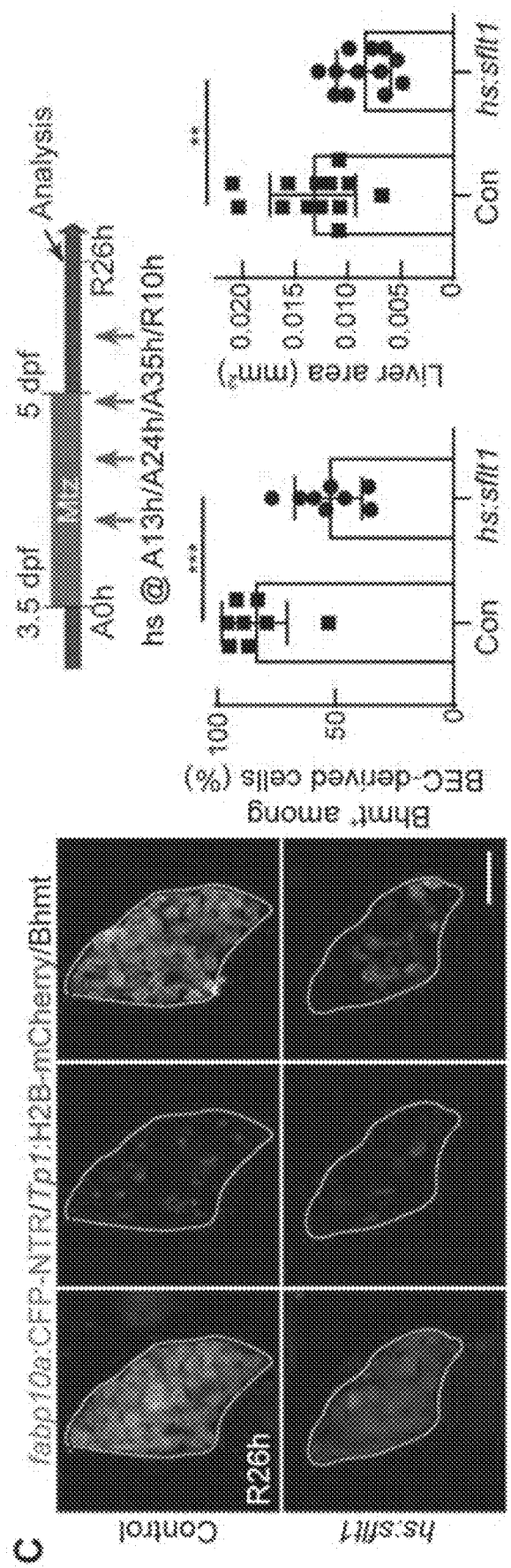

VEGFR Signaling Regulates BEC-to-Hepatocyte Conversion During Liver Regeneration in Zebrafish To investigate the molecular mechanisms underlying BEC-driven liver regeneration, the inventors had previously performed a chemical screen[46] using the zebrafish hepatocyte ablation model, Tg(fabp10a:CFP-NTR)$^{s93}$, in which metronidazole (Mtz) treatment specifically ablates virtually all nitroreductase (NTR)-expressing fabp10a$^+$ hepatocytes, thereby eliciting BEC-driven liver regeneration[35]. Through this screen, the inventors reported that suppressing VEGFR signaling with two VEGFR inhibitors, SU5416[47] and SU4312[48], significantly reduced the size of regenerating livers but did not affect the induction of early hepatocyte markers Prox1 and HNF4α in BEC-derived liver progenitor cells (LPCs)[46], showing normal BEC-to-LPC dedifferentiation. The inventors here sought to determine whether VEGFR signaling regulates the next step in BEC-driven liver regeneration, LPC-to-hepatocyte differentiation. To distinguish BEC-derived hepatocytes, the inventors used a Notch zebrafish reporter line, Tg(Tp1:H2B-mCherry)s939, which expresses histone 2B (H2B) and mCherry fusion proteins in BECs[35]. A long half-life of H2B-mCherry allows for tracing the lineage of BECs; thus, BECs are strong H2B-mCherry+ and BEC-derived hepatocytes are weak H2B-mCherry+[35]. Treating Tg(fabp10a:CFP-NTR) larvae with SU5416 from ablation 18 hours (A18h) to regeneration 24 hours (R24h) significantly reduced the size of regenerating livers (FIG. 1a), as reported[46]. Importantly, the SU5416 treatment greatly suppressed the expression of the hepatocyte marker Bhmt at R24h (FIG. 1A), showing a defect in LPC-to-hepatocyte differentiation. This defect was confirmed with two additional hepatocyte markers, gc and f5 (FIG. 1B). Complimentary to the pharmacological inhibition, the inventors genetically block VEGFR signaling using the Tg(hs:sflt1)bns80 line, which expresses a soluble form of VEGFR1 (sFlt1), a decoy receptor for VEGFA, VEGFB, and PlGF[41], upon heat-shock[49]. sFlt1 overexpression also reduced Bhmt expression and liver size in regenerating livers at R26h (FIG. 1C), phenocopying the effects of the SU5416 treatment.

Figure 1D:
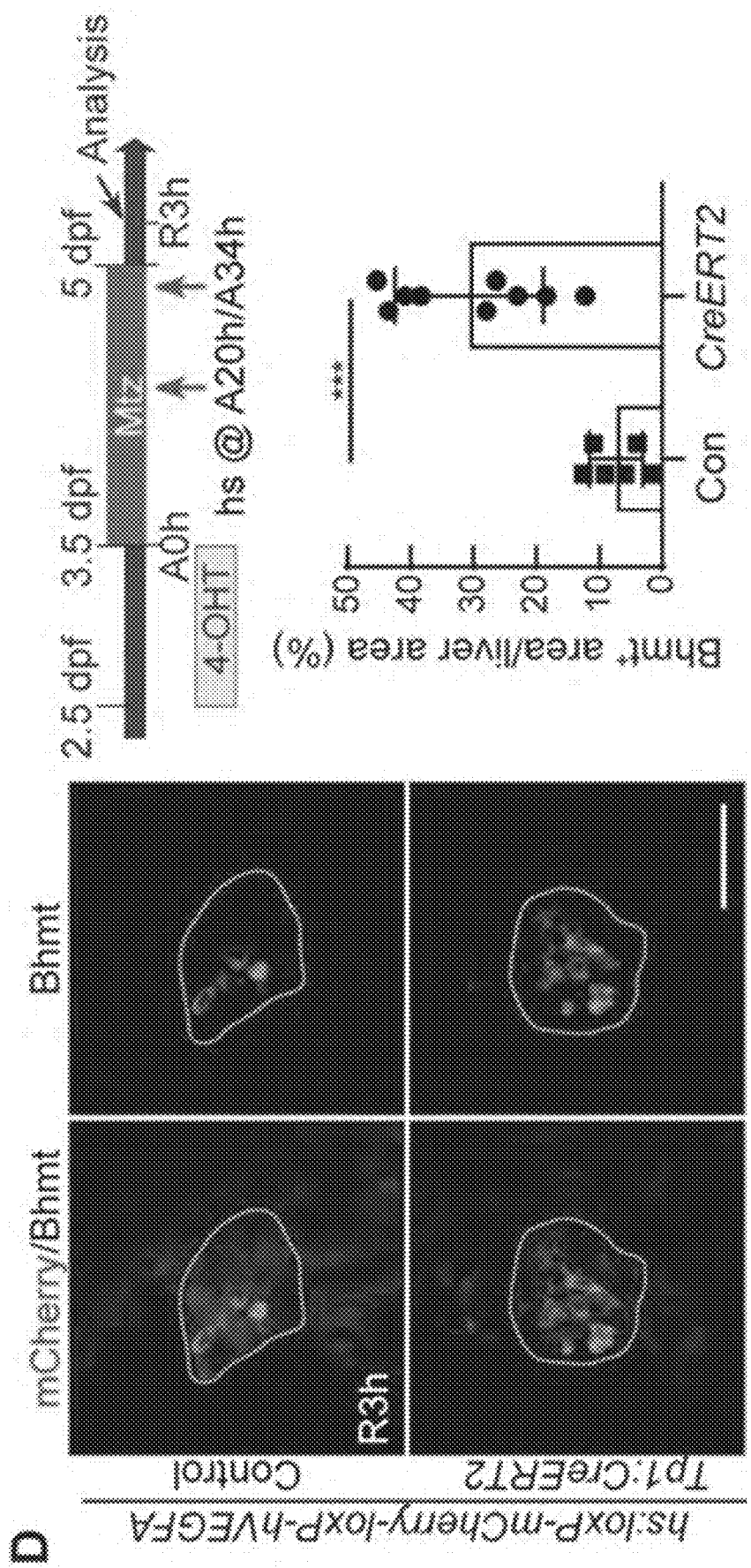

Inversely, the inventors next investigated if the overactivation of VEGFR signaling could promote LPC-to-hepatocyte differentiation. The inventors used the Tg(hs:loxP-mCherry-loxP-hVEGFA)$^{nm32}$ line, which expresses human VEGFA165 upon heat-shock following Cre-mediated, mCherry-loxP excision[50], together with the Tg(Tp1:Cre-ERT2)s959 line that expresses CreERT2 in BECs. Larvae were treated with 4-OHT from 2.5 to 3.5 days post-fertilization (dpf) to induce the Cre-mediated excision of mCherry-loxP in BECs, heat-shocked twice at A20h and A34h to trigger expression of VEGFA165, and harvested at R3h. hVEGFA expression in a subset of BEC-derived cells (BECs and LPCs) increased Bhmt expression in regenerating livers at R3h compared with controls (FIG. 1D), indicating that VEGFR overactivation is sufficient to promote LPC-to-hepatocyte differentiation. Altogether, the zebrafish data demonstrate the essential role of VEGFR signaling in BEC-driven liver regeneration, particularly in LPC-to-hepatocyte differentiation.

Figure 2A:
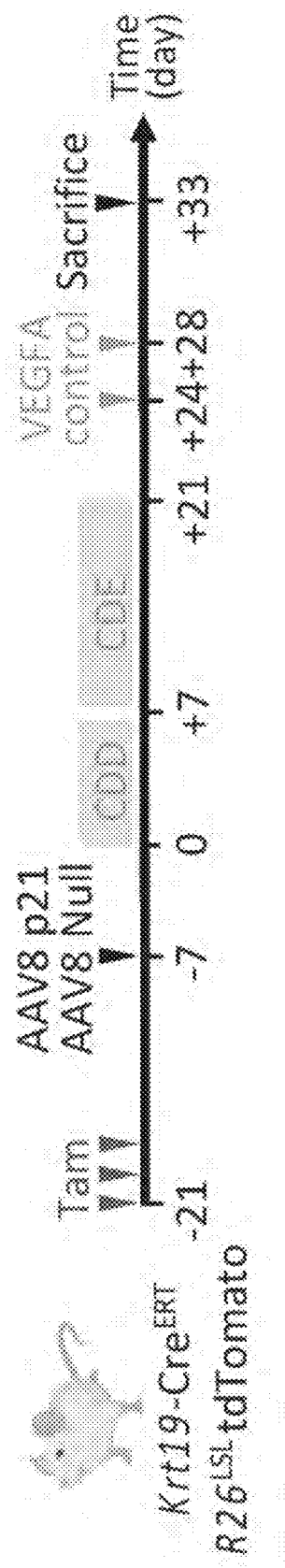
FIGS. 2A-2I depict VEGFA mRNA-LNP administration inducing BEC-to-hepatocyte conversion and promoting liver repair in CDE/p21-induced chronic liver injury in mice.
Figure 2B:
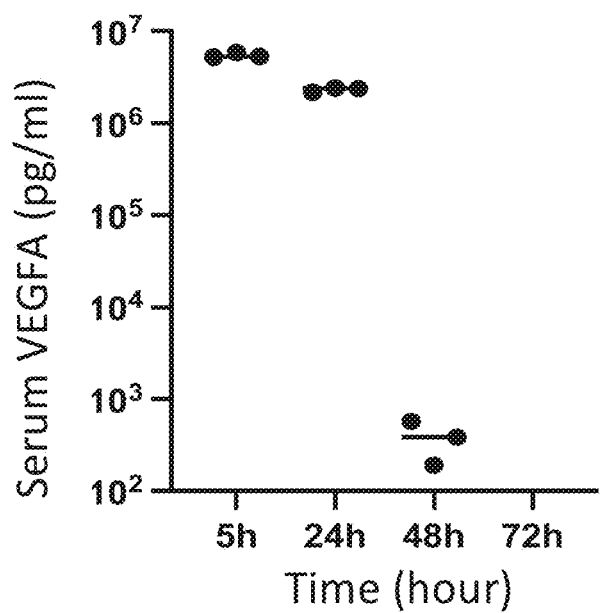
Figure 2B:
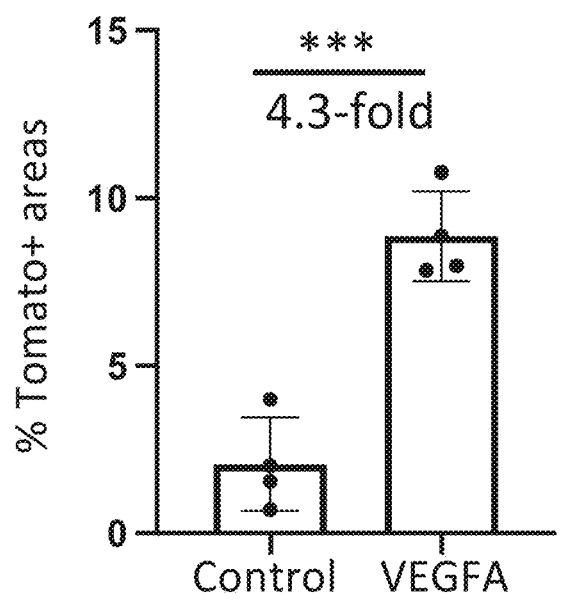
Figure 2C:
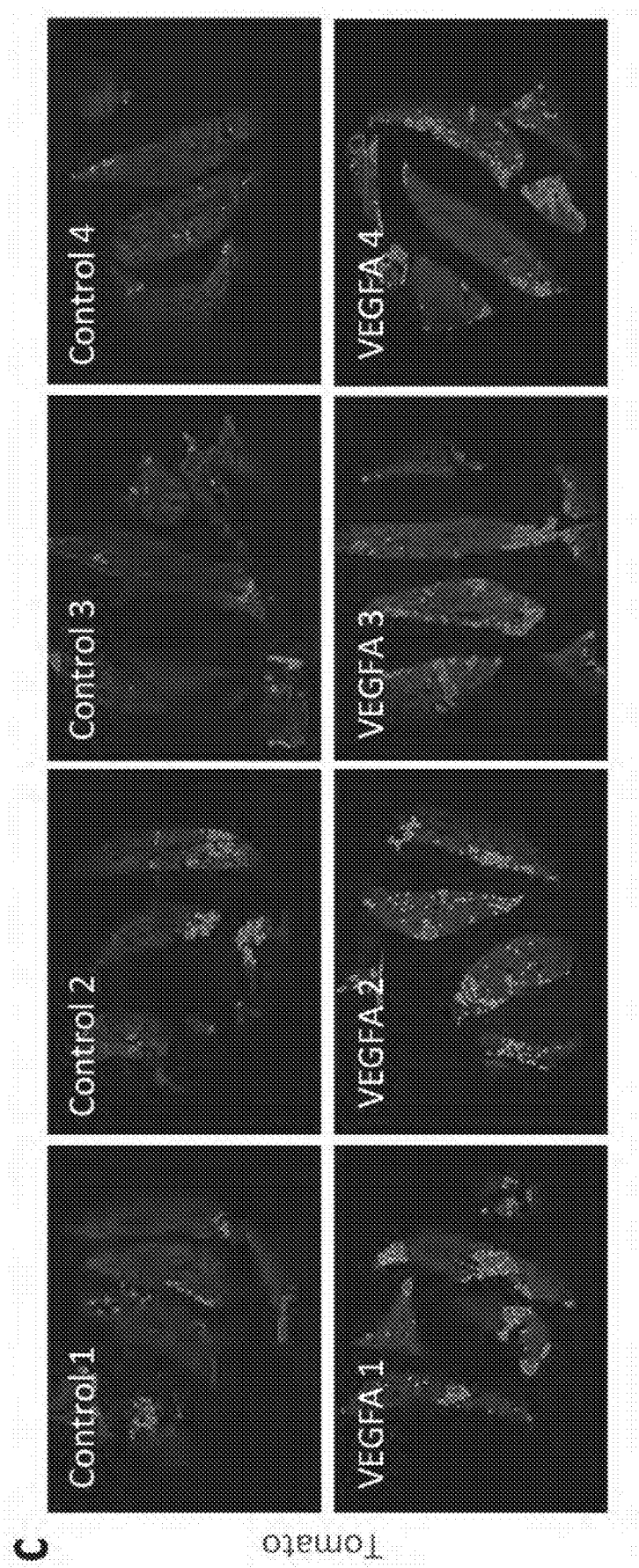
Figure 2D:
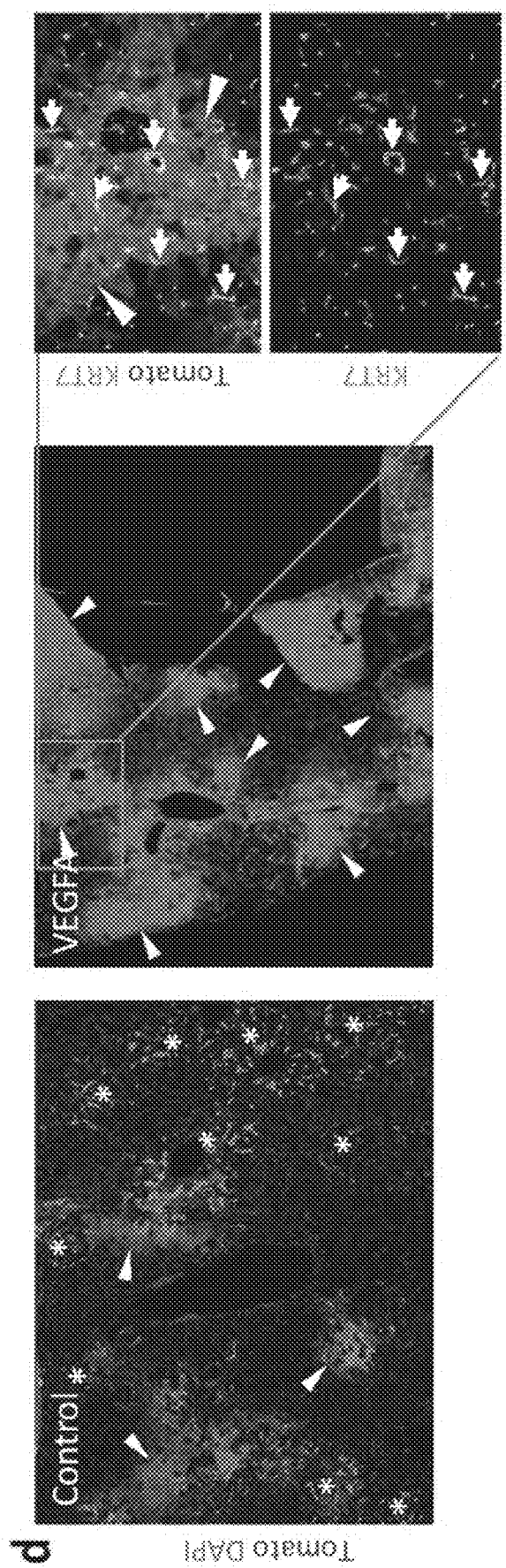
Figure 2E:
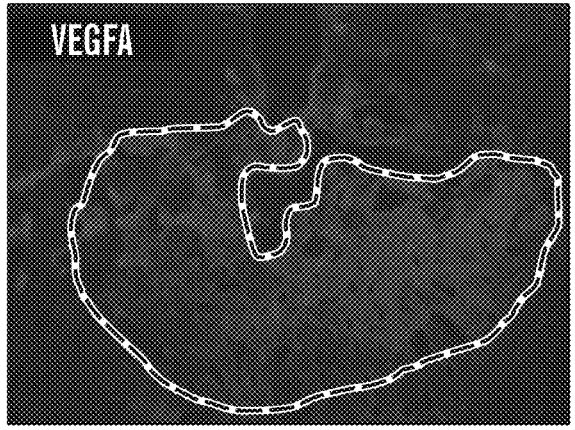
Figure 2E:
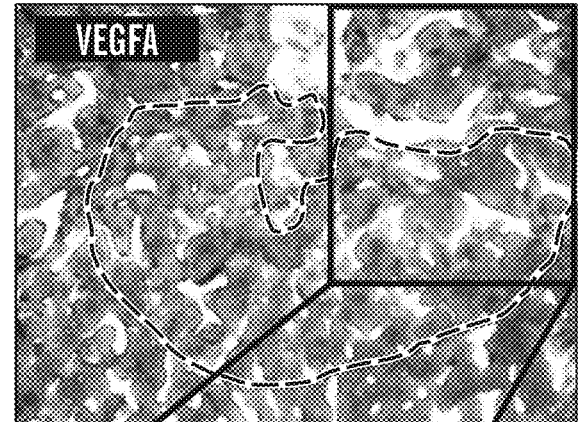
Figure 2E:
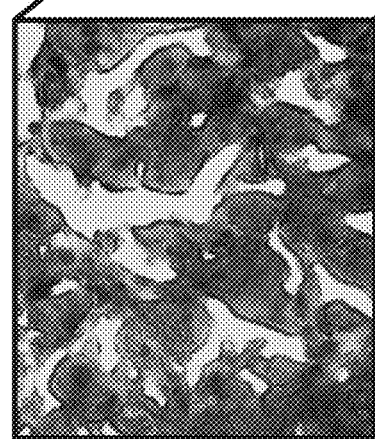
Figure 2F:
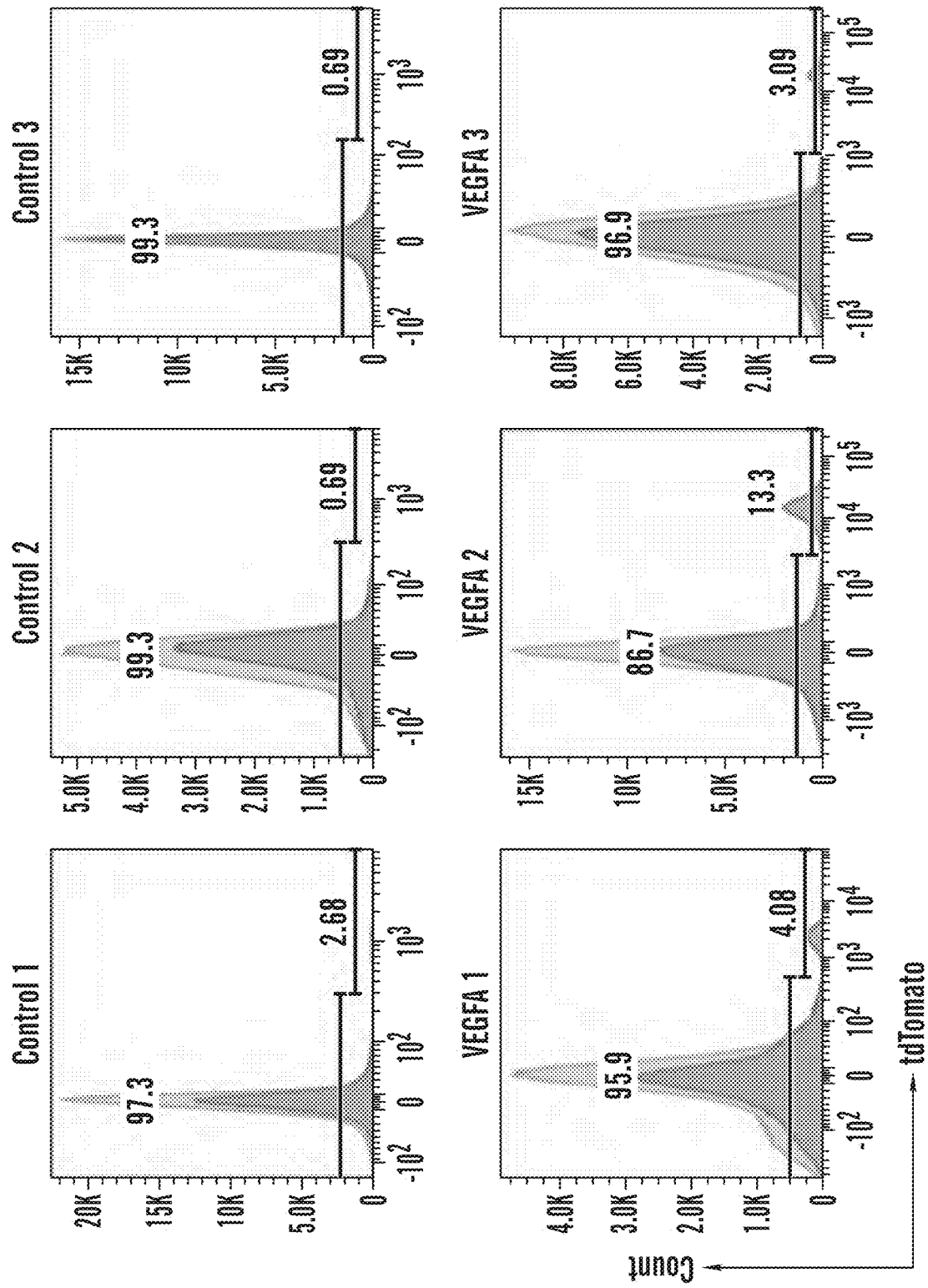
Figure 2F:
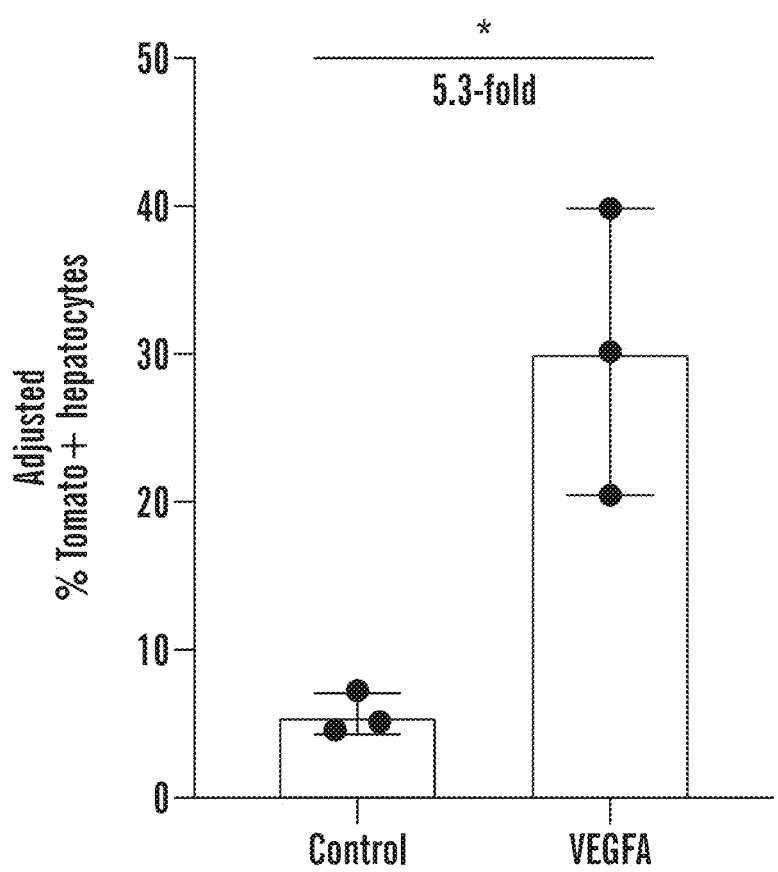
Figures 2G, 2H:
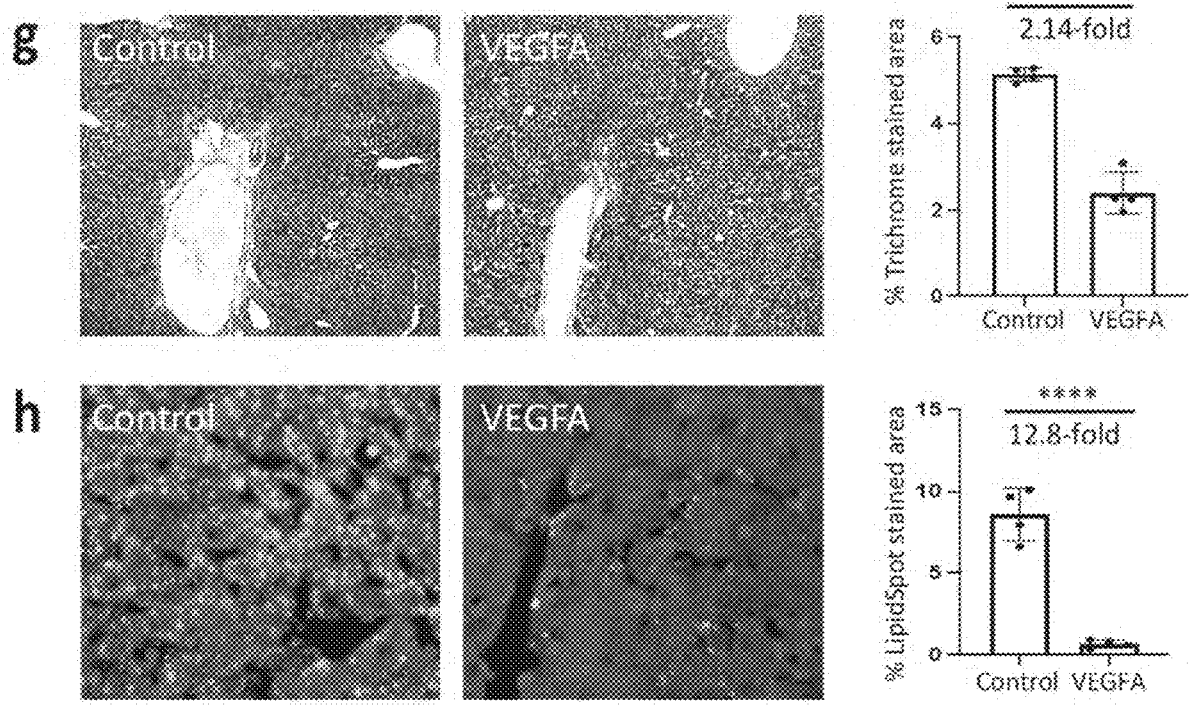
Figure 2I:
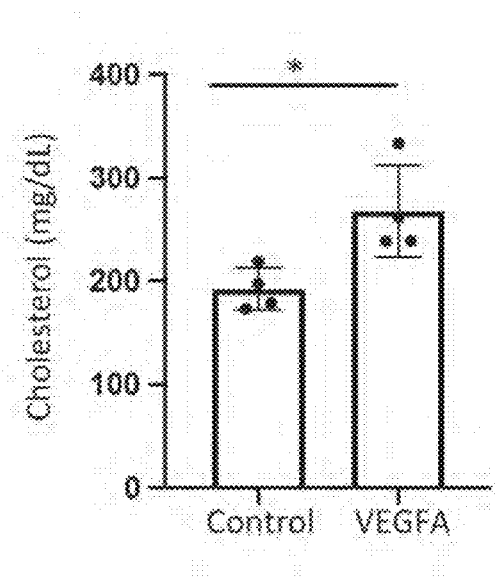
Figure 7A:
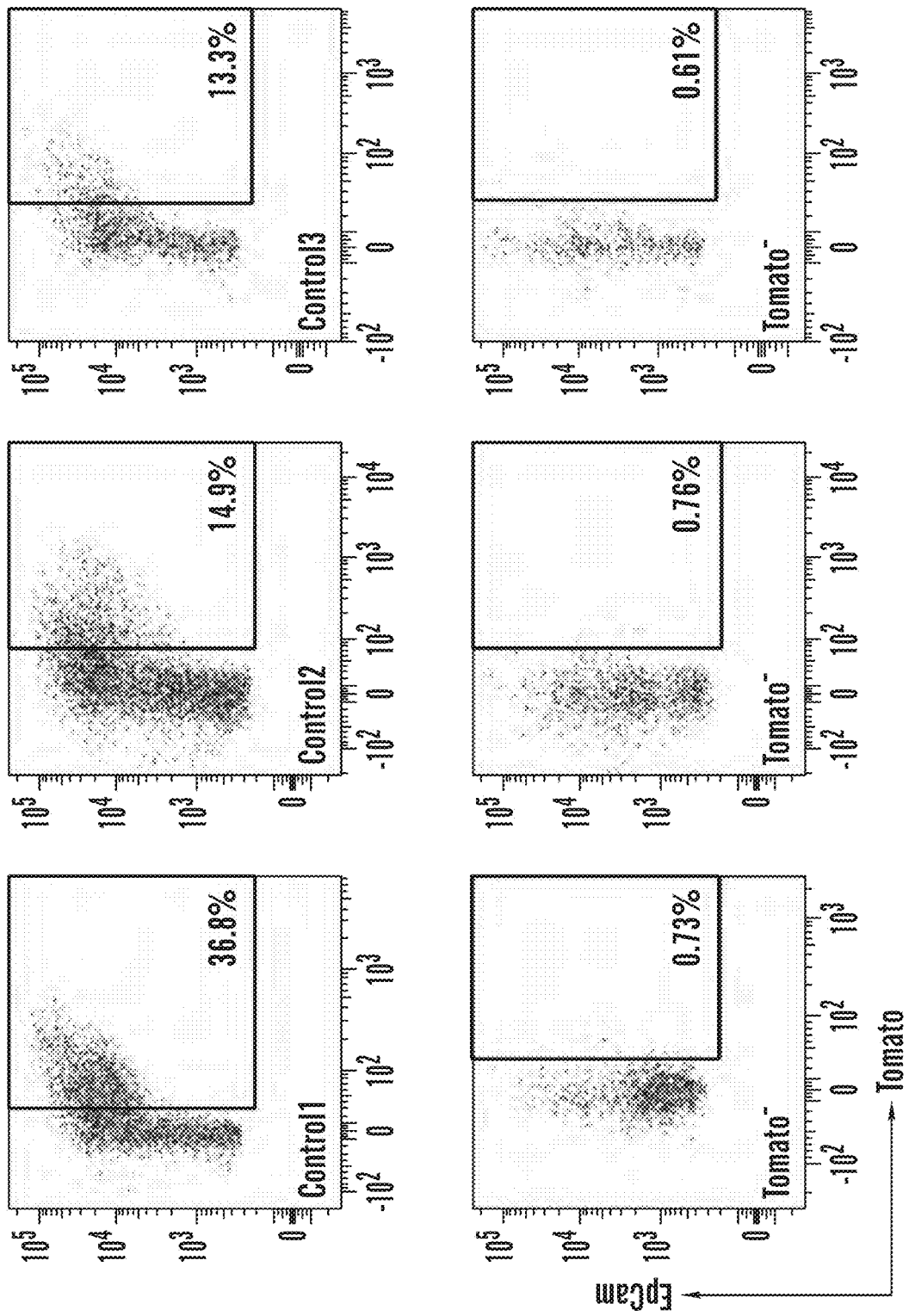
FIGS. 7A-7G depict VEGFA mRNA-LNP administration inducing BEC-to-hepatocyte conversion and promoting liver repair in CDE/p21-induced chronic liver injury in mice (FIG. 7A) Density plots from flow cytometry of non-parenchymal cell (NPC) fraction isolated from mouse livers. The NPC fraction was gated to exclude dead cell, debris, and cells expressing CD11b, CD45, Ter119, CD31. Values show % tdTomato+ EpCAM+ population. Lower panel shows cells from a control non-tdTomato mouse run simultaneously with each experimental mouse.
Figure 7A:
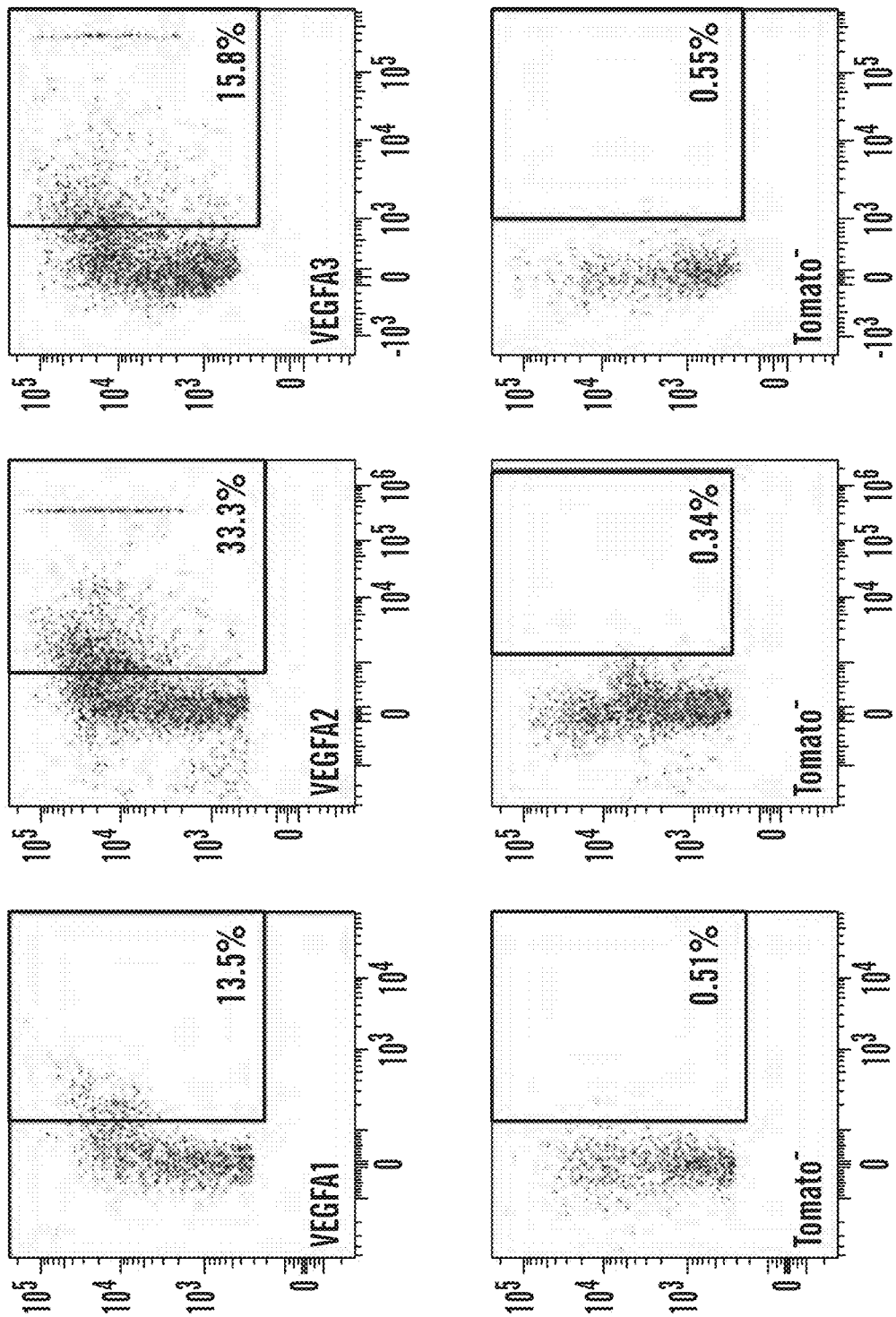
Figure 7B:
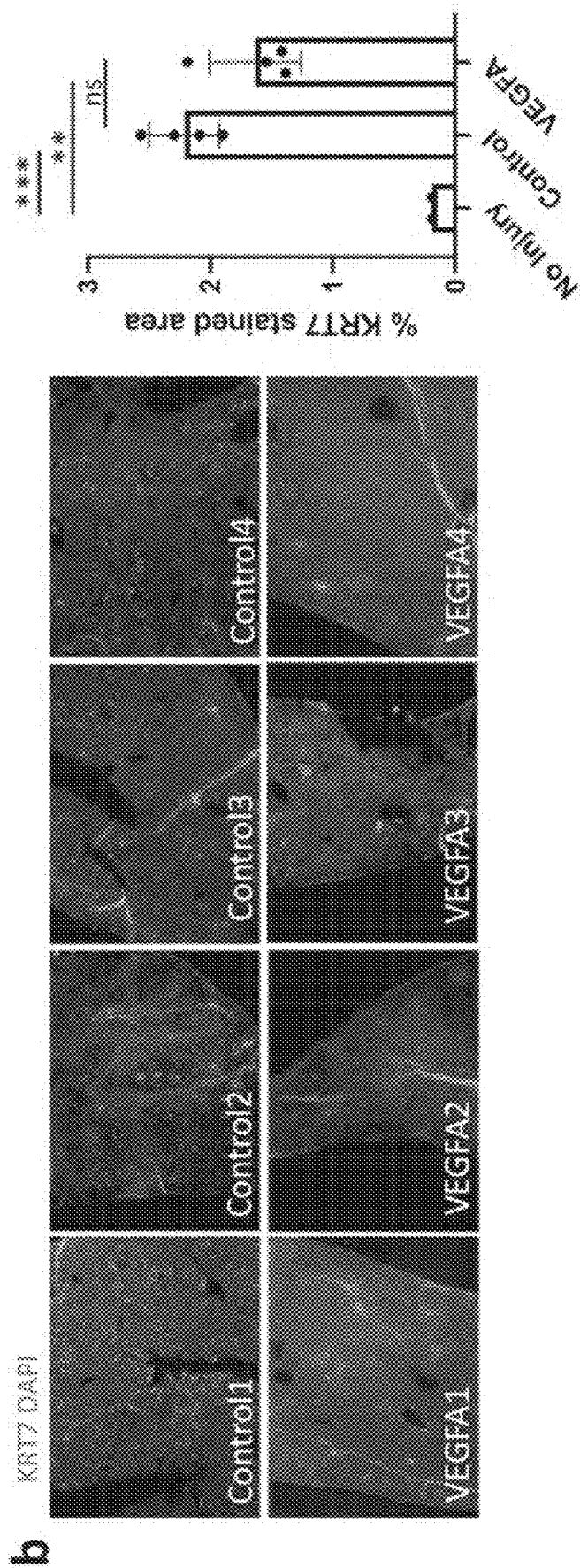
Figure 7C:
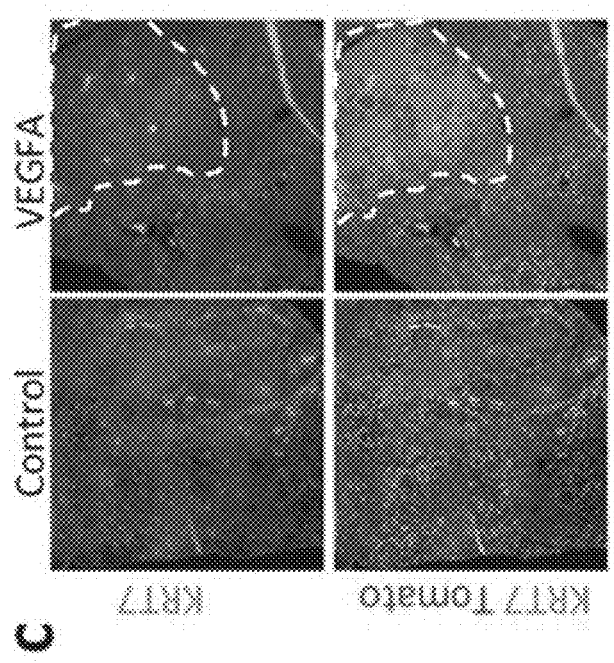

VEGFA mRNA-LNP Induces BEC-to-Hepatocyte Conversion in CDE Diet-Induced Chronic Liver Injury in Mice and Resolves Liver Damage Given the impact of VEGFR activation in promoting BEC-driven liver regeneration in zebrafish, the inventors interrogated its clinical benefit in restoring liver function in a chronic liver injury model in mice. To trace hepatocytic fate of BECs, liver injury was induced in Krt19-Cre$^{ERT}$, R26$^{LSL}$ tdTomato[39] 31 mice with the choline-deficient diet supplemented with 0.1% ethionine (CDE) following a single injection of AAV8-Tbg-p21 (CDE/p21 model)[31] (FIG. 2A), which recapitulates some key features of the human non-alcoholic steatohepatitis (NASH) liver disease including steatosis, fibrosis, hepatocyte senescence, and invasive ductular reaction[31]. Injection of AAV8-Tbg-p21 triggered p21 expression in hepatocytes and was used to induce hepatocyte senescence[31, 32], a common feature seen in human chronic liver disease[51, 52] The inventors chose to deliver VEGFA in mice via injection of nucleoside-modified mRNA-LNP allowing controlled transient expression of VEGFA in the liver for better clinical translation. For the present study, robust levels of VEGFA proteins in the serum were detected as early as 5 hours after one intravenous injection of 10 µg/20 g body weight of VEGFA mRNA-LNPs (FIG. 2B). The levels remained high for the following 24 hours, yet rapidly decreased to baseline levels 48 hours later and were no longer detected by 72 hours. Mice were administered two injections of either VEGFA mRNA-LNP or control LNP (formulated with untranslatable Poly(C) RNA or neutral firefly luciferase-encoding mRNA) after the diet was over. Strikingly, large patches of diffused tdTomato+ clusters appeared in all liver lobes of VEGFA mRNA-LNP-treated mice, representing mostly hepatocytes (FIG. 2C, outline, FIG. 2D). In contrast, in control LNP-treated mice, tdTomato+ clusters were sporadic and small (FIG. 2C, FIG. 2D), with the vast majority composed of BECs (FIG. 2d, see numerous * areas). tdTomato+ hepatocytes (FIG. 2D, arrowheads) were adjacent to tdTomato+ BECs (FIG. 2D, arrows), supporting their BEC origin. Functionally, the tdTomato+ hepatocytes were equally efficient in storing glycogen as the adjacent tdTomato– hepatocytes (FIG. 2E). Quantification of tdTomato+ hepatocytes by flow cytometry confirmed that VEGFA mRNA-LNPs significantly augment BEC-to-hepatocyte conversion (FIG. 2F). Since the lineage tracing efficiency varies greatly among Krt19-Cre$^{ERT}$, R26$^{LSL}$ tdTomato mice, the percent labeled BEC population estimated from the non-parenchymal fraction (FIG. 7A) was used to adjust for lineage tracing discrepancy and define the adjusted % tdTomato+ hepatocytes for each mouse (FIG. 2F). The inventors thus estimated that VEGFA mRNA-LNPs promote 5.3-fold greater % tdTomato+ hepatocytes as compared to control LNP-treated mice. In contrast to the reported role of VEGFA in promoting BEC proliferation[41], here the extent of DR was similar between the two groups (FIG. 7B), most likely due to greater BEC-to-hepatocyte conversion in VEGFA treated group, as supported by lower density of KRT7+ BECs in areas associated with tdTomato+ hepatocytes (FIG. 7C). Importantly, for clinical translation of VEGFA mRNA-LNP, VEGFA-mediated conversion of BECs to hepatocytes was consistently associated with complete reversion of fibrosis and steatosis (FIG. 2G, 2H) as quantified with trichrome and LipidSpot staining, respectively. In line with these findings, the serum levels of cholesterol in the VEGFA mRNA-LNP-treated group were significantly higher, validating increased lipid clearance from hepatocytes as compared to control LNP-treated group (FIG. 2I). Overall, treatment of the CDE/p21 mouse model with two injections of VEGFA mRNA-LNP fully reverts steatosis and fibrosis, the two key features observed in NASH patients, suggesting a potential clinical benefit of VEGFA mRNA-LNP to alleviate the human NASH disease.

Figure 7D:
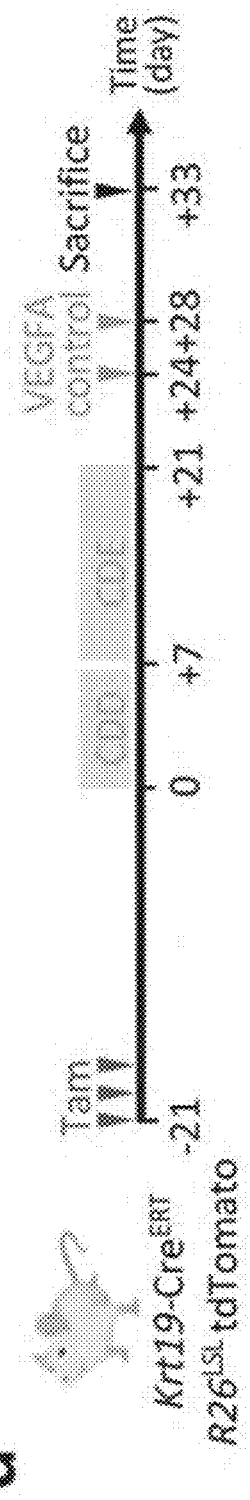
Figure 7E:
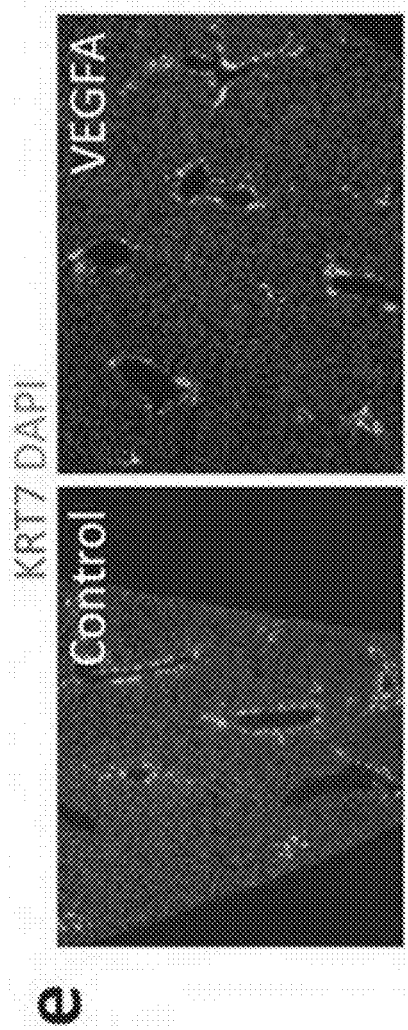
Figure 7F:
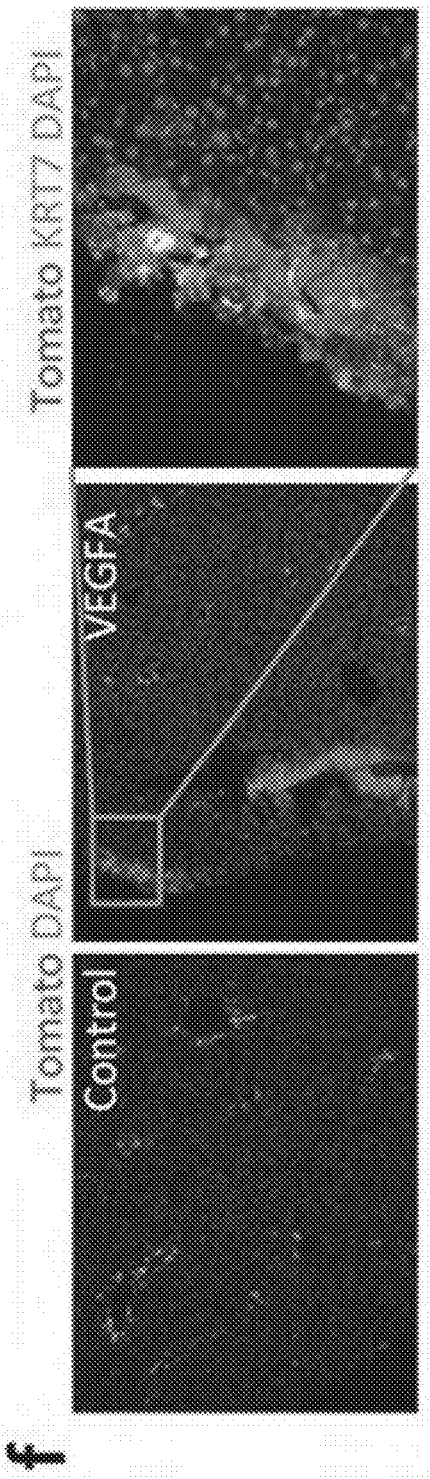
Figure 7G:
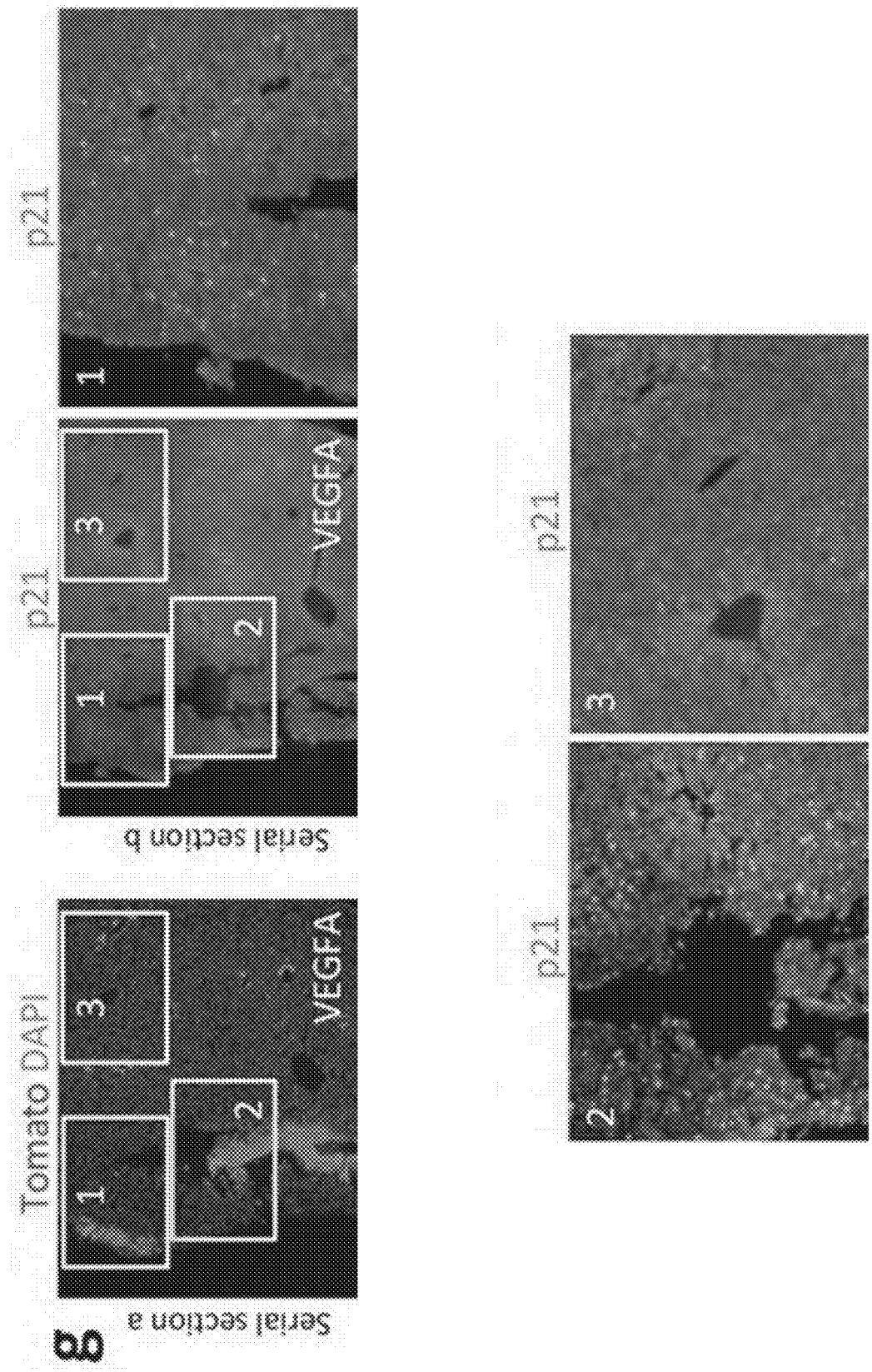

Since VEGFA significantly promotes emergence of BEC-derived hepatocyte in the CDE/p21 mice, the inventors questioned the significance of p21-induced hepatocyte senescence in this process. Indeed, it has been reported by many groups that BEC-driven liver repair occurs almost exclusively in mouse models in which hepatocyte proliferation was impaired[30-32]. Therefore, the inventors asked whether suppression of hepatocyte proliferation was a prerequisite for VEGFA-mediated BEC-to-hepatocyte conversion. The inventors thus administered VEGFA mRNA-LNP in CDE-fed mice that were not pre-injected with AAV8-Tbg-p21 (FIG. 7D). In both control-LNP- and VEGFA mRNA-LNP-treated groups, the DR was much lower than in AAV8-Tbg-p21 administered mice (compare FIG. 7E and FIG. 7B), indicating that hepatocyte senescence accelerates BEC expansion. Control-LNPs group did not generate any tdTomato+ hepatocytes as expected[31]. However, the inventors consistently observed emergence of tdTomato+ hepatocyte clusters in the VEGFA mRNA-LNP-treated group, although sparse, in a specific spatial pattern (FIG. 7F). The clusters were always adjacent to hepatocytes that naturally induced endogenous p21 expression (FIG. 7G, panel 1,2,3). These results demonstrate that p21-mediated suppression of hepatocyte proliferation not only promotes BEC proliferation but also their conversion to hepatocytes. Importantly, VEGFA mRNA-LNP in the presence of hepatocyte proliferation can still trigger BEC-to-hepatocyte conversion, yet combined with suppression of hepatocyte proliferation, potentializes cell conversion to a clinically relevant extent and reverses steatosis and fibrosis.

Figure 3B:
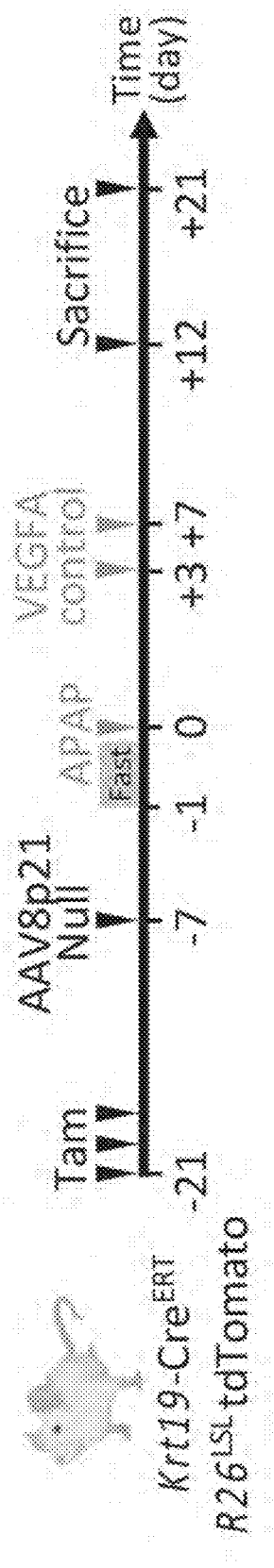
Figure 3B:
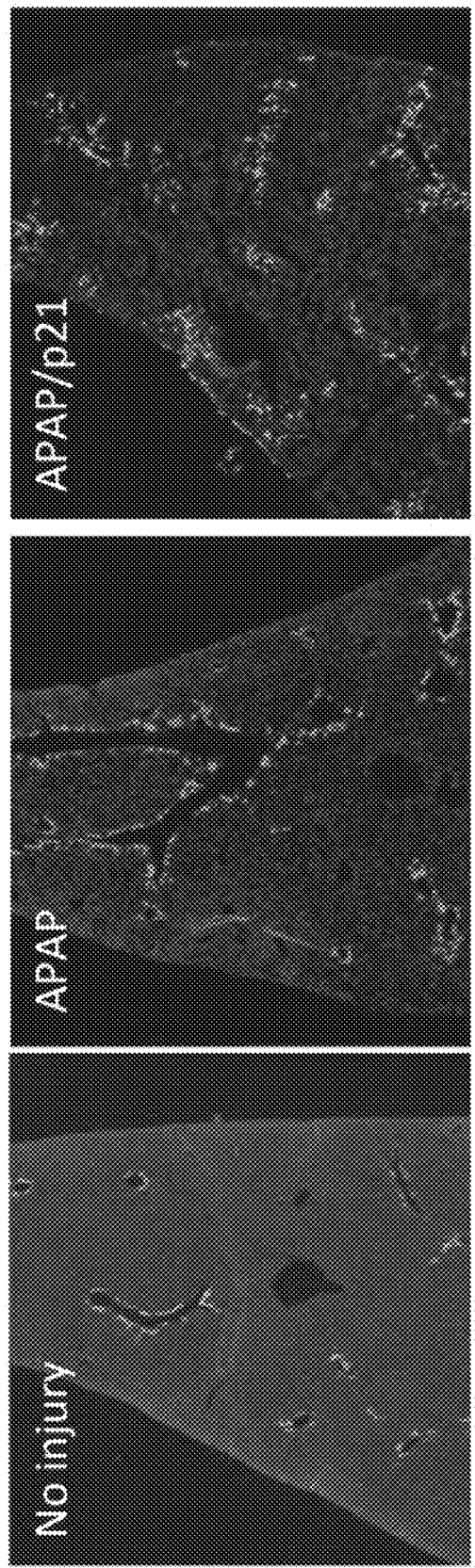
Figure 3C:
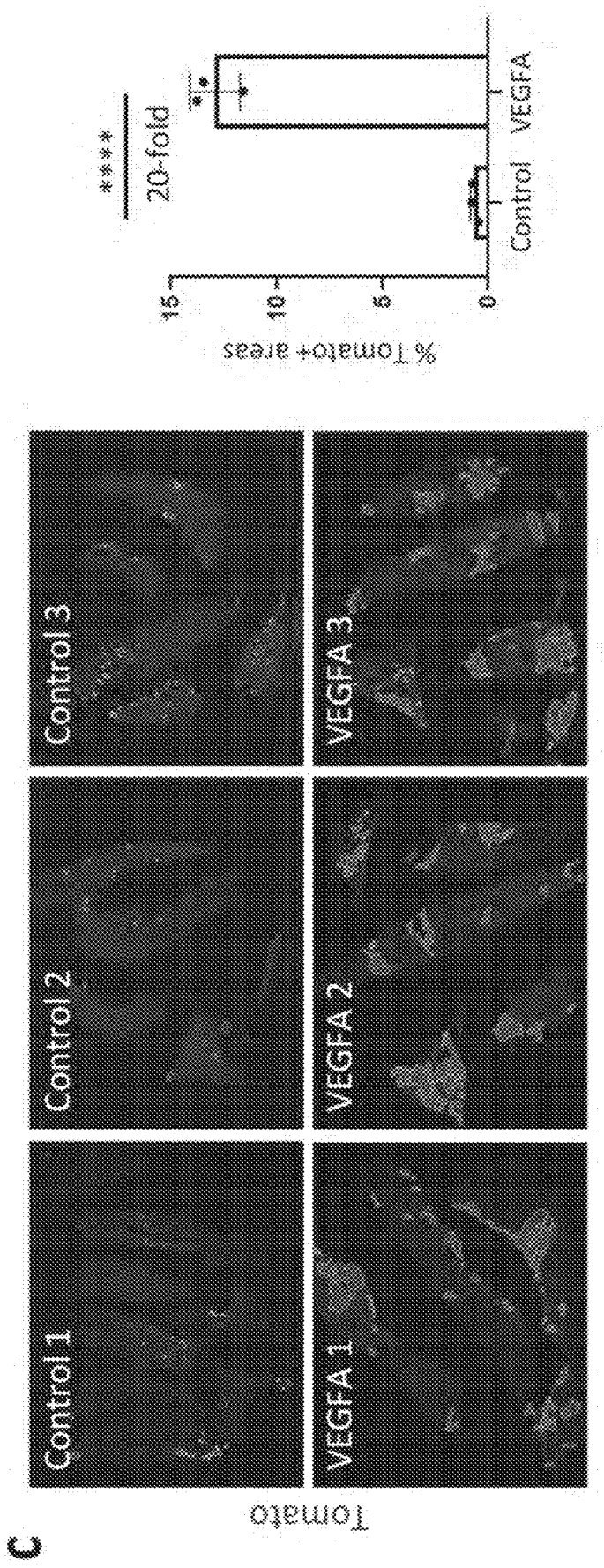
Figure 3D:
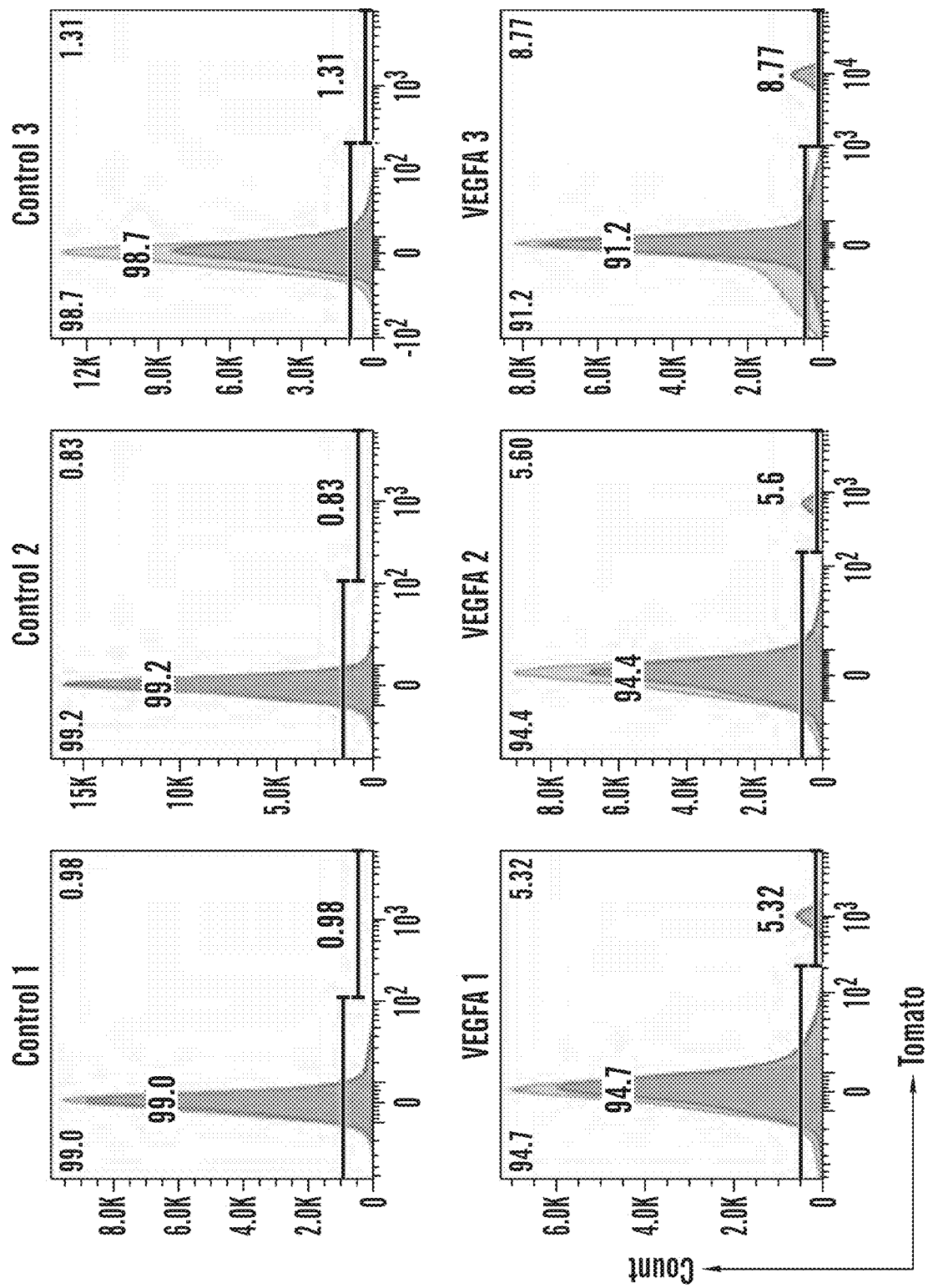
Figure 3D:
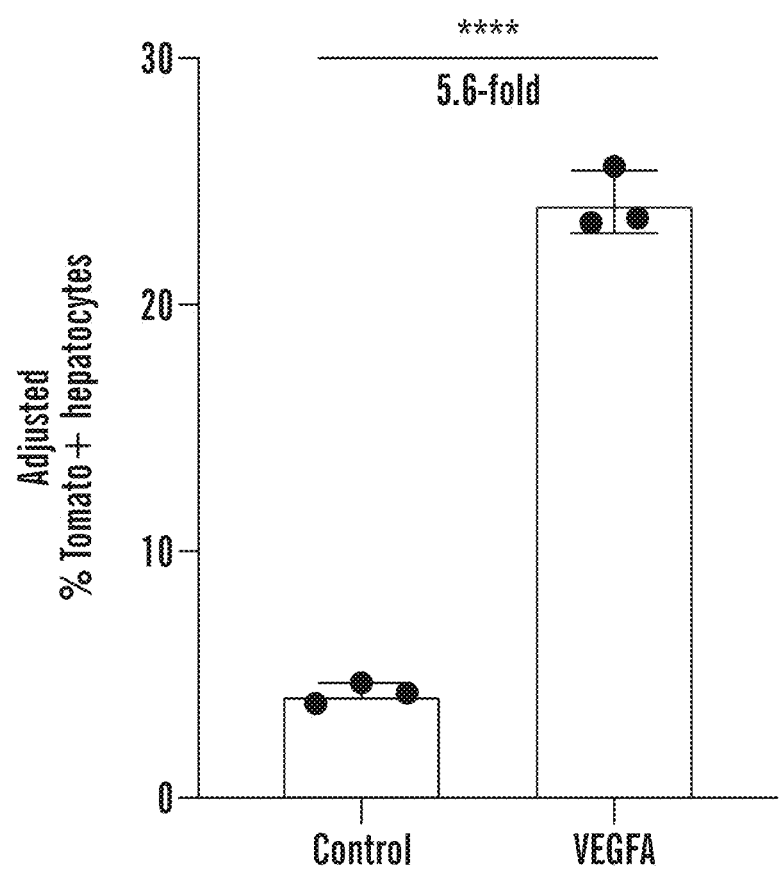
Figure 3E:
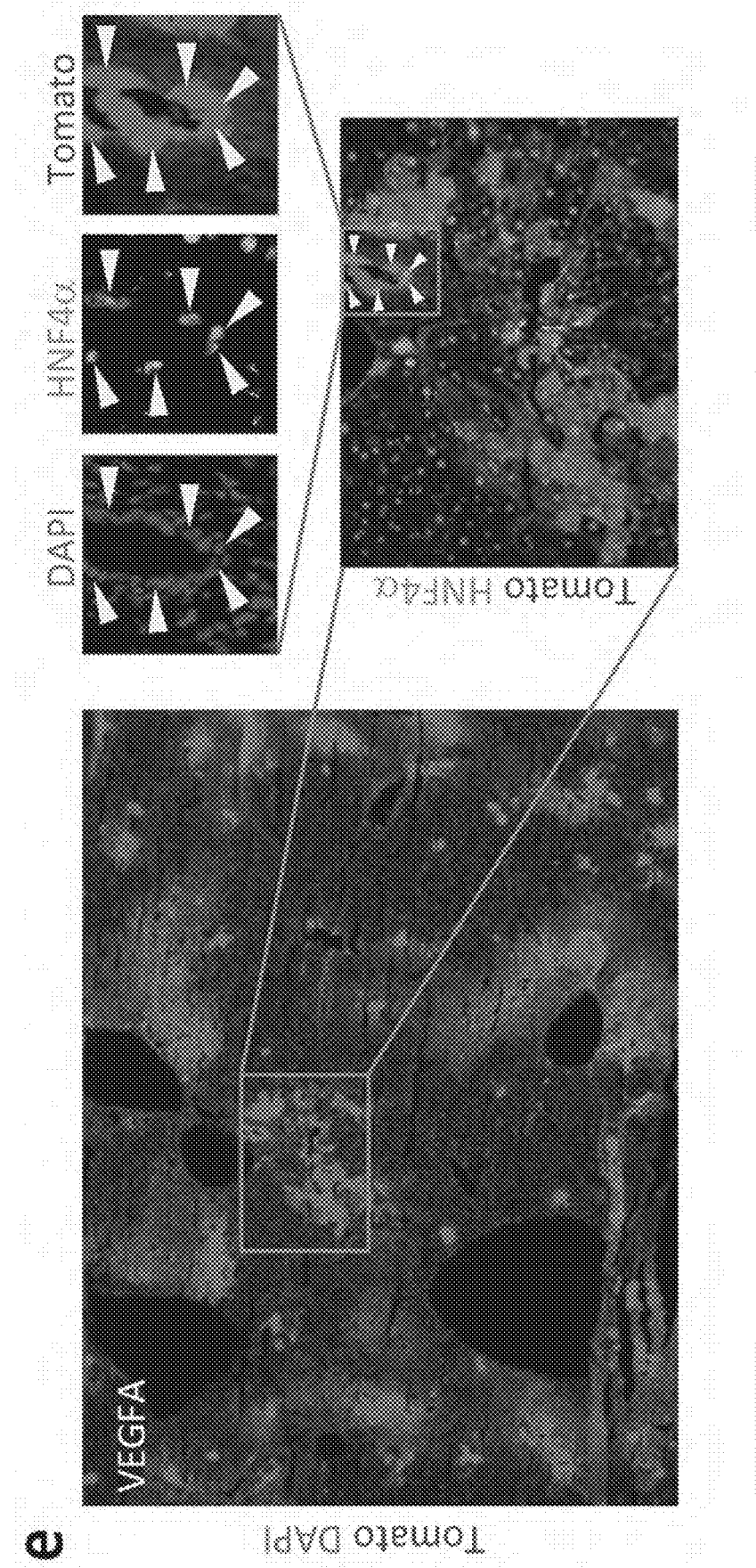
Figure 3F:
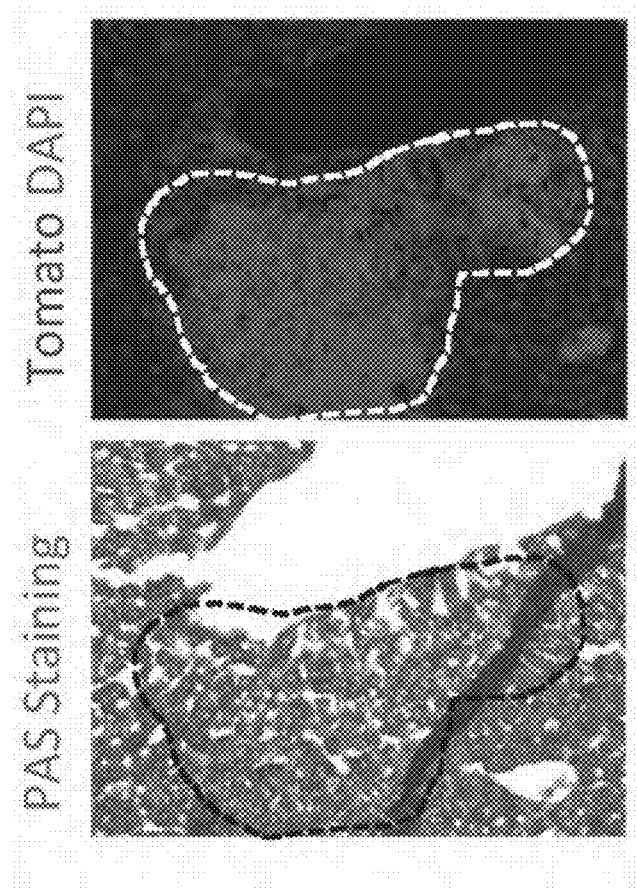
Figure 8A:
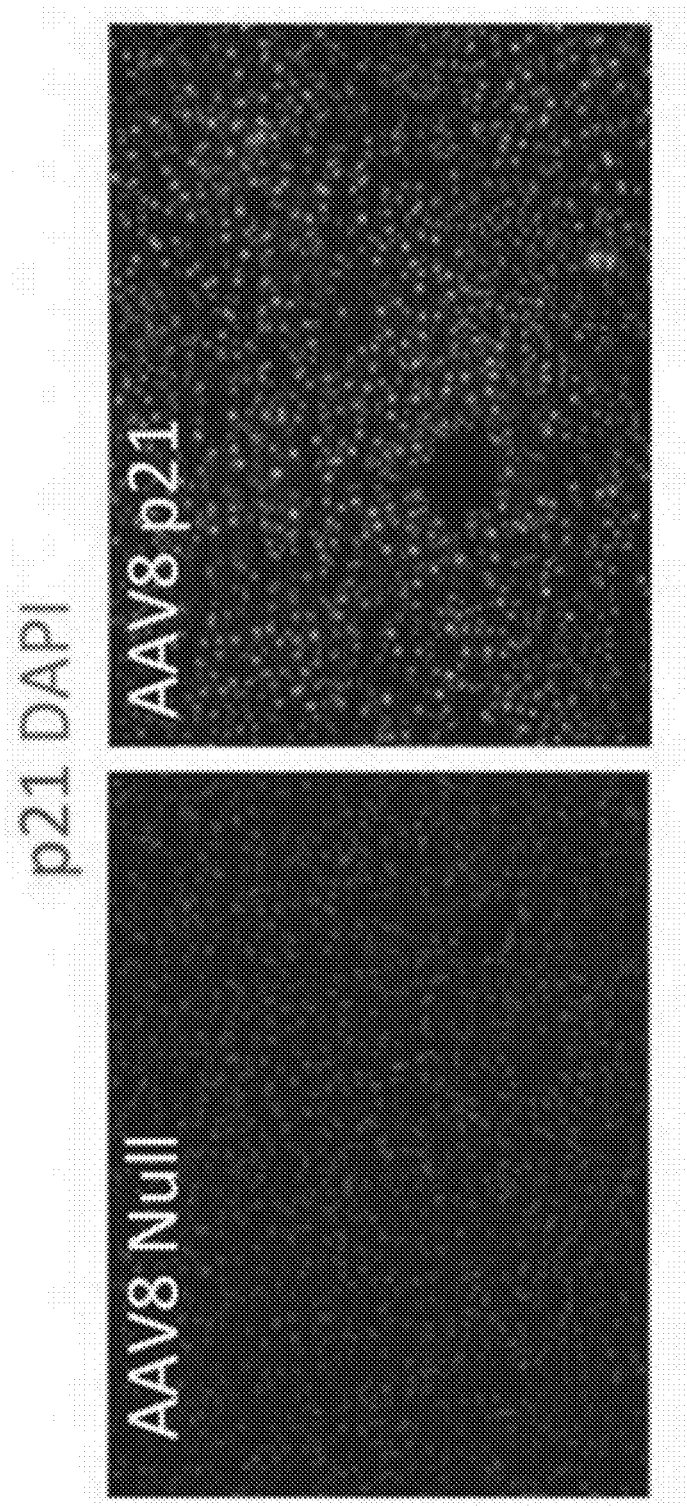
FIGS. 8A-8D depict VEGFA mRNA-LNP administration inducing BEC-to-hepatocyte conversion in APAP/p21-induced acute liver injury in mice.
Figure 8B:
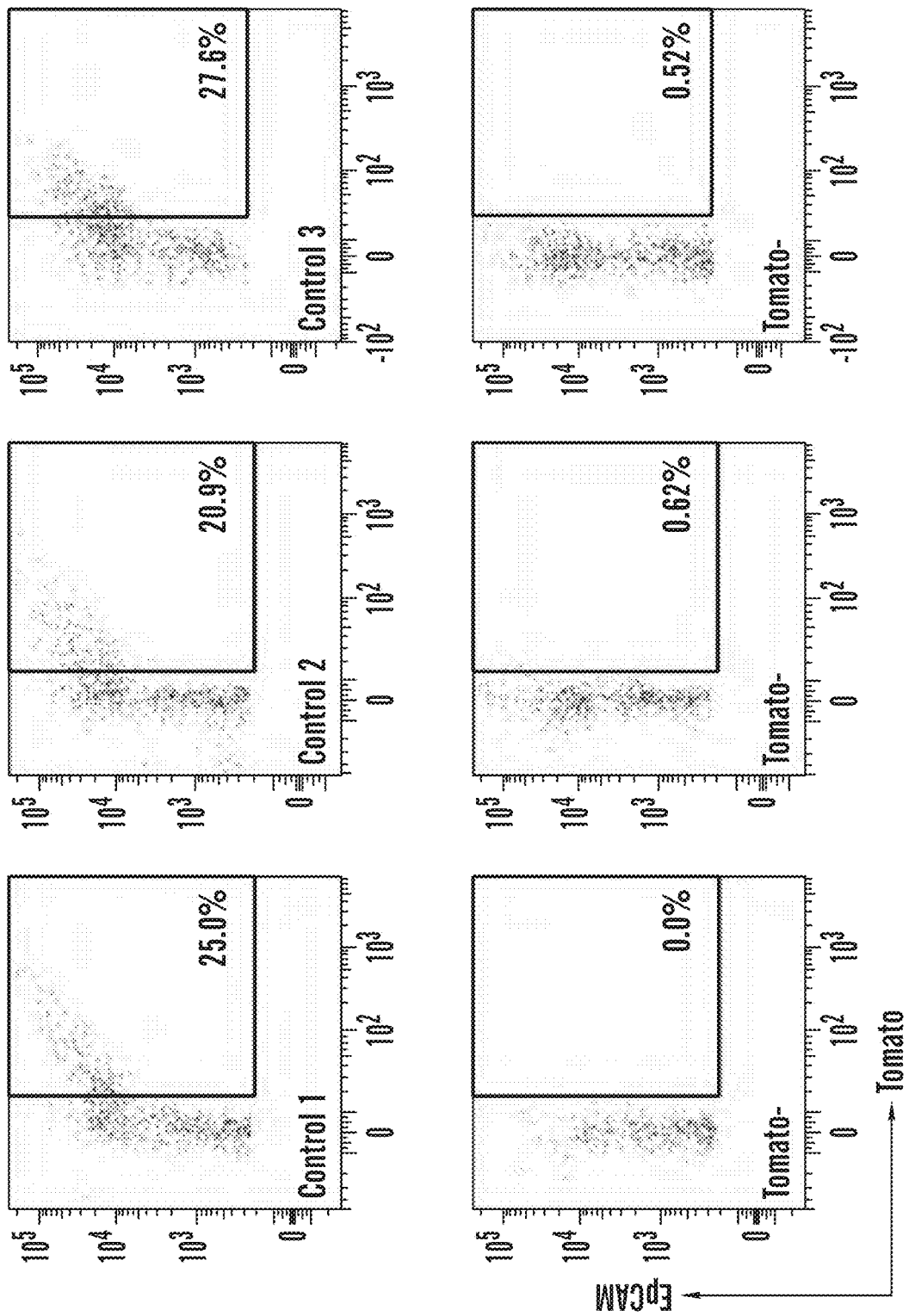
Figure 8B:
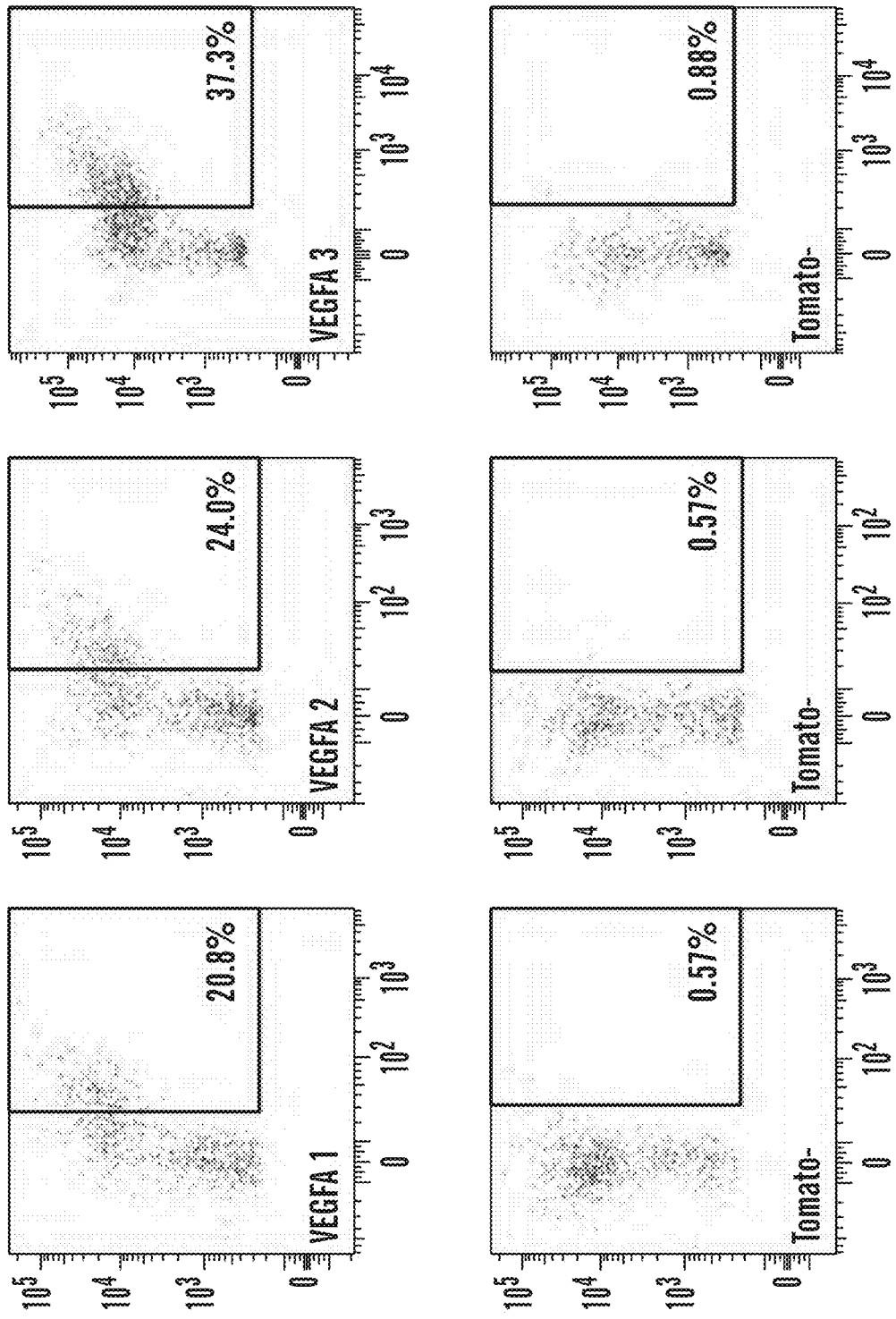
Figure 8C:
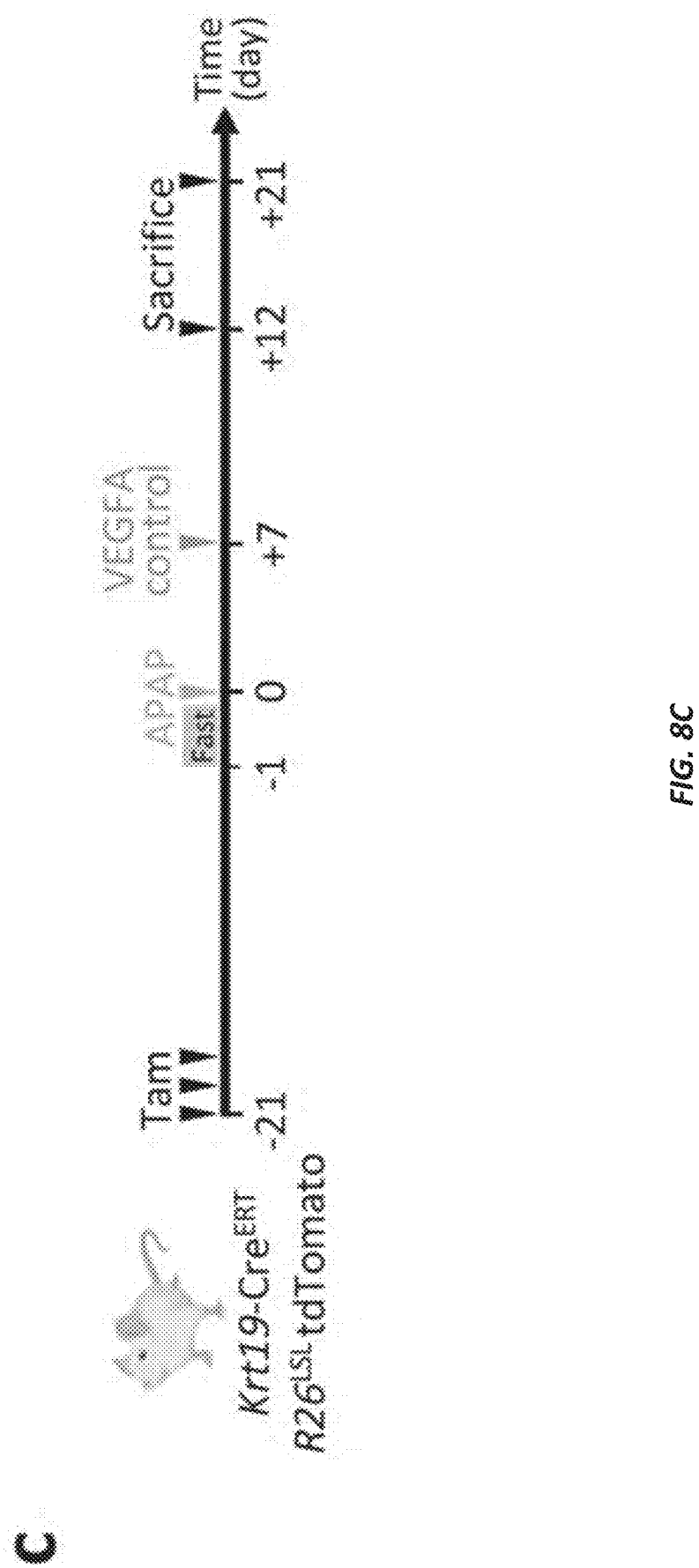
Figure 8D:
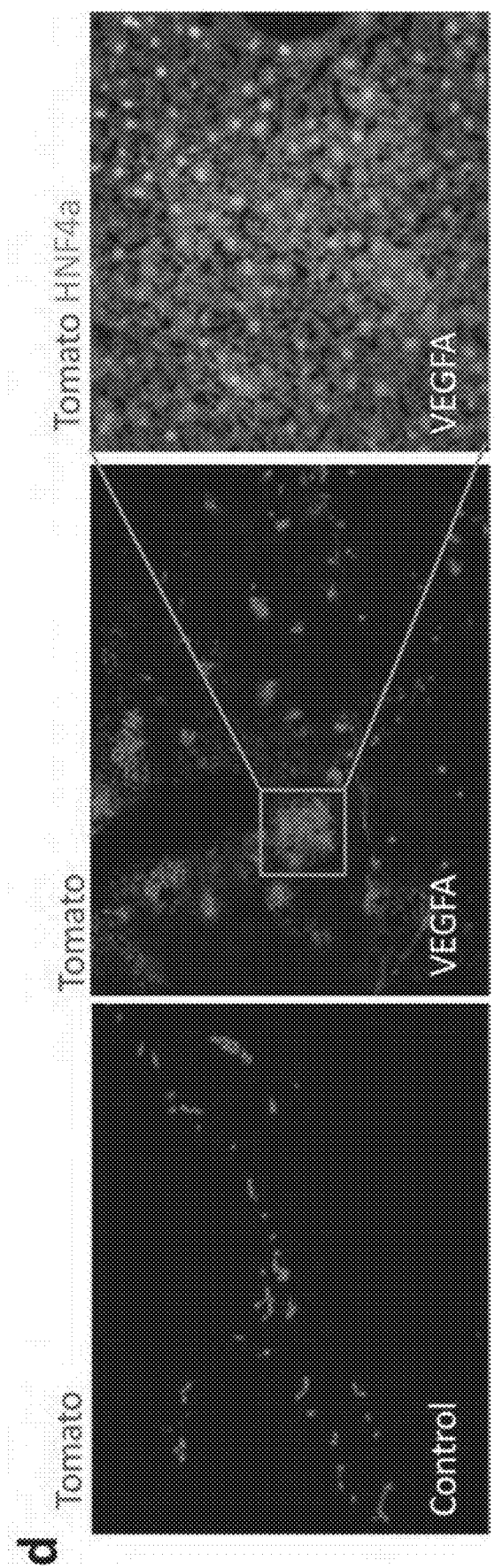

VEGFA Promotes BEC-to-Hepatocyte Conversion in APAP-Induced Acute Liver Injury in Mice Given that acute acetaminophen (APAP) toxicity induces ductular reaction in mice[55, 56], the inventors investigated whether VEGFA could also promote generation of de novo hepatocytes from the expanded pool of BECs. If effective, VEGFA treatment could serve for the nearly 30% of severe cases of APAP overdose requiring liver transplantation[57] as an alternative treatment to the drug NAC currently used in the clinic to neutralize APAP toxic metabolite NAPQI. Evidence of emergence of intermediate hepatocytes from BECs in severe intoxication in humans has been reported[56], yet the process of BEC-to-hepatocyte conversion must be accelerated to become a viable and effective treatment for acute liver injuries, as proposed here with VEGFA mRNA-LNP. To better reflect clinical cases of human severe acute APAP intoxication in which hepatocyte senescence is consistently observed[56, 58], Krt19-Cre$^{ERT}$, R26$^{LSL}$ tdTomato mice were injected with AAV8-Tbg-p21 one week prior to APAP administration (FIG. 3A). p21 was expressed in nearly 70% of hepatocytes (FIG. 8A). APAP/p21 injury induced a ductular response strictly localized around the portal vein areas (FIG. 3B), which was milder in the absence of AAV8-Tbg-p21 as expected. Two consecutive injections of VEGFA mRNA-LNP after APAP administration triggered remarkable BEC-to-hepatocyte conversion (FIG. 3C). Numerous large clusters of tdTomato+ hepatocytes were evenly scattered in all liver lobes of VEGFA mRNA-LNP-treated mice, with a % of tdTomato+ areas 20-fold greater than in control LNP-treated mice (FIG. 3C). Quantification of tdTomato+ hepatocytes was evaluated using flow cytometry analysis (FIG. 3d) and was further adjusted for lineage tracing efficiency discrepancy (FIG. 3D, 8B). Adjusted % tdTomato+ hepatocytes were 5.6-fold greater in VEGFA mRNA-LNP-treated group compared to control LNP-treated mice (FIG. 3d). BEC-derived hepatocytes were identified by co-expression of HNF4α (FIG. 3E), and their BEC origin was supported by their proximity to bile ducts (FIG. 3e). Interestingly, a few bi-phenotypic tdTomato+ BECs within a bile duct (FIG. 3E, arrowheads) were visualized by co-expression of the hepatocytic marker HNF4α as previously described[17]. Periodic acid-Schiff staining of serial liver sections illustrated the ability of tdTomato+ hepatocytes to store glycogen as efficiently as adjacent tdTomato− hepatocytes (FIG. 3F). Similar to the chronic CDE/p21 injury model, BEC-to-hepatocyte conversion did not occur in APAP injured mice in the absence of p21-induced hepatic senescence in control LNP-treated mice, while small clusters of tdTomato+ hepatocytes were consistently detected in all VEGFA mRNA-LNP-treated mice (FIGS. 8C, 8D). the inventors' data demonstrate the ability of VEGFA mRNA-LNP treatment to trigger BEC-to-hepatocyte conversion that can be further amplified in the presence of hepatocyte senescence in an acute liver injury, showing VEGFA mRNA-LNP as an alternative treatment for severe APAP intoxication that would prevent liver failure and, thus, the need for transplantation.

Figure 4A:
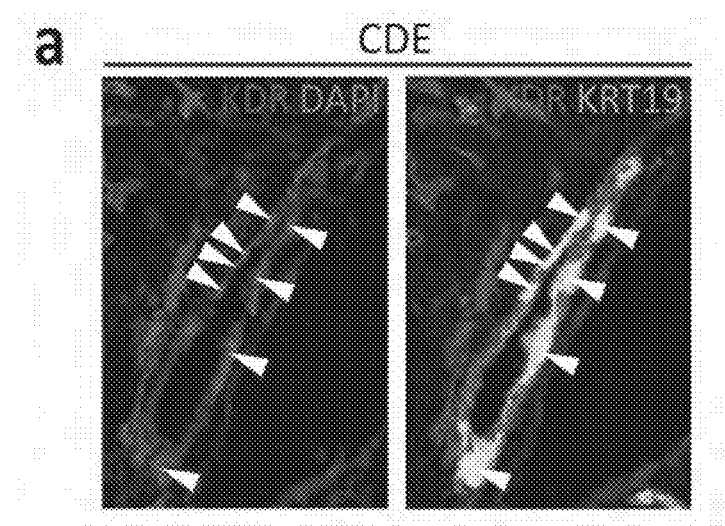
FIGS. 4A-4H depict VEGFA mRNA-LNP administration inducing BEC-to-hepatocyte conversion in CDE/p21-induced chronic liver injury in Kdr-2A-Cre$^{ERT2}$-2A-eYFP mice.
Figure 4B:
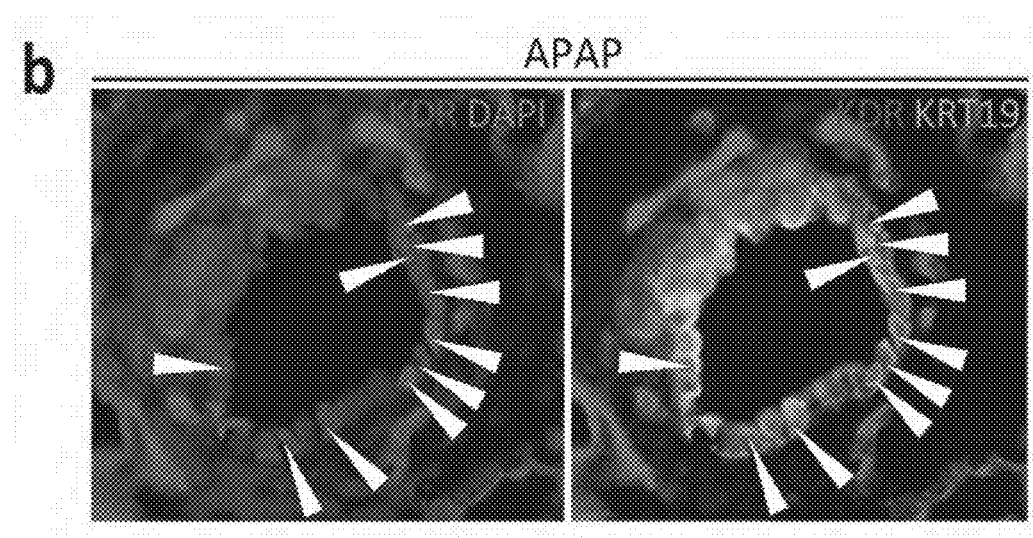
Figure 4C:
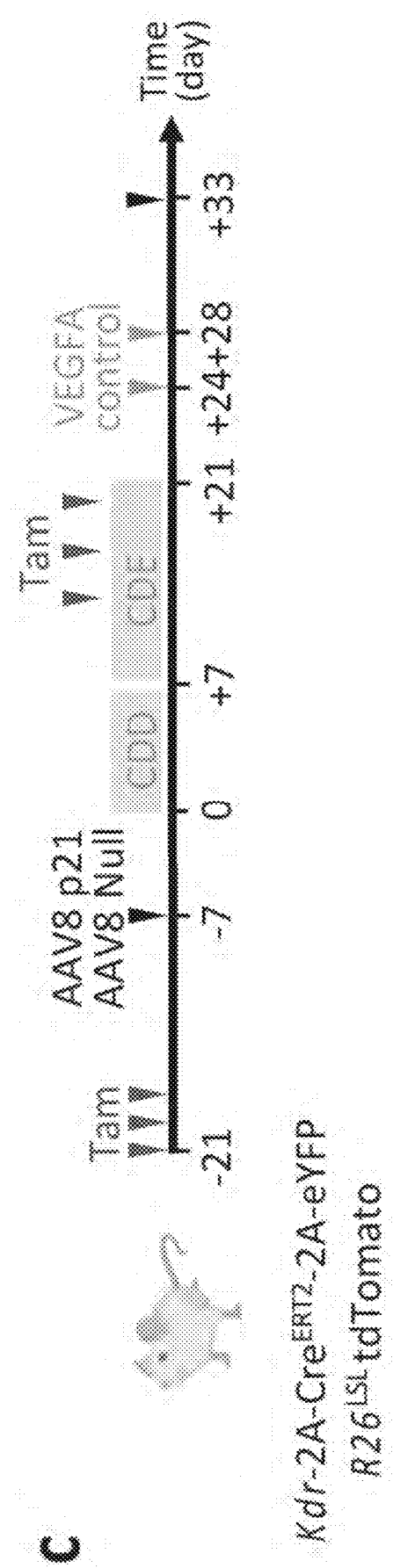
Figure 4D:
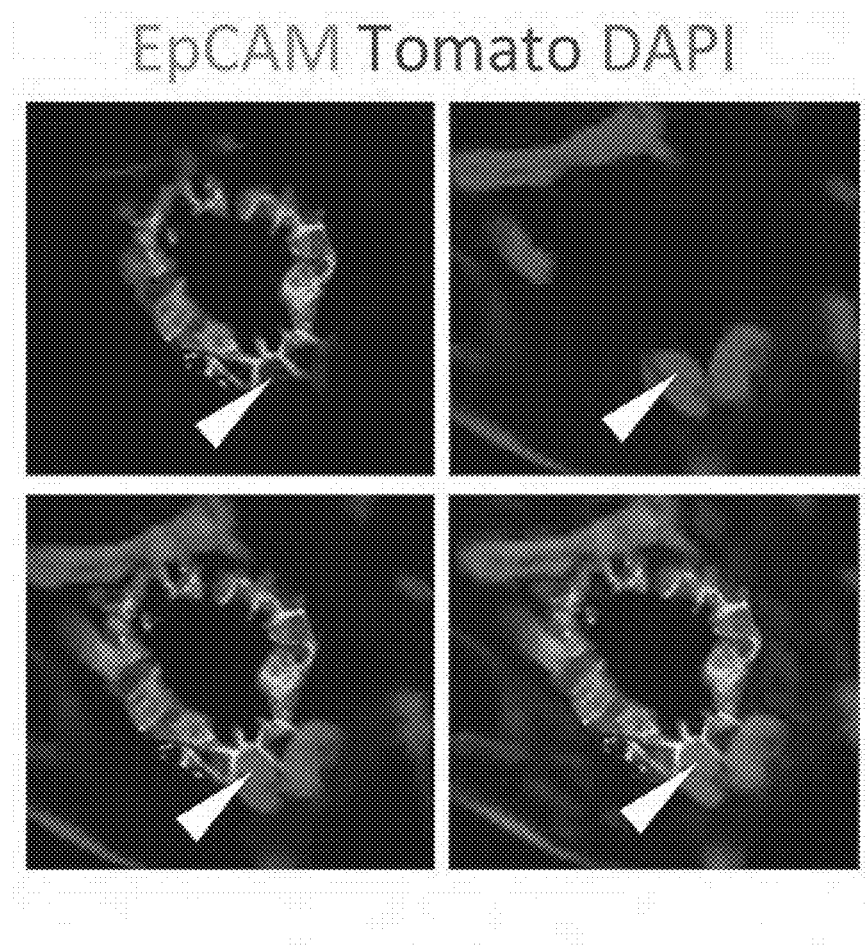
Figure 4E:
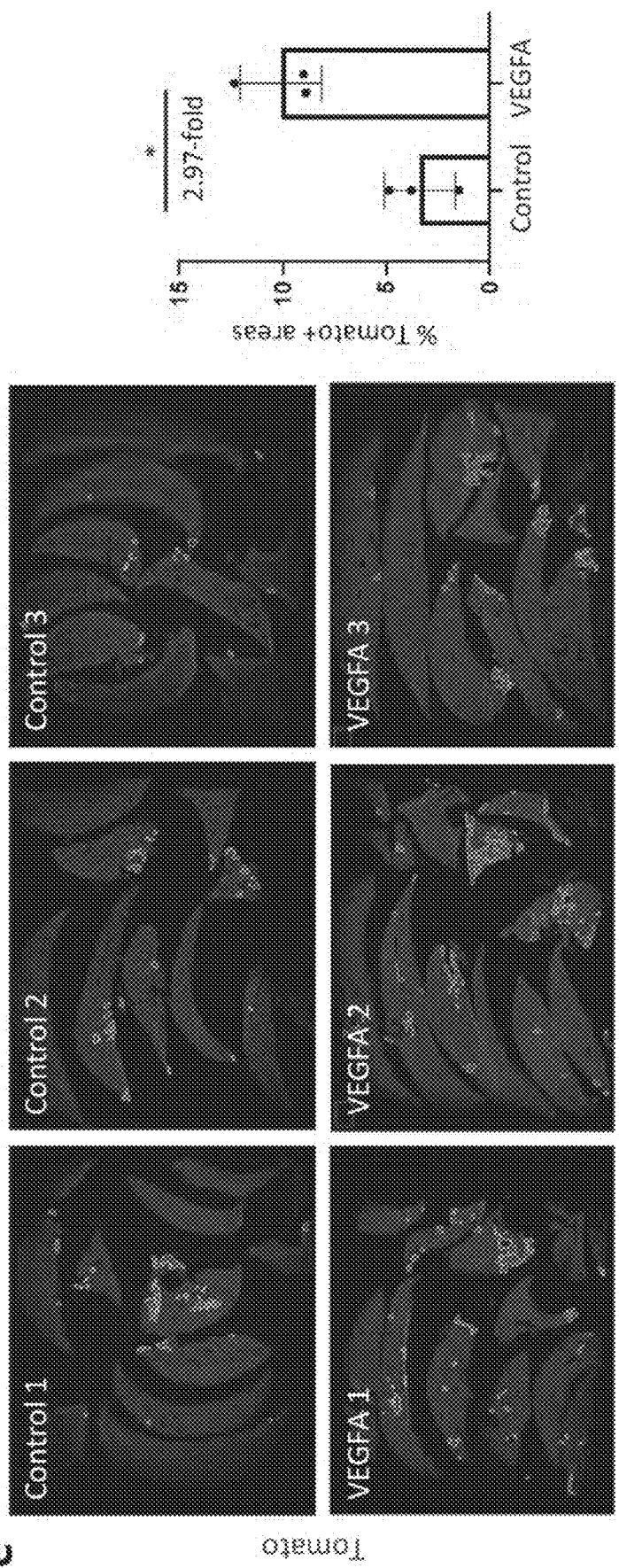
Figure 4F:
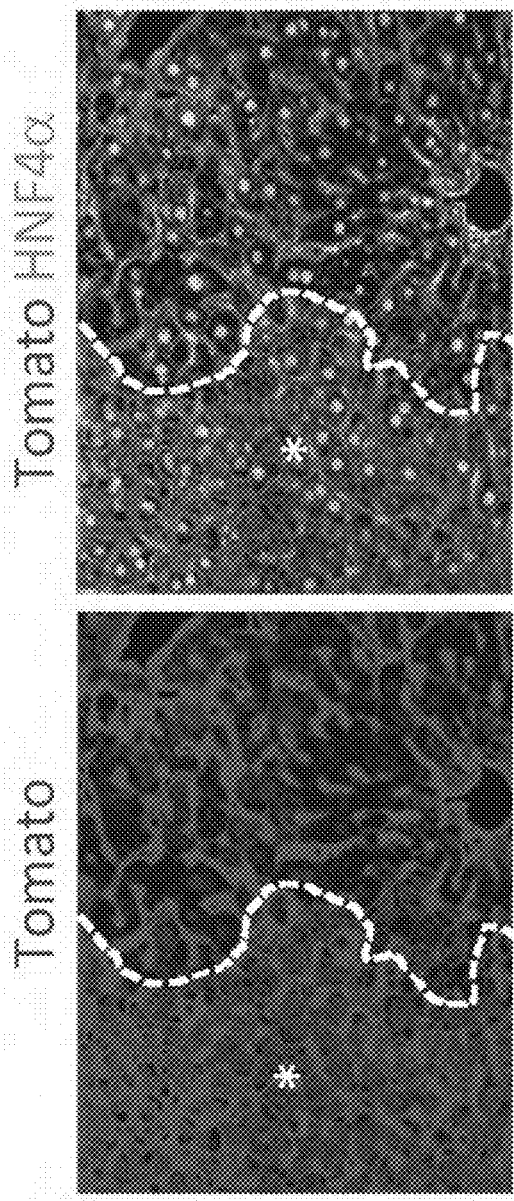
Figure 4G:
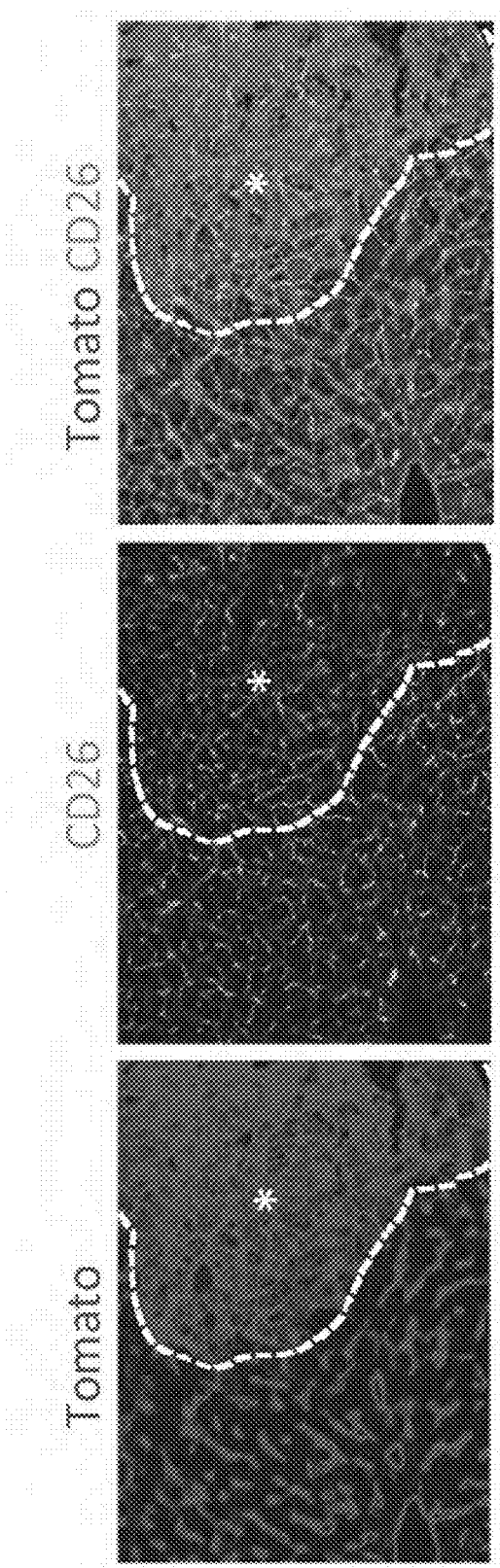
Figure 4H:
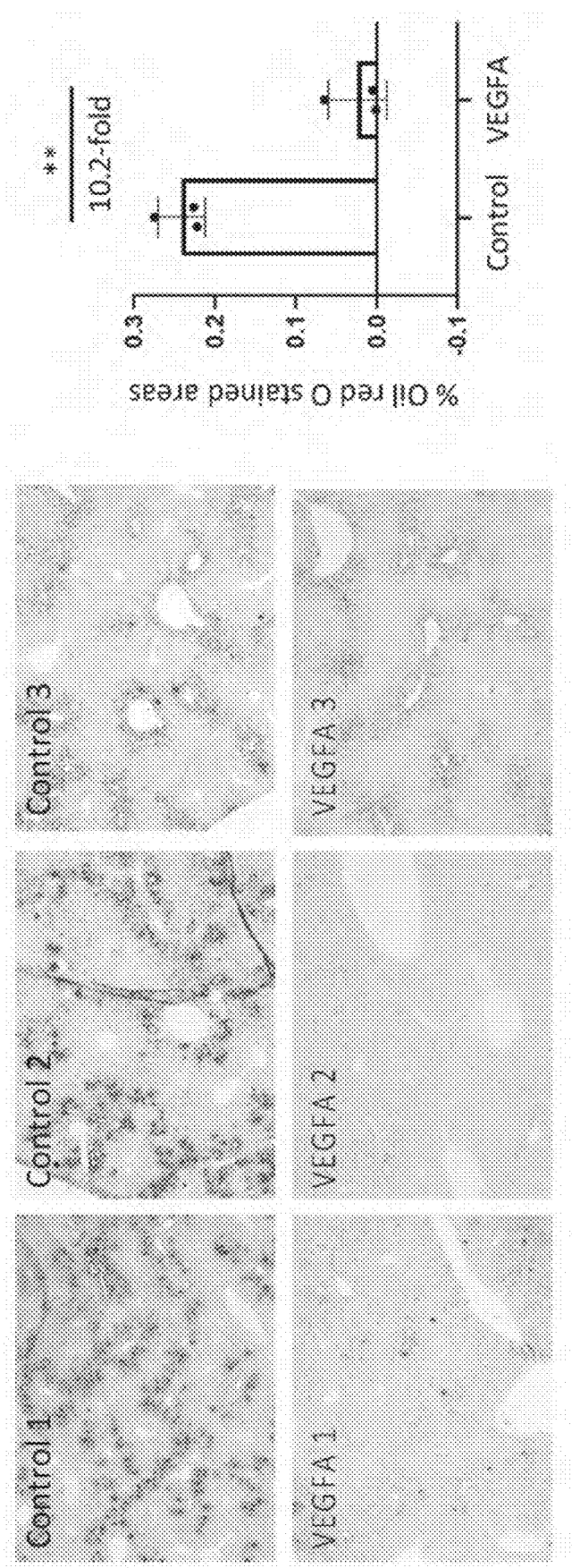
Figure 9C:
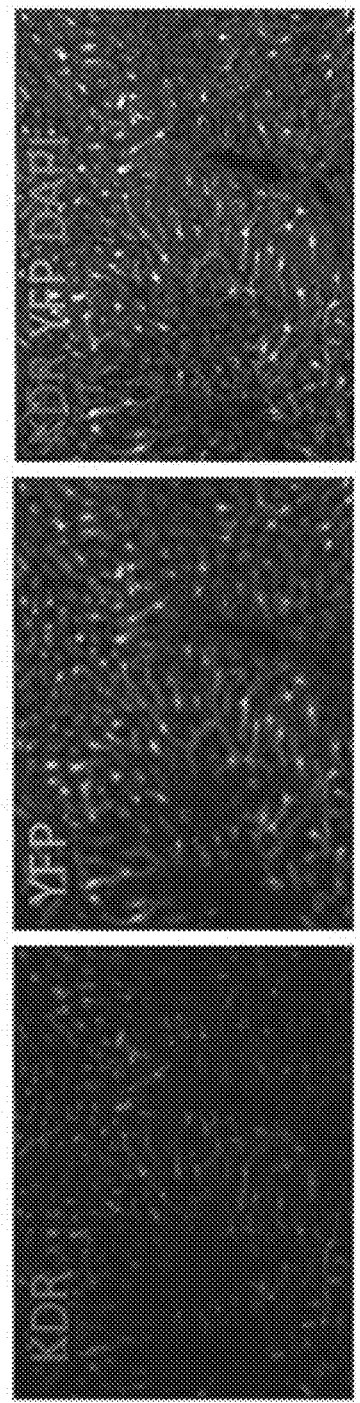
Figure 9D:
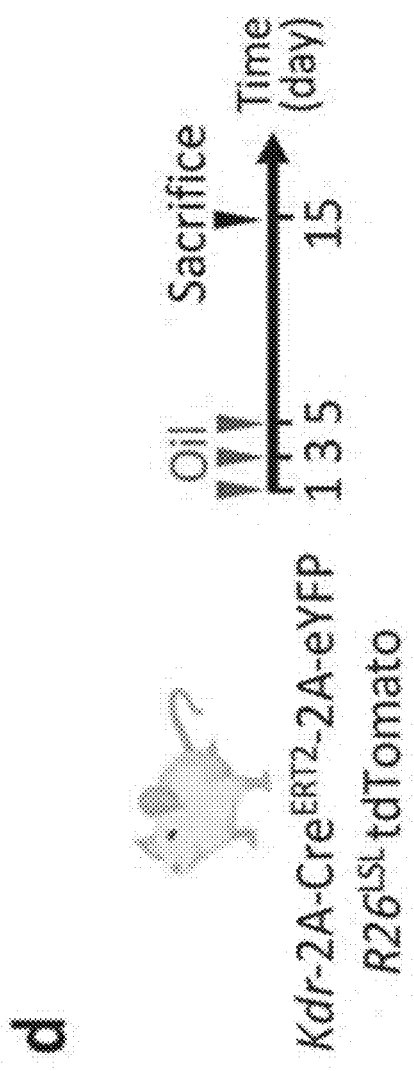
Figure 9E:
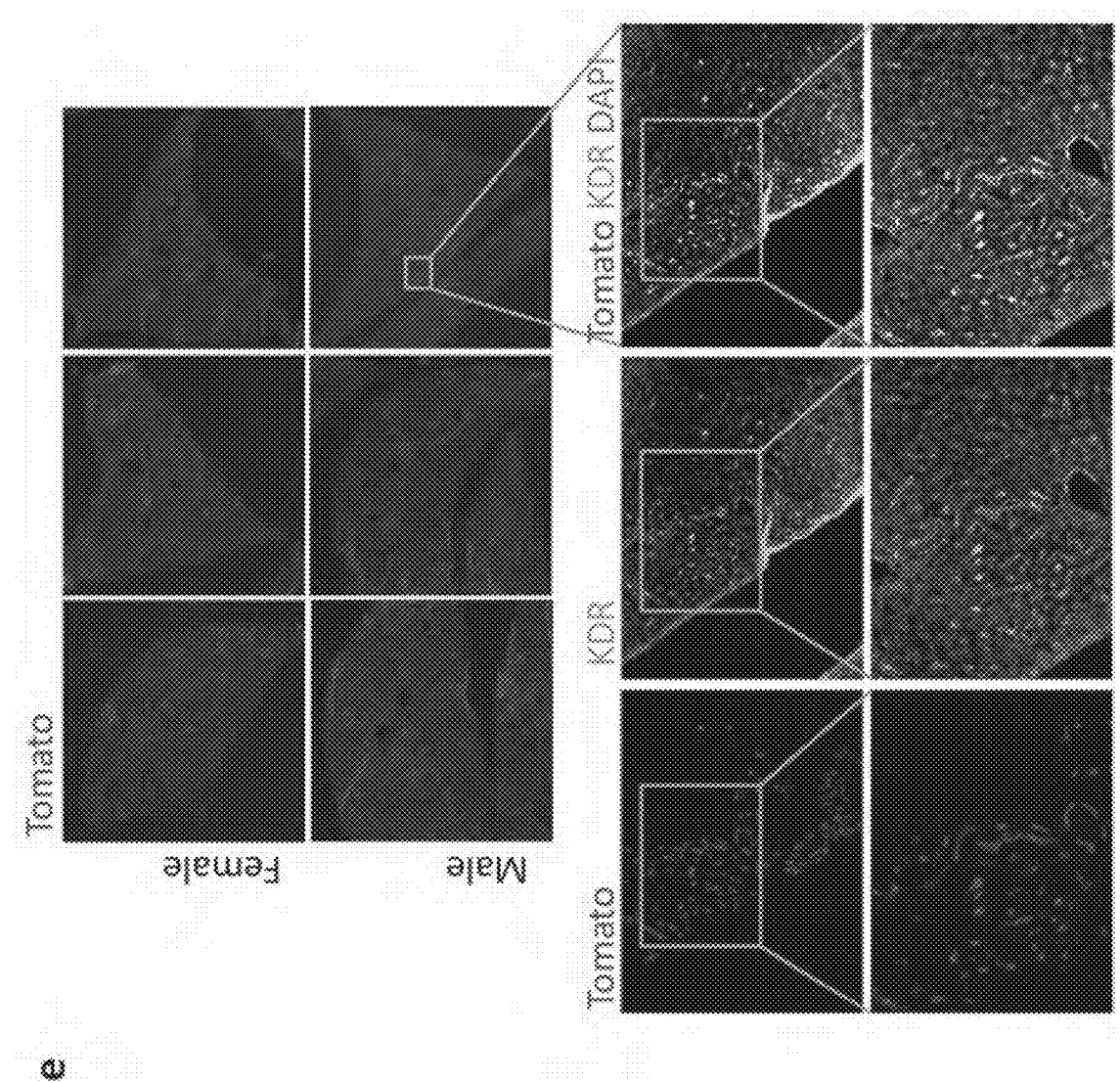
Figure 10A:
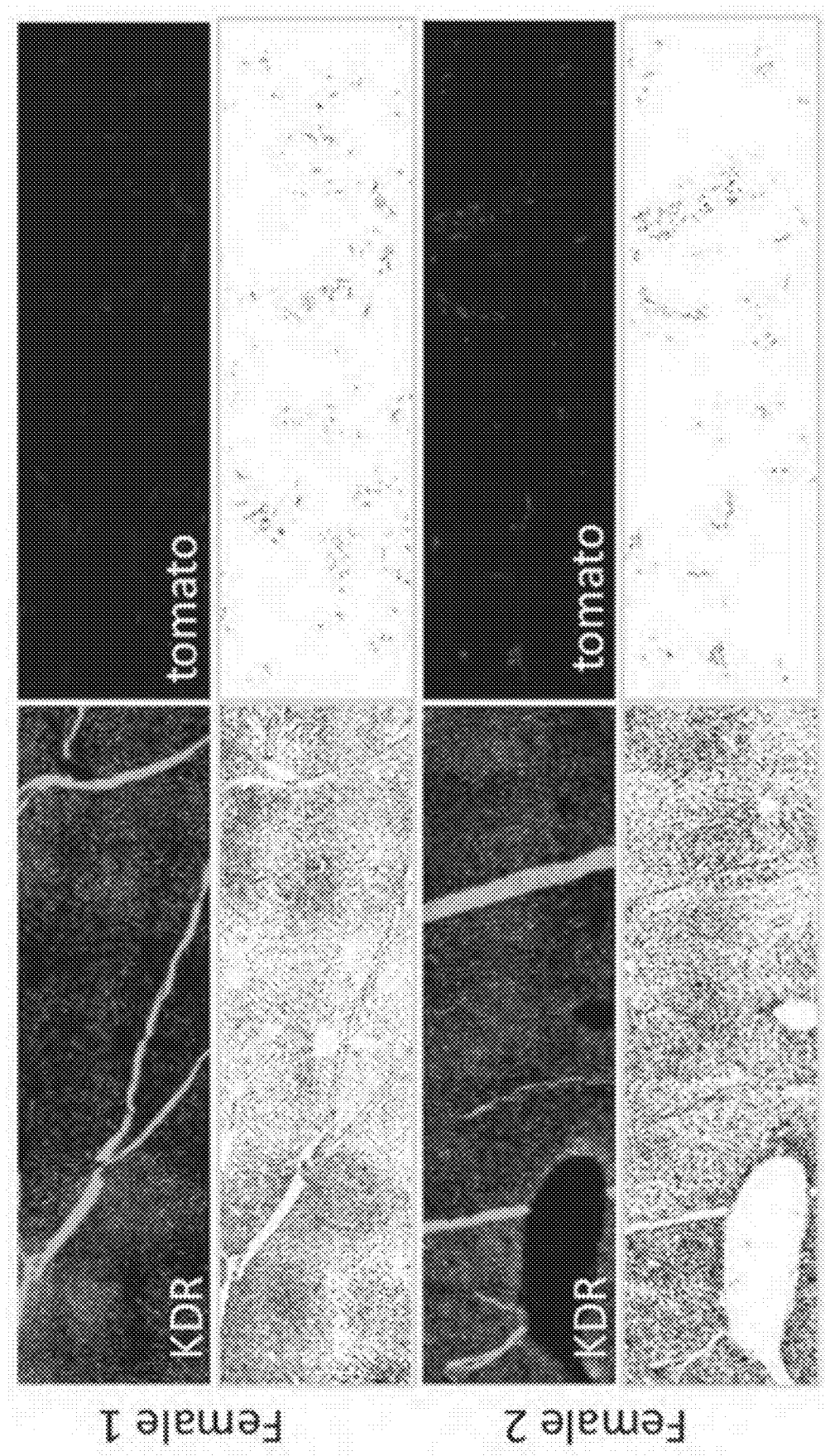
FIGS. 10A-10D depict hepatocytes in Kdr-2A-Cre$^{ERT2}$-2A-eYFP mice.
Figure 10B:
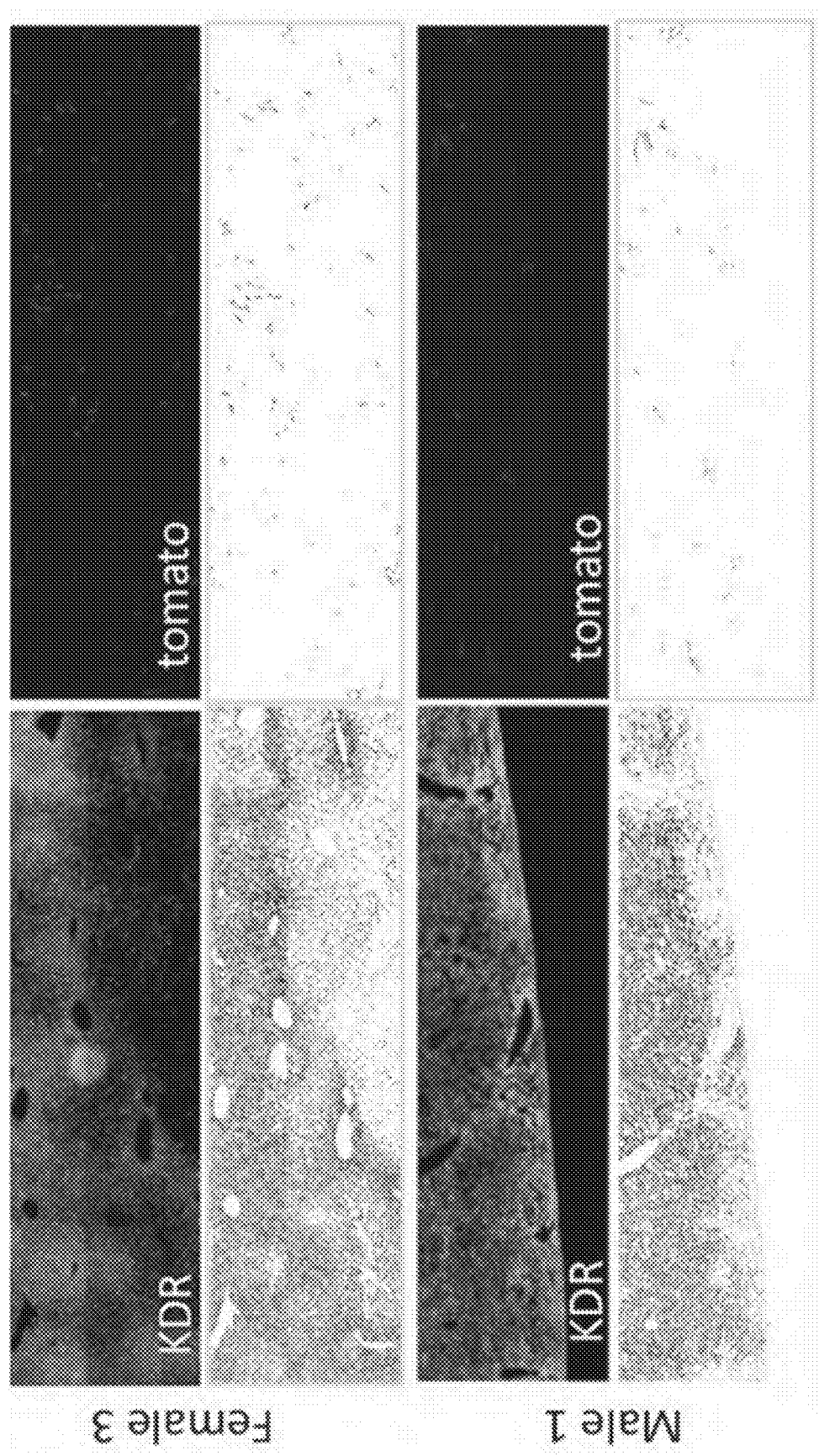
Figure 10C:
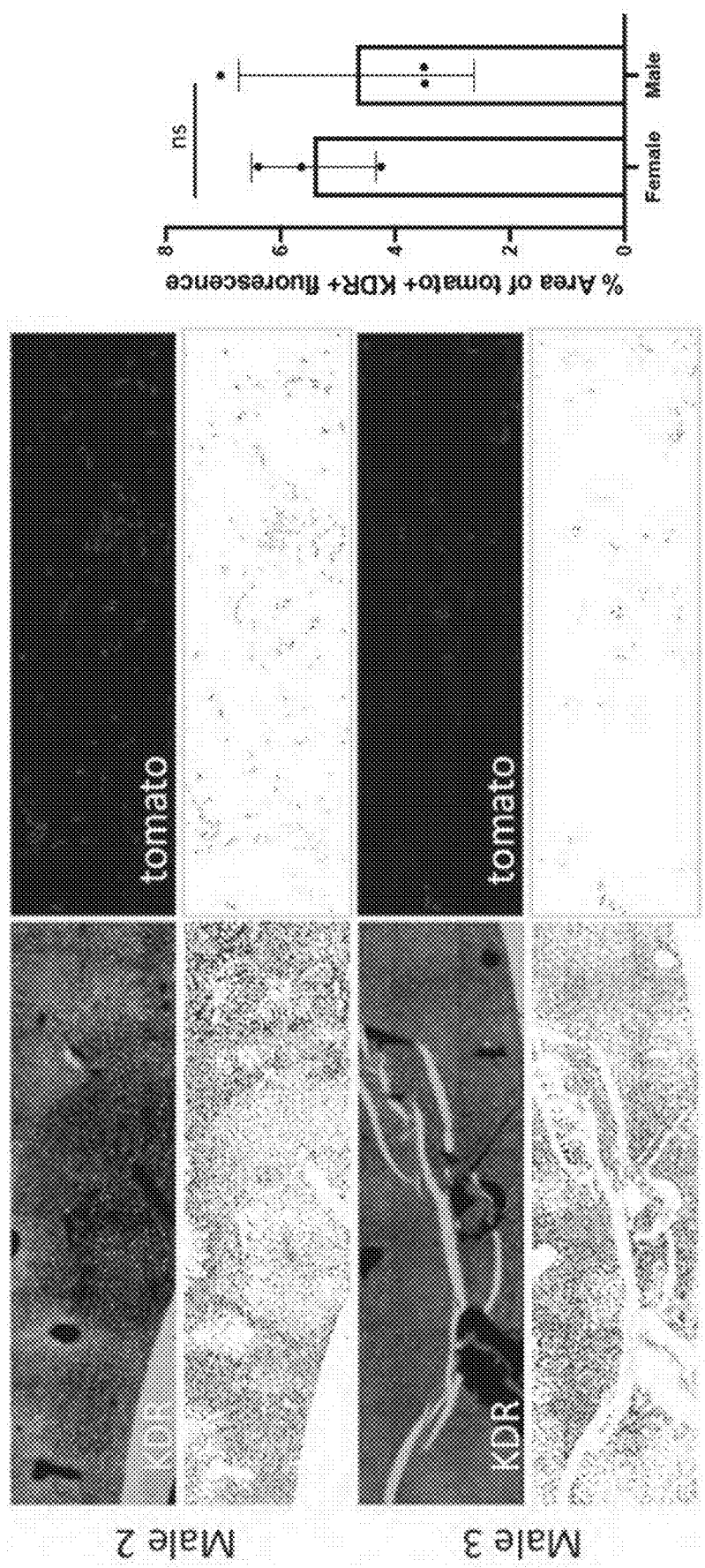
Figure 10D:
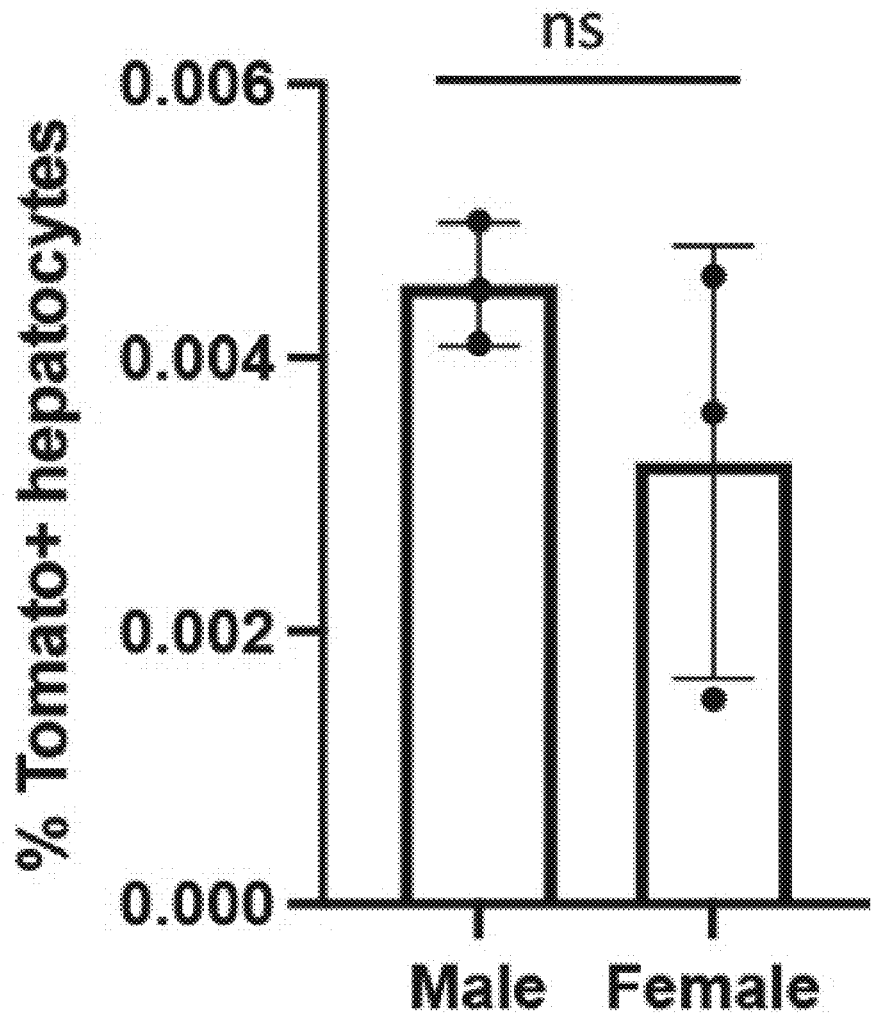
Figure 11A:
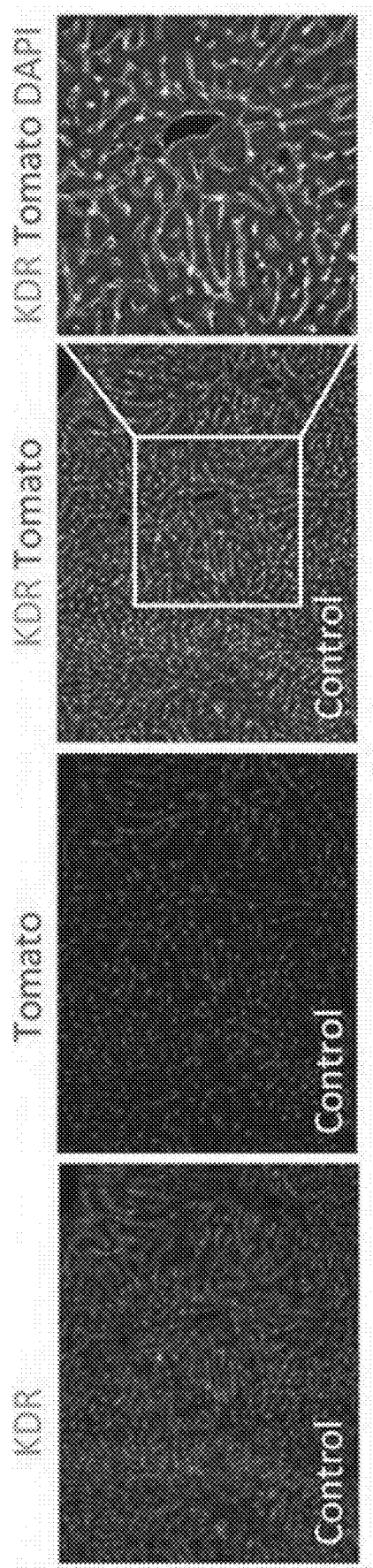
FIGS. 11A-11D depict VEGFA mRNA-LNP administration inducing BEC-to-hepatocyte conversion in chronic and acute liver injury in Kdr-2A-Cre$^{ERT2}$-2A-eYFP mice.
Figure 11B:
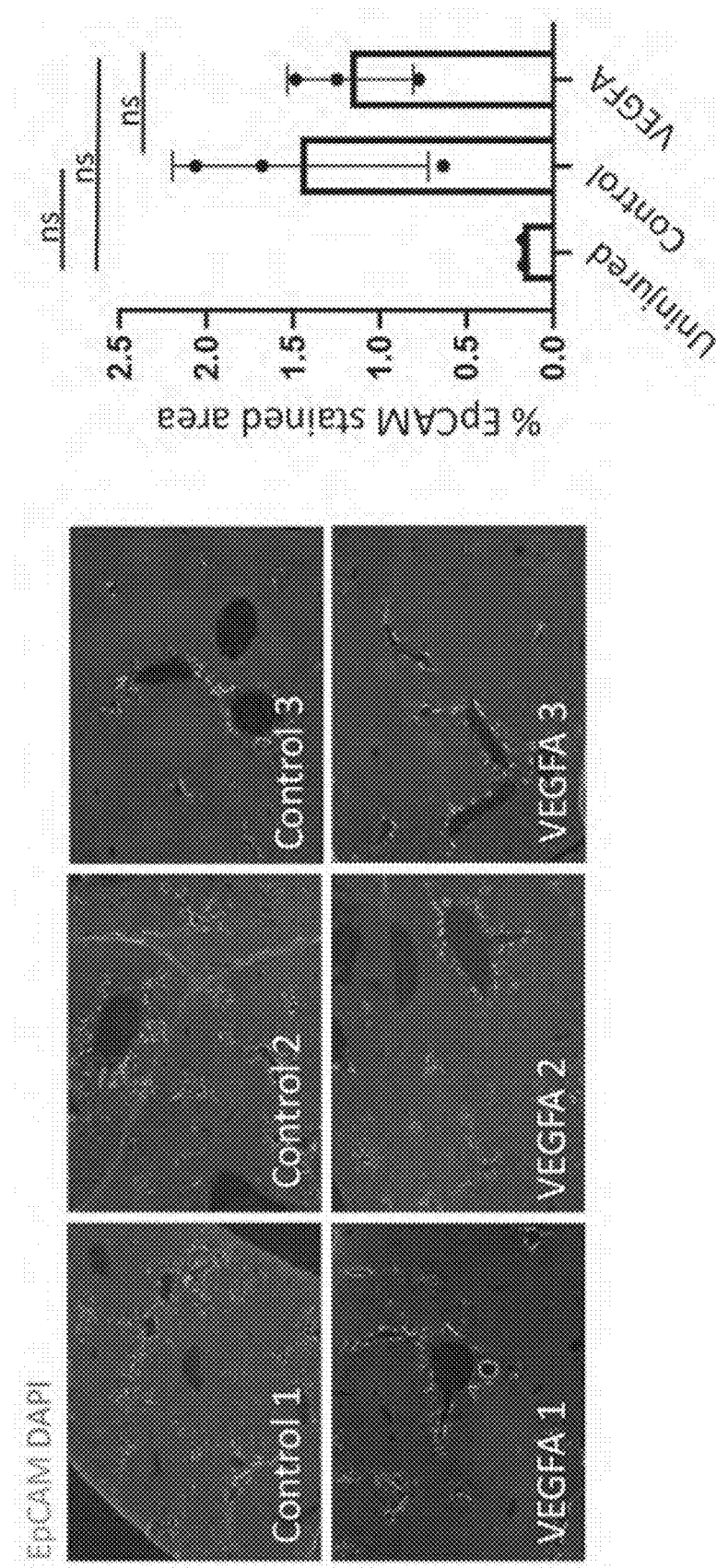

VEGFA Induces Hepatocyte Generation from KDR Expressing Cells in Murine Acute and Chronic Liver Injury Models and Improves Liver Function To further understand the regenerative role of VEGFA in mice, the inventors identified the liver cell types expressing VEGFR2, also known as KDR, the main functional receptor for VEGFA[59]. As expected, endothelial cells, identified with CD31 expression, are the main liver cells expressing KDR as assessed by immunostaining on liver sections of non-injured mice (FIG. 9A). Given that BECs have been reported to express KDR in rodent and human diseased livers[41, 43], the inventors searched for KDR expression in BECs in the chronic CDE/p21 and acute APAP/p21 liver injury mouse models. In both models, the inventors consistently observed expression of KDR in a subpopulation of BECs (FIG. 4A, 4B) that was absent in control uninjured mice (not shown), suggesting that KDR marks a subset of BECs that may represent a facultative LPC that could be directly stimulated by VEGFA to generate hepatocytes. To test this hypothesis, the inventors used an inducible KDR lineage tracing line, Kdr-2A-Cre$^{ERT2}$-2A-eYFP (FIG. 9B) allowing cell fate mapping of KDR-expressing cells with time as well as marking KDR-expressing cells with YFP. Given that the 2A-Cre$^{ERT2}$-2A-eYFP cassette was introduced downstream of the last exon of Kdr gene, this approach did not affect KDR expression, and therefore homozygous Cre/Cre survive, as opposed to the lethal KDR knockout mice[60]. YFP is an accurate tool to track KDR expression as shown with overlapping co-staining marking endothelial cells (FIG. 9C). In the absence of tamoxifen, in oil-treated mice, some reporter activity was detected in 5.42±1% and 4.68±2% of endothelial cells in females and males, respectively (FIGS. 9D, 9E, 10A-10C), while leakiness in hepatocytes was almost nonexistent with rare tdTomato+ cells detected in <1:25,000 hepatocytes scanned in all liver lobes from 6 mice (FIG. 10D). The inventors were therefore confident to use the Kdr-2A-Cre$^{ERT2}$-2A-eYFP; R26-tdTomato mice to map the hepatocyte fate of KDR expressing cells. Given the transient expression of KDR on BECs in response to injury, additional tamoxifen injections were included during the period of injury. In the CDE/p21 model, tamoxifen was injected 3 times over 5 days, starting from the fifth day of the diet (FIG. 4C). The endothelial cell lineage mapping was robust in all mice, as virtually all endothelial cells were tdTomato+ (FIG. 11A). The inventors confirmed expression of KDR in a subset of BECs with the Kdr lineage tracing model by the presence of tdTomato+ BEC within biliary ducts (FIG. 4D). Analyses of all liver lobes of each mouse revealed an even pattern of tdTomato+ cells representing endothelial cells (FIG. 4E). Strikingly, some areas were much brighter (FIG. 4E, areas within dotted line), and were identified as tdTomato+ hepatocytes with co-expression of HNF4v (FIG. 4F) and CD26 (FIG. 4G). The tdTomato+ hepatocyte clusters were significantly larger and more numerous in VEGFA mRNA-LNP-treated mice with a 2.97-fold greater surface area (FIG. 4E). As CD26 is a bile canalicular enzyme that depicts functional polarization of hepatocytes, its expression supports functional maturation of tdTomato+ hepatocytes derived from KDR+ cells. As noticed for the KRT19 lineage tracing model, extent of DR was similar between the two groups (FIG. 11B), most likely due to greater BEC-to-hepatocyte conversion in the VEGFA mRNA-LNP-treated group. Importantly, the inventors confirmed that VEGFA mRNA-LNP treatment significantly reversed steatosis as compared to control-LNP treated mice (FIG. 4H) as seen in the CDE/p21-treated Krt19 lineage tracing mice.

Figure 11C:
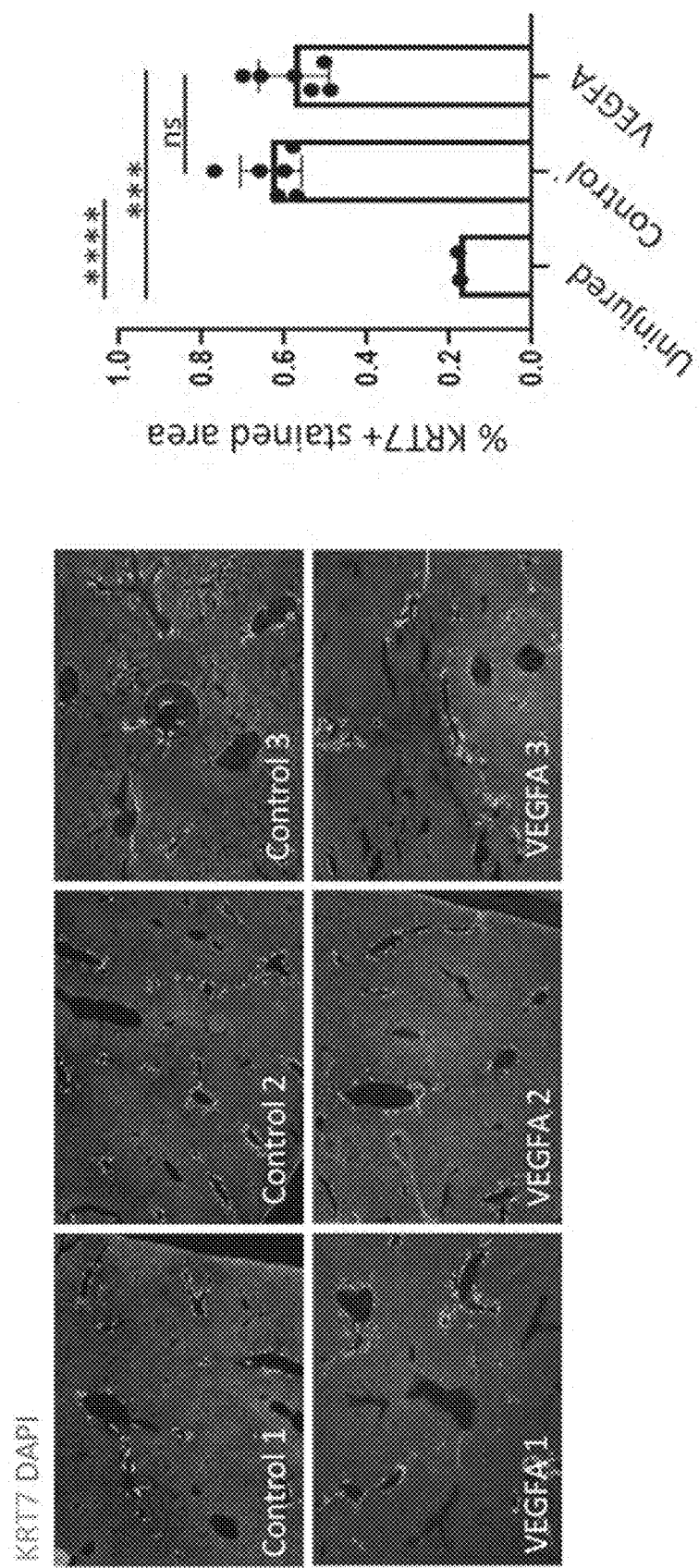
Figure 11D:
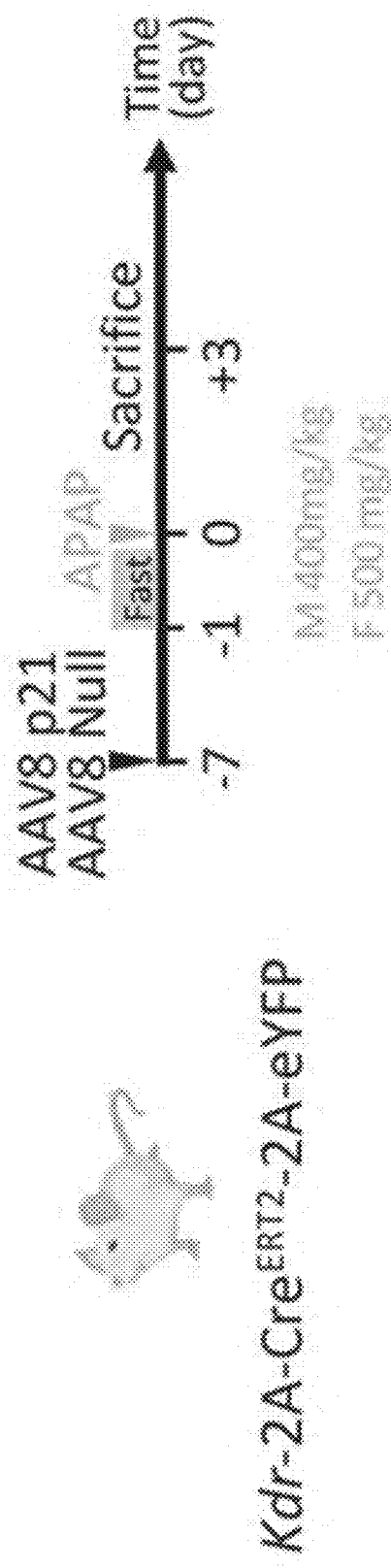

The findings were further supported in the acute APAP/ p21-induced liver injury (FIG. 5). Tamoxifen was additionally injected 3 times, 1 day prior and 1 and 3 days after APAP administration to capture the emerging KDR+ BECs upon injury (FIG. 5A). VEGFA mRNA-LNPs significantly promoted emergence of bright tdTomato+ areas (FIG. 5B, 6.7-fold increase) identified as hepatocytes with co-staining for HNF4α (FIG. 5C) and CD26 (FIG. 5D) as compared to control-LNP-treated mice. Quantification of the KRT7+ BEC areas in both control-LNP- and VEGFA mRNA-LNP-treated mice confirmed again that these numbers were not significantly different (FIG. 11C) as found in the CDE/p21 model. These data are reminiscent to observations made in humans following acetaminophen intoxications in which the ductular reaction decreases as BEC-to-hepatocyte conversion occurs[56]. To capture early events of KDR+ BEC conversion into hepatocytes during APAP/p21 injury, the inventors examined injured Kdr-2A-Cre$^{ERT2}$-2A-eYFP mice (in absence of lineage tracing, FIG. 11D) three days following APAP administration (FIG. 5E). The inventors detected many YFP+ BECs in areas indicative of early regeneration featured by endothelial cell ablation and newly generated hepatocytes with intact DAPI staining (FIG. 5E, area delineated with dotted line). The presence of large YFP+ hepatocyte-like cells (FIG. 5E, arrows) suggests their differentiation from YFP+KDR+ BECs (FIG. 5E, arrowheads). Observation of YFP+ hepatocyte-like cells was most likely possible because of the longer half-life of YFP protein compared to that from KDR protein.

Overall, findings from complementary Krt19- and Kdr-lineage tracing models demonstrate the conversion of KDR+ expressing cells, most likely BECs, into hepatocytes which is significantly augmented after VEGFA mRNA-LNP administration, a therapeutic strategy that could be leveraged in the clinic to treat acute and chronic liver diseases.

Identification of KDR-Expressing BECs with Evidence of BEC-to-Hepatocyte Conversion from Explanted Cirrhotic Liver Specimens with End-Stage Liver Disease (ESLD) and Child-Pugh Score B/C.

Figure 5A:
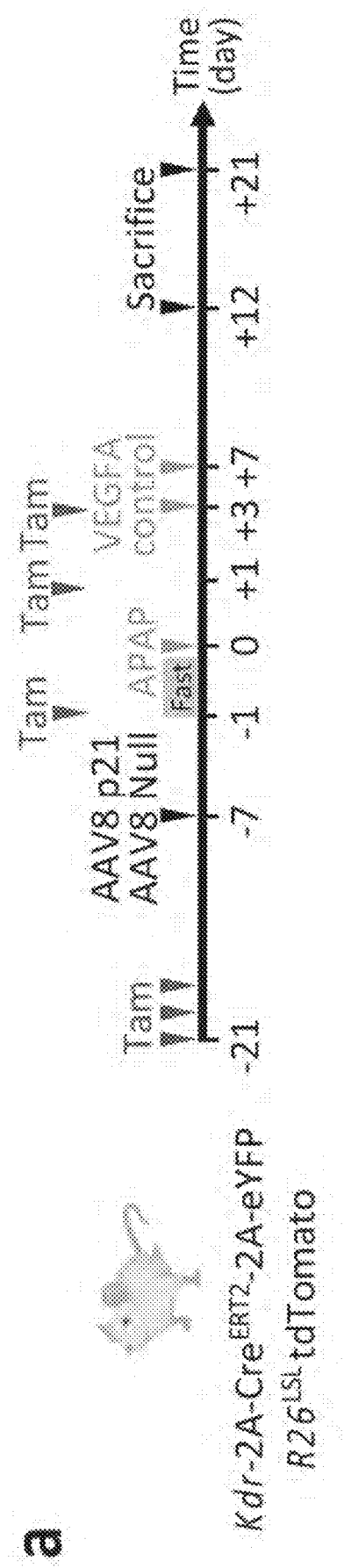
FIGS. 5A-5E depict VEGFA mRNA-LNP administration inducing BEC-to-hepatocyte conversion in APAP/p21-induced acute liver injury in Kdr-2A-Cre$^{ERT2}$-2A-eYFP mice.
Figure 5B:
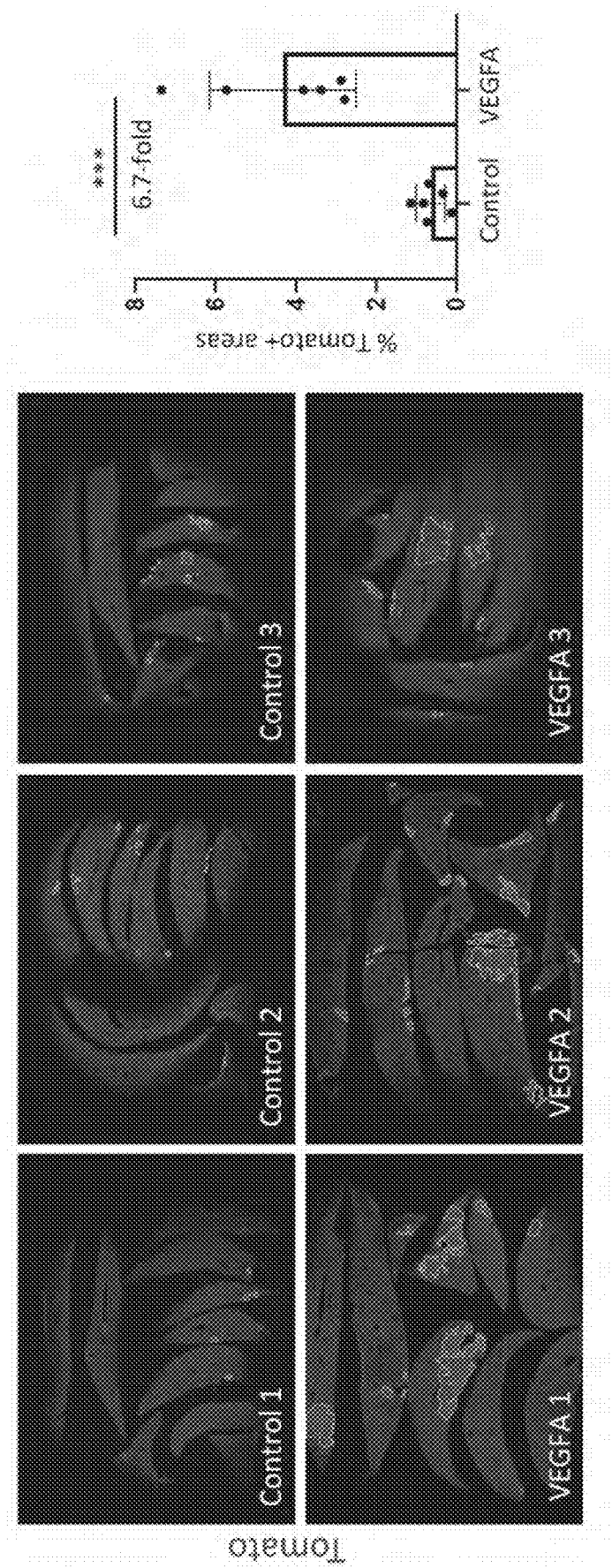
Figure 5C:
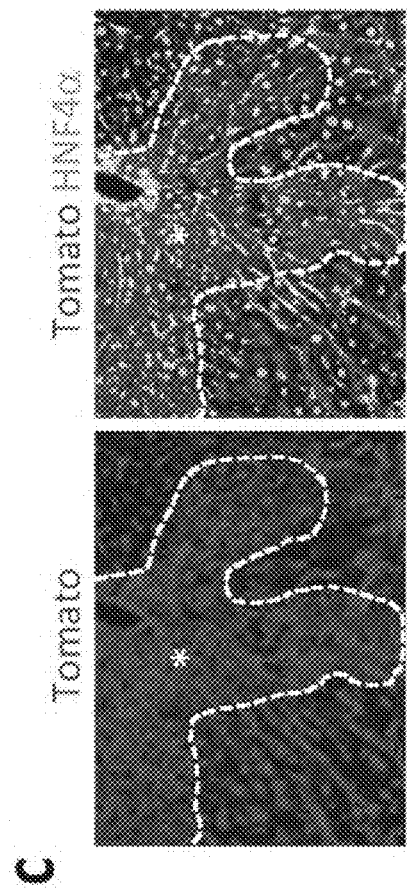
Figure 5D:
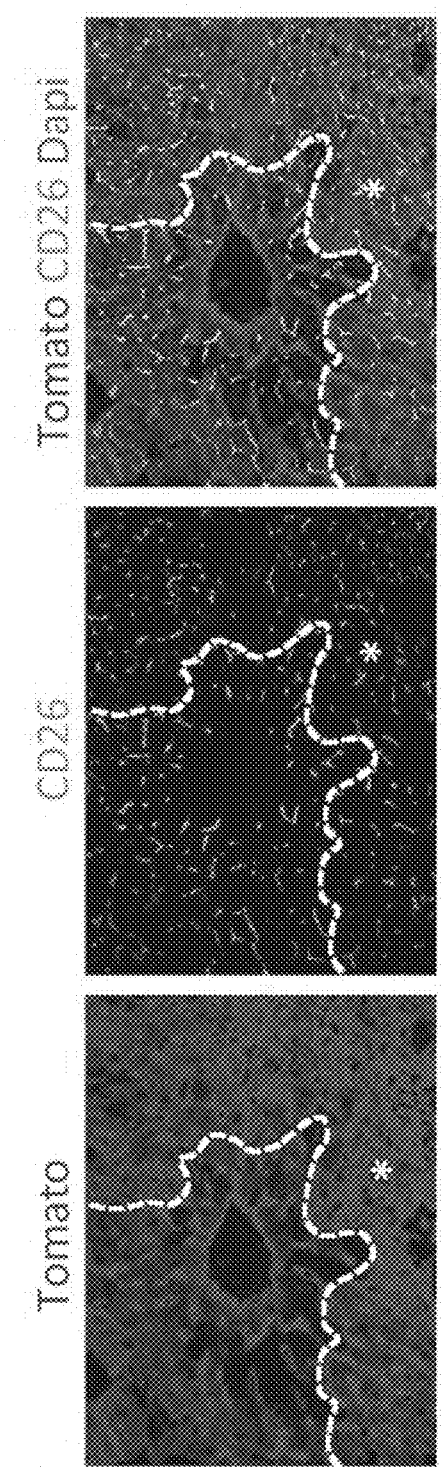
Figure 5E:
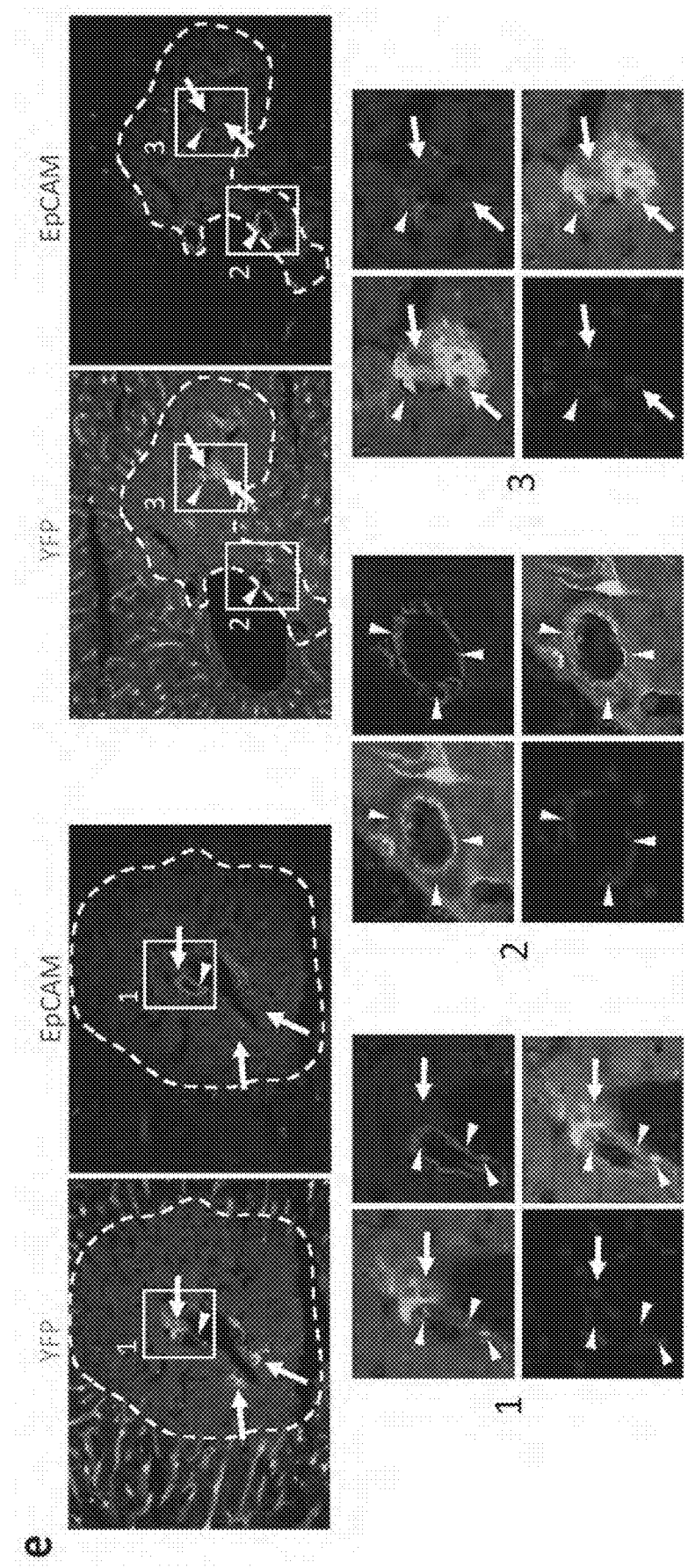
Figure 6A:
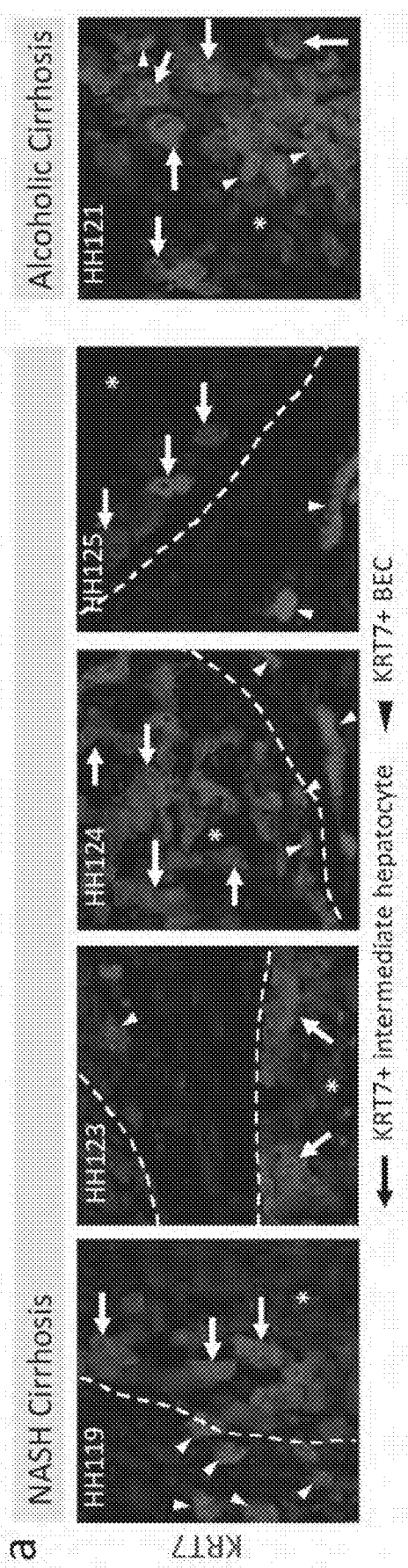
FIGS. 6A-6E depict evidence of BEC-to-hepatocyte conversion and KDR expression in human liver samples from non-alcoholic steatohepatitis (NASH) cirrhosis and alcoholic cirrhosis with ESLD patients.
Figure 6B:
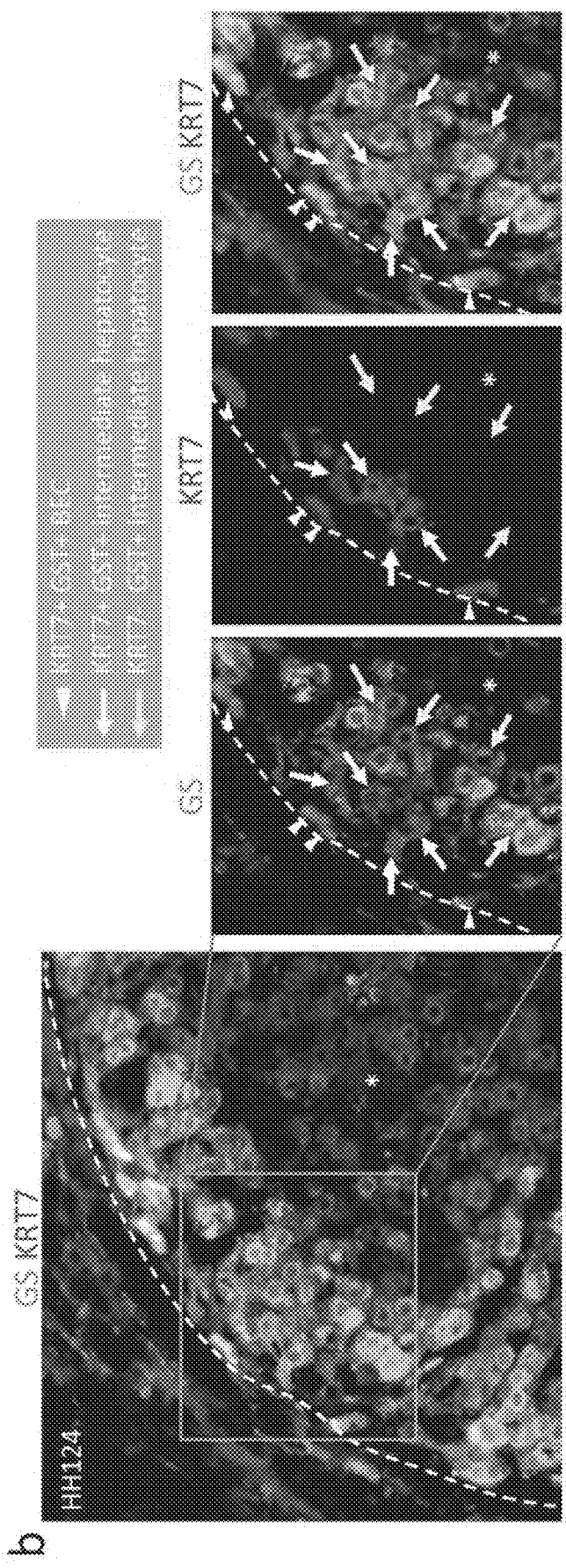
Figure 6C:
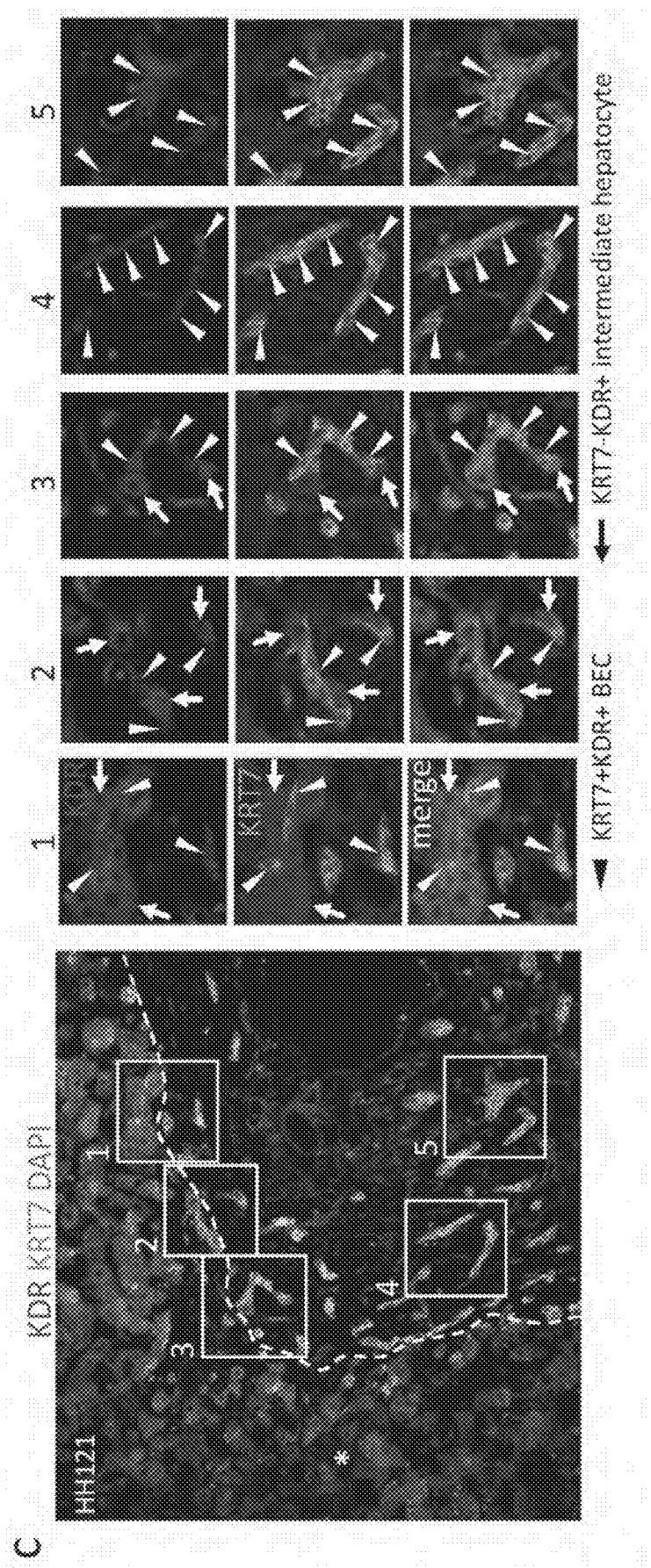
Figure 6D:
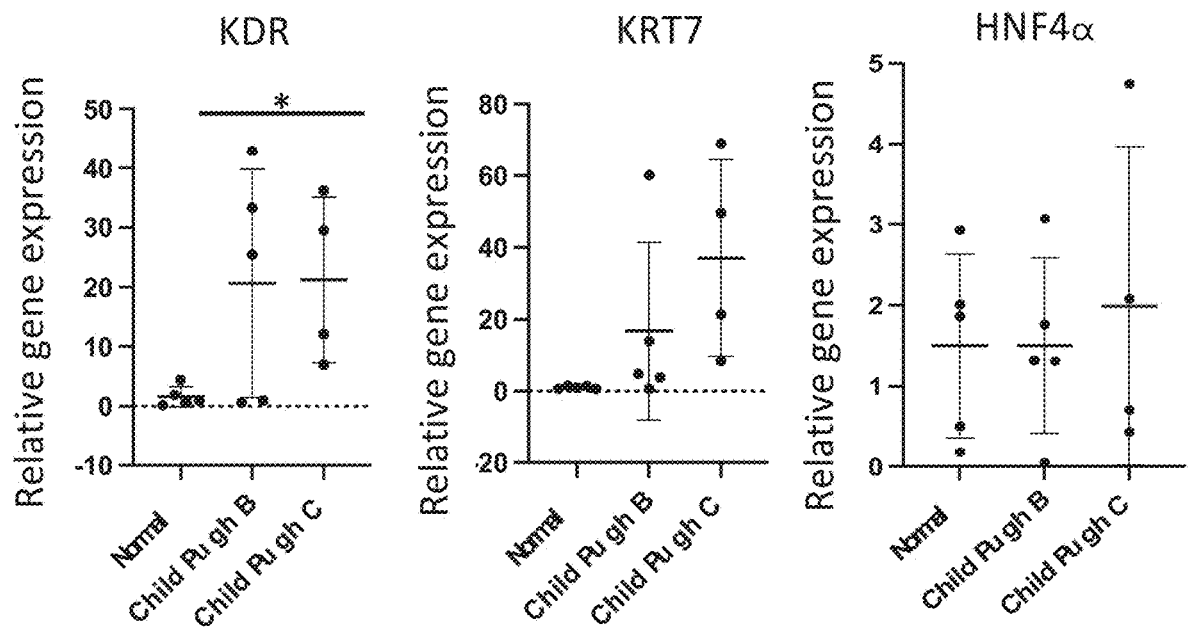
Figure 6E:
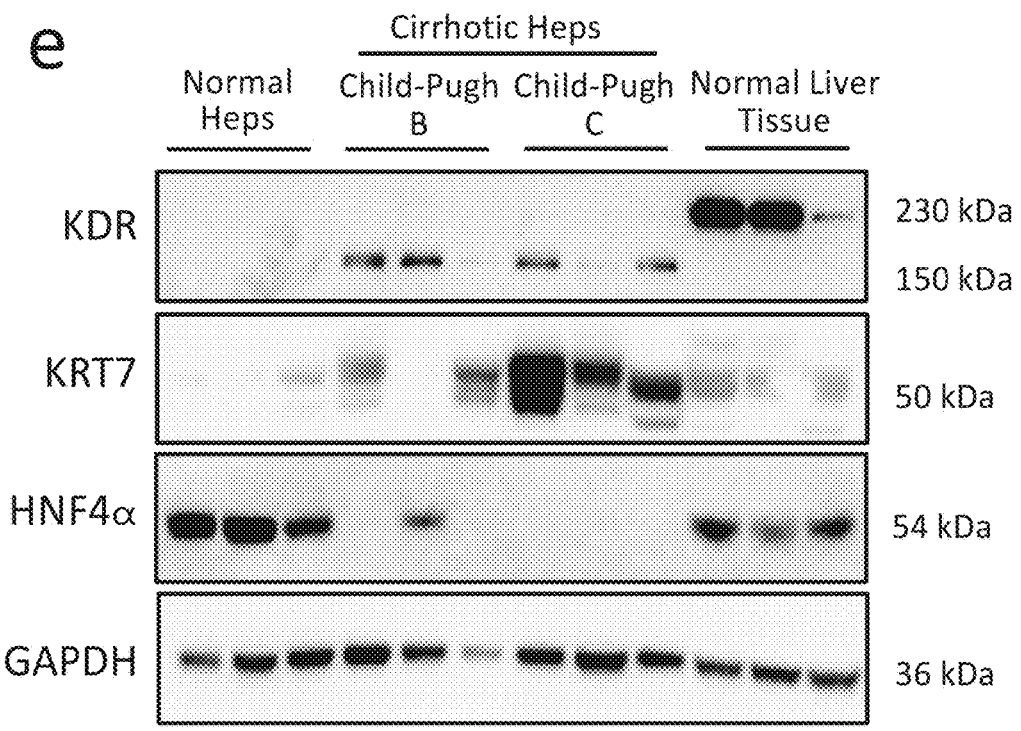
Figure 12A:
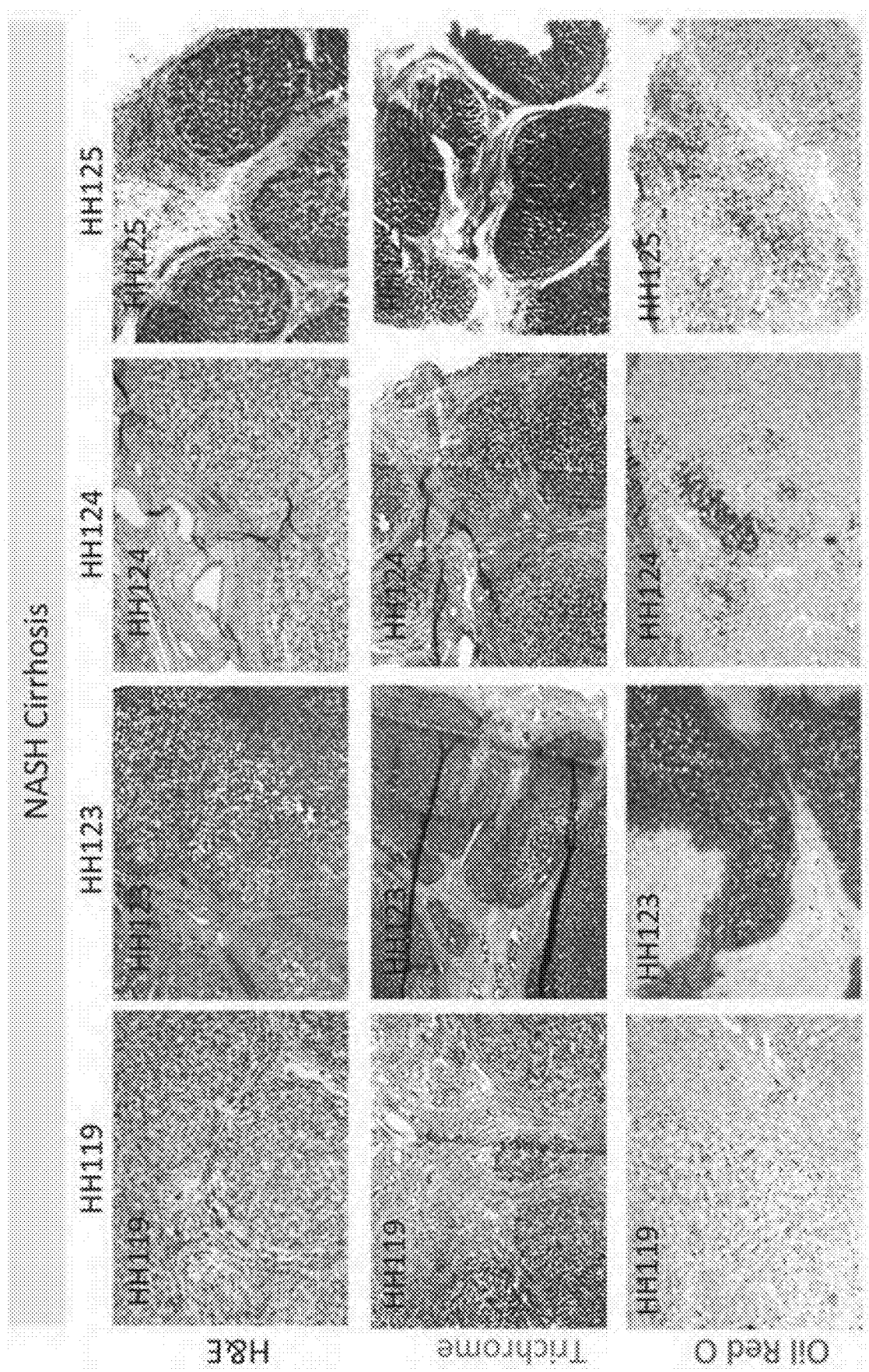
FIGS. 12A-12C depict histopathological examination of human liver specimens with ESLD.
Figure 12B:
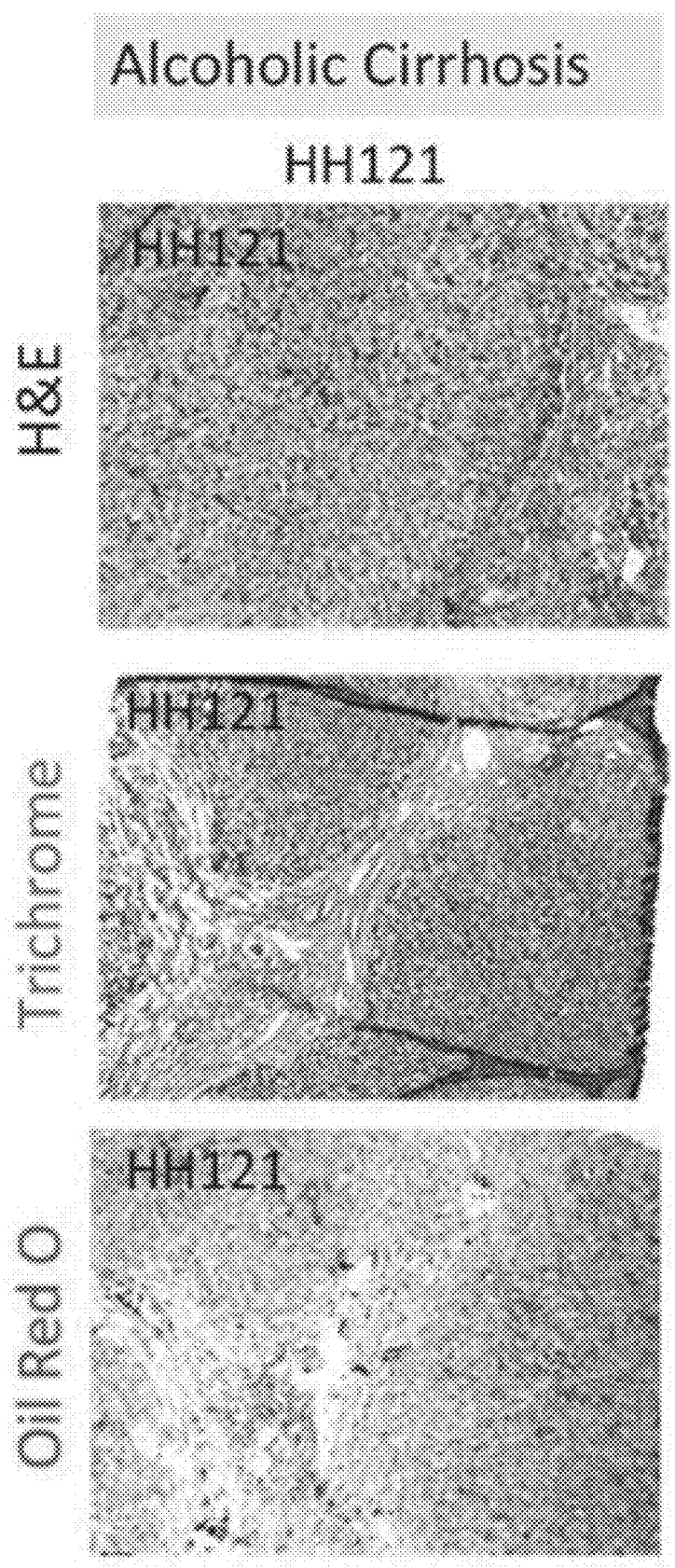
Figure 12C:
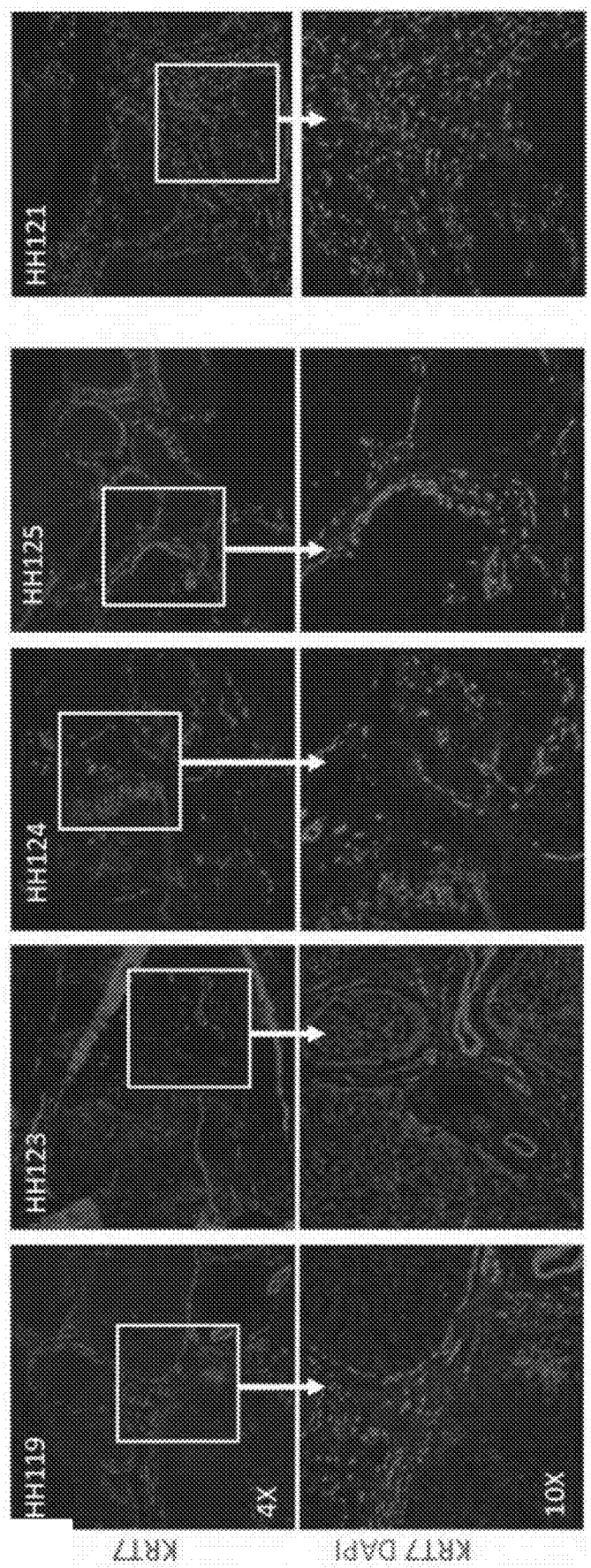
Figures 13A, 13B, 13C:
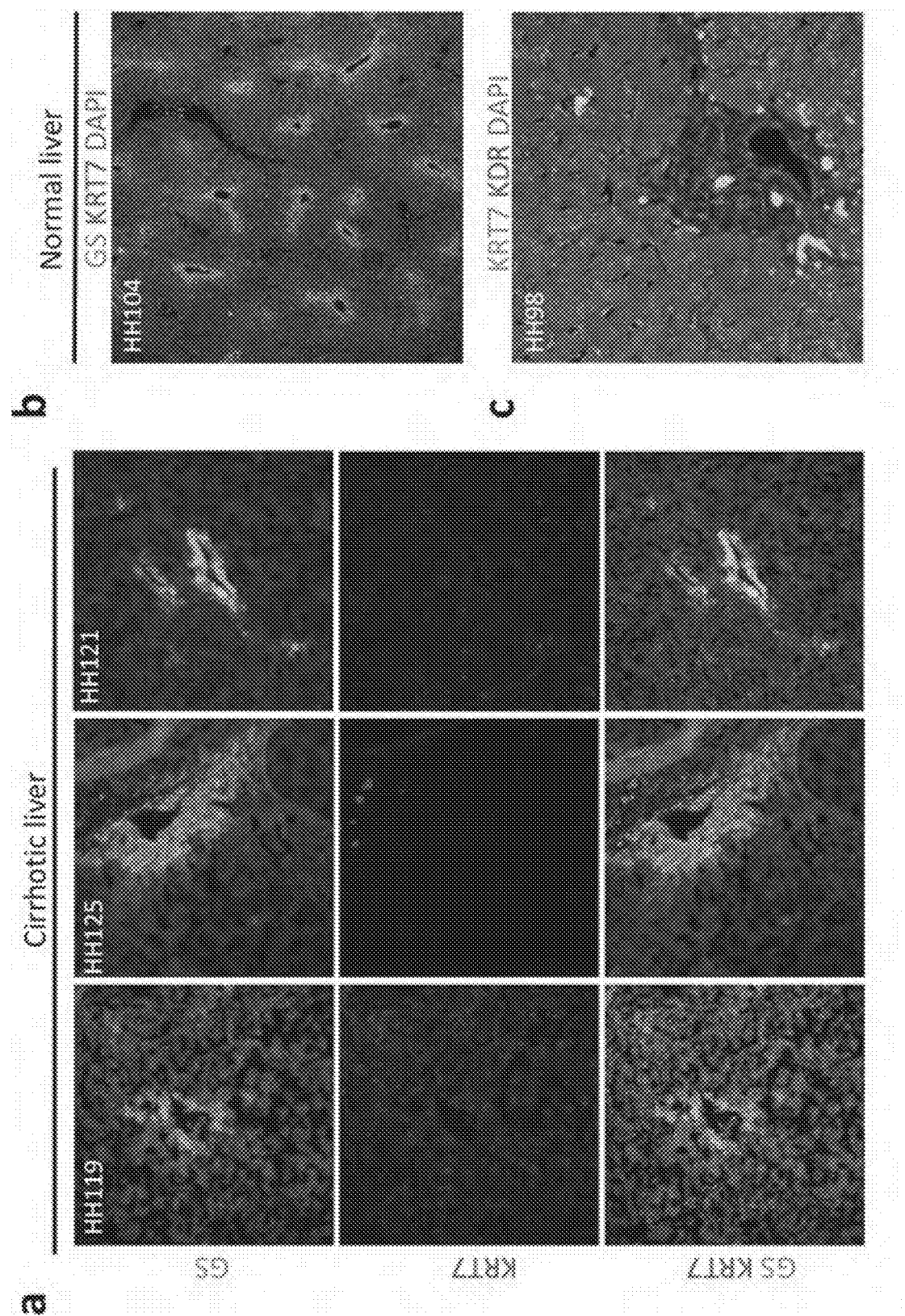
FIGS. 13A-13E depict evidence of BEC-to-hepatocyte conversion and KDR expression in human liver samples from non-alcoholic steatohepatitis (NASH) cirrhosis and alcoholic cirrhosis with ESLD patients.
Figure 13D:
Figure 13E:
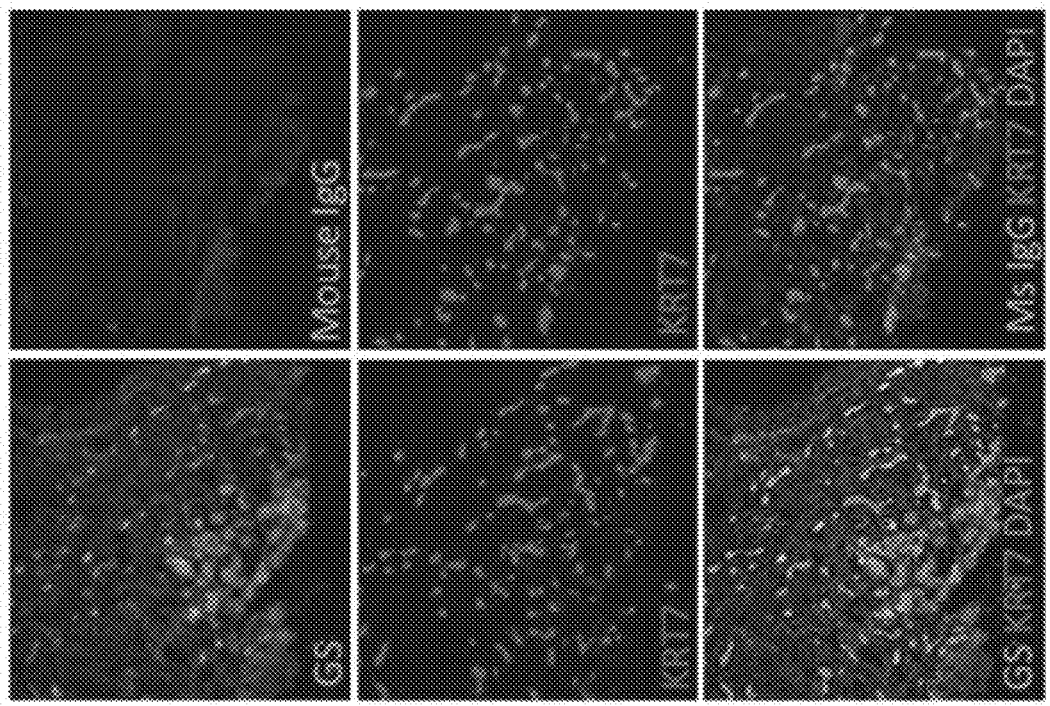

To investigate the clinical relevance of findings from the zebrafish and mouse models, the inventors sought to identify KDR-expressing BECs associated with evidence of BEC-to-hepatocyte conversion in specimens from human cirrhotic livers with ESLD recovered from patients with NASH cirrhosis or alcoholic cirrhosis and terminal liver failure (n=5) (Child-Pugh B and C), as well as three normal specimens (Table 4). Histopathological examination confirmed that all five diseased specimens exhibited features of ESLD such as hepatocyte-containing regenerative nodules surrounded with fibrotic septa (FIG. 12A) associated with various degrees of steatosis (FIG. 12A) and ductular reaction (FIG. 12C). Numerous KRT7+ cells were also found near the margin of, as well as within, the regenerative nodules (FIG. 6A), suggesting the presence of KRT7+ intermediate hepatocyte-like cells derived from KRT7+ BECs as previously speculated in humans[61]. As expected, expression of glutamine synthetase (GS) in hepatocytes around central vein areas was detected in diseased specimens as found in normal specimens (FIGS. 13A, 13B, 13D). However, aberrant GS expression was also found in KRT7+ BECs within the DR and in the adjacent transitioning KRT7+ hepatocytes as well as their neighbors and most likely progeny KRT7− hepatocytes (FIG. 6B) as described[19, 23]. GS expression became weaker as hepatocytes were further away from the DR, toward the center of the regenerative nodule (FIG. 6B, asterisk). Large GS+ hepatocyte-like cells were often seen budding from strings of smaller KRT7+ BECs (FIG. 6B, arrows). Importantly, while KDR expression was not detected in BECs from normal specimens (FIG. 13C), numerous KRT7+ KDR+ BECs were identified histologically in 2 out of 5 cirrhotic specimens (specimens HH125 and HH121, FIG. 6C, frames 4 and 5, arrowheads). Strikingly, KRT7− KDR+ hepatocyte-like cells (FIG. 6C, frames 2 and 3, arrows) were seen budding from the strings of KRT7+KDR+ BECs (FIG. 6C, arrowheads), as observed in mice in the APAP/p21 injury model (Kdr-2A-Cre$^{ERT2}$-2A-eYFP) in which YFP+ hepatocytes were found adjacent to the YFP+KDR+ BECs (FIG. 5E, arrows). Expression of cytoplasmic KDR was also found in a subset of hepatocytes adjacent to KDR+ BECs (FIG. 6C, frame 1, arrows). The inventors further validated KDR expression in purified human hepatocytes from 9 explanted cirrhotic livers (NASH or alcoholic) patients that underwent liver transplantation due to decompensated hepatic function (Child-Pugh score B/C) and compared to normal human liver specimens (Table 5) as previously described[62] at the transcript (FIG. 6D, 9 specimens) and protein (FIG. 6E, 6 specimens) levels. The inventors first validated the hepatocyte identity of the purified cell preparation with the similar levels of mRNA HNF4α transcript representing promoter P1- and P2-derived HNF4α isoforms in the 3 types of specimens including hepatocytes purified from normal and both Child-Pugh score B or C diseased specimens (FIG. 6D). As expected, protein levels of P1-derived adult HNF4α isoforms were critically downregulated in diseased hepatocytes compared to those in normal hepatocytes (Heps) or normal liver tissue[63-65]. Importantly, KDR and KRT7 transcript as well as protein levels were upregulated in purified diseased hepatocytes (FIG. 6D, 6E, FIG. 13E) compared to normal human hepatocytes. Of note, diseased hepatocytes expressed the distinct 150 KDa non-glycosylated isoform of KDR (FIG. 6E), that was not detected in purified normal hepatocytes nor the normal liver tissue specimens. These results support the specificity of KDR to diseased hepatocytes as opposed to potential contaminant endothelial cells from the preparation of purified hepatocytes. Indeed, the 230 KDa isoform of KDR was the only variant detected in normal liver tissues that include endothelial cells. The 150 KDa KDR isoform is known to remain in the cytoplasm as an inactive receptor[66] which is consistent with the cytoplasmic staining of KDR observed in specimen sections (FIG. 6C, arrowheads). In line with the notion of VEGFA as a therapeutic target for advanced liver diseases, a recent study has shown a significant correlation between high levels of serum VEGF and lower fibrosis score in a NAFLD cohort[67], suggesting a protective effect of VEGFA against progression of the disease. Yet, the study indicates that levels of serum VEGF tend to decrease when NASH develops, offering a potential therapeutic intervention for VEGFA mRNA-LNP to mitigate the liver disease.

Altogether, identification in human ESLD specimens of KDR+ BECs associated with evidence of BEC-to-hepatocyte conversion supported by the presence of KRT7+GS+ hepatocytes and KDR+ hepatocyte-like cells budding from KRT7+GS+ BECs and KRT7+KDR+ BECs, respectively, provides a clinical application for VEGFA mRNA-LNP to stimulate BEC-driven liver repair for human liver disease intervention.

Discussion

Hepatocyte-driven repair fails in the face of severe acute injury or years of build-up of chronic liver damage, unveiling the possible clinical benefit of an alternative repair mechanism mediated by BECs. Decades of literature from analyses of human chronic liver disease specimens identified hepatocytes within regenerative nodules or adjacent to portal vein triads, that harbor BEC marker expression such as KRT7 or EpCAM[16, 56, 68, 69] as well as BECs within the DR turning on a hepatocyte signature with concomitant expression of HNF4α, HNF6 or GS[18-23, 69] Given the clinical context of these human advanced chronic liver disease specimens in which proliferation of senescence gene-expressing hepatocytes is exhausted[51, 52, 56, 58], these observations suggest the BEC origin of the bi-phenotypic hepatocyte-like cells. More recent lineage tracing studies in zebrafish and mouse models of liver injuries have recapitulated the generation of DR and demonstrated BEC-to-hepatocyte conversion when hepatocyte proliferation is compromised[17, 30-35] However, the presence of DR in human advanced chronic liver diseases has been associated with poor prognosis[61], casting a doubt on the BEC ability to promote liver repair and thus questioning their clinical benefit as facultative progenitor cells. Indeed, BECs within DR release profibrogenic factors that may instead aggravate the chronic liver disease features[70, 71]. Yet, a recent study showed that aberrant GS positivity in hepatocytes adjacent to portal tracts is significantly associated with regressed cirrhosis in humans[24], suggesting, in contrast, a positive clinical outcome from BEC-derived hepatocytes in resolving human cirrhosis. One of the most convincing studies in humans illustrating the ability of BECs to convert into hepatocytes was attempted by lineage tracing the BECs among the DRs in human cirrhotic livers using mutational analysis in mitochondrial DNA encoding cytochrome c oxidase enzyme, and showed the descent of hepatocytes within monoclonal regenerative nodules from adjacent BEC-associated DRs[25]. Altogether, experimental animal model studies combined with analyses of human specimens raise the possibility of leveraging the naturally occurring DR and associated BEC-to-hepatocyte conversion as a therapy if the BEC-driven repair mechanism could be harnessed. This would have a tremendous impact on the treatment of acute and chronic liver diseases and would circumvent liver transplantation and accompanying challenges and complications.

The current challenge for the efficient therapeutic use of BECs is the inability to reliably identify a true progenitor population among them and to, thus, define a druggable pathway that would accelerate their differentiation into functional hepatocytes. Here, using complementary mouse and zebrafish liver injury models, it is demonstrated that VEGFA potentializes BEC-driven liver regeneration by promoting BEC-to-hepatocyte conversion with a 5-fold increase on average. The presence of KDR-expressing BECs in advanced cirrhotic human liver specimens as well as adjacent KDR-expressing hepatocytes, most likely progeny of the KDR-expressing BECs, suggests that BEC-to-hepatocyte conversion occurs in humans and is possibly mediated through KDR activation on KDR-expressing BECs. Therefore, if augmented with VEGFA mRNA-LNP, BEC-driven liver repair may become an efficient therapy in humans to prevent progression of the chronic liver disease and promote its regression, or to prevent liver failure in acute disease overcoming the necessity for liver transplantation.

Figure 14:
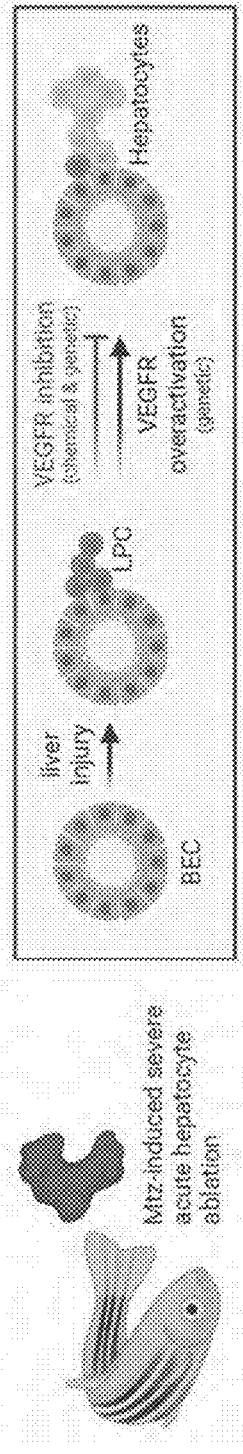
FIG. 14 depicts a graphical summary of using VEGFA mRNA-LNP to induce liver repair. 1) In zebrafish, VEGFR signaling regulates LPC-to-hepatocyte conversion during liver regeneration in the Mtz-induced severe acute hepatocyte ablation. Chemical or genetic inhibition of VEGFR prevents cell conversion, while VEGFR overactivation via overexpression of VEGFA genetically promotes it. 2) During acute and chronic liver injuries in mice, administration of VEGFA via mRNA-LNP promotes BEC-to-hepatocyte conversion or KDR-expressing cell (mostly BECs)-to-hepatocyte conversion and reverts liver fibrosis and steatosis. Transient cytoplasmic KDR-expressing hepatocytes are detected, and are mostly descendant of KDR-expressing BECs. 3) In human ESLD cirrhotic livers, the presence of KDR-expressing BECs in septa is associated with identification of cytoplasmic KDR-expressing hepatocytes at the margin of the regenerative nodules near the septa and with transitioning hepatocytes from KRT7+GS+, KRT7–GS+, to KRT7–GS– phenotype toward the center of the nodule, strongly suggesting their BEC origin.
Figure 14:
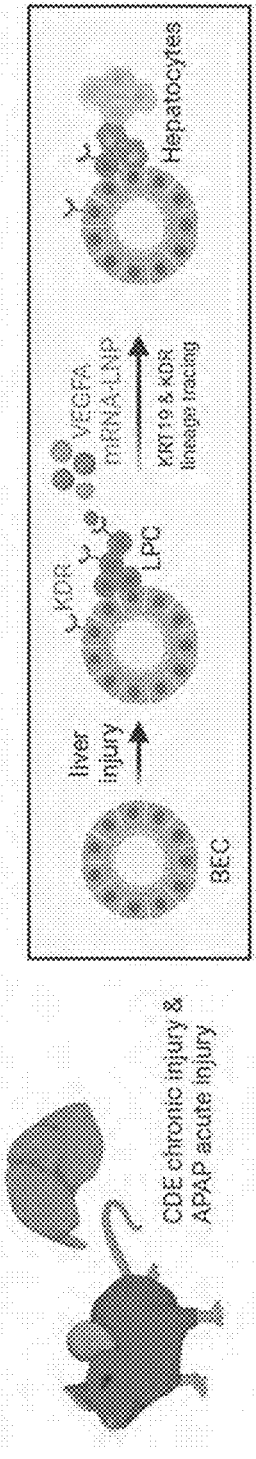
Figure 14:
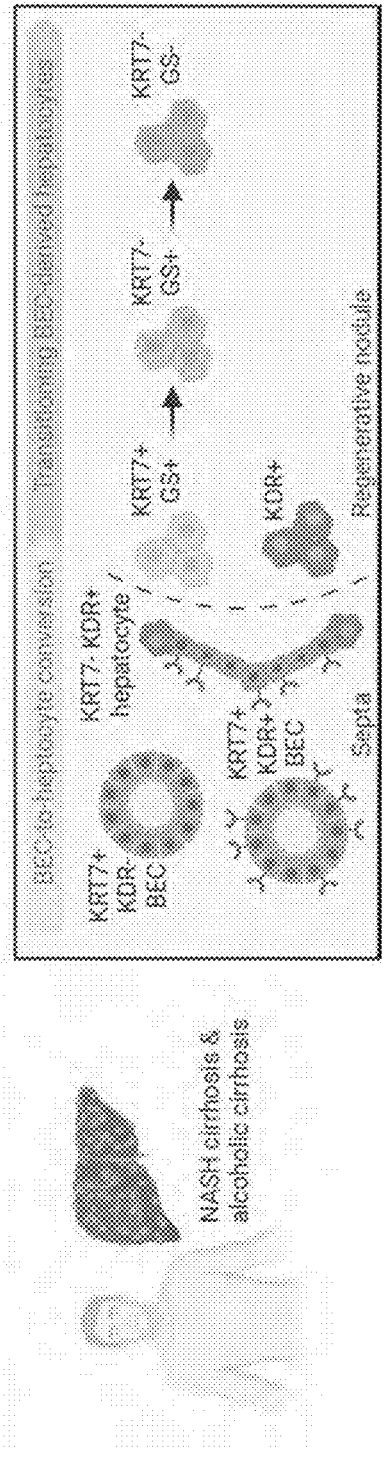

The precise identity of BEC liver progenitor cells remains elusive. Although, there is no evidence for a direct relationship between fetal progenitor hepatoblasts and adult liver progenitor cells, they do share the same clonogenic features with capacity to differentiate into hepatocytes and BECs, as well as share several cell surface markers including DLK1, CD133 and EpCAM[72-81, 82, 83]. However, since these markers are expressed on all BECs in adult livers, it is therefore difficult to identify the clonogenic progenitors amongst the non-clonogenic BECs. Other markers such Lgr5[84], TROP2[77], Fox11[85], and ST14[86] have been reported to define BEC progenitors, yet their cell fate mapping during regeneration have not been fully performed or the ability of their progeny to restore liver function fully demonstrated. The studies using the mouse and the human embryonic stem cell (ESC) differentiation system revealed that KDR+ fetal hepatic progenitors are bonafide hepatoblast precursors and that KDR activation is required for hepatic specification of the human ESC-derived KDR+ hepatic progenitor. KDR+ BECs was identified in mouse liver injury models as well as the ability of KDR+ cells to generate hepatocytes using the Kdr lineage tracing model (FIG. 14). Importantly, as found in mice, KDR expression was also detected on BECs in human cirrhotic ESLD specimens as well as on hepatocytes budding from strings of KRT7+ BECs. Presence of KDR+ hepatocytes in human cirrhotic ESLD specimens or YFP+ hepatocytes in injured livers in mice carrying the YFP reporter under the Kdr promoter supported their identity as progeny of KDR+ BECs. This study introduces KDR+ BEC as a novel facultative liver progenitor cell. Moreover, the use of clinically relevant, non-integrative mRNA-LNP, whose safety has been clinically validated[87] and further supported by the current COVID-19 vaccines, to transiently deliver VEGFA in the liver may potentially have key clinical significance to treat chronic and acute liver diseases.

REFERENCES

1. Michalopoulos, G K. Hepatostat: Liver regeneration and normal liver tissue maintenance. Hepatology 2017, 65:1384-1392. PMID: 27997988.
2. Duncan, A W, C Dorrell and M Grompe. Stem cells and liver regeneration. Gastroenterology 2009, 137:466-481. PMID: 19470389.
3. Stanger, B Z. Cellular homeostasis and repair in the Mammalian liver. Annu Rev Physiol 2015, 77:179-200. PMID: 25668020.
4. Rodrigo-Torres, D, S Affo, M Coll, O Morales-Ibanez, C Millan, D Blaya, A Alvarez-Guaita, C Rentero, J J Lozano, M A Maestro, M Solar, V Arroyo, J Caballeria, L A van Grunsven, C Enrich, P Gines, R Bataller and P Sancho-Bru. The biliary epithelium gives rise to liver progenitor cells. Hepatology 2014, 60:1367-1377. PMID: 24700364.
5. Shin, S and K H Kaestner. The origin, biology, and therapeutic potential of facultative adult hepatic progenitor cells. Curr Top Dev Biol 2014, 107:269-292. PMID: 24439810.
6. Sato, K, M Marzioni, F Meng, H Francis, S Glaser and G Alpini. Ductular Reaction in Liver Diseases: Pathological Mechanisms and Translational Significances. Hepatology 2019, 69:420-430. PMID: 30070383; PMCID: PMC6324973.
7. Boulter, L, W Y Lu and S J Forbes. Differentiation of progenitors in the liver: a matter of local choice. J Clin Invest 2013, 123:1867-1873. PMID: 23635784; PMCID: 3635730.
8. Gouw, A S, A D Clouston and N D Theise. Ductular reactions in human liver: diversity at the interface. Hepatology 2011, 54:1853-1863. PMID: 21983984.
9. Roskams, T A, ND Theise, C Balabaud, G Bhagat, P S Bhathal, P Bioulac-Sage, E M Brunt, J M Crawford, H A Crosby, V Desmet, M J Finegold, S A Geller, A S Gouw, P Hytiroglou, A S Knisely, M Kojiro, J H Lefkowitch, Y Nakanuma, J K Olynyk, Y N Park, B Portmann, R Saxena, P J Scheuer, A J Strain, S N Thung, I R Wanless and A B West. Nomenclature of the finer branches of the biliary tree: canals, ductules, and ductular reactions in human livers. Hepatology 2004, 39:1739-1745. PMID: 15185318.
10. Roskams, T and V Desmet. Ductular reaction and its diagnostic significance. Semin Diagn Pathol 1998, 15:259-269. PMID: 9845427.
11. Popper, H, G Kent and R Stein. Ductular cell reaction in the liver in hepatic injury. J Mt Sinai Hosp N Y 1957, 24:551-556. PMID: 13476145.
12. Turanyi, E, K Dezso, J Csomor, Z Schaff, S Paku and P Nagy. Immunohistochemical classification of ductular reactions in human liver. Histopathology 2010, 57:607-614. PMID: 20875072.
13. Lowes, K N, BA Brennan, G C Yeoh and J K Olynyk. Oval cell numbers in human chronic liver diseases are directly related to disease severity. Am J Pathol 1999, 154:537-541. PMID: 10027411; PMCID: 1849988.
14. Van Haele, M, J Snoeck and T Roskams. Human Liver Regeneration: An Etiology Dependent Process. Int J Mol Sci 2019, 20. PMID: 31083462; PMCID: PMC6539121.
15. Roskams, T A, L Libbrecht and V J Desmet. Progenitor cells in diseased human liver. Semin Liver Dis 2003, 23:385-396. PMID: 14722815.
16. Yoon, S M, D Gerasimidou, R Kuwahara, P Hytiroglou, J E Yoo, Y N Park and N D Theise. Epithelial cell adhesion molecule (EpCAM) marks hepatocytes newly derived from stem/progenitor cells in humans. Hepatology 2011, 53:964-973. PMID: 21319194.
17. Deng, X, X Zhang, W Li, RX Feng, L Li, GR Yi, X N Zhang, C Yin, H Y Yu, JP Zhang, B Lu, L Hui and W F Xie. Chronic Liver Injury Induces Conversion of Biliary Epithelial Cells into Hepatocytes. Cell Stem Cell 2018, 23:114-122.e113. PMID: 29937200.
18. Haque, S, Y Haruna, K Saito, M A Nalesnik, E Atillasoy, S N Thung and MA Gerber. Identification of bipotential progenitor cells in human liver regeneration. Lab Invest 1996, 75:699-705. PMID: 8941215.

19. Stueck, A E and I R Wanless. Hepatocyte buds derived from progenitor cells repopulate regions of parenchymal extinction in human cirrhosis. Hepatology 2015, 61:1696-1707. PMID: 25644399.
20. Hytiroglou, P and N D Theise. Regression of human cirrhosis: an update, 18 years after the pioneering article by Wanless et al. Virchows Archive: an international journal of pathology 2018, 473:15-22. PMID: 29589101.
21. Wanless, I R, E Nakashima and M Sherman. Regression of human cirrhosis. Morphologic features and the genesis of incomplete septal cirrhosis. Arch Pathol Lab Med 2000, 124:1599-1607. PMID: 11079009.
22. Falkowski, O, H J An, I A Ianus, L Chiriboga, H Yee, A B West and N D Theise. Regeneration of hepatocyte 'buds' in cirrhosis from intrabiliary stem cells. J Hepatol 2003, 39:357-364. PMID: 12927921.
23. Fleming, K E and I R Wanless. Glutamine synthetase expression in activated hepatocyte progenitor cells and loss of hepatocellular expression in congestion and cirrhosis. Liver Int 2013, 33:525-534. PMID: 23362937.
24. Hadi, R, K Shin, N Reder, L Alpert, L Koch, WT Choi, P E Swanson, J Hart and M Westerhoff. Utility of glutamine synthetase immunohistochemistry in identifying features of regressed cirrhosis. Mod Pathol 2020, 33:448-455. PMID: 31391527.
25. Lin, W R, S N Lim, S A McDonald, T Graham, V L Wright, C L Peplow, A Humphries, H M Kocher, N A Wright, A P Dhillon and M R Alison. The histogenesis of regenerative nodules in human liver cirrhosis. Hepatology 2010, 51:1017-1026. PMID: 20198634.
26. Malato, Y, S Naqvi, N Schurmann, R Ng, B Wang, J Zape, MA Kay, D Grimm and H Willenbring. Fate tracing of mature hepatocytes in mouse liver homeostasis and regeneration. J Clin Invest 2011, 121:4850-4860. PMID: 22105172; PMCID: 3226005.
27. Yanger, K, D Knigin, Y Zong, L Maggs, G Gu, H Akiyama, E Pikarsky and B Z Stanger. Adult hepatocytes are generated by self-duplication rather than stem cell differentiation. Cell Stem Cell 2014, 15:340-349. PMID: 25130492.
28. Overturf, K, M al-Dhalimy, C N Ou, M Finegold and M Grompe. Serial transplantation reveals the stem-cell-like regenerative potential of adult mouse hepatocytes. Am J Pathol 1997, 151:1273-1280. PMID: 9358753.
29. Schaub, J R, Y Malato, C Gormond and H Willenbring. Evidence against a stem cell origin of new hepatocytes in a common mouse model of chronic liver injury. Cell Rep 2014, 8:933-939. PMID: 25131204; PMCID: PMC4376310.
30. Lu, W Y, T G Bird, L Boulter, A Tsuchiya, A M Cole, T Hay, R V Guest, D Wojtacha, T Y Man, A Mackinnon, R A Ridgway, T Kendall, MJ Williams, T Jamieson, A Raven, DC Hay, J P Iredale, AR Clarke, O J Sansom and S J Forbes. Hepatic progenitor cells of biliary origin with liver repopulation capacity. Nat Cell Biol 2015, 17:971-983. PMID: 26192438; PMCID: 4612439.
31. Raven, A, W Y Lu, T Y Man, S Ferreira-Gonzalez, E O'Duibhir, B J Dwyer, J P Thomson, R R Meehan, R Bogorad, V Koteliansky, Y Kotelevtsev, C Ffrench-Constant, L Boulter and S J Forbes. Cholangiocytes act as facultative liver stem cells during impaired hepatocyte regeneration. Nature 2017, 547:350-354. PMID: 28700576; PMCID: PMC5522613.
32. Russell, J O, W Y Lu, H Okabe, M Abrams, M Oertel, M Poddar, S Singh, S J Forbes and S P Monga. Hepatocyte-specific beta-catenin deletion during severe liver injury provokes cholangiocytes to differentiate into hepatocytes. Hepatology 2018. PMID: 30215850.
33. Manco, R, L A Clerbaux, S Verhulst, M Bou Nader, C Sempoux, J Ambroise, B Bearzatto, J L Gala, Y Horsmans, L van Grunsven, C Desdouets and I Leclercq. Reactive cholangiocytes differentiate into proliferative hepatocytes with efficient DNA repair in mice with chronic liver injury. J Hepatol 2019, 70:1180-1191. PMID: 30794890.
34. He, J, H Lu, Q Zou and L Luo. Regeneration of liver after extreme hepatocyte loss occurs mainly via biliary transdifferentiation in zebrafish. Gastroenterology 2014, 146:789-800.e788. PMID: 24315993.
35. Choi, T Y, N Ninov, D Y Stainier and D Shin. Extensive conversion of hepatic biliary epithelial cells to hepatocytes after near total loss of hepatocytes in zebrafish. Gastroenterology 2014, 146:776-788. PMID: 24148620; PMCID: PMC3943869.
36. LeCouter, J, D R Moritz, B Li, GL Phillips, X H Liang, HP Gerber, K J Hillan and N Ferrara. Angiogenesis-independent endothelial protection of liver: role of VEGFR-1. Science 2003, 299:890-893. PMID: 12574630.
37. Bockhorn, M, M Goralski, D Prokofiev, P Dammann, P Grunewald, M Trippler, A Biglarnia, M Kamler, E M Niehues, A Frilling, C E Broelsch and J F Schlaak. VEGF is important for early liver regeneration after partial hepatectomy. J Surg Res 2007, 138:291-299. PMID: 17275844.
38. Ding, B S, D J Nolan, J M Butler, D James, A O Babazadeh, Z Rosenwaks, V Mittal, H Kobayashi, K Shido, D Lyden, T N Sato, S Y Rabbany and S Rafii. Inductive angiocrine signals from sinusoidal endothelium are required for liver regeneration. Nature 2010, 468:310-315. PMID: 21068842; PMCID: 3058628.
39. Yang, L, J Kwon, Y Popov, G B Gajdos, T Ordog, R A Brekken, D Mukhopadhyay, D Schuppan, Y Bi, D Simonetto and V H Shah. Vascular endothelial growth factor promotes fibrosis resolution and repair in mice. Gastroenterology 2014, 146:1339-1350.e1331. PMID: 24503129; PMCID: PMC4001704.
40. Oe, H, T Kaido, A Mon, H Onodera and M Imamura. Hepatocyte growth factor as well as vascular endothelial growth factor gene induction effectively promotes liver regeneration after hepatectomy in Solt-Farber rats. Hepatogastroenterology 2005, 52:1393-1397. PMID: 16201081.
41. Gaudio, E, B Barbaro, D Alvaro, S Glaser, H Francis, Y Ueno, C J Meininger, A Franchitto, P Onori, M Marzioni, S Taffetani, G Fava, G Stoica, J Venter, R Reichenbach, S De Morrow, R Summers and G Alpini. Vascular endothelial growth factor stimulates rat cholangiocyte proliferation via an autocrine mechanism. Gastroenterology 2006, 130:1270-1282. PMID: 16618418.
42. Dianat, N, H Dubois-Pot-Schneider, C Steichen, C Desterke, P Leclerc, A Raveux, L Combettes, A Weber, A Corlu and A Dubart-Kupperschmitt. Generation of functional cholangiocyte-like cells from human pluripotent stem cells and HepaRG cells. Hepatology 2014, 60:700-714. PMID: 24715669; PMCID: PMC4315871.
43. Fabris, L, M Cadamuro, R Fiorotto, T Roskams, C Spirli, S Melero, A Sonzogni, R E Joplin, L Okolicsanyi and M Strazzabosco. Effects of angiogenic factor overexpression by human and rodent cholangiocytes in polycystic liver diseases. Hepatology 2006, 43:1001-1012. PMID: 16628643.

44. Goldman, O, S Han, M Sourrisseau, N Dziedzic, W Hamou, B Comeo, S D'Souza, T Sato, D N Kotton, K D Bissig, T Kalir, A Jacobs, T Evans, MJ Evans and V Gouon-Evans. KDR Identifies a Conserved Human and Murine Hepatic Progenitor and Instructs Early Liver Development. Cell Stem Cell 2013, 12:748-760. PMID: 23746980.

45. Pardi, N, S Tuyishime, H Muramatsu, K Kariko, B L Mui, Y K Tam, T D Madden, M J Hope and D Weissman. Expression kinetics of nucleoside-modified mRNA delivered in lipid nanoparticles to mice by various routes. J Control Release 2015, 217:345-351. PMID: 26264835; PMCID: 4624045.

46. Ko, S, T Y Choi, J O Russell, J So, S P S Monga and D Shin. Bromodomain and extraterminal (BET) proteins regulate biliary-driven liver regeneration. J Hepatol 2016, 64:316-325. PMID: 26505118; PMCID: PMC4718879.

47. Fong, T A, L K Shawver, L Sun, C Tang, H App, T J Powell, Y H Kim, R Schreck, X Wang, W Risau, A Ullrich, K P Hirth and G McMahon. SU5416 is a potent and selective inhibitor of the vascular endothelial growth factor receptor (Flk-1/KDR) that inhibits tyrosine kinase catalysis, tumor vascularization, and growth of multiple tumor types. Cancer Res 1999, 59:99-106. PMID: 9892193.

48. Sun, L, N Tran, F Tang, H App, P Hirth, G McMahon and C Tang. Synthesis and biological evaluations of 3-substituted indolin-2-ones: a novel class of tyrosine kinase inhibitors that exhibit selectivity toward particular receptor tyrosine kinases. J Med Chem 1998, 41:2588-2603. PMID: 9651163.

49. Matsuoka, R L, A Rossi, O A Stone and D Y R Stainier. CNS-resident progenitors direct the vascularization of neighboring tissues. Proc Natl Acad Sci USA 2017, 114:10137-10142. PMID: 28855341; PMCID: PMC5617242.

50. Hoeppner, L H, K N Phoenix, K J Clark, R Bhattacharya, X Gong, T E Sciuto, P Vohra, S Suresh, S Bhattacharya, A M Dvorak, S C Ekker, H F Dvorak, K P Claffey and D Mukhopadhyay. Revealing the role of phospholipase Cβ3 in the regulation of VEGF-induced vascular permeability. Blood 2012, 120:2167-2173. PMID: 22674805; PMCID: PMC3447777.

51. Marshall, A, S Rushbrook, S E Davies, L S Morris, I S Scott, S L Vowler, N Coleman and G Alexander. Relation between hepatocyte G1 arrest, impaired hepatic regeneration, and fibrosis in chronic hepatitis C virus infection. Gastroenterology 2005, 128:33-42. PMID: 15633121.

52. Richardson, M M, J R Jonsson, E E Powell, E M Brunt, B A Neuschwander-Tetri, P S Bhathal, J B Dixon, M D Weltman, H Tilg, A R Moschen, D M Purdie, A J Demetris and A D Clouston. Progressive fibrosis in nonalcoholic steatohepatitis: association with altered regeneration and a ductular reaction. Gastroenterology 2007, 133:80-90. PMID: 17631134.

53. Everton, E, F Rizvi, A R Smith, M Beattie, Y Tam, N Pardi, D Weissman and V Gouon-Evans. Transient yet Robust Expression of Proteins in the Mouse Liver via Intravenous Injection of Lipid Nanoparticle-encapsulated Nucleoside-modified mRNA. Bio Protoc 2021, 11:e4184. PMID: 34722830; PMCID: PMC8517647.

54. Rizvi, F, E Everton, A R Smith, H Liu, E Osota, M Beattie, Y Tam, N Pardi, D Weissman and V Gouon-Evans. Murine liver repair via transient activation of regenerative pathways in hepatocytes using lipid nanoparticle-complexed nucleoside-modified mRNA. Nat Commun 2021, 12:613. PMID: 33504774; PMCID: PMC7840919

55. Kofman, A V, G Morgan, A Kirschenbaum, J Osbeck, M Hussain, S Swenson and N D Theise. Dose- and time-dependent oval cell reaction in acetaminophen-induced murine liver injury. Hepatology 2005, 41:1252-1261. PMID: 15880565.

56. Katoonizadeh, A, F Nevens, C Verslype, J Pirenne and T Roskams. Liver regeneration in acute severe liver impairment: a clinicopathological correlation study. Liver Int 2006, 26:1225-1233. PMID: 17105588.

57. Yoon, E, A Babar, M Choudhary, M Kutner and N Pyrsopoulos. Acetaminophen-Induced Hepatotoxicity: a Comprehensive Update. Journal of clinical and translational hepatology 2016, 4:131-142. PMID: 27350943; PMCID: PMC4913076.

58. Bird, T G, M Muller, L Boulter, D F Vincent, R A Ridgway, E Lopez-Guadamillas, W Y Lu, T Jamieson, O Govaere, A D Campbell, S Ferreira-Gonzalez, A M Cole, T Hay, K J Simpson, W Clark, A Hedley, M Clarke, P Gentaz, C Nixon, S Bryce, C Kiourtis, J Sprangers, R J B Nibbs, N Van Rooijen, L Bartholin, S R McGreal, U Apte, S T Barry, J P Iredale, A R Clarke, M Serrano, T A Roskams, O J Sansom and S J Forbes. TGFbeta inhibition restores a regenerative response in acute liver injury by suppressing paracrine senescence. Sci Transl Med 2018, 10. PMID: 30111642.

59. Holmes, K, O L Roberts, A M Thomas and M J Cross. Vascular endothelial growth factor receptor-2: structure, function, intracellular signalling and therapeutic inhibition. Cell Signal 2007, 19:2003-2012. PMID: 17658244.

60. Shalaby, F, J Rossant, T P Yamaguchi, M Gertsenstein, X F Wu, M L Breitman and A C Schuh. Failure of blood-island formation and vasculogenesis in Flk-1-deficient mice. Nature 1995, 376:62-66. PMID: 7596435.

61. Sancho-Bru, P, J Altamirano, D Rodrigo-Torres, M Coll, C Millin, J Jos6 Lozano, R Miquel, V Arroyo, J Caballería, P Ginès and R Bataller. Liver progenitor cell markers correlate with liver damage and predict short-term mortality in patients with alcoholic hepatitis. Hepatology 2012, 55:1931-1941. PMID: 22278680.

62. Gramignoli, R, M L Green, V Tahan, K Dorko, K J Skvorak, F Marongiu, W Zao, R Venkataramanan, E C Ellis, D Geller, A G Breite, F E Dwulet, R C McCarthy and S C Strom. Development and application of purified tissue dissociation enzyme mixtures for human hepatocyte isolation. Cell Transplant 2012, 21:1245-1260. PMID: 22080793.

63. Aguila, H L, K Akashi, J Domen, K L Gandy, E Lagasse, R E Mebius, S J Morrison, J Shizuru, S Strober, N Uchida, D E Wright and I L Weissman. From stem cells to lymphocytes: biology and transplantation. Immunol Rev 1997, 157:13-40. PMID: 9255619.

64. Nishikawa, T, A Bell, J M Brooks, K Setoyama, M Melis, B Han, K Fukumitsu, K Handa, J Tian, K H Kaestner, Y Vodovotz, J Locker, A Soto-Gutierrez and I J Fox. Resetting the transcription factor network reverses terminal chronic hepatic failure. J Clin Invest 2015, 125:1533-1544. PMID: 25774505; PMCID: PMC4396487.

65. Guzman-Lepe, J, E Cervantes-Alvarez, A Collin de l'Hortet, Y Wang, W M Mars, Y Oda, Y Bekki, M Shimokawa, H Wang, T Yoshizumi, Y Maehara, A Bell, I J Fox, K Takeishi and A Soto-Gutierrez. Liver-enriched transcription factor expression relates to chronic hepatic 66. Takahashi, T and M Shibuya. The 230 kDa mature form of KDR/Flk-1 (VEGF receptor-2) activates the PLC-gamma pathway and partially induces mitotic signals in NIH3T3 fibroblasts. Oncogene 1997, 14:2079-2089. PMID: 9160888.
67. Papageorgiou, M V, E Hadziyannis, D Tiniakos, A Georgiou, A Margariti, A Kostas and G V Papatheodoridis. Serum levels of vascular endothelial growth factor in non-alcoholic fatty liver disease. Ann Gastroenterol 2017, 30:209-216. PMID: 28243042; PMCID: PMC5320034.
68. Vandersteenhoven, A M, J Burchette and G Michalopoulos. Characterization of ductular hepatocytes in end-stage cirrhosis. Arch Pathol Lab Med 1990, 114:403-406. PMID: 2322100.
69. Limaye, P B, G Alarcón, A L Walls, M A Nalesnik, G K Michalopoulos, A J Demetris and E R Ochoa. Expression of specific hepatocyte and cholangiocyte transcription factors in human liver disease and embryonic development. Lab Invest 2008, 88:865-872. PMID: 18574450; PMCID: PMC2631390.
70. Kaur, S, H Siddiqui and MH Bhat. Hepatic Progenitor Cells in Action: Liver Regeneration or Fibrosis? Am J Pathol 2015, 185:2342-2350. PMID: 26255773.
71. Glaser, S S, E Gaudio, T Miller, D Alvaro and G Alpini. Cholangiocyte proliferation and liver fibrosis. Expert Rev Mol Med 2009, 11:e7. PMID: 19239726; PMCID: PMC2675635.
72. Kamiya, A, S Kakinuma, Y Yamazaki and H Nakauchi. Enrichment and clonal culture of progenitor cells during mouse postnatal liver development in mice. Gastroenterology 2009, 137:1114-1126, 1126 e1111-1114. PMID: 19524574.
73. Schmelzer, E, L Zhang, A Bruce, E Wauthier, J Ludlow, H L Yao, N Moss, A Melhem, R McClelland, W Turner, M Kulik, S Sherwood, T Tallheden, N Cheng, ME Furth and LM Reid. Human hepatic stem cells from fetal and postnatal donors. J Exp Med 2007, 204:1973-1987. PMID: 17664288; PMCID: 2118675.
74. Tanaka, M, M Okabe, K Suzuki, Y Kamiya, Y Tsukahara, S Saito and A Miyajima. Mouse hepatoblasts at distinct developmental stages are characterized by expression of EpCAM and DLK1: drastic change of EpCAM expression during liver development. Mech Dev 2009, 126:665-676. PMID: 19527784.
75. Rountree, C B, L Barsky, S Ge, J Zhu, S Senadheera and G M Crooks. A CD133-expressing murine liver oval cell population with bilineage potential. Stem Cells 2007, 25:2419-2429. PMID: 17585168.
76. Suzuki, A, S Sekiya, M Onishi, N Oshima, H Kiyonari, H Nakauchi and H Taniguchi. Flow cytometric isolation and clonal identification of self-renewing bipotent hepatic progenitor cells in adult mouse liver. Hepatology 2008, 48:1964-1978. PMID: 18837044.
77. Okabe, M, Y Tsukahara, M Tanaka, K Suzuki, S Saito, Y Kamiya, T Tsujimura, K Nakamura and A Miyajima. Potential hepatic stem cells reside in EpCAM+ cells of normal and injured mouse liver. Development 2009, 136:1951-1960. PMID: 19429791.
78. Dorrell, C, L Erker, J Schug, J L Kopp, P S Canaday, A J Fox, O Smirnova, A W Duncan, M J Finegold, M Sander, K H Kaestner and M Grompe. Prospective isolation of a bipotential clonogenic liver progenitor cell in adult mice. Genes Dev 2011, 25:1193-1203. PMID: 21632826; PMCID: 3110957.
79. Yovchev, M I, P N Grozdanov, H Zhou, H Racherla, C Guha and M D Dabeva. Identification of adult hepatic progenitor cells capable of repopulating injured rat liver. Hepatology 2008, 47:636-647. PMID: 18023068.
80. Jensen, C H, El Jauho, E Santoni-Rugiu, U Holmskov, B Teisner, N Tygstrup and HC Bisgaard. Transit-amplifying ductular (oval) cells and their hepatocytic progeny are characterized by a novel and distinctive expression of delta-like protein/preadipocyte factor 1/fetal antigen 1. Am J Pathol 2004, 164:1347-1359. PMID: 15039222; PMCID: 1615354.
81. Qiu, Q, J C Hemandez, A M Dean, P H Rao and G J Darlington. CD24-positive cells from normal adult mouse liver are hepatocyte progenitor cells. Stem Cells Dev 2011, 20:2177-2188. PMID: 21361791; PMCID: 3225069.
82. So, J, A Kim, S H Lee and D Shin. Liver progenitor cell-driven liver regeneration. Exp Mol Med 2020, 52:1230-1238. PMID: 32796957; PMCID: PMC8080804.
83. Ko, S, J O Russell, L M Molina and S P Monga. Liver Progenitors and Adult Cell Plasticity in Hepatic Injury and Repair: Knowns and Unknowns. Annu Rev Pathol 2020, 15:23-50. PMID: 31399003; PMCID: PMC7212705.
84. Huch, M, C Dorrell, S F Boj, J H van Es, V S Li, M van de Wetering, T Sato, K Hamer, N Sasaki, M J Finegold, A Haft, R G Vries, M Grompe and H Clevers. In vitro expansion of single Lgr5(+) liver stem cells induced by Wnt-driven regeneration. Nature 2013. PMID: 23354049.
85. Shin, S, G Walton, R Aoki, K Brondell, J Schug, A Fox, O Smirnova, C Dorrell, L Erker, A S Chu, R G Wells, M Grompe, L E Greenbaum and K H Kaestner. Fox11-Cre-marked adult hepatic progenitors have clonogenic and bilineage differentiation potential. Genes Dev 2011, 25:1185-1192. PMID: 21632825; PMCID: 3110956.
86. Li, B, C Dorrell, P S Canaday, C Pelz, A Haft, M Finegold and M Grompe. Adult Mouse Liver Contains Two Distinct Populations of Cholangiocytes. Stem Cell Reports 2017, 9:478-489. PMID: 28689996; PMCID: PMC5549808.
87. Weissman, D. mRNA transcript therapy. Expert Rev Vaccines 2015, 14:265-281. PMID: 25359562.

TABLE 4

Details of human tissue samples for histology evaluation.

| Code | Age | Sex | Diagnosis | Child-Pugh Score |
|---|---|---|---|---|
| HH98 | 15 years | male | Donor liver | NA |
| HH104 | 11 years | male | Donor liver | NA |
| HH09 | 37 years | female | FNH/No chemo | NA |
| HH119 | 59 years | male | NASH cirrhosis | B |
| HH123 | 58 years | male | NASH cirrhosis | C |
| HH124 | 63 years | male | NASH cirrhosis | B |
| HH125 | 66 years | male | NASH cirrhosis | B |
| HH121 | 71 years | male | Alcoholic cirrhosis | C |

TABLE 5

Details of human tissue samples from cirrhotic and normal liver from which hepatocytes were recovered for gene and protein expression analysis.

| Code | Age | Sex | Diagnosis | Child-Pugh Score |
|---|---|---|---|---|
| HH48 | 33 years | female | HCA "normal" | NA |
| HH55 | 61 years | male | ICCA "normal" | NA |
| HH16 | 44 years | male | Colon Ca "normal" | NA |

TABLE 5-continued

Details of human tissue samples from cirrhotic and normal liver from which hepatocytes were recovered for gene and protein expression analysis.

| Code | Age | Sex | Diagnosis | Child-Pugh Score |
|---|---|---|---|---|
| HH36 | 47 years | female | EHE "normal" | NA |
| HH98 | 15 years | male | Donor liver "normal" | NA |
| HH32 | 71 years | female | NASH cirrhosis | B |
| HH72 | 48 years | male | Alcoholic cirrhosis | B |
| HH49 | 50 years | female | NASH cirrhosis | B |
| HH62 | 67 years | male | NASH cirrhosis | B |
| HH22 | 53 years | male | NASH cirrhosis | B |
| HH26 | 52 years | male | Alcoholic cirrhosis | C |
| HH29 | 68 yo | female | NASH cirrhosis | C |
| HH97 | 62 yo | female | NASH cirrhosis | C |
| HH123 | 58 yo | male | NASH cirrhosis | C |

TABLE 6

DNA sequences used as template to in vitro transcribe nucleoside modified mRNA.

```
Human VEGF165-SEQ ID NO: 12
ATGAACTTCCTGCTGTCCTGGGTGCACTGGTCCCTGGCCCTGCTGCTGT

ACCTGCACCACGCCAAGTGGTCCCAGGCCGCCCCCATGGCCGAGGGCGG

CGGCCAGAACCACCACGAGGTGGTGAAGTTCATGGACGTGTACCAGCGg

TCCTACTGCCACCCCATCGAGACCCTGGTGGACATCTTCCAGGAGTACC

CCGACGAGATCGAGTACATCTTCAAGCCCTCCTGCGTGCCCCTGATGCG

CTGCGGCGGCTGCTGCAACGACGAGGGCCTGGAGTGCGTGCCCACCGAG

GAGTCCAACATCACCATGCAGATCATGCGCATCAAGCCCCACCAGGGCC

AGCACATCGGCGAGATGTCCTTCCTGCAGCACAACAAGTGCGAGTGCCG

CCCCAAGAAGGACCGCGCCCGCCAGGAGAACCCCTGCGGCCCCTGCTCC

GAGCGCCGCAAGCACCTGTTCGTGCAGGACCCCCAGACCTGCAAGTGCT

CCTGCAAGAACACCGACTCCCGCTGCAAGGCCCGCCAGCTGGAGCTGAA

CGAGCGCACCTGCCGCTGCGACAAGCCCCGCCGCTAA
```

TABLE 7

List of primary and secondary antibodies used in tissue immunostaining.

| Antibody | Dilution | Cat. No. | Company | Antigen Retrieval |
|---|---|---|---|---|
| RFP | 1:300 | 600-401-379S | Rockland | — |
| EpCAM | 1:100 | 552370 | BD Pharmingen | — |
| KRT7 | 1:1000 | ab181598 | Abcam | pH = 9 for 20 min at 95° C. for human tissue |
| KDR | 1:100 | 2479s | Cell signaling | pH = 9 for 20 min at 95° C. for human tissue |
| HNF4a | 1:200 | ab201460 | Abcam | — |
| CD26 | 1:100 | AF954-SP | R&D | — |
| KRT19 | 1:100 | 602-670 | Abbomax | — |
| YFP/GFP | 1:300 | A10262 | Life technologies | — |
| GS | 1:500 | MA5-27749 | Invitrogen | pH = 9 for 20 min at 95° C. for human tissue |
| p21 | 1:500 | ab188224 | Abcam | — |
| CD31 | 1:100 | 557355 | BD Pharmingen | — |

TABLE 8

List of conjugated antibodies used in flow cytometry.

| Antibody | Dilution | Cat. No. | Company |
|---|---|---|---|
| APC anti-mouse CD45 | 1:100 | 103112 | Biolegend |
| APC anti-mouse TER-119 | 1:100 | 116211 | Biolegend |
| APC anti-mouse CD31 | 1:100 | 102409 | Biolegend |
| APC anti-mouse/human CD11b | 1:100 | 101211 | Biolegend |
| BV605 Rat Anti-Mouse CD26 | 1:100 | BDB745125 | BD OptiBuild |
| APC/Cyanine7 anti-mouse CD326 (EpCAM) | 1:100 | 118217 | Biolegend |
| Rat anti-mouse CD16/32 (Fc Block) | 1:50 | 553141 | BD Pharmingen |

TABLE 9

Transgenic zebrafish lines used in this study.

| Names used in this study | Official names (ZFIN database) | Allele # | Reference |
|---|---|---|---|
| Tg(Tp1:H2B-mCherry) | Tg(EPV.Tp1-Mmu.Hbb:hist2h2l-mCherry) | s939 | [1] |
| Tg(fabp10a:CFP-NTR) | Tg(fabp10a:CFP-NTR) | s931 | [1] |
| Tg(hs:sflt1) | Tg(hsp70l:flt1, cryaa:Cerulean) | bns80 | [2] |
| Tg(Tp1:CreERT2) | Tg(EPV.Tp1-Mmu.Hbb:Cre-ERT2, cryaa:mCherry) | s959 | [1] |
| Tg(hs:loxP-mCherry-loxP-hVEGFA) | Tg(hsp70l:LOXP-mCherry-LOXP-Hsa.VEGFA, XIa.Cryg:EGFP) | mn32 | [3] |

TABLE 10

List of conjugated antibodies used in western blot.

| Antibody | Host | Company | Cat. No. | Dilution |
|---|---|---|---|---|
| HNF4A | Mouse | Abcam | Ab41898 | 1:1000 |
| KDR | Rabbit | Cell Signaling | 2479s | 1:1000 |
| CD31 | Rabbit | Abcam | Ab32457 | 1:2500 |
| KRT19 | Mouse | Progen | 61029 | 1:500 |
| KRT7 | Mouse | Novus Biologicals | NBP2-44814 | 1:2000 |
| GAPDH | Mouse | Proteintech | 60004-1 | 1:10000 |

TABLE 11

List of human primers used for gene expression analysis in isolated human hepatocytes.

| Gene | | Primer Sequence | Amplicon length |
|---|---|---|---|
| hKRT7 | F: | GGACATCGAGATCGCCACCT (SEQ ID NO: 32) | 124 |
| | R: | ACCGCCACTGCTACTGCCA (SEQ ID NO: 33) | |
| h18s rRNA | F: | CTCAACACGGGAAACCTCAC (SEQ ID NO: 34) | 110 |
| | R: | CGCTCCACCAACTAAGAACG (SEQ ID NO: 35) | |
| hKDR | F: | ACTTTGGAAGACAGAACCAAATTATCTC (SEQ ID NO: 36) | 52 |
| | R: | TGGGCACCATTCCACCA (SEQ ID NO: 37) | |
| hAlbumin | F: | GTGAAACACAAGCCCAAGGCAACA (SEQ ID NO: 38) | 116 |
| | R: | TCCTCGGCAAAGCAGGTCTC (SEQ ID NO: 39) | |
| hHNF4a | F: | GGTGTCCATACGCATCCTTGAC (SEQ ID NO: 40) | 144 |
| | R: | AGCCGCTTGATCTTCCCTGGAT (SEQ ID NO: 41) | |

REFERENCES

1. Choi, T. Y., et al., *Extensive conversion of hepatic biliary epithelial cells to hepatocytes after near total loss of hepatocytes in zebrafish.* Gastroenterology, 2014. 146(3): p. 776-88.
2. Matsuoka, R. L., et al., *CNS-resident progenitors direct the vascularization of neighboring tissues.* Proc Natl Acad Sci USA, 2017. 114(38): p. 10137-10142.
3. Hoeppner, L. H., et al., *Revealing the role of phospholipase Cbeta3 in the regulation of VEGF-induced vascular permeability.* Blood, 2012. 120(11): p. 2167-73.

Methods

In vivo studies: All animal studies were approved by the Boston University IACUC and were consistent with local, state, and federal regulations as applicable. All experiments were done in an age and sex-controlled fashion unless otherwise noted. Krt19-Cre$^{ERT\ 1}$ and R26$^{LSL}$ tdTomato lines were obtained from Jackson Labs. Animals were housed under standard conditions with a 12-hour day/night cycle, in a pathogen-free environment with access to food and water ad libitum.

Generation of Kdr-2A-Cre$^{ERT2}$-2A-eYFP lines: The Kdr knock-in mouse allele was generated using direct delivery of CRISPR-Cas9 reagents to mouse zygotes. Nucleotide changes in the mouse Kdr gene (Ensembl Gene UID ENSMUSG00000062960) were introduced in the Ensembl Kdr-201 transcript (ENSMUST00000113516.1). The mutant allele inserts the Kdr-P2A-CRE.ERT2-P2A-YFP.

Gene Editing Design: Analysis of genomic DNA sequence surrounding the target region, using the Benchling (available on the world wide web at benchling.com) guide RNA (gRNA) design tool, identified one gRNA sequence with a suitable target endonuclease site in exon 30. Predicted off-target sites for the gRNA (sgRNA2-ACCTCCTGTT-TAAATGGAAG (SEQ ID NO: 42)) were identified using the specificity model developed and documented by Hsu and colleagues and embedded in the Benchling gRNA design tool[2]. Design considerations for off-target editing were as follows: higher off-target editing risk was considered when the "Score" is >2.0 with a canonical SpCas9 PAM (NGG), >50.0 with a chromosomally unlinked non-canonical PAM (NAG), or >20.0 with a linked non-canonical PAM yet in an annotated protein coding region. These "Score" thresholds were based on empirical targeted sequencing analysis of 20 different predicted off-target loci in 15 different mouse zygote gene editing experiments.

sgRNAs and plasmid donor DNA repair templates: *Streptococcus pyogenes* Cas9 (SpCas9) mRNA was purchased from Trilink (Product #L-7606, Trilink, USA). sgRNAs were synthesized as described[3]. The sequence of the double stranded DNA donor plasmid, that functions as the DNA repair template, was synthesized by Genscript. Features included asymmetric homology arm lengths of 3 kb and 2.2 kb, flanking the 2.8 kb insertion sequence.

In vitro cell line gRNA evaluation: Using a mouse kidney cell line and a T7 endonuclease cleavage assay, individual gRNA duplexes were evaluated for their ability to direct SpCas9 protein to the target locus and induce a double stranded DNA cleavage event. The immortalized mouse kidney cell line MK4 was infected with a lentivirus construct expressing a SpCas9-P2A-EGFP transgene. Infected cells were selected for high GFP expression using flow cytometry. 200 ng of the sgRNA duplexes were transfected into 50,000 MK4-SpCas9-P2A-EGFP transgenic cells in a 24 well plate using MessengerMax (Product #LMRNA015, ThermoFisher-Invitrogen, USA) according to manufacturer's instructions; 200 ng mCherry mRNA (Product #L-7203, Trilink Biotechnologies, USA) was transfected in a separate well as a control. 24-48 hrs post-transfection, DNA lysates were prepared, and PCR was performed with primers flanking the DNA cleavage target site. PCR products were evaluated on agarose gels.

For evaluating the gRNA activity, the presence of small insertions/deletions (INDELs) in the population of PCR products was detected by denaturation and re-annealing of the PCR product and subsequent treatment with T7 endonuclease (Product #E3321, New England Biolabs, USA). T7 endonuclease cleaves heteroduplex DNA resulting from various INDELs in the population. Unique DNA cleavage products resulting from T7 endonuclease activity were resolved by agarose gel electrophoresis and compared to control transfection PCR products.

Preparation of gene editing reagents for mouse embryo microinjection: The gene editing reagents were prepared for microinjection as described previously[3]. Briefly, 500 ng/ul of Cas9 mRNA, 500 ng/ul of sgRNA and 500 ng/ul donor plasmid were assembled in DNase/RNase free TE buffer, centrifuged and the supernatant collected and delivered for microinjection, all kept on ice or at 4° C.

Zygote isolation, microinjection and embryo transfer: All animal work was approved by the Jackson Laboratory Animal Care and Use Committee and adhered to the standards of the Guide for the Care and Use of Laboratory Animals set forth by the NIH. Fertilized mouse embryos were generated via natural mating and cultured as described previously[3]. C57BL/6J (Stock #000664, The Jackson Laboratory, USA) donor female mice (3-4 weeks of age) were superovulated by administration of 5 IU of pregnant mare serum gonadotrophin (PMSG) via intraperitoneal (ip) injection (Product #HOR-272 ProSpec, Israel) followed 47 hr later by 5 IU (ip) human chorionic gonadotrophin (hCG) (Product #HOR-250, ProSpec, Israel). Immediately post-administration of hCG, the female was mated 1:1 with a C57BL/6J stud male and 22 hr later checked for the presence of a copulation plug. Female mice displaying a copulation plug were sacrificed, the oviducts excised, and embryos collected. Microinjection was performed as described[3]. In brief, zygotes were microinjected on a Zeiss AxioObserver.D1™ using Eppendorf NK2 micromanipulators in conjunction with Narashige IM-5A injectors. Embryos were immediately transferred into B6Qsi5F1 pseudopregnant female mice, a F1 hybrid strain produced by breeding C57BL/6J female mice with the inbred Quackenbush Swiss line 5 (QSi5) mouse strain.

Sequence characterization of Founder and N1 mice: PCR primers flanking the gRNA target site, but outside the repair template homology arms, were used to amplify the region of interest from founder progeny. PCR amplicons were subjected to Sanger sequencing to identify founders with precise desired changes. Founders carrying desired mutations were bred with C57BL/6J mice (Stock #000664, The Jackson Laboratory, USA) to produce N1 progeny. N1 animals were confirmed by the same PCR-Sanger sequence analysis the founder population was subjected to. In contrast to founders, N1 animals are obligate heterozygotes, with one allele derived from an un-manipulated chromosome, enabling deconvolution of the two alleles in the mixed PCR amplicon.

Acetaminophen (APAP) induced acute injury model: Mice were fasted overnight for a period of 14-15 h prior to APAP injections. APAP was administered at a concentration of 20 mg/ml, which was freshly dissolved in sterile PBS at 56° C. After complete dissolution, the stock was cooled down to room temperature. A single intraperitoneal injection was administered to male and female mice which received either 300 mg/kg or 500 mg/kg body weight of APAP, respectively, unless otherwise mentioned. Mice were maintained on normal chow diet and water ad libitum after APAP injections.

CDE diet induced chronic injury model: For inducing the liver injury 7 to 8 week-old male or female mice were given choline-deficient diet (EnvigoTeklad Diets, TD.140207 Choline Deficient Diet with 20% Lard and Irradiated) for one week and then supplemented with 0.10% ethionine in drinking water (Acros Organics, 146170100) for another 2 weeks. The mice were either sacrificed at the end of diet or changed to choline-sufficient diet along with normal drinking water until termination.

Tamoxifen administration and viral infections: Tamoxifen (Sigma-Aldrich) was dissolved in corn oil. For experiments involving Krt19-Cre$^{ER}$T2×R26$^{LSL}$ tdTomato lines, three individual intraperitoneal tamoxifen injections (20 mg/ml) were given at a dose of 4 mg/20 gm body weight of mice for three alternate days. The AAV8 viral vectors were administered 2 weeks after the last tamoxifen injection. p21 plasmid was packaged into the AAV8.TBG vector by the Penn Vector Core. The null vector, AAV8-Ctrl plasmid (AAV8.TBG.PI.Null.bGH, Cat No: AV-8-PV0148) was also obtained from the Penn Vector Core. Viral vectors were diluted in sterile PBS and administered by tail vein or retro-orbital injections with BD Ultra-Fine Insulin Syringes at a viral titer of 5×10$^{11}$ copies in total volume of 100 uL. For experiments involving Kdr-2A-Cre$^{ERT2}$-2A-eYFP, R26$^{LSL}$tdTomato lines, additional 3 tamoxifen injections were given to the mice around the injury as indicated in FIG. 4C and FIG. 5A.

mRNA-LNP formulation and delivery: mRNAs were produced as previously described[4] using T7 RNA polymerase (Megascript, Ambion) on a linearized plasmid encoding codon-optimized[5] vascular endothelial growth factor A (VEGFA) (Table 6) or firefly luciferas. mRNAs were transcribed to contain 101 nucleotide-long poly(A) tails. One-methylpseudouridine (m1Ψ)-5'-triphosphate (TriLink) instead of UTP was used to generate modified nucleoside-containing mRNA. RNAs were capped using the m7G capping kit with 2'-O-methyltransferase (ScriptCap™, CellScript™) to obtain cap1. mRNAs were purified by Fast Protein Liquid Chromatography (FPLC) (Akta Purifier, GE Healthcare) or with cellulose purification as described[6]. All mRNAs were analyzed by agarose gel electrophoresis and were stored frozen at −20° C. All nucleoside-modified mRNA are available from the company RNAx. Poly(C) RNA (Sigma) and purified m1Ψ-containing VEGFA and luciferase mRNAs were encapsulated in LNP using a self-assembly process in which an aqueous solution of mRNA at pH=4.0 is rapidly mixed with a solution of an ionizable cationic lipid, phosphatidylcholine, cholesterol, and polyethylene glycol-lipid dissolved in ethanol[7]. The ionizable cationic lipid (pKa in the range of 6.0-6.5, proprietary to Acuitas Therapeutics) and LNP composition are described in the patent application WO 2017/004143. They had a diameter of ~80 nm with a polydispersity index of <0.1 as measured by dynamic light scattering using a Zetasizer Nano ZS™ (Malvern Instruments Ltd, Malvern, UK) instrument and an encapsulation efficiency of ~95% as determined using a Ribogreen™ assay. mRNA-LNP formulations were stored at −80° C. at a concentration of mRNA of ~1 g/l. VEGFA-mRNA-LNP as well as control Poly(C) RNA-LNP and Luciferase mRNA-LNP were delivered intravenously through retro-orbital sinus. Prior to administration, mRNA-LNPs were thawed and diluted on ice in Dulbecco's Phosphate Buffered Saline (PBS). Mice were injected with 50 µL of diluted mRNA-LNP (10 µg) intravenously by retro-orbital injections using BD Ultra-Fine Insulin Syringes.

Animal tissue harvesting, cryopreservation and serum collection: Mice were sacrificed at their indicated endpoints. The liver was separated into its respective lobes, collected directly in 4% paraformaldehyde (PFA), and kept overnight at 4° C. prior to OCT embedding. For cryopreservation, tissues were washed thrice with PBS and dipped in 15% sucrose solution for 15 min and transferred to and kept in 30% sucrose solution till they sunk to the bottom. The tissues were then embedded in OCT. The cryopreserved blocks were stored at −80° C. Livers were sectioned at 5 μm thickness using a cryostat (model CM3050 S™; Leica, Wetzlar, Germany) and stored at −20° C. until required for subsequent staining. For serum separation, blood was collected immediately after euthanizing the mice and prior to liver extraction and kept at room temperature for 30 min. Serum was separated from blood cells by centrifugation at 2500×g for 15 min.

Histology, immunohistochemistry and immunofluorescence image analysis: The frozen sections were allowed to defrost and dry at room temperature for 30 min. The slides were dipped in PBS for 10 min and permeabilized using 0.3% triton X in PBS for 10 min. The slides were rinsed thrice in PBS, 10 minutes each, and blocked with 3% normal donkey serum for 30 min. The sections were then incubated overnight at 4° C. with appropriate antibody diluted in PBS at concentrations indicated in Table 7. Following primary antibody incubations, the slides were washed thrice with PBS, 10 min each, and incubated with the corresponding fluorescent labeled secondary antibodies for 1 h at room temperature protected from light. The slides were finally washed, incubated with Dapi for 3-5 min, rinsed, and mounted using FluorSave™ reagent (EMD Millipore Corp., 345789). ImageJ™ version 2.3.0/1.53f was used for image analysis as well as quantifications.

Periodic acid-Schiff staining: For staining hepatic glycogen, PAS Staining kit from Sigma Aldrich (395B) was used. Briefly, PFA-fixed, frozen tissue sections were brought to room temperature and hydrated with $dH_2O$ for 10 min. Subsequently, sections were oxidized in 1% periodic acid for 5 min, rinsed in several changes of $dH_2O$ and incubated in Schiff's Reagent for 15 min. After rinsing in $dH_2O$ twice for 5 min each, the tissue was counterstained with hematoxylin for 15 seconds, rinsed, and dehydrated before mounting with permanent mounting solution.

H&E staining: PFA-fixed frozen sections were washed in tap water and dipped for 5 min in hematoxylin (Gill's or Harris), followed by washing in tap water twice for 2 min. Sections were treated with Bluing Reagent (ammonia water) for 10-15 seconds, washed twice and dipped in 100% ethanol. Eosin was applied to sections for 15 sec, thereafter, the slides were washed several times in 100% ethanol, cleared with Histoclear for 5 min, and mounted using permanent mounting media.

Oil Red O staining: Lipid staining was performed on frozen-fixed liver tissue sections using the isopropanol method. Briefly, sections were rinsed with 60% isopropanol and stained with freshly prepared Oil Red O (Sigma) solution for 15 min. Slides were rinsed twice with 60% isopropanol and nuclei were lightly stained using hematoxylin solution. Slides were washed, mounted, and observed under bright-field microscope.

LipidSpot staining: To detect lipid accumulation in liver tissue, another method based on fluorescent detection of lipids was performed using LipidSpot™ Lipid Droplet Stains from Biotium (70065-T). Liver sections were defrosted for 30 minutes at room temperature, followed by an immersion in 1×PBS for 10 minutes at room temperature. Sections were then incubated with a mixture of LipidSpot™ (1:1000) and Dapi (1:3000) diluted in PBS for 10 minutes at room temperature. The slides were washed twice with PBS for 10 minutes and then mounted with FluorSave™ mounting media (Calbiochem) and imaged on Nikon Eclipse Ni-E upright fluorescent microscope.

Trichrome staining: Connective Tissue Staining was performed using Trichrome Staining kit (ab150686, Abcam) following the manufacturer's instructions. All materials were equilibrated and prepared at room temperature just prior to use. Frozen sections were hydrated in distilled water prior to staining.

Serum cholesterol assay: Serum analysis was performed using commercially available Total Cholesterol kit from FUJIFILM Wako Diagnostics (999-02601). Briefly, total cholesterol assay was adapted for a 96-well plate by using 5 uL of serum with 200 uL of test reagent. After incubation at 37° C. for 5 minutes, reactions were read at 600 nm and cholesterol levels were calculated from standard curve.

Human VEGFA (hVEGFA) ELISA with mouse serum: To detect protein expression from hVEGFA-mRNA, serum levels of hVEGFA were analyzed using VEGFA human ELISA Kit (ab119566, Abcam) following the manufacturer's instructions. Mice (n=3) were injected with hVEGFA mRNA-LNP (10 μg) through retro-orbital sinus injection and their serum was collected 5 h, 24 h, 48 h, and 72 h post-injection through submandibular bleed. Serum samples collected at 5 h were diluted 10000-fold, 24 h samples were diluted 5000-fold, 48 h samples were diluted 10-fold while those collected 72 h post-injection were diluted 2-fold. Prior to use all reagents were prepared and equilibrated at room temperature. Samples along with the standards were processed according to the manufacturers protocol and the hVEGFA concentrations were calculated from the standard curve.

Flow cytometry of isolated non-parenchymal cells and hepatocytes: Liver was perfused according to the previously published method[8]. Hepatocyte and non-parenchymal cell fractions were seeded into 100 μl wells and treated with 1 μg/100 μl Fc Block (BD Pharmingen #553141) for 10 minutes at room temperature. Wells were then incubated with primary conjugated antibodies for 20 minutes at room temperature (Table 8). Following antibody incubation, cells were washed and resuspended in FACS buffer. Dapi (1:100, Invitrogen, R37606) was added to the flow tubes 5 min prior to flow run. Cells were run on BD LSR II SORP™ flow cytometer and data analyzed with FlowJo v10 software. Care was taken to include appropriate compensation controls for each run. UltraComp eBeads (Invitrogen, 01-2222-42) were used for running compensation controls for APC, APC-Cyanine7 and BV605 conjugated antibodies, while Dapi treated non-parenchymal cell (NPC) fractions from a non-tdTomato mouse were used to compensate Dapi channel. Likewise, unlabeled NPCs from tdTomato mouse were used to compensate for tdTomato channel. At least 1,00,000 cells were analyzed for each fraction. Cells in both the hepatocyte fraction or non-parenchymal cell fraction were first gated to eliminate dead cells positive for Dapi. The SSC and FSC parameters were used to eliminate cell debris. The cells were then gated to exclude blood cells positive for Ter119/CD45/CD11b/CD31. The remaining cells in NPC fraction were gated for EpCAM+ and then evaluated for tdtomato positive cells as shown in the gating strategy Supplementary FIG. 15a, while those in hepatocyte fractions were analyzed for tdtomato (FIG. 15B).

Experiments on zebrafish: All zebrafish experiments were performed under the approval of the IACUC at the University of Pittsburgh. Embryos and adult fish were raised and maintained under standard laboratory conditions. The following transgenic lines were used: Tg(fabp10a:CFP-NTR) s931, Tg(Tp1:H2B-mCherry)s939, Tg(hs:sflt1)bns80, Tg(Tp1:CreERT2)s959, and Tg(hs:loxP-mCherry-loxP-hVEGFA)mn32. Their full and official names are listed in Table 9.

Hepatocyte ablation using the Tg(fabp10a:CFP-NTR) line: Hepatocyte ablation was performed by treating Tg(fabp10a:CFP-NTR) larvae with 10 mM Mtz in egg water supplemented with 0.2% DMSO and 0.2 mM 1-phenyl-2-thiourea from 3.5 to 5 dpf for 36 hours, as previously described[9].

SU5416 treatment: SU5416 (MedChemExpress, Monmouth Junction, NJ) was used at 1.5 µM.

Heat-shock conditions for zebrafish larvae: Both Tg(hs:sflt1) and Tg(hs:loxP-mCherry-loxP-hVEGFA) larvae were heat-shocked by transferring them into egg water prewarmed to 38.5° C. and keeping them at this temperature for 20 minutes, as previously described[10].

Whole-mount in situ hybridization and immunostaining in zebrafish: Whole-mount in situ hybridization was performed, as previously described[11], with gc[12] and f5 probes. For f5 probe synthesis, cDNA from 5-dpf larvae was used as a template together with a forward (5'-CCCTCCTGGCATTCCTGTGTC-3' (SEQ ID NO: 43)) and a reverse (5'-TAATACGACTCACTATAGGG-CATGGTGGGTCTGCAGCTGT-3' (SEQ ID NO: 44)) primer pair to amplify f5; its PCR products were used to make in situ probes. [Bold is T7 primer sequence.] Whole-mount immunostaining was performed, as previously described[13], with mouse anti-Bhmt (1:500; gift from Jinrong Peng at Zhejiang University) and Alexa Fluor 647-conjugated secondary antibodies (1:500; Thermo Fisher Scientific, Waltham, MA).

Quantification of Bhmt+ cell number and Bhmt+ area in the zebrafish liver: For the quantification of Bhmt+ cell number, confocal projection images consisting of 6 optical-section images, with 3-µm interval, were used. Bhmt+ and Tp1:H2B-mCherry+ cells were manually counted; the number of Bhmt/Tp:H2B-mCherry double-positive cells was divided by the number of Tp1:H2B-mCherry+ cells. For the quantification of Bhmt+ liver area, confocal projection images showing Bhmt and fabp10a:CFP-NTR expression were used. Both Bhmt+ and fabp10a:CFP-NTR+ areas in the liver were calculated by ImageJ and the former area was divided by the latter.

Image acquisition, processing, and statistical analysis of zebrafish data: Zeiss LSM700 confocal and Leica MZ16 microscopes were used to obtain image data. Confocal stacks were analyzed using the Zen 2009 software. All figures, labels, scale bars and outlines were assembled or drawn using the Adobe Illustrator software. Statistical analyses were performed using the GraphPad Prism™ software. Differences between groups were tested by unpaired Student's t-tests and considered statistically significant when P<0.05 (*P<0.05, P<0.01, *P<0.001, ****P<0.0001). Quantitative data were shown as mean±standard error of the mean (SEM).

Collection of human liver specimens and hepatocyte isolation: Adult human liver cells were obtained from the Human Synthetic Liver Biology Core at the Pittsburgh Liver Research Center. The Institutional Review Board at the University of Pittsburgh has approved the protocol and given the Not Human Research Determination. The IRB #STUDY20090069. Hepatocytes were isolated using a three-step collagenase digestion technique as previously described[14]. Cell viability was assessed after isolation as previously described using trypan blue exclusion, and only cell preparations with viability >80% were used for the analysis. Information about the human liver specimens and hepatocytes used in this study can be found in Table 4 and 5.

Human liver tissue staining: Paraffin-embedded liver samples from diseased donors were used as normal liver tissue (n=3). Liver samples from patients with NASH (n=4) and alcoholic cirrhosis (n=1) were fixed overnight in 4% paraformaldehyde (PFA) at 4 C. For cryopreservation, tissues were washed thrice with PBS and dipped in 15% sucrose solution for 15 min and transferred to and kept in 30% sucrose solution till they sunk to the bottom. The tissues were then embedded in OCT. The cryopreserved blocks were stored at −80° C. Livers were sectioned at 5 µm thickness using a cryostat (model CM3050 S; Leica, Wetzlar, Germany) and stored at −20° C. until required for subsequent staining. For all immunofluorescence staining on human liver tissues, antigen-retrieval was performed in Tris-EDTA buffer ph=9 (Vector Labs) for 20 min at 95 C followed by conventional permeabilization, blocking and antibody incubation steps as detailed earlier.

Western blot: Details regarding the antibodies and their corresponding dilutions are listed in Supplementary Table 7. All samples were incubated with RIPA lysis buffer (Sigma-Aldrich, Saint Louis, MO) containing 1× Halt™ Protease and Phosphatase Inhibitor Cocktail (Thermo Fisher Scientific, Waltham, MA) and incubated for 30 min at 4° C. Samples were centrifuged at 13,000×g for 10 min at 4° C. The supernatant from each sample was then transferred to a new microfuge tube and was used as the whole cell lysate. Protein concentrations were determined by comparison with a known concentration of bovine serum albumin using a Pierce BCA Protein Assay Kit (Thermo Fisher Scientific, Waltham, MA). About 30 µg of lysate were loaded per lane into 10% Mini-PROTEAN TGX gel (BioRad, Hercules, CA). After SDS-PAGE, proteins were transferred onto PVDF membrane (Thermo Fisher Scientific, Waltham, MA). Membranes were incubated with primary antibody solution overnight and then washed. Membranes were incubated for 1 hour in secondary antibody solution and then washed. Target antigens were finally detected using SuperSignal™ West Pico PLUS chemiluminescent substrate (Thermo Fisher Scientific, Waltham, MA). Images were scanned and analyzed using ImageJ™ software.

Real-time PCR: cDNA samples from human cirrhotic and normal hepatocytes were generated from 2 ug of RNA using the RevertAid™ First Strand cDNA Synthesis Kit (Thermo Scientific, #K1621). Commercially available human liver total RNA (Invitrogen, AM7960) was used as positive control. Information regarding primers used in the study are provided in Table 11. Real-time PCR reaction was performed using SYBR Green PCR Master Mix (Applied Biosystem, 4309155) following manufacturers protocol and run on QuantStudio 6 Flex™ Real-Time PCR System (Applied Biosystem).

Statistical analyses: All statistical analyses were performed using GraphPad Prism™ 9. For comparison between two mean values a 2-tailed Student's t-test was used to calculate statistical significance. For comparing multiple groups to a reference group one-way ANOVA followed by Tukey's multi-comparison test was performed. Quantitative data are shown as mean standard deviation (SD) and are considered statistically significant when p<0.05 (*p<0.05, p<0.01, *p<0.001, ****p<0.0001).

REFERENCES

1. Means, A. L., Xu, Y., Zhao, A., Ray, K. C. & Gu, G. A CK19 (CreERT) knockin mouse line allows for condi- 1. tional DNA recombination in epithelial cells in multiple endodermal organs. *Genesis* 46, 318-323 (2008).
2. Hsu, P. D. et al. DNA targeting specificity of RNA-guided Cas9 nucleases. *Nat Biotechnol* 31, 827-832 (2013).
3. Qin, W. et al. Efficient CRISPR/Cas9-Mediated Genome Editing in Mice by Zygote Electroporation of Nuclease. *Genetics* 200, 423-430 (2015).
4. Pardi, N., Muramatsu, H., Weissman, D. & Kariko, K. In vitro transcription of long RNA containing modified nucleosides. *Methods Mol Biol* 969, 29-42 (2013).
5. Thess, A. et al. Sequence-engineered mRNA Without Chemical Nucleoside Modifications Enables an Effective Protein Therapy in Large Animals. *Mol Ther* 23, 1456-1464 (2015).
6. Weissman, D., Pardi, N., Muramatsu, H. & Kariko, K. HPLC purification of in vitro transcribed long RNA. *Methods Mol Biol* 969, 43-54 (2013).
7. Pardi, N. et al. Expression kinetics of nucleoside-modified mRNA delivered in lipid nanoparticles to mice by various routes. *J Control Release* 217, 345-351 (2015).
8. Everton, E. et al. Transient yet Robust Expression of Proteins in the Mouse Liver via Intravenous Injection of Lipid Nanoparticle-encapsulated Nucleoside-modified mRNA. *Bio Protoc* 11, e4184 (2021).
9. Choi, T. Y., Ninov, N., Stainier, D. Y. & Shin, D. Extensive conversion of hepatic biliary epithelial cells to hepatocytes after near total loss of hepatocytes in zebrafish. *Gastroenterology* 146, 776-788 (2014).
10. Shin, D. et al. Bmp and Fgf signaling are essential for liver specification in zebrafish. *Development* 134, 2041-2050 (2007).
11. Alexander, J., Stainier, D. Y. & Yelon, D. Screening mosaic F1 females for mutations affecting zebrafish heart induction and patterning. *Dev Genet* 22, 288-299 (1998).
12. Noel, E. S., Reis, M. D., Arain, Z. & Ober, E. A. Analysis of the Albumin/alpha-Fetoprotein/Afamin/Group specific component gene family in the context of zebrafish liver differentiation. *Gene Expr Patterns* 10, 237-243 (2010).
13. Choi, T. Y., Khaliq, M., Ko, S., So, J. & Shin, D. Hepatocyte-specific ablation in zebrafish to study biliary-driven liver regeneration. *J Vis Exp*, e52785 (2015).
14. Gramignoli, R. et al. Development and application of purified tissue dissociation enzyme mixtures for human hepatocyte isolation. *Cell Transplant* 21, 1245-1260 (2012).

Example 2: Growth Hormone Accelerates Recovery from Acetaminophen-Induced Murine Liver Injury Background and Aims: Acetaminophen (APAP) overdose is the leading cause of acute liver failure, with one available treatment, N-acetyl cysteine (NAC). Yet, NAC effectiveness diminishes about ten hours after APAP overdose, urging for therapeutic alternatives. This study addresses this need by deciphering a mechanism of sexual dimorphism in APAP-induced liver injury, and leveraging it to accelerate liver recovery via growth hormone (GH) treatment. GH secretory patterns, pulsatile in males and near-continuous in females, determine the sex bias in many liver metabolic functions. Here, the inventors establish GH as a novel therapy to treat APAP hepatotoxicity.

Approach and Results: The inventors demonstrate sex-dependent APAP toxicity, with females showing reduced liver cell death and faster recovery than males. Single-cell RNA sequencing analyses reveal that female hepatocytes have significantly greater levels of GH receptor expression and GH pathway activation compared to males. In harnessing this female-specific advantage, the inventors demonstrate that a single injection of recombinant human GH protein accelerates liver recovery, promotes survival in males following sub-lethal dose of APAP, and is superior to standard-of-care NAC. Alternatively, slow-release delivery of human GH via the safe non-integrative lipid nanoparticle-encapsulated nucleoside-modified mRNA (mRNA-LNP), a technology validated by widely used COVID-19 vaccines, rescues males from APAP-induced death that otherwise occurred in control mRNA-LNP-treated mice.

Discussion: The inventors demonstrate a sexually dimorphic liver repair advantage in females following APAP overdose, leveraged by establishing GH as an alternative treatment, delivered either as recombinant protein or mRNA-LNP, to prevent liver failure and liver transplant in APAP-overdosed patients.

Introduction

Acetaminophen (acetyl-para-aminophenol, APAP) is consumed by over 60 million Americans weekly, making it the most frequently used analgesic and antipyretic in the US. Yet, APAP overdose is the most common cause of acute liver failure in the US[1]. Hepatotoxicity occurs when excess APAP overwhelms the urinary excretory pathway and is activated by the cytochrome P450 CYP2E1 metabolic pathway, generating the toxic metabolite N-acetyl-p-benzoquinone imine (NAPQI)[2-4]. Glutathione (GSH) binds and neutralizes NAPQI to a non-toxic metabolite; however, under overdose conditions, the rate of GSH synthesis is insufficient, leading to hepatocyte cell death[5-7]. The only treatment currently available is the administration of oral and intravenous N-acetyl cysteine (NAC), a precursor for GSH. However, NAC effectiveness rapidly diminishes within ten hours after APAP overdose[6-8], when organ toxicity is frequently still asymptomatic[9]. Here, the inventors address this unmet clinical need by taking advantage of the clinical[10-16] and pre-clinical[17-20] observation that females are more resistant to APAP toxicity, and in general to most liver diseases than males. Sex-specific hormones and their receptors drive sexual dimorphism in many liver processes in mice[18,21-24] including hepatocyte proliferation, GSH synthesis, drug metabolism, and cell cycle inhibition. Specifically, gonadal steroid-controlled pituitary GH secretory patterns, pulsatile in males and persistent/near-continuous in females[25], a pattern also observed in rodents[26-28], is the basis of sex bias in liver function, including metabolic activity and disease susceptibility[29]. Namely, STAT5b has been reported to be an essential transcriptional regulator of the sex-biased actions of GH in the liver contributing to 90% of differences in liver transcriptome[30]. The inventors demonstrate that females are more resistant to APAP toxicity than males. Single-cell RNA sequencing (scRNA-seq) analyses reveal that female hepatocytes express significantly higher levels of GH receptor (GHR) and GH pathway activation in comparison to male cells. As a result, the inventors leverage this sexually dimorphic response to APAP and demonstrate the therapeutic benefit of recombinant GH protein treatment over the standard-of-care NAC treatment to significantly and rapidly repair the liver in both sexes following sex-specific sub-lethal doses of APAP, albeit in a milder fashion in females. Importantly, the inventors also introduces the use of nucleoside-modified mRNA encoding GH complexed to lipid nanoparticles (mRNA-LNP) for safe and slow-release delivery to the liver as an alternative to recombinant protein bolus for treatment of APAP overdose, a delivery platform recently validated in mRNA-based COVID-19 vaccines.

Methods

Acetaminophen-induced liver injury mouse model. All mice used for the liver injury models are 10-12 week-old males and females inbred C57BL/6J from Jackson Laboratory. All animal studies were approved by the Boston University IACUC and were consistent with all local, state, and federal regulations as applicable. Mice were housed under standard conditions with a 12-hour day/night cycle, in a pathogen-free environment with access to food and water ad libitum. Acetaminophen (APAP; Spectrum Chemical Manufacturing Corporation cat #AC100125GM) was dissolved in sterile PBS to 20 mg/ml concentration at 56° C., then cooled to room temperature. APAP was injected intraperitoneally at 10 am for all experiments to remove circadian rhythm as a potential variable, following the Whitten effect[31-33] in which female mice were placed in cages with soiled male bedding 48 hours prior to injury, and a 14-hour fast, to allow synchronization of estrus cycle which may influence APAP-induced liver injury and repair, and to normalize glutathione levels from the diet that may influence liver damage among the mice, respectively. Mice were maintained on normal chow diet and water ad libitum after APAP injections. Mice were euthanized as per IACUC regulation using isoflurane and cervical dislocation. Liver tissue and blood serum were collected from each mouse at the respective day of sacrifice.

Results

APAP-Induced Liver Injury and Subsequent Repair are Sexually Dimorphic

Figures 16A, 16B:
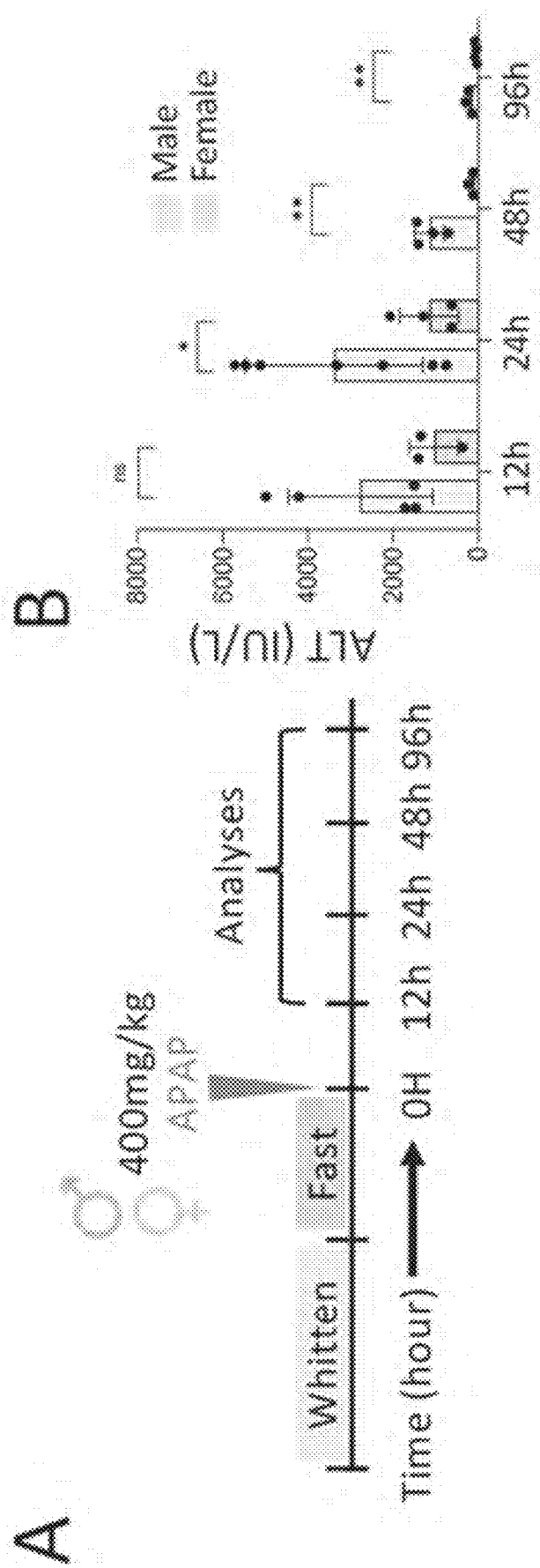
FIGS. 16A-16E depict liver necrosis and cell death are sexually dimorphic following administration of equivalent doses of APAP.
Figure 16C:
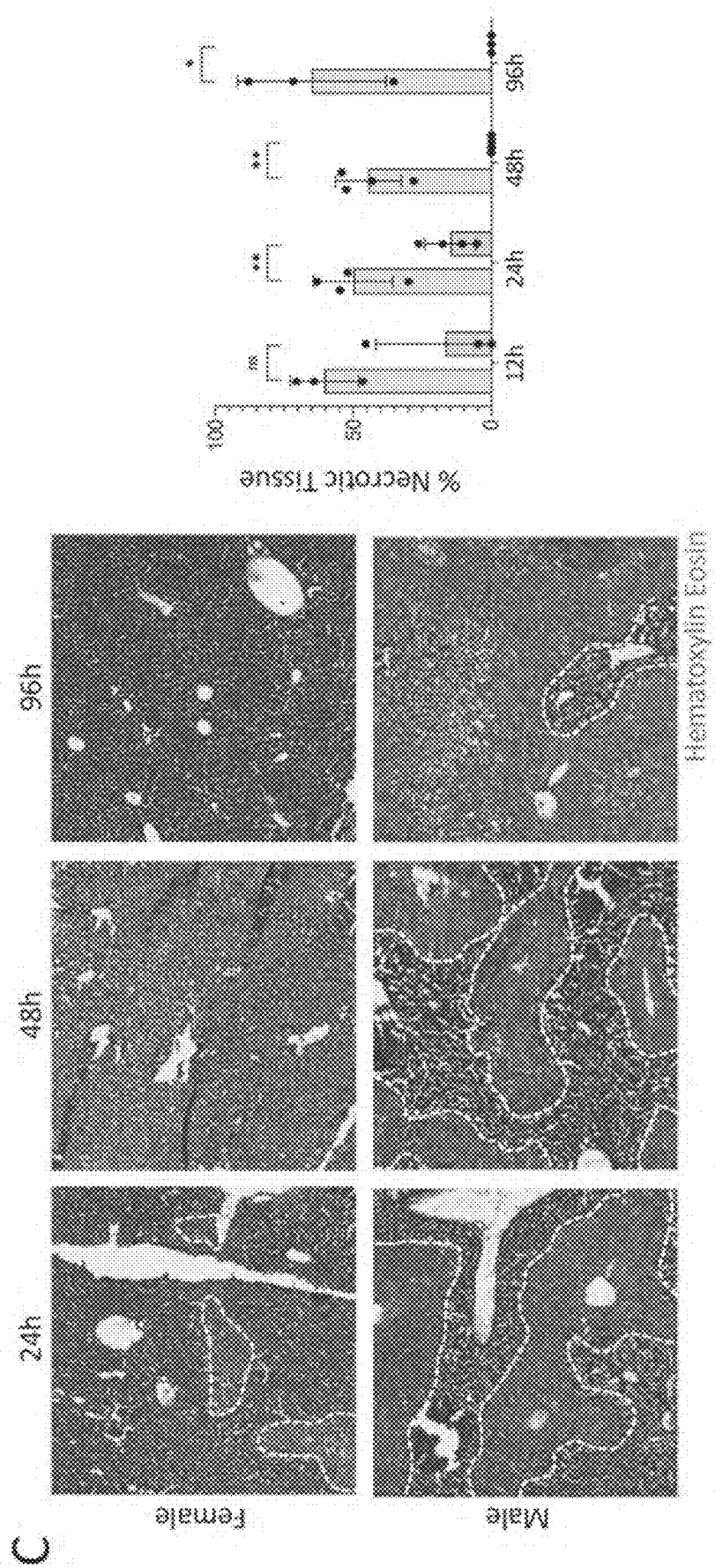
Figure 16D:
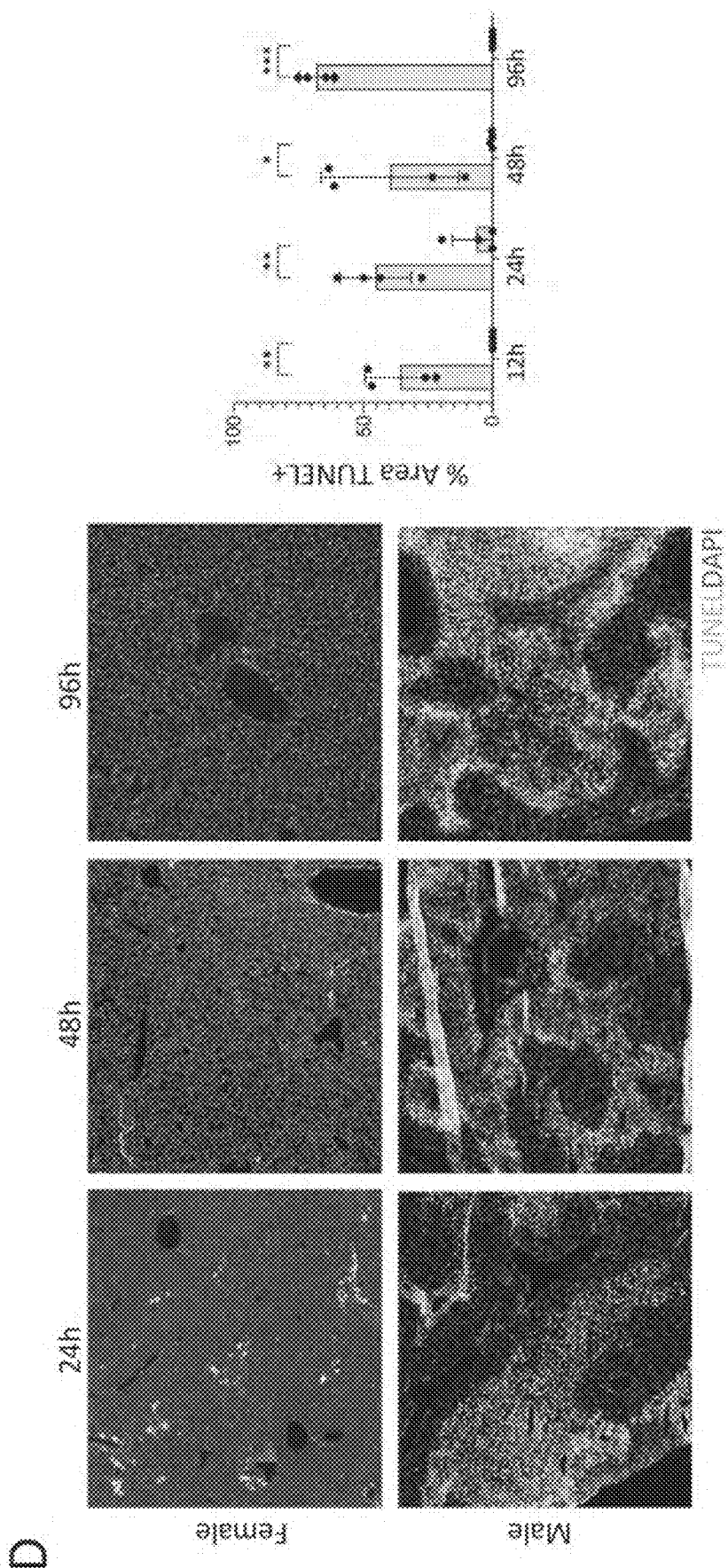
Figure 16E:
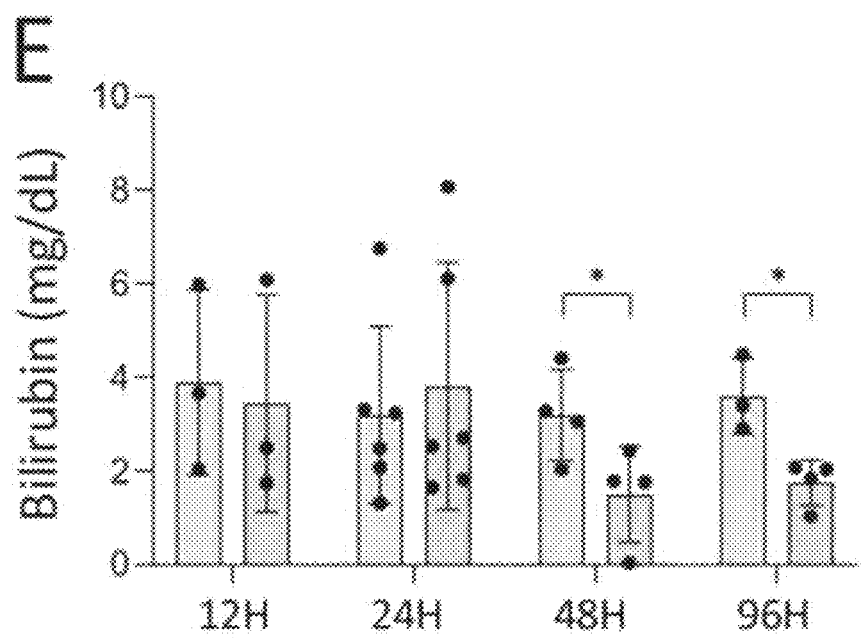

In dose response experiments in both sexes using a range of APAP doses from 300-650 mg/kg, previously validated by others mostly in male mice[34,35], the inventors found that 400 mg/kg APAP induces injury in both sexes without lethality up to 96 hours after APAP administration (FIGS. 16A-16E). Female mice were subjected to the Whitten effect, by replacing the female cage bedding with soiled male bedding to normalize estrus cycles of female mice[31-33], as variability in estrogen levels may impact liver regeneration[10,12,36-39] All mice were then fasted for 14 hours prior to APAP injection to bring liver metabolism to a baseline level and thus help normalize injury[34,35] (FIG. 16A). Sexually mature male and female mice were injected intraperitoneally (IP) with APAP or PBS vehicle control, and euthanized 12, 24, 48, and 96 hours later. Serum alanine aminotransferase (ALT) levels, indicative of liver damage, were consistently higher in males than in females at all-time points post-24 hours (FIG. 16B). Acute central vein area necrosis was seen in both sexes 24 hours after APAP injection, consistent with the localization of CYP enzymes metabolizing APAP[3,40]. Necrosis was more extensive in male livers and progressively increased overtime, whereas female livers fully recovered by 48 hours (FIG. 16C). Cell death, as indicated by TUNEL assay, showed a similar sex difference (FIG. 16D). Consistent with the histological data, serum bilirubin persisted for 96 hours in males but decreased after 48 hours in females, supporting recovery in females that is not seen in males (FIG. 16E). Thus, males are more susceptible than females to APAP hepatotoxicity as characterized by progressive, unresolved necrosis and apoptosis that most likely prevent liver regeneration.

Figures 17A, 17B:
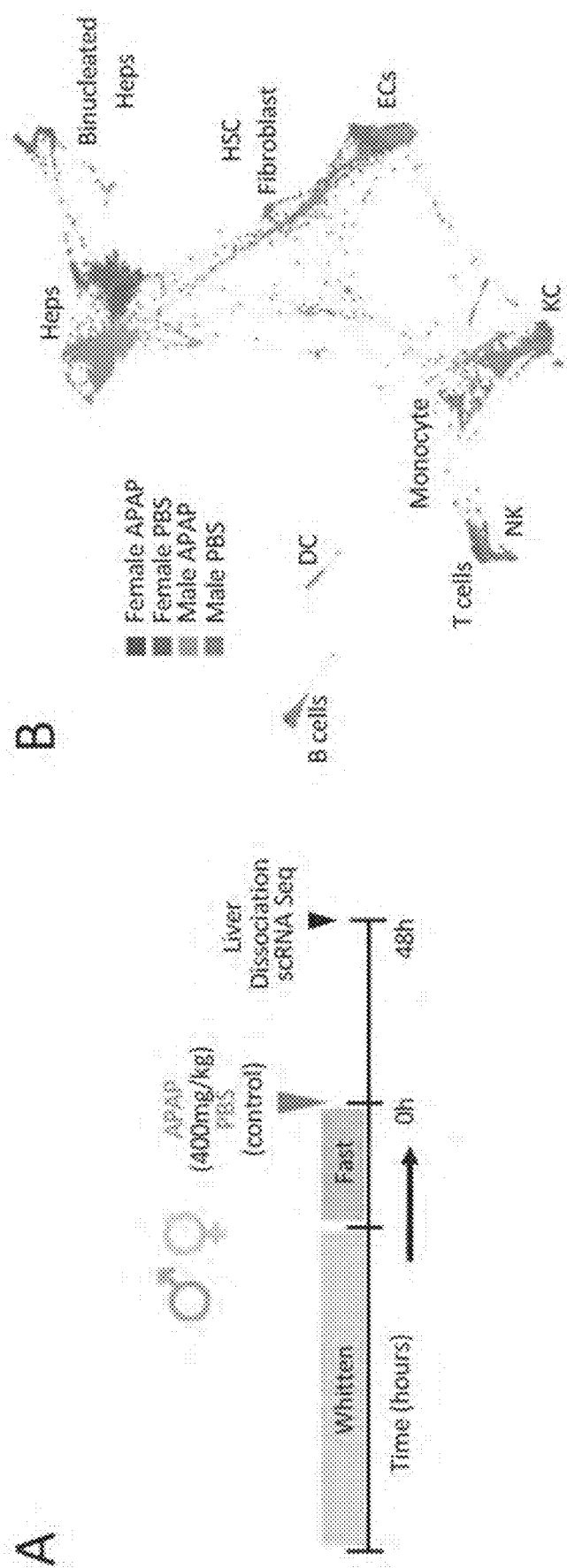
FIGS. 17A-17E depict male and female livers exhibit distinct transcriptional responses to acetaminophen-induced liver injury.
Figure 17C:
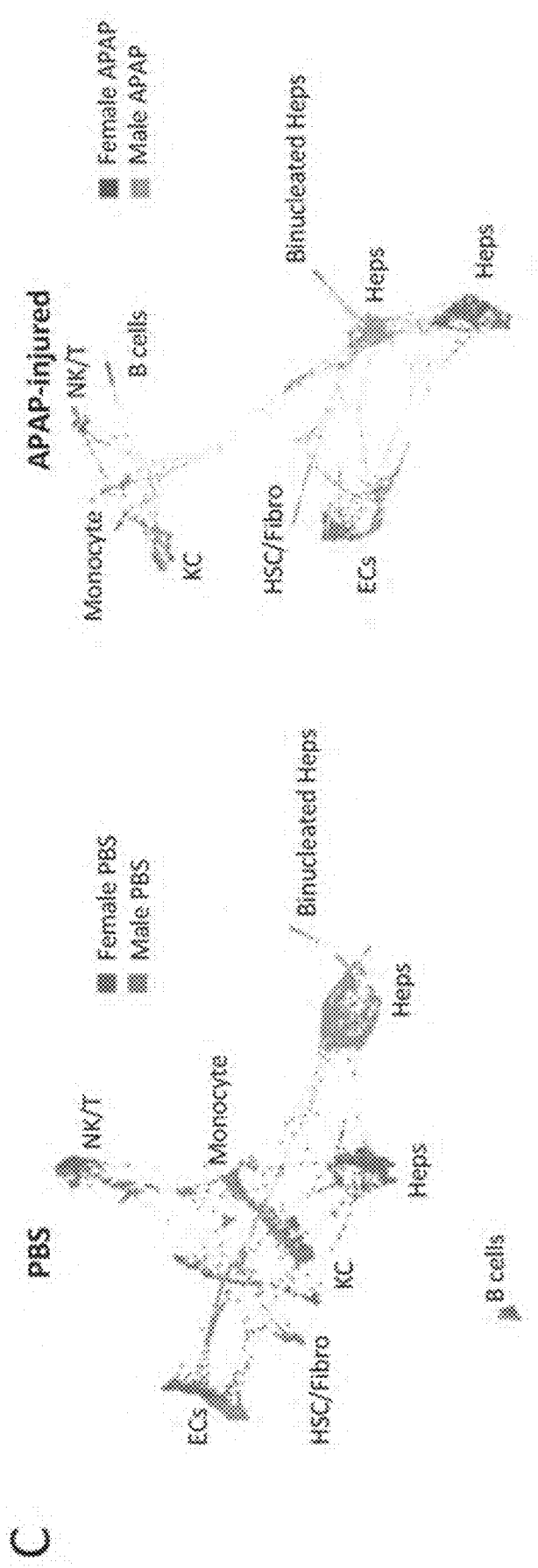
Figure 17D:
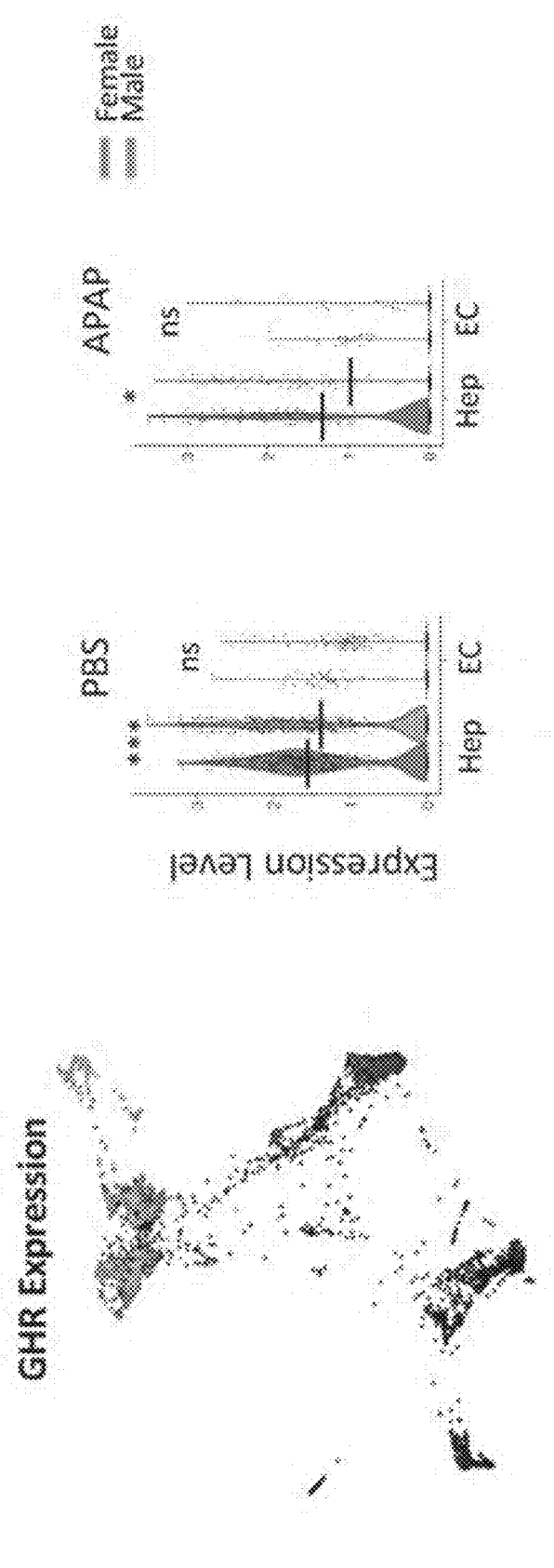
Figure 17E:
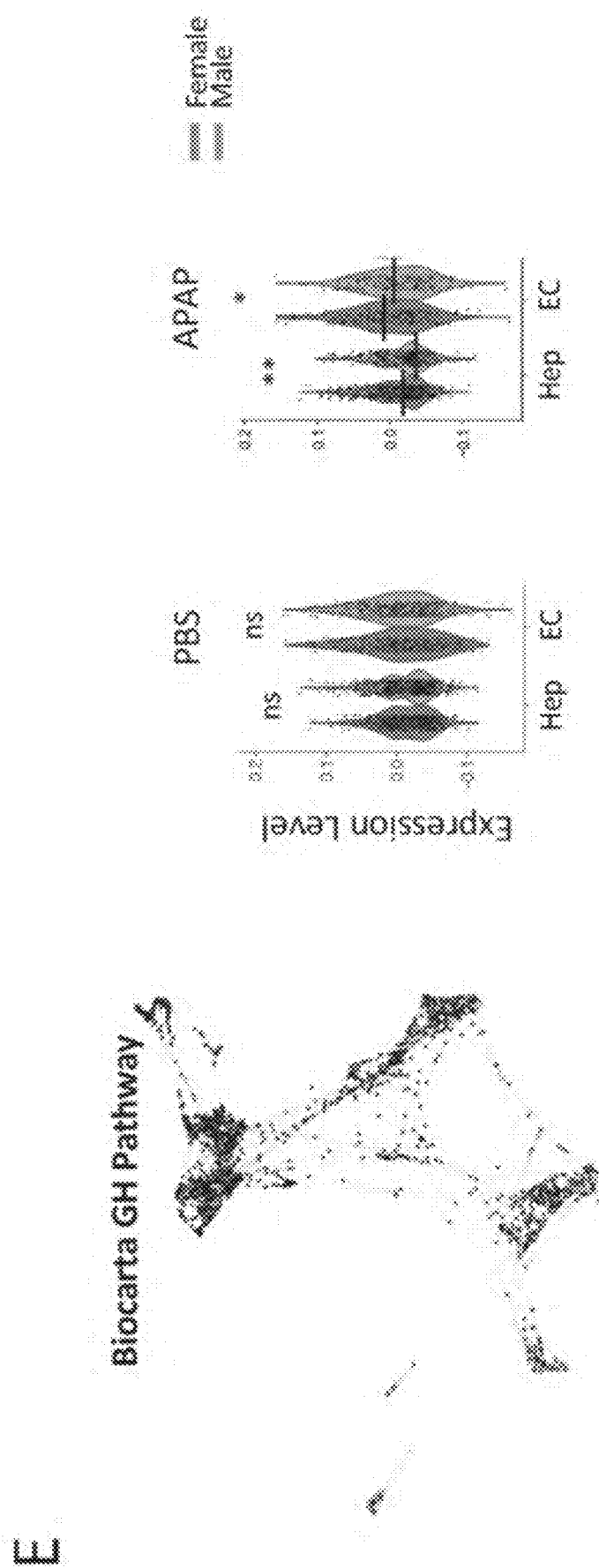
Figure 21A:
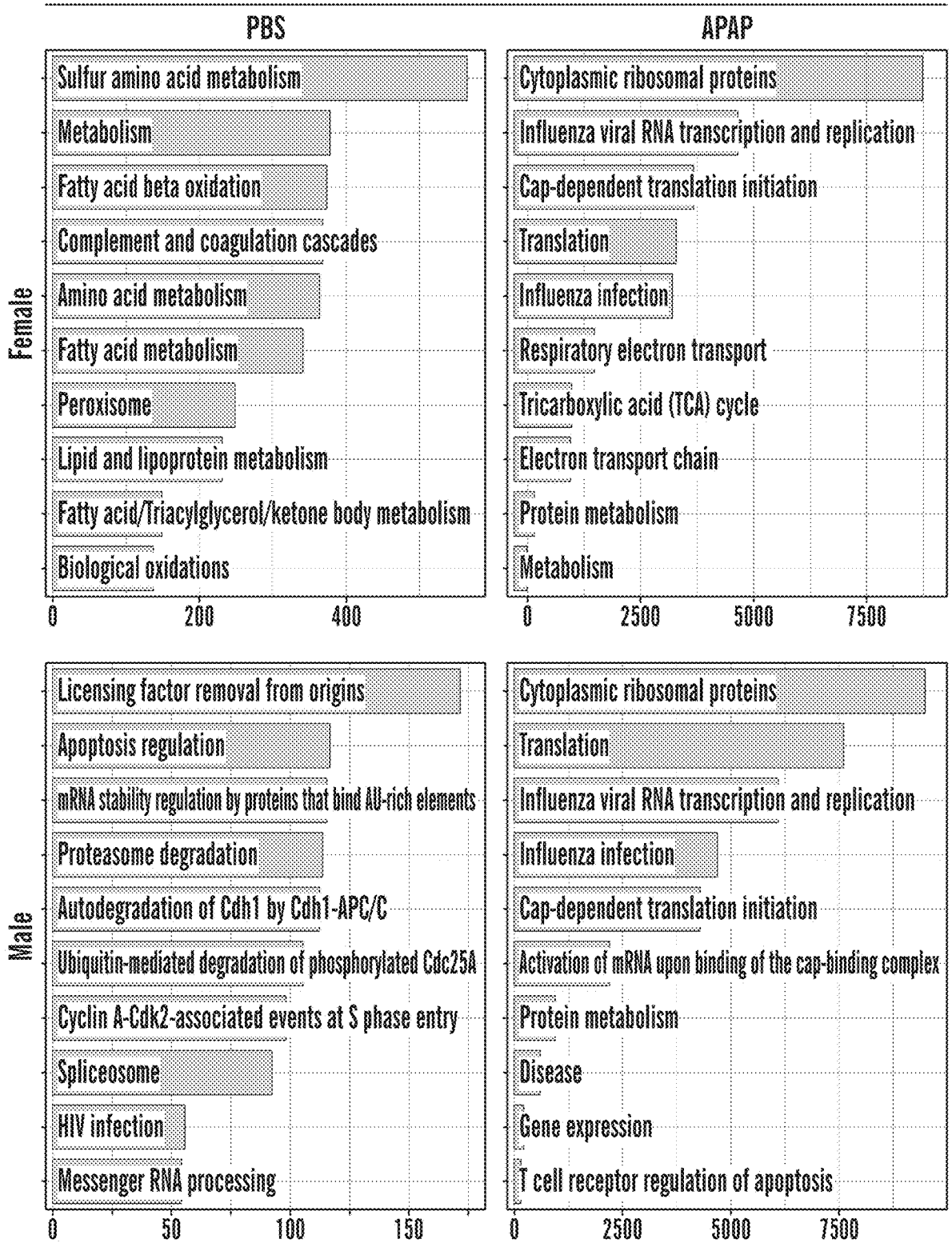
FIG. 21A-21C depict Male and female hepatocytes and endothelial cells are transcriptionally distinct.
Figure 21A:
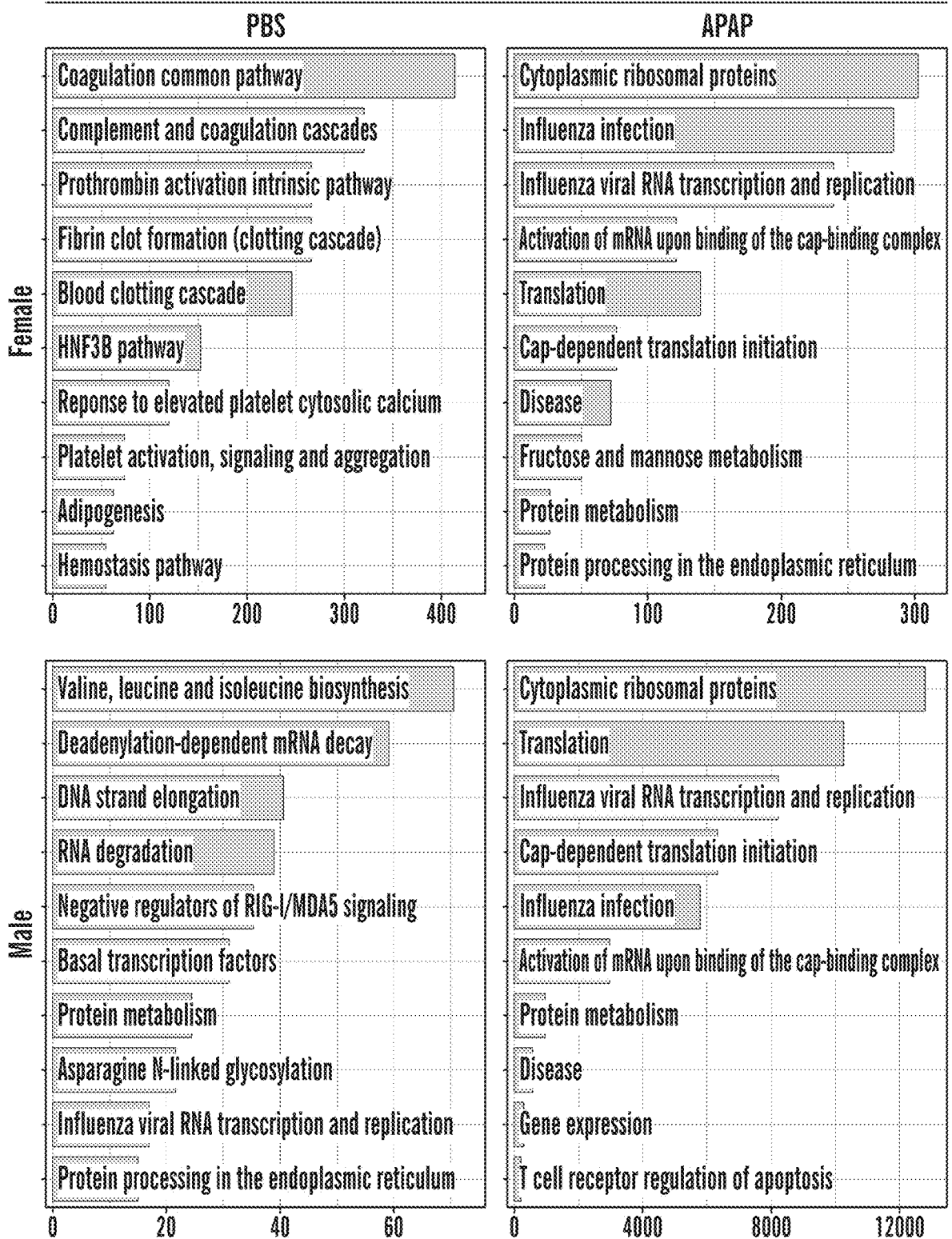
Figure 21B:
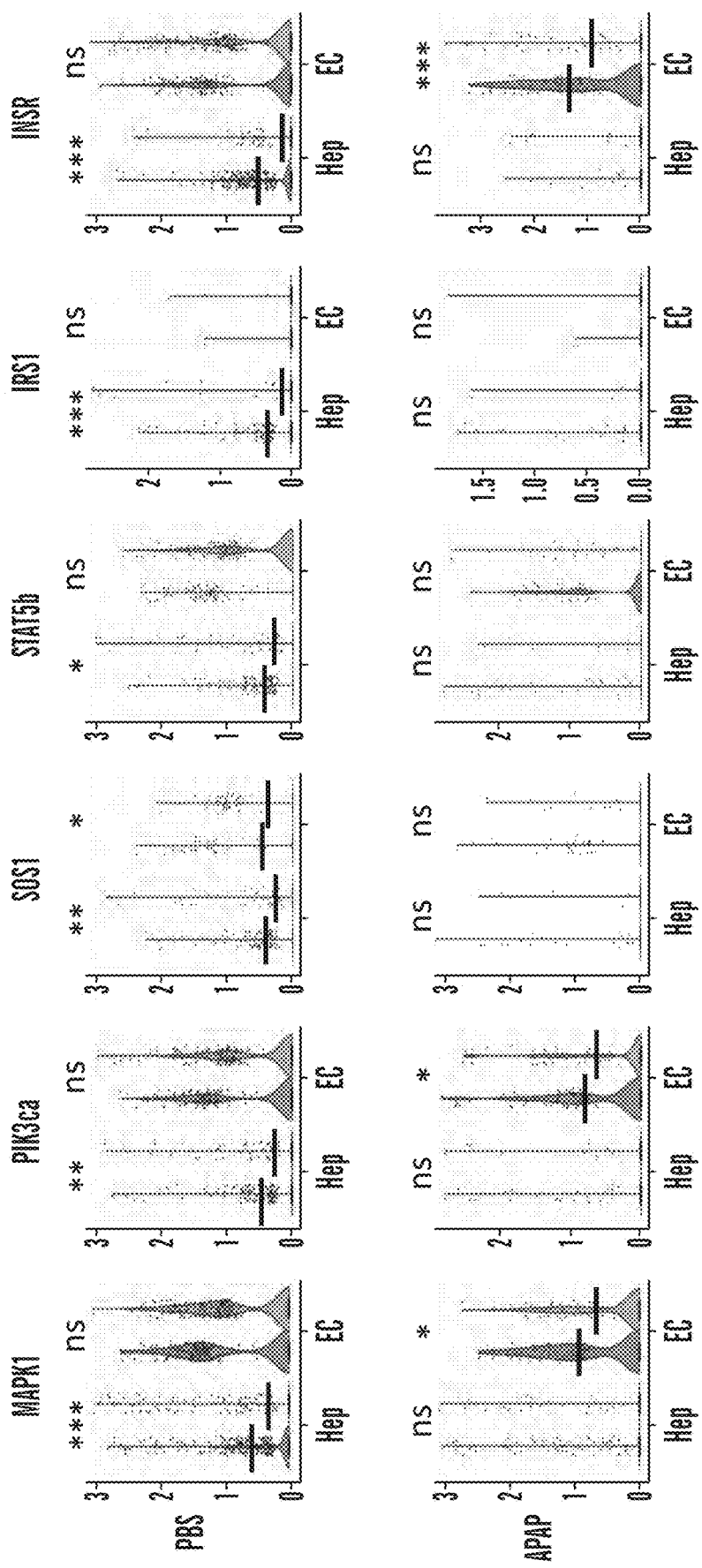
Figure 21C:
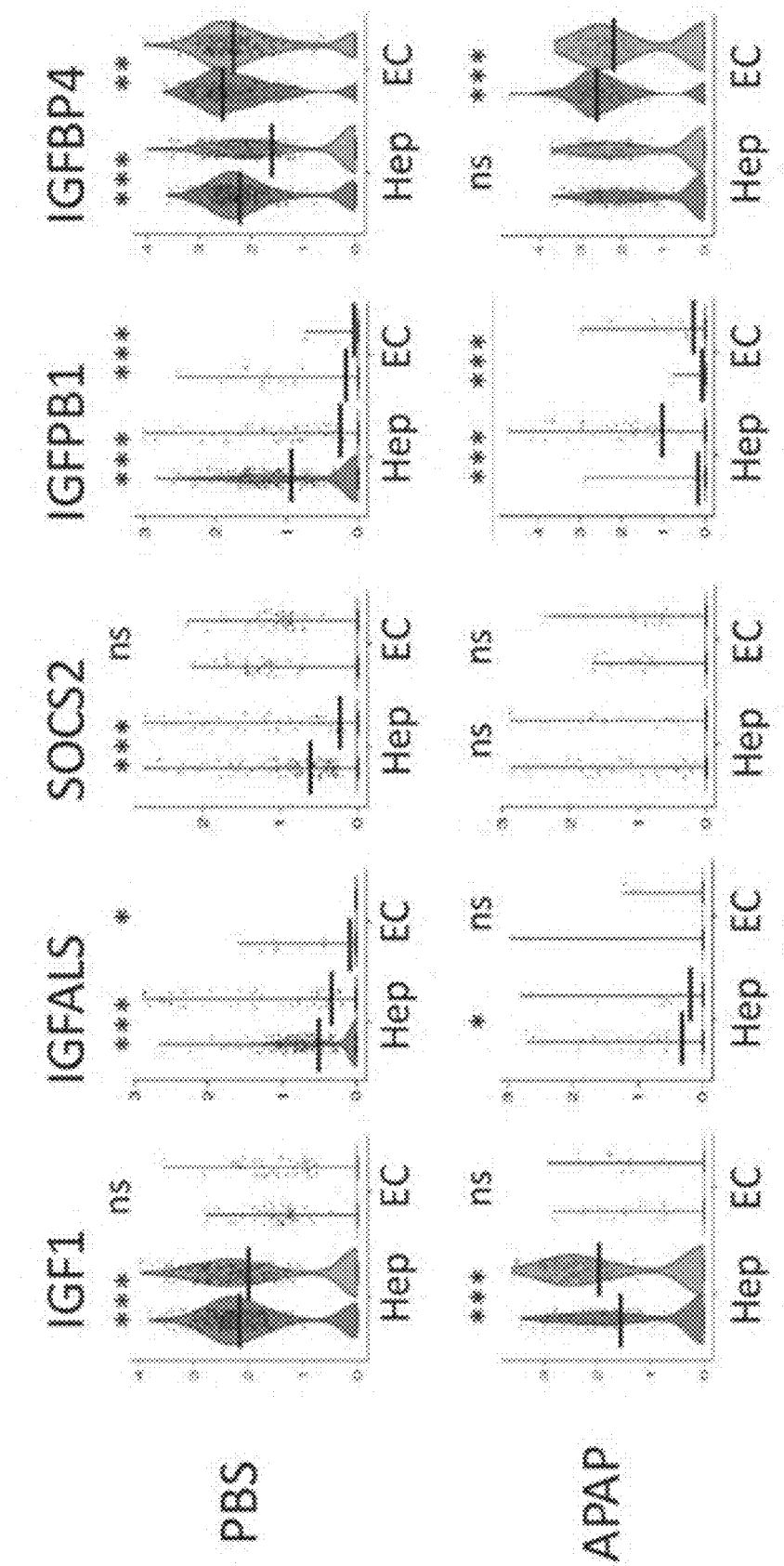

Growth Hormone Receptor Pathway Activation is More Enriched in Female Livers To identify druggable sexually dimorphic pathways activated in females that promote liver repair after APAP overdose, the inventors performed a scRNA-seq analysis for male and female liver cells, treated with PBS control or 400 mg/kg APAP at 48 hours post-injection (FIG. 17A). Single liver cells were collected as per a modified protocol[41], to obtain a mix of ~40% hepatocytes (Hep) and ~60% non-parenchymal cells (NPC) including immune cells, endothelial cells (EC), and fibroblasts/hepatic stellate cells (HSC). Following scRNA-seq of the four samples, data were combined (FIG. 17B) or grouped based on treatment (FIG. 17C), analyzed using the Seurat package, and imported into SPRING software[42] (FIGS. 17B, 17C). Interestingly, hepatocytes (Heps) and endothelial cells (ECs) segregated separately based on their sex prior to injury, then transcriptionally shifted closer to the other sex following injury as indicated with the SPRING plots (FIGS. 17B, 17C) and ENRICHR-based pathway analyses (Supplemental FIG. 21A). Bulk RNA-seq analyses have reported sexual dimorphism of liver transcriptomes[43-45], and both periportal and pericentral hepatocytes were recently identified as the main cell types contributing to the disparity[46]. The single-cell data reveal that not only do hepatocytes harbor distinct transcriptomes based on sex, but ECs do as well. Given the known sex differences in GH secretion patterns and their impact on liver metabolism[29,43,47,48], the inventors specifically examined the GHR pathway in single cells. Violin plots show that female Heps express significantly higher levels of GHR than male cells, both before and after APAP injection. Only a small percentage of ECs express GHR in both sexes (FIG. 17D). Importantly, the enrichment in BioCarta gene sets related to GH/GHR pathway activation was globally greater in Heps and ECs from female mice than from male mice after APAP injection (FIG. 17E), yet levels of a set of specific GH/GHR-pathway activation related genes was also significantly greater in females cells compared to their male counterparts prior to APAP injury (FIG. 21B includes genes from the BioCarta GH pathway activation; FIG. 21C includes additional genes key in the GH pathway activation). These data illustrate the association between GH/GHR pathway activation and accelerated liver regeneration seen in females, suggesting that given the known GH-dependent sexual dimorphism of liver metabolism, administration of GH could improve recovery after acute liver injury caused by APAP overdose.

Figures 18A, 18B:
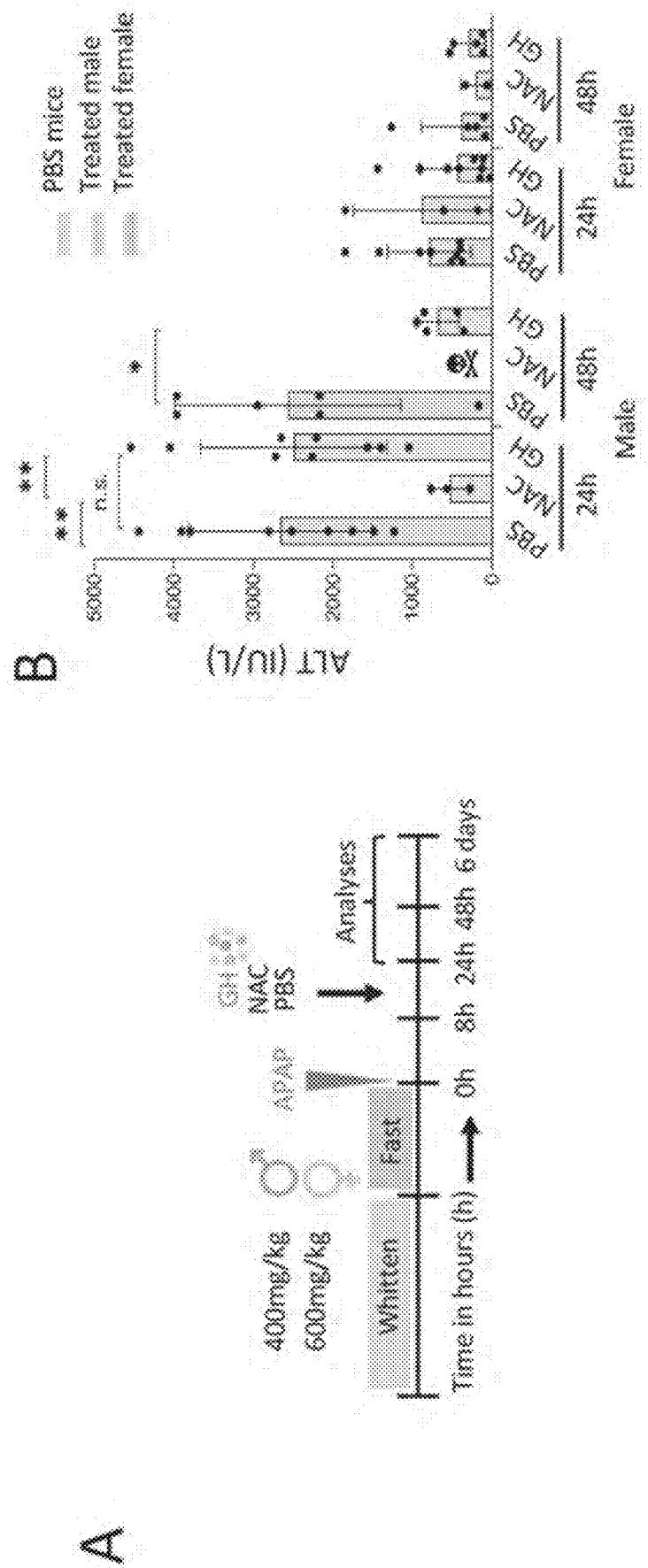
FIGS. 18A-18F depict exogenous human growth hormone treatment promotes liver recovery from APAP-induced injury and more efficiently than NAC.
Figure 18D:
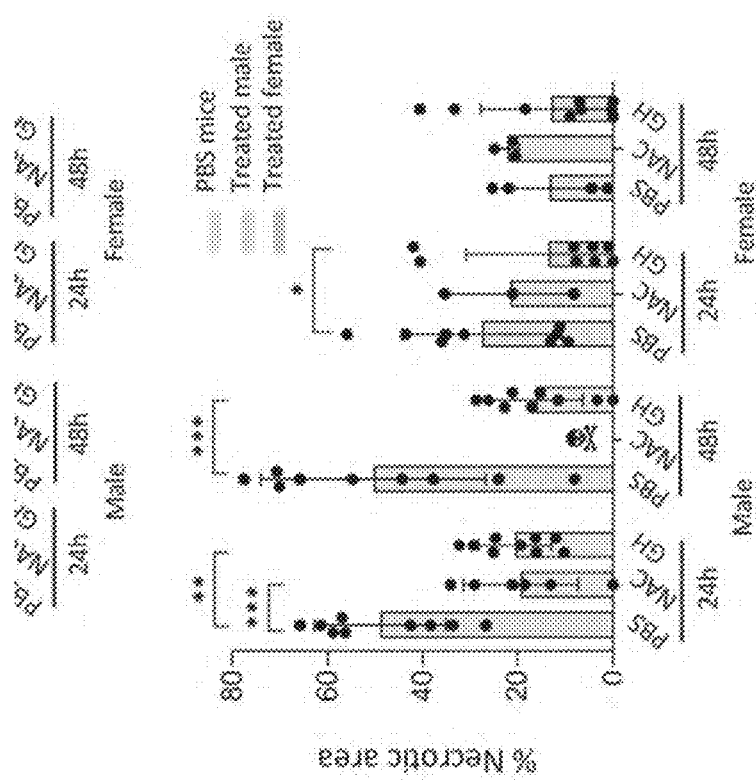
Figure 18C:
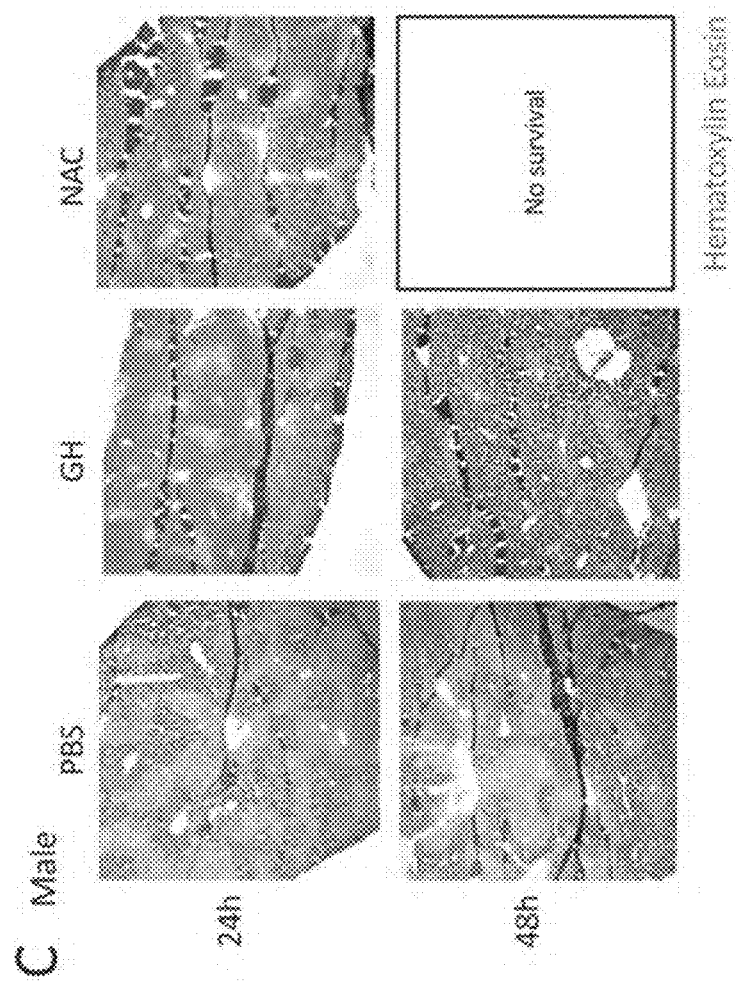
Figures 18E, 18F:
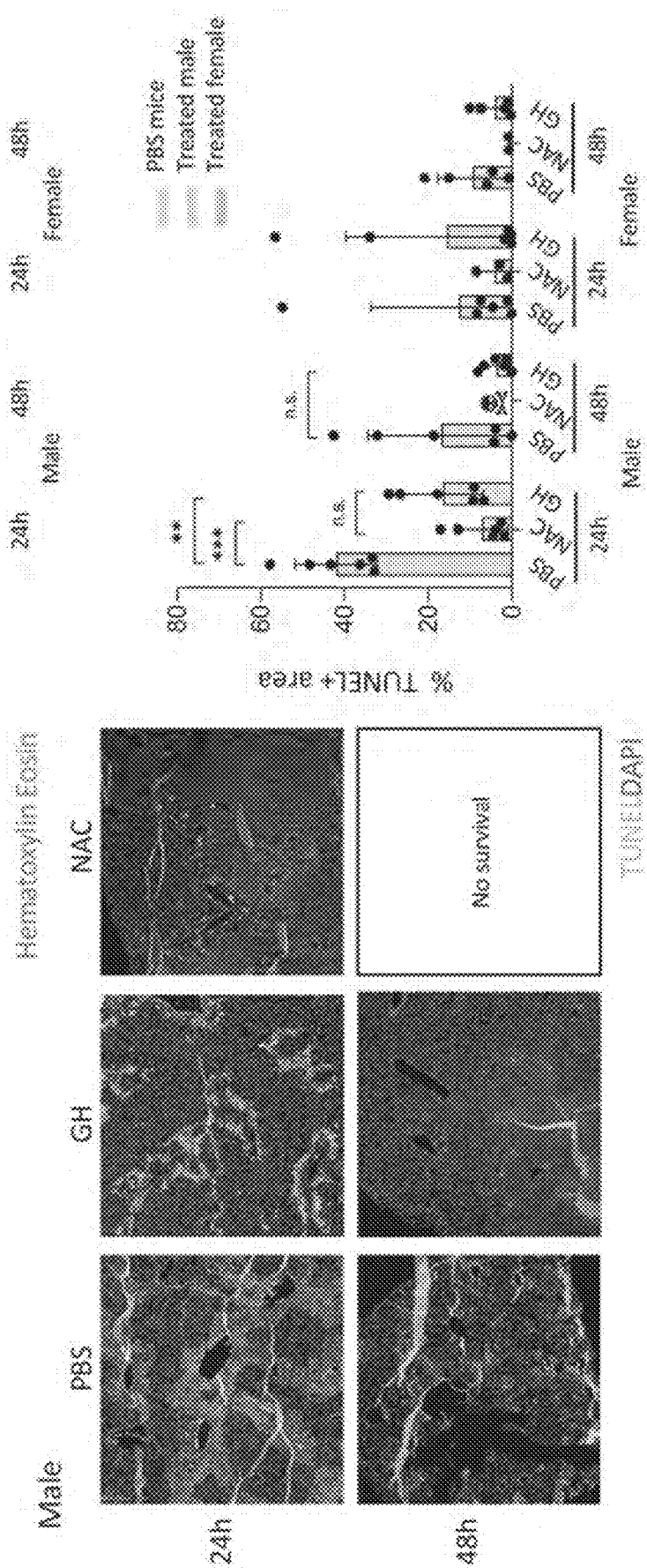
Figures 22A, 22B, 22C, 22D:
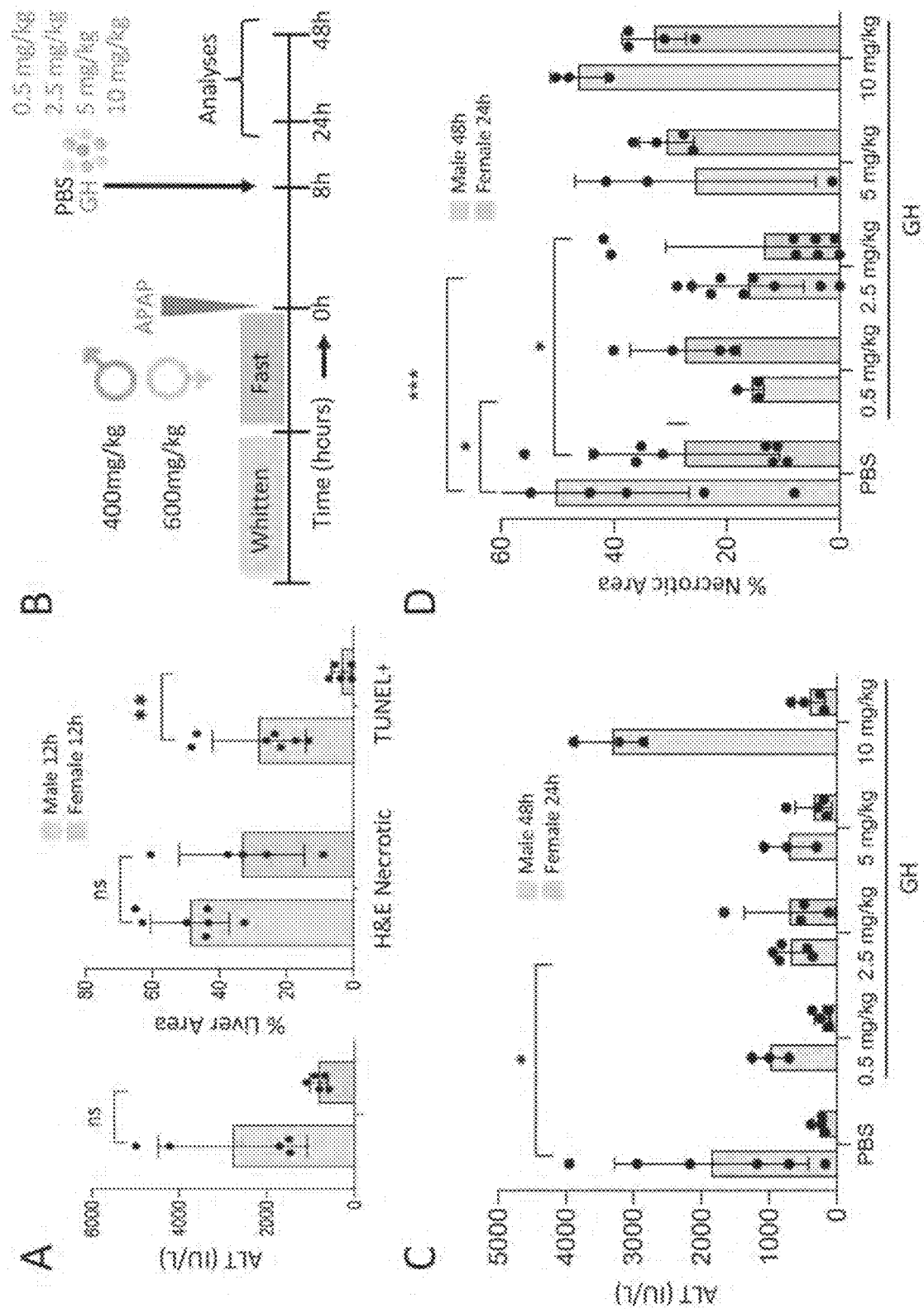
FIGS. 22A-22E depict Median dosage of 2.5 mg/kg GH is most beneficial for treatment post APAP injection.
Figure 22E:
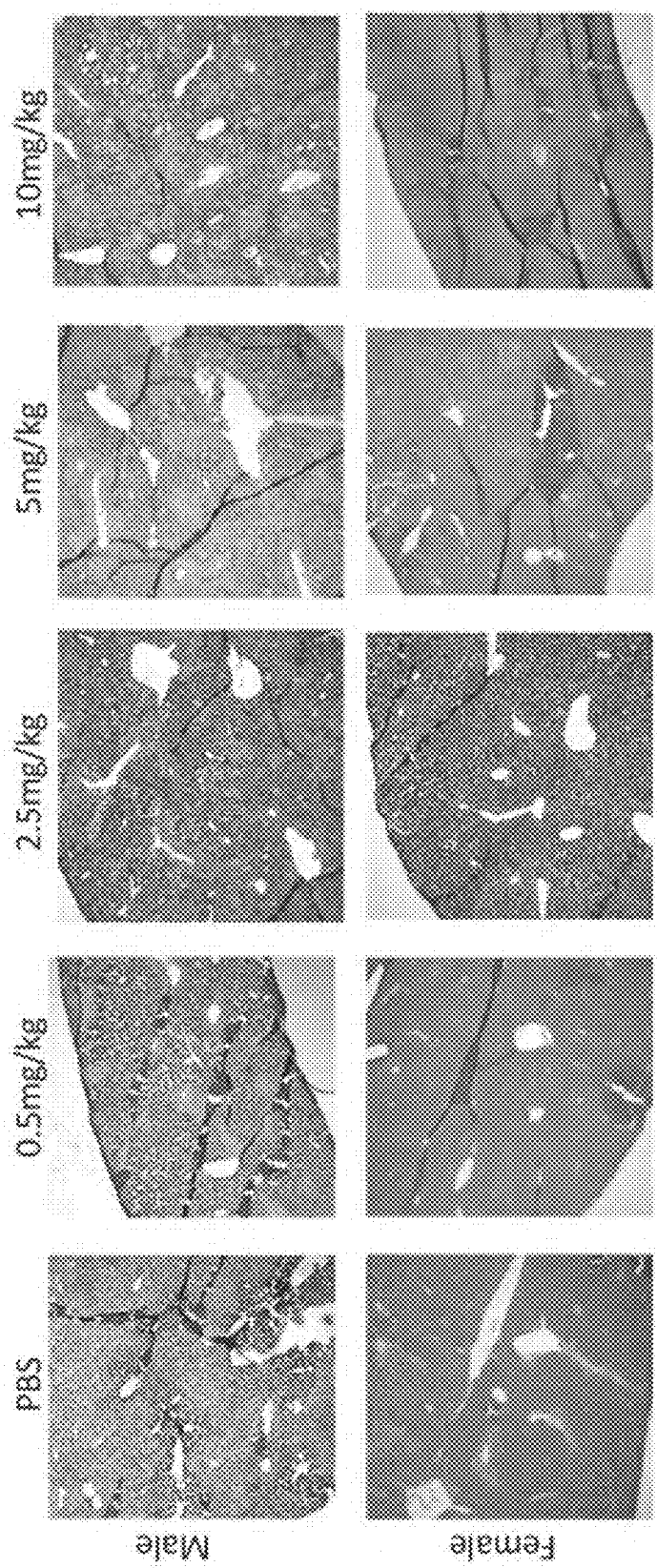
Figure 23A:
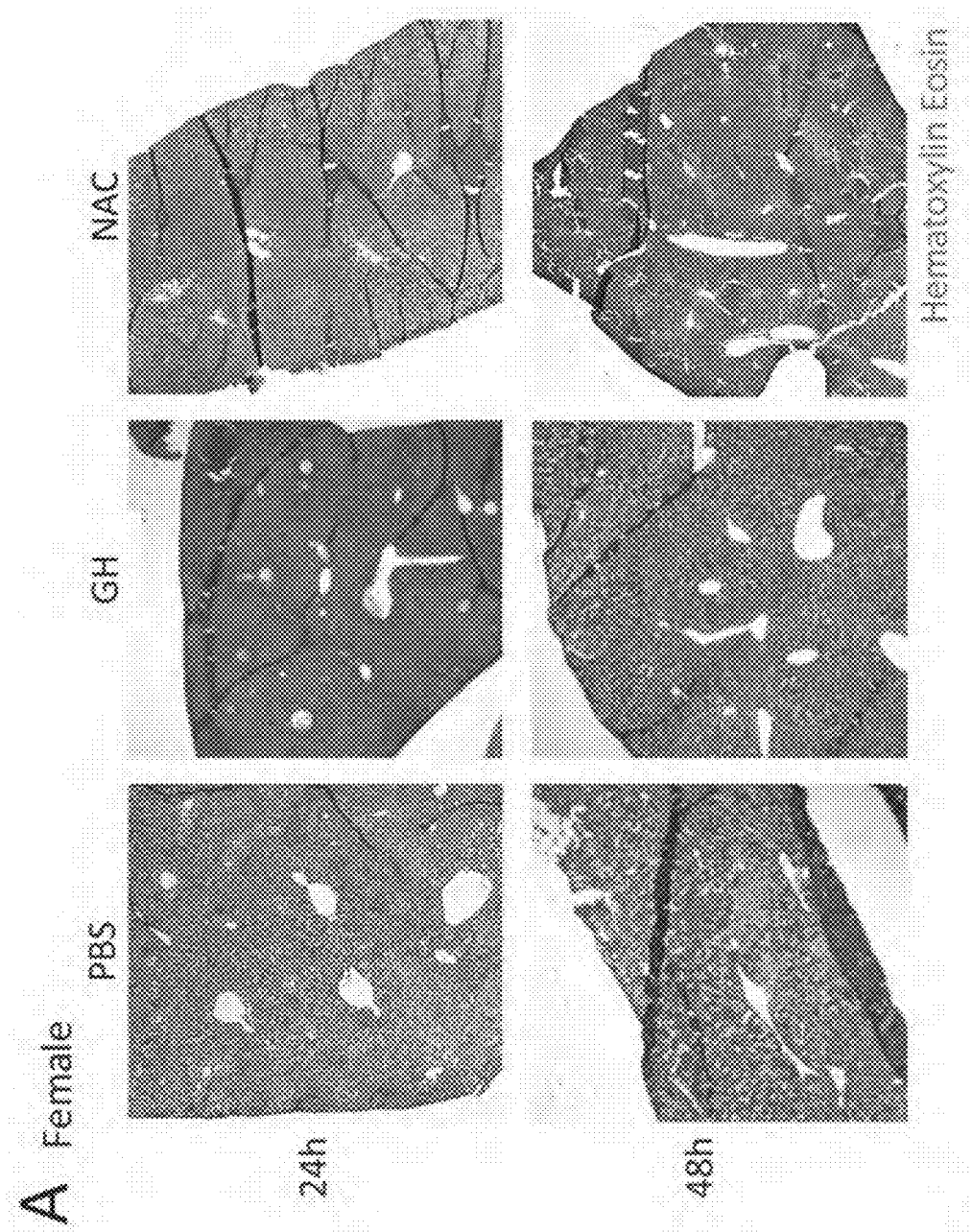
FIGS. 23A-23C depict GH treatment promotes recovery to a lesser extent in females.
Figure 23B:
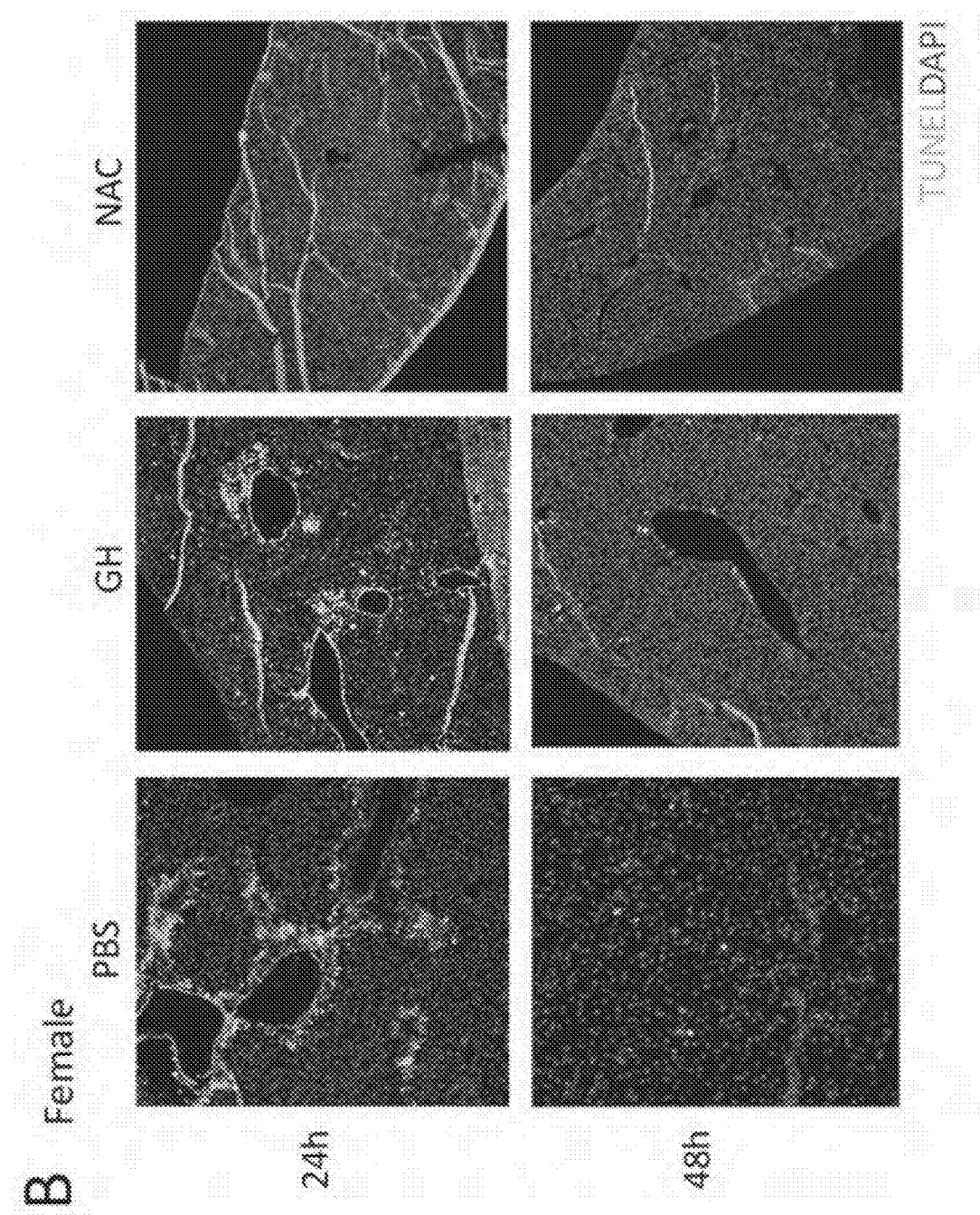

A Single Injection of Recombinant Human GH Accelerates Liver Repair after APAP Overdose As a first approach to investigate the clinical benefit of GH, the inventors tested the efficiency of a single injection of human recombinant GH to promote liver repair in both sexes after female and male livers were similarly injured with APAP. To achieve this, male and female mice were injected with sex-specific sub-lethal doses of APAP selected to achieve a similar level of toxicity in each sex, namely 400 mg/kg for males and 600 mg/kg for females. Eight hours later mice were given a single subcutaneous injection of recombinant human GH (2.5 mg/kg) or control PBS, then analyzed 24 and 48 hours after APAP overdose, and observed for up to 6 days to compare survival between the sexes and treatments (FIG. 18A). The inventors confirmed that the sex-specific APAP doses chosen induced a similar degree of liver injury in both sexes 12 hours after APAP overdose, when the injury is the greatest (FIG. 22A), as shown with no significant difference in serum ALT levels and necrotic areas, although the expansion of apoptotic TUNEL+ area was significantly lower in females. To determine the minimum effective dose of GH, doses were tested (0.5, 2.5, 5, 10 mg/kg) ranging from 0.5 mg/kg[49,50] to 10 mg/kg[51,52] (FIG. 22B), including the average dose of 1 mg/kg, used for adolescents treated daily with GH for short stature therapy[53] (which in mice translates to ~12.3 mg/kg using an inter-species dose conversion factor[54]). It was found that 2.5 mg/kg GH was the minimum dose that significantly decreased necrosis in both sexes and serum ALT levels in males as compared to PBS controls (FIG. 22C, 22D); this dose was therefore used in all subsequent studies. The highest GH dose, 10 mg/kg, was found toxic in both sexes as indicated by high serum ALT levels in males and expansion of necrotic tissue in both sexes similar to that found in PBS controls (FIGS. 22C-22E). 2.5 mg/kg of GH significantly lowered serum ALT levels 48 hours after APAP administration in males compared to PBS-treated males (FIG. 18B), an effect that was not seen in females, most likely due to ALT levels already being lowered in females at both time points. The beneficial effect of GH in males was further illustrated by the sharp and significant GH-dependent decreases in necrotic areas at both time points and in apoptotic TUNEL+ area 24 hours post-APAP (FIG. 18C-18D, 18E-18F; FIG. 23A, 22B). The effect of GH in females was less pronounced, most likely due to the continuous endogenous GH secretion already present in females, yet injection of GH significantly and specifically decreased the necrotic areas 24 hours post-APAP compared to PBS-treated females (FIG. 18C-18D, FIG. 23A). Six-day survival data showed that of 5 APAP-treated mice in each sex, 1 PBS-treated female died (80% survival) and 2 PBS-treated males died (60% survival), while GH increased mouse survival up to 100% for females and 80% to males. Overall, GH treatment sharply and significantly decreases liver injury and accelerates regeneration when given 8 hours post-APAP in both sexes, with a more substantial effect in males.

Figure 23C:
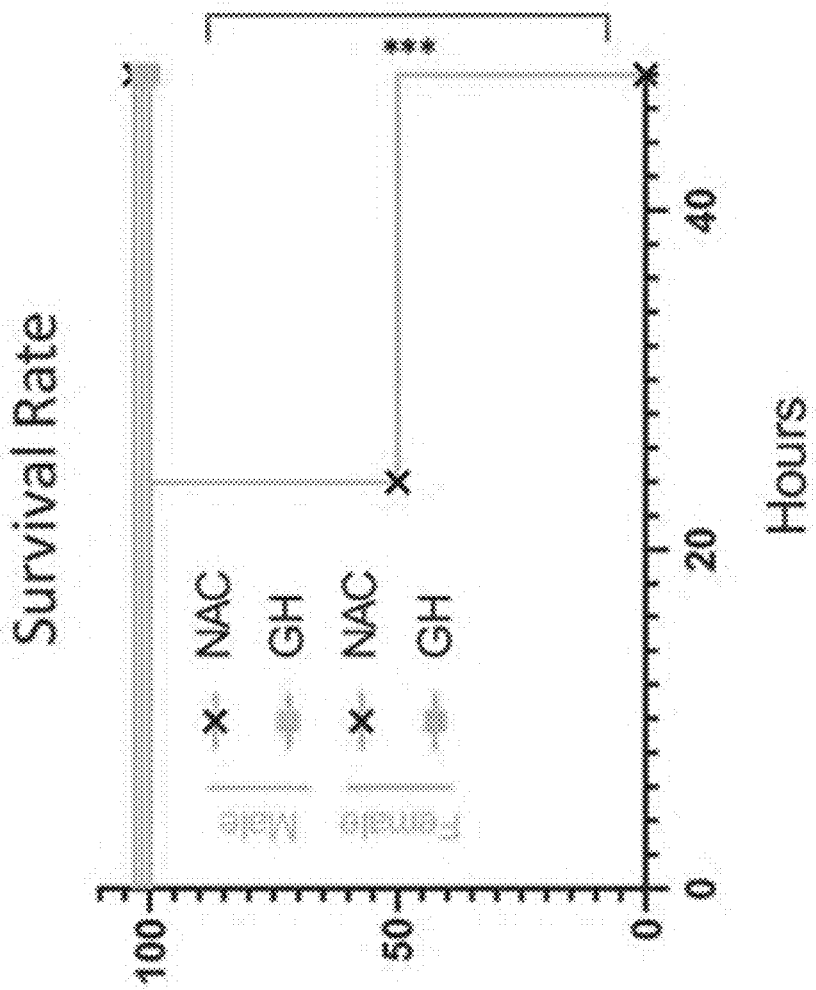

Human Growth Hormone Treatment Accelerates Liver Recovery Better than Administration of NAC For potential clinical translation, the inventors compared the efficacy of GH treatment to that of the clinical standard-of-care treatment with NAC to accelerate liver regeneration post-APAP overdose in the same sets of experiments (FIG. 18A-18F; FIGS. 23A-13C). Sex-specific sub-lethal doses of APAP were administered to mice, which were then treated 8 hours later with either GH (2.5 mg/kg), NAC (1000 mg/kg, the average dose reported in murine APAP overdose to mitigate liver injury in murine APAP overdose studies[55-59]), or PBS control. Impressively, all NAC-treated males died by 48 hours post-APAP, while all males treated with GH or control PBS survived (FIG. 23C) suggesting a toxic effect of NAC in males. In contrast, all females survived regardless of the treatment. For the male mice that survived 24 hours post-APAP, NAC significantly diminished necrotic and TUNEL+ areas, although these mice did not survive by 48 hours post-APAP (FIGS. 18C-18F). This indicates that the beneficial effect of NAC is short-lived when compared to that of GH, which significantly decreased necrotic and apoptotic areas in males and necrotic areas in females compared to PBS (FIGS. 18C-18F; 23A). The deleterious effect of NAC treatment may be due to an anaphylactoid reaction, which has been reported in up to 18% of patients receiving intravenous NAC[60], or to an increase in clotting time[61]. In females, NAC did not show the beneficial effect of reducing necrotic tissue seen with GH (FIGS. 18C-18F, FIGS. 23A, 23B). Altogether, when given 8 hours post-APAP, GH is more efficient in accelerating liver repair in both sexes, as compared to a short-lived beneficial effect of the standard-of-care NAC seen only in males. This suggests that GH may have complementary clinical benefit for APAP-overdosed patients that present late in the ER after NAC loses its efficacy.

Figures 19A, 19B, 19C, 19D:
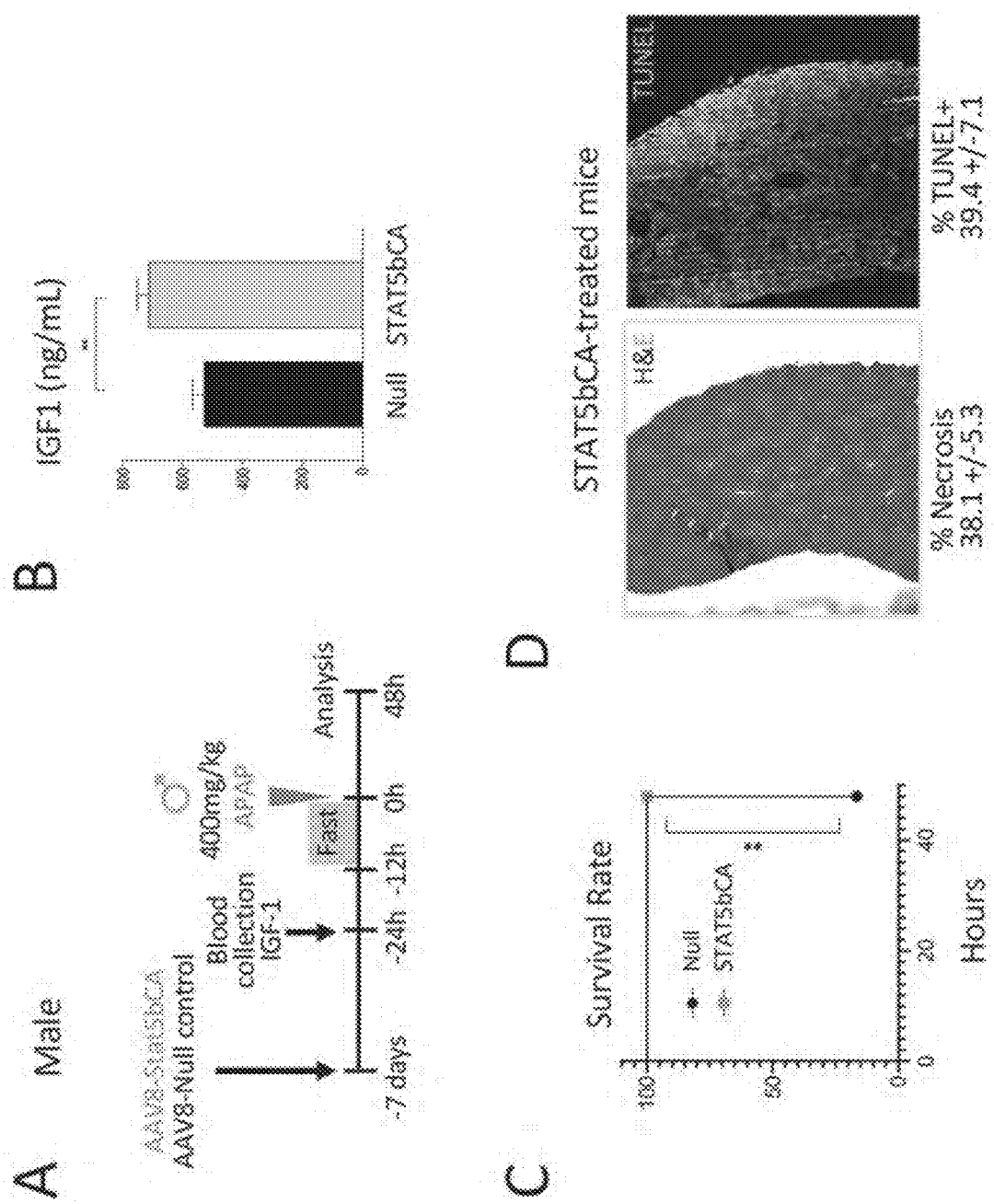
FIGS. 19A-19D depict constitutive activation of the downstream GH/GHR pathway mediator STAT5b rescues males from APAP hepatotoxicity.

Constitutive Activation of the Downstream GH/GHR Pathway Mediator STAT5b Rescues Males from APAP Hepatotoxicity To further validate the clinical benefit of GH treatment in accelerating liver repair, the inventors investigated whether constitutive activation in hepatocytes of the known downstream GH/GHR pathway mediator, transcriptional regulator STAT5b[30,47,48] (STAT5bCA) responsible for the major effects of GH on sex differences in the liver[48,62], would have a protective role prior to APAP injury. Male mice, in which GH treatment was the most significant, were injected with AAV8-TBG-STAT5bCA to induce TBG promoter-driven hepatocyte-specific expression[63-65] of the mutated STAT5b (STAT5bCA) which is constitutively active even in the absence of GHR activation with GH[30] (FIGS. 19A-19C). STAT5bCA has been reported to mimic the response of endogenous liver STAT5b to the female, persistent circulating GH profile and thereby feminizes gene expression in the liver[30]. Seven days later, mice were fasted, given 400 mg/kg APAP, and sacrificed 48 hours post-APAP treatment (FIG. 19A). Expression and function of STAT5bCA in hepatocytes through AAV8-TBG-STAT5bCA injection was validated by a significant increase in plasma IGF1 concentration as previously reported[30] compared to control AAV8-Null-treated mice 6 days post-AAV8 injection (FIG. 19B). Remarkably, while only one of the 6 AAV8-Null-treated control mice survived after 48 hours, all 6 AAV8-STAT5bCA-treated mice survived (FIG. 19C), although necrosis and apoptosis were still visible (FIG. 19D). These findings demonstrate that persistent activation of hepatocytic STAT5b, as normally occurs in female liver, confers a striking protective effect from APAP-induced liver injury, and further support the clinical benefit of GH administration to rapidly promote liver recovery from APAP hepatotoxicity.

Figure 20A:
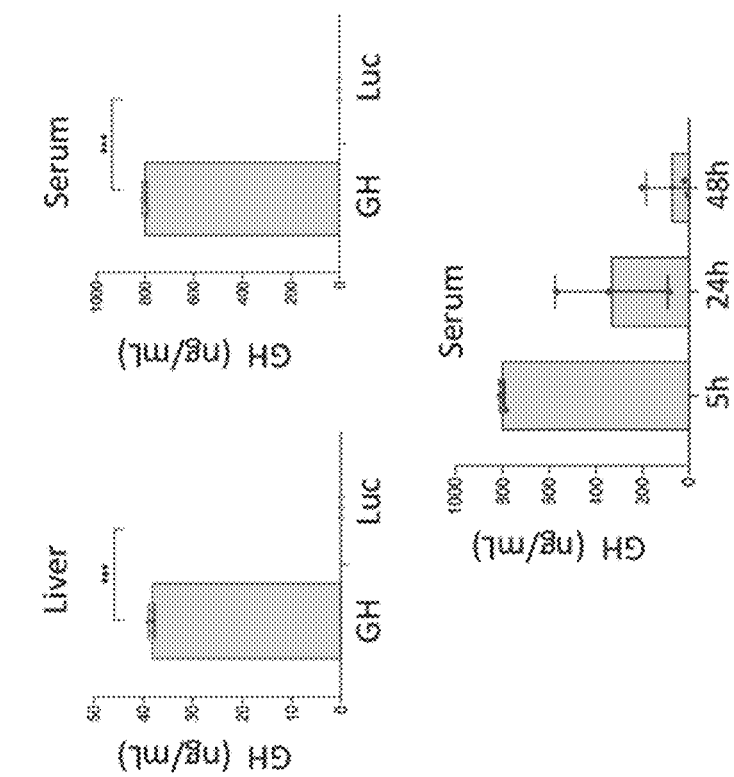
Figure 20B:
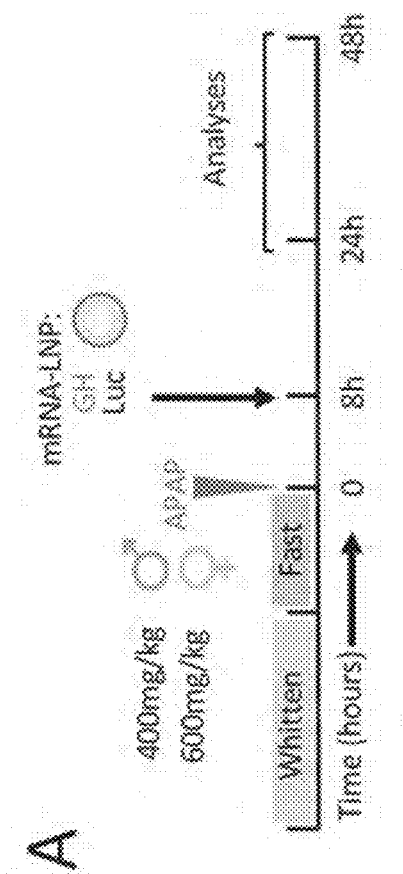

Nucleoside-Modified mRNA-LNP Delivery of GH Induces Sustained GH Expression Over the Course of Liver Injury and Promotes Recovery from APAP Overdose The inventors next investigated the efficacy of nucleoside-modified mRNA encoding human GH encapsulated in lipid nanoparticles (GH mRNA-LNP) for slow-release delivery to the liver as an alternative to recombinant GH protein bolus. mRNA-LNP is a liver-targeted delivery technology that the inventors recently implemented to express regenerative factors in the liver to promote liver regeneration and treat features of murine acute and chronic liver disease[66]. mRNA-LNP is a safe, non-integrative and non-immunogenic technology that has been widely validated in the form of current mRNA-LNP-based COVID-19 vaccines, and allows for robust yet transient expression of proteins with slow-release in the liver over the course of the injury induced by APAP. In this experiment, mice were injured with sex-specific sub-lethal doses of APAP, treated with either 10 μg of GH mRNA-LNPs or with control luciferase (Luc) mRNA-LNPs injected retro-orbitally 8 hours after APAP overdose, and then analyzed 24 and 48 hours after the overdose (FIG. 20A). The inventors first verified the efficient expression of human GH in mouse livers 5 hours post-injection (FIG. 20B). A large increase in serum human GH was also seen, as the transfected hepatocytes ultimately secrete hGH in the blood stream as shown previously with other secreted factors delivered with mRNA-LNP[66]. Over time, serum human GH levels decrease, but are still detectable during the first 2 days post-injection, which represents the critical time during which APAP-induced injury occurs, and thus when GH is the most needed (FIG. 20B). Remarkably, a single dose of GH mRNA-LNP rescued males from death, which occurred by 48 hours post-APAP in all control Luc mRNA-LNP-treated mice (FIG. 20C), which was also associated with lower levels of ALT (FIG. 20D). Though, 48 hours was likely too early to observe improvement of the liver tissue architecture (FIGS. 20E, 20F). In females, GH mRNA-LNP treatment showed no significant benefit, as recovery occurred spontaneously by 48 hours. This was not surprising, as serum human GH levels found in mice 5 hours post mRNA-LNP injection were 30-fold lower than serum levels extrapolated from a single injection of 2.5 mg/kg of recombinant GH, as tested in FIG. 18A-18F. This suggests that increasing doses of slow-release GH mRNA-LNP may not only rescue male mice from death, but may further accelerate recovery in both sexes, as an alternative delivery platform to a bolus injection of recombinant GH protein.

Discussion

NAC is the only current treatment for APAP overdose other than liver transplantation, and loses effectiveness ~10 hours after APAP ingestion, when the symptoms of acute liver failure are frequently not yet evident. This study introduces a potential alternative therapeutic strategy to overcome this clinical unmet need for the many overdose cases that present late to the emergency room. This study reveals the sexually dimorphic response to APAP overdose and identifies GH/GHR/STAT5b as a sexually differentially activated and druggable pathway, that may ultimately be leveraged for the establishment of a GH-based therapeutic to accelerate recovery from APAP-induced liver injury. The inventors demonstrated the efficiency of this therapy in mice using a single dose of GH, delivered as a recombinant protein or via mRNA-LNP injection and its superiority to NAC to mitigate injury, accelerate recovery, and promote survival.

The therapeutic capacity of GH to reverse APAP-induced hepatoxicity reported here is supported by earlier work demonstrating the ability of GH to stimulate liver cell proliferation and liver recovery via EGFR signaling in injured liver mouse models affected with partial hepatectomy or liver steatosis[67-70]. Consistent with the protective role of GH in APAP-induced hepatotoxicity, previous studies have shown that inhibition of GH-releasing hormone (GHRH) prior to APAP overdose increases APAP-induced mouse liver toxicity, while GHRH super-agonist partially reverses APAP toxicity[71]. Here, the pretreatment of male mice prior to APAP overdose with a constitutively active mutant form of the GH-activated transcription factor STAT5b, STAT5bCA, largely recapitulated the relative resistance to APAP seen in female, as compared to male mice and conferred striking protection from APAP overdose hepatotoxicity.

GH is most likely not the only sex-dependent factor involved in the sexual dimorphism of APAP-induced injury and recovery, which was illustrated by the consistently slower liver recovery of GH-treated males as compared to females. Estrogens have been reported to have a direct impact on the GH/GHR pathway activation by reducing hepatic production of the GH-effector IGF-1 in response to GH[39] and its sex-dependent pituitary secretory pattern. Interestingly, IGF-1 can also bind in a compensatory manner to estrogen receptor (ERa) under conditions of low systemic estrogen concentrations[72]. In addition to influencing the GH pathway, estrogen also contributes to liver function independently, for example, by increasing glutathione synthesis[21] and by repressing mitochondrial expression of SH3 domain-binding protein that preferentially associates with Btk (SAB) in hepatocytes, thereby preventing liver injury from APAP overdose[18]. These protective effects of estrogen contribute to the persistent sex differences in APAP-induced liver injury observed even after GH administration, either directly via ERa expressed in hepatocytes, or indirectly, via its effect on pituitary GH secretion patterns[22-24].

This study introduces GH delivery via intravenous injection of nucleoside-modified mRNA-LNP to induce production of GH protein throughout the duration of APAP-induced injury in order to accelerate recovery and increase survival. The use of mRNA-LNP to harness tissue regeneration following acute injury, such as that induced by APAP overdose, departs from its original applications for immunization in vaccines[73] or protein replacement for diseases in which proteins are deficient or defective[74]. Given the short half-life of circulating GH after subcutaneous injection which ranges from 2 to 3 hours with a biological half-life of about 12 hours considering the downstream effects[75], mRNA-LNP delivery of GH offers a wider timeframe of expression of at least 48 hours after a single injection, which should cover the duration of the acute liver damage caused by APAP. Following a single injection of GH mRNA-LNP (10 μg/mouse), the serum level of GH reached about 800 ng/mL, which is about 30× lower than was extrapolated when recombinant GH protein was injected. This suggests that the initial dose of GH mRNA-LNP used in this study can be increased and carefully fine-tuned based on severity and persistence of liver disease. Therefore, delivery of GH via mRNA-LNP may be a promising alternative method to recombinant GH protein therapy for future clinical studies to treat acute liver failure.

This study demonstrates a sexually dimorphic liver repair process following APAP overdose benefitting female mice, which was leveraged by establishing GH as an alternative treatment to improve repair in males and accelerate it in females. This innovative advancement may prove critical in clinical translation for preventing liver failure and liver transplant for APAP-overdosed patients that present late in the ER, for whom NAC loses its therapeutic efficiency. In a clinical setting, GH administration can be paired with standard-of-care NAC treatment as a complementary therapy activating broader mechanisms of repair to prevent liver failure or the need for transplant. Additionally, this study introduces the use of the safe non-integrative nucleoside-modified mRNA-LNP platform for delivering GH in a robust and sustained, yet controllable, transient manner, which was validated as safe with the recent mRNA-based COVID-19 vaccines[73,76-78].

REFERENCES

1. Ostapowicz G, Fontana R J, Schiodt F V, et al. Results of a prospective study of acute liver failure at 17 tertiary care centers in the United States. *Ann Intern Med.* 2002; 137(12):947-954. doi:10.7326/0003-4819-137-12-200212170-00007
2. Laine J E, Auriola S, Pasanen M, Juvonen R O. Acetaminophen bioactivation by human cytochrome P450 enzymes and animal microsomes. *Xenobiotica.* 2009; 39(1):11-21. doi:10.1080/00498250802512830
3. Manyike P T, Kharasch E D, Kalhorn T F, Slattery J T. Contribution of CYP2E1 and CYP3A to acetaminophen reactive metabolite formation. *Clin Pharmacol Ther.* 2000; 67(3):275-282. doi:10.1067/mcp.2000.104736

4. Jaeschke H. Acetaminophen: Dose-Dependent Drug Hepatotoxicity and Acute Liver Failure in Patients. *Dig Dis.* 2015; 33(4):464-471. doi:10.1159/000374090
5. McClain C J, Kromhout J P, Peterson F J, Holtzman J L. Potentiation of acetaminophen hepatotoxicity by alcohol. *JAMA.* 1980; 244(3):251-253.
6. Prescott L F. Paracetamol, alcohol and the liver. *Br J Clin Pharmacol.* 2000; 49(4):291-301. doi:10.1046/j.1365-2125.2000.00167.x
7. Yoon E, Babar A, Choudhary M, Kutner M, Pyrsopoulos N. Acetaminophen-Induced Hepatotoxicity: a Comprehensive Update. *J Clin Transl Hepatol.* 2016; 4(2):131-142. doi:10.14218/JCTH.2015.00052
8. Heard K J. Acetylcysteine for acetaminophen poisoning. *N Engl J Med.* 2008; 359(3):285-292. doi:10.1056/NEJMct0708278
9. Jóźwiak-Bebenista M, Nowak J Z. Paracetamol: mechanism of action, applications and safety concern. *Acta Pol Pharm.* 2014; 71(1):11-23.
10. Naugler W E, Sakurai T, Kim S, et al. Gender Disparity in Liver Cancer Due to Sex Differences in MyD88-Dependent IL-6 Production. *Science (80).* 2007; 317 (5834):121 LP-124. http://science.sciencemag.org/content/317/5834/121.abstract.
11. Lavoie J-M, Pighon A. NAFLD, Estrogens, and Physical Exercise: The Animal Model. Magkos F, ed. *J Nutr Metab.* 2012; 2012:914938. doi:10.1155/2012/914938
12. Zheng B, Zhu Y-J, Wang H-Y, Chen L. Gender disparity in hepatocellular carcinoma (HCC): multiple underlying mechanisms. *Sci China Life Sci.* 2017; 60(6):575-584. doi:10.1007/s11427-016-9043-9
13. Mennecozzi M, Landesmann B, Palosaari T, Harris G, Whelan M. Sex Differences in Liver Toxicity-Do Female and Male Human Primary Hepatocytes React Differently to Toxicants In Vitro? Guillou H, ed. *PLoS One.* 2015; 10(4):e0122786. doi:10.1371/journal.pone.0122786
14. Russo M W, Galanko J A, Shrestha R, Fried M W, Watkins P. Liver transplantation for acute liver failure from drug induced liver injury in the United States. *Liver Transplant.* 2004; 10(8):1018-1023. doi:https://doi.org/10.1002/lt.20204
15. Tan C J-Y, Sklar G E. Characterisation and outcomes of adult patients with paracetamol overdose presenting to a tertiary hospital in Singapore. *Singapore Med J.* 2017; 58(12):695-702. doi:10.11622/smedj.2016170
16. Rubin J B, Hameed B, Gottfried M, Lee W M, Sarkar M. Acetaminophen-induced Acute Liver Failure Is More Common and More Severe in Women. *Clin Gastroenterol Hepatol Off Clin Pract J Am Gastroenterol Assoc.* 2018; 16(6):936-946. doi:10.1016/j.cgh.2017.11.042
17. Masubuchi Y, Nakayama J, Watanabe Y. Sex difference in susceptibility to acetaminophen hepatotoxicity is reversed by buthionine sulfoximine. *Toxicology.* 2011; 287(1):54-60. doi:https://doi.org/10.1016/j.tox.2011.05.018
18. Win S, Min R W, Chen C Q, et al. Expression of mitochondrial membrane-linked SAB determines severity of sex-dependent acute liver injury. *J Clin Invest.* October 2019. doi:10.1172/JCI128289
19. Du K, Williams C D, McGill M R, Jaeschke H. Lower susceptibility of female mice to acetaminophen hepatotoxicity: Role of mitochondrial glutathione, oxidant stress and c-jun N-terminal kinase. *Toxicol Appl Pharmacol.* 2014; 281(1):58-66. doi:10.1016/j.taap.2014.09.002
20. Chandrasekaran V R M, Periasamy S, Liu L-L, Liu M-Y. 17β-Estradiol protects against acetaminophen-overdose-induced acute oxidative hepatic damage and increases the survival rate in mice. *Steroids.* 2011; 76(1-2):118-124. doi:10.1016/j.steroids.2010.09.008
21. Liu H, Wang H, Shenvi S, Hagen T M, Liu R-M. Glutathione metabolism during aging and in Alzheimer disease. *Ann N Y Acad Sci.* 2004; 1019:346-349. doi:10.1196/annals.1297.059
22. Avtanski D, Novaira H J, Wu S, et al. Both estrogen receptor α and β stimulate pituitary GH gene expression. *Mol Endocrinol.* 2014; 28(1):40-52. doi:10.1210/me.2013-1245
23. Addison M L, Rissman E F. Sexual dimorphism of growth hormone in the hypothalamus: regulation by estradiol. *Endocrinology.* 2012; 153(4):1898-1907. doi:10.1210/en.2011-1982
24. Veldhuis J D, Bowers C Y. Regulated recovery of pulsatile growth hormone secretion from negative feedback: a preclinical investigation. *Am J Physiol Regul Integr Comp Physiol.* 2011; 301(4):R1143-R1152. doi:10.1152/ajpregu.00293.2011
25. Farhy L S, Bowers C Y, Veldhuis J D. Model-projected mechanistic bases for sex differences in growth hormone regulation in humans. *Am J Physiol Regul Integr Comp Physiol.* 2007; 292(4):R1577-93. doi:10.1152/ajpregu.00584.2006
26. Wong J H, Dukes J, Levy R E, et al. Sex differences in thrombosis in mice are mediated by sex-specific growth hormone secretion patterns. *J Clin Invest.* 2008; 118(8): 2969-2978. doi:10.1172/JCI34957
27. Adams J M, Otero-Corchon V, Hammond G L, Veldhuis J D, Qi N, Low M J. Somatostatin is essential for the sexual dimorphism of GH secretion, corticosteroid-binding globulin production, and corticosterone levels in mice. *Endocrinology.* 2015; 156(3):1052-1065. doi:10.1210/en.2014-1429
28. Jansson J O, Eden S, Isaksson O. Sexual dimorphism in the control of growth hormone secretion. *Endocr Rev.* 1985; 6(2):128-150. doi:10.1210/edrv-6-2-128
29. Waxman D J, Holloway M G. Sex Differences in the Expression of Hepatic Drug Metabolizing Enzymes. *Mol Pharmacol.* 2009; 76(2):215 LP-228. doi:10.1124/mol.109.056705
30. Lau-Corona D, Ma H, Vergato C, et al. Constitutively Active STAT5b Feminizes Mouse Liver Gene Expression. *Endocrinol (United States).* 2022; 163(5): 2022.02.14.480424. doi:10.1210/endocr/bqac046
31. Jemiolo B, Harvey S, Novotny M. Promotion of the Whitten effect in female mice by synthetic analogs of male urinary constituents. *Proc Natl Acad Sci USA.* 1986; 83(12):4576-4579. doi:10.1073/pnas.83.12.4576
32. WHITTEN W K. Modification of the oestrous cycle of the mouse by external stimuli associated with the male. *J Endocrinol.* 1956; 13(4):399-404. doi:10.1677/joe.0.0130399
33. Dalal S J, Estep J S, Valentin-Bon I E, Jerse A E. Standardization of the Whitten Effect to induce susceptibility to *Neisseria gonorrhoeae* in female mice. *Contemp Top Lab Anim Sci.* 2001; 40(2):13-17.
34. Bhushan B, Apte U. Liver Regeneration after Acetaminophen Hepatotoxicity: Mechanisms and Therapeutic Opportunities. *Am J Pathol.* 2019; 189(4):719-729. doi:10.1016/J.AJPATH.2018.12.006
35. Bhushan B, Walesky C, Manley M, et al. Pro-regenerative signaling after acetaminophen-induced acute liver injury in mice identified using a novel incremental dose model. *Am J Pathol.* 2014; 184(11):3013-3025. doi:10.1016/j.ajpath.2014.07.019

36. Kao T-L, Kuan Y-P, Cheng W-C, et al. Estrogen receptors orchestrate cell growth and differentiation to facilitate liver regeneration. *Theranostics.* 2018; 8(10):2672-2682. doi:10.7150/thno.23624
37. Batmunkh B, Choijookhuu N, Srisowanna N, et al. Estrogen Accelerates Cell Proliferation through Estrogen Receptor a during Rat Liver Regeneration after Partial Hepatectomy. *Acta Histochem Cytochem.* 2017; 50(1):39-48. doi:10.1267/ahc.17003
38. Uebi T, Umeda M, Imai T. Estrogen induces estrogen receptor alpha expression and hepatocyte proliferation in the livers of male mice. *Genes Cells.* 2015; 20(3):217-223. doi:10.1111/gtc.12214
39. Ho K K Y, Gibney J, Johannsson G, Wolthers T. Regulating of growth hormone sensitivity by sex steroids: implications for therapy. *Front Horm Res.* 2006; 35:115-128. doi:10.1159/000094314
40. Wolf K K, Wood S G, Allard J L, et al. Role of CYP3A and CYP2E1 in alcohol-mediated increases in acetaminophen hepatotoxicity: comparison of wild-type and Cyp2e1(−/−) mice. *Drug Metab Dispos.* 2007; 35(7):1223-1231. doi:10.1124/dmd.107.014738
41. Li B, Dorrell C, Canady P S, Wakefield L. Identification and Isolation of Clonogenic Cholangiocyte in Mouse. *Methods Mol Biol.* 2019; 1905:19-27. doi:10.1007/978-1-4939-8961-4_3
42. Weinreb C, Wolock S, Klein A M. SPRING: a kinetic interface for visualizing high dimensional single-cell expression data. *Bioinformatics.* 2018; 34(7):1246-1248. doi:10.1093/bioinformatics/btx792
43. Lau-Corona D, Bae W K, Hennighausen L, Waxman D J. Sex-biased genetic programs in liver metabolism and liver fibrosis are controlled by EZH1 and EZH2. *PLOS Genet.* 2020; 16(5):e1008796. https://doi.org/10.1371/journal.pgen.1008796.
44. Lowe R, Gemma C, Rakyan V K, Holland M L. Sexually dimorphic gene expression emerges with embryonic genome activation and is dynamic throughout development. *BMC Genomics.* 2015; 16(1):295. doi:10.1186/s12864-015-1506-4
45. Goldfarb C N, Waxman D J. Global analysis of expression, maturation and subcellular localization of mouse liver transcriptome identifies novel sex-biased and TCPOBOP-responsive long non-coding RNAs. *BMC Genomics.* 2021; 22(1):212. doi:10.1186/s12864-021-07478-5
46. Goldfarb C N, Karri K, Pyatkov M, Waxman D J. Interplay Between GH-regulated, Sex-biased Liver Transcriptome and Hepatic Zonation Revealed by Single-Nucleus RNA Sequencing. *Endocrinology.* 2022; 163(7). doi:10.1210/endocr/bqac059
47. Waxman D J, O'Connor C. Growth Hormone Regulation of Sex-Dependent Liver Gene Expression. *Mol Endocrinol.* 2006; 20(11):2613-2629. doi:10.1210/me.2006-0007
48. Clodfelter K H, Holloway M G, Hodor P, Park S-H, Ray W J, Waxman D J. Sex-dependent liver gene expression is extensive and largely dependent upon signal transducer and activator of transcription 5b (STAT5b): STAT5b-dependent activation of male genes and repression of female genes revealed by microarray analysis. *Mol Endocrinol.* 2006; 20(6):1333-1351. doi:10.1210/me.2005-0489
49. Rudling M, Angelin B. Growth hormone reduces plasma cholesterol in LDL receptor-deficient mice. *FASEB J.* 2001; 15(8):1350-1356. doi:https://doi.org/10.1096/fj.00-0715com
50. Westwood M, Maqsood A R, Solomon M, et al. The effect of different patterns of growth hormone administration on the IGF axis and somatic and skeletal growth of the dwarf rat. *Am J Physiol Endocrinol Metab.* 2010; 298(3):E467-E476. doi:10.1152/ajpendo.00234.2009
51. Wei L, Chang J, Han Z, Wang R, Song L. Recombinant human growth hormone (rhGH) treatment of MKN-45 xenograft mice improves nutrition status and strengthens immune function without promoting tumor growth. *PLoS One.* 2019; 14(1):e0210613. doi:10.1371/journal.pone.0210613
52. Ruixian T, Francesco A, M. M S, H. H H. Human Growth Hormone Increases Apo(a) Expression in Transgenic Mice. *Arterioscler Thromb Vasc Biol.* 1999; 19(10):2439-2447. doi:10.1161/01.ATV.19.10.2439
53. Guyda H J. Four Decades of Growth Hormone Therapy for Short Children: What Have We Achieved? *J Clin Endocrinol Metab.* 1999; 84(12):4307-4316. doi:10.1210/jcem.84.12.6189
54. Nair A B, Jacob S. A simple practice guide for dose conversion between animals and human. *J basic Clin Pharm.* 2016; 7(2):27-31. doi:10.4103/0976-0105.177703
55. Tersteeg C, Roodt J, Van Rensburg W J, et al. N-acetylcysteine in preclinical mouse and baboon models of thrombotic thrombocytopenic purpura. *Blood.* 2017; 129(8):1030-1038. doi:10.1182/blood-2016-09-738856
56. James L P, McCullough S S, Lamps L W, Hinson J A. Effect of N-acetylcysteine on acetaminophen toxicity in mice: relationship to reactive nitrogen and cytokine formation. *Toxicol Sci.* 2003; 75(2):458-467. doi:10.1093/toxsci/kfg181
57. Kane A E, Huizer-Pajkos A, Mach J, et al. N-Acetyl cysteine does not prevent liver toxicity from chronic low-dose plus subacute high-dose paracetamol exposure in young or old mice. *Fundam Clin Pharmacol.* 2016; 30(3):263-275. doi:10.1111/fcp.12184
58. Saito C, Zwingmann C, Jaeschke H. Novel mechanisms of protection against acetaminophen hepatotoxicity in mice by glutathione and N-acetylcysteine. *Hepatology.* 2010; 51(1):246-254. doi:https://doi.org/10.1002/hep.23267
59. McConnachie L A, Mohar I, Hudson F N, et al. Glutamate cysteine ligase modifier subunit deficiency and gender as determinants of acetaminophen-induced hepatotoxicity in mice. *Toxicol Sci.* 2007; 99(2):628-636. doi:10.1093/toxsci/kfm165
60. Kerr F, Dawson A, Whyte I M, et al. The Australasian Clinical Toxicology Investigators Collaboration randomized trial of different loading infusion rates of N-acetylcysteine. *Ann Emerg Med.* 2005; 45(4):402-408. doi:10.1016/j.annemergmed.2004.08.040
61. Jepsen S, Hansen A B. The influence of N-acetylcysteine on the measurement of prothrombin time and activated partial thromboplastin time in healthy subjects. *Scand J Clin Lab Invest.* 1994; 54(7):543-547. doi:10.3109/00365519409088566
62. Hao P, Waxman D J. STAT5 Regulation of Sex-Dependent Hepatic CpG Methylation at Distal Regulatory Elements Mapping to Sex-Biased Genes. *Mol Cell Biol.* 2021; 41(2). doi:10.1128/MCB.00166-20
63. Fang C-C, Wu C-F, Liao Y-J, Huang S-F, Chen M, Chen Y-M A. AAV serotype 8-mediated liver specific GNMT expression delays progression of hepatocellular carcinoma and prevents carbon tetrachloride-induced liver damage. *Sci Rep.* 2018; 8(1):13802. doi:10.1038/s41598-018-30800-3

64. Sands M S. AAV-mediated liver-directed gene therapy. *Methods Mol Biol.* 2011; 807:141-157. doi:10.1007/978-1-61779-370-7_6
65. Nakai H, Fuess S, Storm T A, Muramatsu S, Nara Y, Kay M A. Unrestricted hepatocyte transduction with adeno-associated virus serotype 8 vectors in mice. *J Virol.* 2005; 79(1):214-224. doi:10.1128/JVI.79.1.214-224.2005
66. Rizvi F, Everton E, Smith A R, et al. Murine liver repair via transient activation of regenerative pathways in hepatocytes using lipid nanoparticle-complexed nucleoside-modified mRNA. *Nat Commun.* 2021; 12(1):613. doi:10.1038/s41467-021-20903-3
67. Pennisi P A, Kopchick J J, Thorgeirsson S, LeRoith D, Yakar S. Role of growth hormone (GH) in liver regeneration. *Endocrinology.* 2004; 145(10):4748-4755. doi:10.1210/en.2004-0655
68. Zerrad-Saadi A, Lambert-Blot M, Mitchell C, et al. GH receptor plays a major role in liver regeneration through the control of EGFR and ERK1/2 activation. *Endocrinology.* 2011; 152(7):2731-2741. doi:10.1210/en.2010-1193
69. Collin de l'Hortet A, Zerrad-Saadi A, Prip-Buus C, et al. GH administration rescues fatty liver regeneration impairment by restoring GH/EGFR pathway deficiency. *Endocrinology.* 2014; 155(7):2545-2554. doi:10.1210/en.2014-1010
70. Wang M, Chen M, Zheng G, et al. Transcriptional activation by growth hormone of HNF-6-regulated hepatic genes, a potential mechanism for improved liver repair during biliary injury in mice. *Am J Physiol Gastrointest Liver Physiol.* 2008; 295(2):G357-66. doi:10.1152/ajpgi.00581.2007
71. Wang T, Hai J, Chen X, et al. Inhibition of GHRH aggravated acetaminophen-induced acute mice liver injury through GH/IGF-I axis. *Endocr J.* 2012; 59(7):579-587. doi:10.1507/endocrj.EJ11-0356
72. Bleach R, Sherlock M, O'Reilly M W, McIlroy M. Growth Hormone/Insulin Growth Factor Axis in Sex Steroid Associated Disorders and Related Cancers. *Front Cell Dev Biol.* 2021; 9. https://www.frontiersin.org/article/10.3389/fcell.2021.630503.
73. Pardi N, Hogan M J, Porter F W, Weissman D. mRNA vaccines—a new era in vaccinology. *Nat Rev Drug Discov.* 2018; 17(4):261-279. doi:10.1038/nrd.2017.243
74. Trepotec Z, Lichtenegger E, Plank C, Aneja M K, Rudolph C. Delivery of mRNA Therapeutics for the Treatment of Hepatic Diseases. *Mol Ther.* 2019; 27(4): 794-802. doi:10.1016/j.ymthe.2018.12.012
75. Cai Y, Xu M, Yuan M, Liu Z, Yuan W. Developments in human growth hormone preparations: sustained-release, prolonged half-life, novel injection devices, and alternative delivery routes. *Int J Nanomedicine.* 2014; 9:3527-3538. doi:10.2147/IJN.S63507
76. Weissman D. mRNA transcript therapy. *Expert Rev Vaccines.* 2015; 14(2):265-281. doi:10.1586/14760584.2015.973859
77. Hou X, Zaks T, Langer R, Dong Y. Lipid nanoparticles for mRNA delivery. *Nat Rev Mater.* 2021; 6(12):1078-1094. doi:10.1038/s41578-021-00358-0
78. Hogan M J, Pardi N. mRNA Vaccines in the COVID-19 Pandemic and Beyond. *Annu Rev Med.* 2022; 73:17-39. doi:10.1146/annurev-med-042420-112725

Supplemental Information

Mouse Treatments

Eight hours following APAP injury, mice were treated with recombinant human growth hormone (Invitrogen cat #PIRP10928) or NAC (Alfa Aesar cat #A1540914). GH and NAC were both diluted in sterile PBS. GH was diluted to a concentration of 1 mg/mL and given at dosage indicated, subcutaneously with a 0.5 mL insulin syringe. NAC was diluted to a concentration of 50 mg/mL and given at 1000 mg/kg dosage, intraperitoneally with a 1 mL insulin syringe.

For STAT5b activation experiments, 7 days prior to APAP injury, 10-12 week old male mice were treated with a single retroorbital injection of $7.5 \times 10^{10}$ genome copies (GC) of AAV8-TBG-STAT5bCA[30] or AAV8-TBG-Null diluted in 100 µL of sterile PBS. To validate the activity of STAT5bCA, IGF1 was measured in plasma obtained from a lateral tail vein blood sample, collected the day prior to APAP injection.

For mRNA-LNP experiments, mRNA-LNPs were thawed and freshly diluted on ice in sterile Dulbecco's Phosphate Buffered Saline (PBS) prior to each experiment. Mice were administered once 10 g mRNA-LNP in 50 d sterile PBS intravenously by retro-orbital injection under isoflurane anesthesia using a ½cc lo-dose insulin syringes (EXELINT) 8 hours after APAP injection.

mRNA-LNP Production mRNA production was performed as described[79]. Briefly, sequences of the firefly luciferase and human growth hormone were codon-optimized, synthesized (GenScript), and cloned into an mRNA production plasmid. mRNAs were produced from linearized plasmids to contain 101 nucleotide-long poly(A) tails. m1Ψ-5' triphosphate instead of UTP was used to generate modified nucleoside-containing mRNA. Capping of the in vitro transcribed mRNAs was performed co-transcriptionally using the trinucleotide cap1 analog, CleanCap™. mRNA was purified by cellulose purification, as described[80]. mRNAs were analyzed by agarose gel electrophoresis and were stored frozen at $-20°$ C. Cellulose-purified m1Ψ-containing RNAs were encapsulated in LNPs using a self-assembly process as previously described wherein an ethanolic lipid mixture of ionizable cationic lipid, phosphatidylcholine, cholesterol and polyethylene glycol-lipid was rapidly mixed with an aqueous solution containing mRNA at acidic pH[81]. The LNP formulation used in this study contains an ionizable cationic lipid (pKa in the range of 6.0-6.5, proprietary to Acuitas Therapeutics)/phosphatidylcholine/cholesterol/PEG-lipid[81,82]. The proprietary lipid and LNP composition are described in US patent U.S. Pat. No. 10,221,127 entitled "Lipids and lipid nanoparticle formulations for delivery of nucleic acids" (available on the world wide web at lens.org/lens/patent/183-348-727-217-109)6. They had a diameter of ~80 nm as measured by dynamic light scattering using a Zetasizer Nano™ ZS (Malvern Instruments Ltd, Malvern, UK) instrument. The RNA-loaded particles were characterized and subsequently stored at $-80°$ C. at an RNA concentration of ~1 µg µl$^{-1}$. diameter of mRNA-LNPs was ~80 nm with a polydispersity index of 0.02-0.06 and an encapsulation efficiency of ~95%. The DNA sequences of nucleoside-modified mRNA are listed in the Table 12

Tissue Sources and Immunohistochemistry on Frozen Sections

Livers were collected directly in 4% paraformaldehyde (PFA) for overnight fixation at $4°$ C. prior to OCT frozen block processing. For cryopreservation, tissues were washed thrice with PBS, dipped in 15% sucrose for 15 min, and then transferred to and kept in 30% sucrose solution until they sank to the bottom. The liver lobes were then cut in half lengthwise and embedded in OCT. 5 m liver sections were cut using CM1950 Leica cryostat and slides were stored at $-20°$ C. until required for staining.

For tissues from AAV8-TBG-STAT5bCA experiments, livers were isolated into 70% ethanol for paraffin embedding. Livers were then dehydrated with 30 min of 90% ethanol then 100% ethanol, twice each, then 100% xylene. Then livers were switched to 1:1 ratio of xylene and paraffin at 60° C. for 30 min, then vacuum baked in 100% paraffin for 30 min 3× at 60° C. Paraffin blocks were then sectioned with a Leica microtome, and rehydrated with 10 minutes Histoclear/xylene, then 2×5 minutes 100% ethanol, then 1 minute each of 90% ethanol, 70% ethanol, 50% ethanol, then water, when ready for staining.

Liver Dissociation and Single-Cell RNA Sequencing

Liver was perfused according to the previously published method with minor modifications[41,66,83]. All solutions were pre-warmed to 40° C. and delivered at a rate of 4 ml/min. Mice were anaesthetized with ketamine/xylazine and then perfused by cannulation with a 24-gauge catheter through the inferior vena cava with 30 mL 1× Liver Perfusion Medium (Gibco by Life Technologies), while the portal vein was cut to allow the perfusate to flow out. In total, 15 mL of Earle's Balanced Salt Solution (EBSS) containing 10 mM Hepes (Ca++ and Mg++, pH 7.4) was then perfused, and finally followed with 30 mL of Liver Digest Medium (Gibco by Life Technologies) to allow complete dissociation of liver cells in situ. Livers were then extracted and mechanically dissociated in 10 mL of Liver Digest Medium. Cells were filtered through 100 μm cell strainer and filtrate was centrifuged at 50×g for 2 min at 4° C. to obtain hepatocytes in the pellet while the supernatant was collected as the fraction of NPCs. The hepatocyte pellet was resuspended in wash media (Hepatocyte Wash Medium by Gibco+ 0.1 mg/mL DNAse 1+10% FBS) and saved. The cell fraction caught in the 100 m strainer was further digested in NPC Digest Medium (2.5 mg/mL Collagenase IV+0.1 mg/mL DNAse 1), filtered through a 40 μm strainer, then centrifuged at 300×g for 5 min at 4° C. The supernatant was discarded, pellet was resuspended in wash media, and solution was added to the other collection of NPCs. This NPC fraction was used for the single-cell RNA sequencing analysis.

Cell concentration was counted via hemocytometer, in triplicate, then the NPC fraction was pelleted, and resuspended in a buffer of PBS+10% FBS to a concentration of 1000 cells/uL, as per 10× Genomics cell prep protocol. Cell concentration after resuspension was checked again via hemocytometer to confirm. Single cells were captured for sequencing library preparation at the BU scRNA Seq facility using the Chromium Single Cell 3' platform (10× Genomics). Barcoded sequencing libraries were loaded on a NextSeq500™ (Illumina) with a custom sequencing setting (26 bp for Read 1, 98 bp for Read 2), to obtain a mean sequencing depth ranging from 20K to 70K mean reads per cell. All four samples were sequenced in parallel to minimize batch-to-batch variability. Cell doublets were excluded from analysis, i.e., cells containing more than 25% of mitochondrial RNA reads and cells with less than 300 genes detected (indicative of dying cells). 3,000 cells were targeted per sample. However, based on the sex and treatments, the actual numbers of cells sequenced were 1688 for PBS-treated female, 756 for APAP-treated female, 605 for PBA-treated male, and 1772 for APAP-treated male. Samples were normalized using the Seurat™ package[84], with scaling and correction for unwanted sources of variation, like cell degradation, as measured by the percentage of mitochondrial reads in each cell. PCA was used for linear dimensionality reduction and then the first 20 principal components were used for identifying cell clusters in the sample, using the Louvain algorithm. Cell cycle scoring and other molecular signature enrichments were computed using the method from Tirosh et al.[85]. Differential expression tests were run using MAST[86], with gene filters to reduce the burden of multiple test corrections (min.pct=0.25, logfc.threshold=0.25). Contrasts in factorial analyses were also run with limma/edgeR. The individual datasets were subsequently combined in Seurat and re-analyzed using the same defaults as for the individual analyses. A targeted gene set enrichment analysis was done using molecular signatures of interest from the database MsigDB (in particular from the Hallmark and Biocarta collections). Pathways of interest were scored in each cell using the same module scoring method outlined above[85], and t-tests were used to assess differences in gene set scores between groups for each cell type. The scores were displayed in violin plots. Further exploratory analyses were performed after importing the data into SPRING[42] for interactive visualization and further data exploratory analyses. Samples were subplotted by cell type to identify the most highly enriched genes by cell type, which were then analyzed with ENRICHR for pathway analysis, and ranked by z-score of enrichment as defined in the Bioplanet 2019 pathways database.

ALT Assay

For serum assays, blood was isolated from the inferior vena cava or tail tip, then centrifuged at 3000×g for 15 min to separate the serum from the blood cells. Assays were performed using the Pointe Scientific kit (A7526-450) for testing serum ALT levels following manufacturers protocol. Briefly, 10 μl of serum was mixed with supplied reagent mix at 37° C. and readings were measured at 340 nm every 1 min for 5 min using Molecular Devices SpectraMax® i3x Multi-Mode microplate reader.

Hematoxylin & Eosin (H&E) Assay

Histology was performed on frozen-fixed liver tissue sections. Briefly, slides were hydrated with tap water, stained with Gill's Hematoxylin, blued with ammonia, washed in ethanol, stained with 0.25% Eosin Y, then cleared with Histoclear. Slides were mounted with permanent mounting media and observed under bright-field microscope.

TUNEL Assay

Apoptotic and necrotic cells were visualized and quantified using the Invitrogen Click-iT™ Plus TUNEL Assay for In Situ Apoptosis Detection (Alexa Fluor™ 488 dye). The protocol was adapted for use on frozen-fixed tissue sections by scaling up reagent proportions for larger volumes. Sections were counter-stained with DAPI, mounted, and observed under a fluorescence microscope green channel (Nikon Eclipse™ Ni-E microscope).

Histological Analyses

Images from stained sections were visualized and measured at 40× magnification on ImageJ™ (FIJI) using the area measurement tool. 2-3 lobes were measured and averaged per mouse.

ELISA Assay

Human GH concentration in the serum and liver tissue homogenates were measured with Human Growth Hormone Quantikine™ ELISA Kit (R&D Systems cat #DGH00). Serum was diluted 1:1000 in diluent provided, while tissue was diluted 1:100 in diluent provided. Liver tissue was isolated from the right median lobe and mechanically dissociated in 1 mL of sterile PBS for analysis. Murine IGF1 was measured in plasma collected from a lateral tail vein nick prior to APAP injection, using the Mouse/Rat ELISA Kit (22-IG1MS-E01, ALPCO, Salem, NH).

Statistics and Reproducibility

The statistical analyses for the graphs were carried out using two-sided student's t test for unpaired comparisons with GraphPad Prism™. The statistical analyses for the Kaplan-Meier survival curves were carried out using the Log-rank Mantel-Cox test with GraphPad Prism. A p value<0.05 was considered significant, *<0.0001, <0.001, *<0.05, n.s. or no result=not significant. The results are presented as the means±standard error or standard deviation as indicated in legends.

SUPPLEMENTAL REFERENCES

79. Freyn A W, Ramos da Silva J, Rosado V C, et al. A Multi-Targeting, Nucleoside-Modified mRNA Influenza Virus Vaccine Provides Broad Protection in Mice. *Mol Ther.* 2020; 28(7):1569-1584. doi: 10.1016/j.ymthe.2020.04.018
80. Baiersdorfer M, Boros G, Muramatsu H, et al. A Facile Method for the Removal of dsRNA Contaminant from In Vitro-Transcribed mRNA. *Mol Ther Nucleic Acids.* 2019; 15:26-35. doi: 10.1016/j.omtn.2019.02.018
81. Maier M A, Jayaraman M, Matsuda S, et al. Biodegradable lipids enabling rapidly eliminated lipid nanoparticles for systemic delivery of RNAi therapeutics. *Mol Ther.* 2013; 21(8):1570-1578. doi:10.1038/mt.2013.124
82. Jayaraman M, Ansell S M, Mui B L, et al. Maximizing the potency of siRNA lipid nanoparticles for hepatic gene silencing in vivo. *Angew Chem Int Ed Engl.* 2012; 51(34): 8529-8533. doi: 10.1002/anie.201203263
83. Everton E, Rizvi F, Smith A R, et al. Transient yet Robust Expression of Proteins in the Mouse Liver via Intravenous Injection of Lipid Nanoparticle-encapsulated Nucleoside-modified mRNA. *Bio-protocol.* 2021; 11(19):e4184. doi: 10.21769/BioProtoc.4184
84. Butler A, Hoffman P, Smibert P, Papalexi E, Satija R. Integrating single-cell transcriptomic data across different conditions, technologies, and species. *Nat Biotechnol.* 2018; 36(5):411-420. doi:10.1038/nbt.4096
85. Itay T, Benjamin I, M. P S, et al. Dissecting the multicellular ecosystem of metastatic melanoma by single-cell RNA-seq. *Science (80).* 2016; 352(6282):189-196. doi:10.1126/science.aad0501
86. Finak G, McDavid A, Yajima M, et al. MAST: a flexible statistical framework for assessing transcriptional changes and characterizing heterogeneity in single-cell RNA sequencing data. *Genome Biol.* 2015; 16(1):278. doi:10.1186/s13059-015-0844-5

TABLE 12

DNA sequences used as templates to in vitro transcribe nucleoside modified mRNA.

Human Growth Hormone
ATGGCCACCGGCTCCCGCACCTCCCTGCTGCTGGCCTTCGGCCTGCTGT
GCCTGCCCTGGCTGCAGGAGGGCTCCGCCTTCCCCACCATCCCCCTGTC
CCGCCTGTTCGACAACGCCATGCTGCGCGCCCACCGCCTGCACCAGCTG
GCCTTCGACACCTACCAGGAGTTCGAGGAGGCCTACATCCCCAAGGAGC
AGAAGTACTCCTTCCTGCAGAACCCCCAGACCTCCCTGTGCTTCTCCGA
GTCCATCCCCACCCCCTCCAACCGCGAGGAGACCCAGCAGAAGTCCAAC
CTGGAGCTGCTGCGCATCTCCCTGCTGCTGATCCAGTCCTGGCTGGAGC
CCGTGCAGTTCCTGCGCTCCGTGTTCGCCAACTCCCTGGTGTACGGCGC
CTCCGACTCCAACGTGTACGACCTGCTGAAGGACCTGGAGGAGGGCATC
CAGACCCTGATGGGCCGCCTGGAGGACGGCTCCCCCCGCACCGGCCAGA
TCTTCAAGCAGACCTACTCCAAGTTCGACACCAACTCCCAC
(SEQ ID NO: 45)

Firefly Luciferase
ATGGAAGATGCCAAAAACATTAAGAAGGGCCCAGCGCCATTCTACCCAC
TCGAAGACGGGACCGCCGGCGAGCAGCTGCACAAAGCCATGAAGCGCTA
CGCCCTGGTGCCCGGCACCATCGCCTTTACCGACGCACATATCGAGGTG
GACATTACCTACGCCGAGTACTTCGAGATGAGCGTTCGGCTGGCAGAAG
CTATGAAGCGCTATGGGCTGAATACAAACCATCGGATCGTGGTGTGCAG
CGAGAATAGCTTGCAGTTCTTCATGCCCGTGTTGGGTGCCCTGTTCATC TABLE 12-continued DNA sequences used as templates to in vitro transcribe nucleoside modified mRNA.

GGTGTGGCTGTGGCCCCAGCTAACGACATCTACAACGAGCGCGAGCTGC
TGAACAGCATGGGCATCAGCCAGCCCACCGTCGTATTCGTGAGCAAGAA
AGGGCTGCAAAAGATCCTCAACGTGCAAAAGAAGCTACCGATCATACAA
AAGATCATCATCATGGATAGCAAGACCGACTACCAGGGCTTCCAAAGCA
TGTACACCTTCGTGACTTCCCATTTGCCACCCGGCTTCAACGAGTACGA
CTTCGTGCCCGAGAGCTTCGACCGGGACAAACCATCGCCCTGATCATGA
ACAGTAGTGGCAGTACCGGATTGCCCAAGGGCGTAGCCCTACCGCACCG
CACCGCTTGTGTCCGATTCAGTCATGCCCGCGACCCCATCTTCGGCAAC
CAGATCATCCCCGACACCGCTATCCTCAGCGTGGTGCCATTTCACCACG
GCTTCGGCATGTTCACCACGCTGGGCTACTTGACTCTGCGGCTTTCGGG
TCGTGCTCATGTACCGCTTCGAGGAGGAGCTATTCTTGCGCAGCTTGCA
AGACTATAAGATTCAATCTGCCCTGCTGGTGCCCACACTGTTTAGCTTC
TTCGCTAAGAGCACTCTCATCGACAAGTACGACCTAAGCAACTTGCACG
AGATCGCCAGCGGCGGGGCGCCGCTCAGCAAGGAGGTAGGTGAGGCCGT
GGCCAAACGCTTCCACCTACCAGGCATCCGACAGGGCTACGGCCTGACA
GAAACAACCAGCGCCATTCTGATCACCCCCGAAGGGGACGACAAGCCTG
GCGCAGTAGGCAAGGTGGTGCCCTTCTTCGAGGCTAAGGTGGTGGACTT
GGACACCGGTAAGACACTGGGTGTGAACCAGCGCGGCGAGCTGTGCGTC
CGTGGCCCCATGATCATGAGCGGCTACGTTAACAACCCCGAGGCTACAA
ACGCTCTCATCGACAAGGACGGCTGGCTGCACAGCGGCGACATCGCCTA
CTGGGACGAGGACGAGCACTTCTTCATCGTGGACCGGCTGAAGTCCCTG
ATCAAATACAAGGGCTACCAGGTAGCCCCAGCCGAACTGGAGAGCATCC
TGCTGCAACACCCCAACATCTTCGACGCCGGGGTCGCCGGCCTGCCCGA
CGACGATGCCGGCGAGCTGCCCGCCGCAGTCGTCGTGCTGGAACACGGT
AAAACCATGACCGAGAAGGAGATCGTGGACTATGTGGCCAGCCAGGTTA
CAACCGCCAAGAAGCTGCGCGGTGGTGTTGTGTTCGTGGACGAGGTGCC
TAAAGGACTGACCGGCAAGTTGGACGCCCGCAAGATCCGCGAGATTCTC
ATTAAGGCCAAGAAGGGCGGCAAGATCGCCGTG (SEQ ID NO: 46)

Example 3: A Multi-Modular Approach for Human Pluripotent Stem Cell-Based Liver Regeneration Significance Liver disease affects hundreds of millions of patients worldwide. Liver transplantation is the only treatment for end stage liver disease. Currently, more than 6,000 liver transplants are performed each year in the United States, yet over 16,000 Americans are on the waiting list for a liver transplant. Given the scarcity of donor organs, hepatocyte transplantation has been attempted in patients with inherited metabolic liver and acute liver failure as treatment and a bridge for liver transplantation[1-3]. Although the safety of the procedure is well established and the clinical results are encouraging, the application for liver cell therapy is still hampered by poor engraftment of transplanted cells, lack of optimal immunosuppression regiments and most importantly, a limited source of hepatocytes[4-8]. Hepatocytes derived from human induced pluripotent stem cells (hiPSC) could provide an unlimited supply for patient-specific cell replacement therapy[9-11]. However, generation of iPSC-derived hepatocyte-like cells (HLC) that engraft, defined here as the ability to survive and proliferate, and are mature enough to function in a damaged liver remains a challenge[12-14], and a major gap that this application targets. The inventors propose a multi-modular approach that includes (1) a bi-cell therapy composed of HLCs and supportive endothelial cells (ECs), both derived from hiPSCs (2) engineering HLCs with genetic circuits to promote their engraftment and maturation and (3) engineering ECs to support HLC-mediated liver repair.

The inventors initially observed that ECs were always associated with mouse ESC-derived HLC clusters[16], and showed that ECs function as a niche to repress Wnt and Notch signaling to promote HLC specification[17]. Recently, the inventors discovered that the supportive function of ECs is dependent on activation of VEGFR2[18]. It has been shown that a VEGFA-VEGFR2 axis activates sinusoidal ECs in injured mouse livers to induce the expression of endothelial factors such as WNT2 and HGF that trigger hepatocyte proliferation[19]. Similarly, WNT2 and WNT9b secreted by sinusoidal ECs were shown to induce beta catenin-dependent hepatocyte proliferation following partial hepatectomy[20]

Thus, bi-cell therapy with ECs represents a potential strategy to overcome the obstacles of HLC therapies. In addition, the inventors enhance EC supportive functions through modulation of VEGFR2 and downstream factors such as HGF, WNT2 as well as WNT9b. In parallel, the inventors engineer HLCs to activate pathways (HGF/cMET, EGF/EGFR and IL6/IL6R) and express transcription factors (ATF5, PROX1, CEBPA) that are critical for liver development, regeneration[21-24] and the maturation of reprogrammed fibroblast-derived HLCs[25]. The inventors test the ability of these pathways and TFs to accelerate HLC engraftment and maturation following bi-cell therapy. Importantly for clinical translation, VEGFR2, cMET, EGFR and IL6R will be activated in a timely manner in vivo using the non-integrative nucleoside-modified mRNA, delivered with lipid-nanoparticles (mRNA-LNPs), whose safety has been validated in clinical trials for cancer immunotherapy[26]. The inventors validated the use of mRNA-LNPs to timely control robust gene expression in virtually all hepatocytes in the liver to precondition the host liver prior to transplantation. Specifically, data indicate that mRNA-LNP encoding HGF, EGF and IL6 significantly improve HLC survival after transplantation into acute and chronic liver injury models.

Figure 24:
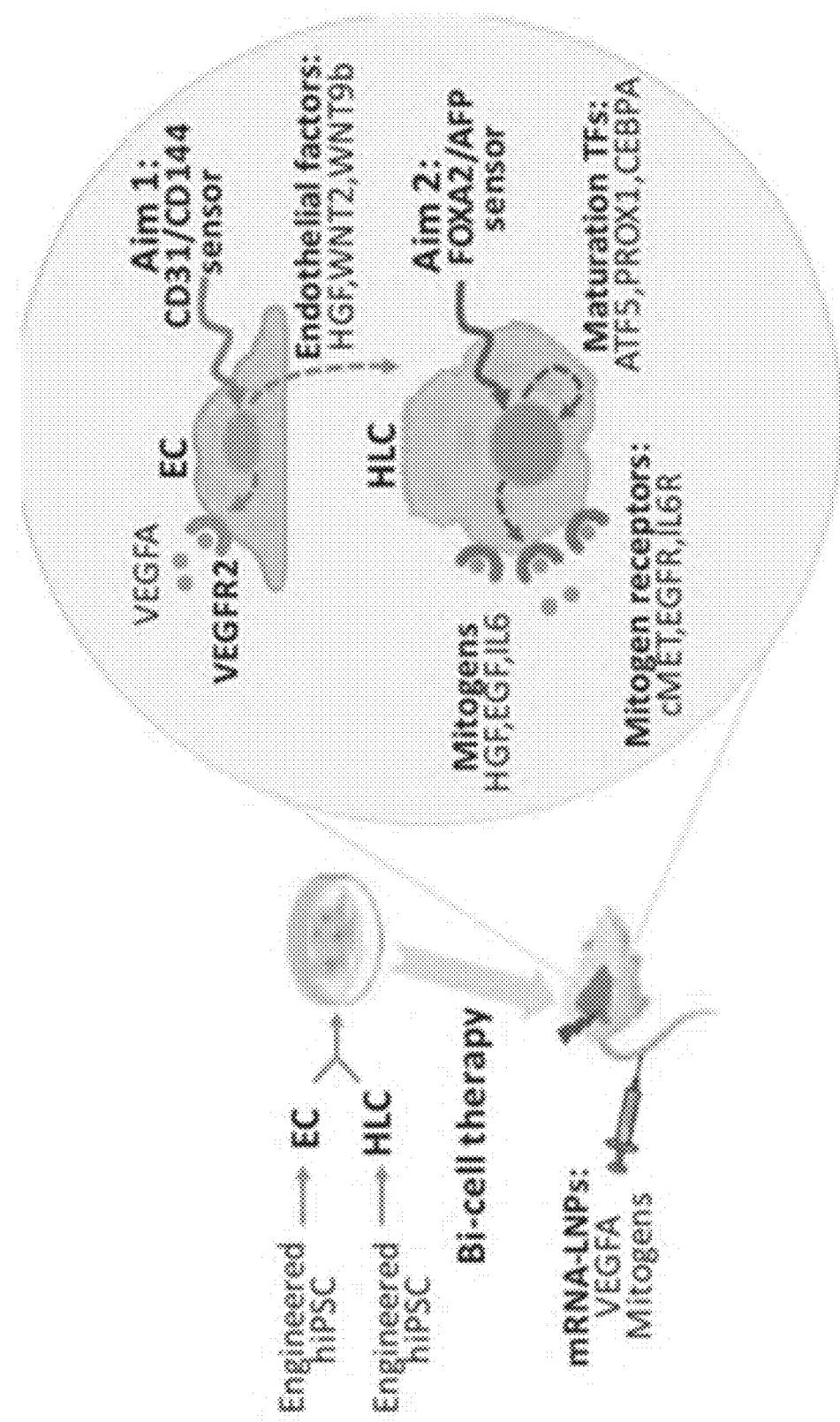
FIG. 24 depicts experimental design of the hiPSC-based bi-cell therapy with engineered HLCs and ECs to treat liver disease models. Aim 1 design will enhance EC supportive functions by engineering ECs to express VEGFR2 and the downstream factors HGF, WNT2, and WNT9b, while the ligand VEGFA will be delivered via mRNA-LNPs. Aim 2 design will promote maturation and engraftment of HLCs that will be engineered to express mitogen receptors and maturation transcription factors (TFs), while mitogens will be delivered via mRNA-LNPs. Experiments in both aims will establish novel engineered hiPSC lines in which genetic circuits will sense ECs via CD31 or CD144 expression, and HLCs via FOXA2 or AFP expression as the cells specify in culture, and subsequently will induce expression of the cell type-specific genes.

Altogether, this multi-modular approach includes innovative technologies that combine engineered hiPSCs with CRISPR/dCas9-based genetic circuits to express multiple cell-specific genes from endogenous loci and timely delivery of factors in vivo via mRNA-LNPs (FIG. 24). ECs are engineered to express sustained and robust levels of VEGFR2, while VEGFA will be timely delivered in the liver via mRNA-LNPs, and the endothelial factors WNT2, HGF and WNT9b to provide functional support for HLCs. HLCs are engineered to express sustained and robust levels of mitogen receptors, while mitogens will be timely delivered via mRNA-LNPs, and key maturation TFs ATF5, PROX1 and CEBPA. This novel cell-type specific gene expression genetic circuit technology is a major advance for the hiPSC field as it is relatively safe with site specific integration, and allows expression of multiple genes from their endogenous loci in specific cells as they develop in hiPSC differentiation cultures. This alleviates technical difficulties encountered when generating hiPSC lines engineered with multiple integrations of cell type specific promoters regulating genes of interest, and preventing any harmful artificial gene overexpression.

This proposal pioneers in the liver regeneration field two technologies, engineered genetic circuit-based hiPSC lines and mRNA-LNPs, and hence has major technical and clinical significance for treating liver diseases. This example uses hiPSC to model bi-cell therapy with patient-specific HLCs and ECs, which extends the clinical significance for treating liver diseases with patient specific cells.

Innovation

The use of hiPSC differentiation cultures to generate functional HLCs for cell therapy of liver diseases remains a challenge[9-15]. The approach is innovative, for 6 major scientific reasons: It is proposed (1) to co-transplant HLCs and supportive ECs to model the known hepatocytes EC niche in vivo during liver regeneration; (2) to enhance the EC niche-HLC crosstalk by engineering both EC and HLCs, (3) engineering ECs to secrete supportive factors to improve HLC repopulation of injured livers, (4) engineering HLCs to enhance their survival, proliferation and maturation; (5) to synergize strategies by cotransplanting HLCs and ECs that will be both engineered, (6) to specifically examine the impact of these strategies on cell engraftment during the first week following cell transplantation, which has been an overlooked time frame, but is a critical time when transplanted cell need engraftment support.

Moreover, innovative experimental strategies include: (1) hiPSC lines expressing luciferase in combination with DsRed to quantify cell engraftment in real-time in live mice and to identify transplanted cells on liver sections; (2) the two clinically relevant and complementary human acute and chronic liver disease; (3) critically, the clinically relevant non-integrative mRNA tool to modulate protein expression in a timely fashion into host livers to synergize liver repair by transplanted cells; (4) the novel engineered hiPSC lines that include EC- or HLC-specific genetic circuits; (5) two key advantages of the genetic circuit-engineered hiPSC lines are the induction of gene expression from endogenous loci preventing any harmful artificial overexpression, and the ability to induce expression of multiple genes in one cell type such as 3 mitogen receptors in HLCs or 3 endothelial factors in ECs.

By pioneering the use of genetic circuit embedded-hiPSCs and mRNA-LNPs to promote the regenerative EC niche-HLC interaction, this project greatly advances the ultimate utility of the patient-derived hiPSC-derived bi-cell HLC-EC therapy to treat liver diseases.

Approach

Preliminary Studies

This application tests that a bi-cell therapy with HLCs and ECs engineered to promote the EC niche-HLC interactions lead to successful HLC-based treatment for liver disease.

Efficient generation of homogenous cultures of HLCs from hiPSCs. The inventors have demonstrated that the resulting HLCs express markers characteristic of fetal hepatoblasts and hepatocytes including alpha fetoprotein (AFP), albumin (ALB), alpha 1 antitrypsin, (AAT), P450 enzymes (Cyp3A4, 3A7), and are positive for Periodic acid Schiff staining indicative of glycogen storage.

Figure 25A:
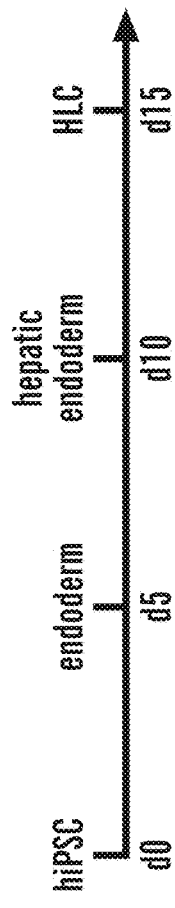
FIGS. 25A-25D depicts efficient generation of HLCs in 2D hiPSC differentiation cultures.
Figure 25B:
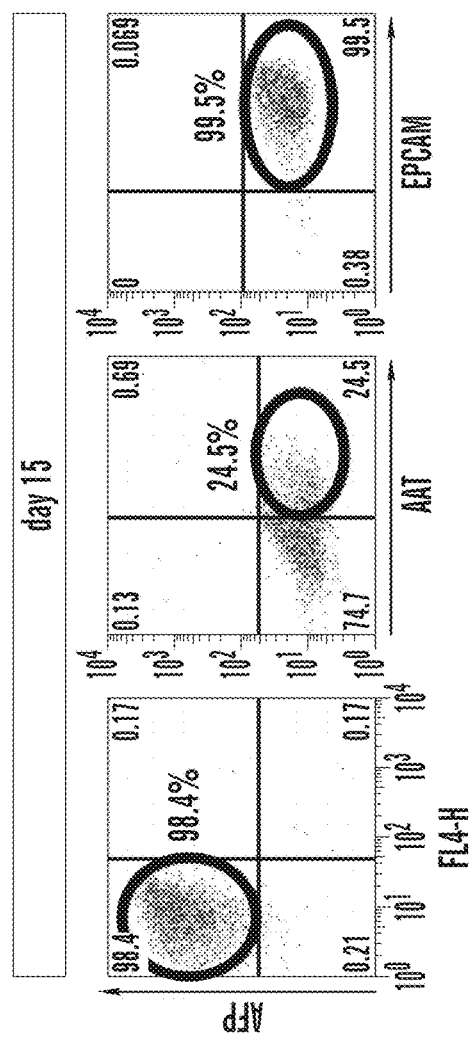
Figure 25B:
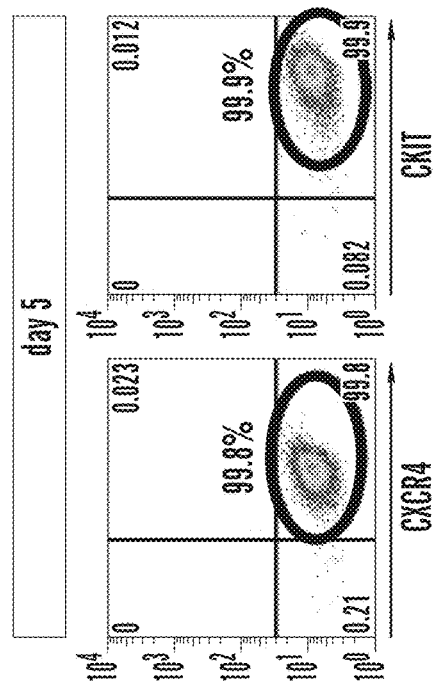
Figure 25C:
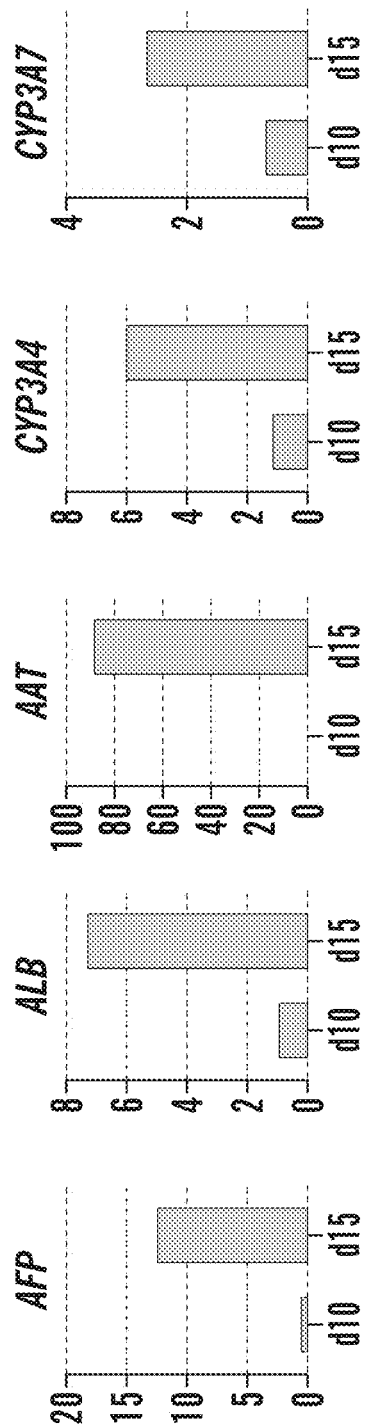
Figure 25D:
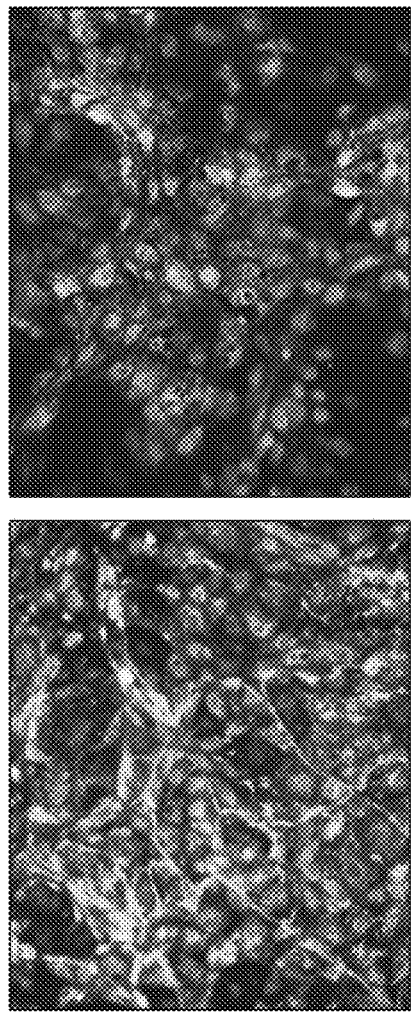
Figures 26A, 26B, 26C, 26D, 26E, 26F:
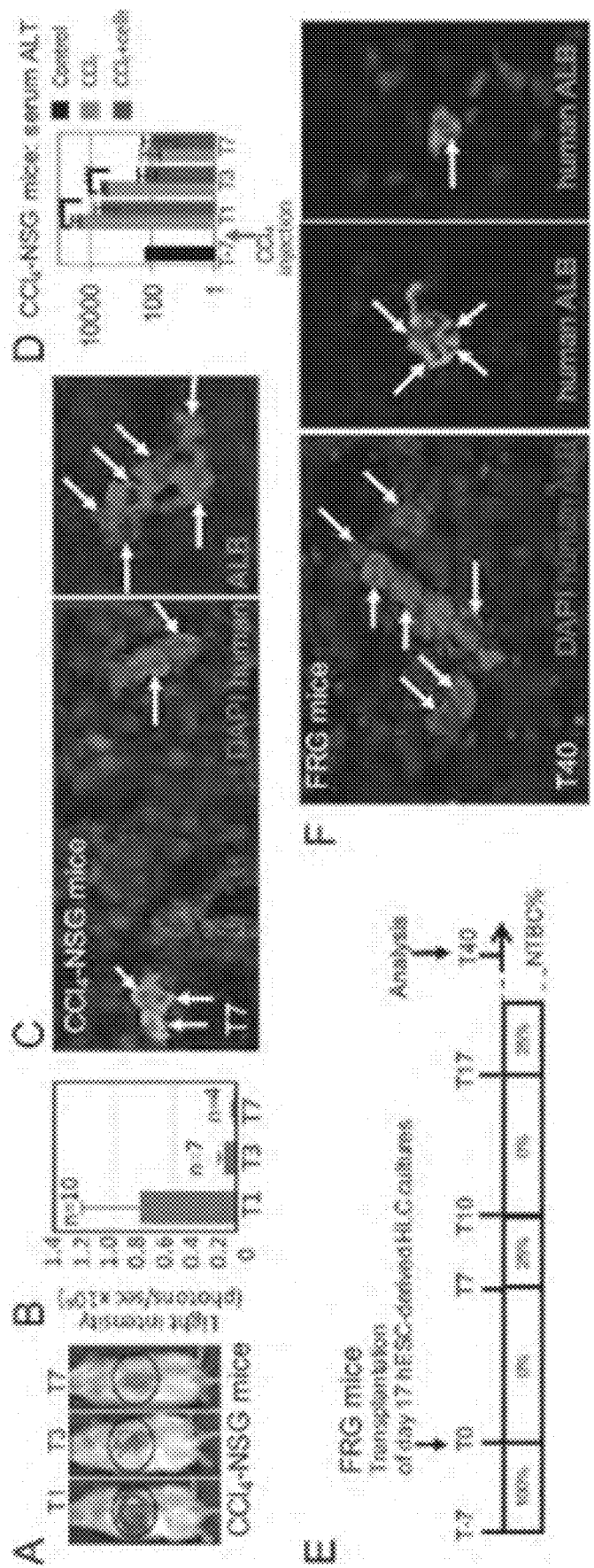
FIGS. 26A-26F depicts integration of day 17 hESC-derived HLCs in CCl4-NSG mice (FIGS. 26A-26D) and FRG mice (FIGS. 26E-26F).

Importantly, HLCs from human ESC and macaque iPSC harbor a unique hepatocyte feature which is to support hepatitis C virus (HCV) replication. The inventors showed that Human[32] and macaque[31] HLCs replicate HCV to levels comparable to the best-case control human hepatoma Huh-7.5 cells. This protocol also generates endoderm-derived hepatic progenitors that express VEGFR2. When further cultured in aggregates (3D), VEGFR2+ progenitors differentiate into HLCs that functionally support HCV replication[32]. Similarly, VEGFR2 expressing liver progenitors were identified in the foregut endoderm in mice and have been shown to give rise to 30-50% fetal hepatoblasts that in turn generated hepatocytes and cholangiocytes in adult mice[32]. In order to strictly generate HLCs in differentiation cultures, the inventors established a modified version of the above hepatic differentiation protocol. This new protocol requires similar specification factors, however, the endoderm program is induced in a 2D monolayer culture instead of the 3D embryoid body culture (FIG. 25A). FIG. 25 illustrates the efficient differentiation of hiPSC monolayers into HLCs. hiPSCs gave rise to a homogenous population of endoderm cells at day 5 expressing the endoderm markers CXCR4 and CKIT, that in turn derived at day 15 homogenous cultures of HLCs composed virtually of ~100% of HLCs expressing AFP and EPCAM (FIG. 25B). Most of HLCs are positive for albumin (ALB), and about ~20% express a1 antitrypsin (AAT) (FIG. 25B, 25D). Expression of hepatic markers in day 15 HLCs was confirmed by qPCR (FIG. 25C).

hESC-derived HLCs are able to integrate into damaged livers of acute and chronic liver injury mouse models. In a first attempt to define the basic level of engraftment of hESC-derived hepatic cell cultures, the inventors used an acute liver injury CCl4-treated NOD/SCID/IL2Rg−/−(NSG) immuno-compromised model. In order to detect hESC-derived HLCs in vivo, the inventors established a stable hESC line (H9DsL) by transducing 2 lentiviruses expressing DsRed and luciferase proteins. Day 17 H9DsL hepatic cultures, comprised of ~80% HLCs and ~20% VEGFR2+ progenitors were transplanted at T0, 1.5 day after CCl4 injection (0.35 ml/kg body weight). Bioluminescence pictures were taken one day (T1), 3 days (T3) and 7 days (T7) following cell transplantation and bioluminescence quantified (FIG. 26A, 26B). Luciferase activity was strongly detected in livers at T1, however it progressively decreased to finally drop to barely detectable levels at T7. Despite low levels of bioluminescence, small clusters of human albumin+ cells were detected at T7 (FIG. 26C). To assess the functionality of HLCs, levels of alanine aminotransferase (ALT) were measured in the serum of transplanted mice. As expected, ALT levels were very low in CCl4-untreated control mice (FIG. 26D, black column), while they were dramatically increased at T1 after CCl4 injection (FIG. 26D, grey column). These levels decreased progressively to finally reach control levels at T7, when livers fully recovered by simple proliferation of hepatocytes. Importantly, in the presence of hESC-derived HLCs, ALT levels dropped to control levels earlier, at T3, indicating an acceleration of liver repair in the presence of hESC HLCs (FIG. 26D). The second mouse model is a chronic liver injury Fumaryl acetoacetate (Fah)−/−, Rag2−/−, IL2Rg−/− (FRG mice[35]) immuno-compromised model. The FRG mouse serves as a model for hereditary tyrosinemia type I in humans. These mice lack the enzyme FAH required for tyrosine catabolism. In the absence of FAH, two metabolites accumulate into hepatocytes that lead to cell death. Treatment with a drug NTBC in the drinking water prevents accumulation of these hepatotoxic metabolites and cell death. Day 17 hESC-derived hepatic cultures were transplanted in FRG mice (FIGS. 26E, 26F). NTBC was then withdrawn from the drinking water to induce liver injury for 7 days, and was subsequently reintroduced at a low concentration for 3 days to prevent weight loss and associated death. The cycle of 7 days without NTBC followed by 3 days with NTBC was reiterated until day 40 when livers were analyzed. Clusters of transplanted HLCs were visualized by immunostaining for human albumin (FIG. 26F). These preliminary data suggest some abilities of hESC-derived HLCs to engraft in vivo. The inventors improve HLC engraftment by co-transplanting HLCs with supportive ECs, both derived from hiPSC and both engineered to promote the EC niche-HLC regenerative interactions.

Figures 27A, 27B, 27C:
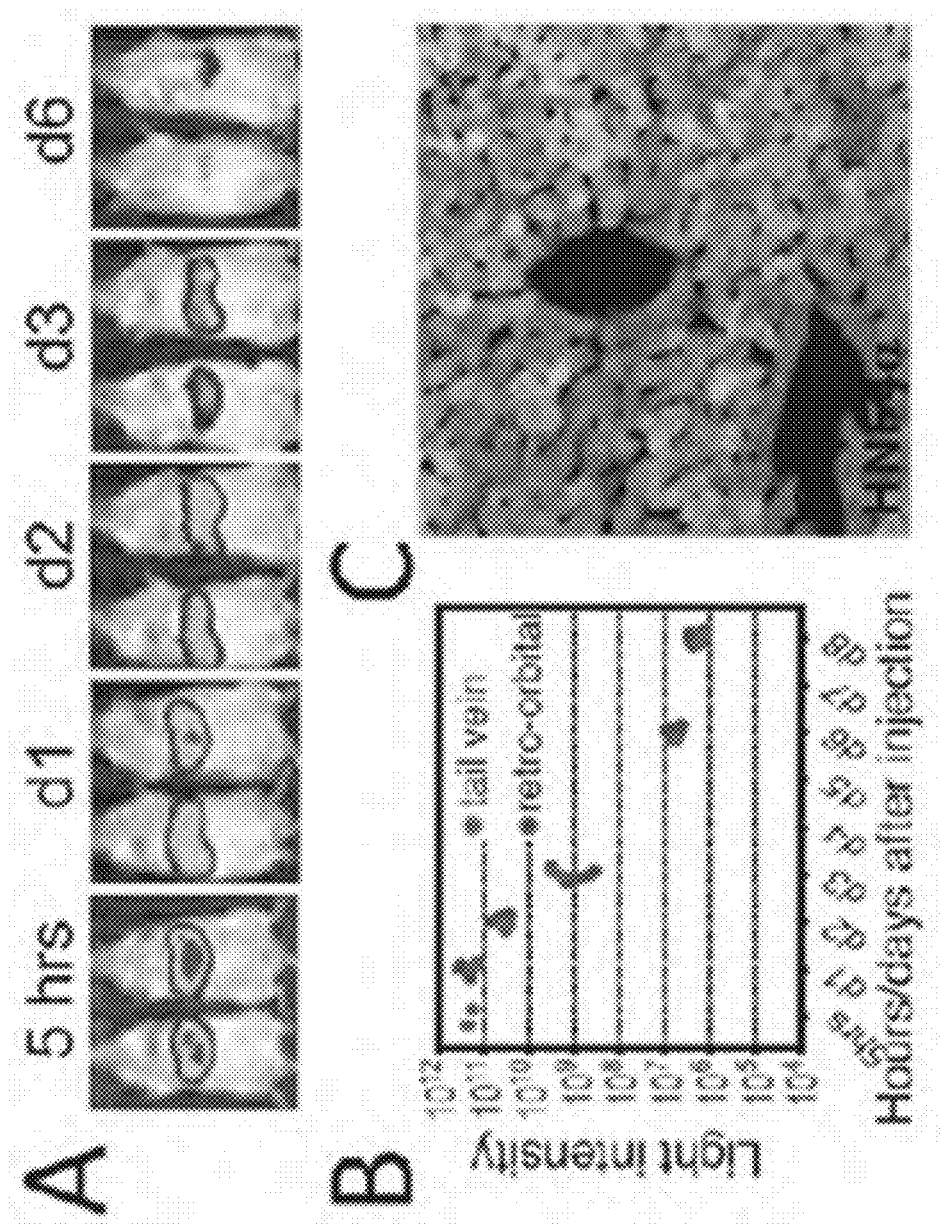
FIGS. 27A-27C depicts mRNA-LNPs are efficiently targeted to the liver.

The mRNA-LNP tool is an efficient, safe technology to transiently express any protein in vivo in the liver. Recently, in vitro-transcribed nucleoside modified mRNA has emerged as a safe therapeutic platform for their non-integrative properties and timely controlled protein expression[36]. Many strategies have been established to improve stability, immune silencing and translatability of mRNAs including 5' cap, optimized 5'- and 3'-UTRs, HPLC purification, modifications of the poly(A)-tail and of the coding sequences with modified nucleosides (pseudouridine or 1-methylpseudouridine, methyl cystidine)[36]. The inventors demonstrate using mRNA-LNP encoding luciferase, that IV injected mRNA-LNPs are specifically and efficiently targeted to the liver, and that their transient expression lasts over a week (FIGS. 27A, 27B). The inventors further showed that mRNAs are specifically transfected into virtually all hepatocytes as detected by GFP after injection of GFP-mRNA-LNPs (FIG. 27C). Delivery in vivo of mRNA-LNP encoding specific ligands to timely activate ECs and HLCs following bi-cell therapy improves HLC engraftment and function in vivo.

Figures 28A, 28B, 28C, 28D, 28E, 28F:
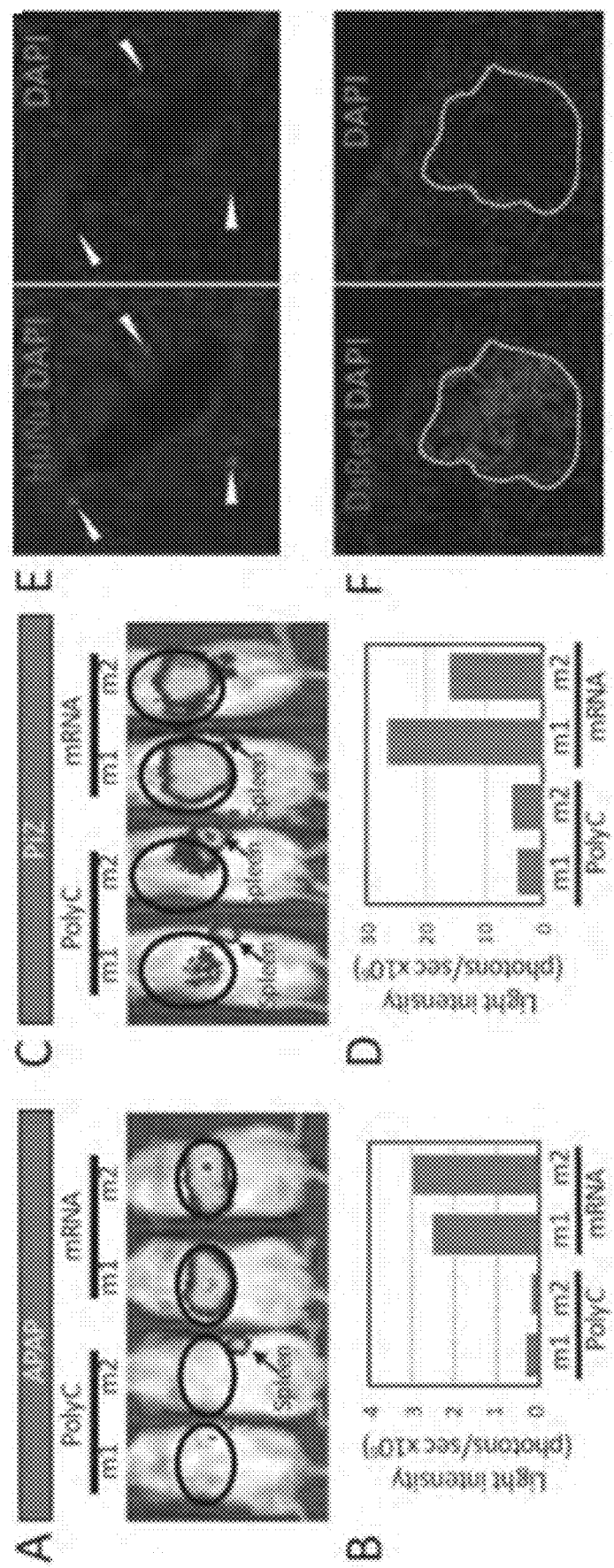
FIGS. 28A-28F depicts mRNA-LNP encoding HGF, EGF, and IL6 efficiently promote hiPSC-derived HLC survival in acute (APAP.

Transient expression of 3 mitogens (HGF, EGF, IL6) via mRNA-LNP supports hiPSC-derived HLC survival in vivo. The inventors have generated data supporting the role of HGF, EGF and IL6, 3 key pathways naturally induced during liver injury in hepatocytes[22-24], in improving transplanted hiPSC HLC survival via mRNA-LNP-ligand delivery. To this end, the inventors used an acute liver injury model in which NSG mice were injected with a single dose of acetaminophen (APAP, 200 mg/kg IP) (FIGS. 28A, 28B) and a chronic liver injury model (PiZ-NSG) that recapitulates the liver disease of a1 antitrypsin deficiency in humans[40] (FIGS. 28C, 28D). $10^6$ luciferase-expressing hiPSC (BU3)-derived HLCs were transplanted through the spleen. Transplantations were performed 24 h00 after APAP injection and in 8-9 week-old PiZ-NSG mice. mRNA-LNPs encoding HGF, EGF and IL6 were injected IV 5 hours prior to cell transplantation as the inventors demonstrated that the highest expression of protein from mRNA-LNPs in liver is obtained 5 hours after administration (FIG. 27). The following day, bioluminescence was significantly greater in mice pre-conditioned with mRNA-LNPs in both injury models, indicating the key impact of the factors in improving transplanted HLC survival (FIG. 28). The inventors observed one day following HLC transplantation into the APAP injury model scattered single transplanted cells or occasionally clusters of HLCs detected either with human nuclei antigen (FIG. 28E) or DsRed (FIG. 28F). The inventors induce sustained and robust expression of mitogen receptors to levels found in primary hepatocytes by engineering hiPSCs in experiments outlined in Aim 2, and roles of each mitogen in improving HLC engraftment are systematically investigated.

ECs are key supportive cells for PSC-derived endoderm commitment to a hepatic fate and further maturation. The inventors observed that ECs were always associated with HLC clusters in mouse ESC hepatic differentiation cultures, and that ECs were required for HLC cluster outgrowth[16]. The inventors further showed that the EC niche functions by repressing Wnt and Notch signaling in HLCs to promote HLC specification[17]. More recently, analyses of RNA seq data revealed that this EC supportive role is mediated through activation of VEGFR2 in ECs[18]. Consistent with the instant data, it has been reported that sinusoidal ECs in the injured mouse liver are activated through the VEGFA-VEGFR2 axis to express endothelial factors WNT2 and HGF that in turn trigger hepatocyte regeneration[19]. Similarly, WNT2 and WNT9 overexpression in sinusoidal ECs has been shown to induce hepatocyte proliferation following partial hepatectomy[20]. Thus, the inventors demonstrate that a bi-cell therapy combining ECs and HLCs represents a potential strategy that will lead to successful HLC-based treatment for liver disease. In this scenario, both HLCs and ECs derive from hiPSCs. The inventors generate hiPSC-derived ECs from a protocol which demonstrated the critical supportive function of hiPSC-ECs to generate HLC-based liver organoids able to engraft and function in mouse models of liver injuries[42,43].

Figure 29A:
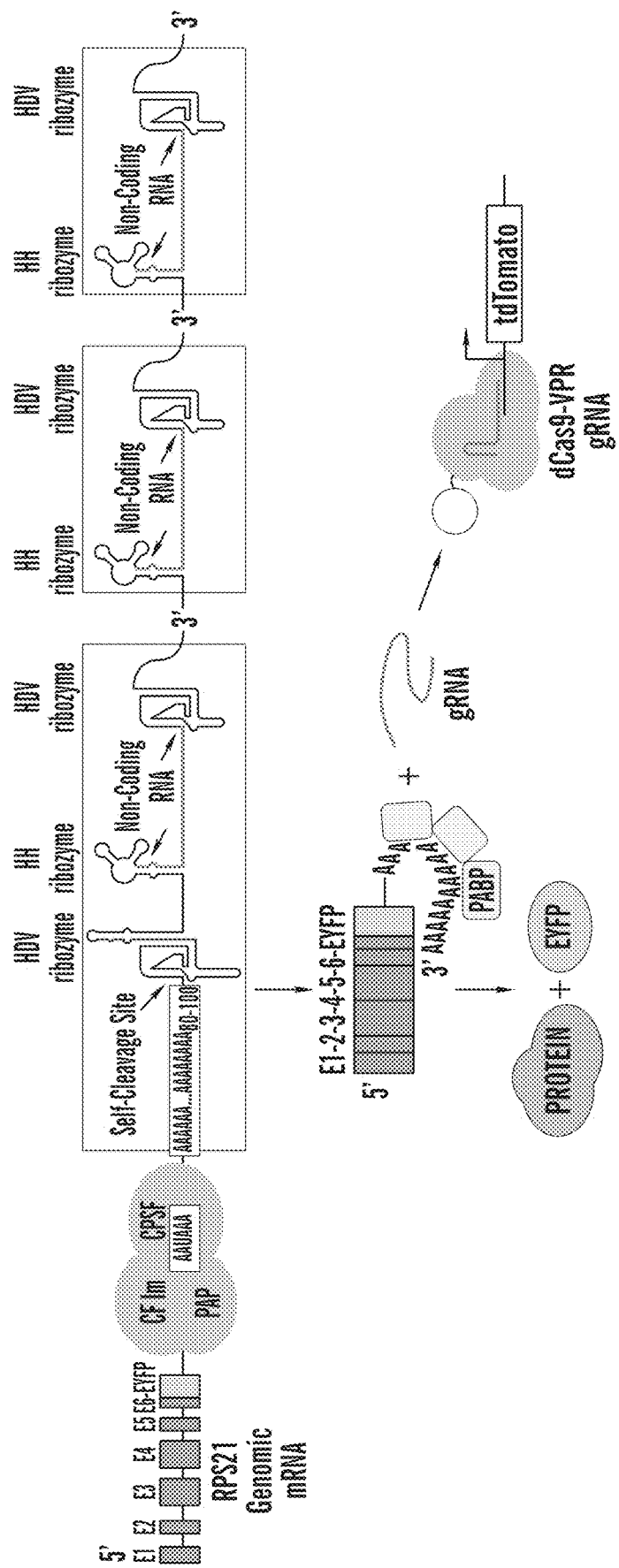
FIGS. 29A-29C depict validation of activation of genetic circuits inducing gene express (actuator: tdTomato) in cells that sense specific gene expression (sensor: RSP21/EYFP) using the CRISPR/dCas9 system.
Figures 29B, 29C:
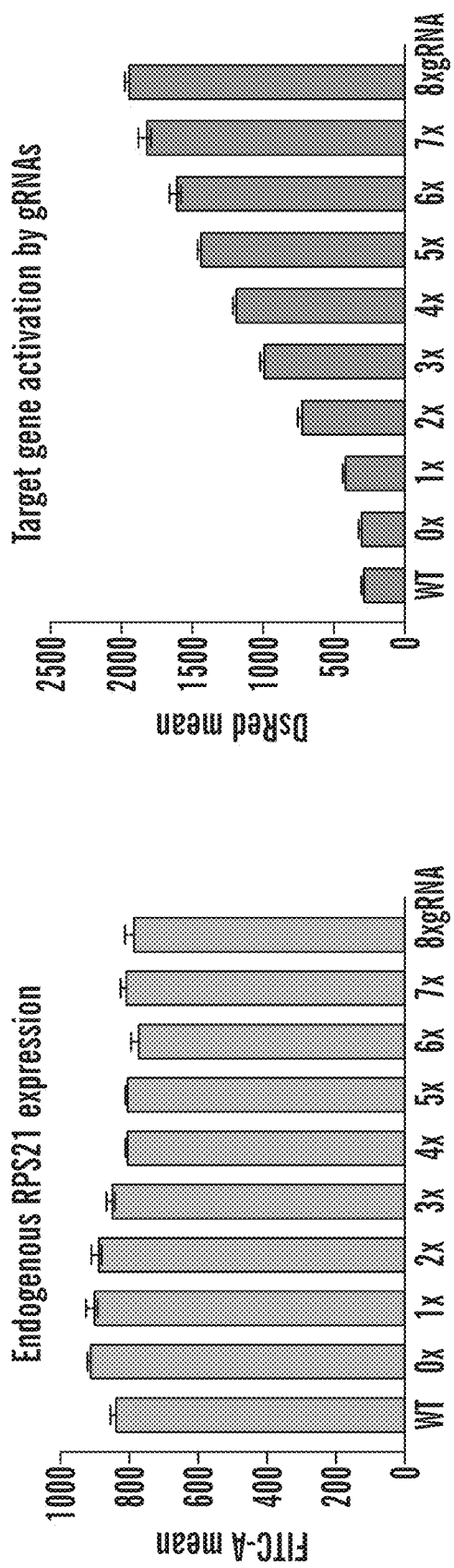

Development of sensor/actuator genetic circuits using CRISPR/dCas9 system that senses specific cell-type gene expression (sensor) to induce expression of a gene of interest (actuator). To accelerate genetic engineering tasks, the inventors construct large mammalian genetic circuits using the CRISPR/Cas9 system and integrate them in various cell lines into chromosomal "landing pads"[44,45] and showed long-term gene expression[46]. The efficiency of sensor/actuator genetic circuits has been recently validated in HEK293FT cells using the RPS21 locus activity as a sensor to express up to 8 guide RNA (gRNA) targeting a synthetic minimal CMV promoter with 7 gRNA target sites driving expression of tdTomato (FIG. 29). Integration of gRNAs downstream of the RPS21 gene coupled with a 2A sequence and the EYFP reporter indicated that gRNA expression didn't affect endogenous RPS21 expression based on the maintenance of EYFP expression regardless of the number of gRNAs integrated (FIG. 29B). Transfection of plasmid encoding dCas9 VPR, complexed with gRNAs produced alongside endogenous RPS21 transcripts and resulted in high levels of expression of tdTomato proportional to the number of gRNAs integrated (FIG. 29B). The inventors build genetic circuits in hiPSC lines in which HLCs (sensed by AFP or FOXA2 expression) or ECs (sensed by CD31 or CD144 expression) in hiPSC differentiation cultures are induced to express specific genes (actuators) from their endogenous loci. This novel cell-type specific gene expression genetic circuit tool is a major advance for the hiPSC field as it allows expression of multiple genes from their endogenous loci in specific cells as they develop in hiPSC or differentiation cultures. This will alleviate technical difficulties encountered when generating hiPSC lines engineered with multiple integrations of cell type specific promoters regulating genes of interest, and preventing any harmful artificial gene overexpression.

Design

Rigor: All in vitro experiments will be performed in triplicate from 3 independent differentiations to allow proper statistical analyses as previously published[31,32,47]. Different groups/conditions will be analyzed by student's t-test. $P<0.05$ will be considered statistically different. Both genders will be used in mouse studies to account for gender variability. Rigorous experimental designs are described in the animal protocol document. The inventors consult the Biostatistics, Epidemiology & Research Design (BERD) program from BU to ensure proper statistical analyses. Both genders hiPSC lines from the CReM will be used in these studies: The hiPSC BU1, BU2 and BU3 are males, while BU7 and BU8 are females.

Aim 1: Engineering the EC Niche to Promote Liver Regeneration in Bi-Cell Therapy with HLCs Rationale: The ability of hiPSC-derived HLCs to repopulate diseased livers remains a major challenge and key gap toward successful regenerative cell therapy[9-11]. To fill this gap, the inventors use co-transplantation of HLCs with supportive hiPSC-derived ECs to facilitate liver regeneration success. The inventors initially observed that ECs were always associated with mouse ESC-derived HLC colonies[16], and showed that ECs function as a niche to repress Wnt and Notch signaling to promote HLC specification[17]. Recently, RNA seq data analyses revealed that this EC supportive function is dependent on activation of VEGFR2[18]. Consistent with this data, it has been shown that a VEGFA-VEGFR2 axis activates sinusoidal ECs in injured mouse livers to induce the expression of endothelial factors such as WNT2 and HGF that trigger hepatocyte proliferation[19]. Similarly, WNT2 and WNT9b secreted by sinusoidal ECs were shown to induce beta catenin-dependent hepatocyte proliferation following partial hepatectomy[20]. Therefore, activation of hiPSC-derived ECs through the VEGFA-VEGFR2 axis in combination with expression of the downstream factors WNT2, HGF as well as WNT9b will promote bi-cell therapy with HLC and engineered ECs. ECs engineered to express robust levels of VEGFR2 as well as WNT2, HGF and WNT9b factors improve survival, proliferation and possibly maturation of HLCs in co-culture in vitro (aim 1 a), and engraftment and function in vivo following bi-cell transplantation (Aim 1 c). Furthermore, the inventors identify novel VEGFR2-induced endothelial factors key for enhancing EC niche-HLC interaction in promoting bi-cell therapy mediated liver repair (Aim 1b)

Figures 30A, 30B:
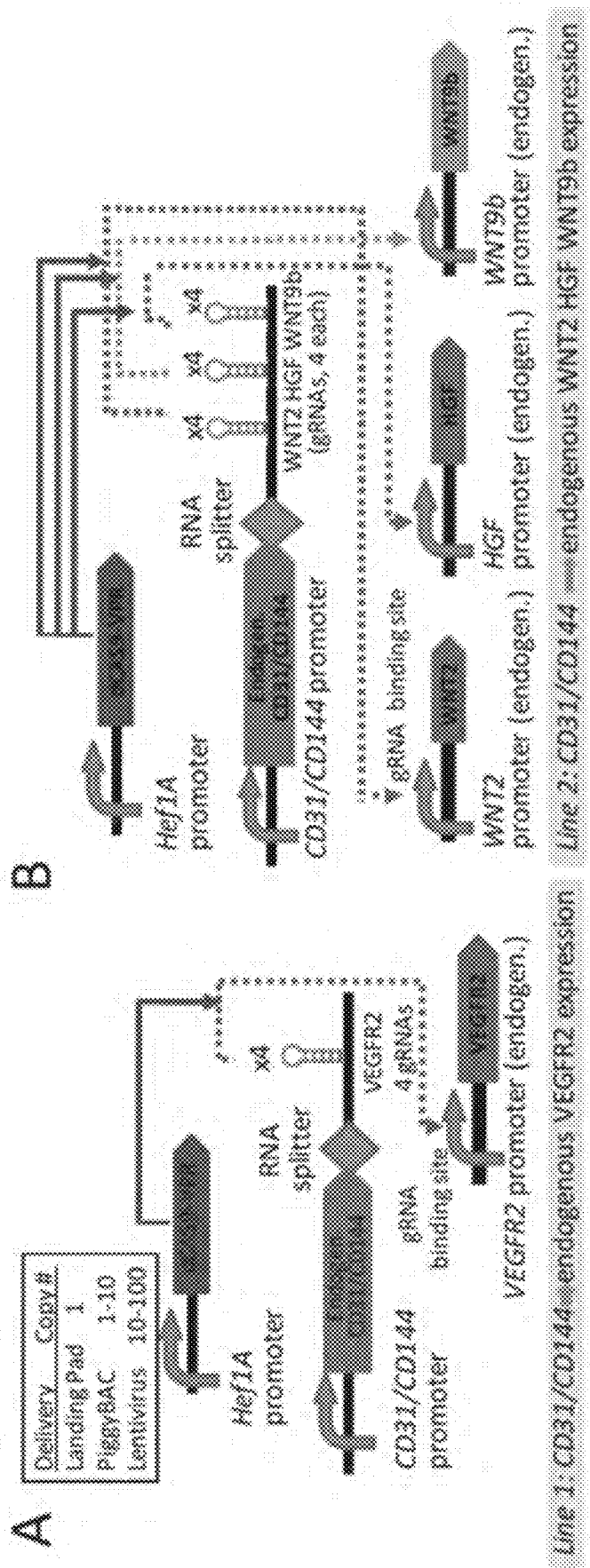
FIGS. 30A-30B depict design of the sensor/actuator genetic circuits in hiPSC lines to express either VEGFR2 (FIG. 30A, line 1) or HGF/WNT2/WNT9b (FIG. 30B, line 2) in CD31 or CD144 (sensor) expressing ECs. Line 3 will express VEGFR2 as well as the 3 endothelial factors in either CD31 or CD144 expressing ECs.

(a) Determine the effects of VEGFR2 activation and expression of 3 endothelial factors in ECs on survival, proliferation and maturation of HLCs upon HLC and engineered EC co-culture in vitro. The inventors established 3 engineered hiPSC lines in which genetic circuits will induce robust and sustained expression of either VEGFR2 (FIG. 30, line 1) or endothelial factors (HGF, WNT2 and WNT9b) (FIG. 30 line 2) or both VEGFR2 and endothelial factors combined together (line 3) specifically in hiPSC-derived ECs. Then the inventors integrate downstream of the CD31 gene or alternatively CD144 gene, 1 set of 4 gRNAs to target the endogenous VEGFR2 promoter in hiPSC line 1, 3 sets of 4 gRNAs to target each endothelial factor promoter in hiPSC line 2, and 4 sets of 4 gRNAs to target VEGFR2 and the 3 endothelial factors in hiPSC line 3. As shown in FIG. 29, the level of gene expression is proportional to the number of gRNAs integrated per gene. Numbers of gRNAs will be increased or decreased as needed to obtain in ECs at least levels of VEGFR2 and endothelial factors obtained in control human umbilical vein endothelial cells (HUVEC) cultured in the presence of (20-50 ng/ml) VEGFA. As a first approach to deliver dCas9, the inventors use the landing pad in the AAVS1 locus to encode 1 copy of dCas9 VPR under the strong and constitutive promoter HeF1a. Alternatively, dCas9-VPR either with the PiggyBAC transposon system or lentiviruses is delivered that will produce 1-10 or 10-100 copies respectively. The expression of VEGFR2 and endothelial factors are strongly induced in the engineered hiPSC-derived ECs compared to the parental hiPSC-derived ECs by flow cytometry (costained CD31+VEGFR2+ cells), western blots and qPCR. By comparing the engineered line and the parental line, the inventors confirm that expression (transcript and protein) of CD31 or alternatively CD144 is not affected by the genetic circuits as expected from the preliminary data (FIG. 29). If it is not the case, the inventors target only one allele to prevent depletion of CD31 or CD144 in the engineered lines and validate activation of VEGFR2 in ECs in vitro in the presence of recombinant VEGFA (20-50 ng/ml) compared to control condition (PBS) by performing western blots and immunostaining in the dish to detect phosphorylated forms of VEGFR2[48].

The inventors differentiate hiPSC into ECs. Briefly, the mesoderm program is induced with BMP4 (25 ng/ml) and CHIR99021 (8 µM) while hiPSC are cultured on laminin 511 E8 fragment. Three days later the endothelial program is induced with high doses of VEGFA (200 ng/ml) and forskolin (2 µM). At day 7, about 85% of the cells express the endothelial markers CD144 and CD31 (protein) and VEGFR2 (transcript). The generated ECs are then expanded on fibronectin in the presence of VEGFA (50 ng/ml) in StemPro-34 based media. For the coculture experiments with HLCs, ECs will be harvested from expansion cultures, and purified by FACS for these 3 receptor expression.

Endothelial identity of ECs is verified by 4 well-established functional assays. Those include wound-healing assay, incorporation of acetylated low-density lipoprotein, formation of tubes in thick matrigel culture, and the ability to induce expression of VCAM, ICAM and E-selectin following TNFa stimulation.

ECs derived from the 3 hiPSC lines and the parental non-engineered hiPSC line (as control) are co-cultured with day 15 hepatic cultures that are composed of virtually ~100% of HLCs. The inventors use a ratio of 70% 30% for HLC/EC in a media that has previously shown to support both hESC and HUVEC culture[32]. Control conditions will include (1) co-cultures of HLCs with HUVEC cells, and (2) monoculture of HLCs. The inventors examine HLC survival, proliferation and maturation in co-culture following 3 and 10 days in the presence of recombinant VEGFA (20-50 ng/ml) or VEGFR2 inhibitory antibody, as extensively used in previous studies[32, 47]. All results are compared to those from bona-fide human primary hepatocytes (purchased from Triangle Research Labs). Specifically, cell proliferation is determined by cell count and incorporation of EdU by flow cytometry associated with CD31/CD144/VEGFR2 expression to track ECs from HLCs, and cell apoptosis is monitored with the TUNEL assay and cleaved caspase 3 staining. HLC maturation is evaluated by validated methods as previously used[31-33, 47]; (1) AFP and ALB expression by immunostaining in the dish and flow cytometry, (2) QPCR for AFP, ALB, AAT, and P450 enzyme expression, and bulk RNA sequencing analyses of purified HLCs based on the hepatic gene signature previously described[49-51], (3) functional assays including human ALB secretion (Bethyl-Laboratories), detection of glycogen storage by Periodic Acid-Schiff's staining[16], ammonia detoxification (Sigma-Aldrich), and P450 activity with fluorescence based assays (Invitrogen)[16,32]. The inventors define in the 3 generated EC populations whether activation of VEGFR2 with VEGFA induces significantly higher levels of the downstream factors WNT2 and HGF as well as WNT9b by western blot and qPCR. Altogether, this set of in vitro experiments determine (1) whether engineered ECs provide better supportive role than non-engineered ECs and HUVECs, and (2) determine which engineered hiPSC line among line 1, 2 and 3, derives the most efficient ECs to support HLCs in the presence or the absence of VEGFA upon co-culture in vitro. The optimized engineered ECs (with either induced expression of VEGFR2 or endothelial factors, or all combined) are then used in vivo as explained below.

(b) Identify novel VEGFR2-induced instructive endothelial factors that support in vitro HLC survival, proliferation and maturation. The inventors identify novel supportive endothelial factors induced by VEGFR2 activation in ECs and the receptor-pathways they activate in HLCs to promote HLC survival, proliferation and maturation. They co-culture for 10 days HLCs with engineered ECs derived from the hiPSC line #1 that induces robust expression of VEGFR2 in the presence of VEGFA or inhibitory VEGFR2 antibody. The 4 populations using VEGFR2/CD31/CD144 expression are purified to separate ECs from HLCs for global transcriptomic analysis. Transcriptomes of activated VEGFR2+ ECs with those from inhibited VEGFR2 ECs (screen #1) as well as those of "indirectly supported" HLCs with those from "indirectly inhibited" HLCs (screen #2) are compared. Screen #1 identifies ligands secreted by VEGFA-activated ECs, while screen #2 identifies receptors and associated pathways activated in HLCs in response to endothelial ligands. mRNA sequencing of the 4 populations is performed with the Illumina NextSeq™ 500 by the Microarray and Sequencing Resource Core at the Boston University Medical Campus. Triplicate RNA samples from 3 independent differentiations are analyzed for rigorous statistical analyses. To systematically map cell fate-specific molecular features, the inventors perform hierarchical clustering and principal component analyses. Gene ontology analyses allows for insights into enriched functional gene categories relevant to activation of VEGFR2 in ECs and to indirect activation of HLCs. Gene network analyses to link changes in gene expression to molecular mechanisms and pathways using algorithms, including Expression2Kinases[52], ChEA[53], KEA[54], Genes2Networks[55] and Enrichr[56] is performed. Briefly, differentially expressed genes are subjected to gene-set enrichment analyses using libraries that include transcription factors and histone modifications created from ENCODE[57] and the Epigenomics Roadmap[58]. The enriched regulators are connected to other proteins through known protein-protein interactions from available databases. Such regulatory complexes could identify links to kinases and other pathways providing important new insights into cell-cell communication including secreted signals in ECs from screen #1 and resulting receptor pathway activation in HLCs from screen #2. To help narrow down the ligand/receptor pathway candidates, the inventors focus on testing differential expression between populations with special attention to ligand/receptor pairs annotated in CellPhoneDB[59], a public repository of curated receptors, ligands and their interactions used to infer populations with complementary receptor-ligand expression profiles. Finally, the inventors select the top 6 candidates for ligand/receptor pairs for functional validations. Verification of the differential expression of candidates is performed at mRNA (QPCR) and protein levels (western blot). Then whether activation/inhibition of the selected ligand/receptor axes improve/repress in vitro survival, proliferation and maturation of HLCs is tested. Activation of ligand/receptor axes is performed by including recombinant protein or activating small molecules (if known), and inhibition with inclusion of receptor inhibitory antibody or inhibitory small molecule or siRNA against the receptor. Activation and inhibition assays are performed on HLCs grown for additional 3 and 10 days. The ligand/receptor axes whose activation promote any of the functions of HLCs are subsequently tested in vivo for enhancing regenerative ability of HLCs in mouse models of liver disease (see next sub-aim). Activation of ligand/receptor axes in vivo is induced either by IV injection of mRNA-LNP encoding ligand as explained in the next sub-aim for VEGF-mRNA-LNPs, and induction of receptor expression with generation of new genetic circuit-embedded hiPSC lines if needed. This subaim identifies new VEGFR2-induced endothelial supportive factors and HLC receptor axes to modulate to potentially improve engraftment and maturation in vivo of transplanted HLCs.

(c) Determine the effects of VEGFR2 activation and expression of downstream endothelial factors in ECs on engraftment and function of HLCs following HLC-EC co-transplantation in liver injury models. Prior to transplantation, HLC and the most supportive engineered ECs are co-cultured (70/30 ratio) for 3 days to prime the HLC-EC crosstalk. Co-cultured cells are then harvested and $10^6$ cells are transplanted through the spleen to target the liver as illustrated in FIG. 28. The inventors test higher numbers of transplanted cells ($2\times10^6$ and $3\times10^6$ cells) to accelerate liver repopulation. Transplanted control populations include: HLCs alone, HLC co-transplanted with non-engineered ECs, primary human hepatocytes alone and co-transplanted with non-engineered ECs or the most efficient ECs as defined above. VEGFR2 expressed on transplanted ECs will be activated by delivering VEGFA-mRNA-LNPs 5 hours prior to cell transplantation (Poly(C)-RNA-LNPs will be used as negative control). The transient expression of mRNA-LNP (see FIG. 27) makes this protein delivery method ideal to timely activate VEGFR2 at the time transplanted cells require engraftment support, yet, additional injections of VEGFA-mRNA-LNPs are performed twice a week until sacrifice to maintain sustained expression of VEGFA in the liver. To ensure uniformity in VEGF expression by mRNA-LNP between mice, concentration of serum VEGFA is tested in each mouse by ELISA. Given that the role of exogenous VEGF in promoting intrinsic liver regeneration after injury in the absence of transplanted cells has been previously reported in rats and mice[60, 61], the inventors compare the efficiency of liver repopulation by HLCs in the presence and in the absence of VEGFA-mRNA-LNP following bi-cell therapy or mono HLC therapy. This comparison determines whether co-transplanted VEGFA-mRNA-LNP-activated ECs improve HLC engraftment and function in vivo.

Figure 31:
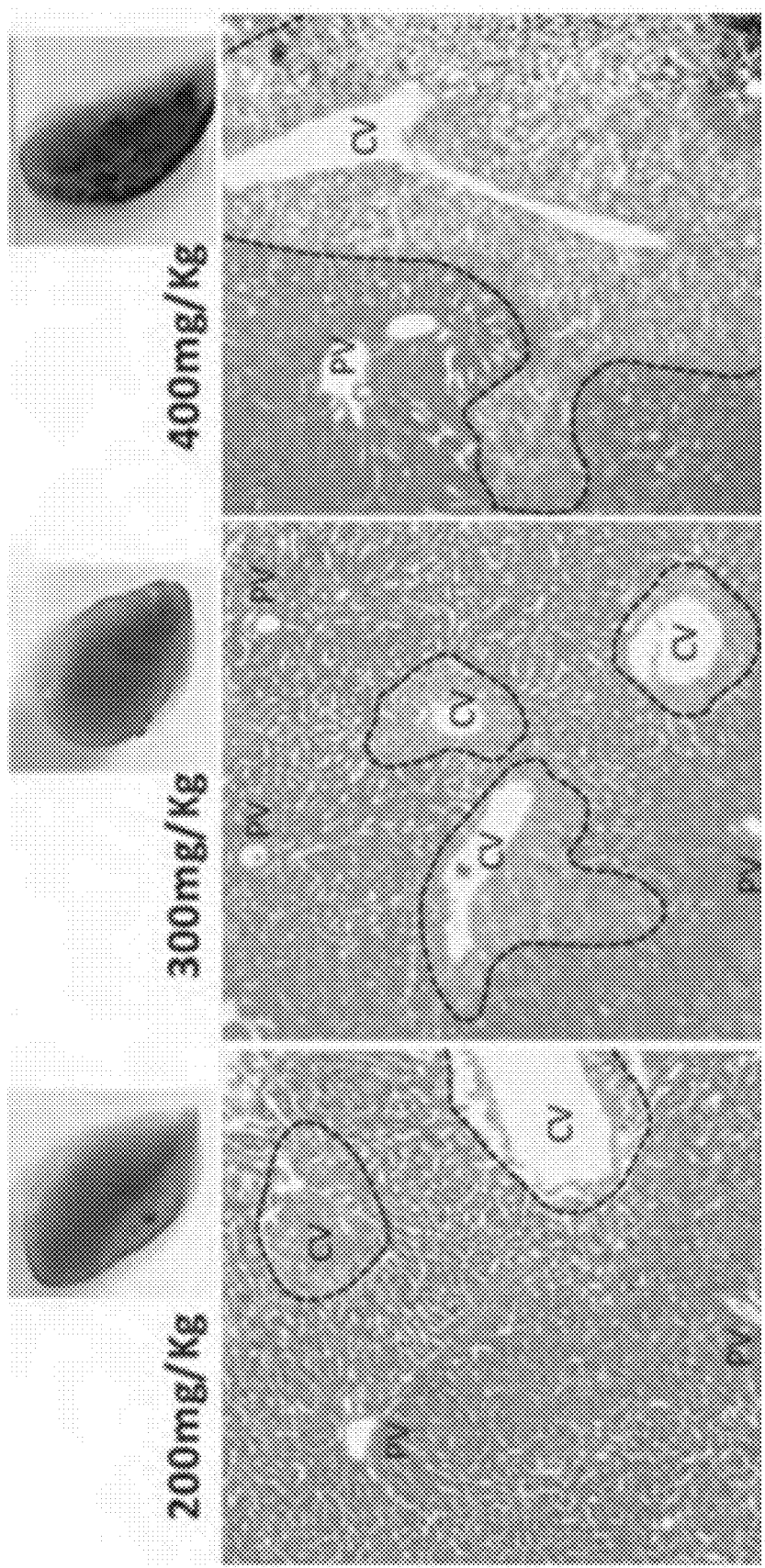
FIG. 31 depicts APAP-NSG liver injury model. 200-400 mg/Kg doses of APAP were tested for centrilobular necrosis 24 h after injection. Gross morphology of the liver as well as H&E staining illustrate the increase liver damage with increasing doses. 400 mg/kg dose triggered severe damage and ultimately death, while 200 mg/Kg-mediated damage was mild.

To determine the efficacy of the bi-cell therapy, the inventors use two clinically relevant mouse models shown in preliminary data. The PiZ-NSG mice model the liver disease of alpha-1 antitrypsin deficiency (AATD) patients by over-expressing a mutant human SERPINA1 gene displaying a single base pair mutation. In humans, this Glu342Lys mutation results in production of misfolded AAT protein known as "Z-AAT". Misfolded Z-AAT proteins form polymers that accumulate in hepatocytes causing injury that manifests as fibrosis and in some cases cirrhosis. PiZ mice were recently crossed into the NSG background for human cell transplantation[40]. The PiZ-NSG model has been shown to provide a growth advantage for transplanted human primary hepatocytes[40] and is therefore an ideal chronic genetically-induced liver injury model to test the regenerative potential of hiPSC-derived bi-cell therapy. The APAP-treated NSG mice have been widely used to recapitulate acetaminophen intoxication, the most common cause of acute liver failure seen in patients, by administrating a single dose of APAP[63]. APAP induces hepatocyte cell death by toxic metabolites, which arise from the cytochrome P450-dependent breakdown. The injury is characterized by centrilobular necrosis with strong immunologic responses, followed by complete regeneration within 7 days by hepatocyte proliferation. The inventors tested various doses of APAP in the NSG background and concluded that 300 mg/kg was the maximum range of sub-lethal dose capable of inducing significant hepatocyte necrosis (FIG. 31), while 400 mg/Kg injections triggered massive necrosis and subsequent death. The inventors additionally test 350 mg/kg doses to determine whether it would provide a stronger injury without killing mice compared to the 300 mg/kg dose. The highest sub-lethal dose will be chosen for further transplantations. Engraftment conditions are optimized using lethal doses to mimic human acute liver failure and test the clinical benefit of the bi-cell therapy to rescue survival. The APAP model is acute and thereby most likely provides stronger regenerative signals but also allows a narrower time frame for transplanted cells to repopulate the tissue over healthy resident hepatocytes compared to the chronic model. Together, both models are complementary as they may probe different cell regenerative potential. These 2 mouse injuries are thus used in parallel to test all strategies proposed in Aim 1 and 2.

Systematic analysis of the different steps of liver repopulation are carried out to define which stages of the regeneration process are improved by bi-cell therapy. Based on preliminary data, it became obvious that engraftment of HLCs during the first week after transplantation was a critical limiting factor (FIG. 26, 28). Therefore, the inventors monitor transplanted cells at 4 time points: 3 and 7 days after transplantation to examine cell survival, proliferation and integration into the liver tissue by the presence of single/doublet cells at day 3 that should become small clusters of 2-4 cells by day 7, as well as 1 and 5 months later to examine sustained cell proliferation with the presence of larger clusters of cells and acceleration of restoration of liver functions. Presence of transplanted cells is validated by immunostainings for human ALB (FIGS. 26C, 26F), for Dsred fluorescence (FIG. 28F) and human nuclei (FIG. 28E)[64]. All hiPSC lines used for HLC generation are engineered to over express luciferase and Dsred as illustrated in FIG. 28F, so that luciferase activity strictly tracks engrafted HLCs. EC survival, spatial association with engrafted HLCs, and integration to the mouse liver vasculature is examined by using specific human CD31 antibodies in combination with human albumin antibody and human nuclei antibody as well as fluorescent dextran injection. EdU is injected into mice prior to sacrifice to assess cell proliferation by staining for EdU and PCNA in combination with transplanted cells markers (DsRed, human ALB, human nuclei, human CD31). Cell apoptosis is analyzed with TUNEL assay and cleaved caspase 3 staining. Global liver functions are determined by measuring serum levels of AST, ALT (FIG. 26), and serum bilirubin levels; and specific HLC functions are evaluated with serum human albumin and AAT ELISA assays (Bethyl Laboratories, GenWay Biotech). Zonation phenotype of engrafted HLCs is examined by immunostaining for zonation markers such as glutamine synthetase and P450 enzymes in pericentral hepatocytes, as well as glucose 6 phosphatase and carbamoylphosphatase synthetase I in periportal hepatocytes[75, 76]. In vivo maturation of transplanted HLCs is further evaluated by bulk RNA sequencing following liver dissociation with collagenases[65], and Dsred hepatocyte purification by FACS. Engrafted HLCs are collected at two different time points (1 and 5 months), and RNA sequencing data is compared to those from cultured cells prior to transplant and to primary human hepatocytes. Degree of maturation of engrafted cells is evaluated based on the hepatic gene signature previously described[49-51]. Overall, the systematic analyses of survival, proliferation and function of HLCs in acute and chronic liver injury models determines (1) the efficiency of the different steps of liver repopulation by HLCs alone, (2) the need for ECs upon bi-cell therapy to improve HLC engraftment, (3) the role of VEGFR2 activation in ECs and secreted endothelial factors to support HLC engraftment and function in vivo.

Experimental Outcomes and Alternative Strategies of Aim 1. Outcomes of Aim 1 are clinically relevant for hiPSC-HLC therapy as they provide strategies to tackle the lack of cell engraftment and maturation. These strategies leverage the known supportive roles of ECs to contribute to hepatocyte development and regenerative abilities and include co-transplantation of HLCs with ECs, both generated from hiPSCs, and innovative technologies to enhance the HLC-EC supportive crosstalk. These technologies include engineering hiPSCs with genetic circuits to generate ECs that express robust levels of VEGFR2 and supportive endothelial factors, combined with VEGFA-mRNA-LNPs to timely deliver the ligand VEGFA in host livers following bi-cell therapy. By comparing the various combination of bi-cell therapy of HLCs or control primary hepatocytes with the different engineered ECs, in the presence or absence of VEGFR2 activation, the inventors (1) evaluate the ability of HLCs alone to regenerate injured livers, (2) examine whether the presence of non-engineered ECs improves their regenerative ability, (3) whether VEGFR2 activation or expression of endothelial factors accelerates it; (4) whether the combination of both synergizes HLC engraftment and function in vivo, and finally (5) determine whether the regenerative ability of HLC-EC therapy is as efficient as that from primary human hepatocyte-EC therapy. The two models of injury used in this proposal clinically recapitulate an acute and a chronic human liver disease, two different liver injury environments in order to probe different cell regenerative potential. Moreover, the inventors identify novel VEGFR2-induced secreted endothelial factors supportive of HLC regenerative ability as new potential interventions to improve engraftment and maturation of HLCs. All transplantations are performed with hiPSC-derived cells as a step forward to test the utility of human patient-specific iPSC derivatives to treat liver diseases. Autologous transplantation of hiPSC-derived hepatic cells should not even require immunosuppression[66]. Therefore, for these various reasons, this approach is a step forward for the utility of the hiPSC-derived HLCs to the clinic to treat liver diseases. Alternatives: (1) For genetic circuits: 3 alternatives to increase endogenous gene expression are: (i) by delivering dCas9-VPR either with the PiggyBAC transposon system or lentiviruses instead of the landing pad strategy, although one copy per cell of dCas9-VPR produced by the landing pad has shown to be potent to active gene expression[67], (ii) by increasing the number of gRNAs per gene candidate, or (iii) by generating homozygous lines for the sensor cassette. Although CD31 promoter will be the first choice to build the EC-specific gene circuits, as CD31 is expressed on all ECs generated, CD144 promoter serves as a second choice as hiPSC-derived ECs also express CD144[43]. In addition, if continuous expression of HGF/WNT2/WNT9b promotes abnormal growth of HLCs, host hepatocytes, or ECs, alternatively, a small molecule-induced Cas9-VPR cassette is used via the ABA inducible system. Finally, potential Off-target effect of CRISPR/dCas9 are tested in ECs by comparing DNA sequencing of parental hiPSC line-ECs with the engineered hiPSC-ECs. (2) Given the non-integrative nature of mRNA and its transient translation to proteins, this tool is highly controllable. However, any hyper dilatation of sinusoids that may occur is controlled, and thus decreasing the frequency of VEGFA-mRNA-LNP injections to once a week can happen if bleeding occurs. (3) In addition to the 70/30 ratio between co-transplanted ECs and HLCs, additional ratios are tested if EC overgrow in cocultures occurs. (4) Even though transplanted cells may not appear as mature as primary hepatocytes after co-culture with ECs in vitro, the inventors still transplant them as they further mature in vivo with the help of in vivo delivery of VEGFA-mRNA-LNPs and through interactions with the damaged liver environment. In vivo cell maturation has previously been reported when fetal hepatoblasts were transplanted into injured livers of rats[70]. In line with this study, fetal progenitors have been found to exhibit a greater repopulation ability compared to that from adult mature hepatocytes into a cirrhosis liver rat model[71].

Aim 2: Enhance Maturation and Engraftment of Engineered HLCs in Bi-Cell Therapy Through Activation of Mitogen and Maturation Pathways Rationale: As a complementary approach to engineering ECs to improve regenerative potential of HLC-EC therapy, in aim 2 HLC are engineers to activate 3 mitogen pathways (HGF/cMET, EGF/EGFR, IL6/IL6R) reported to be critical for hepatocyte survival and proliferation during liver regeneration[22-24] as well as to trigger sustained expression of 3 maturation TFs ATF5, PROX1, CEBPA[21, 25]. Given that transcript levels of the 3 receptors in HLCs from day 10 and day 15 differentiation cultures are approximately 10- to 100-fold less than those in human primary hepatocytes, the inventors engineer hiPSCs for robust and sustained expression of the mitogen receptors in HLCs for efficient mitogen pathways activation with ligand-mRNA-LNPs. The inventors chose to specifically induce expression of ATF5, PROX1 and CEBPA for the following reasons: (1) they are significantly enriched in human adult hepatocytes compared to human fetal liver cells, (2) they are highly and consistently expressed in adult human hepatocytes from different donors compared to other hepatocyte TFs, and (3) they have been reported to constitute the smallest cocktail of maturation TFs tested among others to promote maturation of reprogrammed fibroblasts into HLCs with transcriptional profiles near those from adult human hepatocytes[25]. Given that activation of cMET, EGFR and IL6R also induce cell proliferation, survival, and maturation (for cMET specifically) during various biological processes48,[72-74], the inventors systematically test all these functions in vitro as well as engraftment and roles in restoring liver function in vivo. The inventors test that activation of the mitogen pathways and expression of maturation TFs key pathways in engineered HLCs shows synergic effects with VEGFR2 activation in the most supportive ECs on HLC survival, proliferation and maturation in co-culture in vitro (Aim 2a), and on HLC engraftment and function in vivo (Aim 2b). The inventors use the same mouse liver injury models as described in Aim 1 (APAP and PiZ). Ligands VEGFA, HGF, EGF and IL6 are be delivered in vivo in damaged livers via mRNA-LNPs for timely controlled pathway activation. Preliminary data inducing expression of HGF, EGF and IL6 via mRNA-LNPs into the two liver injury models resulted in improved transplanted HLC survival (FIG. 28), and thus support the plausibility.

Figures 32A, 32B:
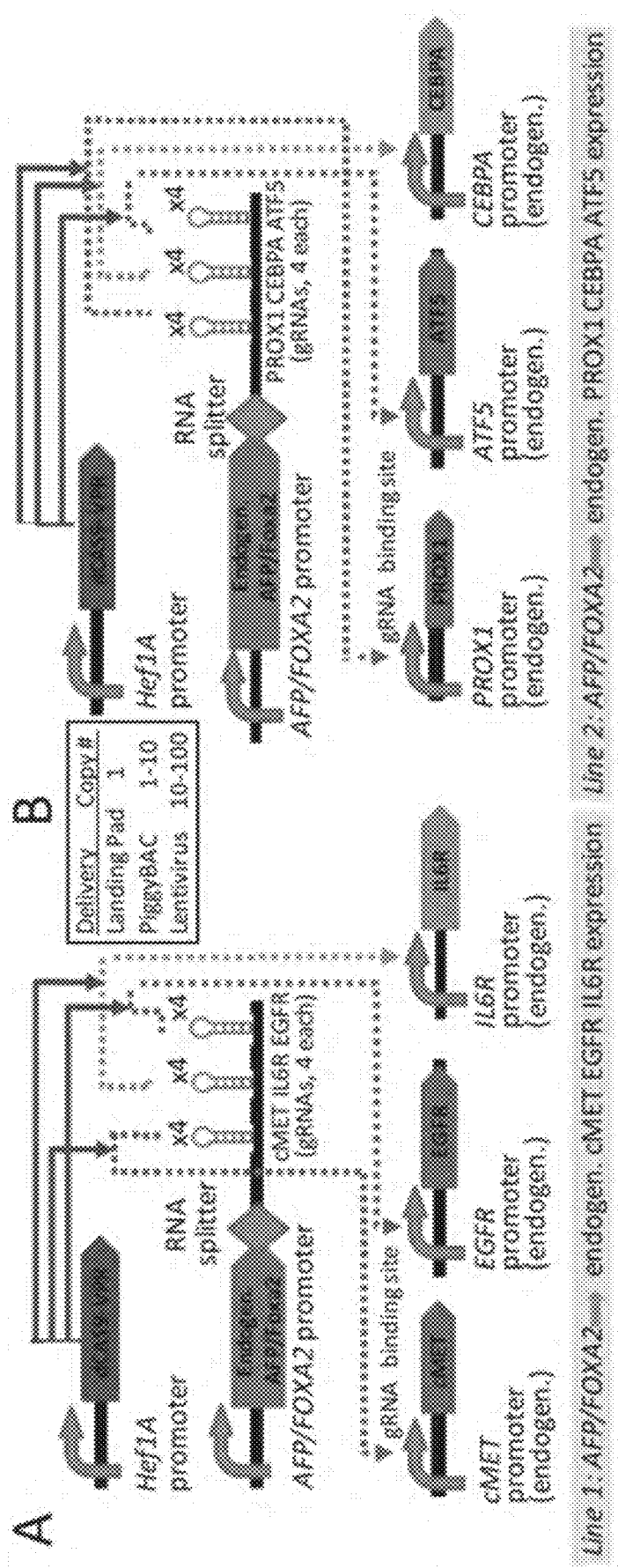
FIGS. 32A-32B depict design of the sensor/actuator genetic circuit in hiPSC line to induce robust expression of either cMET, EGFR and IL6R in hiPSC line 1 (A) and PROX1, CEBPA and ATF5 in hiPSC line 2 (B) in AFP or FOXA2 (sensor) expressing HLCs. A line 3 is also established that will generate HLCs that will express the 3 receptors using FOXA2 expression as sensor as well as the 3 maturation TFs using AFP expression as sensor.

(a) Determine the effects of 3 mitogen receptor activation and 3 maturation TFs on survival, proliferation and maturation in vitro of HLCs in the presence and absence of the most supportive engineered ECs. The inventors establish 3 engineered hiPSC lines in which genetic circuits induce robust and sustained expression specifically in hiPSC-derived HLCs of either mitogen receptors cMET, EGFR and IL6R (FIG. 32, line 1), or maturation TFs PROX1, CEBPA, and ATF5 (FIG. 32 line 2), or both mitogen receptors and maturation TFs combined together (line 3). The inventors integrate downstream of the AFP gene or alternatively FOXA2 gene, 3 sets of 4 gRNAs to target the endogenous promoter of the 3 receptors in hiPSC line 1, 3 sets of 4 gRNAs to target each maturation TF promoter in hiPSC line 2, and 6 sets of 4 gRNAs to target both receptors and TFs in hiPSC line 3. If expression of genes is weakly induced when compared to parental hiPSC line, a separate sensor for each set of genes in line 3 is used. Specifically, the inventors use FOXA2 as a sensor to induce mitogen receptors and the sensor AFP to induce maturation TF expression in line 3. Numbers of gRNAs will be increased or decreased as needed to obtain in HLCs levels of receptors and TFs that equal those from primary hepatocytes. As explained in Aim 1, a first approach to deliver dCas9 is the landing pad integrated in the AAVS1 locus to encode 1 copy of dCas9 VPR under the strong and constitutive promoter HeF1a. Alternatively, dCas9-VPR is delivered either with the PiggyBAC transposon system or lentiviruses that will produce 1-10 or 10-100 copies respectively. Efficiency and restricted induction of expression of the 3 receptors and 3 TFs in AFP+ or FOXA2+ HLCs is examined by co-immunostaining in the dish for AFP or FOXA2 and each receptor and maturation TFs as well as by flow cytometry and qPCR. Assays are performed every other day from day 5 of differentiation when FOXA2 is well expressed until day 10-12 when all HLCs express AFP to determine the time it takes to express high and sustained levels of receptors and TFs that equal those from human primary hepatocytes.

The inventors evaluate using line 1 the roles of activation of the 3 receptors individually and in combination of pairs and the three together on HLC survival, proliferation and maturation using assays described in Aim 1a. HLCs are generated as described in FIG. 25 and recombinant ligands (EGF:10 ng/ml, IL6: 10 ng/ml, HGF: 20 ng/ml) are included in the media from the time receptor expression is highly induced, as defined above. Ligand containing media is changed every 2 days and HLC cultures analyzed just prior to ligand inclusion in the media, 2, 5, and 10 days later. These experiments are performed in the presence and the absence of the most supportive engineered ECs activated or not with VEGFA to determine the synergic effects of activation of mitogen pathways in HLCs with the most supportive engineered ECs in coculture. This defines the minimal combination of mitogen activation needed to result in the best survival, proliferation and maturation of HLCs in the absence and presence of the most supportive engineered ECs. Next the same experiments are performed with HLCs obtained from line 2 and line 3. Comparison of the data determines the benefit of expression of the 3 maturation TFs combined with activation of the minimal cocktail of mitogens in the absence and the presence of the most supportive engineered ECs. Parental lines are the control line for line 2 to define the benefit of expression of the 3 maturation TFs for HLC maturation. This strategy identifies the minimal cocktail of mitogen axes whose activation improves in vitro HLC survival, proliferation, and maturation of HLCs in combination with expression of maturation factors and in the presence of the most supportive engineered ECs activated or not with VEGFA. The minimal cocktail of mitogen activation is thus used in vivo in bi-cell therapy.

Figures 33A, 33B:
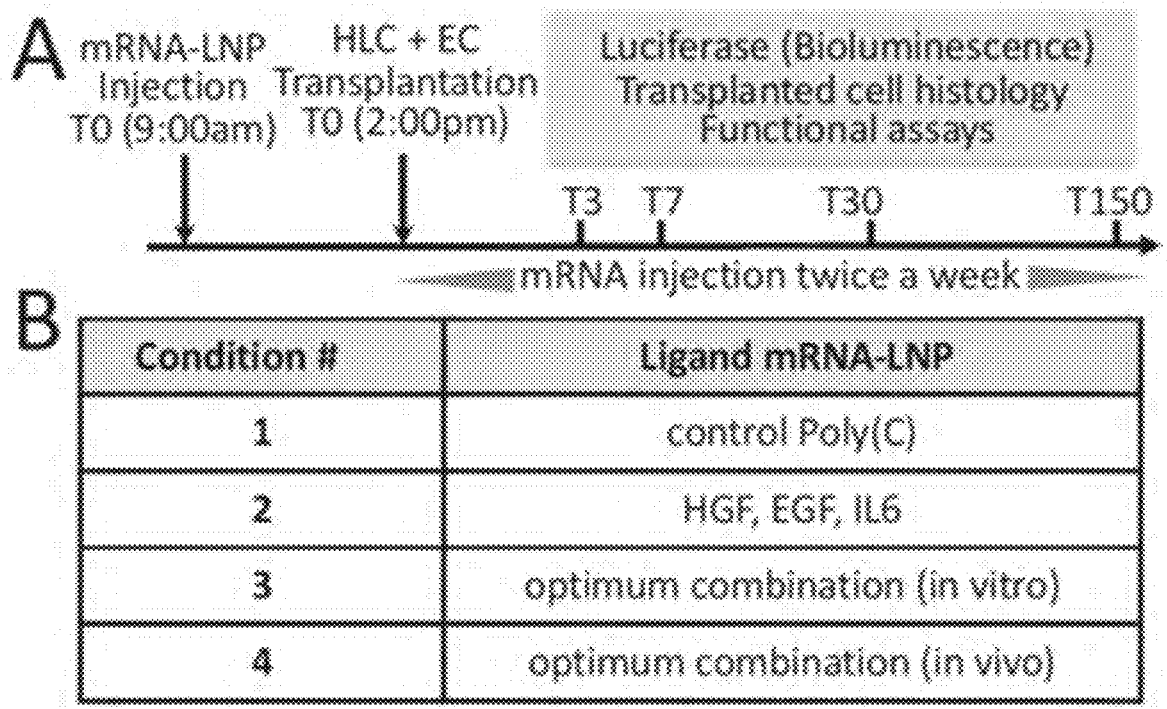
FIGS. 33A-33B depict design of bi-cell transplantation and mRNA-LNP conditions.

(b) Determine the effects of activation of HGF, EGF and IL6 and the 3 maturation TFs on regenerative functions of HLCs in bi-cell therapy in vivo. The inventors use line 3 to generate HLCs that will therefore express the 3 mitogen receptors and the 3 maturation TFs. Prior to transplantation, HLC and the most supportive engineered ECs are co-cultured (70/30 ratio) for 3 days to prime the HLC-EC crosstalk in the treatment condition that is used in vivo. Co-cultured cells are then harvested and $10^6$ cells (or more, as explained in Aim 1) are transplanted through the spleen. The inventors co-transplant the most supportive engineered ECs with hiPSC line 3-derived HLCs (FIG. 33A). The optimum combination of mitogen activation defined in vitro is tested (FIG. 33B, condition #3) in parallel with activation of the 3 mitogens (FIG. 33B, condition #2) as mitogen activity and requirement may differ in a complex in vivo environment compared to that from an in vitro culture. If condition #2 results in better liver regeneration than condition #3, the minimal combination of pairs of mitogen activation (condition #4) is identified to support in vivo HLC-mediated liver repair. To facilitate the optimization process, the luciferase activity is used as read out for HLC engraftment. Injection of PolyC-RNA-LNP serves as controls (FIG. 33B, condition #1). The 4 conditions are tested in the presence and absence of VEGFA-mRNA-LNPs to determine synergic effects of the minimal combination of regenerative pathway activation with VEGFR2 activation on bi-cell therapy success. Additional controls include human primary hepatocytes co-transplanted with the most supportive ECs in condition 1, 2 and 4 to determine whether activation of mitogen pathways also improve primary hepatocyte engraftment and function in vivo. Whether HLCs exhibit similar regenerative functions as those from primary hepatocytes in the same conditions is also determined The design of the mRNA-LNP treatment is as follows: Ligand-mRNA-LNPs are injected IV at T0 at 9:00 am, 5 hours prior to cell transplantation. Co-cultures are transplanted at T0 at 2:00 pm. Injections of ligand-mRNA-LNPs is performed twice a week as protein expression from mRNA is maintained for 3-4 days after injection. Systematic analysis of the different steps of liver regeneration by HLC and ECs is performed as described Aim 1c. Altogether, the systematic analyses of engraftment and function in vivo of bi-cell therapy combined with mRNA-LNP treatment determines the optimum combination of mitogen pathway activation that facilitates HLC engraftment and maturation, and whether the role of regenerative pathway activation is synergic with VEGFR2 activation in ECs.

(c) Experimental Outcomes and Alternative Strategies of Aim 2. Outcomes of Aim 2 are clinically relevant as they address the lack of engraftment and maturation, 2 critical limitations of the use of hiPSC-based HLC therapy for liver regenerative medicine. To overcome this issue, Aim 2 engineers hiPSC lines to produce HLCs that express receptor for 3 known hepatocyte mitogens, while the corresponding ligands are timely delivered in vivo via the safe mRNA-LNPs as well as 3 key hepatocyte maturation TFs. The optimum combination of activation of cMET, EGFR and IL6R on HLCs is identified to enhance engraftment in vivo in bi-cell therapy with the most supportive engineered ECs defined in Aim 1. Combining technologies from Aim 1 and Aim 2 ultimately evaluates the synergy between the 2 strategies by co-transplanting the most supportive engineered ECs from Aim 1 with the optimum engineered HLCs defined in Aim 2. These studies have major clinical implications for treating liver disease, as all receptor activations (cMET, EGFR, IL6R and VEGFR2) are timely induced with the corresponding ligands delivered in vivo via mRNA-LNPs that were proven safe in clinical trials for cancer vaccines[36]. Alternatives: (1) For genetic circuits: The pitfalls and alternatives described in Aim 1 apply to this Aim. Potential Off-target effect of CRISPR/dCas9 are tested in HLCs by comparing DNA sequencing of parental hiPSC line-HLCs with the engineered hiPSC-HLC. (2) Given the non-integrative nature of mRNA and its transient translation to proteins, this tool is highly controllable, minimizing any deleterious effect such as cancer initiation. However, in the context of expression of mitogens, even transient, cancer development in mice after one year following the treatment with the regiment of mRNA-LNPs that successfully improves cell engraftment and maturation is monitored.

This project develops unique strategies to address the 3 key limiting factors for HLC therapy to be successful: poor HLC survival, proliferation and maturation. This project specifically determines the synergy of a bi-cell therapy with HLCs and ECs, both generated from hiPSC lines engineered to promote EC niche-HLC crosstalk to lead to successful HLC-based treatment for liver disease. This project pioneers the use of genetic circuit embedded-hiPSC lines with safe integration into specific site, and mRNA-LNPs whose safety has been validated in clinical trials, to promote the regenerative EC niche-HLC interaction. Therefore, this proposal greatly advances the ultimate utility of the patient-specific hiPSC-derived bi-cell HLC-EC therapy to treat liver diseases.

REFERENCES FROM THE SPECIFIC AIM PAGE AND INTRODUCTION

1. Gouon-Evans, V., Boussemart L, Gadue P, Nierhoff D, Koehler C I, Kubo A, Shafritz D A, Keller G. BMP-4 is required for hepatic specification of mouse embryonic stem cell-derived definitive endoderm. *Nat Biotechnol* 24, 1402-1411 (2006). PMID: 17086172
2. Han, S., Dziedzic, N., Gadue, P., Keller, G. M. & Gouon-Evans, V. An endothelial cell niche induces hepatic specification through dual repression of wnt and notch signaling. *Stem Cells* 29, 217-228 (2011).
3. Han S, Tan C, Ding J, Wang J, Ma'ayan A, Gouon-Evans V. Endothelial cells instruct liver specification of embryonic stem cell-derived endoderm through endothelial VEGFR2 signaling and endoderm epigenetic modifications. *Stem Cell Res* 30, 163-170 (2018). PMID: 29936335
4. Ding B S, Nolan D J, Butler J M, James D, Babazadeh A O, Rosenwaks Z, Mittal V, Kobayashi H, Shido K, Lyden D, Sato T N, Rabbany S Y, Rafii S. Inductive angiocrine signals from sinusoidal endothelium are required for liver regeneration. *Nature* 468, 310-315 (2010).
5. Preziosi, M., Okabe, H., Poddar, M., Singh, S. & Monga, S. P. Endothelial Wnts regulate beta-catenin signaling in murine liver zonation and regeneration: A sequel to the Wnt-Wnt situation. *Hepatology communications* 2, 845-860 (2018).
6. Gordillo, M., Evans, T. & Gouon-Evans, V. Orchestrating liver development. *Development* 142, 20942108 (2015).
7. Bohm, F., Kohler, U. A., Speicher, T. & Werner, S. Regulation of liver regeneration by growth factors and cytokines. *EMBO Mol Med* 2, 294-305 (2010).
8. Michalopoulos, G. K. Liver regeneration after partial hepatectomy: critical analysis of mechanistic dilemmas. *Am J Pathol* 176, 2-13 (2010).
9. Michalopoulos, G. K. Hepatostat: Liver regeneration and normal liver tissue maintenance. *Hepatology* 65, 1384-1392 (2017).
10. Du Y, Wang J, Jia J, Song N, Xiang C, Xu J, Hou Z, Su X, Liu B, Jiang T, Zhao D, Sun Y, Shu J, Guo Q, Yin M, Sun D, Lu S, Shi Y, Deng H. Human hepatocytes with drug metabolic function induced from fibroblasts by lineage reprogramming. *Cell Stem Cell* 14, 394-403 (2014).
11. Weissman, D. & Kariko, K. mRNA: Fulfilling the Promise of Gene Therapy. *Mol Ther* 23, 1416-1417 (2015).

REFERENCES FROM THE RESEARCH STRATEGY

1. Hughes, R. D., Mitry, R. R. & Dhawan, A. Current status of hepatocyte transplantation. *Transplantation* 93, 342-347 (2012).
2. Cantz, T., Sharma, A. D. & Ott, M. Concise review: cell therapies for hereditary metabolic liver diseases-concepts, clinical results, and future developments. *Stem Cells* 33, 1055-1062 (2015).
3. Vacanti, J. P. & Kulig, K. M. Liver cell therapy and tissue engineering for transplantation. *Semin Pediatr Surg* 23, 150-155 (2014).
4. Kawashita, Y. Guha C, Yamanouchi K, Ito Y, Kamohara Y, and Kanematsu T. Liver repopulation: a new concept of hepatocyte transplantation. *Surg Today* 35, 705-710 (2005). PMID: 16133662
5. Puppi, J. Strom S C, Hughes R D, Bansal S, Castell J V, Dagher I, Ellis E C, Nowak G, Ericzon B G, Fox I J, Gómez-Lechón M J, Guha C, Gupta S, Mitry R R, Ohashi K, Ott M, Reid L M, Roy-Chowdhury J, Sokal E, Weber A, Dhawan A. Improving the Techniques for Human Hepatocyte Transplantation: Report from a Consensus Meeting in London. *Cell Transplant* (2011).
6. Dhawan, A., Strom, S. C., Sokal, E. & Fox, I. J. Human hepatocyte transplantation. *Methods Mol Biol* 640, 525-534 (2010).
7. Forbes, S. J., Gupta, S. & Dhawan, A. Cell therapy for liver disease: From liver transplantation to cell factory. *J Hepatol* 62, S157-169 (2015).
8. Squires J E, Soltys K A, McKieman P, Squires R H, Strom S C, Fox I J, Soto-Gutierrez A. Clinical Hepatocyte Transplantation: What Is Next? *Current transplantation reports* 4, 280-289 (2017). PMID: 29732274
9. Rezvani, M., Grimm, A. A. & Willenbring, H. Assessing the therapeutic potential of lab-made hepatocytes. *Hepatology* 64, 287-294 (2016).
10. Roy-Chowdhury, N., Wang, X., Guha, C. & Roy-Chowdhury, J. Hepatocyte-like cells derived from induced pluripotent stem cells. *Hepatol Int* 11, 54-69 (2017).
11. Agarwal, N., Popovic, B., Martucci, N. J., Fraunhoffer, N. A. & Soto-Gutierrez, A. Biofabrication of Autologous Human Hepatocytes for Transplantation: How do we get there? *Gene expression* (2018).
12. Han, S. Bourdon A, Hamou W, Dziedzic N, Goldman O, Gouon-Evans V. Generation of functional hepatic cells from pluripotent stem cells. *J Stem Cell Res* Ther Suppl 10, 1-7 (2012). PMCID: PMC4215546
13. Schwartz, R. E., Fleming, H. E., Khetani, S. R. & Bhatia, S. N. Pluripotent stem cell-derived hepatocyte-like cells. *Biotechnol Adv* 32, 504-513 (2014).
14. Ji, S., Zhang, L. & Hui, L. Cell fate conversion: direct induction of hepatocyte-like cells from fibroblasts. *J Cell Biochem* 114, 256-265 (2013).
15. Goldman, O. & Gouon-Evans, V. Human Pluripotent Stem Cells: Myths and Future Realities for Liver Cell Therapy. *Cell Stem Cell* 18, 703-706 (2016).
16. Gouon-Evans, V., Boussemart L, Gadue P, Nierhoff D, Koehler C I, Kubo A, Shafritz D A, Keller G. BMP-4 is required for hepatic specification of mouse embryonic stem cell-derived definitive endoderm. *Nat Biotechnol* 24, 1402-1411 (2006). PMID: 17086172
17. Han, S., Dziedzic, N., Gadue, P., Keller, G. M. & Gouon-Evans, V. An endothelial cell niche induces hepatic specification through dual repression of wnt and notch signaling. *Stem Cells* 29, 217-228 (2011).
18. Han S, Tan C, Ding J, Wang J, Ma'ayan A, Gouon-Evans V. Endothelial cells instruct liver specification of embryonic stem cell-derived endoderm through endothelial VEGFR2 signaling and endoderm epigenetic modifications. *Stem Cell Res* 30, 163-170 (2018). PMID: 29936335
19. Ding B S, Nolan D J, Butler J M, James D, Babazadeh A O, Rosenwaks Z, Mittal V, Kobayashi H, Shido K, Lyden D, Sato T N, Rabbany S Y, Rafii S. Inductive angiocrine signals from sinusoidal endothelium are required for liver regeneration. *Nature* 468, 310-315 (2010).

20. Preziosi, M., Okabe, H., Poddar, M., Singh, S. & Monga, S. P. Endothelial Wnts regulate beta-catenin signaling in murine liver zonation and regeneration: A sequel to the Wnt-Wnt situation. *Hepatology communications* 2, 845-860 (2018).
21. Gordillo, M., Evans, T. & Gouon-Evans, V. Orchestrating liver development. *Development* 142, 20942108 (2015).
22. Bohm, F., Kohler, U. A., Speicher, T. & Werner, S. Regulation of liver regeneration by growth factors and cytokines. *EMBO Mol Med* 2, 294-305 (2010).
23. Michalopoulos, G. K. Liver regeneration after partial hepatectomy: critical analysis of mechanistic dilemmas. *Am J Pathol* 176, 2-13 (2010).
24. Michalopoulos, G. K. Hepatostat: Liver regeneration and normal liver tissue maintenance. *Hepatology* 65, 1384-1392 (2017).
25. Du Y, Wang J, Jia J, Song N, Xiang C, Xu J, Hou Z, Su X, Liu B, Jiang T, Zhao D, Sun Y, Shu J, Guo Q, Yin M, Sun D, Lu S, Shi Y, Deng H. Human hepatocytes with drug metabolic function induced from fibroblasts by lineage reprogramming. *Cell Stem Cell* 14, 394-403 (2014).
26. Weissman, D. & Kariko, K. mRNA: Fulfilling the Promise of Gene Therapy. *Mol Ther* 23, 1416-1417 (2015).
27. Kiani S, Chavez A, Tuttle M, Hall R N, Chari R, Ter-Ovanesyan D, Qian J, Pruitt B W, Beal J, Vora S, Buchthal J, Kowal E J, Ebrahimkhani M R, Collins J J, Weiss R, Church G. Cas9 gRNA engineering for genome editing, activation and repression. *Nat Methods* 12, 1051-1054 (2015).
28. Gadue, P., Gouon-Evans V, Cheng X, Wandzioch E, Zaret K S, Grompe M, Streeter P R, Keller G M. Generation of monoclonal antibodies specific for cell surface molecules expressed on early mouse endoderm. *Stem Cells* 27, 2103-2113 (2009). PMCID: PMC2890285
29. Green, M. D., Chen A, Nostro M C, d'Souza S L, Schaniel C, Lemischka I R, Gouon-Evans V, Keller G, Snoeck H W. Generation of anterior foregut endoderm from human embryonic and induced pluripotent stem cells. *Nat Biotechnol* 29, 267-272 (2011). PMCID: PMC4866999derm from human embryonic and induced pluripotent stem cells. *Nat Biotechnol* 29, 267-272 (2011).
30. Christodoulou, C., Longmire T A, Shen S S, Bourdon A, Sommer C A, Gadue P, Spira A,
31. Gouon-Evans V, Murphy G J, Mostoslavsky G, Kotton D N. Mouse E S and iPS cells can form similar definitive endoderm despite differences in imprinted genes. *J Clin Invest* 121, 2313-2325 (2011). PMCID: PMC3104741
32. Sourisseau, M., Goldman O, He W, Gori J L, Kiem H P, Gouon-Evans V, Evans M J. Hepatic Cells Derived From Induced Pluripotent Stem Cells of Pigtail Macaques Support Hepatitis C Virus Infection. *Gastroenterology* (2013). PMCID: PMC3805793
33. Goldman, O., Han S, Sourisseau M, Dziedzic N, Hamou W, Comeo B, D'Souza S, Sato T, Kotton D N, Bissig K D, Kalir T, Jacobs A, Evans T, Evans M J, Gouon-Evans V. KDR Identifies a Conserved Human and Murine Hepatic Progenitor and Instructs Early Liver Development. *Cell Stem Cell* 12, 748-760 (2013). PMCID: PMC3922205
34. Goldman, O., Cohen, I. & Gouon-Evans, V. Functional Blood Progenitor Markers in Developing Human Liver Progenitors. *Stem Cell Reports* 7, 158-166 (2016).
35. Goldman, O., Valdes, V. J., Ezhkova, E. & Gouon-Evans, V. The mesenchymal transcription factor SNAI-1 instructs human liver specification. *Stem Cell Res* 17, 62-68 (2016).
36. Azuma H, Paulk N, Ranade A, Dorrell C, Al-Dhalimy M, Ellis E, Strom S, Kay M A, Finegold M, Grompe M. Robust expansion of human hepatocytes in Fah(−/−)/Rag2(−/−)/Il2rg(−/−) mice. *Nat Biotechnol* 25, 903-910 (2007).
37. Weissman, D. mRNA transcript therapy. *Expert Rev Vaccines* 14, 265-281 (2015).
38. Kariko, K., Buckstein, M., Ni, H. & Weissman, D. Suppression of RNA recognition by Toll-like receptors: the impact of nucleoside modification and the evolutionary origin of RNA. *Immunity* 23, 165-175 (2005).
39. Karikó K, Muramatsu H, Welsh F A, Ludwig J, Kato H, Akira S, Weissman D. Incorporation of pseudouridine into mRNA yields superior nonimmunogenic vector with increased translational capacity and biological stability. *Mol Ther* 16, 1833-1840 (2008).
40. Pardi N, Tuyishime S, Muramatsu H, Kariko K, Mui B L, Tam Y K, Madden T D, Hope M J, Weissman D. Expression kinetics of nucleoside-modified mRNA delivered in lipid nanoparticles to mice by various routes. *J Control Release* 217, 345-351 (2015).
41. Borel F, Tang Q, Gemoux G, Greer C, Wang Z, Barzel A, Kay M A, Shultz L D, Greiner D L, Flotte T R, Brehm M A, Mueller C. Survival Advantage of Both Human Hepatocyte Xenografts and Genome-Edited Hepatocytes for Treatment of alpha-1 Antitrypsin Deficiency. *Mol Ther* 25, 2477-2489 (2017). PMID: 29032169
42. Matsumoto, K., Yoshitomi, H., Rossant, J. & Zaret, K. S. Liver organogenesis promoted by endothelial cells prior to vascular function. *Science* 294, 559-563 (2001).
43. Takebe T, Sekine K, Enomura M, Koike H, Kimura M, Ogaeri T, Zhang R R, Ueno Y, Zheng Y W, Koike N, Aoyama S, Adachi Y, Taniguchi H. Vascularized and functional human liver from an iPSC-derived organ bud transplant. *Nature* 499, 481-484 (2013).
44. Takebe T, Sekine K, Kimura M, Yoshizawa E, Ayano S, Koido M, Funayama S, Nakanishi N, Hisai T, Kobayashi T, Kasai T, Kitada R, Mori A, Ayabe H, Ejiri Y, Amimoto N, Yamazaki Y, Ogawa S, Ishikawa M, Kiyota Y, Sato Y, Nozawa K, Okamoto S, Ueno Y, Taniguchi H. Massive and Reproducible Production of Liver Buds Entirely from Human Pluripotent Stem Cells. *Cell Rep* 21, 2661-2670 (2017).
45. Wroblewska L, Kitada T, Endo K, Siciliano V, Stillo B, Saito H, Weiss R. Mammalian synthetic circuits with RNA binding proteins for RNA-only delivery. *Nat Biotechnol* 33, 839-841 (2015).
46. Guye, P., Li, Y., Wroblewska, L., Duportet, X. & Weiss, R. Rapid, modular and reliable construction of complex mammalian gene circuits. *Nucleic Acids Res* 41, e156 (2013).
47. Gouon, V., Tucker, G. C., Kraus-Berthier, L., Atassi, G. & Kieffer, N. Up-regulated expression of the beta3 integrin and the 92-kDa gelatinase in human HT-144 melanoma cell tumors grown in nude mice. *Int J Cancer* 68, 650-662 (1996).
48. Goldman, O., Han S, Hamou W, Jodon de Villeroche V, Uzan G, Lickert H, Gouon-Evans V. Endoderm generates endothelial cells during liver development. *Stem Cell Reports* 3, 556-565 (2014). PMCID: PMC4223703
49. Koch, S. & Claesson-Welsh, L. Signal transduction by vascular endothelial growth factor receptors. *Cold Spring Harb Perspect Med* 2, a006502 (2012).

50. DeLaForest A, Nagaoka M, Si-Tayeb K, Noto F K, Konopka G, Battle M A, Duncan S A. HNF4A is essential for specification of hepatic progenitors from human pluripotent stem cells. *Development* 138, 4143-4153 (2011). PMID: 21852396
51. Wilson A A, Ying L, Liesa M, Segeritz C P, Mills J A, Shen S S, Jean J, Lonza G C, Liberti D C, Lang A H, Nazaire J, Gower A C, Mueller F J, Mehta P, Ordóñez A, Lomas D A, Vallier L, Murphy G J, Mostoslavsky G, Spira A, Shirihai O S, Ramirez M I, Gadue P, Kotton D N. Emergence of a stage-dependent human liver disease signature with directed differentiation of alpha-1 antitrypsin-deficient iPS cells. *Stem Cell Reports* 4, 873-885 (2015). PMID: 25843048
52. Pashos E E, Park Y, Wang X, Raghavan A, Yang W, Abbey D, Peters D T, Arbelaez J, Hernandez M, Kuperwasser N, Li W, Lian Z, Liu Y, Lv W, Lytle-Gabbin S L, Marchadier D H, Rogov P, Shi J, Slovik K J, Stylianou I M, Wang L, Yan R, Zhang X, Kathiresan S, Duncan S A, Mikkelsen T S, Morrisey E E, Rader D J, Brown C D, Musunuru K. Large, Diverse Population Cohorts of hiPSCs and Derived Hepatocyte-like Cells Reveal Functional Genetic Variation at Blood Lipid-Associated Loci. *Cell Stem Cell* 20, 558570.e510 (2017). PMID: 28388432
53. Chen, E. Y., Xu H, Gordonov S, Lin M P, Perkins M H, Ma'ayan A. Expression2Kinases: mRNA profiling linked to multiple upstream regulatory layers. *Bioinformatics* 28, 105-111 (2012).
54. Lachmann, A. & Ma'ayan, A. Lists2Networks: Integrated analysis of gene/protein lists. *BMC Bioinformatics* 11, 87.
55. Lachmann, A. & Ma'ayan, A. KEA: kinase enrichment analysis. *Bioinformatics* 25, 684-686 (2009).
56. Berger, S. I., Posner, J. M. & Ma'ayan, A. Genes2Networks: connecting lists of gene symbols using mammalian protein interactions databases. *BMC Bioinformatics* 8, 372 (2007).
57. Chen, E. Y., Tan C M, Kou Y, Duan Q. Wang Z, Meirelles C V, Clark N R, Ma'ayan A, Enrichr: interactive and collaborative HTML5 gene list enrichment analysis tool. *BMC Bioinformatics* 14, 128(2013). PMCID: PMC3637064
58. A user's guide to the encyclopedia of DNA elements (ENCODE). *PLoS Biol* 9, e1001046 (2011).
59. Bernstein, B. E. et al. The NIH Roadmap Epigenomics Mapping Consortium. *Nat Biotechnol* 28, 10451048 (2010).
60. CellPhoneDB v2.0: Inferring cell-cell communication from combined expression of multi-subunit receptor-ligand complexes Efremova M, Vento-Tormo M, Teichmann S, Vento-Tormo R. bioRxiv 2019
61. LeCouter, J., Moritz D R, Li B, Phillips G L, Liang X H. Gerber H P, Hillan K J, Ferrara N. Angiogenesis-independent endothelial protection of liver: role of VEGFR-1. *Science* 299, 890-893 (2003). PMID: 12574630
62. Marino, G., Piazzese E, Gruttadauria S, Nicotra G, Guarnaccia M, Emmanuele G, Bartoloni G, Messina A, Travali S, Famnulari C, Gruttadauria G. New model of liver regeneration induced through use of vascular endothelial growth factor. *Transplant Proc* 38, 1193-1194 (2006). PMID: 16757304
63. Carlson J A, Rogers B B, Sifers R N, Finegold M J, Clift S M, DeMayo F J, Bullock D W, Woo S L. Accumulation of PiZ alpha 1-antitrypsin causes liver damage in transgenic mice. *J Clin Invest* 83, 11831190 (1989). PMID: 2784798
64. Maes, M., Vinken, M. & Jaeschke, H. Experimental models of hepatotoxicity related to acute liver failure. *Toxicology and applied pharmacology* 290, 86-97 (2016).
65. Bissig-Choisat B, Wang L, Legras X, Saha P K, Chen L, Bell P, Pankowicz F P, Hill M C, Barzi M, Kettlun Leyton C, Leung H C, Kruse R L, Himes R W, Goss J A, Wilson J M, Chan L, Lagor W R, Bissig K D. Development and rescue of human familial hypercholesterolaemia in a xenograft mouse model. *Nat Commun* 6, 7339 (2015). PMID: 26081744
66. Li B, Dorrell C, Canaday P S, Pelz C, Haft A, Finegold M, Grompe M. Adult Mouse Liver Contains Two Distinct Populations of Cholangiocytes. *Stem Cell Reports* 9, 478-489 (2017). PMID: 28689996
67. Zhao, T., Zhang, Z. N., Rong, Z. & Xu, Y. Immunogenicity of induced pluripotent stem cells. *Nature* 474, 212-215 (2011).
68. Gam, J. J., Babb, J. & Weiss, R. A mixed antagonistic/synergistic miRNA repression model enables accurate predictions of multi-input miRNA sensor activity. *Nat Commun* 9, 2430 (2018).
69. Leonid Gaidukov, Liliana Wroblewska, Brian Teague, Tom Nelson, Xin Zhang, Yan Liu, Kalpana Jagtap, Selamawit Mamo[1], Wen Allen Tseng[1], Alexis Lowe, Jishnu Das, Kalpanie Bandara, Swetha Baijuraj, Nevin M Summers[1], Timothy K Lu, Lin Zhang, Ron Weiss. A multi-landing pad DNA integration platform for mammalian cell engineering. *Nucleic Acids Res* 46, 4072-4086 (2018).
70. Michelle M Chang, Leonid Gaidukov, Giyoung Jung, Wen Allen Tseng, John J Scarcelli, Richard Cornell, Jeffrey K Marshall, Jonathan L Lyles, Paul Sakorafas, An-Hsiang Adam Chu, Kaffa Cote, Boriana Tzvetkova, Sepideh Dolatshahi, Madhuresh Sumit, Bhanu Chandra Mulukutla, Douglas A Lauffenburger, Bruno Figueroa Jr, Nevin M Summers, Timothy K Lu, Ron Weiss. Small-molecule control of antibody N-glycosylation in engineered mammalian cells. *Nat Chem Biol* 15, 730-736 (2019).
71. Oertel, M., Menthena, A., Dabeva, M. D. & Shafritz, D. A. Cell competition leads to a high level of normal liver reconstitution by transplanted fetal liver stem/progenitor cells. *Gastroenterology* 130, 507-520; quiz 590 (2006).
72. Yovchev, M. I., Xue, Y., Shafritz, D. A., Locker, J. & Oertel, M. Repopulation of the fibrotic/cirrhotic rat liver by transplanted hepatic stem/progenitor cells and mature hepatocytes. *Hepatology* 59, 284-295 (2014).
73. Jorissen, R. N., Walker F, Pouliot N, Garrett T P, Ward C W, Burgess A W. Epidermal growth factor receptor: mechanisms of activation and signalling. *Exp Cell Res* 284, 31-53 (2003). PMID: 12648464
74. Ma, P. C., Maulik, G., Christensen, J. & Salgia, R. c-Met: structure, functions and potential for therapeutic inhibition. *Cancer Metastasis Rev* 22, 309-325 (2003).
75. Ataie-Kachoie, P., Pourgholami, M. H., Richardson, D. R. & Morris, D. L. Gene of the month: Interleukin 6 (IL-6). *J Cin Pathol* 67, 932-937 (2014).
75 Halpern K B, Shenhav R, Matcovitch-Natan O, Tóth B, Lemze D, Golan M, Massasa E E, Baydatch S, Landen S, Moor A E, Brandis A, Giladi A, Stokar-Avihail A, David E, Amit I, Itzkovitz S. Single-cell spatial reconstruction reveals global division of labour in the mammalian liver. *Nature* 542 (7641):352356 (2017). PMID: 28297709
76 Rolf Gebhardt and Madlen Matz-Soja. Liver zonation: Novel aspects of its regulation and its impact on homeostasis. World J Gastroenterol. July 14; 20(26):8491-504. (2014). PMID: 25024605.

Figure 34B:
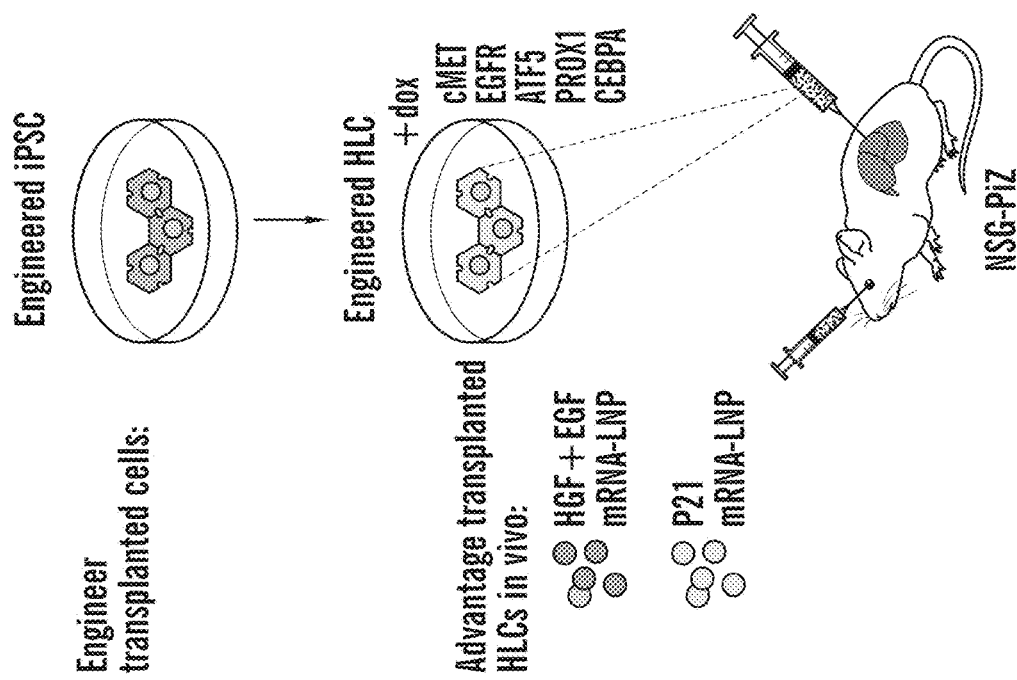
FIGS. 34A-34B depict proposal overview.
Figure 34A:
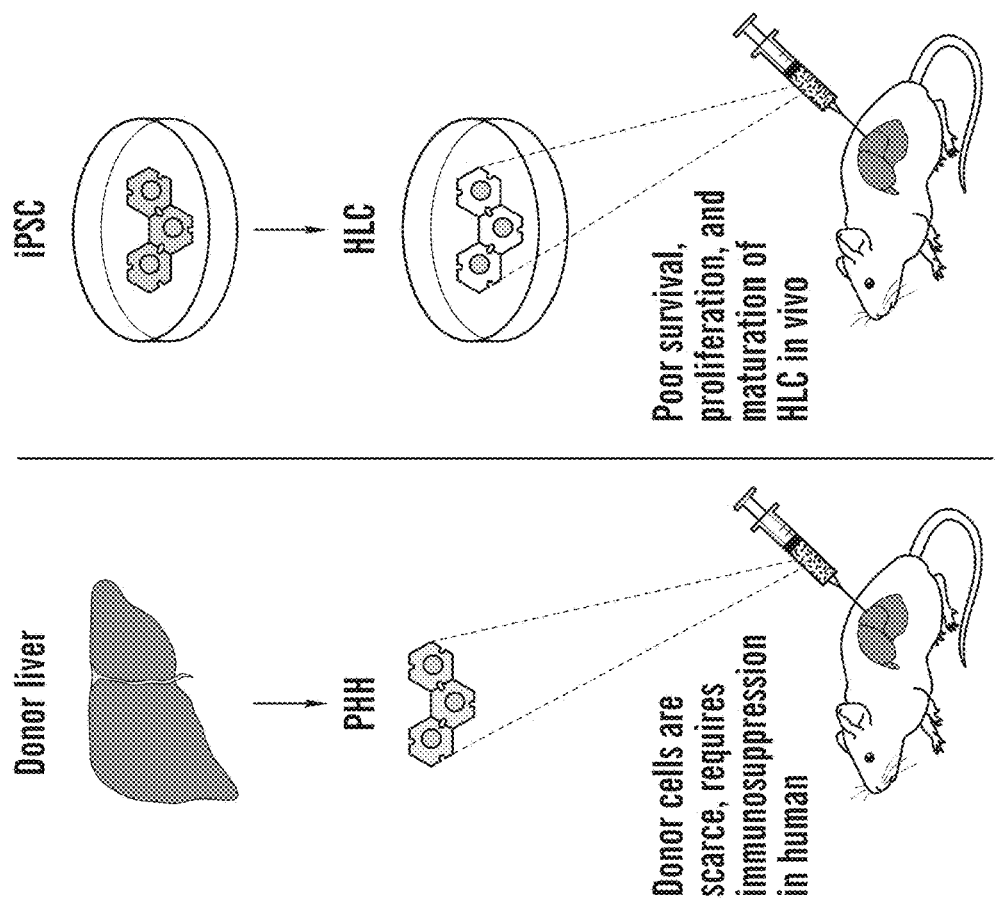

Example 4: Multimodular Approach to Improve Hepatocyte Transplantation to Treat Alpha-1 Antitrypsin Deficiency (AATD) Associated Liver Disease Significance AATD is an autosomal co-dominant condition that increases risk for liver and lung disease. Wildtype M-AAT protein encoded by the SERPINA1 gene is mainly produced by hepatocytes[2], secreted into the blood, and functions to protect the lungs from protease activity[23]. The most common mutation is a single amino acid substitution[24], called the PiZ allele, that causes the protein to misfold into the Z-AAT form and polymerize in the endoplasmic reticulum of hepatocytes, leading to hepatocyte death, cirrhosis, and hepatocellular carcinoma[3]. Curing AATD requires replacing diseased ZZ hepatocytes with wild type MM, but donor organs for whole liver transplantation are scarce. PHH cell therapy is safe and used for metabolic and acute liver diseases in humans[25,26], but this therapy is restricted by immunosuppression and limited hepatocyte supply[27] (FIG. 34A). Alternatively, patient-specific iPSCs that have been gene corrected at the PiZ allele could provide an unlimited source of M-AAT producing autologous HLCs for transplantation without the burden of immune rejection. However, factors that limit HLC engraftment are not fully understood, but include poor survival, proliferation, and maturation of transplanted cells[11,26-30] (FIG. 34A). Generation of HLCs that engraft and are mature enough to function in vivo remains a major gap that this project targets. To fill this gap the inventors propose a multimodular approach that includes (1) enhancing HLC survival, proliferation, and maturation in vitro by engineering HLCs to express increased levels of key mitogen receptors (cMET, EGFR) and maturation transcription factors (ATF5, PROX1, CEBPA) and (2) advantaging HLC repopulation in vivo by inducing post-transplantation maturation, stimulating proliferation in transplanted cells with HGF+EGF, and preventing proliferation in the host liver with P21 (FIG. 34B).

To determine the therapeutic efficacy of HLCs, they are compared to PHHs which are known to largely repopulate the liver in many different mouse models of liver diseases[30]. The feasibility of iPSC-derived HLCs as a cell replacement therapy has been demonstrated in various animal models of liver disease such as NOD/SCID[9], MUP-uPA/SCID/Bg[7], and Gunn rats[8]. Yet, HLCs are less effective than PHHs and do not achieve nearly the same level of repopulation, suggesting impaired engraftment[30]. This is most likely due to the challenges reviewed here[26,31-33] which include poor maturation, survival, proliferation, phenotypic stability, and function of transplanted cells in comparison to PHHs. Previously, two studies used HLCs in different AATD mouse models[4,10] than proposed here; however, these studies are only a proof-of-principle, as the therapeutic threshold for liver and/or lung has not yet been reached.

There is an urgent need for a liver specific therapy for AATD patients, as no therapeutic option currently exists other than supportive care and liver transplantation[34]. The progression of lung disease associated with AATD can be slowed with weekly protein augmentation of exogenous M-AAT, for which there are US FDA approved drugs available[35,36]. Several ongoing clinical and pre-clinical studies aim to ameliorate AATD liver disease by designing small molecules to prevent Z-AAT misfolding[37], editing or silencing the mutated allele in vitro[20] and in vivo[5], and increasing the liver's ability to break down accumulated Z-AAT with rapamycin[38] and carbamazepine[39,40]. However, in this proposal, efficient repopulation and maturation of HLCs in vivo lead to engraftment of functional HLCs that secrete normal M-AAT protein. This would effectively replace diseased Z-AAT burdened hepatocytes and restore secreted M-AAT in the blood, relieving both the liver and lung phenotype of AATD with one single therapy.

Innovation

This proposal has significant clinical implications for treating AATD associated liver disease, underlined by three main innovative concepts: (1) Use of AATD patient iPSCs that have been gene corrected at the PiZ allele to generate healthy HLCs engineered to express physiological levels of 5 genes that are key for survival, proliferation, and maturation of hepatocytes. The inventors use inventive dox-inducible expression of these genes to initiate maturation of transplanted cells in vivo, giving insight to creating more functional HLCs. (2) The inventors seek HLC repopulation in vivo using transient, safe, non-integrative mRNA-LNP to deliver HGF+EGF to stimulate proliferation. Using the same technique, the inventors precondition the host liver with P21 mRNA-LNP to block host cell proliferation. This is the first use of this clinically relevant tool to help improve liver cell therapies. (3) Importantly, the inventors closely examine early time points within the first week post transplantation of HLCs in vivo, which has been neglected in other published studies[30]. This is a crucial time point in which a majority of HLCs are lost, which may also be an issue for PHH transplantation as only a fraction (~10%) of cells transplanted are detected in the host[41].

Approach

1 Preliminary Studies

Figures 35A, 35B:
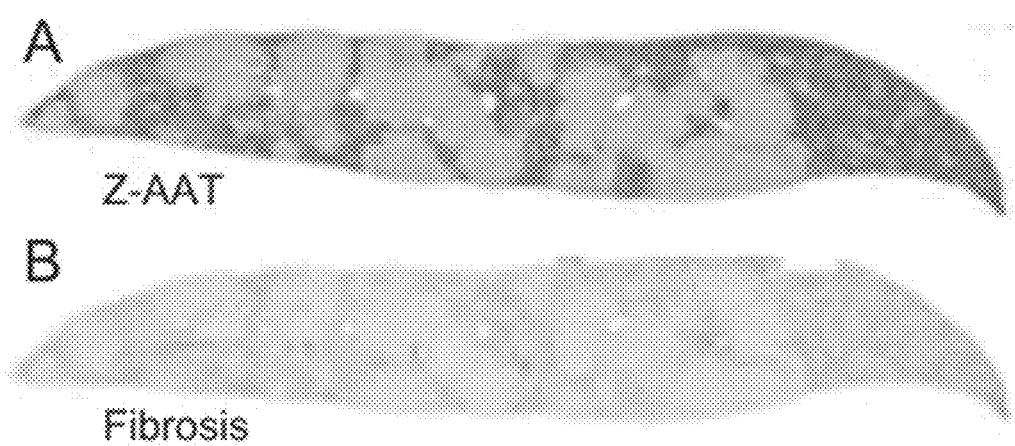
FIGS. 35A-35B depict NSG-PIZ mice recapitulate AATD liver phenotype.

NSG-PiZ mice recapitulate AATD liver phenotype: The liver disease associated with AATD is recapitulated in transgenic NOD/SCID/IL2R −/−(NSG)-PiZ mice. NSG-PiZ mice express the human PiZ allele on a severe immune deficient background, and have been characterized to have heterogeneous Z-AAT accumulation in hepatocytes (FIG. 35A) and liver fibrosis (FIG. 35B). Male and female 7-10 week old NSG-PiZ mice are the recipient strain in all hepatocyte xenotransplantation studies. Age matched NSG mice serve as controls.

Figure 36A:
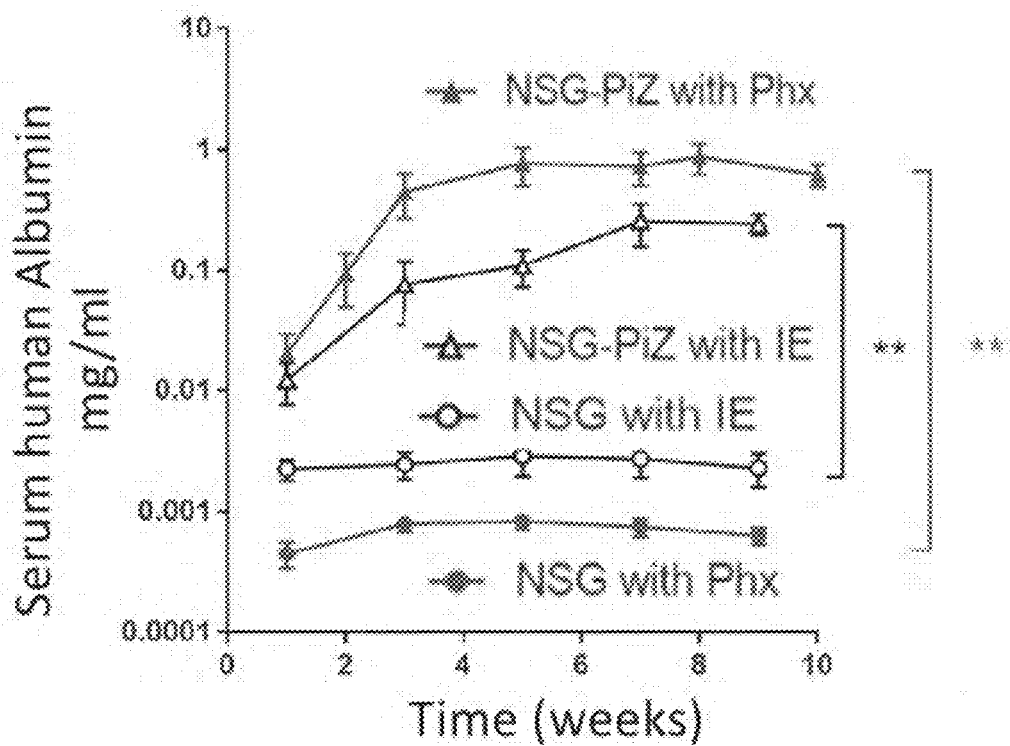
FIGS. 36A-36D depict Wildtype PHHs repopulate the NSG-PiZ mouse liver.
Figure 36B:
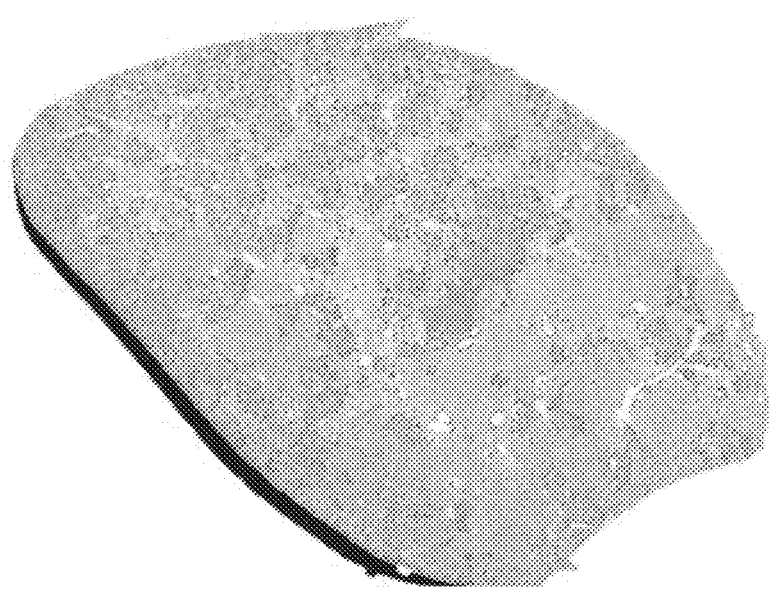
Figure 36C:
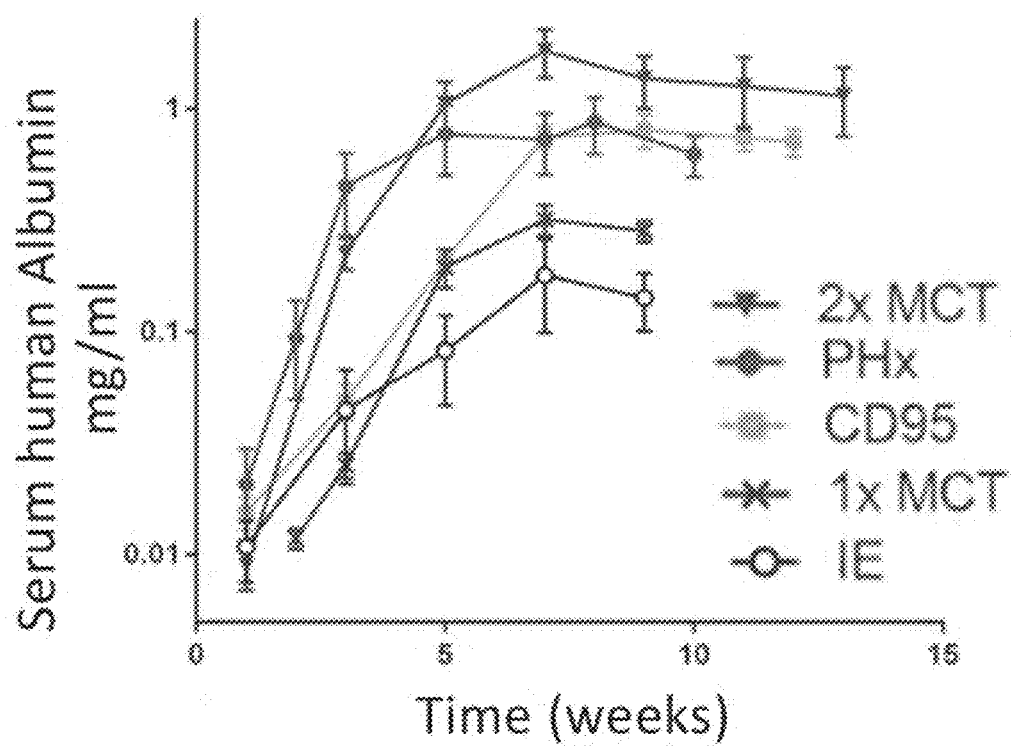
Figure 36D:
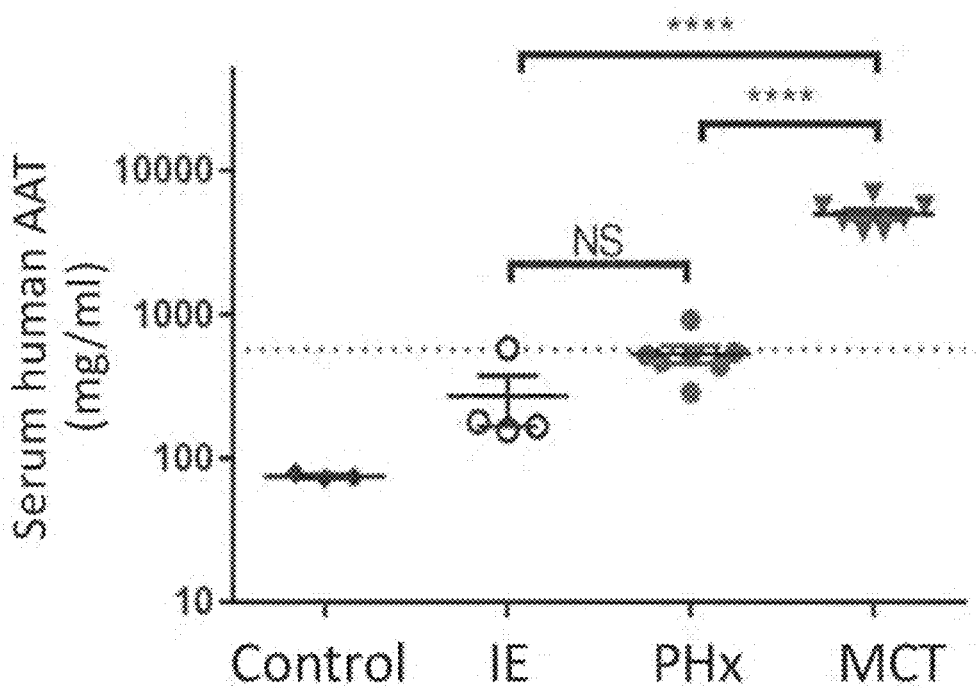

PHHs repopulate the NSG-PiZ mouse liver: Wild type mouse hepatocytes have a growth advantage over PiZ mouse hepatocytes transplanted in NSG-PiZ mice, confirming that the host liver undergoes enough turnover to provide healthy hepatocytes opportunity to repopulate it. Wild type PHHs can also repopulate the NSG-PiZ liver by transplanting $10^6$ cells via intrasplenic injection into these immune deficient hosts. Human serum albumin levels are monitored biweekly as a measure of liver repopulation with human cells (FIG. 36A). Human chimerism is significantly higher in NSG-PiZ mice than NSG controls, demonstrating that Z-AAT burden creates a niche for PHH repopulation. Increasing cell turnover via partial hepatectomy (PHx) also leads to increased liver repopulation versus intrasplenic engraftment (IE) alone (FIG. 36A). PHHs are able to repopulate a significant area of NSG-PiZ livers (FIG. 36B). To optimize PHH repopulation, monocrotaline (MCT) and anti-CD95 antibody are used to increase cell turnover. MCT induces endothelial toxicity and repopulation in the liver[42], and anti-CD95 antibody is known to induce hepatocyte apoptosis[43]. The highest level of two MCT doses (FIG. 36C). Importantly, FDA-accepted therapeutic levels of AAT secretion were achieved with PHH transplantation when paired with PHx and MCT (FIG. 36D). PHH repopulation will serve as a control for HLC repopulation, with the goal of achieving similar therapeutic benefit.

iPSC-derived HLCs have immature gene signature: To differentiate human iPSCs into HLCs, the endoderm program is induced, followed by hepatic specification, and maturation as previously described in[44] (FIG. 35A). High levels of activin-A are used to efficiently induce definitive endoderm, confirmed by cKIT+/CXCR4+ cellular phenotype on day 5 (FIG. 35B). Cells are then exposed to hepatic specification media containing rhBMP4, rhFGF-2, rhHGF, rhEGF, rhVEGF, rhTGFa, and dexamethasone in complete serum free differentiation media[44]. Identity of cultures through directed differentiation are confirmed by immunostaining in the dish for pluripotency marker OCT4, endoderm marker FOXA2, early hepatic marker alpha fetoprotein (AFP), and later stage hepatic marker albumin (ALB) (FIG. 35C). HLCs have some characteristics of PHHs, but considering function and metabolic activity our HLCs, as well as those derived in other labs, are more similar to immature hepatocytes[45,46]. In comparison to PHHs, the inventors find that these HLCs have much lower gene expression of cMET and EGFR (FIG. 35D), two mitogen receptors that are key in liver regeneration[13]. Similarly, these HLCs have much lower transcript levels of ATF5, PROX1, and CEBPA (FIG. 35D), all of which are necessary for HLC maturation[15]. This protocol is used to generate day 15 HLCs for transplantation in the proposed HLC engineering and transplantation studies.

Figures 38A, 38B, 38C:
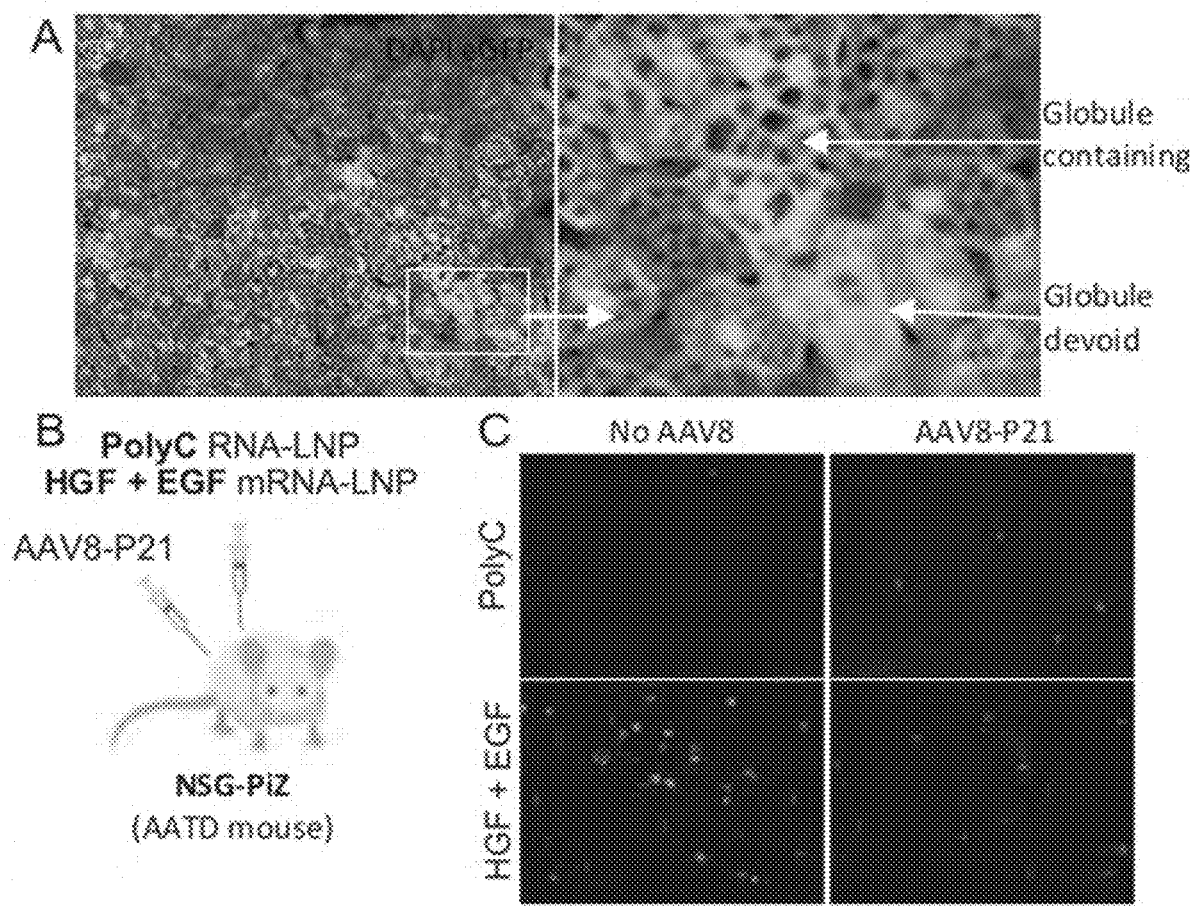
FIGS. 38A-38E depict mRNA-LNP express proteins in the liver.
Figure 38D:
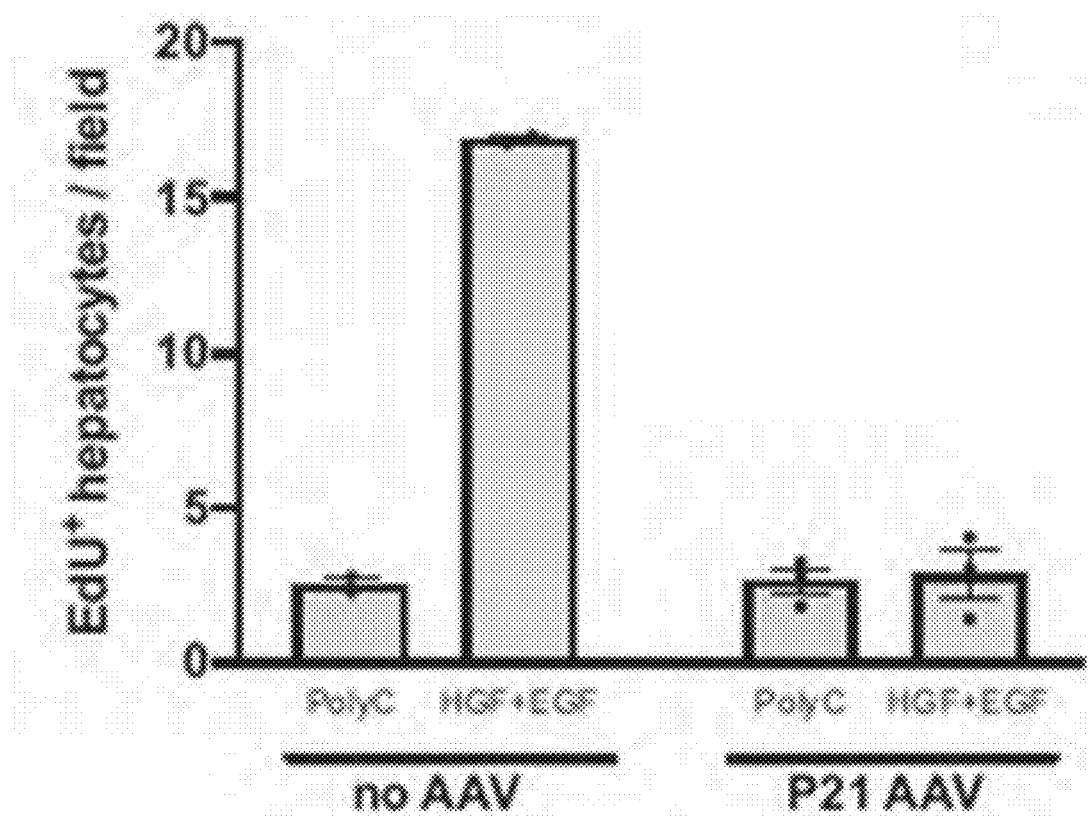
Figure 38E:
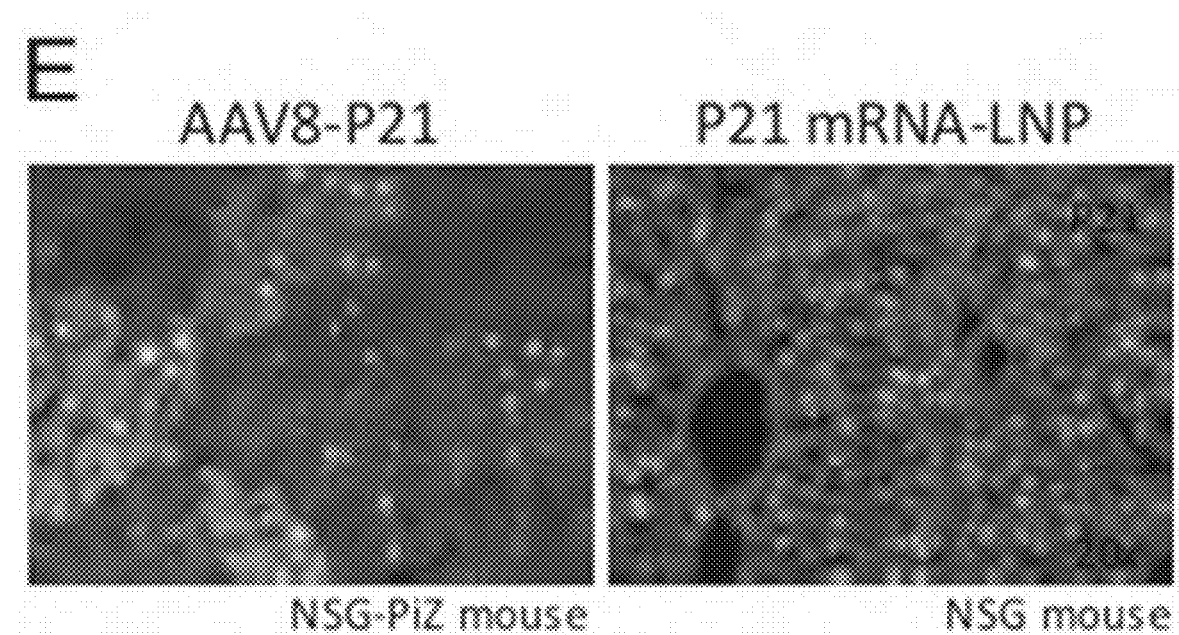

Gene correction of AATD patient iPSCs: HLCs derived from AATD patient iPSCs maintain the disease signature[21]. An important proof-of-principle study shows that the Z mutation in these iPSCs can be genetically corrected, demonstrating the ability to generate cells for autologous cell therapies[47]. To demonstrate the feasibility and clinical relevance of patient specific cell therapy, the inventors use the cell lines corrected at the PiZ allele, in the engineering and transplantation experiments.

mRNA-LNPs transiently express proteins of interest in the liver: The inventors use mRNA-LNP to transiently express proteins in the liver. It was recently shown that a single IV injection of mRNA-LNP leads to robust protein expression in the liver and hepatocytes are the main cell type transfected[19]. All hepatocytes in the NSG-PiZ mouse are transfected with mRNA-LNP and efficiently express protein, regardless of the amount of Z-AAT accumulation (FIG. 38A). A single IV injection of HGF+EGF mRNA-LNP functions in vivo to induce hepatocyte proliferation, as shown by incorporation of EdU into proliferating cells in comparison to the PolyC untranslatable control RNA which induced little proliferation (FIG. 38B, 38C). This data is quantified as EdU+ hepatocytes by morphology per field (FIG. 38D). Furthermore, the inventors show that by constitutively expressing P21 cell cycle regulator in the host mouse using adeno-associated virus, they are able to block the proliferation induced by HGF+EGF (FIGS. 38C, 38D). This is a proof-of-principle demonstrating block of host hepatocyte proliferation, which can be leveraged to induce proliferation only in transplanted HLCs. The inventors also show that P21 expression is possible using clinically relevant mRNA-LNP, but further experiments will be necessary to determine if this method can also block EGF+EGF induced proliferation in the host tissue (FIG. 38E). This mRNA-LNP technology will be used to pre-condition the host liver and stimulate survival and proliferation in HLCs in vivo.

HGF+EGF mRNA-LNP treatment increases PHH cluster size in male NSG-PiZ mice: Five hours prior to transplantation, host animals are injected IV with HGF+EGF mRNA-LNP or PolyC control. Cryopreserved PHH (BioIVT) are thawed and immediately transplanted into the NSG-PiZ mouse via intrasplenic injection protocol as previously described[16]. HGF+EGF mRNA-LNP injections are administered weekly for 9 weeks after transplantation. Importantly, the inventors see a trend that transplanted PHH clusters in male NSG-PiZ mice are larger in the HGF+EGF treated mouse, suggesting that these mitogens could improve transplanted PHH proliferation in vivo (FIG. 39), though further experiments will be required to achieve significance and explore sex differences.

Figure 40A:
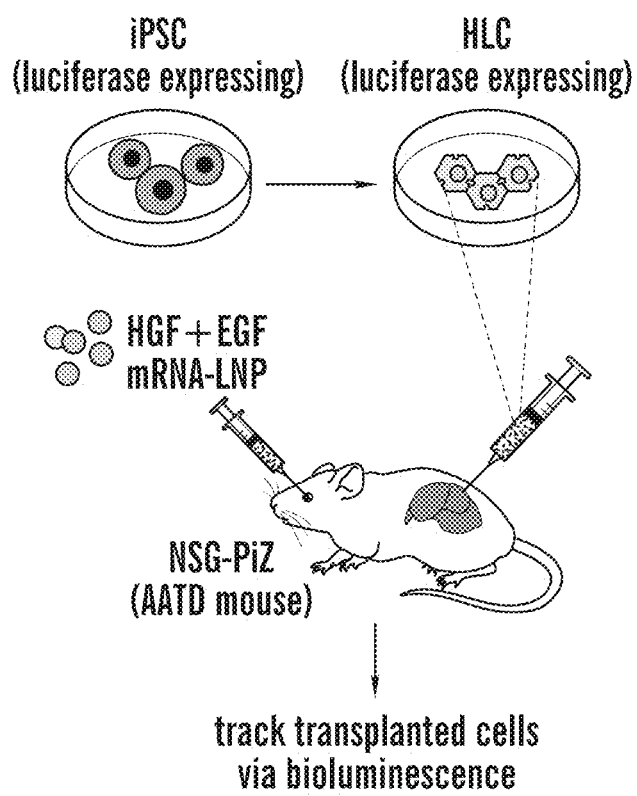
FIGS. 40A-40C depict HGF+EGF mRNA-LNP transiently improves survival of HLCs in NSG-PiZ mice.
Figure 40B:
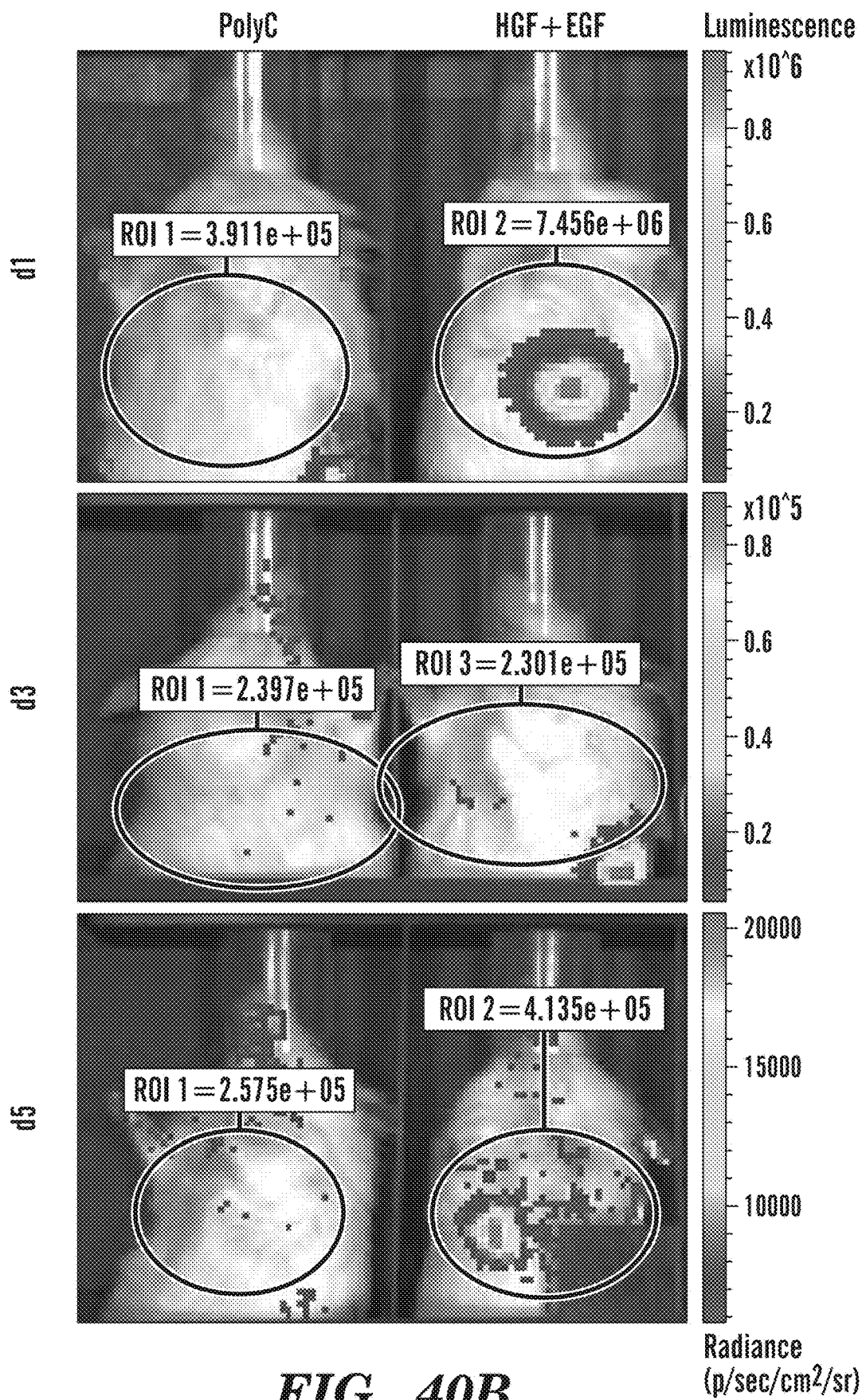
Figure 40C:
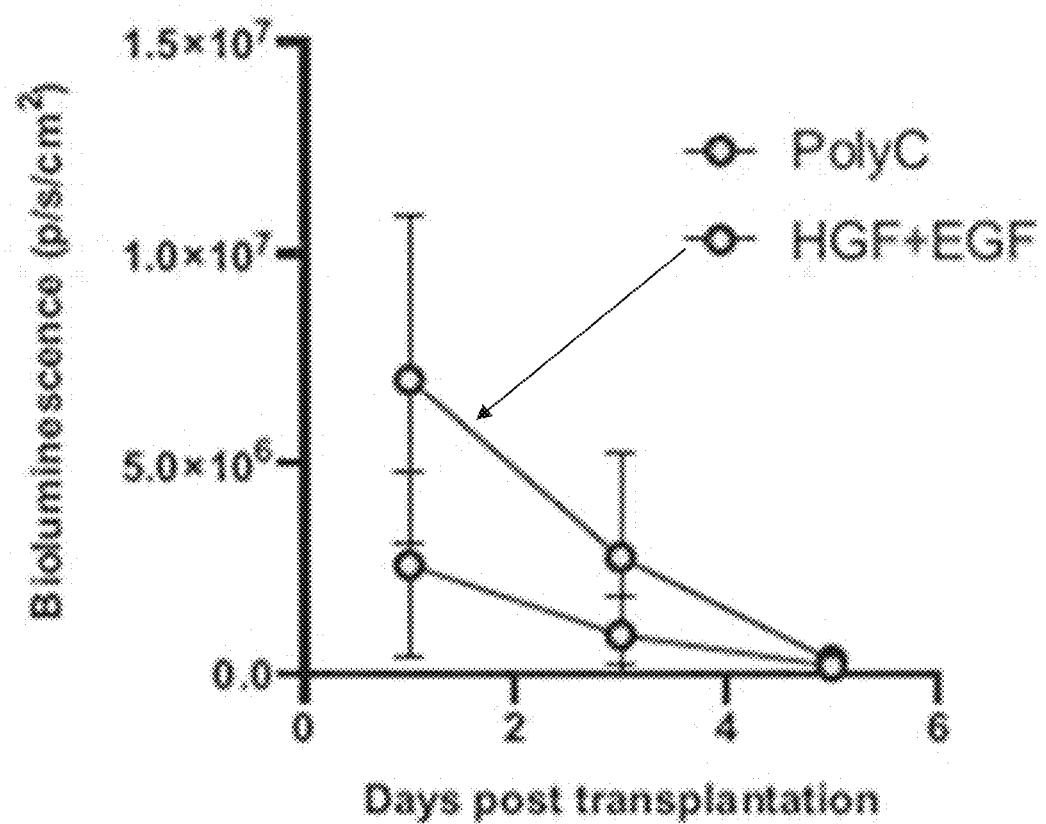

HGF+EGF mRNA-LNP treatment transiently improves HLC survival in NSG-PiZ mice: When HLCs are transplanted into mice, the inventors use luciferase expressing iPSCs to make HLCs that are trackable in vivo using bioluminescence (FIG. 40A). Here, it is shown that HGF+EGF mRNA-LNP administered 5 hours prior transplantation transiently improves HLC survival in the first few days after transplantation in comparison to control PolyC (FIG. 40B). Quantification of bioluminescence over time shows a trend that HGF+EGF treated mice have higher HLC survival, but most cells die after a few days (FIG. 40C).

2 Experimental Design

Statistics, Rigor, and Reproducibility: In vitro experiments include data from at least three independent experiments performed as technical replicates on different days. For the purpose of reproducibility, it is important to use multiple iPSC lines to substantiate findings. Unless otherwise stated, in vivo experiments and follow up assays include at least 8 mice per group (4 males and 4 females) as biological replicates. LaMorte's Power Calculations is used to determine the minimum number of animals needed to achieve statistical significance based on predicted results for each analysis. Both sexes are used in mouse studies to account for the known difference in liver diseases between males and females. A threshold of $p<0.05$ is used to determine statistical significance. A student's t test is used when comparing 2 groups, while an ANOVA is used when comparing more than 2 data sets. Consultation from the BU CTSI Biostatics, Epidemiology, & Research Design program ensures appropriate statistical analyses.

Aim 1: To Enhance iPSC-Derived HLC Survival, Proliferation, and Maturation In Vitro, Engineered HLCs are Used to Express Increased Levels of Key Mitogen Receptors (cMET, EGFR) and Maturation Transcription Factors (ATF5, PROX1, CEBPA).

Figure 37A:
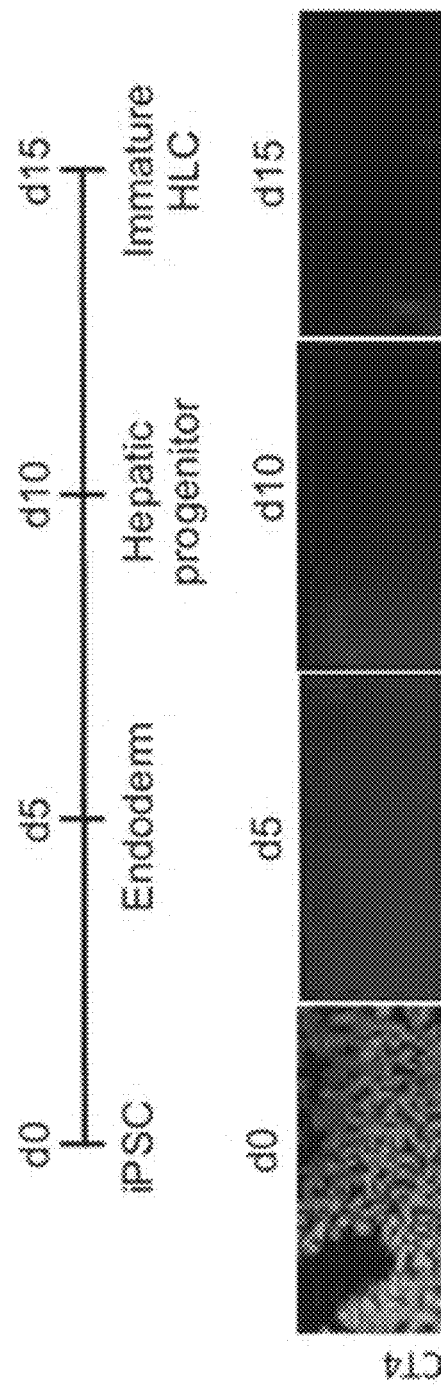
FIGS. 37A-37D depict HLCs have immature gene signature.
Figure 37B:
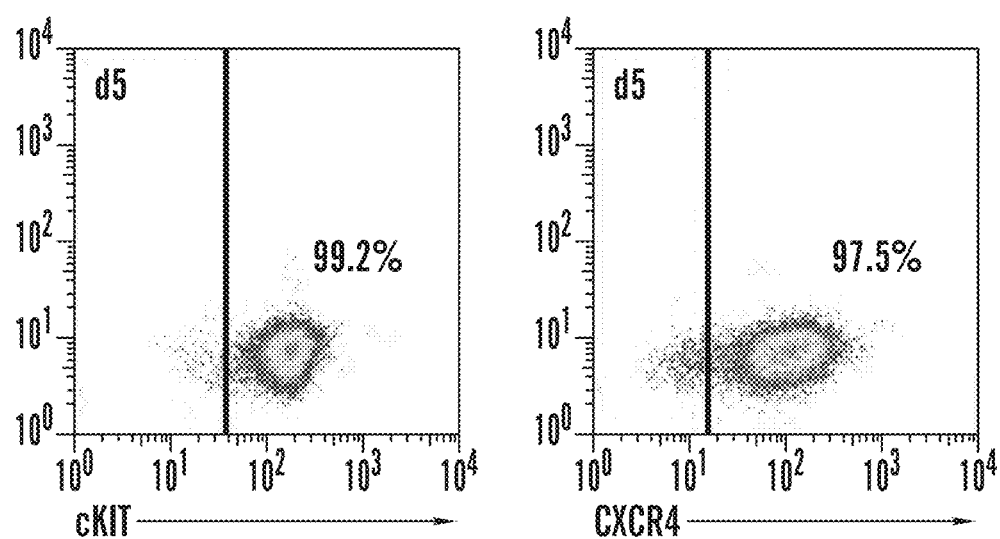
Figure 37C:
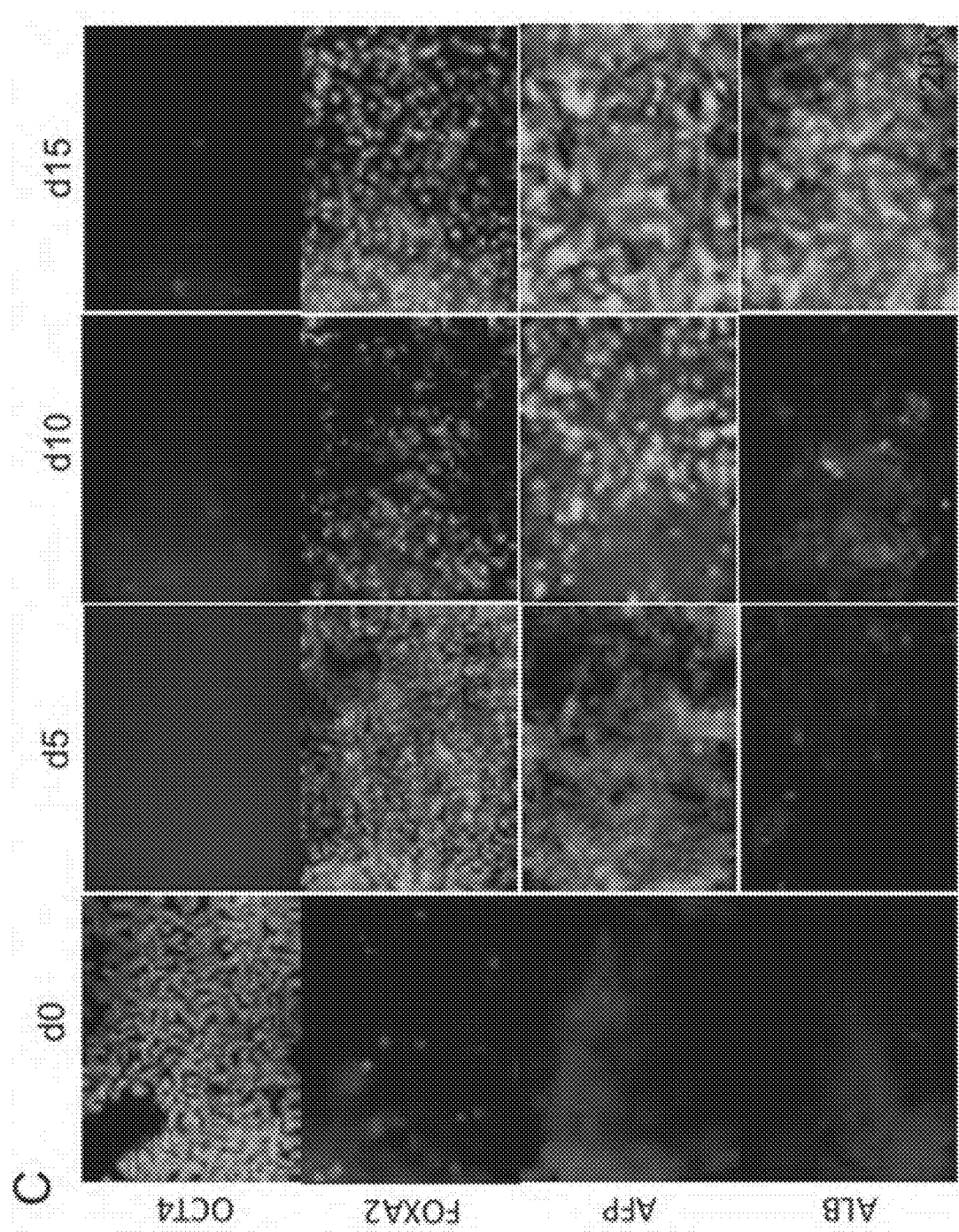
Figure 37D:
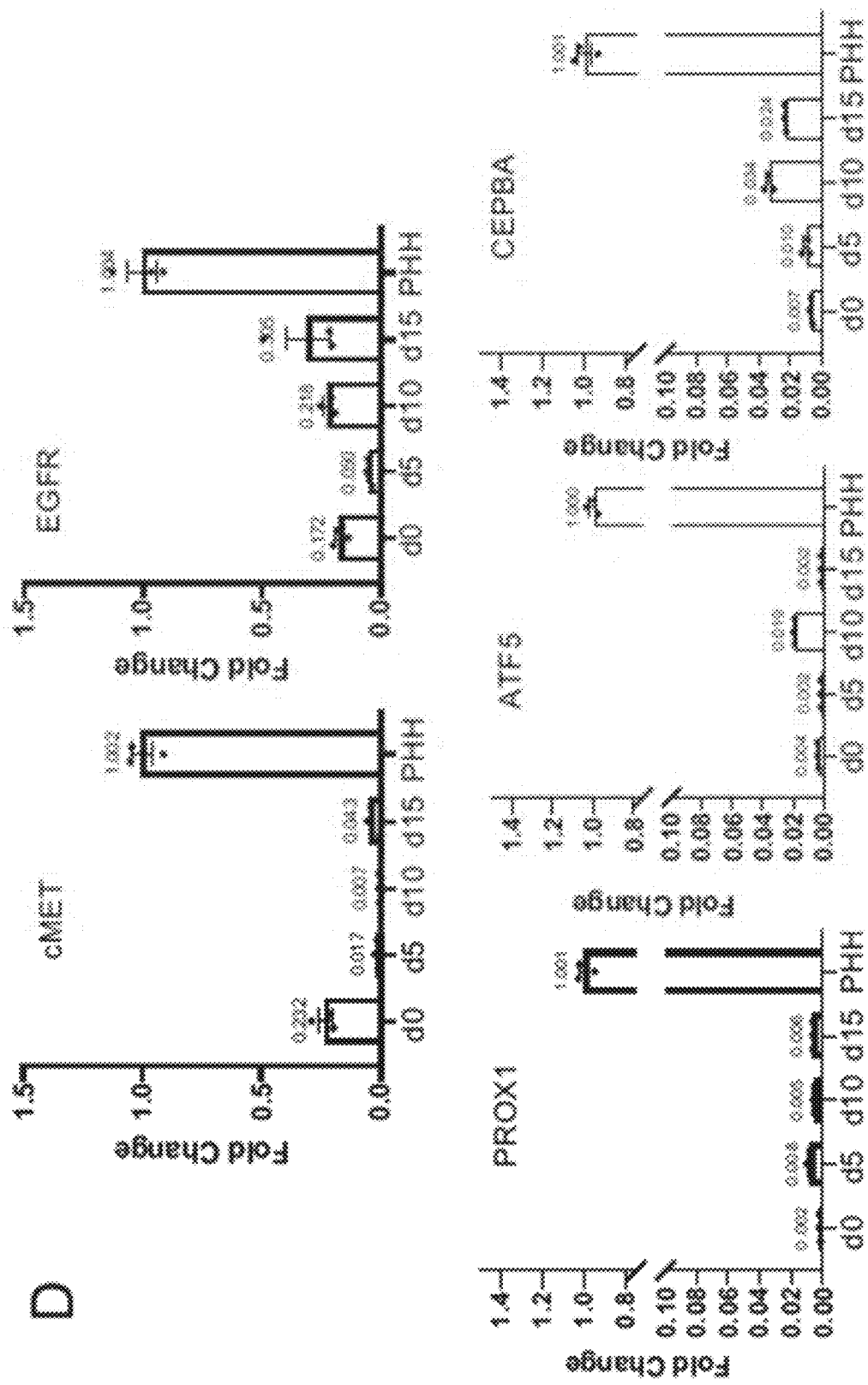

Rationale: Creating HLCs for cell therapy to repopulate a diseased liver remains a challenge and major gap that this project targets. Studies suggest that the root causes of poor engraftment may be lack of proliferation and maturation of transplanted cells[28,30,48]. To overcome these obstacles, in Aim 1 the inventors engineer HLCs to activate mitogen pathways (HGF/cMET and EGF/EGFR) that are known to be crucial for hepatocyte survival, proliferation, and migration during liver development and regeneration[13,14,49]. It is well know that HLCs maintain an immature phenotype in comparison to primary controls[45,46]. Accordingly, here it is seen that HLCs have 10-100 fold lower expression of these important receptors (FIG. 37D), which motivates this aim. The inventors also aim to engineer HLCs to have persistent expression of transcription factors (ATF5, PROX1, CEBPA)[5] to facilitate the maturation of HLCs in vitro and in vivo in downstream transplantation applications in Aim 2. The inventors induce expression of ATF5, PROX1, and CEBPA for several reasons: these genes are enriched in adult hepatocytes in comparison to fetal, they are highly enriched in adult hepatocytes in comparison to other transcription factors, they are the smallest cocktail necessary to promote maturation of fibroblasts reprogrammed to hepatocytes, and HLCs express considerably lower levels in comparison to PHHs (FIG. 37D)[11,15,50]. These genes are integrated into corrected AATD patient iPSCs using PiggyBac transposons because they can carry inserts of up to 100 kb and they rarely produce genomic footprints[51-53]. 5 genes of interest are expressed via dox-induction to control when the genes are expressed in a dose dependent way, so as to avoid spontaneous differentiation throughout definitive endoderm and hepatic specification. Thus, the inventors test that by engineering iPSC lines to have these 5 factors increases their expression in HLCs and improves HLC survival, proliferation, and maturation in vitro. These cell lines, if more viable, proliferative, and mature in vitro, are used in Aim 2 transplantation studies.

Figure 41:
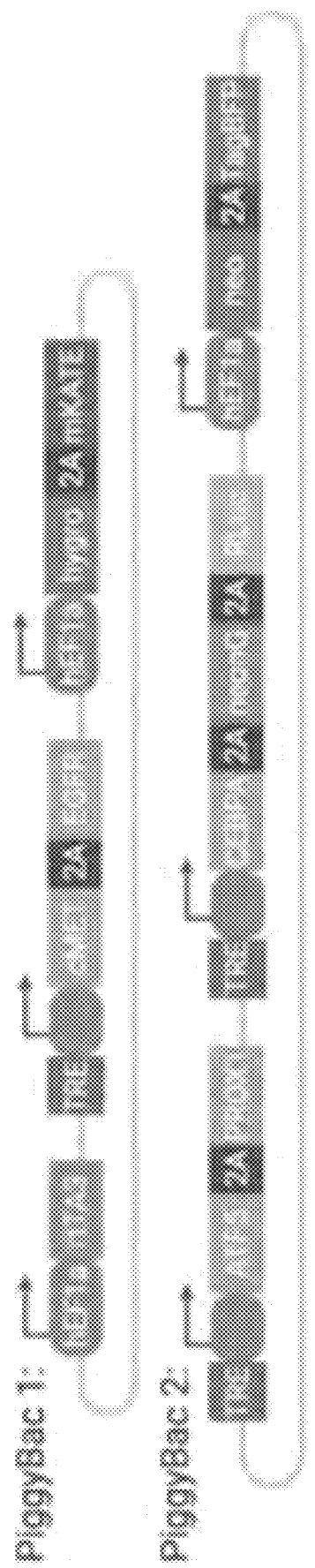
FIG. 41 depicts PiggyBac based non-viral gene delivery of doxycycline-inducible genetic constructs.

(A) Design a doxycycline-inducible gene expression system: The inventors transfect the gene corrected AATD patient iPSC lines, integrate the constructs using PiggyBac transposons, differentiate into HLCs using the protocol above (FIG. 37), and turn on gene expression with dox in the media. The proposed construct design is as follows (FIG. 41): PiggyBac 1—The first transcription unit (TU) encodes rtTA3 under the constitutive hEF1a promoter. When added in the media, dox and rtTa3 bind and activate dose dependent gene expression at all the tetracycline response elements (TRE) elsewhere in the constructs. The second TU encodes the mitogen receptors cMET and EGFR under a TRE. Transcripts fused by a 2A sequence will produce two separate proteins via ribosomal skipping. The third TU encodes a hygromycin resistant gene and fluorescent protein mKATE under the constitutive hEF1a promoter. Hygromycin resistance allows selection in the dish for cells that have integrated PiggyBac 1, and mKATE allows for detection of transfected cells under the microscope and sorting based on copy number via flow cytometry. PiggyBac 2—The first TU encodes the transcription factors ATF5 and PROX1 under a TRE. The second TU encodes transcription factor CEBPA, fluorescent protein neonGreen, and bioluminescent renilla luciferase (RLuc) under a TRE. The fluorescent protein neonGreen allows for the detection of dox activation in vitro, and the RLuc will aid the detection of dox activation in vivo (Aim 2). The third TU encodes a neomycin resistant gene and fluorescent protein TagBFP for selection, detection, and sorting of cells transfected with PiggyBac 2.

(B) Integrate, establish, and validate engineered cell lines: Gene corrected AATD patient iPSCs are seeded as single cells at low density. Lipofectamine stem reagent (Invitrogen) is used to transfect both PiggyBac constructs (FIG. 41) along with a PiggyBac transposase plasmid that facilitates integration into cells. Hygromycin and neomycin in media is used to select cells that integrate both constructs. Following directed differentiation into day 15 HLCs (FIG. 37), a range of dox concentrations is added in the media to induce gene expression. Expression of the genes of interest is validated and characterized using qPCR, flow cytometry, and immunostaining in the dish for cMET, EGFR, ATF5, PROX1, and CEBPA. Engineered HLCs are compared to original HLCs and PHH controls to establish the effects of dox dose and determine what condition yields gene expression on par with PHHs.

(C) Characterize survival, proliferation, and maturation of engineered HLCs: The ability of engineered HLCs to survive, proliferate, and mature in comparison to original HLCs and PHH controls is evaluated using the following assays. These experiments are performed with an optimized range of dox doses established in (B) as well as with and without recombinant ligands added in the media (HGF: 20 ng/ml, EGF 10 ng/ml) to stimulate the mitogen receptors. To test survival, an MTT assay[54] measures HLC viability and a TUNEL assay (Invitrogen) will examine apoptosis. To test proliferation, population doubling is observed, EdU incorporation (Invitrogen) is detected via flow cytometry, and immunostaining in the dish shows proliferation marker Ki67. To test maturation, methods previously described[i'''17,18,45,55] are used including immunostaining in the dish, qPCR, and flow cytometry quantification for fetal liver marker alpha-fetoprotein (AFP) and more mature liver markers albumin (ALB), alpha-1 antitrypsin (AAT), and cytochrome P450 enzymes (CYP). The transcriptomes of original HLCs, engineered HLCs, and PHHs are compared using bulk RNA sequencing. To test function, ALB (Bethyl) and AAT secretion ELISA[5], glycogen storage via PAS staining[55], ammonia detoxification (Sigma), urea secretion (BioAssay), and CYP activity fluorescent kits (Invitrogen) is used.

Experimental Outcomes and Alternatives: Altogether these in vitro experiments integrate these constructs into iPSCs, validate dose dependent expression of the 5 genes in HLCs, and characterize the effects of these genes on survival, proliferation, and maturation in vitro. Using PiggyBac integration, 1-10 copies of each construct is integrated randomly into each cell. If PiggyBac 1 and 2 are integrated, the cells become resistant to hygromycin and neomycin and to see mKATE and TagBFP expression in accordance with the number of copies integrated. Upon addition of dox, there is an increase in expression of cMET, EGFR, ATF5, PROX1, CEBPA, and fluorescent neonGreen in a dose dependent way. The inventors anticipate that engineered HLCs with higher expression of these genes are more viable, proliferative, mature, and functional than un-engineered HLCs, measured by the assays outlined above. Optimal HLCs are achieved when dox induced gene expression closely mimics that of PHHs. However, even higher expression of these genes may be beneficial. The inventors use the engineered HLC characterization done here to inform in vivo experiments in Aim 2. Even without gene expression that is on par with PHHs, the engineered cells are still viable candidates for transplantation studies, as fetal liver progenitor cells are able to repopulate a damaged liver[56,57]. When integrating constructs randomly into the genome of iPSCs and subjecting them to major chromatin remodeling via directed differentiation, silencing is an obvious concern. The inventors have previously experienced minimal silencing of luciferase lentiviral integration in the BU3 iPSC line. Regardless, keeping selective pressure on engineered cells using hygromycin and neomycin is essential. Choosing clones that demonstrate robust sustained expression of constructs is also an alternative to a polyclonal population. Otherwise, the inventors use site specific integration of the constructs into the AAVS1 safe harbor landing pad. A single dox dose may not appropriate for both receptor and transcription factor expression, as all the other genes of interest are combined in a single, interdependent dox-inducible system. Rather than entirely remodeling the constructs, it is possible to sort the cells into high and low integration levels of both plasmids. For example, low mKATE (PiggyBac 1) and high TagBFP (PiggyBac 2) cell populations may allow for tuning the HLCs to favor expression of PiggyBac 2 over 1. Finally, the order of genes in each TU can also affect expression, as higher expression of the first gene in each TU is usually observed.

Aim 2: To Advantage HLC Repopulation In Vivo, Maturation Genes are Expressed, Expansion of Transplanted Cells with HGF+EGF is Stimulated, and Proliferation of the Host Liver with P21 is Prevented.

Figure 39:
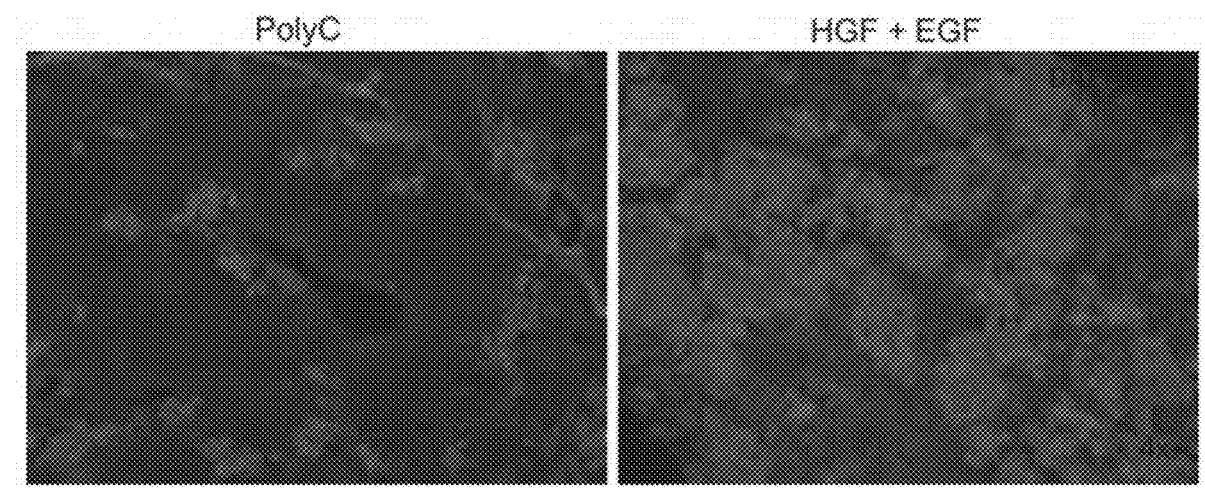
FIG. 39 depicts HGF+EGF mRNA-LNP increases cluster size of PHHs in NSG-PiZ male mice. Mice were transplanted with $10^6$ PHHs. PolyC or HGF+EGF mRNA-LNP injections were given once a week post transplantation. Livers were harvested after 9 weeks. hALB shows PHHs, n=1.

Rationale: Proof-of-principle has been established for liver cell therapy in NSG-PiZ mice (FIG. 36), where the Z-AAT burdened liver provides a growth advantage to PHHs and wildtype murine heptocytes[5]. Achieving repopulation using iPSC-derived HLCs may be possible, however this technology is currently limited by poor survival and proliferation[6,10]. To overcome these obstacles in vivo, the inventors promote post transplantation maturation using dox-inducible gene expression of ATF5, PROX1, and CEBPA using engineered HLCs established in Aim 1. Promoting HLC maturation after transplantation is ideal because fetal liver progenitors have a higher capacity for liver repopulation than mature cells[56,57]. Simultaneously, expression of the receptors cMET and EGFR in HLCs is induced by providing doxycycline in the drinking water of host mice. The corresponding ligands, HGF and EGF, are delivered in vivo with mRNA-LNP. mRNA-LNP is advantageous because it is transient, non-integrative, in vitro transcribed, and modified to prevent immunogenicity and increase stability. The inventors have demonstrated the in vivo function of HGF+EGF to induce proliferation (FIG. 38). The inventors identified a trend that HGF+EGF increases transplanted PHH cluster size in male NSG-PiZ mice, likely because PHHs express high levels of cMET and EGFR (FIG. 39). Promisingly, there is a transient improvement in HLC survival post transplantation with HGF+EGF treatment (FIG. 40). Other cell therapy applications have used an adenovector expressing HGF[4] or a cMET agonist antibody[58] to accelerate liver repopulation, making this axis an appealing target. Prior studies use techniques such as partial hepatectomy, monocrotaline, anti CD95, liver irradiation, and acute injury to increase host hepatocyte turnover to create a niche for transplanted cells to repopulate[5,8,58,59]. PHH repopulation can even reach the FDA accepted therapeutic threshold of normal AAT secretion when NSG-PiZ host cell turnover is increased with partial hepatectomy or monocortaline[5]. Yet, using these practices on human patients to improve HLC repopulation is unethical. To further advantage HLC repopulation in a safe way, the inventors block host mouse hepatocyte proliferation using cell cycle regulator P21 mRNA-LNP. P21 has been noted to halt liver regeneration by blocking proliferation[60,61] and other cell therapy studies have used knockout of other cell cycle regulators to advantage the proliferation of transplanted cells[62]. Thus, the inventors test that expressing maturation genes in HLCs, stimulating proliferation of HLCs, and preventing proliferation of the host liver will advantage HLC repopulation in vivo.

(A) Stimulate maturation of HLCs in vivo using expression of ATF5, PROX1, CEBPA: Using intrasplenic injection of $10^6$ cells[16], repopulation of the NSG-PiZ mouse liver is compared among optimized engineered HLCs from Aim 1, original HLCs, and PHHs. A range of dox doses is administered in the drinking water. Induction of the genes of interest is observed via RLuc bioluminescent activity in vivo and assessed by qPCR and immunostaining for ATF5, PROX1, CEBPA, cMET, and EGFR. To validate liver repopulation, the inventors use immunostaining for hALB and human nuclear protein (HuNu) on liver sections. To test maturation, human cells are re-isolated from the host liver and RNA sequenced to compare their hepatic gene signature to non-transplanted cells and PHHs. In addition, co-immunostaining and flow cytometry for human cell markers HuNu or Ku80 along with fetal liver marker AFP and more mature liver markers ALB, AAT, CYP identify maturity of transplanted HLCs. To test function of HLCs, ALB and AAT secretion are measured with ELISA (Bethyl). To test global liver function, serum AST, ALT, and bilirubin assays are used.

(B) Promote survival and proliferation of HLCs with HGF+EGF mRNA-LNP: Using the best dose of dox determined in (A), the inventors then systematically examine the effects of HGF+EGF mRNA-LNP treatment on the survival and proliferation of transplanted engineered HLCs, original HLCs, and PHHs. HGF+EGF mRNA-LNP (5 ug each) are injected intravenously 5 hours prior to transplantation, and weekly thereafter. To validate liver repopulation, the inventors use the same technique as in (A). To test survival of HLCs, the inventors look at Luciferase activity in vivo as a surrogate for HLC count and use the TUNEL assay (Invitrogen) on liver sections to look at apoptosis of transplanted cells. To test proliferation, the inventors inject EdU into mice 2 hours prior to sacrifice and use the EdU incorporation assay (Invitrogen) on liver sections, as well as flow cytometry and immunostaining for proliferation marker Ki67. The size of transplanted cell clusters is also compared. To test function of HLCs and to test global liver function, the same assays described in (A) are used.

(C) Block host hepatocyte proliferation with P21 mRNA-LNP: The inventors have shown that HGF+EGF mRNA-LNP stimulates proliferation in the host animal liver (FIG. 38C), however, here the aim is to only advantage transplanted HLC proliferation. Using the best dose of dox determined in (A) and the most proliferative and functional condition from (B), the inventors then systematically examine the effects of P21 mRNA-LNP preconditioning to halt host hepatocyte proliferation. P21 mRNA-LNP (10 ug) is injected into NSG-PiZ mice 1 day prior to transplantation of engineered HLCs, original HLCs, or PHHs. HGF+EGF mRNA-LNP (5 ug each) is injected intravenously 5 hours prior to transplantation and weekly thereafter. To validate liver repopulation, test survival of HLCs, test proliferation, test function of HLCs, and test global liver function, the same assays described in (A) and (B) are used. In particular, the inventors closely examine the proliferative tendencies of host tissue and transplanted cells when treated with P21 and HGF+EGF, and its effects on the overall repopulation of the liver.

Experimental Outcomes and Alternatives: Altogether, this set of in vivo experiments establish dox-inducible gene expression, characterize maturation, survival, and proliferation of transplanted cells, and block host hepatocyte proliferation. Dox in the drinking water of mice stimulates RLuc expression in engineered HLCs which can be detected via bioluminescence. Higher dox dose elicits higher expression of the 5 genes engineered into HLCs. Thus, these cells cease expression of fetal liver markers and adopt a more mature gene signature. Likewise, more mature HLCs in vivo will also function better to secrete ALB and AAT which goes hand-in-hand with improved overall liver function. Dox does affect un-engineered HLC and PHH maturation in vivo. HGF+EGF mRNA-LNP treatment significantly improves survival and proliferation of engineered HLCs and PHHs, as they both express the corresponding receptors. This is seen by the size of clusters of transplanted cells as demonstrated previously (FIG. 39). Accordingly, there is a significant increase in hALB secretion in these groups. HGF+EGF does not affect original HLC transplantation short term (FIG. 40). P21 mRNA-LNP preconditioning of the host liver temporarily halts host hepatocyte proliferation. Thus, this boosts engineered HLC, original HLC, and PHH repopulation. This is evident by higher percent liver repopulation, improved HLC function, and better overall liver function. Importantly, even if the engineered HLCs established in Aim 1 fail to express the genes of interest in vivo, the HGF+EGF and P21 mRNA-LNP treatment scheme improves PHH transplantation in a clinically relevant way. This discovery still has meaningful impact on the liver cell therapy field and inform future PHH cell therapy treatments.

REFERENCES

1. Brantly M, Campos M, Davis A M, et al. Detection of alpha-1 antitrypsin deficiency: the past, present and future. *Orphanet J Rare Dis.* 2020; 15:96. doi:10.1186/s13023-020-01352-5
2. Carlson J A, Rogers B B, Sifers R N, et al. Accumulation of PiZ alpha 1-antitrypsin causes liver damage in transgenic mice. *J Clin Invest.* 1989; 83(4):1183-1190. doi: 10.1172/JCI113999
3. Eriksson S, Carlson J, Velez R. Risk of cirrhosis and primary liver cancer in alpha 1-antitrypsin deficiency. NEngl *J Med.* 1986; 314(12):736-739. doi:10.1056/NEJM198603203141202
4. Ding J, Yannam G R, Roy-Chowdhury N, et al. Spontaneous hepatic repopulation in transgenic mice expressing mutant human α1-antitrypsin by wild-type donor hepatocytes. *J Cin Invest.* 2011; 121(5):19301934. doi: 10.1172/JCI45260
5. Borel F, Tang O, Gemoux G, et al. Survival Advantage of Both Human Hepatocyte Xenografts and Genome-Edited Hepatocytes for Treatment of α-1 Antitrypsin Deficiency. *Mol Ther.* 2017; 25(11):24772489. doi:10.1016/j.ymthe.2017.09.020
6. Chen Y, Li R, Zhang L, Gan L, Ding J. Treatment of α-1 antitrypsin deficiency using hepatic-specified cells derived from human-induced pluripotent stem cells. *Am J Transl Res.* 2021; 13(4):2710-2716.
7. Carpentier A, Tesfaye A, Chu V, et al. Engrafted human stem cell-derived hepatocytes establish an infectious HCV murine model. *J Clin Invest.* 2014; 124(11):4953-4964. doi:10.1172/JCI75456
8. Chen Y, Li Y, Wang X, et al. Amelioration of Hyperbilirubinemia in Gunn Rats after Transplantation of Human Induced Pluripotent Stem Cell-Derived Hepatocytes. *Stem Cell Rep.* 2015; 5(1):22-30. doi:10.1016/j.stemcr.2015.04.017
9. Takebe T, Sekine K, Enomura M, et al. Vascularized and functional human liver from an iPSC-derived organ bud transplant. *Nature.* 2013; 499(7459):481-484. doi: 10.1038/nature12271
10. Sauer V, Tchaikovskaya T, Wang X, et al. Human Urinary Epithelial Cells as a Source of Engraftable Hepatocyte-Like Cells Using Stem Cell Technology. *Cell Transplant.* 2016; 25(12):2221-2243. doi: 10.3727/096368916X692014
11. Goldman O, Gouon-Evans V. Human Pluripotent Stem Cells: Myths and Future Realities for Liver Cell Therapy. *Cell Stem Cell.* 2016; 18(6):703-706. doi:10.1016/j.stem.2016.05.019
12. Paranjpe S, Bowen W C, Mars W M, et al. Combined systemic elimination of MET and epidermal growth factor receptor signaling completely abolishes liver regeneration and leads to liver decompensation. *Hepatol Baltim Md.* 2016; 64(5):1711-1724. doi:10.1002/hep.28721
13. Michalopoulos G K. Hepatostat: Liver regeneration and normal liver tissue maintenance. *Hepatology.* 2017; 65(4):1384-1392. doi:10.1002/hep.28988
14. Michalopoulos G K. Liver Regeneration after Partial Hepatectomy. *Am J Pathol.* 2010; 176(1):2-13. doi: 10.2353/ajpath.2010.090675
15. Du Y, Wang J, Jia J, et al. Human Hepatocytes with Drug Metabolic Function Induced from Fibroblasts by Lineage Reprogramming. *Cell Stem Cell.* 2014; 14(3):394-403. doi:10.1016/j.stem.2014.01.008
16. Tang O, Gemoux G, Cheng Y, Flotte T, Mueller C. Engraftment of Human Hepatocytes in the PiZ-NSG Mouse Model. In: Aouadi M, Azzimato V, eds. *Kupffer Cells.* Vol 2164. Methods in Molecular Biology. Springer U S; 2020:75-85. doi:10.1007/978-1-0716-0704-6_9
17. Han S, Bourdon A, Hamou W, Dziedzic N, Goldman O, Gouon-Evans V. Generation of functional hepatic cells from pluripotent stem cells. *J Stem Cell Res Ther.* 2012; Suppl 10(8):1-7. doi: 10.4172/2157-7633.S10-008
18. Sourisseau M, Goldman O, He W, et al. Hepatic cells derived from induced pluripotent stem cells of pigtail macaques support hepatitis C virus infection. *Gastroenterology.* 2013; 145(5):966-969.e7. doi: 10.1053/j.gastro.2013.07.026
19. Rizvi F, Everton E, Smith A R, et al. Murine liver repair via transient activation of regenerative pathways in hepatocytes using lipid nanoparticle-complexed nucleoside-modified mRNA. *Nat Commun.* 2021; 12(1):613. doi: 10.1038/s41467-021-20903-3
20. Werder R B, Kaserman J E, Packer M S, et al. Adenine Base Editing Reduces Misfolded Protein Accumulation and Toxicity in Alpha-1 Antitrypsin Deficient Patient iPSC-Hepatocytes. *Mol Ther.* Published online Jul. 2, 2021. doi: 10.1016/j.ymthe.2021.06.021
21. Wilson A A, Ying L, Liesa M, et al. Emergence of a Stage-Dependent Human Liver Disease Signature with Directed Differentiation of Alpha-1 Antitrypsin-Deficient iPS Cells. *Stem Cell Rep.* 2015; 4(5):873-885. doi: 10.1016/j.stemcr.2015.02.021
22. Kitada T, DiAndreth B, Teague B, Weiss R. Programming gene and engineered-cell therapies with synthetic biology. *Science.* 2018; 359(6376):eaad1067. doi: 10.1126/science.aad1067
23. Takeda K, Kim S-H, Joetham A, Petrache I, Gelfand E W. Therapeutic benefits of recombinant alpha1-antitrypsin IgG1 Fc-fusion protein in experimental emphysema. *Respir Res.* 2021; 22:207. doi:10.1186/s12931-021-01784-y
24. Sifers R N, Carlson J A, Clift S M, DeMayo F J, Bullock D W, Woo S L. Tissue specific expression of the human alpha-1-antitrypsin gene in transgenic mice. *Nucleic Acids Res.* 1987; 15(4):1459-1475. doi: 10.1093/nar/15.4.1459
25. Fox I J, Chowdhury J R, Kaufman S S, et al. Treatment of the Crigler-Najjar syndrome type I with hepatocyte transplantation. *N Engl J Med.* 1998; 338(20):1422-1426. doi: 10.1056/NEJM199805143382004
26. Cantz T, Sharma A D, Ott M. Concise review: cell therapies for hereditary metabolic liver diseases-concepts, clinical results, and future developments. *Stem Cells Dayt Ohio.* 2015; 33(4):1055-1062. doi:10.1002/stem.1920
27. Puppi J, Strom S C, Hughes R D, et al. Improving the techniques for human hepatocyte transplantation: report from a consensus meeting in London. *Cell Transplant.* 2012; 21(1):1-10. doi: 10.3727/096368911X566208
28. Agarwal N, Popovic B, Martucci N J, Fraunhoffer N A, Soto-Gutierrez A. Biofabrication of Autologous Human Hepatocytes for Transplantation: How Do We Get There? *Gene Expr.* 2019; 19(2):89-95. doi:10.3727/105221618X15350366478989

29. Yu Y, Liu H, Ikeda Y, et al. Hepatocyte-like cells differentiated from human induced pluripotent stem cells: Relevance to cellular therapies. *Stem Cell Res.* 2012; 9(3):196-207. doi: 10.1016/j.scr.2012.06.004

30. Rezvani M, Grimm A A, Willenbring H. Assessing the therapeutic potential of lab-made hepatocytes. *Hepatol Baltim Md.* 2016; 64(1):287-294. doi:10.1002/hep.28569

31. Bhatia S N, Underhill G H, Zaret K S, Fox I J. Cell and Tissue Engineering for Liver Disease. *Sci Transl Med.* 2014; 6(245):245sr2. doi: 10.1126/scitranslmed.3005975

32. Sokal E M. Treating inborn errors of liver metabolism with stem cells: current clinical development. *J Inherit Metab Dis.* 2014; 37(4):535-539. doi:10.1007/s10545-014-9691-x 33. Forbes S J, Gupta S, Dhawan A. Cell therapy for liver disease: From liver transplantation to cell factory. *J Hepatol.* 2015; 62(1 Suppl):S157-169. doi:10.1016/j.jhep.2015.02.040

34. Teckman J H. Liver Disease in Alpha-1 Antitrypsin Deficiency: Current Understanding and Future Therapy. *COPD J Chronic Obstr Pulm Dis.* 2013; 10(sup1):35-43. doi: 10.3109/15412555.2013.765839

35. Chapman K R, Stockley R A, Dawkins C, Wilkes M M, Navickis R J. Augmentation therapy for alpha1 antitrypsin deficiency: a meta-analysis. *COPD.* 2009; 6(3): 177-184. doi: 10.1080/15412550902905961

36. Chapman K R, Burdon J G W, Piitulainen E, et al. Intravenous augmentation treatment and lung density in severe al antitrypsin deficiency (RAPID): a randomised, double-blind, placebo-controlled trial. *Lancet Lond Engl.* 2015; 386(9991):360-368. doi:10.1016/S0140-6736(15) 60860-1

37. Vertex Pharmaceuticals Incorporated. *A Phase 2, Randomized, Double-Blind, Placebo-Controlled Study of the Efficacy and Safety of VX-864 in PiZZ Subjects.* clinicaltrials.gov; 2021. *Accessed* Sep. 4, 2021. clinicaltrials.gov/ct2/show/NCT04474197

38. Kaushal S, Annamali M, Blomenkamp K, et al. Rapamycin reduces intrahepatic alpha-1-antitrypsin mutant Z protein polymers and liver injury in a mouse model. *Exp Biol Med* Maywood NJ. 2010; 235(6):700-709. doi:10.1258/ebm.2010.009297

39. Washington University School of Medicine. *A Preliminary Study of the Efficacy and Safety of Carbamazepine in Severe Liver Disease Due to Alpha-1 Antitrypsin Deficiency.* clinicaltrials.gov; 2019. *Accessed* Sep. 4, 2021. clinicaltrials.gov/ct2/show/NCTO1379469

40. Hidvegi T, Ewing M, Hale P, et al. An autophagy-enhancing drug promotes degradation of mutant alpha1-antitrypsin Z and reduces hepatic fibrosis. *Science.* 2010; 329(5988):229-232. doi: 10.1126/science.1190354

41. Azuma H, Paulk N, Ranade A, et al. Robust expansion of human hepatocytes in Fah−/−/Rag2−/−/Il2rg−/−mice. *Nat Biotechnol.* 2007; 25(8):903-910. doi: 10.1038/nbt1326

42. Shah M, Patel K, Sehgal P B. Monocrotaline pyrrole-induced endothelial cell megalocytosis involves a Golgi blockade mechanism. *Am J Physiol-Cell Physiol.* 2005; 288(4):C850-C862. doi:10.1152/ajpcell.00327.2004

43. Ogasawara J, Watanabe-Fukunaga R, Adachi M, et al. Lethal effect of the anti-Fas antibody in mice. *Nature.* 1993; 364(6440):806-809. doi:10.1038/364806a0

44. Kaserman J E, Wilson A A. Protocol for Directed Differentiation of Human Induced Pluripotent Stem Cells (iPSCs) to a Hepatic Lineage. *Methods Mol Biol* Clifton N J. 2017; 1639:151-160. doi:10.1007/978-1-4939-7163-3 15

45. Schwartz R E, Fleming H E, Bhatia S N. Pluripotent Stem Cell-Derived Hepatocyte-Like Cells. *Biotechnol Adv.* 2014; 32(2):504-513. doi:10.1016/j.biotechadv.2014.01.003

46. Baxter M, Withey S, Harrison S, et al. Phenotypic and functional analyses show stem cell-derived hepatocyte-like cells better mimic fetal rather than adult hepatocytes. *J Hepatol.* 2015; 62(3):581-589. doi:10.1016/j.jhep.2014.10.016

47. Yusa K, Rashid S T, Strick-Marchand H, et al. Targeted gene correction of α1-antitrypsin deficiency in induced pluripotent stem cells. *Nature.* 2011; 478(7369):391-394. doi: 10.1038/nature10424

48. Roy-Chowdhury N, Wang X, Guha C, Roy-Chowdhury J. Hepatocyte-like cells derived from induced pluripotent stem cells. *Hepatol Int.* 2017; 11(1):54-69. doi:10.1007/s12072-016-9757-y 49. Böhm F, Köhler U A, Speicher T, Werner S. Regulation of liver regeneration by growth factors and cytokines. *EMBO Mol Med.* 2010; 2(8):294-305. doi: 10.1002/emmm.201000085

50. Huang P, Zhang L, Gao Y, et al. Direct reprogramming of human fibroblasts to functional and expandable hepatocytes. *Cell Stem Cell.* 2014; 14(3):370-384. doi: 10.1016/j.stem.2014.01.003

51. Rostovskaya M, Fu J, Obst M, et al. Transposon-mediated BAC transgenesis in human ES cells. *Nucleic Acids Res.* 2012; 40(19):e150-e150. doi: 10.1093/nar/gks643

52. Sandoval-Villegas N, Nurieva W, Amberger M, Ivics Z. Contemporary Transposon Tools: A Review and Guide through Mechanisms and Applications of Sleeping Beauty, piggyBac and Tol2 for Genome Engineering. *Int J Mol Sci.* 2021; 22(10):5084. doi: 10.3390/ijms22105084

53. Yusa K, Zhou L, Li M A, Bradley A, Craig N L. A hyperactive piggyBac transposase for mammalian applications. *Proc Natl Acad Sci.* Published online Jan. 4, 2011. doi: 10.1073/pnas.1008322108

54. Schiller C D, Kainz A, Mynett K, Gescher A. Assessment of viability of hepatocytes in suspension using the MTT assay. *Toxicol Vitro Int J Publ Assoc BIBRA.* 1992; 6(6):575-578. doi:10.1016/0887-2333(92)90070-8

55. Si-Tayeb K, Noto F K, Nagaoka M, et al. Highly efficient generation of human hepatocyte-like cells from induced pluripotent stem cells. *Hepatol Baltim Md.* 2010; 51(1): 297-305. doi: 10.1002/hep.23354

56. Oertel M, Menthena A, Dabeva M D, Shafritz D A. Cell competition leads to a high level of normal liver reconstitution by transplanted fetal liver stem/progenitor cells. *Gastroenterology.* 2006; 130(2):507-520; quiz 590. doi: 10.1053/j.gastro.2005.10.049

57. Oertel M, Menthena A, Chen Y-Q, Teisner B, Jensen C H, Shafritz D A. Purification of fetal liver stem/progenitor cells containing all the repopulation potential for normal adult rat liver. *Gastroenterology.* 2008; 134(3):823-832. doi:10.1053/j.gastro.2008.01.007

58. Yuan L, Zhang Y, Liu X, et al. Agonist c-Met Monoclonal Antibody Augments the Proliferation of hiPSC-derived Hepatocyte-Like Cells and Improves Cell Transplantation Therapy for Liver Failure in Mice. *Theranostics.* 2019; 9(7):2115-2128. doi:10.7150/thno.30009

59. Yamanouchi K, Zhou H, Roy-Chowdhury N, et al. Hepatic irradiation augments engraftment of donor cells following hepatocyte transplantation. *Hepatol Baltim Md.* 2009; 49(1):258-267. doi: 10.1002/hep.22573

60. Arthur L M, Heber-Katz E. The role of p21 in regulating mammalian regeneration. *Stem Cell Res Ther.* 2011; 2(3): 30. doi:10.1186/scrt71

61. Stepniak E, Ricci R, Eferl R, et al. c-Jun/AP-1 controls liver regeneration by repressing p53/p21 and p38 MAPK activity. *Genes Dev.* 2006; 20(16):2306-2314. doi: 10.1101/gad.390506

62. Yuan R-H, Ogawa A, Ogawa E, Neufeld D, Zhu L, Shafritz D A. p27Kip1 inactivation provides a proliferative advantage to transplanted hepatocytes in DPPIV/Rag2 double knockout mice after repeated host liver injury. *Cell Transplant.* 2003; 12(8):907-919. doi: 10.3727/000000003771000147

Example 5: Investigation of the Role of VEGFA in Harnessing Cholangiocyte-Driven Liver Regeneration Research Strategy
A. Significance End stage liver disease (ESLD) is the 12$^{th}$ most common cause of death in the United States. As the result of a chronic damage of the liver tissue, ESLD begins as steatosis and inflammation and progresses to fibrosis and irreversible cirrhosis, and ultimately hepatocellular carcinoma. The current therapies to prevent the progression of the liver disease are designed to eliminate the underlying causes of injury including obesity or hepatitis C virus infection[4-6]. Although some anti-fibrotic drugs are presently tested in clinical trials, none of them have been approved by the FDA. Liver transplantation remains the only treatment for ESLD, which is critically challenged by the shortage of liver donors. An alternative to this strategy would be to promote regeneration of injured liver tissues through endogenous mechanisms. The inventors establish cholangiocyte-mediated regeneration as a mechanism that could be exploited as a novel therapeutic target.

The remarkable ability of the liver to regenerate by proliferation of mature hepatocytes is well documented[9], yet in the case of acute severe hepatocyte death or chronic liver injury, proliferation of mature cells becomes exhausted[10,11]. In these cases, the presence of alternative precursors of hepatocytes that derive from cholangiocytes/biliary epithelial cells (named hereafter BEC) has been postulated, and these cells have been referred to by various names, including liver progenitor cells (LPCs)[12]. Expansion of LPCs from the BEC compartment, a process described as ductular reaction (DR), is present in virtually all chronic and acute human liver diseases, suggesting an alternative regeneration process by which BECs proliferate and differentiate into hepatocytes[13-23], the BEC-driven liver regeneration. The evidence for the contribution of BECs to de novo hepatocytes in humans is illustrated by the presence of hepatocytes expressing the BEC marker EpCAM emerging from highly proliferative DR areas in advanced cirrhotic livers[24], detection of "bi-phenotypic cells"[25] or "ductular hepatocytes"[26] positive for both the BEC marker KRT19 and the hepatocyte marker HNF4α[25] or HepPar1[26], and observation of budding of hepatocyte-like cells expressing the hepatocytic marker glutamine synthetase from BECs within the DRs[27-31]. Specifically, a recent study quantified the emerging immature hepatocytes budding from CK19+ BECs within the septa developed in human cirrhotic livers. They found that the BEC budding maturation sequence was a major mechanism for repopulation of cirrhotic livers with de novo hepatocytes that represented up to 70% of hepatocytes. In line with the reconstitution of cirrhotic livers through BEC budding, bud numbers significantly decreased in biliary diseases associated with duct loss or cholestatic destruction of nascent buds[27]. Importantly, a recent study showed that aberrant glutamine synthetase positivity adjacent to portal tracts is significantly associated with regressed cirrhosis in humans[32], suggesting the clinical benefit of LPC-derived hepatocytes in resolving human cirrhosis. In an attempt to lineage trace the LPCs among the DRs in human cirrhotic livers, another study used mutational analysis in mitochondrial DNA encoding cytochrome c oxidase enzyme, and convincingly showed the descent of hepatocytes within monoclonal regenerative nodules from adjacent LPC-associated DRs[33]. In mice, lineage tracing studies have confirmed that the first and massive response to liver injury is the proliferation of mature hepatocytes[34-37]. Yet, consistent with an alternative BEC-mediated liver repair identified in human liver diseases, the BEC origin of de novo hepatocytes has been demonstrated in mouse models in which hepatocyte proliferation was significantly impaired by lack of Mdm2[38], deficiency in b1 integrin[39] or b-catenin[40], overexpression of p21 in hepatocytes[39] or following long-term chronic injuries[41]. In these studies, percentages of non-hepatocyte-derived hepatocytes varied between 20-70%[40,41] and percentages of specifically BEC-derived hepatocytes averaged 15%394. In the same line of evidence, lineage tracing studies in zebrafish robustly demonstrated the BEC origin of the majority of hepatocytes after near complete ablation of hepatocytes[2].

This emerging literature raises the exciting possibility that BECs could be harnessed for therapeutic purposes to produce de novo hepatocytes and restore liver function. This would serve as an alternative solution to liver transplantation. The current limitation for the efficient therapeutic use of BECs is the need to force BEC differentiation into hepatocytes by discovery of druggable pathways that efficiently trigger this cell conversion. To address this limitation, the inventors test that VEGFA promotes BEC-to-hepatocyte conversion and rescues liver function using complementary mouse and zebrafish liver injury models.

Preliminary data provide key evidence that transient delivery of VEGFA in injured mouse livers via the non-integrative and safe nucleoside modified mRNA complexed with lipid nanoparticles (mRNA-LNP) induces robust BEC conversion to hepatocytes as well as reversion of steatosis and fibrosis. Furthermore, the inventors found that expression of the main receptor for VEGFA, VEGFR2, is induced in a subset of BECs in these liver injury mouse models, suggesting that VEGFR2-expressing BECs may be directly activated by VEGFA for the cell conversion. In line with these data, the inventors found that blocking VEGFR2 signaling or downstream mediators PI3K/AKT abrogates BEC-driven liver regeneration in zebrafish, suggesting the key contribution of the VEGFR2/PI3K/AKT axis in this process. The data is in line with previous studies providing evidence for the role of VEGFA in improving liver regeneration after injury in rodents[43-46] and for the contribution of the VEGFA-VEGFR2 axis in this process[45,46]. The last two studies indicated that VEGFA binds VEGFR2 expressed on liver sinusoidal endothelial cells (EC) that in turn secrete hepatocyte mitogens, thereby promoting the proliferation of hepatocytes. The role of VEGFA in accelerating BEC-driven regeneration was suggested in a rat injury model in which hepatocyte proliferation was compromised[47]; however, it is not known yet if VEGFA promotes BEC-to-hepatocyte conversion. A direct effect of VEGFA on the BEC lineage is possible as VEGFR2 is expressed in BECs following liver injury in rats[48], in developing BECs generated from human induced pluripotent stem cells[49], and in ductal plates in the developing human fetal biliary system[50]. Similarly, examination of published single cell RNA-Sequencing (scRNA-Seq) studies identifies VEGFR2/KDR transcripts in 8.3% of human BECs[51].

Figure 42:
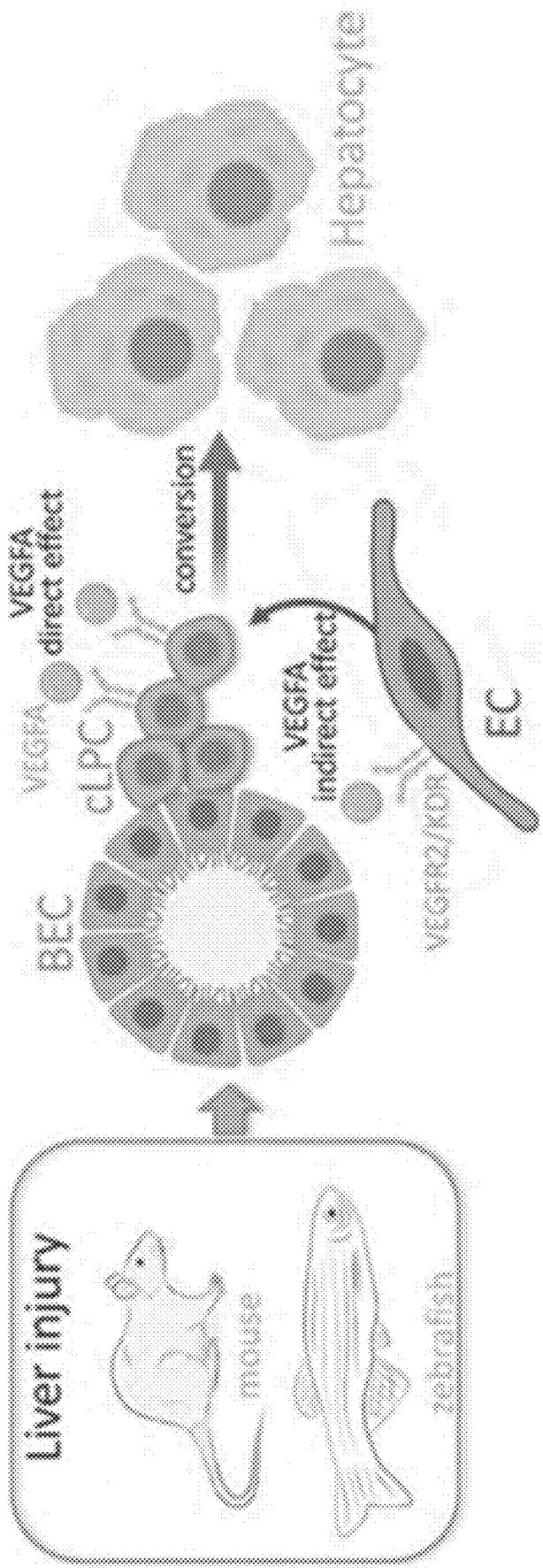
FIG. 42 depicts mechanisms of action of the VEGFA-VEGFR2 axis on BEC-to-hepatocyte conversion and restoration of liver function in mouse and zebrafish models. BEC: biliary epithelial cells, EC: endothelial cells, LPC: liver progenitor cells.

Therefore the inventors propose that (1) VEGFA treatment in vivo triggers BEC-to-hepatocyte conversion to replenish the lost cell mass and restores liver function, and that (2) VEGFA acts either directly on BECs and/or indirectly on ECs that express VEGFR2 (FIG. 42). The inventors further define the VEGFR2 downstream pathways responsible for the BEC-driven liver regeneration that may potentially serve as additional therapeutic targets to accelerate liver repair. Completion of this study will be highly significant as it may have clinical implications establishing a possible treatment to mitigate the liver disease, a currently unmet national health concern[4-6], by exploiting and optimizing the alternative intrinsic regenerative ability of the liver via BEC-driven liver regeneration using clinically safe mRNA-LNPs[52] currently used for FDA-approved COVID-19 vaccines.

Innovation

The proposed research is scientifically innovative for 3 main reasons: (1) It reveals the novel therapeutic benefit of VEGFA to harness BEC-driven liver regeneration to treat chronic and acute liver diseases because compromised hepatocyte-driven liver regeneration due to senescence is consistently observed in these human diseases[53-56], (2) it uncovers the downstream mediators of VEGFA-VEGFR2 that may serve as new therapeutic targets to harness BEC-driven liver regeneration, and (3) it identifies the VEGFR2-expressing BECs as functional LPCs, a unique BEC population that has yet been uncovered, or alternatively define the indirect mechanism of EC-mediated BEC-driven liver regeneration. Innovative experimental strategies include: (1) A unique juxtaposition of the mouse models, as a step forward to pre-clinical studies for the therapeutic benefit of VEGFA in liver diseases, and the zebrafish models suitable for pharmacologic screens and genetic modulations to interrogate the mechanisms of action of VEGFA. (2) The use of 2 complementary mouse liver injury models that recapitulate various stages of acute[57] and chronic[58] human liver diseases to define the role of VEGFA in restoring a broad range of liver function. (3) Versatility of the two complementary zebrafish models of BEC-driven liver regeneration exhibiting either a fast[2] or slow[7] liver recovery that allow for testing factors that abrogate or accelerate the regeneration, respectively. (4) Cell-specific genetic modulations of the VEGFA-VEGFR2 axis in mouse and zebrafish models to distinguish the direct from indirect effect of VEGFA on BEC-driven liver regeneration. (5) The experimental p21-mediated hepatocyte senescence strategy to define the threshold of hepatocyte senescence required for successful VEGFA-mediated BEC-driven liver regeneration, which will importantly define the clinical context (abundance of senescence) for which VEGFA will be therapeutically beneficial. (6) The generation of a new mouse line Kdr-2A-Cre$^{ERT2}$-2A-eYFP to map the fate of KDR/VEGFR2+ cells. (7) The use of clinically relevant, non-integrative mRNA-LNP, whose safety has been clinically validated[52] and currently used for COVID-19 vaccines, to transiently deliver VEGFA in the liver.

Approach

RIGOR: All in vitro assays and bulk RNA-Seq analyses are performed in triplicate. Both sexes are examined to possibly identify sex dimorphism. Numbers of mice and zebrafish for each group have been calculated based on power analyses.

Figure 43:
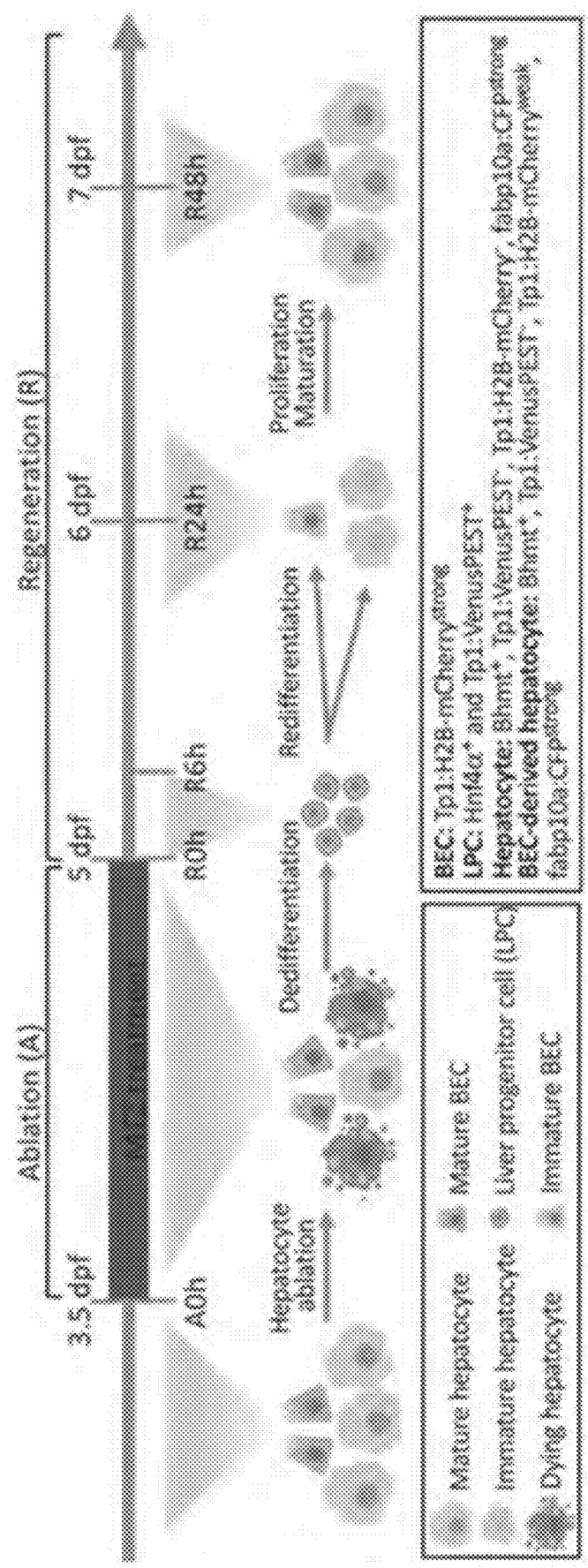
FIG. 43 depicts schematic of the process of BEC-driven liver regeneration in the zebrafish NTR-mediated hepatocyte ablation model. Tg(fabp10a:CFP-NTR) larvae were treated with 10 mM Mtz from 3.5 days post-fertilization (dpf) for 36 hours, followed by Mtz washout. A0h stands for ablation 0 hour; R0h, regeneration 0 hour; R48h, regeneration 48 hours.
Figure 44A:
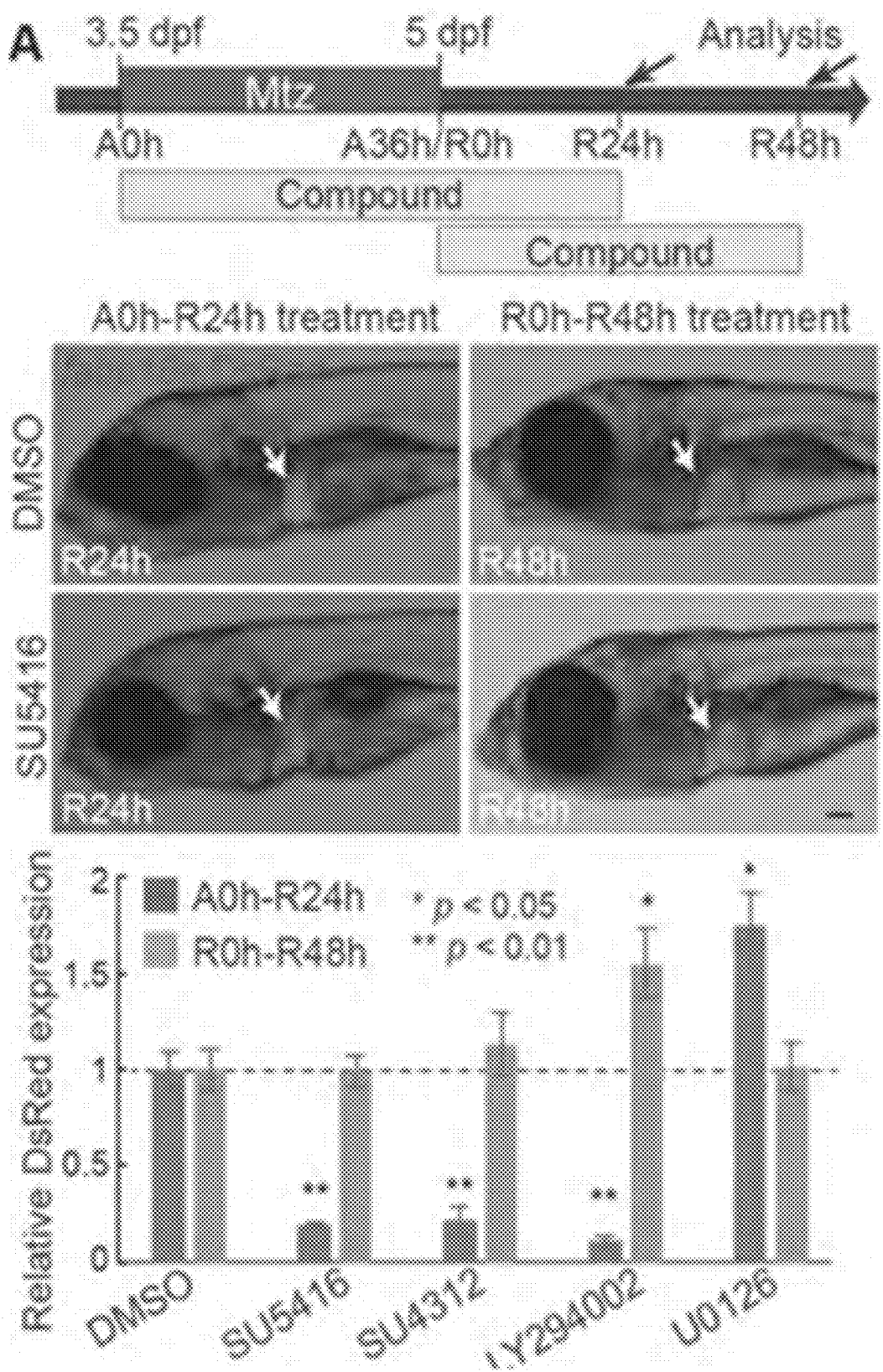
FIG. 44A-44C depict VEGFR2 inhibition impairs BEC-driven liver regeneration in zebrafish.
Figures 44B, 44C:
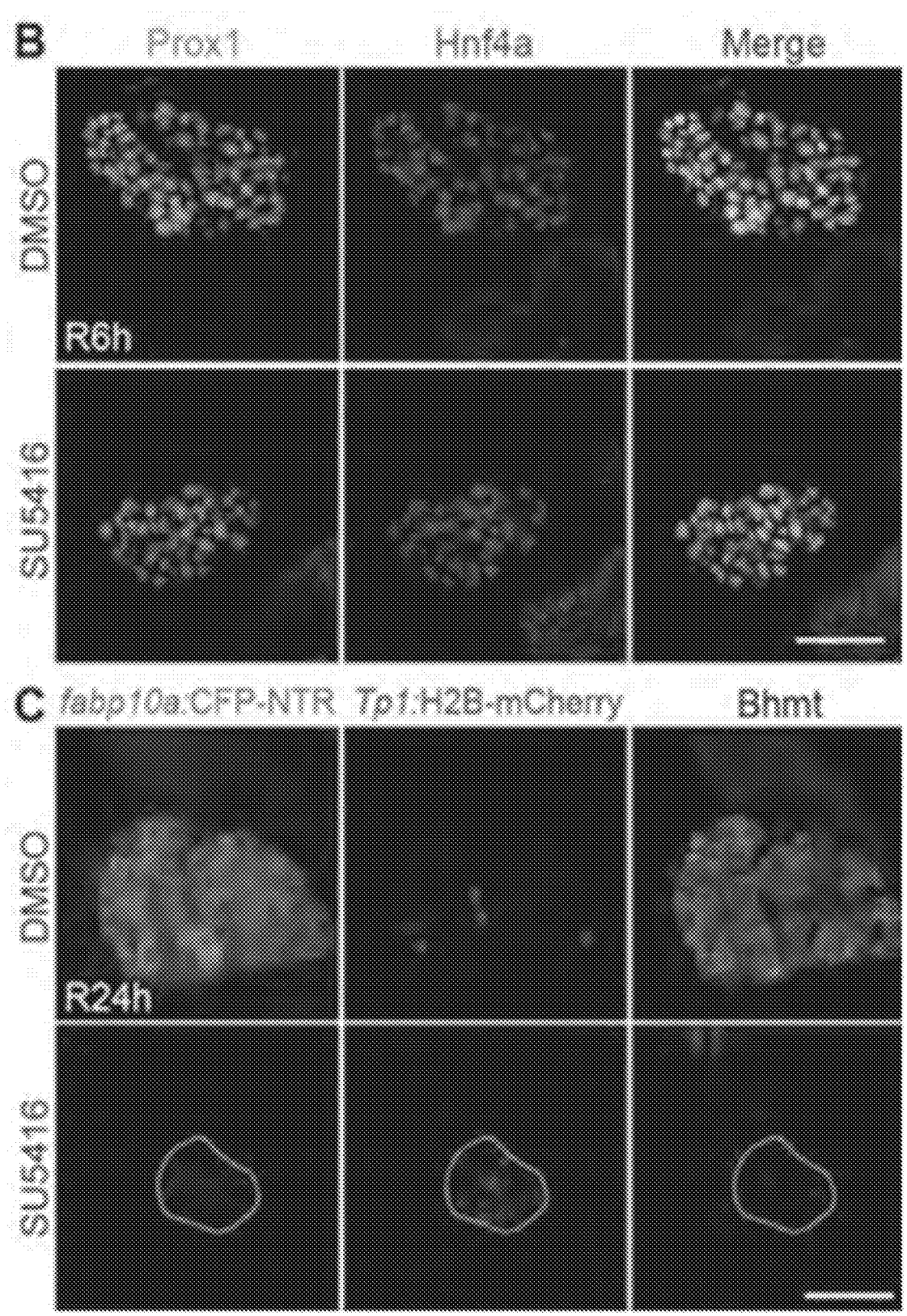
Figures 45A, 45B, 45C, 45D, 45E, 45F, 45G:
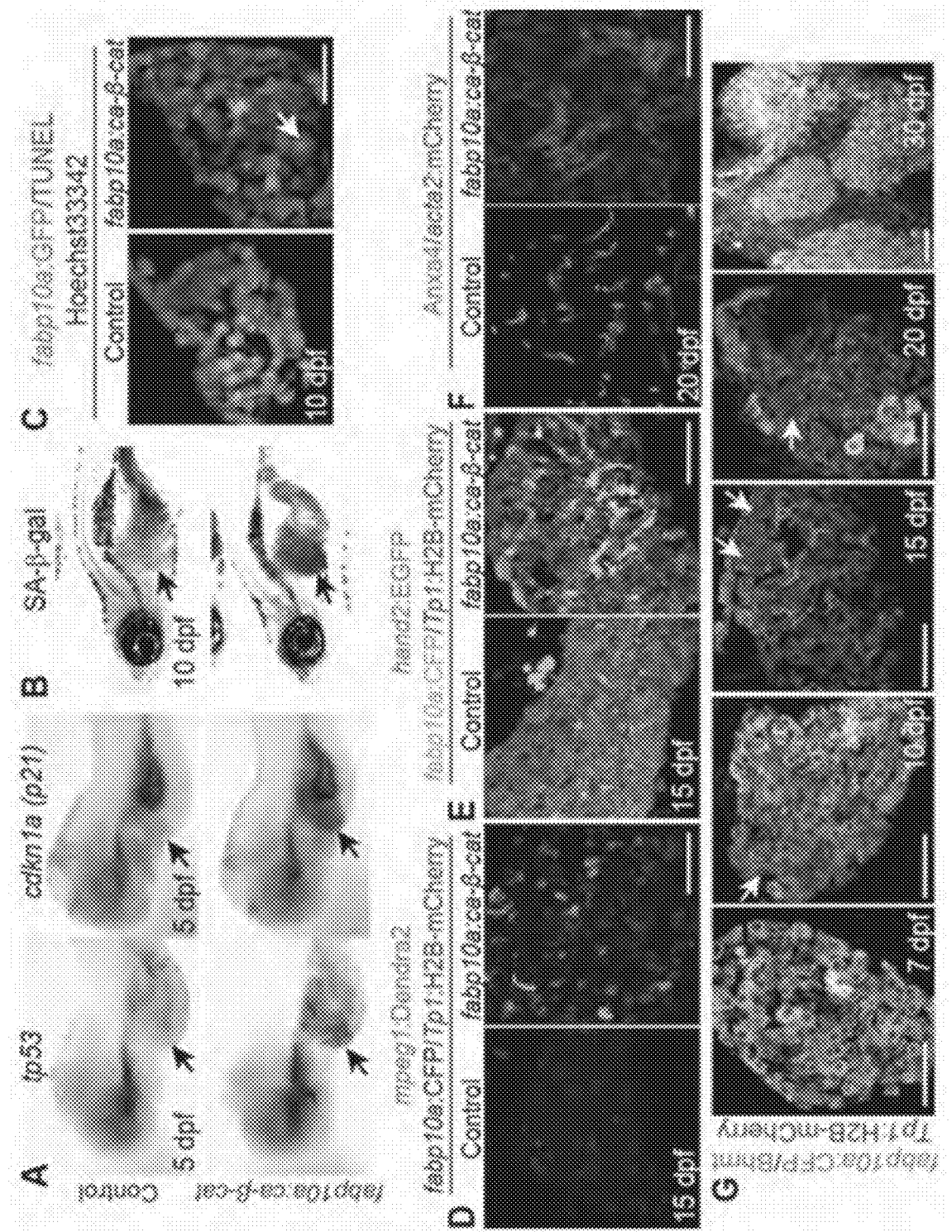
FIGS. 45A-45G depict the oncogene-induced liver injury model of LPC-mediated liver regeneration, Tg(fabp10a:ca-β-catenin).

Aim 1: Determine the Roles of VEGFA in BEC-to-Hepatocyte Conversion and Recovery of Liver Function Post Injury Preliminary Data a. A zebrafish hepatocyte ablation model of BEC-driven liver regeneration with rapid regeneration 2. This model is instrumental to test agents (chemicals or molecules) that prevent BEC-driven liver regeneration. In the Tg(fabp10a: CFP-NTR)$^{59 31}$ zebrafish line, bacterial nitroreductase (NTR) is expressed under the hepatocyte-specific fabp10a promoter[2]. Since the NTR enzyme converts the non-toxic prodrug, metronidazole (Mtz), into a cytotoxic drug[59, 60] treating the transgenic zebrafish with Mtz specifically ablates hepatocytes. In this model, upon severe hepatocyte loss, BECs first dedifferentiate into LPCs, then re-differentiate into either hepatocytes or BECs, thereby leading to full liver recovery[2]. This recovery is rapid: BEC-derived hepatocytes are detected within 24 hours and the liver fully recovers within 3 days following severe hepatocyte ablation (FIG. 43). In addition to this rapidity, the process of BEC-driven liver regeneration is well characterized and synchronized among the animals, making this model extremely valuable to qualitatively identify hepatocytes, BECs, LPCs and BEC-derived hepatocytes as well as quantitatively examine the effect of any factor that prevents the regeneration process.

b. EGFR2 inhibition impairs BEC-driven liver regeneration. Upon targeted chemical screening using the NTR/Mtz model[61], the inventors examined the effect of VEGFR2 inhibition on BEC-driven liver regeneration. The inventors used the Notch reporter line Tg(Tp1:H2B-mCherry)$^{9 39}$ that expresses H2B-mCherry fusion proteins in BECs. Given the long half-life of the histone 2B protein, the line allows us to trace cells derived from BECs within a few days after Notch signaling turns off BECs are Tp1:H2B-mCherry$^{strong}$, whereas hepatocytes derived from BECs are Tp1:H2B-mCherry$^{faint}$. This fate was confirmed using Cre-loxP-mediated lineage tracing[2]. Treating Tg(fabp10a:CFP-NTR) larvae with VEGFR2 inhibitors (2 µM SU5416 or SU4312) from A0h, but not R0h, to R24h significantly reduced the size of regenerating livers (FIG. 44A). SU5416-treated livers exhibited the normal expression of Prox1 and Hnf4a in LPCs at R6h (FIG. 44B), suggesting normal BEC-to-LPC dedifferentiation. However, SU5416-treated livers exhibited almost no expression of the hepatocyte marker Bhmt and very weak expression of fabp10a:CFP-NTR at R24h (FIG. 44C), suggesting a defect in LPC-to-hepatocyte differentiation.

c. A zebrafish oncogene-induced liver injury model of BEC/LPC-mediated liver regeneration with slow regeneration[7]. To validate the beneficial effect of VEGFA overexpression or VEGFA-VEGFR2 downstream mediator overactivation on BEC/LPC-mediated liver regeneration in zebrafish, the inventors use an oncogene-induced liver injury model, Tg(fabp10a:ca-β-catenin)$^{s704}$, in which BEC/LPC-mediated liver regeneration occurs slowly[7]. In this model, the hepatocyte-specific expression of the stable form of mutated β-catenin (ca-β-catenin) elicits oncogene-induced senescence and death in hepatocytes (FIGS. 45A-45C) followed by inflammation, fibrosis and BEC/LPC activation (FIGS. 45D-45G). Progressive death of hepatocytes and their dedifferentiation were tracked by gradual loss of Bhmt expression that was barely detected at 15 dpf (FIG. 45G). Here, LPCs are identified as fabp10a:CFP$^{1Neak}$/Tp1: H2B-mCherry$^{1Neak}$ cells (FIG. 45G, arrows). After near-complete loss of Bhmt expression at 15 dpf, its expression slowly reappeared: at 20 dpf, small clusters of cells expressed Bhmt, while at 30 dpf, ~70% of the liver region was covered by Bhmt+ hepatocytes (FIG. 45G), indicating that LPCs slowly and gradually differentiate into hepatocytes over 10 days. Lineage tracing of preexisting hepatocytes and BECs revealed that in 30-dpf Tg(fabp10a:ca-β-catenin) livers, ~60% of hepatocytes originated from preexisting hepatocytes via LPCs and ~40% of hepatocytes originated from BECs[7]. Compared to the NTR/Mtz model, the slow LPC-to-hepatocyte differentiation makes this ca-β-catenin-overexpressing model ideal for identifying factors that promote BEC/LPC-mediated liver regeneration by specifically tracing BEC-derived LPC fate.

Figure 46A:
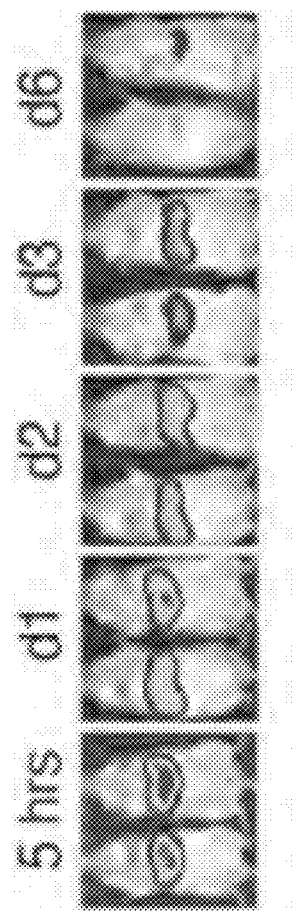
FIGS. 46A-46E depict mRNA-LNPs are efficiently transfected in virtually all hepatocytes.
Figure 46B:
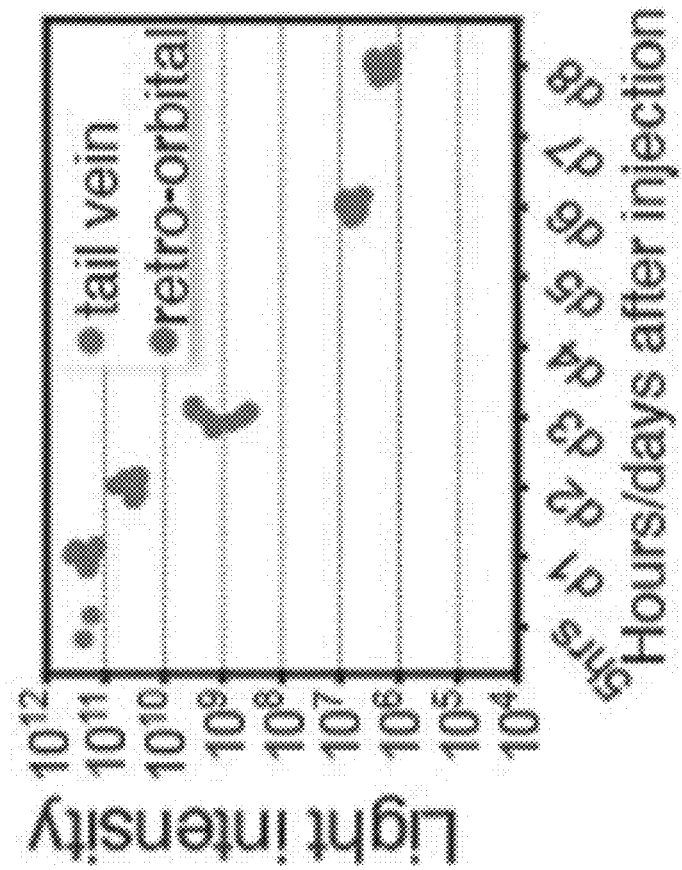
Figure 47:
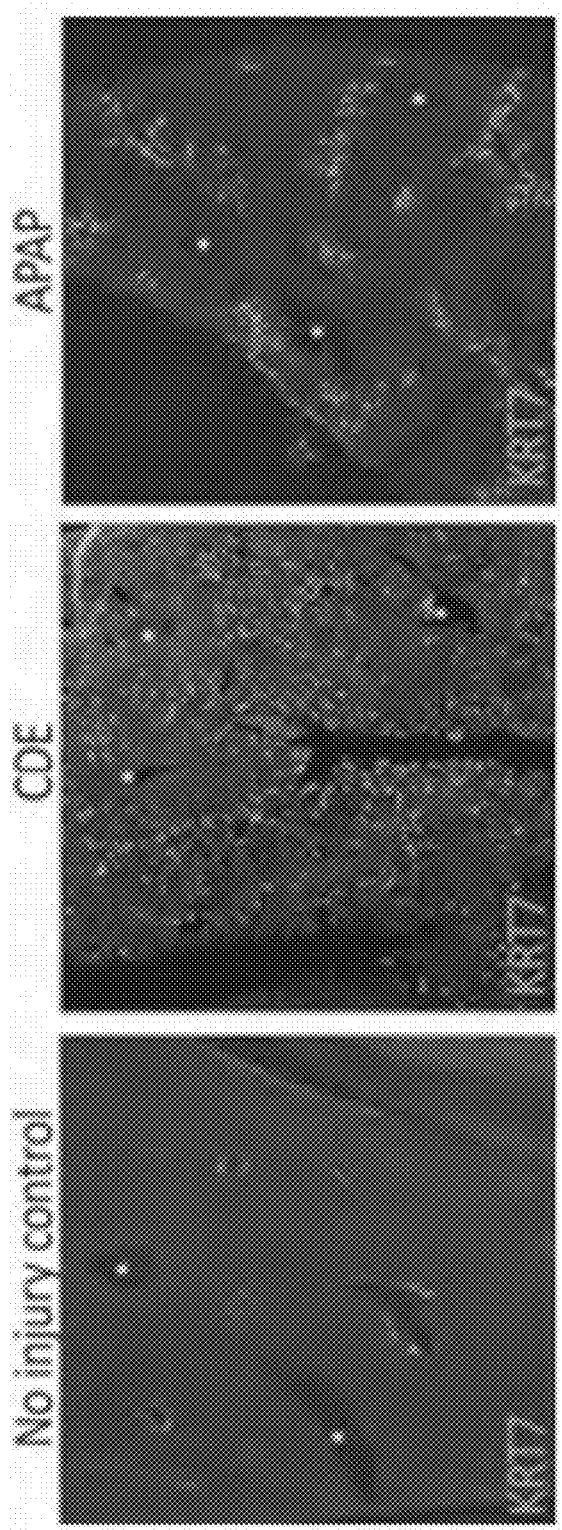
FIG. 47 depicts DR develops in both chronic CDE diet and acute APAP liver injury in the presence of AAV8-Tbg-p21. Expansion of KRT7+ BECs from the portal triads is greater in the CDE model compared to the APAP model. *Central vein areas.
Figures 48A, 48B, 48C:
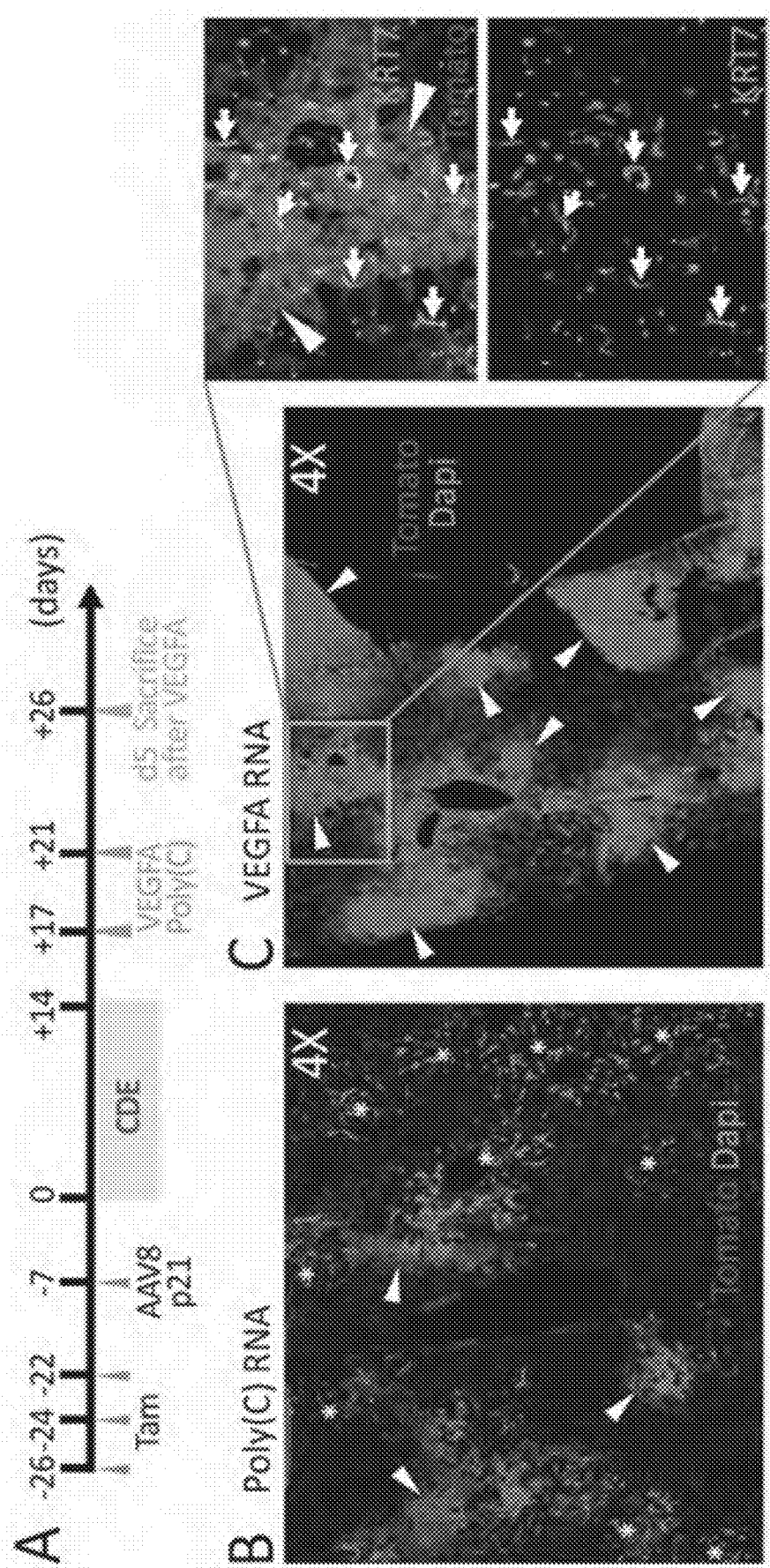
FIGS. 48A-48C depict VEGFA induces BEC-to-hepatocyte conversion in CDE-fed/p21-injected mice.
Figures 49A, 49B, 49C, 49D:
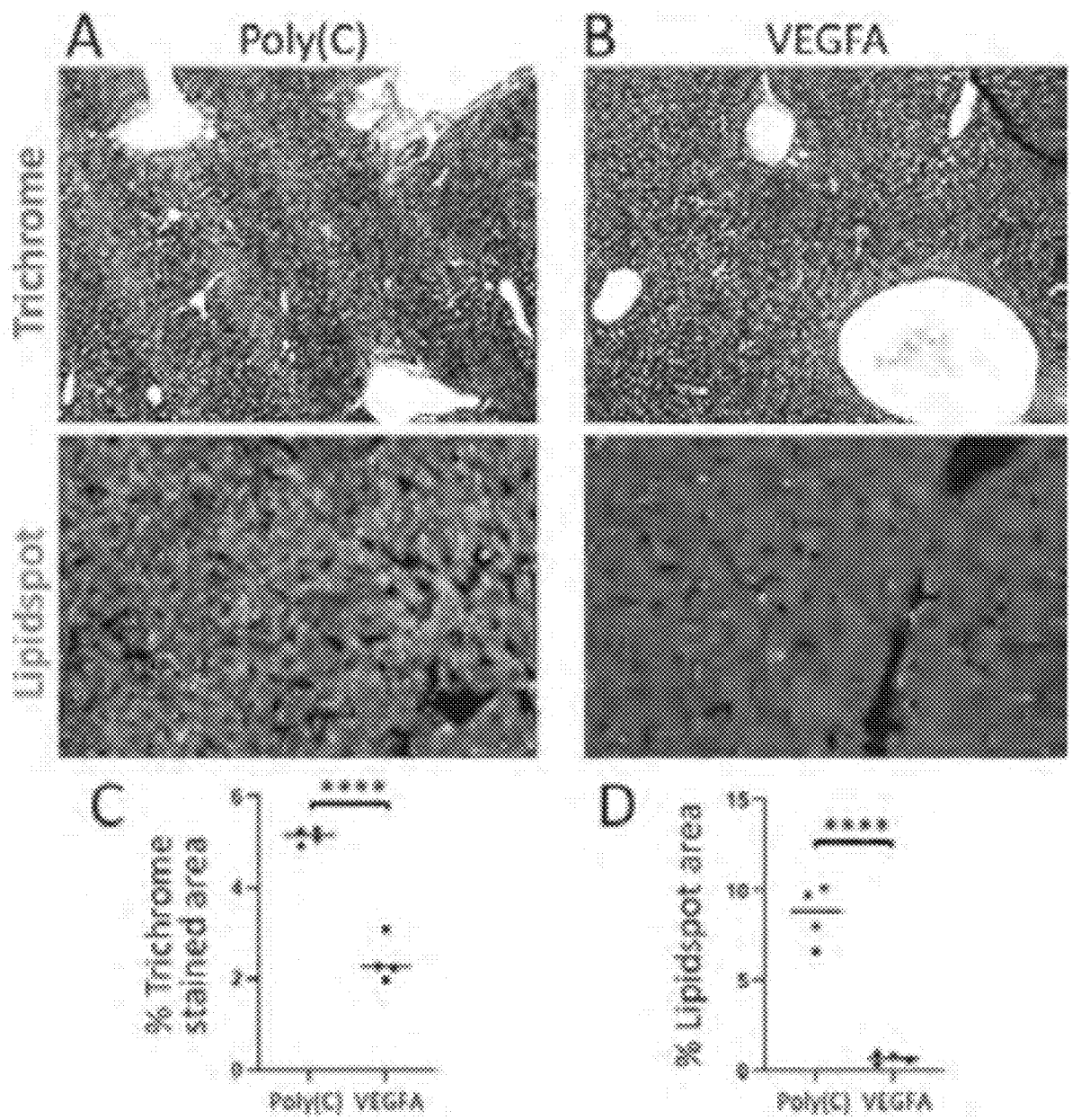
FIG. 49A-49D depict VEGFA reverts fibrosis and steatosis in CDE-fed/p21-injected mice. Trichrome and lipidspot assays were performed (FIGS. 49A, 49B) and quantified (FIGS. 49C, 49D) on mice treated with either Poly(C) RNA-LNPs (FIG. 49A, n=4) or VEGFA mRNA-LNPs (FIG. 49B, n=4).
Figures 50A, 50B:
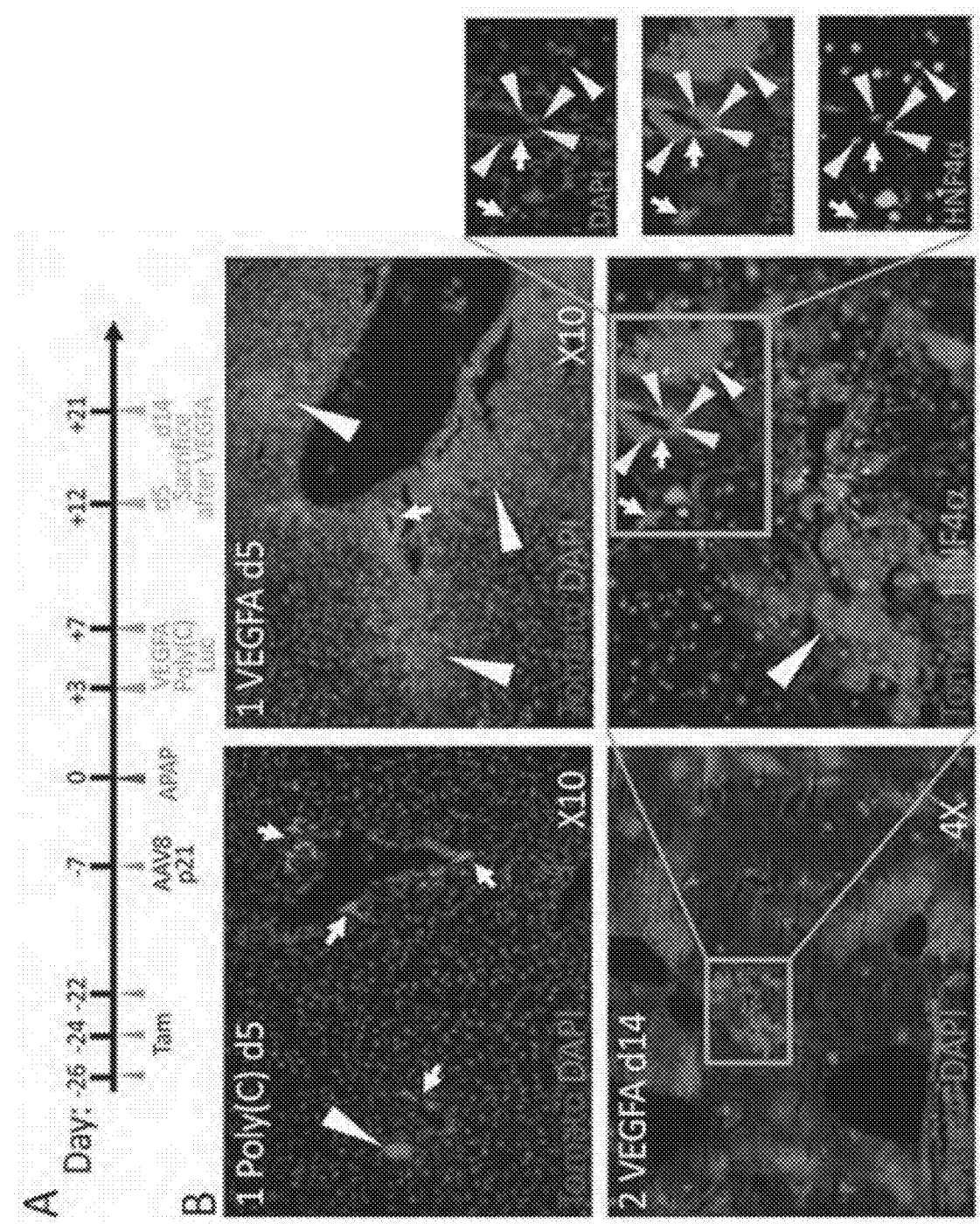
FIGS. 50A-50D depict VEGFA induces BEC-to-hepatocyte conversion in APAP/p21 treated mice.
Figure 50C:
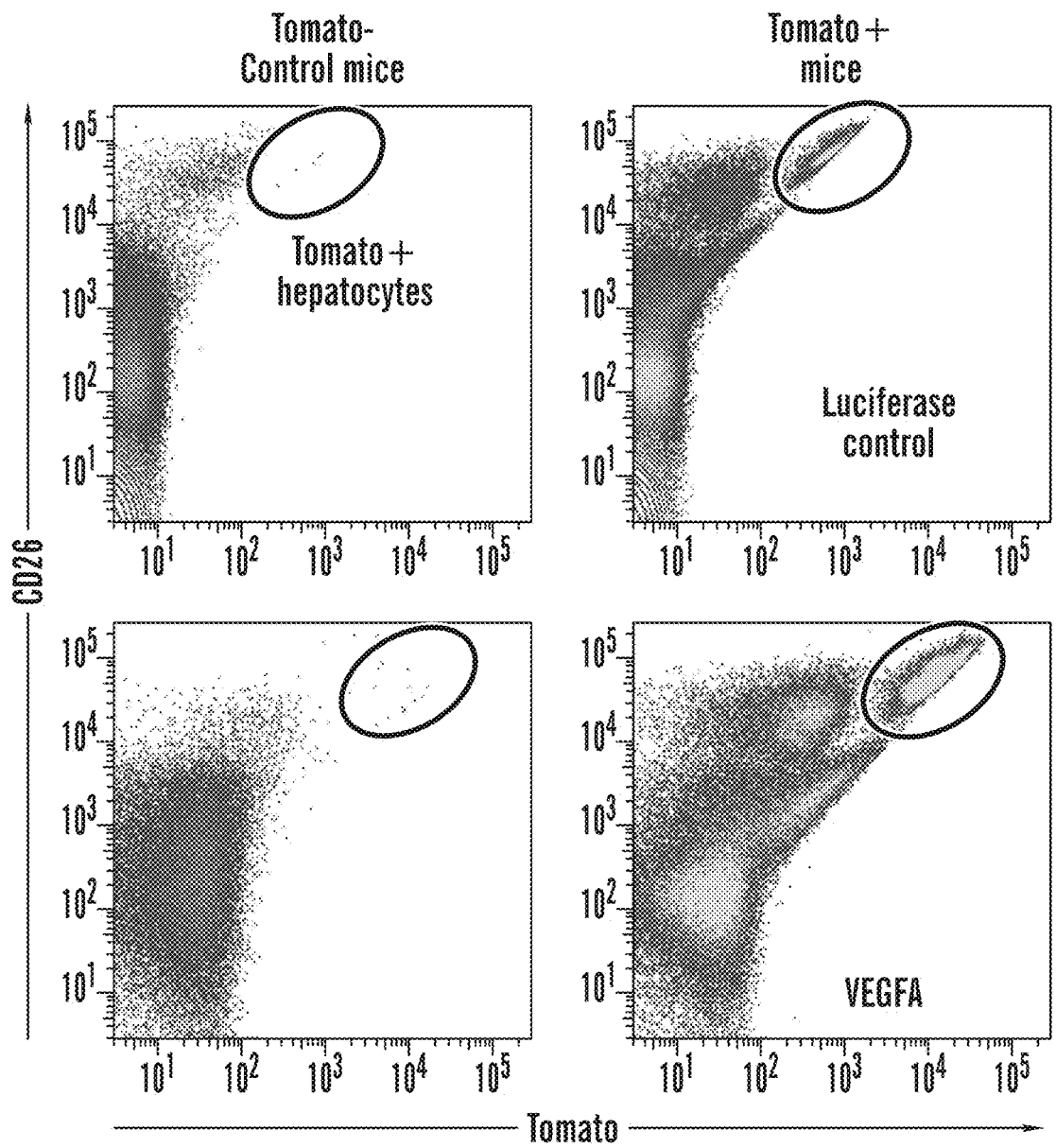
Figure 50D:
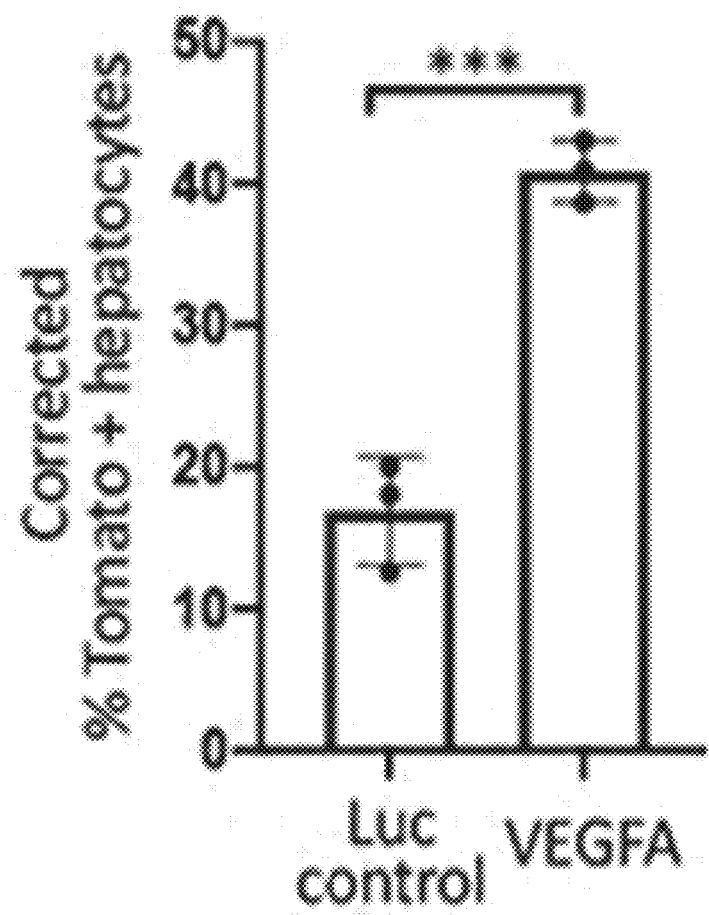

Contribution of the zebrafish model in Aim 1: The slow zebrafish model will be used to interrogate the mechanism by which overexpression of VEGFA induces BEC-to-hepatocyte liver repair by identifying the improved steps in this process.

d. The mRNA-LNP is an efficient, non-integrative strategy to transiently yet robustly express any protein in vivo in the liver. mRNA-LNP is a tool that transiently delivers any protein to the liver[3]. As proof-of-principle, the inventors demonstrated using intravenous (IV) injection of luciferase mRNA-LNPs that mRNA-LNPs are specifically and efficiently targeted to the liver, and that their translation into proteins can last up to a week (FIGS. 46A, 46B). eGFP mRNA-LNP injections indicated that nearly all hepatocytes are transfected along with 70.7±9% of CD31+ ECs and 41.5±14.6% CD11b+ macrophage/Kupffer cells (FIGS. 46C, 46D) following non-parenchymal cell fraction isolation[62]. Once human VEGFA mRNA-LNPs are injected, the levels of expression in vivo are quantified by ELISA assays as VEGFA is secreted by hepatocytes into the blood circulation (FIG. 46E). mRNA-LNPs represent thus an unprecedented tool to temporally deliver VEGFA to the liver.

e. Transient expression of VEGFA in livers via mRNA-LNP promotes BEC-to-hepatocyte conversion and restores liver function. The inventors used a BEC lineage-tracing model (Krt19-Cre$^{ERT}$R26$^{LSL}$ tdTomato)[39] to demonstrate injections of VEGFA mRNA-LNPs induce conversion of KRT19+ BECs to hepatocytes. Mice were fed a choline-deficient diet supplemented with ethionine (CDE)[58] to induce chronic liver injury, or injected with a single dose of N-acetyl-paraminophen, (APAP, 500 mg/Kg in female)[57] to induce acute liver injury. To suppress hepatocyte proliferation, the inventors induced senescence of hepatocytes by overexpressing the senescence gene p21 in hepatocytes via IV injections of AAV8-Tbg-p21 under the hepatocyte promoter thyroxine-binding globulin (Tbg) as previously published[39,40]. As previously documented[58,57], the CDE diet triggers a strong DR marked with KRT7 that is highly invasive toward central vein areas, while the APAP-induced DR is milder and localized around the portal vein areas (FIG. 47). Of note, the DR was significantly milder in both injury models without AAV8-Tbg-p21 injection (control AAV8.Tbg.PI.Null.bGH-treated mice), indicating that hepatocyte senescence promotes further DRs as expected. Strikingly, large patches of Tomato+ hepatocytes appeared when CDE-fed mice were injected with 2 doses of VEGFA mRNA-LNPs (FIGS. 48A, 48C, arrowheads). In contrast, in control Poly(C) RNA-LNP-treated mice, Tomato+ hepatocyte areas were sporadic and small (FIGS. 48A, 48B, arrowheads), and the majority of Tomato+ cells were BECs (see numerous * areas). Tomato+ hepatocytes were adjacent to Tomato+ BECs, supporting their BEC origin. Importantly, VEGFA-mediated conversion of BECs to hepatocytes was consistently associated with reversion of fibrosis and steatosis (FIG. 49). Similar to the CDE model, VEGFA triggered remarkable BEC-to-hepatocyte conversion in the APAP model (FIG. 50). While very few Tomato+ hepatocytes were detected in Poly(C) RNA-LNP-treated mice, they were numerous following one injection of VEGFA mRNA-LNP (FIGS. 50A, 50B, day5). Two injections of VEGFA significantly increased the size and abundance of Tomato+ hepatocyte areas two weeks after the last dose of VEGFA (FIGS. 50B, 50C, 50D, day14). BEC-derived hepatocytes (white arrowheads) emerged near the bile ducts (white arrows). Interestingly, a few Tomato+ cells within the bile ducts (yellow arrowheads) expressed HNF4α, and were reminiscent of the reported HNF4α+/KRT19+bi-phenotypic cells, indicative of transitioning BECs[25]. These key preliminary data support the hypothesis that the delivery of VEGFA in the liver triggers BEC-to-hepatocyte conversion.

Contribution of the mouse models in Aim 1: While the fish model is instrumental in defining which phase of BEC-driven liver repair is harnessed by VEGFA, the mouse models is key to examine the pre-clinical impact of VEGFA on rescuing various liver disease features.

Design:

Rationale: BEC/LPC expansion from biliary ducts has been reported in virtually all human chronic liver diseases and acute acetaminophen intoxication[16-23]. While there is some evidence that BEC-to-hepatocyte conversion occurs in humans when proliferation of hepatocytes is exhausted[24-33], this alternative regeneration may be insufficient to alleviate liver diseases. Experiments in Aim 1 demonstrate the therapeutic benefit of VEGFA in harnessing BEC-to-hepatocyte conversion to replenish the loss of hepatocyte mass and restore liver function. Key preliminary data supporting this is the robust VEGFA-mediated conversion of BEC-to-hepatocytes in two (acute and chronic) liver injury mouse models associated with reversion of fibrosis and steatosis in the chronic model, supported by the VEGFR2 inhibition study in the liver injury zebrafish model. Experimental design of Aim 1 use the same 2 injury mouse models that cover many aspects of the chronic and acute liver disease stages including DR (CDE[58], APAP[57]), necrosis (APAP), hepatocyte cell death (CDE, APAP), steatosis (CDE), fibrosis (CDE), as well as the slow recovery zebrafish model developing hepatocyte cell death, and fibrosis[7]. Therefore, Aim 1 first determines the effectiveness of VEGFA to induce BEC-to-hepatocyte conversion, liver damage reversion and liver function recovery in different contexts of liver diseases in mice and zebrafish, as well as elucidate in both fish and mice whether VEGFA functions to expand BECs, to induce emergence of bi-phenotypic cells/LPCs and VEGFR2+ BECs, and/or to promote BEC-to-hepatocyte conversion and subsequent proliferation (Aim 1a). Secondly, Aim 1 defines the threshold of hepatocyte senescence (with increasing MOI of AAV8-Tbg-p21) in mice and thus the liver disease context in which therapeutic benefit of VEGFA-induced BEC-driven liver regeneration may be successful (Aim 1b).

a. Determine the Role of VEGFA to Harness BEC-to-Hepatocyte Conversion and Restore Liver Function in Liver Disease Mouse and Zebrafish Models Experimental design in mice (FIG. 5I): The chronic CDE- and acute APAP-induced liver injuries as shown in the preliminary data are further used in this aim. The rationale for using these 2 injury models is motivated by the unmet clinical needs to prevent progression of chronic liver disease before it reaches the irreversible stage of decompensated cirrhosis, and to search for an alternative treatment for acute APAP intoxication that is currently responsible for 20-30% of liver transplantation in the US[63, 64] The diversity of liver disease features represented in the 2 liver injury models allows for interrogation of the therapeutic value of VEGFA to enhance BEC-to-hepatocyte conversion and to alleviate a broad range of stages of liver diseases. To quantify BEC-derived hepatocytes, the Krt19 lineage mouse model Krt19-Cre$^{ERT}$, R26$^{LSL}$tdTomato[65] is used (FIGS. 48-50). The inventors verified that the CreERT system is not leaky after CDE and APAP-induced injuries by the lack of Tomato expression in the absence of Tamoxifen (Tam). Tam is administered 4 weeks before injury (4 mg/20 g BW three times every other day as shown in FIGS. 48-50). AAV8-Tbg-p21 ($7.5 \times 10^{11}$ viral particles/mouse) is injected IV one week prior to CDE diet and APAP injection to induce hepatocyte senescence as previously shown[39,40] (FIGS. 48-50). AAV8.Tbg.PI.Null.bGH (Addgene, #105536) is used as control for AAV8-Tbg-p21. Timing of injury: Mice are fed CDE (choline-deficient diet from Teklad supplemented with 0.1% ethionine drinking water from Acros Organics) for 3 weeks[34, 35, 39-41] to allow expansion of BEC-derived hepatocytes without interfering with concomitant cell death of the de novo hepatocytes[39-41]. Control diets for CDE is the choline-sufficient diet from Teklad. Effects of continuous injury without recovery are also examined to recapitulate a chronic clinical context. Non-lethal doses of APAP (350 mg/kg for males[66] and 500 mg/kg for females (FIG. 50)) are injected IP following a 12 hr-fasting period allowing for even cell damage; control mice are injected with PBS. Lethal doses (450-500/650-700 mg/kg for male/female respectively)[66] are additionally used to test the ability of VEGFA to improve animal survival associated with BEC-driven liver regeneration. VEGFA mRNA-LNP treatment and timing of analyses: Mice are treated twice with VEGFA mRNA-LNPs or control Poly(C) RNA-LNPs (5p g/mouse) at 3 days and 7 days during the recovery time after injury ends or during the continuous injury after the initial 3-week diet. Mice are euthanized at the end of the diet (to define the extent of the liver injury) and at 2, 6 and 12 weeks of recovery (to define the kinetic of cell conversion and liver function). Matching time points will be used for continuous injury. Mice are treated with mRNA-LNPs at 3 and 7 days following the single dose of APAP and euthanized at 2 and 3 weeks after APAP injection, as recovery is completed by that time. Importantly, the inventors optimize the frequency of VEGFA mRNA-LNP injections needed to enhance generation of Tomato+ hepatocytes. After the initial 2 doses of mRNA-LNP, the inventors perform additional injections once a week until sacrifice. The time frame of mRNA-LNP injection after lethal injection of APAP that will rescue mice is also defined. To ensure uniformity in VEGFA expression between mice, concentration of serum VEGFA is tested by ELISA (as shown, FIG. 46E). Importantly, the inventors include all controls such as Poly(C) RNA-LNP control for VEGFA mRNA-LNP, AAV8.Tbg.PI.Null.bGH for AAV8-Tbg-p21 and, no injury (PBS for APAP and choline-sufficient diet for CDE diet). The inventors thus determine the effect of VEGFA alone and in combination with AAV8-Tbg-p21 and injury on all aspects of BEC-driven liver repair.

Figure 46C:
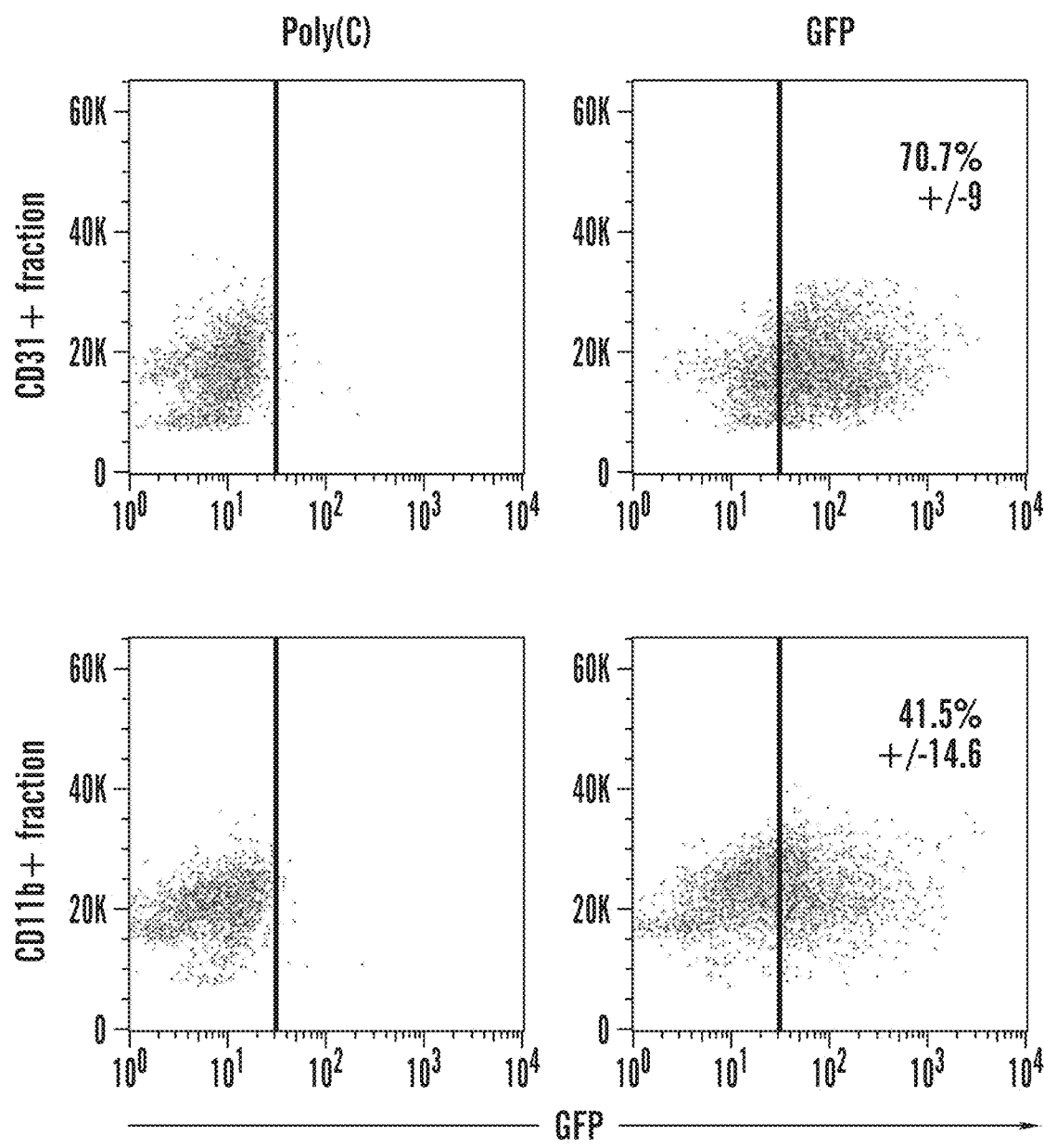
Figure 46E:
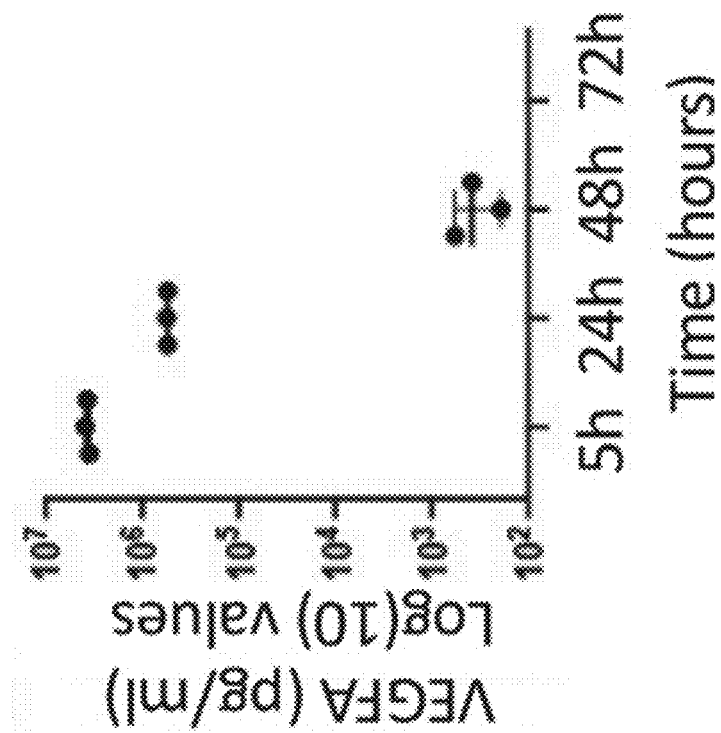
Figure 46D:
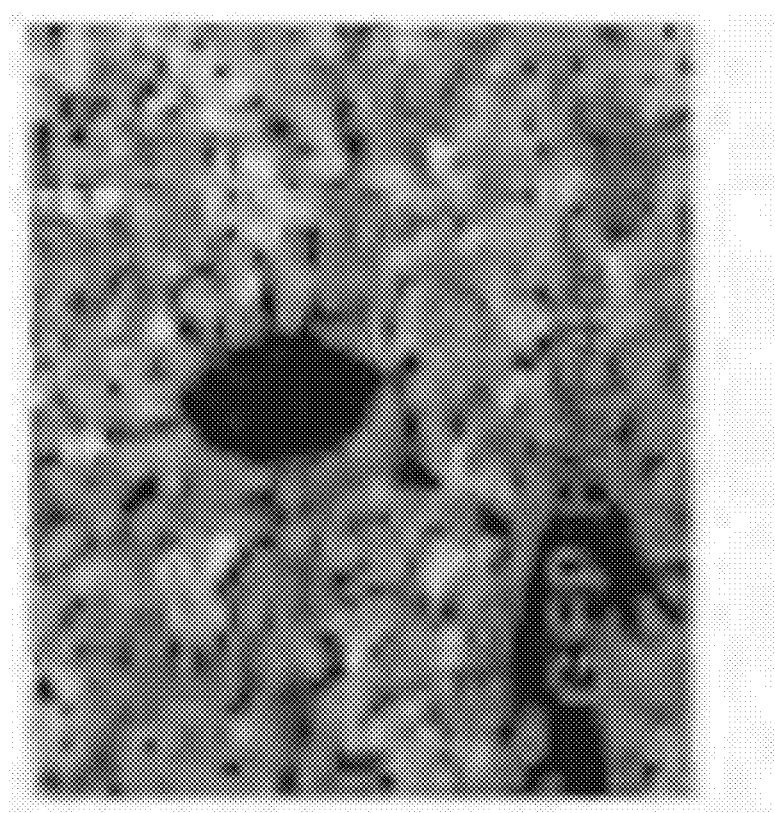
Figure 51:
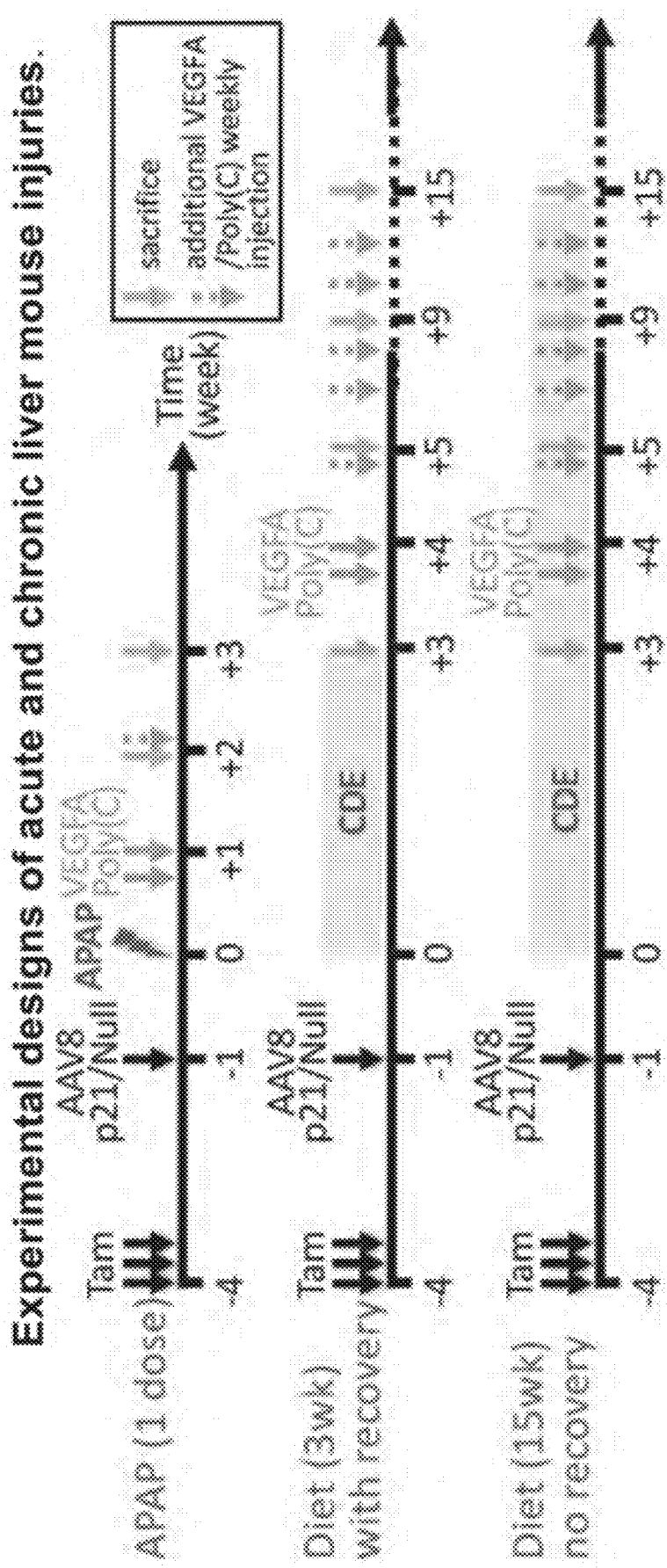
FIG. 51 depicts experimental designs of acute and chronic liver mouse injuries.
Figure 52:
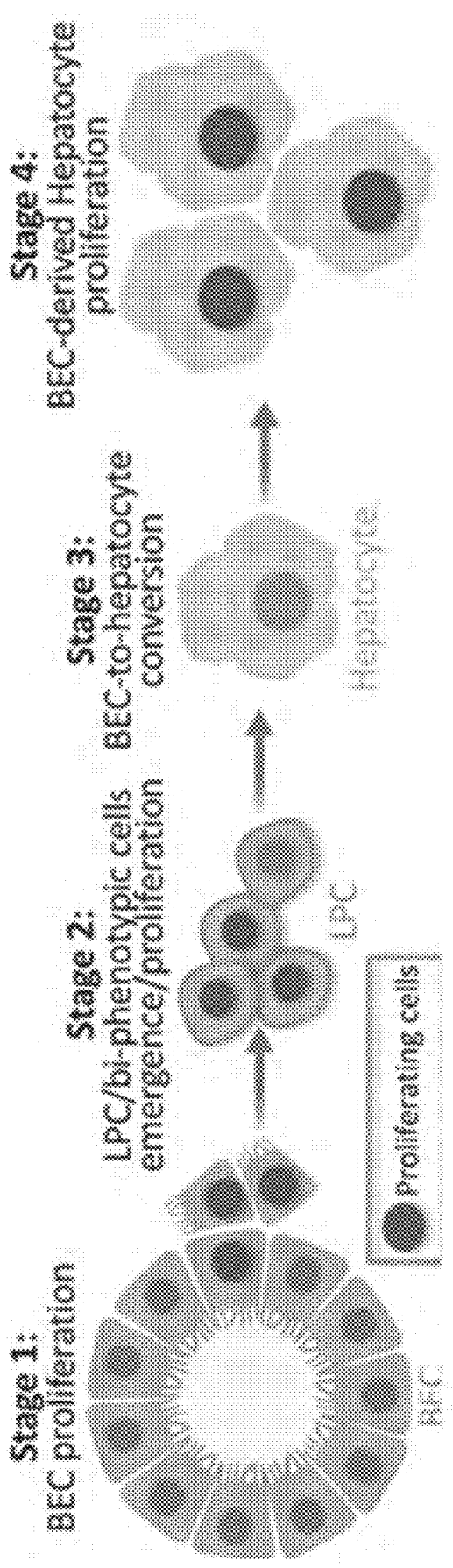
FIG. 52 depicts analyses of VEGFA effects on BEC characteristics, BEC expansion (stage 1) and emergence/proliferation of LPCs and KDR+ BEC (phase 2), BEC-to-hepatocyte conversion (phase 3) and subsequent de novo hepatocyte proliferation (phase 4).

Analyses of BEC-driven liver regeneration in mice: Roles of VEGFA on BEC characteristics, BEC expansion (Phase 1), and emergence of bi-phenotypic cells/LPCs and VEGFR2+ BECs (phase 2), BEC-to-hepatocyte conversion (phase 3), and subsequent de novo hepatocyte proliferation (phase 4) (FIG. 52) are examined. Given that VEGFA has been reported to positively regulate the proliferation of BECs in biliary tract disease48,[67], the inventors quantify in the Krt19-Cre$^{ERT}$; R26$^{LSL}$tdTomato mice treated with VEGFA mRNA-LNP or Poly(C) RNA-LNP, BEC proliferation (EdU, Ki67), morphological intrahepatic bile duct mass[68], senescence (SA-β-GAL, p21, p16)[69], apoptosis (TUNEL, cleaved caspase 3), and BEC/hepatocyte function (bile acid and bilirubin serum levels)[70, 71]. The inventors analyze, in both liver injuries, functional transcript profiles of BECs as defined using bulk RNA seq analysis after purification of BECs (EpCAM+/CD31−/CD45− cells) from the non-parenchymal fraction (FIG. 46C and[62]). To then specifically examine the 4 phases of BEC-driven repair, the numbers of BECs (CK19+/EpCAM+/Tomato+), bi-phenotypic cells (HNF4ct+/CK19+/Tomato+), VEGFR2-expressing BECs (VEGFR2+/CK19+/EpCAM+/Tomato+), and Tomato+/HNF4ct+ hepatocytes are quantified. The inventors define whether the VEGFR2-expressing BECs are bi-phenotypic (HNF4ct+), which suggest their LPC potential. The inventors also characterize these cells for proliferation, senescence and apoptosis. Time-course analyses are performed as indicated in FIG. 51 by immunofluorescence on liver sections and by flow cytometry. This determines which phase(s) (1-4) of BEC-driven liver regeneration VEGFA promotes. Quantification of Tomato+ BEC-derived hepatocytes is performed by defining percentages of Tomato+/HNF4ct+vs. Tomato−/HNF4ct+ hepatocytes as well as percentages of Tomato+ vs Tomato− CK19+ BEC (to define the lineage tracing efficiency) on blinded co-stained sections from all liver lobes. Systematic counting is carried out on 5 high magnification sections separated from each other by at least 100 μm as published[39]. Corrected % Tomato+ hepatocytes are then extrapolated based on the lineage tracing efficiency for each mouse as previously reported[39]. Importantly, the inventors examine both Tomato+ and Tomato−hepatocytes for proliferation (EdU, Ki67), apoptosis (TUNEL, cleaved caspase 3), and senescence (SA-13-Gal, p21). Percentage of Tomato+/CD26+[74] hepatocytes among all CD26+ hepatocytes are also determined by flow cytometry within the parenchymal cell fraction obtained following differential centrifugations[62] (FIG. 46C). Again, corrected % Tomato+ hepatocytes is extrapolated based on the % of Tomato+ EpCAM+ BECs found by flow for each mouse as shown (FIG. 50D). Hepatocyte function: To further characterize the degree of maturation and proliferative status of Tomato+ hepatocytes compared to those from the Tomato−hepatocyte counterparts, bulk RNA-Seq analyses as previously assessed[39] is performed. Hepatocytes are isolated at an early and late time points to characterize cell maturation with time. RNA sequencing data of hepatocytes from 3 different mice for each group are analyzed to ensure robustness of data. Highly expressed genes are identified and then focused on with relation to metabolic functions[39, 41, 75] and cell cycle, using the gene set enrichment analysis[76]. The inventors also spatially examine by immunostaining whether Tomato+ hepatocytes in central vein or portal vein areas acquire pericentral marker expression (Cyp2e1 and GS) and periportal marker expression (CPS1), respectively. Liver function tests include serum levels of ALT[3], AST, bilirubin and albumin[39]. Fibrosis is assessed histologically with the Picro Sirius red[25], Masson's trichrome[77] (FIGS. 49, 44), and collagen/ctSMA/desmin staining[78] and by western blot from whole liver protein homogenates. Steatosis is evaluated with the lipidspot and Oil Red O staining (FIG. 49) as well as serum triglyceride concentration[3].

Figure 53:
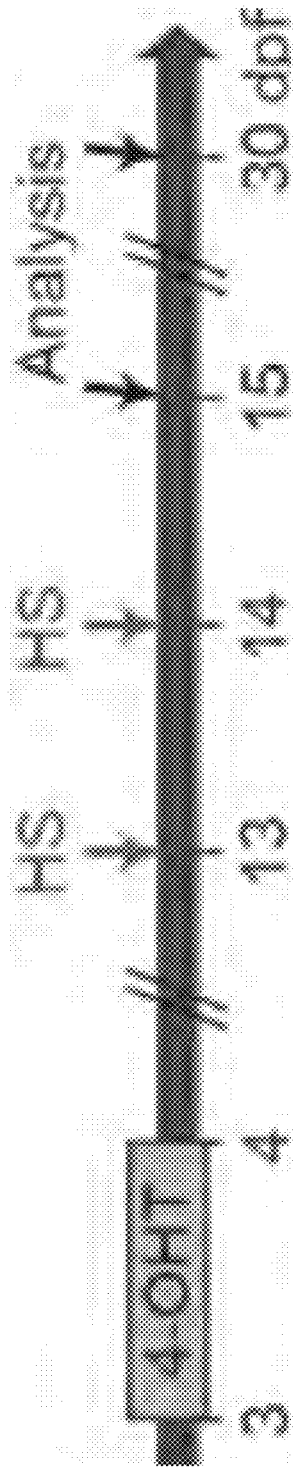
FIG. 53 depicts scheme of VEGFA overexpression experiments. Tg(fabp10a:ca-β-catenin); Tg(hsp70l: loxP-mCherry-loxP-VEGFA); Tg(Tp1: CreERT2); Tg(ubb:loxP-CFP-STOP-loxP-H2B-mCherry) quadruple transgenic larvae will be treated with 10 μM 4-OHT from 3 to 4 dpf and heat-shocked (HS) twice at 13 and 14 dpf. The larvae will be harvested at 15 or 30 dpf for liver analysis.
Figure 54:
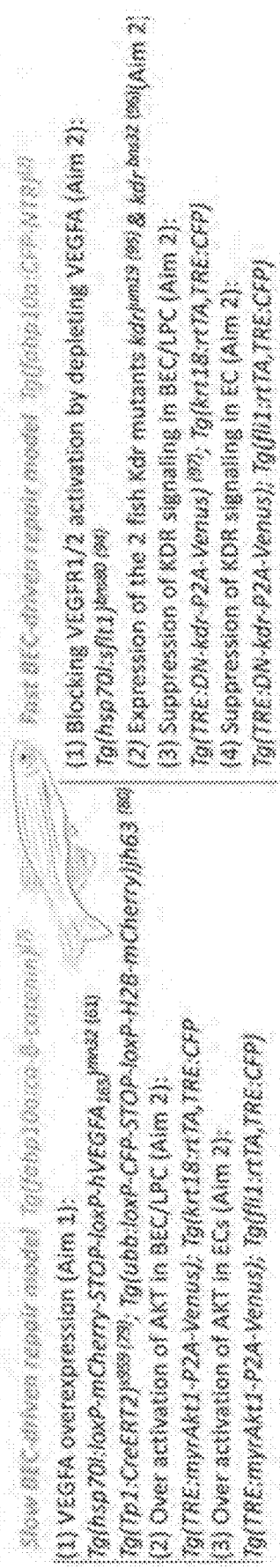
FIG. 54 depicts proposed genetic zebrafish models associated with the slow or fast BEC-driven regeneration models.

Experimental design in fish: The inventors determine the effect of VEGFA overexpression on BEC/LPC-mediated liver regeneration using Tg(fabp10a:ca-b-catenin) fish. To overexpress VEGFA in the liver, the inventors use the Tg(hsp70l:loxP-mCherry-STOP-loxP-hVEGFA165)

mn32[61] and Tg(Tp1:CreERT2)s959 79 lines. The Tg(ubb:loxP-CFP-STOP-loxP-H2B-mCherry)[ih63] line[80] is also used to reveal BEC-derived cells. Larvae containing all four transgenes are treated with 10 µM 4-OHT from 3 to 4 dpf for 24 hours to delete the STOP cassettes in BECs, and heat-shocked twice at 13 and 14 dpf to induce VEGFA expression in BECs and BEC-derived LPCs (FIG. 53). Although both hsp70l:mCherry and ubb:H2B-mCherry expression are detected in the larvae, the latter is in the nucleus and is much stronger than the former, permitting one to distinguish BEC-derived H2B-mCherry+ cells from the other cells. Control fish are not heat-shocked and therefore will not express VEGFA. Induction and absence of hVEGFA is validated by immunofluorescence with anti-human VEGFA antibody. All genetic zebrafish models used in the proposal are summarized in FIG. 54.

Analyses of BEC-Driven Liver Regeneration in Fish:

Roles of VEGFA on Phase 1-4 of BEC-mediated liver repair: As explained above, the zebrafish model provides a more synchronous liver injury animal model compared to mouse models, ideal for identification and quantification of each step of BEC-to-hepatocyte process. LPCs are identified with co-expression of HNF4α and H2B-mCherry and absence of Bhmt expression, and BEC-derived hepatocytes with co-expression of HNF4α, H2B-mCherry and Bhmt, while hepatocyte-derived hepatocytes with HNF4α and Bhmt (H2B-mCherry-). The inventors examine BEC/LPC/hepatocyte proliferation at 15 dpf (PCNA, EdU), apoptosis (cleaved caspase 3, TUNEL), and senescence (SA-b-Gal, p21) as well as examine bile flow in the bile ducts using fluorescent lipids[81] for each step.

Quantification of BEC-derived hepatocytes: Larvae are harvested at 15 dpf and the expression of multiple hepatocyte markers is analyzed by immunostaining (Bhmt) and in situ hybridization (ces2, ces3, gc, tdo2a, serpina1, cyp2ad2) that reflect their hepatic maturation. BEC-derived cells are marked by nuclear H2B-mCherry expression. Percentages of H2B-mCherry+ Bhmt+ hepatocytes among all hepatocytes is defined. However, these numbers are underestimated as the labeling efficiency of the Tp1:CreERT2 line is ~70%[82].

Reversion of liver damage: Larvae are analyzed at 30 dpf to determine the long-term consequence of the temporal VEGFA overexpression. H&E staining reveals the overall liver structure. Abundance of cells expressing mpeg1:Dendra2, hand2:EGFP, and acta2:mCherry are defined to quantify inflammation, hepatic stellate cell activation, and fibrosis respectively.

b. Define the degree of hepatocyte senescence and thus the liver disease context required for successful VEGFA-mediated BEC-driven liver regeneration in mice. Most chronic and acute human liver diseases, including APAP intoxication, are associated with hepatocyte senescence[53-56], and differentiation of LPCs seems to correlate with a certain threshold of damage of hepatocytes when moderate to severe inflammation is reached[83, 84]. This has been recapitulated in mouse models with long-term chronic liver injuries' 4, supporting the clinical relevance of overexpressing p21 in the short-term liver injury models. The inventors take advantage of the experimental p21-induced hepatocyte senescence to determine the threshold of the percentage of senescent p21+ hepatocytes required for revealing the therapeutic benefit of VEGFA to efficiently trigger BEC-driven liver regeneration. Expression of p21 in hepatocytes is fine-tuned via injection of two intermediate doses of AAV8-Tbg-p21, resulting in 20% and 50% of hepatocyte transduction. Effects of the intermediate doses on cell conversion, subsequent proliferation and liver function are compared to those from mice treated with the high dose used in the preliminary data (FIGS. 48-50) and published by others[40,39] and from mice treated with the control AAV8.Tbg.PI.Null.bGH (in the absence of p21). This experiment is performed in parallel to those described in section (a) with the 2 injuries (CDE, and APAP) as p21-induced hepatocyte senescence may differently affect VEGFA-mediated BEC-driven liver regeneration based on the injury Experimental Outcomes and Alternative Strategies for Aim 1: The main outcome of this aim is clinically relevant as it determines the therapeutic value of the safe VEGFA mRNA-LNPs (in mice) or genetic overexpression (in fish) to stimulate BEC-to-hepatocyte conversion and to reverse a broad range of liver disease features using 3 liver injury animal models. The inventors specifically address key pre-clinical points: (1) does VEGFA function similarly or uniquely to reverse an acute or chronic liver disease features? (2) does VEGFA promote BEC proliferation (DR) (or BEC senescence), BEC-to-hepatocyte conversion, and/or proliferation of the de novo hepatocytes? (3) is cell proliferation abrogated after termination of VEGFA mRNA-LNP injections by examining mice a year after VEGFA treatment (to prevent hyperplasia)? (4) Does VEGFA rescue animal survival following a lethal dose of APAP, and how late VEGFA can be administered to provide a beneficial effect? (5) Does VEGFA promote BEC-driven liver regeneration when hepatocytes are continuously injured? (6) What is the threshold of hepatocyte senescence required for successful VEGFA therapy via BEC-driven liver regeneration? (7) Is hepatocyte senescence needed for VEGFA-mediated BEC-to-hepatocyte conversion and/or subsequent de novo hepatocyte proliferation? These results dictate clinical contexts in which VEGFA treatments will be the most beneficial to treat liver diseases.

Figures 55A, 55B, 55C:
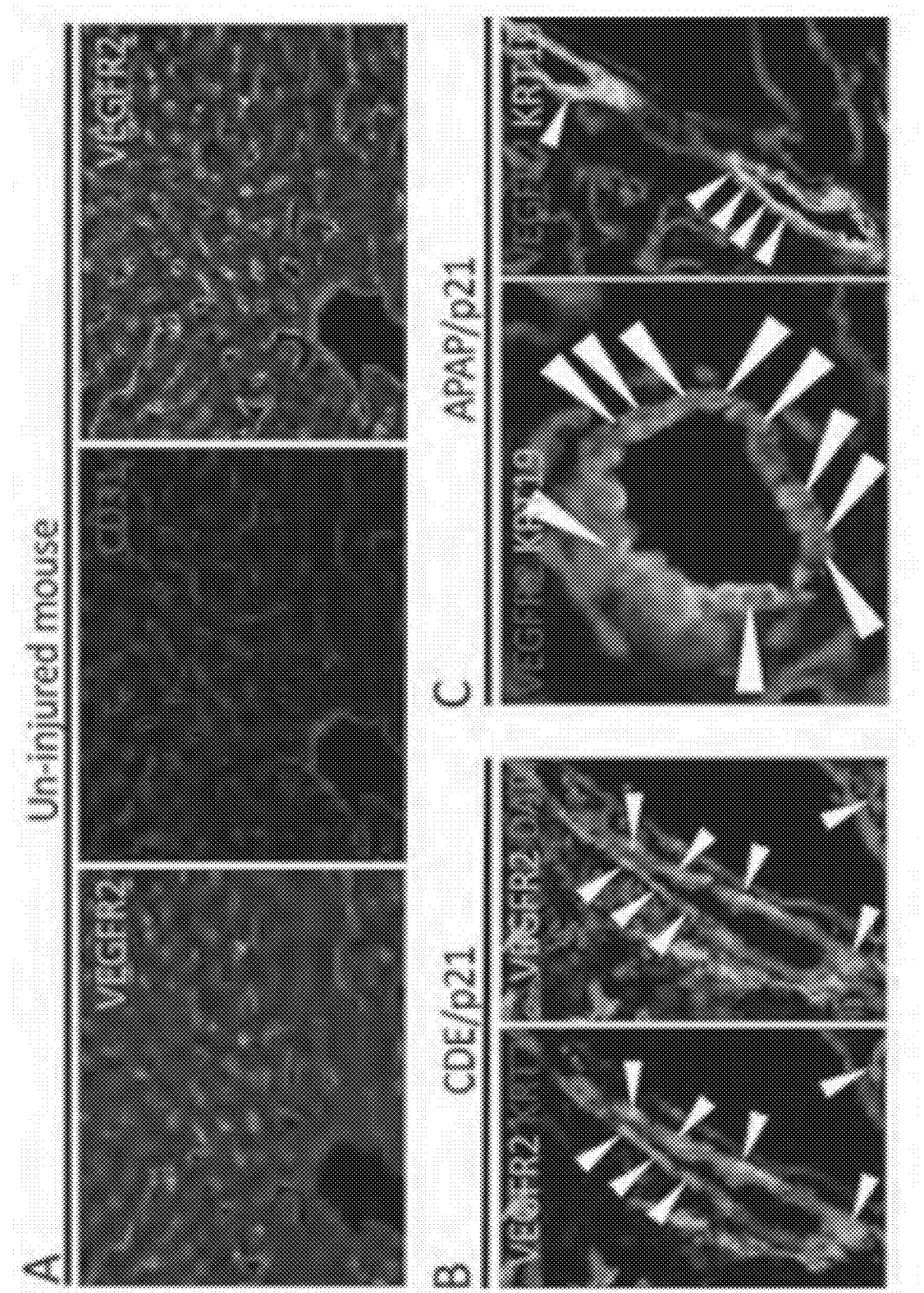
FIGS. 55A-55C depict expression of VEGFR2 in ECs (FIG. 55A) and BECs (FIGS. 55B, 55C) from the CDE diet (FIGS. 55A, 55B) and the APAP (FIG. 55C) induced liver injuries in the presence of AAV8-Tbg-p21. Detection of KRT19+ or KRT7+ BECs positive for VEGFR2 (arrowhead) in CDE (FIG. 55B) and APAP (FIG. 55C) models.
Figures 56A, 56B, 56C, 56D:
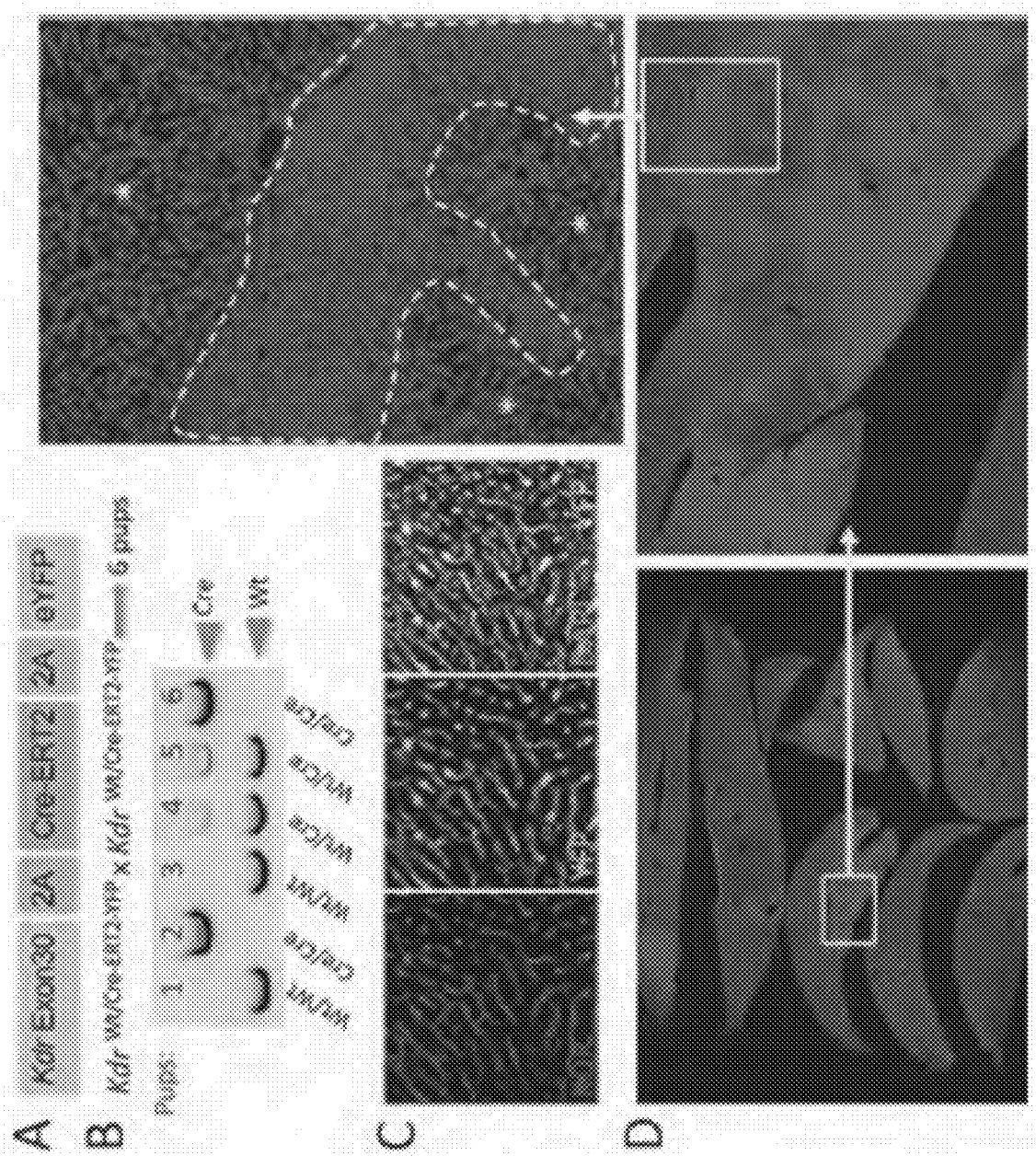
FIGS. 56A-56D depict validation of the Kdr-2A-Cre$^{ERT2}$-2A-eYFP mouse.

Alternatives: Several technical alternatives have been discussed above. Those include examination of continuous injury vs. injury with recovery, use of lethal doses of APAP (specific for each sex), and modulation of hepatocyte senescence in injury models. Efficiency of BEC-lineage tracing in the Krt19-Cre[ERT] line varies between 40-70%. The percentage of BEC-derived hepatocytes is thus extrapolated in each mouse based on the labeling efficiency defined by flow cytometry as shown (FIG. 50D) and staining on liver sections as previously published[39]. Alternatively, the inventors use the Hnf1b-Cre[ERT2] line[85] (Jackson Laboratory) that is reported to label more than 84% of BECs. For the zebrafish experiments, the inventors use the published lines, Tg(hsp70l:loxP-mCherry-STOP-loxP-hVEGFA165)[mn32] and Tg(ubb:loxP-CFP-STOP-loxP-H2B-mCherry)[ih63]. An alternative, VEGFA line to use is Tg(hsp70l:hVEGFA165-P2A-Venus), which express hVEGFA165 and Venus upon heat-shock. AIM 2: Define the cellular and molecular mechanisms of action of VEGFA in BEC-driven liver regeneration PRELIMINARY DATA a. VEGFR2 is expressed in ECs in healthy and injured livers and in a subset of BECs after liver injury in mice. To understand the regenerative role of VEGFA, the liver cell types expressing VEGFR2, the main functional receptor for VEGFA[86] were identified. As expected, ECs, identified with CD31 staining, are the main liver cells expressing VEGFR2 (Kdr) as assessed by immunostaining on liver sections of un-injured mice (FIG. 55A). Although other cell types such as hepatic stellate cells (HSC) or Kupffer cells (KC) may express VEGFR2 as previously reported especially after liver injury[87] cannot be ruled out. Given that BECs have been reported to express VEGFR2 following bile duct ligation in rats[48] and in polycystic liver diseases from human and the Pkd2$^{WS25/-}$ mouse model[50], the inventors searched for VEGFR2 expression in BECs in CDE-fed mice and APAP-treated mice injected with AAV8-Tbg-p21. They found in both models expression of VEGFR2 in a subpopulation of BECs (FIGS. 55B, 55C) that was absent in control uninjured mice (not shown). In line with these data, the examination of published scRNA-Seq studies identifies KDR transcripts in 8.3% of human BECs[51]. Altogether, these key data suggest that VEGFA can act either through activation of ECs indirectly or BECs directly and that VEGFR2 marks a subset of BECs that may represent candidate facultative LPCs.

b. Validation of a Kdr-Cre$^{ERT2}$-eYFP mouse line to fate map VEGFR2-expressing cells. To test that VEGFR2+ BECs generate de novo hepatocytes, the inventors used inducible Kdr lineage tracing line, Kdr-2A-Cre$^{ERT2}$-2A-eYFP (FIG. 56A). Given that the "2A-Cre$^{ERT2}$-2A-eYFP" cassette was introduced downstream of the last exon, this approach allowed transcription of mRNA encoding all exons of Kdr and the cassette. The line was validated as the cross from 2 heterozygous mice resulted in a litter of 6 pups including 2 homozygous (FIG. 56B) confirming that KDR expression is preserved as Kdr knockout mice are lethal[88]. Further confirmation was that VEGFR2 expression perfectly overlaps with YFP, as both are detected by immunostaining on liver section (FIG. 56C). The high efficiency of EC mapping was verified by tracking Tomato expression in ECs when the Cre$^{ERT2}$ line was crossed with the reporter R26$^{LSL}$tdTomato line and treated with the same regiment of Tam, AAV-p21, APAP, and VEGFA as shown in FIG. 9 (FIG. 56D). Tam was injected 3 times every other day starting from the day APAP was injected to capture the emerging VEGFR2+ BECs after injury. Analyses of all liver lobes of one mouse revealed an even pattern of Tomato+ cells representing ECs (see areas with asterisk in the close-up). Strikingly, some areas were much brighter, and may represent hepatocytes derived from VEGFR2+ cells (areas with a dotted line in the close-up). Aim 2 carefully examines the identity of the Tomato+ cells.

Figures 57A, 57B:
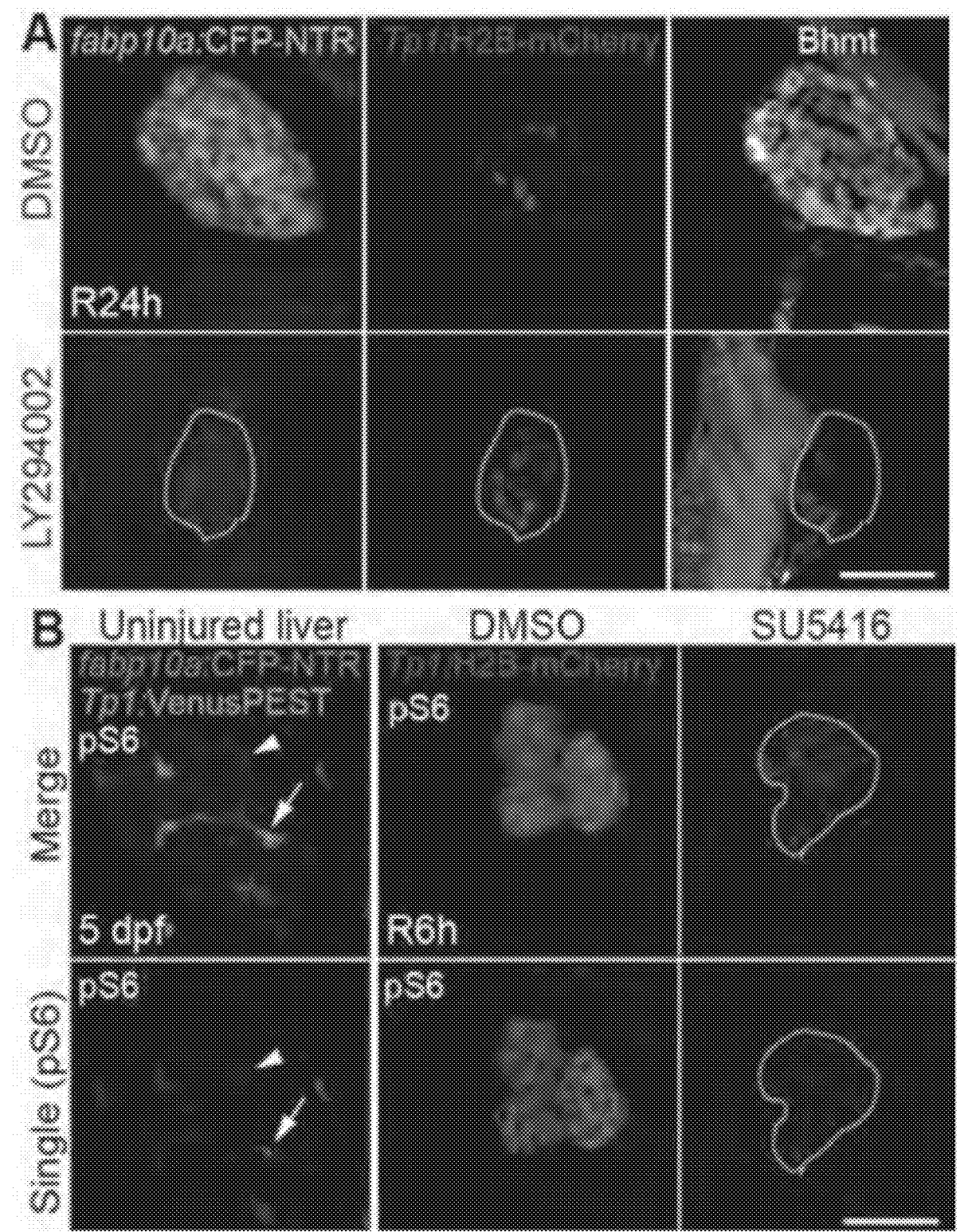
FIGS. 57A-57B depict the PI3K-AKT-mTORC1 axis controls BEC-driven liver regeneration.
Figure 58:
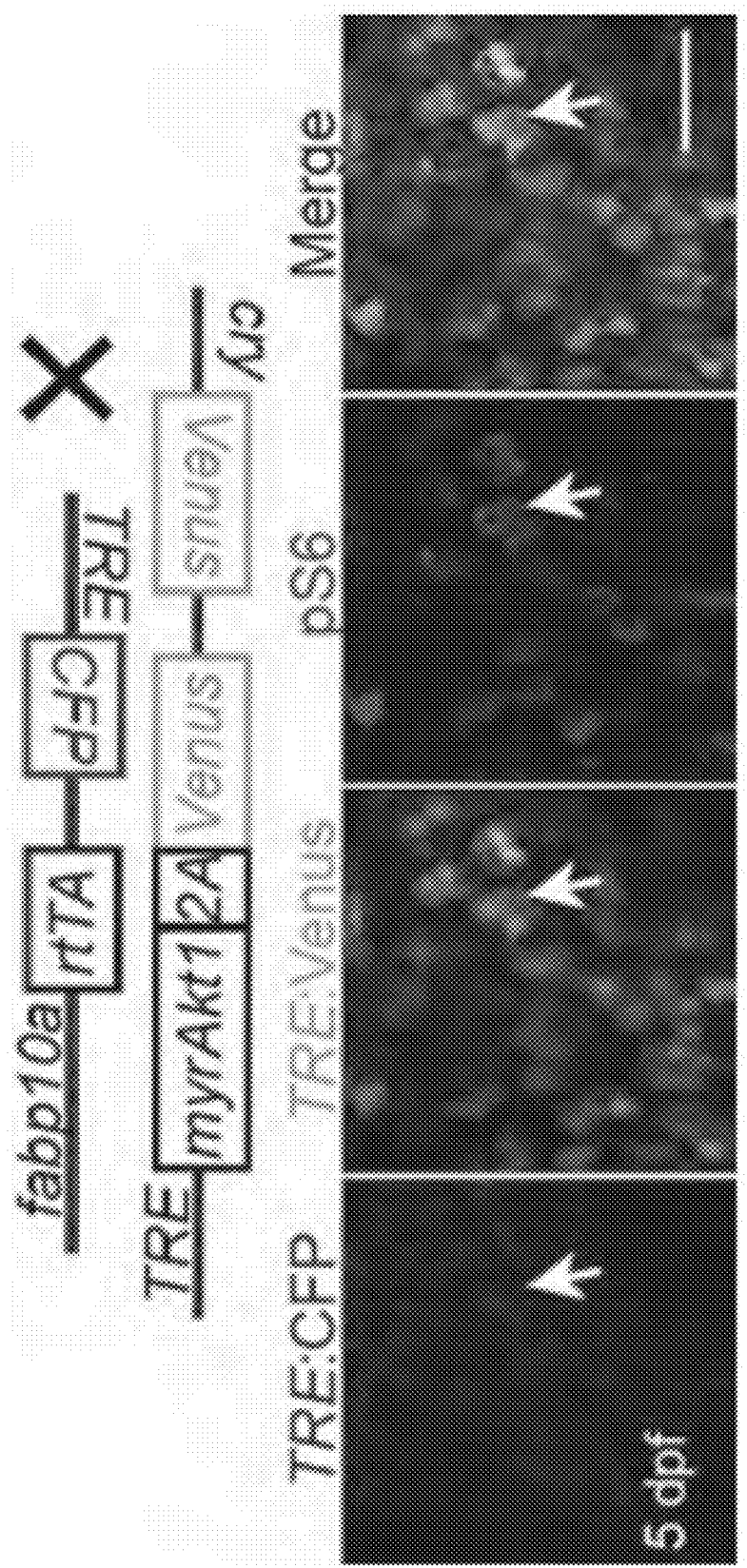
FIG. 58 depicts generation of genetic tools for AKT activation. Confocal images showing the expression of TRE:CFP, TRE:myrAkt1-P2A-Venus, and pS6 in the liver at 5 dpf. pS6 expression was observed in TRE:Venus$^+$ hepatocytes (arrows). The larva was treated with 10 μg/ml Dox from 4 to 5 dpf. Scale bar, 50 μm.

Contribution of the mouse models in Aim 2: The identification of putative facultative VEGFR2+ LPCs is carried out in mice using the Kdr-2A-Cre$^{ERT2}$-2A-eYFP; R26$^{LSL}$tdTomato model. The VEGFA-VEGFR2 downstream mediator contribution in the VEGFA-mediated BEC-to-hepatocyte liver repair identified in zebrafish models is then validated in mice using cell type-specific knock out models.

c. The PI3K-AKT-mTORC1 axis controls BEC-driven liver regeneration in fish. Given that VEGFR2 functions via at least two major signaling branches, PI3K/AKT and MEK/ERK1/2, the inventors tested which downstream branch controls BEC-driven liver regeneration using their specific inhibitors (LY294002 for PI3K and U0126 for MEK1/2). PI3K, but not MEK1/2, inhibition impaired BEC-driven liver regeneration as did VEGRF2 inhibition (FIGS. 44A, 57A), suggesting the PI3K/AKT branch as the downstream mediator of VEGFR2 activation in BEC-driven liver regeneration. Given the well-known cascade of PI3K-AKT-mTOR, the inventors further examined mTOR activity in the regenerating livers. As assessed by the expression of pS6, a reliable marker for mTORC1 activation[89], LPCs at R6h clearly expressed pS6 (FIG. 57B). Importantly, this pS6 expression was absent in SU5416-treated regenerating livers (FIG. 57B), suggesting the VEGFR2-PI3K-AKT-mTORC1 axis acting in LPCs.

d. Generation of genetic tools for the inducible and cell-type-specific activation of AKT signaling in fish. Given the possibility that VEGFR2 signaling regulates BEC-driven liver regeneration via PI3K/AKT, the inventors determine if AKT overactivation promotes LPC-to-hepatocyte differentiation as does VEGFA overexpression. To do so, genetic tools that allow for cell-type-specific activation of AKT signaling are used: Tg(fabp10a:rtTA, TRE:CFP), Tg(krt18:rtTA, TRE:CFP), and Tg(TRE:myrAkt1-P2A-Venus, cry:Venus). In this tetracycline-inducible system (Tet-ON), reverse tetracycline-controlled transactivator (rtTA) is expressed in hepatocytes/LPCs (fabp10a:rtTA) or BECs/LPCs (krt18:rtTA). Both the myristoylated, active form of AKT1 (myrAKT1) and Venus are expressed under the control of the tetracycline response element (TRE). In zebrafish, krt18 is restrictively expressed in BECs[90]. Upon doxycycline (Dox) treatment, Tg(fabp10a:rtTA, TRE:CFP); Tg(TRE:myrAkt1-P2A-Venus) larvae displayed uniform CFP but mosaic Venus expression in the liver (FIG. 58). Importantly, pS6 expression was detected in TRE:myrAkt1-P2A-Venus+ cells (FIG. 58, arrows), validating the transgenic line for AKT activation.

Contribution of the fish models in Aim 2: Given the easiness of targeted pharmacologic screens and genetic modifications in zebrafish, these models will be key to identify the VEGFA-VEGFR2 downstream mediators responsible for VEGFA-mediated BEC-to-hepatocyte liver repair. Results from the fish studies will guide the mouse studies for generation of the cell specific knockout VEGFA-VEGFR2 downstream mediators.

Design:

Rationale: The preliminary data provide strong evidence that VEGFA harnesses BEC-driven liver regeneration in mice and fish. Here, the cellular and molecular mechanism of action of VEGFA in this process are deciphered. Specifically, the inventors define whether VEGFR2+ BECs are facultative LPC candidates using a lineage tracing strategy in mice (Aim 2a). They determine the direct (via VEGFR2+ BECs) or indirect (via VEGFR2-expressing ECs and potentially stellate cells and KCs/macrophages) effect of VEGFA on BEC-driven liver regeneration and identify the VEGFR2 downstream signaling involved in this process (Aim 2b). To do so, a combination of a targeted chemical screen in fish, and genetic strategies are used in both mice and fish to knock out or modulate the identified VEGFR2 downstream targets in BECs and ECs to validate their role in VEGFA-dependent BEC-driven liver repair.

a. Contribution of VEGFR2+ BECs to de novo hepatocytes and BECs after liver injury in mice. To track the hepatocyte or BEC fate of VEGFR2+ cells, the Kdr-2A-Cre$^{ERT2}$-2A-eYFP; R26$^{LSL}$tdTomato[65] mice are used. The inventors verify that the inducible Cre system is not leaky in the absence of Tam by the lack of Tomato expression. Tam is injected IP (4 mg/20 g BW three times every other day) as soon as VEGFR2+ BECs are detected. Careful examination of kinetic of VEGFR2 expression in BECs is thus carried out in both injury models to define the timing of injection of Tam. Mice are pretreated with AAV8-Tbg-p21 and injected with 2 doses of VEGFA mRNA-LNPs (same as FIG. 48-50) to allow optimal conversion of BECs to hepatocytes. Expansion of VEGFR2+ BECs (eYFP+/KRT19+/Tomato+) and their ability to differentiate into hepatocytes (Tomato+/HNF4α+/CD26+74/eYFP−) or BECs (Tomato+/KRT19+/EpCAM+74/eYFP−) is quantified by immunostaining and flow cytometry, and their proliferative/apoptosis/senescence status and function is examined (as explained in Aim 1a). As ECs identified as CD31+ cells are also tracked with Tomato, CD31+ cells are excluded from flow cytometry analyses. The comparison of data from VEGFA mRNA-LNP-vs. Poly(C) RNA-LNP-treated mice reveals the requirement of VEGFR2 activation in BEC-driven liver regeneration. Clonal ability of VEGFR2+ BECs to expand and differentiate is further studied using the confetti reporter mice[91] as recently used[41]. VEGFR2 activation in BECs is assessed by the phosphorylation status of VEGFR2 with immunofluorescence and Western Blotting (on purified VEGFR2+/eYFP+/EpCAM+ BECs) using antibodies against phosphorylated forms of VEGFR2. Liver function is examined as explained in Aim 1a. Transcript profiles of the purified de novo hepatocytes (Tomato+/CD26+/eYFP−) and BECs (Tomato+/EpCAM+/eYFP−) in the presence of VEGFA is compared to those from their Tomato− counterparts using bulk RNA-Seq analyses at two different time points to define their maturation and proliferative/apoptosis/senescence status with time (see Aim 1a). The inventors analyze functional transcript profiles as reported for hepatocytes39,[41] and BECs[49, 72, 73] Hepatocytes are obtained from the parenchymal fraction, and BECs purified from the non-parenchymal fraction EpCAM+/CD31−/CD45− cells (FIG. 46C). It is verified that other VEGFR2-expressing cells than BECs are not the source of the tdTomato hepatocytes by mapping the fate of ECs, KC and HSCs using Cre lines for these lineages (Cdh5-Cre$^{ERT2}$ for ECs[92], Lrat-Cre for HSC[78], Csf1r-Mer-iCre-Mer[93] for KCs, all available from the Jackson Laboratory or Taconic. In the unexpected case that these other liver cell specific lineage tracing models show contribution of hepatocytes, the mechanism of cell conversion into hepatocytes will be thoroughly examined as described above.

b. Cellular and Molecular Mechanism of VEGFA in BEC-Driven Liver Regeneration Fish Study:

Define the expression of the component genes of VEGFR2 signaling in regenerating livers. Using in situ hybridization, the expression of the following genes implicated in VEGFR2 signaling in regenerating livers is first examined: kdrl, kdr, vegfaa, vegfab, vegfc, nrp1a, and nrp1b. For the Tg(fabp10a:CFP-NTR) model, their expression is examined at R6h; for the Tg(fabp10a:ca-b-catenin) model, at 15 dpf when LPCs are prevalent. Once their expression in the regenerating livers is identified, double labeling using RNAscope is used to determine which cell type expresses the genes. BEC/LPCs is revealed by Tp1: H2B-mCherry or Tp1:VenusPEST expression, ECs by fli1: GFP, stellate cells by hand2:GFP, and macrophages by mpeg1:Dendra2. Moreover, the inventors examine their expression, particularly kdrl and kdr, at multiple stages (e.g., A18h, A24h, A30h, A36h/R0h, and R6h for the Tg(fabp10a: CFP-NTR) model) to determine when they start to be induced in BECs.

Loss-of-function experiments using the Tg(fabp10a:CFP-NTR) model. The inventors observed two distinct defects in BEC-driven liver regeneration in SU5416-treated regenerating larvae: reduced liver size and impaired LPC-to-hepatocyte differentiation (FIG. 44). These phenotypes are analyzed in detail with various liver markers. Both SU5416 and SKLB1002 are used to inhibit VEGFR2 signaling. For the size phenotype, the proliferation of BEC-derived cells is first examined at R6h and R24h (EdU, anti-pH3). Then the death of BEC-derived cells (TUNEL assay, active caspase-3) is examined. For the differentiation phenotype, the expression of multiple hepatocyte markers is examined, including cp, sepp1b, gc, and Bhmt, at R24h. Their expression is examined later at R48h and R72h to determine whether LPC-to-hepatocyte differentiation in VEGFR2-suppressed larvae is just delayed or completely blocked. Complementary to the pharmacological inhibition, the inventors use genetic tools to suppress VEGFR2 signaling: (1) the Tg(hsp70l:sflt1)$^{bns80}$ line, which upon heat-shock expresses a soluble form of VEGFR1 that sequesters VEGFA, thereby blocking VEGFR1/2 signaling[94], and (2) kdr!$^{mn19}$ and kdr$^{bns32}$ mutant lines95, [96] corresponding to the two zebrafish orthologs of the mammalian Kdr. Both liver size and LPC-to-hepatocyte differentiation are assessed in these genetic backgrounds, as described for the pharmacological studies. Moreover, to suppress VEGFR2 signaling in a cell-type-specific manner, the inventors generate a Tg(TRE:DN-kdr-P2A-Venus) line, which expresses Kdr without its intracellular domain (DN-Kdr) under the TRE promoter. The DN-Kdr makes a dimer with its wild-type receptors, thereby blocking VEGFR2 signaling in cells that express DN-Kdr, i.e., cell-autonomously[97]. For BEC/LPC-specific suppression of VEGFR2 signaling, the Tg(krt18:rtTA, TRE:CFP) line is used; for its endothelial-specific suppression, a Tg(fli1:rtTA, TRE:CFP) line is generated. In the cases when kdr or kdrl is also expressed in HSCs and macrophages, a TgBAC(hand2: rtTA) line is generated using transposon-mediated BAC transgenesis[98] and Tg(mpeg1:rtTA, TRE:CFP) line using the 1.86-kb mpeg1 promoter[99] for HSC and macrophage overexpression of DN-Kdr, respectively.

Determine the downstream mediator of VEGFR2 activation in BEC-driven liver regeneration. The preliminary data show the PI3K/AKT/mTOR axis as the downstream mediator of VEGFR2 activation in BEC-driven liver regeneration. This is tested by manipulating the activity of PI3K, AKT, and mTORC1. First, the effect of the inhibition of each component on BEC-driven liver regeneration is investigated, particularly on liver size and LPC-to-hepatocyte differentiation, as described for SU5416 treatment studies. LY294002, MK-2206, and rapamycin is used to inhibit PI3K, AKT, and mTORC1, respectively. Since p38 MAPK is another key downstream mediator of VEGFR2 activation, the inventors also investigate if p38 inhibition impairs BEC-driven liver regeneration using the pan-p38 inhibitor SB203580. Second, the effect of VEGFA overexpression on promoting LPC-to-hepatocyte differentiation is investigated for if it is through PI3K activation. To do so, Tg(fabp10a: ca-b-catenin) larvae overexpressing VEGFA (FIG. 53) are treated with LY294002 from 13 to 15 dpf and Bhmt expression is assessed at 15 dpf Third, AKT overactivation is investigated for if it promotes LPC-to-hepatocyte differentiation, and if VEGFA overexpression does the same, using the mosaic Tg(TRE:myrAkt1-P2A-Venus) line (FIG. 58). Tg(TRE:myrAkt1-P2A-Venus); Tg(krt18:rtTA, TRE:CFP); Tg(fabp10a:ca-b-catenin) larvae will be treated with 10 μg/ml Dox from 13 dpf onwards, harvested at 15 dpf, and processed for Bhmt immunostaining. Complementary to this BEC/LPC-specific AKT activation, endothelial-specific AKT activation is achieved using a Tg(fli1:rtTA, TRE:CFP) line. Similarly, the transgenic lines indicated above for HSC- and macrophage-specific activation of AKT are used if needed.

Mouse Study:

Define the direct effects of VEGFA on VEGFR2+ BECs and indirect effects on VEGFR2+ ECs and uncover the key VEGFR2 downstream targets. The inventors investigate the key requirement of VEGFR2 in BEC-driven liver regeneration using Kdr conditional knockout mice. To reveal a direct effect of VEGFA on BECs, they delete Kdr using triple (Osteopontin) Opn-iCre$^{ERT2}$ [100]; Kdr$^{fl/fl}$; R26$^{LSL}$Tomato mice. The Opn-iCre$^{ERT2}$ line[100] has been reported to virtually label all BECs[100]. These experiments are first performed with the liver injury that generates the most VEGFR2+ BEC-derived hepatocytes after pretreatment with AAV8-Tbg-p21 and following the optimal injection protocol of VEGFA mRNA-LNPs as defined in FIG. 51. In this protocol, Tam is injected 4 weeks prior to injury. Non-specific labeling from ectopic expression of Opn reported in small subsets of hepatocytes and other liver cells upon chronic liver injury[101-103] is not expected. The liver function is examined and the percentage of Tomato+ hepatocytes is determined. Decreased numbers of Tomato+ hepatocytes in Kdrfl/fl mice compared to Kdrwt/wt is expected if VEGFR2 expressed in BECs is key in BEC-driven liver regeneration. To reveal an indirect effect of VEGFA via ECs, or possibly KCs and HSCs, Kdr is deleted using Cre lines for these lineages as listed in Aim 2a. BEC-derived hepatocytes are identified indirectly by tracking eGFP-negative hepatocytes in mice pre-treated with AAV8-Tbg-eGFP (Addgene, #105535) to specifically and efficiently mark all hepatocytes as previously reported[35]. Comparison of the abundance of eGFP-negative hepatocytes in the 4 Cre lines (Kdr, Cdh5, Lrat, Csf1r) by indirect BEC fate mapping combined with the analyses of the direct BEC tracing with Opn-iCre$^{ERT2}$ is very informative in discriminating the direct from indirect effect of VEGFR2 activation on BEC-driven liver regeneration. To demonstrate the key role of the specific downstream targets of VEGFR2 activation identified in the zebrafish studies, the inventors delete the target gene in the same cells indicated above by crossing the specific Cre lines with floxed mice of the downstream target gene. For instance, Akt1-, 2-, 3-floxed mice are all available from the Jackson Laboratory.

Experimental Outcomes and Alternative Strategies for Aim 2: Outcomes of Aim 2 identify the common or distinct mechanisms by which VEGFA harnesses BEC-driven liver regeneration in acute and chronic models recapitulating a broad range of liver diseases. Importantly, the inventors discriminate between the direct effect of VEGFA on BECs and its indirect effect via activation of ECs or other cell types. Moreover, given the easiness of chemical screens and genetic modulations in fish, findings from zebrafish not only support findings from mice but also are instrumental in providing the molecular mechanism by which VEGFA promotes BEC-driven liver regeneration, and thus in identifying novel roles of VEGFR2 downstream mediators such as AKT that may serve as additional therapeutic targets to accelerate BEC-driven liver regeneration. Alternatives: (1) Although the induction of VEGFR2 expression has been reported in BECs/LPCs in injured mouse and diseased human livers[48, 50], it is possible that VEGFR2 expressed on BECs is not functionally instrumental in promoting BEC-driven liver regeneration. As indicated in section (b), the inventors alternatively identify in mice and fish other liver cell types expressing VEGFR2 (ECs, HSCs and macrophages/KCs) whose activation is key in this process. (2) Although VEGFR2 is known to be the main functional receptor for VEGFA and the preliminary data support the key contribution of VEGFR2 in BEC-driven liver regeneration in zebrafish, there is a slight chance that VEGFR2 knockout mice do not show reduced BEC-driven liver regeneration. In this case, the inventors examine the additional contribution of VEGFR1 (Flt1) in this process by identifying the liver cell types expressing Flt1. Cell type-specific Flt1 deletion is performed using Flt1-floxed mice (Jackson Laboratory) and the flt1$^{bns29}$ mutant fish line[94], as explained for Kdr deletion. (3) All zebrafish lines are available except Tg(TRE:DN-kdr-P2A-Venus) and Tg(fli1:rtTA, TRE:CFP) lines.

A major strength of the proposal is the use of complementary pre-clinical mouse models and zebrafish models suitable for pharmacologic screens and genetic modulations to demonstrate the therapeutic impact and cellular and molecular mechanisms of action of VEGFA-VEGFR2 axis activation to harness BEC-driven liver regeneration, and identify potential downstream mediators that serve as additional therapeutic targets to accelerate the regeneration. This proposal has high potential for clinical impact as it provides a novel therapeutic intervention to treat human chronic or severe acute liver diseases that are consistently characterized by compromised hepatocyte proliferation. Importantly, this proposal will pioneer the clinically validated and currently used for COVID-19 vaccines mRNA-LNP as a safe means to transiently deliver VEGFA to the liver to exploit and optimize the alternative intrinsic BEC-driven liver repair.

REFERENCES

1. Ko, S, T Y Choi, J O Russell, J So, S P Monga and D Shin. Bromodomain and extraterminal (BET) proteins regulate biliary-driven liver regeneration. J Hepatol 2016, 64:316-325. PMID: WOS: 000368280200010.
2. Choi, T Y, N Ninov, D Y Stainier and D Shin. Extensive conversion of hepatic biliary epithelial cells to hepatocytes after near total loss of hepatocytes in zebrafish. Gastroenterology 2014, 146:776-788. PMID: 24148620; PMCID: PMC3943869.
3. Rizvi, F, E Everton, A R Smith, H Liu, E Osota, M Beattie, Y Tam, N Pardi, D Weissman and V Gouon-Evans. Murine liver repair via transient activation of regenerative pathways in hepatocytes using lipid nanoparticle-complexed nucleoside-modified mRNA. Nat Commun 2021, 12:613. PMID: 33504774; PMCID: PMC7840919
4. Ebrahimi, H, M Naderian and A A Sohrabpour. New Concepts on Reversibility and Targeting of Liver Fibrosis; A Review Article. Middle East journal of digestive diseases 2018, 10:133-148. PMID: 30186577; PMCID: PMC6119836.
5. Schuppan, D, M Ashfaq-Khan, A T Yang and Y O Kim. Liver fibrosis: Direct antifibrotic agents and targeted therapies. Matrix biology: journal of the International Society for Matrix Biology 2018, 68-69:435-451. PMID: 29656147.
6. Trautwein, C, S L Friedman, D Schuppan and M Pinzani. Hepatic fibrosis: Concept to treatment. J Hepatol 2015, 62:S15-24. PMID: 25920084.
7. So, J, M Kim, S H Lee, S Ko, D A Lee, H Park, M Azuma, M J Parsons, D Prober and D Shin. Attenuating the EGFR-ERK-SOX9 axis promotes liver progenitor cell-mediated liver regeneration in zebrafish. Hepatology 2020: Accepted.
8. Jung, K, M Kim, J So, S H Lee, S Ko and D Shin. Farnesoid X receptor activation impairs liver progenitor cell-mediated liver regeneration via the PTEN-PI3K-AKT-mTOR axis in zebrafish. Hepatology 2020. PMID: 33314176.
9. Michalopoulos, G K. Hepatostat: Liver regeneration and normal liver tissue maintenance. Hepatology 2017, 65:1384-1392. PMID: 27997988.
10. Duncan, A W, C Dorrell and M Grompe. Stem cells and liver regeneration. Gastroenterology 2009, 137:466481. PMID: 19470389.
11. Stanger, B Z. Cellular homeostasis and repair in the Mammalian liver. Annu Rev Physiol 2015, 77:179-200. PMID: 25668020.

12. Rodrigo-Torres, D, S Affo, M Coll, O Morales-Ibanez, C Millan, D Blaya, A Alvarez-Guaita, C Rentero, J J Lozano, M A Maestro, M Solar, V Arroyo, J Caballeria, L A van Grunsven, C Enrich, P Gines, R Bataller and P Sancho-Bru. The biliary epithelium gives rise to liver progenitor cells. Hepatology 2014, 60:1367-1377. PMID: 24700364.
13. Shin, S and K H Kaestner. The origin, biology, and therapeutic potential of facultative adult hepatic progenitor cells. Curr Top Dev Biol 2014, 107:269-292. PMID: 24439810.
14. Sato, K, M Marzioni, F Meng, H Francis, S Glaser and G Alpini. Ductular Reaction in Liver Diseases: Pathological Mechanisms and Translational Significances. Hepatology 2019, 69:420-430. PMID: 30070383; PMCID: PMC6324973.
15. Boulter, L, W Y Lu and S J Forbes. Differentiation of progenitors in the liver: a matter of local choice. J Clin Invest 2013, 123:1867-1873. PMID: 23635784; PMCID: 3635730.
16. Gouw, A S, A D Clouston and N D Theise. Ductular reactions in human liver: diversity at the interface. Hepatology 2011, 54:1853-1863. PMID: 21983984.
17. Roskams, T A, N D Theise, C Balabaud, G Bhagat, P S Bhathal, P Bioulac-Sage, E M Brunt, J M Crawford, H A Crosby, V Desmet, M J Finegold, SA Geller, A S Gouw, P Hytiroglou, A S Knisely, M Kojiro, J H Lefkowitch, Y Nakanuma, J K Olynyk, Y N Park, B Portmann, R Saxena, P J Scheuer, A J Strain, S N Thung, I R Wanless and A B West. Nomenclature of the finer branches of the biliary tree: canals, ductules, and ductular reactions in human livers. Hepatology 2004, 39:1739-1745. PMID: 15185318.
18. Roskams, T and V Desmet. Ductular reaction and its diagnostic significance. Semin Diagn Pathol 1998, 15:259-269. PMID: 9845427.
19. Popper, H, G Kent and R Stein. Ductular cell reaction in the liver in hepatic injury. J Mt Sinai Hosp N Y 1957, 24:551-556. PMID: 13476145.
20. Turanyi, E, K Dezso, J Csomor, Z Schaff, S Paku and P Nagy. Immunohistochemical classification of ductular reactions in human liver. Histopathology 2010, 57:607-614. PMID: 20875072.
21. Lowes, K N, B A Brennan, G C Yeoh and J K Olynyk. Oval cell numbers in human chronic liver diseases are directly related to disease severity. Am J Pathol 1999, 154:537-541. PMID: 10027411; PMCID: 1849988.
22. Van Haele, M, J Snoeck and T Roskams. Human Liver Regeneration: An Etiology Dependent Process. Int J Mol Sci 2019, 20. PMID: 31083462; PMCID: PMC6539121.
23. Roskams, T A, L Libbrecht and V J Desmet. Progenitor cells in diseased human liver. Semin Liver Dis 2003, 23:385-396. PMID: 14722815.
24. Yoon, S M, D Gerasimidou, R Kuwahara, P Hytiroglou, J E Yoo, Y N Park and N D Theise. Epithelial cell adhesion molecule (EpCAM) marks hepatocytes newly derived from stem/progenitor cells in humans. Hepatology 2011, 53:964-973. PMID: 21319194.
25. Deng, X, X Zhang, W Li, R X Feng, L Li, G R Yi, X N Zhang, C Yin, H Y Yu, J P Zhang, B Lu, L Hui and W F Xie. Chronic Liver Injury Induces Conversion of Biliary Epithelial Cells into Hepatocytes. Cell Stem Cell 2018, 23:114-122.e113. PMID: 29937200.
26. Haque, S, Y Haruna, K Saito, M A Nalesnik, E Atillasoy, S N Thung and M A Gerber. Identification of bipotential progenitor cells in human liver regeneration. Lab Invest 1996, 75:699-705. PMID: 8941215.
27. Stueck, A E and I R Wanless. Hepatocyte buds derived from progenitor cells repopulate regions of parenchymal extinction in human cirrhosis. Hepatology 2015, 61:1696-1707. PMID: 25644399.
28. Hytiroglou, P and N D Theise. Regression of human cirrhosis: an update, 18 years after the pioneering article by Wanless et al. Virchows Archive: an international journal of pathology 2018, 473:15-22. PMID: 29589101.
29. Wanless, I R, E Nakashima and M Sherman. Regression of human cirrhosis. Morphologic features and the genesis of incomplete septal cirrhosis. Arch Pathol Lab Med 2000, 124:1599-1607. PMID: 11079009.
30. Falkowski, O, H J An, I A Ianus, L Chiriboga, H Yee, A B West and N D Theise. Regeneration of hepatocyte 'buds' in cirrhosis from intrabiliary stem cells. J Hepatol 2003, 39:357-364. PMID: 12927921.
31. Fleming, K E and I R Wanless. Glutamine synthetase expression in activated hepatocyte progenitor cells and loss of hepatocellular expression in congestion and cirrhosis. Liver Int 2013, 33:525-534. PMID: 23362937.
32. Hadi, R, K Shin, N Reder, L Alpert, L Koch, W T Choi, P E Swanson, J Hart and M Westerhoff. Utility of glutamine synthetase immunohistochemistry in identifying features of regressed cirrhosis. Mod Pathol 2020, 33:448-455. PMID: 31391527.
33. Lin, W R, S N Lim, S A McDonald, T Graham, V L Wright, C L Peplow, A Humphries, H M Kocher, N A Wright, A P Dhillon and M R Alison. The histogenesis of regenerative nodules in human liver cirrhosis. Hepatology 2010, 51:1017-1026. PMID: 20198634.
34. Malato, Y, S Naqvi, N Schurmann, R Ng, B Wang, J Zape, M A Kay, D Grimm and H Willenbring. Fate tracing of mature hepatocytes in mouse liver homeostasis and regeneration. J Clin Invest 2011, 121:4850-4860. PMID: 22105172; PMCID: 3226005.
35. Yanger, K, D Knigin, Y Zong, L Maggs, G Gu, H Akiyama, E Pikarsky and B Z Stanger. Adult hepatocytes are generated by self-duplication rather than stem cell differentiation. Cell Stem Cell 2014, 15:340-349. PMID: 25130492.
36. Overturf, K, M al-Dhalimy, C N Ou, M Finegold and M Grompe. Serial transplantation reveals the stem-cell-like regenerative potential of adult mouse hepatocytes. Am J Pathol 1997, 151:1273-1280. PMID: 9358753.
37. Schaub, J R, Y Malato, C Gormond and H Willenbring. Evidence against a stem cell origin of new hepatocytes in a common mouse model of chronic liver injury. Cell Rep 2014, 8:933-939. PMID: 25131204; PMCID: PMC4376310.
38. Lu, W Y, T G Bird, L Boulter, A Tsuchiya, A M Cole, T Hay, R V Guest, D Wojtacha, T Y Man, A Mackinnon, R A Ridgway, T Kendall, M J Williams, T Jamieson, A Raven, D C Hay, J P Iredale, A R Clarke, O J Sansom and S J Forbes. Hepatic progenitor cells of biliary origin with liver repopulation capacity. Nat Cell Biol 2015, 17:971983. PMID: 26192438; PMCID: 4612439.
39. Raven, A, W Y Lu, T Y Man, S Ferreira-Gonzalez, E O'Duibhir, B J Dwyer, J P Thomson, R R Meehan, R Bogorad, V Koteliansky, Y Kotelevtsev, C Ffrench-Constant, L Boulter and S J Forbes. Cholangiocytes act as facultative liver stem cells during impaired hepatocyte regeneration. Nature 2017, 547:350-354. PMID: 28700576; PMCID: PMC5522613.
40. Russell, J O, W Y Lu, H Okabe, M Abrams, M Oertel, M Poddar, S Singh, S J Forbes and S P Monga. Hepatocyte-specific beta-catenin deletion during severe liver injury provokes cholangiocytes to differentiate into hepatocytes. Hepatology 2018. PMID: 30215850.
41. Manco, R, L A Clerbaux, S Verhulst, M Bou Nader, C Sempoux, J Ambroise, B Bearzatto, J L Gala, Y Horsmans, L van Grunsven, C Desdouets and I Leclercq. Reactive cholangiocytes differentiate into proliferative hepatocytes with efficient DNA repair in mice with chronic liver injury. J Hepatol 2019, 70:1180-1191. PMID: 30794890.
42. He, J, H Lu, Q Zou and L Luo. Regeneration of liver after extreme hepatocyte loss occurs mainly via biliary transdifferentiation in zebrafish. Gastroenterology 2014, 146:789-800.e788. PMID: 24315993.
43. LeCouter, J, D R Moritz, B Li, G L Phillips, X H Liang, H P Gerber, K J Hillan and N Ferrara. Angiogenesis-independent endothelial protection of liver: role of VEGFR-1. Science 2003, 299:890-893. PMID: 12574630.
44. Bockhorn, M, M Goralski, D Prokofiev, P Dammann, P Grunewald, M Trippler, A Biglarnia, M Kamler, E M Niehues, A Frilling, C E Broelsch and J F Schlaak. VEGF is important for early liver regeneration after partial hepatectomy. J Surg Res 2007, 138:291-299. PMID: 17275844.
45. Ding, B S, D J Nolan, J M Butler, D James, A O Babazadeh, Z Rosenwaks, V Mittal, H Kobayashi, K Shido, D Lyden, T N Sato, S Y Rabbany and S Rafii. Inductive angiocrine signals from sinusoidal endothelium are required for liver regeneration. Nature 2010, 468:310-315. PMID: 21068842; PMCID: 3058628.
46. Yang, L, J Kwon, Y Popov, G B Gajdos, T Ordog, R A Brekken, D Mukhopadhyay, D Schuppan, Y Bi, D Simonetto and V H Shah. Vascular endothelial growth factor promotes fibrosis resolution and repair in mice. Gastroenterology 2014, 146:1339-1350.e1331. PMID: 24503129; PMCID: PMC4001704.
47. Oe, H, T Kaido, A Mon, H Onodera and M Imamura. Hepatocyte growth factor as well as vascular endothelial growth factor gene induction effectively promotes liver regeneration after hepatectomy in Solt-Farber rats. Hepatogastroenterology 2005, 52:1393-1397. PMID: 16201081.
48. Gaudio, E, B Barbaro, D Alvaro, S Glaser, H Francis, Y Ueno, C J Meininger, A Franchitto, P Onori, M Marzioni, S Taffetani, G Fava, G Stoica, J Venter, R Reichenbach, S De Morrow, R Summers and G Alpini. Vascular endothelial growth factor stimulates rat cholangiocyte proliferation via an autocrine mechanism. Gastroenterology 2006, 130:1270-1282. PMID: 16618418.
49. Dianat, N, H Dubois-Pot-Schneider, C Steichen, C Desterke, P Leclerc, A Raveux, L Combettes, A Weber, A Corlu and A Dubart-Kupperschmitt. Generation of functional cholangiocyte-like cells from human pluripotent stem cells and HepaRG cells. Hepatology 2014, 60:700-714. PMID: 24715669; PMCID: PMC4315871.
50. Fabris, L, M Cadamuro, R Fiorotto, T Roskams, C Spirli, S Melero, A Sonzogni, R E Joplin, L Okolicsanyi and M Strazzabosco. Effects of angiogenic factor overexpression by human and rodent cholangiocytes in polycystic liver diseases. Hepatology 2006, 43:1001-1012. PMID: 16628643.
51. Segal, J M, D Kent, D J Wesche, S S Ng, M Serra, B Oules, G Kar, G Emerton, SJI Blackford, S Darmanis, R Miquel, T V Luong, R Yamamoto, A Bonham, W Jassem, N Heaton, A Vigilante, A King, R Sancho, S Teichmann, SR Quake, H Nakauchi and ST Rashid. Single cell analysis of human foetal liver captures the transcriptional profile of hepatobiliary hybrid progenitors. Nat Commun 2019, 10:3350. PMID: 31350390; PMCID: PMC6659636.
52. Weissman, D. mRNA transcript therapy. Expert Rev Vaccines 2015, 14:265-281. PMID: 25359562.
53. Richardson, M M, J R Jonsson, E E Powell, E M Brunt, B A Neuschwander-Tetri, P S Bhathal, J B Dixon, M D Weltman, H Tilg, A R Moschen, D M Purdie, A J Demetris and A D Clouston. Progressive fibrosis in nonalcoholic steatohepatitis: association with altered regeneration and a ductular reaction. Gastroenterology 2007, 133:8090. PMID: 17631134.
54. Marshall, A, S Rushbrook, S E Davies, L S Morris, I S Scott, S L Vowler, N Coleman and G Alexander. Relation between hepatocyte G1 arrest, impaired hepatic regeneration, and fibrosis in chronic hepatitis C virus infection. Gastroenterology 2005, 128:33-42. PMID: 15633121.
55. Bird, T G, M Muller, L Boulter, D F Vincent, R A Ridgway, E Lopez-Guadamillas, W Y Lu, T Jamieson, O Govaere, A D Campbell, S Ferreira-Gonzalez, A M Cole, T Hay, K J Simpson, W Clark, A Hedley, M Clarke, P Gentaz, C Nixon, S Bryce, C Kiourtis, J Sprangers, R J B Nibbs, N Van Rooijen, L Bartholin, S R McGreal, U Apte, S T Barry, J P Iredale, A R Clarke, M Serrano, T A Roskams, O J Sansom and S J Forbes. TGFbeta inhibition restores a regenerative response in acute liver injury by suppressing paracrine senescence. Sci Transl Med 2018, 10. PMID: 30111642.
56. Wiemann, S U, A Satyanarayana, M Tsahuridu, H L Tillmann, L Zender, J Klempnauer, P Flemming, S Franco, M A Blasco, M P Manns and K L Rudolph. Hepatocyte telomere shortening and senescence are general markers of human liver cirrhosis. Fasebj 2002, 16:935-942. PMID: 12087054.
57. Kofman, A V, G Morgan, A Kirschenbaum, J Osbeck, M Hussain, S Swenson and N D Theise. Dose- and time-dependent oval cell reaction in acetaminophen-induced murine liver injury. Hepatology 2005, 41:12521261. PMID: 15880565.
58. Akhurst, B, E J Croager, C A Farley-Roche, J K Ong, M L Dumble, B Knight and G C Yeoh. A modified choline-deficient, ethionine-supplemented diet protocol effectively induces oval cells in mouse liver. Hepatology 2001, 34:519-522. PMID: 11526537.
59. Curado, S, D Y R Stainier and R M Anderson. Nitroreductase-mediated cell/tissue ablation in zebrafish: a spatially and temporally controlled ablation method with applications in developmental and regeneration studies. Nature Protocols 2008, 3:948-954. PMID: ISI: 000258423700003.
60. Curado, S, R M Anderson, B Jungblut, J Mumm, E Schroeter and D Y R Stainier. Conditional targeted cell ablation in zebrafish: A new tool for regeneration studies. Developmental Dynamics 2007, 236:1025-1035. PMID: ISI: 000245883700011.
61. Hoeppner, L H, K N Phoenix, K J Clark, R Bhattacharya, X Gong, T E Sciuto, P Vohra, S Suresh, S Bhattacharya, A M Dvorak, S C Ekker, H F Dvorak, K P Claffey and D Mukhopadhyay. Revealing the role of phospholipase C$\beta$3 in the regulation of VEGF-induced vascular permeability. Blood 2012, 120:2167-2173. PMID: 22674805; PMCID: PMC3447777.
62. Dorrell, C, L Erker, J Schug, J L Kopp, P S Canaday, A J Fox, O Smirnova, A W Duncan, M J Finegold, M Sander, K H Kaestner and M Grompe. Prospective isolation of a bipotential clonogenic liver progenitor cell in 63. Lee, W M. Acetaminophen (APAP) hepatotoxicity-Isn't it time for APAP to go away? J Hepatol 2017, 67:13241331. PMID: 28734939; PMCID: PMC5696016.
64. Yoon, E, A Babar, M Choudhary, M Kutner and N Pyrsopoulos. Acetaminophen-Induced Hepatotoxicity: a Comprehensive Update. Journal of clinical and translational hepatology 2016, 4:131-142. PMID: 27350943; PMCID: PMC4913076.
65. Madisen, L, T A Zwingman, S M Sunkin, S W Oh, H A Zariwala, H Gu, L L Ng, R D Palmiter, M J Hawrylycz, A R Jones, E S Lein and H Zeng. A robust and high-throughput Cre reporting and characterization system for the whole mouse brain. Nature neuroscience 2010, 13:133-140. PMID: 20023653; PMCID: PMC2840225.
66. Bhushan, B, C Walesky, M Manley, T Gallagher, P Borude, G Edwards, S P Monga and U Apte. Pro-regenerative signaling after acetaminophen-induced acute liver injury in mice identified using a novel incremental dose model. Am J Pathol 2014, 184:3013-3025. PMID: 25193591; PMCID: PMC4215032.
67. Glaser, S S, E Gaudio and G Alpini. Vascular factors, angiogenesis and biliary tract disease. Current opinion in gastroenterology 2010, 26:246-250. PMID: 20061944; PMCID: PMC2893138.
68. Glaser, S S, E Gaudio, A Rao, L M Pierce, P Onori, A Franchitto, H L Francis, D E Dostal, J K Venter, S DeMorrow, R Mancinelli, G Carpino, D Alvaro, S E Kopriva, J M Savage and G D Alpini. Morphological and functional heterogeneity of the mouse intrahepatic biliary epithelium. Lab Invest 2009, 89:456-469. PMID: 19204666; PMCID: PMC2662046.
69. Meadows, V, L Kennedy, L Hargrove, J Demieville, F Meng, S Virani, E Reinhart, K Kyritsi, P Invernizzi, Z Yang, N Wu, S Liangpunsakul, G Alpini and H Francis. Downregulation of hepatic stem cell factor by Vivo-Morpholino treatment inhibits mast cell migration and decreases biliary damage/senescence and liver fibrosis in Mdr2(-/-) mice. Biochimica et biophysica acta Molecular basis of disease 2019, 1865:165557. PMID: 31521820; PMCID: PMC6878979.
70. Okabe, H, J Yang, K Sylakowski, M Yovchev, Y Miyagawa, S Nagarajan, M Chikina, M Thompson, M Oertel, H Baba, S P Monga and K N Nejak-Bowen. Wnt signaling regulates hepatobiliary repair following cholestatic liver injury in mice. Hepatology 2016, 64:1652-1666. PMID: 27533619; PMCID: PMC5074849.
71. Zhou, T, N Wu, F Meng, J Venter, T K Giang, H Francis, K Kyritsi, C Wu, A Franchitto, D Alvaro, M Marzioni, P Onori, R Mancinelli, E Gaudio, S Glaser and G Alpini. Knockout of secretin receptor reduces biliary damage and liver fibrosis in Mdr2(-/-) mice by diminishing senescence of cholangiocytes. Lab Invest 2018, 98:1449-1464. PMID: 29977037; PMCID: PMC6214714.
72. Ogawa, M, S Ogawa, C E Bear, S Ahmadi, S Chin, B Li, M Grompe, G Keller, B M Kamath and A Ghanekar. Directed differentiation of cholangiocytes from human pluripotent stem cells. Nat Biotechnol 2015, 33:853-861. PMID: 26167630.
73. Sampaziotis, F, M C de Brito, P Madrigal, A Bertero, K Saeb-Parsy, FAC Soares, E Schrumpf, E Melum, T H Karlsen, J A Bradley, W T Gelson, S Davies, A Baker, A Kaser, G J Alexander, NRF Hannan and L Vallier. Cholangiocytes derived from human induced pluripotent stem cells for disease modeling and drug validation. Nat Biotechnol 2015, 33:845-852. PMID: 26167629; PMCID: PMC4768345.
74. Li, B, C Dorrell, P S Canaday, C Pelz, A Haft, M Finegold and M Grompe. Adult Mouse Liver Contains Two Distinct Populations of Cholangiocytes. Stem Cell Reports 2017, 9:478-489. PMID: 28689996; PMCID: PMC5549808.
75. DeLaForest, A, M Nagaoka, K Si-Tayeb, F K Noto, G Konopka, M A Battle and S A Duncan. HNF4A is essential for specification of hepatic progenitors from human pluripotent stem cells. Development 2011, 138:4143-4153. PMID: 21852396; PMCID: 3171218.
76. Korotkevich G, Sukhov V, Sergushichev A (2019). "Fast gene set enrichment analysis." bioRxiv. doi: 10.1101/060012
77. Abdelghany, A H, M A BaSalamah, S Idris, J Ahmad and B Refaat. The fibrolytic potentials of vitamin D and thymoquinone remedial therapies: insights from liver fibrosis established by CCl4 in rats. Journal of translational medicine 2016, 14:281. PMID: 27681697; PMCID: PMC5041560.
78. Mederacke, I, C C Hsu, J S Troeger, P Huebener, X Mu, D H Dapito, J P Pradere and R F Schwabe. Fate tracing reveals hepatic stellate cells as dominant contributors to liver fibrosis independent of its aetiology. Nat Commun 2013, 4:2823. PMID: 24264436; PMCID: 4059406.
79. Ninov, N, D Hesselson, P Gut, A Zhou, K Fidelin and D Y Stainier. Metabolic regulation of cellular plasticity in the pancreas. Curr Biol 2013, 23:1242-1250. PMID: 23791726; PMCID: PMC4206552.
80. Wang, Y J, J T Park, M J Parsons and S D Leach. Fate mapping of ptf1a-expressing cells during pancreatic organogenesis and regeneration in zebrafish. Dev Dyn 2015, 244:724-735. PMID: 25773748; PMCID: PMC4838417.
81. So, J, M Khaliq, K Evason, N Ninov, B L Martin, D Y R Stainier and D Shin. Wnt/β-catenin signaling controls intrahepatic biliary network formation in zebrafish by regulating notch activity. Hepatology 2018, 67:2352-2366. PMID: 29266316; PMCID: PMC5991997.
82. So, J, M Kim, S H Lee, S Ko, D A Lee, H Park, M Azuma, M J Parsons, D Prober and D Shin. Attenuating the Epidermal Growth Factor Receptor-Extracellular Signal-Regulated Kinase-Sex-Determining Region Y-Box 9 Axis Promotes Liver Progenitor Cell-Mediated Liver Regeneration in Zebrafish. Hepatology 2021, 73:1494-1508. PMID: 32602149; PMCID: PMC7769917.
83. Libbrecht, L, V Desmet, B Van Damme and T Roskams. Deep intralobular extension of human hepatic 'progenitor cells' correlates with parenchymal inflammation in chronic viral hepatitis: can 'progenitor cells' migrate? J Pathol 2000, 192:373-378. PMID: 11054721.
84. Roskams, T, S Q Yang, A Koteish, A Durnez, R DeVos, X Huang, R Achten, C Verslype and A M Diehl. Oxidative stress and oval cell accumulation in mice and humans with alcoholic and nonalcoholic fatty liver disease. Am J Pathol 2003, 163:1301-1311. PMID: 14507639; PMCID: PMC1868311.
85. Jors, S, P Jeliazkova, M Ringelhan, J Thalhammer, S Durl, J Ferrer, M Sander, M Heikenwalder, R M Schmid, J T Siveke and F Geisler. Lineage fate of ductular reactions in liver injury and carcinogenesis. J Clin Invest 2015, 125:2445-2457. PMID: 25915586; PMCID: 4497753.
86. Poisson, J, S Lemoinne, C Boulanger, F Durand, R Moreau, D Valla and P E Rautou. Liver sinusoidal endothelial cells: Physiology and role in liver diseases. J Hepatol 2017, 66:212-227. PMID: 27423426.
87. Novo, E, S Cannito, E Zamara, L Valfrè di Bonzo, A Caligiuri, C Cravanzola, A Compagnone, S Colombatto, F Marra, M Pinzani and M Parola. Proangiogenic cytokines as hypoxia-dependent factors stimulating migration of human hepatic stellate cells. Am J Pathol 2007, 170:1942-1953. PMID: 17525262; PMCID: PMC1899450.
88. Shalaby, F, J Ho, W L Stanford, K D Fischer, A C Schuh, L Schwartz, A Bernstein and J Rossant. A requirement for Flk1 in primitive and definitive hematopoiesis and vasculogenesis. Cell 1997, 89:981-990. PMID: 9200616.
89. Yang, L, L Miao, F Liang, H Huang, X Teng, S Li, J Nuriddinov, M E Selzer and Y Hu. The mTORC1 effectors S6K1 and 4E-B P play different roles in CNS axon regeneration. Nat Commun 2014, 5:5416. PMID: 25382660; PMCID: PMC4228696.
90. Wilkins, B J, W Gong and M Pack. A novel keratin18 promoter that drives reporter gene expression in the intrahepatic and extrahepatic biliary system allows isolation of cell-type specific transcripts from zebrafish liver. Gene Expr Patterns 2014, 14:62-68. PMID: 24394404; PMCID: PMC4677818.
91. Snippert, H J, L G van der Flier, T Sato, J H van Es, M van den Born, C Kroon-Veenboer, N Barker, A M Klein, J van Rheenen, B D Simons and H Clevers. Intestinal crypt homeostasis results from neutral competition between symmetrically dividing Lgr5 stem cells. Cell 2010, 143:134-144. PMID: 20887898.
92. Ding, B S, Z Cao, R Lis, D J Nolan, P Guo, M Simons, M E Penfold, K Shido, S Y Rabbany and S Rafii. Divergent angiocrine signals from vascular niche balance liver regeneration and fibrosis. Nature 2014, 505:97102. PMID: 24256728; PMCID: PMC4142699.
93. Qian, B Z, J Li, H Zhang, T Kitamura, J Zhang, L R Campion, E A Kaiser, L A Snyder and J W Pollard. CCL2 recruits inflammatory monocytes to facilitate breast-tumour metastasis. Nature 2011, 475:222-225. PMID: 21654748; PMCID: PMC3208506.
94. Matsuoka, R L, M Marass, A Avdesh, C S Helker, H M Maischein, A S Grosse, H Kaur, N D Lawson, W Herzog and D Y Stainier. Radial glia regulate vascular patterning around the developing spinal cord. Elife 2016, 5. PMID: 27852438; PMCID: PMC5123865.
95. Covassin, L D, A F Siekmann, M C Kacergis, E Laver, J C Moore, J A Villefranc, B M Weinstein and N D Lawson. A genetic screen for vascular mutants in zebrafish reveals dynamic roles for Vegf/Plcg1 signaling during artery development. Dev Biol 2009, 329:212-226. PMID: 19269286; PMCID: PMC2791107.
96. Mullapudi, S T, G L M Boezio, A Rossi, M Marass, R L Matsuoka, H Matsuda, C S M Helker, Y H C Yang and D Y R Stainier. Disruption of the pancreatic vasculature in zebrafish affects islet architecture and function. Development 2019, 146. PMID: 31597659.
97. Millauer, B, L K Shawver, K H Plate, W Risau and A Ullrich. Glioblastoma growth inhibited in vivo by a dominant-negative Flk-1 mutant. Nature 1994, 367:576-579. PMID: 8107827.
98. Bussmann, J and S Schulte-Merker. Rapid BAC selection for tol2-mediated transgenesis in zebrafish. Development 2011, 138:4327-4332. PMID: 21865323.
99. Ellett, F, L Pase, J W Hayman, A Andrianopoulos and G J Lieschke. mpeg1 promoter transgenes direct macrophage-lineage expression in zebrafish. Blood 2011, 117: e49-56. PMID: 21084707; PMCID: PMC3056479.
100. Espanol-Suner, R, R Carpentier, N Van Hul, V Legry, Y Achouri, S Cordi, P Jacquemin, F Lemaigre and I A Leclercq. Liver progenitor cells yield functional hepatocytes in response to chronic liver injury in mice. Gastroenterology 2012, 143:1564-1575 e1567. PMID: 22922013.
101. Arriazu, E, X Ge, T M Leung, F Magdaleno, A Lopategi, Y Lu, N Kitamura, R Urtasun, N Theise, D J Antoine and N Nieto. Signalling via the osteopontin and high mobility group box-1 axis drives the fibrogenic response to liver injury. Gut 2017, 66:1123-1137. PMID: 26818617; PMCID: PMC5532463.
102. Wang, X, A Lopategi, X Ge, Y Lu, N Kitamura, R Urtasun, T M Leung, M I Fiel and N Nieto. Osteopontin induces ductular reaction contributing to liver fibrosis. Gut 2014, 63:1805-1818. PMID: 24496779.
103. Kawashima, R, S Mochida, A Matsui, Z Y YouLuTu, K Ishikawa, K Toshima, F Yamanobe, M Inao, H Ikeda, A Ohno, S Nagoshi, T Uede and K Fujiwara. Expression of osteopontin in Kupffer cells and hepatic macrophages and Stellate cells in rat liver after carbon tetrachloride intoxication: a possible factor for macrophage migration into hepatic necrotic areas. Biochem Biophys Res Commun 1999, 256:527-531. PMID: 10080931.

Example 6: Growth Hormone-Driven Regeneration in the Sexually Dimorphic Acetaminophen-Injured Liver Model Research Strategy A. Significance Acetaminophen (acetyl-para-aminophenol, APAP) is the most common analgesic and antipyretic in the United States, consumed by over 60 million Americans weekly. Yet, APAP overdose is the most common cause of acute liver failure in the US[2]. Around 30,000 Americans are hospitalized yearly for acute liver failure from APAP overdose, nearly 30% of whom require liver transplants[4]. APAP is extensively conjugated by UDP-glucuronosyl transferases and sulfotransferases in hepatocytes, with conversion to metabolites eliminated in urine. The remaining ~10% of APAP is metabolized by several hepatic cytochromes P450, including CYP2E1, via phase I oxidation, generating N-acetyl-p-benzoquinone imine (NAPQI), a highly reactive, toxic metabolite[5,7]. NAPQI can be neutralized by glutathione (GSH) to form a non-toxic metabolite; however, under APAP overdose conditions, or when exacerbated by oxidative stress, mitochondrial dysfunction, or chronic alcoholism, the rate of GSH replenishment is insufficient, resulting in NAPQI-induced hepatocyte cell death[4,8,9]. The only current treatment for APAP overdose is N-acetyl cysteine (NAC), a precursor for GSH. However, the effectiveness of this treatment rapidly diminishes ten hours after APAP overdose[9,10], when liver toxicity is frequently still asymptomatic[11]. Mortality rates within this time period reach up to 40%[10]. Although NAC increases cellular cysteine concentrations required for GSH synthesis, glutamate-cysteine ligase, required for this conversion, is still a limiting factor[12]. Therefore, alternative therapies to treat APAP intoxication are urgently needed. This proposal addresses this gap by deciphering and leveraging the mechanisms of sexual dimorphism of injury and repair from APAP overdose to establish a sex-hormone-based therapy that accelerates recovery in both sexes.

Clinical studies have reported the prevalence of sexual dimorphism in many human liver diseases, including hepatocellular carcinoma, non-alcoholic fatty liver disease, cirrhosis, non-alcoholic steatohepatitis, and liver graft rejection[13-16]. Menopause increases the prevalence of these diseases in females, consistent with a role for hormonal factors, such as circulating β-estradiol[17]. Clinical data on sexual dimorphism for APAP overdose are inconclusive. While some studies report that women more frequently experience APAP overdose, comprising 60-70% of cases, retrospective investigations have identified confounding factors, such as more frequent drug interactions and a higher reporting bias in women[2, 16, 18] When absolute numbers of APAP intoxication patients are compared to the proportion of patients that go on to experience acute liver failure or require liver transplantation, the numbers are similar in both sexes, with a tendency to increase in males[19-21]. Given the rarity of liver biopsies due to its invasiveness, the question of human sex differences in APAP-induced liver injury remains inconclusive, yet most likely follows the overall tendency seen for all other liver diseases and toxicities, which is a higher prevalence in males.

In mice, over 1,200 sex-biased genes have been identified in the liver, including many genes active in drug, steroid, and fatty acid metabolism[22]. Several studies have reported that females are better protected than males from APAP-mediated liver injury[23-26]. One proposed mechanism for this protection is that APAP increases levels of glutamate-cysteine ligase in females, which produces GSH and neutralizes NAPQI, and hence prevents hepatotoxicity[24, 26]. Furthermore, estrogen increases GSH synthesis[27] and can repress mitochondrial SAB expression in hepatocytes, thereby preventing liver injury from APAP overdose[25]. These protective effects of estrogen may contribute to the sex differences in APAP-induced liver injury either directly, via estrogen receptor ERα expressed in hepatocytes, or indirectly, as is investigated here, via its effect on the sexual dimorphism of pituitary growth hormone (GH) secretion patterns[28-30], which is the major proximal regulator of liver sex differences[22]. Women exhibit a more frequent (near continuous) pituitary GH secretory pattern, whereas a pulsatile GH release pattern is seen in men[31], a pattern also observed in rodents[32-34]. These sex-specific GH secretion patterns directly regulate the sex-specific expression of many hepatic cytochromes P450 and other drug-metabolizing enzymes[22] through complex transcriptional and epigenetic regulatory mechanisms[35, 36]. Importantly, GH and its key mediator, insulin like growth factor 1 (IGF1), have been implicated in responses to various liver injuries and regeneration pathways, and have been tested in clinical trials for efficacy in treating non-alcoholic fatty liver disease and cirrhosis[37-41]. In mice, blocking GH signaling in hepatocytes significantly delays liver regeneration following partial hepatectomy[42]. Consistent with clinical trials using GH to alleviate chronic liver disease, GH also inhibits steatosis and liver injury in mice in a sex-dependent, yet in an IGF1-independent manner[43].

In line with these findings, preliminary data demonstrate that male mice exhibit higher sensitivity to increasing doses of APAP than females, as shown by higher levels of tissue necrosis and cell death for longer periods post-overdose. Moreover, single-cell RNA sequencing (scRNA Seq) analyses reveal that female hepatocytes express significantly higher levels of GH receptor (GHR) and the GH pathway reactome, while female liver endothelial cells (ECs) greater levels of receptor for the key GH pathway effector IGF1, and its associated binding proteins IGFBP4 and IGFBP7, than their counterpart male cells, particularly post-APAP injury. Importantly, GH treatment significantly and rapidly restores liver tissue architecture, mitigates hepatocyte cell death, and increases survival following APAP injury in both sexes. These key data indicate a critical role for the GH pathway in liver regeneration, which can be leveraged by exogenous GH treatment to therapeutically accelerate recovery following APAP overdose. Thus, preliminary data support the scientific premise of this proposal that there is a sexual dimorphism in APAP susceptibility driven by the sexually distinct GH secretion pattern, and consequently, GH can serve as a therapy to accelerate recovery from acute liver failure in both sexes. This proposed study is significant as it has important clinical implications by establishing the therapeutic value of GH therapy to more efficiently treat APAP overdose compared to the standard-of-care NAC treatment. These novel insights into mechanisms underlying sexual dimorphism in APAP overdose therefore contribute to the long-term goal of advancing liver regenerative medicine via GH therapy.

B. Innovation

Figure 59:
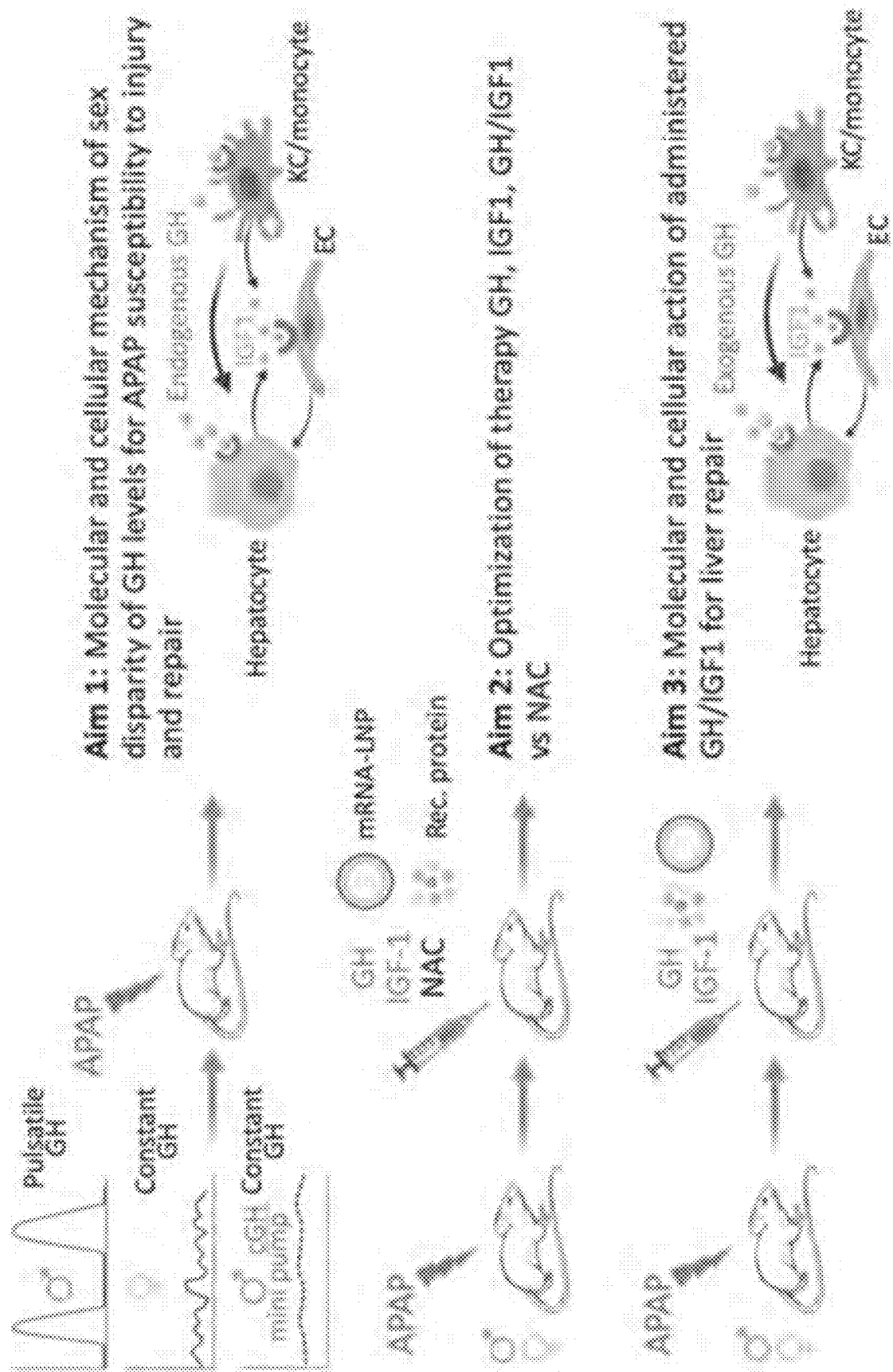
FIG. 59 depicts mechanisms of action of GH pathway on susceptibility and recovery from APAP-induced liver injury. Aim 1 will test whether sex-specific GH level disparity is a key determinant of the susceptibility of APAP-induced injury and subsequent repair. Aim 2 will establish an optimum therapy to treat APAP-induced liver damage by injection of GH, IGF1, and GH/IGF1 vs the standard-of-care NAC therapy. Aim 3 will identify the molecular and cellular actions of GH/IGF1 therapy to promote liver repair after APAP overdose.

Although the NIH and FDA have required researchers and clinicians to sex-match experimental trials since 2014[18, 44], females are still understudied regarding adverse drug reactions, 74% of which occur in the neglected females[16]. Yet still, less than 40% of researchers report the sex of animals used in experimental models[16]. Therefore, it is crucial that drugs as widely used as APAP must be studied in both sexes in order to fully understand the mechanisms that sensitize and/or protect each sex from APAP toxicity and prevent further adverse drug reactions. The proposed research is thus scientifically innovative for the three main reasons: (1) It tackles an unmet clinical need in understanding the cellular and molecular mechanism underlying the sex-based disparity in susceptibility to APAP-induced liver injury and repair mediated by sex-specific differences in plasma GH profiles (FIG. 59 Aim 1). (2) It elucidates the novel therapeutic benefit of GH therapy, and determines the potential role of IGF1, its main mediator, in stimulating liver regeneration to treat APAP overdose and prevent liver failure in both sexes (FIG. 59, Aim 2). (3) It uncovers the molecular and cellular mechanisms driving GH/IGF1 therapy-mediated liver repair and identifies novel downstream therapeutic targets to harness liver regeneration following APAP overdose (FIG. 59, Aim 3). This study lead to a clinically translational innovation by establishing the therapeutic value of GH/IGF1 to treat APAP overdose, especially in later time points when the standard-of-care NAC is not efficient, which is thus a critically unmet clinical need. Innovative experimental strategies include: (1) Comprehensive analyses of the sexually dimorphic liver injury and regenerative response to APAP and of the regenerative benefit of exogenous GH/IGF1 in protecting the liver and accelerating tissue repair. (2) scRNA Seq analyses to define the cell-specific mechanism of action of exogenous GH/IGF1 and identification of GH/IGF1-mediated pathways and candidate factors that are targets to modulate to further prevent injury and accelerate recovery from APAP injury. (3) Novel combination of conditional liver cell-specific knockout mouse models with GH/IGF1 therapy to identify the liver cell types responsible for GH/IGF1 therapy-mediated liver recovery following APAP injury. (4) Versatility of using complementary recombinant protein and mRNA-LNP technologies to deliver GH and IGF-1 into the liver to accelerate regeneration. (5) The use of clinically relevant, non-integrative mRNA-LNP, whose safety has been clinically validated[45] and is currently used for COVID-19 mRNA vaccines, to transiently deliver GH, IGF1 in vivo.

C. Approach

C1. Preliminary Data

Figure 60C:
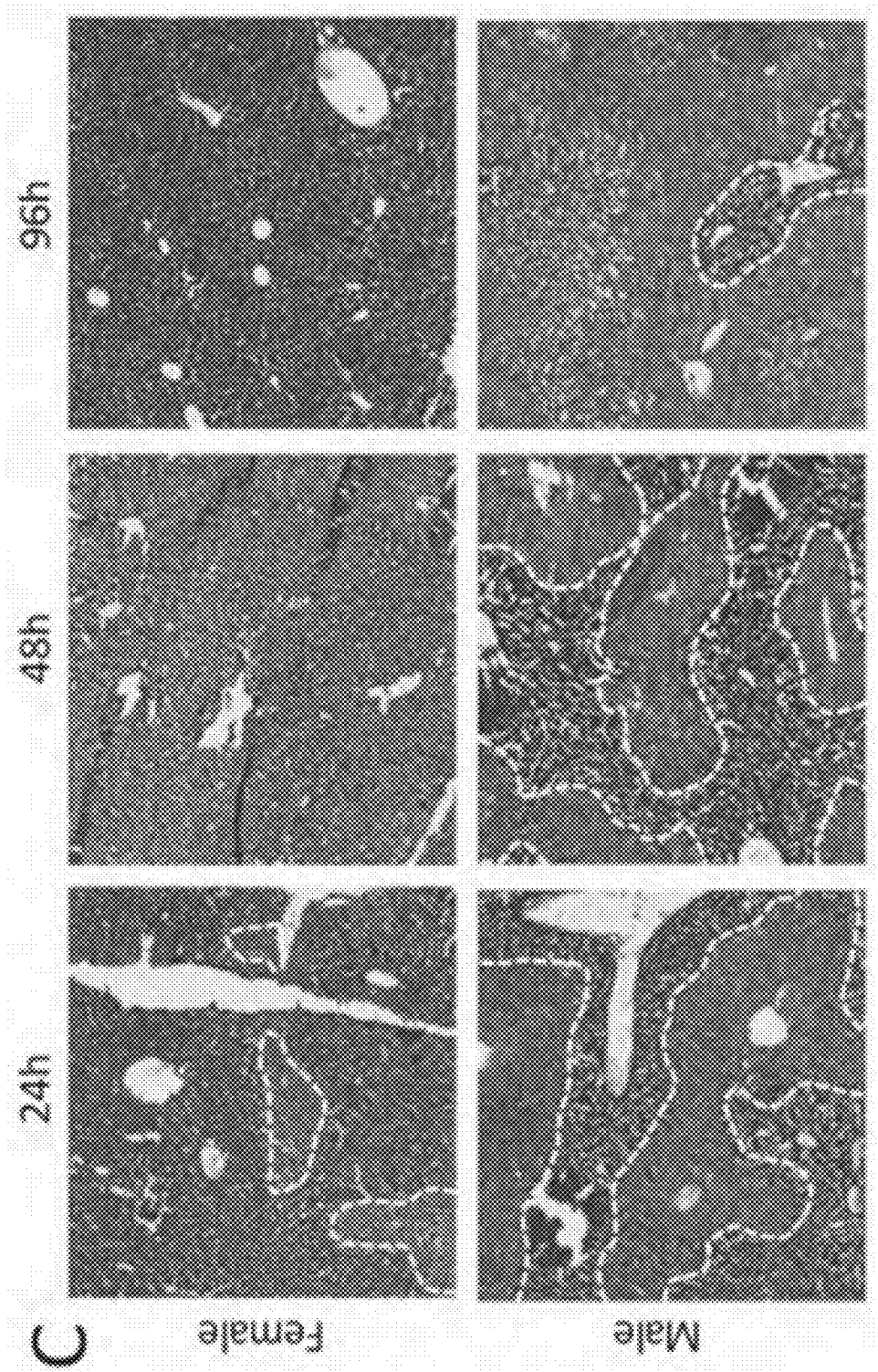
Figure 60D:
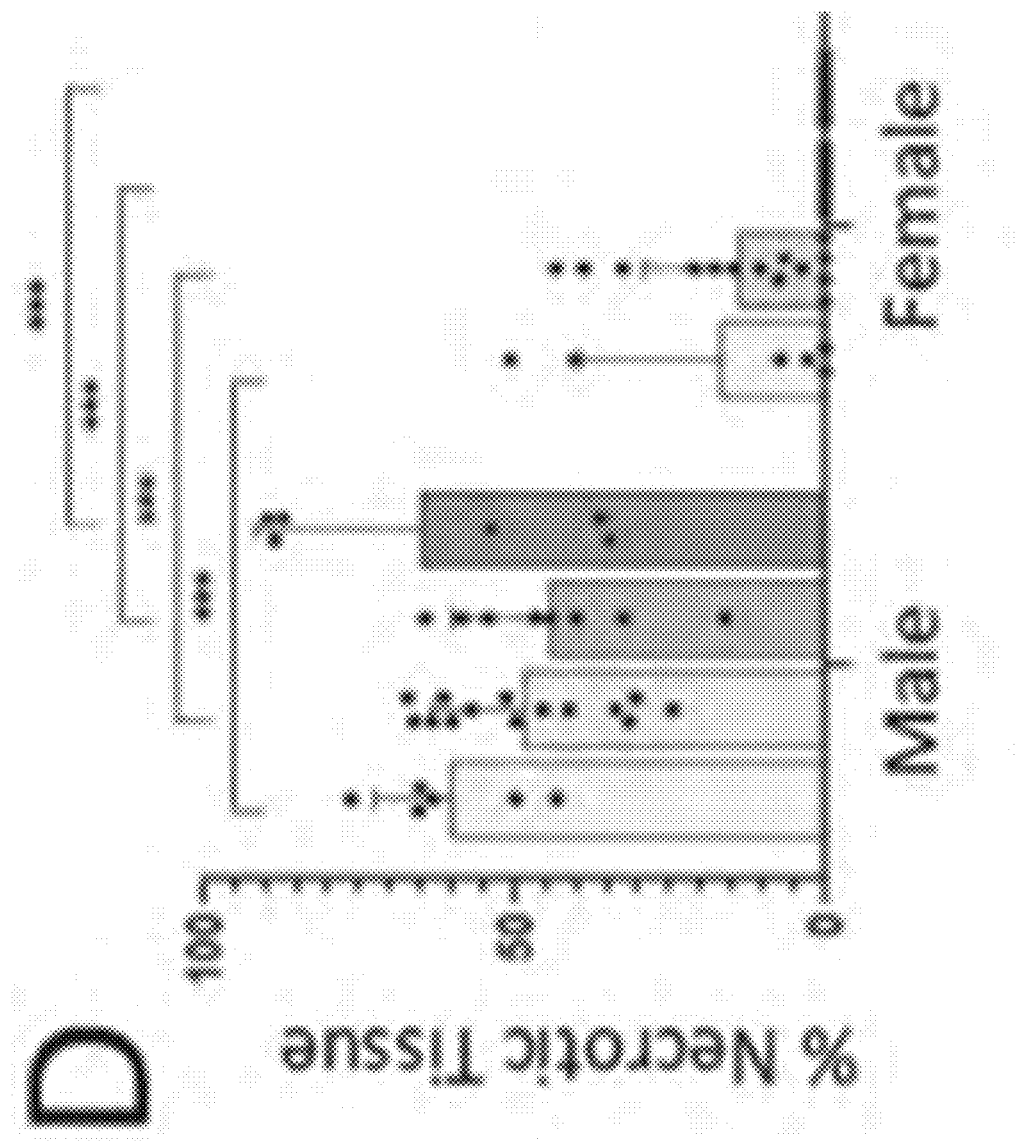
Figure 60E:
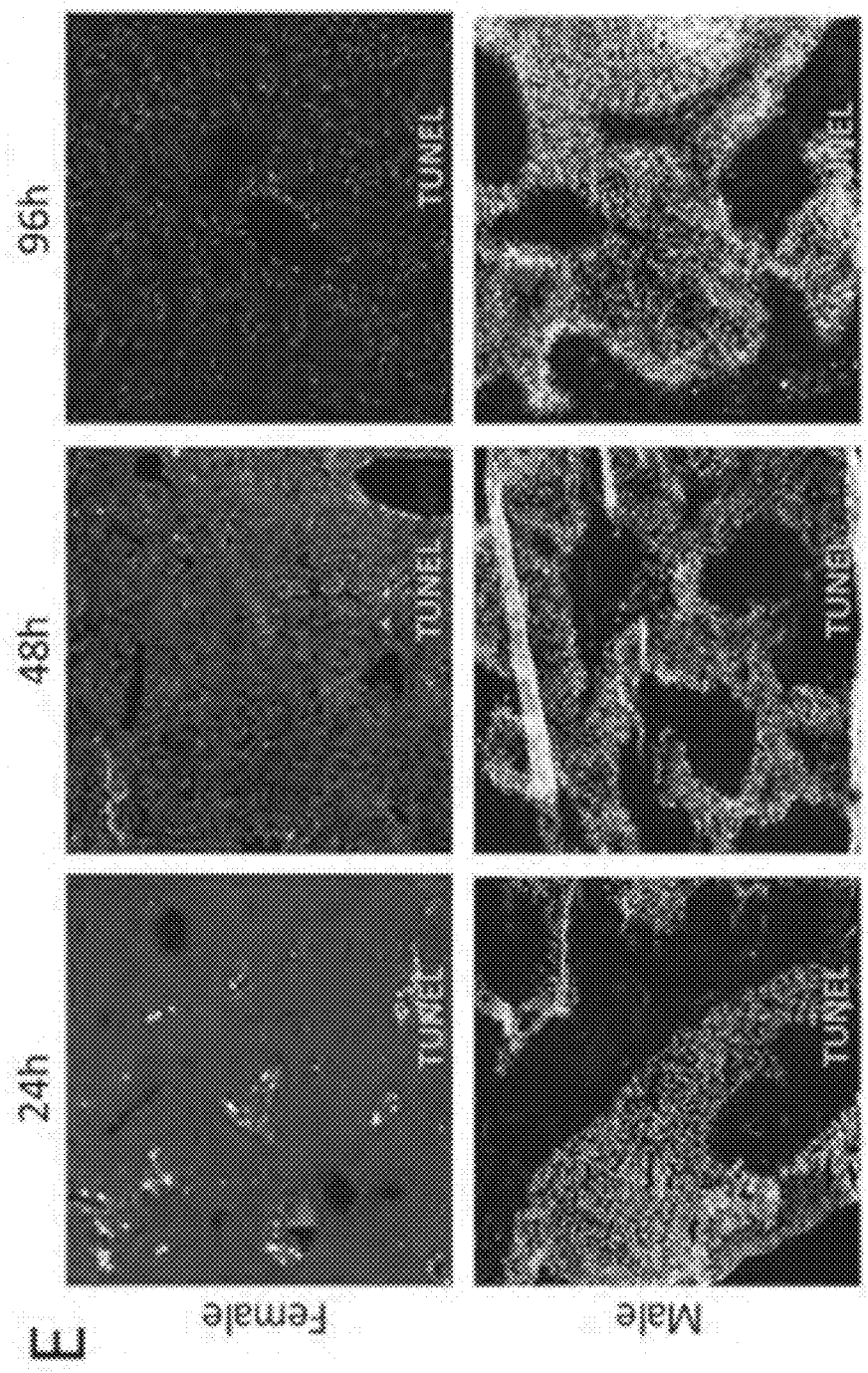
Figures 60F, 60G:
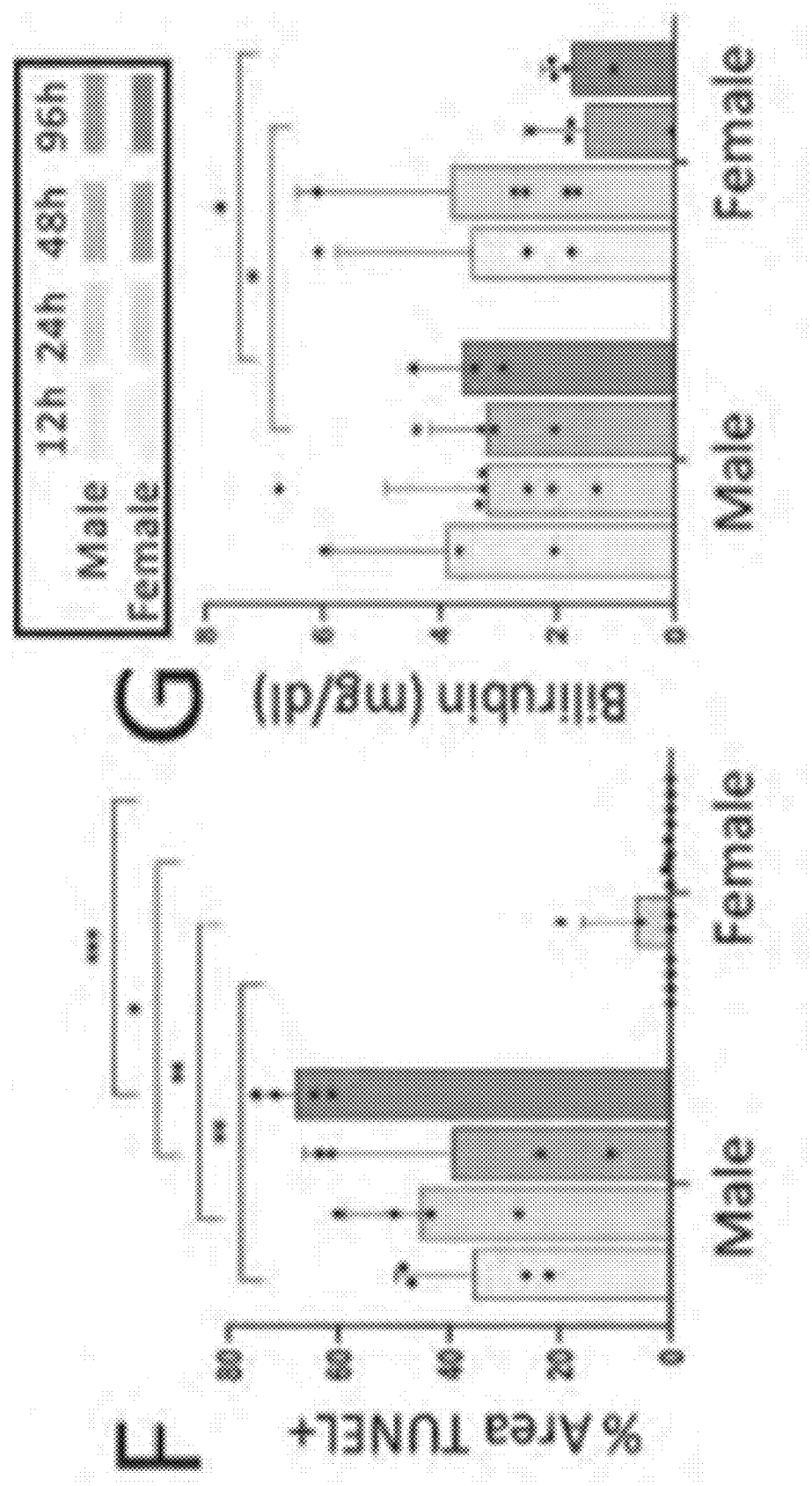

1. Sex differences in APAP-induced liver necrosis, hepatocyte apoptosis and tissue recovery. In dose-response experiments in both sexes using APAP doses from 300-650 mg/kg, previously validated by others[46, 47] 400 mg/kg APAP is shown to induce injury in both sexes without lethality up to 96 hours after APAP administration. Sexually mature male and female (12-15-week-old) C57BL/6 mice were injected intraperitoneally (IP) with APAP (or PBS vehicle control), and euthanized 12, 24, 48, and 96 hours later. Mice were subjected to the Whitten effect, by replacing the female cage bedding with soiled male bedding to normalize estrus cycles of female mice[48], as variability in estrogen levels may impact liver regeneration. Female and male mice were then fasted for 12 hours prior to APAP injection to bring liver metabolism to a baseline level for all mice and thus normalize injury[46] (FIG. 60A). Serum alanine aminotransferase (ALT) levels, indicative of liver damage, were consistently higher in males than in females at each time point analyzed (FIG. 60B). Hematoxylin and eosin (H&E) staining indicated acute necrosis in central vein areas in both sexes 24 hours after APAP injection, although in a milder manner in females than in males. Moreover, while female livers fully recovered by 48 hours, male livers progressed in injury over time (FIG. 60C), and at a significantly higher level than females at all-time points (FIG. 60D). Cell death was significantly increased in male livers compared to female livers, and progressed over time (FIGS. 60E and 60F). Consistent with these histology data, serum bilirubin persisted for 96 hours in males but decreased after 48 hours in females, suggesting recovery in females not seen in males (FIG. 60G). Altogether, males are more susceptible than females to APAP as characterized by unresolved necrosis and apoptosis that most likely prevent liver regeneration. These data support Aim 1, which specifically tests whether sexual dimorphism in susceptibility to APAP is mediated by sex-specific plasma GH profiles.

Figure 61:
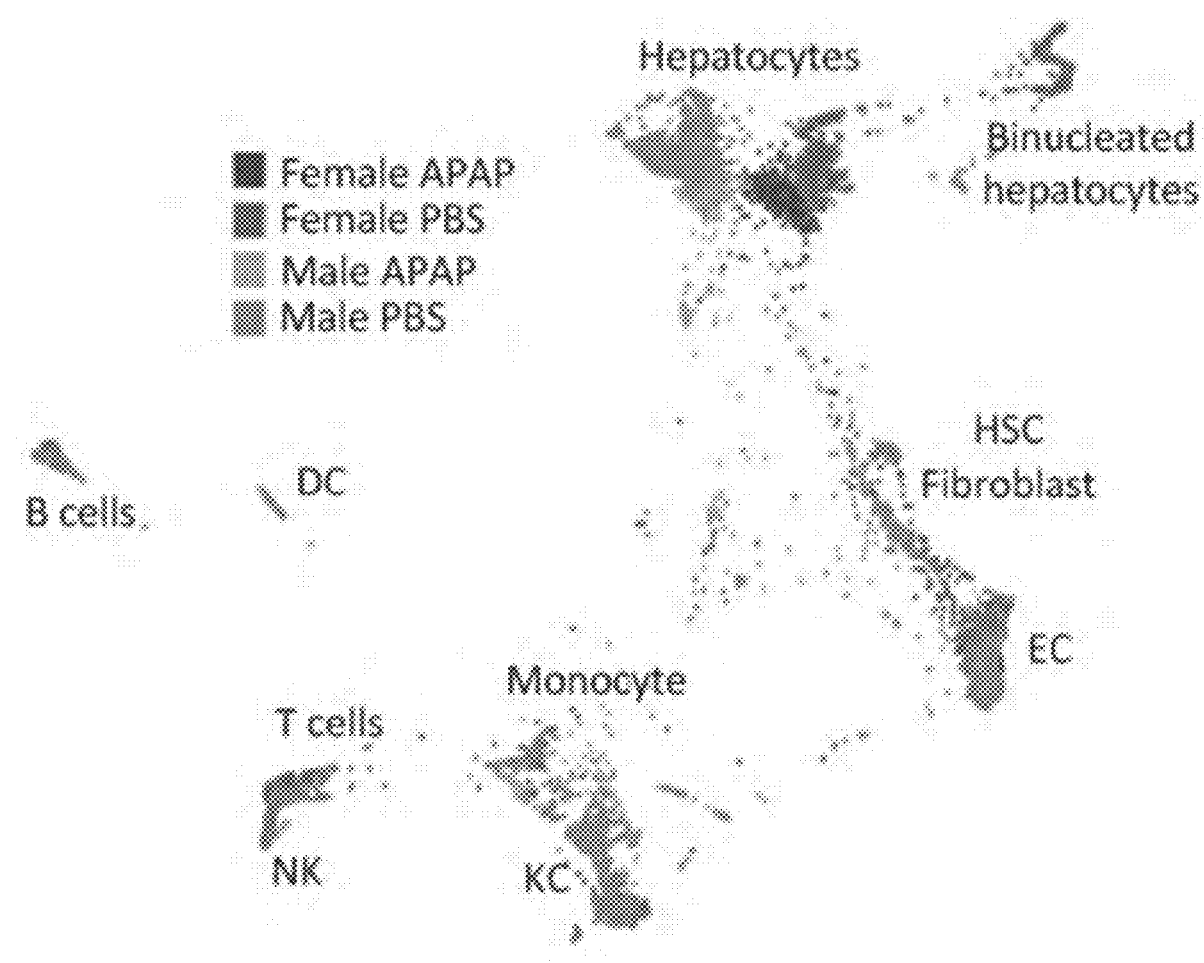
FIG. 61 depicts SPRING plot of scRNA Seq analyses of liver cells from APAP- and PBS-treated males and females. 10 putative cell types are resolved.
Figure 62A:
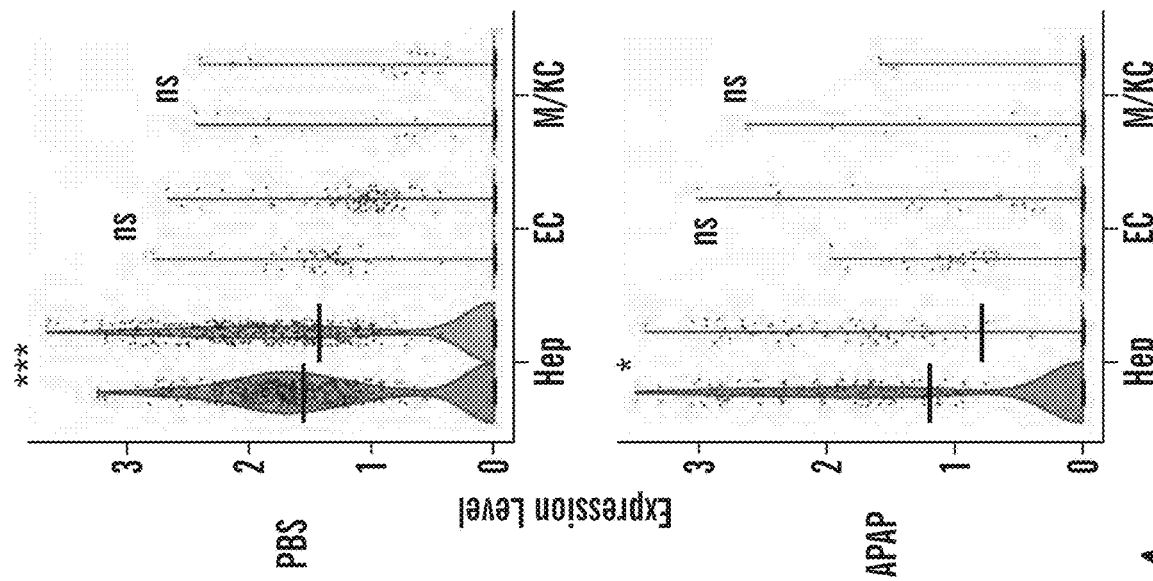
FIGS. 62A-62G depict APAP triggers greater activity of GHR in female hepatocytes and ECs compared to their male counterparts.
Figure 62A:
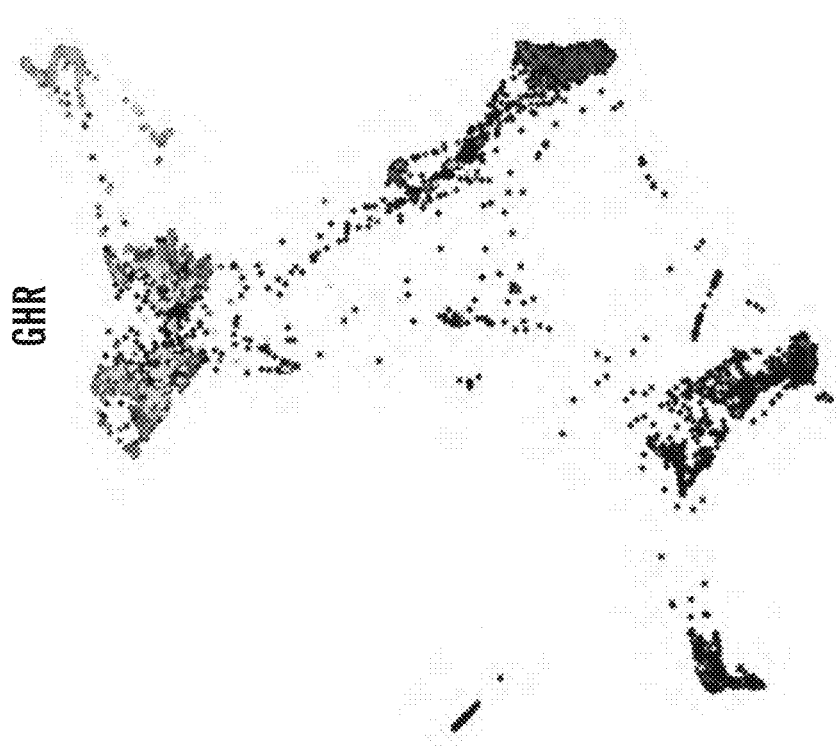
Figure 62B:
Figure 62B:
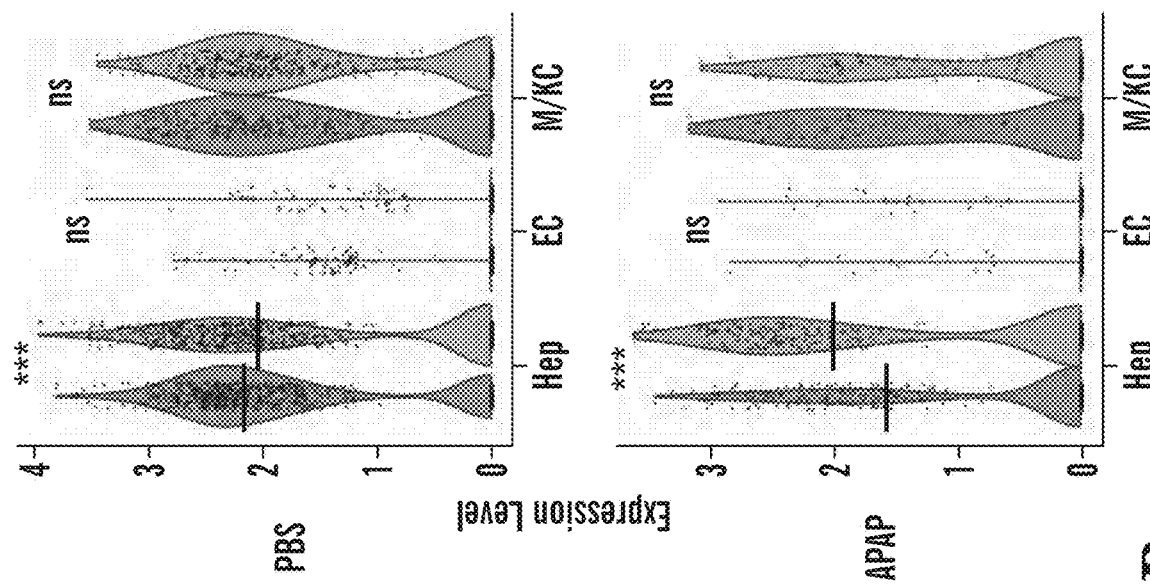
Figure 62C:
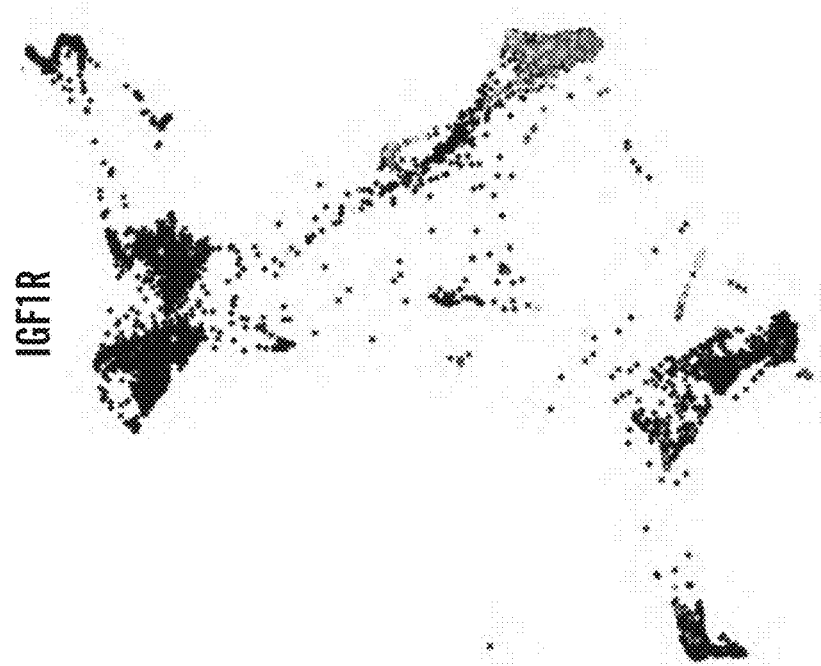
Figure 62C:
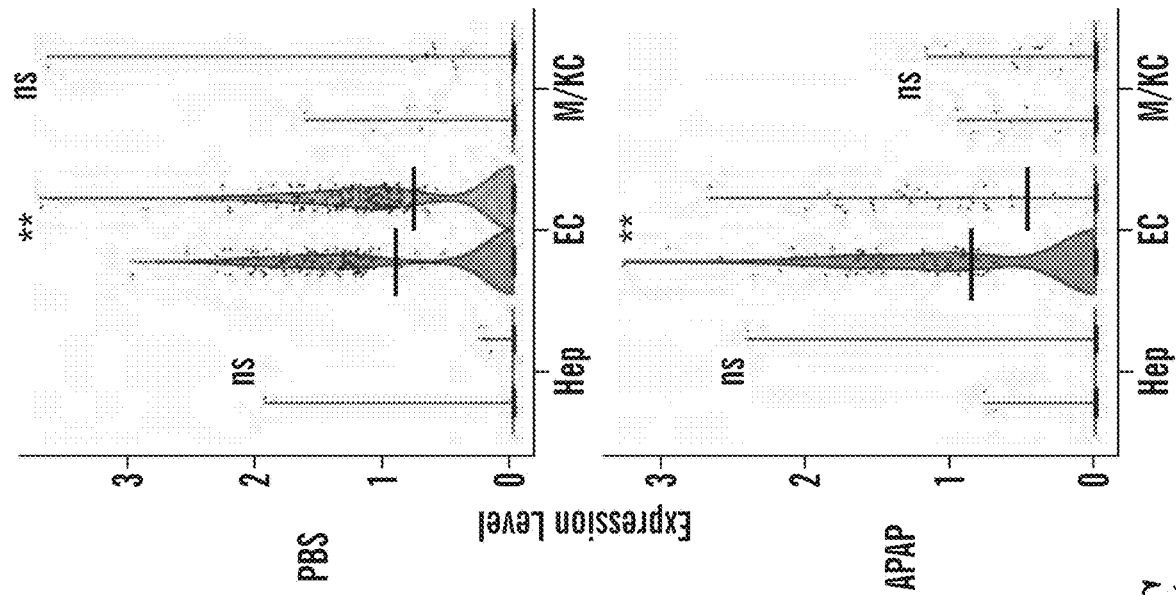
Figure 62D:
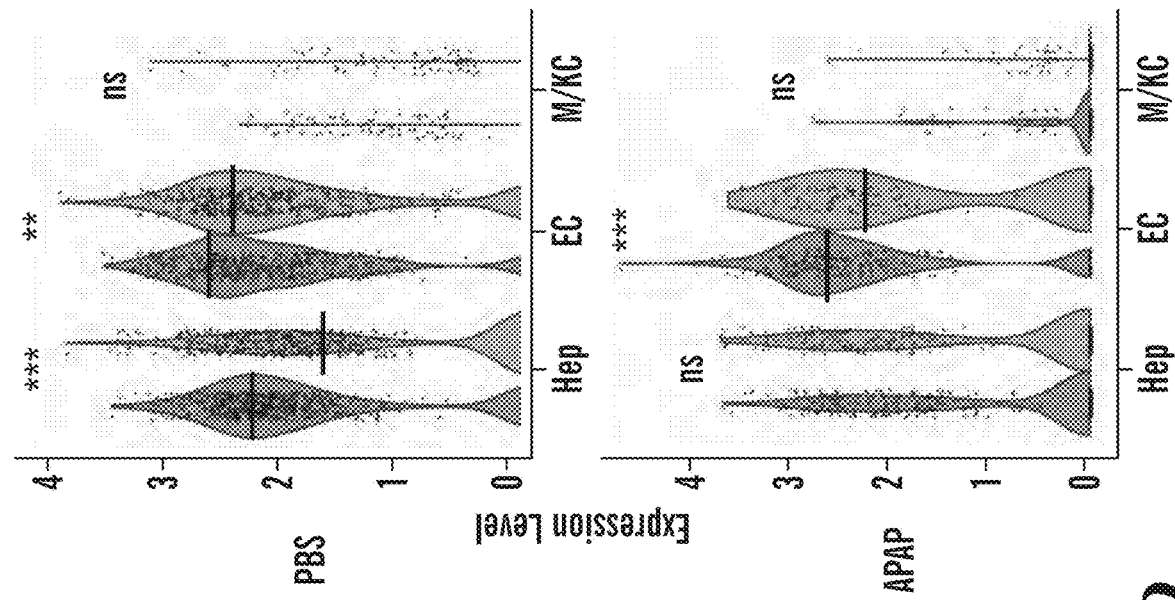
Figure 62D:
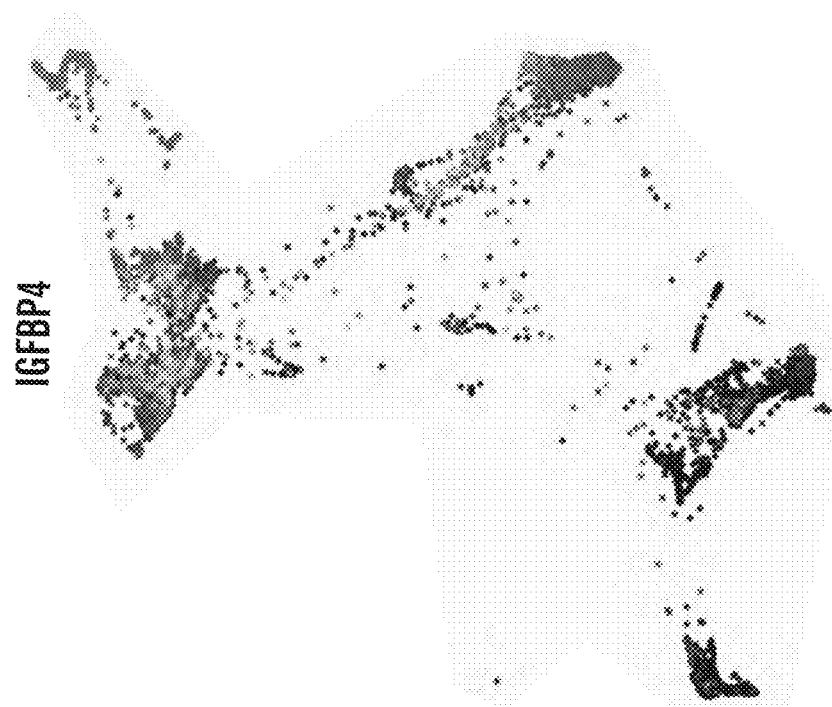
Figure 62E:
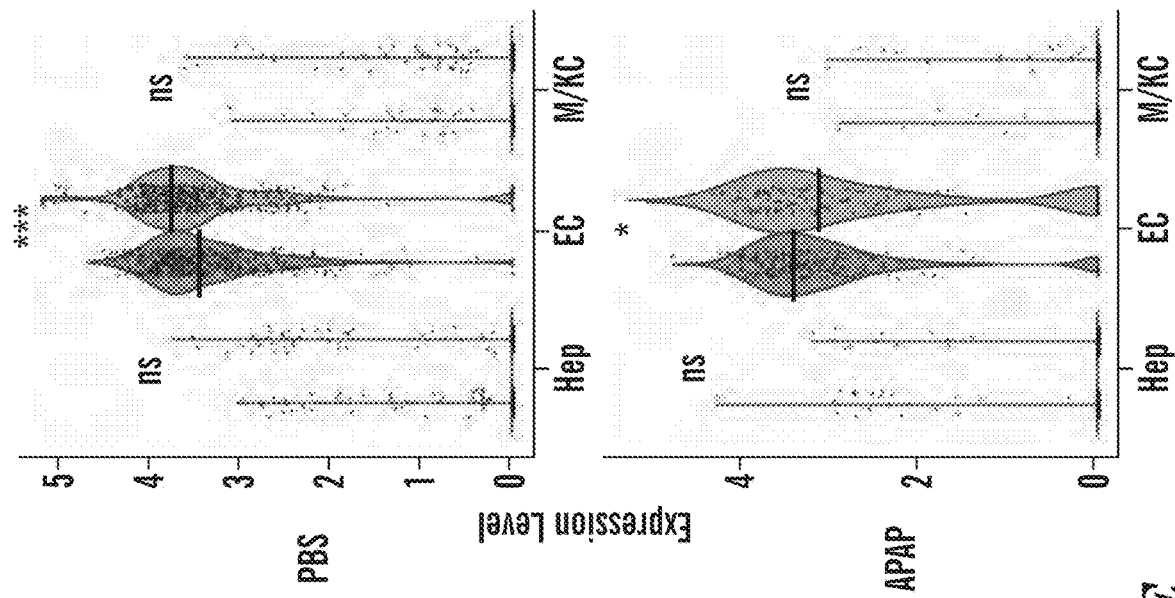
Figure 62E:
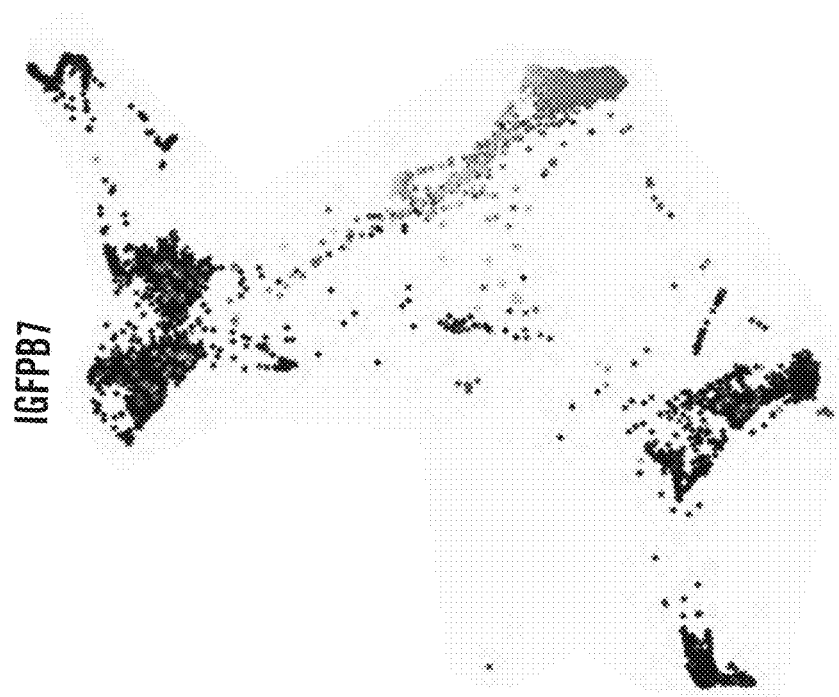
Figure 62F:
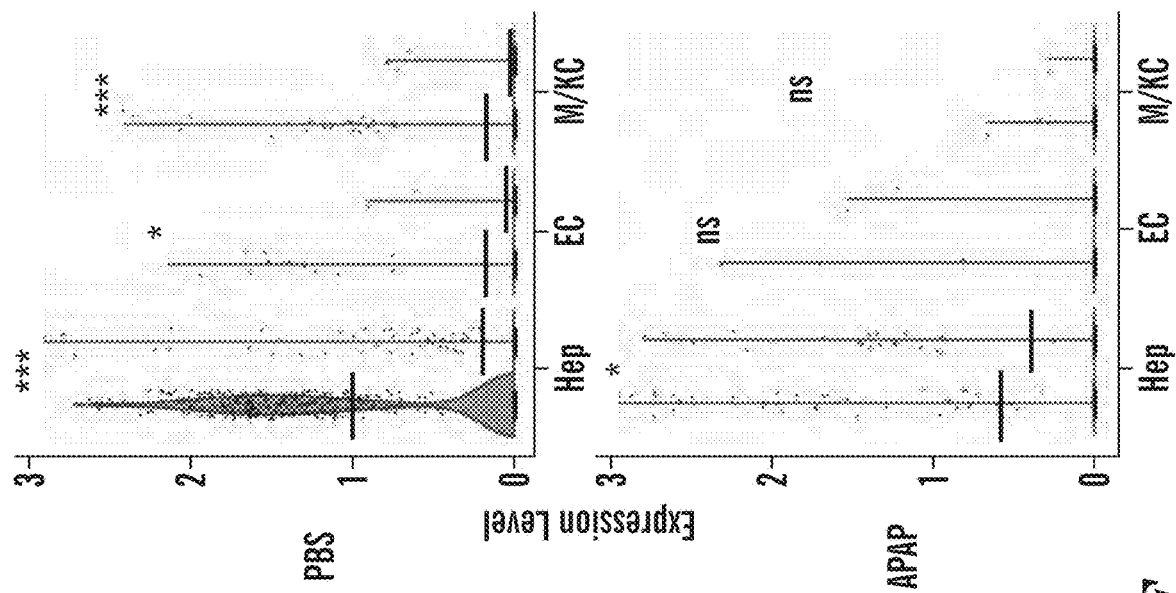
Figure 62F:
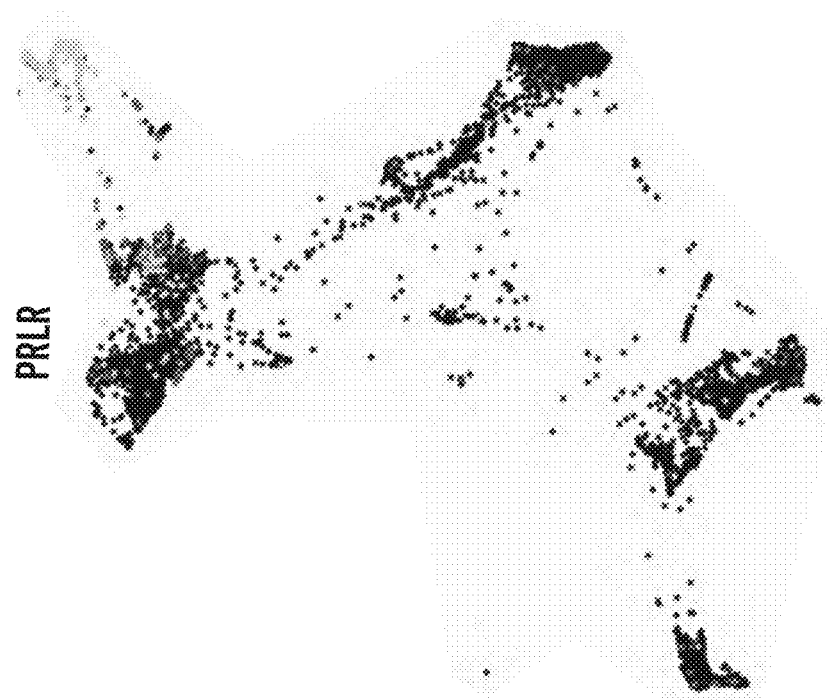
Figure 62G:
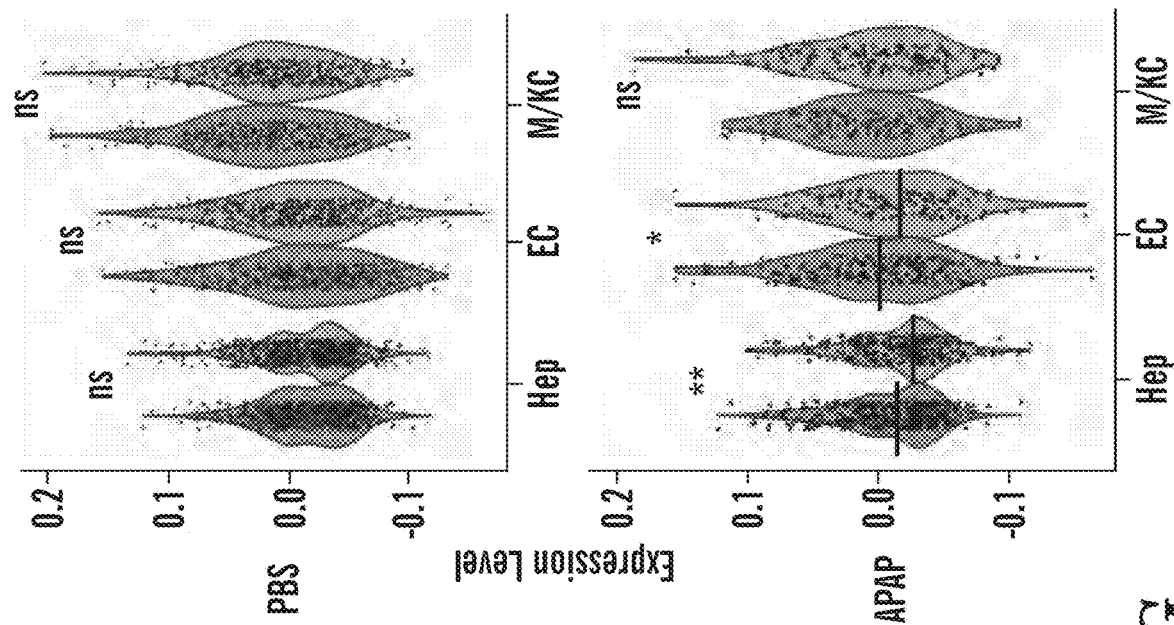
Figure 62G:
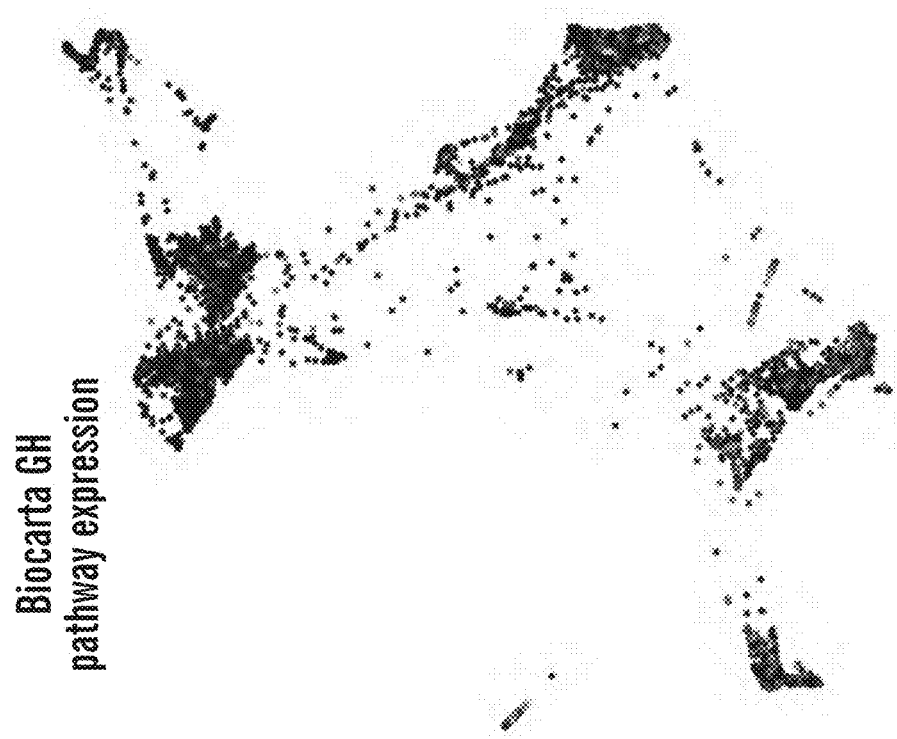

2. APAP triggers greater activity of GHR in female hepatocytes and subsequently GHR effector activity in female as compared to male ECs: Liver single cell suspensions were collected from 4 mice (2 males, 2 females) 48 hours after injection of either 400 mg/kg APAP or PBS. The rationale for using this intermediate dose at that time point was to induce significant injury in both sexes to capture the differential regenerative response without triggering death (FIG. 60). Liver cells were collected, to obtain a mix of ~40% of hepatocytes and ~60% of non-parenchymal cells (NPC) (FIG. 61). Single cells were captured for sequencing library preparation at the BU scRNA Seq facility, and transcriptomic libraries were prepared using a 10× Genomics Chromium Single Cell 3' System. Barcoded sequencing libraries were loaded on a NextSeq500 (Illumina) with a custom sequencing setting (26 bp for Read 1, 98 bp for Read 2), to obtain a sequencing depth of ~100K reads per cell. All four samples were sequenced in parallel to minimize batch-to-batch variability. Cell doublets, cells containing >25% mitochondrial RNA content and cells with less than 300 genes detected (indicative of dying cells) were excluded from analysis. 3,000 cells per sample were targeted. Samples were combined and analyzed using the Seurat package, and imported into SPRING software[50] for interactive visualization (FIG. 61). Data from the 4 samples were normalized to account for differences in sequencing depth and degradation. Interestingly, hepatocytes (Heps) and endothelial cells (ECs) segregated separately based on their sex prior to injury, then shifted closer to the other sex following injury. Previous studies using bulk RNA Seq analyses have reported sex-dimorphism of liver transcriptome[35, 51, 52] yet the cell types contributing to the disparity are not fully identified. Single cell data reveal that not only hepatocytes harbor distinct transcriptomes based on sex, but ECs do as well. Specifically, violin plots show that female hepatocytes express significantly higher levels of GHR than male cells, both before and after APAP injection. Only a small percentage of ECs and Kupffer cells (KC)/monocytes express GHR in both sexes. Importantly, the enrichment in Biocarta gene sets related to GHR pathway activation was greater in hepatocytes and ECs from female mice than from male mice after APAP injection (FIGS. 62A, 62G). Expression levels of IGF1, a key mediator of the GH pathway activation[53], were higher in female hepatocytes prior to APAP injection, however this pattern was reversed after APAP administration. IGF1 expression was the highest in KC/monocytes, both prior and after injury, but without a sex difference. Importantly, IGF1R was most highly expressed in ECs, where its levels were significantly higher in females than in males. Together, these data suggest that GH-driven liver protection and regeneration involves a complex cell crosstalk between hepatocytes, ECs and KC/monocytes, with hepatocytes and KC/monocytes being the main sources of IGF1, and ECs the main cell type for IGF1R-mediated responses. Given these studies use human GH, to recapitulate more closely a human clinical scenario, the inventors examined prolactin receptor (PRLR) expression in male and female livers, as human GH binds to both GHR and PRLR, as opposed to mouse GH that exclusively binds to GHR[54]. PRLR expression is significantly higher in female hepatocytes, ECs and KC/monocytes than in male cells, and that PRLR levels remain significantly higher in female hepatocytes than in male hepatocytes after APAP injury (FIGS. 62A-62F). These data demonstrate that PRLR activation in females may likely contribute to the effect of exogenous human GH used in Aim 2 in mitigating liver injury and promoting liver repair after APAP overdose. The inventors further test the contribution of PRLR in this process in the alternative experimental design proposed in Aim 3. Overall, the scRNA Seq preliminary data indicate a sexual dimorphism for the APAP-mediated GH-IGF1 axis expression and activation is associated with accelerated liver recovery (FIG. 60) in females. Aim 1 and Aim 3 further dissect the cell-cell crosstalk between hepatocytes, ECs and KC/monocytes in the distinct endogenous GH level-driven susceptibility to APAP (Aim 1) and following exogenous GH/IGF1 therapy (Aim 3).

Figures 63A, 63B:
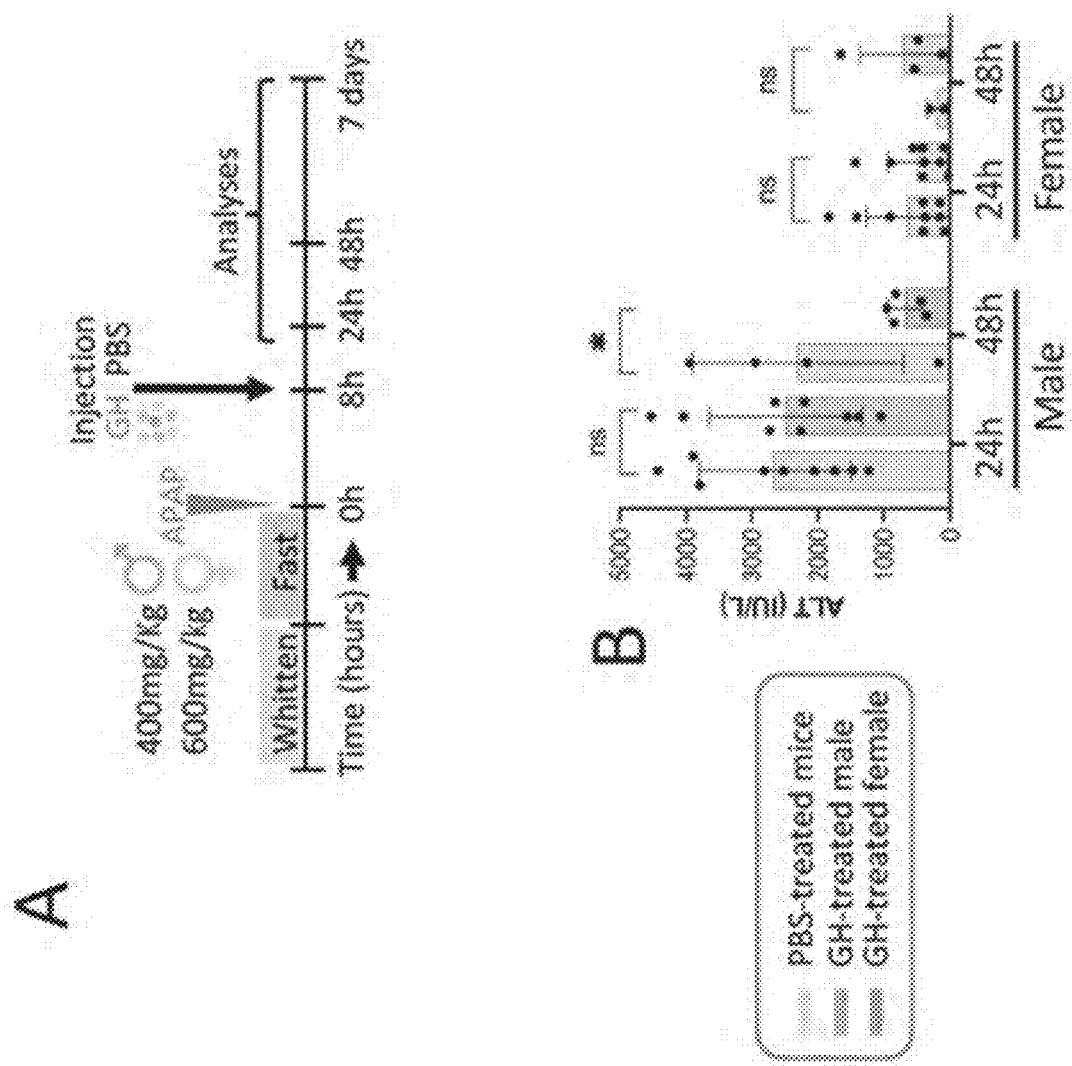
FIGS. 63A-63F depict a single injection of GH sharply reduces injury and accelerates liver regeneration following similar level of APAP-induced liver damage in both sexes.
Figure 63C:
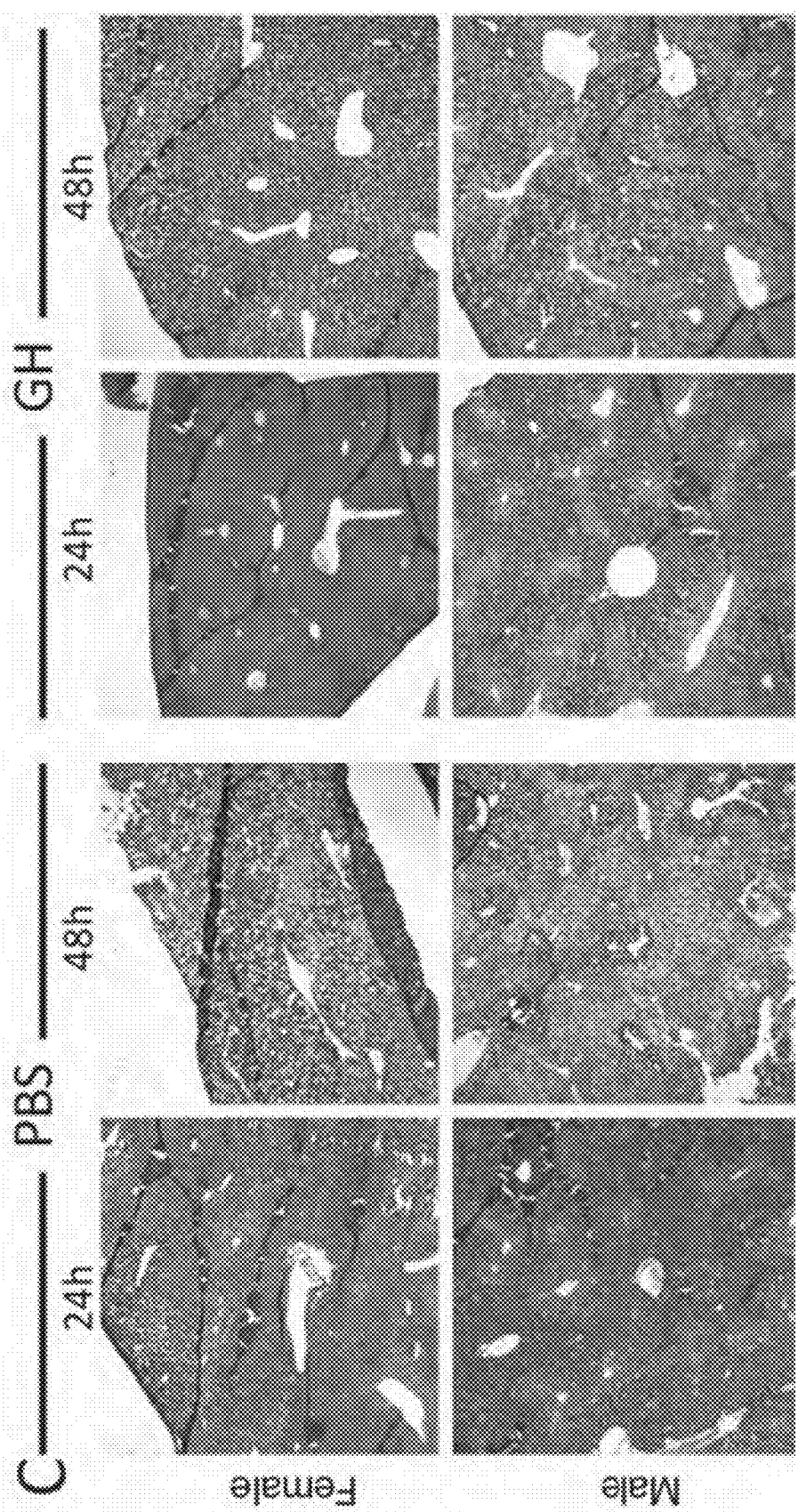
Figure 63D:
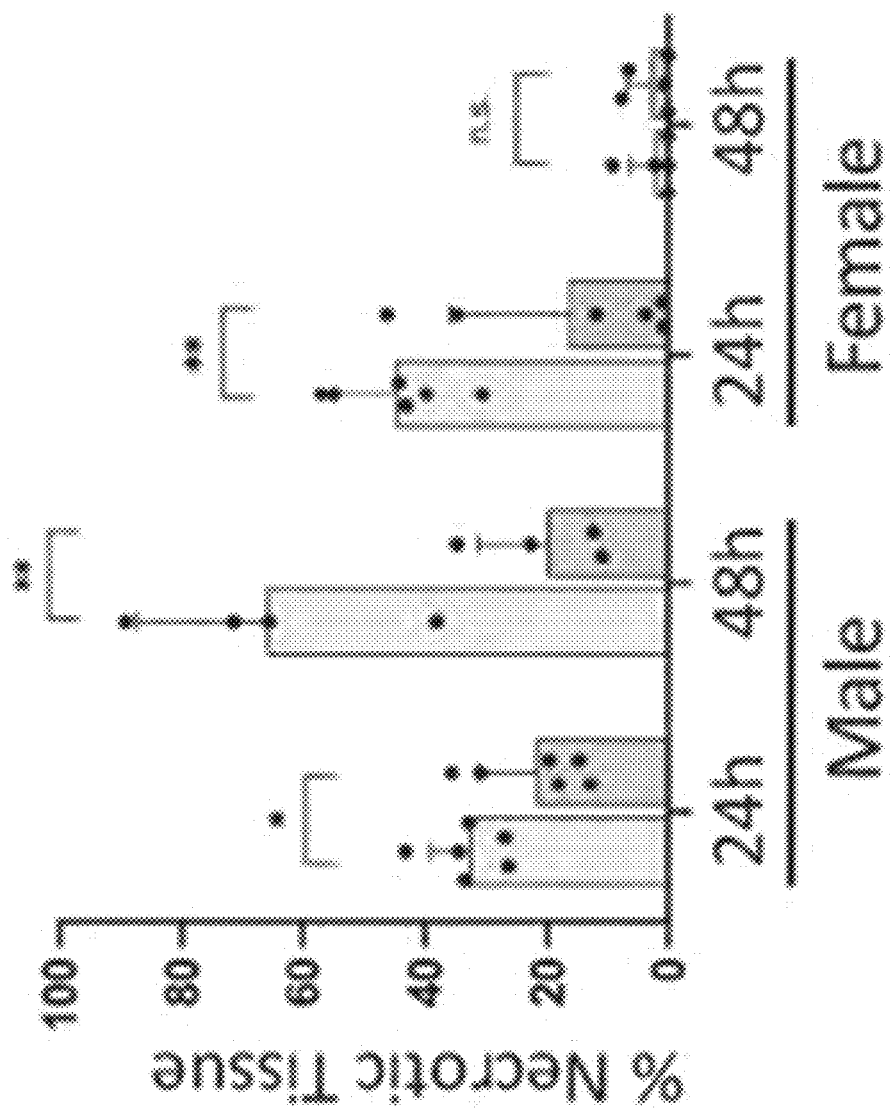
Figure 63E:
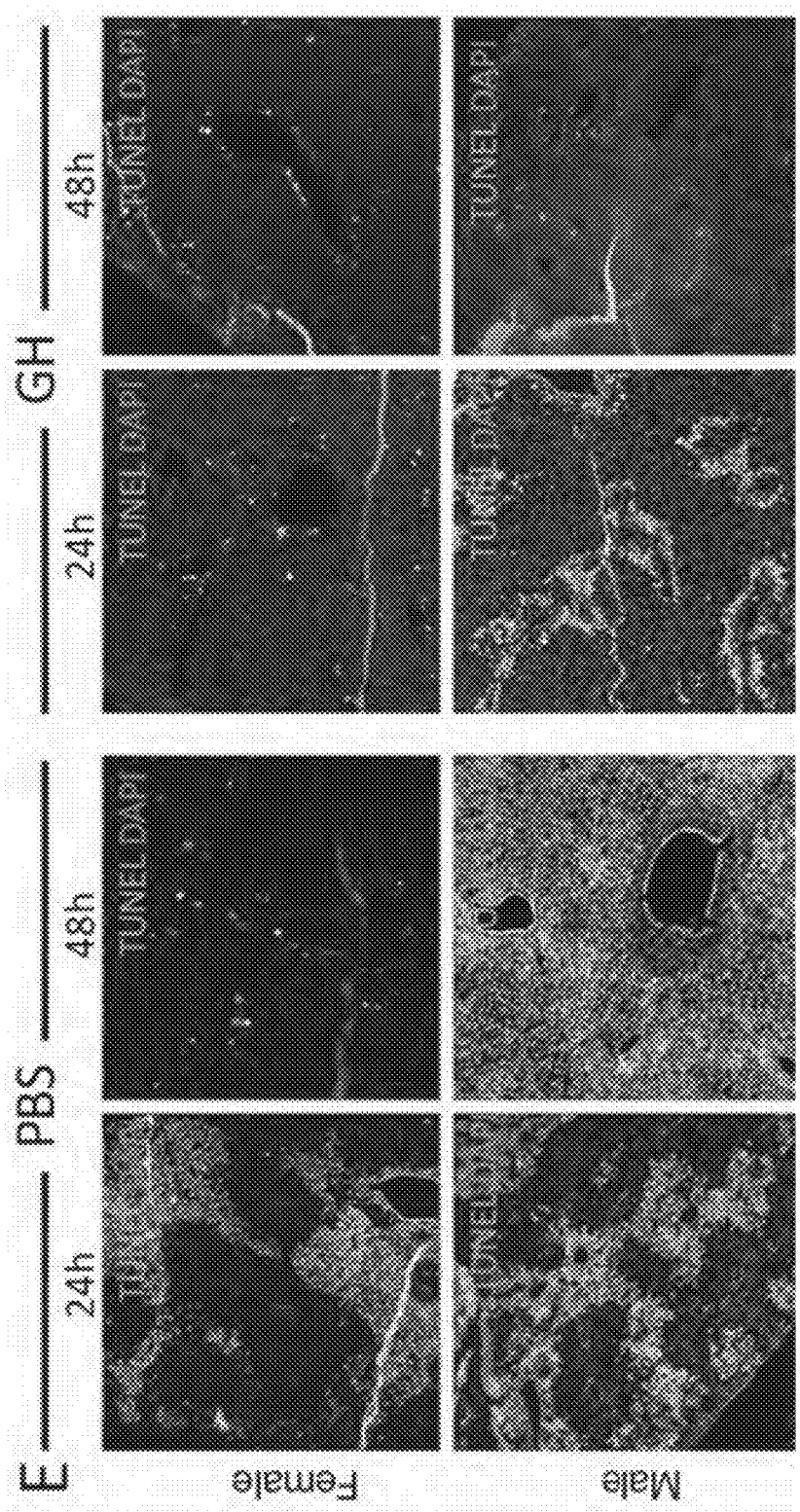
Figure 63F:
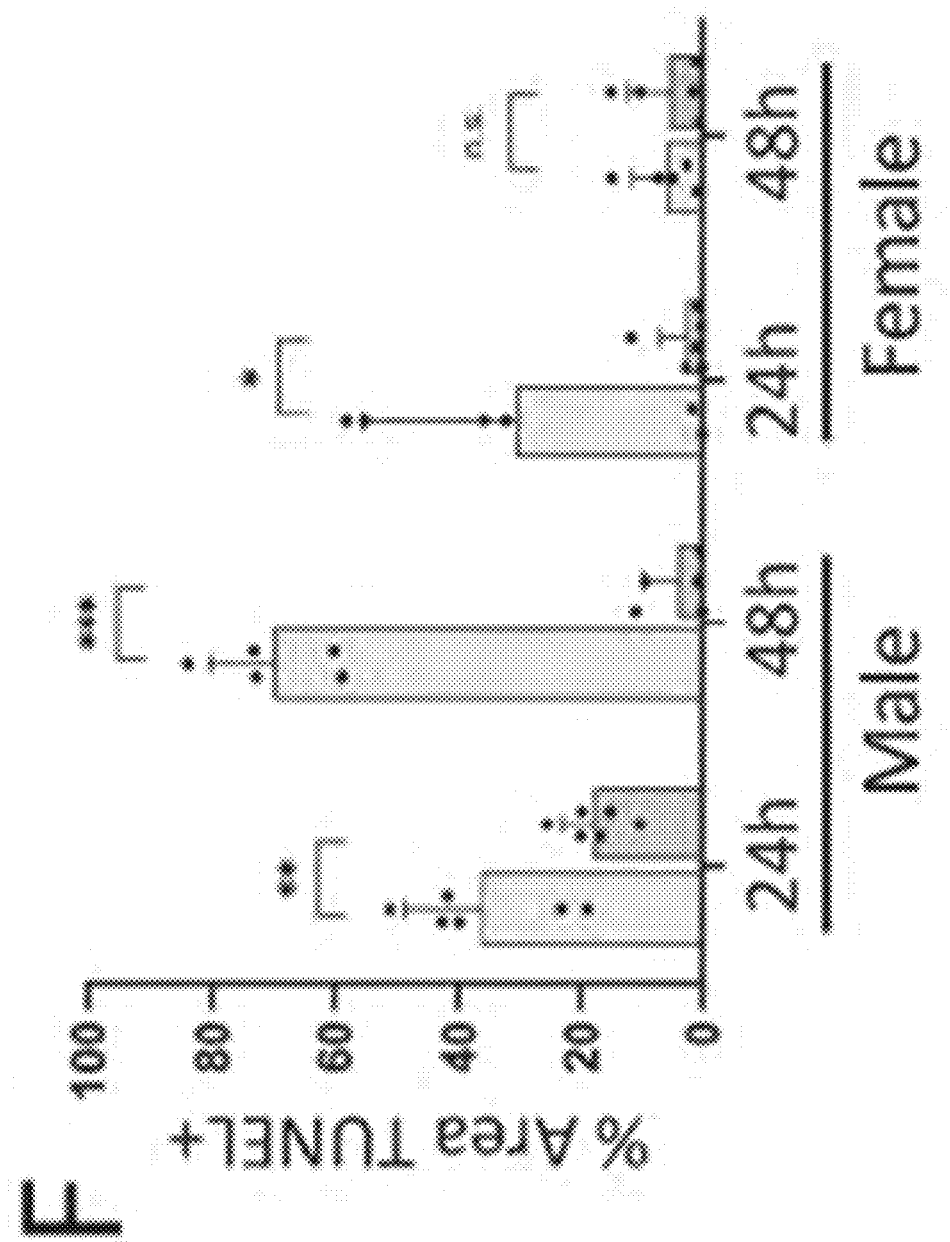

3. Single injection of GH sharply reduces injury and accelerates liver regeneration when using sex-specific APAP doses, to obtain a similar level of APAP-induced liver damage in each sex: The rationale for using human GH to induce liver recovery is to better emulate a clinical scenario in which human GH is used. Mechanistically, human GH binds to both GHR and PRLR[55], which is unique to human GH, as rat/mouse GH only bind GHR receptor. Aim 2 and Aim 3 determine the therapeutic benefit of GH to treat APAP overdose and identify the associated mechanisms. Therefore, both Aim 2 and Aim 3 use human GH to carefully recapitulate the mode of action of GH in human. Data in FIG. 63 demonstrate the effectiveness of human GH on murine GHR, demonstrating that interspecies specificity will not be an issue for the proposed studies, as validated by others[56-59]. Given that preferential activation of GHR by female cells following APAP injury was associated with a better liver recovery, the inventors tested the ability of exogenous human recombinant GH to mitigate injury and accelerate liver repair when female and male livers were similarly damaged by APAP. To achieve this, male and female mice were injected with sex-appropriate sub-lethal doses of APAP (400 mg/kg and 600 mg/kg, respectively), and 8 hours later were given a single subcutaneous injection of recombinant human GH (2.5 mg/kg in PBS[56-59]) or PBS control. Mice were euthanized 24 hours and 48 hours after APAP injection, or observed for up to 7 days to compare survival between the sexes in the presence and absence of GH (FIG. 63A). Serum ALT levels were significantly lower 48 h after APAP administration in GH-treated males compared to those in APAP+PBS-treated males (FIG. 63B), an effect that was not seen in females, most likely due to ALT levels already being low in females at these time points. Although ALT female levels were low 24 hours after APAP administration, H&E and TUNEL assays indicated a similar liver injury in both sexes at this early time point as expected (FIGS. 63C, 63D, 63, 63F). Importantly, both histology assays (FIGS. 63C, 63D, 63E, 63F) showed that GH significantly decreased liver injury and accelerated liver regeneration in both male and female mice compared to PBS-treated control mice with time, with females recovering faster than males. Thus, GH treatment sharply and significantly decreased liver injury and accelerated regeneration when given 8 hours post-APAP, in both sexes. Moreover, preliminary 7-day survival data show that of 5 APAP-treated mice in each sex, 1 PBS-treated female died (80% survival) and 2 PBS-treated males died (60% survival), while GH increased mouse survival up to 100% for females and 80% to males. Aim 2 tests whether human GH therapy, alone or combined with IGF1 after optimization, is superior to the clinical standard-of-care NAC, and Aim 3 thoroughly dissects the cellular and molecular mechanisms by which GH/IGF1 accelerates liver recovery.

Figures 64A, 64B:
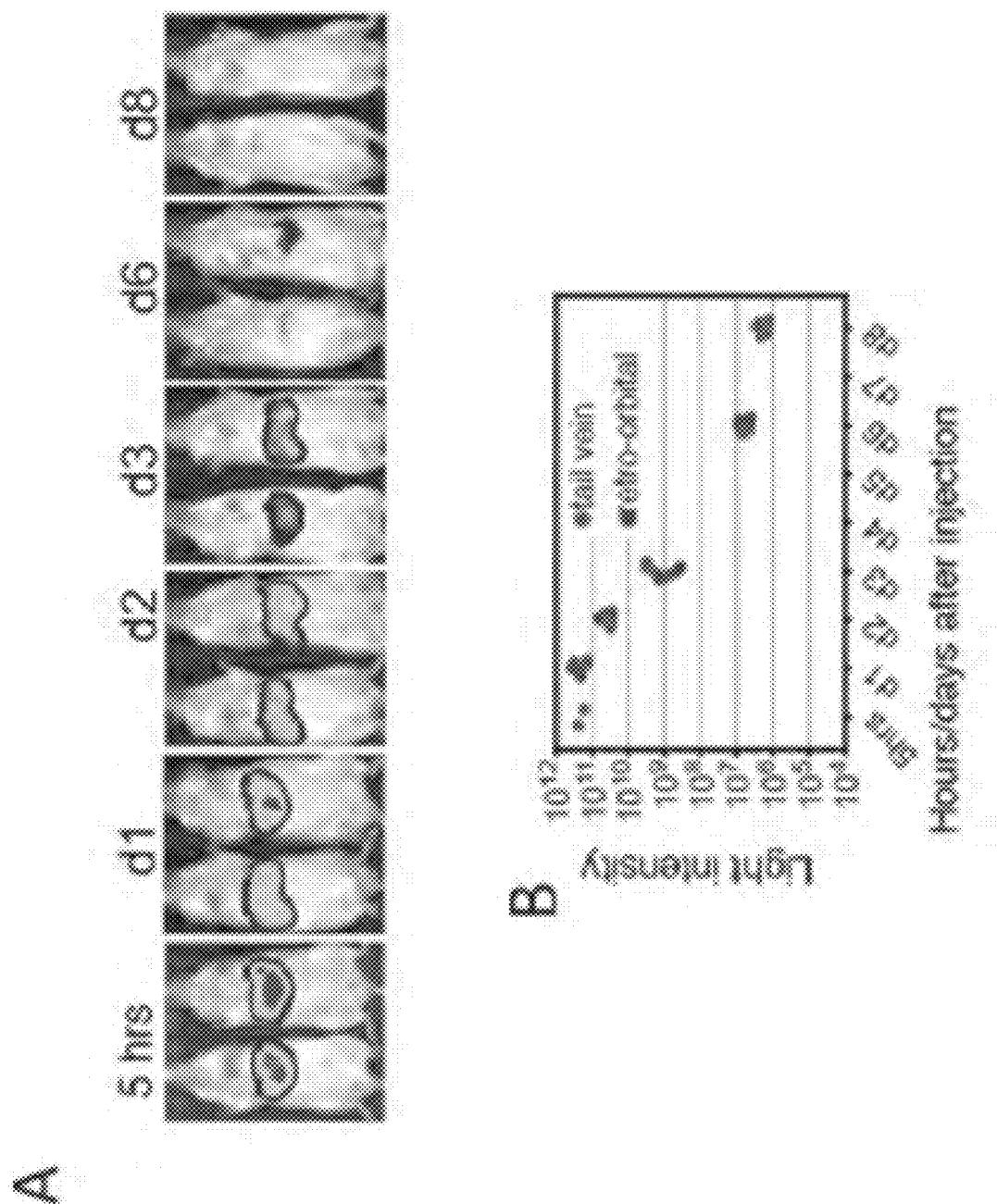
FIGS. 64A-64D depict mRNA-LNPs are efficiently transfected in virtually all hepatocytes and a subpopulation of ECs and macrophage/KCs[1].
Figure 64C:
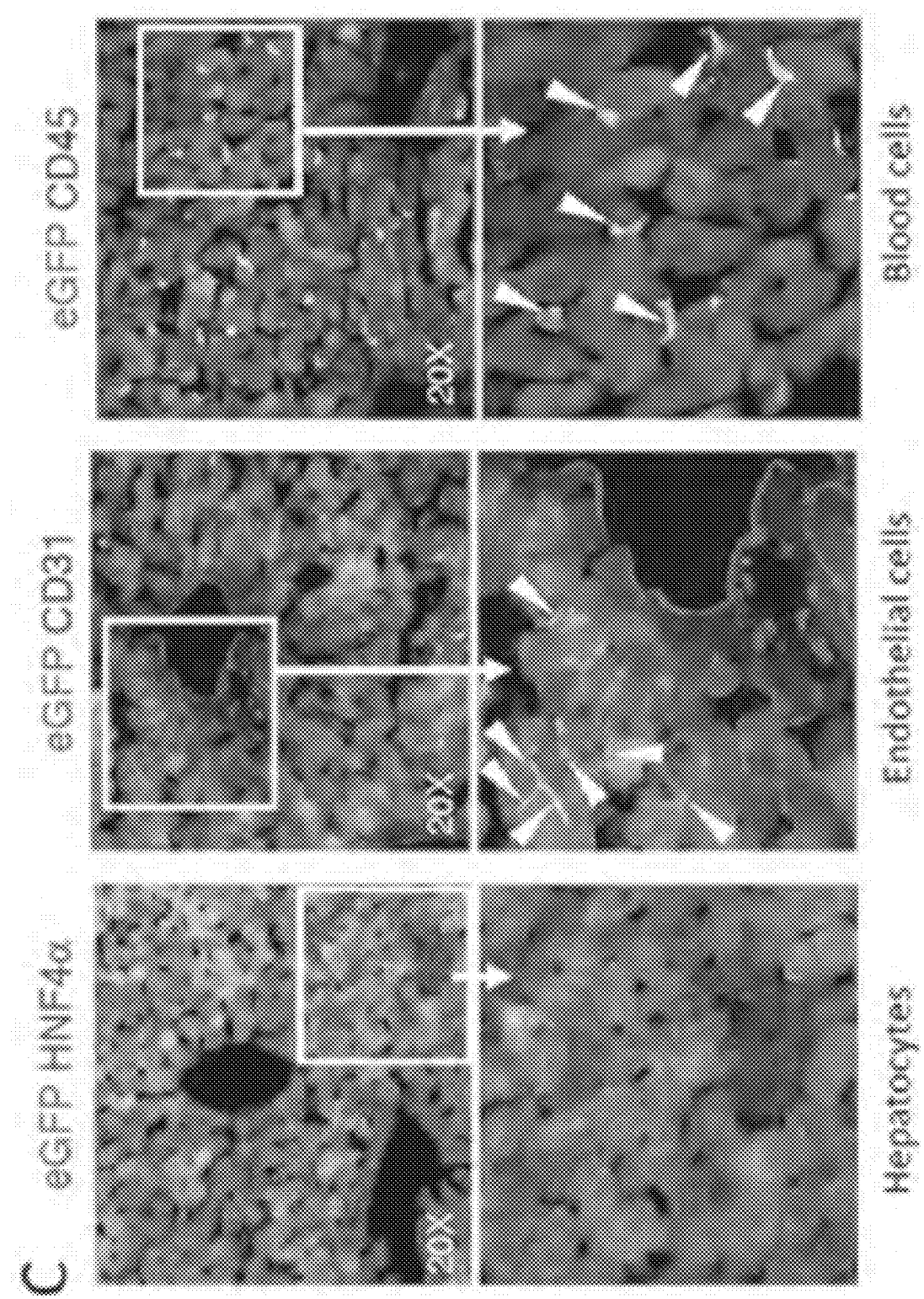
Figure 64D:
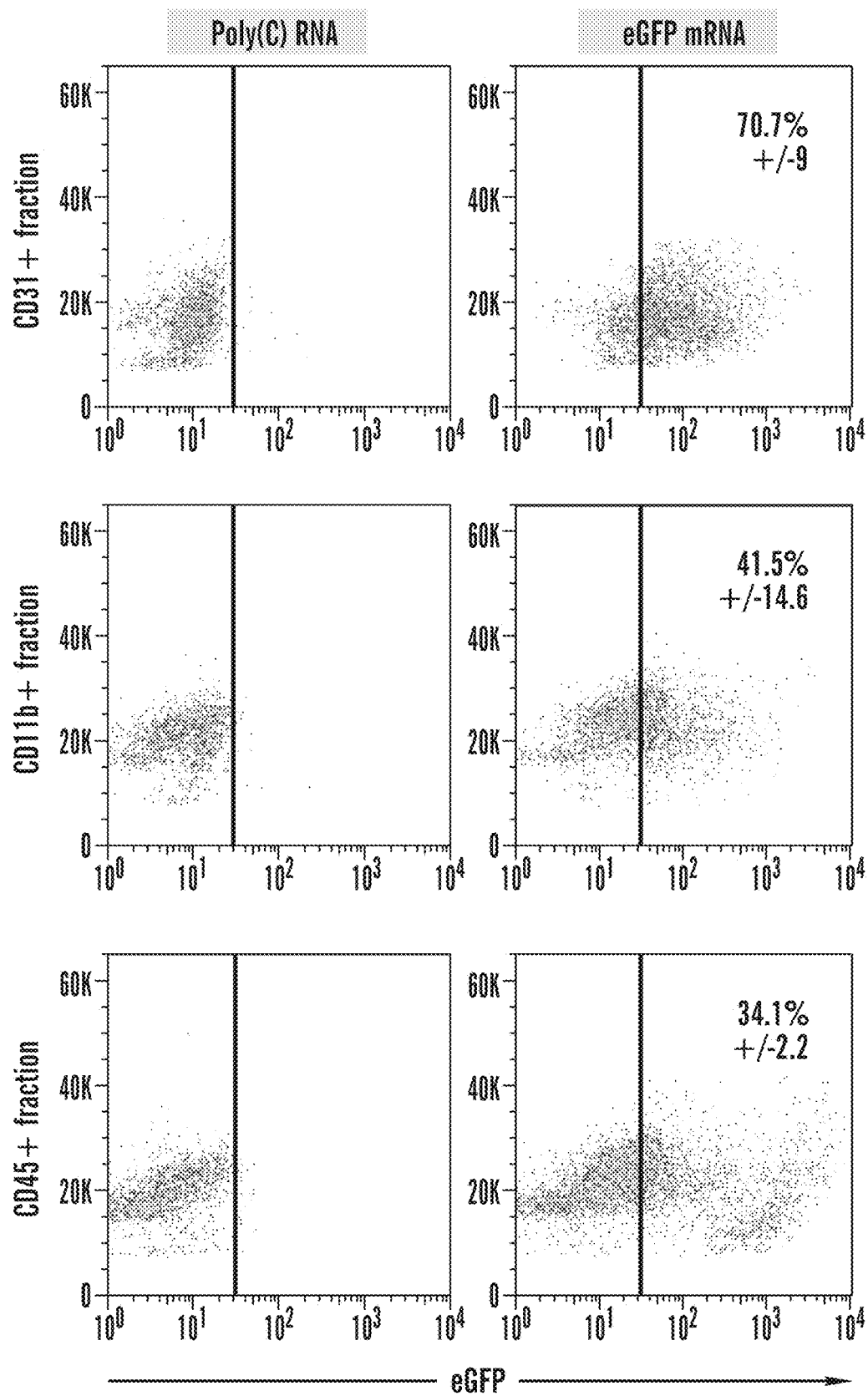

4. mRNA-LNP is a safe and efficient, non-integrative strategy to transiently yet robustly express any protein in vivo in the liver. mRNA-LNP is a tool that can transiently deliver any protein to the liver. As proof-of-principle, the inventors demonstrated using intravenous (IV) injection of luciferase mRNA-LNPs, that mRNA-LNPs are specifically and efficiently targeted to the liver, and that their translation into proteins can last about 4 days (FIGS. 64A, 64B). Nearly all hepatocytes were transfected with eGFP mRNA-LNP (FIG. 64C), along with 70.7±9% of CD31+ ECs and 41.5±14.6% of CD11b+ macrophage/KCs (FIG. 64D) following enrichment of non-parenchymal cells[49]. mRNA-LNPs represent thus an unprecedented tool to temporally yet effectively deliver GH and its effector IGF1 to the liver, as is tested in Aim 2.

C2. Design

RIGOR: Both sexes are examined to fully characterize the sexual dimorphism in APAP-mediated liver injury and regeneration. Numbers of mice for each group have been calculated based on power analyses. Accordingly, all ex vivo assays are performed with tissue from a minimum of 5-6 mice per group to allow proper statistical analyses[1, 46, 47, 60]. Statistical significance between different groups/conditions is analyzed using either the two tailed t-test, or ANOVA for the mouse studies, and Welch's two sample t-test for the scRNA Seq analyses. scRNA Seq is performed on n=4 biological replicates from which 2 transcriptional libraries are generated (each include 2 biological replicates) to account for biological and technical variables. The Biostatistics, Epidemiology & Research Design (BERD) program from BU ensures proper statistical analyses.

Aim 1: Define the Mechanism for Sexually Dimorphic GH Profile Effects on APAP Susceptibility to Liver Injury and Repair.1

Rationale: A few studies[24-26] as well as the preliminary data showed that male mice are more susceptible to APAP-induced liver damage than female mice; yet the mechanism driving this sex disparity remains largely unknown. Similarly, it is not known whether the sex difference is due to greater tissue injury and or defective liver regeneration in males. The sexually distinct GH secretion pattern, pulsatile in males and near-continuous in females, has been reported to be the major proximal regulator of liver sex differences[22]. Clinical trials using GH have shown improvement of non-alcoholic fatty liver disease and cirrhosis[37, 40], an effect of GH also observed in mice[43]. In line with these reports, preliminary data generated from (1) scRNA Seq analyses indicating elevated GHR activity in female hepatocytes and higher expression of its main effector IGF1 in female ECs at homeostasis, and from (2) the rescue of APAP-induced liver damage with exogenous GH, are in support of the key role for GH in the male susceptibility to APAP. Aim 1 therefore tests that APAP not only induces more severe liver damage in males, but also that the ability of males to regenerate the liver is deficient compared that of females. Importantly, Aim 1 also tests that the sexually distinct plasma GH profiles contribute to the sex disparity of APAP susceptibility. To test these, the inventors systematically compare the kinetics of liver damage and regeneration between males, females, and males given a continuous infusion of GH (cGH) via a slow release osmotic minipump (Aim 1a). This cGH treatment generates a female-like plasma GH pattern and feminizes liver gene expression on a near global scale within 7-14 days[61]. Further, the inventors determine the molecular mechanisms, including key pathways and cellular crosstalk associated with cGH-driven liver protection from APAP, and additional critical pathways (beside GH signaling) are discovered associated with female-specific liver protection (Aim 1b).

Figure 65:
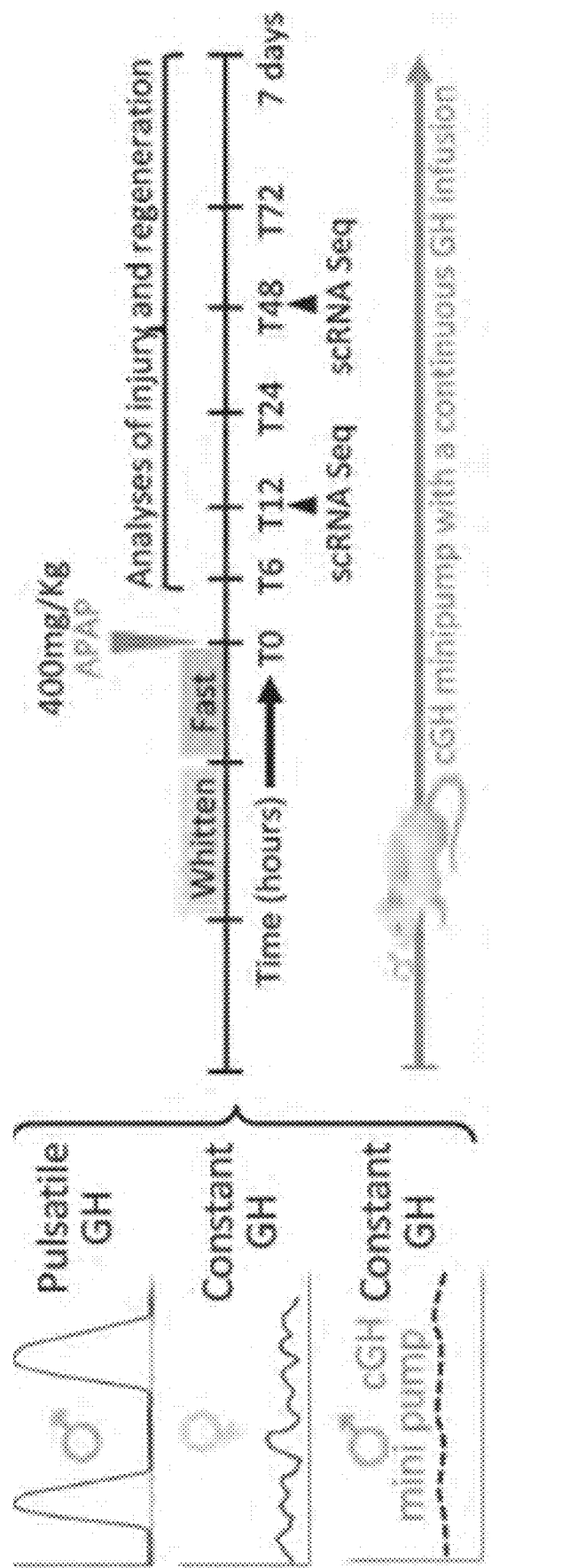
FIG. 65 depicts timeline of the experimental design to investigate the phenotypic sexual disparity of GH levels in APAP susceptibility to liver injury and repair.

Aim 1a: Determine the impact of sexually dimorphic GH profiles on APAP susceptibility to liver injury and repair. Injury and repair are systematically compared in males, in females, and in males given GH by continuous infusion (cGH) beginning two weeks prior to APAP injection. The experimental design to deliver in mice the interspecies compatible rat recombinant GH via minipump at a dose that recapitulates the plasma profiles[62] and biological functions of GH found in females[61] was validated. Briefly, rat GH dissolved in buffer (30 mM $NaHCO_3$, 0.15 M NaCl, 0.1 mg/ml rat albumin) is infused at 25 ng/g BW/hr using Alzet osmotic minipumps (model #2004, up to 28 day delivery) over a 2-week period prior to APAP administration and then during a 7 day period to monitor liver injury and liver regeneration (FIG. 65). Vehicle-filled minipumps are used as control. Under these conditions, cGH treatment substantially feminizes the expression of 92% of liver sex-biased genes, including CYP450 and other metabolic enzymes, by suppressing male-biased genes and inducing female-biased genes[61]. Mice are injected IP with 400 mg/Kg APAP, or PBS vehicle control, as described in the instant data (FIG. 60). The inventors examine livers and sera of mice from 6 hr, 12 hr, 24 hr, 48 hr, 72 hr and 7 days after APAP injection for cell apoptosis, senescence, necrosis, proliferation, and liver function. Injury occurs within the first few hours and peaks around 12 hours after APAP injection[46], while regeneration peaks around 48 hours after APAP injection, as indicated by the presence of the highest numbers of mitotic and PCNA+ hepatocytes[46]. Complete recovery, when injecting sub-lethal doses of APAP, is within 7 days. Liver injury and regeneration are analyzed using a complementary set of assays. Specifically, hepatocyte proliferation is examined and quantified by EdU incorporation, Ki67 and PCNA immunostaining associated with the hepatocyte marker HNF4α. Hepatocyte apoptosis is evaluated by TUNEL assay and immunostaining for cleaved caspase 3 co-stained with HNF4α, cell senescence by senescence-associated p3-galactosidase assay, and necrosis by H&E staining. Immunohistological assays are supported by Western blots for cleaved caspase 3 for apoptosis, HMGB1 for necrosis, and p21 for hepatocyte senescence[63, 64]. Global liver function is evaluated by serum levels of ALT, bilirubin, glutamate dehydrogenase, albumin, and glutathione[1, 65]. Immune cell influx is characterized by immunostaining: F4/80 for macrophages, Clec4F for liver-resident Kupffer Cells, Ly6G/Gr-1 for pro-inflammatory neutrophils, MARCO for anti-inflammatory macrophages[66], and CD45 for all leukocytes. Additionally, expression of markers for injury such as cell-cycle inhibitor p53, necrotic marker HMGB1, apoptotic marker Bax, and cell death marker TNFα, are examined by RT-qPCR. cGH-treated males behave similarly to females, i.e., will be less susceptible than control males to APAP-induced injury, and regenerate quicker. Further tested for is the resistance of cGH-treated males to APAP, by evaluating APAP doses of 500-600 mg/kg, which are lethal to male but not female mice.

Figure 66:
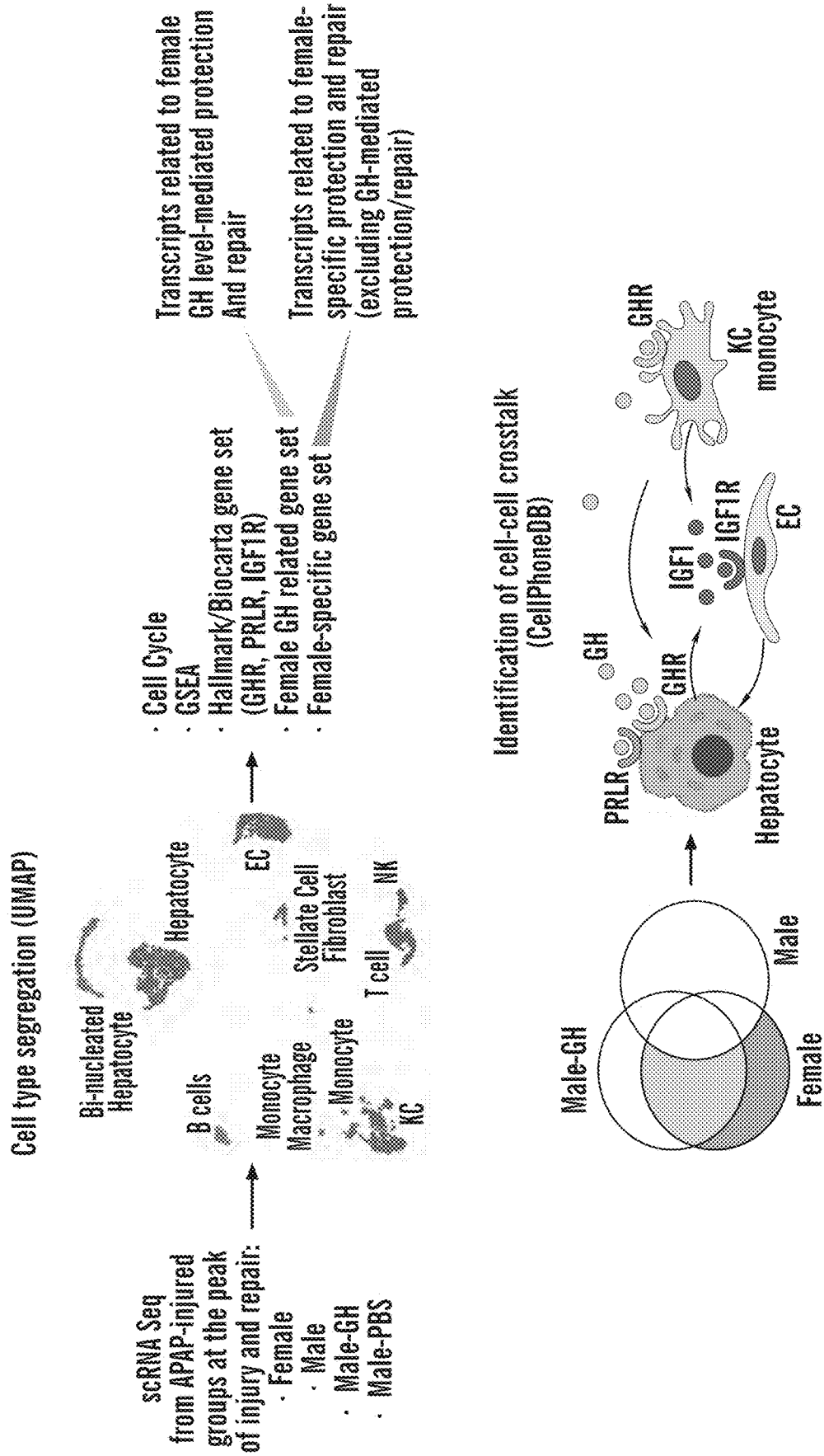
FIG. 66 depicts strategy of scRNA Seq analyses to investigate the role of sex-differential GH profiles in APAP susceptibility to liver injury and repair. For each cell type identified, the 4 transcriptomes (female, male, and cGH or PBS minipump treated male (Male-GH or Male-PBS) will be analyzed for cell cycle, GSEA, specific Hallmark/Biocarta gene set related to GH pathway. They will be compared to obtain the set of transcripts related to female GH level-mediated protection/repair (green), as well as the set of transcripts related to female-specific protection/repair, excluding genes related to GH-mediated protection/repair (purple) (see Venn diagram). Cell-cell crosstalk will be identified using the CellPhoneDB algorithm.

Aim 1b. Define molecular mechanisms by which sexually dimorphic GH profiles determine susceptibility to APAP. In parallel to the phenotypic analyses of the above 4 groups administered with APAP (females, males and cGH-pretreated males or vehicle controls), scRNA Seq analyses is performed at the peak times of liver injury (12 hr) and repair (48 hr)[46] to elucidate the associated molecular mechanisms. The rationale for using scRNA Seq rather than bulk RNA Seq is its ability to examine multiple liver cell populations at the same time, to identify heterogeneity within each population, for instance by associating GH signaling activation and cell survival/proliferation, and finally to dissect cell-cell interactions within the liver. Liver cells are harvested as described in FIG. 61 to resolve multiple clusters of non-parenchymal liver cells in addition to hepatocytes. Single cells are captured for sequencing library preparation using 10× Genomics technology at the BU scRNA Seq facility. Barcoded sequencing libraries are loaded on a NextSeq500™ instrument (Illumina) with a custom sequencing setting to obtain a sequencing depth of ~200K reads per cell. The inventors capture 6,000 cells per group, derived from livers from 4 mice from which 2 transcriptional libraries are generated to account for biological and technical variations. The analysis uses Louvain clustering and visualization of the various cell types and color-coded based on sample origin with reduction algorithms (UMAP and SPRING; see FIGS. 61, 62A-62G). Gene set enrichment analysis (GSEA) is used to identify pathways differentially activated after APAP in each cell lineage in females, males and in cGH or vehicle-pretreated males. The inventors also quantify and visualize within each cell population apoptotic and proliferative cells, which will be classified separately from quiescent cells using the cell cycle scoring strategy of Tirosh et al[67]. Specifically, enrichment in Hallmark and Biocarta gene sets related to GHR, IGF1R and PRLR pathway activation is examined and scored in each cell type using a procedure analogous to that used for the cell cycle[67], to identify cell types contributing to GH response. A GH-mediated pathway (FIG. 66) that could potentially be used alone or combined with GH as a co-therapy for APAP-induced liver injury is identified.

Figure 67A:
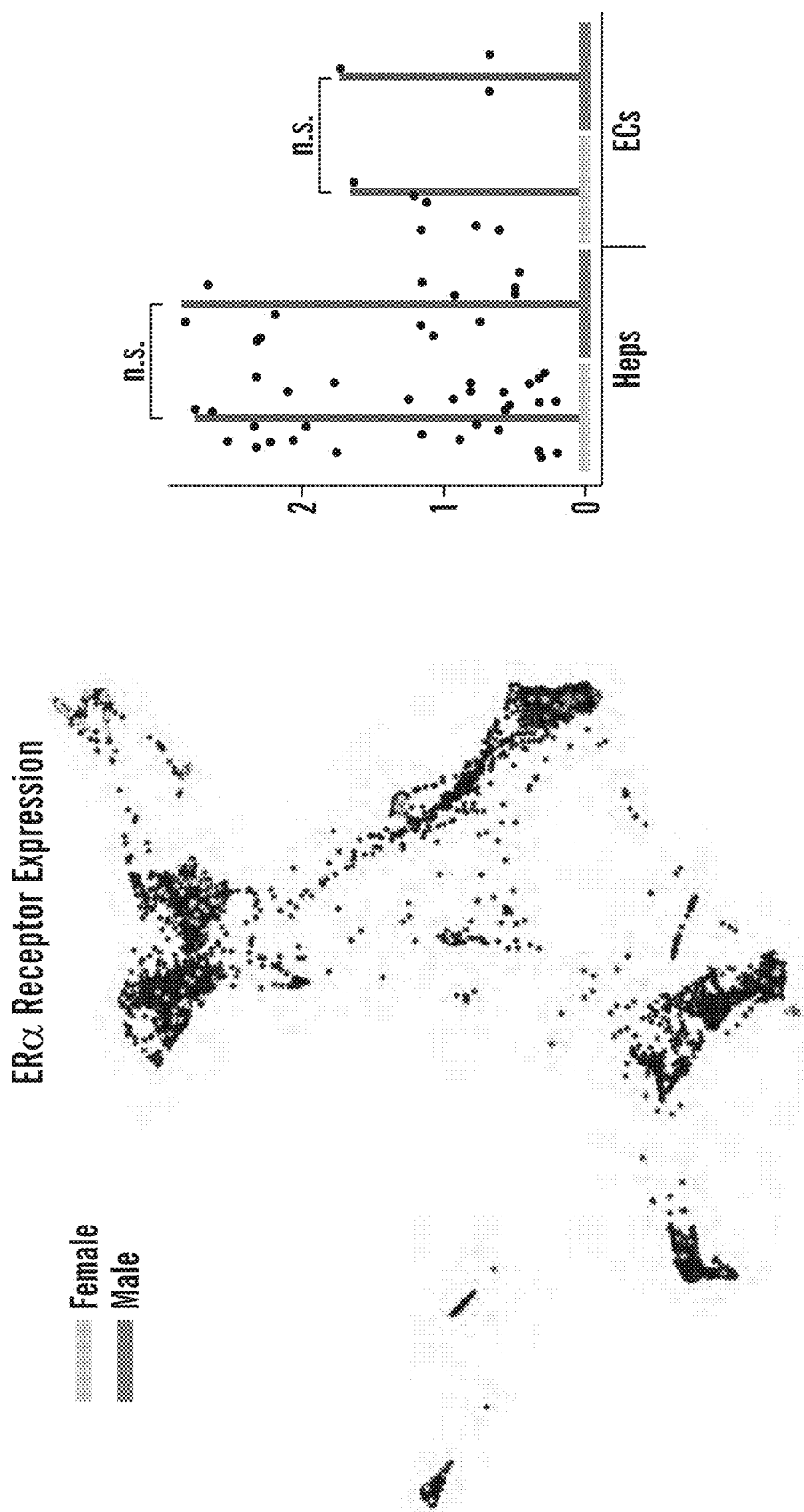
FIGS. 67A-67E depicts identification from the scRNA Seq data early and late estrogen pathway[3] as a candidate female-specific pathway whose activation is associated with resistance to APAP liver injury.
Figure 67B:
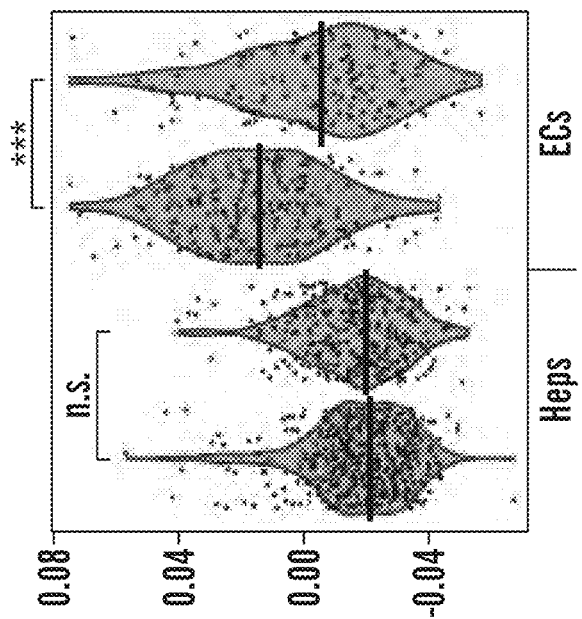
Figure 67B:
Figure 67C:
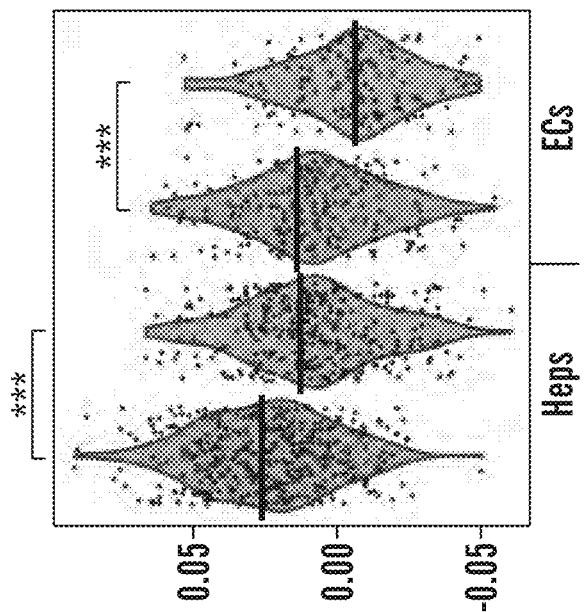
Figure 67C:
Figure 67D:
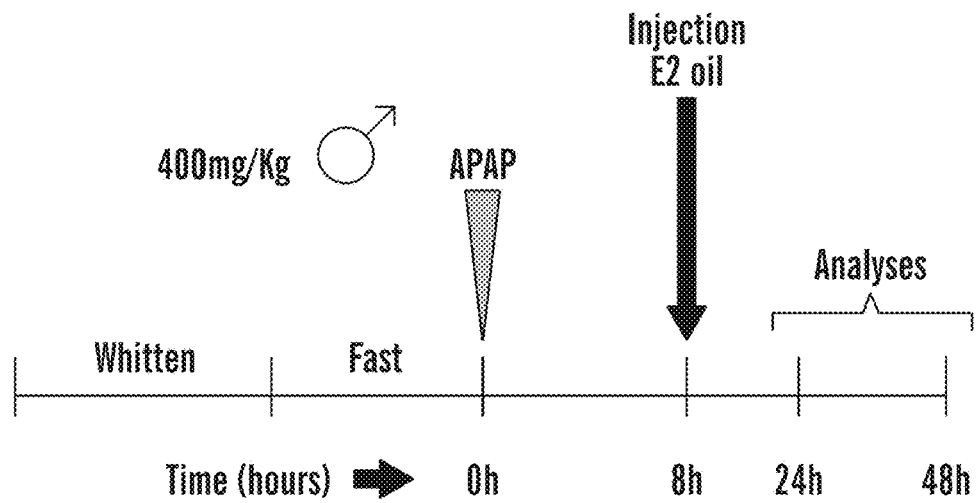
Figure 67E:
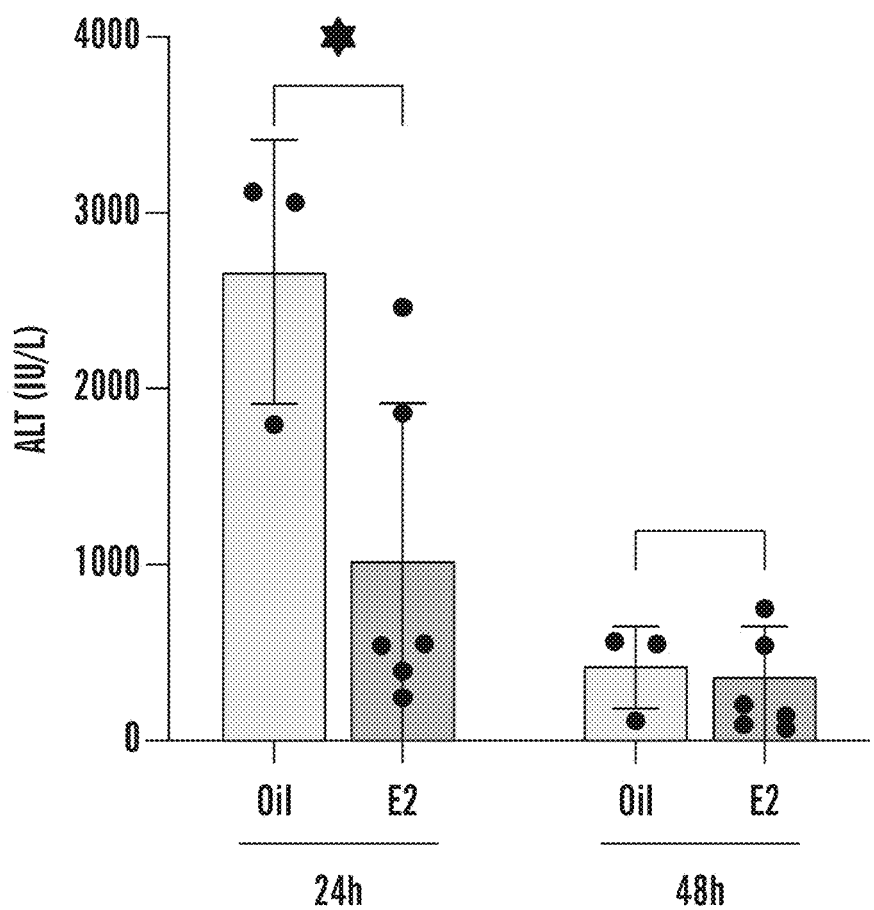

The inventors also identify other pathways, distinct from those mediated by GH pathway activation, that are associated with protection in females (from data analyzed at the peak of injury) or with accelerated repair (from data analyzed at the peak of repair). These additional pathways are identified by their differential activation/expression between female and male cells, combined with similar activation/expression between male and cGH minipump-pretreated male cells. Estrogen signaling was identified as an example of a pathway differentially activated in female hepatocytes and ECs compared to their male counterparts, although ERα itself was similarly expressed between sexes in these two cell types (FIGS. 67A-67C). Preliminary data showed that b-estradiol treatment (IP injection of 0.5 mg/kg in corn oil) in males significantly decreased ALT levels 24 hours following APAP injection (FIGS. 67E, 67E), suggesting a potential therapeutic role for b-estradiol to protect males from APAP susceptibility. Estrogen may contribute to the sex differences in APAP-induced liver injury either directly on ERα-expressing hepatocytes, or perhaps indirectly, via its effect on the sexual dimorphism of pituitary growth hormone (GH) secretion patterns[28-30]. The estrogen pathway is further examined. Using these 2 sets of differentially expressed genes (DEGs), the crosstalk between cell types required for female GH-mediated protection and repair (green DEGs), and those required for female-specific protection and repair excluding the GH-dependent protection/repair (purple DEGs) (FIG. 66) is determined. Given that the preliminary data indicate that hepatocyte and EC transcriptomes are sexually dimorphic, especially prior to APAP injury, and that GHR/GH pathway activation as well as expression of the downstream mediator IGF1, and IGFR, are observed in hepatocytes, ECs and/or KC/monocytes, the analyses of these 3 cell types is prioritized. The inventors examine the expression of each ligand-receptor gene pair between these cell types in each set of DEGs, as annotated in CellPhoneDB, a public repository of curated receptors, ligands and their interactions[68]. This uncovers pairs of complementary ligand-receptor expression profiles whose activity is induced: (1) by GH; or (2) by pathways specific to female liver but in a GH-independent manner. The top 3 most highly differentially expressed/activated pathways are chosen for further validation. As explained above, the estrogen pathway is the top candidate if identified in the DEGs analyses.

Validation of the top 3 pathways and expression of associated ligands and receptors is performed with immunostaining on liver sections of ligands, receptors, phosphorylated receptors, ELISA assay from serum for ligands that are secreted in serum, and flow cytometry on dissociated livers. Functionally, contributions of the identified pathways to the protection from APAP vs susceptibility to APAP are tested pharmacologically and/or by mRNA-LNP delivery using activation and inhibitory assays. Pharmacologic assays include use of commercially available compounds, recombinant proteins, inhibitory and activating antibodies. If needed to improve the duration of delivery of the candidate protein in vivo, mice are treated with one injection of the corresponding mRNA-LNPs that enable expression in ~100% of hepatocytes, ~70% of ECs and ~40% of KC/monocytes, an efficient technology that has been validated[1] (FIG. 64). The candidate pathways pharmacologically are activated/inhibited, as indicated above, and by delivery using mRNA-LNP, which enables future clinical translation. Subsequently, the inventors further validate the functionality of the top 3 candidate pathway factors in protecting male and female mice from APAP.

Expected outcomes and alternative strategies for Aim 1. Outcomes: Aim 1 advances the understanding of the observation of greater liver damage caused by APAP in males compared to females. Given that the APAP-liver injury mouse model recapitulates thoroughly the human disease[7], the findings from Aim 1 provide value to possible clinical translation to reveal the mechanism driving APAP to not only induce more severe liver damage in males than in females, but also to define whether the male ability to regenerate the liver is deficient compared to that in females. Importantly, the extent to which circulating GH profiles are a determinant of the sexually dimorphic susceptibility to APAP is defined. The inventors identify and validate the function of key GH-dependent pathways and the required associated cell-cell interactions. Aim 1 also identifies additional pathways, independent from GH pathway activation, that confer in males better protection to APAP as seen in females. Estrogen pathway is one candidate example from the preliminary data. The top 3 GH-dependent and/or -independent pathways are tested for their ability to protect from APAP liver injury. Alternatives: It is possible that results from Aim 1a reveal that the cGH-minipump only partly mitigates APAP-induced injury or only partially accelerates repair in APAP-treated males. In this case, scRNA Seq data from Aim 1b focuses on identifying pathways independent from GH activation as explained above (FIG. 67).

Aim 2: Determine the Therapeutic Efficacy of GH and IGF-1 Treatment Compared to Clinical Standard-of-Care NAC for APAP-Induced Liver Injury.

Rationale: NAC, the only current treatment for APAP overdose aside from liver transplantation, loses effectiveness by ~10 hours after acetaminophen ingestion, when the symptoms of acute liver failure are frequently not yet evident[10]. Therefore, there is an urgent need to find an alternative treatment that can be effective for the many overdose cases brought to the clinic after this time point. The promising results of GH treatment in humans to mitigate the sexually dimorphic non-alcoholic fatty liver disease and cirrhosis[37, 40], and similarly in mice to alleviate steatosis[43], prompted the investigation into the therapeutic value of GH to treat APAP overdose. Moreover, scRNA Seq data revealed higher expression of GHR in female hepatocytes compared to male cells, as well as significant enrichment of the GH pathway activation in female hepatocytes and ECs compared to male cells following APAP injection. Most importantly, the data showed that a single injection of human GH after APAP injury significantly reduces liver injury and accelerates repair in both sexes. Aim 2 therefore tests that GH treatment alone or in association with the key GH pathway mediator IGF1[53], is more effective than the standard-of-care NAC treatment for APAP-induced liver damage. The efficacy of GH and/or IGF1 treatment as compared to NAC is validated and the doses of GH and IGF1 (Aim 2a), and the time frame for treatment in both sexes of liver injury after sub-lethal and lethal doses of APAP (Aim 2b) are optimized. Importantly, the efficacy of recombinant GH or IGF1 vs non-integrative mRNA-LNP encoding GH or IGF-1, a liver targeted delivery technology recently implemented[1] is compared. Use of mRNA-LNP also enable the evaluation of therapies based on IGF-1 transcripts that generate different protein isoforms differing in their localization and function[69], being either secreted locally to the liver matrix or to the bloodstream, to identify the most effective means of resolving APAP-induced liver injury while minimizing potential systemic secondary effects, a key step for clinical translation. In contrast to Aim 1, which investigates the mechanism of GH levels in APAP susceptibility, Aim 2 and Aim 3 identifies the optimum GH treatment and associated mechanisms to rapidly revert APAP-induced liver injury. Injections of human GH are used in Aim 2 and Aim 3, for practicability to treat an acute disease such as APAP overdose, as opposed to the slow release cGH minipump that was appropriate in Aim 1.

Figure 68:
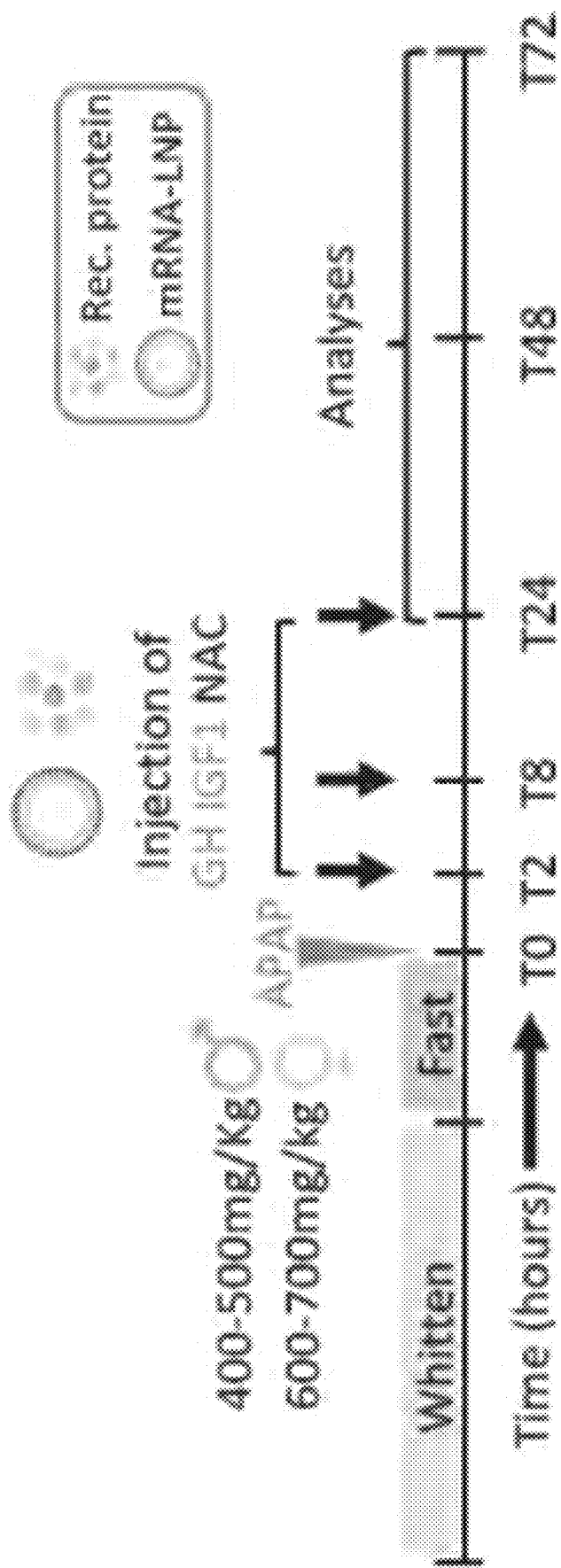
FIG. 68 depicts experimental design for comparison of efficacy of GH/IGF1 treatment using recombinant protein or mRNA-LNP vs clinical standard-of-care NAC post-APAP.

Aim 2a. Define the efficacy of GH/IGF-1 treatment using recombinant protein vs mRNA-LNP as compared to standard-of-care NAC and optimize the GH/IGF-1 doses in both sexes: The same injury model shown in FIG. 63 is followed, and mice are treated with a range of doses of recombinant proteins GH (Invitrogen) and IGF1 (R&D Systems), as well as NAC (Alfa Aesar, Fisher) 8 hours following sex-specific sub-lethal APAP injection (400 mg/kg for males, 600 mg/kg for females, and a vehicle PBS control group in each sex). GH doses tested (0.5, 2.5, 10 mg/kg) range from 0.5 mg/kg70,[71] to 10 mg/kg59,[72] including the average dose for adolescents treated daily with GH for short stature therapy, 1 mg/kg[73], which in mice would translate to ~12.3 mg/Kg considering the inter-species dose conversion factor[74] (FIG. 68). IGF1 doses tested include 2, 10, and 50 µg/kg[75-81], as previously reported in human and rodents. NAC doses tested are 300, 900 and 1200 mg/kg[82-86] as described in rodents. Given that human recombinant GH is efficient in promoting regeneration (FIG. 63) and has the unique ability to activate both GHR and PRLR, for clinical translation purposes, the use of human GH is continued. IGF1 does not show species-specific receptor binding properties, so mouse IGF1 is used to ensure compatibility with the endogenous mouse receptor. These experiments determine the optimal "minimal" effective dose of GH, IGF1 and NAC, compared to vehicle control, when administered alone. Studies are performed in both sexes, as GH, IGF1 and NAC may be variably effective in males vs. females. Vehicle-injected mice serve as a negative control for APAP-treatment (no injury) to help identify any toxic responses to GH, IGF1 and NAC over the dose ranges to be tested. Given that high doses of GH or IGF1 can cause hypoglycemia[87], glycemia after fasting and after administration of glucose (glucose tolerance test, using blood glucose test strips; Precision Xtra systems) is assayed in each group. Additive anabolic effect between GH and IGF1 have been reported[80, 87, 88]; therefore, the combination of GH and IGF1 is assessed for accelerating hepatocyte proliferation and liver tissue repair when using the optimal doses defined above. For the combination therapies, the above-defined optimal doses for GH, IGF1 and NAC are tested; if toxicities are observed, the dose of each factor in the combination is optimized by progressively decreasing its concentration (as tested with individual factor treatment). The results are then compared from the liver injury and regeneration assays outlined in Aim 1b for GH-, IGF1-, NAC-, PBS-, and combined GH/IGF1-treated groups following APAP administration. If NAC is beneficial when administered 8 hours or beyond APAP injection, the effect of the combined best hormone cocktail is tested with NAC. The 3 doses of IGF1 are first tested at 48 hours after APAP injection, a timepoint when GH was clearly beneficial.

A similar set of experiments are performed using mRNA-LNPs encoding GH and IGF1 in place of recombinant proteins to compare their efficiency in restoring liver integrity as well as their possible toxicity. mRNA-LNP doses of 0.1, 1, and 5 µg/20 g mouse body weight for GH and IGF1, both individually and in combination, in both sexes are investigated. A key advantage of using mRNA-LNP over recombinant protein is the robust and continuous production of the therapeutic protein for at least 3 days, and the ability to produce distinct IGF1 transcripts[89, 90], which show unique properties with respect to local secretion in the extracellular matrix versus systemic secretion in serum[69], and may thus harbor different bioactivities for liver regeneration vs. deleterious effects due to systemic secretion. Specifically, it has been reported that the isoform IGF1 Ea, which includes the Ea-peptide, has high affinity for extracellular matrix when overexpressed in muscle, heart or skin in transgenic mice[69, 91-96]. In these studies, local expression of IGF1 Ea was associated with tissue regeneration and absence of secretion in serum, while transgene lacking the E-peptide didn't produce any local effect but rather increased expression in serum[94]. Therefore, the bioactivity of 2 transcripts, mature IGF1, which is devoid of E-peptide and highly secreted in the serum, and isoform IGF1 Ea are initially tested. IGF1 Ea binds to the liver extracellular matrix to act on sinusoidal ECs, while mature IGF1 is secreted in the serum with limited bioactivity in the liver. Regarding GH, the 22K-GH transcript derived from the GH1 gene, which encodes the principal and most abundant pituitary GH and whose biological activities are the most characterized and generally shared by other GH isoforms[97] is used. The signal peptide sequence is included with the 22K-GH to allow proper secretion. Western blot and ELISA assays are performed to define the levels of protein expressed in liver vs serum[69] to better understand its secretion pattern, which are associated with efficacy in local liver repair and possibly systemic toxicity.

Aim 2b. Evaluate the time frame of GH/IGF1 treatment efficacy in both sexes after sub-lethal and lethal APAP administration as compared to standard-of-care NAC. After optimum doses of recombinant protein and mRNA-LNP have been identified, as in FIG. 63, mice are treated with the optimal GH, IGF1 or combined GH/IGF1 dose or NAC given either 2 hours, 8 hours or 24 hours post-sublethal APAP injection (400 mg/kg for males, 600 mg/kg for females) (FIG. 68). Data related to liver injury and liver regeneration is compared 24, 48 and 72 hours post APAP injection in each experimental group (GH-, IGF-1-, GH/IGF1-, NAC-treated mice), and vehicle control groups. Similarly, mice are administered sex-specific lethal doses of APAP (450-500 mg/kg for males, 650-700 mg/kg for females[46]) to determine whether any of the treatments rescue liver failure.

Expected outcomes and alternative strategies for Aim 1 and Aim 2: Outcomes: Aim 2 has a direct clinical application as it determines the clinical benefit of GH alone, or when combined with IGF1, to treat APAP intoxication compared to the standard-of-care NAC, which quickly loses its effectiveness in combatting overdose and has a variable rate of effectiveness even within the 10 hours treatment window[9, 10]. The optimum doses of GH and IGF-1 are defined for females and males as is the time frame of efficacy to treat liver damage induced by sub-lethal doses of APAP, and to rescue liver failure after lethal doses of APAP. Any possible additive therapeutic benefit of combining GH/IGF1 with NAC treatment is also determined. The inventors also test the top 3 candidate target pathways identified in Aim 1 as indicated in Aim 1. Alternatives: (1) The preliminary data (FIG. 63) support the feasibility of the experimental design, however, dose modification occurs if mRNA-LNP dose used is too potent and therefore toxic. Using ELISA assay when mRNA-LNP is tested, allows for adjustment of the dose of mRNA-LNP injected to reach serum concentrations that approach physiological serum levels. In contrast, GH and IGF1 recombinant proteins are administered daily to optimize liver repair. (2) Given that in vitro and in vivo studies and epidemiologic observations provide some evidence that the GH-IGF1 axis is associated with tumorigenesis[98, 99], liver cancer development are monitored 6 months and 1 year following the optimum treatment; (3) It is possible that IGF1 does not contribute to GH-driven acceleration of liver regeneration after APAP-mediated liver injury, as a few studies reported an IGF1-independent role of GH in mitigating chronic liver injury[43], or in promoting hepatocyte proliferation after partial hepatectomy via activation of EGF receptor and ERK1/2[100, 101]. These alternative pathways and mediators are considered in Aim 3a.

Aim 3: Investigate Mechanism of GH/IGF1 Treatment-Mediated Recovery from APAP-Induced Liver Injury.

Rationale: The preliminary data convincingly demonstrate the benefit of exogenous administration of human GH to accelerate liver repair following APAP-induced injury. Moreover, the scRNA Seq analyses reveal that female hepatocytes express significantly higher levels GHR and Biocarta GH pathway expression, and female endothelial cells greater levels of Biocarta GH pathway expression and receptor for the key GH pathway effector IGF-1, than their counterpart male cells. Moreover, KC/monocytes and hepatocytes are the main source of IGF1, both prior and after GH injection. Aim 3 investigates the molecular and cellular mechanisms of GH-IGF1 axis activation-driven accelerated recovery. The inventors specifically test that GH/IGF1 treatment mitigates injury and promotes liver repair in male and female mice post-injury, working through hepatocyte, EC and KC/monocyte activation. To do so, liver cell transcriptomes of APAP-injured male and female mice are compared in the presence and absence of GH/IGF1 (Aim 3a), and hepatocyte-, EC- and KC/monocyte-specific mouse knock-out models for GHR, IGF1R and IGF1 are analyzed to identify the key liver cells involved in GH/IGF1 axis-driven liver regeneration (Aim 3b).

Aim 3a. Determine the sex-common and sex-differential transcriptomic mechanisms associated with GH/IGF1-driven regeneration following APAP overdose. To understand the transcriptional mechanism driving GH/IGF1-mediated liver recovery, the inventors perform scRNA Seq analyses of male and female livers post sub-lethal APAP overdose, following the optimum GH/IGF1-based combination treatment defined in Aim 2 (Cocktail) or PBS vehicle treatment. Following the same injury scheme outlined in FIG. 63A, females and males are injected with 600 and 400 mg/kg APAP respectively, to induce sex-specific sub-lethal liver injury (FIG. 69A). 8 hours later, mice receive the optimum sex-specific cocktail dose defined in Aim 2 (default GH dose will be 2.5 mg/kg, as used in FIG. 63) or PBS. 24 hours post-APAP, when injury is still apparent but repair has been initiated in GH-treated mice, and injury still occurring in PBS-treated mice in both sexes (FIG. 63), livers are dissociated into single-cell suspensions for scRNA Seq analyses as described in Aim 1b. Louvain clustering is applied and liver cell types are visualized with the dimensionality reduction algorithms UMAP and SPRING. GSEA is performed to identify DEGs related to cell death, proliferation, injury response, and inflammatory, regeneration between cocktail- and PBS-treated males and females, and to define how the cocktail treatment affects specifically the hepatocyte, EC and KC/monocyte fractions in males and females commonly and differently, as described in Aim 1b. Common cocktail-mediated pathway activation that induces repair in both sexes are identified, as well as differential candidate pathways or factors related to the faster cocktail-mediated recovery observed in females. Specific enrichment in Hallmark and Biocarta gene sets related to GHR, IGF1R, and PRLR and pathway activation are scored in each cell type to identify cell types contributing to the cocktail response. The expression of each ligand-receptor gene pair between these cell types as annotated in CellPhoneDB[68] is examined, as explained in Aim 1b, thus uncovering pairs of complementary ligand-receptor expression profiles whose activity is induced by the cocktail in common in females and males, or only in females. Validation of the expression of ligands and receptors, and activation and functional contribution of the top 3 pathways to the cocktail-driven repair is performed as detailed in Aim 1b. The top 3 pathways identified in Aim 1 are prioritized as key pathways for protecting males from APAP injury. Pathways that can revert APAP susceptibility will likely accelerate repair after APAP overdose. These findings reveal mechanisms of action of exogenous cocktail GH/IGF1, and help identify the cocktail-mediated pathway candidates in hepatocytes, ECs and KC/monocytes that can further modulate to improve the cocktail GH/IGF1-driven recovery from APAP injury.

Figures 69A, 69B:
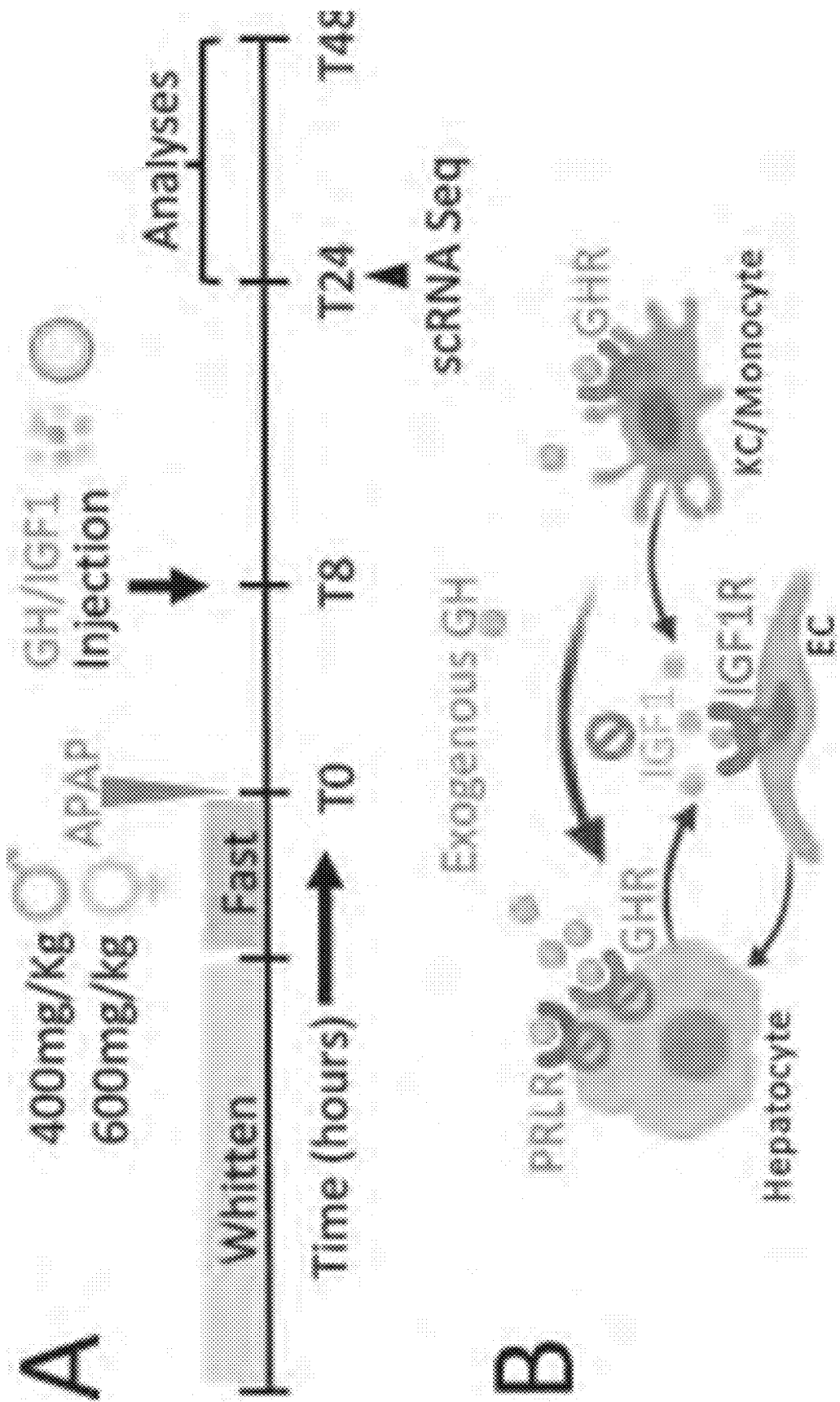
FIGS. 69A-69B depicts experimental design prior to collection of liver cell suspensions for scRNA sequencing analyses and liver function assays (FIG. 69A), as well as for cell-specific knock-out models for which examples are shown (FIG. 69B).
Figure 70:
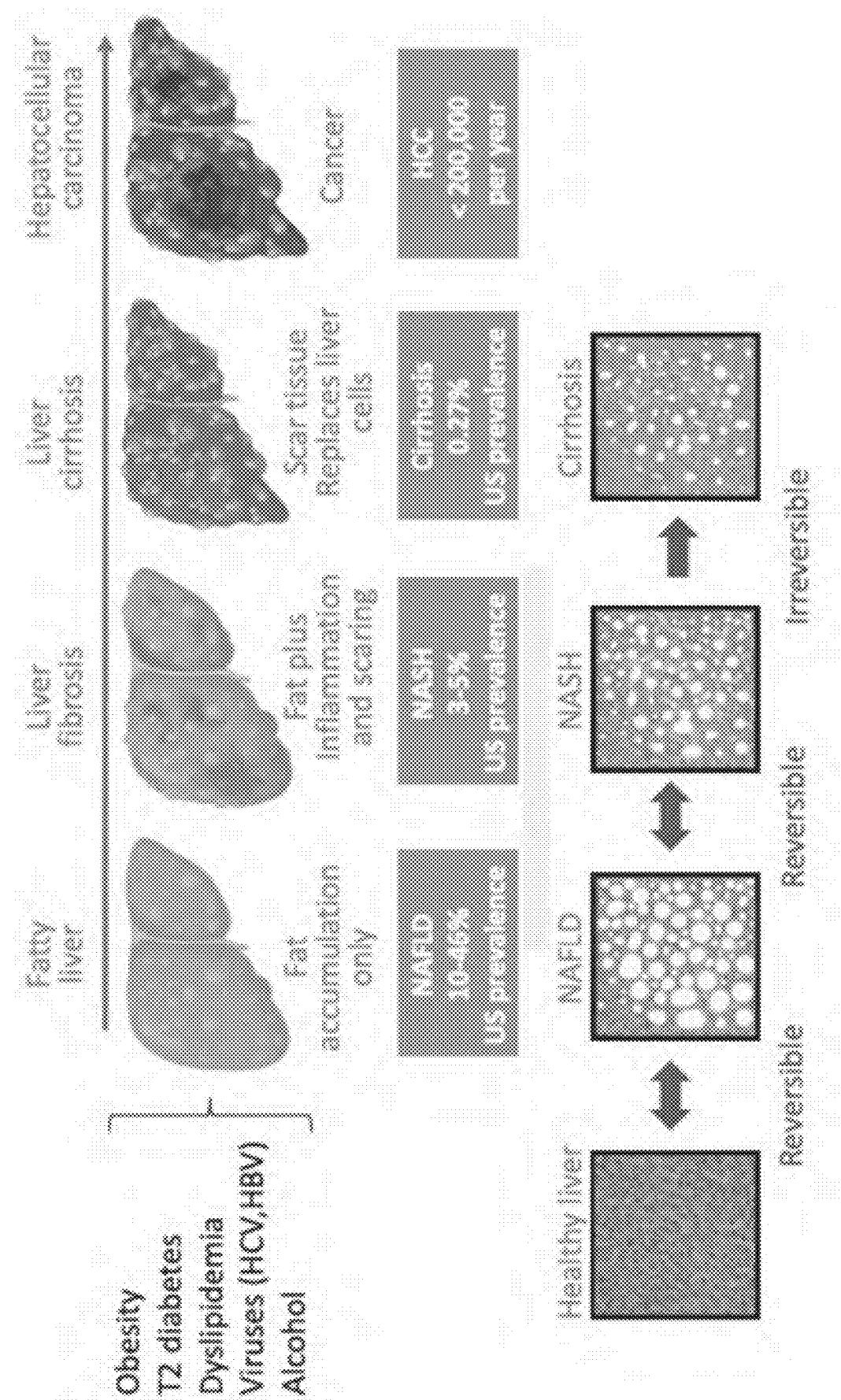
FIG. 70 depicts chronic liver disease is a critical health burden in the USA. NAFLD is the first stem of chronic liver disease and can eventually lead into irreversible cirrhosis.
Figure 71:
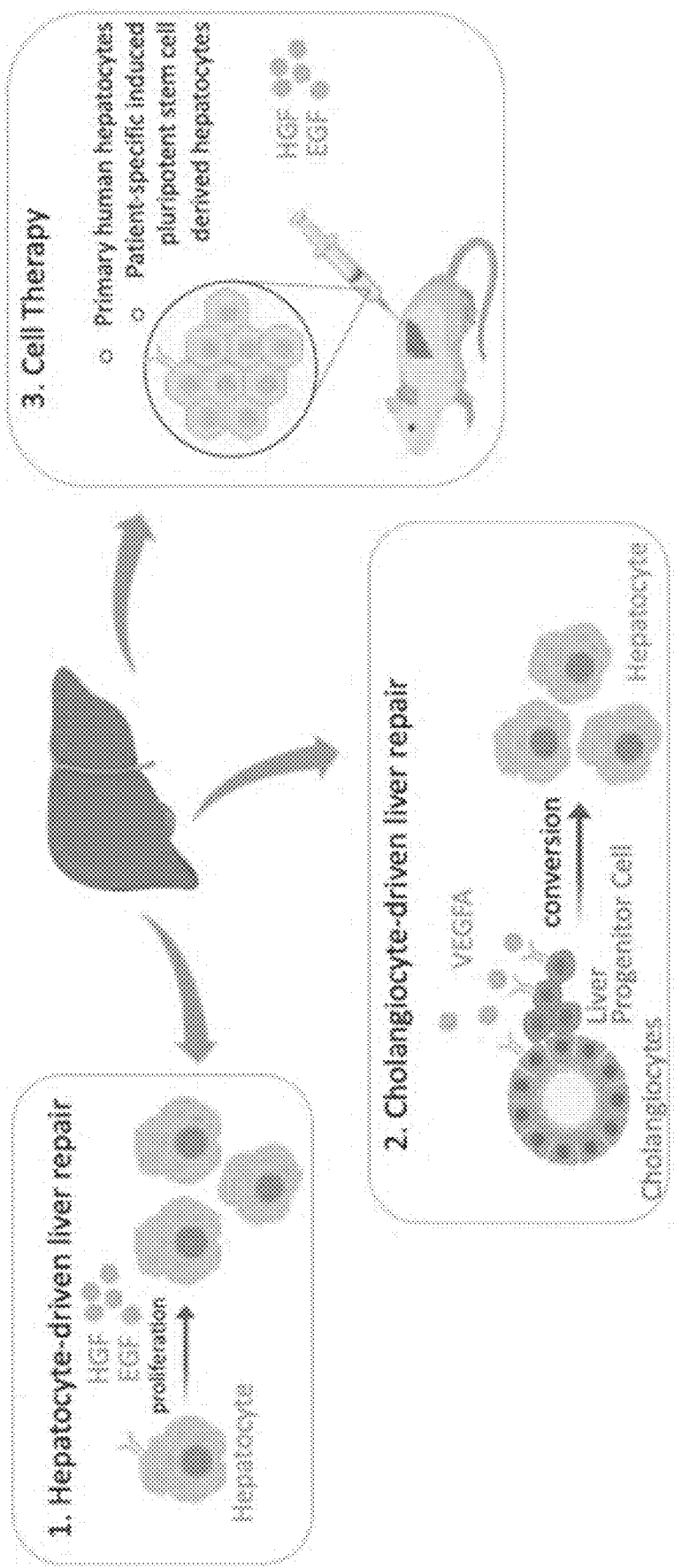
FIG. 71 depicts strategies to harness liver regeneration. Strategies include hepatocyte-driven liver repair in which hepatocytes proliferate to compensate for loss of liver tissue; cholangiocyte-driven liver repair when hepatocyte proliferation is exhausted is case of chronic or acute injury; and cell therapy using primary human hepatocytes and patient specific induced pluripotent stem cell derived hepatocytes. To do so HGF, EGF, and VEGFA can be utilized to promote hepatocyte survival and proliferation and to activate liver progenitor cells to produce de novo functional hepatocytes.
Figure 72A:
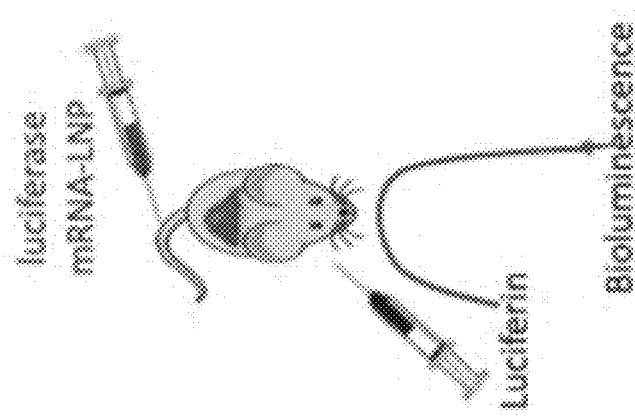
FIGS. 72A-72C depict intravenous injection of nucleoside modified mRNA encoding luciferase complexed to lipid nanoparticles target the liver specifically.
Figure 72B:
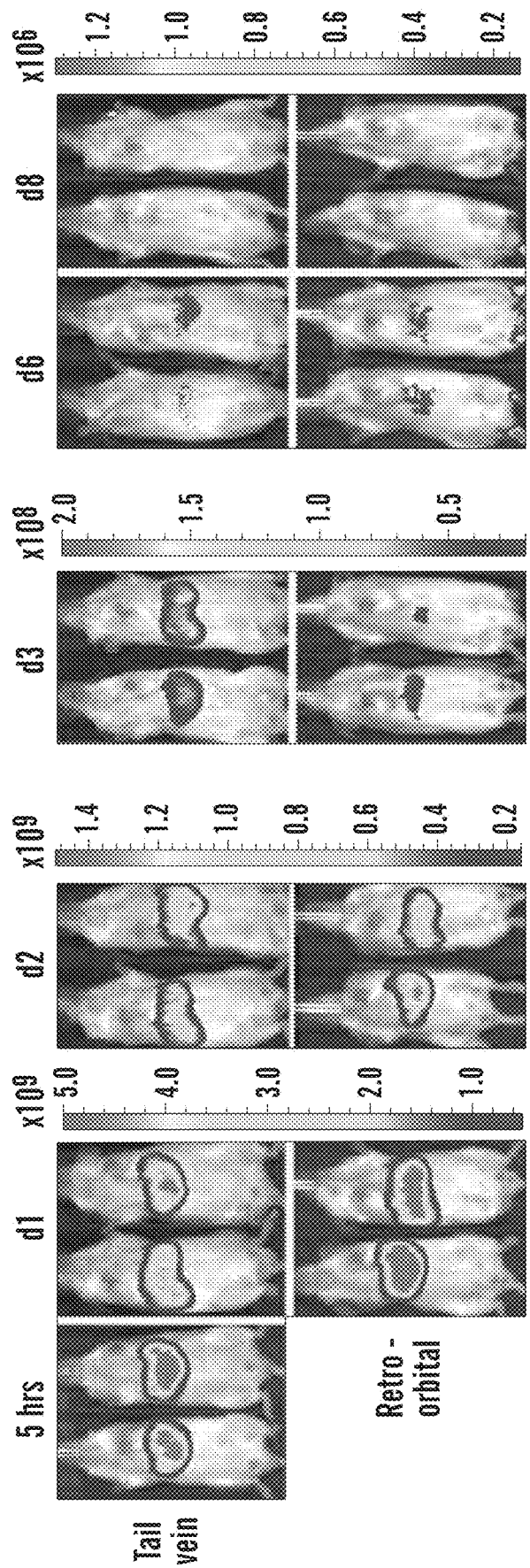
Figure 72C:
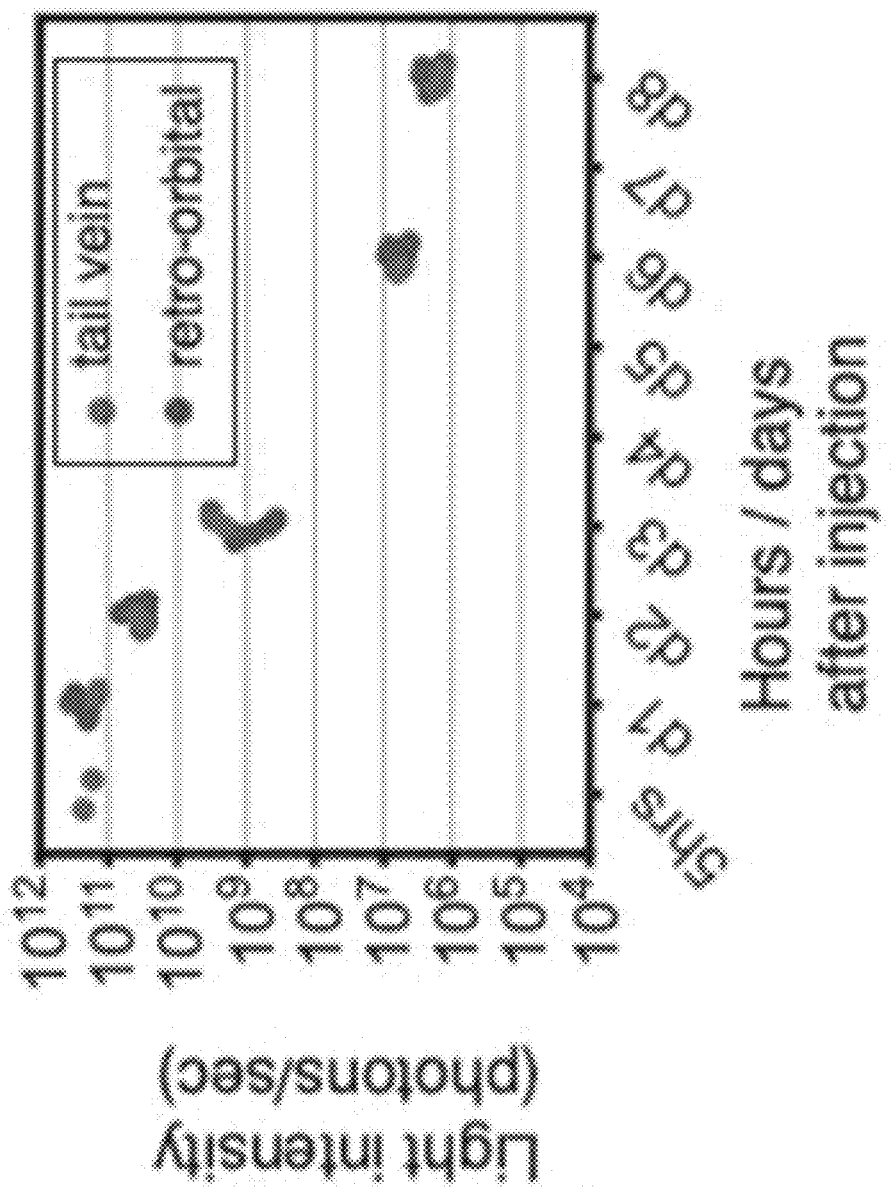
Figure 73A:
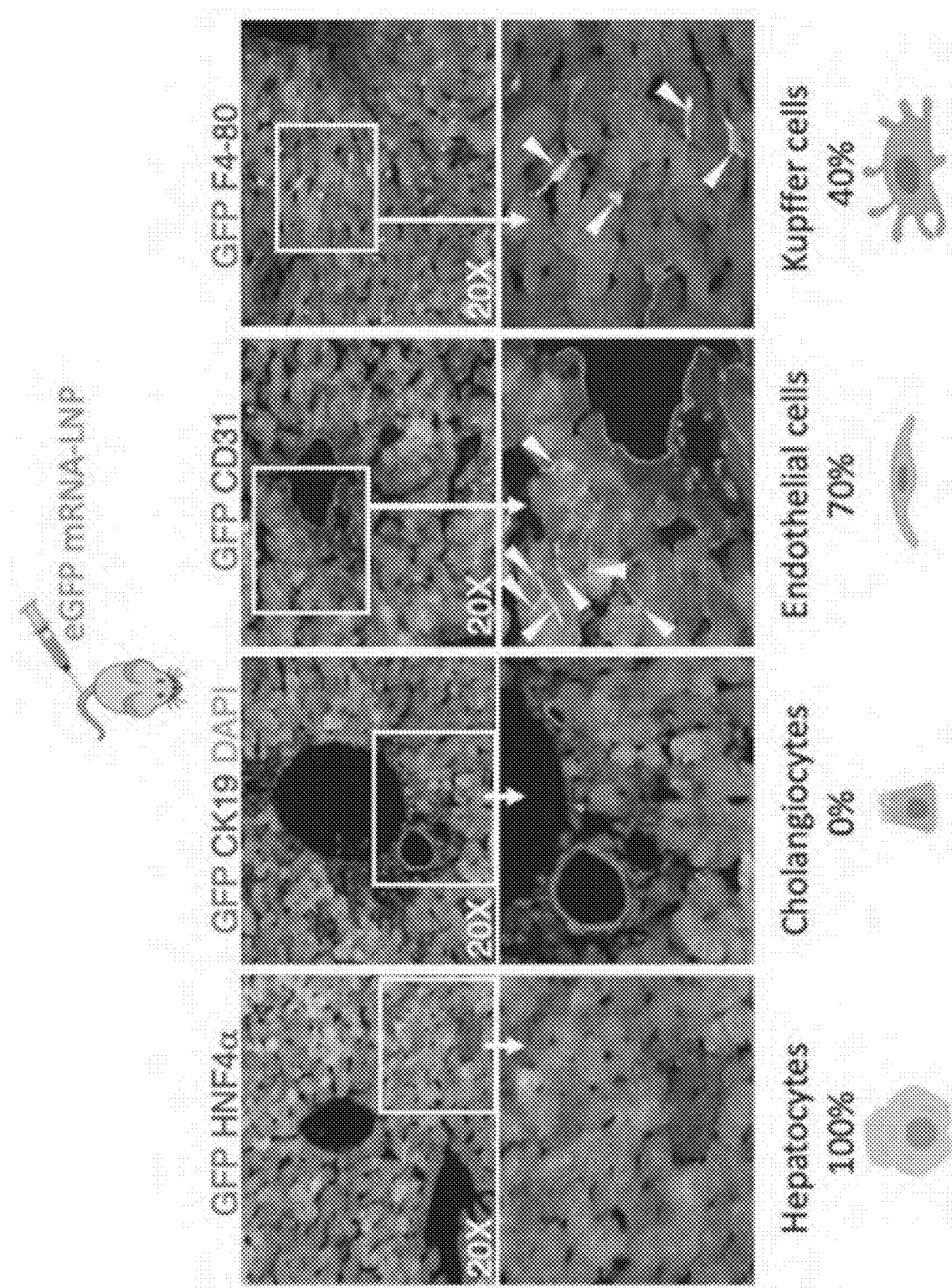
FIGS. 73A-73B depict cells transfected by mRNA-LNP encoding enhanced GFP. After intravenous injection of eGFP mRNA-LNP, virtually all HNF4α+ hepatocytes were transfected, while cholangiocytes, the CK19 positive cells were not. In addition to hepatocytes, about 70% of CD31+ endothelial cells and 40% s of the F4/80 Kupffer cells, the macrophages of the liver, were also transfected. This was quantified by flow cytometry after dissociation of the liver.
Figure 73B:
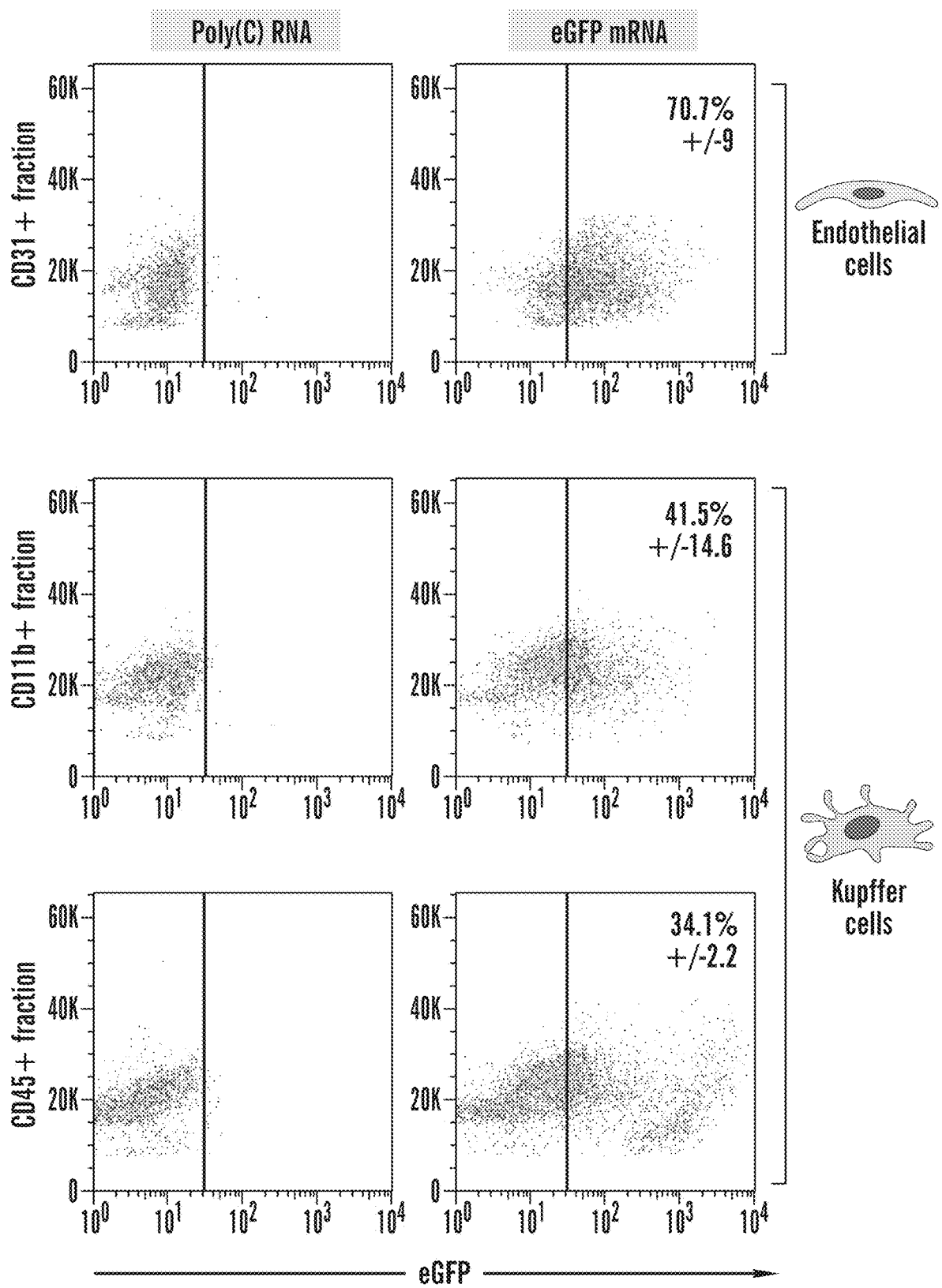
Figure 74A:
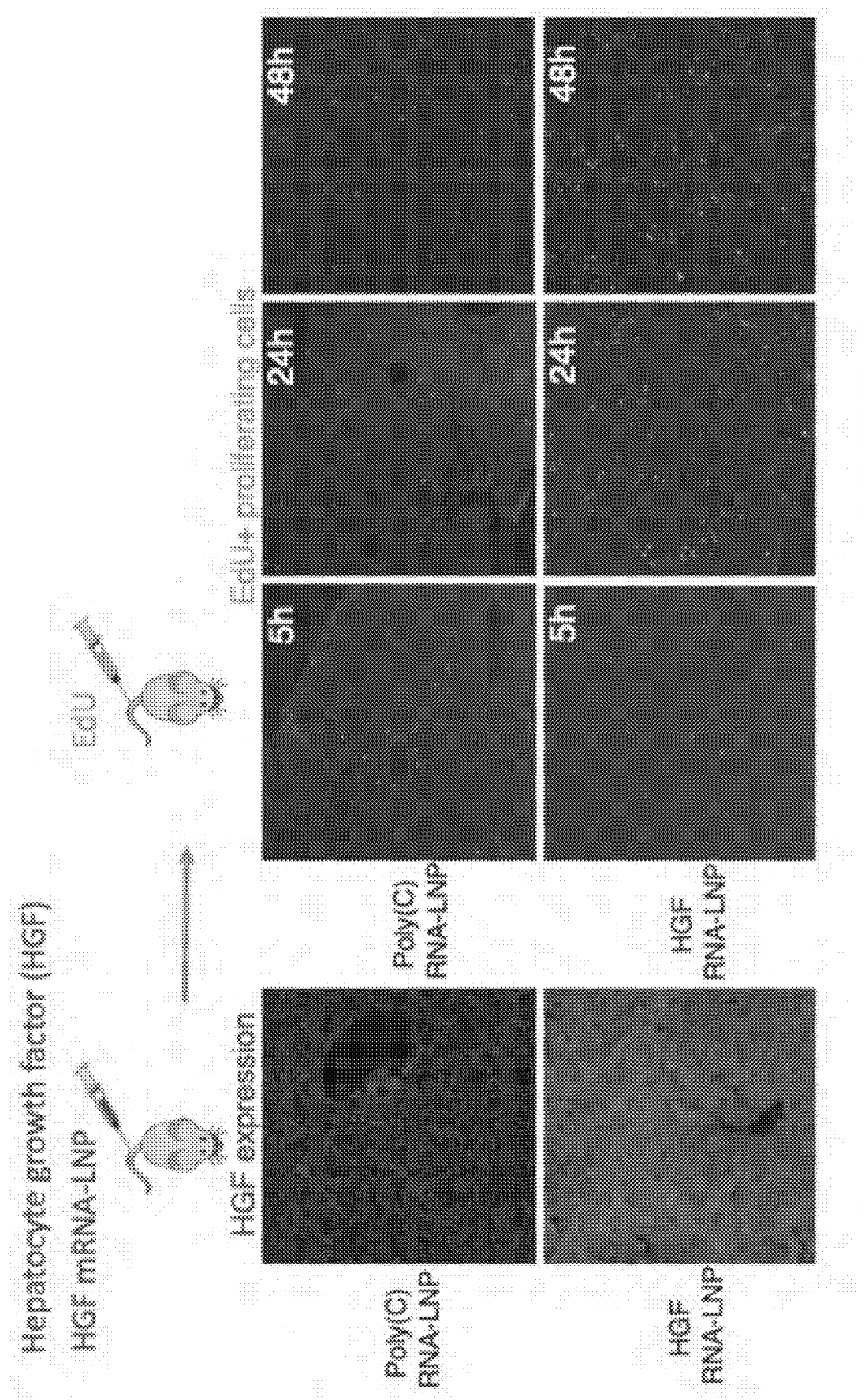
FIGS. 74A-74B depicts HGF mRNA-LNPs induce hepatocyte proliferation in homeostasis condition. 5 hours after HGF mRNA-injection, HGF expression was very intense in all hepatocytes. Hepatocyte proliferation was seen 24 h00 and 48H00 after injection as assessed with staining of incorporated Edu. Quantification shows that more than 60% of the Edu+ cells are hepatocytes in the HGF treated group and that the number of proliferative hepatocytes was 121 fold greater in this group compared to numbers found in the control PolyC treated group.
Figure 74B:
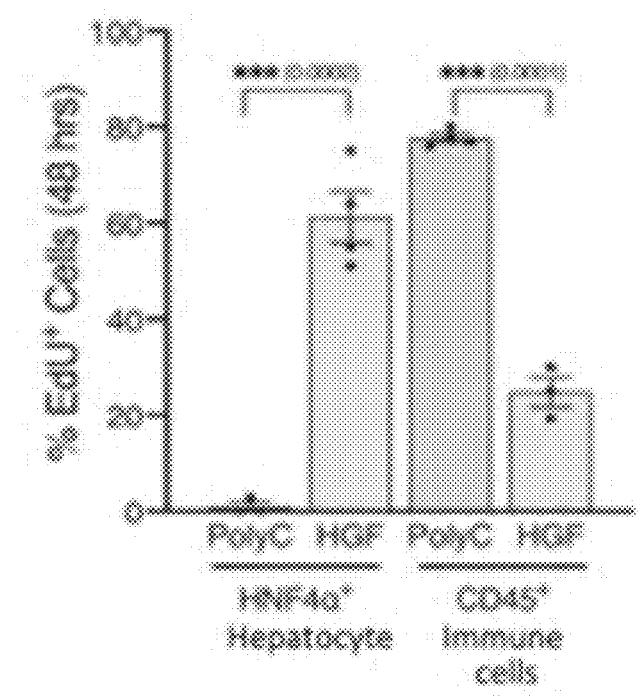
Figure 74B:
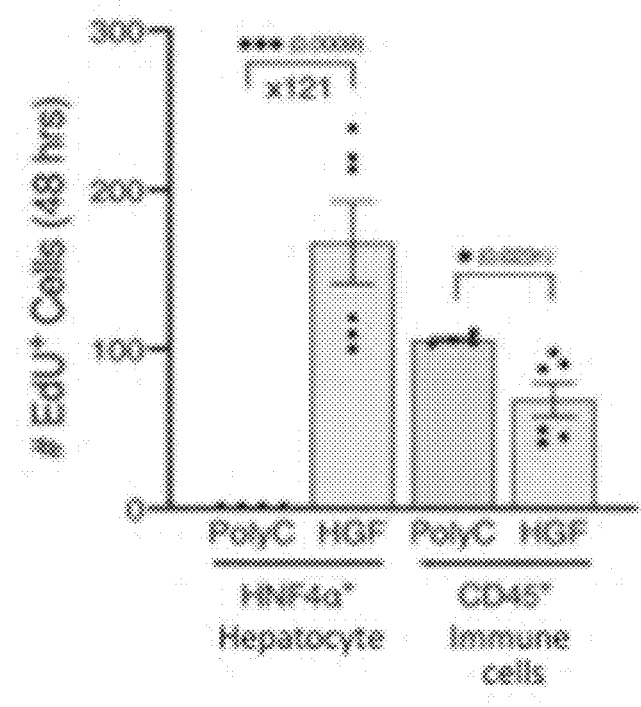

Aim 3b. Identify liver cell crosstalk contributing to GH/IGF1-mediated liver recovery. The cell types in which GHR, IGF1R and PRLR are expressed, and in which IGF1 is induced following the cocktail injection are identified, then conditional knockout mice to validate the key requirement of these cell-specific receptors, and the IGF1 cell source supporting the cocktail-driven liver regeneration (only if the cocktail does not include IGF1) are used. Conditional gene knockout is achieved by crossing mice floxed for GHR (GHR$^{f/f}$ mice from MMRRC[102]), IGF1 (IGF$^{f/f}$ mice from Jackson Laboratory[103]) IGF1R (IGF1R$^{f/f}$ from Jackson Laboratory[104]), and PRLR (PRLR$^{f/f}$ mice from Dr. Dai[105]) with the cell type-specific CreERT2 mouse lines. Those lines include VE-Cadherin-Cre$^{ERT2}$ mice[106] (Taconic) and Csf1r-Mer-iCre-Mer[107] (Jackson Laboratory), which are specific to ECs and KC/monocytes, respectively. Conveniently, IV floxed mice are injected with AAV8.TBG.PI.Cre.rBG virus (AAV8.TBG.PI.Cre.rBG and control AAV8.Tbg.PI.Null.bGH, commercially available from Addgene), which specifically and virtually targets all hepatocytes[108,109]. Double knockout mouse lines are created as required. For instance, to resolve the distinct contribution of IGF1 from hepatocytes and KC/monocytes in the cocktail-driven repair (if the cocktail only includes GH), the 2 single knockout mice with the double knockout IGF1$^{f/f}$, Csf1r-Mer-iCre-Mer mice, injected with AAV8.TBG.PI.Cre.rBG are compared. Examples of cell-specific knock-out models based on the preliminary data are illustrated in FIG. 69B. Knockout mice and their littermate controls are treated with a sex-specific sub-lethal dose of APAP and treated with either the cocktail or PBS 8 hours after APAP injection (FIG. 69A). Mice are euthanized 24 and 48 hours after APAP injection, and liver injury and regeneration is analyzed using assays listed in Aim 1a. If GH acts via IGF1, there is a delay or prevention of GH-induced liver repair when GHR is knocked out in hepatocytes, or when IGF1 is depleted in hepatocytes and (or in) KC/monocytes. This set of experiments identifies the critical liver cell crosstalk responsible for GH/IGF1-driven liver regeneration.

Expected outcomes and alternative strategies for Aim 3. Outcomes: Aim 3 comprehensively determines the molecular and cellular mechanisms that drive exogenous GH to accelerate liver regeneration following APAP injury. Whether male and female GH treatment-driven repair mechanisms are similar and involve the same cell crosstalk mechanisms is determined. Common activated pathways to the GH-mediated recovery seen in both sexes is identified, and differential pathway candidates associated with the faster GH-mediated recovery observed in females for potential therapeutic use are discovered. The top 3 candidates are further tested and then validated in vivo for their ability to accelerate liver recovery following APAP in wild type and knock-out mouse models. Similarly, pathway candidates identified in Aim 1b associated with greater recovery in APAP-injured females (vs APAP-treated males) are further validated in the knock-out models. By comparing the list of liver repair-associated candidates from scRNA Seq analyses from Aim 1 and Aim 3, common and distinct pathways activated by physiologic endogenous and supra-physiologic exogenous levels of GH associated with liver regeneration for potential therapeutic use are identified. Whether the GH-driven repair mechanism is IGF1-dependent or independent is also identified, revealing mediator factor/pathways that may present novel GH co-treatment options. As mentioned in Aim 2, there is also investigation into the alternative route of action of GH via activation of EGF receptor and ERK1/2, as previously reported after partial hepatectomy[100,101] Alternatives: (1) Although GHR is the main functional receptor for GH and the preliminary data support the contribution of GHR, GHR knockout mice might not show reduced repair. Given that human GH also binds mouse prolactin receptor[55], it is possible that loss of GHR will not affect liver regeneration. As an alternative, PRLR is depleted genetically in hepatocytes, or the activity of all prolactin receptors is pharmacologically blocked with injection in vivo of the ligand-competitive antagonist Δ1-9-G129R-hPRL[110,111] or the potent anti-PRLR neutralizing antibody LFA[102,112]. (2) It is possible that the transcriptomic profiles of immune cells, hepatic stellate cells and fibroblasts are altered after GH/IGF1 treatment. In this case, the role of these cells as described for hepatocytes, ECs and KC/monocytes is investigated.

Understanding the mechanisms driving the sexual disparity in APAP-induced liver injury, regeneration, and modulation by GH and IGF-1 provides insights into the preclinical efficacy of a novel GH/IGF-1 therapeutic intervention to treat APAP overdose in both sexes, a currently unmet clinical need. Importantly, this proposal introduces the use of a safe mRNA-LNP tool, largely validated with the recent COVID-19 vaccines, to treat APAP overdose.

REFERENCES

1. Rizvi, F, E Everton, A R Smith, H Liu, E Osota, M Beattie, Y Tam, N Pardi, D Weissman and V Gouon-Evans. Murine liver repair via transient activation of regenerative pathways in hepatocytes using lipid nanoparticle-complexed nucleoside-modified mRNA. Nat Commun 2021, 12:613. PMID: 33504774; PMCID: PMC7840919.
2. Ostapowicz, G, R J Fontana, F V Schiødt, A Larson, T J Davern, S H Han, T M McCashland, A O Shakil, J E Hay, L Hynan, J S Crippin, A T Blei, G Samuel, J Reisch and W M Lee. Results of a prospective study of acute liver failure at 17 tertiary care centers in the United States. Ann Intern Med 2002, 137:947-954. PMID: 12484709.
3. Björnström, L and M Sjöberg. Mechanisms of estrogen receptor signaling: convergence of genomic and nongenomic actions on target genes. Mol Endocrinol 2005, 19:833-842. PMID: 15695368.
4. Yoon, E, A Babar, M Choudhary, M Kutner and N Pyrsopoulos. Acetaminophen-Induced Hepatotoxicity: a Comprehensive Update. Journal of clinical and translational hepatology 2016, 4:131-142. PMID: 27350943; PMCID: PMC4913076.

5. Lame, J E, S Auriola, M Pasanen and R O Juvonen. Acetaminophen bioactivation by human cytochrome P450 enzymes and animal microsomes. Xenobiotica 2009, 39:11-21. PMID: 19219744.
6. Manyike, P T, E D Kharasch, T F Kalhorn and J T Slattery. Contribution of CYP2E1 and CYP3A to acetaminophen reactive metabolite formation. Clin Pharmacol Ther 2000, 67:275-282. PMID: 10741631.
7. Jaeschke, H. Acetaminophen: Dose-Dependent Drug Hepatotoxicity and Acute Liver Failure in Patients. Dig Dis 2015, 33:464-471. PMID: 26159260; PMCID: PMC4520394.
8. McClain, C J, J P Kromhout, F J Peterson and J L Holtzman. Potentiation of acetaminophen hepatotoxicity by alcohol. Jama 1980, 244:251-253. PMID: 7382090.
9. Prescott, L F. Paracetamol, alcohol and the liver. British journal of clinical pharmacology 2000, 49:291-301. PMID: 10759684; PMCID: PMC2014937.
10. Heard, K J. Acetylcysteine for acetaminophen poisoning. N Engl J Med 2008, 359:285-292. PMID: 18635433; PMCID: PMC2637612.
11. Jóźwiak-Bebenista, M and J Z Nowak. Paracetamol: mechanism of action, applications and safety concern. Acta Pol Pharm 2014, 71:11-23. PMID: 24779190.
12. Botta, D, S Shi, C C White, M J Dabrowski, C L Keener, S L Srinouanprachanh, F M Farin, C B Ware, W C Ladiges, R H Pierce, N Fausto and T J Kavanagh. Acetaminophen-induced liver injury is attenuated in male glutamate-cysteine ligase transgenic mice. J Biol Chem 2006, 281:28865-28875. PMID: 16840778.
13. Naugler, W E, T Sakurai, S Kim, S Maeda, K Kim, A M Elsharkawy and M Karin. Gender disparity in liver cancer due to sex differences in MyD88-dependent IL-6 production. Science 2007, 317:121-124. PMID: 17615358.
14. Lavoie, J M and A Pighon. NAFLD, Estrogens, and Physical Exercise: The Animal Model. J Nutr Metab 2012, 2012:914938. PMID: 21845221; PMCID: PMC3154523.
15. Zheng, B, Y J Zhu, H Y Wang and L Chen. Gender disparity in hepatocellular carcinoma (HCC): multiple underlying mechanisms. Sci China Life Sci 2017, 60:575-584. PMID: 28547581.
16. Mennecozzi, M, B Landesmann, T Palosaari, G Harris and M Whelan. Sex differences in liver toxicity-do female and male human primary hepatocytes react differently to toxicants in vitro? PloS one 2015, 10:e0122786. PMID: 25849576; PMCID: PMC4388670.
17. Lee, C, J Kim and Y Jung. Potential Therapeutic Application of Estrogen in Gender Disparity of Nonalcoholic Fatty Liver Disease/Nonalcoholic Steatohepatitis. Cells 2019, 8. PMID: 31619023; PMCID: PMC6835656.
18. Liu, K A and N A Mager. Women's involvement in clinical trials: historical perspective and future implications. Pharm Pract (Granada) 2016, 14:708. PMID: 27011778; PMCID: PMC4800017.
19. Russo, M W, J A Galanko, R Shrestha, M W Fried and P Watkins. Liver transplantation for acute liver failure from drug induced liver injury in the United States. Liver Transpl 2004, 10:1018-1023. PMID: 15390328.
20. Tan, C J and G E Sklar. Characterisation and outcomes of adult patients with paracetamol overdose presenting to a tertiary hospital in Singapore. Singapore Med J 2017, 58:695-702. PMID: 27752704; PMCID: PMC5917055.
21. Rubin, J B, B Hameed, M Gottfried, W M Lee and M Sarkar. Acetaminophen-induced Acute Liver Failure Is More Common and More Severe in Women. Clin Gastroenterol Hepatol 2018, 16:936-946. PMID: 29199145; PMCID: PMC5962381.
22. Waxman, D J and M G Holloway. Sex differences in the expression of hepatic drug metabolizing enzymes. Mol Pharmacol 2009, 76:215-228. PMID: 19483103; PMCID: PMC2713118.
23. Chandrasekaran, V R, S Periasamy, L L Liu and M Y Liu. 17β-Estradiol protects against acetaminophen-overdose-induced acute oxidative hepatic damage and increases the survival rate in mice. Steroids 2011, 76:118-124. PMID: 20933533.
24. Masubuchi, Y, J Nakayama and Y Watanabe. Sex difference in susceptibility to acetaminophen hepatotoxicity is reversed by buthionine sulfoximine. Toxicology 2011, 287:54-60. PMID: 21672600.
25. Win, S, R W Min, C Q Chen, J Zhang, Y Chen, M Li, A Suzuki, M F Abdelmalek, Y Wang, M Aghajan, F W Aung, A M Diehl, R J Davis, T A Than and N Kaplowitz. Expression of mitochondrial membrane-linked SAB determines severity of sex-dependent acute liver injury. J Clin Invest 2019. PMID: 31487267.
26. Du, K, C D Williams, M R McGill and H Jaeschke. Lower susceptibility of female mice to acetaminophen hepatotoxicity: Role of mitochondrial glutathione, oxidant stress and c-jun N-terminal kinase. Toxicology and applied pharmacology 2014, 281:58-66. PMID: 25218290; PMCID: PMC4362889.
27. Liu, H, H Wang, S Shenvi, T M Hagen and R M Liu. Glutathione metabolism during aging and in Alzheimer disease. Ann N Y Acad Sci 2004, 1019:346-349. PMID: 15247041.
28. Avtanski, D, H J Novaira, S Wu, C J Romero, R Kineman, R M Luque, F Wondisford and S Radovick. Both estrogen receptor α and β stimulate pituitary GH gene expression. Mol Endocrinol 2014, 28:40-52. PMID: 24284820; PMCID: PMC3874459.
29. Addison, M L and E F Rissman. Sexual dimorphism of growth hormone in the hypothalamus: regulation by estradiol. Endocrinology 2012, 153:1898-1907. PMID: 22315455; PMCID: PMC3320260.
30. Veldhuis, J D and C Y Bowers. Regulated recovery of pulsatile growth hormone secretion from negative feedback: a preclinical investigation. Am J Physiol Regul Integr Comp Physiol 2011, 301:R1143-1152. PMID: 21795635; PMCID: PMC3197337.
31. Farhy, L S, C Y Bowers and J D Veldhuis. Model-projected mechanistic bases for sex differences in growth hormone regulation in humans. Am J Physiol Regul Integr Comp Physiol 2007, 292:R1577-1593. PMID: 17185408.
32. Wong, J H, J Dukes, R E Levy, B Sos, S E Mason, T S Fong and E J Weiss. Sex differences in thrombosis in mice are mediated by sex-specific growth hormone secretion patterns. J Clin Invest 2008, 118:2969-2978. PMID: 18618017; PMCID: PMC2447928.
33. Adams, J M, V Otero-Corchon, G L Hammond, J D Veldhuis, N Qi and M J Low. Somatostatin is essential for the sexual dimorphism of GH secretion, corticosteroid-binding globulin production, and corticosterone levels in mice. Endocrinology 2015, 156:1052-1065. PMID: 25551181; PMCID: PMC4330306.
34. Jansson, J O, S Edén and O Isaksson. Sexual dimorphism in the control of growth hormone secretion. Endocr Rev 1985, 6:128-150. PMID: 2861084.
35. Lau-Corona, D, W K Bae, L Hennighausen and D J Waxman. Sex-biased genetic programs in liver metabolism and liver fibrosis are controlled by EZH1 and EZH2. PLoS Genet 2020, 16:e1008796. PMID: 32428001; PMCID: PMC7263639.

36. Connerney, J, D Lau-Corona, A Rampersaud and D J Waxman. Activation of Male Liver Chromatin Accessibility and STAT5-Dependent Gene Transcription by Plasma Growth Hormone Pulses. Endocrinology 2017, 158:1386-1405. PMID: 28323953; PMCID: PMC6283433.

37. Wallace, J D, W J Abbott-Johnson, D H Crawford, R Barnard, J M Potter and R C Cuneo. GH treatment in adults with chronic liver disease: a randomized, double-blind, placebo-controlled, cross-over study. J Clin Endocrinol Metab 2002, 87:2751-2759. PMID: 12050245.

38. Sandahl, T D, N K Aagaard, K L Thomsen, T Grofte, J Greisen, J S Christiansen and H Vilstrup. Effects of insulin-like growth factor-I administration on in vivo regulation of urea synthesis in normal subjects and patients with cirrhosis. Liver Int 2011, 31:132-137. PMID: 21040412.

39. Adamek, A and A Kasprzak. Insulin-Like Growth Factor (IGF) System in Liver Diseases. Int J Mol Sci 2018, 19. PMID: 29702590; PMCID: PMC5983723.

40. Nishizawa, H, G Iguchi, A Murawaki, H Fukuoka, Y Hayashi, H Kaji, M Yamamoto, K Suda, M Takahashi, Y Seo, Y Yano, R Kitazawa, S Kitazawa, M Koga, Y Okimura, K Chihara and Y Takahashi. Nonalcoholic fatty liver disease in adult hypopituitary patients with GH deficiency and the impact of GH replacement therapy. Eur J Endocrinol 2012, 167:67-74. PMID: 22535644.

41. Moller, N and J O Jorgensen. Effects of growth hormone on glucose, lipid, and protein metabolism in human subjects. Endocr Rev 2009, 30:152-177. PMID: 19240267.

42. Pennisi, P A, J J Kopchick, S Thorgeirsson, D LeRoith and S Yakar. Role of growth hormone (G H) in liver regeneration. Endocrinology 2004, 145:4748-4755. PMID: 15242989.

43. Sarmento-Cabral, A, M Del Rio-Moreno, M C Vazquez-Borrego, M Mahmood, E Gutierrez-Casado, N Pelke, G Guzman, P V Subbaiah, J Cordoba-Chacon, S Yakar and R D Kineman. G H directly inhibits steatosis and liver injury in a sex-dependent and IGF1-independent manner. J Endocrinol 2021, 248:31-44. PMID: 33112796; PMCID: PMC7785648.

44. McCullough, L D, G J de Vries, V M Miller, J B Becker, K Sandberg and M M McCarthy. NIH initiative to balance sex of animals in preclinical studies: generative questions to guide policy, implementation, and metrics. Biol Sex Differ 2014, 5:15. PMID: 25780556; PMCID: PMC4360141.

45. Weissman, D. mRNA transcript therapy. Expert Rev Vaccines 2015, 14:265-281. PMID: 25359562.

46. Bhushan, B, C Walesky, M Manley, T Gallagher, P Borude, G Edwards, S P Monga and U Apte. Pro-regenerative signaling after acetaminophen-induced acute liver injury in mice identified using a novel incremental dose model. Am J Pathol 2014, 184:3013-3025. PMID: 25193591; PMCID: PMC4215032.

47. Bhushan, B and U Apte. Liver Regeneration after Acetaminophen Hepatotoxicity: Mechanisms and Therapeutic Opportunities. Am J Pathol 2019, 189:719-729. PMID: 30653954; PMCID: PMC6446224.

48. Jemiolo, B, S Harvey and M Novotny. Promotion of the Whitten effect in female mice by synthetic analogs of male urinary constituents. Proc Natl Acad Sci USA 1986, 83:4576-4579. PMID: 3459193; PMCID: PMC323778.

49. Dorrell, C, L Erker, J Schug, J L Kopp, P S Canaday, A J Fox, O Smirnova, A W Duncan, M J Finegold, M Sander, K H Kaestner and M Grompe. Prospective isolation of a bipotential clonogenic liver progenitor cell in adult mice. Genes Dev 2011, 25:1193-1203. PMID: 21632826; PMCID: 3110957.

50. Weinreb, C, S Wolock and A M Klein. SPRING: a kinetic interface for visualizing high dimensional single-cell expression data. Bioinformatics 2018, 34:1246-1248. PMID: 29228172; PMCID: PMC6030950.

51. Goldfarb, C N and D J Waxman. Global analysis of expression, maturation and subcellular localization of mouse liver transcriptome identifies novel sex-biased and TCPOBOP-responsive long non-coding RNAs. BMC Genomics 2021, 22:212. PMID: 33761883; PMCID: PMC7992343.

52. Lowe, R, C Gemma, V K Rakyan and M L Holland. Sexually dimorphic gene expression emerges with embryonic genome activation and is dynamic throughout development. BMC Genomics 2015, 16:295. PMID: 25888192; PMCID: PMC4410000.

53. Dehkhoda, F, C M M Lee, J Medina and A J Brooks. The Growth Hormone Receptor: Mechanism of Receptor Activation, Cell Signaling, and Physiological Aspects. Front Endocrinol (Lausanne) 2018, 9:35. PMID: 29487568; PMCID: PMC5816795.

54. Brooks, C L. Molecular mechanisms of prolactin and its receptor. Endocr Rev 2012, 33:504-525. PMID: 22577091; PMCID: PMC3410225.

55. Bartke, A and J J Kopchick. The forgotten lactogenic activity of growth hormone: important implications for rodent studies. Endocrinology 2015, 156:1620-1622. PMID: 25730109; PMCID: PMC4398757.

56. Kalu, D N, P B Orhii, C Chen, D Y Lee, G B Hubbard, S Lee and Y Olatunji-Bello. Aged-rodent models of long-term growth hormone therapy: lack of deleterious effect on longevity. J Gerontol A Biol Sci Med Sci 1998, 53:B452-463. PMID: 9823743.

57. Higuti, E, C R Cecchi, N A Oliveira, D P Vieira, T G Jensen, A A Jorge, P Bartolini and C N Peroni. Growth responses following a single intra-muscular hGH plasmid administration compared to daily injections of hGH in dwarf mice. Curr Gene Ther 2012, 12:437-443. PMID: 22974419.

58. Mastemak, M M, J A Panici, F Wang, Z Wang and A Spong. The effects of growth hormone (GH) treatment on GH and insulin/IGF-1 signaling in long-lived Ames dwarf mice. J Gerontol A Biol Sci Med Sci 2010, 65:24-30. PMID: 19906822; PMCID: PMC2796883.

59. Wei, L, J Chang, Z Han, R Wang and L Song. Recombinant human growth hormone (rhGH) treatment of MKN-45 xenograft mice improves nutrition status and strengthens immune function without promoting tumor growth. PLoS One 2019, 14:e0210613. PMID: 30673747; PMCID: PMC6343934

60. Mossanen, J C and F Tacke. Acetaminophen-induced acute liver injury in mice. Laboratory animals 2015, 49:30-36. PMID: 25835736.

61. Lau-Corona, D, A Suvorov and D J Waxman. Feminization of Male Mouse Liver by Persistent Growth Hormone Stimulation: Activation of Sex-Biased Transcriptional Networks and Dynamic Changes in Chromatin States. Mol Cell Biol 2017, 37. PMID: 28694329; PMCID: PMC5599723.

62. Waxman, D J, N A Pampori, P A Ram, A K Agrawal and B H Shapiro. Interpulse interval in circulating growth hormone patterns regulates sexually dimorphic expression of hepatic cytochrome P450. Proc Natl Acad Sci USA 1991, 88:6868-6872. PMID: 1862110; PMCID: PMC52190.
63. Deng, S, S Tang, C Dai, Y Zhou, X Yang, D Li and X Xiao. P21(Waf1/Cip1) plays a critical role in furazolidone-induced apoptosis in HepG2 cells through influencing the caspase-3 activation and ROS generation. Food Chem Toxicol 2016, 88:1-12. PMID: 26687534.
64. Yang, M, D J Antoine, J L Weemhoff, R E Jenkins, A Farhood, B K Park and H Jaeschke. Biomarkers distinguish apoptotic and necrotic cell death during hepatic ischemia/reperfusion injury in mice. Liver Transpl 2014, 20:1372-1382. PMID: 25046819; PMCID: PMC4213307.
65. Bhushan, B and U Apte. Acetaminophen Test Battery (ATB): A Comprehensive Method to Study Acetaminophen-Induced Acute Liver Injury. Gene expression 2020, 20:125-138. PMID: 32443984; PMCID: PMC7650012.
66. MacParland, S A, J C Liu, X Z Ma, B T Innes, A M Bartczak, B K Gage, J Manuel, N Khuu, J Echeverri, I Linares, R Gupta, M L Cheng, L Y Liu, D Camat, S W Chung, R K Seliga, Z Shao, E Lee, S Ogawa, M Ogawa, M D Wilson, J E Fish, M Selzner, A Ghanekar, D Grant, P Greig, G Sapisochin, N Selzner, N Winegarden, O Adeyi, G KellerGD Bader and I D McGilvray. Single cell RNA sequencing of human liver reveals distinct intrahepatic macrophage populations. Nat Commun 2018, 9:4383. PMID: 30348985; PMCID: PMC6197289.
67. Tirosh, I, B Izar, S M Prakadan, M H Wadsworth, 2nd, D Treacy, J J Trombetta, A Rotem, C Rodman, C Lian, G Murphy, M Fallahi-Sichani, K Dutton-Regester, J R Lin, O Cohen, P Shah, D Lu, A S Genshaft, T K Hughes, C G Ziegler, S W Kazer, A Gaillard, K E Kolb, A C Villani, C M Johannessen, A Y Andreev, E M Van Allen, M Bertagnolli, P K Sorger, R J Sullivan, K T Flaherty, D T Frederick, J Jane-Valbuena, C H Yoon, O Rozenblatt-Rosen, A K Shalek, A Regev and L A Garraway. Dissecting the multicellular ecosystem of metastatic melanoma by single-cell RNA-seq. Science 2016, 352:189-196. PMID: 27124452; PMCID: PMC4944528.
68. Efremova, M, M Vento-Tormo, S A Teichmann and R Vento-Tormo. CellPhoneDB: inferring cell-cell communication from combined expression of multi-subunit ligand-receptor complexes. Nat Protoc 2020, 15:1484-1506. PMID: 32103204.
69. Hede, M S, E Salimova, A Piszczek, E Perlas, N Winn, T Nastasi and N Rosenthal. E-peptides control bioavailability of IGF-1. PLoS One 2012, 7:e51152. PMID: 23251442; PMCID: PMC3519493
70. Rudling, M and B Angelin. Growth hormone reduces plasma cholesterol in LDL receptor-deficient mice. Faseb j 2001, 15:1350-1356. PMID: 11387232.
71. Westwood, M, A R Maqsood, M Solomon, A J Whatmore, J R Davis, R C Baxter, E F Gevers, I C Robinson and P E Clayton. The effect of different patterns of growth hormone administration on the IGF axis and somatic and skeletal growth of the dwarf rat. Am J Physiol Endocrinol Metab 2010, 298:E467-476. PMID: 19861588; PMCID: PMC2838527.
72. Tao, R, F Acquati, S M Marcovina and H H Hobbs. Human growth hormone increases apo(a) expression in transgenic mice. Arterioscler Thromb Vase Biol 1999, 19:2439-2447. PMID: 10521374.
73. Guyda, H J. Four decades of growth hormone therapy for short children: what have we achieved? J Clin Endocrinol Metab 1999, 84:4307-4316. PMID: 10599680.
74. Nair, A B and S Jacob. A simple practice guide for dose conversion between animals and human. J Basic Clin Pharm 2016, 7:27-31. PMID: 27057123; PMCID: PMC4804402.
75. Lara-Diaz, V J, I Castilla-Cortazar, I Martin-Estal, M García-Magariño, G A Aguirre, J E Puche, R G de la Garza, L A Morales and U Muñoz. IGF-1 modulates gene expression of proteins involved in inflammation, cytoskeleton, and liver architecture. J Physiol Biochem 2017, 73:245-258. PMID: 28124277; PMCID: PMC5399066.
76. Morales-Garza, L A, J E Puche, G A Aguirre, U Muñoz, M García-Magariño, R G De la Garza and I Castilla-Cortazar. Experimental approach to IGF-1 therapy in CCl(4)-induced acute liver damage in healthy controls and mice with partial IGF-1 deficiency. Journal of translational medicine 2017, 15:96. PMID: 28472963; PMCID: PMC5418730.
77. Asakawa, K, N Hizuka, K Takano, R Horikawa, I Sukegawa, C Toyoda and K Shizume. Human growth hormone stimulates liver regeneration in rats. J Endocrinol Invest 1989, 12:343-347. PMID: 2768759.
78. Rosenbloom, A L. Insulin-like growth factor-I (rhIGF-I) therapy of short stature. J Pediatr Endocrinol Metab 2008, 21:301-315. PMID: 18556960.
79. Collett-Solberg, P F and M Misra. The role of recombinant human insulin-like growth factor-I in treating children with short stature. J Clin Endocrinol Metab 2008, 93:10-18. PMID: 18165284.
80. Kupfer, S R, L E Underwood, R C Baxter and D R Clemmons. Enhancement of the anabolic effects of growth hormone and insulin-like growth factor I by use of both agents simultaneously. J Clin Invest 1993, 91:391-396. PMID: 7679407; PMCID: PMC287936.
81. Fan, Y, R K Menon, P Cohen, D Hwang, T Clemens, D J DiGirolamo, J J Kopchick, D Le Roith, M Trucco and M A Sperling. Liver-specific deletion of the growth hormone receptor reveals essential role of growth hormone signaling in hepatic lipid metabolism. J Biol Chem 2009, 284:19937-19944. PMID: 19460757; PMCID: PMC2740419.
82. Tersteeg, C, J Roodt, W J Van Rensburg, C Dekimpe, N Vandeputte, I Pareyn, A Vandenbulcke, B Plaimauer, S Lamprecht, H Deckmyn, J A Lopez, S F De Meyer and K Vanhoorelbeke. N-acetylcysteine in preclinical mouse and baboon models of thrombotic thrombocytopenic purpura. Blood 2017, 129:1030-1038. PMID: 28011677.
83. James, L P, S S McCullough, L W Lamps and J A Hinson. Effect of N-acetylcysteine on acetaminophen toxicity in mice: relationship to reactive nitrogen and cytokine formation. Toxicol Sci 2003, 75:458-467. PMID: 12883092.
84. Kane, A E, A Huizer-Pajkos, J Mach, C McKenzie, S J Mitchell, R de Cabo, B Jones, V Cogger, D G Le Couteur and S N Hilmer. N-Acetyl cysteine does not prevent liver toxicity from chronic low-dose plus subacute high-dose paracetamol exposure in young or old mice. Fundam Clin Pharmacol 2016, 30:263-275. PMID: 26821200; PMCID: PMC4864111.
85. Saito, C, C Zwingmann and H Jaeschke. Novel mechanisms of protection against acetaminophen hepatotoxicity in mice by glutathione and N-acetylcysteine. Hepatology 2010, 51:246-254. PMID: 19821517; PMCID: PMC2977522.
86. McConnachie, L A, I Mohar, F N Hudson, C B Ware, W C Ladiges, C Fernandez, S Chatterton-Kirchmeier, C C White, R H Pierce and T J Kavanagh. Glutamate cysteine ligase modifier subunit deficiency and gender as determi- 87. Richmond, E J and A D Rogol. Recombinant human insulin-like growth factor-I therapy for children with growth disorders. Adv Ther 2008, 25:1276-1287. PMID: 19066756.
88. Clark, R G. Recombinant human insulin-like growth factor I (IGF-I): risks and benefits of normalizing blood IGF-I concentrations. Horm Res 2004, 62 Suppl 1:93-100. PMID: 15761240.
89. Oberbauer, A M. The Regulation of IGF-1 Gene Transcription and Splicing during Development and Aging. Front Endocrinol (Lausanne) 2013, 4:39. PMID: 23533068; PMCID: PMC3607797.
90. Simmons, J G, J J Van Wyk, E C Hoyt and P K Lund. Multiple transcription start sites in the rat insulin-like growth factor-I gene give rise to IGF-I mRNAs that encode different IGF-I precursors and are processed differently in vitro. Growth Factors 1993, 9:205-221. PMID: 8274298.
91. Coleman, M E, F DeMayo, K C Yin, H M Lee, R Geske, C Montgomery and R J Schwartz. Myogenic vector expression of insulin-like growth factor I stimulates muscle cell differentiation and myofiber hypertrophy in transgenic mice. J Biol Chem 1995, 270:12109-12116. PMID: 7744859.
92. Rabinovsky, E D, E Gelir, S Gelir, H Lui, M Kattash, F J DeMayo, S M Shenaq and R J Schwartz. Targeted expression of IGF-1 transgene to skeletal muscle accelerates muscle and motor neuron regeneration. Faseb j 2003, 17:53-55. PMID: 12424223.
93. Musarb, A, K McCullagh, A Paul, L Houghton, G Dobrowolny, M Molinaro, E R Barton, H L Sweeney and N Rosenthal. Localized Igf-1 transgene expression sustains hypertrophy and regeneration in senescent skeletal muscle. Nat Genet 2001, 27:195-200. PMID: 11175789.
94. Shavlakadze, T, J M Boswell, D W Burt, E A Asante, F M Tomas, M J Davies, J D White, M D Grounds and C Goddard. Rskalpha-actin/hIGF-1 transgenic mice with increased IGF-I in skeletal muscle and blood: impact on regeneration, denervation and muscular dystrophy. Growth Horm IGF Res 2006, 16:157-173. PMID: 16716629.
95. Santini, M P, N Winn and N Rosenthal. Signalling pathways in cardiac regeneration. Novartis Found Symp 2006, 274:228-238; discussion 239-243, 272-226. PMID: 17019815.
96. Semenova, E, H Koegel, S Hasse, J E Klatte, E Slonimsky, D Bilbao, R Paus, S Werner and N Rosenthal. Overexpression of mIGF-1 in keratinocytes improves wound healing and accelerates hair follicle formation and cycling in mice. Am J Pathol 2008, 173:1295-1310. PMID: 18832567; PMCID: PMC2570121.
97. Baumann, G P. Growth hormone isoforms. Growth Horm IGF Res 2009, 19:333-340. PMID: 19467614.
98. Banerjee, I and P E Clayton. Growth hormone treatment and cancer risk. Endocrinol Metab Clin North Am 2007, 36:247-263. PMID: 17336744.
99. Chesnokova, V and S Melmed. Growth hormone in the tumor microenvironment. Arch Endocrinol Metab 2019, 63:568-575. PMID: 31939481; PMCID: PMC7025769.
100. Zerrad-Saadi, A, M Lambert-Blot, C Mitchell, H Bretes, A Collin de l'Hortet, V Baud, F Chereau, A Sotiropoulos, J J Kopchick, L Liao, J Xu, H Gilgenkrantz and J E Guidotti. G H receptor plays a major role in liver regeneration through the control of EGFR and ERK1/2 activation. Endocrinology 2011, 152:2731-2741. PMID: 21540290.
101. González, L, M E Diaz, J G Miquet, Al Sotelo and F P Dominici. Growth Hormone Modulation of Hepatic Epidermal Growth Factor Receptor Signaling. Trends Endocrinol Metab 2021, 32:403-414. PMID: 33838976.
102. Skames, W C, B Rosen, A P West, M Koutsourakis, W Bushell, V Iyer, A O Mujica, M Thomas, J Harrow, T Cox, D Jackson, J Severin, P Biggs, J Fu, M Nefedov, P J de Jong, A F Stewart and A Bradley. A conditional knockout resource for the genome-wide study of mouse gene function. Nature 2011, 474:337-342. PMID: 21677750; PMCID: PMC3572410.
103. Liu, J L, A Grinberg, H Westphal, B Sauer, D Accili, M Karas and D LeRoith. Insulin-like growth factor-I affects perinatal lethality and postnatal development in a gene dosage-dependent manner: manipulation using the Cre/loxP system in transgenic mice. Mol Endocrinol 1998, 12:1452-1462. PMID: 9731712.
104. Dietrich, P, I Dragatsis, S Xuan, S Zeitlin and A Efstratiadis. Conditional mutagenesis in mice with heat shock promoter-driven cre transgenes. Mamm Genome 2000, 11:196-205. PMID: 10723724.
105. Nteeba, J, K Kubota, W Wang, H Zhu, J Vivian, G Dai and M Soares. Pancreatic prolactin receptor signaling regulates maternal glucose homeostasis. J Endocrinol 2019. PMID: 30798322; PMCID: PMC7189340.
106. Sorensen, I, R H Adams and A Gossler. DLL1-mediated Notch activation regulates endothelial identity in mouse fetal arteries. Blood 2009, 113:5680-5688. PMID: 19144989.
107. Qian, B Z, J Li, H Zhang, T Kitamura, J Zhang, L R Campion, E A Kaiser, L A Snyder and J W Pollard. CCL2 recruits inflammatory monocytes to facilitate breast-tumour metastasis. Nature 2011, 475:222-225. PMID: 21654748; PMCID: PMC3208506.
108. Ballantyne, L L, Y Y Sin, O Y Al-Dirbashi, X Li, D J Hurlbut and C D Funk. Liver-specific knockout of arginase-1 leads to a profound phenotype similar to inducible whole body arginase-1 deficiency. Mol Genet Metab Rep 2016, 9:54-60. PMID: 27761413; PMCID: PMC5065044.
109. Yanger, K, D Knigin, Y Zong, L Maggs, G Gu, H Akiyama, E Pikarsky and B Z Stanger. Adult hepatocytes are generated by self-duplication rather than stem cell differentiation. Cell Stem Cell 2014, 15:340-349. PMID: 25130492.
110. Ferraris, J, S Bernichtein, D Pisera and V Goffin. Use of prolactin receptor antagonist to better understand prolactin regulation of pituitary homeostasis. Neuroendocrinology 2013, 98:171-179. PMID: 23969780.
111. Goffin, V, S Bernichtein, P Touraine and P A Kelly. Development and potential clinical uses of human prolactin receptor antagonists. Endocr Rev 2005, 26:400-422. PMID: 15814850.
112. Damiano, J S, K G Rendahl, C Karim, M G Embry, M Ghoddusi, J Holash, A Fanidi, T J Abrams and J A Abraham. Neutralization of prolactin receptor function by monoclonal antibody LFA102, a novel potential therapeutic for the treatment of breast cancer. Mol Cancer Ther 2013, 12:295-305. PMID: 23270929.

What is claimed herein is:

1. A composition comprising at least one engineered liver regenerative factor mRNA, the at least one engineered liver regenerative factor mRNA comprising a Vascular Endothelial Growth Factor A (VEGFA)-encoding nucleotide sequence having at least 95% sequence identity to the nucleotide sequence set forth in SEQ ID NO: 12.

2. The composition of claim 1, wherein the at least one engineered liver regenerative factor mRNA further comprises at least one modified nucleoside.

3. The composition of claim 2, wherein the at least one modified nucleoside comprises at least one non-natural nucleoside.

4. The composition of claim 2, wherein the at least one modified nucleoside is selected from the group consisting of: pseudouridine, N1-methylpseudouridine, 2-thiouridine, 4'-thiouridine, 5-methylcytosine, 2-thio-1-methyl-1-deaza-pseudouridine, 2-thio-1-methyl-pseudouridine, 2-thio-5-aza-uridine, 2-thio-dihydropseudouridine, 2-thio-dihydrouridine, 2-thio-pseudouridine, 4-methoxy-pseudouridine, 4-thio-1-methyl-pseudouridine, 4-thio-pseudouridine, 5-aza-uridine, dihydropseudouridine, 5-methyluridine, 5-methoxyuridine, 2'-O-methyluridine, and combinations thereof.

5. The composition of claim 2, wherein the at least one modified nucleoside comprises at least one N1-methylpseudouridine (m1Ψ).

6. The composition of claim 1, wherein the at least one engineered liver regenerative factor mRNA comprises the nucleotide sequence set forth in SEQ ID NO: 12.

7. The composition of claim 1, further comprising one or more engineered liver regenerative factor mRNA selected from the group consisting of:
a) an engineered liver regenerative factor mRNA encoding Growth Hormone (GH);
b) an engineered liver regenerative factor mRNA encoding Epidermal Growth Factor (EGF);
c) an engineered liver regenerative factor mRNA encoding Hepatocyte Growth Factor (HGF);
d) an engineered liver regenerative factor mRNA encoding Cyclin-Dependent Kinase Inhibitor 1A (p21);
e) an engineered liver regenerative factor mRNA encoding Insulin-like Growth Factor 1 (IGF-1);
f) an engineered liver regenerative factor mRNA encoding signal transducer and activator of transcription 5B (Stat5b);
g) an engineered liver regenerative factor mRNA encoding beta catenin (CTNNB1);
h) an engineered liver regenerative factor mRNA encoding yes-associated protein 1 (YAP);
i) an engineered liver regenerative factor mRNA encoding wingless-type MMTV integration site family, member 2 (WNT2); and
j) an engineered liver regenerative factor mRNA encoding wingless-type MMTV integration site family, member 9B (WNT9b).

8. The composition of claim 7, wherein the one or more liver regenerative factor mRNA is selected from the group consisting of: an engineered liver regenerative factor mRNA encoding HGF; an engineered liver regenerative factor mRNA encoding GH; an engineered liver regenerative factor mRNA encoding EGF; and an engineered liver regenerative factor mRNA encoding p21.

9. The composition of claim 7, wherein the one or more regenerative factor mRNA is selected from the group consisting of: an engineered liver regenerative factor mRNA encoding HGF; an engineered liver regenerative factor mRNA encoding GH; and an engineered liver regenerative factor mRNA encoding EGF.

10. The composition of claim 7, wherein:
a) the liver regenerative factor mRNA encoding GH comprises a nucleotide sequence having at least 95% sequence identity to the nucleotide sequence set forth in SEQ ID NO: 8;
b) the liver regenerative factor mRNA encoding EGF comprises a nucleotide sequence having at least 95% sequence identity to the nucleotide sequence set forth in SEQ ID NO: 9 or 15;
c) the liver regenerative factor mRNA encoding HGF comprises a nucleotide sequence having at least 95% sequence identity to the nucleotide sequence set forth in SEQ ID NO: 10;
d) the liver regenerative factor mRNA encoding p21 comprises a nucleotide sequence having at least 95% sequence identity to the nucleotide sequence set forth in SEQ ID NO: 11;
e) the liver regenerative factor mRNA encoding IGF-1 comprises a nucleotide sequence having at least 95% sequence identity to the nucleotide sequence set forth in SEQ ID NO: 13 or 14;
f) the liver regenerative factor mRNA encoding Stat5b comprises a nucleotide sequence having at least 95% sequence identity to the nucleotide sequence set forth in SEQ ID NO: 16;

g) the liver regenerative factor mRNA encoding beta catenin comprises a nucleotide sequence having at least 95% sequence identity to the nucleotide sequence set forth in SEQ ID NO: 21;
h) the liver regenerative factor mRNA encoding YAP comprises a nucleotide sequence having at least 95% sequence identity to the nucleotide sequence set forth in SEQ ID NO: 25;
i) the liver regenerative factor mRNA encoding WNT2 comprises a nucleotide sequence having at least 95% sequence identity to the nucleotide sequence set forth in SEQ ID NO: 26; or
j) the liver regenerative factor mRNA encoding WNT9b comprises a nucleotide sequence having at least 95% sequence identity to the nucleotide sequence set forth in SEQ ID NO: 27.

11. The composition of claim 7, wherein:
a) the liver regenerative factor mRNA encoding GH comprises a nucleotide sequence having the nucleotide sequence set forth in SEQ ID NO: 8;
b) the liver regenerative factor mRNA encoding EGF comprises a nucleotide sequence having the nucleotide sequence set forth in SEQ ID NO: 9 or 15;
c) the liver regenerative factor mRNA encoding HGF comprises a nucleotide sequence having the nucleotide sequence set forth in SEQ ID NO: 10;
d) the liver regenerative factor mRNA encoding p21 comprises a nucleotide sequence having the nucleotide sequence set forth in SEQ ID NO: 11;
e) the liver regenerative factor mRNA encoding IGF-1 comprises a nucleotide sequence having the nucleotide sequence set forth in SEQ ID NO: 13 or 14;
f) the liver regenerative factor mRNA encoding Stat5b comprises a nucleotide sequence having the nucleotide sequence set forth in SEQ ID NO: 16;
g) the liver regenerative factor mRNA encoding beta catenin comprises a nucleotide sequence having the nucleotide sequence set forth in SEQ ID NO: 21;
h) the liver regenerative factor mRNA encoding YAP comprises a nucleotide sequence having the nucleotide sequence set forth in SEQ ID NO: 25;
i) the liver regenerative factor mRNA encoding WNT2 comprises a nucleotide sequence having the nucleotide sequence set forth in SEQ ID NO: 26; or
j) the liver regenerative factor mRNA encoding WNT9b comprises a nucleotide sequence having the nucleotide sequence set forth in SEQ ID NO: 27.

12. The composition of claim 1, wherein the composition further comprises a carrier complexed with the at least one engineered liver regenerative factor mRNA.

13. The composition of claim 12, wherein the carrier is a nanoparticle.

14. The composition of claim 12, wherein the carrier is a polymer nanoparticle.

15. The composition of claim 12, wherein the nanoparticle is a lipid nanoparticle (LNP).

16. The composition of claim 1, further comprising N-acetyl cysteine (NAC).

17. A combination of the composition of claim 1 and N-acetyl cysteine (NAC).

18. A method of treating liver injury or liver disease, or accelerating intrinsic liver repair, in a subject in need thereof, the method comprising administering the composition of claim 1 to the subject.

19. The method of claim 18, wherein the subject is a subject in need of treatment for acute liver disease, chronic liver disease, or acetaminophen (acetyl-para-aminophenol, APAP) overdose.

20. The method of claim 18, further comprising administering N-acetyl cysteine (NAC) to the subject.

21. A method of engrafting cells in a live of a subject, the method comprising transplanting the cells into the liver and administering the composition of claim 1 to the subject.

22. The method of claim 21, wherein the cells are primary human hepatocytes (PHH) or hepatocytes derived from human induced pluripotent stem cells (hiPSC).

* * * * *